US012398186B2

(12) United States Patent
Wong

(10) Patent No.: US 12,398,186 B2
(45) Date of Patent: Aug. 26, 2025

(54) MULTI-CHAIN CHIMERIC POLYPEPTIDES AND USES THEREOF

(71) Applicant: ImmunityBio, Inc., San Diego, CA (US)

(72) Inventor: Hing Wong, Miramar, FL (US)

(73) Assignee: ImmunityBio, Inc., San Diego, CA (US)

( * ) Notice: Subject to any disclaimer, the term of this patent is extended or adjusted under 35 U.S.C. 154(b) by 203 days.

(21) Appl. No.: 18/047,751

(22) Filed: Oct. 19, 2022

(65) Prior Publication Data

US 2023/0128292 A1 Apr. 27, 2023

Related U.S. Application Data

(62) Division of application No. 16/555,689, filed on Aug. 29, 2019, now Pat. No. 11,518,792.

(60) Provisional application No. 62/881,088, filed on Jul. 31, 2019, provisional application No. 62/817,230, filed on Mar. 12, 2019, provisional application No. 62/817,241, filed on Mar. 12, 2019, provisional application No. 62/816,683, filed on Mar. 11, 2019, provisional application No. 62/749,506, filed on Oct. 23, 2018, provisional application No. 62/749,007, filed on Oct. 22, 2018, provisional application No. 62/746,832, filed on Oct. 17, 2018, provisional application No. 62/724,969, filed on Aug. 30, 2018, provisional application No. 62/725,043, filed on Aug. 30, 2018, provisional application No. 62/725,010, filed on Aug. 30, 2018.

(51) Int. Cl.

| | |
|---|---|
| ***C07K 14/54*** | (2006.01) |
| ***C07K 14/71*** | (2006.01) |
| ***C07K 14/715*** | (2006.01) |
| ***C07K 14/745*** | (2006.01) |
| ***C07K 16/28*** | (2006.01) |

(52) U.S. Cl.

CPC .......... *C07K 14/5434* (2013.01); *C07K 14/54* (2013.01); *C07K 14/5418* (2013.01); *C07K 14/71* (2013.01); *C07K 14/7155* (2013.01); *C07K 14/745* (2013.01); *C07K 16/283* (2013.01); *C07K 2317/622* (2013.01); *C07K 2319/02* (2013.01); *C07K 2319/03* (2013.01); *C07K 2319/30* (2013.01)

(58) Field of Classification Search

CPC ........................ C07K 2319/30; C07K 14/5443

See application file for complete search history.

(56) References Cited

U.S. PATENT DOCUMENTS

| | | | | |
|---|---|---|---|---|
| 5,595,756 | A | 1/1997 | Bally et al. | |
| 6,117,980 | A | 9/2000 | Gonzalez et al. | |
| 7,452,537 | B2 | 11/2008 | Bauer et al. | |
| 7,482,436 | B2 | 1/2009 | Sugimura et al. | |
| 7,488,802 | B2 | 2/2009 | Collins et al. | |
| 7,521,051 | B2 | 4/2009 | Collins et al. | |
| 7,612,181 | B2 | 11/2009 | Wu et al. | |
| 7,691,380 | B2 | 4/2010 | Thorpe et al. | |
| 7,723,482 | B2 | 5/2010 | Soulillou et al. | |
| 7,968,094 | B2 | 6/2011 | Jiao et al. | |
| 8,007,795 | B2 | 8/2011 | Jiao et al. | |
| 8,133,485 | B2 | 3/2012 | Levi-Schaffer et al. | |
| 8,217,149 | B2 | 7/2012 | Irving et al. | |
| 8,258,268 | B2 | 9/2012 | Wu et al. | |
| 8,475,792 | B2 * | 7/2013 | Dall'Acqua | A61P 37/00 530/387.9 |
| 8,552,156 | B2 | 10/2013 | Takayanagi et al. | |
| 8,586,714 | B2 | 11/2013 | Ghayur et al. | |
| 8,716,450 | B2 | 5/2014 | Ghayur et al. | |
| 8,722,855 | B2 | 5/2014 | Ghayur et al. | |
| 8,735,546 | B2 | 5/2014 | Ghayur et al. | |
| 8,741,604 | B2 | 6/2014 | Campbell et al. | |
| 8,753,640 | B2 | 6/2014 | Wu et al. | |
| 8,759,494 | B2 | 6/2014 | Bachmann et al. | |
| 8,822,645 | B2 | 9/2014 | Ghayur et al. | |
| 9,035,026 | B2 | 5/2015 | Hoffmann et al. | |
| 9,067,997 | B2 | 6/2015 | Romagne et al. | |

(Continued)

FOREIGN PATENT DOCUMENTS

| | | |
|---|---|---|
| CN | 1844150 | 10/2006 |
| CN | 101653603 | 2/2010 |

(Continued)

OTHER PUBLICATIONS

Chan et al., "Molecular mechanisms of natural killer cell activation in response to cellular stress," Cell Death & Differentiation, Jan. 2014, 21(1):5-14.

(Continued)

*Primary Examiner* — Vanessa L. Ford
*Assistant Examiner* — Sandra Carter
(74) *Attorney, Agent, or Firm* — Sheridan Ross P.C.

(57) ABSTRACT

Provided herein are multi-chain chimeric polypeptides that include:

(a) a first chimeric polypeptide including a first target-binding domain, a soluble tissue factor domain, and a first domain of a pair of affinity domains; and (b) a second chimeric polypeptide including a second domain of a pair of affinity domains and a second target-binding domain, where the first chimeric polypeptide and the second chimeric polypeptide associate through the binding of the first domain and the second domain of the pair of affinity domains. Also provided here are methods of using these multi-chain chimeric polypeptides and nucleic acids encoding these multi-chain chimeric polypeptides.

29 Claims, 95 Drawing Sheets

Specification includes a Sequence Listing.

(56) References Cited

U.S. PATENT DOCUMENTS

| | | | |
|---|---|---|---|
| 9,085,623 | B2 | 7/2015 | Rother et al. |
| 9,090,684 | B2 | 7/2015 | Borras et al. |
| 9,226,962 | B2 | 1/2016 | Le Gall et al. |
| 9,238,084 | B2 | 1/2016 | Liu et al. |
| 9,273,136 | B2 | 3/2016 | Rader et al. |
| 9,371,395 | B2 | 6/2016 | Takahashi et al. |
| 9,441,034 | B2 | 9/2016 | Sivakumar et al. |
| 9,505,843 | B2 | 11/2016 | Kim et al. |
| 9,617,345 | B2 | 4/2017 | Berne et al. |
| 9,701,758 | B2 | 7/2017 | Cooper et al. |
| 11,518,792 | B2 | 12/2022 | Wong |
| 11,672,826 | B2 | 6/2023 | Wong |
| 11,730,762 | B2 | 8/2023 | Wong |
| 11,738,052 | B2 | 8/2023 | Wong |
| 2001/0044427 | A1 | 11/2001 | Mazel et al. |
| 2003/0124678 | A1 | 7/2003 | Epstein et al. |
| 2003/0219441 | A1 | 11/2003 | Thorpe et al. |
| 2005/0014224 | A1 | 1/2005 | Collins et al. |
| 2006/0159655 | A1 | 7/2006 | Collins et al. |
| 2007/0160579 | A1 | 7/2007 | Schmitz et al. |
| 2008/0025979 | A1 | 1/2008 | Honjo et al. |
| 2009/0148942 | A1 | 6/2009 | McDonagh et al. |
| 2012/0171197 | A1 | 7/2012 | Eriksson et al. |
| 2012/0264920 | A1 | 10/2012 | Wang et al. |
| 2013/0274446 | A1 | 10/2013 | Kumagai et al. |
| 2014/0242077 | A1 | 8/2014 | Choi |
| 2015/0218274 | A1 | 8/2015 | Sabatos-Peyton et al. |
| 2015/0259429 | A1 | 9/2015 | Benaroch et al. |
| 2016/0175397 | A1 | 6/2016 | Umana et al. |
| 2016/0340413 | A1 | 11/2016 | Duerner et al. |
| 2016/0367664 | A1 | 12/2016 | Wang et al. |
| 2017/0051063 | A1 | 2/2017 | Baum et al. |
| 2017/0198042 | A1 | 7/2017 | Williams et al. |
| 2017/0283499 | A1 | 10/2017 | Delhem et al. |
| 2018/0200366 | A1 | 7/2018 | Wong |
| 2019/0078082 | A1 | 3/2019 | Amorese et al. |
| 2019/0092846 | A1 | 3/2019 | Ibebunjo et al. |
| 2019/0177406 | A1 | 6/2019 | Ledbetter et al. |
| 2019/0315850 | A1 | 10/2019 | Bedinger et al. |
| 2020/0123607 | A1 | 4/2020 | Serrano Marugan et al. |
| 2020/0190174 | A1 | 6/2020 | Wong |
| 2020/0392221 | A1 | 12/2020 | Van Snick et al. |
| 2020/0399358 | A1 | 12/2020 | Shapiro et al. |
| 2021/0060064 | A1 | 3/2021 | Wong |
| 2021/0061897 | A1 | 3/2021 | Ledbetter et al. |
| 2021/0100840 | A1 | 4/2021 | Wong et al. |
| 2021/0137981 | A1 | 5/2021 | Wong |
| 2021/0268022 | A1 | 9/2021 | Wong et al. |
| 2021/0277054 | A1 | 9/2021 | Wong et al. |
| 2021/0338724 | A1 | 11/2021 | Wong |
| 2021/0355204 | A1 | 11/2021 | Bedinger et al. |
| 2021/0403545 | A1 | 12/2021 | Van Snick et al. |
| 2022/0073578 | A1 | 3/2022 | Wong et al. |
| 2023/0023389 | A1 | 1/2023 | Wong |
| 2023/0039157 | A1 | 2/2023 | Wong |
| 2023/0174666 | A1 | 6/2023 | Wong et al. |
| 2023/0372399 | A1 | 11/2023 | Wong |
| 2023/0372444 | A1 | 11/2023 | Wong et al. |
| 2023/0381238 | A1 | 11/2023 | Wong |
| 2023/0398151 | A1 | 12/2023 | Wong |

FOREIGN PATENT DOCUMENTS

| | | |
|---|---|---|
| CN | 101965364 | 2/2011 |
| CN | 102153653 | 8/2011 |
| CN | 106255703 | 12/2016 |
| CN | 109513003 | 3/2019 |
| EP | 1245676 | 10/2002 |
| EP | 1719528 | 11/2006 |
| EP | 2537933 | 12/2012 |
| EP | 3029069 | 6/2016 |
| EP | 3348276 | 7/2018 |
| JP | 2005-124568 | 5/2005 |
| JP | 2008-536487 | 9/2008 |
| JP | 2009-512433 | 3/2009 |
| JP | 4361133 | 8/2009 |
| KR | 2016/0127688 | 11/2016 |
| KR | 101778439 | 9/2017 |
| WO | WO 1995/015341 | 6/1995 |
| WO | WO 1996/001653 | 1/1996 |
| WO | WO 2001/083755 | 11/2001 |
| WO | WO 2002/083152 | 10/2002 |
| WO | WO 2003/037911 | 5/2003 |
| WO | WO 2003/104425 | 12/2003 |
| WO | WO 2004/076488 | 9/2004 |
| WO | WO 2006/096828 | 9/2006 |
| WO | WO 2006/097743 | 9/2006 |
| WO | WO 2006/119897 | 11/2006 |
| WO | WO 2008/096158 | 8/2008 |
| WO | WO 2011/127324 | 10/2011 |
| WO | WO 2012/040323 | 3/2012 |
| WO | WO 2012/120125 | 9/2012 |
| WO | WO 2012/170470 | 12/2012 |
| WO | WO 2012/175222 | 12/2012 |
| WO | WO 2012/175692 | 12/2012 |
| WO | WO 2013/068946 | 5/2013 |
| WO | WO 2014/007513 | 1/2014 |
| WO | WO 2014/026054 | 2/2014 |
| WO | WO 2014/095808 | 6/2014 |
| WO | WO 2014/130635 | 8/2014 |
| WO | WO 2014/159531 | 10/2014 |
| WO | WO 2015/089881 | 6/2015 |
| WO | WO 2016/106221 | 6/2016 |
| WO | WO 2016/154585 | 9/2016 |
| WO | WO 2016/166348 | 10/2016 |
| WO | WO 2017/053748 | 3/2017 |
| WO | WO 2017/083612 | 5/2017 |
| WO | WO 2017/149538 | 9/2017 |
| WO | WO 2017/189526 | 11/2017 |
| WO | WO 2018/067825 | 4/2018 |
| WO | WO 2018/075989 | 4/2018 |
| WO | WO 2018/129007 | 7/2018 |
| WO | WO 2018/158350 | 9/2018 |
| WO | WO 2018/183169 | 10/2018 |
| WO | WO 2018/165208 | 12/2018 |
| WO | WO 2019/046313 | 3/2019 |
| WO | WO 2020/047333 | 3/2020 |
| WO | WO 2020/047462 | 3/2020 |
| WO | WO 2020/047473 | 3/2020 |
| WO | WO 2021/163369 | 8/2021 |

OTHER PUBLICATIONS

Chang et al., "The dock and lock method: a novel platform technology for building multivalent, multifunctional structures of defined composition with retained bioactivity," Clinical cancer research, Sep. 15, 2007, 13(18):5586s-5591s.

Hui et al., "Butyrate inhibit collagen-induced arthritis via Treg/IL-10/Th17 axis," International immunopharmacology, Mar. 1, 2019, 68: Abstract 1 page.

Li et al., "Lipid metabolism fuels cancer's spread," Cell metabolism, Feb. 7, 2017, 25(2):228-230.

Wilchek et al., "Essentials of biorecognition: The (strept) avidin-biotin system as a model for protein-protein and protein-ligand interaction," Immunology letters, Feb. 28, 2006, 103(1): Abstract 2 pages.

Zhang et al., "Depletion of NK cells improves cognitive function in the Alzheimer disease mouse model, " The Journal of Immunology, Jul. 15, 2020, 205(2): 10pages.

Chen et al., "A novel idea for establishing Parkinson's disease mouse model by intranasal administration of paraquat" Neurological Research, 43(4):267-277, 2021.

Igarashi et al., "VEGF-C and TGF-β reciprocally regulate mesenchymal stem cell commitment to differentiation into lymphatic endothelial or osteoblastic phenotypes," International journal of molecular medicine, 37(4):1005-1013, Apr. 1, 2016.

Infante-Duarte et al., "New developments in understanding and treating neuroinflammation" Journal of Molecular Medicine, 86:975-985, Sep. 2008.

International Search Report and Written Opinion in International Appln. No. PCT/US2023/065745, mailed on Jun. 26, 2023, 14 pages.

(56) References Cited

OTHER PUBLICATIONS

Janeway et al., "The interaction of the antibody molecule with specific antigen" In Immunobiology: The Immune System in Health and Disease, 5th edition, 5 pages, 2001.
Matsuura et al., "Pole test is a useful method for evaluating the mouse movement disorder caused by striatal dopamine depletion" Journal of neuroscience methods, 73(1):45-48, 1997.
Reddy et al., "Linkers in the structural biology of protein-protein interactions" Protein science, 22(2):153-167, 2013.
Ross et al., "Signaling and function of interleukin-2 in T lymphocytes" Annual review of immunology, 36:411-433, 2018.
Van Bockstaele et al., "The development of nanobodies for therapeutic applications" Current opinion in investigational drugs, 10(11):1212-1224, 2009.
[No Author Listed], "CN Br-activated Sepharose 4 Fast Flow," 1999, Affinity Chromatography, 4 pages.
Brämer et al., "Membrane adsorber for the fast purification of a monoclonal antibody using protein a chromatography," Membranes, Nov. 27, 2019, 9(12):159, 15 pages.
Chabannon et al., "Manufacturing natural killer cells as medicinal products," Frontiers in Immunology, Nov. 15, 2016, 7(504): 1-9.
Guha et al., "Affinity purification of human tissue factor: interaction of factor VII and tissue factor in detergent micelles," Proceedings of the National Academy of Sciences, Jan. 1986, 83(2):299-302.
Hélie et al., "Application of the Protein Maker as a platform purification system for therapeutic antibody research and development," Computational and Structural Biotechnology Journal, Jan. 1, 2016, 14:238-244.
info.gbiosciences.com [Online], "G-Biosciences, The Basics of Affinity Purification/Affinity Chromatography," Jul. 31, 2018, retrieved on Apr. 18, 2023, retrieved from URL<https://info.gbiosciences.com/blog/the-basics-of-affinity-purification/affinity-chromatography?utm_campaign-G-Bio+Search+Ads&utm term=&utm_source-adwords&utm_medium=ppc&hsa_src=g&hsa_ver=3&hsa_cam=737902488&hsa kw=&hsa_ad=621736020174&hsa_tgt-dsa-460355902483&hsa mt=&hsa acc-6752996364&hsa_grp=92226101427&hsa_net-adwords&gclid-CjwKCAjwihBhADEiwAXEazJvXifVFgeRGV_W99XbY72eRROhWnHtdd695ydPgyh8qdvTwd9ikGIRoCdecQAvD_BwE>, 5 pages.
Klingemann et al., "Natural killer cells for immunotherapy-advantages of the NK-92 cell line over blood NK cells, " Frontiers in Immunology, Mar. 14, 2016, 7(91): 1-7.
Kozlowska et al., "Adoptive transfer of osteoclast-expanded natural killer cells for immunotherapy targeting cancer stem-like cells in humanized mice," Cancer Immunology, Immunotherapy, Jul. 2016, 65:835-845.
Putnam et al., "Clinical grade manufacturing of human alloantigen-reactive regulatory T cells for use in transplantation," American Journal of Transplantation, Nov. 1, 2013, 13(11):3010-3020.
ThermoFisher.com [Online], "Covalent Immobilization of Affinity Ligands," 2018, retrieved on Apr. 18, 2023, retrieved from <URLhttps://www.thermofisher.com/us/en/home/life-science/protein-biology/protein-biology-learning-center/protein-biology-resource-library/pierce-protein-methods/covalent-immobilization-affinity-ligands.html>, 13 pages.
Uppendahl et al., "Natural killer cell-based immunotherapy in gynecologic malignancy: a review," Frontiers in Immunology, Jan. 5, 2018, 8(1825): 1-15.
Urh et al., "Affinity chromatography: general methods," Methods in Enzymology, Jan. 1, 2009, 463: 23 pages.
Veluchamy et al., "The rise of allogeneic natural killer cells as a platform for cancer immunotherapy: recent innovations and future developments," Frontiers in Immunology, May 31, 2017, 8(631): 1-20.
Zhou, "Emerging mechanisms and applications of low-dose IL-2 therapy in autoimmunity," Cytokine & Growth Factor Reviews, Jun. 30, 2022, 67: 80-88.
Fernando et al., "Targeting tumor endothelial marker 8 in the tumor vasculature of colorectal carcinomas in mice," Cancer Research, Jun. 15, 2009, 69(12):5126-5132.
Mortier et al., "Soluble interleukin-15 receptor α (IL-15Rα)-sushi as a selective and potent agonist of IL-15 action through IL-15Rβ/γ: hyperagonist IL-15. IL-15Rα fusion proteins," Journal of Biological Chemistry, Jan. 20, 2006, 281(3): 1612-1619.
Wong et al., "Interleukin-15: Interleukin-15 receptor a scaffold for creation of multivalent targeted immune molecules," Protein Engineering, Design & Selection, Apr. 1, 2011, 24(4):373-383.
International Preliminary Report on Patentability in International Appln. No. PCT/US2020/035598, mailed Dec. 6, 2022, 7 pages.
International Preliminary Report on Patentability in International Appln. No. PCT/US2021/035285, mailed Dec. 15, 2022, 7 pages.
Shen et al., "Engineering peptide linkers for scFv immunosensors," Anal Chem., Mar. 2008, 80(6):1910-1917.
Bartscht et al., "Dasatinib blocks transcriptional and promigratory responses to transforming growth factor-beta in pancreatic adenocarcinoma cells through inhibition of Smad signalling: implications for in vivo mode of action," Molecular Cancer, Dec. 2015, 14(199):1-12.
Bird et al., "TGFβ inhibition restores a regenerative response in acute liver injury by suppressing paracrine senescence," Science translational medicine, Aug. 15, 2018, 10(454):eaan 1230, 15 pages.
Cai et al., "Quercetin inhibits transforming growth factor β1-induced epithelial-mesenchymal transition in human retinal pigment epithelial cells via the Smad pathway," Drug design, development and therapy, Dec. 6, 2018, 12:4149-4161.
Abbott et al., "Genomic organization, exact localization, and tissue expression of the human CD26 (dipeptidyl peptidase IV) gene," Immunogentics, Sep. 1994, 40(5):331-338.
Abdul-Aziz et al., "Acute myeloid leukemia induces protumoral p16INK4a-driven senescence in the bone marrow microenvironment," Blood, Jan. 31, 2019, 133(5):446-456.
Aertgeerts et al., "Crystal structure of human dipeptidyl peptidase IV in complex with a decapeptide reveals details on substrate specificity and tetrahedral intermediate formation, " Protein Science, Feb. 2004, 13(2):412-421.
Ait-Oufella el al., "Natural regulatory T cells control the development of atherosclerosis in mice," Nature Medicine, Feb. 5, 2006, 12:178-180.
Akbari, et al., "Design, expression and evaluation of a novel humanized single chain antibody against epidermal growth factor receptor (EGFR)," Protein Expr. Purif., 2016, 127:8-15.
Ali et al., "Regulatory T cells in skin," Immunology, Jul. 12, 2017, 152(3):372-381.
Angevin et al., "First-in-human phase 1 of YS110, a monoclonal antibody directed against CD26 in advanced CD26-expressing cancers," British Journal of Cancer, Mar. 14, 2017, 116(9):1126-1134.
Bachelet et al., "Mast Cell Costimulation by CD226/CD112 (DNAM-1/Nectin-2) A Novel Interface in the Allergic Process," Journal of Biological Chemistry, Sep. 15, 2006, 281(37):27190-6.
Baker et al., "Chronic treatment with the beta(2)-adrenoceptor agonist prodrug BRL-47672 impairs rat skeletal muscle function by inducing a comprehensive shift to a faster muscle phenotype," J Pharmacol Exp Ther., Oct. 2006, 319(1):439-446.
Baker et al., "Effects of conjugated linoleic acid (CLA) on tissue composition parameters in a murine cachexia model," The FASEB Journal, Mar. 2006, 20(4), 2 pages (Abstract Only).
Baker, et al., "Clearance of p16Ink4a-positive senescent cells delays ageing-associated disorders," Nature, 2011, 479(7372): 232-236.
Bennett et al., "Erratum: Killing the old: cell senescence in atherosclerosis," Nature Reviews Cardiology, Jan. 12, 2017, 14(3):132.
Bennett et al., "Killing the old: cell senescence in atherosclerosis," Nature Reviews Cardiology, Dec. 12, 2016, 14(1):8-9, 2 pages.
Bentebibel et al., "A First-in-Human Study and Biomarker Analysis of NKTR-214, a Novel IL2Raf Biased Cytokine, in Patients with Advanced or Metastatic Solid Tumors," Cancer Discovery, Jun. 2019, 9(6):711-721.
Berry et al., "Cancer Anorexia and Cachexia: Screening in an Ambulatory Infusion Service and Nutrition Consultation, " Clin J Oncol Nurs., 2018, 22(1):63-68.
Bhat et al., "Astrocyte Senescence as a Component of Alzheimer's Disease, " PLoS One, Sep. 12, 2012, 7(9):e45069, 10 pages.

(56) References Cited

OTHER PUBLICATIONS

Biran et al., "Senescent cells communicate via intercellular protein transfer," Genes & Development, Apr. 8, 2015, 29(8):791-802, 13 pages.
Borea et al., "Pharmacology of Adenosine Receptors: The State of the Art," Physiological Reviews 98(3):1591-1625, 2018.
Borgerding et al., "B-lymphoma cells escape rituximab-triggered elimination by NK cells through increased HLA class I expression," Experimental Hematology, Mar. 1, 2010, 38(3):213-21.
Bork, "Powers and Pitfalls in Sequence Analysis: The 70% Hurdle," Genome Research, 2000, 10:398-400.
Bourgeois et al., "Regulation of cellular senescence via the FOXO4-p53 axis, " FEBS Lett., 2018, 592(12): 2083-2097.
Bowie et al., "Deciphering the Message in Protein Sequences: Tolerance to Amino Acid Substitutions," Science, 1990, 247:1306-1310.
Boyman et al., "IL-7/Anti-IL-7 mAb Complexes Restore T Cell Development and Induce Homeostatic T Cell Expansion without Lymphopenia, " The Journal of Immunology, Jun. 1, 2008, 180:7265-7275.
Boyman et al., "Selective Stimulation of T Cell Subsets with Antibody-Cytokine Immune Complexes," Science, Mar. 31, 2006, 311(5769):1924-1927.
Brennan et al., "Structural determination of lipid antigens captured at the CD1d-T-cell receptor interface," PNAS, 2017, 114(31):8348-8353.
Brighton et al., "Clearance of senescent decidual cells by uterine natural killer cells in cycling human endometrium," Elife, Dec. 11, 2017, 6:e31274, 23 pages.
Brooks et al., "Combined inhibition of PD1 and CD96 checkpoints improves survival in a resectable murine model of pancreatic cancer," European Journal of Cancer, Jul. 1, 2016, 61:S189, 1 page.
Broxmeyer et al., "Modulation of Hematopoietic Chemokine Effects In Vitro and In Vivo by DPP-4/CD26," Stem Cells and Development, Mar. 4, 2016, 25(8):575-585.
Brunstein et al., "Infusion of Ex Vivo Expanded T Regulatory Cells in Adults Transplanted with Umbilical Cord Blood: Safety Profile and Detection Kinetics," Blood, Jan. 20, 2011, 117(3):1061-1070.
Brunstein et al., "Umbilical cord blood-derived T regulatory cells to prevent GVHD:kinetics, toxicity profile, and clinical effect," Blood, Feb. 25, 2016, 127(8):1044-1051.
Buhling et al., "Functional role of CD26 on human B lymphocytes," Immunology Letters, Feb. 1995, 45(1-2):47-51.
Burgess et al., "Possible Dissociation of the Heparin-binding and Mitogenic Activities of Heparin-binding (Acidic Fibroblast) GrowthFactor-1 from Its Receptor-binding Activities by Site-directed Mutagenesis of a Single Lysine Residue," J. Cell Biol., 1990, 111:2129-2138.
Bussian et al., "Clearance of senescent glial cells prevents tau-dependent pathology and cognitive decline," Nature, Sep. 19, 2018, 562(7728):578-582, 21 pages.
Cai et al., "Chibby suppresses aerobic glycolysis and proliferation of nasopharyngeal carcinoma via the Wnt/β-catenin-Lin28/let7-PDK1 cascade," Journal of Experimental & Clinical Cancer Research, Dec. 1, 2018, 37(1):104.
Cao et al., "Expression and characterization of recombinant humanized anti-HER2 single-chain antibody in Pichia pastoris for targeted cancer therapy," Biotechnology Letters, Jul. 1, 2015, 37(7):1347-54.
Cao, "Self-regulation and cross-regulation of pattern-recognition receptor signaling in health and disease," Nature Reviews Immunology, Dec. 29, 2015, 16(1):35-50.
Carr et al., "NK Cell-Mediated Lysis of Autologous HCMV-Infected Skin Fibroblasts Is Highly Variable among NK Cell Clones and Polyclonal NK Cell Lines," Clinical Immunology, Nov. 2002, 105(2):126-140.
Catania et al., "The tumor-targeting immunocytokine F16-IL2 in combination with doxorubicin: dose escalation in patients with advanced solid tumors and expansion into patients with metastatic breast cancer," Cell Adhesion and Migration, Jan.-Apr. 2015, 9(1-2):14-21.
Cavinato et al., "Molecular mechanisms of UVB-induced senescence of dermal fibroblasts and its relevance for photoaging of the human skin," Experimental Gerontology. Aug. 2017, 94:78-82.
Chalan et al., "Expression of Lectin-Like Transcript 1, the Ligand for CD161, in Rheumatoid Arthritis," PLoS ONE, 2015, 10(7):e0132436.
Chambers et al., "Can blocking inflammation enhance immunity during aging?," Journal of Allergy and Clinical Immunology, May 2020, 145(5):1323-1331.
Chance et al., "A simple and rapid assay of oxidative phosphorylation," Nature, Jun. 1955, 175(4469):1120-1121.
Chandrudu et al., "Chemical methods for peptide and protein production," Molecules, 2013, 18(4):4373-4388.
Chang et al., "Association Between Sarcopenia and Cognitive Impairment: A Systematic Review and Meta-Analysis," J Am Med Dir Assoc., Dec. 1, 2016, 17(12):1164e7-1164e15, 9 pages.
Chattopadyhay et al., "Structural Basis of Inducible Costimulator Ligand Costimulatory Function: Determination of the Cell Surface Oligomeric State and Functional Mapping of the Receptor Binding Site of the Protein1," J Immunol., 2006, 3920-3929.
Chen et al., "Circulating levels of resistin and risk of type 2 diabetes in men and women: results from two prospective cohorts," Diabetes Care, Feb. 2009, 32(2):329-334.
Chen et al., "Sterile inflammation: sensing and reacting to damage," Nature Reviews Immunology, Nov. 19, 2010, 10(12):826-837.
Chichili et al., "Linkers in the structural biology of protein-protein interactions," Protein Science, Feb. 2013, 22(2):153-67.
Childs et al., "Senescent cells: an emerging target for diseases of ageing," Nature Reviews Drug Discovery, Jul. 21, 2017, 16(10):718-735, 18 pages.
Childs et al., "Senescent intimal foam cells are deleterious at all stages of atherosclerosis," Science, Oct. 28, 2016, 354(6311):472-477.
Chinta, et al., "Cellular senescence is induced by the environmental neurotoxin paraquat and bontributes to neuropathology linked to Parkinson's Disease," Cell Rep., 2018, 22(4): 930-940.
Chong et al., "CD36 initiates the secretory phenotype during the establishment of cellular senescence, " EMBO Rep., May 18, 2018, 19(6):e45274, 13 pages.
Ciaglia, et al., "Recognition by natural killer cells of N6-isopentenyladensoine-treated human glioma cell lines," Int. J. Cancer, 2018 142(1): 176-190.
Cichocki et al., "GSK3 inhibition drives maturation of NK cells and enhances their antitumor activity," Cancer Research, Oct. 15, 2017, 77(20):5664-75.
Cifaldi et al., "Boosting Natural Killer Cell-Based Immunotherapy with Anticancer Drugs: a Perspective," Trends Molecular Medicine, Dec. 2017, 23(12):1156-1175, 20 pages.
Cipriani et al., "Hippocampal Radial Glial Subtypes and Their Neurogenic Potential in Human Fetuses and Healthy and Alzheimer's Disease Adults," Cerebral Cortex, May 2, 2018, 28(7):2458-2478, 21 pages.
Clayton et al.,"Soluble T Cell Immunoglobulin Mucin Domain 3 Is Shed from CD8 T Cells by the Sheddase ADAM10, Is Increased in Plasma during Untreated HIV Infection, and Correlates with HIV Disease Progression," J Viral., 2015, 89(7):3723-3736.
Collado et al., "Senescence in tumours: evidence from mice and humans," Nature Reviews Cancer, Jan. 2010, 10(1):51-57.
Conarello et al., "Mice lacking dipeptidyl peptidase IV are protected against obesity and insulin resistance," Proc. Natl. Acad. Sci. U.S.A., May 27, 2003, 100(11):6825-6830.
Conlon et al., "Abstract CT082: Phase (Ph) I/Ib study of NIZ985 with and without spartalizumab (PDR001) in patients (pts) with metastatic/unresectable solid tumors," Cancer Res. 79(13 Suppl. ):CT082, Jul. 1, 2019, 2 pages.
Coppe et al., "Tumor Suppressor and Aging Biomarker p16INK4a Induces Cellular Senescence without the Associated Inflammatory Secretory Phenotype," Journal of Biological Chemistry, Oct. 21, 2011, 286(42): 36396-36403.
Cosgrove et al., "Usher protein functions in hair cells and photoreceptors," Int J Biochem Cell Biol., Jan. 2014, 46:80-89.

(56) References Cited

OTHER PUBLICATIONS

Cosman et al., "ULBPs, novel MHC class I-related molecules, bind to CMV glycoprotein UL16 and stimulate NK cytotoxicity through the NKG2D receptor," Immunity, Feb. 1, 2001, 14(2):123-33.
Costa et al., "Targeting the epidermal growth factor receptor can counteract the inhibition of natural killer cell function exerted by colorectal tumor-associated fibroblasts," Frontiers in Immunology, May 29, 2018, 9:1150, 14 pages.
Crews et al., "Molecular mechanisms of neurodegeneration in Alzheimer's disease," Human Molecular Genetics, Apr. 22, 2010, 19(R1):R12-R20, 9 pages.
Cromie et al., "Nanobodies and their use in GPCR drug discovery," Current Topics in Medicinal Chemistry, Dec. 1, 2015, 15(24):2543-57.
Czaja et al., "A comprehensive analysis of the binding of anti-KIR antibodies to activating KIRs," Genes and Immunity, Jan. 2014, 15(1), 15 pages.
Da Silva et al., "Dipeptidylpeptidase 4 inhibition enhances lymphocyte trafficking, improving both naturally occurring tumor immunity and immunotherapy," Nature Immunology, Jun. 15, 2015, 16(8):850-858, 11 pages.
Dall'Era et al., "Adoptive Regulatory T Cell Therapy in a Patient with Systemic Lupus Erythematosus," Arthritis Rheumatology, Mar. 2019, 71(3):431-440.
De Crescenzo et al., "Engineering TGF-β Traps: Artificially Dimerized Receptor Ectodomains as High-affinity Blockers of TGF-β Action," Transforming Growth Factor-β in Cancer Therapy, vol. II, 2008, Humana Press, 671-84.
De Genst et al., "Antibody repertoire development in camelids," Developmental & Comparative Immunology, Jan. 1, 2006, 30(1-2):187-98.
De Meyer et al., "Nanobody-based products as research and diagnostic tools," Trends in Biotechnology, May 1, 2014, 32(5):263-70.
De Stefano et al., "Establishing pathological cut-offs of brain atrophy rates in multiple sclerosis," Journal of Neurology, Neurosurgery, and Psychiatry, Jan. 2016, 87(1):93-99.
Deacon, "Physiology and Pharmacology of DPP-4 in Glucose Homeostasis and the Treatment of Type 2 Diabetes," Frontiers in Endocrinology, Feb. 2019, 10:80, 14 pages.
Deaglio et al., "Adenosine generation catalyzed by CD39 and CD73 expressed on regulatory T cells mediates immune suppression," Journal of Experimental Medicine, May 14, 2007, 204(6):1257-1265.
Demaria et al., "An Essential Role for Senescent Cellsin Optimal Wound Healingthrough Secretion of PDGF-AA," Developmental Cell, Dec. 22, 2014, 31(6):722-733.
Deyev et al., "Design of multivalent complexes using the barnase· barstar module," Nature Biotechnology, Dec. 2003, 21(12):1486-92.
Di Ianni et al., "Tregs prevent GVHD and promote immune reconstitution inHLA-haploidentical transplantation, " Blood, Apr. 7, 2011, 117(14):3921-3928.
Dietel et al., "Decreased Nos. of regulatory T cells are associated with human atherosclerotic lesion vulnerability and inversely correlate with infiltrated mature dendritic cells," Atherosclerosis, Sep. 2013, 230:92-99.
DiGiammarino et al., "Design and generation of DVD-Ig™ molecules for dual-specific targeting," Therapeutic Proteins: Methods and Protocols, Methods in Molecular Biology, 2012, Humana Press, Totowa, NJ., 899:145-516.
Dikov et al., "New fluorescent method for the histochemical detection of tripeptidyl peptidase I using glycyl-1-prolyl-1-met-2-anthraquinonyl hydrazide as substrate," Cellular and Molecular Biology, Jan. 1, 2004, 50 Online Pub: OL565-568, 1 page (Abstract Only).
Dimri et al., "A biomarker that identifies senescent human cells in culture and in aging skin in vivo," Proceedings of the National Academy of Sciences, Sep. 29, 1995, 92(20):9363-9367.
Dinarello, "Interleukin 1 and interleukin 18 as mediators of inflammation and the aging process," The American Journal of Clinical Nutrition, Feb. 1, 2006, 83(2):447S-455S.
Docagne et al., "A soluble transforming growth factor-β (TGF-β) type I receptor mimics TGF-β responses," Journal of Biological Chemistry, Dec. 7, 2001, 276(49):46243-50.
Dong et al., "Characterization of adenosine deaminase binding to human CD26 on T cells and its biologic role in immune response," Journal of Immunology, Feb. 15, 1996, 156(4):1349-1355.
Dong et al., "Determination of adenosine deaminase binding domain on CD26 and its immunoregulatory effect on T cell activation," Journal of Immunology, Dec. 15, 1997, 159(12):6070-6076.
Dong et al., "Loss of methylation at theIFNGpromoter and CNS-1 is associated with the development of functional IFN-γ memory in human CD4+T lymphocytes," European Journal of Immunology, 2013, 43(3), 793-804.
Dou et al., "Cytoplasmic chromatin triggers inflammation in senescence and cancer," Nature, Oct. 4, 2017, 550(7676):402-406, 21 pages.
Drees, et al., "Soluble production of a biologically active single-chain antibody against murine PD-L1 in *Escherichia coli*, " Protein Express. Purif., 2014, 94:60-66.
Dubois et al., "Preassociation of IL-15 with IL-15Rα-IgG1-Fc Enhances Its Activity on Proliferation of NK and CD8+/CD44high T Cells and Its Antitumor Action," The Journal of Immunology, Feb. 15, 2008, 180:2099-2106.
Edwardraja et al., "Redesigning of anti-c-met single chain Fv antibody for the cytoplasmic folding and its structural analysis," Biotechnology and Bioengineering, Jun. 15, 2010, 106(3):367-75.
Eisenhut et al., "Ion Channels in Inflammation," Pflugers Archive, Jan. 29, 2011, 461(4):401-421.
Elgueta et al., "Molecular mechanism and function of CD40/CD40L engagement in the immune system," Immunological Reviews, 2009, 229(1):152-172 doi.org/10.1111/j.1600-065X.2009.00782.x.
Elpek et al., "Mature natural killer cells with phenotypic and functional alterations accumulate upon sustained stimulation with IL-15/IL-15Rα complexes," Proceedings of the National Academy of Science, Dec. 14, 2010, 107: 21647-21652.
Engel et al., "The crystal structure of dipeptidyl peptidase IV (CD26) reveals its functional regulation and enzymatic mechanism," Proc. Natl. Acad. Sci. U.S.A., Apr. 29, 2003, 100(9):5063-5068.
Epardaud et al., "Interleukin-15/Interleukin-15RA Complexes Promote Destruction of Established Tumors by Reviving Tumor-Resident CD8+ T Cells," Cancer Research 68: Apr. 15, 2008, 2972-2983.
Esensten et al., "Regulatory T-cell therapy for autoimmune and autoinflammatory diseases: The next frontier," The Journal of Allergy and Clinical Immunology, Dec. 1, 2018, 142(6):1710-1718.
Farr, et al., "Targeting cellular senescence prevents age-related bone loss in mice," Nat. Med., 2017, 23(9): 1072-1079.
Fehniger et al., "A Phase 1 Trial of CNDO-109-Activated Natural Killer Cells in Patients with High-Risk Acute Myeloid Leukemia," Biology of Blood and Marrow Transplantation, Aug. 2018, 24(8):1581-1589.
Feng et al., "The yin and yang functions of extracellular ATP and adenosine in tumor immunity," Cancer Cell International, Apr. 7, 2020, 20:110, 11 pages.
Ferreira et al., "Next-generation regulatory T cell therapy," Nature Reviews Drug Discovery, Sep. 20, 2019, 18(10):749-769, 21 pages.
Ferrucci et al., "The origins of age-related proinflammatory state," Blood, Mar. 15, 2005, 105(6):2294-2299.
Finkelman et al., "Anti-cytokine antibodies as carrier proteins. Prolongation of in vivo effects of exogenous cytokines by injection of cytokine-anti-cytokine antibody complexes," The Journal of Immunology, Aug. 1, 1993, 151:1235-1244.
Finkelstein et al., "Obesity and Severe Obesity Forecasts Through 2030," American Journal of Preventative Medicine, Jun. 2012, 42(6):563-570.
Ford et al., "TREM and TREM-like receptors in inflammation and disease," Current Opinion in Immunology, Feb. 21, 2009, 21(1):38-46.

(56) References Cited

OTHER PUBLICATIONS

Franceschi et al., "Inflamm-aging. An evolutionary perspective on immunosenescence," Annals of the New York Academy of Sciences, Jun. 2000, 908:244-254.
Frutoso et al., "Emergence of NK Cell Hyporesponsiveness after Two IL-15 Stimulation Cycles," Journal of Immunology, May 30, 2018, 201: 493-506.
Ganesh et al., "TGF-β Inhibition and Immunotherapy: Checkmate," Immunity, Apr. 17, 2018, 48(4):626-628.
Garber, "Bispecific antibodies rise again," Nat. Rev. Drug Discov., 2014, 13:799-801.
Gaulton et al., "Characterization of a monoclonal rat anti-mouse interleukin 2 (IL-2) receptor antibody and its use in the biochemical characterization of the murine IL-2 receptor," Clinical Immunology and Immunopathology, Jul. 1, 1985, 36(1):18-29.
Gejima et al., "Human single-chain Fv (scFv) antibody specific to human IL-6 with the inhibitory activity on IL-6-signaling," Human Antibodies, Jan. 1, 2002, 11(4):121-9.
Geng et al., "A novel anti-TNF scFv constructed with human antibody frameworks and antagonistic peptides," Immunol. Res. 62(3):377-385, 2015.
Georgilis et al., "PTBP1-Mediated Alternative Splicing Regulates the Inflammatory Secretome and the Pro-tumorigenic Effects of Senescent Cells," Cancer Cell, Jul. 9, 2018, 34(1):85-102.
Ghosh et al., "The Senescence-Associated Secretory Phenotype: Critical Effector in SkinCancer and Aging," Journal of Investigative Dermatology, Nov. 2016, 136(11):2133-2139.
Gibbs et al., "Identification of the factor VIIa binding site on tissue factor by homologous loop swap and alanine scanning mutagenesis," Biochemistry, Nov. 1, 1994, 33(47):14003-10.
Gong et al., "DAMP-sensing receptors in sterile inflammation and inflammatory diseases," Nature Reviews Immunology, Sep. 26, 2019, 20(2):95-112.
Gorrell et al., "Expression of the rat CD26 Antigen (dipeptidyl peptidase IV) on subpopulations of rat lymphocytes," Cellular Immunology, Apr. 15, 1991, 134(1):205-215.
Greenspan et al., "Defining epitopes: Its not as easy as it seems," Nature Biotechnology, 1999, 17:936-937.
Grupp et al., "Chimeric Antigen Receptor-Modified T Cells for Acute Lymphoid Leukemia," The New England Journal of Medicine, Apr. 18, 2013, 368(16):1509-1518.
Gu et al., "Human CD39hi regulatory T cells present stronger stability and function under inflammatory conditions," Cellular and Molecular Immunology, Jul. 4, 2016, 14(6):521-528.
Guo et al., "Immunobiology of the IL-15-IL-15R complex as an antitumor and antiviral agent," 2017, Cytokine & Growth Factor Reviews, 38:10-21.
Gutschmidt et al., "A quantitative histochemical study of dipeptidyl peptidase IV (DPP IV)," Histochemistry, 1981, 73(2):285-304.
Haile et al., "Soluble CD80 Restores T Cell Activation and Overcomes Tumor Cell Programmed Death Ligand 1-Mediated Immune Suppression," J. Immunol., 2013, 191(5):2829-2836.
Hayflick et al., "The serial cultivation of human diploid cell strains, " Experimental Cell Research, Dec. 1961, 25:585-621.
He et al., "Senescence in Health and Disease," Cell, Jun. 1, 2017, 169(6):1000-1011.
Hebbar et al., "Detection of circulating soluble CD28 in patients with systemic lupus erythematosus, primary Sjögren's syndrome and systemic sclerosis," Clinical & Experimental Immunology, May 2004, 136(2):388-92.
Helfrich et al., "A rapid and versatile method for harnessing scFv antibody fragments with varous biological effector functions," Journal of Immunological methods, 2000, 237(1-2):131-145 DOI:1O.1O16/S0022-1759(99)OO220-3.
Helman et al., "Effects of ageing and senescence on pancreatic β-cell function," Diabetes Obes Metab., Sep. 2016, 18(Suppl. 1):58-62.
Heneka et al., "Inflammasome signaling in brain function and neurodegenerative disease," Nature Reviews Neuroscience, Sep. 11, 2018, 19(10):610-621.
Heneka et al., "NLRP3 is activated in Alzheimer's disease and contributes to pathology in APP/PS1 mice," Nature, Jan. 31, 2013, 493(7434):674-678, 8 pages.
Heng et al., "G Protein-Coupled Receptors Revisited: Therapeutic Applications Inspired by Synthetic Biology," Annual Review of Pharmacology and Toxicology, Jan. 2014, 54:227-249.
Heng et al., Sophea, et al. "Multiple soluble TGF-β receptors in addition to soluble endoglin are elevated in preeclamptic serum and they synergistically inhibit TGF-β signalling." Placenta, 2017 57: 320 (1 page).
Highfill et al., "Overcoming Challenges in Process Development of Cellular Therapies," Current Hematologic Malignancy Reports, Jul. 6, 2019, 14(4):269-277, 9 pages.
Hoare et al., "The Power Behind the Throne: Senescence and the Hallmarks of Cancer," Annual Review of Cancer Biology, 2018, 2:175-194.
Hoffmann et al., "Large-scale in vitro expansion of polyclonal human CD4+CD25high regulatory T Cells," Blood, Aug. 2004, 104(3):895-903.
Hollande et al., "Inhibition of the dipeptidyl peptidase DPP4 (CD26) reveals IL-33-dependent eosinophil-mediated control of tumor growth," Nature Immunology, Feb. 18, 2019, 20(3):257-264.
Hombach et al., "Generation of the single chain antibody fragment conserves the idiotypic profile of the anti-CD30 monoclonal antibody HRS3," Scandinavian Journal of Immunology, Nov. 1998, 48(5):497-501.
Hu et al., "Discovery of a novel IL-15 based protein with improved developability and efficacy for cancer immunotherapy," Scientific Reports, 2018, 8:7675, 11 pages.
Huang et al., "Substrate recognition by tissue factor-factor VIIa Evidence for interaction of residues Lys165 and Lys166 of tissue factor with the 4-carboxyglutamate-rich domain of factor X," Journal of Biological Chemistry, Sep. 6, 1996, 271(36):21752-7.
Huang et al., "Targeting the vasculature of colorectal carcinoma with a fused protein of (RGD) 3-tTF" The Scientific World Journal, 2013(637086): 1-11, 2013.
Hudak et al., "Glycocalyx engineering reveals a Siglec-based mechanism for NK cell immunoevasion," Nature Chemical Biology, Jan. 2014, 10(1), 20 pages.
Hudson et al., "Targeting RAGE Signaling in Inflammatory Disease," Annual Review of Medicine, Jan. 2018, 69:349-364, 16 pages.
Huell et al., "Interleukin-6 is present in early stages of plaque formation and is restricted to the brains of Alzheimer's disease patients," Acta Neuropathologica, Nov. 1995, 89(6):544-551.
Hughes, et al., "Transfer of a TCR gene derived from a patient with a marked antitumor response conveys highly active T-cell effector functions," Hum. Gene Ther., 2005, 16:457-72.
Hynes et al., "In vitro analysis of cell metabolism using a long-decay pH-sensitive lanthanide probe and extracellular acidification assay," Analytical biochemistry, Jul. 1, 2009, 390(1):21-28.
Iannello et al., "p53-dependent chemokine production by senescent tumor cells supports NKG2D-dependent tumor elimination by natural killer cells," Journal of Experimental Medicine, Sep. 23, 2013, 210(10):2057-69.
Iihoshi et al., "Aclarubicin, an anthracycline anti-cancer drug, fluorescently contrasts mitochondria and reduces the oxygen consumption rate in living human cells," Toxicology Letters, Aug. 5, 2017, 277:109-114, 22 pages.
Inzucchi et al., "New Drugs for the Treatment of Diabetes, Part II: Incretin-Based Therapy and Beyond, " Circulation, Jan. 29, 2008, 117(4):574-584, 21 pages.
Jain et al., "Mitochondrial Reactive Oxygen Species Regulate Transforming Growth Factor-β Signaling," Journal of Biological Chemistry, Jan. 11, 2013, 288(2):770-777.
Jakob et al., "Structure reveals function of the dual variable domain immunoglobulin (DVD-Ig™) molecule," Mabs, May 1, 2013, Taylor & Francis, 5(3):358-63.
Janeway, "Approaching the Asymptote? Evolution and Revolution in Immunology," Cold Spring Harbor Symposia on Quantitative Biology, 1989, 54 Pt 1:1-13.
Jeannin et al., "Soluble CD86 Is a Costimulatory Moleculefor Human T Lymphocytes," Immunity, 2000, 13(3):303-312.

(56) References Cited

OTHER PUBLICATIONS

Jeon et al., "Local clearance of senescent cells attenuates the development of post-traumatic osteoarthritis and creates a pro-regenerative environment," Nat Med., Jun. 2017, 23(6):775-781.
Jin et al., "Novel Insights Into the NLRP3 Inflammasome in Atherosclerosis," Journal of the American Heart Association, Jun. 11, 2019, 8(12):e012219, 12 pages.
Justice et al., "Senolytics in idiopathic pulmonary fibrosis: Results from a first-in-human, open-label, pilot study," EBioMedicine, Feb. 2019, 40:554-563.
Kain et al., "The identification of the endogenous ligands of natural killer T cells reveals the presence of mammalian α-linked glycosylceramides," Immunity, Oct. 16, 2014, 41(4):543-54.
Karin et al., "Senescent cell turnover slows with age providing an explanation for the Gompertz law," Nature Communications, 10:5495, 9 pages, Dec. 2, 2019.
Karkera et al., "The anti-interleukin-6 antibody siltuximab down-regulates genes implicated in tumorigenesis in prostate cancer patients from a phase I study," The Prostate, Feb. 14, 2011, 71(13):1455-1465.
Katsuumi et al., "Vascular Senescence in Cardiovascular and Metabolic Diseases," Frontiers in Cardiovascular Medicine, 5:18, 13 pages, Mar. 5, 2018.
Kellner et al., "Enhancing natural killer cell-mediated lysis of lymphoma cells by combining therapeutic antibodies with CD20-specific immunoligands engaging NKG2D or NKp30," Oncoimmunology, Jan. 2, 2016, 5(1):e1058459, 12 pages.
Kijanka et al., "Nanobody-based cancer therapy of solid tumors, " Nanomedicine, Jan. 2015, 10(1):161-74.
Kim et al., "Experimental malaria infection triggers early expansion of natural killer cells," Infection and Immunity, Dec. 1, 2008, 76(12):5873-82.
Kim et al., "Identification of senescent cell surface targetable protein DPP4," Genes & Development, 2017, 31(15):1529-1534.
Kim et al., "Insulin resistance, inflammation, and nonalcoholic fatty liver disease in non-obese adults without metabolic syndrome components," Hepatol Int., Jun. 2013, 7(2):586-591.
Kim et al., "SCAMP4 enhances the senescent cell secretome," Genes & Development, 2018, 32(13-14):909-914.
Kirchhofer et al., "The tissue factor region that interacts with substrates factor IX and factor X," Biochemistry, Jun. 27, 2000, 39(25):7380-7.
Kirkland et al., "Cellular Senescence: A Translational Perspective," EBioMedicine, Jul. 2017, 21:21-28.
Klein et al., "Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines," Oncoimmunology, 2017 6(3):e1277306, 15 pages.
Klein et al., "Design and characterization of structured protein linkers with differing flexibilities," Protein Engineering, Design & Selection, 2014, 27(10):325-30.
Klemann et al., "Cut to the chase: a review of CD26/dipeptidyl peptidase-4's (DPP4) entanglement in the immune system," Clinical and Experimental Immunology, Feb. 25, 2016, 185(1):1-21.
Klingenberg et al., "Depletion of FOXP3+ regulatory T cells promotes hypercholesterolemia and atherosclerosis," The Journal of Clinical Investigation, Feb. 15, 2013, 123:1323-1334.
Kondo et al., "Requirements for the functional expression of OX40 ligand on human activated CD4+ and CD8+ T cells," Human Immunology, 2007, 68(7):563-571.
Kovaleva et al., "Shark variable new antigen receptor biologics-a novel technology platform for therapeutic drug development," Expert Opinion on Biological Therapy, Oct. 1, 2014, 14(10):1527-39.
Krah et al., "Single-domain antibodies for biomedical applications," Immunopharmacology and Immunotoxicology, Jan. 2, 2016, 38(1):21-8.
Kritsilis et al., "Ageing, Cellular Senescence and Neurodegenerative Disease," International Journal of Molecular Sciences, Sep. 27, 2018, 19(10):2937, 37 pages.
Krizhanovsky et al., "Senescence of activated stellate cells limits liver fibrosis," Cell, Aug. 22, 2008, 134(4):657-67.
Kumagai et al., "Monitoring of glutamate-induced excitotoxicity by mitochondrial oxygen consumption," Synapse, Jan. 2019, 73(1):e22067, 24 Pages.
Kuyinu et al., "Animal models of osteoarthritis: classification, update, and measurement of outcomes," J Orthop Surg Res., Feb. 2, 2016, 11:19, 27 pages.
Lambeir et al., "Dipeptidyl-Peptidase IV from Bench to Bedside: An Update on Structural Properties, Functions, and Clinical Aspects of the Enzyme DPP IV," Critical Reviews in Clinical Laboratory Sciences, Sep. 29, 2003, 40(3):209-294.
Lamkanfi et al., "Mechanisms and Functions of Inflammasomes," Cell, May 22, 2014, 157(5):1013-1022.
Lansigan et al., "DI-Leu16-IL2, an Anti-CD20-Interleukin-2 Immunocytokine, Is Safe and Active in Patients with Relapsed and Refractory B-Cell Lymphoma: A Report of Maximum Tolerated Dose, Optimal Biologic Dose, and Recommended Phase 2 Dose," Blood, Dec. 2, 2016, 128(22):620, 3 pages (Abstract Only).
Latz et al., "Activation and regulation of the inflammasomes," Nature Reviews Immunology, May 24, 2013, 13(6):397-411.
Latz et al., "NLRP3 inflammasome activation in inflammaging," Seminars in Immunology, Dec. 2018, 40:61-73, 13 pages.
Lau et al., "RNA-associated autoantigens activate B cells by combined B cell antigen receptor/Toll-like receptor 7 engagement," The Journal of Experimental Medicine, Oct. 31, 2005, 202(9):1171-1177.
Lazar et al., "Transforming Growth Factor Alpha: Mutation of Aspartic Acid 47 and Leucine 48 Results in Different Biological Activities," Mol. Cell. Biol., 1988, 8:1247-1252.
Li et al., "A Novel I L2-based Irrmunotherapeutic Protein Prevents the Development of Atherosclerosis in ApoE-/mice and LDLR-/-mice," Journal of Immunology, May 1, 2020, 204(1):Supplement (Abstract Only), 2 pages.
Li et al., "Adoptive transfer of natural killer cells in combination with chemotherapy improves outcomes of patients with locally advanced colon carcinoma," Cytotherapy, Jan. 2018, 20(1): 134-148, 15 pages.
Li et al., "The cGAS-cGAMP-STING pathway connects DNA damage to inflammation, senescence, and cancer," Journal of Experimental Medicine, Apr. 5, 2018, 215(5):1287-1299.
Li et al., "Transforming Growth Factor-β Regulation of Immune Responses," Annu. Rev. Immunol., 2006, 24:99-146.
Liton et al., "Cellular senescence in the glaucomatous outflow pathway," Experimental Gerontology, August-Sep. 2005, 40(8-9):745-748.
Liu et al., "A Novel Fusion of ALT-803 (IL-15 Superagonist) with an Antibody Demonstrates Antigen-specific Antitumor Responses," Journal of Biological Chemistry, 2016, 291(46):23869-23881.
Liu et al., "Evaluation of the biological activities of the IL-15 superagonist complex, ALT-803, following intravenous versus subcutaneous administration in murine models," Cytokine, Jul. 2018, 107: 105-112, 8 pages.
Loster et al., "The Cysteine-Rich Region of Dipeptidyl Peptidase IV (CD 26) Is the Collagen Binding Site," Biochemical and Biophysical Research Communications, Dec. 5, 1995, 217(1):341-348.
Lu et al., "Molecular basis of binding between novel human coronavirus MERS-CoV and its receptor CD26," Nature, Jul. 7, 2013, 500(7461):227-231.
Lujambio et al., "Non-Cell-Autonomous Tumor Suppression by p53," Cell, Apr. 11, 2013, 153(2):449-460.
Maeda et al., "Original Ligand for LTβR Is LIGHT: Insight into Evolution of the LT/LTβR System," J Immunol., 2018, 201(1):202-214.
Maganto-García et al., "Dynamic Changes in Regulatory T Cells Are Linked to Levels of Diet-Induced Hypercholesterolemia," Circulation, Jun. 20, 2011, 124:185-195.
Mandelboim et al., "Recognition of haemagglutinins on virus-infected cells by NKp46 activates lysis by human NK cells," Nature, Feb. 2001, 409(6823):1055.

(56) References Cited

OTHER PUBLICATIONS

Marguet et al., "Enhanced insulin secretion and improved glucose tolerance in mice lacking CD26," Proc. Natl. Acad. Sci. U.S.A., Jun. 6, 2000, 97(12):6874-6879.
Martelli et al., "HLA-haploidentical transplantation with regulatory and conventionalT-cell adoptive immunotherapy prevents acute leukemia relapse," Blood, Jul. 24, 2014, 124(4):638-644.
Masoumi et al., "The role of hypoxia as the driving force for non-erythroid production of globin chains in preeclamptic placentas," Placenta. 2017;57:320.
McCarron et al., "TGF-β prevents T follicular helper cell accumulation and B cell autoreactivity," J Clin Invest., 2014, 124(10):4375-4386.
McHugh et al., "Senescence and aging: Causes, consequences, and therapeutic avenues," Journal of Cellular Biology, Nov. 7, 2017, 217(1):65-77.
Mehta et al., "Why do trials for Alzheimer's disease drugs keep failing? A discontinued drug perspective for 2010-2015," Expert Opinion on Investigational Drugs, May 2017, 26(6):735-739.
Melk et al., "Expression of p16INK4a and other cell cycle regulator and senescence associated genes in aging human kidney," Kidney Int., Feb. 2004, 65(2):510-520.
Melk et al., "Senescence of renal cells: molecular basis and clinical implications," Nephrology Dialysis Transplantation, Dec. 2003, 18(12):2474-2478.
Menshawy et al., "CD58; leucocyte function adhesion-3 (LFA-3) could be used as a differentiating marker between immune and non-immune thyroid disorders," Comparative Clinical Pathology, 2018, 27(3), 721-727, doi.org/10.1007/s00580-018-2657-x.
Mentlein et al., "Dipeptidyl-peptidase IV (CD26)-role in the inactivation of regulatory peptides," Regulatory Peptides, Nov. 30, 1999, 85(1):9-24.
Miah et al., "KIR2DL4 differentially signals downstream functions in human NK cells through distinct structural modules," The Journal of Immunology, Mar. 1, 2008, 180(5):2922-32.
Michelet et al., "Metabolic reprogramming of natural killer cells in obesity limits antitumor responses," Nature Immunology, Nov. 12, 2018, 19(12):1330-1340.
Mikayama et al., "Molecular cloning and functional expression of a cDNA encoding glycosylation-inhibiting factor," Proc. Natl. Acad. Sci. USA, Nov. 1, 1993, 90(21):10056-10060.
Milanovic et al., "Senescence-associated reprogramming promotes cancer stemness," Nature, Dec. 20, 2017, 553(7686):96-100.
Milanovic et al., "The Senescence-Stemness Alliance—A Cancer-Hijacked Regeneration Principle," Trends in Cellular Biology, Dec. 2018, 28(12): 1049-1061, 13 pages.
Miller et al., "Soluble CD70: a novel immunotherapeutic agent for experimental glioblastoma," J Neurosurg., 2010, 113(2):280-285.
Miller et al., "Successful adoptive transfer and in vivo expansion of human haploidentical NK cells in patients with cancer," Blood, Apr. 15, 2005, 105(8):3051-3057.
Minamino et al., "A crucial role for adipose tissue p53 in the regulation of insulin resistance," Nature Medicine, Aug. 30, 2009, 15(9):1082-1087.
Mitterberger et al., "Adipogenic Differentiation Is Impaired in Replicative Senescent Human Subcutaneous Adipose-Derived Stromal/Progenitor Cells," The Journals of Gerontology: Series A, Biological Sciences and Medical Sciences, Jan. 2014, 69(1):13-24.
Miyazaki et al., "Abstract 3265: NKTR-255, a polymer-conjugated IL-15 enhances anti-tumor NK cell responses and synergizes with monoclonal antibodies to provide long-term survival in human lymphoma model," Proceedings: AACR Annual Meeting 2019, Atlanta, GA, Mar. 29-Apr. 3, 2019, 1 page.
Moesta et al., "Targeting CD39 in cancer," Nature Reviews Immunology, Jul. 29, 2020, 20(12):739-755, 17 pages.
Moiseeva et al., "Metformin inhibits the senescence-associated secretory phenotype by interfering with IKK/NF-κB activation," Aging Cell, Mar. 23, 2013, 12(3):489-498.
Molema et al., "The use of bispecific antibodies in tumor cell and tumor vasculature directed immunotherapy," Journal of Controlled Release, 2000, 64(1-3):229-239.
Molgora et al., "Regulatory role of IL-1R8 in immunity and disease, " Frontiers in Immunology, Apr. 20, 2016, 7:149.
Mookerjee et al., "Measurement and Analysis of Extracellular Acid Production to Determine Glycolytic Rate," Journal of Visualized Experiments : Jove, Dec. 2015, (106):e53464, 9 Pages.
Moore et al., "Macrophages in atherosclerosis: a dynamic balance," Nature Reviews Immunology, Sep. 2, 2013, 13:709-721, 13 pages.
Moreno et al., "Molecular Evidence of Adenosine Deaminase Linking Adenosine A2A Receptor and CD26 Proteins," Frontiers in Pharmacology, Feb. 15, 2018, 9:106, 18 pages.
Moretta et al., "CD69-mediated pathway of lymphocyte activation: anti-CD69 monoclonal antibodies trigger the cytolytic activity of different lymphoid effector cells with the exception of cytolytic T lymphocytes expressing T cell receptor alpha/beta," Journal of Experimental Medicine, Dec. 1, 1991, 174(6):1393-8.
Mujić-Delić et al., "GPCR-targeting nanobodies: attractive research tools, diagnostics, and therapeutics," Trends in Pharmacological Sciences, May 1, 2014, 35(5):247-55.
Muller et al., "Antibody fusions with immunomodulatory proteins for cancer therapy," Pharmacology and Therapeutics, 2015, 154:57-66.
Mulvihill et al., "Pharmacology, Physiology, and Mechanisms of Action of Dipeptidyl Peptidase-4 Inhibitors," Endocrine Reviews, Dec. 1, 2014, 35(6):992-1019.
Munoz-Espin et al., "Cellular senescence: from physiology to pathology," Nature Reviews Molecular Cellular Biology, Jun. 23, 2014, 15(7):482-496.
Munoz-Espin et al., "Programmed Cell Senescence during Mammalian Embryonic Development," Cell, Nov. 21, 2013, 155(5):1104-1118.
Musi et al., "Tau protein aggregation is associated with cellular senescence in the brain," Aging Cell, Aug. 20, 2018, 17(6):e12840, 13 pages.
Must et al., "The Disease Burden Associated with Overweight and Obesity," Endotext, Feingold et al. (eds.), South Dartmouth, MA, 2000, 35 pages.
Muyldermans et al., "Recognition of antigens by single-domain antibody fragments: the superfluous luxury of paired domains," Trends in Biochemical Sciences, Apr. 1, 2001, 26(4):230-5.
Muyldermans, "Nanobodies: natural single-domain antibodies," Annual Review of Biochemistry, Jun. 2, 2013, 82:775-97.
Muyldermans, "Single domain camel antibodies: current status," Reviews in Molecular Biotechnology, Jun. 1, 2001, 74(4):277-302.
Myung et al., "Evidence of DNA damage in Alzheimer disease: phosphorylation of histone H2AX in astrocytes," Age, Apr. 23, 2008, 30(4):209-215.
Nag et al., "Soluble MHC II-peptide complexes induce antigen-specific apoptosis in T cells," Cellular Immunology, May 25, 1996, 170(1):25-33.
Nayyar et al., "Overcoming Resistance to Natural Killer Cell Based Immunotherapies for Solid Tumors, " Frontiers in Oncology, 2019, 9: DOI:10.3389/fonc.2019.00051.
Nelson et al., "A senescent cell bystander effect: senescence-induced senescence," Aging Cell, Feb. 9, 2012, 11(2):345-349.
Nilsson et al., "Targeted delivery of tissue factor to the ED-B domain of fibronectin, a marker of angiogenesis, mediates the infarction of solid tumors in mice," Cancer Research, American Association for Cancer Researc, Proceddings: AACR 107th Annual Meeting, 2016, Apr. 16-20, 2016, New Orleans, LA 61(2):711-716.
Nishida et al., "CD26 is a potential therapeutic target by humanized monoclonal antibody for the treatment of multiple myeloma," Blood Cancer Journal, Oct. 22, 2018, 8(11):99, 17 pages.
O'Sullivan et al., "Natural Killer Cell Memory," Immunity, Oct. 20, 2015, 43(4):634-645.
Oberle et al., "Rapid Suppression of Cytokine Transcription in Human CD4+CD25-T Cells by CD4+Foxp3+ Regulatory T Cells: Independence of IL-2 Consumption, TGF-β, and Various Inhibitors of TCR Signaling," The Journal of Immunology, Sep. 15, 2007, 179(6):3578-3587.

(56) References Cited

OTHER PUBLICATIONS

Ogrodnik et al., "Cellular senescence drives age-dependent hepatic steatosis," Nat Commun. Jun. 1, 20173;8:15691, 12 pages.
Ogrodnik et al., "Obesity-Induced Cellular Senescence Drives Anxiety and Impairs Neurogenesis," Cell Metabolism, May 2019, 29(5):1061-1077, 25 pages.
Ohnuma et al., "Blockade of CD26-mediated T cell costimulation with soluble caveolin-1-Ig fusion protein induces anergy in CD4+T cells," Biochemical and Biophysics Research Communications, Aug. 21, 2009, 386(2):327-332.
Ohnuma et al., "CD26 Mediates Dissociation of Tollip and IRAK-1 from Caveolin-1 and Induces Upregulation of CD86 on Antigen-Presenting Cells," Molecular and Cellular Biology, Sep. 1, 2005, 25(17):7743-7757.
Ohnuma et al., "CD26 up-regulates expression of CD86 on antigen-presenting cells by means of caveolin-1," Proc. Natl. Acad. Sci. U.S.A., Sep. 28, 2004, 101(39):14186-14191.
Ohnuma et al., "Role of CD26/dipeptidyl peptidase IV in human T cell activation and function," Frontiers in Bioscience, Jan. 1, 2008, 13:2299-2310.
Ohnuma et al., "Soluble CD26/Dipeptidyl Peptidase IV Induces T Cell Proliferation Through CD86 Up-Regulation on APCs," Journal of Immunology, Dec. 15, 2001, 167(12):6745-6755.
Ovadya et al., "Strategies targeting cellular senescence," The Journal of Clinical Investigation, Apr. 2, 2018, 128(4):1247-54.
Owicki et al., "Biosensors based on the energy metabolism of living cells: the physical chemistry and cell biology of extracellular acidification," Biosensors and Bioelectronics, Jan. 1, 1992, 7(4):255-272.
Padutsch et al., "Superior Treg-Expanding Properties of a Novel Dual-Acting Cytokine Fusion Protein," Frontiers in Pharmacology, Dec. 18, 2019, 10:1490, 10 pages.
Palmer et al., "Cellular Senescence in Type 2 Diabetes: A Therapeutic Opportunity," Diabetes, Jul. 2015, 64(7):2289-2298.
Parker et al., "Design, production, and characterization of a single-chain variable fragment (ScFv) derived from the prostate specific membrane antigen (PSMA) monoclonal antibody J591," Protein Expression and Purification, Jun. 1, 2013, 89(2):136-45.
PCT International Preliminary Report on Patentability in International Appln. No. PCT/US2019/048881, dated Mar. 11, 2021, 7 pages.
PCT International Preliminary Report on Patentability in International Appln. No. PCT/US2019/048930, dated Mar. 11, 2021, 9 pages.
PCT International Preliminary Report on Patentability in International Appln. No. PCT/US2019/049142, dated Mar. 11, 2021, 11 pages.
PCT International Preliminary Report on Patentability in International Appln. No. PCT/US2019/049158, dated Mar. 11, 2021, 8 pages.
PCT International Preliminary Report on Patentability in International Appln. No. PCT/US2020/038717, dated Dec. 30, 2021, 9 pages.
PCT International Preliminary Report on Patentability in International Appln. No. PCT/US2021/017620, dated Aug. 25, 2022, 12 pages.
PCT International Preliminary Report on Patentability in International Appln. No. PCT/US2021/017621, dated Aug. 25, 2022, 8 pages.
PCT International Preliminary Report on Patentability in International Appln. No. PCT/US2021/017714, dated Aug. 25, 2022, 12 pages.
PCT International Preliminary Report on Patentability in International Appln. No. PCT/US2021/029920, dated Nov. 10, 2022, 11 pages.
PCT International Search Report and Written Opinion in International Appln. No. PCT/US2019/048881, dated Nov. 9, 2019, 16 pages.
PCT International Search Report and Written Opinion in International Appln. No. PCT/US2019/048930, dated Nov. 20, 2019, 18 pages.
PCT International Search Report and Written Opinion in International Appln. No. PCT/US2019/04912, dated Jun. 23, 2020, 20 pages.
PCT International Search Report and Written Opinion in International Appln. No. PCT/US2019/049158, dated Jan. 20, 2020, 18 pages.
PCT International Search Report and Written Opinion in International Appln. No. PCT/US2020/035598, dated Feb. 18, 2021, 12 pages.
PCT International Search Report and Written Opinion in International Appln. No. PCT/US2020/038717, dated Oct. 16, 2020, 17 pages.
PCT International Search Report and Written Opinion in International Appln. No. PCT/US2021/017620, dated Aug. 6, 2021, 22 pages.
PCT International Search Report and Written Opinion in International Appln. No. PCT/US2021/017621, dated Jun. 9, 2021, 15 pages.
PCT International Search Report and Written Opinion in International Appln. No. PCT/US2021/017714, dated Aug. 27, 2021, 22 pages.
PCT International Search Report and Written Opinion in International Appln. No. PCT/US2021/029920, dated Oct. 6, 2021, 21 pages.
PCT International Search Report and Written Opinion in International Appln. No. PCT/US2021/035285, dated Oct. 18, 2021, 14 pages.
Peipp et al., "HER2-specific immunoligands engaging NKp30 or NKp80 trigger NK-cell-mediated lysis of tumor cells and enhance antibody-dependent cell-mediated cytotoxicity," Oncotarget, Oct. 13, 2015, 6(31):32075.
Pittayapruek et al., "Role of Matrix Metalloproteinases in Photoaging and Photocarcinogenesis," International Journal of Molecular Sciences, 2016, 17(6):868, 20 pages.
Price et al., "Comparison of collagenase-cleaved articular cartilage collagen in mice in the naturally occurring STR/ort model of osteoarthritis and in collagen-induced arthritis," Osteoarthritis Cartilage, Mar. 2002, 10(3):172-179.
Priyanka et al., "Linkers in the structural biology of protein-protein interactions," Protein Sci., 2013, 22(2):153-167.
Purohit et al., "Smad3-dependent regulation of type I collagen in human dermal fibroblasts: Impact on human skin connective tissue aging, " Journal of Dermatological Science, Jul. 2016, 83(1):80-83, 4 pages.
Qin et al., "Critical Role of P2Y12 Receptor in Regulation of Th17 Differentiation and Experimental Autoimmune Encephalomyelitis Pathogenesis," The Journal of Immunology, Jul. 1, 2017, 199(1):72-81.
Rafei et al., "Off-the-shelf virus specific T-cells for therapy of adenovirus disease in immunosuppressed patients," Journal of Clinical Oncology, May 26, 2019, 37(15 Suppl.):7008, 2 pages.
Rahbarizadeh et al., "Nanobody; an old concept and new vehicle for immunotargeting," Immunological Investigations, Jan. 1, 2011, 40(3):299-338.
Raj et al., "Adenosine Deaminase Acts as a Natural Antagonist for Dipeptidyl Peptidase 4-Mediated Entry of the Middle East Respiratory Syndrome Coronavirus," Journal of Virology, Feb. 2014, 88(3):1834-1838, 7 pages.
Ranganathan et al., "Pinpointing the putative heparin/sialic acid-binding residues in the 'sushi' domain 7 of factor H: a molecular modeling study," Biocomputing 2000, 1999, 155-67.
Rao et al., "Purification and characterization of rabbit tissue factor," Thrombosis Research, Oct. 1, 1989, 56(1):109-118.
Rasmussen et al., "Crystal structure of human dipeptidyl peptidase IV/CD26 in complex with a substrate analog," Nature Structural and Molecular Biology, 2003, 10(1):19-25.
Raz et al., "Efficacy and safety of the dipeptidyl peptidase-4 inhibitor sitagliptin as monotherapy in patients with type 2 diabetes mellitus," Diabetologia, Sep. 26, 2006, 49(11):2564-2571.

(56) References Cited

OTHER PUBLICATIONS

Resta et al., "Ecto-enzyme and signaling functions of lymphocyte CD 7 3," Immunological Reviews, 1998, 161:95-109.
Rhein et al., "Characterization of Human and Murine T-Cell Immunoglobulin Mucin Domain 4 (TIM-4) IgV Domain Residues Critical for Ebola Virus Entry," J Viral., 2016, 90(13):6097-6111.
Rippmann et al., "Fusion of the Tissue Factor Extracellular Domain to a Tumor Stromaspecific Single-Chain Fragment Variable Antibody Results in an Antigen-Specific Coagulation-Promoting Molecule," Biochemical Journal, 2000, 349(3):805-812.
Rittie et al., "Natural and Sun-Induced Aging of Human Skin," Cold Spring Harbor Perspective in Medicine, 2015, 5(1):a015370, 15 pages.
Rocha et al., "A novel immunofluorescent assay to investigate oxidative phosphorylation deficiency in mitochondrial myopathy: understanding mechanisms and improving diagnosis," Scientific reports, Oct. 15, 2015, 5:15037, 17 Pages.
Rodier et al., "Persistent DNA damage signaling triggers senescence-associated inflammatory cytokine secretion," Nature Cell Biology, Jul. 13, 2009, 11(8): 973-979, 15 pages.
Rogge et al., "Antibodies to the IL-12 receptor β2 chain mark human Th1 but not Th2 cells in vitro and in vivo," The Journal of Immunology, Apr. 1, 1999, 162(7):3926-3932.
Roh et al., "Damage-Associated Molecular Patterns in Inflammatory Diseases," Immune Network, Aug. 2018, 18(4):e27, 14 pages.
Romano et al., "Past, Present, and Future of Regulatory T Cell Therapy in Transplantation and Autoimmunity," Frontiers in Immunology, Jan. 1, 2019, 10:43, 14 pages.
Romee et al., "Cytokine activation induces human memory-like NK cells," Blood, Dec. 6, 2012, 120(24):4751-4760.
Rossi et al., "Complex and defined biostructures with the dock-and-lock method," Trends in Pharmacological Sciences, Sep. 1, 2012, 33(9):474-81.
Rossi et al., "Stably tethered multifunctional structures of defined composition made by the dock and lock method for use in cancer targeting," Proceedings of the National Academy of Sciences, May 2, 2006, 103(18):6841-6.
Rubinstein et al., "Converting IL-15 to a superagonist by binding to soluble IL-15Rα," Proceedings of the National Academy of Sciences U.S.A., Jun. 13, 2006, 103(24):9166-9171.
Ruf et al., "Cofactor residues lysine 165 and 166 are critical for protein substrate recognition by the tissue factor-factor VIIa protease complex," Journal of Biological Chemistry, Mar. 25, 1992, 267(9):6375-81.
Ruf et al., "Tissue factor residues 157-167 are required for efficient proteolytic activation of factor X and factor VII," Journal of Biological Chemistry, Nov. 5, 1992, 267(31):22206-10.
Ruscetti et al., "NK cell-mediated cytotoxicity contributes to tumor control by a cytostatic drug combination," Science, Dec. 21, 2018, 362(6421):1416-1422, 8 pages.
Sagiv et al., "Granule exocytosis mediates immune surveillance of senescent cells," Oncogene, 2013, 32(15):1971-1977.
Sakaguchi et al., "Regulatory T Cells and Human Disease," Annual Review of Immunology, Apr. 26, 2020, 38:541-566.
Sakaguchi et al., "Regulatory T Cells and Immune Tolerance," Cell, May 30, 2008, 133(5):775-787.
Sakaguchi et al., "Regulatory T cells: how do they suppress immune responses?" International Immunology, Sep. 7, 2009, 21(10):1105-1111.
Sakamoto et al., "Phase I clinical trial of autologous NK cell therapy using novel expansion method in patients with advanced digestive cancer," Journal of Translational Medicine, Aug. 25, 2015, 13:277, 13 pages.
Sakamuri et al., "Measurement of respiratory function in isolated cardiac mitochondria using Seahorse XFe24 Analyzer: applications for aging research," Geroscience, Jun. 1, 2018, 40(3):347-356.
Salminen et al., "Emerging role of NF-κB signaling in the induction of senescence-associated secretory phenotype (SASP)," Cellular Signaling, Apr. 2012, 24(4):835-845.
Sandusky et al., "Regulation of 2B4 (CD244)-mediated NK cell activation by ligand-induced receptor modulation," European Journal of Immunology, Dec. 2006, 36(12):3268-76.
Sato et al., "Recombinant soluble murine IL-4 receptor can inhibit or enhance IgE responses in vivo," The Journal of Immunology, Apr. 1, 1993, 150:2717-2723.
Schafer et al., "Cellular senescence mediates fibrotic pulmonary disease," Nat Commun., Feb. 2017, 8:14532, 11 pages.
Schullek et al., "Key ligand interface residues in tissue factor contribute independently to factor VIIa binding," Journal of Biological Chemistry, Jul. 29, 1994, 269(30):19399-403.
Schwoppe et al., "Tissue-factor fusion proteins induce occlusion of tumor vessels," Thrombosis Research, Apr. 1, 2010, 125:S143-S150.
Seo et al., "Positive Feedback Loop between Plasminogen Activator Inhibitor-1 and Transforming Growth Factor-Beta1 during Renal Fibrosis in Diabetes," American Journal of Nephrology, Sep. 25, 2009, 30:481-490.
Sharkey et al., "Improved Therapeutic Results by Pretargeted Radioimmunotherapy of Non-Hodgkin's Lymphoma with a New Recombinant, Trivalent, Anti-CD20, Bispecific Antibody," Cancer Research, Jul. 1, 2008, 68(13):5282-90.
Sharma et al., "Regulatory T Cells License Macrophage Pro Resolving Functions During Atherosclerosis Regression," Circulation Research, Apr. 27, 2020, 127:335-353.
Smith et al., "Antigen Nature and Complexity Influence Human Antibody Light Chain Usage and Specificity," Vaccine, 2016, 34(25): 2813-2820.
Smith et al., "Development and evaluation of an optimal human single-chain variable fragment-derived BCMA-targeted CAR T cell vector," Molecular Therapy, Jun. 6, 2018, 26(6):1447-56.
Soerensen et al., "Safety, PK/PD, and anti-tumor activity of RO6874281, an engineered variant of interleukin-2 (IL-2v) targeted to tumor-associated fibroblasts via binding to fibroblast activation protein (FAP)," Journal of Clinical Oncology, Jun. 1, 2018, 36(No. 15 Suppl.):e15155, 2 pages.
Sondel et al., "Combination Therapy with Interleukin-2 and Antitumor Monoclonal Antibodies," Cancer Journal from Scientific American, Jan. 1, 1997, 3(Suppl. 1):S121-S127.
Sone et al., "Pancreatic beta cell senescence contributes to the pathogenesis of type 2 diabetes in high-fat diet-induced diabetic mice," Diabetologia, 2005, 48(1):58-67.
Song et al., "IL-12/IL-18-preactivated donor NK cells enhance GVL effects and mitigate GvHD after allogeneic hematopoietic stem cell transplantation," European Journal of Immunology, Apr. 2018, 48(4):670-682.
Soriani et al., "ATM-ATR-dependent up-regulation of DNAM-1 and NKG2D ligands on multiple myeloma cells by therapeutic agents results in enhanced NK-cell susceptibility and is associated with a senescent phenotype," Blood, Apr. 9, 2009, 113(15):3503-11.
Sousa-Victor et al., "Geroconversion of aged muscle stem cells under regenerative pressure," Cell Cycle, Oct. 15, 2014, 13(20):3183-3190.
Spiess et al., "Alternative molecular formats and therapeutic applications for bispecific antibodies, " Molecular Immunology, Oct. 1, 2015, 67(2):95-106.
Stoklasek et al., "Combined IL-15/IL-15Rα Immunotherapy Maximizes IL-15 Activity In Vivo," The Journal of Immunology, Nov. 1, 2006, 177(9):6072-6080.
Storer et al., "Senescence Is a Developmental Mechanism that Contributes to Embryonic Growth and Patterning," Cell, Nov. 21, 2013, 155(5):1119-1130.
Stryer, Biochemistry Fourth Edition, W. H. Freeman and Company, New York, 1995, pp. 18-23, 8 pages.
Swanson et al., "The NLRP3 inflammasome: molecular activation and regulation to therapeutics," Nature Reviews Immunology, Apr. 29, 2019, 19(8):477-489, 13 pages.
Szalay et al., "Cutting edge: anti-CD1 monoclonal antibody treatment reverses the production patterns of TGF-β2 and Th1 cytokines and ameliorates listeriosis in mice," The Journal of Immunology, Jun. 15, 1999, 162(12):6955-8.

(56) References Cited

OTHER PUBLICATIONS

Tahara-Hanaoka et al., "Functional characterization of DNAM-1 (CD226) interaction with its ligands PVR (CD155) and nectin-2 (PRR-2/CD112)," International Immunology, Apr. 1, 2004, 16(4):533-8.
Takahashi et al., "Downregulation of cytoplasmic DNases is implicated in cytoplasmic DNA accumulation and SASP in senescent cells," Nature Communications, Mar. 28, 2018, 9:1249, 12 pages.
Takahashi et al., "Simple and inexpensive technique for measuring oxygen consumption rate in adherent cultured cells," The Journal of Physiological Sciences, Nov. 2017, 67(6):731-737.
Takeda et al., "Phase I study of YS110, a recombinant humanized monoclonal antibody to CD26, in Japanese patients with advanced malignant pleural mesothelioma," Lung Cancer, Nov. 2019, 137:64-70.
Tam et al., "Methods and strategies of peptide ligation," Peptide Science: Original Research on Biomolecules, 2001, 60(3):194-205.
Tanaka et al., "Cloning and functional expression of the T cell activation antigen CD26," Journal of Immunology, Jul. 15, 1992, 149(2):481-486.
Tang et al., "The Foxp3+ regulatory T cell: a jack of all trades, master of regulation," Nature Immunology, Feb. 19, 2008, 9(3):239-244.
Teissier et al., "The receptor for advanced glycation end-products (RAGE) is an important pattern recognition receptor (PRR) for inflammaging," Biogerontology, Apr. 9, 2019, 20(3):279-301, 23 pages.
Teng et al., "Structural assessment of the effects of amino acid substitutions on protein stability and protein proteininteraction," International journal of computational biology and drug design, Feb. 7, 2011, 3(4):334-349.
Theil et al., "Adoptive transfer of allogeneic regulatory T cells into patients with chronic graft-versus-host disease," Cytotherapy, Apr. 2015, 17(4):473-486, 14 pages.
Thonhoff et al., "Expanded autologous regulatory T-lymphocyte infusions in ALS," Neurology Neuroimmunology Neuroinflammation, May 18, 2018, 5(4):e465, 8 pages.
Tobin et al., "NK cells in childhood obesity are activated, metabolically stressed, and functionally deficient," JCI Insight, Dec. 21, 2017, 2(24):e94939, 9 pages.
Tomala et al., "In Vivo Expansion of Activated Naive CD8+ T Cells and NK Cells Driven by Complexes of IL-2 and Anti-IL-2 Monoclonal Antibody As Novel Approach of Cancer Immunotherapy," The Journal of Immunology, Oct. 15, 2009, 183:4904-4912.
Tominaga et al., "TGF-β Signaling in Cellular Senescence and Aging-Related Pathology," International Journal of Molecular Sciences, Oct. 10, 2019, 20(20):5002, 18 pages.
Trevani et al., "Extracellular acidification induces human neutrophil activation," The Journal of Immunology, Apr. 15, 1999, 162(8):4849-4857.
Tse et al., "ABT-263: A Potent and Orally Bioavailable Bcl-2 Family Inhibitor," Cancer Research, May 2008, 68(9):3421-3428.
Uryga et al., "Ageing induced vascular smooth muscle cell senescence in atherosclerosis," Journal of Physiology, Apr. 15, 2016, 594(8):2115-2124.
Vaishampayan et al., "A phase I trial of ALKS 4230, an engineered cytokine activator of NK and effector T cells, in patients with advanced solid tumors," Journal of Clinical Oncology, 2017, 35(15 Suppl.):TPS3111, 4 pages (Abstract Only).
Van Audenhove et al., "Nanobodies as versatile tools to understand, diagnose, visualize and treat cancer," EBioMedicine, Jun. 1, 2016, 8:40-8.
Van den Bergh et al., "IL-15 receptor alpha as the magic wand to boost the success of IL-15 antitumor therapies: The upswing of IL-15 transpresentation," Pharmacology and Therapeutics, 2017, 170:73-79.
Van Deursen, "The role of senescent cells in ageing, " Nature, May 21, 2014, 509(7501):439-446.
Vankadari et al., "Emerging COVID-19 coronavirus: glycan shield and structure prediction of spike glycoprotein and its interaction with human CD26," Emerging Microbes and Infection, Mar. 17, 2020, 9(1):601-604.
Vidarsson et al., "IgG subclasses and allotypes: from structure to effector functions," Frontiers in immunology, Oct. 20, 2014, 5:520, 17 Pages.
Vincke et al., "Introduction to heavy chain antibodies and derived Nanobodies," Single Domain Antibodies, Humana Press, Totowa, NJ, 2012, pp. 15-26.
Voelker et al., "Anti-TGF-β1 Antibody Therapy in Patients with Diabetic Nephropathy," J Am Soc Nephrol., 2017, 28:953-962.
Voet et al., Biochemistry, John Wiley & Sons, Inc., 1990, pp. 126-128 and 228-234, 12 pages.
Von Kobbe, "Cellular senescence: a view throughout organismal life," Cellular and Molecular Life Sciences, Jul. 20, 2018, 75:3553-3567, 15 pages.
Waaijer et al., "Do senescence markers correlate in vitro and in situ within individual human donors?," Aging Feb. 2018, 10(2):278-289.
Wallace et al., "B lymphocytes confer immune tolerance via cell surface GARP-TGF-β complex," JCI Insight., 2018, 3(7):e99863, 19 pages.
Walsh et al., "Inflammasomes in the CNS," Nature Reviews Neuroscience, Jan. 8, 2014, 15(2):84-97, 14 pages.
Wang et al., A New Recombinant Single Chain Trispecific Antibody Recruits T Lymphocytes to Kill CEA (Carcinoma Embryonic Antigen) Positive Tumor Cells In Vitro Efficiently, Journal of Biochemisty, 2004, 135(4):555-565 DOI: 10.1093/jb/mvh065.
Wang et al., "Biomarkers of Cellular Senescence and Skin Aging," Frontiers in Genetics, Aug. 23, 2018, 9:247, 14 pages.
Wang et al., "Loss of lamin B1 is a biomarker to quantify cellular senescence in photoaged skin," Scientific Reports, Nov. 15, 2017, 7(1):15678, 8 pages.
Wang et al., "Recombinant human CD137L for cancer immunotherapy: effects of different fusions and linkers on its activity," Cancer Immunol Immunother., 2012, 61(4):489-495.
Washburn et al., "A potential role for shed soluble major histocompatibility class I molecules as modulators of neurite outgrowth," PLoS One, Mar. 31, 2011, 6(3):e18439.
Weber et al., "Specific low-affinity recognition of major histocompatibility complex plus peptide by soluble T-cell receptor," Nature, Apr. 1992, 356(6372):793.
Weihermann et al., "Elastin structure and its involvement in skin photoageing," International Journal of Cosmetic Science, Jun. 2017, 39(3):241-247.
Weihofen et al., "Crystal Structure of CD26/Dipeptidyl-peptidase IV in Complex with Adenosine Deaminase Reveals a Highly Amphiphilic Interface, " Journal of Biological Chemistry, Oct. 2004, 279(41):43330-43335.
Weiner et al., "Antibody-based immunotherapy of cancer," Cell, Mar. 16, 2012, 148(6):1081-4.
Weiss et al., "Formyl-Peptide Receptors in Infection, Inflammation, and Cancer," Trends in Immunology, Oct. 2018, 39(10):815-829, 15 pages.
Wesolowski et al., "Single domain antibodies: promising experimental and therapeutic tools in infection and immunity," Medical Microbiology and Immunology. Aug. 1, 2009, 198(3):157-174.
Wiemann et al., "Hepatocyte telomere shortening and senescence are general markers of human liver cirrhosis," The FASEB Journal, Jul. 2002, 16(9):935-942.
Wiley et al., "Mitochondrial Dysfunction Induces Senescence with a Distinct Secretory Phenotype," Cell Metabolism, Feb. 9, 2016, 23(2):303-314.
Witkowsa et al., "Soluble intercellular adhesion molecule-1 (sICAM-1): an overview," Eur Cytokine Netw. 2004, 15(2):91-98.
Xiong et al., "Maternal uterine NK cell-activating receptor KIR2DS1 enhances placentation," The Journal of Clinical Investigation, Oct. 1, 2013, 123(10):4264-4272.
Xu et al., "Celecoxib attenuates cachectic events in mice by modulating the expression of vascular endothelial growth factor," Mol Med Rep., Jan. 2015, 11(1):289-294.

(56) References Cited

OTHER PUBLICATIONS

Xu et al., "JAK inhibition alleviates the cellular senescence-associated secretory phenotype and frailty in old age," Proceedings of the National Academy of Sciences U.S.A., Nov. 17, 2015, 112(46):E6301-6310, 10 pages.
Xu et al., "Senolytics improve physical function and increase lifespan in old age," Nature Medicine, Aug. 2018, 24(8):1246, 15 pages.
Xu et al., "Transplanted senescent cells induce an osteoarthritis-like condition in mice," The Journals of Gerontology: Series A, Jun. 1, 2017, 72(6):780-5.
Yamamoto et al., "Measurement of glucose uptake in cultured cells," Curr Protoc Pharmacol, Dec. 2011, Chapter 12:12.14.1-12.14.22.
Yamazaki et al., "Vascular Cell Senescence Contributes to Blood-Brain Barrier Breakdown," Stroke, Feb. 16, 2016, 47(4):1068-1077, 15 pages.
Yan et al., "Obesity- and aging-induced excess of central transforming growth factor-β potentiates diabetic development via an RNA stress response," Nature Medicine, Aug. 3, 2014, 20:1001-1008, 9 pages.
Yanai et al., "Cellular senescence-like features of lung fibroblasts derived from idiopathic pulmonary fibrosis patients," Aging (Albany NY), Sep. 2015, 7(9):664-672.
Yigit et al., "A combination of an anti-SLAMF6 antibody and ibrutinib efficiently abrogates expansion of chronic lymphocytic leukemia cells," Oncotarget, May 3, 2016, 7(18):26346.
Yousefzadeh et al., "An aged immune system drives senescence and ageing of solid organs," Nature, May 12, 2021, 594:100-105, 34 pages.
Yu et al., "Targeting the Senescence-Overriding Cooperative Activity of Structurally Unrelated H3K9 Demethylases in Melanoma," Cancer Cell, Feb. 12, 2018, 33(2):322-336, 23 pages.
Yu et al., "The dipeptidyl peptidase IV family in cancer and cell biology," FEBS Journal, Feb. 5, 2010, 277(5):1126-1144.
Yun et al., "Recurrent turnover of senescent cells during regeneration of a complex structure," Elife, May 5, 2015, 4:e05505, 16 pages.
Yung et al., "A selective transforming growth factor-β ligand trap attenuates pulmonary hypertension," American Journal of Respiratory and Critical Care Medicine, Nov. 1, 2016, 194(9):1140-51.
Zhang et al., "AAED1 modulates proliferation and glycolysis in gastric cancer," Oncology Reports, Aug. 1, 2018, 40(2):1156-1164.
Zhang et al., "The bone anabolic effects of irisin are through preferential stimulation of aerobic glycolysis, " Bone, Sep. 1, 2018, 114:150-160.
Zhao et al., "Histone Deacetylase-3 Modification of MicroRNA-31 Promotes Cell Proliferation and Aerobic Glycolysis in Breast Cancer and Is Predictive of Poor Prognosis," Journal of breast cancer, Jun. 1, 2018, 21(2):112-123.
Zheng et al., "Acquisition of Suppressive Function by Activated Human CD4+CD25- T Cells Is Associated with the Expression of CTLA-4 Not FoxP3," The Journal of Immunology, Aug. 1, 2008, 181(3):1683-1691.
Zhong et al., "A Potential Role for Dendritic Cell/Macrophage-Expressing DPP4 in Obesity-Induced Visceral Inflammation," Diabetes, Jan. 2013, 62(1):149-157.
Zhou et al., "A novel chimeric antigen receptor redirecting T-cell specificity towards CD26cancer cells," Leukemia, Apr. 2020, 35(1):119-129, 11 pages.
Zhu et al., "New agents that target senescent cells: the flavone, fisetin, and the BCL-XL inhibitors, A1331852 and A1155463," Aging (Albany NY), Mar. 2017, 9(3):955-963.
Zhu et al., "Novel Human Interleukin-15 Agonists," The Journal of Immunology, Sep. 15, 2009, 183(6):3598-3607.
Zou et al., "2-NBDG as a fluorescent indicator for direct glucose uptake measurement," Journal of biochemical and biophysical methods, Sep. 30, 2005, 64(3):207-215.
Zwaagstra et al., "Engineering and therapeutic application of single-chain bivalent TGF-β family traps," Molecular Cancer Therapeutics, Jul. 1, 2012, 11(7):1477-1487.
Auerbach et al., "Angiogenesis assays: problems and pitfalls," Cancer and Metastasis Reviews, 2000, vol. 19, pp. 167-172.
Beans, "Targeting metastasis to halt cancer's spread," Proceedings of the National Academy of Sciences, 2018, vol. 115(50), pp. 12539-12543.
Brown et al., Tolerance to Single, but Not Multiple, Amino Acid Replacements in Antibody VH CDR2, Journal of Immunology, May 1996, vol. 156(9), pp. 3285-3291.
Christiansen et al., "Biological impediments to monoclonal antibody-based cancer immunotherapy," Molecular Cancer Therapeutics, 2004, vol. 3, pp. 1493-1501.
Gravanis et al., "The changing world of cancer drug development: the regulatory bodies' perspective," Chinese Clinical Oncology, 2014, vol. 3, pp. 1-5.
Gura, "Systems for identifying new drugs are often faulty," Science, 1997, vol. 278(5340), pp. 1041-1042.
Hait, "Anticancer drug development: the grand challenges," Nature Reviews/Drug Discovery, 2010, vol. 9, pp. 253-254.
Heppner et al., "Tumor heterogeneity: biological implications and therapeutic consequences," Cancer Metastasis Review, 1983, vol. 2, pp. 5-23.
Jain, "Barriers to drug delivery in solid tumors," Scientific American, Jul. 1994, pp. 58-65.
Kulmanov et al., "DeepGO: predicting protein functions from sequence and interactions using a deep ontology-aware classifier," Bioinformatics, 2018, vol. 34(4), pp. 660-668.
Miosge et al., "Comparison of predicted and actual consequences of missense mutations," Proceedings of the National Academy of Sciences USA, Sep. 15, 2015, vol. 112(37), pp. E5189-98.
Ng et al., "Stimulation of Natural Killer Cell-Mediated Tumor Immunity by an IL 15/TGFβ- Neutralizing Fusion Protein," Cancer Research, Oct. 1, 2016, vol. 76(19), pp. 5683-5695.
Quatromoni et al., "The timing of TGF-β inhibition affects the generation of antigen-specific CD8+ T Cells," BMC Immunology, 2013, vol. 14(30), 16 pages.
Skolnick et al., "From genes to protein structure and function: novel applications of computational approaches in the genomic era," Trends in Biotechnology, Jan. 2000, vol. 18(1), pp. 34-39.
Sporn et al., "Chemoprevention of Cancer," Carcinogenesis, 2000, vol. 21(3), pp. 525-530.
Topp et al., "Antibody transport in cultured tumor cell layers," Journal of Controlled Release, 1998, vol. 53, pp. 15-23.
Vajdos et al., "Comprehensive Functional Maps of the Antigen-binding Site of an Anti-ErbB2 Antibody Obtained with Shotgun Scanning Mutagenesis," Journal of Molecular Biology, Jul. 5, 2002, vol. 320(2), pp. 415-428.

* cited by examiner

DTX (10 mg/kg), TGFRt15-TGFRs (3mg/kg), TA99 (200 µg)

SEQUENCE LISTING

```
Sequence total quantity: 226
SEQ ID NO: 1            moltype = AA  length = 219
FEATURE                 Location/Qualifiers
REGION                  1..219
                        note = source = /note="Tissue factor"
source                  1..219
                        mol_type = protein
                        organism = Homo sapiens
SEQUENCE: 1
SGTTNTVAAY NLTWKSTNFK TILEWEPKPV NQVYTVQIST KSGDWKSKCF YTTDTECDLT  60
DEIVKDVKQT YLARVFSYPA GNVESTGSAG EPLYENSPEF TPYLETNLGQ PTIQSFEQVG  120
```

-continued

```
TKVNVTVEDE RTLVRRNNTF LSLRDVFGKD LIYTLYYWKS SSSGKKTAKT NTNEFLIDVD  180
KGENYCFSVQ AVIPSRTVNR KSTDSPVECM GQEKGEFRE                         219

SEQ ID NO: 2           moltype = DNA  length = 657
FEATURE                Location/Qualifiers
misc_feature           1..657
                       note = source = /note="Tissue factor"
source                 1..657
                       mol_type = genomic DNA
                       organism = Homo sapiens
SEQUENCE: 2
agcggcacaa ccaacacagt cgctgcctat aacctcactt ggaagagcac caacttcaaa  60
accatcctcg aatgggaacc caaacccgtt aaccaagttt acaccgtgca gatcagcacc  120
aagtccggcg actggaagtc caaatgtttc tataccaccg acaccgagtg cgatctcacc  180
gatgagatcg tgaaagatgt gaaacagacc tacctcgccc gggtgtttag ctaccccgcc  240
ggcaatgtgg agagcactgg ttccgctggc gagcctttat acgagaacag ccccgaattt  300
accccttacc tcgagaccaa tttaggacag cccaccatcc aaagctttga gcaagttggc  360
acaaaggtga atgtgacagt ggaggacgag cggactttag tgcggcggaa caacaccttt  420
ctcagcctcc gggatgtgtt cggcaaagat ttaatctaca cactgtatta ctggaagtcc  480
tcttcctccg gcaagaagac agctaaaacc aacacaaacg agtttttaat cgacgtggat  540
aaaggcgaaa actactgttt cagcgtgcaa gctgtgatcc cctcccggac cgtgaatagg  600
aaaagcaccg atagccccgt tgagtgcatg ggccaagaaa agggcgagtt ccgggag     657

SEQ ID NO: 3           moltype = AA  length = 219
FEATURE                Location/Qualifiers
REGION                 1..219
                       note = source = /note="Tissue factor"
source                 1..219
                       mol_type = protein
                       organism = Homo sapiens
SEQUENCE: 3
SGTTNTVAAY NLTWKSTNFA TALEWEPKPV NQVYTVQIST KSGDWKSKCF YTTDTECALT  60
DEIVKDVKQT YLARVFSYPA GNVESTGSAG EPLYENSPEF TPYLETNLGQ PTIQSFEQVG  120
TKVNVTVEDE RTLVARNNTA LSLRDVFGKD LIYTLYYWKS SSSGKKTAKT NTNEFLIDVD  180
KGENYCFSVQ AVIPSRTVNR KSTDSPVECM GQEKGEFRE                         219

SEQ ID NO: 4           moltype = AA  length = 219
FEATURE                Location/Qualifiers
REGION                 1..219
                       note = source = /note="Tissue factor"
source                 1..219
                       mol_type = protein
                       organism = Homo sapiens
SEQUENCE: 4
SGTTNTVAAY NLTWKSTNFA TALEWEPKPV NQVYTVQIST KSGDAKSKCF YTTDTECALT  60
DEIVKDVKQT YLARVFSYPA GNVESTGSAG EPLAENSPEF TPYLETNLGQ PTIQSFEQVG  120
TKVNVTVEDE RTLVARNNTA LSLRDVFGKD LIYTLYYWKS SSSGKKTAKT NTNEFLIDVD  180
KGENYCFSVQ AVIPSRTVNR KSTDSPVECM GQEKGEFRE                         219

SEQ ID NO: 5           moltype = AA  length = 223
FEATURE                Location/Qualifiers
REGION                 1..223
                       note = source = /note="Tissue factor"
source                 1..223
                       mol_type = protein
                       organism = Mus musculus
SEQUENCE: 5
AGIPEKAFNL TWISTDFKTI LEWQPKPTNY TYTVQISDRS RNWKNKCFST TDTECDLTDE  60
IVKDVTWAYE AKVLSVPRRN SVHGDGDQLV IHGEEPPFTN APKFLPYRDT NLGQPVIQQF  120
EQDGRKLNVV VKDSLTLVRK NGTFLTLRQV FGKDLGYIIT YRKGSSTGKK TNITNTNEFS  180
IDVEEGVSYC FFVQAMIFSR KTNQNSPGSS TVCTEQWKSF LGE                    223

SEQ ID NO: 6           moltype = AA  length = 224
FEATURE                Location/Qualifiers
REGION                 1..224
                       note = source = /note="Tissue factor"
source                 1..224
                       mol_type = protein
                       organism = Rattus rattus
SEQUENCE: 6
AGTPPGKAFN LTWISTDFKT ILEWQPKPTN YTYTVQISDR SRNWKYKCTG TTDTECDLTD  60
EIVKDVNWTY EARVLSVPWR NSTHGKETLF GTHGEEPPFT NARKFLPYRD TKIGQPVIQK  120
YEQGGTKLKV TVKDSFTLVR KNGTFLTLRQ VFGNDLGYIL TYRKDSSTGR KTNTTHTNEF  180
LIDVEKGVSY CFFAQAVIFS RKTNHKSPES ITKCTEQWKS VLGE                   224

SEQ ID NO: 7           moltype = AA  length = 15
FEATURE                Location/Qualifiers
REGION                 1..15
                       note = source = /note="Description of Artificial Sequence:
```

```
                        SyntheticLinker sequence"
source                  1..15
                        mol_type = protein
                        organism = synthetic construct
SEQUENCE: 7
GGGGSGGGGS GGGGS                                                   15

SEQ ID NO: 8            moltype = DNA  length = 45
FEATURE                 Location/Qualifiers
misc_feature            1..45
                        note = source = /note="Description of Artificial Sequence:
                         SyntheticLinker sequence"
source                  1..45
                        mol_type = other DNA
                        organism = synthetic construct
SEQUENCE: 8
ggcggtggag gatccggagg aggtggctcc ggcggcggag gatct                  45

SEQ ID NO: 9            moltype = AA  length = 133
FEATURE                 Location/Qualifiers
REGION                  1..133
                        note = source = /note="IL-2"
source                  1..133
                        mol_type = protein
                        organism = Homo sapiens
SEQUENCE: 9
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 10           moltype = AA  length = 133
FEATURE                 Location/Qualifiers
REGION                  1..133
                        note = source = /note="IL-3"
source                  1..133
                        mol_type = protein
                        organism = Homo sapiens
SEQUENCE: 10
APMTQTTPLK TSWVNCSNMI DEIITHLKQP PLPLLDFNNL NGEDQDILME NNLRRPNLEA  60
FNRAVKSLQN ASAIESILKN LLPCLPLATA APTRHPIHIK DGDWNEFRRK LTFYLKTLEN  120
AQAQQTTLSL AIF                                                     133

SEQ ID NO: 11           moltype = AA  length = 152
FEATURE                 Location/Qualifiers
REGION                  1..152
                        note = source = /note="IL-7"
source                  1..152
                        mol_type = protein
                        organism = Homo sapiens
SEQUENCE: 11
DCDIEGKDGK QYESVLMVSI DQLLDSMKEI GSNCLNNEFN FFKRHICDAN KEGMFLFRAA  60
RKLRQFLKMN STGDFDLHLL KVSEGTTILL NCTGQVKGRK PAALGEAQPT KSLEENKSLK  120
EQKKLNDLCF LKRLLQEIKT CWNKILMGTK EH                                152

SEQ ID NO: 12           moltype = AA  length = 79
FEATURE                 Location/Qualifiers
REGION                  1..79
                        note = source = /note="IL-8"
source                  1..79
                        mol_type = protein
                        organism = Homo sapiens
SEQUENCE: 12
EGAVLPRSAK ELRCQCIKTY SKPFHPKFIK ELRVIESGPH CANTEIIVKL SDGRELCLDP  60
KENWVQRVVE KFLKRAENS                                               79

SEQ ID NO: 13           moltype = AA  length = 160
FEATURE                 Location/Qualifiers
REGION                  1..160
                        note = source = /note="IL-10"
source                  1..160
                        mol_type = protein
                        organism = Homo sapiens
SEQUENCE: 13
SPGQGTQSEN SCTHFPGNLP NMLRDLRDAF SRVKTFFQMK DQLDNLLLKE SLLEDFKGYL  60
GCQALSEMIQ FYLEEVMPQA ENQDPDIKAH VNSLGENLKT LRLRLRRCHR FLPCENKSKA  120
VEQVKNAFNK LQEKGIYKAM SEFDIFINYI EAYMTMKIRN                        160

SEQ ID NO: 14           moltype = AA  length = 114
FEATURE                 Location/Qualifiers
```

-continued

```
REGION                  1..114
                        note = source = /note="IL-15"
source                  1..114
                        mol_type = protein
                        organism = Homo sapiens
SEQUENCE: 14
NWVNVISDLK KIEDLIQSMH IDATLYTESD VHPSCKVTAM KCFLLELQVI SLESGDASIH  60
DTVENLIILA NNSLSSNGNV TESGCKECEE LEEKNIKEFL QSFVHIVQMF INTS        114

SEQ ID NO: 15           moltype = AA  length = 132
FEATURE                 Location/Qualifiers
REGION                  1..132
                        note = source = /note="IL-17"
source                  1..132
                        mol_type = protein
                        organism = Homo sapiens
SEQUENCE: 15
GITIPRNPGC PNSEDKNFPR TVMVNLNIHN RNTNTNPKRS SDYYNRSTSP WNLHRNEDPE  60
RYPSVIWEAK CRHLGCINAD GNVDYHMNSV PIQQEILVLR REPPHCPNSF RLEKILVSVG  120
CTCVTPIVHH VA                                                      132

SEQ ID NO: 16           moltype = AA  length = 157
FEATURE                 Location/Qualifiers
REGION                  1..157
                        note = source = /note="IL-18"
source                  1..157
                        mol_type = protein
                        organism = Homo sapiens
SEQUENCE: 16
YFGKLESKLS VIRNLNDQVL FIDQGNRPLF EDMTDSDCRD NAPRTIFIIS MYKDSQPRGM  60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                           157

SEQ ID NO: 17           moltype = AA  length = 352
FEATURE                 Location/Qualifiers
REGION                  1..352
                        note = source = /note="PDGF-DD"
source                  1..352
                        mol_type = protein
                        organism = Homo sapiens
SEQUENCE: 17
RDTSATPQSA SIKALRNANL RRDESNHLTD LYRRDETIQV KGNGYVQSPR FPNSYPRNLL  60
LTWRLHSQEN TRIQLVFDNQ FGLEEAENDI CRYDFVEVED ISETSTIIRG RWCGHKEVPP  120
RIKSRTNQIK ITFKSDDYFV AKPGFKIYYS LLEDFQPAAA SETNWESVTS SISGVSYNSP  180
SVTDPTLIAD ALDKKIAEFD TVEDLLKYFN PESWQEDLEN MYLDTPRYRG RSYHDRKSKV  240
DLDRLNDDAK RYSCTPRNYS VNIREELKLA NVVFFPRCLL VQRCGGNCGC GTVNWRSCTC  300
NSGKTVKKYH EVLQFEPGHI KRRGRAKTMA LVDIQLDHHE RCDCICSSRP PR          352

SEQ ID NO: 18           moltype = AA  length = 248
FEATURE                 Location/Qualifiers
REGION                  1..248
                        note = source = /note="SCF"
source                  1..248
                        mol_type = protein
                        organism = Homo sapiens
SEQUENCE: 18
EGICRNRVTN NVKDVTKLVA NLPKDYMITL KYVPGMDVLP SHCWISEMVV QLSDSLTDLL  60
DKFSNISEGL SNYSIIDKLV NIVDDLVECV KENSSKDLKK SFKSPEPRLF TPEEFFRIFN  120
RSIDAFKDFV VASETSDCVV SSTLSPEKDS RVSVTKPFML PPVAASSLRN DSSSSNRKAK  180
NPPGDSSLHW AAMALPALFS LIIGFAFGAL YWKKRQPSLT RAVENIQINE EDNEISMLQE  240
KEREFQEV                                                           248

SEQ ID NO: 19           moltype = AA  length = 209
FEATURE                 Location/Qualifiers
REGION                  1..209
                        note = source = /note="FLT3L"
source                  1..209
                        mol_type = protein
                        organism = Homo sapiens
SEQUENCE: 19
TQDCSFQHSP ISSDFAVKIR ELSDYLLQDY PVTVASNLQD EELCGGLWRL VLAQRWMERL  60
KTVAGSKMQG LLERVNTEIH FVTKCAFQPP PSCLRFVQTN ISRLLQETSE QLVALKPWIT  120
RQNFSRCLEL QCQPDSSTLP PPWSPRPLEA TAPTAPQPPL LLLLLLPVGL LLLAAAWCLH  180
WQRTRRRTPR PGEQVPPVPS PQDLLLVEH                                    209

SEQ ID NO: 20           moltype = AA  length = 360
FEATURE                 Location/Qualifiers
REGION                  1..360
                        note = source = /note="MICA"
```

-continued

```
source                 1..360
                       mol_type = protein
                       organism = Homo sapiens
SEQUENCE: 20
EPHSLRYNLT VLSWDGSVQS GFLTEVHLDG QPFLRCDRQK CRAKPQGQWA EDVLGNKTWD  60
RETRDLTGNG KDLRMTLAHI KDQKEGLHSL QEIRVCEIHE DNSTRSSQHF YYDGELFLSQ  120
NLETKEWTMP QSSRAQTLAM NVRNFLKEDA MKTKTHYHAM HADCLQELRR YLKSGVVLRR  180
TVPPMVNVTR SEASEGNITV TCRASGFYPW NITLSWRQDG VSLSHDTQQW GDVLPDGNGT  240
YQTWVATRIC QGEEQRFTCY MEHSGNHSTH PVPSGKVLVL QSHWQTFHVS AVAAAAIFVI  300
IIFYVRCCKK KTSAAEGPEL VSLQVLDQHP VGTSDHRDAT QLGFQPLMSD LGSTGSTEGA  360

SEQ ID NO: 21          moltype = AA  length = 361
FEATURE                Location/Qualifiers
REGION                 1..361
                       note = source = /note="MICB"
source                 1..361
                       mol_type = protein
                       organism = Homo sapiens
SEQUENCE: 21
AEPHSLRYNL MVLSQDESVQ SGFLAEGHLD GQPFLRYDRQ KRRAKPQGQW AEDVLGAKTW  60
DTETEDLTEN GQDLRRTLTH IKDQKGGLHS LQEIRVCEIH EDSSTRGSRH FYYDGELFLS  120
QNLETQESTV PQSSRAQTLA MNVTNFWKED AMKTKTHYRA MQADCLQKLQ RYLKSGVAIR  180
RTVPPMVNVT CSEVSEGNIT VTCRASSFYP RNITLTWRQD GVSLSHNTQQ WGDVLPDGNG  240
TYQTWVATRI RQGEEQRFTC YMEHSGNHGT HPVPSGKVLV LQSQRTDFPY VSAAMPCFVI  300
IIILCVPCCK KKTSAAEGPE LVSLQVLDQH PVGTGDHRDA AQLGFQPLMS ATGSTGSTEG  360
A                                                                 361

SEQ ID NO: 22          moltype = AA  length = 190
FEATURE                Location/Qualifiers
REGION                 1..190
                       note = source = /note="ULBP1"
source                 1..190
                       mol_type = protein
                       organism = Homo sapiens
SEQUENCE: 22
WVDTHCLCYD FIITPKSRPE PQWCEVQGLV DERPFLHYDC VNHKAKAFAS LGKKVNVTKT  60
WEEQTETLRD VVDFLKGQLL DIQVENLIPI EPLTLQARMS CEHEAHGHGR GSWQFLFNGQ  120
KFLLFDSNNR KWTALHPGAK KMTEKWEKNR DVTMFFQKIS LGDCKMWLEE FLMYWEQMLD  180
PTKPPSLAPG                                                        190

SEQ ID NO: 23          moltype = AA  length = 191
FEATURE                Location/Qualifiers
REGION                 1..191
                       note = source = /note="ULBP2"
source                 1..191
                       mol_type = protein
                       organism = Homo sapiens
SEQUENCE: 23
GRADPHSLCY DITVIPKFRP GPRWCAVQGQ VDEKTFLHYD CGNKTVTPVS PLGKKLNVTT  60
AWKAQNPVLR EVVDILTEQL RDIQLENYTP KEPLTLQARM SCEQKAEGHS SGSWQFSFDG  120
QIFLLFDSEK RMWTTVHPGA RKMKEKWEND KVVAMSFHYF SMGDCIGWLE DFLMGMDSTL  180
EPSAGAPLAM S                                                      191

SEQ ID NO: 24          moltype = AA  length = 188
FEATURE                Location/Qualifiers
REGION                 1..188
                       note = source = /note="ULBP3"
source                 1..188
                       mol_type = protein
                       organism = Homo sapiens
SEQUENCE: 24
DAHSLWYNFT IIHLPRHGQQ WCEVQSQVDQ KNFLSYDCGS DKVLSMGHLE EQLYATDAWG  60
KQLEMLREVG QRLRLELADT ELEDFTPSGP LTLQVRMSCE CEADGYIRGS WQFSFDGRKF  120
LLFDSNNRKW TVVHAGARRM KEKWEKDSGL TTFFKMVSMR DCKSWLRDFL MHRKKRLEPT  180
APPTMAPG                                                          188

SEQ ID NO: 25          moltype = AA  length = 233
FEATURE                Location/Qualifiers
REGION                 1..233
                       note = source = /note="ULBP4"
source                 1..233
                       mol_type = protein
                       organism = Homo sapiens
SEQUENCE: 25
HSLCFNFTIK SLSRPGQPWC EAQVFLNKNL FLQYNSDNNM VKPLGLLGKK VYATSTWGEL  60
TQTLGEVGRD LRMLLCDIKP QIKTSDPSTL QVEMFCQREA ERCTGASWQF ATNGEKSLLF  120
DAMNMTWTVI NHEASKIKET WKKDRGLEKY FRKLSKGDCD HWLREFLGHW EAMPEPTVSP  180
VNASDIHWSS SSLPDRWIIL GAFILLVLMG IVLICVWWQN GEWQAGLWPL RTS        233
```

```
SEQ ID NO: 26          moltype = AA  length = 193
FEATURE                Location/Qualifiers
REGION                 1..193
                       note = source = /note="ULBP5"
source                 1..193
                       mol_type = protein
                       organism = Homo sapiens
SEQUENCE: 26
GLADPHSLCY DITVIPKFRP GPRWCAVQGQ VDEKTFLHYD CGSKTVTPVS PLGKKLNVTT  60
AWKAQNPVLR EVVDILTEQL LDIQLENYIP KEPLTLQARM SCEQKAEGHG SGSWQLSFDG  120
QIFLLFDSEN RMWTTVHPGA RKMKEKWEND KDMTMSFHYI SMGDCTGWLE DFLMGMDSTL  180
EPSAGAPPTM SSG                                                   193

SEQ ID NO: 27          moltype = AA  length = 193
FEATURE                Location/Qualifiers
REGION                 1..193
                       note = source = /note="ULBP6"
source                 1..193
                       mol_type = protein
                       organism = Homo sapiens
SEQUENCE: 27
RRDDPHSLCY DITVIPKFRP GPRWCAVQGQ VDEKTFLHYD CGNKTVTPVS PLGKKLNVTM  60
AWKAQNPVLR EVVDILTEQL LDIQLENYTP KEPLTLQARM SCEQKAEGHS SGSWQFSIDG  120
QTFLLFDSEK RMWTTVHPGA RKMKEKWEND KDVAMSFHYI SMGDCIGWLE DFLMGMDSTL  180
EPSAGAPLAM SSG                                                   193

SEQ ID NO: 28          moltype = AA  length = 65
FEATURE                Location/Qualifiers
REGION                 1..65
                       note = source = /note="IL15Ralpha"
source                 1..65
                       mol_type = protein
                       organism = Homo sapiens
SEQUENCE: 28
ITCPPPMSVE HADIWVKSYS LYSRERYICN SGFKRKAGTS SLTECVLNKA TNVAHWTTPS  60
LKCIR                                                            65

SEQ ID NO: 29          moltype = DNA  length = 195
FEATURE                Location/Qualifiers
misc_feature           1..195
                       note = source = /note="IL15Ralpha"
source                 1..195
                       mol_type = genomic DNA
                       organism = Homo sapiens
SEQUENCE: 29
attacatgcc cccctcccat gagcgtggag cacgccgaca tctgggtgaa gagctatagc  60
ctctacagcc gggagaggta tatctgtaac agcggcttca agaggaaggc cggcaccagc  120
agcctcaccg agtgcgtgct gaataaggct accaacgtgg ctcactggac aacaccctct  180
ttaaagtgca tccgg                                                 195

SEQ ID NO: 30          moltype = DNA  length = 342
FEATURE                Location/Qualifiers
misc_feature           1..342
                       note = source = /note="IL-15"
source                 1..342
                       mol_type = genomic DNA
                       organism = Homo sapiens
SEQUENCE: 30
aactgggtga acgtcatcag cgatttaaag aagatcgaag atttaattca gtccatgcat  60
atcgacgcca ctttatacac agaatccgac gtgcacccct cttgtaaggt gaccgccatg  120
aaatgttttt tactggagct gcaagttatc tctttagaga gcggagacgc tagcatccac  180
gacaccgtgg agaatttaat cattttagcc aataactctt tatccagcaa cggcaacgtg  240
acagagtccg gctgcaagga gtgcgaagag ctggaggaga agaacatcaa ggagtttctg  300
caatcctttg tgcacattgt ccagatgttc atcaatacct cc                   342

SEQ ID NO: 31          moltype = AA  length = 18
FEATURE                Location/Qualifiers
REGION                 1..18
                       note = source = /note="Description of Artificial Sequence:
                        Syntheticpeptide"
source                 1..18
                       mol_type = protein
                       organism = synthetic construct
SEQUENCE: 31
MKWVTFISLL FLFSSAYS                                              18

SEQ ID NO: 32          moltype = DNA  length = 54
FEATURE                Location/Qualifiers
misc_feature           1..54
```

```
                        note = source = /note="Description of Artificial Sequence:
                         Syntheticoligonucleotide"
source                  1..54
                        mol_type = other DNA
                        organism = synthetic construct
SEQUENCE: 32
atgaaatggg tgacctttat ttctttactg ttcctcttta gcagcgccta ctcc        54

SEQ ID NO: 33           moltype = DNA  length = 54
FEATURE                 Location/Qualifiers
misc_feature            1..54
                        note = source = /note="Description of Artificial Sequence:
                         Syntheticoligonucleotide"
source                  1..54
                        mol_type = other DNA
                        organism = synthetic construct
SEQUENCE: 33
atgaagtggg tcacatttat ctctttactg ttcctcttct ccagcgccta cagc        54

SEQ ID NO: 34           moltype = DNA  length = 54
FEATURE                 Location/Qualifiers
misc_feature            1..54
                        note = source = /note="Description of Artificial Sequence:
                         Syntheticoligonucleotide"
source                  1..54
                        mol_type = other DNA
                        organism = synthetic construct
SEQUENCE: 34
atgaaatggg tgacctttat ttctttactg ttcctcttta gcagcgccta ctcc        54

SEQ ID NO: 35           moltype = AA  length = 16
FEATURE                 Location/Qualifiers
REGION                  1..16
                        note = source = /note="Description of Artificial Sequence:
                         Syntheticpeptide"
source                  1..16
                        mol_type = protein
                        organism = synthetic construct
SEQUENCE: 35
MKCLLYLAFL FLGVNC                                                  16

SEQ ID NO: 36           moltype = AA  length = 58
FEATURE                 Location/Qualifiers
REGION                  1..58
                        note = source = /note="Description of Artificial Sequence:
                         Syntheticpolypeptide"
source                  1..58
                        mol_type = protein
                        organism = synthetic construct
SEQUENCE: 36
MGQIVTMFEA LPHIIDEVIN IVIIVLIIIT SIKAVYNFAT CGILALVSFL FLAGRSCG    58

SEQ ID NO: 37           moltype = AA  length = 97
FEATURE                 Location/Qualifiers
REGION                  1..97
                        note = source = /note="Description of Artificial Sequence:
                         Syntheticpolypeptide"
source                  1..97
                        mol_type = protein
                        organism = synthetic construct
SEQUENCE: 37
MPNHQSGSPT GSSDLLLSGK KQRPHLALRR KRRREMRKIN RKVRRMNLAP IKEKTAWQHL  60
QALISEAEEV LKTSQTPQNS LTLFLALLSV LGPPVTG                           97

SEQ ID NO: 38           moltype = AA  length = 30
FEATURE                 Location/Qualifiers
REGION                  1..30
                        note = source = /note="Description of Artificial Sequence:
                         Syntheticpolypeptide"
source                  1..30
                        mol_type = protein
                        organism = synthetic construct
SEQUENCE: 38
MDSKGSSQKG SRLLLLLVVS NLLLCQGVVS                                   30

SEQ ID NO: 39           moltype = AA  length = 15
FEATURE                 Location/Qualifiers
REGION                  1..15
                        note = source = /note="Description of Artificial Sequence:
```

```
                         SyntheticAviTag sequence"
source                  1..15
                        mol_type = protein
                        organism = synthetic construct
SEQUENCE: 39
GLNDIFEAQK IEWHE                                                    15

SEQ ID NO: 40           moltype = AA  length = 26
FEATURE                 Location/Qualifiers
REGION                  1..26
                        note = source = /note="Description of Artificial Sequence:
                         SyntheticTag sequence"
source                  1..26
                        mol_type = protein
                        organism = synthetic construct
SEQUENCE: 40
KRRWKKNFIA VSAANRFKKI SSSGAL                                        26

SEQ ID NO: 41           moltype = AA  length = 7
FEATURE                 Location/Qualifiers
REGION                  1..7
                        note = source = /note="Description of Artificial Sequence:
                         SyntheticTag sequence"
source                  1..7
                        mol_type = protein
                        organism = synthetic construct
SEQUENCE: 41
EEEEEET                                                             7

SEQ ID NO: 42           moltype = AA  length = 13
FEATURE                 Location/Qualifiers
REGION                  1..13
                        note = source = /note="Description of Artificial Sequence:
                         SyntheticTag sequence"
source                  1..13
                        mol_type = protein
                        organism = synthetic construct
SEQUENCE: 42
GAPVPYPDPL EPR                                                      13

SEQ ID NO: 43           moltype = AA  length = 8
FEATURE                 Location/Qualifiers
REGION                  1..8
                        note = source = /note="Description of Artificial Sequence:
                         SyntheticTag sequence"
source                  1..8
                        mol_type = protein
                        organism = synthetic construct
SEQUENCE: 43
DYKDDDDK                                                            8

SEQ ID NO: 44           moltype = AA  length = 9
FEATURE                 Location/Qualifiers
REGION                  1..9
                        note = source = /note="Description of Artificial Sequence:
                         SyntheticTag sequence"
source                  1..9
                        mol_type = protein
                        organism = synthetic construct
SEQUENCE: 44
YPYDVPDYA                                                           9

SEQ ID NO: 45           moltype = AA  length = 5
FEATURE                 Location/Qualifiers
REGION                  1..5
                        note = source = /note="Description of Artificial Sequence:
                         SyntheticTag sequence"
source                  1..5
                        mol_type = protein
                        organism = synthetic construct
SEQUENCE: 45
HHHHH                                                               5

SEQ ID NO: 46           moltype = AA  length = 6
FEATURE                 Location/Qualifiers
REGION                  1..6
                        note = source = /note="Description of Artificial Sequence:
                         SyntheticTag sequence"
source                  1..6
```

-continued

```
                        mol_type = protein
                        organism = synthetic construct
SEQUENCE: 46
HHHHHH                                                          6

SEQ ID NO: 47           moltype = AA  length = 7
FEATURE                 Location/Qualifiers
REGION                  1..7
                        note = source = /note="Description of Artificial Sequence:
                         SyntheticTag sequence"
source                  1..7
                        mol_type = protein
                        organism = synthetic construct
SEQUENCE: 47
HHHHHHH                                                         7

SEQ ID NO: 48           moltype = AA  length = 8
FEATURE                 Location/Qualifiers
REGION                  1..8
                        note = source = /note="Description of Artificial Sequence:
                         SyntheticTag sequence"
source                  1..8
                        mol_type = protein
                        organism = synthetic construct
SEQUENCE: 48
HHHHHHHH                                                        8

SEQ ID NO: 49           moltype = AA  length = 9
FEATURE                 Location/Qualifiers
REGION                  1..9
                        note = source = /note="Description of Artificial Sequence:
                         SyntheticTag sequence"
source                  1..9
                        mol_type = protein
                        organism = synthetic construct
SEQUENCE: 49
HHHHHHHHH                                                       9

SEQ ID NO: 50           moltype = AA  length = 10
FEATURE                 Location/Qualifiers
REGION                  1..10
                        note = source = /note="Description of Artificial Sequence:
                         SyntheticTag sequence"
source                  1..10
                        mol_type = protein
                        organism = synthetic construct
SEQUENCE: 50
HHHHHHHHHH                                                      10

SEQ ID NO: 51           moltype = AA  length = 10
FEATURE                 Location/Qualifiers
REGION                  1..10
                        note = source = /note="Description of Artificial Sequence:
                         SyntheticTag sequence"
source                  1..10
                        mol_type = protein
                        organism = synthetic construct
SEQUENCE: 51
EQKLISEEDL                                                      10

SEQ ID NO: 52           moltype = AA  length = 18
FEATURE                 Location/Qualifiers
REGION                  1..18
                        note = source = /note="Description of Artificial Sequence:
                         SyntheticTag sequence"
source                  1..18
                        mol_type = protein
                        organism = synthetic construct
SEQUENCE: 52
TKENPRSNQE ESYDDNES                                             18

SEQ ID NO: 53           moltype = AA  length = 15
FEATURE                 Location/Qualifiers
REGION                  1..15
                        note = source = /note="Description of Artificial Sequence:
                         SyntheticTag sequence"
source                  1..15
                        mol_type = protein
                        organism = synthetic construct
```

```
SEQUENCE: 53
KETAAAKFER QHMDS                                                  15

SEQ ID NO: 54           moltype = AA  length = 38
FEATURE                 Location/Qualifiers
REGION                  1..38
                        note = source = /note="Description of Artificial Sequence:
                         SyntheticTag sequence"
source                  1..38
                        mol_type = protein
                        organism = synthetic construct
SEQUENCE: 54
MDEKTTGWRG GHVVEGLAGE LEQLRARLEH HPQGQREP                         38

SEQ ID NO: 55           moltype = AA  length = 13
FEATURE                 Location/Qualifiers
REGION                  1..13
                        note = source = /note="Description of Artificial Sequence:
                         SyntheticTag sequence"
source                  1..13
                        mol_type = protein
                        organism = synthetic construct
SEQUENCE: 55
SLAELLNAGL GGS                                                    13

SEQ ID NO: 56           moltype = AA  length = 8
FEATURE                 Location/Qualifiers
REGION                  1..8
                        note = source = /note="Description of Artificial Sequence:
                         SyntheticTag sequence"
source                  1..8
                        mol_type = protein
                        organism = synthetic construct
SEQUENCE: 56
TQDPSRVG                                                          8

SEQ ID NO: 57           moltype = AA  length = 12
FEATURE                 Location/Qualifiers
REGION                  1..12
                        note = source = /note="Description of Artificial Sequence:
                         SyntheticTag sequence"
source                  1..12
                        mol_type = protein
                        organism = synthetic construct
SEQUENCE: 57
PDRVRAVSHW SS                                                     12

SEQ ID NO: 58           moltype = AA  length = 8
FEATURE                 Location/Qualifiers
REGION                  1..8
                        note = source = /note="Description of Artificial Sequence:
                         SyntheticTag sequence"
source                  1..8
                        mol_type = protein
                        organism = synthetic construct
SEQUENCE: 58
WSHPQFEK                                                          8

SEQ ID NO: 59           moltype = AA  length = 6
FEATURE                 Location/Qualifiers
REGION                  1..6
                        note = source = /note="Description of Artificial Sequence:
                         SyntheticTag sequence"
source                  1..6
                        mol_type = protein
                        organism = synthetic construct
SEQUENCE: 59
CCPGCC                                                            6

SEQ ID NO: 60           moltype = AA  length = 10
FEATURE                 Location/Qualifiers
REGION                  1..10
                        note = source = /note="Description of Artificial Sequence:
                         SyntheticTag sequence"
source                  1..10
                        mol_type = protein
                        organism = synthetic construct
SEQUENCE: 60
EVHTNQDPLD                                                        10
```

```
SEQ ID NO: 61          moltype = AA  length = 14
FEATURE                Location/Qualifiers
REGION                 1..14
                       note = source = /note="Description of Artificial Sequence:
                        SyntheticTag sequence"
source                 1..14
                       mol_type = protein
                       organism = synthetic construct
SEQUENCE: 61
GKPIPNPLLG LDST                                                   14

SEQ ID NO: 62          moltype = AA  length = 11
FEATURE                Location/Qualifiers
REGION                 1..11
                       note = source = /note="Description of Artificial Sequence:
                        SyntheticTag sequence"
source                 1..11
                       mol_type = protein
                       organism = synthetic construct
SEQUENCE: 62
YTDIEMNRLG K                                                      11

SEQ ID NO: 63          moltype = AA  length = 8
FEATURE                Location/Qualifiers
REGION                 1..8
                       note = source = /note="Description of Artificial Sequence:
                        SyntheticTag sequence"
source                 1..8
                       mol_type = protein
                       organism = synthetic construct
SEQUENCE: 63
DLYDDDDK                                                          8

SEQ ID NO: 64          moltype = AA  length = 10
FEATURE                Location/Qualifiers
REGION                 1..10
                       note = source = /note="Description of Artificial Sequence:
                        SyntheticTag sequence"
source                 1..10
                       mol_type = protein
                       organism = synthetic construct
SEQUENCE: 64
EQKLISEEDL                                                        10

SEQ ID NO: 65          moltype = DNA  length = 471
FEATURE                Location/Qualifiers
misc_feature           1..471
                       note = source = /note="IL-18"
source                 1..471
                       mol_type = genomic DNA
                       organism = Homo sapiens
SEQUENCE: 65
tacttcggca aactggaatc caagctgagc gtgatccgga atttaaacga ccaagttctg  60
tttatcgatc aaggtaaccg gcctctgttc gaggacatga ccgactccga ttgccgggac  120
aatgcccccc ggaccatctt cattatctcc atgtacaagg acagccagcc ccggggcatg  180
gctgtgacaa ttagcgtgaa gtgtgagaaa atcagcactt tatcttgtga gaacaagatc  240
atctccttta aggaaatgaa cccccccgat aacatcaagg acaccaagtc cgatatcatc  300
ttcttccagc ggtccgtgcc cggtcacgat aacaagatgc agttcgaatc ctcctcctac  360
gagggctact ttttagcttg tgaaaaggag agggatttat tcaagctgat cctcaagaag  420
gaggacgagc tgggcgatcg ttccatcatg ttcaccgtcc aaaacgagga t           471

SEQ ID NO: 66          moltype = AA  length = 306
FEATURE                Location/Qualifiers
REGION                 1..306
                       note = source = /note="IL-12Beta"
source                 1..306
                       mol_type = protein
                       organism = Homo sapiens
SEQUENCE: 66
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCS                                                            306

SEQ ID NO: 67          moltype = DNA  length = 918
FEATURE                Location/Qualifiers
```

-continued

```
misc_feature          1..918
                      note = source = /note="IL-12Beta"
source                1..918
                      mol_type = genomic DNA
                      organism = Homo sapiens
SEQUENCE: 67
atttgggaac tgaagaagga cgtctacgtg gtcgaactgg actggtatcc cgatgctccc  60
ggcgaaatgg tggtgctcac ttgtgacacc cccgaagaag acggcatcac ttggaccctc  120
gatcagagca gcgaggtgct gggctccgga aagaccctca caatccaagt taaggagttc  180
ggagacgctg gccaatacac atgccacaag ggaggcgagg tgctcagcca ttccttatta  240
ttattacaca agaaggaaga cggaatctgg tccaccgaca ttttaaaaga tcagaaggag  300
cccaagaata agaccttttt aaggtgtgag gccaaaaact acagcggtcg tttcacttgt  360
tggtggctga ccaccatttc caccgattta accttctccg tgaaaagcag ccggggaagc  420
tccgaccctc aaggtgtgac atgtggagcc gctaccctca gcgctgagag ggttcgtggc  480
gataacaagg aatacgagta cagcgtggag tgccaagaag atagcgcttg tcccgctgcc  540
gaagaatctt tacccattga ggtgatggtg gacgccgtgc acaaactcaa gtacgagaac  600
tacacctcct ccttctttat ccgggacatc attaagcccg atcctcctaa gaatttacag  660
ctgaagcctc tcaaaaatag ccggcaagtt gaggtctctt gggaatatcc cgacacttgg  720
agcacacccc acagctactt ctctttaacc ttttgtgtgc aagttcaagg taaaagcaag  780
cgggagaaga aagaccgggt gtttaccgac aaaaccagcg ccaccgtcat ctgtcggaag  840
aacgcctcca tcagcgtgag ggctcaagat cgttattact ccagcagctg gtccgagtgg  900
gccagcgtgc cttgttcc                                                918

SEQ ID NO: 68         moltype = AA  length = 197
FEATURE               Location/Qualifiers
REGION                1..197
                      note = source = /note="IL-12alpha"
source                1..197
                      mol_type = protein
                      organism = Homo sapiens
SEQUENCE: 68
RNLPVATPDP GMFPCLHHSQ NLLRAVSNML QKARQTLEFY PCTSEEIDHE DITKDKTSTV  60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRAVTIDRV MSYLNAS                                                 197

SEQ ID NO: 69         moltype = DNA  length = 591
FEATURE               Location/Qualifiers
misc_feature          1..591
                      note = source = /note="IL-12alpha"
source                1..591
                      mol_type = genomic DNA
                      organism = Homo sapiens
SEQUENCE: 69
cgtaacctcc ccgtggctac ccccgatccc ggaatgttcc cttgtttaca ccacagccag  60
aatttactga gggccgtgag caacatgctg cagaaagcta ggcagacttt agaattttac  120
ccttgcacca gcgaggagat cgaccatgaa gatatcacca aggacaagac atccaccgtg  180
gaggcttgtt tacctctgga gctgacaaag aacgagtctt gtctcaactc tcgtgaaacc  240
agcttcatca caaatggctc ttgtttagct tcccggaaga cctcctttat gatggcttta  300
tgcctcagct ccatctacga ggatttaaag atgtaccaag tggagttcaa gaccatgaac  360
gccaagctgc tcatggaccc taaacggcag atctttttag accagaacat gctggctgtg  420
attgatgagc tgatgcaagc tttaaacttc aactccgaga ccgtccctca gaagtcctcc  480
ctcgaggagc ccgattttta caagacaaag atcaaactgt gcattttact ccacgccttt  540
aggatccggg ccgtgaccat tgaccgggtc atgagctatt taaacgccag c           591

SEQ ID NO: 70         moltype = AA  length = 490
FEATURE               Location/Qualifiers
REGION                1..490
                      note = source = /note="Description of Artificial Sequence:
                       Synthetic18t15-12s sequence"
source                1..490
                      mol_type = protein
                      organism = synthetic construct
SEQUENCE: 70
YFGKLESKLS VIRNLNDQVL FIDQGNRPLF EDMTDSDCRD NAPRTIFIIS MYKDSQPRGM  60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNEDSGT TNTVAAYNLT WKSTNFKTIL  180
EWEPKPVNQV YTVQISTKSG DWKSKCFYTT DTECDLTDEI VKDVKQTYLA RVFSYPAGNV  240
ESTGSAGEPL YENSPEFTPY LETNLGQPTI QSFEQVGTKV NVTVEDERTL VRRNNTFLSL  300
RDVFGKDLIY TLYYWKSSSS GKKTAKTNTN EFLIDVDKGE NYCFSVQAVI PSRTVNRKST  360
DSPVECMGQE KGEFRENWVN VISDLKKIED LIQSMHIDAT LYTESDVHPS CKVTAMKCFL  420
LELQVISLES GDASIHDTVE NLIILANNSL SSNGNVTESG CKECEELEEK NIKEFLQSFV  480
HIVQMFINTS                                                         490

SEQ ID NO: 71         moltype = DNA  length = 1470
FEATURE               Location/Qualifiers
misc_feature          1..1470
                      note = source = /note="Description of Artificial Sequence:
                       Synthetic18t15-12s sequence"
```

```
source                  1..1470
                        mol_type = other DNA
                        organism = synthetic construct
SEQUENCE: 71
tacttcggca aactggaatc caagctgagc gtgatccgga atttaaacga ccaagttctg  60
tttatcgatc aaggtaaccg gcctctgttc gaggacatga ccgactccga ttgccgggac  120
aatgcccccc ggaccatctt cattatctcc atgtacaagg acagccagcc ccggggcatg  180
gctgtgacaa ttagcgtgaa gtgtgagaaa atcagcactt tatcttgtga gaacaagatc  240
atctccttta aggaaatgaa cccccccgat aacatcaagg acaccaagtc cgatatcatc  300
ttcttccagc ggtccgtgcc cggtcacgat aacaagatgc agttcgaatc ctcctcctac  360
gagggctact ttttagcttg tgaaaaggag agggatttat tcaagctgat cctcaagaag  420
gaggacgagc tgggcgatcg ttccatcatg ttcaccgtcc aaaacgagga tagcggcaca  480
accaacacag tcgctgccta taacctcact tggaagagca ccaacttcaa aaccatcctc  540
gaatgggaac ccaaacccgt taaccaagtt tacaccgtgc agatcagcac caagtccggc  600
gactggaagt ccaaatgttt ctataccacc gacaccgagt gcgatctcac cgatgagatc  660
gtgaaagatg tgaaacagac ctacctcgcc cgggtgttta gctaccccgc cggcaatgtg  720
gagagcactg gttccgctgg cgagccttta tacgagaaca gccccgaatt taccccttac  780
ctcgagacca atttaggaca gcccaccatc caaagctttg agcaagttgg cacaaaggtg  840
aatgtgacag tggaggacga gcggacttta gtgcggcgga acaacacctt tctcagcctc  900
cgggatgtgt tcggcaaaga tttaatctac acactgtatt actggaagtc ctcttcctcc  960
ggcaagaaga cagctaaaac caacacaaac gagtttttaa tcgacgtgga taaaggcgaa  1020
aactactgtt tcagcgtgca agctgtgatc ccctcccgga ccgtgaatag gaaaagcacc  1080
gatagccccg ttgagtgcat gggccaagaa aagggcgagt tccgggagaa ctgggtgaac  1140
gtcatcagcg atttaaagaa gatcgaagat ttaattcagt ccatgcatat cgacgccact  1200
ttatacacag aatccgacgt gcacccctct tgtaaggtga ccgccatgaa atgtttttta  1260
ctggagctgc aagttatctc tttagagagc ggagacgcta gcatccacga caccgtggag  1320
aatttaatca ttttagccaa taactcttta tccagcaacg gcaacgtgac agagtccggc  1380
tgcaaggagt gcgaagagct ggaggagaag aacatcaagg agtttctgca atcctttgtg  1440
cacattgtcc agatgttcat caatacctcc                                  1470

SEQ ID NO: 72           moltype = AA  length = 508
FEATURE                 Location/Qualifiers
REGION                  1..508
                        note = source = /note="Description of Artificial Sequence:
                         Synthetic18t15-12s sequence"
source                  1..508
                        mol_type = protein
                        organism = synthetic construct
SEQUENCE: 72
MKWVTFISLL FLFSSAYSYF GKLESKLSVI RNLNDQVLFI DQGNRPLFED MTDSDCRDNA  60
PRTIFIISMY KDSQPRGMAV TISVKCEKIS TLSCENKIIS FKEMNPPDNI KDTKSDIIFF  120
QRSVPGHDNK MQFESSSYEG YFLACEKERD LFKLILKKED ELGDRSIMFT VQNEDSGTTN  180
TVAAYNLTWK STNFKTILEW EPKPVNQVYT VQISTKSGDW KSKCFYTTDT ECDLTDEIVK  240
DVKQTYLARV FSYPAGNVES TGSAGEPLYE NSPEFTPYLE TNLGQPTIQS FEQVGTKVNV  300
TVEDERTLVR RNNTFLSLRD VFGKDLIYTL YYWKSSSSGK KTAKTNTNEF LIDVDKGENY  360
CFSVQAVIPS RTVNRKSTDS PVECMGQEKG EFRENWVNVI SDLKKIEDLI QSMHIDATLY  420
TESDVHPSCK VTAMKCFLLE LQVISLESGD ASIHDTVENL IILANNSLSS NGNVTESGCK  480
ECEELEEKNI KEFLQSFVHI VQMFINTS                                    508

SEQ ID NO: 73           moltype = DNA  length = 1524
FEATURE                 Location/Qualifiers
misc_feature            1..1524
                        note = source = /note="Description of Artificial Sequence:
                         Synthetic18t15-12s sequence"
source                  1..1524
                        mol_type = other DNA
                        organism = synthetic construct
SEQUENCE: 73
atgaagtggg tcacatttat ctctttactg ttcctcttct ccagcgccta cagctacttc  60
ggcaaactgg aatccaagct gagcgtgatc cggaatttaa acgaccaagt tctgtttatc  120
gatcaaggta accggcctct gttcgaggac atgaccgact ccgattgccg ggacaatgcc  180
ccccggacca tcttcattat ctccatgtac aaggacagcc agccccgggg catggctgtg  240
acaattagcg tgaagtgtga gaaaatcagc actttatctt gtgagaacaa gatcatctcc  300
tttaaggaaa tgaacccccc cgataacatc aaggacacca agtccgatat catcttcttc  360
cagcggtccg tgcccggtca cgataacaag atgcagttcg aatcctcctc ctacgagggc  420
tactttttag cttgtgaaaa ggagagggat ttattcaagc tgatcctcaa gaaggaggac  480
gagctgggcg atcgttccat catgttcacc gtccaaaacg aggatagcgg cacaaccaac  540
acagtcgctg cctataacct cacttggaag agcaccaact tcaaaaccat cctcgaatgg  600
gaacccaaac ccgttaacca agtttacacc gtgcagatca gcaccaagtc cggcgactgg  660
aagtccaaat gtttctatac caccgacacc gagtgcgatc tcaccgatga gatcgtgaaa  720
gatgtgaaac agacctacct cgcccgggtg tttagctacc ccgccggcaa tgtggagagc  780
actggttccg ctggcgagcc tttatacgag aacagccccg aatttacccc ttacctcgag  840
accaatttag gacagcccac catccaaagc tttgagcaag ttggcacaaa ggtgaatgtg  900
acagtggagg acgagcggac tttagtgcgg cggaacaaca cctttctcag cctccgggat  960
gtgttcggca aagatttaat ctacacactg tattactgga agtcctcttc ctccggcaag  1020
aagacagcta aaaccaacac aaacgagttt ttaatcgacg tggataaagg cgaaaactac  1080
tgtttcagcg tgcaagctgt gatcccctcc cggaccgtga ataggaaaag caccgatagc  1140
cccgttgagt gcatgggcca agaaaagggc gagttccggg agaactgggt gaacgtcatc  1200
agcgatttaa agaagatcga agatttaatt cagtccatgc atatcgacgc cactttatac  1260
```

```
acagaatccg acgtgcaccc ctcttgtaag gtgaccgcca tgaaatgttt tttactggag  1320
ctgcaagtta tctctttaga gagcggagac gctagcatcc acgacaccgt ggagaattta  1380
atcattttag ccaataactc tttatccagc aacggcaacg tgacagagtc cggctgcaag  1440
gagtgcgaag agctggagga gaagaacatc aaggagtttc tgcaatcctt tgtgcacatt  1500
gtccagatgt tcatcaatac ctcc                                         1524

SEQ ID NO: 74          moltype = AA  length = 583
FEATURE                Location/Qualifiers
REGION                 1..583
                       note = source = /note="Description of Artificial Sequence:
                        Synthetic18t15-12s sequence"
source                 1..583
                       mol_type = protein
                       organism = synthetic construct
SEQUENCE: 74
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRNLPVATPD PGMFPCLHHS QNLLRAVSNM LQKARQTLEF  360
YPCTSEEIDH EDITKDKTST VEACLPLELT KNESCLNSRE TSFITNGSCL ASRKTSFMMA  420
LCLSSIYEDL KMYQVEFKTM NAKLLMDPKR QIFLDQNMLA VIDELMQALN FNSETVPQKS  480
SLEEPDFYKT KIKLCILLHA FRIRAVTIDR VMSYLNASIT CPPPMSVEHA DIWVKSYSLY  540
SRERYICNSG FKRKAGTSSL TECVLNKATN VAHWTTPSLK CIR                    583

SEQ ID NO: 75          moltype = DNA  length = 1749
FEATURE                Location/Qualifiers
misc_feature           1..1749
                       note = source = /note="Description of Artificial Sequence:
                        Synthetic18t15-12s sequence"
source                 1..1749
                       mol_type = other DNA
                       organism = synthetic construct
SEQUENCE: 75
atttgggaac tgaagaagga cgtctacgtg gtcgaactgg actggtatcc cgatgctccc  60
ggcgaaatgg tggtgctcac ttgtgacacc cccgaagaag acggcatcac ttggaccctc  120
gatcagagca gcgaggtgct gggctccgga aagaccctca caatccaagt taaggagttc  180
ggagacgctg gccaatacac atgccacaag ggaggcgagg tgctcagcca ttccttatta  240
ttattacaca agaaggaaga cggaatctgg tccaccgaca ttttaaaaga tcagaaggag  300
cccaagaata agaccttttt aaggtgtgag gccaaaaact acagcggtcg tttcacttgt  360
tggtggctga ccaccatttc caccgattta accttctccg tgaaaagcag ccggggaagc  420
tccgaccctc aaggtgtgac atgtggagcc gctaccctca gcgctgagag ggttcgtggc  480
gataacaagg aatacgagta cagcgtggag tgccaagaag atagcgcttg tcccgctgcc  540
gaagaatctt tacccattga ggtgatggtg gacgccgtgc acaaactcaa gtacgagaac  600
tacacctcct ccttctttat ccgggacatc attaagcccg atcctcctaa gaatttacag  660
ctgaagcctc tcaaaaatag ccggcaagtt gaggtctctt gggaatatcc cgacacttgg  720
agcacacccc acagctactt ctctttaacc ttttgtgtgc aagttcaagg taaaagcaag  780
cgggagaaga aagaccgggt gtttaccgac aaaaccagcg ccaccgtcat ctgtcggaag  840
aacgcctcca tcagcgtgag ggctcaagat cgttattact ccagcagctg gtccgagtgg  900
gccagcgtgc cttgttccgg cggtggagga tccggaggag gtggctccgg cggcggagga  960
tctcgtaacc tccccgtggc tacccccgat cccggaatgt tcccttgttt acaccacagc  1020
cagaatttac tgagggccgt gagcaacatg ctgcagaaag ctaggcagac tttagaattt  1080
tacccttgca ccagcgagga gatcgaccat gaagatatca ccaaggacaa gacatccacc  1140
gtggaggctt gtttacctct ggagctgaca aagaacgagt cttgtctcaa ctctcgtgaa  1200
accagcttca tcacaaatgg ctcttgttta gcttcccgga agacctcctt tatgatggct  1260
ttatgcctca gctccatcta cgaggattta aagatgtacc aagtggagtt caagaccatg  1320
aacgccaagc tgctcatgga ccctaaacgg cagatctttt tagaccagaa catgctggct  1380
gtgattgatg agctgatgca agctttaaac ttcaactccg agaccgtccc tcagaagtcc  1440
tccctcgagg agcccgattt ttacaagaca aagatcaaac tgtgcatttt actccacgcc  1500
tttaggatcc gggccgtgac cattgaccgg gtcatgagct atttaaacgc cagcattaca  1560
tgcccccctc ccatgagcgt ggagcacgcc gacatctggg tgaagagcta tagcctctac  1620
agccgggaga ggtatatctg taacagcggc ttcaagagga aggccggcac cagcagcctc  1680
accgagtgcg tgctgaataa ggctaccaac gtggctcact ggacaacacc ctctttaaag  1740
tgcatccgg                                                          1749

SEQ ID NO: 76          moltype = AA  length = 601
FEATURE                Location/Qualifiers
REGION                 1..601
                       note = source = /note="Description of Artificial Sequence:
                        Synthetic18t15-12s sequence"
source                 1..601
                       mol_type = protein
                       organism = synthetic construct
SEQUENCE: 76
MKWVTFISLL FLFSSAYSIW ELKKDVYVVE LDWYPDAPGE MVVLTCDTPE EDGITWTLDQ  60
SSEVLGSGKT LTIQVKEFGD AGQYTCHKGG EVLSHSLLLL HKKEDGIWST DILKDQKEPK  120
NKTFLRCEAK NYSGRFTCWW LTTISTDLTF SVKSSRGSSD PQGVTCGAAT LSAERVRGDN  180
KEYEYSVECQ EDSACPAAEE SLPIEVMVDA VHKLKYENYT SSFFIRDIIK PDPPKNLQLK  240
```

```
PLKNSRQVEV SWEYPDTWST PHSYFSLTFC VQVQGKSKRE KKDRVFTDKT SATVICRKNA  300
SISVRAQDRY YSSSWSEWAS VPCSGGGGSG GGGSGGGGSR NLPVATPDPG MFPCLHHSQN  360
LLRAVSNMLQ KARQTLEFYP CTSEEIDHED ITKDKTSTVE ACLPLELTKN ESCLNSRETS  420
FITNGSCLAS RKTSFMMALC LSSIYEDLKM YQVEFKTMNA KLLMDPKRQI FLDQNMLAVI  480
DELMQALNFN SETVPQKSSL EEPDFYKTKI KLCILLHAFR IRAVTIDRVM SYLNASITCP  540
PPMSVEHADI WVKSYSLYSR ERYICNSGFK RKAGTSSLTE CVLNKATNVA HWTTPSLKCI  600
R                                                                 601

SEQ ID NO: 77          moltype = DNA  length = 1803
FEATURE                Location/Qualifiers
misc_feature           1..1803
                       note = source = /note="Description of Artificial Sequence:
                        Synthetic18t15-12s sequence"
source                 1..1803
                       mol_type = other DNA
                       organism = synthetic construct
SEQUENCE: 77
atgaaatggg tgacctttat ttctttactg ttcctcttta gcagcgccta ctccatttgg  60
gaactgaaga aggacgtcta cgtggtcgaa ctggactggt atcccgatgc tcccggcgaa  120
atggtggtgc tcacttgtga cacccccgaa gaagacggca tcacttggac cctcgatcag  180
agcagcgagg tgctgggctc cggaaagacc ctcacaatcc aagttaagga gttcggagac  240
gctggccaat acacatgcca caagggaggc gaggtgctca gccattcctt attattatta  300
cacaagaagg aagacggaat ctggtccacc gacattttaa aagatcagaa ggagcccaag  360
aataagacct ttttaaggtg tgaggccaaa aactacagcg gtcgtttcac ttgttggtgg  420
ctgaccacca tttccaccga tttaaccttc tccgtgaaaa gcagccgggg aagctccgac  480
cctcaaggtg tgacatgtgg agccgctacc ctcagcgctg agagggttcg tggcgataac  540
aaggaatacg agtacagcgt ggagtgccaa gaagatagcg cttgtcccgc tgccgaagaa  600
tctttaccca ttgaggtgat ggtggacgcc gtgcacaaac tcaagtacga gaactacacc  660
tcctccttct ttatccggga catcattaag cccgatcctc ctaagaattt acagctgaag  720
cctctcaaaa atagccggca agttgaggtc tcttgggaat atcccgacac ttggagcaca  780
ccccacagct acttctcttt aaccttttgt gtgcaagttc aaggtaaaag caagcgggag  840
aagaaagacc gggtgtttac cgacaaaacc agcgccaccg tcatctgtcg gaagaacgcc  900
tccatcagcg tgagggctca agatcgttat tactccagca gctggtccga gtgggccagc  960
gtgccttgtt ccggcggtgg aggatccgga ggaggtggct ccggcggcgg aggatctcgt  1020
aacctccccg tggctacccc cgatcccgga atgttccctt gtttacacca cagccagaat  1080
ttactgaggg ccgtgagcaa catgctgcag aaagctaggc agactttaga atttaccct  1140
tgcaccagcg aggagatcga ccatgaagat atcaccaagg acaagacatc caccgtggag  1200
gcttgtttac ctctggagct gacaaagaac gagtcttgtc tcaactctcg tgaaaccagc  1260
ttcatcacaa atggctcttg tttagcttcc cggaagacct cctttatgat ggctttatgc  1320
ctcagctcca tctacgagga tttaaagatg taccaagtgg agttcaagac catgaacgcc  1380
aagctgctca tggaccctaa acggcagatc tttttagacc agaacatgct ggctgtgatt  1440
gatgagctga tgcaagcttt aaacttcaac tccgagaccg tccctcagaa gtcctccctc  1500
gaggagcccg atttttacaa gacaaagatc aaactgtgca ttttactcca cgcctttagg  1560
atccgggccg tgaccattga ccgggtcatg agctatttaa acgccagcat tacatgcccc  1620
cctcccatga gcgtggagca cgccgacatc tgggtgaaga gctatagcct ctacagccgg  1680
gagaggtata tctgtaacag cggcttcaag aggaaggccg gcaccagcag cctcaccgag  1740
tgcgtgctga ataaggctac caacgtggct cactggacaa caccctcttt aaagtgcatc  1800
cgg                                                               1803

SEQ ID NO: 78          moltype = AA  length = 133
FEATURE                Location/Qualifiers
REGION                 1..133
                       note = source = /note="IL-21"
source                 1..133
                       mol_type = protein
                       organism = Homo sapiens
SEQUENCE: 78
QGQDRHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH  120
QHLSSRTHGS EDS                                                    133

SEQ ID NO: 79          moltype = DNA  length = 399
FEATURE                Location/Qualifiers
misc_feature           1..399
                       note = source = /note="Description of Artificial Sequence:
                        SyntheticIL7RA MCP insert sequence"
source                 1..399
                       mol_type = other DNA
                       organism = synthetic construct
SEQUENCE: 79
cagggccagg acaggcacat gatccggatg aggcagctca tcgacatcgt cgaccagctg  60
aagaactacg tgaacgacct ggtgcccgag tttctgcctg cccccgagga cgtggagacc  120
aactgcgagt ggtccgcctt ctcctgcttt cagaaggccc agctgaagtc cgccaacacc  180
ggcaacaacg agcggatcat caacgtgagc atcaagaagc tgaagcggaa gcctccctcc  240
acaaacgccg gcaggaggca gaagcacagg ctgacctgcc ccagctgtga ctcctacgag  300
aagaagcccc ccaaggagtt cctggagagg ttcaagtccc tgctgcagaa gatgatccat  360
cagcacctgt cctccaggac ccacggctcc gaggactcc                         399

SEQ ID NO: 80          moltype = AA  length = 136
```

```
FEATURE                Location/Qualifiers
REGION                 1..136
                       note = source = /note="TGFRbetaRII"
source                 1..136
                       mol_type = protein
                       organism = Homo sapiens
SEQUENCE: 80
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPD                                                  136

SEQ ID NO: 81          moltype = AA  length = 136
FEATURE                Location/Qualifiers
REGION                 1..136
                       note = source = /note="TGFRbetaRII"
source                 1..136
                       mol_type = protein
                       organism = Homo sapiens
SEQUENCE: 81
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPD                                                  136

SEQ ID NO: 82          moltype = DNA  length = 408
FEATURE                Location/Qualifiers
misc_feature           1..408
                       note = source = /note="TGFRbetaRII"
source                 1..408
                       mol_type = genomic DNA
                       organism = Homo sapiens
SEQUENCE: 82
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcacgatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgat               408

SEQ ID NO: 83          moltype = DNA  length = 408
FEATURE                Location/Qualifiers
misc_feature           1..408
                       note = source = /note="TGFRbetaRII"
source                 1..408
                       mol_type = genomic DNA
                       organism = Homo sapiens
SEQUENCE: 83
attcctcccc acgtgcagaa gagcgtgaat aatgacatga tcgtgaccga taacaatggc  60
gccgtgaaat ttccccagct gtgcaaattc tgcgatgtga ggttttccac ctgcgacaac  120
cagaagtcct gtatgagcaa ctgcacaatc acctccatct gtgagaagcc tcaggaggtg  180
tgcgtggctg tctggcggaa gaatgacgag aatatcaccc tggaaaccgt ctgccacgat  240
cccaagctgc cctaccacga tttcatcctg gaagacgccg ccagccctaa gtgcatcatg  300
aaagagaaaa agaagcctgg cgagaccttt ttcatgtgct cctgcagcag cgacgaatgc  360
aacgacaata tcatctttag cgaggaatac aataccagca accccgac               408

SEQ ID NO: 84          moltype = DNA  length = 960
FEATURE                Location/Qualifiers
misc_feature           1..960
                       note = source = /note="TGFRbetaRII"
source                 1..960
                       mol_type = genomic DNA
                       organism = Homo sapiens
SEQUENCE: 84
aactgggtga atgtgatcag cgacctgaag aagatcgagg atctgatcca gagcatgcac  60
attgatgcca ccctgtacac agaatctgat gtgcacccta tccccccccca tgtgcaaaag  120
agcgtgaaca acgatatgat cgtgaccgac aacaacggcg ccgtgaagtt tccccagctc  180
tgcaagttct gcgatgtcag gttcagcacc tgcgataatc agaagtcctg catgtccaac  240
tgcacgatca cctccatctg cgagaagccc caagaagtgt gcgtggccgt gtggcggaaa  300
aatgacgaga acatcaccct ggagaccgtg tgtcacgacc ccaagctccc ttatcacgac  360
ttcattctgg aggacgctgc ctcccccaaa tgcatcatga aggagaagaa gaagcccgga  420
gagaccttct ttatgtgttc ctgtagcagc gacgagtgta acgacaacat catcttcagc  480
gaagagtaca acaccagcaa ccctgatgga ggtggcggat ccggaggtgg aggttctggt  540
ggaggtggga gtattcctcc ccacgtgcag aagagcgtga ataatgacat gatcgtgacc  600
gataacaatg gcgccgtgaa atttccccag ctgtgcaaat tctgcgatgt gaggttttcc  660
acctgcgaca accagaagtc ctgtatgagc aactgcacaa tcacctccat ctgtgagaag  720
cctcaggagg tgtgcgtggc tgtctggcgg aagaatgacg agaatatcac cctggaaacc  780
gtctgccacg atcccaagct gccctaccac gatttcatcc tggaagacgc cgccagccct  840
aagtgcatca tgaaagagaa aaagaagcct ggcgagacct ttttcatgtg ctcctgcagc  900
agcgacgaat gcaacgacaa tatcatcttt agcgaggaat acaataccag caaccccgac  960
```

```
SEQ ID NO: 85            moltype = AA  length = 287
FEATURE                  Location/Qualifiers
REGION                   1..287
                         note = source = /note="TGFRbetaRII"
source                   1..287
                         mol_type = protein
                         organism = Homo sapiens
SEQUENCE: 85
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPD                287

SEQ ID NO: 86            moltype = AA  length = 466
FEATURE                  Location/Qualifiers
REGION                   1..466
                         note = source = /note="Description of Artificial Sequence:
                          Synthetic21t15-TGFRs sequence"
source                   1..466
                         mol_type = protein
                         organism = synthetic construct
SEQUENCE: 86
QGQDRHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH  120
QHLSSRTHGS EDSSGTTNTV AAYNLTWKST NFKTILEWEP KPVNQVYTVQ ISTKSGDWKS  180
KCFYTTDTEC DLTDEIVKDV KQTYLARVFS YPAGNVESTG SAGEPLYENS PEFTPYLETN  240
LGQPTIQSFE QVGTKVNVTV EDERTLVRRN NTFLSLRDVF GKDLIYTLYY WKSSSSGKKT  300
AKTNTNEFLI DVDKGENYCF SVQAVIPSRT VNRKSTDSPV ECMGQEKGEF RENWVNVISD  360
LKKIEDLIQS MHIDATLYTE SDVHPSCKVT AMKCFLLELQ VISLESGDAS IHDTVENLII  420
LANNSLSSNG NVTESGCKEC EELEEKNIKE FLQSFVHIVQ MFINTS                 466

SEQ ID NO: 87            moltype = DNA  length = 1398
FEATURE                  Location/Qualifiers
misc_feature             1..1398
                         note = source = /note="Description of Artificial Sequence:
                          Synthetic21t15-TGFRs sequence"
source                   1..1398
                         mol_type = other DNA
                         organism = synthetic construct
SEQUENCE: 87
cagggccagg acaggcacat gatccggatg aggcagctca tcgacatcgt cgaccagctg  60
aagaactacg tgaacgacct ggtgcccgag tttctgcctg cccccgagga cgtggagacc  120
aactgcgagt ggtccgcctt ctcctgcttt cagaaggccc agctgaagtc cgccaacacc  180
ggcaacaacg agcggatcat caacgtgagc atcaagaagc tgaagcggaa gcctccctcc  240
acaaacgccg gcaggaggca gaagcacagg ctgacctgcc ccagctgtga ctcctacgag  300
aagaagcccc ccaaggagtt cctggagagg ttcaagtccc tgctgcagaa gatgatccat  360
cagcacctgt cctccaggac ccacggctcc gaggactcct ccggcaccac caataccgtg  420
gccgcttata acctcacatg gaagagcacc aacttcaaga caattctgga atgggaaccc  480
aagcccgtca atcaagttta caccgtgcag atctccacca aatccggaga ctggaagagc  540
aagtgcttct acacaacaga caccgagtgt gatttaaccg acgaaatcgt caaggacgtc  600
aagcaaacct atctggctcg ggtcttttcc taccccgctg gcaatgtcga gtccaccggc  660
tccgctggcg agcctctcta cgagaattcc cccgaattca ccccttattt agagaccaat  720
ttaggccagc ctaccatcca gagcttcgag caagttggca ccaaggtgaa cgtcaccgtc  780
gaggatgaaa ggactttagt gcggcggaat aacacatttt tatccctccg ggatgtgttc  840
ggcaaagacc tcatctacac actgtactat tggaagtcca gctcctccgg caaaaagacc  900
gctaagacca acaccaacga gtttttaatt gacgtggaca aaggcgagaa ctactgcttc  960
agcgtgcaag ccgtgatccc ttctcgtacc gtcaaccgga agagcacaga ttcccccgtt  1020
gagtgcatgg gccaagaaaa gggcgagttc cgggagaact gggtgaacgt catcagcgat  1080
ttaaagaaga tcgaagattt aattcagtcc atgcatatcg acgccacttt atacacagaa  1140
tccgacgtgc accctcttg taaggtgacc gccatgaaat gtttttact ggagctgcaa  1200
gttatctctt tagagagcgg agacgctagc atccacgaca ccgtggagaa tttaatcatt  1260
ttagccaata actctttatc cagcaacggc aacgtgacag agtccggctg caaggagtgc  1320
gaagagctgg aggagaagaa catcaaggag tttctgcaat cctttgtgca cattgtccag  1380
atgttcatca atacctcc                                                1398

SEQ ID NO: 88            moltype = AA  length = 484
FEATURE                  Location/Qualifiers
REGION                   1..484
                         note = source = /note="Description of Artificial Sequence:
                          Synthetic21t15-TGFRs sequence"
source                   1..484
                         mol_type = protein
                         organism = synthetic construct
SEQUENCE: 88
MKWVTFISLL FLFSSAYSQG QDRHMIRMRQ LIDIVDQLKN YVNDLVPEFL PAPEDVETNC  60
EWSAFSCFQK AQLKSANTGN NERIINVSIK KLKRKPPSTN AGRRQKHRLT CPSCDSYEKK  120
PPKEFLERFK SLLQKMIHQH LSSRTHGSED SSGTTNTVAA YNLTWKSTNF KTILEWEPKP  180
```

```
VNQVYTVQIS TKSGDWKSKC FYTTDTECDL TDEIVKDVKQ TYLARVFSYP AGNVESTGSA  240
GEPLYENSPE FTPYLETNLG QPTIQSFEQV GTKVNVTVED ERTLVRRNNT FLSLRDVFGK  300
DLIYTLYYWK SSSSGKKTAK TNTNEFLIDV DKGENYCFSV QAVIPSRTVN RKSTDSPVEC  360
MGQEKGEFRE NWVNVISDLK KIEDLIQSMH IDATLYTESD VHPSCKVTAM KCFLLELQVI  420
SLESGDASIH DTVENLIILA NNSLSSNGNV TESGCKECEE LEEKNIKEFL QSFVHIVQMF  480
INTS                                                              484

SEQ ID NO: 89          moltype = DNA  length = 1452
FEATURE                Location/Qualifiers
misc_feature           1..1452
                       note = source = /note="Description of Artificial Sequence:
                        Synthetic21t15-TGFRs sequence"
source                 1..1452
                       mol_type = other DNA
                       organism = synthetic construct
SEQUENCE: 89
atgaagtggg tgaccttcat cagcctgctg ttcctgttct ccagcgccta ctcccagggc  60
caggacaggc acatgatccg gatgaggcag ctcatcgaca tcgtcgacca gctgaagaac  120
tacgtgaacg acctggtgcc cgagtttctg cctgcccccg aggacgtgga gaccaactgc  180
gagtggtccg ccttctcctg ctttcagaag gcccagctga agtccgccaa caccggcaac  240
aacgagcgga tcatcaacgt gagcatcaag aagctgaagc ggaagcctcc ctccacaaac  300
gccggcagga ggcagaagca caggctgacc tgccccagct gtgactccta cgagaagaag  360
ccccccaagg agttcctgga gaggttcaag tccctgctgc agaagatgat ccatcagcac  420
ctgtcctcca ggacccacgg ctccgaggac tcctccggca ccaccaatac cgtggccgct  480
tataacctca catggaagag caccaacttc aagacaattc tggaatggga acccaagccc  540
gtcaatcaag tttacaccgt gcagatctcc accaaatccg gagactggaa gagcaagtgc  600
ttctacacaa cagacaccga gtgtgattta accgacgaaa tcgtcaagga cgtcaagcaa  660
acctatctgg ctcgggtctt ttcctacccc gctggcaatg tcgagtccac cggctccgct  720
ggcgagcctc tctacgagaa ttcccccgaa ttcacccctt atttagagac caatttaggc  780
cagcctacca tccagagctt cgagcaagtt ggcaccaagg tgaacgtcac cgtcgaggat  840
gaaaggactt tagtgcggcg gaataacaca tttttatccc tccgggatgt gttcggcaaa  900
gacctcatct acacactgta ctattggaag tccagctcct ccggcaaaaa gaccgctaag  960
accaacacca acgagttttt aattgacgtg gacaaaggcg agaactactg cttcagcgtg  1020
caagccgtga tcccttctcg taccgtcaac cggaagagca cagattcccc cgttgagtgc  1080
atgggccaag aaaagggcga gttccgggag aactgggtga acgtcatcag cgatttaaag  1140
aagatcgaag atttaattca gtccatgcat atcgacgcca ctttatacac agaatccgac  1200
gtgcacccct cttgtaaggt gaccgccatg aaatgttttt tactggagct gcaagttatc  1260
tctttagaga gcggagacgc tagcatccac gacaccgtgg agaatttaat catttttagcc  1320
aataactctt tatccagcaa cggcaacgtg acagagtccg gctgcaagga gtgcgaagag  1380
ctggaggaga agaacatcaa ggagtttctg caatcctttg tgcacattgt ccagatgttc  1440
atcaatacct cc                                                      1452

SEQ ID NO: 90          moltype = AA  length = 352
FEATURE                Location/Qualifiers
REGION                 1..352
                       note = source = /note="Description of Artificial Sequence:
                        Synthetic21t15-TGFRs sequence"
source                 1..352
                       mol_type = protein
                       organism = synthetic construct
SEQUENCE: 90
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPDITC PPPMSVEHAD  300
IWVKSYSLYS RERYICNSGF KRKAGTSSLT ECVLNKATNV AHWTTPSLKC IR          352

SEQ ID NO: 91          moltype = DNA  length = 1056
FEATURE                Location/Qualifiers
misc_feature           1..1056
                       note = source = /note="Description of Artificial Sequence:
                        Synthetic21t15-TGFRs sequence"
source                 1..1056
                       mol_type = other DNA
                       organism = synthetic construct
SEQUENCE: 91
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcacgatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggttttc cacctgcgac aaccagaagt cctgtatgag caactgcaca  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
```

```
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
tacaatacca gcaaccccga catcacgtgt cctcctccta tgtccgtgga acacgcagac  900
atctgggtca agagctacag cttgtactcc agggagcggt acatttgtaa ctctggtttc  960
aagcgtaaag ccggcacgtc cagcctgacg gagtgcgtgt tgaacaaggc cacgaatgtc  1020
gcccactgga caaccccccag tctcaaatgt attaga                            1056

SEQ ID NO: 92           moltype = AA  length = 370
FEATURE                 Location/Qualifiers
REGION                  1..370
                        note = source = /note="Description of Artificial Sequence:
                         Synthetic21t15-TGFRs sequence"
source                  1..370
                        mol_type = protein
                        organism = synthetic construct
SEQUENCE: 92
MKWVTFISLL FLFSSAYSIP PHVQKSVNND MIVTDNNGAV KFPQLCKFCD VRFSTCDNQK  60
SCMSNCSITS ICEKPQEVCV AVWRKNDENI TLETVCHDPK LPYHDFILED AASPKCIMKE  120
KKKPGETFFM CSCSSDECND NIIFSEEYNT SNPDGGGGSG GGGSGGGGSI PPHVQKSVNN  180
DMIVTDNNGA VKFPQLCKFC DVRFSTCDNQ KSCMSNCSIT SICEKPQEVC VAVWRKNDEN  240
ITLETVCHDP KLPYHDFILE DAASPKCIMK EKKKPGETFF MCSCSSDECN DNIIFSEEYN  300
TSNPDITCPP PMSVEHADIW VKSYSLYSRE RYICNSGFKR KAGTSSLTEC VLNKATNVAH  360
WTTPSLKCIR                                                          370

SEQ ID NO: 93           moltype = DNA  length = 1110
FEATURE                 Location/Qualifiers
misc_feature            1..1110
                        note = source = /note="Description of Artificial Sequence:
                         Synthetic21t15-TGFRs sequence"
source                  1..1110
                        mol_type = other DNA
                        organism = synthetic construct
SEQUENCE: 93
atgaagtggg tgaccttcat cagcctgctg ttcctgttct ccagcgccta ctccatcccc  60
ccccatgtgc aaaagagcgt gaacaacgat atgatcgtga ccgacaacaa cggcgccgtg  120
aagtttcccc agctctgcaa gttctgcgat gtcaggttca gcacctgcga taatcagaag  180
tcctgcatgt ccaactgcac gatcacctcc atctgcgaga agccccaaga agtgtgcgtg  240
gccgtgtggc ggaaaaatga cgagaacatc accctggaga ccgtgtgtca cgaccccaag  300
ctcccttatc acgacttcat tctggaggac gctgcctccc ccaaatgcat catgaaggag  360
aagaagaagc ccggagagac cttctttatg tgttcctgta gcagcgacga gtgtaacgac  420
aacatcatct tcagcgaaga gtacaacacc agcaaccctg atggaggtgg cggatccgga  480
ggtggaggtt ctggtggagg tgggagtatt cctccccacg tgcagaagag cgtgaataat  540
gacatgatcg tgaccgataa caatggcgcc gtgaaatttc cccagctgtg caaattctgc  600
gatgtgaggt tttccacctg cgacaaccag aagtcctgta tgagcaactg cacaatcacc  660
tccatctgtg agaagcctca ggaggtgtgc gtggctgtct ggcggaagaa tgacgagaat  720
atcaccctgg aaaccgtctg ccacgatccc aagctgccct accacgattt catcctggaa  780
gacgccgcca gccctaagtg catcatgaaa gagaaaaaga agcctggcga gacctttttc  840
atgtgctcct gcagcagcga cgaatgcaac gacaatatca tctttagcga ggaatacaat  900
accagcaacc ccgacatcac gtgtcctcct cctatgtccg tggaacacgc agacatctgg  960
gtcaagagct acagcttgta ctccagggag cggtacattt gtaactctgg tttcaagcgt  1020
aaagccggca cgtccagcct gacggagtgc gtgttgaaca aggccacgaa tgtcgcccac  1080
tggacaaccc ccagtctcaa atgtattaga                                    1110

SEQ ID NO: 94           moltype = DNA  length = 399
FEATURE                 Location/Qualifiers
misc_feature            1..399
                        note = source = /note="IL-21"
source                  1..399
                        mol_type = genomic DNA
                        organism = Homo sapiens
SEQUENCE: 94
caaggtcaag atcgccacat gattagaatg cgtcaactta tagatattgt tgatcagctg  60
aaaaattatg tgaatgactt ggtccctgaa tttctgccag ctccagaaga tgtagagaca  120
aactgtgagt ggtcagcttt ttcctgtttt cagaaggccc aactaaagtc agcaaataca  180
ggaaacaatg aaaggataat caatgtatca attaaaaagc tgaagaggaa accaccttcc  240
acaaatgcag ggagaagaca gaaacacaga ctaacatgcc cttcatgtga ttcttatgag  300
aaaaaaccac ccaaagaatt cctagaaaga ttcaaatcac ttctccaaaa gatgattcat  360
cagcatctgt cctctagaac acacggaagt gaagattcc                          399

SEQ ID NO: 95           moltype = DNA  length = 456
FEATURE                 Location/Qualifiers
misc_feature            1..456
                        note = source = /note="Description of Artificial Sequence:
                         SyntheticIL-7 sequence"
source                  1..456
                        mol_type = other DNA
                        organism = synthetic construct
SEQUENCE: 95
gattgtgata ttgaaggtaa agatggcaaa caatatgaga gtgttctaat ggtcagcatc  60
```

-continued

```
gatcaattat tggacagcat gaaagaaatt ggtagcaatt gcctgaataa tgaatttaac  120
ttttttaaaa gacatatctg tgatgctaat aaggaaggta tgtttttatt ccgtgctgct  180
cgcaagttga ggcaatttct taaaatgaat agcactggtg attttgatct ccacttatta  240
aaagtttcag aaggcacaac aatactgttg aactgcactg gccaggttaa aggaagaaaa  300
ccagctgccc tgggtgaagc ccaaccaaca aagagtttgg aagaaaataa atctttaaag  360
gaacagaaaa aactgaatga cttgtgtttc ctaaagagac tattacaaga gataaaaact  420
tgttggaata aaattttgat gggcactaaa gaacac                            456

SEQ ID NO: 96           moltype = AA  length = 466
FEATURE                 Location/Qualifiers
REGION                  1..466
                        note = source = /note="Description of Artificial Sequence:
                         Syntheticpolypeptide"
source                  1..466
                        mol_type = protein
                        organism = synthetic construct
SEQUENCE: 96
QGQDRHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH  120
QHLSSRTHGS EDSSGTTNTV AAYNLTWKST NFKTILEWEP KPVNQVYTVQ ISTKSGDWKS  180
KCFYTTDTEC DLTDEIVKDV KQTYLARVFS YPAGNVESTG SAGEPLYENS PEFTPYLETN  240
LGQPTIQSFE QVGTKVNVTV EDERTLVRRN NTFLSLRDVF GKDLIYTLYY WKSSSSGKKT  300
AKTNTNEFLI DVDKGENYCF SVQAVIPSRT VNRKSTDSPV ECMGQEKGEF RENWVNVISD  360
LKKIEDLIQS MHIDATLYTE SDVHPSCKVT AMKCFLLELQ VISLESGDAS IHDTVENLII  420
LANNSLSSNG NVTESGCKEC EELEEKNIKE FLQSFVHIVQ MFINTS                 466

SEQ ID NO: 97           moltype = DNA  length = 1398
FEATURE                 Location/Qualifiers
misc_feature            1..1398
                        note = source = /note="Description of Artificial Sequence:
                         Synthetic21t15-7s sequence"
source                  1..1398
                        mol_type = other DNA
                        organism = synthetic construct
SEQUENCE: 97
caaggtcaag atcgccacat gattagaatg cgtcaactta tagatattgt tgatcagctg  60
aaaaattatg tgaatgactt ggtccctgaa tttctgccag ctccagaaga tgtagagaca  120
aactgtgagt ggtcagcttt ttcctgtttt cagaaggccc aactaaagtc agcaaataca  180
ggaaacaatg aaaggataat caatgtatca attaaaaagc tgaagaggaa accaccttcc  240
acaaatgcag ggagaagaca gaaacacaga ctaacatgcc cttcatgtga ttcttatgag  300
aaaaaaccac ccaaagaatt cctagaaaga ttcaaatcac ttctccaaaa gatgattcat  360
cagcatctgt cctctagaac acacggaagt gaagattcct caggcactac aaatactgtg  420
gcagcatata atttaacttg gaaatcaact aatttcaaga caattttgga gtgggaaccc  480
aaacccgtca atcaagtcta cactgttcaa ataagcacta agtcaggaga ttggaaaagc  540
aaatgctttt acacaacaga cacagagtgt gacctcaccg acgagattgt gaaggatgtg  600
aagcagacgt acttggcacg ggtcttctcc tacccggcag ggaatgtgga gagcaccggt  660
tctgctgggg agcctctgta tgagaactcc ccagagttca caccttacct ggagacaaac  720
ctcggacagc caacaattca gagttttgaa caggtgggaa caaaagtgaa tgtgaccgta  780
gaagatgaac ggactttagt cagaaggaac aacactttcc taagcctccg ggatgttttt  840
ggcaaggact taatttatac actttattat tggaaatctt caagttcagg aaagaaaaca  900
gccaaaacaa acactaatga gtttttgatt gatgtggata aaggagaaaa ctactgtttc  960
agtgttcaag cagtgattcc ctcccgaaca gttaaccgga agagtacaga cagcccggta  1020
gagtgtatgg gccaggagaa aggggaattc agagaaaact gggtgaacgt catcagcgat  1080
ttaaagaaga tcgaagattt aattcagtcc atgcatatcg acgccacttt atacacagaa  1140
tccgacgtgc acccctcttg taaggtgacc gccatgaaat gtttttttact ggagctgcaa  1200
gttatctctt tagagagcgg agacgctagc atccacgaca ccgtggagaa tttaatcatt  1260
ttagccaata actctttatc cagcaacggc aacgtgacag agtccggctg caaggagtgc  1320
gaagagctgg aggagaagaa catcaaggag tttctgcaat cctttgtgca cattgtccag  1380
atgttcatca atacctcc                                                1398

SEQ ID NO: 98           moltype = AA  length = 483
FEATURE                 Location/Qualifiers
REGION                  1..483
                        note = source = /note="Description of Artificial Sequence:
                         Synthetic21t15-7s sequence"
source                  1..483
                        mol_type = protein
                        organism = synthetic construct
SEQUENCE: 98
MGVKVLFALI CIAVAEAQGQ DRHMIRMRQL IDIVDQLKNY VNDLVPEFLP APEDVETNCE  60
WSAFSCFQKA QLKSANTGNN ERIINVSIKK LKRKPPSTNA GRRQKHRLTC PSCDSYEKKP  120
PKEFLERFKS LLQKMIHQHL SSRTHGSEDS SGTTNTVAAY NLTWKSTNFK TILEWEPKPV  180
NQVYTVQIST KSGDWKSKCF YTTDTECDLT DEIVKDVKQT YLARVFSYPA GNVESTGSAG  240
EPLYENSPEF TPYLETNLGQ PTIQSFEQVG TKVNVTVEDE RTLVRRNNTF LSLRDVFGKD  300
LIYTLYYWKS SSSGKKTAKT NTNEFLIDVD KGENYCFSVQ AVIPSRTVNR KSTDSPVECM  360
GQEKGEFREN WVNVISDLKK IEDLIQSMHI DATLYTESDV HPSCKVTAMK CFLLELQVIS  420
LESGDASIHD TVENLIILAN NSLSSNGNVT ESGCKECEEL EEKNIKEFLQ SFVHIVQMFI  480
NTS                                                                483
```

```
SEQ ID NO: 99          moltype = DNA  length = 1449
FEATURE                Location/Qualifiers
misc_feature           1..1449
                       note = source = /note="Description of Artificial Sequence:
                        Synthetic21t15-7s sequence"
source                 1..1449
                       mol_type = other DNA
                       organism = synthetic construct
SEQUENCE: 99
atgggagtga aagttctttt tgcccttatt tgtattgctg tggccgaggc ccaaggtcaa  60
gatcgccaca tgattagaat gcgtcaactt atagatattg ttgatcagct gaaaaattat  120
gtgaatgact tggtccctga atttctgcca gctccagaag atgtagagac aaactgtgag  180
tggtcagctt tttcctgttt tcagaaggcc caactaaagt cagcaaatac aggaaacaat  240
gaaaggataa tcaatgtatc aattaaaaag ctgaagagga aaccaccttc cacaaatgca  300
gggagaagac agaaacacag actaacatgc ccttcatgtg attcttatga gaaaaaacca  360
cccaaagaat tcctagaaag attcaaatca cttctccaaa agatgattca tcagcatctg  420
tcctctagaa cacacggaag tgaagattcc tcaggcacta caaatactgt ggcagcatat  480
aatttaactt ggaaatcaac taatttcaag acaattttgg agtgggaacc caaacccgtc  540
aatcaagtct acactgttca aataagcact aagtcaggag attggaaaag caaatgcttt  600
tacacaacag acacagagtg tgacctcacc gacgagattg tgaaggatgt gaagcagacg  660
tacttggcac gggtcttctc ctacccggca gggaatgtgg agagcaccgg ttctgctggg  720
gagcctctgt atgagaactc cccagagttc acaccttacc tggagacaaa cctcggacag  780
ccaacaattc agagttttga acaggtggga acaaaagtga atgtgaccgt agaagatgaa  840
cggactttag tcagaaggaa caacactttc ctaagcctcc gggatgtttt tggcaaggac  900
ttaatttata cactttatta ttggaaatct tcaagttcag gaaagaaaac agccaaaaca  960
aacactaatg agtttttgat tgatgtggat aaaggagaaa actactgttt cagtgttcaa  1020
gcagtgattc cctcccgaac agttaaccgg aagagtacag acagcccggt agagtgtatg  1080
ggccaggaga aaggggaatt cagagaaaac tgggtgaacg tcatcagcga tttaaagaag  1140
atcgaagatt taattcagtc catgcatatc gacgccactt tatacacaga atccgacgtg  1200
cacccctctt gtaaggtgac cgccatgaaa tgtttttttac tggagctgca agttatctct  1260
ttagagagcg gagacgctag catccacgac accgtggaga atttaatcat tttagccaat  1320
aactctttat ccagcaacgg caacgtgaca gagtccggct gcaaggagtg cgaagagctg  1380
gaggagaaga acatcaagga gtttctgcaa tcctttgtgc acattgtcca gatgttcatc  1440
aatacctcc                                                          1449

SEQ ID NO: 100         moltype = AA  length = 217
FEATURE                Location/Qualifiers
REGION                 1..217
                       note = source = /note="Description of Artificial Sequence:
                        Synthetic21t15-7s sequence"
source                 1..217
                       mol_type = protein
                       organism = synthetic construct
SEQUENCE: 100
DCDIEGKDGK QYESVLMVSI DQLLDSMKEI GSNCLNNEFN FFKRHICDAN KEGMFLFRAA  60
RKLRQFLKMN STGDFDLHLL KVSEGTTILL NCTGQVKGRK PAALGEAQPT KSLEENKSLK  120
EQKKLNDLCF LKRLLQEIKT CWNKILMGTK EHITCPPPMS VEHADIWVKS YSLYSRERYI  180
CNSGFKRKAG TSSLTECVLN KATNVAHWTT PSLKCIR                            217

SEQ ID NO: 101         moltype = DNA  length = 651
FEATURE                Location/Qualifiers
misc_feature           1..651
                       note = source = /note="Description of Artificial Sequence:
                        Synthetic21t15-7s sequence"
source                 1..651
                       mol_type = other DNA
                       organism = synthetic construct
SEQUENCE: 101
gattgtgata ttgaaggtaa agatggcaaa caatatgaga gtgttctaat ggtcagcatc  60
gatcaattat tggacagcat gaaagaaatt ggtagcaatt gcctgaataa tgaatttaac  120
ttttttaaaa gacatatctg tgatgctaat aaggaaggta tgtttttatt ccgtgctgct  180
cgcaagttga ggcaatttct taaaatgaat agcactggtg attttgatct ccacttatta  240
aaagtttcag aaggcacaac aatactgttg aactgcactg gccaggttaa aggaagaaaa  300
ccagctgccc tgggtgaagc ccaaccaaca aagagtttgg aagaaaataa atctttaaag  360
gaacagaaaa aactgaatga cttgtgtttc ctaaagagac tattacaaga gataaaaact  420
tgttggaata aaattttgat gggcactaaa gaacacatca cgtgccctcc ccccatgtcc  480
gtggaacacg cagacatctg ggtcaagagc tacagcttgt actccaggga gcggtacatt  540
tgtaactctg gtttcaagcg taaagccggc acgtccagcc tgacggagtg cgtgttgaac  600
aaggccacga atgtcgccca ctggacaacc cccagtctca aatgcattag a           651

SEQ ID NO: 102         moltype = AA  length = 234
FEATURE                Location/Qualifiers
REGION                 1..234
                       note = source = /note="Description of Artificial Sequence:
                        Synthetic21t15-7s sequence"
source                 1..234
                       mol_type = protein
                       organism = synthetic construct
SEQUENCE: 102
```

-continued

```
MGVKVLFALI CIAVAEADCD IEGKDGKQYE SVLMVSIDQL LDSMKEIGSN CLNNEFNFFK  60
RHICDANKEG MFLFRAARKL RQFLKMNSTG DFDLHLLKVS EGTTILLNCT GQVKGRKPAA  120
LGEAQPTKSL EENKSLKEQK KLNDLCFLKR LLQEIKTCWN KILMGTKEHI TCPPPMSVEH  180
ADIWVKSYSL YSRERYICNS GFKRKAGTSS LTECVLNKAT NVAHWTTPSL KCIR        234

SEQ ID NO: 103         moltype = DNA  length = 702
FEATURE                Location/Qualifiers
misc_feature           1..702
                       note = source = /note="Description of Artificial Sequence:
                        Synthetic21t15-7s sequence"
source                 1..702
                       mol_type = other DNA
                       organism = synthetic construct
SEQUENCE: 103
atgggagtga aagttctttt tgcccttatt tgtattgctg tggccgaggc cgattgtgat  60
attgaaggta aagatggcaa acaatatgag agtgttctaa tggtcagcat cgatcaatta  120
ttggacagca tgaaagaaat tggtagcaat tgcctgaata atgaatttaa ctttttttaaa  180
agacatatct gtgatgctaa taaggaaggt atgtttttat tccgtgctgc tcgcaagttg  240
aggcaatttc ttaaaatgaa tagcactggt gattttgatc tccacttatt aaaagtttca  300
gaaggcacaa caatactgtt gaactgcact ggccaggtta aaggaagaaa accagctgcc  360
ctgggtgaag cccaaccaac aaagagtttg gaagaaaata aatctttaaa ggaacagaaa  420
aaactgaatg acttgtgttt cctaaagaga ctattacaag agataaaaac ttgttggaat  480
aaaattttga tgggcactaa agaacacatc acgtgccctc cccccatgtc cgtggaacac  540
gcagacatct gggtcaagag ctacagcttg tactccaggg agcggtacat ttgtaactct  600
ggtttcaagc gtaaagccgg cacgtccagc ctgacggagt gcgtgttgaa caaggccacg  660
aatgtcgccc actggacaac ccccagtctc aaatgcatta ga                    702

SEQ ID NO: 104         moltype = AA  length = 485
FEATURE                Location/Qualifiers
REGION                 1..485
                       note = source = /note="Description of Artificial Sequence:
                        Synthetic7t15-21s sequence"
source                 1..485
                       mol_type = protein
                       organism = synthetic construct
SEQUENCE: 104
DCDIEGKDGK QYESVLMVSI DQLLDSMKEI GSNCLNNEFN FFKRHICDAN KEGMFLFRAA  60
RKLRQFLKMN STGDFDLHLL KVSEGTTILL NCTGQVKGRK PAALGEAQPT KSLEENKSLK  120
EQKKLNDLCF LKRLLQEIKT CWNKILMGTK EHSGTTNTVA AYNLTWKSTN FKTILEWEPK  180
PVNQVYTVQI STKSGDWKSK CFYTTDTECD LTDEIVKDVK QTYLARVFSY PAGNVESTGS  240
AGEPLYENSP EFTPYLETNL GQPTIQSFEQ VGTKVNVTVE DERTLVRRNN TFLSLRDVFG  300
KDLIYTLYYW KSSSSGKKTA KTNTNEFLID VDKGENYCFS VQAVIPSRTV NRKSTDSPVE  360
CMGQEKGEFR ENWVNVISDL KKIEDLIQSM HIDATLYTES DVHPSCKVTA MKCFLLELQV  420
ISLESGDASI HDTVENLIIL ANNSLSSNGN VTESGCKECE ELEEKNIKEF LQSFVHIVQM  480
FINTS                                                             485

SEQ ID NO: 105         moltype = DNA  length = 1455
FEATURE                Location/Qualifiers
misc_feature           1..1455
                       note = source = /note="Description of Artificial Sequence:
                        Synthetic7t15-21s sequence"
source                 1..1455
                       mol_type = other DNA
                       organism = synthetic construct
SEQUENCE: 105
gattgcgaca tcgagggcaa ggacggcaag cagtacgaga gcgtgctgat ggtgtccatc  60
gaccagctgc tggacagcat gaaggagatc ggctccaact gcctcaacaa cgagttcaac  120
ttcttcaagc ggcacatctg cgacgccaac aaggagggca tgttcctgtt cagggccgcc  180
aggaaactgc ggcagttcct gaagatgaac tccaccggcg acttcgacct gcacctgctg  240
aaggtgtccg agggcaccac catcctgctg aactgcaccg gacaggtgaa gggccggaaa  300
cctgctgctc tgggagaggc ccaacccacc aagagcctgg aggagaacaa gtccctgaag  360
gagcagaaga agctgaacga cctgtgcttc ctgaagaggc tgctgcagga gatcaagacc  420
tgctggaaca agatcctgat gggcaccaag gagcatagcg gcacaaccaa cacagtcgct  480
gcctataacc tcacttggaa gagcaccaac ttcaaaacca tcctcgaatg ggaacccaaa  540
cccgttaacc aagtttacac cgtgcagatc agcaccaagt ccggcgactg gaagtccaaa  600
tgtttctata ccaccgacac cgagtgcgat ctcaccgatg agatcgtgaa agatgtgaaa  660
cagacctacc tcgcccgggt gtttagctac cccgccggca atgtggagag cactggttcc  720
gctggcgagc ctttatacga gaacagcccc gaatttaccc cttacctcga gaccaattta  780
ggacagccca ccatccaaag ctttgagcaa gttggcacaa aggtgaatgt gacagtggag  840
gacgagcgga ctttagtgcg gcggaacaac acctttctca gcctccggga tgtgttcggc  900
aaagatttaa tctacacact gtattactgg aagtcctctt cctccggcaa gaagacagct  960
aaaaccaaca caaacgagtt tttaatcgac gtggataaag gcgaaaacta ctgtttcagc  1020
gtgcaagctg tgatcccctc ccggaccgtg aataggaaaa gcaccgatag ccccgttgag  1080
tgcatgggcc aagaaaaggg cgagttccgg gagaactggg tgaacgtcat cagcgattta  1140
aagaagatcg aagatttaat tcagtccatg catatcgacg ccactttata cacagaatcc  1200
gacgtgcacc cctcttgtaa ggtgaccgcc atgaaatgtt ttttactgga gctgcaagtt  1260
atctctttag agagcggaga cgctagcatc cacgacaccg tggagaattt aatcatttta  1320
gccaataact ctttatccag caacggcaac gtgacagagt ccggctgcaa ggagtgcgaa  1380
gagctggagg agaagaacat caaggagttt ctgcaatcct ttgtgcacat tgtccagatg  1440
```

```
ttcatcaata cctcc                                                    1455

SEQ ID NO: 106         moltype = AA  length = 503
FEATURE                Location/Qualifiers
REGION                 1..503
                       note = source = /note="Description of Artificial Sequence:
                        Synthetic7t15-21s sequence"
source                 1..503
                       mol_type = protein
                       organism = synthetic construct
SEQUENCE: 106
MKWVTFISLL FLFSSAYSDC DIEGKDGKQY ESVLMVSIDQ LLDSMKEIGS NCLNNEFNFF  60
KRHICDANKE GMFLFRAARK LRQFLKMNST GDFDLHLLKV SEGTTILLNC TGQVKGRKPA  120
ALGEAQPTKS LEENKSLKEQ KKLNDLCFLK RLLQEIKTCW NKILMGTKEH SGTTNTVAAY  180
NLTWKSTNFK TILEWEPKPV NQVYTVQIST KSGDWKSKCF YTTDTECDLT DEIVKDVKQT  240
YLARVFSYPA GNVESTGSAG EPLYENSPEF TPYLETNLGQ PTIQSFEQVG TKVNVTVEDE  300
RTLVRRNNTF LSLRDVFGKD LIYTLYYWKS SSSGKKTAKT NTNEFLIDVD KGENYCFSVQ  360
AVIPSRTVNR KSTDSPVECM GQEKGEFREN WVNVISDLKK IEDLIQSMHI DATLYTESDV  420
HPSCKVTAMK CFLLELQVIS LESGDASIHD TVENLIILAN NSLSSNGNVT ESGCKECEEL  480
EEKNIKEFLQ SFVHIVQMFI NTS                                           503

SEQ ID NO: 107         moltype = DNA  length = 1508
FEATURE                Location/Qualifiers
misc_feature           1..1508
                       note = source = /note="Description of Artificial Sequence:
                        Synthetic7t15-21s sequence"
source                 1..1508
                       mol_type = other DNA
                       organism = synthetic construct
SEQUENCE: 107
atgaagtggg tgaccttcat cagcctgctg ttcctgttct ccagcgccta ctccgattgc  60
gacatcgagg gcaaggacgg caagcagtac gagagcgtgc tgatggtgtc catcgaccag  120
ctgctggaca gcatgaagga gatcggctcc aactgcctca acaacgagtt caacttcttc  180
aagcggcaca tctgcgacgc caacaaggag ggcatgttcc tgttcagggc cgccaggaaa  240
ctgcggcagt tcctgaagat gaactccacc ggcgacttcg acctgcacct gctgaaggtg  300
tccgagggca ccaccatcct gctgaactgc accggacagg tgaagggccg gaaacctgct  360
gctctgggag aggcccaacc caccaagagc ctggaggaga acaagtccct gaaggagcag  420
aagaagctga acgacctgtg cttcctgaag aggctgctgc aggagatcaa gacctgctgg  480
aacaagatcc tgatgggcac caaggagcat agcggcacaa ccaacacagt cgctgcctat  540
aacctcactt ggaagagcac caacttcaaa accatcctcg aatgggaacc caaacccgtt  600
aaccaagttt acaccgtgca gatcagcacc aagtccggcg actggaagtc caaatgtttc  660
tataccaccg acaccgagtg cgatctcacc gatgagatcg tgaaagatgt gaaacagacc  720
tacctcgccc gggtgtttag ctaccccgcc ggcaatgtgg agagcactgg ttccgctggc  780
gagcctttat acgagaacag ccccgaattt accccttacc tcgagaccaa tttaggacag  840
cccaccatcc aaagctttga gcaagttggc acaaaggtga atgtgacagt ggaggacgag  900
cggactttag tgcggcggaa caacaccttt ctcagcctcc gggatgtgtt cggcaaagat  960
ttaatctaca cactgtatta ctggaagtcc tcttcctccg gcaagaagac agctaaaacc  1020
aacacaaacg agtttttaat cgacgtggat aaaggcgaaa actactgttt cagcgtgcaa  1080
gctgtgatcc cctcccggac cgtgaatagg aaaagcaccg atagccccgt tgagtgcatg  1140
ggccaagaaa agggcgagtt ccgggagaac tgggtgaacg tcatcagcga tttaaagaag  1200
atcgaagatt taattcagtc catgcatatc gacgccactt tatacacaga atccgacgtg  1260
cacccctctt gtaaggtgac cgccatgaaa tgtttttttac tggagctgca agttatctct  1320
ttagagagcg gagacgctag catccacgac accgtggaga atttaatcat tttagccaat  1380
aactctttat ccagcaacgg caacgtgaca gagtccggct gcaaggagtg cgaagagctg  1440
gaggagaaga acatcaagga gtttctgcaa tcctttgtgc acattgtcca gatgttcatc  1500
aatacctc                                                            1508

SEQ ID NO: 108         moltype = AA  length = 198
FEATURE                Location/Qualifiers
REGION                 1..198
                       note = source = /note="Description of Artificial Sequence:
                        Synthetic7t15-21s sequence"
source                 1..198
                       mol_type = protein
                       organism = synthetic construct
SEQUENCE: 108
QGQDRHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH  120
QHLSSRTHGS EDSITCPPPM SVEHADIWVK SYSLYSRERY ICNSGFKRKA GTSSLTECVL  180
NKATNVAHWT TPSLKCIR                                                 198

SEQ ID NO: 109         moltype = DNA  length = 594
FEATURE                Location/Qualifiers
misc_feature           1..594
                       note = source = /note="Description of Artificial Sequence:
                        Synthetic7t15-21s sequence"
source                 1..594
                       mol_type = other DNA
                       organism = synthetic construct
```

SEQUENCE: 109
cagggccagg acaggcacat gatccggatg aggcagctca tcgacatcgt cgaccagctg 60
aagaactacg tgaacgacct ggtgcccgag tttctgcctg cccccgagga cgtggagacc 120
aactgcgagt ggtccgcctt ctcctgcttt cagaaggccc agctgaagtc cgccaacacc 180
ggcaacaacg agcggatcat caacgtgagc atcaagaagc tgaagcggaa gcctccctcc 240
acaaacgccg gcaggaggca gaagcacagg ctgacctgcc ccagctgtga ctcctacgag 300
aagaagcccc ccaaggagtt cctggagagg ttcaagtccc tgctgcagaa gatgatccat 360
cagcacctgt cctccaggac ccacggctcc gaggactcca ttacatgccc ccctcccatg 420
agcgtggagc acgccgacat ctgggtgaag agctatagcc tctacagccg ggagaggtat 480
atctgtaaca gcggcttcaa gaggaaggcc ggcaccagca gcctcaccga gtgcgtgctg 540
aataaggcta ccaacgtggc tcactggaca acaccctctt taaagtgcat ccgg 594

SEQ ID NO: 110 moltype = AA length = 216
FEATURE Location/Qualifiers
REGION 1..216
note = source = /note="Description of Artificial Sequence: Synthetic7t15-21s sequence"
source 1..216
mol_type = protein
organism = synthetic construct
SEQUENCE: 110
MKWVTFISLL FLFSSAYSQG QDRHMIRMRQ LIDIVDQLKN YVNDLVPEFL PAPEDVETNC 60
EWSAFSCFQK AQLKSANTGN NERIINVSIK KLKRKPPSTN AGRRQKHRLT CPSCDSYEKK 120
PPKEFLERFK SLLQKMIHQH LSSRTHGSED SITCPPPMSV EHADIWVKSY SLYSRERYIC 180
NSGFKRKAGT SSLTECVLNK ATNVAHWTTP SLKCIR 216

SEQ ID NO: 111 moltype = DNA length = 648
FEATURE Location/Qualifiers
misc_feature 1..648
note = source = /note="Description of Artificial Sequence: Synthetic7t15-21s sequence"
source 1..648
mol_type = other DNA
organism = synthetic construct
SEQUENCE: 111
atgaagtggg tgaccttcat cagcctgctg ttcctgttct ccagcgccta ctcccagggc 60
caggacaggc acatgatccg gatgaggcag ctcatcgaca tcgtcgacca gctgaagaac 120
tacgtgaacg acctggtgcc cgagtttctg cctgcccccg aggacgtgga gaccaactgc 180
gagtggtccg ccttctcctg ctttcagaag gcccagctga agtccgccaa caccggcaac 240
aacgagcgga tcatcaacgt gagcatcaag aagctgaagc ggaagcctcc ctccacaaac 300
gccggcagga ggcagaagca caggctgacc tgccccagct gtgactccta cgagaagaag 360
ccccccaagg agttcctgga gaggttcaag tccctgctgc agaagatgat ccatcagcac 420
ctgtcctcca ggacccacgg ctccgaggac tccattacat gcccccctcc catgagcgtg 480
gagcacgccg acatctgggt gaagagctat agcctctaca gccgggagag gtatatctgt 540
aacagcggct tcaagaggaa ggccggcacc agcagcctca ccgagtgcgt gctgaataag 600
gctaccaacg tggctcactg gacaacaccc tctttaaagt gcatccgg 648

SEQ ID NO: 112 moltype = AA length = 108
FEATURE Location/Qualifiers
REGION 1..108
note = source = /note="Description of Artificial Sequence: SyntheticCD16 LC sequence"
source 1..108
mol_type = protein
organism = synthetic construct
SEQUENCE: 112
SELTQDPAVS VALGQTVRIT CQGDSLRSYY ASWYQQKPGQ APVLVIYGKN NRPSGIPDRF 60
SGSSSGNTAS LTITGAQAED EADYYCNSRD SSGNHVVFGG GTKLTVGH 108

SEQ ID NO: 113 moltype = DNA length = 324
FEATURE Location/Qualifiers
misc_feature 1..324
note = source = /note="Description of Artificial Sequence: SyntheticCD16 LC sequence"
source 1..324
mol_type = other DNA
organism = synthetic construct
SEQUENCE: 113
tccgagctga cccaggaccc tgctgtgtcc gtggctctgg gccagaccgt gaggatcacc 60
tgccagggcg actccctgag gtcctactac gcctcctggt accagcagaa gcccggccag 120
gctcctgtgc tggtgatcta cggcaagaac aacaggccct ccggcatccc tgacaggttc 180
tccggatcct cctccggcaa caccgcctcc ctgaccatca caggcgctca ggccgaggac 240
gaggctgact actactgcaa ctccagggac tcctccggca accatgtggt gttcggcggc 300
ggcaccaagc tgaccgtggg ccat 324

SEQ ID NO: 114 moltype = AA length = 117
FEATURE Location/Qualifiers
REGION 1..117
note = source = /note="Description of Artificial Sequence:

-continued

```
                         SyntheticCD16 HC sequence"
source                  1..117
                        mol_type = protein
                        organism = synthetic construct
SEQUENCE: 114
EVQLVESGGG VVRPGGSLRL SCAASGFTFD DYGMSWVRQA PGKGLEWVSG INWNGGSTGY  60
ADSVKGRFTI SRDNAKNSLY LQMNSLRAED TAVYYCARGR SLLFDYWGQG TLVTVSR     117

SEQ ID NO: 115          moltype = DNA  length = 351
FEATURE                 Location/Qualifiers
misc_feature            1..351
                        note = source = /note="Description of Artificial Sequence:
                         SyntheticCD16 HC sequence"
source                  1..351
                        mol_type = other DNA
                        organism = synthetic construct
SEQUENCE: 115
gaggtgcagc tggtggagtc cggaggagga gtggtgaggc ctggaggctc cctgaggctg  60
agctgtgctg cctccggctt caccttcgac gactacggca tgtcctgggt gaggcaggct  120
cctggaaagg gcctggagtg ggtgtccggc atcaactgga acggcggatc caccggctac  180
gccgattccg tgaagggcag gttcaccatc agcagggaca acgccaagaa ctccctgtac  240
ctgcagatga actccctgag ggccgaggac accgccgtgt actactgcgc caggggcagg  300
tccctgctgt tcgactactg gggacagggc accctggtga ccgtgtccag g           351

SEQ ID NO: 116          moltype = AA  length = 490
FEATURE                 Location/Qualifiers
REGION                  1..490
                        note = source = /note="Description of Artificial Sequence:
                         Synthetic18t15-12s16 sequence"
source                  1..490
                        mol_type = protein
                        organism = synthetic construct
SEQUENCE: 116
YFGKLESKLS VIRNLNDQVL FIDQGNRPLF EDMTDSDCRD NAPRTIFIIS MYKDSQPRGM  60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNEDSGT TNTVAAYNLT WKSTNFKTIL  180
EWEPKPVNQV YTVQISTKSG DWKSKCFYTT DTECDLTDEI VKDVKQTYLA RVFSYPAGNV  240
ESTGSAGEPL YENSPEFTPY LETNLGQPTI QSFEQVGTKV NVTVEDERTL VRRNNTFLSL  300
RDVFGKDLIY TLYYWKSSSS GKKTAKTNTN EFLIDVDKGE NYCFSVQAVI PSRTVNRKST  360
DSPVECMGQE KGEFRENWVN VISDLKKIED LIQSMHIDAT LYTESDVHPS CKVTAMKCFL  420
LELQVISLES GDASIHDTVE NLIILANNSL SSNGNVTESG CKECEELEEK NIKEFLQSFV  480
HIVQMFINTS                                                        490

SEQ ID NO: 117          moltype = DNA  length = 1470
FEATURE                 Location/Qualifiers
misc_feature            1..1470
                        note = source = /note="Description of Artificial Sequence:
                         Synthetic18t15-12s16 sequence"
source                  1..1470
                        mol_type = other DNA
                        organism = synthetic construct
SEQUENCE: 117
tacttcggca aactggaatc caagctgagc gtgatccgga atttaaacga ccaagttctg  60
tttatcgatc aaggtaaccg gcctctgttc gaggacatga ccgactccga ttgccgggac  120
aatgcccccc ggaccatctt cattatctcc atgtacaagg acagccagcc ccggggcatg  180
gctgtgacaa ttagcgtgaa gtgtgagaaa atcagcactt tatcttgtga gaacaagatc  240
atctccttta aggaaatgaa cccccccgat aacatcaagg acaccaagtc cgatatcatc  300
ttcttccagc ggtccgtgcc cggtcacgat aacaagatgc agttcgaatc ctcctcctac  360
gagggctact ttttagcttg tgaaaaggag agggatttat tcaagctgat cctcaagaag  420
gaggacgagc tgggcgatcg ttccatcatg ttcaccgtcc aaaacgagga tagcggcaca  480
accaacacag tcgctgccta taacctcact tggaagagca ccaacttcaa aaccatcctc  540
gaatgggaac ccaaacccgt taaccaagtt tacaccgtgc agatcagcac caagtccggc  600
gactggaagt ccaaatgttt ctataccacc gacaccgagt gcgatctcac cgatgagatc  660
gtgaaagatg tgaaacagac ctacctcgcc cgggtgttta gctaccccgc cggcaatgtg  720
gagagcactg gttccgctgg cgagccttta tacgagaaca gccccgaatt taccccttac  780
ctcgagacca atttaggaca gcccaccatc caaagctttg agcaagttgg cacaaaggtg  840
aatgtgacag tggaggacga gcggacttta gtgcggcgga acaacacctt tctcagcctc  900
cgggatgtgt tcggcaaaga tttaatctac acactgtatt actggaagtc ctcttcctcc  960
ggcaagaaga cagctaaaac caacacaaac gagtttttaa tcgacgtgga taaaggcgaa  1020
aactactgtt tcagcgtgca agctgtgatc cccctcccgga ccgtgaatag gaaaagcacc  1080
gatagccccg ttgagtgcat gggccaagaa aagggcgagt tccgggagaa ctgggtgaac  1140
gtcatcagcg atttaaagaa gatcgaagat ttaattcagt ccatgcatat cgacgccact  1200
ttatacacag aatccgacgt gcacccctct tgtaaggtga ccgccatgaa atgtttttta  1260
ctggagctgc aagttatctc tttagagagc ggagacgcta gcatccacga caccgtggag  1320
aatttaatca ttttagccaa taactcttta tccagcaacg gcaacgtgac agagtccggc  1380
tgcaaggagt gcgaagagct ggaggagaag aacatcaagg agtttctgca atcctttgtg  1440
cacattgtcc agatgttcat caatacctcc                                  1470

SEQ ID NO: 118          moltype = AA  length = 508
```

```
FEATURE                Location/Qualifiers
REGION                 1..508
                       note = source = /note="Description of Artificial Sequence:
                        Synthetic18t15-12s16 sequence"
source                 1..508
                       mol_type = protein
                       organism = synthetic construct
SEQUENCE: 118
MKWVTFISLL FLFSSAYSYF GKLESKLSVI RNLNDQVLFI DQGNRPLFED MTDSDCRDNA  60
PRTIFIISMY KDSQPRGMAV TISVKCEKIS TLSCENKIIS FKEMNPPDNI KDTKSDIIFF  120
QRSVPGHDNK MQFESSSYEG YFLACEKERD LFKLILKKED ELGDRSIMFT VQNEDSGTTN  180
TVAAYNLTWK STNFKTILEW EPKPVNQVYT VQISTKSGDW KSKCFYTTDT ECDLTDEIVK  240
DVKQTYLARV FSYPAGNVES TGSAGEPLYE NSPEFTPYLE TNLGQPTIQS FEQVGTKVNV  300
TVEDERTLVR RNNTFLSLRD VFGKDLIYTL YYWKSSSSGK KTAKTNTNEF LIDVDKGENY  360
CFSVQAVIPS RTVNRKSTDS PVECMGQEKG EFRENWVNVI SDLKKIEDLI QSMHIDATLY  420
TESDVHPSCK VTAMKCFLLE LQVISLESGD ASIHDTVENL IILANNSLSS NGNVTESGCK  480
ECEELEEKNI KEFLQSFVHI VQMFINTS                                    508

SEQ ID NO: 119         moltype = DNA  length = 1524
FEATURE                Location/Qualifiers
misc_feature           1..1524
                       note = source = /note="Description of Artificial Sequence:
                        Synthetic18t15-12s16 sequence"
source                 1..1524
                       mol_type = other DNA
                       organism = synthetic construct
SEQUENCE: 119
atgaagtggg tcacatttat ctctttactg ttcctcttct ccagcgccta cagctacttc  60
ggcaaactgg aatccaagct gagcgtgatc cggaatttaa acgaccaagt tctgtttatc  120
gatcaaggta accggcctct gttcgaggac atgaccgact ccgattgccg ggacaatgcc  180
ccccggacca tcttcattat ctccatgtac aaggacagcc agccccgggg catggctgtg  240
acaattagcg tgaagtgtga gaaaatcagc actttatctt gtgagaacaa gatcatctcc  300
tttaaggaaa tgaacccccc cgataacatc aaggacacca agtccgatat catcttcttc  360
cagcggtccg tgcccggtca cgataacaag atgcagttcg aatcctcctc ctacgagggc  420
tactttttag cttgtgaaaa ggagagggat ttattcaagc tgatcctcaa gaaggaggac  480
gagctgggcg atcgttccat catgttcacc gtccaaaacg aggatagcgg cacaaccaac  540
acagtcgctg cctataacct cacttggaag agcaccaact tcaaaaccat cctcgaatgg  600
gaacccaaac ccgttaacca agtttacacc gtgcagatca gcaccaagtc cggcgactgg  660
aagtccaaat gtttctatac caccgacacc gagtgcgatc tcaccgatga gatcgtgaaa  720
gatgtgaaac agacctacct cgcccgggtg tttagctacc ccgccggcaa tgtggagagc  780
actggttccg ctggcgagcc tttatacgag aacagccccg aatttacccc ttacctcgag  840
accaatttag gacagcccac catccaaagc tttgagcaag ttggcacaaa ggtgaatgtg  900
acagtggagg acgagcggac tttagtgcgg cggaacaaca cctttctcag cctccgggat  960
gtgttcggca aagatttaat ctacacactg tattactgga agtcctcttc ctccggcaag  1020
aagacagcta aaaccaacac aaacgagttt ttaatcgacg tggataaagg cgaaaactac  1080
tgtttcagcg tgcaagctgt gatcccctcc cggaccgtga ataggaaaag caccgatagc  1140
cccgttgagt gcatgggcca agaaaagggc gagttccggg agaactgggt gaacgtcatc  1200
agcgatttaa agaagatcga agatttaatt cagtccatgc atatcgacgc cactttatac  1260
acagaatccg acgtgcaccc ctcttgtaag gtgaccgcca tgaaatgttt tttactggag  1320
ctgcaagtta tctctttaga gagcggagac gctagcatcc acgacaccgt ggagaattta  1380
atcattttag ccaataactc tttatccagc aacggcaacg tgacagagtc cggctgcaag  1440
gagtgcgaag agctggagga gaagaacatc aaggagtttc tgcaatcctt tgtgcacatt  1500
gtccagatgt tcatcaatac ctcc                                        1524

SEQ ID NO: 120         moltype = AA  length = 823
FEATURE                Location/Qualifiers
REGION                 1..823
                       note = source = /note="Description of Artificial Sequence:
                        Synthetic18t15-12s16 sequence"
source                 1..823
                       mol_type = protein
                       organism = synthetic construct
SEQUENCE: 120
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRNLPVATPD PGMFPCLHHS QNLLRAVSNM LQKARQTLEF  360
YPCTSEEIDH EDITKDKTST VEACLPLELT KNESCLNSRE TSFITNGSCL ASRKTSFMMA  420
LCLSSIYEDL KMYQVEFKTM NAKLLMDPKR QIFLDQNMLA VIDELMQALN FNSETVPQKS  480
SLEEPDFYKT KIKLCILLHA FRIRAVTIDR VMSYLNASIT CPPPMSVEHA DIWVKSYSLY  540
SRERYICNSG FKRKAGTSSL TECVLNKATN VAHWTTPSLK CIRSELTQDP AVSVALGQTV  600
RITCQGDSLR SYYASWYQQK PGQAPVLVIY GKNNRPSGIP DRFSGSSSGN TASLTITGAQ  660
AEDEADYYCN SRDSSGNHVV FGGGTKLTVG HGGGGSGGGG SGGGGSEVQL VESGGGVVRP  720
GGSLRLSCAA SGFTFDDYGM SWVRQAPGKG LEWVSGINWN GGSTGYADSV KGRFTISRDN  780
AKNSLYLQMN SLRAEDTAVY YCARGRSLLF DYWGQGTLVT VSR                   823

SEQ ID NO: 121         moltype = DNA  length = 2469
```

```
FEATURE               Location/Qualifiers
misc_feature          1..2469
                      note = source = /note="Description of Artificial Sequence:
                       Synthetic18t15-12s16 sequence"
source                1..2469
                      mol_type = other DNA
                      organism = synthetic construct
SEQUENCE: 121
atttgggaac tgaagaagga cgtctacgtg gtcgaactgg actggtatcc cgatgctccc  60
ggcgaaatgg tggtgctcac ttgtgacacc cccgaagaag acggcatcac ttggaccctc  120
gatcagagca gcgaggtgct gggctccgga aagaccctca caatccaagt taaggagttc  180
ggagacgctg gccaatacac atgccacaag ggaggcgagg tgctcagcca ttccttatta  240
ttattacaca agaaggaaga cggaatctgg tccaccgaca ttttaaaaga tcagaaggag  300
cccaagaata agaccttttt aaggtgtgag gccaaaaact acagcggtcg tttcacttgt  360
tggtggctga ccaccatttc caccgattta accttctccg tgaaaagcag ccggggaagc  420
tccgaccctc aaggtgtgac atgtggagcc gctaccctca gcgctgagag ggttcgtggc  480
gataacaagg aatacgagta cagcgtggag tgccaagaag atagcgcttg tcccgctgcc  540
gaagaatctt tacccattga ggtgatggtg gacgccgtgc acaaactcaa gtacgagaac  600
tacacctcct ccttctttat ccgggacatc attaagcccg atcctcctaa gaatttacag  660
ctgaagcctc tcaaaaatag ccggcaagtt gaggtctctt gggaatatcc cgacacttgg  720
agcacacccc acagctactt ctctttaacc ttttgtgtgc aagttcaagg taaaagcaag  780
cgggagaaga aagaccgggt gtttaccgac aaaaccagcg ccaccgtcat ctgtcggaag  840
aacgcctcca tcagcgtgag ggctcaagat cgttattact ccagcagctg gtccgagtgg  900
gccagcgtgc cttgttccgg cggtggagga tccggaggag gtggctccgg cggcggagga  960
tctcgtaacc tccccgtggc tacccccgat cccggaatgt tcccttgttt acaccacagc  1020
cagaatttac tgagggccgt gagcaacatg ctgcagaaag ctaggcagac tttagaattt  1080
taccettgca ccagcgagga gatcgaccat gaagatatca ccaaggacaa gacatccacc  1140
gtggaggctt gtttacctct ggagctgaca aagaacgagt cttgtctcaa ctctcgtgaa  1200
accagcttca tcacaaatgg ctcttgttta gcttcccgga agacctcctt tatgatggct  1260
ttatgcctca gctccatcta cgaggattta aagatgtacc aagtggagtt caagaccatg  1320
aacgccaagc tgctcatgga ccctaaacgg cagatctttt tagaccagaa catgctggct  1380
gtgattgatg agctgatgca agctttaaac ttcaactccg agaccgtccc tcagaagtcc  1440
tccctcgagg agcccgattt ttacaagaca aagatcaaac tgtgcatttt actccacgcc  1500
tttaggatcc gggccgtgac cattgaccgg gtcatgagct atttaaacgc cagcattaca  1560
tgccccccctc ccatgagcgt ggagcacgcc gacatctggg tgaagagcta tagcctctac  1620
agccgggaga ggtatatctg taacagcggc ttcaagagga aggccggcac cagcagcctc  1680
accgagtgcg tgctgaataa ggctaccaac gtggctcact ggacaacacc ctctttaaag  1740
tgcatccggt ccgagctgac ccaggaccct gctgtgtccg tggctctggg ccagaccgtg  1800
aggatcacct gccagggcga ctccctgagg tcctactacg cctcctggta ccagcagaag  1860
cccggccagg ctcctgtgct ggtgatctac ggcaagaaca acaggccctc cggcatccct  1920
gacaggttct ccggatcctc ctccggcaac accgcctccc tgaccatcac aggcgctcag  1980
gccgaggacg aggctgacta ctactgcaac tccagggact cctccggcaa ccatgtggtg  2040
ttcggcggcg gcaccaagct gaccgtgggc catggcggcg gcggctccgg aggcggcggc  2100
agcggcggag gaggatccga ggtgcagctg gtggagtccg gaggaggagt ggtgaggcct  2160
ggaggctccc tgaggctgag ctgtgctgcc tccggcttca ccttcgacga ctacggcatg  2220
tcctgggtga ggcaggctcc tggaaagggc ctggagtggg tgtccggcat caactggaac  2280
ggcggatcca ccggctacgc cgattccgtg aagggcaggt tcaccatcag cagggacaac  2340
gccaagaact ccctgtacct gcagatgaac tccctgaggg ccgaggacac cgccgtgtac  2400
tactgcgcca ggggcaggtc cctgctgttc gactactggg gacagggcac cctggtgacc  2460
gtgtccagg                                                          2469

SEQ ID NO: 122        moltype = AA  length = 841
FEATURE               Location/Qualifiers
REGION                1..841
                      note = source = /note="Description of Artificial Sequence:
                       Synthetic18t15-12s16 sequence"
source                1..841
                      mol_type = protein
                      organism = synthetic construct
SEQUENCE: 122
MKWVTFISLL FLFSSAYSIW ELKKDVYVVE LDWYPDAPGE MVVLTCDTPE EDGITWTLDQ  60
SSEVLGSGKT LTIQVKEFGD AGQYTCHKGG EVLSHSLLLL HKKEDGIWST DILKDQKEPK  120
NKTFLRCEAK NYSGRFTCWW LTTISTDLTF SVKSSRGSSD PQGVTCGAAT LSAERVRGDN  180
KEYEYSVECQ EDSACPAAEE SLPIEVMVDA VHKLKYENYT SSFFIRDIIK PDPPKNLQLK  240
PLKNSRQVEV SWEYPDTWST PHSYFSLTFC VQVQGKSKRE KKDRVFTDKT SATVICRKNA  300
SISVRAQDRY YSSSWSEWAS VPCSGGGGSG GGGSGGGGSR NLPVATPDPG MFPCLHHSQN  360
LLRAVSNMLQ KARQTLEFYP CTSEEIDHED ITKDKTSTVE ACLPLELTKN ESCLNSRETS  420
FITNGSCLAS RKTSFMMALC LSSIYEDLKM YQVEFKTMNA KLLMDPKRQI FLDQNMLAVI  480
DELMQALNFN SETVPQKSSL EEPDFYKTKI KLCILLHAFR IRAVTIDRVM SYLNASITCP  540
PPMSVEHADI WVKSYSLYSR ERYICNSGFK RKAGTSSLTE CVLNKATNVA HWTTPSLKCI  600
RSELTQDPAV SVALGQTVRI TCQGDSLRSY YASWYQQKPG QAPVLVIYGK NNRPSGIPDR  660
FSGSSSGNTA SLTITGAQAE DEADYYCNSR DSSGNHVVFG GGTKLTVGHG GGGSGGGGSG  720
GGGSEVQLVE SGGGVVRPGG SLRLSCAASG FTFDDYGMSW VRQAPGKGLE WVSGINWNGG  780
STGYADSVKG RFTISRDNAK NSLYLQMNSL RAEDTAVYYC ARGRSLLFDY WGQGTLVTVS  840
R                                                                  841

SEQ ID NO: 123        moltype = DNA  length = 2523
FEATURE               Location/Qualifiers
misc_feature          1..2523
```

```
                         note = source = /note="Description of Artificial Sequence:
                          Synthetic18t15-12s16 sequence"
source                   1..2523
                         mol_type = other DNA
                         organism = synthetic construct
SEQUENCE: 123
atgaaatggg tgacctttat ttctttactg ttcctcttta gcagcgccta ctccatttgg  60
gaactgaaga aggacgtcta cgtggtcgaa ctggactggt atcccgatgc tcccggcgaa  120
atggtggtgc tcacttgtga cacccccgaa gaagacggca tcacttggac cctcgatcag  180
agcagcgagg tgctgggctc cggaaagacc ctcacaatcc aagttaagga gttcggagac  240
gctggccaat acacatgcca caagggaggc gaggtgctca gccattcctt attattatta  300
cacaagaagg aagacggaat ctggtccacc gacattttaa aagatcagaa ggagcccaag  360
aataagacct ttttaaggtg tgaggccaaa aactacagcg gtcgtttcac ttgttggtgg  420
ctgaccacca tttccaccga tttaaccttc tccgtgaaaa gcagccgggg aagctccgac  480
cctcaaggtg tgacatgtgg agccgctacc ctcagcgctg agagggttcg tggcgataac  540
aaggaatacg agtacagcgt ggagtgccaa gaagatagcg cttgtcccgc tgccgaagaa  600
tctttaccca ttgaggtgat ggtggacgcc gtgcacaaac tcaagtacga gaactacacc  660
tcctccttct ttatccggga catcattaag cccgatcctc ctaagaattt acagctgaag  720
cctctcaaaa atagccggca agttgaggtc tcttgggaat atcccgacac ttggagcaca  780
ccccacagct acttctcttt aaccttttgt gtgcaagttc aaggtaaaag caagcgggag  840
aagaaagacc gggtgtttac cgacaaaacc agcgccaccg tcatctgtcg gaagaacgcc  900
tccatcagcg tgagggctca agatcgttat tactccagca gctggtccga gtgggccagc  960
gtgccttgtt ccggcggtgg aggatccgga ggaggtggct ccggcggcgg aggatctcgt  1020
aacctccccg tggctacccc cgatcccgga atgttccctt gtttacacca cagccagaat  1080
ttactgaggg ccgtgagcaa catgctgcag aaagctaggc agactttaga attttaccct  1140
tgcaccagcg aggagatcga ccatgaagat atcaccaagg acaagacatc caccgtggag  1200
gcttgtttac ctctggagct gacaaagaac gagtcttgtc tcaactctcg tgaaaccagc  1260
ttcatcacaa atggctcttg tttagcttcc cggaagacct cctttatgat ggctttatgc  1320
ctcagctcca tctacgagga tttaaagatg taccaagtgg agttcaagac catgaacgcc  1380
aagctgctca tggaccctaa acggcagatc tttttagacc agaacatgct ggctgtgatt  1440
gatgagctga tgcaagcttt aaacttcaac tccgagaccg tccctcagaa gtcctccctc  1500
gaggagcccg atttttacaa gacaaagatc aaactgtgca ttttactcca cgcctttagg  1560
atccgggccg tgaccattga ccgggtcatg agctatttaa acgccagcat tacatgcccc  1620
cctcccatga gcgtggagca cgccgacatc tgggtgaaga gctatagcct ctacagccgg  1680
gagaggtata tctgtaacag cggcttcaag aggaaggccg gcaccagcag cctcaccgag  1740
tgcgtgctga ataaggctac caacgtggct cactggacaa caccctcttt aaagtgcatc  1800
cggtccgagc tgacccagga ccctgctgtg tccgtggctc tgggccagac cgtgaggatc  1860
acctgccagg gcgactccct gaggtcctac tacgcctcct ggtaccagca gaagcccggc  1920
caggctcctg tgctggtgat ctacggcaag aacaacaggc cctccggcat ccctgacagg  1980
ttctccggat cctcctccgg caacaccgcc tccctgacca tcacaggcgc tcaggccgag  2040
gacgaggctg actactactg caactccagg gactcctccg gcaaccatgt ggtgttcggc  2100
ggcggcacca agctgaccgt gggccatggc ggcggcggct ccggaggcgg cggcagcggc  2160
ggaggaggat ccgaggtgca gctggtggag tccggaggag gagtggtgag gcctggaggc  2220
tccctgaggc tgagctgtgc tgcctccggc ttcaccttcg acgactacgg catgtcctgg  2280
gtgaggcagg ctcctggaaa gggcctggag tgggtgtccg gcatcaactg gaacggcgga  2340
tccaccggct acgccgattc cgtgaagggc aggttcacca tcagcaggga caacgccaag  2400
aactccctgt acctgcagat gaactccctg agggccgagg acaccgccgt gtactactgc  2460
gccaggggca ggtccctgct gttcgactac tggggacagg gcaccctggt gaccgtgtcc  2520
agg                                                                2523

SEQ ID NO: 124           moltype = DNA  length = 456
FEATURE                  Location/Qualifiers
misc_feature             1..456
                         note = source = /note="Description of Artificial Sequence:
                          SyntheticIL-7 sequence"
source                   1..456
                         mol_type = other DNA
                         organism = synthetic construct
SEQUENCE: 124
gattgcgaca tcgagggcaa ggacggcaag cagtacgaga gcgtgctgat ggtgtccatc  60
gaccagctgc tggacagcat gaaggagatc ggctccaact gcctcaacaa cgagttcaac  120
ttcttcaagc ggcacatctg cgacgccaac aaggagggca tgttcctgtt cagggccgcc  180
aggaaactgc ggcagttcct gaagatgaac tccaccggcg acttcgacct gcacctgctg  240
aaggtgtccg agggcaccac catcctgctg aactgcaccg gacaggtgaa gggccggaaa  300
cctgctgctc tgggagaggc ccaacccacc aagagcctgg aggagaacaa gtccctgaag  360
gagcagaaga agctgaacga cctgtgcttc ctgaagaggc tgctgcagga gatcaagacc  420
tgctggaaca agatcctgat gggcaccaag gagcat                            456

SEQ ID NO: 125           moltype = AA  length = 485
FEATURE                  Location/Qualifiers
REGION                   1..485
                         note = source = /note="Description of Artificial Sequence:
                          Synthetic7t15-16s21 sequence"
source                   1..485
                         mol_type = protein
                         organism = synthetic construct
SEQUENCE: 125
DCDIEGKDGK QYESVLMVSI DQLLDSMKEI GSNCLNNEFN FFKRHICDAN KEGMFLFRAA  60
RKLRQFLKMN STGDFDLHLL KVSEGTTILL NCTGQVKGRK PAALGEAQPT KSLEENKSLK  120
```

```
EQKKLNDLCF LKRLLQEIKT CWNKILMGTK EHSGTTNTVA AYNLTWKSTN FKTILEWEPK  180
PVNQVYTVQI STKSGDWKSK CFYTTDTECD LTDEIVKDVK QTYLARVFSY PAGNVESTGS  240
AGEPLYENSP EFTPYLETNL GQPTIQSFEQ VGTKVNVTVE DERTLVRRNN TFLSLRDVFG  300
KDLIYTLYYW KSSSSGKKTA KTNTNEFLID VDKGENYCFS VQAVIPSRTV NRKSTDSPVE  360
CMGQEKGEFR ENWVNVISDL KKIEDLIQSM HIDATLYTES DVHPSCKVTA MKCFLLELQV  420
ISLESGDASI HDTVENLIIL ANNSLSSNGN VTESGCKECE ELEEKNIKEF LQSFVHIVQM  480
FINTS                                                             485

SEQ ID NO: 126          moltype = DNA  length = 1455
FEATURE                 Location/Qualifiers
misc_feature            1..1455
                        note = source = /note="Description of Artificial Sequence:
                         Synthetic7t15-16s21 sequence"
source                  1..1455
                        mol_type = other DNA
                        organism = synthetic construct
SEQUENCE: 126
gattgcgaca tcgagggcaa ggacggcaag cagtacgaga gcgtgctgat ggtgtccatc  60
gaccagctgc tggacagcat gaaggagatc ggctccaact gcctcaacaa cgagttcaac  120
ttcttcaagc ggcacatctg cgacgccaac aaggagggca tgttcctgtt cagggccgcc  180
aggaaactgc ggcagttcct gaagatgaac tccaccggcg acttcgacct gcacctgctg  240
aaggtgtccg agggcaccac catcctgctg aactgcaccg gacaggtgaa gggccggaaa  300
cctgctgctc tgggagaggc ccaacccacc aagagcctgg aggagaacaa gtccctgaag  360
gagcagaaga agctgaacga cctgtgcttc ctgaagaggc tgctgcagga gatcaagacc  420
tgctggaaca agatcctgat gggcaccaag gagcatagcg gcacaaccaa cacagtcgct  480
gcctataacc tcacttggaa gagcaccaac ttcaaaacca tcctcgaatg ggaacccaaa  540
cccgttaacc aagtttacac cgtgcagatc agcaccaagt ccggcgactg gaagtccaaa  600
tgtttctata ccaccgacac cgagtgcgat ctcaccgatg agatcgtgaa agatgtgaaa  660
cagacctacc tcgcccgggt gtttagctac cccgccggca atgtggagag cactggttcc  720
gctggcgagc ctttatacga gaacagcccc gaatttaccc cttacctcga gaccaattta  780
ggacagccca ccatccaaag ctttgagcaa gttggcacaa aggtgaatgt gacagtggag  840
gacgagcgga ctttagtgcg gcggaacaac acctttctca gcctccggga tgtgttcggc  900
aaagatttaa tctacacact gtattactgg aagtcctctt cctccggcaa gaagacagct  960
aaaaccaaca caaacgagtt tttaatcgac gtggataaag gcgaaaacta ctgtttcagc  1020
gtgcaagctg tgatcccctc ccggaccgtg aataggaaaa gcaccgatag ccccgttgag  1080
tgcatgggcc aagaaaaggg cgagttccgg gagaactggg tgaacgtcat cagcgattta  1140
aagaagatcg aagatttaat tcagtccatg catatcgacg ccactttata cacagaatcc  1200
gacgtgcacc cctcttgtaa ggtgaccgcc atgaaatgtt ttttactgga gctgcaagtt  1260
atctctttag agagcggaga cgctagcatc cacgacaccg tggagaattt aatcatttta  1320
gccaataact ctttatccag caacggcaac gtgacagagt ccggctgcaa ggagtgcgaa  1380
gagctggagg agaagaacat caaggagttt ctgcaatcct ttgtgcacat tgtccagatg  1440
ttcatcaata cctcc                                                  1455

SEQ ID NO: 127          moltype = AA  length = 503
FEATURE                 Location/Qualifiers
REGION                  1..503
                        note = source = /note="Description of Artificial Sequence:
                         Synthetic7t15-16s21 sequence"
source                  1..503
                        mol_type = protein
                        organism = synthetic construct
SEQUENCE: 127
MKWVTFISLL FLFSSAYSDC DIEGKDGKQY ESVLMVSIDQ LLDSMKEIGS NCLNNEFNFF  60
KRHICDANKE GMFLFRAARK LRQFLKMNST GDFDLHLLKV SEGTTILLNC TGQVKGRKPA  120
ALGEAQPTKS LEENKSLKEQ KKLNDLCFLK RLLQEIKTCW NKILMGTKEH SGTTNTVAAY  180
NLTWKSTNFK TILEWEPKPV NQVYTVQIST KSGDWKSKCF YTTDTECDLT DEIVKDVKQT  240
YLARVFSYPA GNVESTGSAG EPLYENSPEF TPYLETNLGQ PTIQSFEQVG TKVNVTVEDE  300
RTLVRRNNTF LSLRDVFGKD LIYTLYYWKS SSSGKKTAKT NTNEFLIDVD KGENYCFSVQ  360
AVIPSRTVNR KSTDSPVECM GQEKGEFREN WVNVISDLKK IEDLIQSMHI DATLYTESDV  420
HPSCKVTAMK CFLLELQVIS LESGDASIHD TVENLIILAN NSLSSNGNVT ESGCKECEEL  480
EEKNIKEFLQ SFVHIVQMFI NTS                                         503

SEQ ID NO: 128          moltype = DNA  length = 1509
FEATURE                 Location/Qualifiers
misc_feature            1..1509
                        note = source = /note="Description of Artificial Sequence:
                         Synthetic7t15-16s21 sequence"
source                  1..1509
                        mol_type = other DNA
                        organism = synthetic construct
SEQUENCE: 128
atgaagtggg tgaccttcat cagcctgctg ttcctgttct ccagcgccta ctccgattgc  60
gacatcgagg gcaaggacgg caagcagtac gagagcgtgc tgatggtgtc catcgaccag  120
ctgctggaca gcatgaagga gatcggctcc aactgcctca acaacgagtt caacttcttc  180
aagcggcaca tctgcgacgc caacaaggag ggcatgttcc tgttcagggc cgccaggaaa  240
ctgcggcagt tcctgaagat gaactccacc ggcgacttcg acctgcacct gctgaaggtg  300
tccgagggca ccaccatcct gctgaactgc accggacagg tgaagggccg gaaacctgct  360
gctctgggag aggcccaacc caccaagagc ctggaggaga acaagtccct gaaggagcag  420
aagaagctga acgacctgtg cttcctgaag aggctgctgc aggagatcaa gacctgctgg  480
```

-continued

```
aacaagatcc tgatgggcac caaggagcat agcggcacaa ccaacacagt cgctgcctat  540
aacctcactt ggaagagcac caacttcaaa accatcctcg aatgggaacc caaacccgtt  600
aaccaagttt acaccgtgca gatcagcacc aagtccggcg actggaagtc caaatgtttc  660
tataccaccg acaccgagtg cgatctcacc gatgagatcg tgaaagatgt gaaacagacc  720
tacctcgccc gggtgtttag ctaccccgcc ggcaatgtgg agagcactgg ttccgctggc  780
gagcctttat acgagaacag ccccgaattt accccttacc tcgagaccaa tttaggacag  840
cccaccatcc aaagctttga gcaagttggc acaaaggtga atgtgacagt ggaggacgag  900
cggactttag tgcggcggaa caacaccttt ctcagcctcc gggatgtgtt cggcaaagat  960
ttaatctaca cactgtatta ctggaagtcc tcttcctccg gcaagaagac agctaaaacc  1020
aacacaaacg agtttttaat cgacgtggat aaaggcgaaa actactgttt cagcgtgcaa  1080
gctgtgatcc cctcccggac cgtgaatagg aaaagcaccg atagccccgt tgagtgcatg  1140
ggccaagaaa agggcgagtt ccgggagaac tgggtgaacg tcatcagcga tttaaagaag  1200
atcgaagatt taattcagtc catgcatatc gacgccactt tatacacaga atccgacgtg  1260
cacccctctt gtaaggtgac cgccatgaaa tgtttttttac tggagctgca agttatctct  1320
ttagagagcg gagacgctag catccacgac accgtggaga atttaatcat tttagccaat  1380
aactctttat ccagcaacgg caacgtgaca gagtccggct gcaaggagtg cgaagagctg  1440
gaggagaaga acatcaagga gtttctgcaa tcctttgtgc acattgtcca gatgttcatc  1500
aatacctcc                                                          1509

SEQ ID NO: 129         moltype = AA  length = 438
FEATURE                Location/Qualifiers
REGION                 1..438
                       note = source = /note="Description of Artificial Sequence:
                        Synthetic7t15-16s21 sequence"
source                 1..438
                       mol_type = protein
                       organism = synthetic construct
SEQUENCE: 129
SELTQDPAVS VALGQTVRIT CQGDSLRSYY ASWYQQKPGQ APVLVIYGKN NRPSGIPDRF  60
SGSSSGNTAS LTITGAQAED EADYYCNSRD SSGNHVVFGG GTKLTVGHGG GGSGGGGSGG  120
GGSEVQLVES GGGVVRPGGS LRLSCAASGF TFDDYGMSWV RQAPGKGLEW VSGINWNGGS  180
TGYADSVKGR FTISRDNAKN SLYLQMNSLR AEDTAVYYCA RGRSLLFDYW GQGTLVTVSR  240
ITCPPPMSVE HADIWVKSYS LYSRERYICN SGFKRKAGTS SLTECVLNKA TNVAHWTTPS  300
LKCIRQGQDR HMIRMRQLID IVDQLKNYVN DLVPEFLPAP EDVETNCEWS AFSCFQKAQL  360
KSANTGNNER IINVSIKKLK RKPPSTNAGR RQKHRLTCPS CDSYEKKPPK EFLERFKSLL  420
QKMIHQHLSS RTHGSEDS                                                438

SEQ ID NO: 130         moltype = DNA  length = 1314
FEATURE                Location/Qualifiers
misc_feature           1..1314
                       note = source = /note="Description of Artificial Sequence:
                        Synthetic7t15-16s21 sequence"
source                 1..1314
                       mol_type = other DNA
                       organism = synthetic construct
SEQUENCE: 130
tccgagctga cccaggaccc tgctgtgtcc gtggctctgg gccagaccgt gaggatcacc  60
tgccagggcg actccctgag gtcctactac gcctcctggt accagcagaa gcccggccag  120
gctcctgtgc tggtgatcta cggcaagaac aacaggccct ccggcatccc tgacaggttc  180
tccggatcct cctccggcaa caccgcctcc ctgaccatca caggcgctca ggccgaggac  240
gaggctgact actactgcaa ctccagggac tcctccggca accatgtggt gttcggcggc  300
ggcaccaagc tgaccgtggg ccatggcggc ggcggctccg gaggcggcgg cagcggcgga  360
ggaggatccg aggtgcagct ggtggagtcc ggaggaggag tggtgaggcc tggaggctcc  420
ctgaggctga gctgtgctgc ctccggcttc accttcgacg actacggcat gtcctgggtg  480
aggcaggctc ctggaaaggg cctggagtgg gtgtccggca tcaactggaa cggcggatcc  540
accggctacg ccgattccgt gaagggcagg ttcaccatca gcagggacaa cgccaagaac  600
tccctgtacc tgcagatgaa ctccctgagg gccgaggaca ccgccgtgta ctactgcgcc  660
aggggcaggt ccctgctgtt cgactactgg ggacagggca ccctggtgac cgtgtccagg  720
attacatgcc cccctcccat gagcgtggag cacgccgaca tctgggtgaa gagctatagc  780
ctctacagcc gggagaggta tatctgtaac agcggcttca agaggaaggc cggcaccagc  840
agcctcaccg agtgcgtgct gaataaggct accaacgtgg ctcactggac aacaccctct  900
ttaaagtgca tccggcaggg ccaggacagg cacatgatcc ggatgaggca gctcatcgac  960
atcgtcgacc agctgaagaa ctacgtgaac gacctggtgc ccgagtttct gcctgccccc  1020
gaggacgtgg agaccaactg cgagtggtcc gccttctcct gctttcagaa ggcccagctg  1080
aagtccgcca acaccggcaa caacgagcgg atcatcaacg tgagcatcaa gaagctgaag  1140
cggaagcctc cctccacaaa cgccggcagg aggcagaagc acaggctgac ctgccccagc  1200
tgtgactcct acgagaagaa gccccccaag gagttcctgg agaggttcaa gtccctgctg  1260
cagaagatga tccatcagca cctgtcctcc aggacccacg gctccgagga ctcc        1314

SEQ ID NO: 131         moltype = AA  length = 456
FEATURE                Location/Qualifiers
REGION                 1..456
                       note = source = /note="Description of Artificial Sequence:
                        Synthetic7t15-16s21 sequence"
source                 1..456
                       mol_type = protein
                       organism = synthetic construct
SEQUENCE: 131
MKWVTFISLL FLFSSAYSSE LTQDPAVSVA LGQTVRITCQ GDSLRSYYAS WYQQKPGQAP  60
```

```
VLVIYGKNNR PSGIPDRFSG SSSGNTASLT ITGAQAEDEA DYYCNSRDSS GNHVVFGGGT  120
KLTVGHGGGG SGGGGSGGGG SEVQLVESGG GVVRPGGSLR LSCAASGFTF DDYGMSWVRQ  180
APGKGLEWVS GINWNGGSTG YADSVKGRFT ISRDNAKNSL YLQMNSLRAE DTAVYYCARG  240
RSLLFDYWGQ GTLVTVSRIT CPPPMSVEHA DIWVKSYSLY SRERYICNSG FKRKAGTSSL  300
TECVLNKATN VAHWTTPSLK CIRQGQDRHM IRMRQLIDIV DQLKNYVNDL VPEFLPAPED  360
VETNCEWSAF SCFQKAQLKS ANTGNNERII NVSIKKLKRK PPSTNAGRRQ KHRLTCPSCD  420
SYEKKPPKEF LERFKSLLQK MIHQHLSSRT HGSEDS                            456

SEQ ID NO: 132         moltype = DNA  length = 1368
FEATURE                Location/Qualifiers
misc_feature           1..1368
                       note = source = /note="Description of Artificial Sequence:
                        Synthetic7t15-16s21 sequence"
source                 1..1368
                       mol_type = other DNA
                       organism = synthetic construct
SEQUENCE: 132
atgaagtggg tgaccttcat cagcctgctg ttcctgttct ccagcgccta ctcctccgag  60
ctgacccagg accctgctgt gtccgtggct ctgggccaga ccgtgaggat cacctgccag  120
ggcgactccc tgaggtccta ctacgcctcc tggtaccagc agaagcccgg ccaggctcct  180
gtgctggtga tctacggcaa gaacaacagg ccctccggca tccctgacag gttctccgga  240
tcctcctccg gcaacaccgc ctccctgacc atcacaggcg ctcaggccga ggacgaggct  300
gactactact gcaactccag ggactcctcc ggcaaccatg tggtgttcgg cggcggcacc  360
aagctgaccg tgggccatgg cggcggcggc tccggaggcg gcggcagcgg cggaggagga  420
tccgaggtgc agctggtgga gtccggagga ggagtggtga ggcctggagg ctccctgagg  480
ctgagctgtg ctgcctccgg cttcaccttc gacgactacg gcatgtcctg ggtgaggcag  540
gctcctggaa agggcctgga gtgggtgtcc ggcatcaact ggaacggcgg atccaccggc  600
tacgccgatt ccgtgaaggg caggttcacc atcagcaggg acaacgccaa gaactccctg  660
tacctgcaga tgaactccct gagggccgag gacaccgccg tgtactactg cgccaggggc  720
aggtccctgc tgttcgacta ctggggacag ggcaccctgg tgaccgtgtc caggattaca  780
tgcccccctc ccatgagcgt ggagcacgcc gacatctggg tgaagagcta tagcctctac  840
agccgggaga ggtatatctg taacagcggc ttcaagagga aggccggcac cagcagcctc  900
accgagtgcg tgctgaataa ggctaccaac gtggctcact ggacaacacc ctctttaaag  960
tgcatccggc agggccagga caggcacatg atccggatga ggcagctcat cgacatcgtc  1020
gaccagctga agaactacgt gaacgacctg gtgcccgagt ttctgcctgc ccccgaggac  1080
gtggagacca actgcgagtg gtccgccttc tcctgctttc agaaggccca gctgaagtcc  1140
gccaacaccg gcaacaacga gcggatcatc aacgtgagca tcaagaagct gaagcggaag  1200
cctccctcca caaacgccgg caggaggcag aagcacaggc tgacctgccc cagctgtgac  1260
tcctacgaga agaagccccc caaggagttc ctggagaggt tcaagtccct gctgcagaag  1320
atgatccatc agcacctgtc ctccaggacc cacggctccg aggactcc              1368

SEQ ID NO: 133         moltype = AA  length = 620
FEATURE                Location/Qualifiers
REGION                 1..620
                       note = source = /note="Description of Artificial Sequence:
                        SyntheticTGFRt15-16s21 sequence"
source                 1..620
                       mol_type = protein
                       organism = synthetic construct
SEQUENCE: 133
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPDSGT TNTVAAYNLT  300
WKSTNFKTIL EWEPKPVNQV YTVQISTKSG DWKSKCFYTT DTECDLTDEI VKDVKQTYLA  360
RVFSYPAGNV ESTGSAGEPL YENSPEFTPY LETNLGQPTI QSFEQVGTKV NVTVEDERTL  420
VRRNNTFLSL RDVFGKDLIY TLYYWKSSSS GKKTAKTNTN EFLIDVDKGE NYCFSVQAVI  480
PSRTVNRKST DSPVECMGQE KGEFRENWVN VISDLKKIED LIQSMHIDAT LYTESDVHPS  540
CKVTAMKCFL LELQVISLES GDASIHDTVE NLIILANNSL SSNGNVTESG CKECEELEEK  600
NIKEFLQSFV HIVQMFINTS                                              620

SEQ ID NO: 134         moltype = DNA  length = 1860
FEATURE                Location/Qualifiers
misc_feature           1..1860
                       note = source = /note="Description of Artificial Sequence:
                        SyntheticTGFRt15-16s21 sequence"
source                 1..1860
                       mol_type = other DNA
                       organism = synthetic construct
SEQUENCE: 134
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcagcatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
```

```
aataatgaca tgatcgtgac cgataacaat ggcgccgtga aatttcccca gctgtgcaaa  540
ttctgcgatg tgaggttttc cacctgcgac aaccagaagt cctgtatgag caactgctcc  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
tacaatacca gcaaccccga cagcggcaca accaacacag tcgctgccta taacctcact  900
tggaagagca ccaacttcaa aaccatcctc gaatgggaac ccaaacccgt taaccaagtt  960
tacaccgtgc agatcagcac caagtccggc gactggaagt ccaaatgttt ctataccacc  1020
gacaccgagt gcgatctcac cgatgagatc gtgaaagatg tgaaacagac ctacctcgcc  1080
cgggtgttta gctaccccgc cggcaatgtg gagagcactg gttccgctgg cgagccttta  1140
tacgagaaca gccccgaatt taccccttac ctcgagacca atttaggaca gccccaccatc  1200
caaagctttg agcaagttgg cacaaaggtg aatgtgacag tggaggacga gcggacttta  1260
gtgcggcgga acaacacctt tctcagcctc cgggatgtgt tcggcaaaga tttaatctac  1320
acactgtatt actggaagtc ctcttcctcc ggcaagaaga cagctaaaac caacacaaac  1380
gagtttttaa tcgacgtgga taaaggcgaa aactactgtt tcagcgtgca agctgtgatc  1440
ccctcccgga ccgtgaatag gaaaagcacc gatagccccg ttgagtgcat gggccaagaa  1500
aagggcgagt tccgggagaa ctgggtgaac gtcatcagcg atttaaagaa gatcgaagat  1560
ttaattcagt ccatgcatat cgacgccact ttatacacag aatccgacgt gcacccctct  1620
tgtaaggtga ccgccatgaa atgtttttta ctggagctgc aagttatctc tttagagagc  1680
ggagacgcta gcatccacga caccgtggag aatttaatca ttttagccaa taactcttta  1740
tccagcaacg gcaacgtgac agagtccggc tgcaaggagt gcgaagagct ggaggagaag  1800
aacatcaagg agtttctgca atcctttgtg cacattgtcc agatgttcat caatacctcc  1860
```

SEQ ID NO: 135 moltype = AA length = 638
FEATURE Location/Qualifiers
REGION 1..638
note = source = /note="Description of Artificial Sequence: SyntheticTGFRt15-16s21 sequence"
source 1..638
mol_type = protein
organism = synthetic construct
SEQUENCE: 135

```
MKWVTFISLL FLFSSAYSIP PHVQKSVNND MIVTDNNGAV KFPQLCKFCD VRFSTCDNQK  60
SCMSNCSITS ICEKPQEVCV AVWRKNDENI TLETVCHDPK LPYHDFILED AASPKCIMKE  120
KKKPGETFFM CSCSSDECND NIIFSEEYNT SNPDGGGGSG GGGSGGGGSI PPHVQKSVNN  180
DMIVTDNNGA VKFPQLCKFC DVRFSTCDNQ KSCMSNCSIT SICEKPQEVC VAVWRKNDEN  240
ITLETVCHDP KLPYHDFILE DAASPKCIMK EKKKPGETFF MCSCSSDECN DNIIFSEEYN  300
TSNPDSGTTN TVAAYNLTWK STNFKTILEW EPKPVNQVYT VQISTKSGDW KSKCFYTTDT  360
ECDLTDEIVK DVKQTYLARV FSYPAGNVES TGSAGEPLYE NSPEFTPYLE TNLGQPTIQS  420
FEQVGTKVNV TVEDERTLVR RNNTFLSLRD VFGKDLIYTL YYWKSSSSGK KTAKTNTNEF  480
LIDVDKGENY CFSVQAVIPS RTVNRKSTDS PVECMGQEKG EFRENWVNVI SDLKKIEDLI  540
QSMHIDATLY TESDVHPSCK VTAMKCFLLE LQVISLESGD ASIHDTVENL IILANNSLSS  600
NGNVTESGCK ECEELEEKNI KEFLQSFVHI VQMFINTS  638
```

SEQ ID NO: 136 moltype = DNA length = 1914
FEATURE Location/Qualifiers
misc_feature 1..1914
note = source = /note="Description of Artificial Sequence: SyntheticTGFRt15-16s21 sequence"
source 1..1914
mol_type = other DNA
organism = synthetic construct
SEQUENCE: 136

```
atgaagtggg tgaccttcat cagcctgctg ttcctgttct ccagcgccta ctccatcccc  60
ccccatgtgc aaaagagcgt gaacaacgat atgatcgtga ccgacaacaa cggcgccgtg  120
aagtttcccc agctctgcaa gttctgcgat gtcaggttca gcacctgcga taatcagaag  180
tcctgcatgt ccaactgcag catcacctcc atctgcgaga agccccaaga agtgtgcgtg  240
gccgtgtggc ggaaaaatga cgagaacatc accctggaga ccgtgtgtca cgacccccaag  300
ctcccttatc acgacttcat tctggaggac gctgcctccc ccaaatgcat catgaaggag  360
aagaagaagc ccggagagac cttctttatg tgttcctgta gcagcgacga gtgtaacgac  420
aacatcatct tcagcgaaga gtacaacacc agcaaccctg atggaggtgg cggatccgga  480
ggtggaggtt ctggtggagg tgggagtatt cctccccacg tgcagaagag cgtgaataat  540
gacatgatcg tgaccgataa caatggcgcc gtgaaatttc cccagctgtg caaattctgc  600
gatgtgaggt tttccacctg cgacaaccag aagtcctgta tgagcaactg ctccatcacc  660
tccatctgtg agaagcctca ggaggtgtgc gtggctgtct ggcggaagaa tgacgagaat  720
atcaccctgg aaaccgtctg ccacgatccc aagctgccct accacgattt catcctggaa  780
gacgccgcca gccctaagtg catcatgaaa gagaaaaaga agcctggcga gaccttttttc  840
atgtgctcct gcagcagcga cgaatgcaac gacaatatca tctttagcga ggaatacaat  900
accagcaacc ccgacagcgg cacaaccaac acagtcgctg cctataacct cacttggaag  960
agcaccaact tcaaaaccat cctcgaatgg gaacccaaac ccgttaacca agtttacacc  1020
gtgcagatca gcaccaagtc cggcgactgg aagtccaaat gtttctatac caccgacacc  1080
gagtgcgatc tcaccgatga gatcgtgaaa gatgtgaaac agacctacct cgcccgggtg  1140
tttagctacc ccgccggcaa tgtggagagc actggttccg ctggcgagcc tttatacgag  1200
aacagccccg aatttacccc ttacctcgag accaatttag gacagcccac catccaaagc  1260
tttgagcaag ttggcacaaa ggtgaatgtg acagtggagg acgagcggac tttagtgcgg  1320
cggaacaaca cctttctcag cctccgggat gtgttcggca aagatttaat ctacacactg  1380
tattactgga agtcctcttc ctccggcaag aagacagcta aaaccaacac aaacgagttt  1440
ttaatcgacg tggataaagg cgaaaactac tgtttcagcg tgcaagctgt gatcccctcc  1500
```

```
cggaccgtga ataggaaaag caccgatagc cccgttgagt gcatgggcca agaaaagggc  1560
gagttccggg agaactgggt gaacgtcatc agcgatttaa agaagatcga agatttaatt  1620
cagtccatgc atatcgacgc cactttatac acagaatccg acgtgcaccc ctcttgtaag  1680
gtgaccgcca tgaaatgttt tttactggag ctgcaagtta tctctttaga gagcggagac  1740
gctagcatcc acgacaccgt ggagaattta atcattttag ccaataactc tttatccagc  1800
aacggcaacg tgacagagtc cggctgcaag gagtgcgaag agctggagga gaagaacatc  1860
aaggagtttc tgcaatcctt tgtgcacatt gtccagatgt tcatcaatac ctcc        1914

SEQ ID NO: 137         moltype = AA  length = 438
FEATURE                Location/Qualifiers
REGION                 1..438
                       note = source = /note="Description of Artificial Sequence:
                        SyntheticTGFRt15-16s21 sequence"
source                 1..438
                       mol_type = protein
                       organism = synthetic construct
SEQUENCE: 137
SELTQDPAVS VALGQTVRIT CQGDSLRSYY ASWYQQKPGQ APVLVIYGKN NRPSGIPDRF  60
SGSSSGNTAS LTITGAQAED EADYYCNSRD SSGNHVVFGG GTKLTVGHGG GGSGGGGSGG  120
GGSEVQLVES GGGVVRPGGS LRLSCAASGF TFDDYGMSWV RQAPGKGLEW VSGINWNGGS  180
TGYADSVKGR FTISRDNAKN SLYLQMNSLR AEDTAVYYCA RGRSLLFDYW GQGTLVTVSR  240
ITCPPPMSVE HADIWVKSYS LYSRERYICN SGFKRKAGTS SLTECVLNKA TNVAHWTTPS  300
LKCIRQGQDR HMIRMRQLID IVDQLKNYVN DLVPEFLPAP EDVETNCEWS AFSCFQKAQL  360
KSANTGNNER IINVSIKKLK RKPPSTNAGR RQKHRLTCPS CDSYEKKPPK EFLERFKSLL  420
QKMIHQHLSS RTHGSEDS                                                438

SEQ ID NO: 138         moltype = DNA  length = 1314
FEATURE                Location/Qualifiers
misc_feature           1..1314
                       note = source = /note="Description of Artificial Sequence:
                        SyntheticTGFRt15-16s21 sequence"
source                 1..1314
                       mol_type = other DNA
                       organism = synthetic construct
SEQUENCE: 138
tccgagctga cccaggaccc tgctgtgtcc gtggctctgg gccagaccgt gaggatcacc  60
tgccagggcg actccctgag gtcctactac gcctcctggt accagcagaa gcccggccag  120
gctcctgtgc tggtgatcta cggcaagaac aacaggccct ccggcatccc tgacaggttc  180
tccggatcct cctccggcaa caccgcctcc ctgaccatca caggcgctca ggccgaggac  240
gaggctgact actactgcaa ctccagggac tcctccggca accatgtggt gttcggcggc  300
ggcaccaagc tgaccgtggg ccatggcggc ggcggctccg gaggcggcgg cagcggcgga  360
ggaggatccg aggtgcagct ggtggagtcc ggaggaggag tggtgaggcc tggaggctcc  420
ctgaggctga gctgtgctgc ctccggcttc accttcgacg actacggcat gtcctgggtg  480
aggcaggctc ctggaaaggg cctggagtgg gtgtccggca tcaactggaa cggcggatcc  540
accggctacg ccgattccgt gaagggcagg ttcaccatca gcagggacaa cgccaagaac  600
tccctgtacc tgcagatgaa ctccctgagg gccgaggaca ccgccgtgta ctactgcgcc  660
aggggcaggt ccctgctgtt cgactactgg ggacagggca ccctggtgac cgtgtccagg  720
attacatgcc cccctcccat gagcgtggag cacgccgaca tctgggtgaa gagctatagc  780
ctctacagcc gggagaggta tatctgtaac agcggcttca agaggaaggc cggcaccagc  840
agcctcaccg agtgcgtgct gaataaggct accaacgtgg ctcactggac aacaccctct  900
ttaaagtgca tccggcaggg ccaggacagg cacatgatcc ggatgaggca gctcatcgac  960
atcgtcgacc agctgaagaa ctacgtgaac gacctggtgc ccgagtttct gcctgccccc  1020
gaggacgtgg agaccaactg cgagtggtcc gccttctcct gctttcagaa ggcccagctg  1080
aagtccgcca acaccggcaa caacgagcgg atcatcaacg tgagcatcaa gaagctgaag  1140
cggaagcctc cctccacaaa cgccggcagg aggcagaagc acaggctgac ctgccccagc  1200
tgtgactcct acgagaagaa gccccccaag gagttcctgg agaggttcaa gtccctgctg  1260
cagaagatga tccatcagca cctgtcctcc aggacccacg gctccgagga ctcc        1314

SEQ ID NO: 139         moltype = AA  length = 456
FEATURE                Location/Qualifiers
REGION                 1..456
                       note = source = /note="Description of Artificial Sequence:
                        SyntheticTGFRt15-16s21 sequence"
source                 1..456
                       mol_type = protein
                       organism = synthetic construct
SEQUENCE: 139
MKWVTFISLL FLFSSAYSSE LTQDPAVSVA LGQTVRITCQ GDSLRSYYAS WYQQKPGQAP  60
VLVIYGKNNR PSGIPDRFSG SSSGNTASLT ITGAQAEDEA DYYCNSRDSS GNHVVFGGGT  120
KLTVGHGGGG SGGGGSGGGG SEVQLVESGG GVVRPGGSLR LSCAASGFTF DDYGMSWVRQ  180
APGKGLEWVS GINWNGGSTG YADSVKGRFT ISRDNAKNSL YLQMNSLRAE DTAVYYCARG  240
RSLLFDYWGQ GTLVTVSRIT CPPPMSVEHA DIWVKSYSLY SRERYICNSG FKRKAGTSSL  300
TECVLNKATN VAHWTTPSLK CIRQGQDRHM IRMRQLIDIV DQLKNYVNDL VPEFLPAPED  360
VETNCEWSAF SCFQKAQLKS ANTGNNERII NVSIKKLKRK PPSTNAGRRQ KHRLTCPSCD  420
SYEKKPPKEF LERFKSLLQK MIHQHLSSRT HGSEDS                            456

SEQ ID NO: 140         moltype = DNA  length = 1368
FEATURE                Location/Qualifiers
misc_feature           1..1368
```

```
                         note = source = /note="Description of Artificial Sequence:
                          SyntheticTGFRt15-16s21 sequence"
source                   1..1368
                         mol_type = other DNA
                         organism = synthetic construct
SEQUENCE: 140
atgaagtggg tgaccttcat cagcctgctg ttcctgttct ccagcgccta ctcctccgag  60
ctgacccagg accctgctgt gtccgtggct ctgggccaga ccgtgaggat cacctgccag  120
ggcgactccc tgaggtccta ctacgcctcc tggtaccagc agaagcccgg ccaggctcct  180
gtgctggtga tctacggcaa gaacaacagg ccctccggca tccctgacag gttctccgga  240
tcctcctccg gcaacaccgc ctccctgacc atcacaggcg ctcaggccga ggacgaggct  300
gactactact gcaactccag ggactcctcc ggcaaccatg tggtgttcgg cggcggcacc  360
aagctgaccg tgggccatgg cggcggcggc tccggaggcg gcggcagcgg cggaggagga  420
tccgaggtgc agctggtgga gtccggagga ggagtggtga ggcctggagg ctccctgagg  480
ctgagctgtg ctgcctccgg cttcaccttc gacgactacg gcatgtcctg ggtgaggcag  540
gctcctggaa agggcctgga gtgggtgtcc ggcatcaact ggaacggcgg atccaccggc  600
tacgccgatt ccgtgaaggg caggttcacc atcagcaggg acaacgccaa gaactccctg  660
tacctgcaga tgaactccct gagggccgag gacaccgccg tgtactactg cgccaggggc  720
aggtccctgc tgttcgacta ctggggacag ggcaccctgg tgaccgtgtc caggattaca  780
tgcccccctc ccatgagcgt ggagcacgcc gacatctggg tgaagagcta tagcctctac  840
agccgggaga ggtatatctg taacagcggc ttcaagagga aggccggcac cagcagcctc  900
accgagtgcg tgctgaataa ggctaccaac gtggctcact ggacaacacc ctctttaaag  960
tgcatccggc agggccagga caggcacatg atccggatga ggcagctcat cgacatcgtc  1020
gaccagctga agaactacgt gaacgacctg gtgcccgagt ttctgcctgc cccccgaggac  1080
gtggagacca actgcgagtg gtccgccttc tcctgctttc agaaggccca gctgaagtcc  1140
gccaacaccg gcaacaacga gcggatcatc aacgtgagca tcaagaagct gaagcggaag  1200
cctccctcca caaacgccgg caggaggcag aagcacaggc tgacctgccc cagctgtgac  1260
tcctacgaga agaagccccc caaggagttc ctggagaggt tcaagtccct gctgcagaag  1320
atgatccatc agcacctgtc ctccaggacc cacggctccg aggactcc              1368

SEQ ID NO: 141           moltype = AA  length = 485
FEATURE                  Location/Qualifiers
REGION                   1..485
                         note = source = /note="Description of Artificial Sequence:
                          Synthetic7t15-7s sequence"
source                   1..485
                         mol_type = protein
                         organism = synthetic construct
SEQUENCE: 141
DCDIEGKDGK QYESVLMVSI DQLLDSMKEI GSNCLNNEFN FFKRHICDAN KEGMFLFRAA  60
RKLRQFLKMN STGDFDLHLL KVSEGTTILL NCTGQVKGRK PAALGEAQPT KSLEENKSLK  120
EQKKLNDLCF LKRLLQEIKT CWNKILMGTK EHSGTTNTVA AYNLTWKSTN FKTILEWEPK  180
PVNQVYTVQI STKSGDWKSK CFYTTDTECD LTDEIVKDVK QTYLARVFSY PAGNVESTGS  240
AGEPLYENSP EFTPYLETNL GQPTIQSFEQ VGTKVNVTVE DERTLVRRNN TFLSLRDVFG  300
KDLIYTLYYW KSSSSGKKTA KTNTNEFLID VDKGENYCFS VQAVIPSRTV NRKSTDSPVE  360
CMGQEKGEFR ENWVNVISDL KKIEDLIQSM HIDATLYTES DVHPSCKVTA MKCFLLELQV  420
ISLESGDASI HDTVENLIIL ANNSLSSNGN VTESGCKECE ELEEKNIKEF LQSFVHIVQM  480
FINTS                                                              485

SEQ ID NO: 142           moltype = DNA  length = 1455
FEATURE                  Location/Qualifiers
misc_feature             1..1455
                         note = source = /note="Description of Artificial Sequence:
                          Synthetic7t15-7s sequence"
source                   1..1455
                         mol_type = other DNA
                         organism = synthetic construct
SEQUENCE: 142
gattgcgaca tcgagggcaa ggacggcaag cagtacgaga gcgtgctgat ggtgtccatc  60
gaccagctgc tggacagcat gaaggagatc ggctccaact gcctcaacaa cgagttcaac  120
ttcttcaagc ggcacatctg cgacgccaac aaggagggca tgttcctgtt cagggccgcc  180
aggaaactgc ggcagttcct gaagatgaac tccaccggcg acttcgacct gcacctgctg  240
aaggtgtccg agggcaccac catcctgctg aactgcaccg gacaggtgaa gggccggaaa  300
cctgctgctc tgggagaggc ccaacccacc aagagcctgg aggagaacaa gtccctgaag  360
gagcagaaga agctgaacga cctgtgcttc ctgaagaggc tgctgcagga gatcaagacc  420
tgctggaaca agatcctgat gggcaccaag gagcatagcg gcacaaccaa cacagtcgct  480
gcctataacc tcacttggaa gagcaccaac ttcaaaacca tcctcgaatg ggaacccaaa  540
cccgttaacc aagtttacac cgtgcagatc agcaccaagt ccggcgactg gaagtccaaa  600
tgtttctata ccaccgacac cgagtgcgat ctcaccgatg agatcgtgaa agatgtgaaa  660
cagacctacc tcgcccgggt gtttagctac cccgccggca atgtggagag cactggttcc  720
gctggcgagc ctttatacga gaacagcccc gaatttaccc cttacctcga gaccaattta  780
ggacagccca ccatccaaag ctttgagcaa gttggcacaa aggtgaatgt gacagtggag  840
gacgagcgga ctttagtgcg gcggaacaac acctttctca gcctccggga tgtgttcggc  900
aaagatttaa tctacacact gtattactgg aagtcctctt cctccggcaa gaagacagct  960
aaaaccaaca caaacgagtt tttaatcgac gtggataaag gcgaaaacta ctgtttcagc  1020
gtgcaagctg tgatcccctc ccggaccgtg aataggaaaa gcaccgatag ccccgttgag  1080
tgcatgggcc aagaaaaggg cgagttccgg gagaactggg tgaacgtcat cagcgattta  1140
aagaagatcg aagatttaat tcagtccatg catatcgacg ccactttata cacagaatcc  1200
gacgtgcacc cctcttgtaa ggtgaccgcc atgaaatgtt ttttactgga gctgcaagtt  1260
```

-continued

```
atctctttag agagcggaga cgctagcatc cacgacaccg tggagaattt aatcatttta  1320
gccaataact ctttatccag caacggcaac gtgacagagt ccggctgcaa ggagtgcgaa  1380
gagctggagg agaagaacat caaggagttt ctgcaatcct ttgtgcacat tgtccagatg  1440
ttcatcaata cctcc                                                   1455

SEQ ID NO: 143         moltype = AA  length = 503
FEATURE                Location/Qualifiers
REGION                 1..503
                       note = source = /note="Description of Artificial Sequence:
                        Synthetic7t15-7s sequence"
source                 1..503
                       mol_type = protein
                       organism = synthetic construct
SEQUENCE: 143
MKWVTFISLL FLFSSAYSDC DIEGKDGKQY ESVLMVSIDQ LLDSMKEIGS NCLNNEFNFF  60
KRHICDANKE GMFLFRAARK LRQFLKMNST GDFDLHLLKV SEGTTILLNC TGQVKGRKPA  120
ALGEAQPTKS LEENKSLKEQ KKLNDLCFLK RLLQEIKTCW NKILMGTKEH SGTTNTVAAY  180
NLTWKSTNFK TILEWEPKPV NQVYTVQIST KSGDWKSKCF YTTDTECDLT DEIVKDVKQT  240
YLARVFSYPA GNVESTGSAG EPLYENSPEF TPYLETNLGQ PTIQSFEQVG TKVNVTVEDE  300
RTLVRRNNTF LSLRDVFGKD LIYTLYYWKS SSSGKKTAKT NTNEFLIDVD KGENYCFSVQ  360
AVIPSRTVNR KSTDSPVECM GQEKGEFREN WVNVISDLKK IEDLIQSMHI DATLYTESDV  420
HPSCKVTAMK CFLLELQVIS LESGDASIHD TVENLIILAN NSLSSNGNVT ESGCKECEEL  480
EEKNIKEFLQ SFVHIVQMFI NTS                                          503

SEQ ID NO: 144         moltype = DNA  length = 1509
FEATURE                Location/Qualifiers
misc_feature           1..1509
                       note = source = /note="Description of Artificial Sequence:
                        Syntheticpolynucleotide"
source                 1..1509
                       mol_type = other DNA
                       organism = synthetic construct
SEQUENCE: 144
atgaagtggg tgaccttcat cagcctgctg ttcctgttct ccagcgccta ctccgattgc  60
gacatcgagg gcaaggacgg caagcagtac gagagcgtgc tgatggtgtc catcgaccag  120
ctgctggaca gcatgaagga gatcggctcc aactgcctca acaacgagtt caacttcttc  180
aagcggcaca tctgcgacgc caacaaggag ggcatgttcc tgttcagggc cgccaggaaa  240
ctgcggcagt tcctgaagat gaactccacc ggcgacttcg acctgcacct gctgaaggtg  300
tccgagggca ccaccatcct gctgaactgc accggacagg tgaagggccg gaaacctgct  360
gctctgggag aggcccaacc caccaagagc ctggaggaga acaagtccct gaaggagcag  420
aagaagctga acgacctgtg cttcctgaag aggctgctgc aggagatcaa gacctgctgg  480
aacaagatcc tgatgggcac caaggagcat agcggcacaa ccaacacagt cgctgcctat  540
aacctcactt ggaagagcac caacttcaaa accatcctcg aatgggaacc caaacccgtt  600
aaccaagttt acaccgtgca gatcagcacc aagtccggcg actggaagtc caaatgtttc  660
tataccaccg acaccgagtg cgatctcacc gatgagatcg tgaaagatgt gaaacagacc  720
tacctcgccc gggtgtttag ctaccccgcc ggcaatgtgg agagcactgg ttccgctggc  780
gagcctttat acgagaacag ccccgaattt accccttacc tcgagaccaa tttaggacag  840
cccaccatcc aaagctttga gcaagttggc acaaaggtga atgtgacagt ggaggacgag  900
cggactttag tgcggcggaa caacaccttt ctcagcctcc gggatgtgtt cggcaaagat  960
ttaatctaca cactgtatta ctggaagtcc tcttcctccg gcaagaagac agctaaaacc  1020
aacacaaacg agtttttaat cgacgtggat aaaggcgaaa actactgttt cagcgtgcaa  1080
gctgtgatcc cctcccggac cgtgaatagg aaaagcaccg atagccccgt tgagtgcatg  1140
ggccaagaaa agggcgagtt ccgggagaac tgggtgaacg tcatcagcga tttaaagaag  1200
atcgaagatt taattcagtc catgcatatc gacgccactt tatacacaga atccgacgtg  1260
cacccctctt gtaaggtgac cgccatgaaa tgttttttac tggagctgca agttatctct  1320
ttagagagcg gagacgctag catccacgac accgtggaga atttaatcat tttagccaat  1380
aactctttat ccagcaacgg caacgtgaca gagtccggct gcaaggagtg cgaagagctg  1440
gaggagaaga acatcaagga gtttctgcaa tcctttgtgc acattgtcca gatgttcatc  1500
aatacctcc                                                          1509

SEQ ID NO: 145         moltype = AA  length = 217
FEATURE                Location/Qualifiers
REGION                 1..217
                       note = source = /note="Description of Artificial Sequence:
                        Synthetic7t15-7s sequence"
source                 1..217
                       mol_type = protein
                       organism = synthetic construct
SEQUENCE: 145
DCDIEGKDGK QYESVLMVSI DQLLDSMKEI GSNCLNNEFN FFKRHICDAN KEGMFLFRAA  60
RKLRQFLKMN STGDFDLHLL KVSEGTTILL NCTGQVKGRK PAALGEAQPT KSLEENKSLK  120
EQKKLNDLCF LKRLLQEIKT CWNKILMGTK EHITCPPPMS VEHADIWVKS YSLYSRERYI  180
CNSGFKRKAG TSSLTECVLN KATNVAHWTT PSLKCIR                            217

SEQ ID NO: 146         moltype = DNA  length = 651
FEATURE                Location/Qualifiers
misc_feature           1..651
                       note = source = /note="Description of Artificial Sequence:
                        Synthetic7t15-7s sequence"
```

```
source                  1..651
                        mol_type = other DNA
                        organism = synthetic construct
SEQUENCE: 146
gattgtgata ttgaaggtaa agatggcaaa caatatgaga gtgttctaat ggtcagcatc  60
gatcaattat tggacagcat gaaagaaatt ggtagcaatt gcctgaataa tgaatttaac  120
ttttttaaaa gacatatctg tgatgctaat aaggaaggta tgtttttatt ccgtgctgct  180
cgcaagttga ggcaatttct taaaatgaat agcactggtg attttgatct ccacttatta  240
aaagtttcag aaggcacaac aatactgttg aactgcactg gccaggttaa aggaagaaaa  300
ccagctgccc tgggtgaagc ccaaccaaca aagagtttgg aagaaaataa atctttaaag  360
gaacagaaaa aactgaatga cttgtgtttc ctaaagagac tattacaaga gataaaaact  420
tgttggaata aaattttgat gggcactaaa gaacacatca cgtgccctcc ccccatgtcc  480
gtggaacacg cagacatctg ggtcaagagc tacagcttgt actccaggga gcggtacatt  540
tgtaactctg gtttcaagcg taaagccggc acgtccagcc tgacggagtg cgtgttgaac  600
aaggccacga atgtcgccca ctggacaacc cccagtctca aatgcattag a           651

SEQ ID NO: 147          moltype = AA  length = 235
FEATURE                 Location/Qualifiers
REGION                  1..235
                        note = source = /note="Description of Artificial Sequence:
                         Synthetic7t15-7s sequence"
source                  1..235
                        mol_type = protein
                        organism = synthetic construct
SEQUENCE: 147
MKWVTFISLL FLFSSAYSDC DIEGKDGKQY ESVLMVSIDQ LLDSMKEIGS NCLNNEFNFF  60
KRHICDANKE GMFLFRAARK LRQFLKMNST GDFDLHLLKV SEGTTILLNC TGQVKGRKPA  120
ALGEAQPTKS LEENKSLKEQ KKLNDLCFLK RLLQEIKTCW NKILMGTKEH ITCPPPMSVE  180
HADIWVKSYS LYSRERYICN SGFKRKAGTS SLTECVLNKA TNVAHWTTPS LKCIR       235

SEQ ID NO: 148          moltype = DNA  length = 705
FEATURE                 Location/Qualifiers
misc_feature            1..705
                        note = source = /note="Description of Artificial Sequence:
                         Synthetic7t15-7s sequence"
source                  1..705
                        mol_type = other DNA
                        organism = synthetic construct
SEQUENCE: 148
atgaagtggg tgaccttcat cagcctgctg ttcctgttct ccagcgccta ctccgattgc  60
gacatcgagg gcaaggacgg caagcagtac gagagcgtgc tgatggtgtc catcgaccag  120
ctgctggaca gcatgaagga gatcggctcc aactgcctca acaacgagtt caacttcttc  180
aagcggcaca tctgcgacgc caacaaggag ggcatgttcc tgttcagggc cgccaggaaa  240
ctgcggcagt tcctgaagat gaactccacc ggcgacttcg acctgcacct gctgaaggtg  300
tccgagggca ccaccatcct gctgaactgc accggacagg tgaagggccg gaaacctgct  360
gctctgggag aggcccaacc caccaagagc ctggaggaga acaagtccct gaaggagcag  420
aagaagctga acgacctgtg cttcctgaag aggctgctgc aggagatcaa gacctgctgg  480
aacaagatcc tgatgggcac caaggagcat attacatgcc cccctcccat gagcgtggag  540
cacgccgaca tctgggtgaa gagctatagc ctctacagcc gggagaggta tatctgtaac  600
agcggcttca agaggaaggc cggcaccagc agcctcaccg agtgcgtgct gaataaggct  660
accaacgtgg ctcactggac aacaccctct ttaaagtgca tccgg                  705

SEQ ID NO: 149          moltype = AA  length = 620
FEATURE                 Location/Qualifiers
REGION                  1..620
                        note = source = /note="Description of Artificial Sequence:
                         SyntheticTGFRt15-TGFR sequence"
source                  1..620
                        mol_type = protein
                        organism = synthetic construct
SEQUENCE: 149
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPDSGT TNTVAAYNLT  300
WKSTNFKTIL EWEPKPVNQV YTVQISTKSG DWKSKCFYTT DTECDLTDEI VKDVKQTYLA  360
RVFSYPAGNV ESTGSAGEPL YENSPEFTPY LETNLGQPTI QSFEQVGTKV NVTVEDERTL  420
VRRNNTFLSL RDVFGKDLIY TLYYWKSSSS GKKTAKTNTN EFLIDVDKGE NYCFSVQAVI  480
PSRTVNRKST DSPVECMGQE KGEFRENWVN VISDLKKIED LIQSMHIDAT LYTESDVHPS  540
CKVTAMKCFL LELQVISLES GDASIHDTVE NLIILANNSL SSNGNVTESG CKECEELEEK  600
NIKEFLQSFV HIVQMFINTS                                              620

SEQ ID NO: 150          moltype = DNA  length = 1860
FEATURE                 Location/Qualifiers
misc_feature            1..1860
                        note = source = /note="Description of Artificial Sequence:
                         SyntheticTGFRt15-TGFR sequence"
source                  1..1860
```

```
                        mol_type = other DNA
                        organism = synthetic construct
SEQUENCE: 150
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcagcatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggttttc cacctgcgac aaccagaagt cctgtatgag caactgctcc  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
tacaatacca gcaaccccga cagcggcaca accaacacag tcgctgccta taacctcact  900
tggaagagca ccaacttcaa aaccatcctc gaatgggaac ccaaacccgt taaccaagtt  960
tacaccgtgc agatcagcac caagtccggc gactggaagt ccaaatgttt ctataccacc  1020
gacaccgagt gcgatctcac cgatgagatc gtgaaagatg tgaaacagac ctacctcgcc  1080
cgggtgttta gctaccccgc cggcaatgtg gagagcactg gttccgctgg cgagccttta  1140
tacgagaaca gccccgaatt taccccttac ctcgagacca atttaggaca gcccaccatc  1200
caaagctttg agcaagttgg cacaaaggtg aatgtgacag tggaggacga gcggacttta  1260
gtgcggcgga acaacacctt tctcagcctc cgggatgtgt tcggcaaaga tttaatctac  1320
acactgtatt actggaagtc ctcttcctcc ggcaagaaga cagctaaaac caacacaaac  1380
gagtttttaa tcgacgtgga taaaggcgaa aactactgtt tcagcgtgca agctgtgatc  1440
cctcccgga ccgtgaatag gaaaagcacc gatagccccg ttgagtgcat gggccaagaa  1500
aagggcgagt tccgggagaa ctgggtgaac gtcatcagcg atttaaagaa gatcgaagat  1560
ttaattcagt ccatgcatat cgacgccact ttatacacag aatccgacgt gcacccctct  1620
tgtaaggtga ccgccatgaa atgtttttta ctggagctgc aagttatctc tttagagagc  1680
ggagacgcta gcatccacga caccgtggag aatttaatca ttttagccaa taactcttta  1740
tccagcaacg gcaacgtgac agagtccggc tgcaaggagt gcgaagagct ggaggagaag  1800
aacatcaagg agtttctgca atcctttgtg cacattgtcc agatgttcat caatacctcc  1860

SEQ ID NO: 151          moltype = AA  length = 638
FEATURE                 Location/Qualifiers
REGION                  1..638
                        note = source = /note="Description of Artificial Sequence:
                         SyntheticTGFRt15-TGFR sequence"
source                  1..638
                        mol_type = protein
                        organism = synthetic construct
SEQUENCE: 151
MKWVTFISLL FLFSSAYSIP PHVQKSVNND MIVTDNNGAV KFPQLCKFCD VRFSTCDNQK  60
SCMSNCSITS ICEKPQEVCV AVWRKNDENI TLETVCHDPK LPYHDFILED AASPKCIMKE  120
KKKPGETFFM CSCSSDECND NIIFSEEYNT SNPDGGGGSG GGGSGGGGSI PPHVQKSVNN  180
DMIVTDNNGA VKFPQLCKFC DVRFSTCDNQ KSCMSNCSIT SICEKPQEVC VAVWRKNDEN  240
ITLETVCHDP KLPYHDFILE DAASPKCIMK EKKKPGETFF MCSCSSDECN DNIIFSEEYN  300
TSNPDSGTTN TVAAYNLTWK STNFKTILEW EPKPVNQVYT VQISTKSGDW KSKCFYTTDT  360
ECDLTDEIVK DVKQTYLARV FSYPAGNVES TGSAGEPLYE NSPEFTPYLE TNLGQPTIQS  420
FEQVGTKVNV TVEDERTLVR RNNTFLSLRD VFGKDLIYTL YYWKSSSSGK KTAKTNTNEF  480
LIDVDKGENY CFSVQAVIPS RTVNRKSTDS PVECMGQEKG EFRENWVNVI SDLKKIEDLI  540
QSMHIDATLY TESDVHPSCK VTAMKCFLLE LQVISLESGD ASIHDTVENL IILANNSLSS  600
NGNVTESGCK ECEELEEKNI KEFLQSFVHI VQMFINTS                        638

SEQ ID NO: 152          moltype = DNA  length = 1914
FEATURE                 Location/Qualifiers
misc_feature            1..1914
                        note = source = /note="Description of Artificial Sequence:
                         SyntheticTGFRt15-TGFR sequence"
source                  1..1914
                        mol_type = other DNA
                        organism = synthetic construct
SEQUENCE: 152
atgaagtggg tgaccttcat cagcctgctg ttcctgttct ccagcgccta ctccatcccc  60
ccccatgtgc aaaagagcgt gaacaacgat atgatcgtga ccgacaacaa cggcgccgtg  120
aagtttcccc agctctgcaa gttctgcgat gtcaggttca gcacctgcga taatcagaag  180
tcctgcatgt ccaactgcag catcacctcc atctgcgaga agccccaaga agtgtgcgtg  240
gccgtgtggc ggaaaaatga cgagaacatc accctggaga ccgtgtgtca cgaccccaag  300
ctcccttatc acgacttcat tctggaggac gctgcctccc ccaaatgcat catgaaggag  360
aagaagaagc ccggagagac cttctttatg tgttcctgta gcagcgacga gtgtaacgac  420
aacatcatct tcagcgaaga gtacaacacc agcaaccctg atggaggtgg cggatccgga  480
ggtggaggtt ctggtggagg tgggagtatt cctccccacg tgcagaagag cgtgaataat  540
gacatgatcg tgaccgataa caatggcgcc gtgaaatttc cccagctgtg caaattctgc  600
gatgtgaggt tttccacctg cgacaaccag aagtcctgta tgagcaactg ctccatcacc  660
tccatctgtg agaagcctca ggaggtgtgc gtggctgtct ggcggaagaa tgacgagaat  720
atcaccctgg aaaccgtctg ccacgatccc aagctgccct accacgattt catcctggaa  780
gacgccgcca gccctaagtg catcatgaaa gagaaaaaga agcctggcga gaccttttc  840
```

-continued

```
atgtgctcct gcagcagcga cgaatgcaac gacaatatca tctttagcga ggaatacaat  900
accagcaacc ccgacagcgg cacaaccaac acagtcgctg cctataacct cacttggaag  960
agcaccaact tcaaaaccat cctcgaatgg gaacccaaac ccgttaacca agtttacacc  1020
gtgcagatca gcaccaagtc cggcgactgg aagtccaaat gtttctatac caccgacacc  1080
gagtgcgatc tcaccgatga gatcgtgaaa gatgtgaaac agacctacct cgcccgggtg  1140
tttagctacc ccgccggcaa tgtggagagc actggttccg ctggcgagcc tttatacgag  1200
aacagccccg aatttacccc ttacctcgag accaatttag gacagcccac catccaaagc  1260
tttgagcaag ttggcacaaa ggtgaatgtg acagtggagg acgagcggac tttagtgcgg  1320
cggaacaaca cctttctcag cctccgggat gtgttcggca aagatttaat ctacacactg  1380
tattactgga agtcctcttc ctccggcaag aagacagcta aaaccaacac aaacgagttt  1440
ttaatcgacg tggataaagg cgaaaactac tgtttcagcg tgcaagctgt gatcccctcc  1500
cggaccgtga ataggaaaag caccgatagc cccgttgagt gcatgggcca agaaaagggc  1560
gagttccggg agaactgggt gaacgtcatc agcgatttaa agaagatcga agatttaatt  1620
cagtccatgc atatcgacgc cactttatac acagaatccg acgtgcaccc ctcttgtaag  1680
gtgaccgcca tgaaatgttt tttactggag ctgcaagtta tctctttaga gagcggagac  1740
gctagcatcc acgacaccgt ggagaattta atcattttag ccaataactc tttatccagc  1800
aacggcaacg tgacagagtc cggctgcaag gagtgcgaag agctggagga gaagaacatc  1860
aaggagtttc tgcaatcctt tgtgcacatt gtccagatgt tcatcaatac ctcc        1914

SEQ ID NO: 153          moltype = AA  length = 352
FEATURE                 Location/Qualifiers
REGION                  1..352
                        note = source = /note="Description of Artificial Sequence:
                         SyntheticTGFRt15-TGFR sequence"
source                  1..352
                        mol_type = protein
                        organism = synthetic construct
SEQUENCE: 153
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPDITC PPPMSVEHAD  300
IWVKSYSLYS RERYICNSGF KRKAGTSSLT ECVLNKATNV AHWTTPSLKC IR          352

SEQ ID NO: 154          moltype = DNA  length = 1056
FEATURE                 Location/Qualifiers
misc_feature            1..1056
                        note = source = /note="Description of Artificial Sequence:
                         SyntheticTGFRt15-TGFR sequence"
source                  1..1056
                        mol_type = other DNA
                        organism = synthetic construct
SEQUENCE: 154
atccccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcagcatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggttttc cacctgcgac aaccagaagt cctgtatgag caactgctcc  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
tacaatacca gcaaccccga cattacatgc ccccctccca tgagcgtgga gcacgccgac  900
atctgggtga agagctatag cctctacagc cgggagaggt atatctgtaa cagcggcttc  960
aagaggaagg ccggcaccag cagcctcacc gagtgcgtgc tgaataaggc taccaacgtg  1020
gctcactgga caacaccctc tttaaagtgc atccgg                            1056

SEQ ID NO: 155          moltype = AA  length = 370
FEATURE                 Location/Qualifiers
REGION                  1..370
                        note = source = /note="Description of Artificial Sequence:
                         SyntheticTGFRt15-TGFR sequence"
source                  1..370
                        mol_type = protein
                        organism = synthetic construct
SEQUENCE: 155
MKWVTFISLL FLFSSAYSIP PHVQKSVNND MIVTDNNGAV KFPQLCKFCD VRFSTCDNQK  60
SCMSNCSITS ICEKPQEVCV AVWRKNDENI TLETVCHDPK LPYHDFILED AASPKCIMKE  120
KKKPGETFFM CSCSSDECND NIIFSEEYNT SNPDGGGGSG GGGSGGGGSI PPHVQKSVNN  180
DMIVTDNNGA VKFPQLCKFC DVRFSTCDNQ KSCMSNCSIT SICEKPQEVC VAVWRKNDEN  240
ITLETVCHDP KLPYHDFILE DAASPKCIMK EKKKPGETFF MCSCSSDECN DNIIFSEEYN  300
TSNPDITCPP PMSVEHADIW VKSYSLYSRE RYICNSGFKR KAGTSSLTEC VLNKATNVAH  360
WTTPSLKCIR                                                         370
```

```
SEQ ID NO: 156         moltype = DNA  length = 1110
FEATURE                Location/Qualifiers
misc_feature           1..1110
                       note = source = /note="Description of Artificial Sequence:
                        SyntheticTGFRt15-TGFR sequence"
source                 1..1110
                       mol_type = other DNA
                       organism = synthetic construct
SEQUENCE: 156
atgaagtggg tgaccttcat cagcctgctg ttcctgttct ccagcgccta ctccatcccc  60
ccccatgtgc aaaagagcgt gaacaacgat atgatcgtga ccgacaacaa cggcgccgtg  120
aagtttcccc agctctgcaa gttctgcgat gtcaggttca gcacctgcga taatcagaag  180
tcctgcatgt ccaactgcag catcacctcc atctgcgaga agccccaaga agtgtgcgtg  240
gccgtgtggc ggaaaaatga cgagaacatc accctggaga ccgtgtgtca cgaccccaag  300
ctccccttatc acgacttcat tctggaggac gctgcctccc ccaaatgcat catgaaggag  360
aagaagaagc ccggagagac cttctttatg tgttcctgta gcagcgacga gtgtaacgac  420
aacatcatct tcagcgaaga gtacaacacc agcaaccctg atggaggtgg cggatccgga  480
ggtggaggtt ctggtggagg tgggagtatt cctccccacg tgcagaagag cgtgaataat  540
gacatgatcg tgaccgataa caatggcgcc gtgaaatttc cccagctgtg caaattctgc  600
gatgtgaggt tttccacctg cgacaaccag aagtcctgta tgagcaactg ctccatcacc  660
tccatctgtg agaagcctca ggaggtgtgc gtggctgtct ggcggaagaa tgacgagaat  720
atcaccctgg aaaccgtctg ccacgatccc aagctgccct accacgattt catcctggaa  780
gacgccgcca gccctaagtg catcatgaaa gagaaaaaga agcctggcga gacctttttc  840
atgtgctcct gcagcagcga cgaatgcaac gacaatatca tctttagcga ggaatacaat  900
accagcaacc ccgacattac atgcccccct cccatgagcg tggagcacgc cgacatctgg  960
gtgaagagct atagcctcta cagccgggag aggtatatct gtaacagcgg cttcaagagg  1020
aaggccggca ccagcagcct caccgagtgc gtgctgaata aggctaccaa cgtggctcac  1080
tggacaacac cctctttaaa gtgcatccgg                                1110

SEQ ID NO: 157         moltype = AA  length = 184
FEATURE                Location/Qualifiers
REGION                 1..184
                       note = source = /note="CD137L"
source                 1..184
                       mol_type = protein
                       organism = Homo sapiens
SEQUENCE: 157
REGPELSPDD PAGLLDLRQG MFAQLVAQNV LLIDGPLSWY SDPGLAGVSL TGGLSYKEDT  60
KELVVAKAGV YYVFFQLELR RVVAGEGSGS VSLALHLQPL RSAAGAAALA LTVDLPPASS  120
EARNSAFGFQ GRLLHLSAGQ RLGVHLHTEA RARHAWQLTQ GATVLGLFRV TPEIPAGLPS  180
PRSE                                                            184

SEQ ID NO: 158         moltype = DNA  length = 552
FEATURE                Location/Qualifiers
misc_feature           1..552
                       note = source = /note="CD137L"
source                 1..552
                       mol_type = genomic DNA
                       organism = Homo sapiens
SEQUENCE: 158
cgcgagggtc ccgagctttc gcccgacgat cccgccggcc tcttggacct gcggcagggc  60
atgtttgcgc agctggtggc ccaaaatgtt ctgctgatcg atgggcccct gagctggtac  120
agtgacccag gcctggcagg cgtgtccctg acgggggggc tgagctacaa agaggacacg  180
aaggagctgg tggtggccaa ggctggagtc tactatgtct tctttcaact agagctgcgg  240
cgcgtggtgg ccggcgaggg ctcaggctcc gtttcacttg cgctgcacct gcagccactg  300
cgctctgctg ctggggccgc cgccctggct ttgaccgtgg acctgccacc cgcctcctcc  360
gaggctcgga actcggcctt cggtttccag ggccgcttgc tgcacctgag tgccggccag  420
cgcctgggcg tccatcttca cactgaggcc agggcacgcc atgcctggca gcttacccag  480
ggcgccacag tcttgggact cttccgggtg acccccgaaa tcccagccgg actcccttca  540
ccgaggtcgg aa                                                   552

SEQ ID NO: 159         moltype = AA  length = 165
FEATURE                Location/Qualifiers
REGION                 1..165
                       note = source = /note="CD137L"
source                 1..165
                       mol_type = protein
                       organism = Homo sapiens
SEQUENCE: 159
DPAGLLDLRQ GMFAQLVAQN VLLIDGPLSW YSDPGLAGVS LTGGLSYKED TKELVVAKAG  60
VYYVFFQLEL RRVVAGEGSG SVSLALHLQP LRSAAGAAAL ALTVDLPPAS SEARNSAFGF  120
QGRLLHLSAG QRLGVHLHTE ARARHAWQLT QGATVLGLFR VTPEI               165

SEQ ID NO: 160         moltype = DNA  length = 495
FEATURE                Location/Qualifiers
misc_feature           1..495
                       note = source = /note="CD137L"
source                 1..495
```

```
                         mol_type = genomic DNA
                         organism = Homo sapiens
SEQUENCE: 160
gatcccgccg gcctcttgga cctgcggcag ggcatgtttg cgcagctggt ggcccaaaat  60
gttctgctga tcgatgggcc cctgagctgg tacagtgacc caggcctggc aggcgtgtcc  120
ctgacggggg gcctgagcta caaagaggac acgaaggagc tggtggtggc caaggctgga  180
gtctactatg tcttctttca actagagctg cggcgcgtgg tggccggcga gggctcaggc  240
tccgtttcac ttgcgctgca cctgcagcca ctgcgctctg ctgctggggc cgccgccctg  300
gctttgaccg tggacctgcc acccgcctcc tccgaggctc ggaactcggc cttcggtttc  360
cagggccgct tgctgcacct gagtgccggc cagcgcctgg gcgtccatct tcacactgag  420
gccagggcac gccatgcctg gcagcttacc cagggcgcca cagtcttggg actcttccgg  480
gtgacccccg aaatc                                                  495

SEQ ID NO: 161           moltype = AA  length = 485
FEATURE                  Location/Qualifiers
REGION                   1..485
                         note = source = /note="Description of Artificial Sequence:
                          Synthetic7t15-21s137L sequence"
source                   1..485
                         mol_type = protein
                         organism = synthetic construct
SEQUENCE: 161
DCDIEGKDGK QYESVLMVSI DQLLDSMKEI GSNCLNNEFN FFKRHICDAN KEGMFLFRAA  60
RKLRQFLKMN STGDFDLHLL KVSEGTTILL NCTGQVKGRK PAALGEAQPT KSLEENKSLK  120
EQKKLNDLCF LKRLLQEIKT CWNKILMGTK EHSGTTNTVA AYNLTWKSTN FKTILEWEPK  180
PVNQVYTVQI STKSGDWKSK CFYTTDTECD LTDEIVKDVK QTYLARVFSY PAGNVESTGS  240
AGEPLYENSP EFTPYLETNL GQPTIQSFEQ VGTKVNVTVE DERTLVRRNN TFLSLRDVFG  300
KDLIYTLYYW KSSSSGKKTA KTNTNEFLID VDKGENYCFS VQAVIPSRTV NRKSTDSPVE  360
CMGQEKGEFR ENWVNVISDL KKIEDLIQSM HIDATLYTES DVHPSCKVTA MKCFLLELQV  420
ISLESGDASI HDTVENLIIL ANNSLSSNGN VTESGCKECE ELEEKNIKEF LQSFVHIVQM  480
FINTS                                                             485

SEQ ID NO: 162           moltype = DNA  length = 1455
FEATURE                  Location/Qualifiers
misc_feature             1..1455
                         note = source = /note="Description of Artificial Sequence:
                          Synthetic7t15-21s137L sequence"
source                   1..1455
                         mol_type = other DNA
                         organism = synthetic construct
SEQUENCE: 162
gattgcgaca tcgagggcaa ggacggcaag cagtacgaga gcgtgctgat ggtgtccatc  60
gaccagctgc tggacagcat gaaggagatc ggctccaact gcctcaacaa cgagttcaac  120
ttcttcaagc ggcacatctg cgacgccaac aaggagggca tgttcctgtt cagggccgcc  180
aggaaactgc ggcagttcct gaagatgaac tccaccggcg acttcgacct gcacctgctg  240
aaggtgtccg agggcaccac catcctgctg aactgcaccg gacaggtgaa gggccggaaa  300
cctgctgctc tgggagaggc ccaacccacc aagagcctgg aggagaacaa gtccctgaag  360
gagcagaaga agctgaacga cctgtgcttc ctgaagaggc tgctgcagga gatcaagacc  420
tgctggaaca agatcctgat gggcaccaag gagcatagcg gcacaaccaa cacagtcgct  480
gcctataacc tcacttggaa gagcaccaac ttcaaaacca tcctcgaatg ggaacccaaa  540
cccgttaacc aagtttacac cgtgcagatc agcaccaagt ccggcgactg gaagtccaaa  600
tgtttctata ccaccgacac cgagtgcgat ctcaccgatg agatcgtgaa agatgtgaaa  660
cagacctacc tcgcccgggt gtttagctac cccgccggca atgtggagag cactggttcc  720
gctggcgagc ctttatacga gaacagcccc gaatttaccc cttacctcga gaccaattta  780
ggacagccca ccatccaaag ctttgagcaa gttggcacaa aggtgaatgt gacagtggag  840
gacgagcgga ctttagtgcg gcggaacaac acctttctca gcctccggga tgtgttcggc  900
aaagatttaa tctacacact gtattactgg aagtcctctt cctccggcaa gaagacagct  960
aaaaccaaca caaacgagtt tttaatcgac gtggataaag gcgaaaacta ctgtttcagc  1020
gtgcaagctg tgatccccctc ccggaccgtg aataggaaaa gcaccgatag ccccgttgag  1080
tgcatgggcc aagaaaaggg cgagttccgg gagaactggg tgaacgtcat cagcgattta  1140
aagaagatcg aagatttaat tcagtccatg catatcgacg ccactttata cacagaatcc  1200
gacgtgcacc cctcttgtaa ggtgaccgcc atgaaatgtt ttttactgga gctgcaagtt  1260
atctctttag agagcggaga cgctagcatc cacgacaccg tggagaattt aatcatttta  1320
gccaataact ctttatccag caacggcaac gtgacagagt ccggctgcaa ggagtgcgaa  1380
gagctggagg agaagaacat caaggagttt ctgcaatcct ttgtgcacat tgtccagatg  1440
ttcatcaata cctcc                                                  1455

SEQ ID NO: 163           moltype = AA  length = 503
FEATURE                  Location/Qualifiers
REGION                   1..503
                         note = source = /note="Description of Artificial Sequence:
                          Synthetic7t15-21s137L sequence"
source                   1..503
                         mol_type = protein
                         organism = synthetic construct
SEQUENCE: 163
MKWVTFISLL FLFSSAYSDC DIEGKDGKQY ESVLMVSIDQ LLDSMKEIGS NCLNNEFNFF  60
KRHICDANKE GMFLFRAARK LRQFLKMNST GDFDLHLLKV SEGTTILLNC TGQVKGRKPA  120
ALGEAQPTKS LEENKSLKEQ KKLNDLCFLK RLLQEIKTCW NKILMGTKEH SGTTNTVAAY  180
```

```
NLTWKSTNFK TILEWEPKPV NQVYTVQIST KSGDWKSKCF YTTDTECDLT DEIVKDVKQT  240
YLARVFSYPA GNVESTGSAG EPLYENSPEF TPYLETNLGQ PTIQSFEQVG TKVNVTVEDE  300
RTLVRRNNTF LSLRDVFGKD LIYTLYYWKS SSSGKKTAKT NTNEFLIDVD KGENYCFSVQ  360
AVIPSRTVNR KSTDSPVECM GQEKGEFREN WVNVISDLKK IEDLIQSMHI DATLYTESDV  420
HPSCKVTAMK CFLLELQVIS LESGDASIHD TVENLIILAN NSLSSNGNVT ESGCKECEEL  480
EEKNIKEFLQ SFVHIVQMFI NTS                                         503

SEQ ID NO: 164         moltype = DNA  length = 1509
FEATURE                Location/Qualifiers
misc_feature           1..1509
                       note = source = /note="Description of Artificial Sequence:
                        Synthetic7t15-21s137L sequence"
source                 1..1509
                       mol_type = other DNA
                       organism = synthetic construct
SEQUENCE: 164
atgaagtggg tgaccttcat cagcctgctg ttcctgttct ccagcgccta ctccgattgc  60
gacatcgagg gcaaggacgg caagcagtac gagagcgtgc tgatggtgtc catcgaccag  120
ctgctggaca gcatgaagga gatcggctcc aactgcctca acaacgagtt caacttcttc  180
aagcggcaca tctgcgacgc caacaaggag ggcatgttcc tgttcagggc cgccaggaaa  240
ctgcggcagt tcctgaagat gaactccacc ggcgacttcg acctgcacct gctgaaggtg  300
tccgagggca ccaccatcct gctgaactgc accggacagg tgaagggccg gaaacctgct  360
gctctgggag aggcccaacc caccaagagc ctggaggaga acaagtccct gaaggagcag  420
aagaagctga acgacctgtg cttcctgaag aggctgctgc aggagatcaa gacctgctgg  480
aacaagatcc tgatgggcac caaggagcat agcggcacaa ccaacacagt cgctgcctat  540
aacctcactt ggaagagcac caacttcaaa accatcctcg aatgggaacc caaacccgtt  600
aaccaagttt acaccgtgca gatcagcacc aagtccggcg actggaagtc caaatgtttc  660
tataccaccg acaccgagtg cgatctcacc gatgagatcg tgaaagatgt gaaacagacc  720
tacctcgccc gggtgtttag ctaccccgcc ggcaatgtgg agagcactgg ttccgctggc  780
gagcctttat acgagaacag ccccgaattt accccttacc tcgagaccaa tttaggacag  840
cccaccatcc aaagctttga gcaagttggc acaaaggtga atgtgacagt ggaggacgag  900
cggactttag tgcggcggaa caacaccttt ctcagcctcc gggatgtgtt cggcaaagat  960
ttaatctaca cactgtatta ctggaagtcc tcttcctccg gcaagaagac agctaaaacc  1020
aacacaaacg agtttttaat cgacgtggat aaaggcgaaa actactgttt cagcgtgcaa  1080
gctgtgatcc cctcccggac cgtgaatagg aaaagcaccg atagccccgt tgagtgcatg  1140
ggccaagaaa agggcgagtt ccgggagaac tgggtgaacg tcatcagcga tttaaagaag  1200
atcgaagatt taattcagtc catgcatatc gacgccactt tatacacaga atccgacgtg  1260
cacccctctt gtaaggtgac cgccatgaaa tgtttttac tggagctgca agttatctct  1320
ttagagagcg gagacgctag catccacgac accgtggaga atttaatcat tttagccaat  1380
aactctttat ccagcaacgg caacgtgaca gagtccggct gcaaggagtg cgaagagctg  1440
gaggagaaga acatcaagga gtttctgcaa tcctttgtgc acattgtcca gatgttcatc  1500
aatacctcc                                                         1509

SEQ ID NO: 165         moltype = AA  length = 397
FEATURE                Location/Qualifiers
REGION                 1..397
                       note = source = /note="Description of Artificial Sequence:
                        Synthetic7t15-21s137L sequence"
source                 1..397
                       mol_type = protein
                       organism = synthetic construct
SEQUENCE: 165
QGQDRHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH  120
QHLSSRTHGS EDSITCPPPM SVEHADIWVK SYSLYSRERY ICNSGFKRKA GTSSLTECVL  180
NKATNVAHWT TPSLKCIRGG GGSGGGGSGG GGSREGPELS PDDPAGLLDL RQGMFAQLVA  240
QNVLLIDGPL SWYSDPGLAG VSLTGGLSYK EDTKELVVAK AGVYYVFFQL ELRRVVAGEG  300
SGSVSLALHL QPLRSAAGAA ALALTVDLPP ASSEARNSAF GFQGRLLHLS AGQRLGVHLH  360
TEARARHAWQ LTQGATVLGL FRVTPEIPAG LPSPRSE                          397

SEQ ID NO: 166         moltype = DNA  length = 1191
FEATURE                Location/Qualifiers
misc_feature           1..1191
                       note = source = /note="Description of Artificial Sequence:
                        Synthetic7t15-21s137L sequence"
source                 1..1191
                       mol_type = other DNA
                       organism = synthetic construct
SEQUENCE: 166
cagggccagg acaggcacat gatccggatg aggcagctca tcgacatcgt cgaccagctg  60
aagaactacg tgaacgacct ggtgcccgag tttctgcctg cccccgagga cgtggagacc  120
aactgcgagt ggtccgcctt ctcctgcttt cagaaggccc agctgaagtc cgccaacacc  180
ggcaacaacg agcggatcat caacgtgagc atcaagaagc tgaagcggaa gcctccctcc  240
acaaacgccg gcaggaggca gaagcacagg ctgacctgcc ccagctgtga ctcctacgag  300
aagaagcccc ccaaggagtt cctggagagg ttcaagtccc tgctgcagaa gatgatccat  360
cagcacctgt cctccaggac ccacggctcc gaggactcca ttacatgccc ccctcccatg  420
agcgtggagc acgccgacat ctgggtgaag agctatagcc tctacagccg ggagaggtat  480
atctgtaaca gcggcttcaa gaggaaggcc ggcaccagca gcctcaccga gtgcgtgctg  540
aataaggcta ccaacgtggc tcactggaca acaccctctt taaagtgcat ccggggcggt  600
```

```
ggaggatccg gaggaggtgg ctccggcggc ggaggatctc gcgagggtcc cgagctttcg  660
cccgacgatc ccgccggcct cttggacctg cggcagggca tgtttgcgca gctggtggcc  720
caaaatgttc tgctgatcga tgggcccctg agctggtaca gtgacccagg cctggcaggc  780
gtgtccctga cgggggggcct gagctacaaa gaggacacga aggagctggt ggtggccaag  840
gctggagtct actatgtctt ctttcaacta gagctgcggc gcgtggtggc cggcgagggc  900
tcaggctccg tttcacttgc gctgcacctg cagccactgc gctctgctgc tggggccgcc  960
gccctggctt tgaccgtgga cctgccaccc gcctcctccg aggctcggaa ctcggccttc  1020
ggtttccagg gccgcttgct gcacctgagt gccggccagc gcctgggcgt ccatcttcac  1080
actgaggcca gggcacgcca tgcctggcag cttacccagg gcgccacagt cttgggactc  1140
ttccgggtga cccccgaaat cccagccgga ctcccttcac cgaggtcgga a           1191
```

```
SEQ ID NO: 167         moltype = AA  length = 415
FEATURE                Location/Qualifiers
REGION                 1..415
                       note = source = /note="Description of Artificial Sequence:
                        Synthetic7t15-21s137L sequence"
source                 1..415
                       mol_type = protein
                       organism = synthetic construct
SEQUENCE: 167
MKWVTFISLL FLFSSAYSQG QDRHMIRMRQ LIDIVDQLKN YVNDLVPEFL PAPEDVETNC  60
EWSAFSCFQK AQLKSANTGN NERIINVSIK KLKRKPPSTN AGRRQKHRLT CPSCDSYEKK  120
PPKEFLERFK SLLQKMIHQH LSSRTHGSED SITCPPPMSV EHADIWVKSY SLYSRERYIC  180
NSGFKRKAGT SSLTECVLNK ATNVAHWTTP SLKCIRGGGG SGGGGSGGGG SREGPELSPD  240
DPAGLLDLRQ GMFAQLVAQN VLLIDGPLSW YSDPGLAGVS LTGGLSYKED TKELVVAKAG  300
VYYVFFQLEL RRVVAGEGSG SVSLALHLQP LRSAAGAAAL ALTVDLPPAS SEARNSAFGF  360
QGRLLHLSAG QRLGVHLHTE ARARHAWQLT QGATVLGLFR VTPEIPAGLP SPRSE       415
```

```
SEQ ID NO: 168         moltype = DNA  length = 1245
FEATURE                Location/Qualifiers
misc_feature           1..1245
                       note = source = /note="Description of Artificial Sequence:
                        Synthetic7t15-21s137L sequence"
source                 1..1245
                       mol_type = other DNA
                       organism = synthetic construct
SEQUENCE: 168
atgaagtggg tgaccttcat cagcctgctg ttcctgttct ccagcgccta ctcccagggc  60
caggacaggc acatgatccg gatgaggcag ctcatcgaca tcgtcgacca gctgaagaac  120
tacgtgaacg acctggtgcc cgagtttctg cctgcccccg aggacgtgga gaccaactgc  180
gagtggtccg ccttctcctg ctttcagaag gcccagctga agtccgccaa caccggcaac  240
aacgagcgga tcatcaacgt gagcatcaag aagctgaagc ggaagcctcc ctccacaaac  300
gccggcagga ggcagaagca caggctgacc tgccccagct gtgactccta cgagaagaag  360
ccccccaagg agttcctgga gaggttcaag tccctgctgc agaagatgat ccatcagcac  420
ctgtcctcca ggacccacgg ctccgaggac tccattacat gcccccctcc catgagcgtg  480
gagcacgccg acatctgggt gaagagctat agcctctaca gccgggagag gtatatctgt  540
aacagcggct tcaagaggaa ggccggcacc agcagcctca ccgagtgcgt gctgaataag  600
gctaccaacg tggctcactg gacaacaccc tctttaaagt gcatccgggg cggtggagga  660
tccggaggag gtggctccgg cggcggagga tctcgcgagg gtcccgagct ttcgcccgac  720
gatcccgccg gcctcttgga cctgcggcag ggcatgtttg cgcagctggt ggcccaaaat  780
gttctgctga tcgatgggcc cctgagctgg tacagtgacc caggcctggc aggcgtgtcc  840
ctgacggggg gcctgagcta caaagaggac acgaaggagc tggtggtggc caaggctgga  900
gtctactatg tcttctttca actagagctg cggcgcgtgg tggccggcga gggctcaggc  960
tccgtttcac ttgcgctgca cctgcagcca ctgcgctctg ctgctggggc cgccgccctg  1020
gctttgaccg tggacctgcc acccgcctcc tccgaggctc ggaactcggc cttcggtttc  1080
cagggccgct tgctgcacct gagtgccggc cagcgcctgg gcgtccatct tcacactgag  1140
gccagggcac gccatgcctg gcagcttacc cagggcgcca cagtcttggg actcttccgg  1200
gtgacccccg aaatcccagc cggactccct tcaccgaggt cggaa                  1245
```

```
SEQ ID NO: 169         moltype = AA  length = 378
FEATURE                Location/Qualifiers
REGION                 1..378
                       note = source = /note="Description of Artificial Sequence:
                        Synthetic7t15-21s137L sequence"
source                 1..378
                       mol_type = protein
                       organism = synthetic construct
SEQUENCE: 169
QGQDRHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH  120
QHLSSRTHGS EDSITCPPPM SVEHADIWVK SYSLYSRERY ICNSGFKRKA GTSSLTECVL  180
NKATNVAHWT TPSLKCIRGG GGSGGGGSGG GGSDPAGLLD LRQGMFAQLV AQNVLLIDGP  240
LSWYSDPGLA GVSLTGGLSY KEDTKELVVA KAGVYYVFFQ LELRRVVAGE GSGSVSLALH  300
LQPLRSAAGA AALALTVDLP PASSEARNSA FGFQGRLLHL SAGQRLGVHL HTEARARHAW  360
QLTQGATVLG LFRVTPEI                                                378
```

```
SEQ ID NO: 170         moltype = DNA  length = 1134
FEATURE                Location/Qualifiers
misc_feature           1..1134
```

```
                         note = source = /note="Description of Artificial Sequence:
                          Synthetic7t15-21s137L sequence"
source                   1..1134
                         mol_type = other DNA
                         organism = synthetic construct
SEQUENCE: 170
cagggccagg acaggcacat gatccggatg aggcagctca tcgacatcgt cgaccagctg  60
aagaactacg tgaacgacct ggtgcccgag tttctgcctg cccccgagga cgtggagacc  120
aactgcgagt ggtccgcctt ctcctgcttt cagaaggccc agctgaagtc cgccaacacc  180
ggcaacaacg agcggatcat caacgtgagc atcaagaagc tgaagcggaa gcctccctcc  240
acaaacgccg gcaggaggca gaagcacagg ctgacctgcc ccagctgtga ctcctacgag  300
aagaagcccc ccaaggagtt cctggagagg ttcaagtccc tgctgcagaa gatgatccat  360
cagcacctgt cctccaggac ccacggctcc gaggactcca ttacatgccc ccctcccatg  420
agcgtggagc acgccgacat ctgggtgaag agctatagcc tctacagccg ggagaggtat  480
atctgtaaca gcggcttcaa gaggaaggcc ggcaccagca gcctcaccga gtgcgtgctg  540
aataaggcta ccaacgtggc tcactggaca acaccctctt taaagtgcat ccggggcggt  600
ggaggatccg gaggaggtgg ctccggcggc ggaggatctg atcccgccgg cctcttggac  660
ctgcggcagg gcatgtttgc gcagctggtg gcccaaaatg ttctgctgat cgatgggccc  720
ctgagctggt acagtgaccc aggcctggca ggcgtgtccc tgacgggggg cctgagctac  780
aaagaggaca cgaaggagct ggtggtggcc aaggctggag tctactatgt cttctttcaa  840
ctagagctgc ggcgcgtggt ggccggcgag ggctcaggct ccgtttcact tgcgctgcac  900
ctgcagccac tgcgctctgc tgctggggcc gccgccctgg ctttgaccgt ggacctgcca  960
cccgcctcct ccgaggctcg gaactcggcc ttcggtttcc agggccgctt gctgcacctg  1020
agtgccggcc agcgcctggg cgtccatctt cacactgagg ccagggcacg ccatgcctgg  1080
cagcttaccc agggcgccac agtcttggga ctcttccggg tgacccccga aatc        1134

SEQ ID NO: 171           moltype = AA  length = 396
FEATURE                  Location/Qualifiers
REGION                   1..396
                         note = source = /note="Description of Artificial Sequence:
                          Synthetic7t15-21s137L sequence"
source                   1..396
                         mol_type = protein
                         organism = synthetic construct
SEQUENCE: 171
MKWVTFISLL FLFSSAYSQG QDRHMIRMRQ LIDIVDQLKN YVNDLVPEFL PAPEDVETNC  60
EWSAFSCFQK AQLKSANTGN NERIINVSIK KLKRKPPSTN AGRRQKHRLT CPSCDSYEKK  120
PPKEFLERFK SLLQKMIHQH LSSRTHGSED SITCPPPMSV EHADIWVKSY SLYSRERYIC  180
NSGFKRKAGT SSLTECVLNK ATNVAHWTTP SLKCIRGGGG SGGGGSGGGG SDPAGLLDLR  240
QGMFAQLVAQ NVLLIDGPLS WYSDPGLAGV SLTGGLSYKE DTKELVVAKA GVYYVFFQLE  300
LRRVVAGEGS GSVSLALHLQ PLRSAAGAAA LALTVDLPPA SSEARNSAFG FQGRLLHLSA  360
GQRLGVHLHT EARARHAWQL TQGATVLGLF RVTPEI                            396

SEQ ID NO: 172           moltype = DNA  length = 1188
FEATURE                  Location/Qualifiers
misc_feature             1..1188
                         note = source = /note="Description of Artificial Sequence:
                          Synthetic7t15-21s137L sequence"
source                   1..1188
                         mol_type = other DNA
                         organism = synthetic construct
SEQUENCE: 172
atgaagtggg tgaccttcat cagcctgctg ttcctgttct ccagcgccta ctcccagggc  60
caggacaggc acatgatccg gatgaggcag ctcatcgaca tcgtcgacca gctgaagaac  120
tacgtgaacg acctggtgcc cgagtttctg cctgcccccg aggacgtgga gaccaactgc  180
gagtggtccg ccttctcctg ctttcagaag gcccagctga agtccgccaa caccggcaac  240
aacgagcgga tcatcaacgt gagcatcaag aagctgaagc ggaagcctcc ctccacaaac  300
gccggcagga ggcagaagca caggctgacc tgccccagct gtgactccta cgagaagaag  360
ccccccaagg agttcctgga gaggttcaag tccctgctgc agaagatgat ccatcagcac  420
ctgtcctcca ggacccacgg ctccgaggac tccattacat gcccccctcc catgagcgtg  480
gagcacgccg acatctgggt gaagagctat agcctctaca gccgggagag gtatatctgt  540
aacagcggct tcaagaggaa ggccggcacc agcagcctca ccgagtgcgt gctgaataag  600
gctaccaacg tggctcactg gacaacaccc tctttaaagt gcatccgggg cggtggagga  660
tccggaggag gtggctccgg cggcggagga tctgatcccg ccggcctctt ggacctgcgg  720
cagggcatgt ttgcgcagct ggtggcccaa aatgttctgc tgatcgatgg gcccctgagc  780
tggtacagtg acccaggcct ggcaggcgtg tccctgacgg ggggcctgag ctacaaagag  840
gacacgaagg agctggtggt ggccaaggct ggagtctact atgtcttctt tcaactagag  900
ctgcggcgcg tggtggccgg cgagggctca ggctccgttt cacttgcgct gcacctgcag  960
ccactgcgct ctgctgctgg ggccgccgcc ctggctttga ccgtggacct gccacccgcc  1020
tcctccgagg ctcggaactc ggccttcggt ttccagggcc gcttgctgca cctgagtgcc  1080
ggccagcgcc tgggcgtcca tcttcacact gaggccaggg cacgccatgc ctggcagctt  1140
acccagggcg ccacagtctt gggactcttc cgggtgaccc ccgaaatc                1188

SEQ ID NO: 173           moltype = AA  length = 485
FEATURE                  Location/Qualifiers
REGION                   1..485
                         note = source = /note="Description of Artificial Sequence:
                          Synthetic7t15-TGFRs sequence"
source                   1..485
```

```
                        mol_type = protein
                        organism = synthetic construct
SEQUENCE: 173
DCDIEGKDGK QYESVLMVSI DQLLDSMKEI GSNCLNNEFN FFKRHICDAN KEGMFLFRAA  60
RKLRQFLKMN STGDFDLHLL KVSEGTTILL NCTGQVKGRK PAALGEAQPT KSLEENKSLK  120
EQKKLNDLCF LKRLLQEIKT CWNKILMGTK EHSGTTNTVA AYNLTWKSTN FKTILEWEPK  180
PVNQVYTVQI STKSGDWKSK CFYTTDTECD LTDEIVKDVK QTYLARVFSY PAGNVESTGS  240
AGEPLYENSP EFTPYLETNL GQPTIQSFEQ VGTKVNVTVE DERTLVRRNN TFLSLRDVFG  300
KDLIYTLYYW KSSSSGKKTA KTNTNEFLID VDKGENYCFS VQAVIPSRTV NRKSTDSPVE  360
CMGQEKGEFR ENWVNVISDL KKIEDLIQSM HIDATLYTES DVHPSCKVTA MKCFLLELQV  420
ISLESGDASI HDTVENLIIL ANNSLSSNGN VTESGCKECE ELEEKNIKEF LQSFVHIVQM  480
FINTS                                                             485

SEQ ID NO: 174          moltype = DNA  length = 1455
FEATURE                 Location/Qualifiers
misc_feature            1..1455
                        note = source = /note="Description of Artificial Sequence:
                         Synthetic7t15-TGFRs sequence"
source                  1..1455
                        mol_type = other DNA
                        organism = synthetic construct
SEQUENCE: 174
gattgcgaca tcgagggcaa ggacggcaag cagtacgaga gcgtgctgat ggtgtccatc  60
gaccagctgc tggacagcat gaaggagatc ggctccaact gcctcaacaa cgagttcaac  120
ttcttcaagc ggcacatctg cgacgccaac aaggagggca tgttcctgtt cagggccgcc  180
aggaaactgc ggcagttcct gaagatgaac tccaccggcg acttcgacct gcacctgctg  240
aaggtgtccg agggcaccac catcctgctg aactgcaccg gacaggtgaa gggccggaaa  300
cctgctgctc tgggagaggc ccaacccacc aagagcctgg aggagaacaa gtccctgaag  360
gagcagaaga agctgaacga cctgtgcttc ctgaagaggc tgctgcagga gatcaagacc  420
tgctggaaca agatcctgat gggcaccaag gagcatagcg gcacaaccaa cacagtcgct  480
gcctataacc tcacttggaa gagcaccaac ttcaaaacca tcctcgaatg ggaacccaaa  540
cccgttaacc aagtttacac cgtgcagatc agcaccaagt ccggcgactg gaagtccaaa  600
tgtttctata ccaccgacac cgagtgcgat ctcaccgatg agatcgtgaa agatgtgaaa  660
cagacctacc tcgcccgggt gtttagctac cccgccggca atgtggagag cactggttcc  720
gctggcgagc ctttatacga gaacagcccc gaatttaccc cttacctcga gaccaattta  780
ggacagccca ccatccaaag ctttgagcaa gttggcacaa aggtgaatgt gacagtggag  840
gacgagcgga ctttagtgcg gcggaacaac acctttctca gcctccggga tgtgttcggc  900
aaagatttaa tctacacact gtattactgg aagtcctctt cctccggcaa gaagacagct  960
aaaaccaaca caaacgagtt tttaatcgac gtggataaag gcgaaaacta ctgtttcagc  1020
gtgcaagctg tgatcccctc ccggaccgtg aataggaaaa gcaccgatag ccccgttgag  1080
tgcatgggcc aagaaaaggg cgagttccgg gagaactggg tgaacgtcat cagcgattta  1140
aagaagatcg aagatttaat tcagtccatg catatcgacg ccactttata cacagaatcc  1200
gacgtgcacc cctcttgtaa ggtgaccgcc atgaaatgtt ttttactgga gctgcaagtt  1260
atctctttag agagcggaga cgctagcatc cacgacaccg tggagaattt aatcatttta  1320
gccaataact ctttatccag caacggcaac gtgacagagt ccggctgcaa ggagtgcgaa  1380
gagctggagg agaagaacat caaggagttt ctgcaatcct ttgtgcacat tgtccagatg  1440
ttcatcaata cctcc                                                  1455

SEQ ID NO: 175          moltype = AA  length = 502
FEATURE                 Location/Qualifiers
REGION                  1..502
                        note = source = /note="Description of Artificial Sequence:
                         Synthetic7t15-TGFRs sequence"
source                  1..502
                        mol_type = protein
                        organism = synthetic construct
SEQUENCE: 175
MKWVTFISLL FLFSSAYSDC DIEGKDGKQY ESVLMVSIDQ LLDSMKEIGS NCLNNEFNFF  60
KRHICDANKE GMFLFRAARK LRQFLKMNST GDFDLHLLKV SEGTTILLNC TGQVKGRKPA  120
ALGEAQPTKS LEENKSLKEQ KKLNDLCFLK RLLQEIKTCW NKILMGTKEH SGTTNTVAAY  180
NLTWKSTNFK TILEWEPKPV NQVYTVQIST KSGDWKSKCF YTTDTECDLT DEIVKDVKQT  240
YLARVFSYPA GNVESTGSAG EPLYENSPEF TPYLETNLGQ PTIQSFEQVG TKVNVTVEDE  300
RTLVRRNNTF LSLRDVFGKD LIYTLYYWKS SSSGKKTAKT NTNEFLIDVD KGENYCFSVQ  360
AVIPSRTVNR KSTDSPVECM GQEKGEFREN WVNVISDLKK IEDLIQSMHI DATLYTESDV  420
HPSCKVTAMK CFLLELQVIS LESGDASIHD TVENLIILAN NSLSSNGNVT ESGCKECEEL  480
EEKNIKEFLQ SFVHIVQMFI NT                                          502

SEQ ID NO: 176          moltype = DNA  length = 1509
FEATURE                 Location/Qualifiers
misc_feature            1..1509
                        note = source = /note="Description of Artificial Sequence:
                         Synthetic7t15-TGFRs sequence"
source                  1..1509
                        mol_type = other DNA
                        organism = synthetic construct
SEQUENCE: 176
atgaagtggg tgaccttcat cagcctgctg ttcctgttct ccagcgccta ctccgattgc  60
gacatcgagg gcaaggacgg caagcagtac gagagcgtgc tgatggtgtc catcgaccag  120
ctgctggaca gcatgaagga gatcggctcc aactgcctca acaacgagtt caacttcttc  180
```

-continued

```
aagcggcaca tctgcgacgc caacaaggag ggcatgttcc tgttcagggc cgccaggaaa  240
ctgcggcagt tcctgaagat gaactccacc ggcgacttcg acctgcacct gctgaaggtg  300
tccgagggca ccaccatcct gctgaactgc accggacagg tgaagggccg gaaacctgct  360
gctctgggag aggcccaacc caccaagagc ctggaggaga acaagtccct gaaggagcag  420
aagaagctga acgacctgtg cttcctgaag aggctgctgc aggagatcaa gacctgctgg  480
aacaagatcc tgatgggcac caaggagcat agcggcacaa ccaacacagt cgctgcctat  540
aacctcactt ggaagagcac caacttcaaa accatcctcg aatgggaacc caaacccgtt  600
aaccaagttt acaccgtgca gatcagcacc aagtccggcg actggaagtc caaatgtttc  660
tataccaccg acaccgagtg cgatctcacc gatgagatcg tgaaagatgt gaaacagacc  720
tacctcgccc gggtgtttag ctaccccgcc ggcaatgtgg agagcactgg ttccgctggc  780
gagcctttat acgagaacag ccccgaattt accccttacc tcgagaccaa tttaggacag  840
cccaccatcc aaagctttga gcaagttggc acaaaggtga atgtgacagt ggaggacgag  900
cggactttag tgcggcggaa caacaccttt ctcagcctcc gggatgtgtt cggcaaagat  960
ttaatctaca cactgtatta ctggaagtcc tcttcctccg gcaagaagac agctaaaacc  1020
aacacaaacg agtttttaat cgacgtggat aaaggcgaaa actactgttt cagcgtgcaa  1080
gctgtgatcc cctcccggac cgtgaatagg aaaagcaccg atagccccgt tgagtgcatg  1140
ggccaagaaa agggcgagtt ccgggagaac tgggtgaacg tcatcagcga tttaaagaag  1200
atcgaagatt taattcagtc catgcatatc gacgccactt tatacacaga atccgacgtg  1260
cacccctctt gtaaggtgac cgccatgaaa tgtttttac tggagctgca agttatctct  1320
ttagagagcg gagacgctag catccacgac accgtggaga atttaatcat tttagccaat  1380
aactctttat ccagcaacgg caacgtgaca gagtccggct gcaaggagtg cgaagagctg  1440
gaggagaaga acatcaagga gtttctgcaa tcctttgtgc acattgtcca gatgttcatc  1500
aatacctcc                                                          1509
```

```
SEQ ID NO: 177          moltype = AA  length = 352
FEATURE                 Location/Qualifiers
REGION                  1..352
                        note = source = /note="Description of Artificial Sequence:
                         Synthetic7t15-TGFRs sequence"
source                  1..352
                        mol_type = protein
                        organism = synthetic construct
SEQUENCE: 177
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPDITC PPPMSVEHAD  300
IWVKSYSLYS RERYICNSGF KRKAGTSSLT ECVLNKATNV AHWTTPSLKC IR          352
```

```
SEQ ID NO: 178          moltype = DNA  length = 1056
FEATURE                 Location/Qualifiers
misc_feature            1..1056
                        note = source = /note="Description of Artificial Sequence:
                         Synthetic7t15-TGFRs sequence"
source                  1..1056
                        mol_type = other DNA
                        organism = synthetic construct
SEQUENCE: 178
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcagcatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggttttc cacctgcgac aaccagaagt cctgtatgag caactgctcc  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
tacaatacca gcaaccccga cattacatgc ccccctccca tgagcgtgga gcacgccgac  900
atctgggtga agagctatag cctctacagc cgggagaggt atatctgtaa cagcggcttc  960
aagaggaagg ccggcaccag cagcctcacc gagtgcgtgc tgaataaggc taccaacgtg  1020
gctcactgga caacaccctc tttaaagtgc atccgg                            1056
```

```
SEQ ID NO: 179          moltype = AA  length = 370
FEATURE                 Location/Qualifiers
REGION                  1..370
                        note = source = /note="Description of Artificial Sequence:
                         Synthetic7t15-TGFRs sequence"
source                  1..370
                        mol_type = protein
                        organism = synthetic construct
SEQUENCE: 179
MKWVTFISLL FLFSSAYSIP PHVQKSVNND MIVTDNNGAV KFPQLCKFCD VRFSTCDNQK  60
SCMSNCSITS ICEKPQEVCV AVWRKNDENI TLETVCHDPK LPYHDFILED AASPKCIMKE  120
```

```
KKKPGETFFM CSCSSDECND NIIFSEEYNT SNPDGGGGSG GGGSGGGGSI PPHVQKSVNN  180
DMIVTDNNGA VKFPQLCKFC DVRFSTCDNQ KSCMSNCSIT SICEKPQEVC VAVWRKNDEN  240
ITLETVCHDP KLPYHDFILE DAASPKCIMK EKKKPGETFF MCSCSSDECN DNIIFSEEYN  300
TSNPDITCPP PMSVEHADIW VKSYSLYSRE RYICNSGFKR KAGTSSLTEC VLNKATNVAH  360
WTTPSLKCIR                                                         370

SEQ ID NO: 180          moltype = DNA  length = 1110
FEATURE                 Location/Qualifiers
misc_feature            1..1110
                        note = source = /note="Description of Artificial Sequence:
                         Synthetic7t15-TGFRs sequence"
source                  1..1110
                        mol_type = other DNA
                        organism = synthetic construct
SEQUENCE: 180
atgaagtggg tgaccttcat cagcctgctg ttcctgttct ccagcgccta ctccatcccc  60
ccccatgtgc aaaagagcgt gaacaacgat atgatcgtga ccgacaacaa cggcgccgtg  120
aagtttcccc agctctgcaa gttctgcgat gtcaggttca gcacctgcga taatcagaag  180
tcctgcatgt ccaactgcag catcacctcc atctgcgaga agccccaaga agtgtgcgtg  240
gccgtgtggc ggaaaaatga cgagaacatc accctggaga ccgtgtgtca cgaccccaag  300
ctcccttatc acgacttcat tctggaggac gctgcctccc ccaaatgcat catgaaggag  360
aagaagaagc ccggagagac cttctttatg tgttcctgta gcagcgacga gtgtaacgac  420
aacatcatct tcagcgaaga gtacaacacc agcaaccctg atggaggtgg cggatccgga  480
ggtggaggtt ctggtggagg tgggagtatt cctccccacg tgcagaagag cgtgaataat  540
gacatgatcg tgaccgataa caatggcgcc gtgaaatttc cccagctgtg caaattctgc  600
gatgtgaggt tttccacctg cgacaaccag aagtcctgta tgagcaactg ctccatcacc  660
tccatctgtg agaagcctca ggaggtgtgc gtggctgtct ggcggaagaa tgacgagaat  720
atcaccctgg aaaccgtctg ccacgatccc aagctgccct accacgattt catcctggaa  780
gacgccgcca gccctaagtg catcatgaaa gagaaaaaga agcctggcga gacctttttc  840
atgtgctcct gcagcagcga cgaatgcaac gacaatatca tctttagcga ggaatacaat  900
accagcaacc ccgacattac atgccccccct cccatgagcg tggagcacgc cgacatctgg  960
gtgaagagct atagcctcta cagccgggag aggtatatct gtaacagcgg cttcaagagg  1020
aaggccggca ccagcagcct caccgagtgc gtgctgaata aggctaccaa cgtggctcac  1080
tggacaacac cctctttaaa gtgcatccgg                                   1110

SEQ ID NO: 181          moltype = AA  length = 620
FEATURE                 Location/Qualifiers
REGION                  1..620
                        note = source = /note="Description of Artificial Sequence:
                         SyntheticTGFRt15-21s137L sequence"
source                  1..620
                        mol_type = protein
                        organism = synthetic construct
SEQUENCE: 181
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPDSGT TNTVAAYNLT  300
WKSTNFKTIL EWEPKPVNQV YTVQISTKSG DWKSKCFYTT DTECDLTDEI VKDVKQTYLA  360
RVFSYPAGNV ESTGSAGEPL YENSPEFTPY LETNLGQPTI QSFEQVGTKV NVTVEDERTL  420
VRRNNTFLSL RDVFGKDLIY TLYYWKSSSS GKKTAKTNTN EFLIDVDKGE NYCFSVQAVI  480
PSRTVNRKST DSPVECMGQE KGEFRENWVN VISDLKKIED LIQSMHIDAT LYTESDVHPS  540
CKVTAMKCFL LELQVISLES GDASIHDTVE NLIILANNSL SSNGNVTESG CKECEELEEK  600
NIKEFLQSFV HIVQMFINTS                                              620

SEQ ID NO: 182          moltype = DNA  length = 1860
FEATURE                 Location/Qualifiers
misc_feature            1..1860
                        note = source = /note="Description of Artificial Sequence:
                         SyntheticTGFRt15-21s137L sequence"
source                  1..1860
                        mol_type = other DNA
                        organism = synthetic construct
SEQUENCE: 182
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcagcatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggttttc cacctgcgac aaccagaagt cctgtatgag caactgctcc  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
```

```
tacaatacca gcaaccccga cagcggcaca accaacacag tcgctgccta taacctcact  900
tggaagagca ccaacttcaa aaccatcctc gaatgggaac ccaaacccgt taaccaagtt  960
tacaccgtgc agatcagcac caagtccggc gactggaagt ccaaatgttt ctataccacc  1020
gacaccgagt gcgatctcac cgatgagatc gtgaaagatg tgaaacagac ctacctcgcc  1080
cgggtgttta gctaccccgc cggcaatgtg gagagcactg gttccgctgg cgagccttta  1140
tacgagaaca gccccgaatt taccccttac ctcgagacca atttaggaca gcccaccatc  1200
caaagctttg agcaagttgg cacaaaggtg aatgtgacag tggaggacga gcggacttta  1260
gtgcggcgga acaacacctt tctcagcctc cgggatgtgt tcggcaaaga tttaatctac  1320
acactgtatt actggaagtc ctcttcctcc ggcaagaaga cagctaaaac caacacaaac  1380
gagtttttaa tcgacgtgga taaaggcgaa aactactgtt tcagcgtgca agctgtgatc  1440
ccctccccgga ccgtgaatag gaaaagcacc gatagccccg ttgagtgcat gggccaagaa  1500
aagggcgagt tccgggagaa ctgggtgaac gtcatcagcg atttaaagaa gatcgaagat  1560
ttaattcagt ccatgcatat cgacgccact ttatacacag aatccgacgt gcacccctct  1620
tgtaaggtga ccgccatgaa atgtttttta ctggagctgc aagttatctc tttagagagc  1680
ggagacgcta gcatccacga caccgtggag aatttaatca ttttagccaa taactcttta  1740
tccagcaacg gcaacgtgac agagtccggc tgcaaggagt gcgaagagct ggaggagaag  1800
aacatcaagg agtttctgca atcctttgtg cacattgtcc agatgttcat caatacctcc  1860

SEQ ID NO: 183         moltype = AA  length = 638
FEATURE                Location/Qualifiers
REGION                 1..638
                       note = source = /note="Description of Artificial Sequence:
                        SyntheticTGFRt15-21s137L sequence"
source                 1..638
                       mol_type = protein
                       organism = synthetic construct
SEQUENCE: 183
MKWVTFISLL FLFSSAYSIP PHVQKSVNND MIVTDNNGAV KFPQLCKFCD VRFSTCDNQK  60
SCMSNCSITS ICEKPQEVCV AVWRKNDENI TLETVCHDPK LPYHDFILED AASPKCIMKE  120
KKKPGETFFM CSCSSDECND NIIFSEEYNT SNPDGGGGSG GGGSGGGGSI PPHVQKSVNN  180
DMIVTDNNGA VKFPQLCKFC DVRFSTCDNQ KSCMSNCSIT SICEKPQEVC VAVWRKNDEN  240
ITLETVCHDP KLPYHDFILE DAASPKCIMK EKKKPGETFF MCSCSSDECN DNIIFSEEYN  300
TSNPDSGTTN TVAAYNLTWK STNFKTILEW EPKPVNQVYT VQISTKSGDW KSKCFYTTDT  360
ECDLTDEIVK DVKQTYLARV FSYPAGNVES TGSAGEPLYE NSPEFTPYLE TNLGQPTIQS  420
FEQVGTKVNV TVEDERTLVR RNNTFLSLRD VFGKDLIYTL YYWKSSSSGK KTAKTNTNEF  480
LIDVDKGENY CFSVQAVIPS RTVNRKSTDS PVECMGQEKG EFRENWVNVI SDLKKIEDLI  540
QSMHIDATLY TESDVHPSCK VTAMKCFLLE LQVISLESGD ASIHDTVENL IILANNSLSS  600
NGNVTESGCK ECEELEEKNI KEFLQSFVHI VQMFINTS                        638

SEQ ID NO: 184         moltype = DNA  length = 1914
FEATURE                Location/Qualifiers
misc_feature           1..1914
                       note = source = /note="Description of Artificial Sequence:
                        SyntheticTGFRt15-21s137L sequence"
source                 1..1914
                       mol_type = other DNA
                       organism = synthetic construct
SEQUENCE: 184
atgaagtggg tgaccttcat cagcctgctg ttcctgttct ccagcgccta ctccatcccc  60
ccccatgtgc aaaagagcgt gaacaacgat atgatcgtga ccgacaacaa cggcgccgtg  120
aagtttcccc agctctgcaa gttctgcgat gtcaggttca gcacctgcga taatcagaag  180
tcctgcatgt ccaactgcag catcacctcc atctgcgaga agccccaaga agtgtgcgtg  240
gccgtgtggc ggaaaaatga cgagaacatc accctggaga ccgtgtgtca cgaccccaag  300
ctcccttatc acgacttcat tctggaggac gctgcctccc ccaaatgcat catgaaggag  360
aagaagaagc ccggagagac cttctttatg tgttcctgta gcagcgacga gtgtaacgac  420
aacatcatct tcagcgaaga gtacaacacc agcaaccctg atggaggtgg cggatccgga  480
ggtggaggtt ctggtggagg tgggagtatt cctccccacg tgcagaagag cgtgaataat  540
gacatgatcg tgaccgataa caatggcgcc gtgaaatttc cccagctgtg caaattctgc  600
gatgtgaggt tttccacctg cgacaaccag aagtcctgta tgagcaactg ctccatcacc  660
tccatctgtg agaagcctca ggaggtgtgc gtggctgtct ggcggaagaa tgacgagaat  720
atcaccctgg aaaccgtctg ccacgatccc aagctgccct accacgattt catcctggaa  780
gacgccgcca gccctaagtg catcatgaaa gagaaaaaga agcctggcga gaccttttc  840
atgtgctcct gcagcagcga cgaatgcaac gacaatatca tctttagcga ggaatacaat  900
accagcaacc ccgacagcgg cacaaccaac acagtcgctg cctataacct cacttggaag  960
agcaccaact tcaaaaccat cctcgaatgg gaacccaaac ccgttaacca agtttacacc  1020
gtgcagatca gcaccaagtc cggcgactgg aagtccaaat gtttctatac caccgacacc  1080
gagtgcgatc tcaccgatga gatcgtgaaa gatgtgaaac agacctacct cgcccgggtg  1140
tttagctacc ccgccggcaa tgtggagagc actggttccg ctggcgagcc tttatacgag  1200
aacagccccg aatttacccc ttacctcgag accaatttag gacagcccac catccaaagc  1260
tttgagcaag ttggcacaaa ggtgaatgtg acagtggagg acgagcggac tttagtgcgg  1320
cggaacaaca cctttctcag cctccgggat gtgttcggca aagatttaat ctacacactg  1380
tattactgga agtcctcttc ctccggcaag aagacagcta aaaccaacac aaacgagttt  1440
ttaatcgacg tggataaagg cgaaaactac tgtttcagcg tgcaagctgt gatcccctcc  1500
cggaccgtga ataggaaaag caccgatagc cccgttgagt gcatgggcca agaaaagggc  1560
gagttccggg agaactgggt gaacgtcatc agcgatttaa agaagatcga agatttaatt  1620
cagtccatgc atatcgacgc cactttatac acagaatccg acgtgcaccc ctcttgtaag  1680
gtgaccgcca tgaaatgttt tttactggag ctgcaagtta tctctttaga gagcggagac  1740
gctagcatcc acgacaccgt ggagaattta atcattttag ccaataactc tttatccagc  1800
aacggcaacg tgacagagtc cggctgcaag gagtgcgaag agctggagga gaagaacatc  1860
```

-continued

```
aaggagtttc tgcaatcctt tgtgcacatt gtccagatgt tcatcaatac ctcc       1914

SEQ ID NO: 185          moltype = AA  length = 397
FEATURE                 Location/Qualifiers
REGION                  1..397
                        note = source = /note="Description of Artificial Sequence:
                         SyntheticTGFRt15-21s137L sequence"
source                  1..397
                        mol_type = protein
                        organism = synthetic construct
SEQUENCE: 185
QGQDRHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH  120
QHLSSRTHGS EDSITCPPPM SVEHADIWVK SYSLYSRERY ICNSGFKRKA GTSSLTECVL  180
NKATNVAHWT TPSLKCIRGG GGSGGGGSGG GGSREGPELS PDDPAGLLDL RQGMFAQLVA  240
QNVLLIDGPL SWYSDPGLAG VSLTGGLSYK EDTKELVVAK AGVYYVFFQL ELRRVVAGEG  300
SGSVSLALHL QPLRSAAGAA ALALTVDLPP ASSEARNSAF GFQGRLLHLS AGQRLGVHLH  360
TEARARHAWQ LTQGATVLGL FRVTPEIPAG LPSPRSE                          397

SEQ ID NO: 186          moltype = DNA  length = 1191
FEATURE                 Location/Qualifiers
misc_feature            1..1191
                        note = source = /note="Description of Artificial Sequence:
                         SyntheticTGFRt15-21s137L sequence"
source                  1..1191
                        mol_type = other DNA
                        organism = synthetic construct
SEQUENCE: 186
cagggccagg acaggcacat gatccggatg aggcagctca tcgacatcgt cgaccagctg  60
aagaactacg tgaacgacct ggtgcccgag tttctgcctg cccccgagga cgtggagacc  120
aactgcgagt ggtccgcctt ctcctgcttt cagaaggccc agctgaagtc cgccaacacc  180
ggcaacaacg agcggatcat caacgtgagc atcaagaagc tgaagcggaa gcctccctcc  240
acaaacgccg gcaggaggca gaagcacagg ctgacctgcc ccagctgtga ctcctacgag  300
aagaagcccc ccaaggagtt cctggagagg ttcaagtccc tgctgcagaa gatgatccat  360
cagcacctgt cctccaggac ccacggctcc gaggactcca ttacatgccc ccctcccatg  420
agcgtggagc acgccgacat ctgggtgaag agctatagcc tctacagccg ggagaggtat  480
atctgtaaca gcggcttcaa gaggaaggcc ggcaccagca gcctcaccga gtgcgtgctg  540
aataaggcta ccaacgtggc tcactggaca acaccctctt taaagtgcat ccggggcggt  600
ggaggatccg gaggaggtgg ctccggcggc ggaggatctc gcgagggtcc cgagctttcg  660
cccgacgatc ccgccggcct cttggacctg cggcagggca tgtttgcgca gctggtggcc  720
caaaatgttc tgctgatcga tgggcccctg agctggtaca gtgacccagg cctggcaggc  780
gtgtccctga cggggggcct gagctacaaa gaggacacga aggagctggt ggtggccaag  840
gctggagtct actatgtctt ctttcaacta gagctgcggc gcgtggtggc cggcgagggc  900
tcaggctccg tttcacttgc gctgcacctg cagccactgc gctctgctgc tggggccgcc  960
gccctggctt tgaccgtgga cctgccaccc gcctcctccg aggctcggaa ctcggccttc  1020
ggtttccagg gccgcttgct gcacctgagt gccggccagc gcctgggcgt ccatcttcac  1080
actgaggcca gggcacgcca tgcctggcag cttacccagg gcgccacagt cttgggactc  1140
ttccgggtga cccccgaaat cccagccgga ctcccttcac cgaggtcgga a          1191

SEQ ID NO: 187          moltype = AA  length = 415
FEATURE                 Location/Qualifiers
REGION                  1..415
                        note = source = /note="Description of Artificial Sequence:
                         SyntheticTGFRt15-21s137L sequence"
source                  1..415
                        mol_type = protein
                        organism = synthetic construct
SEQUENCE: 187
MKWVTFISLL FLFSSAYSQG QDRHMIRMRQ LIDIVDQLKN YVNDLVPEFL PAPEDVETNC  60
EWSAFSCFQK AQLKSANTGN NERIINVSIK KLKRKPPSTN AGRRQKHRLT CPSCDSYEKK  120
PPKEFLERFK SLLQKMIHQH LSSRTHGSED SITCPPPMSV EHADIWVKSY SLYSRERYIC  180
NSGFKRKAGT SSLTECVLNK ATNVAHWTTP SLKCIRGGGG SGGGGSGGGG SREGPELSPD  240
DPAGLLDLRQ GMFAQLVAQN VLLIDGPLSW YSDPGLAGVS LTGGLSYKED TKELVVAKAG  300
VYYVFFQLEL RRVVAGEGSG SVSLALHLQP LRSAAGAAAL ALTVDLPPAS SEARNSAFGF  360
QGRLLHLSAG QRLGVHLHTE ARARHAWQLT QGATVLGLFR VTPEIPAGLP SPRSE       415

SEQ ID NO: 188          moltype = DNA  length = 1245
FEATURE                 Location/Qualifiers
misc_feature            1..1245
                        note = source = /note="Description of Artificial Sequence:
                         SyntheticTGFRt15-21s137L sequence"
source                  1..1245
                        mol_type = other DNA
                        organism = synthetic construct
SEQUENCE: 188
atgaagtggg tgaccttcat cagcctgctg ttcctgttct ccagcgccta ctcccagggc  60
caggacaggc acatgatccg gatgaggcag ctcatcgaca tcgtcgacca gctgaagaac  120
tacgtgaacg acctggtgcc cgagtttctg cctgccccccg aggacgtgga gaccaactgc  180
gagtggtccg ccttctcctg ctttcagaag gcccagctga agtccgccaa caccggcaac  240
```

-continued

```
aacgagcgga tcatcaacgt gagcatcaag aagctgaagc ggaagcctcc ctccacaaac  300
gccggcagga ggcagaagca caggctgacc tgccccagct gtgactccta cgagaagaag  360
ccccccaagg agttcctgga gaggttcaag tccctgctgc agaagatgat ccatcagcac  420
ctgtcctcca ggacccacgg ctccgaggac tccattacat gcccccctcc catgagcgtg  480
gagcacgccg acatctgggt gaagagctat agcctctaca gccgggagag gtatatctgt  540
aacagcggct tcaagaggaa ggccggcacc agcagcctca ccgagtgcgt gctgaataag  600
gctaccaacg tggctcactg gacaacaccc tctttaaagt gcatccgggg cggtggagga  660
tccggaggag gtggctccgg cggcggagga tctcgcgagg gtcccgagct ttcgcccgac  720
gatcccgccg gcctcttgga cctgcggcag ggcatgtttg cgcagctggt ggcccaaaat  780
gttctgctga tcgatgggcc cctgagctgg tacagtgacc caggcctggc aggcgtgtcc  840
ctgacggggg gcctgagcta caaagaggac acgaaggagc tggtggtggc caaggctgga  900
gtctactatg tcttctttca actagagctg cggcgcgtgg tggccggcga gggctcaggc  960
tccgtttcac ttgcgctgca cctgcagcca ctgcgctctg ctgctggggc cgccgccctg  1020
gctttgaccg tggacctgcc acccgcctcc tccgaggctc ggaactcggc cttcggtttc  1080
cagggccgct tgctgcacct gagtgccggc cagcgcctgg gcgtccatct tcacactgag  1140
gccagggcac gccatgcctg gcagcttacc cagggcgcca cagtcttggg actcttccgg  1200
gtgacccccg aaatcccagc cggactccct tcaccgaggt cggaa                  1245

SEQ ID NO: 189         moltype = AA  length = 378
FEATURE                Location/Qualifiers
REGION                 1..378
                       note = source = /note="Description of Artificial Sequence:
                        SyntheticTGFRt15-21s137L sequence"
source                 1..378
                       mol_type = protein
                       organism = synthetic construct
SEQUENCE: 189
QGQDRHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH  120
QHLSSRTHGS EDSITCPPPM SVEHADIWVK SYSLYSRERY ICNSGFKRKA GTSSLTECVL  180
NKATNVAHWT TPSLKCIRGG GGSGGGGSGG GGSDPAGLLD LRQGMFAQLV AQNVLLIDGP  240
LSWYSDPGLA GVSLTGGLSY KEDTKELVVA KAGVYYVFFQ LELRRVVAGE GSGSVSLALH  300
LQPLRSAAGA AALALTVDLP PASSEARNSA FGFQGRLLHL SAGQRLGVHL HTEARARHAW  360
QLTQGATVLG LFRVTPEI                                                378

SEQ ID NO: 190         moltype = DNA  length = 1134
FEATURE                Location/Qualifiers
misc_feature           1..1134
                       note = source = /note="Description of Artificial Sequence:
                        SyntheticTGFRt15-21s137L sequence"
source                 1..1134
                       mol_type = other DNA
                       organism = synthetic construct
SEQUENCE: 190
cagggccagg acaggcacat gatccggatg aggcagctca tcgacatcgt cgaccagctg  60
aagaactacg tgaacgacct ggtgcccgag tttctgcctg cccccgagga cgtggagacc  120
aactgcgagt ggtccgcctt ctcctgcttt cagaaggccc agctgaagtc cgccaacacc  180
ggcaacaacg agcggatcat caacgtgagc atcaagaagc tgaagcggaa gcctccctcc  240
acaaacgccg gcaggaggca gaagcacagg ctgacctgcc ccagctgtga ctcctacgag  300
aagaagcccc ccaaggagtt cctggagagg ttcaagtccc tgctgcagaa gatgatccat  360
cagcacctgt cctccaggac ccacggctcc gaggactcca ttacatgccc ccctcccatg  420
agcgtggagc acgccgacat ctgggtgaag agctatagcc tctacagccg ggagaggtat  480
atctgtaaca gcggcttcaa gaggaaggcc ggcaccagca gcctcaccga gtgcgtgctg  540
aataaggcta ccaacgtggc tcactggaca acaccctctt taaagtgcat ccggggcggt  600
ggaggatccg gaggaggtgg ctccggcggc ggaggatctg atcccgccgg cctcttggac  660
ctgcggcagg gcatgtttgc gcagctggtg gcccaaaatg ttctgctgat cgatgggccc  720
ctgagctggt acagtgaccc aggcctggca ggcgtgtccc tgacgggggg cctgagctac  780
aaagaggaca cgaaggagct ggtggtggcc aaggctggag tctactatgt cttctttcaa  840
ctagagctgc ggcgcgtggt ggccggcgag ggctcaggct ccgtttcact tgcgctgcac  900
ctgcagccac tgcgctctgc tgctggggcc gccgccctgg ctttgaccgt ggacctgcca  960
cccgcctcct ccgaggctcg gaactcggcc ttcggtttcc agggccgctt gctgcacctg  1020
agtgccggcc agcgcctggg cgtccatctt cacactgagg ccagggcacg ccatgcctgg  1080
cagcttaccc agggcgccac agtcttggga ctcttccggg tgacccccga aatc        1134

SEQ ID NO: 191         moltype = AA  length = 396
FEATURE                Location/Qualifiers
REGION                 1..396
                       note = source = /note="Description of Artificial Sequence:
                        SyntheticTGFRt15-21s137L sequence"
source                 1..396
                       mol_type = protein
                       organism = synthetic construct
SEQUENCE: 191
MKWVTFISLL FLFSSAYSQG QDRHMIRMRQ LIDIVDQLKN YVNDLVPEFL PAPEDVETNC  60
EWSAFSCFQK AQLKSANTGN NERIINVSIK KLKRKPPSTN AGRRQKHRLT CPSCDSYEKK  120
PPKEFLERFK SLLQKMIHQH LSSRTHGSED SITCPPPMSV EHADIWVKSY SLYSRERYIC  180
NSGFKRKAGT SSLTECVLNK ATNVAHWTTP SLKCIRGGGG SGGGGSGGGG SDPAGLLDLR  240
QGMFAQLVAQ NVLLIDGPLS WYSDPGLAGV SLTGGLSYKE DTKELVVAKA GVYYVFFQLE  300
LRRVVAGEGS GSVSLALHLQ PLRSAAGAAA LALTVDLPPA SSEARNSAFG FQGRLLHLSA  360
```

-continued

```
GQRLGVHLHT EARARHAWQL TQGATVLGLF RVTPEI                          396

SEQ ID NO: 192          moltype = DNA  length = 1188
FEATURE                 Location/Qualifiers
misc_feature            1..1188
                        note = source = /note="Description of Artificial Sequence:
                         SyntheticTGFRt15-21s137L sequence"
source                  1..1188
                        mol_type = other DNA
                        organism = synthetic construct
SEQUENCE: 192
atgaagtggg tgaccttcat cagcctgctg ttcctgttct ccagcgccta ctcccagggc  60
caggacaggc acatgatccg gatgaggcag ctcatcgaca tcgtcgacca gctgaagaac  120
tacgtgaacg acctggtgcc cgagtttctg cctgccccg aggacgtgga gaccaactgc  180
gagtggtccg ccttctcctg ctttcagaag gcccagctga agtccgccaa caccggcaac  240
aacgagcgga tcatcaacgt gagcatcaag aagctgaagc ggaagcctcc ctccacaaac  300
gccggcagga ggcagaagca caggctgacc tgccccagct gtgactccta cgagaagaag  360
ccccccaagg agttcctgga gaggttcaag tccctgctgc agaagatgat ccatcagcac  420
ctgtcctcca ggacccacgg ctccgaggac tccattacat gcccccctcc catgagcgtg  480
gagcacgccg acatctgggt gaagagctat agcctctaca gccgggagag gtatatctgt  540
aacagcggct tcaagaggaa ggccggcacc agcagcctca ccgagtgcgt gctgaataag  600
gctaccaacg tggctcactg gacaacaccc tctttaaagt gcatccgggg cggtggagga  660
tccggaggag gtggctccgg cggcggagga tctgatcccg ccggcctctt ggacctgcgg  720
cagggcatgt ttgcgcagct ggtggcccaa aatgttctgc tgatcgatgg gcccctgagc  780
tggtacagtg acccaggcct ggcaggcgtg tccctgacgg ggggcctgag ctacaaagag  840
gacacgaagg agctggtggt ggccaaggct ggagtctact atgtcttctt tcaactagag  900
ctgcggcgcg tggtggccgg cgagggctca ggctccgttt cacttgcgct gcacctgcag  960
ccactgcgct ctgctgctgg ggccgccgcc ctggctttga ccgtggacct gccacccgcc  1020
tcctccgagg ctcggaactc ggccttcggt ttccagggcc gcttgctgca cctgagtgcc  1080
ggccagcgcc tgggcgtcca tcttcacact gaggccaggg cacgccatgc ctggcagctt  1140
acccagggcg ccacagtctt gggactcttc cgggtgaccc ccgaaatc             1188

SEQ ID NO: 193          moltype = AA  length = 620
FEATURE                 Location/Qualifiers
REGION                  1..620
                        note = source = /note="Description of Artificial Sequence:
                         SyntheticTGFRt15-TGFRs21 sequence"
source                  1..620
                        mol_type = protein
                        organism = synthetic construct
SEQUENCE: 193
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPDSGT TNTVAAYNLT  300
WKSTNFKTIL EWEPKPVNQV YTVQISTKSG DWKSKCFYTT DTECDLTDEI VKDVKQTYLA  360
RVFSYPAGNV ESTGSAGEPL YENSPEFTPY LETNLGQPTI QSFEQVGTKV NVTVEDERTL  420
VRRNNTFLSL RDVFGKDLIY TLYYWKSSSS GKKTAKTNTN EFLIDVDKGE NYCFSVQAVI  480
PSRTVNRKST DSPVECMGQE KGEFRENWVN VISDLKKIED LIQSMHIDAT LYTESDVHPS  540
CKVTAMKCFL LELQVISLES GDASIHDTVE NLIILANNSL SSNGNVTESG CKECEELEEK  600
NIKEFLQSFV HIVQMFINTS                                            620

SEQ ID NO: 194          moltype = DNA  length = 1860
FEATURE                 Location/Qualifiers
misc_feature            1..1860
                        note = source = /note="Description of Artificial Sequence:
                         SyntheticTGFRt15-TGFRs21 sequence"
source                  1..1860
                        mol_type = other DNA
                        organism = synthetic construct
SEQUENCE: 194
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcagcatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggttttc cacctgcgac aaccagaagt cctgtatgag caactgctcc  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
tacaatacca gcaaccccga cagcggcaca accaacacag tcgctgccta taacctcact  900
tggaagagca ccaacttcaa aaccatcctc gaatgggaac ccaaacccgt taaccaagtt  960
tacaccgtgc agatcagcac caagtccggc gactggaagt ccaaatgttt ctataccacc  1020
```

-continued

```
gacaccgagt gcgatctcac cgatgagatc gtgaaagatg tgaaacagac ctacctcgcc  1080
cgggtgttta gctaccccgc cggcaatgtg gagagcactg gttccgctgg cgagccttta  1140
tacgagaaca gccccgaatt tacccccttac ctcgagacca atttaggaca gcccaccatc  1200
caaagctttg agcaagttgg cacaaaggtg aatgtgacag tggaggacga gcggacttta  1260
gtgcggcgga acaacacctt tctcagcctc cgggatgtgt tcggcaaaga tttaatctac  1320
acactgtatt actggaagtc ctcttcctcc ggcaagaaga cagctaaaac caacacaaac  1380
gagtttttaa tcgacgtgga taaaggcgaa aactactgtt tcagcgtgca agctgtgatc  1440
ccctcccgga ccgtgaatag gaaaagcacc gatagccccg ttgagtgcat gggccaagaa  1500
aagggcgagt tccgggagaa ctgggtgaac gtcatcagcg atttaaagaa gatcgaagat  1560
ttaattcagt ccatgcatat cgacgccact ttatacacag aatccgacgt gcacccctct  1620
tgtaaggtga ccgccatgaa atgtttttta ctggagctgc aagttatctc tttagagagc  1680
ggagacgcta gcatccacga caccgtggag aatttaatca ttttagccaa taactcttta  1740
tccagcaacg gcaacgtgac agagtccggc tgcaaggagt gcgaagagct ggaggagaag  1800
aacatcaagg agtttctgca atcctttgtg cacattgtcc agatgttcat caatacctcc  1860
```

```
SEQ ID NO: 195         moltype = AA  length = 638
FEATURE                Location/Qualifiers
REGION                 1..638
                       note = source = /note="Description of Artificial Sequence:
                        SyntheticTGFRt15-TGFRs21 sequence"
source                 1..638
                       mol_type = protein
                       organism = synthetic construct
SEQUENCE: 195
MKWVTFISLL FLFSSAYSIP PHVQKSVNND MIVTDNNGAV KFPQLCKFCD VRFSTCDNQK  60
SCMSNCSITS ICEKPQEVCV AVWRKNDENI TLETVCHDPK LPYHDFILED AASPKCIMKE  120
KKKPGETFFM CSCSSDECND NIIFSEEYNT SNPDGGGGSG GGGSGGGGSI PPHVQKSVNN  180
DMIVTDNNGA VKFPQLCKFC DVRFSTCDNQ KSCMSNCSIT SICEKPQEVC VAVWRKNDEN  240
ITLETVCHDP KLPYHDFILE DAASPKCIMK EKKKPGETFF MCSCSSDECN DNIIFSEEYN  300
TSNPDSGTTN TVAAYNLTWK STNFKTILEW EPKPVNQVYT VQISTKSGDW KSKCFYTTDT  360
ECDLTDEIVK DVKQTYLARV FSYPAGNVES TGSAGEPLYE NSPEFTPYLE TNLGQPTIQS  420
FEQVGTKVNV TVEDERTLVR RNNTFLSLRD VFGKDLIYTL YYWKSSSSGK KTAKTNTNEF  480
LIDVDKGENY CFSVQAVIPS RTVNRKSTDS PVECMGQEKG EFRENWVNVI SDLKKIEDLI  540
QSMHIDATLY TESDVHPSCK VTAMKCFLLE LQVISLESGD ASIHDTVENL IILANNSLSS  600
NGNVTESGCK ECEELEEKNI KEFLQSFVHI VQMFINTS                        638
```

```
SEQ ID NO: 196         moltype = DNA  length = 1914
FEATURE                Location/Qualifiers
misc_feature           1..1914
                       note = source = /note="Description of Artificial Sequence:
                        SyntheticTGFRt15-TGFRs21 sequence"
source                 1..1914
                       mol_type = other DNA
                       organism = synthetic construct
SEQUENCE: 196
atgaagtggg tgaccttcat cagcctgctg ttcctgttct ccagcgccta ctccatcccc  60
ccccatgtgc aaaagagcgt gaacaacgat atgatcgtga ccgacaacaa cggcgccgtg  120
aagtttcccc agctctgcaa gttctgcgat gtcaggttca gcacctgcga taatcagaag  180
tcctgcatgt ccaactgcag catcacctcc atctgcgaga agccccaaga agtgtgcgtg  240
gccgtgtggc ggaaaaatga cgagaacatc accctggaga ccgtgtgtca cgaccccaag  300
ctcccttatc acgacttcat tctggaggac gctgcctccc ccaaatgcat catgaaggag  360
aagaagaagc ccggagagac cttctttatg tgttcctgta gcagcgacga gtgtaacgac  420
aacatcatct tcagcgaaga gtacaacacc agcaaccctg atggaggtgg cggatccgga  480
ggtggaggtt ctggtggagg tgggagtatt cctccccacg tgcagaagag cgtgaataat  540
gacatgatcg tgaccgataa caatggcgcc gtgaaatttc cccagctgtg caaattctgc  600
gatgtgaggt tttccacctg cgacaaccag aagtcctgta tgagcaactg ctccatcacc  660
tccatctgtg agaagcctca ggaggtgtgc gtggctgtct ggcggaagaa tgacgagaat  720
atcaccctgg aaaccgtctg ccacgatccc aagctgccct accacgattt catcctggaa  780
gacgccgcca gccctaagtg catcatgaaa gagaaaaaga agcctggcga gaccttttc  840
atgtgctcct gcagcagcga cgaatgcaac gacaatatca tctttagcga ggaatacaat  900
accagcaacc ccgacagcgg cacaaccaac acagtcgctg cctataacct cacttggaag  960
agcaccaact tcaaaaccat cctcgaatgg gaacccaaac ccgttaacca agtttacacc  1020
gtgcagatca gcaccaagtc cggcgactgg aagtccaaat gtttctatac caccgacacc  1080
gagtgcgatc tcaccgatga gatcgtgaaa gatgtgaaac agacctacct cgcccgggtg  1140
tttagctacc ccgccggcaa tgtggagagc actggttccg ctggcgagcc tttatacgag  1200
aacagccccg aatttacccc ttacctcgag accaatttag gacagcccac catccaaagc  1260
tttgagcaag ttggcacaaa ggtgaatgtg acagtggagg acgagcggac tttagtgcgg  1320
cggaacaaca cctttctcag cctccgggat gtgttcggca aagatttaat ctacacactg  1380
tattactgga agtcctcttc ctccggcaag aagacagcta aaaccaacac aaacgagttt  1440
ttaatcgacg tggataaagg cgaaaactac tgtttcagcg tgcaagctgt gatcccctcc  1500
cggaccgtga ataggaaaag caccgatagc cccgttgagt gcatgggcca agaaaagggc  1560
gagttccggg agaactgggt gaacgtcatc agcgatttaa agaagatcga agatttaatt  1620
cagtccatgc atatcgacgc cactttatac acagaatccg acgtgcaccc ctcttgtaag  1680
gtgaccgcca tgaaatgttt tttactggag ctgcaagtta tctctttaga gagcggagac  1740
gctagcatcc acgacaccgt ggagaattta atcattttag ccaataactc tttatccagc  1800
aacggcaacg tgacagagtc cggctgcaag gagtgcgaag agctggagga gaagaacatc  1860
aaggagtttc tgcaatcctt tgtgcacatt gtccagatgt tcatcaatac ctcc        1914
```

```
SEQ ID NO: 197         moltype = AA  length = 485
```

-continued

```
FEATURE                Location/Qualifiers
REGION                 1..485
                       note = source = /note="Description of Artificial Sequence:
                        SyntheticTGFRt15-TGFRs21 sequence"
source                 1..485
                       mol_type = protein
                       organism = synthetic construct
SEQUENCE: 197
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPDITC PPPMSVEHAD  300
IWVKSYSLYS RERYICNSGF KRKAGTSSLT ECVLNKATNV AHWTTPSLKC IRQGQDRHMI  360
RMRQLIDIVD QLKNYVNDLV PEFLPAPEDV ETNCEWSAFS CFQKAQLKSA NTGNNERIIN  420
VSIKKLKRKP PSTNAGRRQK HRLTCPSCDS YEKKPPKEFL ERFKSLLQKM IHQHLSSRTH  480
GSEDS                                                            485

SEQ ID NO: 198         moltype = DNA  length = 1455
FEATURE                Location/Qualifiers
misc_feature           1..1455
                       note = source = /note="Description of Artificial Sequence:
                        SyntheticTGFRt15-TGFRs21 sequence"
source                 1..1455
                       mol_type = other DNA
                       organism = synthetic construct
SEQUENCE: 198
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcagcatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggttttc cacctgcgac aaccagaagt cctgtatgag caactgctcc  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
tacaatacca gcaaccccga cattacatgc ccccctccca tgagcgtgga gcacgccgac  900
atctgggtga agagctatag cctctacagc cgggagaggt atatctgtaa cagcggcttc  960
aagaggaagg ccggcaccag cagcctcacc gagtgcgtgc tgaataaggc taccaacgtg  1020
gctcactgga caacaccctc tttaaagtgc atccggcagg gccaggacag gcacatgatc  1080
cggatgaggc agctcatcga catcgtcgac cagctgaaga actacgtgaa cgacctggtg  1140
cccgagtttc tgcctgcccc cgaggacgtg gagaccaact gcgagtggtc cgccttctcc  1200
tgctttcaga aggcccagct gaagtccgcc aacaccggca acaacgagcg gatcatcaac  1260
gtgagcatca agaagctgaa gcggaagcct ccctccacaa acgccggcag gaggcagaag  1320
cacaggctga cctgccccag ctgtgactcc tacgagaaga agccccccaa ggagttcctg  1380
gagaggttca agtccctgct gcagaagatg atccatcagc acctgtcctc caggacccac  1440
ggctccgagg actcc                                                 1455

SEQ ID NO: 199         moltype = AA  length = 503
FEATURE                Location/Qualifiers
REGION                 1..503
                       note = source = /note="Description of Artificial Sequence:
                        SyntheticTGFRt15-TGFRs21 sequence"
source                 1..503
                       mol_type = protein
                       organism = synthetic construct
SEQUENCE: 199
MKWVTFISLL FLFSSAYSIP PHVQKSVNND MIVTDNNGAV KFPQLCKFCD VRFSTCDNQK  60
SCMSNCSITS ICEKPQEVCV AVWRKNDENI TLETVCHDPK LPYHDFILED AASPKCIMKE  120
KKKPGETFFM CSCSSDECND NIIFSEEYNT SNPDGGGGSG GGGSGGGGSI PPHVQKSVNN  180
DMIVTDNNGA VKFPQLCKFC DVRFSTCDNQ KSCMSNCSIT SICEKPQEVC VAVWRKNDEN  240
ITLETVCHDP KLPYHDFILE DAASPKCIMK EKKKPGETFF MCSCSSDECN DNIIFSEEYN  300
TSNPDITCPP PMSVEHADIW VKSYSLYSRE RYICNSGFKR KAGTSSLTEC VLNKATNVAH  360
WTTPSLKCIR QGQDRHMIRM RQLIDIVDQL KNYVNDLVPE FLPAPEDVET NCEWSAFSCF  420
QKAQLKSANT GNNERIINVS IKKLKRKPPS TNAGRRQKHR LTCPSCDSYE KKPPKEFLER  480
FKSLLQKMIH QHLSSRTHGS EDS                                        503

SEQ ID NO: 200         moltype = DNA  length = 1509
FEATURE                Location/Qualifiers
misc_feature           1..1509
                       note = source = /note="Description of Artificial Sequence:
                        SyntheticTGFRt15-TGFRs21 sequence"
source                 1..1509
                       mol_type = other DNA
```

-continued

```
                        organism = synthetic construct
SEQUENCE: 200
atgaagtggg tgaccttcat cagcctgctg ttcctgttct ccagcgccta ctccatcccc  60
ccccatgtgc aaaagagcgt gaacaacgat atgatcgtga ccgacaacaa cggcgccgtg  120
aagtttcccc agctctgcaa gttctgcgat gtcaggttca gcacctgcga taatcagaag  180
tcctgcatgt ccaactgcag catcacctcc atctgcgaga agccccaaga agtgtgcgtg  240
gccgtgtggc ggaaaaatga cgagaacatc accctggaga ccgtgtgtca cgaccccaag  300
ctcccttatc acgacttcat tctggaggac gctgcctccc ccaaatgcat catgaaggag  360
aagaagaagc ccggagagac cttctttatg tgttcctgta gcagcgacga gtgtaacgac  420
aacatcatct tcagcgaaga gtacaacacc agcaaccctg atggaggtgg cggatccgga  480
ggtggaggtt ctggtggagg tgggagtatt cctccccacg tgcagaagag cgtgaataat  540
gacatgatcg tgaccgataa caatggcgcc gtgaaatttc cccagctgtg caaattctgc  600
gatgtgaggt tttccacctg cgacaaccag aagtcctgta tgagcaactg ctccatcacc  660
tccatctgtg agaagcctca ggaggtgtgc gtggctgtct ggcggaagaa tgacgagaat  720
atcaccctgg aaaccgtctg ccacgatccc aagctgccct accacgattt catcctggaa  780
gacgccgcca gccctaagtg catcatgaaa gagaaaaaga agcctggcga gacctttttc  840
atgtgctcct gcagcagcga cgaatgcaac gacaatatca tctttagcga ggaatacaat  900
accagcaacc ccgacattac atgcccccct cccatgagcg tggagcacgc cgacatctgg  960
gtgaagagct atagcctcta cagccgggag aggtatatct gtaacagcgg cttcaagagg  1020
aaggccggca ccagcagcct caccgagtgc gtgctgaata aggctaccaa cgtggctcac  1080
tggacaacac cctctttaaa gtgcatccgg cagggccagg acaggcacat gatccggatg  1140
aggcagctca tcgacatcgt cgaccagctg aagaactacg tgaacgacct ggtgcccgag  1200
tttctgcctg cccccgagga cgtggagacc aactgcgagt ggtccgcctt ctcctgcttt  1260
cagaaggccc agctgaagtc cgccaacacc ggcaacaacg agcggatcat caacgtgagc  1320
atcaagaagc tgaagcggaa gcctccctcc acaaacgccg gcaggaggca gaagcacagg  1380
ctgacctgcc ccagctgtga ctcctacgag aagaagcccc ccaaggagtt cctggagagg  1440
ttcaagtccc tgctgcagaa gatgatccat cagcacctgt cctccaggac ccacggctcc  1500
gaggactcc                                                          1509

SEQ ID NO: 201          moltype = AA  length = 620
FEATURE                 Location/Qualifiers
REGION                  1..620
                        note = source = /note="Description of Artificial Sequence:
                         SyntheticTGFRt15-TGFRs16 sequence"
source                  1..620
                        mol_type = protein
                        organism = synthetic construct
SEQUENCE: 201
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPDSGT TNTVAAYNLT  300
WKSTNFKTIL EWEPKPVNQV YTVQISTKSG DWKSKCFYTT DTECDLTDEI VKDVKQTYLA  360
RVFSYPAGNV ESTGSAGEPL YENSPEFTPY LETNLGQPTI QSFEQVGTKV NVTVEDERTL  420
VRRNNTFLSL RDVFGKDLIY TLYYWKSSSS GKKTAKTNTN EFLIDVDKGE NYCFSVQAVI  480
PSRTVNRKST DSPVECMGQE KGEFRENWVN VISDLKKIED LIQSMHIDAT LYTESDVHPS  540
CKVTAMKCFL LELQVISLES GDASIHDTVE NLIILANNSL SSNGNVTESG CKECEELEEK  600
NIKEFLQSFV HIVQMFINTS                                              620

SEQ ID NO: 202          moltype = DNA  length = 1860
FEATURE                 Location/Qualifiers
misc_feature            1..1860
                        note = source = /note="Description of Artificial Sequence:
                         SyntheticTGFRt15-TGFRs16 sequence"
source                  1..1860
                        mol_type = other DNA
                        organism = synthetic construct
SEQUENCE: 202
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcagcatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggttttc cacctgcgac aaccagaagt cctgtatgag caactgctcc  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
tacaatacca gcaaccccga cagcggcaca accaacacag tcgctgccta taacctcact  900
tggaagagca ccaacttcaa aaccatcctc gaatgggaac ccaaacccgt taaccaagtt  960
tacaccgtgc agatcagcac caagtccggc gactggaagt ccaaatgttt ctataccacc  1020
gacaccgagt gcgatctcac cgatgagatc gtgaaagatg tgaaacagac ctacctcgcc  1080
cgggtgttta gctaccccgc cggcaatgtg gagagcactg gttccgctgg cgagccttta  1140
tacgagaaca gccccgaatt taccccttac ctcgagacca atttaggaca gcccaccatc  1200
```

```
caaagctttg agcaagttgg cacaaaggtg aatgtgacag tggaggacga gcggacttta  1260
gtgcggcgga acaacacctt tctcagcctc cgggatgtgt tcggcaaaga tttaatctac  1320
acactgtatt actggaagtc ctcttcctcc ggcaagaaga cagctaaaac caacacaaac  1380
gagtttttaa tcgacgtgga taaaggcgaa aactactgtt tcagcgtgca agctgtgatc  1440
ccctcccgga ccgtgaatag gaaaagcacc gatagccccg ttgagtgcat gggccaagaa  1500
aagggcgagt tccgggagaa ctgggtgaac gtcatcagcg atttaaagaa gatcgaagat  1560
ttaattcagt ccatgcatat cgacgccact ttatacacag aatccgacgt gcacccctct  1620
tgtaaggtga ccgccatgaa atgtttttta ctggagctgc aagttatctc tttagagagc  1680
ggagacgcta gcatccacga caccgtggag aatttaatca ttttagccaa taactcttta  1740
tccagcaacg gcaacgtgac agagtccggc tgcaaggagt gcgaagagct ggaggagaag  1800
aacatcaagg agtttctgca atcctttgtg cacattgtcc agatgttcat caatacctcc  1860
```

```
SEQ ID NO: 203         moltype = AA  length = 638
FEATURE                Location/Qualifiers
REGION                 1..638
                       note = source = /note="Description of Artificial Sequence:
                        SyntheticTGFRt15-TGFRs16 sequence"
source                 1..638
                       mol_type = protein
                       organism = synthetic construct
SEQUENCE: 203
MKWVTFISLL FLFSSAYSIP PHVQKSVNND MIVTDNNGAV KFPQLCKFCD VRFSTCDNQK  60
SCMSNCSITS ICEKPQEVCV AVWRKNDENI TLETVCHDPK LPYHDFILED AASPKCIMKE  120
KKKPGETFFM CSCSSDECND NIIFSEEYNT SNPDGGGGSG GGGSGGGGSI PPHVQKSVNN  180
DMIVTDNNGA VKFPQLCKFC DVRFSTCDNQ KSCMSNCSIT SICEKPQEVC VAVWRKNDEN  240
ITLETVCHDP KLPYHDFILE DAASPKCIMK EKKKPGETFF MCSCSSDECN DNIIFSEEYN  300
TSNPDSGTTN TVAAYNLTWK STNFKTILEW EPKPVNQVYT VQISTKSGDW KSKCFYTTDT  360
ECDLTDEIVK DVKQTYLARV FSYPAGNVES TGSAGEPLYE NSPEFTPYLE TNLGQPTIQS  420
FEQVGTKVNV TVEDERTLVR RNNTFLSLRD VFGKDLIYTL YYWKSSSSGK KTAKTNTNEF  480
LIDVDKGENY CFSVQAVIPS RTVNRKSTDS PVECMGQEKG EFRENWVNVI SDLKKIEDLI  540
QSMHIDATLY TESDVHPSCK VTAMKCFLLE LQVISLESGD ASIHDTVENL IILANNSLSS  600
NGNVTESGCK ECEELEEKNI KEFLQSFVHI VQMFINTS                        638
```

```
SEQ ID NO: 204         moltype = DNA  length = 1914
FEATURE                Location/Qualifiers
misc_feature           1..1914
                       note = source = /note="Description of Artificial Sequence:
                        SyntheticTGFRt15-TGFRs16 sequence"
source                 1..1914
                       mol_type = other DNA
                       organism = synthetic construct
SEQUENCE: 204
atgaagtggg tgaccttcat cagcctgctg ttcctgttct ccagcgccta ctccatcccc  60
ccccatgtgc aaaagagcgt gaacaacgat atgatcgtga ccgacaacaa cggcgccgtg  120
aagtttcccc agctctgcaa gttctgcgat gtcaggttca gcacctgcga taatcagaag  180
tcctgcatgt ccaactgcag catcacctcc atctgcgaga agccccaaga agtgtgcgtg  240
gccgtgtggc ggaaaaatga cgagaacatc accctggaga ccgtgtgtca cgaccccaag  300
ctcccttatc acgacttcat tctggaggac gctgcctccc ccaaatgcat catgaaggag  360
aagaagaagc ccggagagac cttctttatg tgttcctgta gcagcgacga gtgtaacgac  420
aacatcatct tcagcgaaga gtacaacacc agcaaccctg atggaggtgg cggatccgga  480
ggtggaggtt ctggtggagg tgggagtatt cctccccacg tgcagaagag cgtgaataat  540
gacatgatcg tgaccgataa caatggcgcc gtgaaatttc cccagctgtg caaattctgc  600
gatgtgaggt tttccacctg cgacaaccag aagtcctgta tgagcaactg ctccatcacc  660
tccatctgtg agaagcctca ggaggtgtgc gtggctgtct ggcggaagaa tgacgagaat  720
atcaccctgg aaaccgtctg ccacgatccc aagctgccct accacgattt catcctggaa  780
gacgccgcca gccctaagtg catcatgaaa gagaaaaaga agcctggcga gacctttttc  840
atgtgctcct gcagcagcga cgaatgcaac gacaatatca tctttagcga ggaatacaat  900
accagcaacc ccgacagcgg cacaaccaac acagtcgctg cctataacct cacttggaag  960
agcaccaact tcaaaaccat cctcgaatgg gaacccaaac ccgttaacca agtttacacc  1020
gtgcagatca gcaccaagtc cggcgactgg aagtccaaat gtttctatac caccgacacc  1080
gagtgcgatc tcaccgatga gatcgtgaaa gatgtgaaac agacctacct cgcccgggtg  1140
tttagctacc ccgccggcaa tgtggagagc actggttccg ctggcgagcc tttatacgag  1200
aacagccccg aatttacccc ttacctcgag accaatttag gacagcccac catccaaagc  1260
tttgagcaag ttggcacaaa ggtgaatgtg acagtggagg acgagcggac tttagtgcgg  1320
cggaacaaca cctttctcag cctccgggat gtgttcggca aagatttaat ctacacactg  1380
tattactgga agtcctcttc ctccggcaag aagacagcta aaaccaacac aaacgagttt  1440
ttaatcgacg tggataaagg cgaaaactac tgtttcagcg tgcaagctgt gatcccctcc  1500
cggaccgtga ataggaaaag caccgatagc cccgttgagt gcatgggcca agaaaagggc  1560
gagttccggg agaactgggt gaacgtcatc agcgatttaa agaagatcga agatttaatt  1620
cagtccatgc atatcgacgc cactttatac acagaatccg acgtgcaccc ctcttgtaag  1680
gtgaccgcca tgaaatgttt tttactggag ctgcaagtta tctctttaga gagcggagac  1740
gctagcatcc acgacaccgt ggagaattta atcattttag ccaataactc tttatccagc  1800
aacggcaacg tgacagagtc cggctgcaag gagtgcgaag agctggagga gaagaacatc  1860
aaggagtttc tgcaatcctt tgtgcacatt gtccagatgt tcatcaatac ctcc        1914
```

```
SEQ ID NO: 205         moltype = AA  length = 592
FEATURE                Location/Qualifiers
REGION                 1..592
                       note = source = /note="Description of Artificial Sequence:
```

```
                         SyntheticTGFRt15-TGFRs16 sequence"
source                  1..592
                        mol_type = protein
                        organism = synthetic construct
SEQUENCE: 205
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPDITC PPPMSVEHAD  300
IWVKSYSLYS RERYICNSGF KRKAGTSSLT ECVLNKATNV AHWTTPSLKC IRSELTQDPA  360
VSVALGQTVR ITCQGDSLRS YYASWYQQKP GQAPVLVIYG KNNRPSGIPD RFSGSSSGNT  420
ASLTITGAQA EDEADYYCNS RDSSGNHVVF GGGTKLTVGH GGGGSGGGGS GGGGSEVQLV  480
ESGGGVVRPG GSLRLSCAAS GFTFDDYGMS WVRQAPGKGL EWVSGINWNG GSTGYADSVK  540
GRFTISRDNA KNSLYLQMNS LRAEDTAVYY CARGRSLLFD YWGQGTLVTV SR          592

SEQ ID NO: 206          moltype = DNA  length = 1776
FEATURE                 Location/Qualifiers
misc_feature            1..1776
                        note = source = /note="Description of Artificial Sequence:
                         SyntheticTGFRt15-TGFRs16 sequence"
source                  1..1776
                        mol_type = other DNA
                        organism = synthetic construct
SEQUENCE: 206
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcagcatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggttttc cacctgcgac aaccagaagt cctgtatgag caactgctcc  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
tacaatacca gcaaccccga cattacatgc ccccctccca tgagcgtgga gcacgccgac  900
atctgggtga agagctatag cctctacagc cgggagaggt atatctgtaa cagcggcttc  960
aagaggaagg ccggcaccag cagcctcacc gagtgcgtgc tgaataaggc taccaacgtg  1020
gctcactgga caacaccctc tttaaagtgc atccggtccg agctgaccca ggaccctgct  1080
gtgtccgtgg ctctgggcca gaccgtgagg atcacctgcc agggcgactc cctgaggtcc  1140
tactacgcct cctggtacca gcagaagccc ggccaggctc ctgtgctggt gatctacggc  1200
aagaacaaca ggccctccgg catccctgac aggttctccg gatcctcctc cggcaacacc  1260
gcctccctga ccatcacagg cgctcaggcc gaggacgagg ctgactacta ctgcaactcc  1320
agggactcct ccggcaacca tgtggtgttc ggcggcggca ccaagctgac cgtgggccat  1380
ggcggcggcg gctccggagg cggcggcagc ggcggaggag gatccgaggt gcagctggtg  1440
gagtccggag gaggagtggt gaggcctgga ggctccctga ggctgagctg tgctgcctcc  1500
ggcttcacct tcgacgacta cggcatgtcc tgggtgaggc aggctcctgg aaagggcctg  1560
gagtgggtgt ccggcatcaa ctggaacggc ggatccaccg gctacgccga ttccgtgaag  1620
ggcaggttca ccatcagcag ggacaacgcc aagaactccc tgtacctgca gatgaactcc  1680
ctgagggccg aggacaccgc cgtgtactac tgcgccaggg gcaggtccct gctgttcgac  1740
tactggggac agggcaccct ggtgaccgtg tccagg                            1776

SEQ ID NO: 207          moltype = AA  length = 610
FEATURE                 Location/Qualifiers
REGION                  1..610
                        note = source = /note="Description of Artificial Sequence:
                         SyntheticTGFRt15-TGFRs16 sequence"
source                  1..610
                        mol_type = protein
                        organism = synthetic construct
SEQUENCE: 207
MKWVTFISLL FLFSSAYSIP PHVQKSVNND MIVTDNNGAV KFPQLCKFCD VRFSTCDNQK  60
SCMSNCSITS ICEKPQEVCV AVWRKNDENI TLETVCHDPK LPYHDFILED AASPKCIMKE  120
KKKPGETFFM CSCSSDECND NIIFSEEYNT SNPDGGGGSG GGGSGGGGSI PPHVQKSVNN  180
DMIVTDNNGA VKFPQLCKFC DVRFSTCDNQ KSCMSNCSIT SICEKPQEVC VAVWRKNDEN  240
ITLETVCHDP KLPYHDFILE DAASPKCIMK EKKKPGETFF MCSCSSDECN DNIIFSEEYN  300
TSNPDITCPP PMSVEHADIW VKSYSLYSRE RYICNSGFKR KAGTSSLTEC VLNKATNVAH  360
WTTPSLKCIR SELTQDPAVS VALGQTVRIT CQGDSLRSYY ASWYQQKPGQ APVLVIYGKN  420
NRPSGIPDRF SGSSSGNTAS LTITGAQAED EADYYCNSRD SSGNHVVFGG GTKLTVGHGG  480
GGSGGGGSGG GGSEVQLVES GGGVVRPGGS LRLSCAASGF TFDDYGMSWV RQAPGKGLEW  540
VSGINWNGGS TGYADSVKGR FTISRDNAKN SLYLQMNSLR AEDTAVYYCA RGRSLLFDYW  600
GQGTLVTVSR                                                         610

SEQ ID NO: 208          moltype = DNA  length = 1830
FEATURE                 Location/Qualifiers
```

```
misc_feature          1..1830
                      note = source = /note="Description of Artificial Sequence:
                       SyntheticTGFRt15-TGFRs16 sequence"
source                1..1830
                      mol_type = other DNA
                      organism = synthetic construct
SEQUENCE: 208
atgaagtggg tgaccttcat cagcctgctg ttcctgttct ccagcgccta ctccatcccc  60
ccccatgtgc aaaagagcgt gaacaacgat atgatcgtga ccgacaacaa cggcgccgtg  120
aagtttcccc agctctgcaa gttctgcgat gtcaggttca gcacctgcga taatcagaag  180
tcctgcatgt ccaactgcag catcacctcc atctgcgaga agccccaaga agtgtgcgtg  240
gccgtgtggc ggaaaaatga cgagaacatc accctggaga ccgtgtgtca cgaccccaag  300
ctcccttatc acgacttcat tctggaggac gctgcctccc ccaaatgcat catgaaggag  360
aagaagaagc ccggagagac cttctttatg tgttcctgta gcagcgacga gtgtaacgac  420
aacatcatct tcagcgaaga gtacaacacc agcaaccctg atggaggtgg cggatccgga  480
ggtggaggtt ctggtggagg tgggagtatt cctccccacg tgcagaagag cgtgaataat  540
gacatgatcg tgaccgataa caatggcgcc gtgaaatttc cccagctgtg caaattctgc  600
gatgtgaggt tttccacctg cgacaaccag aagtcctgta tgagcaactg ctccatcacc  660
tccatctgtg agaagcctca ggaggtgtgc gtggctgtct ggcggaagaa tgacgagaat  720
atcaccctgg aaaccgtctg ccacgatccc aagctgccct accacgattt catcctggaa  780
gacgccgcca gccctaagtg catcatgaaa gagaaaaaga agcctggcga gaccttttc  840
atgtgctcct gcagcagcga cgaatgcaac gacaatatca tctttagcga ggaatacaat  900
accagcaacc ccgacattac atgcccccct cccatgagcg tggagcacgc cgacatctgg  960
gtgaagagct atagcctcta cagccgggag aggtatatct gtaacagcgg cttcaagagg  1020
aaggccggca ccagcagcct caccgagtgc gtgctgaata aggctaccaa cgtggctcac  1080
tggacaacac cctctttaaa gtgcatccgg tccgagctga cccaggaccc tgctgtgtcc  1140
gtggctctgg gccagaccgt gaggatcacc tgccagggcg actccctgag gtcctactac  1200
gcctcctggt accagcagaa gcccggccag gctcctgtgc tggtgatcta cggcaagaac  1260
aacaggccct ccggcatccc tgacaggttc tccggatcct cctccggcaa caccgcctcc  1320
ctgaccatca caggcgctca ggccgaggac gaggctgact actactgcaa ctccagggac  1380
tcctccggca accatgtggt gttcggcggc ggcaccaagc tgaccgtggg ccatggcggc  1440
ggcggctccg gaggcggcgg cagcggcgga ggaggatccg aggtgcagct ggtggagtcc  1500
ggaggaggag tggtgaggcc tggaggctcc ctgaggctga gctgtgctgc ctccggcttc  1560
accttcgacg actacggcat gtcctgggtg aggcaggctc ctggaaaggg cctggagtgg  1620
gtgtccggca tcaactggaa cggcggatcc accggctacg ccgattccgt gaagggcagg  1680
ttcaccatca gcagggacaa cgccaagaac tccctgtacc tgcagatgaa ctccctgagg  1740
gccgaggaca ccgccgtgta ctactgcgcc aggggcaggt ccctgctgtt cgactactgg  1800
ggacagggca ccctggtgac cgtgtccagg                                1830

SEQ ID NO: 209        moltype = AA  length = 620
FEATURE               Location/Qualifiers
REGION                1..620
                      note = source = /note="Description of Artificial Sequence:
                       SyntheticTGFRt15-TGFRs137 sequence"
source                1..620
                      mol_type = protein
                      organism = synthetic construct
SEQUENCE: 209
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPDSGT TNTVAAYNLT  300
WKSTNFKTIL EWEPKPVNQV YTVQISTKSG DWKSKCFYTT DTECDLTDEI VKDVKQTYLA  360
RVFSYPAGNV ESTGSAGEPL YENSPEFTPY LETNLGQPTI QSFEQVGTKV NVTVEDERTL  420
VRRNNTFLSL RDVFGKDLIY TLYYWKSSSS GKKTAKTNTN EFLIDVDKGE NYCFSVQAVI  480
PSRTVNRKST DSPVECMGQE KGEFRENWVN VISDLKKIED LIQSMHIDAT LYTESDVHPS  540
CKVTAMKCFL LELQVISLES GDASIHDTVE NLIILANNSL SSNGNVTESG CKECEELEEK  600
NIKEFLQSFV HIVQMFINTS                                           620

SEQ ID NO: 210        moltype = DNA  length = 1860
FEATURE               Location/Qualifiers
misc_feature          1..1860
                      note = source = /note="Description of Artificial Sequence:
                       SyntheticTGFRt15-TGFRs137 sequence"
source                1..1860
                      mol_type = other DNA
                      organism = synthetic construct
SEQUENCE: 210
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcagcatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggttttc cacctgcgac aaccagaagt cctgtatgag caactgctcc  600
```

atcacctcca tctgtgagaa gcctcaggag gtgtgcgtgg ctgtctggcg gaagaatgac 660
gagaatatca ccctggaaac cgtctgccac gatcccaagc tgccctacca cgatttcatc 720
ctggaagacg ccgccagccc taagtgcatc atgaaagaga aaaagaagcc tggcgagacc 780
tttttcatgt gctcctgcag cagcgacgaa tgcaacgaca atatcatctt tagcgaggaa 840
tacaatacca gcaaccccga cagcggcaca accaacacag tcgctgccta taacctcact 900
tggaagagca ccaacttcaa aaccatcctc gaatgggaac ccaaacccgt taaccaagtt 960
tacaccgtgc agatcagcac caagtccggc gactggaagt ccaaatgttt ctataccacc 1020
gacaccgagt gcgatctcac cgatgagatc gtgaaagatg tgaaacagac ctacctcgcc 1080
cgggtgttta gctaccccgc cggcaatgtg gagagcactg gttccgctgg cgagccttta 1140
tacgagaaca gccccgaatt taccccttac ctcgagacca atttaggaca gcccaccatc 1200
caaagctttg agcaagttgg cacaaaggtg aatgtgacag tggaggacga gcggacttta 1260
gtgcggcgga acaacacctt tctcagcctc cgggatgtgt tcggcaaaga tttaatctac 1320
acactgtatt actggaagtc ctcttcctcc ggcaagaaga cagctaaaac caacacaaac 1380
gagtttttaa tcgacgtgga taaaggcgaa aactactgtt tcagcgtgca agctgtgatc 1440
cctcccggga ccgtgaatag gaaaagcacc gatagccccg ttgagtgcat gggccaagaa 1500
aagggcgagt tccgggagaa ctgggtgaac gtcatcagcg atttaaagaa gatcgaagat 1560
ttaattcagt ccatgcatat cgacgccact ttatacacag aatccgacgt gcacccctct 1620
tgtaaggtga ccgccatgaa atgtttttta ctggagctgc aagttatctc tttagagagc 1680
ggagacgcta gcatccacga caccgtggag aatttaatca ttttagccaa taactcttta 1740
tccagcaacg gcaacgtgac agagtccggc tgcaaggagt gcgaagagct ggaggagaag 1800
aacatcaagg agtttctgca atcctttgtg cacattgtcc agatgttcat caatacctcc 1860

SEQ ID NO: 211 moltype = AA length = 638
FEATURE Location/Qualifiers
REGION 1..638
note = source = /note="Description of Artificial Sequence:
SyntheticTGFRt15-TGFRs137 sequence"
source 1..638
mol_type = protein
organism = synthetic construct
SEQUENCE: 211
MKWVTFISLL FLFSSAYSIP PHVQKSVNND MIVTDNNGAV KFPQLCKFCD VRFSTCDNQK 60
SCMSNCSITS ICEKPQEVCV AVWRKNDENI TLETVCHDPK LPYHDFILED AASPKCIMKE 120
KKKPGETFFM CSCSSDECND NIIFSEEYNT SNPDGGGGSG GGGSGGGGSI PPHVQKSVNN 180
DMIVTDNNGA VKFPQLCKFC DVRFSTCDNQ KSCMSNCSIT SICEKPQEVC VAVWRKNDEN 240
ITLETVCHDP KLPYHDFILE DAASPKCIMK EKKKPGETFF MCSCSSDECN DNIIFSEEYN 300
TSNPDSGTTN TVAAYNLTWK STNFKTILEW EPKPVNQVYT VQISTKSGDW KSKCFYTTDT 360
ECDLTDEIVK DVKQTYLARV FSYPAGNVES TGSAGEPLYE NSPEFTPYLE TNLGQPTIQS 420
FEQVGTKVNV TVEDERTLVR RNNTFLSLRD VFGKDLIYTL YYWKSSSSGK KTAKTNTNEF 480
LIDVDKGENY CFSVQAVIPS RTVNRKSTDS PVECMGQEKG EFRENWVNVI SDLKKIEDLI 540
QSMHIDATLY TESDVHPSCK VTAMKCFLLE LQVISLESGD ASIHDTVENL IILANNSLSS 600
NGNVTESGCK ECEELEEKNI KEFLQSFVHI VQMFINTS 638

SEQ ID NO: 212 moltype = DNA length = 1914
FEATURE Location/Qualifiers
misc_feature 1..1914
note = source = /note="Description of Artificial Sequence:
SyntheticTGFRt15-TGFRs137 sequence"
source 1..1914
mol_type = other DNA
organism = synthetic construct
SEQUENCE: 212
atgaagtggg tgaccttcat cagcctgctg ttcctgttct ccagcgccta ctccatcccc 60
ccccatgtgc aaaagagcgt gaacaacgat atgatcgtga ccgacaacaa cggcgccgtg 120
aagtttcccc agctctgcaa gttctgcgat gtcaggttca gcacctgcga taatcagaag 180
tcctgcatgt ccaactgcag catcacctcc atctgcgaga agccccaaga agtgtgcgtg 240
gccgtgtggc ggaaaaatga cgagaacatc accctggaga ccgtgtgtca cgaccccaag 300
ctcccttatc acgacttcat tctggaggac gctgcctccc ccaaatgcat catgaaggag 360
aagaagaagc ccggagagac cttctttatg tgttcctgta gcagcgacga gtgtaacgac 420
aacatcatct tcagcgaaga gtacaacacc agcaaccctg atggaggtgg cggatccgga 480
ggtggaggtt ctggtggagg tgggagtatt cctccccacg tgcagaagag cgtgaataat 540
gacatgatcg tgaccgataa caatggcgcc gtgaaatttc cccagctgtg caaattctgc 600
gatgtgaggt tttccacctg cgacaaccag aagtcctgta tgagcaactg ctccatcacc 660
tccatctgtg agaagcctca ggaggtgtgc gtggctgtct ggcggaagaa tgacgagaat 720
atcaccctgg aaaccgtctg ccacgatccc aagctgccct accacgattt catcctggaa 780
gacgccgcca gccctaagtg catcatgaaa gagaaaaaga agcctggcga gacctttttc 840
atgtgctcct gcagcagcga cgaatgcaac gacaatatca tctttagcga ggaatacaat 900
accagcaacc ccgacagcgg cacaaccaac acagtcgctg cctataacct cacttggaag 960
agcaccaact tcaaaaccat cctcgaatgg gaacccaaac ccgttaacca agtttacacc 1020
gtgcagatca gcaccaagtc cggcgactgg aagtccaaat gtttctatac caccgacacc 1080
gagtgcgatc tcaccgatga gatcgtgaaa gatgtgaaac agacctacct cgcccgggtg 1140
tttagctacc ccgccggcaa tgtggagagc actggttccg ctggcgagcc tttatacgag 1200
aacagccccg aatttacccc ttacctcgag accaatttag gacagcccac catccaaagc 1260
tttgagcaag ttggcacaaa ggtgaatgtg acagtggagg acgagcggac tttagtgcgg 1320
cggaacaaca cctttctcag cctccgggat gtgttcggca aagatttaat ctacacactg 1380
tattactgga agtcctcttc ctccggcaag aagacagcta aaaccaacac aaacgagttt 1440
ttaatcgacg tggataaagg cgaaaactac tgtttcagcg tgcaagctgt gatccccctcc 1500
cggaccgtga ataggaaaag caccgatagc cccgttgagt gcatgggcca agaaaagggc 1560
gagttccggg agaactgggt gaacgtcatc agcgatttaa agaagatcga agatttaatt 1620

```
cagtccatgc atatcgacgc cactttatac acagaatccg acgtgcaccc ctcttgtaag  1680
gtgaccgcca tgaaatgttt tttactggag ctgcaagtta tctctttaga gagcggagac  1740
gctagcatcc acgacaccgt ggagaattta atcattttag ccaataactc tttatccagc  1800
aacggcaacg tgacagagtc cggctgcaag gagtgcgaag agctggagga gaagaacatc  1860
aaggagtttc tgcaatcctt tgtgcacatt gtccagatgt tcatcaatac ctcc        1914

SEQ ID NO: 213         moltype = AA  length = 551
FEATURE                Location/Qualifiers
REGION                 1..551
                       note = source = /note="Description of Artificial Sequence:
                        SyntheticTGFRt15-TGFRs137 sequence"
source                 1..551
                       mol_type = protein
                       organism = synthetic construct
SEQUENCE: 213
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPDITC PPPMSVEHAD  300
IWVKSYSLYS RERYICNSGF KRKAGTSSLT ECVLNKATNV AHWTTPSLKC IRGGGGSGGG  360
GSGGGGSREG PELSPDDPAG LLDLRQGMFA QLVAQNVLLI DGPLSWYSDP GLAGVSLTGG  420
LSYKEDTKEL VVAKAGVYYV FFQLELRRVV AGEGSGSVSL ALHLQPLRSA AGAAALALTV  480
DLPPASSEAR NSAFGFQGRL LHLSAGQRLG VHLHTEARAR HAWQLTQGAT VLGLFRVTPE  540
IPAGLPSPRS E                                                       551

SEQ ID NO: 214         moltype = DNA  length = 1653
FEATURE                Location/Qualifiers
misc_feature           1..1653
                       note = source = /note="Description of Artificial Sequence:
                        SyntheticTGFRt15-TGFRs137 sequence"
source                 1..1653
                       mol_type = other DNA
                       organism = synthetic construct
SEQUENCE: 214
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcagcatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggtttc cacctgcgac aaccagaagt cctgtatgag caactgctcc  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
tacaatacca gcaaccccga cattacatgc cccccctccca tgagcgtgga gcacgccgac  900
atctgggtga agagctatag cctctacagc cgggagaggt atatctgtaa cagcggcttc  960
aagaggaagg ccggcaccag cagcctcacc gagtgcgtgc tgaataaggc taccaacgtg  1020
gctcactgga caacaccctc tttaaagtgc atccggggcg gtggaggatc cggaggaggt  1080
ggctccggcg gcggaggatc tcgcgagggt cccgagcttt cgcccgacga tcccgccggc  1140
ctcttggacc tgcggcaggg catgtttgcg cagctggtgg cccaaaatgt tctgctgatc  1200
gatgggcccc tgagctggta cagtgaccca ggcctggcag gcgtgtccct gacgggggc  1260
ctgagctaca aagaggacac gaaggagctg gtggtggcca aggctggagt ctactatgtc  1320
ttctttcaac tagagctgcg gcgcgtggtg gccggcgagg gctcaggctc cgtttcactt  1380
gcgctgcacc tgcagccact gcgctctgct gctggggccg ccgccctggc tttgaccgtg  1440
gacctgccac ccgcctcctc cgaggctcgg aactcggcct tcggtttcca gggccgcttg  1500
ctgcacctga gtgccggcca gcgcctgggc gtccatcttc acactgaggc cagggcacgc  1560
catgcctggc agcttaccca gggcgccaca gtcttgggac tcttccgggt gacccccgaa  1620
atcccagccg gactcccttc accgaggtcg gaa                               1653

SEQ ID NO: 215         moltype = AA  length = 569
FEATURE                Location/Qualifiers
REGION                 1..569
                       note = source = /note="Description of Artificial Sequence:
                        SyntheticTGFRt15-TGFRs137 sequence"
source                 1..569
                       mol_type = protein
                       organism = synthetic construct
SEQUENCE: 215
MKWVTFISLL FLFSSAYSIP PHVQKSVNND MIVTDNNGAV KFPQLCKFCD VRFSTCDNQK  60
SCMSNCSITS ICEKPQEVCV AVWRKNDENI TLETVCHDPK LPYHDFILED AASPKCIMKE  120
KKKPGETFFM CSCSSDECND NIIFSEEYNT SNPDGGGGSG GGGSGGGGSI PPHVQKSVNN  180
DMIVTDNNGA VKFPQLCKFC DVRFSTCDNQ KSCMSNCSIT SICEKPQEVC VAVWRKNDEN  240
ITLETVCHDP KLPYHDFILE DAASPKCIMK EKKKPGETFF MCSCSSDECN DNIIFSEEYN  300
TSNPDITCPP PMSVEHADIW VKSYSLYSRE RYICNSGFKR KAGTSSLTEC VLNKATNVAH  360
```

-continued

```
WTTPSLKCIR GGGGSGGGGS GGGGSREGPE LSPDDPAGLL DLRQGMFAQL VAQNVLLIDG  420
PLSWYSDPGL AGVSLTGGLS YKEDTKELVV AKAGVYYVFF QLELRRVVAG EGSGSVSLAL  480
HLQPLRSAAG AAALALTVDL PPASSEARNS AFGFQGRLLH LSAGQRLGVH LHTEARARHA  540
WQLTQGATVL GLFRVTPEIP AGLPSPRSE                                    569

SEQ ID NO: 216         moltype = DNA  length = 1707
FEATURE                Location/Qualifiers
misc_feature           1..1707
                       note = source = /note="Description of Artificial Sequence:
                        SyntheticTGFRt15-TGFRs137 sequence"
source                 1..1707
                       mol_type = other DNA
                       organism = synthetic construct
SEQUENCE: 216
atgaagtggg tgaccttcat cagcctgctg ttcctgttct ccagcgccta ctccatcccc  60
ccccatgtgc aaaagagcgt gaacaacgat atgatcgtga ccgacaacaa cggcgccgtg  120
aagtttcccc agctctgcaa gttctgcgat gtcaggttca gcacctgcga taatcagaag  180
tcctgcatgt ccaactgcag catcacctcc atctgcgaga agccccaaga agtgtgcgtg  240
gccgtgtggc ggaaaaatga cgagaacatc accctggaga ccgtgtgtca cgaccccaag  300
ctcccttatc acgacttcat tctggaggac gctgcctccc ccaaatgcat catgaaggag  360
aagaagaagc ccggagagac cttctttatg tgttcctgta gcagcgacga gtgtaacgac  420
aacatcatct tcagcgaaga gtacaacacc agcaaccctg atggaggtgg cggatccgga  480
ggtggaggtt ctggtggagg tgggagtatt cctccccacg tgcagaagag cgtgaataat  540
gacatgatcg tgaccgataa caatggcgcc gtgaaatttc cccagctgtg caaattctgc  600
gatgtgaggt tttccacctg cgacaaccag aagtcctgta tgagcaactg ctccatcacc  660
tccatctgtg agaagcctca ggaggtgtgc gtggctgtct ggcggaagaa tgacgagaat  720
atcaccctgg aaaccgtctg ccacgatccc aagctgccct accacgattt catcctggaa  780
gacgccgcca gccctaagtg catcatgaaa gagaaaaaga agcctggcga gacctttttc  840
atgtgctcct gcagcagcga cgaatgcaac gacaatatca tctttagcga ggaatacaat  900
accagcaacc ccgacattac atgcccccct cccatgagcg tggagcacgc cgacatctgg  960
gtgaagagct atagcctcta cagccgggag aggtatatct gtaacagcgg cttcaagagg  1020
aaggccggca ccagcagcct caccgagtgc gtgctgaata aggctaccaa cgtggctcac  1080
tggacaacac cctctttaaa gtgcatccgg ggcggtggag gatccggagg aggtggctcc  1140
ggcggcggag gatctcgcga gggtcccgag ctttcgcccg acgatcccgc cggcctcttg  1200
gacctgcggc agggcatgtt tgcgcagctg gtggcccaaa atgttctgct gatcgatggg  1260
cccctgagct ggtacagtga cccaggcctg gcaggcgtgt ccctgacggg gggcctgagc  1320
tacaaagagg acacgaagga gctggtggtg gccaaggctg gagtctacta tgtcttcttt  1380
caactagagc tgcggcgcgt ggtggccggc gagggctcag gctccgtttc acttgcgctg  1440
cacctgcagc cactgcgctc tgctgctggg gccgccgccc tggctttgac cgtggacctg  1500
ccacccgcct cctccgaggc tcggaactcg gccttcggtt tccagggccg cttgctgcac  1560
ctgagtgccg gccagcgcct gggcgtccat cttcacactg aggccagggc acgccatgcc  1620
tggcagctta cccagggcgc cacagtcttg ggactcttcc gggtgacccc cgaaatccca  1680
gccggactcc cttcaccgag gtcggaa                                      1707

SEQ ID NO: 217         moltype = DNA  length = 720
FEATURE                Location/Qualifiers
misc_feature           1..720
                       note = source = /note="Description of Artificial Sequence:
                        SyntheticIL-18/IL-15RalphaSu sequence"
source                 1..720
                       mol_type = other DNA
                       organism = synthetic construct
SEQUENCE: 217
atgaagtggg tcacatttat ctctttactg ttcctcttct ccagcgccta cagctacttc  60
ggcaaactgg aatccaagct gagcgtgatc cggaatttaa acgaccaagt tctgtttatc  120
gatcaaggta accggcctct gttcgaggac atgaccgact ccgattgccg ggacaatgcc  180
ccccggacca tcttcattat ctccatgtac aaggacagcc agccccgggg catggctgtg  240
acaattagcg tgaagtgtga gaaaatcagc actttatctt gtgagaacaa gatcatctcc  300
tttaaggaaa tgaacccccc cgataacatc aaggacacca agtccgatat catcttcttc  360
cagcggtccg tgcccggtca cgataacaag atgcagttcg aatcctcctc ctacgagggc  420
tactttttag cttgtgaaaa ggagagggat ttattcaagc tgatcctcaa gaaggaggac  480
gagctgggcg atcgttccat catgttcacc gtccaaaacg aggatattac atgcccccct  540
cccatgagcg tggagcacgc cgacatctgg gtgaagagct atagcctcta cagccgggag  600
aggtatatct gtaacagcgg cttcaagagg aaggccggca ccagcagcct caccgagtgc  660
gtgctgaata aggctaccaa cgtggctcac tggacaacac cctctttaaa gtgcatccgg  720

SEQ ID NO: 218         moltype = DNA  length = 2607
FEATURE                Location/Qualifiers
misc_feature           1..2607
                       note = source = /note="Description of Artificial Sequence:
                        SyntheticIL-12/TF/IL-15 sequence"
source                 1..2607
                       mol_type = other DNA
                       organism = synthetic construct
SEQUENCE: 218
atgaaatggg tgacctttat ttctttactg ttcctcttta gcagcgccta ctccatttgg  60
gaactgaaga aggacgtcta cgtggtcgaa ctggactggt atcccgatgc tcccggcgaa  120
atggtggtgc tcacttgtga cacccccgaa gaagacggca tcacttggac cctcgatcag  180
agcagcgagg tgctgggctc cggaaagacc ctcacaatcc aagttaagga gttcggagac  240
```

-continued

```
gctggccaat acacatgcca caagggaggc gaggtgctca gccattcctt attattatta  300
cacaagaagg aagacggaat ctggtccacc gacattttaa aagatcagaa ggagcccaag  360
aataagacct ttttaaggtg tgaggccaaa aactacagcg gtcgtttcac ttgttggtgg  420
ctgaccacca tttccaccga tttaaccttc tccgtgaaaa gcagccgggg aagctccgac  480
cctcaaggtg tgacatgtgg agccgctacc ctcagcgctg agagggttcg tggcgataac  540
aaggaatacg agtacagcgt ggagtgccaa gaagatagcg cttgtcccgc tgccgaagaa  600
tctttaccca ttgaggtgat ggtggacgcc gtgcacaaac tcaagtacga gaactacacc  660
tcctccttct ttatccggga catcattaag cccgatcctc ctaagaattt acagctgaag  720
cctctcaaaa atagccggca agttgaggtc tcttgggaat atcccgacac ttggagcaca  780
ccccacagct acttctcttt aaccttttgt gtgcaagttc aaggtaaaag caagcgggag  840
aagaaagacc gggtgtttac cgacaaaacc agcgccaccg tcatctgtcg gaagaacgcc  900
tccatcagcg tgagggctca agatcgttat tactccagca gctggtccga gtgggccagc  960
gtgccttgtt ccggcggtgg aggatccgga ggaggtggct ccggcggcgg aggatctcgt  1020
aacctccccg tggctacccc cgatcccgga atgttccctt gtttacacca cagccagaat  1080
ttactgaggg ccgtgagcaa catgctgcag aaagctaggc agactttaga attttaccct  1140
tgcaccagcg aggagatcga ccatgaagat atcaccaagg acaagacatc caccgtggag  1200
gcttgtttac ctctggagct gacaaagaac gagtcttgtc tcaactctcg tgaaaccagc  1260
ttcatcacaa atggctcttg tttagcttcc cggaagacct cctttatgat ggctttatgc  1320
ctcagctcca tctacgagga tttaaagatg taccaagtgg agttcaagac catgaacgcc  1380
aagctgctca tggaccctaa acggcagatc tttttagacc agaacatgct ggctgtgatt  1440
gatgagctga tgcaagcttt aaacttcaac tccgagaccg tccctcagaa gtcctccctc  1500
gaggagcccg atttttacaa gacaaagatc aaactgtgca ttttactcca cgcctttagg  1560
atccgggccg tgaccattga ccgggtcatg agctatttaa acgccagcag cggcacaacc  1620
aacacagtcg ctgcctataa cctcacttgg aagagcacca acttcaaaac catcctcgaa  1680
tgggaaccca aacccgttaa ccaagtttac accgtgcaga tcagcaccaa gtccggcgac  1740
tggaagtcca aatgtttcta taccaccgac accgagtgcg atctcaccga tgagatcgtg  1800
aaagatgtga aacagaccta cctcgcccgg gtgtttagct accccgccgg caatgtggag  1860
agcactggtt ccgctggcga gcctttatac gagaacagcc ccgaatttac cccttacctc  1920
gagaccaatt taggacagcc caccatccaa agctttgagc aagttggcac aaaggtgaat  1980
gtgacagtgg aggacgagcg gactttagtg cggcggaaca acacctttct cagcctccgg  2040
gatgtgttcg gcaaagattt aatctacaca ctgtattact ggaagtcctc ttcctccggc  2100
aagaagacag ctaaaaccaa cacaaacgag tttttaatcg acgtggataa aggcgaaaac  2160
tactgtttca gcgtgcaagc tgtgatcccc tcccggaccg tgaataggaa aagcaccgat  2220
agccccgttg agtgcatggg ccaagaaaag ggcgagttcc gggagaactg ggtgaacgtc  2280
atcagcgatt taaagaagat cgaagattta attcagtcca tgcatatcga cgccacttta  2340
tacacagaat ccgacgtgca cccctcttgt aaggtgaccg ccatgaaatg ctttttactg  2400
gagctgcaag ttatctcttt agagagcgga gacgctagca tccacgacac cgtggagaat  2460
ttaatcattt tagccaataa ctctttatcc agcaacggca acgtgacaga gtccggctgc  2520
aaggagtgcg aagagctgga ggagaagaac atcaaggagt ttctgcaatc ctttgtgcac  2580
attgtccaga tgttcatcaa tacctcc                                     2607
```

```
SEQ ID NO: 219          moltype = AA  length = 240
FEATURE                 Location/Qualifiers
REGION                  1..240
                        note = source = /note="Description of Artificial Sequence:
                         SyntheticIL-18/IL-15RalphaSu sequence"
source                  1..240
                        mol_type = protein
                        organism = synthetic construct
SEQUENCE: 219
MKWVTFISLL FLFSSAYSYF GKLESKLSVI RNLNDQVLFI DQGNRPLFED MTDSDCRDNA  60
PRTIFIISMY KDSQPRGMAV TISVKCEKIS TLSCENKIIS FKEMNPPDNI KDTKSDIIFF  120
QRSVPGHDNK MQFESSSYEG YFLACEKERD LFKLILKKED ELGDRSIMFT VQNEDITCPP  180
PMSVEHADIW VKSYSLYSRE RYICNSGFKR KAGTSSLTEC VLNKATNVAH WTTPSLKCIR  240
```

```
SEQ ID NO: 220          moltype = AA  length = 869
FEATURE                 Location/Qualifiers
REGION                  1..869
                        note = source = /note="Description of Artificial Sequence:
                         SyntheticIL-12/TF/IL-15 sequence"
source                  1..869
                        mol_type = protein
                        organism = synthetic construct
SEQUENCE: 220
MKWVTFISLL FLFSSAYSIW ELKKDVYVVE LDWYPDAPGE MVVLTCDTPE EDGITWTLDQ  60
SSEVLGSGKT LTIQVKEFGD AGQYTCHKGG EVLSHSLLLL HKKEDGIWST DILKDQKEPK  120
NKTFLRCEAK NYSGRFTCWW LTTISTDLTF SVKSSRGSSD PQGVTCGAAT LSAERVRGDN  180
KEYEYSVECQ EDSACPAAEE SLPIEVMVDA VHKLKYENYT SSFFIRDIIK PDPPKNLQLK  240
PLKNSRQVEV SWEYPDTWST PHSYFSLTFC VQVQGKSKRE KKDRVFTDKT SATVICRKNA  300
SISVRAQDRY YSSSWSEWAS VPCSGGGGSG GGGSGGGGSR NLPVATPDPG MFPCLHHSQN  360
LLRAVSNMLQ KARQTLEFYP CTSEEIDHED ITKDKTSTVE ACLPLELTKN ESCLNSRETS  420
FITNGSCLAS RKTSFMMALC LSSIYEDLKM YQVEFKTMNA KLLMDPKRQI FLDQNMLAVI  480
DELMQALNFN SETVPQKSSL EEPDFYKTKI KLCILLHAFR IRAVTIDRVM SYLNASSGTT  540
NTVAAYNLTW KSTNFKTILE WEPKPVNQVY TVQISTKSGD WKSKCFYTTD TECDLTDEIV  600
KDVKQTYLAR VFSYPAGNVE STGSAGEPLY ENSPEFTPYL ETNLGQPTIQ SFEQVGTKVN  660
VTVEDERTLV RRNNTFLSLR DVFGKDLIYT LYYWKSSSSG KKTAKTNTNE FLIDVDKGEN  720
YCFSVQAVIP SRTVNRKSTD SPVECMGQEK GEFRENWVNV ISDLKKIEDL IQSMHIDATL  780
YTESDVHPSC KVTAMKCFLL ELQVISLESG DASIHDTVEN LIILANNSLS SNGNVTESGC  840
KECEELEEKN IKEFLQSFVH IVQMFINTS                                   869
```

```
SEQ ID NO: 221          moltype = DNA  length = 1452
FEATURE                 Location/Qualifiers
misc_feature            1..1452
                        note = source = /note="Description of Artificial Sequence:
                         SyntheticIL-21/TF mutant/IL-15 sequence"
source                  1..1452
                        mol_type = other DNA
                        organism = synthetic construct
SEQUENCE: 221
atgaagtggg tgaccttcat cagcctgctg ttcctgttct ccagcgccta ctcccagggc  60
caggacaggc acatgatccg gatgaggcag ctcatcgaca tcgtcgacca gctgaagaac  120
tacgtgaacg acctggtgcc cgagtttctg cctgcccccg aggacgtgga gaccaactgc  180
gagtggtccg ccttctcctg ctttcagaag gcccagctga agtccgccaa caccggcaac  240
aacgagcgga tcatcaacgt gagcatcaag aagctgaagc ggaagcctcc ctccacaaac  300
gccggcagga ggcagaagca caggctgacc tgccccagct gtgactccta cgagaagaag  360
ccccccaagg agttcctgga gaggttcaag tccctgctgc agaagatgat ccatcagcac  420
ctgtcctcca ggacccacgg ctccgaggac tcctccggca ccaccaatac cgtggccgct  480
tataacctca catggaagag caccaacttc gcgacagctc tggaatggga acccaagccc  540
gtcaatcaag tttacaccgt gcagatctcc accaaatccg gagactggaa gagcaagtgc  600
ttctacacaa cagacaccga gtgtgcttta accgacgaaa tcgtcaagga cgtcaagcaa  660
acctatctgg ctcgggtctt ttcctacccc gctggcaatg tcgagtccac cggctccgct  720
ggcgagcctc tctacgagaa ttcccccgaa ttcacccctt atttagagac caatttaggc  780
cagcctacca tccagagctt cgagcaagtt ggcaccaagg tgaacgtcac cgtcgaggat  840
gaaaggactt tagtggcgcg gaataacaca gctttatccc tccgggatgt gttcggcaaa  900
gacctcatct acacactgta ctattggaag tccagctcct ccggcaaaaa gaccgctaag  960
accaacacca acgagttttt aattgacgtg gacaaaggcg agaactactg cttcagcgtg  1020
caagccgtga tcccttctcg taccgtcaac cggaagagca cagattcccc cgttgagtgc  1080
atgggccaag aaaagggcga gttccgggag aactgggtga acgtcatcag cgatttaaag  1140
aagatcgaag atttaattca gtccatgcat atcgacgcca ctttatacac agaatccgac  1200
gtgcacccct cttgtaaggt gaccgccatg aaatgttttt tactggagct gcaagttatc  1260
tctttagaga gcggagacgc tagcatccac gacaccgtgg agaatttaat cattttagcc  1320
aataactctt tatccagcaa cggcaacgtg acagagtccg gctgcaagga gtgcgaagag  1380
ctggaggaga agaacatcaa ggagtttctg caatcctttg tgcacattgt ccagatgttc  1440
atcaatacct cc                                                  1452

SEQ ID NO: 222          moltype = AA  length = 483
FEATURE                 Location/Qualifiers
REGION                  1..483
                        note = source = /note="Description of Artificial Sequence:
                         SyntheticIL-21/TF mutant/IL-15 sequence"
source                  1..483
                        mol_type = protein
                        organism = synthetic construct
SEQUENCE: 222
KWVTFISLLF LFSSAYSQGQ DRHMIRMRQL IDIVDQLKNY VNDLVPEFLP APEDVETNCE  60
WSAFSCFQKA QLKSANTGNN ERIINVSIKK LKRKPPSTNA GRRQKHRLTC PSCDSYEKKP  120
PKEFLERFKS LLQKMIHQHL SSRTHGSEDS SGTTNTVAAY NLTWKSTNFA TALEWEPKPV  180
NQVYTVQIST KSGDWKSKCF YTTDTECALT DEIVKDVKQT YLARVFSYPA GNVESTGSAG  240
EPLYENSPEF TPYLETNLGQ PTIQSFEQVG TKVNVTVEDE RTLVARNNTA LSLRDVFGKD  300
LIYTLYYWKS SSSGKKTAKT NTNEFLIDVD KGENYCFSVQ AVIPSRTVNR KSTDSPVECM  360
GQEKGEFREN WVNVISDLKK IEDLIQSMHI DATLYTESDV HPSCKVTAMK CFLLELQVIS  420
LESGDASIHD TVENLIILAN NSLSSNGNVT ESGCKECEEL EEKNIKEFLQ SFVHIVQMFI  480
NTS                                                            483

SEQ ID NO: 223          moltype = AA  length = 17
FEATURE                 Location/Qualifiers
REGION                  1..17
                        note = source = /note="Description of Artificial Sequence:
                         SyntheticSignal sequence"
source                  1..17
                        mol_type = protein
                        organism = synthetic construct
SEQUENCE: 223
MGVKVLFALI CIAVAEA                                             17

SEQ ID NO: 224          moltype = AA  length = 8
FEATURE                 Location/Qualifiers
REGION                  1..8
                        note = source = /note="Description of Artificial Sequence:
                         SyntheticLinker sequence"
source                  1..8
                        mol_type = protein
                        organism = synthetic construct
SEQUENCE: 224
GGGSGGGS                                                       8

SEQ ID NO: 225          moltype = DNA  length = 1245
FEATURE                 Location/Qualifiers
```

-continued

```
misc_feature          1..1245
                      note = source = /note="Description of Artificial Sequence:
                       Synthetic21s137L sequence"
source                1..1245
                      mol_type = other DNA
                      organism = synthetic construct
SEQUENCE: 225
atgaagtggg tgaccttcat cagcctgctg ttcctgttct ccagcgccta ctcccagggc  60
caggacaggc acatgatccg gatgaggcag ctcatcgaca tcgtcgacca gctgaagaac  120
tacgtgaacg acctggtgcc cgagtttctg cctgcccccg aggacgtgga gaccaactgc  180
gagtggtccg ccttctcctg ctttcagaag gcccagctga agtccgccaa caccggcaac  240
aacgagcgga tcatcaacgt gagcatcaag aagctgaagc ggaagcctcc ctccacaaac  300
gccggcagga ggcagaagca caggctgacc tgccccagct gtgactccta cgagaagaag  360
ccccccaagg agttcctgga gaggttcaag tccctgctgc agaagatgat ccatcagcac  420
ctgtcctcca ggacccacgg ctccgaggac tccattacat gcccccctcc catgagcgtg  480
gagcacgccg acatctgggt gaagagctat agcctctaca gccgggagag gtatatctgt  540
aacagcggct tcaagaggaa ggccggcacc agcagcctca ccgagtgcgt gctgaataag  600
gctaccaacg tggctcactg gacaacaccc tctttaaagt gcatccgggg cggtggagga  660
tccggaggag gtggctccgg cggcggagga tctcgcgagg gtcccgagct ttcgcccgac  720
gatcccgccg gcctcttgga cctgcggcag ggcatgtttg cgcagctggt ggcccaaaat  780
gttctgctga tcgatgggcc cctgagctgg tacagtgacc caggcctggc aggcgtgtcc  840
ctgacggggg gcctgagcta caaagaggac acgaaggagc tggtggtggc caaggctgga  900
gtctactatg tcttctttca actagagctg cggcgcgtgg tggccggcga gggctcaggc  960
tccgtttcac ttgcgctgca cctgcagcca ctgcgctctg ctgctggggc cgccgccctg  1020
gctttgaccg tggacctgcc acccgcctcc tccgaggctc ggaactcggc cttcggtttc  1080
cagggccgct tgctgcacct gagtgccggc cagcgcctgg gcgtccatct tcacactgag  1140
gccagggcac gccatgcctg gcagcttacc cagggcgcca cagtcttggg actcttccgg  1200
gtgacccccg aaatcccagc cggactccct tcaccgaggt cggaa             1245

SEQ ID NO: 226        moltype = AA  length = 415
FEATURE               Location/Qualifiers
REGION                1..415
                      note = source = /note="Description of Artificial Sequence:
                       Synthetic21s137L sequence"
source                1..415
                      mol_type = protein
                      organism = synthetic construct
SEQUENCE: 226
MKWVTFISLL FLFSSAYSQG QDRHMIRMRQ LIDIVDQLKN YVNDLVPEFL PAPEDVETNC  60
EWSAFSCFQK AQLKSANTGN NERIINVSIK KLKRKPPSTN AGRRQKHRLT CPSCDSYEKK  120
PPKEFLERFK SLLQKMIHQH LSSRTHGSED SITCPPPMSV EHADIWVKSY SLYSRERYIC  180
NSGFKRKAGT SSLTECVLNK ATNVAHWTTP SLKCIRGGGG SGGGGSGGGG SREGPELSPD  240
DPAGLLDLRQ GMFAQLVAQN VLLIDGPLSW YSDPGLAGVS LTGGLSYKED TKELVVAKAG  300
VYYVFFQLEL RRVVAGEGSG SVSLALHLQP LRSAAGAAAL ALTVDLPPAS SEARNSAFGF  360
QGRLLHLSAG QRLGVHLHTE ARARHAWQLT QGATVLGLFR VTPEIPAGLP SPRSE       415
```

MULTI-CHAIN CHIMERIC POLYPEPTIDES AND USES THEREOF

CROSS-REFERENCE TO RELATED APPLICATIONS

This application is a divisional of U.S. patent application Ser. No. 16/555,689, filed Aug. 29, 2019, now U.S. Pat. No. 11,518,792, which claims priority to: U.S. Patent Application No. 62/724,969, filed Aug. 30, 2018; U.S. Patent Application No. 62/817,230, filed Mar. 12, 2019; U.S. Patent Application Ser. No. 62/725,043, filed Aug. 30, 2018; U.S. Patent Application Ser. No. 62/725,010, filed Aug. 30, 2018; U.S. Patent Application Ser. No. 62/749,007, filed Oct. 22, 2018; U.S. Patent Application Ser. No. 62/746,832, filed Oct. 17, 2018; U.S. Patent Application Ser. No. 62/749,506, filed Oct. 23, 2018; U.S. Patent Application Ser. No. 62/817,241, filed Mar. 12, 2019; U.S. Patent Application Ser. No. 62/816,683, filed Mar. 11, 2019; and U.S. Patent Application Ser. No. 62/881,088, filed Jul. 31, 2019, each of which is herein incorporated by reference in its entirety.

SEQUENCE LISTING

This application contains a Sequence Listing that has been submitted electronically as an XML file named 47039-0005006_SL_ST26.xml. The XML file, created on Oct. 11, 2022, is 443,149 bytes in size. The material in the XML file is hereby incorporated by reference in its entirety.

TECHNICAL FIELD

The present disclosure relates to the field of biotechnology, and more specifically, to antigen-binding molecules.

BACKGROUND

Tissue factor (TF), a 263 amino acid integral membrane glycoprotein with a molecular weight of ~46 kDa and the trigger protein of the extrinsic blood coagulation pathway, is the primary initiator of coagulation in vivo. Tissue factor, normally not in contact with circulating blood, initiates the coagulation cascade upon exposure to the circulating coagulation serine protease factors. Vascular damage exposes sub-endothelial cells expressing tissue factor, resulting in the formation of a calcium-dependent, high-affinity complex with pre-existing plasma factor VIIa (FVIIa). Binding of the serine protease FVIIa to tissue factor promotes rapid cleavage of FX to FXa and FIX to FIXa. The proteolytic activity of the resulting FXa and an active membrane surface then inefficiently converts a small amount of prothrombin to thrombin. The thrombin generated by FXa initiates platelet activation and activates minute amounts of the pro-cofactors factor V (FV) and factor VIII (FVIII) to become active cofactors, factor Va (FVa) and factor VIIIa (FVIIIa). FIXa complexes with FVIIIa on the platelet surface forming the intrinsic tenase complex, which results in rapid generation of FXa. FXa complexes with FVa to form the pro-thrombinase complex on the activated platelet surface which results in rapid cleavage of prothrombin to thrombin.

In addition to the tissue factor-FVIIa complex, a recent study showed that the tissue factor-FVIIa-FXa complex can activate FVIII, which would provide additional levels of FVIIIa during the initiation phase. The extrinsic pathway is paramount in initiating coagulation via the activation of limited amounts of thrombin, whereas the intrinsic pathway maintains coagulation by dramatic amplification of the initial signal.

Much of the tissue factor expressed on a cell surface is "encrypted," which must be "decrypted" for full participation in coagulation. The mechanism of "decryption" of cell-surface tissue factor is still unclear at this time, however, exposure of anionic phospholipids plays a major role in this process. Healthy cells actively sequester anionic phospholipids such as phosphatidyl serine (PS) to the inner leaflet of the plasma membrane. Following cellular damage, activation, or increased levels of cytosolic $Ca^{2+}$, this bilayer asymmetry is lost, resulting in increased PS exposure on the outer leaflet, which increases the specific activity of cell-surface tissue factor-FVIIa complexes. PS exposure is known to decrease the apparent Km for activation of FIX and FX by tissue factor-FVIIa complexes, but additional mechanisms could include conformational rearrangement of tissue factor or tissue factor-FVIIa and subsequent exposure of substrate binding sites.

SUMMARY

The present invention is based on the discovery that soluble tissue factor can be used as a scaffold for chimeric polypeptides including an antigen-binding domain. Based on this discovery provided herein are multi-chain chimeric polypeptides that include: (a) a first chimeric polypeptide including: (i) a first target-binding domain; (ii) a soluble tissue factor domain; and (iii) a first domain of a pair of affinity domains; and (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains. Also provided herein are compositions that include any of the multi-chain chimeric polypeptides described herein, nucleic acids that encode any of the multi-chain chimeric polypeptides described herein, and cells that include any of the nucleic acids that encode any of the multi-chain chimeric polypeptides described herein. Also provided herein are methods of stimulating an immune cell and methods of treating a subject in need thereof that include the use of any of the multi-chain chimeric polypeptides described herein. Also provided herein are methods of producing any of the multi-chain chimeric polypeptides described herein.

Accordingly, provided herein is a multi-chain chimeric polypeptide comprising:

(a) a first chimeric polypeptide comprising:
  (i) a first target-binding domain;
  (ii) a soluble tissue factor domain; and
  (iii) a first domain of a pair of affinity domains;

(b) a second chimeric polypeptide comprising:
  (i) a second domain of a pair of affinity domains; and
  (ii) a second target-binding domain, wherein the first chimeric polypeptide and the second chimeric polypeptide associate through the binding of the first domain and the second domain of the pair of affinity domains. In some embodiments, the first target-binding domain and the soluble tissue factor domain directly abut each other in the first chimeric polypeptide. In some embodiments, the first chimeric polypeptide further comprises a linker sequence between the first target-binding domain and the soluble tissue factor domain in the first chimeric polypeptide. In some embodiments, the soluble tissue factor domain and the first domain of the pair of affinity domains directly abut each other in the first chimeric polypeptide. In some embodiments, the first chimeric polypeptide further comprises a linker sequence between the soluble tissue factor domain and the first domain of the pair of affinity domains in the first chimeric polypeptide. In some embodiments, the second domain of the pair of affinity domains and the second target-binding domain directly abut each other in the second chimeric polypeptide. In some embodiments, the second chimeric polypeptide further comprises a linker sequence between the second domain of the pair of affinity domains and the second target-binding domain in the second chimeric polypeptide. In some embodiments, the first target-binding domain and the second target-binding domain bind specifically to the same antigen. In some embodiments, the first target-binding domain and the second target-binding domain bind specifically to the same epitope. In some embodiments, the first target-binding domain and the second target-binding domain comprise the same amino acid sequence. In some embodiments, the first target-binding domain and the second target-binding domain bind specifically to different antigens. In some embodiments, one or both of the first target-binding domain and the second target-binding domain is an antigen-binding domain. In some embodiments, the first target-binding domain and the second target-binding domain are each antigen-binding domains. In some embodiments, the antigen-binding domain comprises a scFv or a single domain antibody. In some embodiments, one or both of the first target-binding domain and the second target-binding domain bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHICII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28. In some embodiments, one or both of the first target-binding domain and the second target-binding domain is a soluble interleukin, a soluble cytokine protein, or a ligand protein. In some embodiments, the soluble interleukin, soluble cytokine, or ligand protein is selected from the group consisting of: IL-1, IL-2, IL-3, IL-7, IL-8, IL-10, IL-12, IL-15, IL-17, IL-18, IL-21, PDGF-DD, SCF, and FLT3L. In some embodiments, one or both of the first target-binding domain and the second target-binding domain is a soluble interleukin, a cytokine receptor, or a soluble cell surface receptor. In some embodiments, the soluble receptor is a soluble TGF-β receptor II (TGF-β RII), a soluble TGF-βRIII, a soluble NKG2D, a soluble NKp30, a soluble NKp44, a soluble NKp46, a soluble DNAM-1, a scMHICI, a scMHICII, a scTCR, a soluble CD155, or a soluble CD28. In some embodiments, the first chimeric polypeptide further comprises one or more additional target-binding domain(s), where at least one of the one or more additional antigen-binding domain(s) is positioned between the soluble tissue factor domain and the first domain of the pair of affinity domains. In some embodiments, the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains. In some embodiments, the first chimeric polypeptide further comprises one or more additional target-binding domains at the N-terminal and/or C-terminal end of the first chimeric polypeptide. In some embodiments, at least one of the one or more additional target-binding domains directly abuts the first domain of the pair of affinity domains in the first chimeric polypeptide. In some embodiments, the first chimeric polypeptide further comprises a linker sequence between the at least one of the one or more additional target-binding domains and the first domain of the pair of affinity domains. In some embodiments, the at least one of the one or more additional target-binding domains directly abuts the first target-binding domain in the first chimeric polypeptide. In some embodiments, the first chimeric polypeptide further comprises a linker sequence between the at least one of the one or more additional target-binding domains and the first target-binding domain. In some embodiments, at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide. In some embodiments, the at least one additional target-binding domain of the one or more additional target-binding domains disposed at the N-terminus directly abuts the first target-binding domain or the first domain of the pair of affinity domains in the first chimeric polypeptide. In some embodiments, the first chimeric polypeptide further comprises a linker sequence disposed between the at least one additional target-binding domain and the first target-binding domain or the first domain of the pair of affinity domains in the first chimeric polypeptide. In some embodiments, the at least one additional target-binding domain of the one or more additional target-binding domains disposed at the C-terminus directly abuts the first target-binding domain or the first domain of the pair of affinity domains in the first chimeric polypeptide. In some embodiments, the first chimeric polypeptide further comprises a linker sequence disposed between the at least one additional target-binding domain and the first target-binding domain or the first domain of the pair of affinity domains in the first chimeric polypeptide. In some embodiments, the at least one of the one or more additional target-binding domains positioned between the soluble tissue factor domain and the first domain of the pair of affinity domains, directly abuts the soluble tissue factor domain and/or the first domain of the pair of affinity domains. In some embodiments, the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains. In some embodiments, the second chimeric polypeptide further comprises one or more additional target-binding domains at the N-terminal end or the C-terminal end of the second chimeric polypeptide. In some embodiments, at least one of the one or more additional target-binding domains directly abuts the second domain of the pair of affinity domains in the second chimeric polypeptide. In some embodiments, the second chimeric polypeptide further comprises a linker sequence between at least one of the one or more additional target-binding domains and the second domain of the pair of affinity domains in the second chimeric polypeptide. In some embodiments, at least one of the one or more additional target-binding domains directly abuts the second target-binding domain in the second chimeric polypeptide. In some embodiments, the second chimeric polypeptide further comprises a linker sequence between at least one of the one or more additional target-binding domains and the second target-binding domain in the second chimeric polypeptide. In some embodiments, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence. In some embodiments, the first target-binding domain, the second target-binding domain, and the one or more additional target-binding domains each bind specifically to the same antigen. In some embodiments, the first target-binding domain, the second target-binding domain, and the one or more additional target-binding domains each bind specifically to the same epitope. In some embodiments, the first target-binding domain, the second target-binding domain, and the one or more additional target-binding domains each comprise the same amino acid sequence. In some embodiments, the first target-binding domain, the second target-binding domain, and the one or more additional target-binding domains bind specifically to different antigens. In some embodiments, one or more of the first target-binding domain, the second target-binding domain, and the one or more target-binding domains is an antigen-binding domain. In some embodiments, the first target-binding domain, the second target-binding domain, and the one or more additional target-binding domains are each an antigen-binding domain. In some embodiments, antigen-binding domain comprises a scFv. In some embodiments, one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD3, and a receptor for CD28. In some embodiments, one or more of the first target-binding domain, the second target-binding domain, and the one or more additional target-binding domains is a soluble interleukin, a soluble cytokine protein, or a ligand protein. In some embodiments, the soluble interleukin, soluble cytokine, or ligand protein is selected from the group consisting of: IL-1, IL-2, IL-3, IL-7, IL-8, IL-10, IL-12, IL-15, IL-17, IL-18, IL-21, PDGF-DD, SCF, and FLT3L. In some embodiments, one or more of the first target-binding domain, the second target-binding domain, and the one or more additional target-binding domains is a soluble interleukin or cytokine receptor. In some embodiments, the soluble receptor is a soluble TGF-β receptor II (TGF-β RII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28. In some embodiments, the first chimeric polypeptide further comprises a peptide tag at the N-terminal end or the C-terminal end of the first chimeric polypeptide. In some embodiments, the second chimeric polypeptide further comprises a peptide tag at the N-terminal end or the C-terminal end of the second chimeric polypeptide. In some embodiments, the soluble tissue factor domain is a soluble human tissue factor domain. In some embodiments, the soluble human tissue factor domain comprises a sequence that is at least 80% identical to SEQ ID NO: 1. In some embodiments, the soluble human tissue factor domain comprises a sequence that is at least 90% identical to SEQ ID NO: 1. In some embodiments, the soluble human tissue factor domain comprises a sequence that is at least 95% identical to SEQ ID NO: 1. In some embodiments, the soluble human tissue factor domain does not comprise one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble human tissue factor domain does not comprise any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble tissue factor domain is not capable of binding to Factor VIIa. In some embodiments, the soluble tissue factor domain does not convert inactive Factor X into Factor Xa. In some embodiments, the multi-chain chimeric polypeptide does not stimulate blood coagulation in a mammal. In some embodiments of any of the single-chain chimeric polypeptides provided herein, the human soluble tissue factor domain does not initiate blood coagulation. In some embodiments of any of the single-chain chimeric polypeptides provided herein, the soluble tissue factor domain comprises or consists of a soluble wildtype human tissue factor.

In some embodiments, the pair of affinity domains is a sushi domain from an alpha chain of human IL-15 receptor (IL15Rα) and a soluble IL-15. In some embodiments, the soluble IL15 has a D8N or D8A amino acid substitution. In some embodiments, the human IL15Rα is a mature full-length IL15Rα. In some embodiments, the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25. In some embodiments, the first chimeric polypeptide and/or the second chimeric polypeptide further comprises a signal sequence at its N-terminal end.

In some embodiments, the multi-chain chimeric polypeptide comprises a composition. In some embodiments, the composition is a pharmaceutical composition. In some embodiments, the composition comprises at least one dose of the multi-chain chimeric polypeptide. In some embodiments, a kit comprises at least one dose of the composition.

In some embodiments, provided herein is a method of stimulating an immune cell, the method comprising: contacting an immune cell with an effective amount of any of the multi-chain chimeric polypeptides or compositions described above. In some embodiments, the method comprises contacting the immune cell in vitro. In some embodiments, the method comprises obtaining the immune cell from a subject. In some embodiments, the method comprises obtaining the immune cell from the subject prior to the contacting step. In some embodiments, the method comprises contacting the immune cell in vivo. In some embodiments, the method comprises selecting the immune cell from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a $CD8^+$ T cell, a $CD4^+$ T cell, a natural killer T cell, a mast cell, a macrophage, a neutrophil, a dendritic cell, a basophil, an eosinophil, and a natural killer cell. In some embodiments, the method comprises genetically modifying the immune cell to express a chimeric antigen receptor or a recombinant T-cell receptor. In some embodiments, the method comprises introducing into the immune cell a nucleic acid encoding a chimeric antigen-receptor or a recombinant T-cell receptor after the contacting step. In some embodiments, the method comprises administering the immune cell to a subject in need thereof. In some embodiments, the method comprises identifying or diagnosing the subject as having an age-related disease or condition. In some embodiments, the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some embodiments, the method comprises identifying or diagnosing the subject as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CMIL), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the method comprises diagnosing or identifying the subject as having an infectious disease. In some embodiments, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Also provided herein is a method of inducing or increasing proliferation of an immune cell, the method comprising: contacting an immune cell with an effective amount of any of the multi-chain chimeric polypeptides or compositions described above. In some embodiments, the method comprises contacting the immune cell in vitro. In some embodiments, the method comprises obtaining the immune cell from a subject. In some embodiments, the method comprises obtaining the immune cell from the subject prior to the contacting step. In some embodiments, the method comprises contacting the immune cell in vivo. In some embodiments, the method comprises selecting the immune cell from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a $CD8^+$ T cell, a $CD4^+$ T cell, a natural killer T cell, a mast cell, a macrophage, a neutrophil, a dendritic cell, a basophil, an eosinophil, and a natural killer cell. In some embodiments, the method comprises modifying the immune cell to express a chimeric antigen receptor or a recombinant T-cell receptor. In some embodiments, the method further comprises introducing into the immune cell a nucleic acid encoding a chimeric antigen-receptor or a recombinant T-cell receptor after the contacting step. In some embodiments, the method further comprises administering the immune cell to a subject in need thereof. In some embodiments, the method comprises identifying or diagnosing the subject as having an age-related disease or condition. In some embodiments, the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some embodiments, the method comprises identifying or diagnosing the subject as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the method comprises diagnosing or identifying the subject as having an infectious disease. In some embodiments, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Also provided herein is a method of inducing differentiation of an immune cell into a memory or memory-like immune cell, the method comprising: contacting an immune cell with an effective amount of any of the multi-chain chimeric polypeptides or compositions discussed above. In some embodiments, the method comprises contacting the immune cell in vitro. In some embodiments, the method comprises obtaining the immune cell from a subject. In some embodiments, the method further comprises obtaining the immune cell from the subject prior to the contacting step. In some embodiments, the method comprises contacting the immune cell in vivo. In some embodiments, the immune cell is selected from the group consisting of: an immature thymocyte, a peripheral blood lymphocyte, a naïve T cell, a pluripotent Th cell precursor, a lymphoid progenitor cell, a Treg cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell. In some embodiments, the immune cell has previously been genetically modified to express a chimeric antigen receptor or a recombinant T-cell receptor. In some embodiments, the method further comprises introducing into the immune cell a nucleic acid encoding a chimeric antigen-receptor or a recombinant T-cell receptor after the contacting step. In some embodiments, the method further comprises administering the immune cell to a subject in need thereof. In some embodiments, the method comprises identifying or diagnosing the subject as having an age-related disease or condition. In some embodiments, the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some embodiments, the method comprises identifying or diagnosing the subject as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CMIL), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the method comprises diagnosing or identifying the subject as having an infectious disease. In some embodiments, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Also provided herein is a method of killing a cancer cell, an infected cell, or a senescent cell in a subject in need thereof, the method comprising administering to the subject a therapeutically effective amount of any of the multi-chain chimeric polypeptides or compositions discussed above. In some embodiments, the method comprises identifying or diagnosing the subject as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CMIL), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the method comprises identifying or diagnosing the subject as having an aging-related disease or condition. In some embodiments, the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some embodiments, the method comprises administering to the subject a therapeutically effective amount of any of the multi-chain chimeric polypeptides or compositions discussed above. In some embodiments, the method comprises identifying or diagnosing the subject as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CMIL), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the method comprises identifying or diagnosing the subject as having an aging-related disease or condition. In some embodiments, the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some embodiments, the method comprises diagnosing or identifying the subject as having an infectious disease. In some embodiments, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Also provided herein is a nucleic acid encoding any of the multi-chain chimeric polypeptides discussed above. Some embodiments comprise vector containing any of the nucleic acids discussed above. In some embodiments, the vector is an expression vector. Some embodiments comprise a cell containing any of the nucleic acids discussed above.

Also provided herein is a method of producing a multi-chain chimeric polypeptide, the method comprising: culturing the cell discussed above in a culture medium under conditions sufficient to result in the production of the multi-chain chimeric polypeptide; and recovering the multi-chain chimeric polypeptide from the cell and/or the culture medium. In some embodiments, the method comprises producing a multi-chain chimeric polypeptide by the methods discussed above.

In some embodiments, the mutant soluble human tissue factor domain comprises a sequence that is at least 80% identical to SEQ ID NO: 3. In some embodiments, the soluble human tissue factor domain comprises a sequence that is at least 90% identical to SEQ ID NO: 3. In some embodiments, the soluble human tissue factor domain comprises a sequence that is at least 95% identical to SEQ ID NO: 3. In some embodiments, the soluble human tissue factor domain comprises a sequence that is 100% identical to SEQ ID NO: 3. In some embodiments, the soluble human tissue factor domain comprises a sequence that is at least 80% identical to SEQ ID NO: 4. In some embodiments, the soluble human tissue factor domain comprises a sequence that is at least 90% identical to SEQ ID NO: 4. In some embodiments, the soluble human tissue factor domain comprises a sequence that is at least 95% identical to SEQ ID NO:4. In some embodiments, the soluble human tissue factor domain comprises a sequence that is 100% identical to SEQ ID NO: 4.

As used herein, the term "chimeric" refers to a polypeptide that includes amino acid sequences (e.g., domains) originally derived from two different sources (e.g., two different naturally-occurring proteins, e.g., from the same or different species). For example, a chimeric polypeptide can include domains from at least two different naturally occurring human proteins. In some examples, a chimeric polypeptide can include a domain that is a synthetic sequence (e.g., an scFv) and a domain that is derived from a naturally-occurring protein (e.g., a naturally-occurring human protein). In some embodiments, a chimeric polypeptide can include at least two different domains that are synthetic sequences (e.g., two different scFvs).

An "antigen-binding domain" is one or more protein domain(s) (e.g., formed from amino acids from a single polypeptide or formed from amino acids from two or more polypeptides (e.g., the same or different polypeptides) that is capable of specifically binding to one or more different antigen(s). In some examples, an antigen-binding domain can bind to an antigen or epitope with specificity and affinity similar to that of naturally-occurring antibodies. In some embodiments, the antigen-binding domain can be an antibody or a fragment thereof. In some embodiments, an antigen-binding domain can include an alternative scaffold. Non-limiting examples of antigen-binding domains are described herein. Additional examples of antigen-binding domains are known in the art.

A "soluble tissue factor domain" refers to a polypeptide having at least 70% identity (e.g., at least 75% identity, at least 80% identity, at least 85% identity, at least 90% identity, at least 95% identity, at least 99% identity, or 100% identical) to a segment of a wildtype mammalian tissue factor protein (e.g., a wildtype human tissue factor protein) that lacks the transmembrane domain and the intracellular domain. Non-limiting examples of soluble tissue factor domains are described herein.

The term "soluble interleukin protein" is used herein to refer to a mature and secreted interleukin protein or a biologically active fragment thereof. In some examples, a soluble interleukin protein can include a sequence that is at least 70% identical, at least 75% identical, at least 80% identical, at least 85% identical, at least 90% identical, at least 95% identical, at least 99% identical, or 100% identical to a wildtype mature and secreted mammalian interleukin protein (e.g., a wildtype human interleukin protein) and retains its biological activity. Non-limiting examples of soluble interleukin proteins are described herein.

The term "soluble cytokine protein" is used herein to refer to a mature and secreted cytokine protein or a biologically active fragment thereof. In some examples, a soluble cytokine protein can include a sequence that is at least 70% identical, at least 75% identical, at least 80% identical, at least 85% identical, at least 90% identical, at least 95% identical, at least 99% identical, or 100% identical to a wildtype mature and secreted mammalian interleukin protein (e.g., a wildtype human interleukin protein) and retains its biological activity. Non-limiting examples of soluble cytokine proteins are described herein.

The term "soluble interleukin receptor" is used herein in the broadest sense to refer to a polypeptide that lacks a transmembrane domain (and optionally an intracellular domain) that is capable of binding one or more of its natural ligands (e.g., under physiological conditions, e.g., in phosphate buffered saline at room temperature). For example, a soluble interleukin receptor can include a sequence that is at least 70% identical (e.g., at least 75% identical, at least 80% identical, at least 85% identical, at least 90% identical, at least 95% identical, at least 99% identical, or 100% identical) to an extracellular domain of wildtype interleukin receptor and retains its ability to specifically bind to one or more of its natural ligands, but lacks its transmembrane domain (and optionally, further lacks its intracellular domain). Non-limiting examples of soluble interleukin receptors are described herein.

The term "soluble cytokine receptor" is used herein in the broadest sense to refer to a polypeptide that lacks a transmembrane domain (and optionally an intracellular domain) that is capable of binding one or more of its natural ligands (e.g., under physiological conditions, e.g., in phosphate buffered saline at room temperature). For example, a soluble cytokine receptor can include a sequence that is at least 70% identical (e.g., at least 75% identical, at least 80% identical, at least 85% identical, at least 90% identical, at least 95% identical, at least 99% identical, or 100% identical) to an extracellular domain of wildtype cytokine receptor and retains its ability to specifically bind to one or more of its natural ligands, but lacks its transmembrane domain (and optionally, further lacks its intracellular domain). Non-limiting examples of soluble cytokine receptors are described herein.

The term "antibody" is used herein in its broadest sense and includes certain types of immunoglobulin molecules that include one or more antigen-binding domains that specifically bind to an antigen or epitope. An antibody specifically includes, e.g., intact antibodies (e.g., intact immunoglobulins), antibody fragments, and multi-specific antibodies. One example of an antigen-binding domain is an antigen-binding domain formed by a VH-VL dimer. Additional examples of an antibody are described herein. Additional examples of an antibody are known in the art.

"Affinity" refers to the strength of the sum total of non-covalent interactions between an antigen-binding site and its binding partner (e.g., an antigen or epitope). Unless indicated otherwise, as used herein, "affinity" refers to intrinsic binding affinity, which reflects a 1:1 interaction between members of an antigen-binding domain and an antigen or epitope. The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein. Affinity can be determined, for example, using surface plasmon resonance (SPR) technology (e.g., BIACORE®) or biolayer interferometry (e.g., FORTEBIO®). Additional methods for determining the affinity for an antigen-binding domain and its corresponding antigen or epitope are known in the art.

A "multi-chain polypeptide" as used herein to refers to a polypeptide comprising two or more (e.g., three, four, five, six, seven, eight, nine, or ten) protein chains (e.g., at least a first chimeric polypeptide and a second polypeptide), where the two or more proteins chains associate through non-covalent bonds to form a quaternary structure.

The term "pair of affinity domains" is two different protein domain(s) that bind specifically to each other with a $K_D$ of less than of less than $1\times10^{-7}$ M (e.g., less than $1\times10^{-8}$ M, less than $1\times10^{-9}$ M, less than $1\times10^{-10}$ M, or less than $1\times10^{-11}$ M). In some examples, a pair of affinity domains can be a pair of naturally-occurring proteins. In some embodiments, a pair of affinity domains can be a pair of synthetic proteins. Non-limiting examples of pairs of affinity domains are described herein.

The term "epitope" means a portion of an antigen that specifically binds to an antigen-binding domain. Epitopes can, e.g., consist of surface-accessible amino acid residues and/or sugar side chains and may have specific three-dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. Methods for identifying an epitope to which an antigen-binding domain binds are known in the art.

An "immune effector cell" refers to a cell of the immune system of a mammal that is capable, directly or indirectly, of recognizing and/or causing cytostasis or cell death of a pathogenic cell (e.g., a cancer cell) in the mammal. Non-limiting examples of immune effector cells include macrophages, T-lymphocytes (e.g., cytotoxic T-lymphocytes and T-helper cells), natural killer cells, neutrophils, monocytes, and eosinophils. Additional examples of immune effector cells are known in the art.

The term "treatment" means to ameliorate at least one symptom of a disorder. In some examples, the disorder being treated is cancer and to ameliorate at least one symptom of cancer includes reducing aberrant proliferation, gene expression, signaling, translation, and/or secretion of factors. Generally, the methods of treatment include administering a therapeutically effective amount of composition that reduces at least one symptom of a disorder to a subject who is in need of, or who has been determined to be in need of such treatment.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

FIG. 67A shows binding affinity of TGFRt15-16521 with CHO cells expressing human CD16b. FIG. 67B shows binding affinity of 7t15-21s with CHO cells expressing human CD16b.

FIG. 85A shows spleen weight in mice treated with TGFRt15-TGFRs as compared to PBS control. FIG. 85B shows the percentage of $CD4^+$ T cells, $CD8^+$ T cells, and NK cells in mice treated with TGFRt15-TGFRs as compared to PBS control.

FIG. 86A shows spleen weight of mice treated with TGFRt15-TGFRs at 16, 24, 48, 72, and 92 hours after treatment. FIG. 86B shows the percentages of immune cells in mice treated with TGFRt15-TGFRs at 16, 24, 48, 72, and 92 hours after treatment.

FIG. 96A shows detection of IL15 in 7t15-21s137L (short version) with ELISA. FIG. 96B shows detection of IL21 in 7t15-21s137L (short version) with ELISA. FIG. 96C shows detection of IL7 in 7t15-21s137L (short version) with ELISA.

FIG. 107A shows spleen weight in mice treated with 7t15-TGFRs at various dosages, as compared to PBS control. FIG. 107B shows the percentage of $CD4^+$ T cells, $CD8^+$ T cells, and NK cells in mice treated with 7t15-TGFRs at various dosages, as compared to PBS control.

FIG. 121 shows enhancement of cytotoxicity of splenocytes by TGFRt15-TGFRs21 in C57BL/6 Mice.

FIG. 122 shows a schematic of the TGFRt15-TGFRs16 construct.

FIG. 123 shows an additional schematic of the TGFRt15-TGFRs16 construct.

FIG. 124 shows a schematic of the TGFRt15-TGFRs137L construct.

FIG. 125 shows an additional schematic of the TGFRt15-TGFRs137L construct.

FIG. 126 shows changes in the surface phenotype of lymphocyte populations after stimulation with 18t15-12s, 18t15-12s16, and 7t15-21s.

FIG. 127 shows an increase in phospho-STAT4 and phospho-STAT5 levels in NK cells after stimulation with 18t15-12s.

FIGS. 128A-128C show in vivo stimulation of Tregs, NK cells, and $CD8^+$ T cells in $ApoE^{-/-}$ mice fed with a Western diet and treated with TGFRt15-TGFRs.

FIGS. 129A-129C show immunostimulation in C57BL/6 mice following treatment with TGFRt15-TGFRs.

FIGS. 130A and 130B show in vivo induction of proliferation of NK cells and $CD8^+$ T cells in $ApoE^{-/-}$ mice fed with a Western diet and treated with TGFRt15-TGFRs.

FIGS. 131A and 131B show enhancement of cytotoxicity of NK cells following treatment of NK cells with TGFRt15-TGFRs.

FIGS. 132A and 132B show enhancement of ADCC activity of NK cells following treatment of NK cells with TGFRt15-TGFRs.

FIGS. 133A-133H show antitumor activity of TGFRt15-TGFRs plus anti-TRP1 antibody (TA99) in combination with chemotherapy in a melanoma mouse model.

Figure 134A:
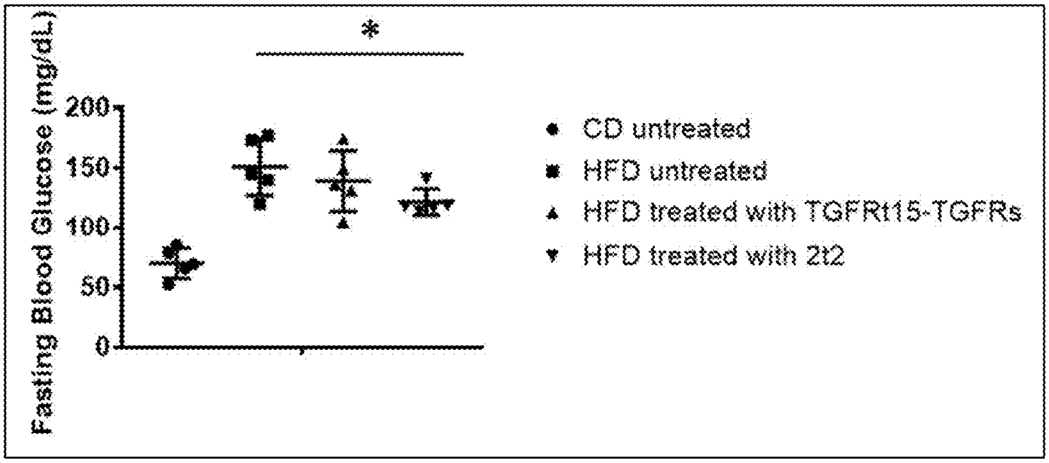
Figure 134B:
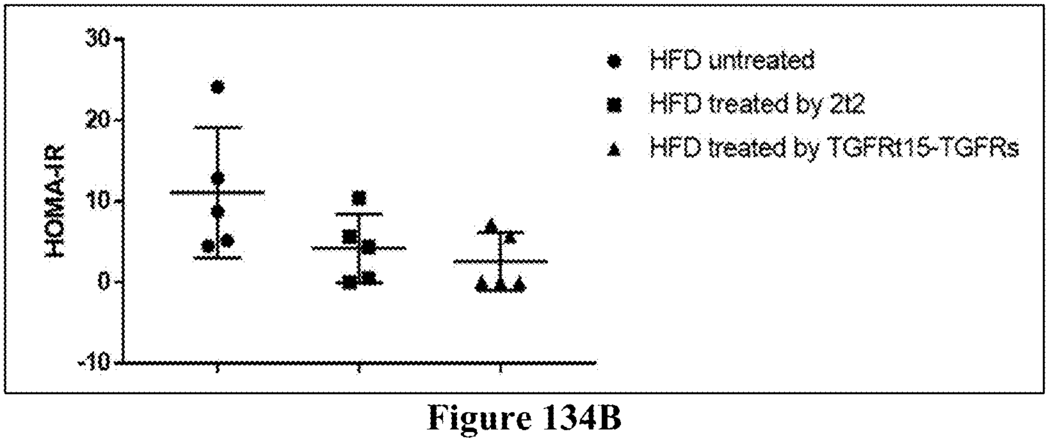
Figure 134C:
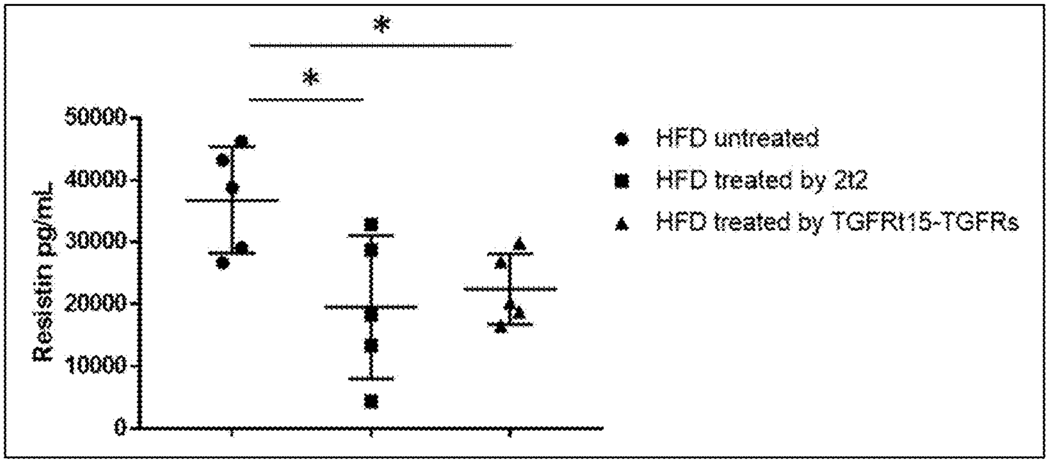

FIGS. 134A-134C show amelioration of the Western diet-induced hyperglycemia in $ApoE^{-/-}$ mice by TGFRt15-TGFRs.

Figure 135:
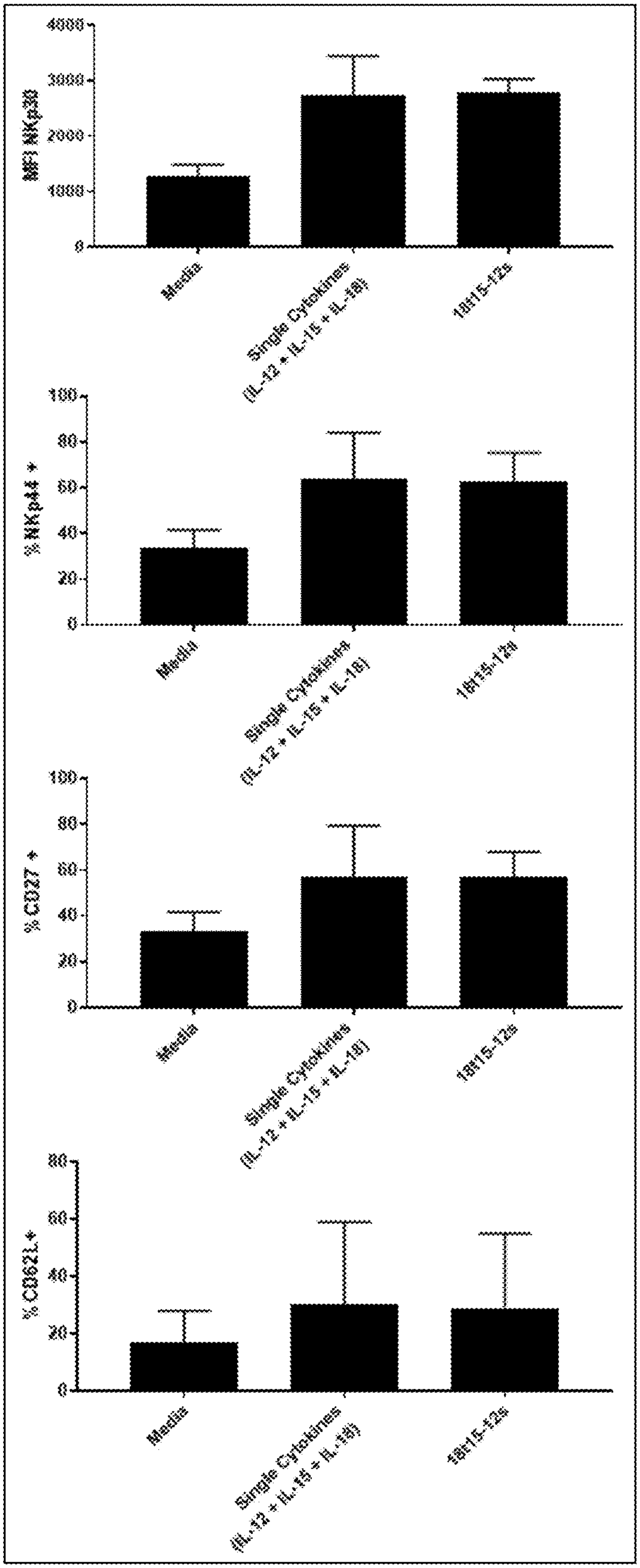

FIG. 135 shows cell surface staining summarizing the differentiation of NK cells into cytokine-induced memory like NK Cells (CIML-NK Cells) after stimulation with 18t15-12s and cultured in rhIL15.

Figure 136:
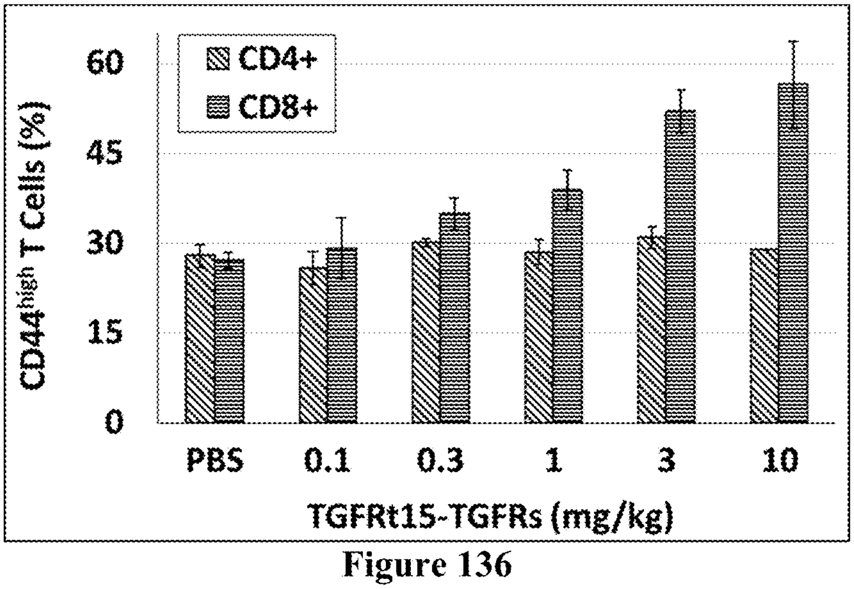

FIG. 136 shows upregulation shows upregulation of CD44hi memory T cells upon treatment with TGFRt15-TGFRs.

Figure 137:
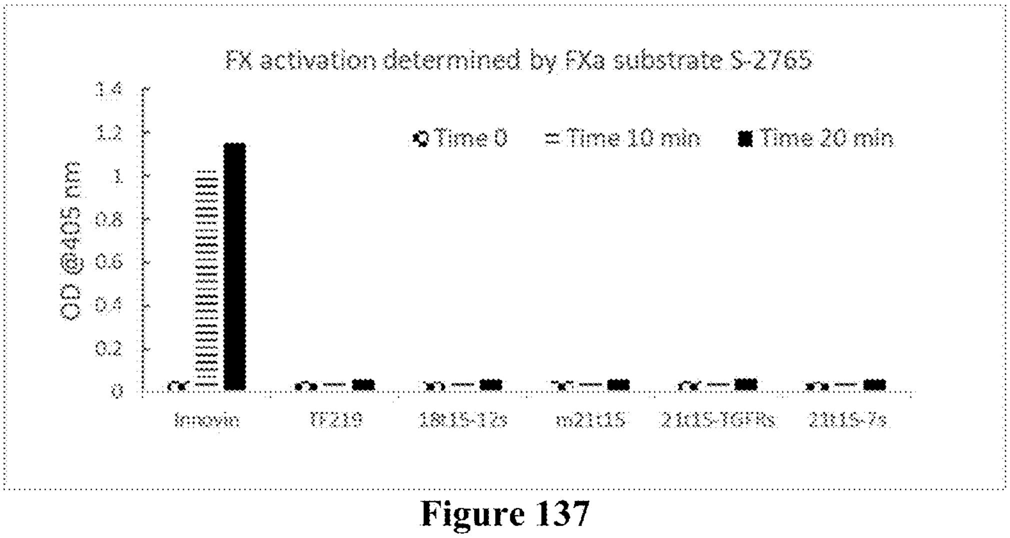

FIG. 137 shows a graph of Factor X (FX) activation following treatment with single-chain or multi-chain chimeric polypeptides.

Figure 138:
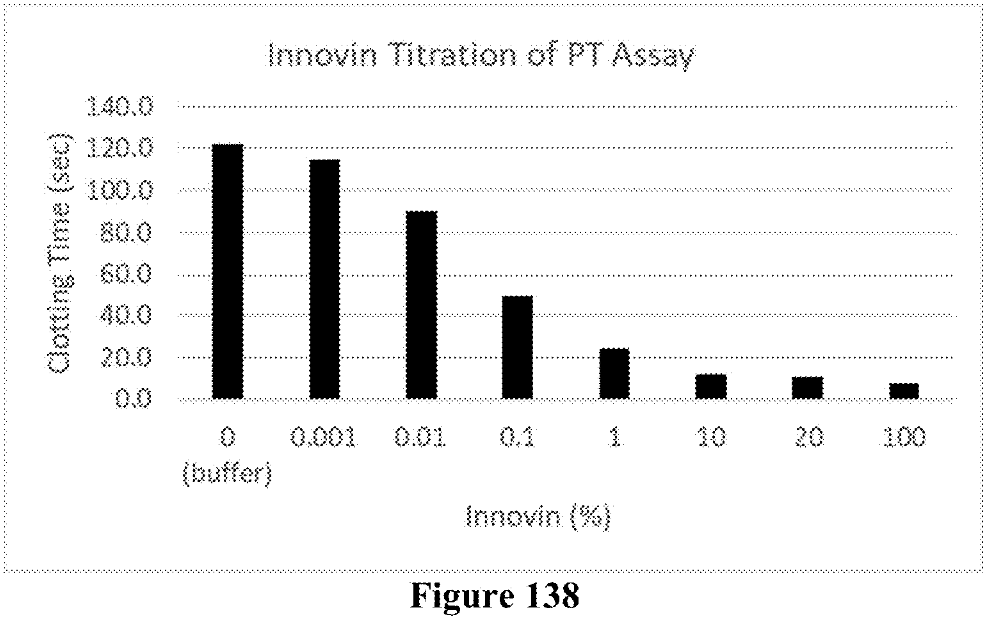

FIG. 138 shows clotting time for a buffer with varying concentrations of Innovin in a prothrombin time (PT) test.

Figure 139:
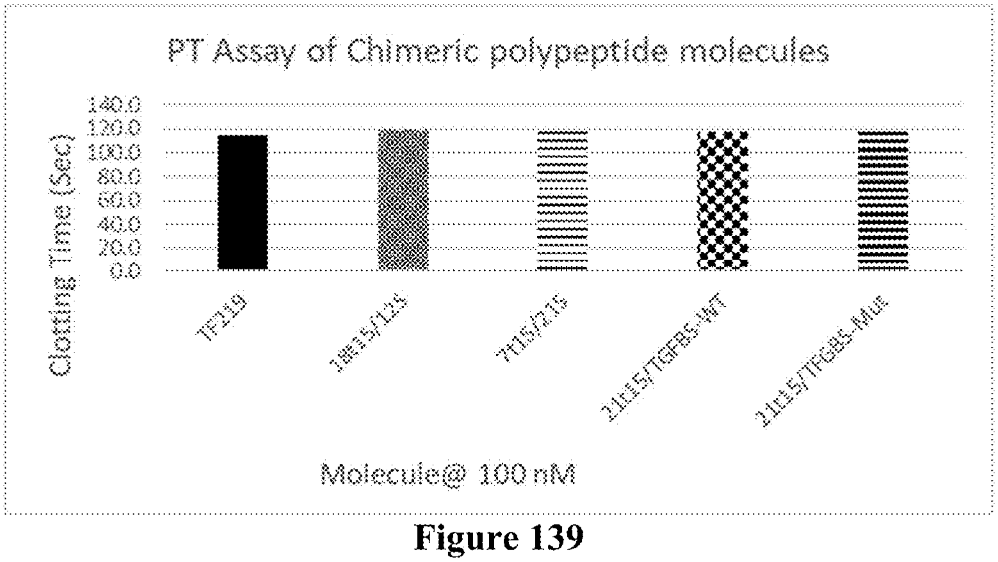

FIG. 139 shows clotting time for multi-chain chimeric polypeptides in a PT Assay.

Figure 140:
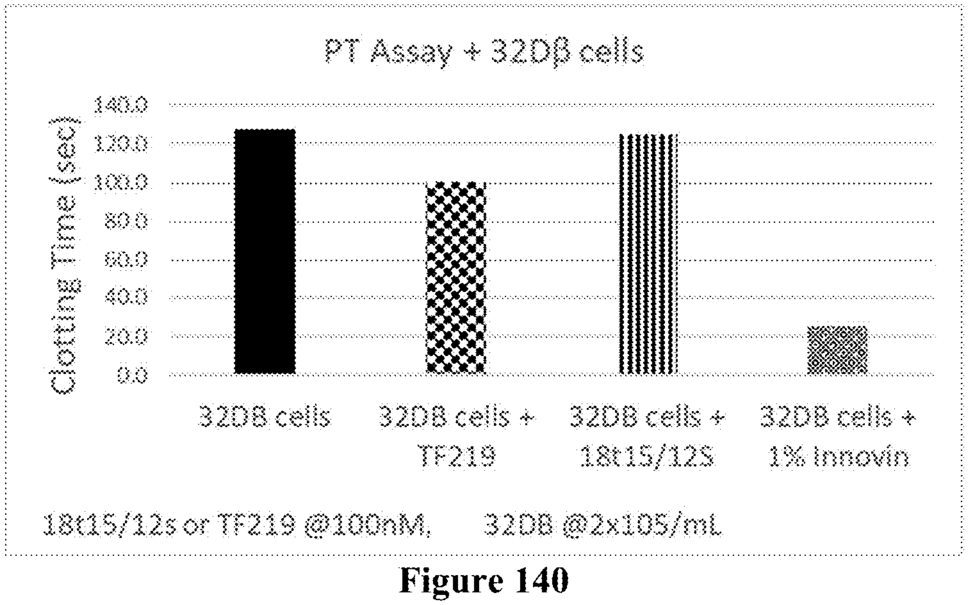

FIG. 140 shows clotting time of the multi-chain chimeric polypeptides in a PT assay when mixed with 32DB cells.

Figure 141:
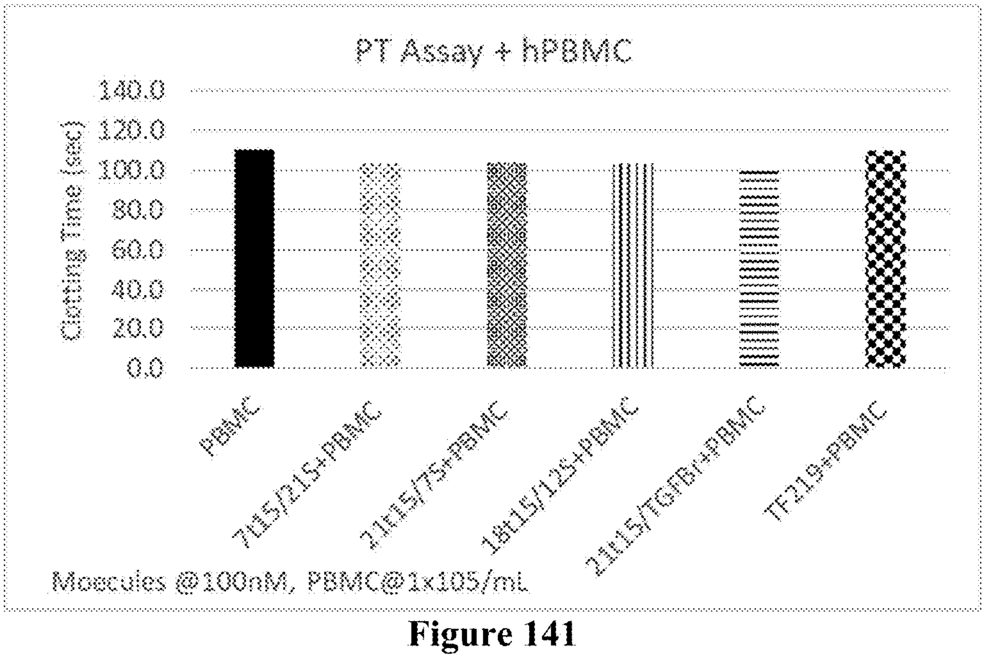

FIG. 141 shows clotting time of multi-chain chimeric polypeptides in a PT assay when mixed with human PBMC.

Figure 142:
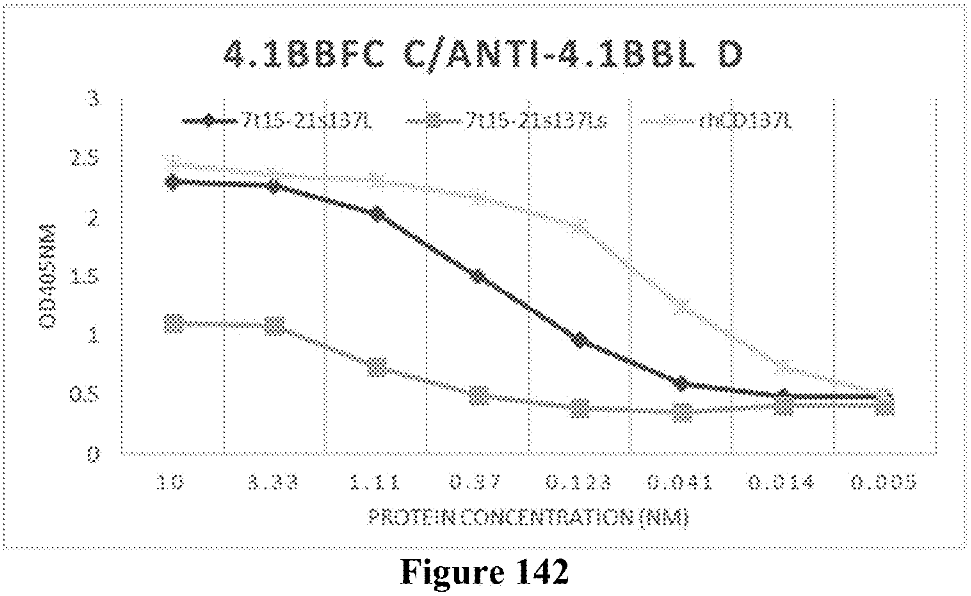
Figure 143A:
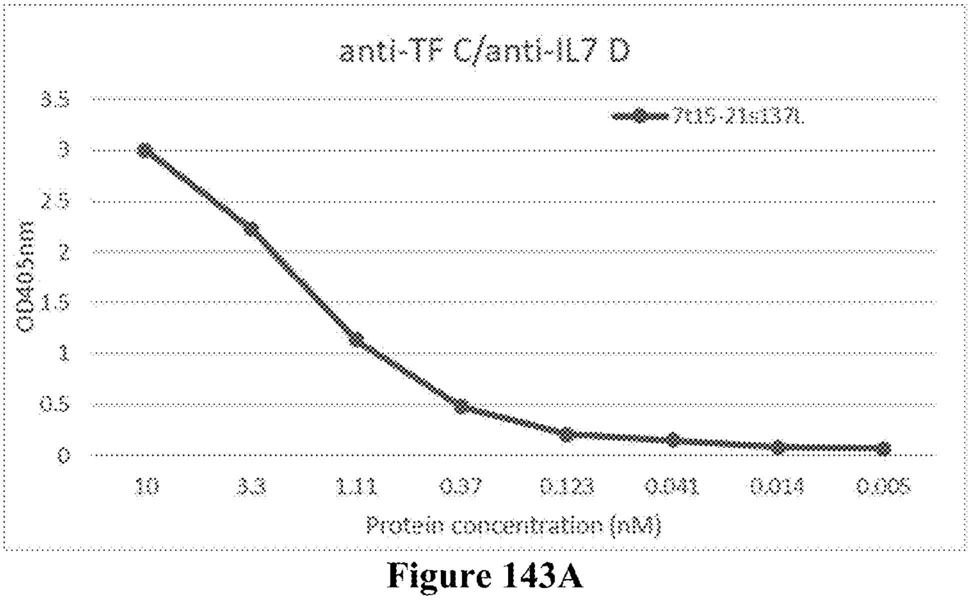
Figure 143B:
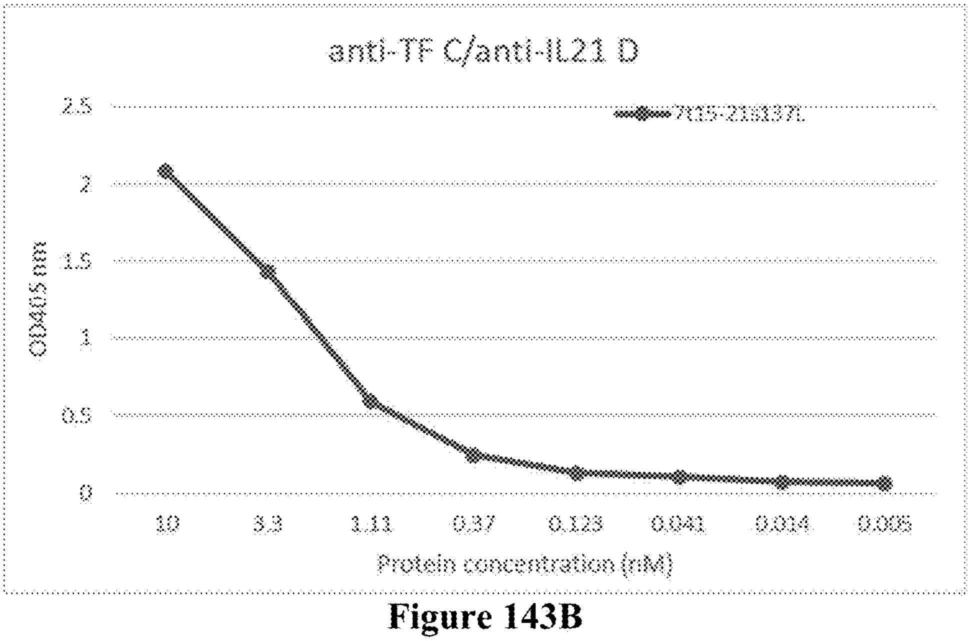
Figure 143C:
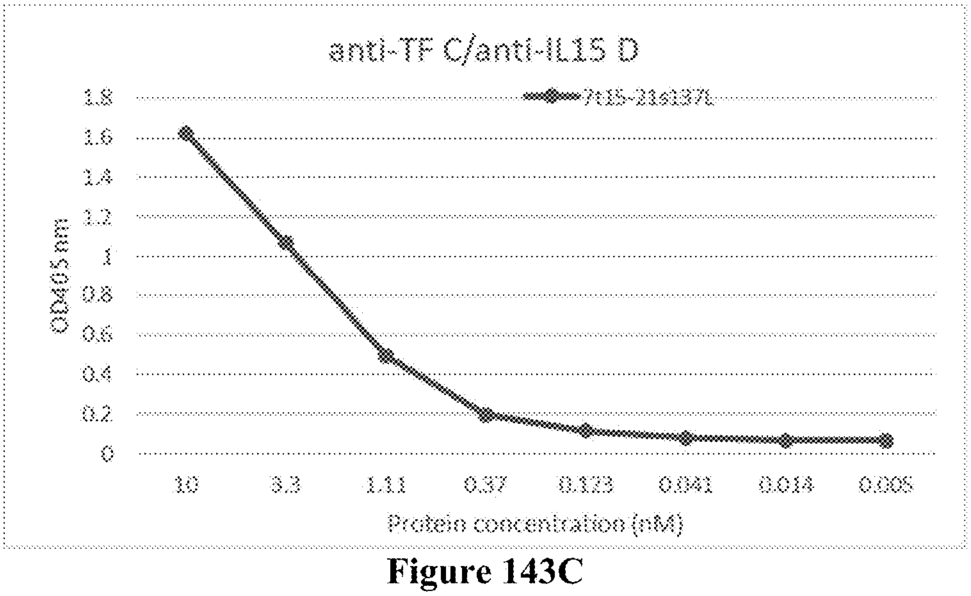
Figure 143D:
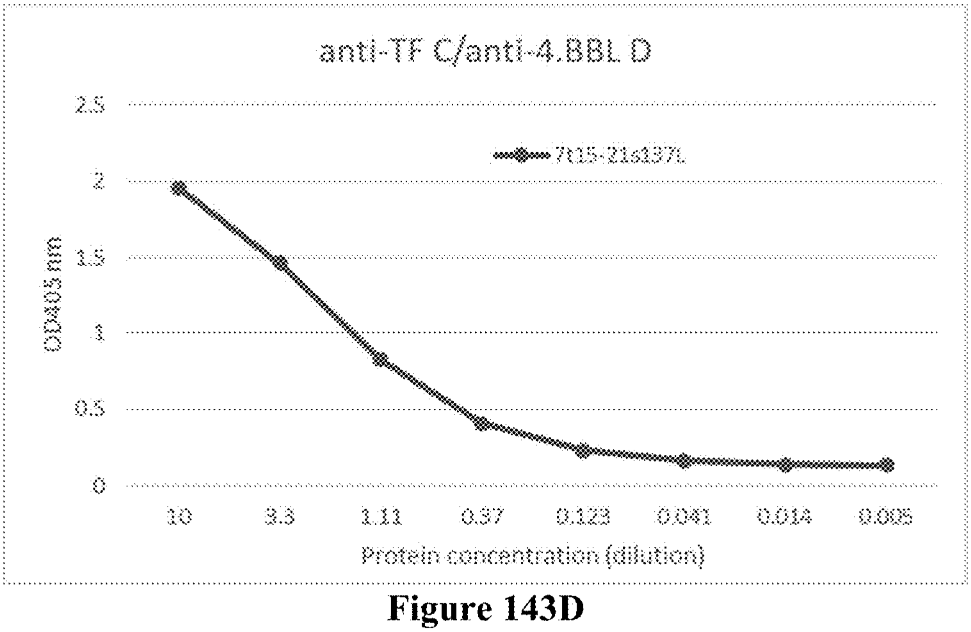

FIG. 142 shows binding of 7t15-21s137L (long version) and 7t15-21s137L (short version) to CD137 (4.1BB).

FIG. 143A-143D show detection of IL7, IL21, IL15, and 4.1BBL in 7t15-21s137L (long version) by the respective antibodies using ELISA.

Figure 144:
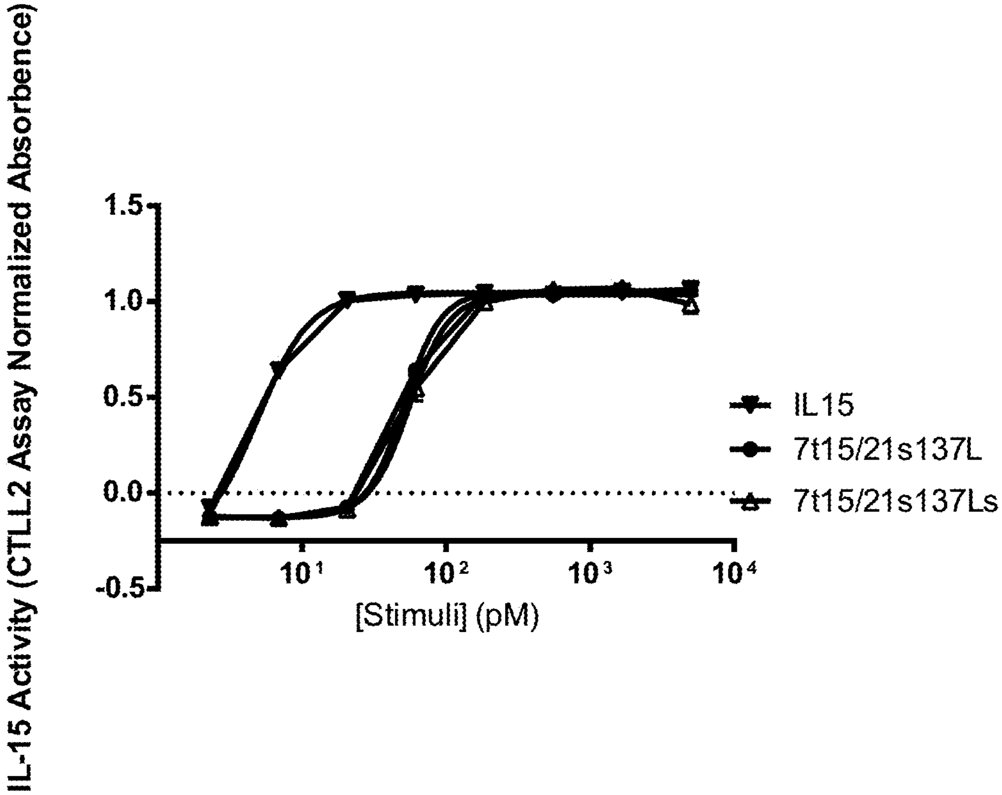

FIG. 144 shows IL-15 activity of 7t15-21s137L (long version) and 7t15-21s137L (short version) as evaluated by a IL2Rαβγ-containing CTLL2 cell proliferation assay.

DETAILED DESCRIPTION

Provided herein are multi-chain chimeric polypeptides that include: (a) a first chimeric polypeptide including: (i) a first target-binding domain; (ii) a soluble tissue factor domain; and (iii) a first domain of a pair of affinity domains; and (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains. Also provided herein are compositions that include any of the multi-chain chimeric polypeptides described herein, nucleic acids that encode any of the multi-chain chimeric polypeptides described herein, and cells that include any of the nucleic acids that encode any of the multi-chain chimeric polypeptides described herein. Also provided herein are methods of stimulating an immune cell and methods of treating a subject in need thereof that include the use of any of the multi-chain chimeric polypeptides described herein. Also provided herein are methods of producing any of the multi-chain chimeric polypeptides described herein.

Figure 1:
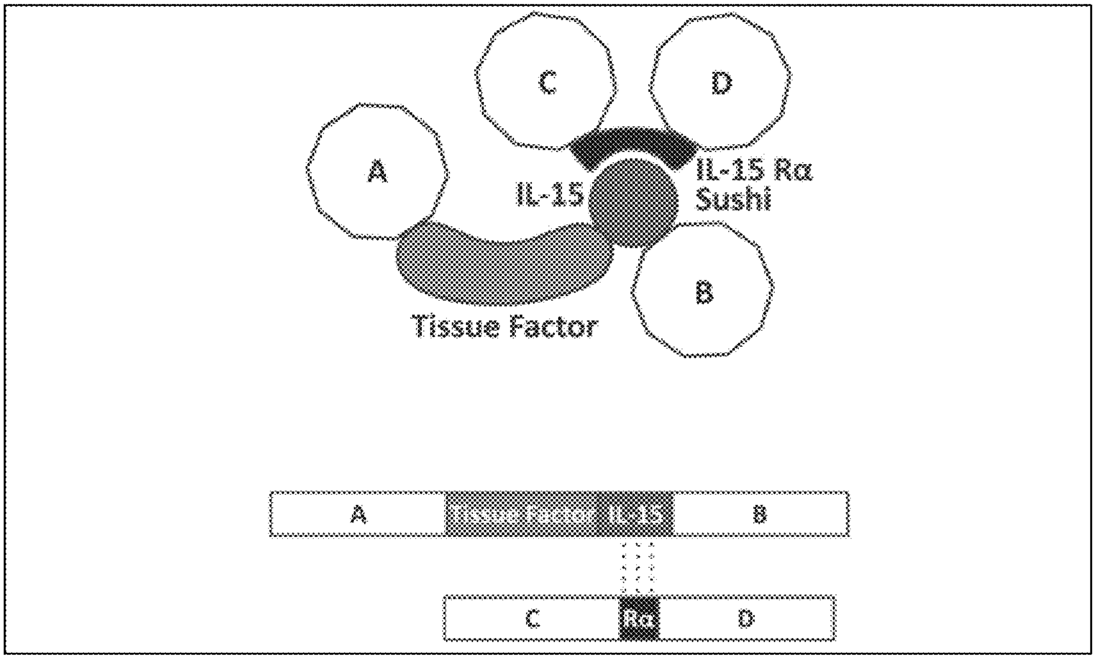
FIG. 1 shows exemplary diagrams for a multi-chain chimeric polypeptide: (i) a first chimeric polypeptide including a first target-binding domain (A), a soluble tissue factor domain, a first domain of an affinity pair of domains (soluble interleukin IL-15), and an additional target-binding domain (B); and (ii) second chimeric polypeptide including a second domain of an affinity pair of domains (IL-15 receptor alpha sushi domain), a second target-binding domain (C), and an additional antigen-binding domain (D). The top cartoon diagram depicts the association of the first and the second chimeric polypeptides through the pair of affinity domains. The bottom schematic diagrams show the order of the domains in the first and second chimeric polypeptides.
Figure 2:
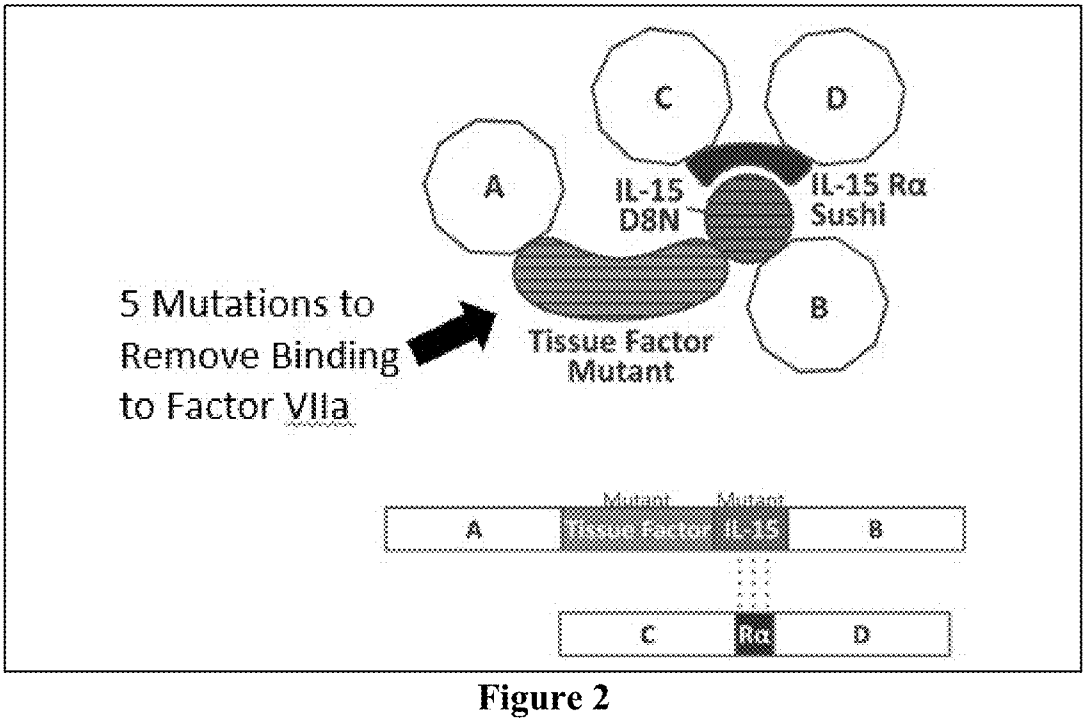
FIG. 2 shows exemplary diagrams for a multi-chain chimeric polypeptide: (i) a first chimeric polypeptide including a first target-binding domain (A), a soluble tissue factor domain including five amino acid substitutions in order to remove binding of the soluble tissue factor domain to FVIIa, a first domain of an affinity pair of domains (soluble interleukin IL-15 including a D8N or D8A amino acid substitution), and an additional target-binding domain (B); and (ii) second chimeric polypeptide including a second domain of an affinity pair of domains (IL-15 receptor alpha sushi domain), a second target-binding domain (C), and an additional antigen-binding domain (D). The top cartoon diagram depicts the association of the first and the second chimeric polypeptides through the pair of affinity domains. The bottom schematic diagrams show the order of the domains in the first and second chimeric polypeptides. In other embodiments of any of the multi-chain chimeric polypeptides described herein the soluble tissue factor domain can comprise or consists of a soluble wildtype human tissue factor domain (comprising or consisting of a contiguous sequence within wildtype human tissue factor).

In some examples of any of the multi-chain chimeric polypeptides described herein the total length of first chimeric polypeptide and/or the second chimeric polypeptide can each independently be about 50 amino acids to about 3000 amino acids, about 50 amino acids to about 2500 amino acids, about 50 amino acids to about 2000 amino acids, about 50 amino acids to about 1500 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 480 amino acids, about 50 amino acids to about 460 amino acids, about 50 amino acids to about 440 amino acids, about 50 amino acids to about 420 amino acids, about 50 amino acids to about 400 amino acids, about 50 amino acids to about 380 amino acids, about 50 amino acids to about 360 amino acids, about 50 amino acids to about 340 amino acids, about 50 amino acids to about 320 amino acids, about 50 amino acids to about 300 amino acids, about 50 amino acids to about 280 amino acids, about 50 amino acids to about 260 amino acids, about 50 amino acids to about 240 amino acids, about 50 amino acids to about 220 amino acids, about 50 amino acids to about 200 amino acids, about 50 amino acids to about 150 amino acids, about 50 amino acids to about 100 amino acids, about 100 amino acids to about 3000 amino acids, about 100 amino acids to about 2500 amino acids, about 100 amino acids to about 2000 amino acids, about 100 amino acids to about 1500 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 480 amino acids, about 100 amino acids to about 460 amino acids, about 100 amino acids to about 440 amino acids, about 100 amino acids to about 420 amino acids, about 100 amino acids to about 400 amino acids, about 100 amino acids to about 380 amino acids, about 100 amino acids to about 360 amino acids, about 100 amino acids to about 340 amino acids, about 100 amino acids to about 320 amino acids, about 100 amino acids to about 300 amino acids, about 100 amino acids to about 280 amino acids, about 100 amino acids to about 260 amino acids, about 100 amino acids to about 240 amino acids, about 100 amino acids to about 220 amino acids, about 100 amino acids to about 200 amino acids, about 100 amino acids to about 150 amino acids, about 150 amino acids to about 3000 amino acids, about 150 amino acids to about 2500 amino acids, about 150 amino acids to about 2000 amino acids, about 150 amino acids to about 1500 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 480 amino acids, about 150 amino acids to about 460 amino acids, about 150 amino acids to about 440 amino acids, about 150 amino acids to about 420 amino acids, about 150 amino acids to about 400 amino acids, about 150 amino acids to about 380 amino acids, about 150 amino acids to about 360 amino acids, about 150 amino acids to about 340 amino acids, about 150 amino acids to about 320 amino acids, about 150 amino acids to about 300 amino acids, about 150 amino acids to about 280 amino acids, about 150 amino acids to about 260 amino acids, about 150 amino acids to about 240 amino acids, about 150 amino acids to about 220 amino acids, about 150 amino acids to about 200 amino acids, about 200 amino acids to about 3000 amino acids, about 200 amino acids to about 2500 amino acids, about 200 amino acids to about 2000 amino acids, about 200 amino acids to about 1500 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 480 amino acids, about 200 amino acids to about 460 amino acids, about 200 amino acids to about 440 amino acids, about 200 amino acids to about 420 amino acids, about 200 amino acids to about 400 amino acids, about 200 amino acids to about 380 amino acids, about 200 amino acids to about 360 amino acids, about 200 amino acids to about 340 amino acids, about 200 amino acids to about 320 amino acids, about 200 amino acids to about 300 amino acids, about 200 amino acids to about 280 amino acids, about 200 amino acids to about 260 amino acids, about 200 amino acids to about 240 amino acids, about 200 amino acids to about 220 amino acids, about 220 amino acids to about 3000 amino acids, about 220 amino acids to about 2500 amino acids, about 220 amino acids to about 2000 amino acids, about 220 amino acids to about 1500 amino acids, about 220 amino acids to about 1000 amino acids, about 220 amino acids to about 950 amino acids, about 220 amino acids to about 900 amino acids, about 220 amino acids to about 850 amino acids, about 220 amino acids to about 800 amino acids, about 220 amino acids to about 750 amino acids, about 220 amino acids to about 700 amino acids, about 220 amino acids to about 650 amino acids, about 220 amino acids to about 600 amino acids, about 220 amino acids to about 550 amino acids, about 220 amino acids to about 500 amino acids, about 220 amino acids to about 480 amino acids, about 220 amino acids to about 460 amino acids, about 220 amino acids to about 440 amino acids, about 220 amino acids to about 420 amino acids, about 220 amino acids to about 400 amino acids, about 220 amino acids to about 380 amino acids, about 220 amino acids to about 360 amino acids, about 220 amino acids to about 340 amino acids, about 220 amino acids to about 320 amino acids, about 220 amino acids to about 300 amino acids, about 220 amino acids to about 280 amino acids, about 220 amino acids to about 260 amino acids, about 220 amino acids to about 240 amino acids, about 240 amino acids to about 3000 amino acids, about 240 amino acids to about 2500 amino acids, about 240 amino acids to about 2000 amino acids, about 240 amino acids to about 1500 amino acids, about 240 amino acids to about 1000 amino acids, about 240 amino acids to about 950 amino acids, about 240 amino acids to about 900 amino acids, about 240 amino acids to about 850 amino acids, about 240 amino acids to about 800 amino acids, about 240 amino acids to about 750 amino acids, about 240 amino acids to about 700 amino acids, about 240 amino acids to about 650 amino acids, about 240 amino acids to about 600 amino acids, about 240 amino acids to about 550 amino acids, about 240 amino acids to about 500 amino acids, about 240 amino acids to about 480 amino acids, about 240 amino acids to about 460 amino acids, about 240 amino acids to about 440 amino acids, about 240 amino acids to about 420 amino acids, about 240 amino acids to about 400 amino acids, about 240 amino acids to about 380 amino acids, about 240 amino acids to about 360 amino acids, about 240 amino acids to about 340 amino acids, about 240 amino acids to about 320 amino acids, about 240 amino acids to about 300 amino acids, about 240 amino acids to about 280 amino acids, about 240 amino acids to about 260 amino acids, about 260 amino acids to about 3000 amino acids, about 260 amino acids to about 2500 amino acids, about 260 amino acids to about 2000 amino acids, about 260 amino acids to about 1500 amino acids, about 260 amino acids to about 1000 amino acids, about 260 amino acids to about 950 amino acids, about 260 amino acids to about 900 amino acids, about 260 amino acids to about 850 amino acids, about 260 amino acids to about 800 amino acids, about 260 amino acids to about 750 amino acids, about 260 amino acids to about 700 amino acids, about 260 amino acids to about 650 amino acids, about 260 amino acids to about 600 amino acids, about 260 amino acids to about 550 amino acids, about 260 amino acids to about 500 amino acids, about 260 amino acids to about 480 amino acids, about 260 amino acids to about 460 amino acids, about 260 amino acids to about 440 amino acids, about 260 amino acids to about 420 amino acids, about 260 amino acids to about 400 amino acids, about 260 amino acids to about 380 amino acids, about 260 amino acids to about 360 amino acids, about 260 amino acids to about 340 amino acids, about 260 amino acids to about 320 amino acids, about 260 amino acids to about 300 amino acids, about 260 amino acids to about 280 amino acids, about 280 amino acids to about 3000 amino acids, about 280 amino acids to about 2500 amino acids, about 280 amino acids to about 2000 amino acids, about 280 amino acids to about 1500 amino acids, about 280 amino acids to about 1000 amino acids, about 280 amino acids to about 950 amino acids, about 280 amino acids to about 900 amino acids, about 280 amino acids to about 850 amino acids, about 280 amino acids to about 800 amino acids, about 280 amino acids to about 750 amino acids, about 280 amino acids to about 700 amino acids, about 280 amino acids to about 650 amino acids, about 280 amino acids to about 600 amino acids, about 280 amino acids to about 550 amino acids, about 280 amino acids to about 500 amino acids, about 280 amino acids to about 480 amino acids, about 280 amino acids to about 460 amino acids, about 280 amino acids to about 440 amino acids, about 280 amino acids to about 420 amino acids, about 280 amino acids to about 400 amino acids, about 280 amino acids to about 380 amino acids, about 280 amino acids to about 360 amino acids, about 280 amino acids to about 340 amino acids, about 280 amino acids to about 320 amino acids, about 280 amino acids to about 300 amino acids, about 300 amino acids to about 3000 amino acids, about 300 amino acids to about 2500 amino acids, about 300 amino acids to about 2000 amino acids, about 300 amino acids to about 1500 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 480 amino acids, about 300 amino acids to about 460 amino acids, about 300 amino acids to about 440 amino acids, about 300 amino acids to about 420 amino acids, about 300 amino acids to about 400 amino acids, about 300 amino acids to about 380 amino acids, about 300 amino acids to about 360 amino acids, about 300 amino acids to about 340 amino acids, about 300 amino acids to about 320 amino acids, about 320 amino acids to about 3000 amino acids, about 320 amino acids to about 2500 amino acids, about 320 amino acids to about 2000 amino acids, about 320 amino acids to about 1500 amino acids, about 320 amino acids to about 1000 amino acids, about 320 amino acids to about 950 amino acids, about 320 amino acids to about 900 amino acids, about 320 amino acids to about 850 amino acids, about 320 amino acids to about 800 amino acids, about 320 amino acids to about 750 amino acids, about 320 amino acids to about 700 amino acids, about 320 amino acids to about 650 amino acids, about 320 amino acids to about 600 amino acids, about 320 amino acids to about 550 amino acids, about 320 amino acids to about 500 amino acids, about 320 amino acids to about 480 amino acids, about 320 amino acids to about 460 amino acids, about 320 amino acids to about 440 amino acids, about 320 amino acids to about 420 amino acids, about 320 amino acids to about 400 amino acids, about 320 amino acids to about 380 amino acids, about 320 amino acids to about 360 amino acids, about 320 amino acids to about 340 amino acids, about 340 amino acids to about 3000 amino acids, about 340 amino acids to about 2500 amino acids, about 340 amino acids to about 2000 amino acids, about 340 amino acids to about 1500 amino acids, about 340 amino acids to about 1000 amino acids, about 340 amino acids to about 950 amino acids, about 340 amino acids to about 900 amino acids, about 340 amino acids to about 850 amino acids, about 340 amino acids to about 800 amino acids, about 340 amino acids to about 750 amino acids, about 340 amino acids to about 700 amino acids, about 340 amino acids to about 650 amino acids, about 340 amino acids to about 600 amino acids, about 340 amino acids to about 550 amino acids, about 340 amino acids to about 500 amino acids, about 340 amino acids to about 480 amino acids, about 340 amino acids to about 460 amino acids, about 340 amino acids to about 440 amino acids, about 340 amino acids to about 420 amino acids, about 340 amino acids to about 400 amino acids, about 340 amino acids to about 380 amino acids, about 340 amino acids to about 360 amino acids, about 360 amino acids to about 3000 amino acids, about 360 amino acids to about 2500 amino acids, about 360 amino acids to about 2000 amino acids, about 360 amino acids to about 1500 amino acids, about 360 amino acids to about 1000 amino acids, about 360 amino acids to about 950 amino acids, about 360 amino acids to about 900 amino acids, about 360 amino acids to about 850 amino acids, about 360 amino acids to about 800 amino acids, about 360 amino acids to about 750 amino acids, about 360 amino acids to about 700 amino acids, about 360 amino acids to about 650 amino acids, about 360 amino acids to about 600 amino acids, about 360 amino acids to about 550 amino acids, about 360 amino acids to about 500 amino acids, about 360 amino acids to about 480 amino acids, about 360 amino acids to about 460 amino acids, about 360 amino acids to about 440 amino acids, about 360 amino acids to about 420 amino acids, about 360 amino acids to about 400 amino acids, about 360 amino acids to about 380 amino acids, about 380 amino acids to about 3000 amino acids, about 380 amino acids to about 2500 amino acids, about 380 amino acids to about 2000 amino acids, about 380 amino acids to about 1500 amino acids, about 380 amino acids to about 1000 amino acids, about 380 amino acids to about 950 amino acids, about 380 amino acids to about 900 amino acids, about 380 amino acids to about 850 amino acids, about 380 amino acids to about 800 amino acids, about 380 amino acids to about 750 amino acids, about 380 amino acids to about 700 amino acids, about 380 amino acids to about 650 amino acids, about 380 amino acids to about 600 amino acids, about 380 amino acids to about 550 amino acids, about 380 amino acids to about 500 amino acids, about 380 amino acids to about 480 amino acids, about 380 amino acids to about 460 amino acids, about 380 amino acids to about 440 amino acids, about 380 amino acids to about 420 amino acids, about 380 amino acids to about 400 amino acids, about 400 amino acids to about 3000 amino acids, about 400 amino acids to about 2500 amino acids, about 400 amino acids to about 2000 amino acids, about 400 amino acids to about 1500 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 480 amino acids, about 400 amino acids to about 460 amino acids, about 400 amino acids to about 440 amino acids, about 400 amino acids to about 420 amino acids, about 420 amino acids to about 3000 amino acids, about 420 amino acids to about 2500 amino acids, about 420 amino acids to about 2000 amino acids, about 420 amino acids to about 1500 amino acids, about 420 amino acids to about 1000 amino acids, about 420 amino acids to about 950 amino acids, about 420 amino acids to about 900 amino acids, about 420 amino acids to about 850 amino acids, about 420 amino acids to about 800 amino acids, about 420 amino acids to about 750 amino acids, about 420 amino acids to about 700 amino acids, about 420 amino acids to about 650 amino acids, about 420 amino acids to about 600 amino acids, about 420 amino acids to about 550 amino acids, about 420 amino acids to about 500 amino acids, about 420 amino acids to about 480 amino acids, about 420 amino acids to about 460 amino acids, about 420 amino acids to about 440 amino acids, about 440 amino acids to about 3000 amino acids, about 440 amino acids to about 2500 amino acids, about 440 amino acids to about 2000 amino acids, about 440 amino acids to about 1500 amino acids, about 440 amino acids to about 1000 amino acids, about 440 amino acids to about 950 amino acids, about 440 amino acids to about 900 amino acids, about 440 amino acids to about 850 amino acids, about 440 amino acids to about 800 amino acids, about 440 amino acids to about 750 amino acids, about 440 amino acids to about 700 amino acids, about 440 amino acids to about 650 amino acids, about 440 amino acids to about 600 amino acids, about 440 amino acids to about 550 amino acids, about 440 amino acids to about 500 amino acids, about 440 amino acids to about 480 amino acids, about 440 amino acids to about 460 amino acids, about 460 amino acids to about 3000 amino acids, about 460 amino acids to about 2500 amino acids, about 460 amino acids to about 2000 amino acids, about 460 amino acids to about 1500 amino acids, about 460 amino acids to about 1000 amino acids, about 460 amino acids to about 950 amino acids, about 460 amino acids to about 900 amino acids, about 460 amino acids to about 850 amino acids, about 460 amino acids to about 800 amino acids, about 460 amino acids to about 750 amino acids, about 460 amino acids to about 700 amino acids, about 460 amino acids to about 650 amino acids, about 460 amino acids to about 600 amino acids, about 460 amino acids to about 550 amino acids, about 460 amino acids to about 500 amino acids, about 460 amino acids to about 480 amino acids, about 480 amino acids to about 3000 amino acids, about 480 amino acids to about 2500 amino acids, about 480 amino acids to about 2000 amino acids, about 480 amino acids to about 1500 amino acids, about 480 amino acids to about 1000 amino acids, about 480 amino acids to about 950 amino acids, about 480 amino acids to about 900 amino acids, about 480 amino acids to about 850 amino acids, about 480 amino acids to about 800 amino acids, about 480 amino acids to about 750 amino acids, about 480 amino acids to about 700 amino acids, about 480 amino acids to about 650 amino acids, about 480 amino acids to about 600 amino acids, about 480 amino acids to about 550 amino acids, about 480 amino acids to about 500 amino acids, about 500 amino acids to about 3000 amino acids, about 500 amino acids to about 2500 amino acids, about 500 amino acids to about 2000 amino acids, about 500 amino acids to about 1500 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 3000 amino acids, about 550 amino acids to about 2500 amino acids, about 550 amino acids to about 2000 amino acids, about 550 amino acids to about 1500 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 3000 amino acids, about 600 amino acids to about 2500 amino acids, about 600 amino acids to about 2000 amino acids, about 600 amino acids to about 1500 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 3000 amino acids, about 650 amino acids to about 2500 amino acids, about 650 amino acids to about 2000 amino acids, about 650 amino acids to about 1500 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 3000 amino acids, about 700 amino acids to about 2500 amino acids, about 700 amino acids to about 2000 amino acids, about 700 amino acids to about 1500 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 3000 amino acids, about 750 amino acids to about 2500 amino acids, about 750 amino acids to about 2000 amino acids, about 750 amino acids to about 1500 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 3000 amino acids, about 800 amino acids to about 2500 amino acids, about 800 amino acids to about 2000 amino acids, about 800 amino acids to about 1500 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 3000 amino acids, about 850 amino acids to about 2500 amino acids, about 850 amino acids to about 2000 amino acids, about 850 amino acids to about 1500 amino acids, about 850 amino acids to about 1000 amino acids, about 850 amino acids to about 950 amino acids, about 850 amino acids to about 900 amino acids, about 900 amino acids to about 3000 amino acids, about 900 amino acids to about 2500 amino acids, about 900 amino acids to about 2000 amino acids, about 900 amino acids to about 1500 amino acids, about 900 amino acids to about 1000 amino acids, about 900 amino acids to about 950 amino acids, about 950 amino acids to about 3000 amino acids, about 950 amino acids to about 2500 amino acids, about 950 amino acids to about 2000 amino acids, about 950 amino acids to about 1500 amino acids, about 950 amino acids to about 1000 amino acids, about 1000 amino acids to about 3000 amino acids, about 1000 amino acids to about 2500 amino acids, about 1000 amino acids to about 2000 amino acids, about 1000 amino acids to about 1500 amino acids, about 1500 amino acids to about 3000 amino acids, about 1500 amino acids to about 2500 amino acids, about 1500 amino acids to about 2000 amino acids, about 2000 amino acids to about 3000 amino acids, about 2000 amino acids to about 2500 amino acids, or about 2500 amino acids to about 3000 amino acids. Diagrams of exemplary multi-chain chimeric polypeptides provided herein are depicted in FIGS. 1 and 2.

In some embodiments of any of the multi-chain chimeric polypeptides described herein, the first target-binding domain (e.g., any of the first target-binding domains described herein) and the soluble tissue factor domain (e.g., any of the exemplary soluble tissue factor domains described herein) directly abut each other in the first chimeric polypeptide. In some embodiments of any of the multi-chain chimeric polypeptides described herein, the first chimeric polypeptide further comprises a linker sequence (e.g., any of the exemplary linker sequences described herein or known in the art) between the first target-binding domain (e.g., any of the exemplary first target-binding domains described herein) and the soluble tissue factor domain (e.g., any of the exemplary soluble tissue factor domains described herein) in the first chimeric polypeptide.

In some embodiments of any of the multi-chain chimeric polypeptides described herein, the soluble tissue factor domain (e.g., any of the exemplary soluble tissue factor domains described herein) and the first domain of the pair of affinity domains (e.g., any of the exemplary first domains of any of the exemplary pairs of affinity domains described herein) directly abut each other in the first chimeric polypeptide. In some embodiments of any of the multi-chain chimeric polypeptides described herein, the first chimeric polypeptide further comprises a linker sequence (e.g., any of the exemplary linker sequences described herein or known in the art) between the soluble tissue factor domain (e.g., any of the exemplary soluble tissue factor domains described herein) and the first domain of the pair of affinity domains (e.g., any of the exemplary first domains of any of the exemplary pairs of affinity domains described herein) in the first chimeric polypeptide.

In some embodiments of any of the multi-chain chimeric polypeptides described herein, the second domain of the pair of affinity domains (e.g., any of the exemplary second domains of any of the exemplary pairs of affinity domains described herein) and the second target-binding domain (e.g., any of the exemplary second target-binding domains described herein) directly abut each other in the second chimeric polypeptide. In some embodiments of any of the multi-chain chimeric polypeptides described herein, the second chimeric polypeptide further comprises a linker sequence (e.g., any of the exemplary linker sequences described herein or known in the art) between the second domain of the pair of affinity domains (e.g., any of the exemplary second domains of any of the exemplary pairs of affinity domains described herein) and the second target-binding domain (e.g., any of the exemplary second target-binding domains described herein) in the second chimeric polypeptide.

Non-limiting aspects of these chimeric polypeptides, nucleic acids, vectors, cells, and methods are described below, and can be used in any combination without limitation. Additional aspects of these chimeric polypeptides, nucleic acids, vectors, cells, and methods are known in the art.

Tissue Factor

Human tissue factor is a 263 amino-acid transmembrane protein containing three domains: (1) a 219-amino acid N-terminal extracellular domain (residues 1-219); (2) a 22-amino acid transmembrane domain (residues 220-242); and (3) a 21-amino acid cytoplasmic C-terminal tail (residues 242-263) ((UniProtKB Identifier Number: P13726). The cytoplasmic tail contains two phosphorylation sites at Ser253 and Ser258, and one S-palmitoylation site at Cys245. Deletion or mutation of the cytoplasmic domain was not found to affect tissue factor coagulation activity. Tissue factor has one S-palmitoylation site in the intracellular domain of the protein at Cys245. The Cys245 is located at the amino acid terminus of the intracellular domain and close to the membrane surface. The tissue factor transmembrane domain is composed of a single-spanning α-helix.

The extracellular domain of tissue factor, composed of two fibronectin type III domains, is connected to the transmembrane domain through a six-amino acid linker. This linker provides conformational flexibility to decouple the tissue factor extracellular domain from its transmembrane and cytoplasmic domains. Each tissue factor fibronectin type III module is composed of two overlapping β sheets with the top sheet domain containing three antiparallel β-strands and the bottom sheet containing four β-strands. The β-strands are connected by β-loops between strand βA and βB, βC and βD, and βE and βF, all of which are conserved in conformation in the two modules. There are three short α-helix segments connecting the β-strands. A unique feature of tissue factor is a 17-amino acid β-hairpin between strand β10 and strand β11, which is not a common element of the fibronectin superfamily. The N-terminal domain also contains a 12 amino acid loop between β6F and β7G that is not present in the C-terminal domain and is unique to tissue factor. Such a fibronectin type III domain structure is a feature of the immunoglobulin-like family of protein folds and is conserved among a wide variety of extracellular proteins.

The zymogen FVII is rapidly converted to FVIIa by limited proteolysis once it binds to tissue to form the active tissue factor-FVIIa complex. The FVIIa, which circulates as an enzyme at a concentration of approximately 0.1 nM (1% of plasma FVII), can also bind directly to tissue factor. The allosteric interaction between tissue factor and FVIIa on the tissue factor-FVIIa complex greatly increases the enzymatic activity of FVIIa: an approximate 20- to 100-fold increase in the rate of hydrolysis of small, chromogenic peptidyl substrates, and nearly a million-fold increase in the rate of activation of the natural macromolecular substrates FIX and FX. In concert with allosteric activation of the active site of FVIIa upon binding to tissue factor, the formation of tissue factor-FVIIa complex on phospholipid bilayer (i.e., upon exposure of phosphatidyl-L-serine on membrane surfaces) increases the rate of FIX or FX activation, in a $Ca^{2+}$-dependent manner, an additional 1,000-fold. The roughly million-fold overall increase in FX activation by tissue factor-FVIIa-phospholipid complex relative to free FVIIa is a critical regulatory point for the coagulation cascade.

FVII is a ~50 kDa, single-chain polypeptide consisting of 406 amino acid residues, with an N-terminal γ-carboxyglutamate-rich (GLA) domain, two epidermal growth factor-like domains (EGF1 and EFG2), and a C-terminal serine protease domain. FVII is activated to FVIIa by a specific proteolytic cleavage of the $Ile\text{-}^{154}\text{-}Arg^{152}$ bond in the short linker region between the EGF2 and the protease domain. This cleavage results in the light and heavy chains being held together by a single disulfide bond of $Cys^{135}$ and $Cys^{262}$. FVIIa binds phospholipid membrane in a $Ca^{2+}$-dependent manner through its N-terminal GLA-domain. Immediately C-terminal to the GLA domain is an aromatic stack and two EGF domains. The aromatic stack connects the GLA to EGF1 domain which binds a single $Ca^{2+}$ ion. Occupancy of this $Ca^{2+}$-binding site increases FVIIa amidolytic activity and tissue factor association. The catalytic triad consist of $His^{193}$, $Asp^{242}$, and $Ser^{344}$, and binding of a single $Ca^{2+}$ ion within the FVIIa protease domain is critical for its catalytic activity. Proteolytic activation of FVII to FVIIa frees the newly formed amino terminus at $Ile^{153}$ to fold back and be inserted into the activation pocket forming a salt bridge with the carboxylate of $Asp^{343}$ to generate the oxyanion hole. Formation of this salt bridge is critical for FVIIa activity. However, oxyanion hole formation does not occur in free FVIIa upon proteolytic activation. As a result, FVIIa circulates in a zymogen-like state that is poorly recognized by plasma protease inhibitors, allowing it to circulate with a half-life of approximately 90 minutes.

Tissue factor-mediated positioning of the FVIIa active site above the membrane surface is important for FVIIa towards cognate substrates. Free FVIIa adopts a stable, extended structure when bound to the membrane with its active site positioned ~80 Å above the membrane surface. Upon FVIIa binding to tissue factor, the FVa active site is repositioned ~6 Å closer to the membrane. This modulation may aid in a proper alignment of the FVIIa catalytic triad with the target substrate cleavage site. Using GLA-domainless FVIIa, it has been shown that the active site was still positioned a similar distance above the membrane, demonstrating that tissue factor is able to fully support FVIIa active site positioning even in the absence of FVIIa-membrane interaction. Additional data showed that tissue factor supported full FVIIa proteolytic activity as long as the tissue factor extracellular domain was tethered in some way to the membrane surface. However, raising the active site of FVIIa greater than 80 Å above the membrane surface greatly reduced the ability of the tissue factor-FVIIa complex to activate FX but did not diminish tissue factor-FVIIa amidolytic activity.

Alanine scanning mutagenesis has been used to assess the role of specific amino acid side chains in the tissue factor extracellular domain for interaction with FVIIa (Gibbs et al., *Biochemistry* 33(47): 14003-14010, 1994; Schullek et al., *J Biol Chem* 269(30): 19399-19403, 1994). Alanine substitution identified a limited number of residue positions at which alanine replacements cause 5- to 10-fold lower affinity for FVIIa binding. Most of these residue side chains were found to be well-exposed to solvent in the crystal structure, concordant with macromolecular ligand interaction. The FVIIa ligand-binding site is located over an extensive region at the boundary between the two modules. In the C-module, residues $Arg^{135}$ and $Phe^{140}$ located on the protruding B-C loop provide an independent contact with FVIIa. $Leu^{133}$ is located at the base of the fingerlike structure and packed into the cleft between the two modules. This provides continuity to a major cluster of important binding residues consisting of $Lys^{20}$, $Thr^{60}$, $Asp^{58}$, and $Ile^{22}$. $Thr^{60}$ is only partially solvent-exposed and may play a local structural role rather than making a significant contact with ligand. The binding site extends onto the concave side of the intermodule angle involving $Glu^{24}$ and $Gln^{110}$, and potentially the more distant residue $Val^{207}$. The binding region extends from Asp58 onto a convex surface area formed by $Lys^{48}$, $Lys^{46}$, $Gln^{37}$, $Asp^{44}$, and $Trp^{45}$. $Trp^{45}$ and $Asp^{44}$ do not interact independently with FVIIa, indicating that the mutational effect at the $Trp^{45}$ position may reflect a structural importance of this side chain for the local packing of the adjacent $Asp^{44}$ and $Gln^{37}$ side chain. The interactive area further includes two surface-exposed aromatic residues, $Phe^{76}$ and $Tyr^{78}$, which form part of the hydrophobic cluster in the N-module.

The known physiologic substrates of tissue factor-FVIIa are FVII, FIX, and FX and certain proteinase-activated receptors. Mutational analysis has identified a number of residues that, when mutated, support full FVIIa amidolytic activity towards small peptidyl substrates but are deficient in their ability to support macromolecular substrate (i.e., FVII, FIX, and FX) activation (Ruf et al., *J Biol Chem* 267(31): 22206-22210, 1992; Ruf et al., *J Biol Chem* 267(9): 6375-6381, 1992; Huang et al., *J Biol Chem* 271(36): 21752-21757, 1996; Kirchhofer et al., *Biochemistry* 39(25): 7380-7387, 2000). The tissue factor loop region at residues 159-165, and residues in or adjacent to this flexible loop have been shown to be critical for the proteolytic activity of the tissue factor-FVIIa complex. This defines the proposed substrate-binding exosite region of tissue factor that is quite distant from the FVIIa active site. A substitution of the glycine residue by a marginally bulkier residue alanine, significantly impairs tissue factor-FVIIa proteolytic activity. This suggests that the flexibility afforded by glycine is critical for the loop of residues 159-165 for tissue factor macromolecular substrate recognition.

The residues $Lys^{165}$ and $Lys^{166}$ have also been demonstrated to be important for substrate recognition and binding. Mutation of either of these residues to alanine results in a significant decrease in the tissue factor co-factor function. $Lys^{165}$ and $Lys^{166}$ face away from each other, with $Lys^{165}$ pointing towards FVIIa in most tissue factor-FVIIa structures, and $Lys^{166}$ pointing into the substrate binding exosite region in the crystal structure. Putative salt bridge formation between $Lys^{165}$ of and $Gla^{35}$ of FVIIa would support the notion that tissue factor interaction with the GLA domain of FVIIa modulates substrate recognition. These results suggest that the C-terminal portion of the tissue factor ectodomain directly interacts with the GLA-domain, the possible adjacent EGF1 domains, of FIX and FX, and that the presence of the FVIIa GLA-domain may modulate these interactions either directly or indirectly.

Soluble Tissue Factor Domain

In some embodiments of any of the polypeptides, compositions, or methods described herein, the soluble tissue factor domain can be a wildtype tissue factor polypeptide lacking the signal sequence, the transmembrane domain, and the intracellular domain. In some examples, the soluble tissue factor domain can be a tissue factor mutant, wherein a wildtype tissue factor polypeptide lacking the signal sequence, the transmembrane domain, and the intracellular domain, and has been further modified at selected amino acids. In some examples, the soluble tissue factor domain can be a soluble human tissue factor domain. In some examples, the soluble tissue factor domain can be a soluble mouse tissue factor domain. In some examples, the soluble tissue factor domain can be a soluble rat tissue factor domain. Non-limiting examples of soluble human tissue factor domains, a mouse soluble tissue factor domain, a rat soluble tissue factor domain, and mutant soluble tissue factor domains are shown below.

```
Exemplary Soluble Human Tissue Factor
Domain
                                  (SEQ ID NO: 1)
SGTTNTVAAYNLTWKSTNFKTILEWEPKPVNQVYT

VQISTKSGDWKSKCFYTTDTECDLTDEIVKDVKQT

YLARVFSYPAGNVESTGSAGEPLYENSPEFTPYLE

TNLGQPTIQSFEQVGTKVNVTVEDERTLVRRNNTF

LSLRDVFGKDLIYTLYYWKSSSSGKKTAKTNTNEF

LIDVDKGENYCFSVQAVIPSRTVNRKSTDSPVECM

GQEKGEFRE
```

```
Exemplary Nucleic Acid Encoding Soluble
Human Tissue Factor Domain
                                  (SEQ ID NO: 2)
AGCGGCACAACCAACACAGTCGCTGCCTATAACCT

CACTTGGAAGAGCACCAACTTCAAAACCATCCTCG

AATGGGAACCCAAACCCGTTAACCAAGTTTACACC

GTGCAGATCAGCACCAAGTCCGGCGACTGGAAGTC

CAAATGTTTCTATACCACCGACACCGAGTGCGATC

TCACCGATGAGATCGTGAAAGATGTGAAACAGACC

TACCTCGCCCGGGTGTTTAGCTACCCCGCCGGCAA

TGTGGAGAGCACTGGTTCCGCTGGCGAGCCTTTAT

ACGAGAACAGCCCCGAATTTACCCCTTACCTCGAG

ACCAATTTAGGACAGCCCACCATCCAAAGCTTTGA

GCAAGTTGGCACAAAGGTGAATGTGACAGTGGAGG

ACGAGCGGACTTTAGTGCGGCGGAACAACACCTTT

CTCAGCCTCCGGGATGTGTTCGGCAAAGATTTAAT

CTACACACTGTATTACTGGAAGTCCTCTTCCTCCG

GCAAGAAGACAGCTAAAACCAACACAAACGAGTTT

TTAATCGACGTGGATAAAGGCGAAAACTACTGTTT

CAGCGTGCAAGCTGTGATCCCCTCCCGGACCGTGA

ATAGGAAAAGCACCGATAGCCCCGTTGAGTGCATG

GGCCAAGAAAAGGGCGAGTTCCGGGAG
```

-continued

```
Exemplary Mutant Soluble Human Tissue
Factor Domain
                                  (SEQ ID NO: 3)
SGTTNTVAAYNLTWKSTNFATALEWEPKPVNQVYT

VQISTKSGDWKSKCFYTTDTECALTDEIVKDVKQT

YLARVFSYPAGNVESTGSAGEPLYENSPEFTPYLE

TNLGQPTIQSFEQVGTKVNVTVEDERTLVARNNTA

LSLRDVFGKDLIYTLYYWKSSSSGKKTAKTNTNEF

LIDVDKGENYCFSVQAVIPSRTVNRKSTDSPVECM

GQEKGEFRE
```

```
Exemplary Mutant Soluble Human Tissue
Factor Domain
                                  (SEQ ID NO: 4)
SGTTNTVAAYNLTWKSTNFATALEWEPKPVNQVYT

VQISTKSGDAKSKCFYTTDTECALTDEIVKDVKQT

YLARVFSYPAGNVESTGSAGEPLAENSPEFTPYLE

TNLGQPTIQSFEQVGTKVNVTVEDERTLVARNNTA

LSLRDVFGKDLIYTLYYWKSSSSGKKTAKTNTNEF

LIDVDKGENYCFSVQAVIPSRTVNRKSTDSPVECM

GQEKGEFRE
```

```
Exemplary Soluble Mouse Tissue Factor
Domain
                                  (SEQ ID NO: 5)
agipekafnltwistdfktilewqpkptnytytvq

isdrsrnwknkcfsttdtecdltdeivkdvtwaye

akvlsvprrnsvhgdgdqlvihgeeppftnapkfI

pyrdtnlgqpviqqfeqdgrklnvvvkdsltlvrk

ngtfItlrqvfgkdlgyiityrkgsstgkktnitn

tnefsidveegvsycffvqamifsrktnqnspgss

tvcteqwksflge
```

```
Exemplary Soluble Rat Tissue Factor
Domain
                                  (SEQ ID NO: 6)
agtppgkafnltwistdfktilewqpkptnytytv

qisdrsrnwkykctgttdtecdltdeivkdvnwty

earvlsvpwrnsthgketlfgthgeeppftnarkf

ipyrdtkigqpviqkyeqggtklkvtvkdsftlvr

kngtfItlrqvfgndlgyiltyrkdsstgrktntt

htneflidvekgvsycffaqavifsrktnhkspes

itkcteqwksvlge
```

In some embodiments, a soluble tissue factor domain can include a sequence that is at least 70% identical, at least 72% identical, at least 74% identical, at least 76% identical, at least 78% identical, at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 1, 3, 4, 5, or 6. In some embodiments, a soluble tissue factor domain can include a sequence of SEQ ID NO: 1, 3, 4, 5, or 6, with one to twenty amino acids (e.g., 2, 3, 4, 5, 6, 7, 8, 9, 10, 11, 12, 13, 14, 15, 16, 17, 18, 19, or 20) amino acids removed from its N-terminus and/or one to twenty amino acids (e.g., 2, 3, 4, 5, 6, 7, 8, 9, 10, 11, 12, 13, 14, 15, 16, 17, 18, 19, or 20) amino acids removed from its C-terminus.

As can be appreciated in the art, one skilled in the art would understand that mutation of amino acids that are conserved between different mammalian species is more likely to decrease the activity and/or structural stability of the protein, while mutation of amino acids that are not conserved between different mammalian species is less likely to decrease the activity and/or structural stability of the protein.

In some examples of any of the multi-chain chimeric polypeptides described herein, the soluble tissue factor domain is not capable of binding to Factor VIIa. In some examples of any of the multi-chain chimeric polypeptides described herein, the soluble tissue factor domain does not convert inactive Factor X into Factor Xa. In some embodiments of any of the multi-chain chimeric polypeptides described herein, the multi-chain chimeric polypeptide does not stimulate blood coagulation in a mammal.

In some examples, the soluble tissue factor domain can be a soluble human tissue factor domain. In some embodiments, the soluble tissue factor domain can be a soluble mouse tissue factor domain. In some embodiments, the soluble tissue factor domain can be a soluble rat tissue factor domain.

In some examples, the soluble tissue factor domain does not include one or more (e.g., two, three, four, five, six, or seven) of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the mutant soluble tissue factor possesses the amino acid sequence of SEQ ID NO: 3 or SEQ ID NO: 4.

In some examples, the soluble tissue factor domain can be encoded by a nucleic acid including a sequence that is at least 70% identical, at least 72% identical, at least 74% identical, at least 76% identical, at least 78% identical, at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 2.

In some embodiments, the soluble tissue factor domain can have a total length of about 20 amino acids to about 220 amino acids, about 20 amino acids to about 215 amino acids, about 20 amino acids to about 210 amino acids, about 20 amino acids to about 205 amino acids, about 20 amino acids to about 200 amino acids, about 20 amino acids to about 195 amino acids, about 20 amino acids to about 190 amino acids, about 20 amino acids to about 185 amino acids, about 20 amino acids to about 180 amino acids, about 20 amino acids to about 175 amino acids, about 20 amino acids to about 170 amino acids, about 20 amino acids to about 165 amino acids, about 20 amino acids to about 160 amino acids, about 20 amino acids to about 155 amino acids, about 20 amino acids to about 150 amino acids, about 20 amino acids to about 145 amino acids, about 20 amino acids to about 140 amino acids, about 20 amino acids to about 135 amino acids, about 20 amino acids to about 130 amino acids, about 20 amino acids to about 125 amino acids, about 20 amino acids to about 120 amino acids, about 20 amino acids to about 115 amino acids, about 20 amino acids to about 110 amino acids, about 20 amino acids to about 105 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 60 amino acids, about 20 amino acids to about 50 amino acids, about 20 amino acids to about 40 amino acids, about 20 amino acids to about 30 amino acids, about 30 amino acids to about 220 amino acids, about 30 amino acids to about 215 amino acids, about 30 amino acids to about 210 amino acids, about 30 amino acids to about 205 amino acids, about 30 amino acids to about 200 amino acids, about 30 amino acids to about 195 amino acids, about 30 amino acids to about 190 amino acids, about 30 amino acids to about 185 amino acids, about 30 amino acids to about 180 amino acids, about 30 amino acids to about 175 amino acids, about 30 amino acids to about 170 amino acids, about 30 amino acids to about 165 amino acids, about 30 amino acids to about 160 amino acids, about 30 amino acids to about 155 amino acids, about 30 amino acids to about 150 amino acids, about 30 amino acids to about 145 amino acids, about 30 amino acids to about 140 amino acids, about 30 amino acids to about 135 amino acids, about 30 amino acids to about 130 amino acids, about 30 amino acids to about 125 amino acids, about 30 amino acids to about 120 amino acids, about 30 amino acids to about 115 amino acids, about 30 amino acids to about 110 amino acids, about 30 amino acids to about 105 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 60 amino acids, about 30 amino acids to about 50 amino acids, about 30 amino acids to about 40 amino acids, about 40 amino acids to about 220 amino acids, about 40 amino acids to about 215 amino acids, about 40 amino acids to about 210 amino acids, about 40 amino acids to about 205 amino acids, about 40 amino acids to about 200 amino acids, about 40 amino acids to about 195 amino acids, about 40 amino acids to about 190 amino acids, about 40 amino acids to about 185 amino acids, about 40 amino acids to about 180 amino acids, about 40 amino acids to about 175 amino acids, about 40 amino acids to about 170 amino acids, about 40 amino acids to about 165 amino acids, about 40 amino acids to about 160 amino acids, about 40 amino acids to about 155 amino acids, about 40 amino acids to about 150 amino acids, about 40 amino acids to about 145 amino acids, about 40 amino acids to about 140 amino acids, about 40 amino acids to about 135 amino acids, about 40 amino acids to about 130 amino acids, about 40 amino acids to about 125 amino acids, about 40 amino acids to about 120 amino acids, about 40 amino acids to about 115 amino acids, about 40 amino acids to about 110 amino acids, about 40 amino acids to about 105 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 60 amino acids, about 40 amino acids to about 50 amino acids, about 50 amino acids to about 220 amino acids, about 50 amino acids to about 215 amino acids, about 50 amino acids to about 210 amino acids, about 50 amino acids to about 205 amino acids, about 50 amino acids to about 200 amino acids, about 50 amino acids to about 195 amino acids, about 50 amino acids to about 190 amino acids, about 50 amino acids to about 185 amino acids, about 50 amino acids to about 180 amino acids, about 50 amino acids to about 175 amino acids, about 50 amino acids to about 170 amino acids, about 50 amino acids to about 165 amino acids, about 50 amino acids to about 160 amino acids, about 50 amino acids to about 155 amino acids, about 50 amino acids to about 150 amino acids, about 50 amino acids to about 145 amino acids, about 50 amino acids to about 140 amino acids, about 50 amino acids to about 135 amino acids, about 50 amino acids to about 130 amino acids, about 50 amino acids to about 125 amino acids, about 50 amino acids to about 120 amino acids, about 50 amino acids to about 115 amino acids, about 50 amino acids to about 110 amino acids, about 50 amino acids to about 105 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 60 amino acids, about 60 amino acids to about 220 amino acids, about 60 amino acids to about 215 amino acids, about 60 amino acids to about 210 amino acids, about 60 amino acids to about 205 amino acids, about 60 amino acids to about 200 amino acids, about 60 amino acids to about 195 amino acids, about 60 amino acids to about 190 amino acids, about 60 amino acids to about 185 amino acids, about 60 amino acids to about 180 amino acids, about 60 amino acids to about 175 amino acids, about 60 amino acids to about 170 amino acids, about 60 amino acids to about 165 amino acids, about 60 amino acids to about 160 amino acids, about 60 amino acids to about 155 amino acids, about 60 amino acids to about 150 amino acids, about 60 amino acids to about 145 amino acids, about 60 amino acids to about 140 amino acids, about 60 amino acids to about 135 amino acids, about 60 amino acids to about 130 amino acids, about 60 amino acids to about 125 amino acids, about 60 amino acids to about 120 amino acids, about 60 amino acids to about 115 amino acids, about 60 amino acids to about 110 amino acids, about 60 amino acids to about 105 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 70 amino acids to about 220 amino acids, about 70 amino acids to about 215 amino acids, about 70 amino acids to about 210 amino acids, about 70 amino acids to about 205 amino acids, about 70 amino acids to about 200 amino acids, about 70 amino acids to about 195 amino acids, about 70 amino acids to about 190 amino acids, about 70 amino acids to about 185 amino acids, about 70 amino acids to about 180 amino acids, about 70 amino acids to about 175 amino acids, about 70 amino acids to about 170 amino acids, about 70 amino acids to about 165 amino acids, about 70 amino acids to about 160 amino acids, about 70 amino acids to about 155 amino acids, about 70 amino acids to about 150 amino acids, about 70 amino acids to about 145 amino acids, about 70 amino acids to about 140 amino acids, about 70 amino acids to about 135 amino acids, about 70 amino acids to about 130 amino acids, about 70 amino acids to about 125 amino acids, about 70 amino acids to about 120 amino acids, about 70 amino acids to about 115 amino acids, about 70 amino acids to about 110 amino acids, about 70 amino acids to about 105 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 80 amino acids to about 220 amino acids, about 80 amino acids to about 215 amino acids, about 80 amino acids to about 210 amino acids, about 80 amino acids to about 205 amino acids, about 80 amino acids to about 200 amino acids, about 80 amino acids to about 195 amino acids, about 80 amino acids to about 190 amino acids, about 80 amino acids to about 185 amino acids, about 80 amino acids to about 180 amino acids, about 80 amino acids to about 175 amino acids, about 80 amino acids to about 170 amino acids, about 80 amino acids to about 165 amino acids, about 80 amino acids to about 160 amino acids, about 80 amino acids to about 155 amino acids, about 80 amino acids to about 150 amino acids, about 80 amino acids to about 145 amino acids, about 80 amino acids to about 140 amino acids, about 80 amino acids to about 135 amino acids, about 80 amino acids to about 130 amino acids, about 80 amino acids to about 125 amino acids, about 80 amino acids to about 120 amino acids, about 80 amino acids to about 115 amino acids, about 80 amino acids to about 110 amino acids, about 80 amino acids to about 105 amino acids, about 80 amino acids to about 100 amino acids, about 80 amino acids to about 95 amino acids, about 80 amino acids to about 90 amino acids, about 90 amino acids to about 220 amino acids, about 90 amino acids to about 215 amino acids, about 90 amino acids to about 210 amino acids, about 90 amino acids to about 205 amino acids, about 90 amino acids to about 200 amino acids, about 90 amino acids to about 195 amino acids, about 90 amino acids to about 190 amino acids, about 90 amino acids to about 185 amino acids, about 90 amino acids to about 180 amino acids, about 90 amino acids to about 175 amino acids, about 90 amino acids to about 170 amino acids, about 90 amino acids to about 165 amino acids, about 90 amino acids to about 160 amino acids, about 90 amino acids to about 155 amino acids, about 90 amino acids to about 150 amino acids, about 90 amino acids to about 145 amino acids, about 90 amino acids to about 140 amino acids, about 90 amino acids to about 135 amino acids, about 90 amino acids to about 130 amino acids, about 90 amino acids to about 125 amino acids, about 90 amino acids to about 120 amino acids, about 90 amino acids to about 115 amino acids, about 90 amino acids to about 110 amino acids, about 90 amino acids to about 105 amino acids, about 90 amino acids to about 100 amino acids, about 100 amino acids to about 220 amino acids, about 100 amino acids to about 215 amino acids, about 100 amino acids to about 210 amino acids, about 100 amino acids to about 205 amino acids, about 100 amino acids to about 200 amino acids, about 100 amino acids to about 195 amino acids, about 100 amino acids to about 190 amino acids, about 100 amino acids to about 185 amino acids, about 100 amino acids to about 180 amino acids, about 100 amino acids to about 175 amino acids, about 100 amino acids to about 170 amino acids, about 100 amino acids to about 165 amino acids, about 100 amino acids to about 160 amino acids, about 100 amino acids to about 155 amino acids, about 100 amino acids to about 150 amino acids, about 100 amino acids to about 145 amino acids, about 100 amino acids to about 140 amino acids, about 100 amino acids to about 135 amino acids, about 100 amino acids to about 130 amino acids, about 100 amino acids to about 125 amino acids, about 100 amino acids to about 120 amino acids, about 100 amino acids to about 115 amino acids, about 100 amino acids to about 110 amino acids, about 110 amino acids to about 220 amino acids, about 110 amino acids to about 215 amino acids, about 110 amino acids to about 210 amino acids, about 110 amino acids to about 205 amino acids, about 110 amino acids to about 200 amino acids, about 110 amino acids to about 195 amino acids, about 110 amino acids to about 190 amino acids, about 110 amino acids to about 185 amino acids, about 110 amino acids to about 180 amino acids, about 110 amino acids to about 175 amino acids, about 110 amino acids to about 170 amino acids, about 110 amino acids to about 165 amino acids, about 110 amino acids to about 160 amino acids, about 110 amino acids to about 155 amino acids, about 110 amino acids to about 150 amino acids, about 110 amino acids to about 145 amino acids, about 110 amino acids to about 140 amino acids, about 110 amino acids to about 135 amino acids, about 110 amino acids to about 130 amino acids, about 110 amino acids to about 125 amino acids, about 110 amino acids to about 120 amino acids, about 110 amino acids to about 115 amino acids, about 115 amino acids to about 220 amino acids, about 115 amino acids to about 215 amino acids, about 115 amino acids to about 210 amino acids, about 115 amino acids to about 205 amino acids, about 115 amino acids to about 200 amino acids, about 115 amino acids to about 195 amino acids, about 115 amino acids to about 190 amino acids, about 115 amino acids to about 185 amino acids, about 115 amino acids to about 180 amino acids, about 115 amino acids to about 175 amino acids, about 115 amino acids to about 170 amino acids, about 115 amino acids to about 165 amino acids, about 115 amino acids to about 160 amino acids, about 115 amino acids to about 155 amino acids, about 115 amino acids to about 150 amino acids, about 115 amino acids to about 145 amino acids, about 115 amino acids to about 140 amino acids, about 115 amino acids to about 135 amino acids, about 115 amino acids to about 130 amino acids, about 115 amino acids to about 125 amino acids, about 115 amino acids to about 120 amino acids, about 120 amino acids to about 220 amino acids, about 120 amino acids to about 215 amino acids, about 120 amino acids to about 210 amino acids, about 120 amino acids to about 205 amino acids, about 120 amino acids to about 200 amino acids, about 120 amino acids to about 195 amino acids, about 120 amino acids to about 190 amino acids, about 120 amino acids to about 185 amino acids, about 120 amino acids to about 180 amino acids, about 120 amino acids to about 175 amino acids, about 120 amino acids to about 170 amino acids, about 120 amino acids to about 165 amino acids, about 120 amino acids to about 160 amino acids, about 120 amino acids to about 155 amino acids, about 120 amino acids to about 150 amino acids, about 120 amino acids to about 145 amino acids, about 120 amino acids to about 140 amino acids, about 120 amino acids to about 135 amino acids, about 120 amino acids to about 130 amino acids, about 120 amino acids to about 125 amino acids, about 125 amino acids to about 220 amino acids, about 125 amino acids to about 215 amino acids, about 125 amino acids to about 210 amino acids, about 125 amino acids to about 205 amino acids, about 125 amino acids to about 200 amino acids, about 125 amino acids to about 195 amino acids, about 125 amino acids to about 190 amino acids, about 125 amino acids to about 185 amino acids, about 125 amino acids to about 180 amino acids, about 125 amino acids to about 175 amino acids, about 125 amino acids to about 170 amino acids, about 125 amino acids to about 165 amino acids, about 125 amino acids to about 160 amino acids, about 125 amino acids to about 155 amino acids, about 125 amino acids to about 150 amino acids, about 125 amino acids to about 145 amino acids, about 125 amino acids to about 140 amino acids, about 125 amino acids to about 135 amino acids, about 125 amino acids to about 130 amino acids, about 130 amino acids to about 220 amino acids, about 130 amino acids to about 215 amino acids, about 130 amino acids to about 210 amino acids, about 130 amino acids to about 205 amino acids, about 130 amino acids to about 200 amino acids, about 130 amino acids to about 195 amino acids, about 130 amino acids to about 190 amino acids, about 130 amino acids to about 185 amino acids, about 130 amino acids to about 180 amino acids, about 130 amino acids to about 175 amino acids, about 130 amino acids to about 170 amino acids, about 130 amino acids to about 165 amino acids, about 130 amino acids to about 160 amino acids, about 130 amino acids to about 155 amino acids, about 130 amino acids to about 150 amino acids, about 130 amino acids to about 145 amino acids, about 130 amino acids to about 140 amino acids, about 130 amino acids to about 135 amino acids, about 135 amino acids to about 220 amino acids, about 135 amino acids to about 215 amino acids, about 135 amino acids to about 210 amino acids, about 135 amino acids to about 205 amino acids, about 135 amino acids to about 200 amino acids, about 135 amino acids to about 195 amino acids, about 135 amino acids to about 190 amino acids, about 135 amino acids to about 185 amino acids, about 135 amino acids to about 180 amino acids, about 135 amino acids to about 175 amino acids, about 135 amino acids to about 170 amino acids, about 135 amino acids to about 165 amino acids, about 135 amino acids to about 160 amino acids, about 135 amino acids to about 155 amino acids, about 135 amino acids to about 150 amino acids, about 135 amino acids to about 145 amino acids, about 135 amino acids to about 140 amino acids, about 140 amino acids to about 220 amino acids, about 140 amino acids to about 215 amino acids, about 140 amino acids to about 210 amino acids, about 140 amino acids to about 205 amino acids, about 140 amino acids to about 200 amino acids, about 140 amino acids to about 195 amino acids, about 140 amino acids to about 190 amino acids, about 140 amino acids to about 185 amino acids, about 140 amino acids to about 180 amino acids, about 140 amino acids to about 175 amino acids, about 140 amino acids to about 170 amino acids, about 140 amino acids to about 165 amino acids, about 140 amino acids to about 160 amino acids, about 140 amino acids to about 155 amino acids, about 140 amino acids to about 150 amino acids, about 140 amino acids to about 145 amino acids, about 145 amino acids to about 220 amino acids, about 145 amino acids to about 215 amino acids, about 145 amino acids to about 210 amino acids, about 145 amino acids to about 205 amino acids, about 145 amino acids to about 200 amino acids, about 145 amino acids to about 195 amino acids, about 145 amino acids to about 190 amino acids, about 145 amino acids to about 185 amino acids, about 145 amino acids to about 180 amino acids, about 145 amino acids to about 175 amino acids, about 145 amino acids to about 170 amino acids, about 145 amino acids to about 165 amino acids, about 145 amino acids to about 160 amino acids, about 145 amino acids to about 155 amino acids, about 145 amino acids to about 150 amino acids, about 150 amino acids to about 220 amino acids, about 150 amino acids to about 215 amino acids, about 150 amino acids to about 210 amino acids, about 150 amino acids to about 205 amino acids, about 150 amino acids to about 200 amino acids, about 150 amino acids to about 195 amino acids, about 150 amino acids to about 190 amino acids, about 150 amino acids to about 185 amino acids, about 150 amino acids to about 180 amino acids, about 150 amino acids to about 175 amino acids, about 150 amino acids to about 170 amino acids, about 150 amino acids to about 165 amino acids, about 150 amino acids to about 160 amino acids, about 150 amino acids to about 155 amino acids, about 155 amino acids to about 220 amino acids, about 155 amino acids to about 215 amino acids, about 155 amino acids to about 210 amino acids, about 155 amino acids to about 205 amino acids, about 155 amino acids to about 200 amino acids, about 155 amino acids to about 195 amino acids, about 155 amino acids to about 190 amino acids, about 155 amino acids to about 185 amino acids, about 155 amino acids to about 180 amino acids, about 155 amino acids to about 175 amino acids, about 155 amino acids to about 170 amino acids, about 155 amino acids to about 165 amino acids, about 155 amino acids to about 160 amino acids, about 160 amino acids to about 220 amino acids, about 160 amino acids to about 215 amino acids, about 160 amino acids to about 210 amino acids, about 160 amino acids to about 205 amino acids, about 160 amino acids to about 200 amino acids, about 160 amino acids to about 195 amino acids, about 160 amino acids to about 190 amino acids, about 160 amino acids to about 185 amino acids, about 160 amino acids to about 180 amino acids, about 160 amino acids to about 175 amino acids, about 160 amino acids to about 170 amino acids, about 160 amino acids to about 165 amino acids, about 165 amino acids to about 220 amino acids, about 165 amino acids to about 215 amino acids, about 165 amino acids to about 210 amino acids, about 165 amino acids to about 205 amino acids, about 165 amino acids to about 200 amino acids, about 165 amino acids to about 195 amino acids, about 165 amino acids to about 190 amino acids, about 165 amino acids to about 185 amino acids, about 165 amino acids to about 180 amino acids, about 165 amino acids to about 175 amino acids, about 165 amino acids to about 170 amino acids, about 170 amino acids to about 220 amino acids, about 170 amino acids to about 215 amino acids, about 170 amino acids to about 210 amino acids, about 170 amino acids to about 205 amino acids, about 170 amino acids to about 200 amino acids, about 170 amino acids to about 195 amino acids, about 170 amino acids to about 190 amino acids, about 170 amino acids to about 185 amino acids, about 170 amino acids to about 180 amino acids, about 170 amino acids to about 175 amino acids, about 175 amino acids to about 220 amino acids, about 175 amino acids to about 215 amino acids, about 175 amino acids to about 210 amino acids, about 175 amino acids to about 205 amino acids, about 175 amino acids to about 200 amino acids, about 175 amino acids to about 195 amino acids, about 175 amino acids to about 190 amino acids, about 175 amino acids to about 185 amino acids, about 175 amino acids to about 180 amino acids, about 180 amino acids to about 220 amino acids, about 180 amino acids to about 215 amino acids, about 180 amino acids to about 210 amino acids, about 180 amino acids to about 205 amino acids, about 180 amino acids to about 200 amino acids, about 180 amino acids to about 195 amino acids, about 180 amino acids to about 190 amino acids, about 180 amino acids to about 185 amino acids, about 185 amino acids to about 220 amino acids, about 185 amino acids to about 215 amino acids, about 185 amino acids to about 210 amino acids, about 185 amino acids to about 205 amino acids, about 185 amino acids to about 200 amino acids, about 185 amino acids to about 195 amino acids, about 185 amino acids to about 190 amino acids, about 190 amino acids to about 220 amino acids, about 190 amino acids to about 215 amino acids, about 190 amino acids to about 210 amino acids, about 190 amino acids to about 205 amino acids, about 190 amino acids to about 200 amino acids, about 190 amino acids to about 195 amino acids, about 195 amino acids to about 220 amino acids, about 195 amino acids to about 215 amino acids, about 195 amino acids to about 210 amino acids, about 195 amino acids to about 205 amino acids, about 195 amino acids to about 200 amino acids, about 200 amino acids to about 220 amino acids, about 200 amino acids to about 215 amino acids, about 200 amino acids to about 210 amino acids, about 200 amino acids to about 205 amino acids, about 205 amino acids to about 220 amino acids, about 205 amino acids to about 215 amino acids, about 205 amino acids to about 210 amino acids, about 210 amino acids to about 220 amino acids, about 210 amino acids to about 215 amino acids, or about 215 amino acids to about 220 amino acids.

Linker Sequences

In some embodiments, the linker sequence can be a flexible linker sequence. Non-limiting examples of linker sequences that can be used are described in Klein et al., *Protein Engineering, Design & Selection* 27(10):325-330, 2014; Priyanka et al., *Protein Sci.* 22(2):153-167, 2013. In some examples, the linker sequence is a synthetic linker sequence.

In some embodiments of any of the multi-chain chimeric polypeptides described herein, the first chimeric polypeptide can include one, two, three, four, five, six, seven, eight, nine, or ten linker sequence(s) (e.g., the same or different linker sequences, e.g., any of the exemplary linker sequences described herein or known in the art). In some embodiments of any of the multi-chain chimeric polypeptides described herein, the second chimeric polypeptide can include one, two, three, four, five, six, seven, eight, nine, or ten linker sequence(s) (e.g., the same or different linker sequences, e.g., any of the exemplary linker sequences described herein or known in the art).

In some embodiments, a linker sequence can have a total length of 1 amino acid to about 100 amino acids, 1 amino acid to about 90 amino acids, 1 amino acid to about 80 amino acids, 1 amino acid to about 70 amino acids, 1 amino acid to about 60 amino acids, 1 amino acid to about 50 amino acids, 1 amino acid to about 45 amino acids, 1 amino acid to about 40 amino acids, 1 amino acid to about 35 amino acids, 1 amino acid to about 30 amino acids, 1 amino acid to about 25 amino acids, 1 amino acid to about 24 amino acids, 1 amino acid to about 22 amino acids, 1 amino acid to about 20 amino acids, 1 amino acid to about 18 amino acids, 1 amino acid to about 16 amino acids, 1 amino acid to about 14 amino acids, 1 amino acid to about 12 amino acids, 1 amino acid to about 10 amino acids, 1 amino acid to about 8 amino acids, 1 amino acid to about 6 amino acids, 1 amino acid to about 4 amino acids, about 2 amino acids to about 100 amino acids, about 2 amino acids to about 90 amino acids, about 2 amino acids to about 80 amino acids, about 2 amino acids to about 70 amino acids, about 2 amino acids to about 60 amino acids, about 2 amino acids to about 50 amino acids, about 2 amino acids to about 45 amino acids, about 2 amino acids to about 40 amino acids, about 2 amino acids to about 35 amino acids, about 2 amino acids to about 30 amino acids, about 2 amino acids to about 25 amino acids, about 2 amino acids to about 24 amino acids, about 2 amino acids to about 22 amino acids, about 2 amino acids to about 20 amino acids, about 2 amino acids to about 18 amino acids, about 2 amino acids to about 16 amino acids, about 2 amino acids to about 14 amino acids, about 2 amino acids to about 12 amino acids, about 2 amino acids to about 10 amino acids, about 2 amino acids to about 8 amino acids, about 2 amino acids to about 6 amino acids, about 2 amino acids to about 4 amino acids, about 4 amino acids to about 100 amino acids, about 4 amino acids to about 90 amino acids, about 4 amino acids to about 80 amino acids, about 4 amino acids to about 70 amino acids, about 4 amino acids to about 60 amino acids, about 4 amino acids to about 50 amino acids, about 4 amino acids to about 45 amino acids, about 4 amino acids to about 40 amino acids, about 4 amino acids to about 35 amino acids, about 4 amino acids to about 30 amino acids, about 4 amino acids to about 25 amino acids, about 4 amino acids to about 24 amino acids, about 4 amino acids to about 22 amino acids, about 4 amino acids to about 20 amino acids, about 4 amino acids to about 18 amino acids, about 4 amino acids to about 16 amino acids, about 4 amino acids to about 14 amino acids, about 4 amino acids to about 12 amino acids, about 4 amino acids to about 10 amino acids, about 4 amino acids to about 8 amino acids, about 4 amino acids to about 6 amino acids, about 6 amino acids to about 100 amino acids, about 6 amino acids to about 90 amino acids, about 6 amino acids to about 80 amino acids, about 6 amino acids to about 70 amino acids, about 6 amino acids to about 60 amino acids, about 6 amino acids to about 50 amino acids, about 6 amino acids to about 45 amino acids, about 6 amino acids to about 40 amino acids, about 6 amino acids to about 35 amino acids, about 6 amino acids to about 30 amino acids, about 6 amino acids to about 25 amino acids, about 6 amino acids to about 24 amino acids, about 6 amino acids to about 22 amino acids, about 6 amino acids to about 20 amino acids, about 6 amino acids to about 18 amino acids, about 6 amino acids to about 16 amino acids, about 6 amino acids to about 14 amino acids, about 6 amino acids to about 12 amino acids, about 6 amino acids to about 10 amino acids, about 6 amino acids to about 8 amino acids, about 8 amino acids to about 100 amino acids, about 8 amino acids to about 90 amino acids, about 8 amino acids to about 80 amino acids, about 8 amino acids to about 70 amino acids, about 8 amino acids to about 60 amino acids, about 8 amino acids to about 50 amino acids, about 8 amino acids to about 45 amino acids, about 8 amino acids to about 40 amino acids, about 8 amino acids to about 35 amino acids, about 8 amino acids to about 30 amino acids, about 8 amino acids to about 25 amino acids, about 8 amino acids to about 24 amino acids, about 8 amino acids to about 22 amino acids, about 8 amino acids to about 20 amino acids, about 8 amino acids to about 18 amino acids, about 8 amino acids to about 16 amino acids, about 8 amino acids to about 14 amino acids, about 8 amino acids to about 12 amino acids, about 8 amino acids to about 10 amino acids, about 10 amino acids to about 100 amino acids, about 10 amino acids to about 90 amino acids, about 10 amino acids to about 80 amino acids, about 10 amino acids to about 70 amino acids, about 10 amino acids to about 60 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 24 amino acids, about 10 amino acids to about 22 amino acids, about 10 amino acids to about 20 amino acids, about 10 amino acids to about 18 amino acids, about 10 amino acids to about 16 amino acids, about 10 amino acids to about 14 amino acids, about 10 amino acids to about 12 amino acids, about 12 amino acids to about 100 amino acids, about 12 amino acids to about 90 amino acids, about 12 amino acids to about 80 amino acids, about 12 amino acids to about 70 amino acids, about 12 amino acids to about 60 amino acids, about 12 amino acids to about 50 amino acids, about 12 amino acids to about 45 amino acids, about 12 amino acids to about 40 amino acids, about 12 amino acids to about 35 amino acids, about 12 amino acids to about 30 amino acids, about 12 amino acids to about 25 amino acids, about 12 amino acids to about 24 amino acids, about 12 amino acids to about 22 amino acids, about 12 amino acids to about 20 amino acids, about 12 amino acids to about 18 amino acids, about 12 amino acids to about 16 amino acids, about 12 amino acids to about 14 amino acids, about 14 amino acids to about 100 amino acids, about 14 amino acids to about 90 amino acids, about 14 amino acids to about 80 amino acids, about 14 amino acids to about 70 amino acids, about 14 amino acids to about 60 amino acids, about 14 amino acids to about 50 amino acids, about 14 amino acids to about 45 amino acids, about 14 amino acids to about 40 amino acids, about 14 amino acids to about 35 amino acids, about 14 amino acids to about 30 amino acids, about 14 amino acids to about 25 amino acids, about 14 amino acids to about 24 amino acids, about 14 amino acids to about 22 amino acids, about 14 amino acids to about 20 amino acids, about 14 amino acids to about 18 amino acids, about 14 amino acids to about 16 amino acids, about 16 amino acids to about 100 amino acids, about 16 amino acids to about 90 amino acids, about 16 amino acids to about 80 amino acids, about 16 amino acids to about 70 amino acids, about 16 amino acids to about 60 amino acids, about 16 amino acids to about 50 amino acids, about 16 amino acids to about 45 amino acids, about 16 amino acids to about 40 amino acids, about 16 amino acids to about 35 amino acids, about 16 amino acids to about 30 amino acids, about 16 amino acids to about 25 amino acids, about 16 amino acids to about 24 amino acids, about 16 amino acids to about 22 amino acids, about 16 amino acids to about 20 amino acids, about 16 amino acids to about 18 amino acids, about 18 amino acids to about 100 amino acids, about 18 amino acids to about 90 amino acids, about 18 amino acids to about 80 amino acids, about 18 amino acids to about 70 amino acids, about 18 amino acids to about 60 amino acids, about 18 amino acids to about 50 amino acids, about 18 amino acids to about 45 amino acids, about 18 amino acids to about 40 amino acids, about 18 amino acids to about 35 amino acids, about 18 amino acids to about 30 amino acids, about 18 amino acids to about 25 amino acids, about 18 amino acids to about 24 amino acids, about 18 amino acids to about 22 amino acids, about 18 amino acids to about 20 amino acids, about 20 amino acids to about 100 amino acids, about 20 amino acids to about 90 amino acids, about 20 amino acids to about 80 amino acids, about 20 amino acids to about 70 amino acids, about 20 amino acids to about 60 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 20 amino acids to about 24 amino acids, about 20 amino acids to about 22 amino acids, about 22 amino acids to about 100 amino acids, about 22 amino acids to about 90 amino acids, about 22 amino acids to about 80 amino acids, about 22 amino acids to about 70 amino acids, about 22 amino acids to about 60 amino acids, about 22 amino acids to about 50 amino acids, about 22 amino acids to about 45 amino acids, about 22 amino acids to about 40 amino acids, about 22 amino acids to about 35 amino acids, about 22 amino acids to about 30 amino acids, about 22 amino acids to about 25 amino acids, about 22 amino acids to about 24 amino acids, about 25 amino acids to about 100 amino acids, about 25 amino acids to about 90 amino acids, about 25 amino acids to about 80 amino acids, about 25 amino acids to about 70 amino acids, about 25 amino acids to about 60 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 100 amino acids, about 30 amino acids to about 90 amino acids, about 30 amino acids to about 80 amino acids, about 30 amino acids to about 70 amino acids, about 30 amino acids to about 60 amino acids, about 30 amino acids to about 50 amino acids, about 30 amino acids to about 45 amino acids, about 30 amino acids to about 40 amino acids, about 30 amino acids to about 35 amino acids, about 35 amino acids to about 100 amino acids, about 35 amino acids to about 90 amino acids, about 35 amino acids to about 80 amino acids, about 35 amino acids to about 70 amino acids, about 35 amino acids to about 60 amino acids, about 35 amino acids to about 50 amino acids, about 35 amino acids to about 45 amino acids, about 35 amino acids to about 40 amino acids, about 40 amino acids to about 100 amino acids, about 40 amino acids to about 90 amino acids, about 40 amino acids to about 80 amino acids, about 40 amino acids to about 70 amino acids, about 40 amino acids to about 60 amino acids, about 40 amino acids to about 50 amino acids, about 40 amino acids to about 45 amino acids, about 45 amino acids to about 100 amino acids, about 45 amino acids to about 90 amino acids, about 45 amino acids to about 80 amino acids, about 45 amino acids to about 70 amino acids, about 45 amino acids to about 60 amino acids, about 45 amino acids to about 50 amino acids, about 50 amino acids to about 100 amino acids, about 50 amino acids to about 90 amino acids, about 50 amino acids to about 80 amino acids, about 50 amino acids to about 70 amino acids, about 50 amino acids to about 60 amino acids, about 60 amino acids to about 100 amino acids, about 60 amino acids to about 90 amino acids, about 60 amino acids to about 80 amino acids, about 60 amino acids to about 70 amino acids, about 70 amino acids to about 100 amino acids, about 70 amino acids to about 90 amino acids, about 70 amino acids to about 80 amino acids, about 80 amino acids to about 100 amino acids, about 80 amino acids to about 90 amino acids, or about 90 amino acids to about 100 amino acids.

In some embodiments, the linker is rich in glycine (Gly or G) residues. In some embodiments, the linker is rich in serine (Ser or S) residues. In some embodiments, the linker is rich in glycine and serine residues. In some embodiments, the linker has one or more glycine-serine residue pairs (GS), e.g., 1, 2, 3, 4, 5, 6, 7, 8, 9, or 10 or more GS pairs. In some embodiments, the linker has one or more Gly-Gly-Gly-Ser (GGGS) sequences, e.g., 1, 2, 3, 4, 5, 6, 7, 8, 9, or 10 or more GGGS sequences. In some embodiments, the linker has one or more Gly-Gly-Gly-Gly-Ser (GGGGS) sequences, e.g., 1, 2, 3, 4, 5, 6, 7, 8, 9, or 10 or more GGGGS sequences. In some embodiments, the linker has one or more Gly-Gly-Ser-Gly (GGSG) sequences, e.g., 1, 2, 3, 4, 5, 6, 7, 8, 9, or 10 or more GGSG sequences.

In some embodiments, the linker sequence can comprise or consist of GGGGSGGGGSGGGGS (SEQ ID NO: 7). In some embodiments, the linker sequence can be encoded by a nucleic acid comprising or consisting of: GGCGGTGGAGGATCCGGAGGAGGTGGCTCCGGCGGCGGAGGATCT (SEQ ID NO: 8). In some embodiments, the linker sequence can comprise or consist of:

```
                                        (SEQ ID NO: 9)
GGGSGGGS.
```

Target-Binding Domains

In some embodiments of any of the multi-chain chimeric polypeptides described herein, the first target-binding domain, the second target-binding domain, and/or the additional one or more target-binding domains can be an antigen-binding domain (e.g., any of the exemplary antigen-binding domains described herein or known in the art), a soluble interleukin or cytokine protein (e.g., any of the exemplary soluble interleukin proteins or soluble cytokine proteins described herein), and a soluble interleukin or cytokine receptor (e.g., any of the exemplary soluble interleukin receptors or soluble cytokine receptors described herein).

In some embodiments of any of the multi-chain chimeric polypeptides described herein, one or more of the first target-binding domain (e.g., any of the exemplary first target binding domains described herein or known in the art), the second target-binding domain (e.g., any of the exemplary second target binding domains described herein or known in the art), and the one or more additional target binding domains can each, independently, bind specifically to a target selected from the group of: bind specifically to a target selected from the group consisting of: CD16a, CD28, CD3 (e.g., one or more of CD3α, CD3β, CD3δ, CD3ε, and CD3γ), CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUCSAC, Trop-2, CMET, EGFR, HER1, HER2, HER3, PSMA, CEA, B7H3, EPCAM, BCMA, P-cadherin, CEACAM5, a UL16-binding protein (e.g., ULBP1, ULBP2, ULBP3, ULBP4, ULBP5, and ULBP6), HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of $NK_p30$, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the multi-chain chimeric polypeptides described herein, the first target-binding domain, the second target-binding domain, and/or the one or more additional target-binding domains can each independent have a total number of amino acids of about 5 amino acids to about 1000 amino acids, about 5 amino acids to about 950 amino acids, about 5 amino acids to about 900 amino acids, about 5 amino acids to about 850 amino acids, about 5 amino acids to about 800 amino acids, about 5 amino acids to about 750 amino acids, about 5 amino acids to about 700 amino acids, about 5 amino acids to about 650 amino acids, about 5 amino acids to about 600 amino acids, about 5 amino acids to about 550 amino acids, about 5 amino acids to about 500 amino acids, about 5 amino acids to about 450 amino acids, about 5 amino acids to about 400 amino acids, about 5 amino acids to about 350 amino acids, about 5 amino acids to about 300 amino acids, about 5 amino acids to about 280 amino acids, about 5 amino acids to about 260 amino acids, about 5 amino acids to about 240 amino acids, about 5 amino acids to about 220 amino acids, about 5 amino acids to about 200 amino acids, about 5 amino acids to about 195 amino acids, about 5 amino acids to about 190 amino acids, about 5 amino acids to about 185 amino acids, about 5 amino acids to about 180 amino acids, about 5 amino acids to about 175 amino acids, about 5 amino acids to about 170 amino acids, about 5 amino acids to about 165 amino acids, about 5 amino acids to about 160 amino acids, about 5 amino acids to about 155 amino acids, about 5 amino acids to about 150 amino acids, about 5 amino acids to about 145 amino acids, about 5 amino acids to about 140 amino acids, about 5 amino acids to about 135 amino acids, about 5 amino acids to about 130 amino acids, about 5 amino acids to about 125 amino acids, about 5 amino acids to about 120 amino acids, about 5 amino acids to about 115 amino acids, about 5 amino acids to about 110 amino acids, about 5 amino acids to about 105 amino acids, about 5 amino acids to about 100 amino acids, about 5 amino acids to about 95 amino acids, about 5 amino acids to about 90 amino acids, about 5 amino acids to about 85 amino acids, about 5 amino acids to about 80 amino acids, about 5 amino acids to about 75 amino acids, about 5 amino acids to about 70 amino acids, about 5 amino acids to about 65 amino acids, about 5 amino acids to about 60 amino acids, about 5 amino acids to about 55 amino acids, about 5 amino acids to about 50 amino acids, about 5 amino acids to about 45 amino acids, about 5 amino acids to about 40 amino acids, about 5 amino acids to about 35 amino acids, about 5 amino acids to about 30 amino acids, about 5 amino acids to about 25 amino acids, about 5 amino acids to about 20 amino acids, about 5 amino acids to about 15 amino acids, about 5 amino acids to about 10 amino acids, about 10 amino acids to about 1000 amino acids, about 10 amino acids to about 950 amino acids, about 10 amino acids to about 900 amino acids, about 10 amino acids to about 850 amino acids, about 10 amino acids to about 800 amino acids, about 10 amino acids to about 750 amino acids, about 10 amino acids to about 700 amino acids, about 10 amino acids to about 650 amino acids, about 10 amino acids to about 600 amino acids, about 10 amino acids to about 550 amino acids, about 10 amino acids to about 500 amino acids, about 10 amino acids to about 450 amino acids, about 10 amino acids to about 400 amino acids, about 10 amino acids to about 350 amino acids, about 10 amino acids to about 300 amino acids, about 10 amino acids to about 280 amino acids, about 10 amino acids to about 260 amino acids, about 10 amino acids to about 240 amino acids, about 10 amino acids to about 220 amino acids, about 10 amino acids to about 200 amino acids, about 10 amino acids to about 195 amino acids, about 10 amino acids to about 190 amino acids, about 10 amino acids to about 185 amino acids, about 10 amino acids to about 180 amino acids, about 10 amino acids to about 175 amino acids, about 10 amino acids to about 170 amino acids, about 10 amino acids to about 165 amino acids, about 10 amino acids to about 160 amino acids, about 10 amino acids to about 155 amino acids, about 10 amino acids to about 150 amino acids, about 10 amino acids to about 145 amino acids, about 10 amino acids to about 140 amino acids, about 10 amino acids to about 135 amino acids, about 10 amino acids to about 130 amino acids, about 10 amino acids to about 125 amino acids, about 10 amino acids to about 120 amino acids, about 10 amino acids to about 115 amino acids, about 10 amino acids to about 110 amino acids, about 10 amino acids to about 105 amino acids, about 10 amino acids to about 100 amino acids, about 10 amino acids to about 95 amino acids, about 10 amino acids to about 90 amino acids, about 10 amino acids to about 85 amino acids, about 10 amino acids to about 80 amino acids, about 10 amino acids to about 75 amino acids, about 10 amino acids to about 70 amino acids, about 10 amino acids to about 65 amino acids, about 10 amino acids to about 60 amino acids, about 10 amino acids to about 55 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 20 amino acids, about 10 amino acids to about 15 amino acids, about 15 amino acids to about 1000 amino acids, about 15 amino acids to about 950 amino acids, about 15 amino acids to about 900 amino acids, about 15 amino acids to about 850 amino acids, about 15 amino acids to about 800 amino acids, about 15 amino acids to about 750 amino acids, about 15 amino acids to about 700 amino acids, about 15 amino acids to about 650 amino acids, about 15 amino acids to about 600 amino acids, about 15 amino acids to about 550 amino acids, about 15 amino acids to about 500 amino acids, about 15 amino acids to about 450 amino acids, about 15 amino acids to about 400 amino acids, about 15 amino acids to about 350 amino acids, about 15 amino acids to about 300 amino acids, about 15 amino acids to about 280 amino acids, about 15 amino acids to about 260 amino acids, about 15 amino acids to about 240 amino acids, about 15 amino acids to about 220 amino acids, about 15 amino acids to about 200 amino acids, about 15 amino acids to about 195 amino acids, about 15 amino acids to about 190 amino acids, about 15 amino acids to about 185 amino acids, about 15 amino acids to about 180 amino acids, about 15 amino acids to about 175 amino acids, about 15 amino acids to about 170 amino acids, about 15 amino acids to about 165 amino acids, about 15 amino acids to about 160 amino acids, about 15 amino acids to about 155 amino acids, about 15 amino acids to about 150 amino acids, about 15 amino acids to about 145 amino acids, about 15 amino acids to about 140 amino acids, about 15 amino acids to about 135 amino acids, about 15 amino acids to about 130 amino acids, about 15 amino acids to about 125 amino acids, about 15 amino acids to about 120 amino acids, about 15 amino acids to about 115 amino acids, about 15 amino acids to about 110 amino acids, about 15 amino acids to about 105 amino acids, about 15 amino acids to about 100 amino acids, about 15 amino acids to about 95 amino acids, about 15 amino acids to about 90 amino acids, about 15 amino acids to about 85 amino acids, about 15 amino acids to about 80 amino acids, about 15 amino acids to about 75 amino acids, about 15 amino acids to about 70 amino acids, about 15 amino acids to about 65 amino acids, about 15 amino acids to about 60 amino acids, about 15 amino acids to about 55 amino acids, about 15 amino acids to about 50 amino acids, about 15 amino acids to about 45 amino acids, about 15 amino acids to about 40 amino acids, about 15 amino acids to about 35 amino acids, about 15 amino acids to about 30 amino acids, about 15 amino acids to about 25 amino acids, about 15 amino acids to about 20 amino acids, about 20 amino acids to about 1000 amino acids, about 20 amino acids to about 950 amino acids, about 20 amino acids to about 900 amino acids, about 20 amino acids to about 850 amino acids, about 20 amino acids to about 800 amino acids, about 20 amino acids to about 750 amino acids, about 20 amino acids to about 700 amino acids, about 20 amino acids to about 650 amino acids, about 20 amino acids to about 600 amino acids, about 20 amino acids to about 550 amino acids, about 20 amino acids to about 500 amino acids, about 20 amino acids to about 450 amino acids, about 20 amino acids to about 400 amino acids, about 20 amino acids to about 350 amino acids, about 20 amino acids to about 300 amino acids, about 20 amino acids to about 280 amino acids, about 20 amino acids to about 260 amino acids, about 20 amino acids to about 240 amino acids, about 20 amino acids to about 220 amino acids, about 20 amino acids to about 200 amino acids, about 20 amino acids to about 195 amino acids, about 20 amino acids to about 190 amino acids, about 20 amino acids to about 185 amino acids, about 20 amino acids to about 180 amino acids, about 20 amino acids to about 175 amino acids, about 20 amino acids to about 170 amino acids, about 20 amino acids to about 165 amino acids, about 20 amino acids to about 160 amino acids, about 20 amino acids to about 155 amino acids, about 20 amino acids to about 150 amino acids, about 20 amino acids to about 145 amino acids, about 20 amino acids to about 140 amino acids, about 20 amino acids to about 135 amino acids, about 20 amino acids to about 130 amino acids, about 20 amino acids to about 125 amino acids, about 20 amino acids to about 120 amino acids, about 20 amino acids to about 115 amino acids, about 20 amino acids to about 110 amino acids, about 20 amino acids to about 105 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 65 amino acids, about 20 amino acids to about 60 amino acids, about 20 amino acids to about 55 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 25 amino acids to about 1000 amino acids, about 25 amino acids to about 950 amino acids, about 25 amino acids to about 900 amino acids, about 25 amino acids to about 850 amino acids, about 25 amino acids to about 800 amino acids, about 25 amino acids to about 750 amino acids, about 25 amino acids to about 700 amino acids, about 25 amino acids to about 650 amino acids, about 25 amino acids to about 600 amino acids, about 25 amino acids to about 550 amino acids, about 25 amino acids to about 500 amino acids, about 25 amino acids to about 450 amino acids, about 25 amino acids to about 400 amino acids, about 25 amino acids to about 350 amino acids, about 25 amino acids to about 300 amino acids, about 25 amino acids to about 280 amino acids, about 25 amino acids to about 260 amino acids, about 25 amino acids to about 240 amino acids, about 25 amino acids to about 220 amino acids, about 25 amino acids to about 200 amino acids, about 25 amino acids to about 195 amino acids, about 25 amino acids to about 190 amino acids, about 25 amino acids to about 185 amino acids, about 25 amino acids to about 180 amino acids, about 25 amino acids to about 175 amino acids, about 25 amino acids to about 170 amino acids, about 25 amino acids to about 165 amino acids, about 25 amino acids to about 160 amino acids, about 25 amino acids to about 155 amino acids, about 25 amino acids to about 150 amino acids, about 25 amino acids to about 145 amino acids, about 25 amino acids to about 140 amino acids, about 25 amino acids to about 135 amino acids, about 25 amino acids to about 130 amino acids, about 25 amino acids to about 125 amino acids, about 25 amino acids to about 120 amino acids, about 25 amino acids to about 115 amino acids, about 25 amino acids to about 110 amino acids, about 25 amino acids to about 105 amino acids, about 25 amino acids to about 100 amino acids, about 25 amino acids to about 95 amino acids, about 25 amino acids to about 90 amino acids, about 25 amino acids to about 85 amino acids, about 25 amino acids to about 80 amino acids, about 25 amino acids to about 75 amino acids, about 25 amino acids to about 70 amino acids, about 25 amino acids to about 65 amino acids, about 25 amino acids to about 60 amino acids, about 25 amino acids to about 55 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 1000 amino acids, about 30 amino acids to about 950 amino acids, about 30 amino acids to about 900 amino acids, about 30 amino acids to about 850 amino acids, about 30 amino acids to about 800 amino acids, about 30 amino acids to about 750 amino acids, about 30 amino acids to about 700 amino acids, about 30 amino acids to about 650 amino acids, about 30 amino acids to about 600 amino acids, about 30 amino acids to about 550 amino acids, about 30 amino acids to about 500 amino acids, about 30 amino acids to about 450 amino acids, about 30 amino acids to about 400 amino acids, about 30 amino acids to about 350 amino acids, about 30 amino acids to about 300 amino acids, about 30 amino acids to about 280 amino acids, about 30 amino acids to about 260 amino acids, about 30 amino acids to about 240 amino acids, about 30 amino acids to about 220 amino acids, about 30 amino acids to about 200 amino acids, about 30 amino acids to about 195 amino acids, about 30 amino acids to about 190 amino acids, about 30 amino acids to about 185 amino acids, about 30 amino acids to about 180 amino acids, about 30 amino acids to about 175 amino acids, about 30 amino acids to about 170 amino acids, about 30 amino acids to about 165 amino acids, about 30 amino acids to about 160 amino acids, about 30 amino acids to about 155 amino acids, about 30 amino acids to about 150 amino acids, about 30 amino acids to about 145 amino acids, about 30 amino acids to about 140 amino acids, about 30 amino acids to about 135 amino acids, about 30 amino acids to about 130 amino acids, about 30 amino acids to about 125 amino acids, about 30 amino acids to about 120 amino acids, about 30 amino acids to about 115 amino acids, about 30 amino acids to about 110 amino acids, about 30 amino acids to about 105 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 65 amino acids, about 30 amino acids to about 60 amino acids, about 30 amino acids to about 55 amino acids, about 30 amino acids to about 50 amino acids, about 30 amino acids to about 45 amino acids, about 30 amino acids to about 40 amino acids, about 30 amino acids to about 35 amino acids, about 35 amino acids to about 1000 amino acids, about 35 amino acids to about 950 amino acids, about 35 amino acids to about 900 amino acids, about 35 amino acids to about 850 amino acids, about 35 amino acids to about 800 amino acids, about 35 amino acids to about 750 amino acids, about 35 amino acids to about 700 amino acids, about 35 amino acids to about 650 amino acids, about 35 amino acids to about 600 amino acids, about 35 amino acids to about 550 amino acids, about 35 amino acids to about 500 amino acids, about 35 amino acids to about 450 amino acids, about 35 amino acids to about 400 amino acids, about 35 amino acids to about 350 amino acids, about 35 amino acids to about 300 amino acids, about 35 amino acids to about 280 amino acids, about 35 amino acids to about 260 amino acids, about 35 amino acids to about 240 amino acids, about 35 amino acids to about 220 amino acids, about 35 amino acids to about 200 amino acids, about 35 amino acids to about 195 amino acids, about 35 amino acids to about 190 amino acids, about 35 amino acids to about 185 amino acids, about 35 amino acids to about 180 amino acids, about 35 amino acids to about 175 amino acids, about 35 amino acids to about 170 amino acids, about 35 amino acids to about 165 amino acids, about 35 amino acids to about 160 amino acids, about 35 amino acids to about 155 amino acids, about 35 amino acids to about 150 amino acids, about 35 amino acids to about 145 amino acids, about 35 amino acids to about 140 amino acids, about 35 amino acids to about 135 amino acids, about 35 amino acids to about 130 amino acids, about 35 amino acids to about 125 amino acids, about 35 amino acids to about 120 amino acids, about 35 amino acids to about 115 amino acids, about 35 amino acids to about 110 amino acids, about 35 amino acids to about 105 amino acids, about 35 amino acids to about 100 amino acids, about 35 amino acids to about 95 amino acids, about 35 amino acids to about 90 amino acids, about 35 amino acids to about 85 amino acids, about 35 amino acids to about 80 amino acids, about 35 amino acids to about 75 amino acids, about 35 amino acids to about 70 amino acids, about 35 amino acids to about 65 amino acids, about 35 amino acids to about 60 amino acids, about 35 amino acids to about 55 amino acids, about 35 amino acids to about 50 amino acids, about 35 amino acids to about 45 amino acids, about 35 amino acids to about 40 amino acids, about 40 amino acids to about 1000 amino acids, about 40 amino acids to about 950 amino acids, about 40 amino acids to about 900 amino acids, about 40 amino acids to about 850 amino acids, about 40 amino acids to about 800 amino acids, about 40 amino acids to about 750 amino acids, about 40 amino acids to about 700 amino acids, about 40 amino acids to about 650 amino acids, about 40 amino acids to about 600 amino acids, about 40 amino acids to about 550 amino acids, about 40 amino acids to about 500 amino acids, about 40 amino acids to about 450 amino acids, about 40 amino acids to about 400 amino acids, about 40 amino acids to about 350 amino acids, about 40 amino acids to about 300 amino acids, about 40 amino acids to about 280 amino acids, about 40 amino acids to about 260 amino acids, about 40 amino acids to about 240 amino acids, about 40 amino acids to about 220 amino acids, about 40 amino acids to about 200 amino acids, about 40 amino acids to about 195 amino acids, about 40 amino acids to about 190 amino acids, about 40 amino acids to about 185 amino acids, about 40 amino acids to about 180 amino acids, about 40 amino acids to about 175 amino acids, about 40 amino acids to about 170 amino acids, about 40 amino acids to about 165 amino acids, about 40 amino acids to about 160 amino acids, about 40 amino acids to about 155 amino acids, about 40 amino acids to about 150 amino acids, about 40 amino acids to about 145 amino acids, about 40 amino acids to about 140 amino acids, about 40 amino acids to about 135 amino acids, about 40 amino acids to about 130 amino acids, about 40 amino acids to about 125 amino acids, about 40 amino acids to about 120 amino acids, about 40 amino acids to about 115 amino acids, about 40 amino acids to about 110 amino acids, about 40 amino acids to about 105 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 65 amino acids, about 40 amino acids to about 60 amino acids, about 40 amino acids to about 55 amino acids, about 40 amino acids to about 50 amino acids, about 40 amino acids to about 45 amino acids, about 45 amino acids to about 1000 amino acids, about 45 amino acids to about 950 amino acids, about 45 amino acids to about 900 amino acids, about 45 amino acids to about 850 amino acids, about 45 amino acids to about 800 amino acids, about 45 amino acids to about 750 amino acids, about 45 amino acids to about 700 amino acids, about 45 amino acids to about 650 amino acids, about 45 amino acids to about 600 amino acids, about 45 amino acids to about 550 amino acids, about 45 amino acids to about 500 amino acids, about 45 amino acids to about 450 amino acids, about 45 amino acids to about 400 amino acids, about 45 amino acids to about 350 amino acids, about 45 amino acids to about 300 amino acids, about 45 amino acids to about 280 amino acids, about 45 amino acids to about 260 amino acids, about 45 amino acids to about 240 amino acids, about 45 amino acids to about 220 amino acids, about 45 amino acids to about 200 amino acids, about 45 amino acids to about 195 amino acids, about 45 amino acids to about 190 amino acids, about 45 amino acids to about 185 amino acids, about 45 amino acids to about 180 amino acids, about 45 amino acids to about 175 amino acids, about 45 amino acids to about 170 amino acids, about 45 amino acids to about 165 amino acids, about 45 amino acids to about 160 amino acids, about 45 amino acids to about 155 amino acids, about 45 amino acids to about 150 amino acids, about 45 amino acids to about 145 amino acids, about 45 amino acids to about 140 amino acids, about 45 amino acids to about 135 amino acids, about 45 amino acids to about 130 amino acids, about 45 amino acids to about 125 amino acids, about 45 amino acids to about 120 amino acids, about 45 amino acids to about 115 amino acids, about 45 amino acids to about 110 amino acids, about 45 amino acids to about 105 amino acids, about 45 amino acids to about 100 amino acids, about 45 amino acids to about 95 amino acids, about 45 amino acids to about 90 amino acids, about 45 amino acids to about 85 amino acids, about 45 amino acids to about 80 amino acids, about 45 amino acids to about 75 amino acids, about 45 amino acids to about 70 amino acids, about 45 amino acids to about 65 amino acids, about 45 amino acids to about 60 amino acids, about 45 amino acids to about 55 amino acids, about 45 amino acids to about 50 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 450 amino acids, about 50 amino acids to about 400 amino acids, about 50 amino acids to about 350 amino acids, about 50 amino acids to about 300 amino acids, about 50 amino acids to about 280 amino acids, about 50 amino acids to about 260 amino acids, about 50 amino acids to about 240 amino acids, about 50 amino acids to about 220 amino acids, about 50 amino acids to about 200 amino acids, about 50 amino acids to about 195 amino acids, about 50 amino acids to about 190 amino acids, about 50 amino acids to about 185 amino acids, about 50 amino acids to about 180 amino acids, about 50 amino acids to about 175 amino acids, about 50 amino acids to about 170 amino acids, about 50 amino acids to about 165 amino acids, about 50 amino acids to about 160 amino acids, about 50 amino acids to about 155 amino acids, about 50 amino acids to about 150 amino acids, about 50 amino acids to about 145 amino acids, about 50 amino acids to about 140 amino acids, about 50 amino acids to about 135 amino acids, about 50 amino acids to about 130 amino acids, about 50 amino acids to about 125 amino acids, about 50 amino acids to about 120 amino acids, about 50 amino acids to about 115 amino acids, about 50 amino acids to about 110 amino acids, about 50 amino acids to about 105 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 65 amino acids, about 50 amino acids to about 60 amino acids, about 50 amino acids to about 55 amino acids, about 55 amino acids to about 1000 amino acids, about 55 amino acids to about 950 amino acids, about 55 amino acids to about 900 amino acids, about 55 amino acids to about 850 amino acids, about 55 amino acids to about 800 amino acids, about 55 amino acids to about 750 amino acids, about 55 amino acids to about 700 amino acids, about 55 amino acids to about 650 amino acids, about 55 amino acids to about 600 amino acids, about 55 amino acids to about 550 amino acids, about 55 amino acids to about 500 amino acids, about 55 amino acids to about 450 amino acids, about 55 amino acids to about 400 amino acids, about 55 amino acids to about 350 amino acids, about 55 amino acids to about 300 amino acids, about 55 amino acids to about 280 amino acids, about 55 amino acids to about 260 amino acids, about 55 amino acids to about 240 amino acids, about 55 amino acids to about 220 amino acids, about 55 amino acids to about 200 amino acids, about 55 amino acids to about 195 amino acids, about 55 amino acids to about 190 amino acids, about 55 amino acids to about 185 amino acids, about 55 amino acids to about 180 amino acids, about 55 amino acids to about 175 amino acids, about 55 amino acids to about 170 amino acids, about 55 amino acids to about 165 amino acids, about 55 amino acids to about 160 amino acids, about 55 amino acids to about 155 amino acids, about 55 amino acids to about 150 amino acids, about 55 amino acids to about 145 amino acids, about 55 amino acids to about 140 amino acids, about 55 amino acids to about 135 amino acids, about 55 amino acids to about 130 amino acids, about 55 amino acids to about 125 amino acids, about 55 amino acids to about 120 amino acids, about 55 amino acids to about 115 amino acids, about 55 amino acids to about 110 amino acids, about 55 amino acids to about 105 amino acids, about 55 amino acids to about 100 amino acids, about 55 amino acids to about 95 amino acids, about 55 amino acids to about 90 amino acids, about 55 amino acids to about 85 amino acids, about 55 amino acids to about 80 amino acids, about 55 amino acids to about 75 amino acids, about 55 amino acids to about 70 amino acids, about 55 amino acids to about 65 amino acids, about 55 amino acids to about 60 amino acids, about 60 amino acids to about 1000 amino acids, about 60 amino acids to about 950 amino acids, about 60 amino acids to about 900 amino acids, about 60 amino acids to about 850 amino acids, about 60 amino acids to about 800 amino acids, about 60 amino acids to about 750 amino acids, about 60 amino acids to about 700 amino acids, about 60 amino acids to about 650 amino acids, about 60 amino acids to about 600 amino acids, about 60 amino acids to about 550 amino acids, about 60 amino acids to about 500 amino acids, about 60 amino acids to about 450 amino acids, about 60 amino acids to about 400 amino acids, about 60 amino acids to about 350 amino acids, about 60 amino acids to about 300 amino acids, about 60 amino acids to about 280 amino acids, about 60 amino acids to about 260 amino acids, about 60 amino acids to about 240 amino acids, about 60 amino acids to about 220 amino acids, about 60 amino acids to about 200 amino acids, about 60 amino acids to about 195 amino acids, about 60 amino acids to about 190 amino acids, about 60 amino acids to about 185 amino acids, about 60 amino acids to about 180 amino acids, about 60 amino acids to about 175 amino acids, about 60 amino acids to about 170 amino acids, about 60 amino acids to about 165 amino acids, about 60 amino acids to about 160 amino acids, about 60 amino acids to about 155 amino acids, about 60 amino acids to about 150 amino acids, about 60 amino acids to about 145 amino acids, about 60 amino acids to about 140 amino acids, about 60 amino acids to about 135 amino acids, about 60 amino acids to about 130 amino acids, about 60 amino acids to about 125 amino acids, about 60 amino acids to about 120 amino acids, about 60 amino acids to about 115 amino acids, about 60 amino acids to about 110 amino acids, about 60 amino acids to about 105 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 60 amino acids to about 65 amino acids, about 65 amino acids to about 1000 amino acids, about 65 amino acids to about 950 amino acids, about 65 amino acids to about 900 amino acids, about 65 amino acids to about 850 amino acids, about 65 amino acids to about 800 amino acids, about 65 amino acids to about 750 amino acids, about 65 amino acids to about 700 amino acids, about 65 amino acids to about 650 amino acids, about 65 amino acids to about 600 amino acids, about 65 amino acids to about 550 amino acids, about 65 amino acids to about 500 amino acids, about 65 amino acids to about 450 amino acids, about 65 amino acids to about 400 amino acids, about 65 amino acids to about 350 amino acids, about 65 amino acids to about 300 amino acids, about 65 amino acids to about 280 amino acids, about 65 amino acids to about 260 amino acids, about 65 amino acids to about 240 amino acids, about 65 amino acids to about 220 amino acids, about 65 amino acids to about 200 amino acids, about 65 amino acids to about 195 amino acids, about 65 amino acids to about 190 amino acids, about 65 amino acids to about 185 amino acids, about 65 amino acids to about 180 amino acids, about 65 amino acids to about 175 amino acids, about 65 amino acids to about 170 amino acids, about 65 amino acids to about 165 amino acids, about 65 amino acids to about 160 amino acids, about 65 amino acids to about 155 amino acids, about 65 amino acids to about 150 amino acids, about 65 amino acids to about 145 amino acids, about 65 amino acids to about 140 amino acids, about 65 amino acids to about 135 amino acids, about 65 amino acids to about 130 amino acids, about 65 amino acids to about 125 amino acids, about 65 amino acids to about 120 amino acids, about 65 amino acids to about 115 amino acids, about 65 amino acids to about 110 amino acids, about 65 amino acids to about 105 amino acids, about 65 amino acids to about 100 amino acids, about 65 amino acids to about 95 amino acids, about 65 amino acids to about 90 amino acids, about 65 amino acids to about 85 amino acids, about 65 amino acids to about 80 amino acids, about 65 amino acids to about 75 amino acids, about 65 amino acids to about 70 amino acids, about 70 amino acids to about 1000 amino acids, about 70 amino acids to about 950 amino acids, about 70 amino acids to about 900 amino acids, about 70 amino acids to about 850 amino acids, about 70 amino acids to about 800 amino acids, about 70 amino acids to about 750 amino acids, about 70 amino acids to about 700 amino acids, about 70 amino acids to about 650 amino acids, about 70 amino acids to about 600 amino acids, about 70 amino acids to about 550 amino acids, about 70 amino acids to about 500 amino acids, about 70 amino acids to about 450 amino acids, about 70 amino acids to about 400 amino acids, about 70 amino acids to about 350 amino acids, about 70 amino acids to about 300 amino acids, about 70 amino acids to about 280 amino acids, about 70 amino acids to about 260 amino acids, about 70 amino acids to about 240 amino acids, about 70 amino acids to about 220 amino acids, about 70 amino acids to about 200 amino acids, about 70 amino acids to about 195 amino acids, about 70 amino acids to about 190 amino acids, about 70 amino acids to about 185 amino acids, about 70 amino acids to about 180 amino acids, about 70 amino acids to about 175 amino acids, about 70 amino acids to about 170 amino acids, about 70 amino acids to about 165 amino acids, about 70 amino acids to about 160 amino acids, about 70 amino acids to about 155 amino acids, about 70 amino acids to about 150 amino acids, about 70 amino acids to about 145 amino acids, about 70 amino acids to about 140 amino acids, about 70 amino acids to about 135 amino acids, about 70 amino acids to about 130 amino acids, about 70 amino acids to about 125 amino acids, about 70 amino acids to about 120 amino acids, about 70 amino acids to about 115 amino acids, about 70 amino acids to about 110 amino acids, about 70 amino acids to about 105 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 70 amino acids to about 75 amino acids, about 75 amino acids to about 1000 amino acids, about 75 amino acids to about 950 amino acids, about 75 amino acids to about 900 amino acids, about 75 amino acids to about 850 amino acids, about 75 amino acids to about 800 amino acids, about 75 amino acids to about 750 amino acids, about 75 amino acids to about 700 amino acids, about 75 amino acids to about 650 amino acids, about 75 amino acids to about 600 amino acids, about 75 amino acids to about 550 amino acids, about 75 amino acids to about 500 amino acids, about 75 amino acids to about 450 amino acids, about 75 amino acids to about 400 amino acids, about 75 amino acids to about 350 amino acids, about 75 amino acids to about 300 amino acids, about 75 amino acids to about 280 amino acids, about 75 amino acids to about 260 amino acids, about 75 amino acids to about 240 amino acids, about 75 amino acids to about 220 amino acids, about 75 amino acids to about 200 amino acids, about 75 amino acids to about 195 amino acids, about 75 amino acids to about 190 amino acids, about 75 amino acids to about 185 amino acids, about 75 amino acids to about 180 amino acids, about 75 amino acids to about 175 amino acids, about 75 amino acids to about 170 amino acids, about 75 amino acids to about 165 amino acids, about 75 amino acids to about 160 amino acids, about 75 amino acids to about 155 amino acids, about 75 amino acids to about 150 amino acids, about 75 amino acids to about 145 amino acids, about 75 amino acids to about 140 amino acids, about 75 amino acids to about 135 amino acids, about 75 amino acids to about 130 amino acids, about 75 amino acids to about 125 amino acids, about 75 amino acids to about 120 amino acids, about 75 amino acids to about 115 amino acids, about 75 amino acids to about 110 amino acids, about 75 amino acids to about 105 amino acids, about 75 amino acids to about 100 amino acids, about 75 amino acids to about 95 amino acids, about 75 amino acids to about 90 amino acids, about 75 amino acids to about 85 amino acids, about 75 amino acids to about 80 amino acids, about 80 amino acids to about 1000 amino acids, about 80 amino acids to about 950 amino acids, about 80 amino acids to about 900 amino acids, about 80 amino acids to about 850 amino acids, about 80 amino acids to about 800 amino acids, about 80 amino acids to about 750 amino acids, about 80 amino acids to about 700 amino acids, about 80 amino acids to about 650 amino acids, about 80 amino acids to about 600 amino acids, about 80 amino acids to about 550 amino acids, about 80 amino acids to about 500 amino acids, about 80 amino acids to about 450 amino acids, about 80 amino acids to about 400 amino acids, about 80 amino acids to about 350 amino acids, about 80 amino acids to about 300 amino acids, about 80 amino acids to about 280 amino acids, about 80 amino acids to about 260 amino acids, about 80 amino acids to about 240 amino acids, about 80 amino acids to about 220 amino acids, about 80 amino acids to about 200 amino acids, about 80 amino acids to about 195 amino acids, about 80 amino acids to about 190 amino acids, about 80 amino acids to about 185 amino acids, about 80 amino acids to about 180 amino acids, about 80 amino acids to about 175 amino acids, about 80 amino acids to about 170 amino acids, about 80 amino acids to about 165 amino acids, about 80 amino acids to about 160 amino acids, about 80 amino acids to about 155 amino acids, about 80 amino acids to about 150 amino acids, about 80 amino acids to about 145 amino acids, about 80 amino acids to about 140 amino acids, about 80 amino acids to about 135 amino acids, about 80 amino acids to about 130 amino acids, about 80 amino acids to about 125 amino acids, about 80 amino acids to about 120 amino acids, about 80 amino acids to about 115 amino acids, about 80 amino acids to about 110 amino acids, about 80 amino acids to about 105 amino acids, about 80 amino acids to about 100 amino acids, about 80 amino acids to about 95 amino acids, about 80 amino acids to about 90 amino acids, about 80 amino acids to about 85 amino acids, about 85 amino acids to about 1000 amino acids, about 85 amino acids to about 950 amino acids, about 85 amino acids to about 900 amino acids, about 85 amino acids to about 850 amino acids, about 85 amino acids to about 800 amino acids, about 85 amino acids to about 750 amino acids, about 85 amino acids to about 700 amino acids, about 85 amino acids to about 650 amino acids, about 85 amino acids to about 600 amino acids, about 85 amino acids to about 550 amino acids, about 85 amino acids to about 500 amino acids, about 85 amino acids to about 450 amino acids, about 85 amino acids to about 400 amino acids, about 85 amino acids to about 350 amino acids, about 85 amino acids to about 300 amino acids, about 85 amino acids to about 280 amino acids, about 85 amino acids to about 260 amino acids, about 85 amino acids to about 240 amino acids, about 85 amino acids to about 220 amino acids, about 85 amino acids to about 200 amino acids, about 85 amino acids to about 195 amino acids, about 85 amino acids to about 190 amino acids, about 85 amino acids to about 185 amino acids, about 85 amino acids to about 180 amino acids, about 85 amino acids to about 175 amino acids, about 85 amino acids to about 170 amino acids, about 85 amino acids to about 165 amino acids, about 85 amino acids to about 160 amino acids, about 85 amino acids to about 155 amino acids, about 85 amino acids to about 150 amino acids, about 85 amino acids to about 145 amino acids, about 85 amino acids to about 140 amino acids, about 85 amino acids to about 135 amino acids, about 85 amino acids to about 130 amino acids, about 85 amino acids to about 125 amino acids, about 85 amino acids to about 120 amino acids, about 85 amino acids to about 115 amino acids, about 85 amino acids to about 110 amino acids, about 85 amino acids to about 105 amino acids, about 85 amino acids to about 100 amino acids, about 85 amino acids to about 95 amino acids, about 85 amino acids to about 90 amino acids, about 90 amino acids to about 1000 amino acids, about 90 amino acids to about 950 amino acids, about 90 amino acids to about 900 amino acids, about 90 amino acids to about 850 amino acids, about 90 amino acids to about 800 amino acids, about 90 amino acids to about 750 amino acids, about 90 amino acids to about 700 amino acids, about 90 amino acids to about 650 amino acids, about 90 amino acids to about 600 amino acids, about 90 amino acids to about 550 amino acids, about 90 amino acids to about 500 amino acids, about 90 amino acids to about 450 amino acids, about 90 amino acids to about 400 amino acids, about 90 amino acids to about 350 amino acids, about 90 amino acids to about 300 amino acids, about 90 amino acids to about 280 amino acids, about 90 amino acids to about 260 amino acids, about 90 amino acids to about 240 amino acids, about 90 amino acids to about 220 amino acids, about 90 amino acids to about 200 amino acids, about 90 amino acids to about 195 amino acids, about 90 amino acids to about 190 amino acids, about 90 amino acids to about 185 amino acids, about 90 amino acids to about 180 amino acids, about 90 amino acids to about 175 amino acids, about 90 amino acids to about 170 amino acids, about 90 amino acids to about 165 amino acids, about 90 amino acids to about 160 amino acids, about 90 amino acids to about 155 amino acids, about 90 amino acids to about 150 amino acids, about 90 amino acids to about 145 amino acids, about 90 amino acids to about 140 amino acids, about 90 amino acids to about 135 amino acids, about 90 amino acids to about 130 amino acids, about 90 amino acids to about 125 amino acids, about 90 amino acids to about 120 amino acids, about 90 amino acids to about 115 amino acids, about 90 amino acids to about 110 amino acids, about 90 amino acids to about 105 amino acids, about 90 amino acids to about 100 amino acids, about 90 amino acids to about 95 amino acids, about 95 amino acids to about 1000 amino acids, about 95 amino acids to about 950 amino acids, about 95 amino acids to about 900 amino acids, about 95 amino acids to about 850 amino acids, about 95 amino acids to about 800 amino acids, about 95 amino acids to about 750 amino acids, about 95 amino acids to about 700 amino acids, about 95 amino acids to about 650 amino acids, about 95 amino acids to about 600 amino acids, about 95 amino acids to about 550 amino acids, about 95 amino acids to about 500 amino acids, about 95 amino acids to about 450 amino acids, about 95 amino acids to about 400 amino acids, about 95 amino acids to about 350 amino acids, about 95 amino acids to about 300 amino acids, about 95 amino acids to about 280 amino acids, about 95 amino acids to about 260 amino acids, about 95 amino acids to about 240 amino acids, about 95 amino acids to about 220 amino acids, about 95 amino acids to about 200 amino acids, about 95 amino acids to about 195 amino acids, about 95 amino acids to about 190 amino acids, about 95 amino acids to about 185 amino acids, about 95 amino acids to about 180 amino acids, about 95 amino acids to about 175 amino acids, about 95 amino acids to about 170 amino acids, about 95 amino acids to about 165 amino acids, about 95 amino acids to about 160 amino acids, about 95 amino acids to about 155 amino acids, about 95 amino acids to about 150 amino acids, about 95 amino acids to about 145 amino acids, about 95 amino acids to about 140 amino acids, about 95 amino acids to about 135 amino acids, about 95 amino acids to about 130 amino acids, about 95 amino acids to about 125 amino acids, about 95 amino acids to about 120 amino acids, about 95 amino acids to about 115 amino acids, about 95 amino acids to about 110 amino acids, about 95 amino acids to about 105 amino acids, about 95 amino acids to about 100 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 450 amino acids, about 100 amino acids to about 400 amino acids, about 100 amino acids to about 350 amino acids, about 100 amino acids to about 300 amino acids, about 100 amino acids to about 280 amino acids, about 100 amino acids to about 260 amino acids, about 100 amino acids to about 240 amino acids, about 100 amino acids to about 220 amino acids, about 100 amino acids to about 200 amino acids, about 100 amino acids to about 195 amino acids, about 100 amino acids to about 190 amino acids, about 100 amino acids to about 185 amino acids, about 100 amino acids to about 180 amino acids, about 100 amino acids to about 175 amino acids, about 100 amino acids to about 170 amino acids, about 100 amino acids to about 165 amino acids, about 100 amino acids to about 160 amino acids, about 100 amino acids to about 155 amino acids, about 100 amino acids to about 150 amino acids, about 100 amino acids to about 145 amino acids, about 100 amino acids to about 140 amino acids, about 100 amino acids to about 135 amino acids, about 100 amino acids to about 130 amino acids, about 100 amino acids to about 125 amino acids, about 100 amino acids to about 120 amino acids, about 100 amino acids to about 115 amino acids, about 100 amino acids to about 110 amino acids, about 100 amino acids to about 105 amino acids, about 105 amino acids to about 1000 amino acids, about 105 amino acids to about 950 amino acids, about 105 amino acids to about 900 amino acids, about 105 amino acids to about 850 amino acids, about 105 amino acids to about 800 amino acids, about 105 amino acids to about 750 amino acids, about 105 amino acids to about 700 amino acids, about 105 amino acids to about 650 amino acids, about 105 amino acids to about 600 amino acids, about 105 amino acids to about 550 amino acids, about 105 amino acids to about 500 amino acids, about 105 amino acids to about 450 amino acids, about 105 amino acids to about 400 amino acids, about 105 amino acids to about 350 amino acids, about 105 amino acids to about 300 amino acids, about 105 amino acids to about 280 amino acids, about 105 amino acids to about 260 amino acids, about 105 amino acids to about 240 amino acids, about 105 amino acids to about 220 amino acids, about 105 amino acids to about 200 amino acids, about 105 amino acids to about 195 amino acids, about 105 amino acids to about 190 amino acids, about 105 amino acids to about 185 amino acids, about 105 amino acids to about 180 amino acids, about 105 amino acids to about 175 amino acids, about 105 amino acids to about 170 amino acids, about 105 amino acids to about 165 amino acids, about 105 amino acids to about 160 amino acids, about 105 amino acids to about 155 amino acids, about 105 amino acids to about 150 amino acids, about 105 amino acids to about 145 amino acids, about 105 amino acids to about 140 amino acids, about 105 amino acids to about 135 amino acids, about 105 amino acids to about 130 amino acids, about 105 amino acids to about 125 amino acids, about 105 amino acids to about 120 amino acids, about 105 amino acids to about 115 amino acids, about 105 amino acids to about 110 amino acids, about 110 amino acids to about 1000 amino acids, about 110 amino acids to about 950 amino acids, about 110 amino acids to about 900 amino acids, about 110 amino acids to about 850 amino acids, about 110 amino acids to about 800 amino acids, about 110 amino acids to about 750 amino acids, about 110 amino acids to about 700 amino acids, about 110 amino acids to about 650 amino acids, about 110 amino acids to about 600 amino acids, about 110 amino acids to about 550 amino acids, about 110 amino acids to about 500 amino acids, about 110 amino acids to about 450 amino acids, about 110 amino acids to about 400 amino acids, about 110 amino acids to about 350 amino acids, about 110 amino acids to about 300 amino acids, about 110 amino acids to about 280 amino acids, about 110 amino acids to about 260 amino acids, about 110 amino acids to about 240 amino acids, about 110 amino acids to about 220 amino acids, about 110 amino acids to about 200 amino acids, about 110 amino acids to about 195 amino acids, about 110 amino acids to about 190 amino acids, about 110 amino acids to about 185 amino acids, about 110 amino acids to about 180 amino acids, about 110 amino acids to about 175 amino acids, about 110 amino acids to about 170 amino acids, about 110 amino acids to about 165 amino acids, about 110 amino acids to about 160 amino acids, about 110 amino acids to about 155 amino acids, about 110 amino acids to about 150 amino acids, about 110 amino acids to about 145 amino acids, about 110 amino acids to about 140 amino acids, about 110 amino acids to about 135 amino acids, about 110 amino acids to about 130 amino acids, about 110 amino acids to about 125 amino acids, about 110 amino acids to about 120 amino acids, about 110 amino acids to about 115 amino acids, about 115 amino acids to about 1000 amino acids, about 115 amino acids to about 950 amino acids, about 115 amino acids to about 900 amino acids, about 115 amino acids to about 850 amino acids, about 115 amino acids to about 800 amino acids, about 115 amino acids to about 750 amino acids, about 115 amino acids to about 700 amino acids, about 115 amino acids to about 650 amino acids, about 115 amino acids to about 600 amino acids, about 115 amino acids to about 550 amino acids, about 115 amino acids to about 500 amino acids, about 115 amino acids to about 450 amino acids, about 115 amino acids to about 400 amino acids, about 115 amino acids to about 350 amino acids, about 115 amino acids to about 300 amino acids, about 115 amino acids to about 280 amino acids, about 115 amino acids to about 260 amino acids, about 115 amino acids to about 240 amino acids, about 115 amino acids to about 220 amino acids, about 115 amino acids to about 200 amino acids, about 115 amino acids to about 195 amino acids, about 115 amino acids to about 190 amino acids, about 115 amino acids to about 185 amino acids, about 115 amino acids to about 180 amino acids, about 115 amino acids to about 175 amino acids, about 115 amino acids to about 170 amino acids, about 115 amino acids to about 165 amino acids, about 115 amino acids to about 160 amino acids, about 115 amino acids to about 155 amino acids, about 115 amino acids to about 150 amino acids, about 115 amino acids to about 145 amino acids, about 115 amino acids to about 140 amino acids, about 115 amino acids to about 135 amino acids, about 115 amino acids to about 130 amino acids, about 115 amino acids to about 125 amino acids, about 115 amino acids to about 120 amino acids, about 120 amino acids to about 1000 amino acids, about 120 amino acids to about 950 amino acids, about 120 amino acids to about 900 amino acids, about 120 amino acids to about 850 amino acids, about 120 amino acids to about 800 amino acids, about 120 amino acids to about 750 amino acids, about 120 amino acids to about 700 amino acids, about 120 amino acids to about 650 amino acids, about 120 amino acids to about 600 amino acids, about 120 amino acids to about 550 amino acids, about 120 amino acids to about 500 amino acids, about 120 amino acids to about 450 amino acids, about 120 amino acids to about 400 amino acids, about 120 amino acids to about 350 amino acids, about 120 amino acids to about 300 amino acids, about 120 amino acids to about 280 amino acids, about 120 amino acids to about 260 amino acids, about 120 amino acids to about 240 amino acids, about 120 amino acids to about 220 amino acids, about 120 amino acids to about 200 amino acids, about 120 amino acids to about 195 amino acids, about 120 amino acids to about 190 amino acids, about 120 amino acids to about 185 amino acids, about 120 amino acids to about 180 amino acids, about 120 amino acids to about 175 amino acids, about 120 amino acids to about 170 amino acids, about 120 amino acids to about 165 amino acids, about 120 amino acids to about 160 amino acids, about 120 amino acids to about 155 amino acids, about 120 amino acids to about 150 amino acids, about 120 amino acids to about 145 amino acids, about 120 amino acids to about 140 amino acids, about 120 amino acids to about 135 amino acids, about 120 amino acids to about 130 amino acids, about 120 amino acids to about 125 amino acids, about 125 amino acids to about 1000 amino acids, about 125 amino acids to about 950 amino acids, about 125 amino acids to about 900 amino acids, about 125 amino acids to about 850 amino acids, about 125 amino acids to about 800 amino acids, about 125 amino acids to about 750 amino acids, about 125 amino acids to about 700 amino acids, about 125 amino acids to about 650 amino acids, about 125 amino acids to about 600 amino acids, about 125 amino acids to about 550 amino acids, about 125 amino acids to about 500 amino acids, about 125 amino acids to about 450 amino acids, about 125 amino acids to about 400 amino acids, about 125 amino acids to about 350 amino acids, about 125 amino acids to about 300 amino acids, about 125 amino acids to about 280 amino acids, about 125 amino acids to about 260 amino acids, about 125 amino acids to about 240 amino acids, about 125 amino acids to about 220 amino acids, about 125 amino acids to about 200 amino acids, about 125 amino acids to about 195 amino acids, about 125 amino acids to about 190 amino acids, about 125 amino acids to about 185 amino acids, about 125 amino acids to about 180 amino acids, about 125 amino acids to about 175 amino acids, about 125 amino acids to about 170 amino acids, about 125 amino acids to about 165 amino acids, about 125 amino acids to about 160 amino acids, about 125 amino acids to about 155 amino acids, about 125 amino acids to about 150 amino acids, about 125 amino acids to about 145 amino acids, about 125 amino acids to about 140 amino acids, about 125 amino acids to about 135 amino acids, about 125 amino acids to about 130 amino acids, about 130 amino acids to about 1000 amino acids, about 130 amino acids to about 950 amino acids, about 130 amino acids to about 900 amino acids, about 130 amino acids to about 850 amino acids, about 130 amino acids to about 800 amino acids, about 130 amino acids to about 750 amino acids, about 130 amino acids to about 700 amino acids, about 130 amino acids to about 650 amino acids, about 130 amino acids to about 600 amino acids, about 130 amino acids to about 550 amino acids, about 130 amino acids to about 500 amino acids, about 130 amino acids to about 450 amino acids, about 130 amino acids to about 400 amino acids, about 130 amino acids to about 350 amino acids, about 130 amino acids to about 300 amino acids, about 130 amino acids to about 280 amino acids, about 130 amino acids to about 260 amino acids, about 130 amino acids to about 240 amino acids, about 130 amino acids to about 220 amino acids, about 130 amino acids to about 200 amino acids, about 130 amino acids to about 195 amino acids, about 130 amino acids to about 190 amino acids, about 130 amino acids to about 185 amino acids, about 130 amino acids to about 180 amino acids, about 130 amino acids to about 175 amino acids, about 130 amino acids to about 170 amino acids, about 130 amino acids to about 165 amino acids, about 130 amino acids to about 160 amino acids, about 130 amino acids to about 155 amino acids, about 130 amino acids to about 150 amino acids, about 130 amino acids to about 145 amino acids, about 130 amino acids to about 140 amino acids, about 130 amino acids to about 135 amino acids, about 135 amino acids to about 1000 amino acids, about 135 amino acids to about 950 amino acids, about 135 amino acids to about 900 amino acids, about 135 amino acids to about 850 amino acids, about 135 amino acids to about 800 amino acids, about 135 amino acids to about 750 amino acids, about 135 amino acids to about 700 amino acids, about 135 amino acids to about 650 amino acids, about 135 amino acids to about 600 amino acids, about 135 amino acids to about 550 amino acids, about 135 amino acids to about 500 amino acids, about 135 amino acids to about 450 amino acids, about 135 amino acids to about 400 amino acids, about 135 amino acids to about 350 amino acids, about 135 amino acids to about 300 amino acids, about 135 amino acids to about 280 amino acids, about 135 amino acids to about 260 amino acids, about 135 amino acids to about 240 amino acids, about 135 amino acids to about 220 amino acids, about 135 amino acids to about 200 amino acids, about 135 amino acids to about 195 amino acids, about 135 amino acids to about 190 amino acids, about 135 amino acids to about 185 amino acids, about 135 amino acids to about 180 amino acids, about 135 amino acids to about 175 amino acids, about 135 amino acids to about 170 amino acids, about 135 amino acids to about 165 amino acids, about 135 amino acids to about 160 amino acids, about 135 amino acids to about 155 amino acids, about 135 amino acids to about 150 amino acids, about 135 amino acids to about 145 amino acids, about 135 amino acids to about 140 amino acids, about 140 amino acids to about 1000 amino acids, about 140 amino acids to about 950 amino acids, about 140 amino acids to about 900 amino acids, about 140 amino acids to about 850 amino acids, about 140 amino acids to about 800 amino acids, about 140 amino acids to about 750 amino acids, about 140 amino acids to about 700 amino acids, about 140 amino acids to about 650 amino acids, about 140 amino acids to about 600 amino acids, about 140 amino acids to about 550 amino acids, about 140 amino acids to about 500 amino acids, about 140 amino acids to about 450 amino acids, about 140 amino acids to about 400 amino acids, about 140 amino acids to about 350 amino acids, about 140 amino acids to about 300 amino acids, about 140 amino acids to about 280 amino acids, about 140 amino acids to about 260 amino acids, about 140 amino acids to about 240 amino acids, about 140 amino acids to about 220 amino acids, about 140 amino acids to about 200 amino acids, about 140 amino acids to about 195 amino acids, about 140 amino acids to about 190 amino acids, about 140 amino acids to about 185 amino acids, about 140 amino acids to about 180 amino acids, about 140 amino acids to about 175 amino acids, about 140 amino acids to about 170 amino acids, about 140 amino acids to about 165 amino acids, about 140 amino acids to about 160 amino acids, about 140 amino acids to about 155 amino acids, about 140 amino acids to about 150 amino acids, about 140 amino acids to about 145 amino acids, about 145 amino acids to about 1000 amino acids, about 145 amino acids to about 950 amino acids, about 145 amino acids to about 900 amino acids, about 145 amino acids to about 850 amino acids, about 145 amino acids to about 800 amino acids, about 145 amino acids to about 750 amino acids, about 145 amino acids to about 700 amino acids, about 145 amino acids to about 650 amino acids, about 145 amino acids to about 600 amino acids, about 145 amino acids to about 550 amino acids, about 145 amino acids to about 500 amino acids, about 145 amino acids to about 450 amino acids, about 145 amino acids to about 400 amino acids, about 145 amino acids to about 350 amino acids, about 145 amino acids to about 300 amino acids, about 145 amino acids to about 280 amino acids, about 145 amino acids to about 260 amino acids, about 145 amino acids to about 240 amino acids, about 145 amino acids to about 220 amino acids, about 145 amino acids to about 200 amino acids, about 145 amino acids to about 195 amino acids, about 145 amino acids to about 190 amino acids, about 145 amino acids to about 185 amino acids, about 145 amino acids to about 180 amino acids, about 145 amino acids to about 175 amino acids, about 145 amino acids to about 170 amino acids, about 145 amino acids to about 165 amino acids, about 145 amino acids to about 160 amino acids, about 145 amino acids to about 155 amino acids, about 145 amino acids to about 150 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 450 amino acids, about 150 amino acids to about 400 amino acids, about 150 amino acids to about 350 amino acids, about 150 amino acids to about 300 amino acids, about 150 amino acids to about 280 amino acids, about 150 amino acids to about 260 amino acids, about 150 amino acids to about 240 amino acids, about 150 amino acids to about 220 amino acids, about 150 amino acids to about 200 amino acids, about 150 amino acids to about 195 amino acids, about 150 amino acids to about 190 amino acids, about 150 amino acids to about 185 amino acids, about 150 amino acids to about 180 amino acids, about 150 amino acids to about 175 amino acids, about 150 amino acids to about 170 amino acids, about 150 amino acids to about 165 amino acids, about 150 amino acids to about 160 amino acids, about 150 amino acids to about 155 amino acids, about 155 amino acids to about 1000 amino acids, about 155 amino acids to about 950 amino acids, about 155 amino acids to about 900 amino acids, about 155 amino acids to about 850 amino acids, about 155 amino acids to about 800 amino acids, about 155 amino acids to about 750 amino acids, about 155 amino acids to about 700 amino acids, about 155 amino acids to about 650 amino acids, about 155 amino acids to about 600 amino acids, about 155 amino acids to about 550 amino acids, about 155 amino acids to about 500 amino acids, about 155 amino acids to about 450 amino acids, about 155 amino acids to about 400 amino acids, about 155 amino acids to about 350 amino acids, about 155 amino acids to about 300 amino acids, about 155 amino acids to about 280 amino acids, about 155 amino acids to about 260 amino acids, about 155 amino acids to about 240 amino acids, about 155 amino acids to about 220 amino acids, about 155 amino acids to about 200 amino acids, about 155 amino acids to about 195 amino acids, about 155 amino acids to about 190 amino acids, about 155 amino acids to about 185 amino acids, about 155 amino acids to about 180 amino acids, about 155 amino acids to about 175 amino acids, about 155 amino acids to about 170 amino acids, about 155 amino acids to about 165 amino acids, about 155 amino acids to about 160 amino acids, about 160 amino acids to about 1000 amino acids, about 160 amino acids to about 950 amino acids, about 160 amino acids to about 900 amino acids, about 160 amino acids to about 850 amino acids, about 160 amino acids to about 800 amino acids, about 160 amino acids to about 750 amino acids, about 160 amino acids to about 700 amino acids, about 160 amino acids to about 650 amino acids, about 160 amino acids to about 600 amino acids, about 160 amino acids to about 550 amino acids, about 160 amino acids to about 500 amino acids, about 160 amino acids to about 450 amino acids, about 160 amino acids to about 400 amino acids, about 160 amino acids to about 350 amino acids, about 160 amino acids to about 300 amino acids, about 160 amino acids to about 280 amino acids, about 160 amino acids to about 260 amino acids, about 160 amino acids to about 240 amino acids, about 160 amino acids to about 220 amino acids, about 160 amino acids to about 200 amino acids, about 160 amino acids to about 195 amino acids, about 160 amino acids to about 190 amino acids, about 160 amino acids to about 185 amino acids, about 160 amino acids to about 180 amino acids, about 160 amino acids to about 175 amino acids, about 160 amino acids to about 170 amino acids, about 160 amino acids to about 165 amino acids, about 165 amino acids to about 1000 amino acids, about 165 amino acids to about 950 amino acids, about 165 amino acids to about 900 amino acids, about 165 amino acids to about 850 amino acids, about 165 amino acids to about 800 amino acids, about 165 amino acids to about 750 amino acids, about 165 amino acids to about 700 amino acids, about 165 amino acids to about 650 amino acids, about 165 amino acids to about 600 amino acids, about 165 amino acids to about 550 amino acids, about 165 amino acids to about 500 amino acids, about 165 amino acids to about 450 amino acids, about 165 amino acids to about 400 amino acids, about 165 amino acids to about 350 amino acids, about 165 amino acids to about 300 amino acids, about 165 amino acids to about 280 amino acids, about 165 amino acids to about 260 amino acids, about 165 amino acids to about 240 amino acids, about 165 amino acids to about 220 amino acids, about 165 amino acids to about 200 amino acids, about 165 amino acids to about 195 amino acids, about 165 amino acids to about 190 amino acids, about 165 amino acids to about 185 amino acids, about 165 amino acids to about 180 amino acids, about 165 amino acids to about 175 amino acids, about 165 amino acids to about 170 amino acids, about 170 amino acids to about 1000 amino acids, about 170 amino acids to about 950 amino acids, about 170 amino acids to about 900 amino acids, about 170 amino acids to about 850 amino acids, about 170 amino acids to about 800 amino acids, about 170 amino acids to about 750 amino acids, about 170 amino acids to about 700 amino acids, about 170 amino acids to about 650 amino acids, about 170 amino acids to about 600 amino acids, about 170 amino acids to about 550 amino acids, about 170 amino acids to about 500 amino acids, about 170 amino acids to about 450 amino acids, about 170 amino acids to about 400 amino acids, about 170 amino acids to about 350 amino acids, about 170 amino acids to about 300 amino acids, about 170 amino acids to about 280 amino acids, about 170 amino acids to about 260 amino acids, about 170 amino acids to about 240 amino acids, about 170 amino acids to about 220 amino acids, about 170 amino acids to about 200 amino acids, about 170 amino acids to about 195 amino acids, about 170 amino acids to about 190 amino acids, about 170 amino acids to about 185 amino acids, about 170 amino acids to about 180 amino acids, about 170 amino acids to about 175 amino acids, about 175 amino acids to about 1000 amino acids, about 175 amino acids to about 950 amino acids, about 175 amino acids to about 900 amino acids, about 175 amino acids to about 850 amino acids, about 175 amino acids to about 800 amino acids, about 175 amino acids to about 750 amino acids, about 175 amino acids to about 700 amino acids, about 175 amino acids to about 650 amino acids, about 175 amino acids to about 600 amino acids, about 175 amino acids to about 550 amino acids, about 175 amino acids to about 500 amino acids, about 175 amino acids to about 450 amino acids, about 175 amino acids to about 400 amino acids, about 175 amino acids to about 350 amino acids, about 175 amino acids to about 300 amino acids, about 175 amino acids to about 280 amino acids, about 175 amino acids to about 260 amino acids, about 175 amino acids to about 240 amino acids, about 175 amino acids to about 220 amino acids, about 175 amino acids to about 200 amino acids, about 175 amino acids to about 195 amino acids, about 175 amino acids to about 190 amino acids, about 175 amino acids to about 185 amino acids, about 175 amino acids to about 180 amino acids, about 180 amino acids to about 1000 amino acids, about 180 amino acids to about 950 amino acids, about 180 amino acids to about 900 amino acids, about 180 amino acids to about 850 amino acids, about 180 amino acids to about 800 amino acids, about 180 amino acids to about 750 amino acids, about 180 amino acids to about 700 amino acids, about 180 amino acids to about 650 amino acids, about 180 amino acids to about 600 amino acids, about 180 amino acids to about 550 amino acids, about 180 amino acids to about 500 amino acids, about 180 amino acids to about 450 amino acids, about 180 amino acids to about 400 amino acids, about 180 amino acids to about 350 amino acids, about 180 amino acids to about 300 amino acids, about 180 amino acids to about 280 amino acids, about 180 amino acids to about 260 amino acids, about 180 amino acids to about 240 amino acids, about 180 amino acids to about 220 amino acids, about 180 amino acids to about 200 amino acids, about 180 amino acids to about 195 amino acids, about 180 amino acids to about 190 amino acids, about 180 amino acids to about 185 amino acids, about 185 amino acids to about 1000 amino acids, about 185 amino acids to about 950 amino acids, about 185 amino acids to about 900 amino acids, about 185 amino acids to about 850 amino acids, about 185 amino acids to about 800 amino acids, about 185 amino acids to about 750 amino acids, about 185 amino acids to about 700 amino acids, about 185 amino acids to about 650 amino acids, about 185 amino acids to about 600 amino acids, about 185 amino acids to about 550 amino acids, about 185 amino acids to about 500 amino acids, about 185 amino acids to about 450 amino acids, about 185 amino acids to about 400 amino acids, about 185 amino acids to about 350 amino acids, about 185 amino acids to about 300 amino acids, about 185 amino acids to about 280 amino acids, about 185 amino acids to about 260 amino acids, about 185 amino acids to about 240 amino acids, about 185 amino acids to about 220 amino acids, about 185 amino acids to about 200 amino acids, about 185 amino acids to about 195 amino acids, about 185 amino acids to about 190 amino acids, about 190 amino acids to about 1000 amino acids, about 190 amino acids to about 950 amino acids, about 190 amino acids to about 900 amino acids, about 190 amino acids to about 850 amino acids, about 190 amino acids to about 800 amino acids, about 190 amino acids to about 750 amino acids, about 190 amino acids to about 700 amino acids, about 190 amino acids to about 650 amino acids, about 190 amino acids to about 600 amino acids, about 190 amino acids to about 550 amino acids, about 190 amino acids to about 500 amino acids, about 190 amino acids to about 450 amino acids, about 190 amino acids to about 400 amino acids, about 190 amino acids to about 350 amino acids, about 190 amino acids to about 300 amino acids, about 190 amino acids to about 280 amino acids, about 190 amino acids to about 260 amino acids, about 190 amino acids to about 240 amino acids, about 190 amino acids to about 220 amino acids, about 190 amino acids to about 200 amino acids, about 190 amino acids to about 195 amino acids, about 195 amino acids to about 1000 amino acids, about 195 amino acids to about 950 amino acids, about 195 amino acids to about 900 amino acids, about 195 amino acids to about 850 amino acids, about 195 amino acids to about 800 amino acids, about 195 amino acids to about 750 amino acids, about 195 amino acids to about 700 amino acids, about 195 amino acids to about 650 amino acids, about 195 amino acids to about 600 amino acids, about 195 amino acids to about 550 amino acids, about 195 amino acids to about 500 amino acids, about 195 amino acids to about 450 amino acids, about 195 amino acids to about 400 amino acids, about 195 amino acids to about 350 amino acids, about 195 amino acids to about 300 amino acids, about 195 amino acids to about 280 amino acids, about 195 amino acids to about 260 amino acids, about 195 amino acids to about 240 amino acids, about 195 amino acids to about 220 amino acids, about 195 amino acids to about 200 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 450 amino acids, about 200 amino acids to about 400 amino acids, about 200 amino acids to about 350 amino acids, about 200 amino acids to about 300 amino acids, about 200 amino acids to about 280 amino acids, about 200 amino acids to about 260 amino acids, about 200 amino acids to about 240 amino acids, about 200 amino acids to about 220 amino acids, about 220 amino acids to about 1000 amino acids, about 220 amino acids to about 950 amino acids, about 220 amino acids to about 900 amino acids, about 220 amino acids to about 850 amino acids, about 220 amino acids to about 800 amino acids, about 220 amino acids to about 750 amino acids, about 220 amino acids to about 700 amino acids, about 220 amino acids to about 650 amino acids, about 220 amino acids to about 600 amino acids, about 220 amino acids to about 550 amino acids, about 220 amino acids to about 500 amino acids, about 220 amino acids to about 450 amino acids, about 220 amino acids to about 400 amino acids, about 220 amino acids to about 350 amino acids, about 220 amino acids to about 300 amino acids, about 220 amino acids to about 280 amino acids, about 220 amino acids to about 260 amino acids, about 220 amino acids to about 240 amino acids, about 240 amino acids to about 1000 amino acids, about 240 amino acids to about 950 amino acids, about 240 amino acids to about 900 amino acids, about 240 amino acids to about 850 amino acids, about 240 amino acids to about 800 amino acids, about 240 amino acids to about 750 amino acids, about 240 amino acids to about 700 amino acids, about 240 amino acids to about 650 amino acids, about 240 amino acids to about 600 amino acids, about 240 amino acids to about 550 amino acids, about 240 amino acids to about 500 amino acids, about 240 amino acids to about 450 amino acids, about 240 amino acids to about 400 amino acids, about 240 amino acids to about 350 amino acids, about 240 amino acids to about 300 amino acids, about 240 amino acids to about 280 amino acids, about 240 amino acids to about 260 amino acids, about 260 amino acids to about 1000 amino acids, about 260 amino acids to about 950 amino acids, about 260 amino acids to about 900 amino acids, about 260 amino acids to about 850 amino acids, about 260 amino acids to about 800 amino acids, about 260 amino acids to about 750 amino acids, about 260 amino acids to about 700 amino acids, about 260 amino acids to about 650 amino acids, about 260 amino acids to about 600 amino acids, about 260 amino acids to about 550 amino acids, about 260 amino acids to about 500 amino acids, about 260 amino acids to about 450 amino acids, about 260 amino acids to about 400 amino acids, about 260 amino acids to about 350 amino acids, about 260 amino acids to about 300 amino acids, about 260 amino acids to about 280 amino acids, about 280 amino acids to about 1000 amino acids, about 280 amino acids to about 950 amino acids, about 280 amino acids to about 900 amino acids, about 280 amino acids to about 850 amino acids, about 280 amino acids to about 800 amino acids, about 280 amino acids to about 750 amino acids, about 280 amino acids to about 700 amino acids, about 280 amino acids to about 650 amino acids, about 280 amino acids to about 600 amino acids, about 280 amino acids to about 550 amino acids, about 280 amino acids to about 500 amino acids, about 280 amino acids to about 450 amino acids, about 280 amino acids to about 400 amino acids, about 280 amino acids to about 350 amino acids, about 280 amino acids to about 300 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 450 amino acids, about 300 amino acids to about 400 amino acids, about 300 amino acids to about 350 amino acids, about 350 amino acids to about 1000 amino acids, about 350 amino acids to about 950 amino acids, about 350 amino acids to about 900 amino acids, about 350 amino acids to about 850 amino acids, about 350 amino acids to about 800 amino acids, about 350 amino acids to about 750 amino acids, about 350 amino acids to about 700 amino acids, about 350 amino acids to about 650 amino acids, about 350 amino acids to about 600 amino acids, about 350 amino acids to about 550 amino acids, about 350 amino acids to about 500 amino acids, about 350 amino acids to about 450 amino acids, about 350 amino acids to about 400 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 450 amino acids, about 450 amino acids to about 1000 amino acids, about 450 amino acids to about 950 amino acids, about 450 amino acids to about 900 amino acids, about 450 amino acids to about 850 amino acids, about 450 amino acids to about 800 amino acids, about 450 amino acids to about 750 amino acids, about 450 amino acids to about 700 amino acids, about 450 amino acids to about 650 amino acids, about 450 amino acids to about 600 amino acids, about 450 amino acids to about 550 amino acids, about 450 amino acids to about 500 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 1000 amino acids, about 850 amino acids to about 950 amino acids, about 850 amino acids to about 900 amino acids, about 900 amino acids to about 1000 amino acids, about 900 amino acids to about 950 amino acids, or about 950 amino acids to about 1000 amino acids.

Any of the target-binding domains described herein can bind to its target with a dissociation equilibrium constant ($K_D$) of less than $1\times10^{-7}$M, less than $1\times10^{-8}$ M, less than $1\times10^{-9}$M, less than $1\times10^{-10}$M, less than $1\times10^{-11}$ M, less than $1\times10^{-12}$ M, or less than $1\times10^{-13}$ M. In some embodiments, the antigen-binding protein construct provided herein can bind to an identifying antigen with a $K_D$ of about $1\times10^{-3}$ M to about $1\times10^{-5}$ M, about $1\times10^{-4}$ M to about $1\times10^{-6}$ M, about $1\times10^{-5}$ M to about $1\times10^{-7}$ M, about $1\times10^{-6}$ M to about $1\times10^{-8}$ M, about $1\times10^{-7}$ M to about $1\times10^{-9}$ M, about $1\times10^{-8}$ M to about $1\times10^{-10}$ M, or about $1\times10^{-9}$ M to about $1\times10^{-11}$ M (inclusive).

Any of the target-binding domains described herein can bind to its target with a $K_D$ of between about 1 pM to about 30 nM (e.g., about 1 pM to about 25 nM, about 1 pM to about 20 nM, about 1 pM to about 15 nM, about 1 pM to about 10 nM, about 1 pM to about 5 nM, about 1 pM to about 2 nM, about 1 pM to about 1 nM, about 1 pM to about 950 pM, about 1 pM to about 900 pM, about 1 pM to about 850 pM, about 1 pM to about 800 pM, about 1 pM to about 750 pM, about 1 pM to about 700 pM, about 1 pM to about 650 pM, about 1 pM to about 600 pM, about 1 pM to about 550 pM, about 1 pM to about 500 pM, about 1 pM to about 450 pM, about 1 pM to about 400 pM, about 1 pM to about 350 pM, about 1 pM to about 300 pM, about 1 pM to about 250 pM, about 1 pM to about 200 pM, about 1 pM to about 150 pM, about 1 pM to about 100 pM, about 1 pM to about 90 pM, about 1 pM to about 80 pM, about 1 pM to about 70 pM, about 1 pM to about 60 pM, about 1 pM to about 50 pM, about 1 pM to about 40 pM, about 1 pM to about 30 pM, about 1 pM to about 20 pM, about 1 pM to about 10 pM, about 1 pM to about 5 pM, about 1 pM to about 4 pM, about 1 pM to about 3 pM, about 1 pM to about 2 pM, about 2 pM to about 30 nM, about 2 pM to about 25 nM, about 2 pM to about 20 nM, about 2 pM to about 15 nM, about 2 pM to about 10 nM, about 2 pM to about 5 nM, about 2 pM to about 2 nM, about 2 pM to about 1 nM, about 2 pM to about 950 pM, about 2 pM to about 900 pM, about 2 pM to about 850 pM, about 2 pM to about 800 pM, about 2 pM to about 750 pM, about 2 pM to about 700 pM, about 2 pM to about 650 pM, about 2 pM to about 600 pM, about 2 pM to about 550 pM, about 2 pM to about 500 pM, about 2 pM to about 450 pM, about 2 pM to about 400 pM, about 2 pM to about 350 pM, about 2 pM to about 300 pM, about 2 pM to about 250 pM, about 2 pM to about 200 pM, about 2 pM to about 150 pM, about 2 pM to about 100 pM, about 2 pM to about 90 pM, about 2 pM to about 80 pM, about 2 pM to about 70 pM, about 2 pM to about 60 pM, about 2 pM to about 50 pM, about 2 pM to about 40 pM, about 2 pM to about 30 pM, about 2 pM to about 20 pM, about 2 pM to about 10 pM, about 2 pM to about 5 pM, about 2 pM to about 4 pM, about 2 pM to about 3 pM, about 5 pM to about 30 nM, about 5 pM to about 25 nM, about 5 pM to about 20 nM, about 5 pM to about 15 nM, about 5 pM to about 10 nM, about 5 pM to about 5 nM, about 5 pM to about 2 nM, about 5 pM to about 1 nM, about 5 pM to about 950 pM, about 5 pM to about 900 pM, about 5 pM to about 850 pM, about 5 pM to about 800 pM, about 5 pM to about 750 pM, about 5 pM to about 700 pM, about 5 pM to about 650 pM, about 5 pM to about 600 pM, about 5 pM to about 550 pM, about 5 pM to about 500 pM, about 5 pM to about 450 pM, about 5 pM to about 400 pM, about 5 pM to about 350 pM, about 5 pM to about 300 pM, about 5 pM to about 250 pM, about 5 pM to about 200 pM, about 5 pM to about 150 pM, about 5 pM to about 100 pM, about 5 pM to about 90 pM, about 5 pM to about 80 pM, about 5 pM to about 70 pM, about 5 pM to about 60 pM, about 5 pM to about 50 pM, about 5 pM to about 40 pM, about 5 pM to about 30 pM, about 5 pM to about 20 pM, about 5 pM to about 10 pM, about 10 pM to about 30 nM, about 10 pM to about 25 nM, about 10 pM to about 20 nM, about 10 pM to about 15 nM, about 10 pM to about 10 nM, about 10 pM to about 5 nM, about 10 pM to about 2 nM, about 10 pM to about 1 nM, about 10 pM to about 950 pM, about 10 pM to about 900 pM, about 10 pM to about 850 pM, about 10 pM to about 800 pM, about 10 pM to about 750 pM, about 10 pM to about 700 pM, about 10 pM to about 650 pM, about 10 pM to about 600 pM, about 10 pM to about 550 pM, about 10 pM to about 500 pM, about 10 pM to about 450 pM, about 10 pM to about 400 pM, about 10 pM to about 350 pM, about 10 pM to about 300 pM, about 10 pM to about 250 pM, about 10 pM to about 200 pM, about 10 pM to about 150 pM, about 10 pM to about 100 pM, about 10 pM to about 90 pM, about 10 pM to about 80 pM, about 10 pM to about 70 pM, about 10 pM to about 60 pM, about 10 pM to about 50 pM, about 10 pM to about 40 pM, about 10 pM to about 30 pM, about 10 pM to about 20 pM, about 15 pM to about 30 nM, about 15 pM to about 25 nM, about 15 pM to about 20 nM, about 15 pM to about 15 nM, about 15 pM to about 10 nM, about 15 pM to about 5 nM, about 15 pM to about 2 nM, about 15 pM to about 1 nM, about 15 pM to about 950 pM, about 15 pM to about 900 pM, about 15 pM to about 850 pM, about 15 pM to about 800 pM, about 15 pM to about 750 pM, about 15 pM to about 700 pM, about 15 pM to about 650 pM, about 15 pM to about 600 pM, about 15 pM to about 550 pM, about 15 pM to about 500 pM, about 15 pM to about 450 pM, about 15 pM to about 400 pM, about 15 pM to about 350 pM, about 15 pM to about 300 pM, about 15 pM to about 250 pM, about 15 pM to about 200 pM, about 15 pM to about 150 pM, about 15 pM to about 100 pM, about 15 pM to about 90 pM, about 15 pM to about 80 pM, about 15 pM to about 70 pM, about 15 pM to about 60 pM, about 15 pM to about 50 pM, about 15 pM to about 40 pM, about 15 pM to about 30 pM, about 15 pM to about 20 pM, about 20 pM to about 30 nM, about 20 pM to about 25 nM, about 20 pM to about 20 nM, about 20 pM to about 15 nM, about 20 pM to about 10 nM, about 20 pM to about 5 nM, about 20 pM to about 2 nM, about 20 pM to about 1 nM, about 20 pM to about 950 pM, about 20 pM to about 900 pM, about 20 pM to about 850 pM, about 20 pM to about 800 pM, about 20 pM to about 750 pM, about 20 pM to about 700 pM, about 20 pM to about 650 pM, about 20 pM to about 600 pM, about 20 pM to about 550 pM, about 20 pM to about 500 pM, about 20 pM to about 450 pM, about 20 pM to about 400 pM, about 20 pM to about 350 pM, about 20 pM to about 300 pM, about 20 pM to about 250 pM, about 20 pM to about 20 pM, about 200 pM to about 150 pM, about 20 pM to about 100 pM, about 20 pM to about 90 pM, about 20 pM to about 80 pM, about 20 pM to about 70 pM, about 20 pM to about 60 pM, about 20 pM to about 50 pM, about 20 pM to about 40 pM, about 20 pM to about 30 pM, about 30 pM to about 30 nM, about 30 pM to about 25 nM, about 30 pM to about 30 nM, about 30 pM to about 15 nM, about 30 pM to about 10 nM, about 30 pM to about 5 nM, about 30 pM to about 2 nM, about 30 pM to about 1 nM, about 30 pM to about 950 pM, about 30 pM to about 900 pM, about 30 pM to about 850 pM, about 30 pM to about 800 pM, about 30 pM to about 750 pM, about 30 pM to about 700 pM, about 30 pM to about 650 pM, about 30 pM to about 600 pM, about 30 pM to about 550 pM, about 30 pM to about 500 pM, about 30 pM to about 450 pM, about 30 pM to about 400 pM, about 30 pM to about 350 pM, about 30 pM to about 300 pM, about 30 pM to about 250 pM, about 30 pM to about 200 pM, about 30 pM to about 150 pM, about 30 pM to about 100 pM, about 30 pM to about 90 pM, about 30 pM to about 80 pM, about 30 pM to about 70 pM, about 30 pM to about 60 pM, about 30 pM to about 50 pM, about 30 pM to about 40 pM, about 40 pM to about 30 nM, about 40 pM to about 25 nM, about 40 pM to about 30 nM, about 40 pM to about 15 nM, about 40 pM to about 10 nM, about 40 pM to about 5 nM, about 40 pM to about 2 nM, about 40 pM to about 1 nM, about 40 pM to about 950 pM, about 40 pM to about 900 pM, about 40 pM to about 850 pM, about 40 pM to about 800 pM, about 40 pM to about 750 pM, about 40 pM to about 700 pM, about 40 pM to about 650 pM, about 40 pM to about 600 pM, about 40 pM to about 550 pM, about 40 pM to about 500 pM, about 40 pM to about 450 pM, about 40 pM to about 400 pM, about 40 pM to about 350 pM, about 40 pM to about 300 pM, about 40 pM to about 250 pM, about 40 pM to about 200 pM, about 40 pM to about 150 pM, about 40 pM to about 100 pM, about 40 pM to about 90 pM, about 40 pM to about 80 pM, about 40 pM to about 70 pM, about 40 pM to about 60 pM, about 40 pM to about 50 pM, about 50 pM to about 30 nM, about 50 pM to about 25 nM, about 50 pM to about 30 nM, about 50 pM to about 15 nM, about 50 pM to about 10 nM, about 50 pM to about 5 nM, about 50 pM to about 2 nM, about 50 pM to about 1 nM, about 50 pM to about 950 pM, about 50 pM to about 900 pM, about 50 pM to about 850 pM, about 50 pM to about 800 pM, about 50 pM to about 750 pM, about 50 pM to about 700 pM, about 50 pM to about 650 pM, about 50 pM to about 600 pM, about 50 pM to about 550 pM, about 50 pM to about 500 pM, about 50 pM to about 450 pM, about 50 pM to about 400 pM, about 50 pM to about 350 pM, about 50 pM to about 300 pM, about 50 pM to about 250 pM, about 50 pM to about 200 pM, about 50 pM to about 150 pM, about 50 pM to about 100 pM, about 50 pM to about 90 pM, about 50 pM to about 80 pM, about 50 pM to about 70 pM, about 50 pM to about 60 pM, about 60 pM to about 30 nM, about 60 pM to about 25 nM, about 60 pM to about 30 nM, about 60 pM to about 15 nM, about 60 pM to about 10 nM, about 60 pM to about 5 nM, about 60 pM to about 2 nM, about 60 pM to about 1 nM, about 60 pM to about 950 pM, about 60 pM to about 900 pM, about 60 pM to about 850 pM, about 60 pM to about 800 pM, about 60 pM to about 750 pM, about 60 pM to about 700 pM, about 60 pM to about 650 pM, about 60 pM to about 600 pM, about 60 pM to about 550 pM, about 60 pM to about 500 pM, about 60 pM to about 450 pM, about 60 pM to about 400 pM, about 60 pM to about 350 pM, about 60 pM to about 300 pM, about 60 pM to about 250 pM, about 60 pM to about 200 pM, about 60 pM to about 150 pM, about 60 pM to about 100 pM, about 60 pM to about 90 pM, about 60 pM to about 80 pM, about 60 pM to about 70 pM, about 70 pM to about 30 nM, about 70 pM to about 25 nM, about 70 pM to about 30 nM, about 70 pM to about 15 nM, about 70 pM to about 10 nM, about 70 pM to about 5 nM, about 70 pM to about 2 nM, about 70 pM to about 1 nM, about 70 pM to about 950 pM, about 70 pM to about 900 pM, about 70 pM to about 850 pM, about 70 pM to about 800 pM, about 70 pM to about 750 pM, about 70 pM to about 700 pM, about 70 pM to about 650 pM, about 70 pM to about 600 pM, about 70 pM to about 550 pM, about 70 pM to about 500 pM, about 70 pM to about 450 pM, about 70 pM to about 400 pM, about 70 pM to about 350 pM, about 70 pM to about 300 pM, about 70 pM to about 250 pM, about 70 pM to about 200 pM, about 70 pM to about 150 pM, about 70 pM to about 100 pM, about 70 pM to about 90 pM, about 70 pM to about 80 pM, about 80 pM to about 30 nM, about 80 pM to about 25 nM, about 80 pM to about 30 nM, about 80 pM to about 15 nM, about 80 pM to about 10 nM, about 80 pM to about 5 nM, about 80 pM to about 2 nM, about 80 pM to about 1 nM, about 80 pM to about 950 pM, about 80 pM to about 900 pM, about 80 pM to about 850 pM, about 80 pM to about 800 pM, about 80 pM to about 750 pM, about 80 pM to about 700 pM, about 80 pM to about 650 pM, about 80 pM to about 600 pM, about 80 pM to about 550 pM, about 80 pM to about 500 pM, about 80 pM to about 450 pM, about 80 pM to about 400 pM, about 80 pM to about 350 pM, about 80 pM to about 300 pM, about 80 pM to about 250 pM, about 80 pM to about 200 pM, about 80 pM to about 150 pM, about 80 pM to about 100 pM, about 80 pM to about 90 pM, about 90 pM to about 30 nM, about 90 pM to about 25 nM, about 90 pM to about 30 nM, about 90 pM to about 15 nM, about 90 pM to about 10 nM, about 90 pM to about 5 nM, about 90 pM to about 2 nM, about 90 pM to about 1 nM, about 90 pM to about 950 pM, about 90 pM to about 900 pM, about 90 pM to about 850 pM, about 90 pM to about 800 pM, about 90 pM to about 750 pM, about 90 pM to about 700 pM, about 90 pM to about 650 pM, about 90 pM to about 600 pM, about 90 pM to about 550 pM, about 90 pM to about 500 pM, about 90 pM to about 450 pM, about 90 pM to about 400 pM, about 90 pM to about 350 pM, about 90 pM to about 300 pM, about 90 pM to about 250 pM, about 90 pM to about 200 pM, about 90 pM to about 150 pM, about 90 pM to about 100 pM, about 100 pM to about 30 nM, about 100 pM to about 25 nM, about 100 pM to about 30 nM, about 100 pM to about 15 nM, about 100 pM to about 10 nM, about 100 pM to about 5 nM, about 100 pM to about 2 nM, about 100 pM to about 1 nM, about 100 pM to about 950 pM, about 100 pM to about 900 pM, about 100 pM to about 850 pM, about 100 pM to about 800 pM, about 100 pM to about 750 pM, about 100 pM to about 700 pM, about 100 pM to about 650 pM, about 100 pM to about 600 pM, about 100 pM to about 550 pM, about 100 pM to about 500 pM, about 100 pM to about 450 pM, about 100 pM to about 400 pM, about 100 pM to about 350 pM, about 100 pM to about 300 pM, about 100 pM to about 250 pM, about 100 pM to about 200 pM, about 100 pM to about 150 pM, about 150 pM to about 30 nM, about 150 pM to about 25 nM, about 150 pM to about 30 nM, about 150 pM to about 15 nM, about 150 pM to about 10 nM, about 150 pM to about 5 nM, about 150 pM to about 2 nM, about 150 pM to about 1 nM, about 150 pM to about 950 pM, about 150 pM to about 900 pM, about 150 pM to about 850 pM, about 150 pM to about 800 pM, about 150 pM to about 750 pM, about 150 pM to about 700 pM, about 150 pM to about 650 pM, about 150 pM to about 600 pM, about 150 pM to about 550 pM, about 150 pM to about 500 pM, about 150 pM to about 450 pM, about 150 pM to about 400 pM, about 150 pM to about 350 pM, about 150 pM to about 300 pM, about 150 pM to about 250 pM, about 150 pM to about 200 pM, about 200 pM to about 30 nM, about 200 pM to about 25 nM, about 200 pM to about 30 nM, about 200 pM to about 15 nM, about 200 pM to about 10 nM, about 200 pM to about 5 nM, about 200 pM to about 2 nM, about 200 pM to about 1 nM, about 200 pM to about 950 pM, about 200 pM to about 900 pM, about 200 pM to about 850 pM, about 200 pM to about 800 pM, about 200 pM to about 750 pM, about 200 pM to about 700 pM, about 200 pM to about 650 pM, about 200 pM to about 600 pM, about 200 pM to about 550 pM, about 200 pM to about 500 pM, about 200 pM to about 450 pM, about 200 pM to about 400 pM, about 200 pM to about 350 pM, about 200 pM to about 300 pM, about 200 pM to about 250 pM, about 300 pM to about 30 nM, about 300 pM to about 25 nM, about 300 pM to about 30 nM, about 300 pM to about 15 nM, about 300 pM to about 10 nM, about 300 pM to about 5 nM, about 300 pM to about 2 nM, about 300 pM to about 1 nM, about 300 pM to about 950 pM, about 300 pM to about 900 pM, about 300 pM to about 850 pM, about 300 pM to about 800 pM, about 300 pM to about 750 pM, about 300 pM to about 700 pM, about 300 pM to about 650 pM, about 300 pM to about 600 pM, about 300 pM to about 550 pM, about 300 pM to about 500 pM, about 300 pM to about 450 pM, about 300 pM to about 400 pM, about 300 pM to about 350 pM, about 400 pM to about 30 nM, about 400 pM to about 25 nM, about 400 pM to about 30 nM, about 400 pM to about 15 nM, about 400 pM to about 10 nM, about 400 pM to about 5 nM, about 400 pM to about 2 nM, about 400 pM to about 1 nM, about 400 pM to about 950 pM, about 400 pM to about 900 pM, about 400 pM to about 850 pM, about 400 pM to about 800 pM, about 400 pM to about 750 pM, about 400 pM to about 700 pM, about 400 pM to about 650 pM, about 400 pM to about 600 pM, about 400 pM to about 550 pM, about 400 pM to about 500 pM, about 500 pM to about 30 nM, about 500 pM to about 25 nM, about 500 pM to about 30 nM, about 500 pM to about 15 nM, about 500 pM to about 10 nM, about 500 pM to about 5 nM, about 500 pM to about 2 nM, about 500 pM to about 1 nM, about 500 pM to about 950 pM, about 500 pM to about 900 pM, about 500 pM to about 850 pM, about 500 pM to about 800 pM, about 500 pM to about 750 pM, about 500 pM to about 700 pM, about 500 pM to about 650 pM, about 500 pM to about 600 pM, about 500 pM to about 550 pM, about 600 pM to about 30 nM, about 600 pM to about 25 nM, about 600 pM to about 30 nM, about 600 pM to about 15 nM, about 600 pM to about 10 nM, about 600 pM to about 5 nM, about 600 pM to about 2 nM, about 600 pM to about 1 nM, about 600 pM to about 950 pM, about 600 pM to about 900 pM, about 600 pM to about 850 pM, about 600 pM to about 800 pM, about 600 pM to about 750 pM, about 600 pM to about 700 pM, about 600 pM to about 650 pM, about 700 pM to about 30 nM, about 700 pM to about 25 nM, about 700 pM to about 30 nM, about 700 pM to about 15 nM, about 700 pM to about 10 nM, about 700 pM to about 5 nM, about 700 pM to about 2 nM, about 700 pM to about 1 nM, about 700 pM to about 950 pM, about 700 pM to about 900 pM, about 700 pM to about 850 pM, about 700 pM to about 800 pM, about 700 pM to about 750 pM, about 800 pM to about 30 nM, about 800 pM to about 25 nM, about 800 pM to about 30 nM, about 800 pM to about 15 nM, about 800 pM to about 10 nM, about 800 pM to about 5 nM, about 800 pM to about 2 nM, about 800 pM to about 1 nM, about 800 pM to about 950 pM, about 800 pM to about 900 pM, about 800 pM to about 850 pM, about 900 pM to about 30 nM, about 900 pM to about 25 nM, about 900 pM to about 30 nM, about 900 pM to about 15 nM, about 900 pM to about 10 nM, about 900 pM to about 5 nM, about 900 pM to about 2 nM, about 900 pM to about 1 nM, about 900 pM to about 950 pM, about 1 nM to about 30 nM, about 1 nM to about 25 nM, about 1 nM to about 20 nM, about 1 nM to about 15 nM, about 1 nM to about 10 nM, about 1 nM to about 5 nM, about 2 nM to about 30 nM, about 2 nM to about 25 nM, about 2 nM to about 20 nM, about 2 nM to about 15 nM, about 2 nM to about 10 nM, about 2 nM to about 5 nM, about 4 nM to about 30 nM, about 4 nM to about 25 nM, about 4 nM to about 20 nM, about 4 nM to about 15 nM, about 4 nM to about 10 nM, about 4 nM to about 5 nM, about 5 nM to about 30 nM, about 5 nM to about 25 nM, about 5 nM to about 20 nM, about 5 nM to about 15 nM, about 5 nM to about 10 nM, about 10 nM to about 30 nM, about 10 nM to about 25 nM, about 10 nM to about 20 nM, about 10 nM to about 15 nM, about 15 nM to about 30 nM, about 15 nM to about 25 nM, about 15 nM to about 20 nM, about 20 nM to about 30 nM, and about 20 nM to about 25 nM).

Any of the target-binding domains described herein can bind to its target with a $K_D$ of between about 1 nM to about 10 nM (e.g., about 1 nM to about 9 nM, about 1 nM to about 8 nM, about 1 nM to about 7 nM, about 1 nM to about 6 nM, about 1 nM to about 5 nM, about 1 nM to about 4 nM, about 1 nM to about 3 nM, about 1 nM to about 2 nM, about 2 nM to about 10 nM, about 2 nM to about 9 nM, about 2 nM to about 8 nM, about 2 nM to about 7 nM, about 2 nM to about 6 nM, about 2 nM to about 5 nM, about 2 nM to about 4 nM, about 2 nM to about 3 nM, about 3 nM to about 10 nM, about 3 nM to about 9 nM, about 3 nM to about 8 nM, about 3 nM to about 7 nM, about 3 nM to about 6 nM, about 3 nM to about 5 nM, about 3 nM to about 4 nM, about 4 nM to about 10 nM, about 4 nM to about 9 nM, about 4 nM to about 8 nM, about 4 nM to about 7 nM, about 4 nM to about 6 nM, about 4 nM to about 5 nM, about 5 nM to about 10 nM, about 5 nM to about 9 nM, about 5 nM to about 8 nM, about 5 nM to about 7 nM, about 5 nM to about 6 nM, about 6 nM to about 10 nM, about 6 nM to about 9 nM, about 6 nM to about 8 nM, about 6 nM to about 7 nM, about 7 nM to about 10 nM, about 7 nM to about 9 nM, about 7 nM to about 8 nM, about 8 nM to about 10 nM, about 8 nM to about 9 nM, and about 9 nM to about 10 nM).

A variety of different methods known in the art can be used to determine the $K_D$ values of any of the antigen-binding protein constructs described herein (e.g., an electrophoretic mobility shift assay, a filter binding assay, surface plasmon resonance, and a biomolecular binding kinetics assay, etc.).

Antigen-Binding Domains

In some embodiments of any of the multi-chain chimeric polypeptides described herein, the first target-binding domain and the second target-binding domain bind specifically to the same antigen. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of any of the multi-chain chimeric polypeptides described herein, the first target-binding domain and the second target-binding domain bind specifically to different antigens.

In some embodiments of any of the multi-chain chimeric polypeptides described herein, one or both of the first target-binding domain and the second target-binding domain is an antigen-binding domain. In some embodiments of any of the multi-chain chimeric polypeptides described herein, the first target-binding domain and the second target-binding domain are each antigen-binding domains.

In some embodiments of any of the multi-chain chimeric polypeptides described herein, the antigen-binding domain includes or is a scFv or a single domain antibody (e.g., a VHH or a VNAR domain).

In some examples, an antigen-binding domain (e.g., any of the antigen-binding domains described herein) can bind specifically to any one of CD16a (see, e.g., those described in U.S. Pat. No. 9,035,026), CD28 (see, e.g., those described in U.S. Pat. No. 7,723,482), CD3 (see, e.g., those described in U.S. Pat. No. 9,226,962), CD33 (see, e.g., those described in U.S. Pat. No. 8,759,494), CD20 (see, e.g., those described in WO 2014/026054), CD19 (see, e.g., those described in U.S. Pat. No. 9,701,758), CD22 (see, e.g., those described in WO 2003/104425), CD123 (see, e.g., those described in WO 2014/130635), IL-1R (see, e.g., those described in U.S. Pat. No. 8,741,604), IL-1 (see, e.g., those described in WO 2014/095808), VEGF (see, e.g., those described in U.S. Pat. No. 9,090,684), IL-6R (see, e.g., those described in U.S. Pat. No. 7,482,436), IL-4 (see, e.g., those described in U.S. Patent Application Publication No. 2012/0171197), IL-10 (see, e.g., those described in U.S. Patent Application Publication No. 2016/0340413), PDL-1 (see, e.g., those described in Drees et al., *Protein Express. Purif* 94:60-66, 2014), TIGIT (see, e.g., those described in U.S. Patent Application Publication No. 2017/0198042), PD-1 (see, e.g., those described in U.S. Pat. No. 7,488,802), TIM3 (see, e.g., those described in U.S. Pat. No. 8,552,156), CTLA4 (see, e.g., those described in WO 2012/120125), MICA (see, e.g., those described in WO 2016/154585), MICB (see, e.g., those described in U.S. Pat. No. 8,753,640), IL-6 (see, e.g., those described in Gejima et al., *Human Antibodies* 11(4): 121-129, 2002), IL-8 (see, e.g., those described in U.S. Pat. No. 6,117,980), TNFα (see, e.g., those described in Geng et al., *Immunol. Res.* 62(3):377-385, 2015), CD26a (see, e.g., those described in WO 2017/189526), CD36 (see, e.g., those described in U.S. Patent Application Publication No. 2015/0259429), ULBP2 (see, e.g., those described in U.S. Pat. No. 9,273,136), CD30 (see, e.g., those described in Homach et al., *Scand. J. Immunol.* 48(5):497-501, 1998), CD200 (see, e.g., those described in U.S. Pat. No. 9,085,623), IGF-1R (see, e.g., those described in U.S. Patent Application Publication No. 2017/0051063), MUC4AC (see, e.g., those described in WO 2012/170470), MUC5AC (see, e.g., those described in U.S. Pat. No. 9,238,084), Trop-2 (see, e.g., those described in WO 2013/068946), CMET (see, e.g., those described in Edwardraja et al., Biotechnol. Bioeng. 106(3):367-375, 2010), EGFR (see, e.g., those described in Akbari et al., *Protein Expr. Purif* 127:8-15, 2016), HER1 (see, e.g., those described in U.S. Patent Application Publication No. 2013/0274446), HER2 (see, e.g., those described in Cao et al., *Biotechnol. Lett.* 37(7):1347-1354, 2015), HER3 (see, e.g., those described in U.S. Pat. No. 9,505,843), PSMA (see, e.g., those described in Parker et al., *Protein Expr. Purif* 89(2):136-145, 2013), CEA (see, e.g., those described in WO 1995/015341), B7H3 (see, e.g., those described in U.S. Pat. No. 9,371,395), EPCAM (see, e.g., those described in WO 2014/159531), BCMA (see, e.g., those described in Smith et al., *Mol. Ther.* 26(6):1447-1456, 2018), P-cadherin (see, e.g., those described in U.S. Pat. No. 7,452,537), CEACAM5 (see, e.g., those described in U.S. Pat. No. 9,617,345), a UL16-binding protein (see, e.g., those described in WO 2017/083612), HLA-DR (see, e.g., Pistillo et al., *Exp. Clin. Immunogenet.* 14(2):123-130, 1997), DLL4 (see, e.g., those described in WO 2014/007513), TYRO3 (see, e.g., those described in WO 2016/166348), AXL (see, e.g., those described in WO 2012/175692), MER (see, e.g., those described in WO 2016/106221), CD122 (see, e.g., those described in U.S. Patent Application Publication No. 2016/0367664), CD155 (see, e.g., those described in WO 2017/149538), or PDGF-DD (see, e.g., those described in U.S. Pat. No. 9,441,034).

The antigen-binding domains present in any of the multi-chain chimeric polypeptides described herein are each independently selected from the group consisting of: a VHH domain, a VNAR domain, and a scFv. In some embodiments, any of the antigen-binding domains described herein is a BiTe, a $(scFv)_2$, a nanobody, a nanobody-HSA, a DART, a TandAb, a scDiabody, a scDiabody-CH3, scFv-CH-CL-scFv, a HSAbody, scDiabody-HAS, or a tandem-scFv. Additional examples of antigen-binding domains that can be used in any of the multi-chain chimeric polypeptide are known in the art.

A VHH domain is a single monomeric variable antibody domain that can be found in camelids. A VNAR domain is a single monomeric variable antibody domain that can be found in cartilaginous fish. Non-limiting aspects of VHH domains and VNAR domains are described in, e.g., Cromie et al., *Curr. Top. Med. Chem.* 15:2543-2557, 2016; De Genst et al., *Dev. Comp. Immunol.* 30:187-198, 2006; De Meyer et al., *Trends Biotechnol.* 32:263-270, 2014; Kijanka et al., *Nanomedicine* 10:161-174, 2015; Kovaleva et al., *Expert. Opin. Biol. Ther.* 14:1527-1539, 2014; Krah et al., *Immunopharmacol. Immunotoxicol.* 38:21-28, 2016; Mujic-Delic et al., *Trends Pharmacol. Sci.* 35:247-255, 2014; Muyldermans, *J. Biotechnol.* 74:277-302, 2001; Muyldermans et al., *Trends Biochem. Sci.* 26:230-235, 2001; Muyldermans, *Ann. Rev. Biochem.* 82:775-797, 2013; Rahbarizadeh et al., *Immunol. Invest.* 40:299-338, 2011; Van Audenhove et al., *EBioMedicine* 8:40-48, 2016; Van Bockstaele et al., *Curr. Opin. Investig. Drugs* 10:1212-1224, 2009; Vincke et al., *Methods Mol. Biol.* 911:15-26, 2012; and Wesolowski et al., *Med. Microbiol. Immunol.* 198:157-174, 2009.

In some embodiments, each of the antigen-binding domains in the multi-chain chimeric polypeptides described herein are both VHH domains, or at least one antigen-binding domain is a VHH domain. In some embodiments, each of the antigen-binding domains in the multi-chain chimeric polypeptides described herein are both VNAR domains, or at least one antigen-binding domain is a VNAR domain. In some embodiments, each of the antigen-binding domains in the multi-chain chimeric polypeptides described herein are both scFv domains, or at least one antigen-binding domain is a scFv domain.

In some embodiments, two or more of polypeptides present in the multi-chain chimeric polypeptide can assemble (e.g., non-covalently assemble) to form any of the antigen-binding domains described herein, e.g., an antigen-binding fragment of an antibody (e.g., any of the antigen-binding fragments of an antibody described herein), a VHH-scAb, a VHH-Fab, a Dual scFab, a F(ab')2, a diabody, a crossMab, a DAF (two-in-one), a DAF (four-in-one), a DutaMab, a DT-IgG, a knobs-in-holes common light chain, a knobs-in-holes assembly, a charge pair, a Fab-arm exchange, a SEEDbody, a LUZ-Y, a Fcab, a KX-body, an orthogonal Fab, a DVD-IgG, a IgG(H)-scFv, a scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig, Zybody, DVI-IgG, Diabody-CH3, a triple body, a miniantibody, a minibody, a TriBi minibody, scFv-CH3 KIH, Fab-scFv, a F(ab')2-scFv2, a scFv-KIH, a Fab-scFv-Fc, a tetravalent HCAb, a scDiabody-Fc, a Diabody-Fc, a tandem scFv-Fc, an Intrabody, a dock and lock, a lmmTAC, an IgG-IgG conjugate, a Cov-X-Body, and a scFv1-PEG-scFv2. See, e.g., Spiess et al., *Mol. Immunol.* 67:95-106, 2015, incorporated in its entirety herewith, for a description of these elements. Non-limiting examples of an antigen-binding fragment of an antibody include an Fv fragment, a Fab fragment, a F(ab')2 fragment, and a Fab' fragment. Additional examples of an antigen-binding fragment of an antibody is an antigen-binding fragment of an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); or an antigen-binding fragment of an IgM (e.g., an antigen-binding fragment of a human or humanized IgM).

An "Fv" fragment includes a non-covalently-linked dimer of one heavy chain variable domain and one light chain variable domain.

A "Fab" fragment includes, the constant domain of the light chain and the first constant domain (CHI) of the heavy chain, in addition to the heavy and light chain variable domains of the Fv fragment.

A "F(ab')2" fragment includes two Fab fragments joined, near the hinge region, by disulfide bonds.

A "dual variable domain immunoglobulin" or "DVD-Ig" refers to multivalent and multispecific binding proteins as described, e.g., in DiGiammarino et al., *Methods Mol. Biol.* 899:145-156, 2012; Jakob et al., *MABs* 5:358-363, 2013; and U.S. Pat. Nos. 7,612,181; 8,258,268; 8,586,714; 8,716,450; 8,722,855; 8,735,546; and 8,822,645, each of which is incorporated by reference in its entirety.

DARTs are described in, e.g., Garber, Nature Reviews Drug Discovery 13:799-801, 2014.

In some embodiments of any of the antigen-binding domains described herein can bind to an antigen selected from the group consisting of: a protein, a carbohydrate, a lipid, and a combination thereof.

Additional examples and aspects of antigen-binding domains are known in the art.

Soluble Interleukin or Cytokine Protein

In some embodiments of any of the multi-chain chimeric polypeptides described herein, one or both of the first target-binding domain and the second target-binding domain can be a soluble interleukin protein or soluble cytokine protein. In some embodiments, the soluble interleukin or soluble cytokine protein is selected from the group of: IL-2, IL-3, IL-7, IL-8, IL-10, IL-12, IL-15, IL-17, IL-18, IL-21, PDGF-DD, SCF, and FLT3L. Non-limiting examples of soluble IL-2, IL-3, IL-7, IL-8, IL-10, IL-15, IL-17, IL-18, IL-21, PDGF-DD, SCF, and FLT3L are provided below.

```
Human Soluble IL-2
                                    (SEQ ID NO: 9)
aptsssstkkt qlqlehllld lqmilnginn yknpkltrml

tfkfympkka telkhlqcle eelkpleevl nlaqsknfhl

rprdlisnin vivlelkgse ttfmceyade tativeflnr

witfcqsiis tlt

Human Soluble IL-3
                                   (SEQ ID NO: 10)
apmtqttplkt swvncsnmid eiithlkqpp lplldfnnln

gedqdilmen nlrrpnleaf nravkslqna saiesilknl

ipclplataa ptrhpihikd gdwnefrrkl tfylktlena

qaqqttlsla if

Human Soluble IL-7
                                   (SEQ ID NO: 11)
dcdiegkdgkqyesv Imvsidqlld smkeigsncl nnefnffkrh

icdankegmf lfraarklrq flkmnstgdf dlhllkvseg
```

-continued ttillnctgq vkgrkpaalg eaqptkslee nkslkeqkkl ndlcflkrll qeiktcwnki lmgtkeh Human Soluble IL-8

(SEQ ID NO: 12)

egavlprsak elrcqcikty skpfhpkfik elrviesgph canteiivkl sdgrelcldp kenwvqrvve kflkraens Human Soluble IL-10

(SEQ ID NO: 13)

spgqgtqsensc thfpgnlpnm lrdlrdafsr vktffqmkdq ldnlllkesl ledfkgylgc qalsemiqfy leevmpqaen qdpdikahvn slgenlktlr l/rlrrchrfl pcenkskave qvknafnklq ekgiykamse fdifinyiea ymtmkirn Human Soluble IL-15

(SEQ ID NO: 14)

Nwvnvisdlkki edliqsmhid atlytesdvh psckvtamkc fllelqvisl esgdasihdt venliilann slssngnvte sgckeceele eknikeflqs fvhivqmfin ts Human Soluble IL-17

(SEQ ID NO: 15)

gitiprn pgcpnsedkn fprtvmvnln ihnrntntnp krssdyynrs tspwnlhrne dperypsviw eakcrhlgci nadgnvdyhm nsvpiqqeil vlrrepphcp nsfrlekilv svgctcvtpi vhhva Human Soluble IL-18

(SEQ ID NO: 16)

yfgklesklsvirn indqvlfidq gnrplfedmt dsdcrdnapr tifiismykd sqprgmavti svkcekistl scenkiisfk emnppdnikd tksdiiffqr svpghdnkmq fesssyegyf lacekerdif klilkkedel gdrsimftvq ned Human Soluble PDGF-DD (SEQ ID NO: 17)

rdtsatpqsasi kalrnanlrr desnhltdly rrdetiqvkg ngyvqsprfp nsyprnlllt wrihsqentr iqlvfdnqfg leeaendicr ydfvevedis etstiirgrw cghkevppri ksrtnqikit fksddyfvak pgfkiyysll edfqpaaase tnwesvtssi sgvsynspsv tdptliadal dkkiaefdtv edllkyfnpe swqedlenmy ldtpryrgrs yhdrkskvdl drlnddakry sctprnysvn ireelklanv vffprcllvq rcggncgcgt vnwrsctcns gktvkkyhev lqfepghikr rgraktmalv diqldhherc dcicssrppr Human Soluble SCF (SEQ ID NO: 18)

egicrnrvtnnvkdv tklvanlpkd ymitlkyvpg mdvlpshcwi semvvqlsds ltdlldkfsn iseglsnysi idklvnivdd lvecvkenss kdlkksfksp eprlftpeef frifnrsida fkdfvvaset sdcvvsstls pekdsrvsvt kpfmlppvaa sslrndssss nrkaknppgd sslhwaamal palfsliigf afgalywkkr qpsltraven iqineednei smlqekeref qev -continued Human Soluble FLT3L (SEQ ID NO: 19)

tqdcsfqhspissd favkirelsd yllqdypvtv asnlqdeelc gglwrlvlaq rwmerlktva gskmqgller vnteihfvtk cafqpppscl rfvqtnisrl lqetseqlva lkpwitrqnf srclelqcqp dsstlpppws prpleatapt apqppllll llpvgllla aawclhwqrt rrrtprpgeq vppvpspqdl llveh Non-limiting examples of soluble MICA, MICB, ULBP1, ULBP2, ULBP3, ULBP4, ULBP5, and ULBP6 are provided below.

Human Soluble MICA (SEQ ID NO: 20)

ephslry nltvlswdgs vqsgfltevh ldgqpflrcd rqkcrakpqg qwaedvlgnk twdretrdlt gngkdlrmtl ahikdqkegl hslqeirvce ihednstrss qhfyydgelf lsqnletkew tmpqssraqt lamnvrnflk edamktkthy hamhadclqe lrrylksgvv lrrtvppmvn vtrseasegn itvtcrasgf ypwnitlswr qdgvslshdt qqwgdvlpdg ngtyqtwvat ricqgeeqrf tcymehsgnh sthpvpsgkv lvlqshwqtf hvsavaaaai fviiifyvre ckkktsaaeg pelvslqvld qhpvgtsdhr datqlgfqpl msdlgstgst ega Human Soluble MICB (SEQ ID NO: 21)

aephslry nlmvlsqdes vqsgflaegh ldgqpflryd rqkrrakpqg qwaedvlgak twdtetedlt engqdlrrtl thikdqkggl hslqeirvce ihedsstrgs rhfyydgelf lsqnletqes tvpqssraqt lamnvtnfwk edamktkthy ramqadclqk lqrylksgva irrtvppmvn vtcsevsegn itvtcrassf yprnitltwr qdgvslshnt qqwgdvlpdg ngtyqtwvat rirqgeeqrf tcymehsgnh gthpvpsgkv lvlqsqrtdf pyvsaampcf viiiilcvpc ckkktsaaeg pelvslqvld qhpvgtgdhr daaqlgfqpl msatgstgst ega Human Soluble ULBP1

(SEQ ID NO: 22)

wvdthclcydfiit pksrpepqwc evqglvderp flhydcvnhk akafaslgkk vnvtktweeq tetlrdvvdf lkgqlldiqv enlipieplt lqarmscehe ahghgrgswq flfngqkfll fdsnnrkwta lhpgakkmte kweknrdvtm ffqkislgdc kmwleeflmy weqmldptkp pslapg -continued

```
Human Soluble ULBP2
                                       (SEQ ID NO: 23)
gradphslcyditvi pkfrpgprwc avqgqvdekt

flhydcgnkt vtpvsplgkk lnvttawkaq npvlrevvdi

lteqlrdiql enytpkeplt lqarmsceqk aeghssgswq

fsfdgqifll fdsekrmwtt vhpgarkmke kwendkvvam

sfhyfsmgdc igwledflmg mdstlepsag aplams

Human Soluble ULBP3
                                       (SEQ ID NO: 24)
dahslwynfti ihlprhgqqw cevqsqvdqk nflsydcgsd

kvlsmghlee qlyatdawgk qlemlrevgq rlrleladte

ledftpsgpl tlqvrmscec eadgyirgsw qfsfdgrkfl

lfdsnnrkwt vvhagarrmk ekwekdsglt tffkmvsmrd

ckswlrdflm hrkkrlepta pptmapg

Human Soluble ULBP4
                                       (SEQ ID NO: 25)
hslcfnftik slsrpgqpwc eaqvflnknl flqynsdnnm

vkplgllgkk vyatstwgel tqtlgevgrd lrmllcdikp

qiktsdpstl qvemfcqrea erctgaswqf atngeksllf

damnmtwtvi nheaskiket wkkdrgleky frklskgdcd

hwlreflghw eampeptvsp vnasdihwss sslpdrwiil

gafillvlmg ivlicvwwqn gewqaglwpl rts

Human Soluble ULBP5
                                       (SEQ ID NO: 26)
gladp hslcyditvi pkfrpgprwc avqgqvdekt

flhydcgskt vtpvsplgkk lnvttawkaq npvlrevvdi

lteqlldiql enyipkeplt lqarmsceqk aeghgsgswq

lsfdgqifll fdsenrmwtt vhpgarkmke kwendkdmtm

sfhyismgdc tgwledflmg mdstlepsag apptmssg

Human Soluble ULBP6
                                       (SEQ ID NO: 27)
rrddp hslcyditvi pkfrpgprwc avqgqvdekt

flhydcgnkt vtpvsplgkk lnvtmawkaq npvlrevvdi

lteqlldiql enytpkeplt lqarmsceqk aeghssgswq

fsidgqtfll fdsekrmwtt vhpgarkmke kwendkdvam

sfhyismgdc igwledflmg mdstlepsag aplamssg
```

Additional examples of soluble interleukin proteins and soluble cytokine proteins are known in the art.

Soluble Receptor

In some embodiments of any of the multi-chain chimeric polypeptides described herein, one or both of the first target-binding domain and the second target-binding domain is a soluble interleukin receptor, a soluble cytokine receptor or a ligand receptor. In some embodiments, the soluble receptor is a soluble TGF-β receptor II (TGF-β RII) (see, e.g., those described in Yung et al., *Am. J. Resp. Crit. Care Med.* 194(9):1140-1151, 2016), a soluble TGF-βRIII (see, e.g., those described in Heng et al., *Placenta* 57:320, 2017), a soluble NKG2D (see, e.g., Cosman et al., *Immunity* 14(2):123-133, 2001; Costa et al., *Front. Immunol., Vol.* 9, Article 1150, May 29, 2018; doi: 10.3389/fimmu.2018.01150), a soluble NKp30 (see, e.g., Costa et al., *Front. Immunol., Vol.* 9, Article 1150, May 29, 2018; doi: 10.3389/fimmu.2018.01150), a soluble NKp44 (see, e.g., those described in Costa et al., *Front. Immunol., Vol.* 9, Article 1150, May 29, 2018; doi: 10.3389/fimmu.2018.01150), a soluble NKp46 (see, e.g., Mandelboim et al., *Nature* 409:1055-1060, 2001; Costa et al., *Front. Immunol., Vol.* 9, Article 1150, May 29, 2018; doi: 10.3389/fimmu.2018.01150), a soluble DNAM-1 (see, e.g., those described in Costa et al., *Front. Immunol., Vol.* 9, Article 1150, May 29, 2018; doi: 10.3389/fimmu.2018.01150), a scMHCI (see, e.g., those described in Washburn et al., *PLoS One* 6(3):e18439, 2011), a scMHCII (see, e.g., those described in Bishwajit et al., *Cellular Immunol.* 170(1):25-33, 1996), a scTCR (see, e.g., those described in Weber et al., *Nature* 356(6372):793-796, 1992), a soluble CD155 (see, e.g., those described in Tahara-Hanaoka et al., *Int. Immunol.* 16(4):533-538, 2004), or a soluble CD28 (see, e.g., Hebbar et al., *Clin. Exp. Immunol.* 136:388-392, 2004).

Additional examples of soluble interleukin receptors and soluble cytokine receptors are known in the art.

Additional Antigen-Binding Domains

In some embodiments of any of the multi-chain chimeric polypeptides, the first chimeric polypeptide further includes one or more (e.g., two, three, four, five, six, seven, eight, nine, or ten) additional target-binding domain(s) (e.g., any of the exemplary target-binding domains described herein or known in the art), where at least one of the one or more additional antigen-binding domain(s) is positioned between the soluble tissue factor domain (e.g., any of the exemplary soluble tissue factor domains described herein or known in the art) and the first domain of the pair of affinity domains (e.g., any of the exemplary first domains of any of the exemplary pairs of affinity domains described herein). In some embodiments, the first chimeric polypeptide can further include a linker sequence (e.g., any of the exemplary linker sequences described herein or known in the art) between the soluble tissue factor domain (e.g., any of the exemplary soluble tissue factor domains described herein) and the at least one of the one or more additional target-binding domain(s) (e.g., any of the exemplary target-binding domains described herein or known in the art), and/or a linker sequence (e.g., any of the exemplary linker sequences described herein or known in the art) between the at least one of the one or more additional target-binding domain(s) (e.g., any of the exemplary target-binding domains described herein or known in the art) and the first domain of the pair of affinity domains (e.g., any of the exemplary first domains described herein of any of the exemplary pairs of affinity domains described herein).

In some embodiments of any of the multi-chain chimeric polypeptides described herein, the first chimeric polypeptide further includes one or more (e.g., two, three, four, five, six, seven, eight, nine, or ten) additional target-binding domains at the N-terminal and/or C-terminal end of the first chimeric polypeptide. In some embodiments, at least one of the one or more additional target-binding domains (e.g., any of the exemplary target-binding domains described herein or known in the art) directly abuts the first domain of the pair of affinity domains (e.g., any of the exemplary first domains described herein of any of the exemplary pairs of affinity domains described herein) in the first chimeric polypeptide. In some embodiments, the first chimeric polypeptide further includes a linker sequence (e.g., any of the exemplary linker sequences described herein or known in the art) between the at least one of the one or more additional target-binding domains (e.g., any of the exemplary target-binding domains described herein or known in the art) and the first domain of the pair of affinity domains (e.g., any of the exemplary first domains described herein of any of the exemplary pairs of affinity domains described herein). In some embodiments, the at least one of the one or more additional target-binding domains (e.g., any of the exemplary target-binding domains described herein or known in the art) directly abuts the first target-binding domain (e.g., any of the exemplary target-binding domains described herein or known in the art) in the first chimeric polypeptide. In some embodiments, the first chimeric polypeptide further comprises a linker sequence (e.g., any of the exemplary linker sequences described herein or known in the art) between the at least one of the one or more additional target-binding domains (e.g., any of the exemplary target-binding domains described herein or known in the art) and the first target-binding domain (e.g., any of the exemplary target-binding domains described herein or known in the art).

In some embodiments of any of the multi-chain chimeric polypeptides described herein, at least one of the one or more additional target-binding domains (e.g., any of the exemplary target-binding domains described herein or known in the art) is disposed at the N- and/or C-terminus of the first chimeric polypeptide, and at least one of the one or more additional target-binding domains (e.g., any of the exemplary target-binding domains described herein or known in the art) is positioned between the soluble tissue factor domain (e.g., any of the exemplary soluble tissue factor domains described herein or known in the art) and the first domain of the pair of affinity domains (e.g., any of the exemplary first domains of any of the exemplary pairs of affinity domains described herein) in the first chimeric polypeptide. In some embodiments, the at least one additional target-binding domain (e.g., any of the exemplary target-binding domains described herein or known in the art) of the one or more additional target-binding domains disposed at the N-terminus directly abuts the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the first chimeric polypeptide further comprises a linker sequence (e.g., any of the linker sequences described herein or known in the art) disposed between the at least one additional target-binding domain (e.g., any of the exemplary target-binding domains described herein or known in the art) and the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the at least one additional target-binding domain (e.g., any of the exemplary target-binding domains described herein or known in the art) of the one or more additional target-binding domains disposed at the C-terminus directly abuts the first target-binding domain (e.g., any of the exemplary target-binding domains described herein or known in the art) or the first domain of the pair of affinity domains (e.g., any of the exemplary first domains of any of the exemplary pairs of affinity domains described herein) in the first chimeric polypeptide. In some embodiments, the first chimeric polypeptide further includes a linker sequence (e.g., any of the exemplary linker sequences described herein or known in the art) disposed between the at least one additional target-binding domain (e.g., any of the exemplary target-binding domains described herein or known in the art) and the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the at least one of the one or more additional target-binding domains (e.g., any of the exemplary target-binding domains described herein or known in the art) positioned between the soluble tissue factor domain (e.g., any of the exemplary soluble tissue factor domains described herein) and the first domain of the pair of affinity domains (e.g., any of the first domains described herein or any of the exemplary pairs of affinity domains described herein), directly abuts the soluble tissue factor domain and/or the first domain of the pair of affinity domains. In some embodiments, the first chimeric polypeptide further comprises a linker sequence (e.g., any of the exemplary linker sequences described herein or known in the art) disposed (i) between the soluble tissue factor domain (e.g., any of the exemplary soluble tissue factor domains described herein) and the at least one of the one or more additional target-binding domains (e.g., any of the exemplary target-binding domains described herein or known in the art) positioned between the soluble tissue factor domain (e.g., any of the exemplary soluble tissue factor domains described herein) and the first domain of the pair of affinity domains (e.g., any of the exemplary first domains of any of the exemplary pairs of affinity domains described herein), and/or (ii) between the first domain of the pair of affinity domains and the at least one of the one or more additional target-binding domains positioned between the soluble tissue factor domain and the first domain of the pair of affinity domains.

In some embodiments of any of the multi-chain chimeric polypeptides described herein, the second chimeric polypeptide further includes one or more (e.g., two, three, four, five, six, seven, eight, nine, or ten) additional target-binding domains (e.g., any of the exemplary target-binding domains described herein or known in the art) at the N-terminal end and/or the C-terminal end of the second chimeric polypeptide. In some embodiments, at least one of the one or more additional target-binding domains (e.g., any of the exemplary target-binding domains described herein or known in the art) directly abuts the second domain of the pair of affinity domains (e.g., any of the exemplary second domains of any of the exemplary pairs of affinity domains described herein) in the second chimeric polypeptide. In some embodiments, the second chimeric polypeptide further includes a linker sequence (e.g., any of the exemplary linker sequences described herein or known in the art) between at least one of the one or more additional target-binding domains (e.g., any of the exemplary target-binding domains described herein or known in the art) and the second domain of the pair of affinity domains (e.g., any of the second domains described herein of any of the exemplary pairs of affinity domains described herein) in the second chimeric polypeptide. In some embodiments, at least one of the one or more additional target-binding domains (e.g., any of the exemplary target-binding domains described herein or known in the art) directly abuts the second target-binding domain (e.g., any of the target-binding domains described herein or known in the art) in the second chimeric polypeptide. In some embodiments, the second chimeric polypeptide further includes a linker sequence (e.g., any of the exemplary linker sequences described herein or known in the art) between at least one of the one or more additional target-binding domains (e.g., any of the exemplary target binding domains described herein or known in the art) and the second target-binding domain (e.g., any of the exemplary target binding domains described herein or known in the art) in the second chimeric polypeptide.

In some embodiments of any of the multi-chain chimeric polypeptides described herein, two or more (e.g., three or more, four or more, five or more, six or more, seven or more, eight or more, nine or more, or ten or more) of the first target-binding domain, the second target-binding domain, and the one or more additional target-binding domains bind specifically to the same antigen. In some embodiments, two or more (e.g., three or more, four or more, five or more, six or more, seven or more, eight or more, nine or more, or ten or more) of the first target-binding domain, the second target-binding domain, and the one or more additional target-binding domains bind specifically to the same epitope. In some embodiments, two or more (e.g., three or more, four or more, five or more, six or more, seven or more, eight or more, nine or more, or ten or more) of the first target-binding domain, the second target-binding domain, and the one or more additional target-binding domains include the same amino acid sequence. In some embodiments, the first target-binding domain, the second target-binding domain, and the one or more additional target-binding domains each bind specifically to the same antigen. In some embodiments, the first target-binding domain, the second target-binding domain, and the one or more additional target-binding domains each bind specifically to the same epitope. In some embodiments, the first target-binding domain, the second target-binding domain, and the one or more additional target-binding domains each include the same amino acid sequence.

In some embodiments of any of the multi-chain chimeric polypeptides described herein, the first target-binding domain, the second target-binding domain, and the one or more additional target-binding domains bind specifically to different antigens. In some embodiments of any of the multi-chain chimeric polypeptides described herein, one or more (e.g., two or more, three or more, four or more, five or more, six or more, seven or more, eight or more, nine or more, or ten or more) of the first target-binding domain, the second target-binding domain, and the one or more target-binding domains is an antigen-binding domain. In some embodiments, the first target-binding domain, the second target-binding domain, and the one or more additional target-binding domains are each an antigen-binding domain (e.g., a scFv or a single-domain antibody).

Pairs of Affinity Domains

In some embodiments, a multi-chain chimeric polypeptide includes: 1) a first chimeric polypeptide that includes a first domain of a pair of affinity domains, and 2) a second chimeric polypeptide that includes a second domain of a pair of affinity domains such that the first chimeric polypeptide and the second chimeric polypeptide associate through the binding of the first domain and the second domain of the pair of affinity domains. In some embodiments, the pair of affinity domains is a sushi domain from an alpha chain of human IL-15 receptor (IL15Rα) and a soluble IL-15. A sushi domain, also known as a short consensus repeat or type 1 glycoprotein motif, is a common motif in protein-protein interaction. Sushi domains have been identified on a number of protein-binding molecules, including complement components C1r, C1s, factor H, and C2m, as well as the nonimmunologic molecules factor XIII and β2-glycoprotein. A typical Sushi domain has approximately 60 amino acid residues and contains four cysteines (Ranganathan, Pac. Symp Biocomput. 2000:155-67). The first cysteine can form a disulfide bond with the third cysteine, and the second cysteine can form a disulfide bridge with the fourth cysteine. In some embodiments in which one member of the pair of affinity domains is a soluble IL-15, the soluble IL15 has a D8N or D8A amino acid substitution. In some embodiments in which one member of the pair of affinity domains is an alpha chain of human IL-15 receptor (IL15Rα), the human IL15Rα is a mature full-length IL15Rα. In some embodiments, the pair of affinity domains is barnase and barnstar. In some embodiments, the pair of affinity domains is a PKA and an AKAP. In some embodiments, the pair of affinity domains is an adapter/docking tag module based on mutated RNase I fragments (Rossi, *Proc Natl Acad Sci USA.* 103: 6841-6846, 2006; Sharkey et al., *Cancer Res.* 68:5282-5290, 2008; Rossi et al., *Trends Pharmacol Sci.* 33:474-481, 2012) or SNARE modules based on interactions of the proteins syntaxin, synaptotagmin, synaptobrevin, and SNAP25 (Deyev et al., *Nat Biotechnol.* 1486-1492, 2003).

In some embodiments, a first chimeric polypeptide of a multi-chain chimeric polypeptide includes a first domain of a pair of affinity domains and a second chimeric polypeptide of the multi-chain chimeric polypeptide includes a second domain of a pair of affinity domains, wherein the first domain of the pair of affinity domains and the second domain of the pair of affinity domains bind to each other with a dissociation equilibrium constant ($K_D$) of less than $1\times10^{-7}$ M, less than $1\times10^{-8}$ M, less than $1\times10^{-9}$ M, less than $1\times10^{-10}$ M, less than $1\times10^{-11}$ M, less than $1\times10^{-12}$ M, or less than $1\times10^{-13}$ M. In some embodiments, the first domain of the pair of affinity domains and the second domain of the pair of affinity domains bind to each other with a $K_D$ of about $1\times10^{-4}$ M to about $1\times10^{-6}$ M, about $1\times10^{-5}$ M to about $1\times10^{-7}$ M, about $1\times10^{-6}$ M to about $1\times10^{-8}$ M, about $1\times10^{-7}$ M to about $1\times10^{-9}$ M, about $1\times10^{-8}$ M to about $1\times10^{-10}$ M, about $1\times10^{-9}$ M to about $1\times10^{-11}$ M, about $1\times10^{-10}$ M to about $1\times10^{-12}$ M, about $1\times10^{-11}$ M to about $1\times10^{-13}$ M, about $1\times10^{-4}$ M to about $1\times10^{-5}$ M, about $1\times10^{-5}$ M to about $1\times10^{-6}$ M, about $1\times10^{-6}$ M to about $1\times10^{-7}$ M, about $1\times10^{-7}$ M to about $1\times10^{-8}$ M, about $1\times10^{-8}$ M to about $1\times10^{-9}$ M, about $1\times10^{-9}$ M to about $1\times10^{-10}$ M, about $1\times10^{-10}$ M to about $1\times10^{-11}$ M, about $1\times10^{-11}$ M to about $1\times10^{-12}$ M, or about $1\times10^{-12}$ M to about $1\times10^{-13}$ M (inclusive). Any of a variety of different methods known in the art can be used to determine the $K_D$ value of the binding of the first domain of the pair of affinity domains and the second domain of the pair of affinity domains (e.g., an electrophoretic mobility shift assay, a filter binding assay, surface plasmon resonance, and a biomolecular binding kinetics assay, etc.).

In some embodiments, a first chimeric polypeptide of a multi-chain chimeric polypeptide includes a first domain of a pair of affinity domains and a second chimeric polypeptide of the multi-chain chimeric polypeptide includes a second domain of a pair of affinity domains, wherein the first domain of the pair of affinity domains, the second domain of the pair of affinity domains, or both is about 10 to 100 amino acids in length. For example, a first domain of a pair of affinity domains, a second domain of a pair of affinity domains, or both can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a first domain of a pair of affinity domains, a second domain of a pair of affinity domains, or both is about 10, 15, 20, 25, 30, 35, 40, 45, 50, 55, 60, 65, 70, 75, 80, 85, 90, 95, or 100 amino acids in length.

In some embodiments, any of the first and/or second domains of a pair of affinity domains disclosed herein can include one or more additional amino acids (e.g., 1, 2, 3, 5, 6, 7, 8, 9, 10, or more amino acids) at its N-terminus and/or C-terminus, so long as the function of the first and/or second domains of a pair of affinity domains remains intact. For example, a sushi domain from an alpha chain of human IL-15 receptor (IL15Rα) can include one or more additional amino acids at the N-terminus and/or the C-terminus, while still retaining the ability to bind to a soluble IL-15. Additionally or alternatively, a soluble IL-15 can include one or more additional amino acids at the N-terminus and/or the C-terminus, while still retaining the ability to bind to a sushi domain from an alpha chain of human IL-15 receptor (IL15Rα).

A non-limiting example of a sushi domain from an alpha chain of IL-15 receptor alpha (IL15Rα) can include a sequence that is at least 70% identical, at least 75% identical, at least 80% identical, at least 85% identical, at least 90% identical, at least 95% identical, at least 99% identical, or 100% identical to ITCPPPMSVEHADIWVKSYSLYSR-ERYICNSGFKRKAGTSSLTECVLNKATNVAH WTTPSLKCIR (SEQ ID NO: 28). In some embodiments, a sushi domain from an alpha chain of IL15Rα can be encoded by a nucleic acid including

```
                                        (SEQ ID NO: 29)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG.
```

In some embodiments, a soluble IL-15 can include a sequence that is at least 70% identical, at least 75% identical, at least 80% identical, at least 85% identical, at least 90% identical, at least 95% identical, at least 99% identical, or 100% identical to NWVNVISDLKKIEDLIQSMHIDAT-LYTESDVHPSCKVTAMKCFLLELQVISLESGD ASIHDTVENLIILANNSLSSNGNVTESGCKE-CEELEEKNIKEFLQSFVHIVQMFINT S (SEQ ID NO: 14). In some embodiments, a soluble IL-15 can be encoded by a nucleic acid including the sequence of

```
                                        (SEQ ID NO: 30)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC.
```

Signal Sequence

In some embodiments, a multi-chain chimeric polypeptide includes a first chimeric polypeptide that includes a signal sequence at its N-terminal end. In some embodiments, a multi-chain chimeric polypeptide includes a second chimeric polypeptide that includes a signal sequence at its N-terminal end. In some embodiments, both the first chimeric polypeptide of a multi-chain chimeric polypeptide and a second chimeric polypeptide of the multi-chain chimeric polypeptide include a signal sequence. As will be understood by those of ordinary skill in the art, a signal sequence is an amino acid sequence that is present at the N-terminus of a number of endogenously produced proteins that directs the protein to the secretory pathway (e.g., the protein is directed to reside in certain intracellular organelles, to reside in the cell membrane, or to be secreted from the cell). Signal sequences are heterogeneous and differ greatly in their primary amino acid sequences. However, signal sequences are typically 16 to 30 amino acids in length and include a hydrophilic, usually positively charged N-terminal region, a central hydrophobic domain, and a C-terminal region that contains the cleavage site for signal peptidase.

In some embodiments, a first chimeric polypeptide of a multi-chain chimeric polypeptide, a second chimeric polypeptide of the multi-chain chimeric polypeptide, or both includes a signal sequence having an amino acid sequence MKWVTFISLLFLFSSAYS (SEQ ID NO: 31). In some embodiments, a first chimeric polypeptide of a multi-chain chimeric polypeptide, a second chimeric polypeptide of the multi-chain chimeric polypeptide, or both includes a signal sequence encoded by the nucleic acid sequence

```
                                        (SEQ ID NO: 32)
ATGAAATGGGTGACCTTTATTTCTTTACTGTTCCTCTTTAGCAGCGCCT

ACTCC,

                                        (SEQ ID NO: 33)
ATGAAGTGGGTCACATTTATCTCTTTACTGTTCCTCTTCTCCAGCGCCT

ACAGC,
or

                                        (SEQ ID NO: 34)
ATGAAATGGGTGACCTTTATTTCTTTACTGTTCCTCTTTAGCAGCGCCT

ACTCC.
```

In some embodiments, a first chimeric polypeptide of a multi-chain chimeric polypeptide, a second chimeric polypeptide of the multi-chain chimeric polypeptide, or both includes a signal sequence having an amino acid sequence MKCLLYLAFLFLGVNC (SEQ ID NO: 35). In some embodiments, a first chimeric polypeptide of a multi-chain chimeric polypeptide, a second chimeric polypeptide of the multi-chain chimeric polypeptide, or both includes a signal sequence having an amino acid sequence MGQIVTMFE-ALPHIIDEVINIVIIVLIIITSIKAVYNFATCGILALVSFL-FLAGRSCG (SEQ ID NO: 36). In some embodiments, a first chimeric polypeptide of a multi-chain chimeric polypeptide, a second chimeric polypeptide of the multi-chain chimeric polypeptide, or both includes a signal sequence having an amino acid sequence (SEQ ID NO: 37)
MPNHQSGSPTGSSDLLLSGKKQRPHLALRRKRRREMRKINRKVRRMNLAP

IKEKTAWQHLQALISEAEEVLKTSQTPQNSLTLFLALLSVLGPPVTG.

In some embodiments, a first chimeric polypeptide of a multi-chain chimeric polypeptide, a second chimeric polypeptide of the multi-chain chimeric polypeptide, or both includes a signal sequence having an amino acid sequence MDSKGSSQKGSRLLLLLVVSNLLLCQGVVS (SEQ ID NO: 38). Those of ordinary skill in the art will be aware of other appropriate signal sequences for use in a first chimeric polypeptide and/or a second chimeric polypeptide of multi-chain chimeric polypeptides described herein.

In some embodiments, a first chimeric polypeptide of a multi-chain chimeric polypeptide, a second chimeric polypeptide of the multi-chain chimeric polypeptide, or both includes a signal sequence that is about 10 to 100 amino acids in length. For example, a signal sequence can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a signal sequence is about 10, 15, 20, 25, 30, 35, 40, 45, 50, 55, 60, 65, 70, 75, 80, 85, 90, 95, or 100 amino acids in length.

In some embodiments, any of the signal sequences disclosed herein can include one or more additional amino acids (e.g., 1, 2, 3, 5, 6, 7, 8, 9, 10, or more amino acids) at its N-terminus and/or C-terminus, so long as the function of the signal sequence remains intact. For example, a signal sequence having the amino acid sequence MKCLLY-LAFLFLGVNC (SEQ ID NO: 35) can include one or more additional amino acids at the N-terminus or C-terminus, while still retaining the ability to direct a first chimeric polypeptide of a multi-chain chimeric polypeptide, a second chimeric polypeptide of the multi-chain chimeric polypeptide, or both to the secretory pathway.

In some embodiments, a first chimeric polypeptide of a multi-chain chimeric polypeptide, a second chimeric polypeptide of the multi-chain chimeric polypeptide, or both includes a signal sequence that directs the multi-chain chimeric polypeptide into the extracellular space. Such embodiments are useful in producing multi-chain chimeric polypeptides that are relatively easy to be isolated and/or purified.

Peptide Tags

In some embodiments, a multi-chain chimeric polypeptide includes a first chimeric polypeptide that includes a peptide tag (e.g., at the N-terminal end or the C-terminal end of the first chimeric polypeptide). In some embodiments, a multi-chain chimeric polypeptide includes a second chimeric polypeptide that includes a peptide tag (e.g., at the N-terminal end or the C-terminal end of the second chimeric polypeptide). In some embodiments, both the first chimeric polypeptide of a multi-chain chimeric polypeptide and a second chimeric polypeptide of the multi-chain chimeric polypeptide include a peptide tag. In some embodiments, a first chimeric polypeptide of a multi-chain chimeric polypeptide, a second chimeric polypeptide of the multi-chain chimeric polypeptide, or both include two or more peptide tags.

Exemplary peptide tags that can be included in a first chimeric polypeptide of a multi-chain chimeric polypeptide, a second chimeric polypeptide of the multi-chain chimeric polypeptide, or both include, without limitation, AviTag (GLNDIFEAQKIEWHE; SEQ ID NO: 39), a calmodulin-tag (KRRWKKNFIAVSAANRFKKISSSGAL; SEQ ID NO: 40), a polyglutamate tag (EEEEEE; SEQ ID NO: 41), an E-tag (GAPVPYPDPLEPR; SEQ ID NO: 42), a FLAG-tag (DYKDDDDK; SEQ ID NO: 43), an HA-tag, a peptide from hemagglutinin (YPYDVPDYA; SEQ ID NO: 44), a his-tag (HHHHH (SEQ ID NO: 45); HHHHHH (SEQ ID NO: 46); HHHHHHH (SEQ ID NO: 47); HHHHHHHHH (SEQ ID NO: 48); HHHHHHHH (SEQ ID NO: 49); or HHHHHHHHHH (SEQ ID NO: 50)), a myc-tag (EQKLI-SEEDL; SEQ ID NO: 51), NE-tag (TKENPRSNQEE-SYDDNES; SEQ ID NO: 52), S-tag, (KETAAAKFER-QHMDS; SEQ ID NO: 53), SBP-tag (MDEKTTGWRGGHVVEGLAGELEQLRAR-LEHHPQGQREP; SEQ ID NO: 54), Softag 1 (SLAEL-LNAGLGGS; SEQ ID NO: 55), Softag 3 (TQDPSRVG; SEQ ID NO: 56), Spot-tag (PDRVRAVSHWSS; SEQ ID NO: 57), Strep-tag (WSHPQFEK; SEQ ID NO: 58), TC tag (CCPGCC; SEQ ID NO: 59), Ty tag (EVHTNQDPLD; SEQ ID NO: 60), V5 tag (GKPIPNPLLGLDST; SEQ ID NO: 61), VSV-tag (YTDIEMNRLGK; SEQ ID NO: 62), and Xpress tag (DLYDDDDK; SEQ ID NO: 63). In some embodiments, tissue factor protein is a peptide tag.

Peptide tags that can be included in a first chimeric polypeptide of a multi-chain chimeric polypeptide, a second chimeric polypeptide of the multi-chain chimeric polypeptide, or both can be used in any of a variety of applications related to the multi-chain chimeric polypeptide. For example, a peptide tag can be used in the purification of a multi-chain chimeric polypeptide. As one non-limiting example, a first chimeric polypeptide of a multi-chain chimeric polypeptide (e.g., a recombinantly expressed first chimeric polypeptide), a second chimeric polypeptide of the multi-chain chimeric polypeptide (e.g., a recombinantly expressed second chimeric polypeptide), or both can include a myc tag; the multi-chain chimeric polypeptide that includes the myc-tagged first chimeric polypeptide, the myc-tagged second chimeric polypeptide, or both can be purified using an antibody that recognizes the myc tag(s). One non-limiting example of an antibody that recognizes a myc tag is 9E10, available from the non-commercial Developmental Studies Hybridoma Bank. As another non-limiting example, a first chimeric polypeptide of a multi-chain chimeric polypeptide (e.g., a recombinantly expressed first chimeric polypeptide), a second chimeric polypeptide of the multi-chain chimeric polypeptide (e.g., a recombinantly expressed second chimeric polypeptide), or both can include a histidine tag; the multi-chain chimeric polypeptide that includes the histidine-tagged first chimeric polypeptide, the histidine-tagged second chimeric polypeptide, or both can be purified using a nickel or cobalt chelate. Those of ordinary skill in the art will be aware of other suitable tags and agent that bind those tags for use in purifying multi-chain chimeric polypeptide. In some embodiments, a peptide tag is removed from the first chimeric polypeptide and/or the second chimeric polypeptide of the multi-chain chimeric polypeptide after purification. In some embodiments, a peptide tag is not removed from the first chimeric polypeptide and/or the second chimeric polypeptide of the multi-chain chimeric polypeptide after purification.

Peptide tags that can be included in a first chimeric polypeptide of a multi-chain chimeric polypeptide, a second chimeric polypeptide of the multi-chain chimeric polypeptide, or both can be used, for example, in immunoprecipitation of the multi-chain chimeric polypeptide, imaging of the multi-chain chimeric polypeptide (e.g., via Western blotting, ELISA, flow cytometry, and/or immunocytochemistry), and/or solubilization of the multi-chain chimeric polypeptide.

In some embodiments, a first chimeric polypeptide of a multi-chain chimeric polypeptide, a second chimeric polypeptide of the multi-chain chimeric polypeptide, or both includes a peptide tag that is about 10 to 100 amino acids in length. For example, a peptide tag can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a peptide tag is about 10, 15, 20, 25, 30, 35, 40, 45, 50, 55, 60, 65, 70, 75, 80, 85, 90, 95, or 100 amino acids in length.

Peptide tags included in a first chimeric polypeptide of a multi-chain chimeric polypeptide, a second chimeric polypeptide of the multi-chain chimeric polypeptide, or both can be of any suitable length. For example, peptide tags can be 5, 6, 7, 8, 9, 10, 11, 12, 13, 14, 15, 16, 17, 18, 19, 20, or more amino acids in length. In embodiments in which a multi-chain chimeric polypeptide includes two or more peptide tags, the two or more peptide tags can be of the same or different lengths. In some embodiments, any of the peptide tags disclosed herein may include one or more additional amino acids (e.g., 1, 2, 3, 5, 6, 7, 8, 9, 10, or more amino acids) at the N-terminus and/or C-terminus, so long as the function of the peptide tag remains intact. For example, a myc tag having the amino acid sequence EQKLISEEDL (SEQ ID NO: 64) can include one or more additional amino acids (e.g., at the N-terminus and/or the C-terminus of the peptide tag), while still retaining the ability to be bound by an antibody (e.g., 9E10).

Exemplary Multi-Chain Chimeric Polypeptides—Type A

In some embodiments of any of the multi-chain chimeric polypeptides described herein, the first target-binding domain and the second targeting-binding domain each independently bind specifically to a receptor of IL-18 or a receptor of IL-12. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is an agonistic antigen-binding domain. In some embodiments of these multi-chain chimeric polypeptides, the first target-binding domain and the second target-binding domain are each agonistic antigen-binding domains. In some embodiments of these multi-chain chimeric polypeptides, the antigen-binding domain includes a scFv or single-domain antibody.

In some embodiments of these multi-chain chimeric polypeptides, one or both of the first target-binding domain and the second target-binding domain is a soluble IL-15 or a soluble IL-18. In some embodiments of these multi-chain chimeric polypeptides, the first target-binding domain and the second target-binding domain are each independently a soluble IL-15 or a soluble IL-18. In some embodiments of these multi-chain chimeric polypeptides, the first target-binding domain and the second target-binding domain both bind specifically to a receptor of IL-18 or a receptor of IL-12. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-12, and the second target-binding domain binds specifically to a receptor for IL-18. In some embodiments of these multi-chain chimeric polypeptides, the first target-binding domain binds specifically to a receptor for IL-18, and the second target-binding domain bind specifically to a receptor for IL-12.

In some embodiments of these multi-chain chimeric polypeptides, the first target-binding domain includes a soluble IL-18 (e.g., a soluble human IL-18).

In some embodiments of these multi-chain chimeric polypeptides, the soluble human IL-18 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 16)
YFGKLESKLSVIRNLNDQVLFIDQGNRPLFEDMTDSDCRDNAPRTIFII

SMYKDSQPRGMAVTISVKCEKISTLSCENKIISFKEMNPPDNIKDTKSD

IIFFQRSVPGHDNKMQFESSSYEGYFLACEKERDLFKLILKKEDELGDR

SIMFTVQNED.

In some embodiments of these multi-chain chimeric polypeptides, the soluble human IL-18 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 65)
TACTTCGGCAAACTGGAATCCAAGCTGAGCGTGATCCGGAATTTAAACG

ACCAAGTTCTGTTTATCGATCAAGGTAACCGGCCTCTGTTCGAGGACAT

GACCGACTCCGATTGCCGGGACAATGCCCCCCGGACCATCTTCATTATC

TCCATGTACAAGGACAGCCAGCCCCGGGGCATGGCTGTGACAATTAGCG

TGAAGTGTGAGAAAATCAGCACTTTATCTTGTGAGAACAAGATCATCTC

CTTTAAGGAAATGAACCCCCCCGATAACATCAAGGACACCAAGTCCGAT

-continued

ATCATCTTCTTCCAGCGGTCCGTGCCCGGTCACGATAACAAGATGCAGT

TCGAATCCTCCTCCTACGAGGGCTACTTTTTAGCTTGTGAAAAGGAGAG

GGATTTATTCAAGCTGATCCTCAAGAAGGAGGACGAGCTGGGCGATCGT

TCCATCATGTTCACCGTCCAAAACGAGGAT.

In some embodiments of these multi-chain chimeric polypeptides, the second target-binding domain includes a soluble IL-12 (e.g., a soluble human IL-12). In some embodiments of these multi-chain chimeric polypeptides, the soluble human IL-15 includes a sequence of soluble human IL-12β (p40) and a sequence of soluble human IL-12α (p35). In some embodiments of these multi-chain chimeric polypeptides, the soluble IL-15 human IL-15 further includes a linker sequence (e.g., any of the exemplary linker sequences described herein) between the sequence of soluble IL-12β (p40) and the sequence of soluble human IL-12α (p35). In some examples of these multi-chain chimeric polypeptides, the linker sequence comprises GGGGSGGGGSGGGGS (SEQ ID NO: 7).

In some embodiments of these multi-chain chimeric polypeptides, the sequence of soluble human IL-12β (p40) comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 66)
IWELKKDVYVVELDWYPDAPGEMVVLTCDTPEEDGITWTLDQSSEVLGS

GKTLTIQVKEFGDAGQYTCHKGGEVLSHSLLLLHKKEDGIWSTDILKDQ

KEPKNKTFLRCEAKNYSGRFTCWWLTTISTDLTFSVKSSRGSSDPQGVT

CGAATLSAERVRGDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSKREKKDRVFTDKTSATVICRKNASISVRAQDRYYS

SSWSEWASVPCS.

In some embodiments of these multi-chain chimeric polypeptides, the soluble human IL-12β (p40) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 67)
ATTTGGGAACTGAAGAAGGACGTCTACGTGGTCGAACTGGACTGGTATC

CCGATGCTCCCGGCGAAATGGTGGTGCTCACTTGTGACACCCCCGAAGA

AGACGGCATCACTTGGACCCTCGATCAGAGCAGCGAGGTGCTGGGCTCC

GGAAAGACCCTCACAATCCAAGTTAAGGAGTTCGGAGACGCTGGCCAAT

ACACATGCCACAAGGGAGGCGAGGTGCTCAGCCATTCCTTATTATTATT

ACACAAGAAGGAAGACGGAATCTGGTCCACCGACATTTTAAAAGATCAG

AAGGAGCCCAAGAATAAGACCTTTTTAAGGTGTGAGGCCAAAAACTACA

-continued

```
GCGGTCGTTTCACTTGTTGGTGGCTGACCACCATTTCCACCGATTTAAC
CTTCTCCGTGAAAAGCAGCCGGGGAAGCTCCGACCCTCAAGGTGTGACA
TGTGGAGCCGCTACCCTCAGCGCTGAGAGGGTTCGTGGCGATAACAAGG
AATACGAGTACAGCGTGGAGTGCCAAGAAGATAGCGCTTGTCCCGCTGC
CGAAGAATCTTTACCCATTGAGGTGATGGTGGACGCCGTGCACAAACTC
AAGTACGAGAACTACACCTCCTCCTTCTTTATCCGGGACATCATTAAGC
CCGATCCTCCTAAGAATTTACAGCTGAAGCCTCTCAAAAATAGCCGGCA
AGTTGAGGTCTCTTGGGAATATCCCGACACTTGGAGCACACCCCACAGC
TACTTCTCTTTAACCTTTTGTGTGCAAGTTCAAGGTAAAAGCAAGCGGG
AGAAGAAAGACCGGGTGTTTACCGACAAAACCAGCGCCACCGTCATCTG
TCGGAAGAACGCCTCCATCAGCGTGAGGGCTCAAGATCGTTATTACTCC
AGCAGCTGGTCCGAGTGGGCCAGCGTGCCTTGTTCC.
```

In some embodiments of these multi-chain chimeric polypeptides, the soluble human IL-12α (p35) includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                      (SEQ ID NO: 68)
RNLPVATPDPGMFPCLHHSQNLLRAVSNMLQKARQTLEFYPCTSEEIDH
EDITKDKTSTVEACLPLELTKNESCLNSRETSFITNGSCLASRKTSFMM
ALCLSSIYEDLKMYQVEFKTMNAKLLMDPKRQIFLDQNMLAVIDELMQA
LNFNSETVPQKSSLEEPDFYKTKIKLCILLHAFRIRAVTIDRVMSYLNA
S.
```

In some embodiments of these multi-chain chimeric polypeptides, the soluble human IL-12α (p35) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                      (SEQ ID NO: 69)
CGTAACCTCCCCGTGGCTACCCCCGATCCCGGAATGTTCCCTTGTTTAC
ACCACAGCCAGAATTTACTGAGGGCCGTGAGCAACATGCTGCAGAAAGC
TAGGCAGACTTTAGAATTTTACCCTTGCACCAGCGAGGAGATCGACCAT
GAAGATATCACCAAGGACAAGACATCCACCGTGGAGGCTTGTTTACCTC
TGGAGCTGACAAAGAACGAGTCTTGTCTCAACTCTCGTGAAACCAGCTT
CATCACAAATGGCTCTTGTTTAGCTTCCCGGAAGACCTCCTTTATGATG
GCTTTATGCCTCAGCTCCATCTACGAGGATTTAAAGATGTACCAAGTGG
AGTTCAAGACCATGAACGCCAAGCTGCTCATGGACCCTAAACGGCAGAT
CTTTTTAGACCAGAACATGCTGGCTGTGATTGATGAGCTGATGCAAGCT
TTAAACTTCAACTCCGAGACCGTCCCTCAGAAGTCCTCCCTCGAGGAGC
```

-continued

```
CCGATTTTTACAAGACAAAGATCAAACTGTGCATTTTACTCCACGCCTT
TAGGATCCGGGCCGTGACCATTGACCGGGTCATGAGCTATTTAAACGCC
AGC.
```

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                      (SEQ ID NO: 70)
YFGKLESKLSVIRNLNDQVLFIDQGNRPLFEDMTDSDCRDNAPRTIFII
SMYKDSQPRGMAVTISVKCEKISTLSCENKIISFKEMNPPDNIKDTKSD
IIFFQRSVPGHDNKMQFESSSYEGYFLACEKERDLFKLILKKEDELGDR
SIMFTVQNEDSGTTNTVAAYNLTWKSTNFKTILEWEPKPVNQVYTVQIS
TKSGDWKSKCFYTTDTECDLTDEIVKDVKQTYLARVFSYPAGNVESTGS
AGEPLYENSPEFTPYLETNLGQPTIQSFEQVGTKVNVTVEDERTLVRRN
NTFLSLRDVFGKDLIYTLYYWKSSSSGKKTAKTNTNEFLIDVDKGENYC
FSVQAVIPSRTVNRKSTDSPVECMGQEKGEFRENWVNVISDLKKIEDLI
QSMHIDATLYTESDVHPSCKVTAMKCFLLELQVISLESGDASIHDTVEN
LIILANNSLSSNGNVTESGCKECEELEEKNIKEFLQSFVHIVQMFINTS.
```

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                      (SEQ ID NO: 71)
TACTTCGGCAAACTGGAATCCAAGCTGAGCGTGATCCGGAATTTAAACG
ACCAAGTTCTGTTTATCGATCAAGGTAACCGGCCTCTGTTCGAGGACAT
GACCGACTCCGATTGCCGGGACAATGCCCCCCGGACCATCTTCATTATC
TCCATGTACAAGGACAGCCAGCCCCGGGGCATGGCTGTGACAATTAGCG
TGAAGTGTGAGAAAATCAGCACTTTATCTTGTGAGAACAAGATCATCTC
CTTTAAGGAAATGAACCCCCCCGATAACATCAAGGACACCAAGTCCGAT
ATCATCTTCTTCCAGCGGTCCGTGCCCGGTCACGATAACAAGATGCAGT
TCGAATCCTCCTCCTACGAGGGCTACTTTTTAGCTTGTGAAAAGGAGAG
GGATTTATTCAAGCTGATCCTCAAGAAGGAGGACGAGCTGGGCGATCGT
TCCATCATGTTCACCGTCCAAAACGAGGATAGCGGCACAACCAACACAG
TCGCTGCCTATAACCTCACTTGGAAGAGCACCAACTTCAAAACCATCCT
CGAATGGGAACCCAAACCCGTTAACCAAGTTTACACCGTGCAGATCAGC
ACCAAGTCCGGCGACTGGAAGTCCAAATGTTTCTATACCACCGACACCG
AGTGCGATCTCACCGATGAGATCGTGAAAGATGTGAAACAGACCTACCT
CGCCCGGGTGTTTAGCTACCCCGCCGGCAATGTGGAGAGCACTGGTTCC
GCTGGCGAGCCTTTATACGAGAACAGCCCCGAATTTACCCCTTACCTCG
```

-continued

AGACCAATTTAGGACAGCCCACCATCCAAAGCTTTGAGCAAGTTGGCAC

AAAGGTGAATGTGACAGTGGAGGACGAGCGGACTTTAGTGCGGCGGAAC

AACACCTTTCTCAGCCTCCGGGATGTGTTCGGCAAAGATTTAATCTACA

CACTGTATTACTGGAAGTCCTCTTCCTCCGGCAAGAAGACAGCTAAAAC

CAACACAAACGAGTTTTTAATCGACGTGGATAAAGGCGAAAACTACTGT

TTCAGCGTGCAAGCTGTGATCCCCTCCCGGACCGTGAATAGGAAAAGCA

CCGATAGCCCCGTTGAGTGCATGGGCCAAGAAAAGGGCGAGTTCCGGGA

GAACTGGGTGAACGTCATCAGCGATTTAAAGAAGATCGAAGATTTAATT

CAGTCCATGCATATCGACGCCACTTTATACACAGAATCCGACGTGCACC

CCTCTTGTAAGGTGACCGCCATGAAATGTTTTTTACTGGAGCTGCAAGT

TATCTCTTTAGAGAGCGGAGACGCTAGCATCCACGACACCGTGGAGAAT

TTAATCATTTTAGCCAATAACTCTTTATCCAGCAACGGCAACGTGACAG

GATCCGGCTGCAAGGAGTGCGAAGAGCTGGAGGAGAAGAACATCAAGGA

GTTTCTGCAATCCTTTGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 72)

MKWVTFISLLFLFSSAYSYFGKLESKLSVIRNLNDQVLFIDQGNRPLFE

DMTDSDCRDNAPRTIFIISMYKDSQPRGMAVTISVKCEKISTLSCENKI

ISFKEMNPPDNIKDTKSDIIFFQRSVPGHDNKMQFESSSYEGYFLACEK

ERDLFKLILKKEDELGDRSIMFTVQNEDSGTTNTVAAYNLTWKSTNFKT

ILEWEPKPVNQVYTVQISTKSGDWKSKCFYTTDTECDLTDEIVKDVKQT

YLARVFSYPAGNVESTGSAGEPLYENSPEFTPYLETNLGQPTIQSFEQV

GTKVNVTVEDERTLVRRNNTFLSLRDVFGKDLIYTLYYWKSSSSGKKTA

KTNTNEFLIDVDKGENYCFSVQAVIPSRTVNRKSTDSPVECMGQEKGEF

RENWVNVISDLKKIEDLIQSMHIDATLYTESDVHPSCKVTAMKCFLLEL

QVISLESGDASIHDTVENLIILANNSLSSNGNVTESGCKECEELEEKNI

KEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical to:

(SEQ ID NO: 73)

ATGAAGTGGGTCACATTTATCTCTTTACTGTTCCTCTTCTCCAGCGCCT

ACAGCTACTTCGGCAAACTGGAATCCAAGCTGAGCGTGATCCGGAATTT

AAACGACCAAGTTCTGTTTATCGATCAAGGTAACCGGCCTCTGTTCGAG

-continued

GACATGACCGACTCCGATTGCCGGGACAATGCCCCCCGGACCATCTTCA

TTATCTCCATGTACAAGGACAGCCAGCCCCGGGGCATGGCTGTGACAAT

TAGCGTGAAGTGTGAGAAAATCAGCACTTTATCTTGTGAGAACAAGATC

ATCTCCTTTAAGGAAATGAACCCCCCCGATAACATCAAGGACACCAAGT

CCGATATCATCTTCTTCCAGCGGTCCGTGCCCGGTCACGATAACAAGAT

GCAGTTCGAATCCTCCTCCTACGAGGGCTACTTTTTAGCTTGTGAAAAG

GAGAGGGATTTATTCAAGCTGATCCTCAAGAAGGAGGACGAGCTGGGCG

ATCGTTCCATCATGTTCACCGTCCAAAACGAGGATAGCGGCACAACCAA

CACAGTCGCTGCCTATAACCTCACTTGGAAGAGCACCAACTTCAAAACC

ATCCTCGAATGGGAACCCAAACCCGTTAACCAAGTTTACACCGTGCAGA

TCAGCACCAAGTCCGGCGACTGGAAGTCCAAATGTTTCTATACCACCGA

CACCGAGTGCGATCTCACCGATGAGATCGTGAAAGATGTGAAACAGACC

TACCTCGCCCGGGTGTTTAGCTACCCCGCCGGCAATGTGGAGAGCACTG

GTTCCGCTGGCGAGCCTTTATACGAGAACAGCCCCGAATTTACCCCTTA

CCTCGAGACCAATTTAGGACAGCCCACCATCCAAAGCTTTGAGCAAGTT

GGCACAAAGGTGAATGTGACAGTGGAGGACGAGCGGACTTTAGTGCGGC

GGAACAACACCTTTCTCAGCCTCCGGGATGTGTTCGGCAAAGATTTAAT

CTACACACTGTATTACTGGAAGTCCTCTTCCTCCGGCAAGAAGACAGCT

AAAACCAACACAAACGAGTTTTTAATCGACGTGGATAAAGGCGAAAACT

ACTGTTTCAGCGTGCAAGCTGTGATCCCCTCCCGGACCGTGAATAGGAA

AAGCACCGATAGCCCCGTTGAGTGCATGGGCCAAGAAAAGGGCGAGTTC

CGGGAGAACTGGGTGAACGTCATCAGCGATTTAAAGAAGATCGAAGATT

TAATTCAGTCCATGCATATCGACGCCACTTTATACACAGAATCCGACGT

GCACCCCTCTTGTAAGGTGACCGCCATGAAATGTTTTTTACTGGAGCTG

CAAGTTATCTCTTTAGAGAGCGGAGACGCTAGCATCCACGACACCGTGG

AGAATTTAATCATTTTAGCCAATAACTCTTTATCCAGCAACGGCAACGT

GACAGAGTCCGGCTGCAAGGAGTGCGAAGAGCTGGAGGAGAAGAACATC

AAGGAGTTTCTGCAATCCTTTGTGCACATTGTCCAGATGTTCATCAATA

CCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 74)

IWELKKDVYVVELDWYPDAPGEMVVLTCDTPEEDGITWTLDQSSEVLGSG

KTLTIQVKEFGDAGQYTCHKGGEVLSHSLLLLHKKEDGIWSTDILKDQKE

PKNKTFLRCEAKNYSGRFTCWWLTTISTDLTFSVKSSRGSSDPQGVTCGA

ATLSAERVRGDNKEYEYSVECQEDSACPAAEESLPIEVMVDAVHKLKYEN

YTSSFFIRDIIKPDPPKNLQLKPLKNSRQVEVSWEYPDTWSTPHSYFSLT

FCVQVQGKSKREKKDRVFTDKTSATVICRKNASISVRAQDRYYSSSWSEW

-continued

ASVPCSGGGGSGGGGSGGGGSRNLPVATPDPGMFPCLHHSQNLLRAVSNM

LQKARQTLEFYPCTSEEIDHEDITKDKTSTVEACLPLELTKNESCLNSRE

TSFITNGSCLASRKTSFMMALCLSSIYEDLKMYQVEFKTMNAKLLMDPKR

QIFLDQNMLAVIDELMQALNFNSETVPQKSSLEEPDFYKTKIKLCILLHA

FRIRAVTIDRVMSYLNASITCPPPMSVEHADIWVKSYSLYSRERYICNSG

FKRKAGTSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 75)

ATTTGGGAACTGAAGAAGGACGTCTACGTGGTCGAACTGGACTGGTATCC

CGATGCTCCCGGCGAAATGGTGGTGCTCACTTGTGACACCCCCGAAGAAG

ACGGCATCACTTGGACCCTCGATCAGAGCAGCGAGGTGCTGGGCTCCGGA

AAGACCCTCACAATCCAAGTTAAGGAGTTCGGAGACGCTGGCCAATACAC

ATGCCACAAGGGAGGCGAGGTGCTCAGCCATTCCTTATTATTATTACACA

AGAAGGAAGACGGAATCTGGTCCACCGACATTTTAAAAGATCAGAAGGAG

CCCAAGAATAAGACCTTTTTAAGGTGTGAGGCCAAAAACTACAGCGGTCG

TTTCACTTGTTGGTGGCTGACCACCATTTCCACCGATTTAACCTTCTCCG

TGAAAAGCAGCCGGGGAAGCTCCGACCCTCAAGGTGTGACATGTGGAGCC

GCTACCCTCAGCGCTGAGAGGGTTCGTGGCGATAACAAGGAATACGAGTA

CAGCGTGGAGTGCCAAGAAGATAGCGCTTGTCCCGCTGCCGAAGAATCTT

TACCCATTGAGGTGATGGTGGACGCCGTGCACAAACTCAAGTACGAGAAC

TACACCTCCTCCTTCTTTATCCGGGACATCATTAAGCCCGATCCTCCTAA

GAATTTACAGCTGAAGCCTCTCAAAAATAGCCGGCAAGTTGAGGTCTCTT

GGGAATATCCCGACACTTGGAGCACACCCCACAGCTACTTCTCTTTAACC

TTTTGTGTGCAAGTTCAAGGTAAAAGCAAGCGGGAGAAGAAAGACCGGGT

GTTTACCGACAAAACCAGCGCCACCGTCATCTGTCGGAAGAACGCCTCCA

TCAGCGTGAGGGCTCAAGATCGTTATTACTCCAGCAGCTGGTCCGAGTGG

GCCAGCGTGCCTTGTTCCGGCGGTGGAGGATCCGGAGGAGGTGGCTCCGG

CGGCGGAGGATCTCGTAACCTCCCCGTGGCTACCCCCGATCCCGGAATGT

TCCCTTGTTTACACCACAGCCAGAATTTACTGAGGGCCGTGAGCAACATG

CTGCAGAAAGCTAGGCAGACTTTAGAATTTTACCCTTGCACCAGCGAGGA

GATCGACCATGAAGATATCACCAAGGACAAGACATCCACCGTGGAGGCTT

GTTTACCTCTGGAGCTGACAAAGAACGAGTCTTGTCTCAACTCTCGTGAA

ACCAGCTTCATCACAAATGGCTCTTGTTTAGCTTCCCGGAAGACCTCCTT

TATGATGGCTTTATGCCTCAGCTCCATCTACGAGGATTTAAAGATGTACC

AAGTGGAGTTCAAGACCATGAACGCCAAGCTGCTCATGGACCCTAAACGG

CAGATCTTTTTAGACCAGAACATGCTGGCTGTGATTGATGAGCTGATGCA

-continued

AGCTTTAAACTTCAACTCCGAGACCGTCCCTCAGAAGTCCTCCCTCGAGG

AGCCCGATTTTTACAAGACAAAGATCAAACTGTGCATTTTACTCCACGCC

TTTAGGATCCGGGCCGTGACCATTGACCGGGTCATGAGCTATTTAAACGC

CAGCATTACATGCCCCCCTCCCATGAGCGTGGAGCACGCCGACATCTGGG

TGAAGAGCTATAGCCTCTACAGCCGGGAGAGGTATATCTGTAACAGCGGC

TTCAAGAGGAAGGCCGGCACCAGCAGCCTCACCGAGTGCGTGCTGAATAA

GGCTACCAACGTGGCTCACTGGACAACACCCTCTTTAAAGTGCATCCGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 76)

MKWVTFISLLFLFSSAYSIWELKKDVYVVELDWYPDAPGEMVVLTCDTPE

EDGITWTLDQSSEVLGSGKTLTIQVKEFGDAGQYTCHKGGEVLSHSLLLL

HKKEDGIWSTDILKDQKEPKNKTFLRCEAKNYSGRFTCWWLTTISTDLTF

SVKSSRGSSDPQGVTCGAATLSAERVRGDNKEYEYSVECQEDSACPAAEE

SLPIEVMVDAVHKLKYENYTSSFFIRDIIKPDPPKNLQLKPLKNSRQVEV

SWEYPDTWSTPHSYFSLTFCVQVQGKSKREKKDRVFTDKTSATVICRKNA

SISVRAQDRYYSSSWSEWASVPCSGGGGSGGGGSGGGGSRNLPVATPDPG

MFPCLHHSQNLLRAVSNMLQKARQTLEFYPCTSEEIDHEDITKDKTSTVE

ACLPLELTKNESCLNSRETSFITNGSCLASRKTSFMMALCLSSIYEDLKM

YQVEFKTMNAKLLMDPKRQIFLDQNMLAVIDELMQALNFNSETVPQKSSL

EEPDFYKTKIKLCILLHAFRIRAVTIDRVMSYLNASITCPPPMSVEHADI

WVKSYSLYSRERYICNSGFKRKAGTSSLTECVLNKATNVAHWTTPSLKCI

R.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 77)

ATGAAATGGGTGACCTTTATTTCTTTACTGTTCCTCTTTAGCAGCGCCTA

CTCCATTTGGGAACTGAAGAAGGACGTCTACGTGGTCGAACTGGACTGGT

ATCCCGATGCTCCCGGCGAAATGGTGGTGCTCACTTGTGACACCCCCGAA

GAAGACGGCATCACTTGGACCCTCGATCAGAGCAGCGAGGTGCTGGGCTC

CGGAAAGACCCTCACAATCCAAGTTAAGGAGTTCGGAGACGCTGGCCAAT

ACACATGCCACAAGGGAGGCGAGGTGCTCAGCCATTCCTTATTATTATTA

CACAAGAAGGAAGACGGAATCTGGTCCACCGACATTTTAAAAGATCAGAA

GGAGCCCAAGAATAAGACCTTTTTAAGGTGTGAGGCCAAAAACTACAGCG

GTCGTTTCACTTGTTGGTGGCTGACCACCATTTCCACCGATTTAACCTTC

-continued

```
TCCGTGAAAAGCAGCCGGGGAAGCTCCGACCCTCAAGGTGTGACATGTGG
AGCCGCTACCCTCAGCGCTGAGAGGGTTCGTGGCGATAACAAGGAATACG
AGTACAGCGTGGAGTGCCAAGAAGATAGCGCTTGTCCCGCTGCCGAAGAA
TCTTTACCCATTGAGGTGATGGTGGACGCCGTGCACAAACTCAAGTACGA
GAACTACACCTCCTCCTTCTTTATCCGGGACATCATTAAGCCCGATCCTC
CTAAGAATTTACAGCTGAAGCCTCTCAAAAATAGCCGGCAAGTTGAGGTC
TCTTGGGAATATCCCGACACTTGGAGCACACCCCACAGCTACTTCTCTTT
AACCTTTTGTGTGCAAGTTCAAGGTAAAAGCAAGCGGGAGAAGAAAGACC
GGGTGTTTACCGACAAAACCAGCGCCACCGTCATCTGTCGGAAGAACGCC
TCCATCAGCGTGAGGGCTCAAGATCGTTATTACTCCAGCAGCTGGTCCGA
GTGGGCCAGCGTGCCTTGTTCCGGCGGTGGAGGATCCGGAGGAGGTGGCT
CCGGCGGCGGAGGATCTCGTAACCTCCCCGTGGCTACCCCCGATCCCGGA
ATGTTCCCTTGTTTACACCACAGCCAGAATTTACTGAGGGCCGTGAGCAA
CATGCTGCAGAAAGCTAGGCAGACTTTAGAATTTTACCCTTGCACCAGCG
AGGAGATCGACCATGAAGATATCACCAAGGACAAGACATCCACCGTGGAG
GCTTGTTTACCTCTGGAGCTGACAAAGAACGAGTCTTGTCTCAACTCTCG
TGAAACCAGCTTCATCACAAATGGCTCTTGTTTAGCTTCCCGGAAGACCT
CCTTTATGATGGCTTTATGCCTCAGCTCCATCTACGAGGATTTAAAGATG
TACCAAGTGGAGTTCAAGACCATGAACGCCAAGCTGCTCATGGACCCTAA
ACGGCAGATCTTTTTAGACCAGAACATGCTGGCTGTGATTGATGAGCTGA
TGCAAGCTTTAAACTTCAACTCCGAGACCGTCCCTCAGAAGTCCTCCCTC
GAGGAGCCCGATTTTTACAAGACAAAGATCAAACTGTGCATTTTACTCCA
CGCCTTTAGGATCCGGGCCGTGACCATTGACCGGGTCATGAGCTATTTAA
ACGCCAGCATTACATGCCCCCCTCCCATGAGCGTGGAGCACGCCGACATC
TGGGTGAAGAGCTATAGCCTCTACAGCCGGGAGAGGTATATCTGTAACAG
CGGCTTCAAGAGGAAGGCCGGCACCAGCAGCCTCACCGAGTGCGTGCTGA
ATAAGGCTACCAACGTGGCTCACTGGACAACACCCTCTTTAAAGTGCATC
CGG.
```

Exemplary Multi-Chain Chimeric Polypeptides—Type B

In some embodiments of any of the multi-chain chimeric polypeptides described herein, the first target-binding domain and the second targeting-binding domain each independently bind specifically to a receptor of IL-21 or to TGF-β. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is a soluble IL-21 (e.g., a soluble human IL-21 polypeptide) or a soluble TGF-β receptor (e.g., a soluble TGFRβRII receptor). In some embodiments of these multi-chain chimeric polypeptides, the first target-binding domain and the second target-binding domain are each independently a soluble IL-21 or a soluble TGF-β receptor (e.g., a soluble TGFRβRII receptor). In some embodiments of these multi-chain chimeric polypeptides, the first target-binding domain and the second target-binding domain both bind specifically to a receptor of IL-21 or to TGF-β. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-21, and the second target-binding domain binds specifically to TGF-β. In some embodiments of these multi-chain chimeric polypeptides, the first target-binding domain binds specifically to TGF-β, and the second target-binding domain bind specifically to a receptor for IL-21.

In some embodiments of these multi-chain chimeric polypeptides, the first target-binding domain includes a soluble IL-21 (e.g., a soluble human IL-21). In some embodiments of these multi-chain chimeric polypeptides, the soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                              (SEQ ID NO: 78)
QGQDRHMIRMRQLIDIVDQLKNYVNDLVPEFLPAPEDVETNCEWSAFSCF
QKAQLKSANTGNNERIINVSIKKLKRKPPSTNAGRRQKHRLTCPSCDSYE
KKPPKEFLERFKSLLQKMIHQHLSSRTHGSEDS.
```

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 79)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCCAAGGAGTTCCTGGAGAGGTTCAAGTCCCTGCTGCAGAA

GATGATCCATCAGCACCTGTCCTCCAGGACCCACGGCTCCGAGGACTCC.

In some embodiments of these multi-chain chimeric polypeptides, the second target-binding domain includes a soluble TGF-β receptor (e.g., a soluble TGFRβRII receptor (e.g., a soluble human TGFRβRII receptor)). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 80)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 81)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 82)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCACGATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT.

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 83)
ATTCCTCCCCACGTGCAGAAGAGCGTGAATAATGACATGATCGTGACCGA

TAACAATGGCGCCGTGAAATTTCCCCAGCTGTGCAAATTCTGCGATGTGA

GGTTTTCCACCTGCGACAACCAGAAGTCCTGTATGAGCAACTGCACAATC

ACCTCCATCTGTGAGAAGCCTCAGGAGGTGTGCGTGGCTGTCTGGCGGAA

GAATGACGAGAATATCACCCTGGAAACCGTCTGCCACGATCCCAAGCTGC

CCTACCACGATTTCATCCTGGAAGACGCCGCCAGCCCTAAGTGCATCATG

AAAGAGAAAAAGAAGCCTGGCGAGACCTTTTTCATGTGCTCCTGCAGCAG

CGACGAATGCAACGACAATATCATCTTTAGCGAGGAATACAATACCAGCA

ACCCCGAC.

In some embodiments of these multi-chain chimeric polypeptides, the soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 84)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCACGATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

-continued

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCACA

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC.

In some embodiments of these multi-chain chimeric polypeptides, the human TGFβRII receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 85)

IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 86)

QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDSSGTTNTVAAYNLTWKST

NFKTILEWEPKPVNQVYTVQISTKSGDWKSKCFYTTDTECDLTDEIVKDV

KQTYLARVFSYPAGNVESTGSAGEPLYENSPEFTPYLETNLGQPTIQSFE

QVGTKVNVTVEDERTLVRRNNTFLSLRDVFGKDLIYTLYYWKSSSSGKKT

AKTNTNEFLIDVDKGENYCFSVQAVIPSRTVNRKSTDSPVECMGQEKGEF

RENWVNVISDLKKIEDLIQSMHIDATLYTESDVHPSCKVTAMKCFLLELQ

-continued

VISLESGDASIHDTVENLIILANNSLSSNGNVTESGCKECEELEEKNIKE

FLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 87)

CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCCAAGGAGTTCCTGGAGAGGTTCAAGTCCCTGCTGCAGAA

GATGATCCATCAGCACCTGTCCTCCAGGACCCACGGCTCCGAGGACTCCT

CCGGCACCACCAATACCGTGGCCGCTTATAACCTCACATGGAAGAGCACC

AACTTCAAGACAATTCTGGAATGGGAACCCAAGCCCGTCAATCAAGTTTA

CACCGTGCAGATCTCCACCAAATCCGGAGACTGGAAGAGCAAGTGCTTCT

ACACAACAGACACCGAGTGTGATTTAACCGACGAAATCGTCAAGGACGTC

AAGCAAACCTATCTGGCTCGGGTCTTTTCCTACCCCGCTGGCAATGTCGA

GTCCACCGGCTCCGCTGGCGAGCCTCTCTACGAGAATTCCCCCGAATTCA

CCCCTTATTTAGAGACCAATTTAGGCCAGCCTACCATCCAGAGCTTCGAG

CAAGTTGGCACCAAGGTGAACGTCACCGTCGAGGATGAAAGGACTTTAGT

GCGGCGGAATAACACATTTTTATCCCTCCGGGATGTGTTCGGCAAAGACC

TCATCTACACACTGTACTATTGGAAGTCCAGCTCCTCCGGCAAAAAGACC

GCTAAGACCAACACCAACGAGTTTTTAATTGACGTGGACAAAGGCGAGAA

CTACTGCTTCAGCGTGCAAGCCGTGATCCCTTCTCGTACCGTCAACCGGA

AGAGCACAGATTCCCCCGTTGAGTGCATGGGCCAAGAAAAGGGCGAGTTC

CGGGAGAACTGGGTGAACGTCATCAGCGATTTAAAGAAGATCGAAGATTT

AATTCAGTCCATGCATATCGACGCCACTTTATACACAGAATCCGACGTGC

ACCCCTCTTGTAAGGTGACCGCCATGAAATGTTTTTTACTGGAGCTGCAA

GTTATCTCTTTAGAGAGCGGAGACGCTAGCATCCACGACACCGTGGAGAA

TTTAATCATTTTAGCCAATAACTCTTTATCCAGCAACGGCAACGTGACAG

AGTCCGGCTGCAAGGAGTGCGAAGAGCTGGAGGAGAAGAACATCAAGGAG

TTTCTGCAATCCTTTGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 88)
MKWVTFISLLFLFSSAYSQGQDRHMIRMRQLIDIVDQLKNYVNDLVPEFL
PAPEDVETNCEWSAFSCFQKAQLKSANTGNNERIINVSIKKLKRKPPSTN
AGRRQKHRLTCPSCDSYEKKPPKEFLERFKSLLQKMIHQHLSSRTHGSED
SSGTTNTVAAYNLTWKSTNFKTILEWEPKPVNQVYTVQISTKSGDWKSKC
FYTTDTECDLTDEIVKDVKQTYLARVFSYPAGNVESTGSAGEPLYENSPE
FTPYLETNLGQPTIQSFEQVGTKVNVTVEDERTLVRRNNTFLSLRDVFGK
DLIYTLYYWKSSSSGKKTAKTNTNEFLIDVDKGENYCFSVQAVIPSRTVN
RKSTDSPVECMGQEKGEFRENWVNVISDLKKIEDLIQSMHIDATLYTESD
VHPSCKVTAMKCFLLELQVISLESGDASIHDTVENLIILANNSLSSNGNV
TESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 89)
ATGAAGTGGGTGACCTTCATCAGCCTGCTGTTCCTGTTCTCCAGCGCCT
ACTCCCAGGGCCAGGACAGGCACATGATCCGGATGAGGCAGCTCATCGA
CATCGTCGACCAGCTGAAGAACTACGTGAACGACCTGGTGCCCGAGTTT
CTGCCTGCCCCCGAGGACGTGGAGACCAACTGCGAGTGGTCCGCCTTCT
CCTGCTTTCAGAAGGCCCAGCTGAAGTCCGCCAACACCGGCAACAACGA
GCGGATCATCAACGTGAGCATCAAGAAGCTGAAGCGGAAGCCTCCCTCC
ACAAACGCCGGCAGGAGGCAGAAGCACAGGCTGACCTGCCCCAGCTGTG
ACTCCTACGAGAAGAAGCCCCCCAAGGAGTTCCTGGAGAGGTTCAAGTC
CCTGCTGCAGAAGATGATCCATCAGCACCTGTCCTCCAGGACCCACGGC
TCCGAGGACTCCTCCGGCACCACCAATACCGTGGCCGCTTATAACCTCA
CATGGAAGAGCACCAACTTCAAGACAATTCTGGAATGGGAACCCAAGCC
CGTCAATCAAGTTTACACCGTGCAGATCTCCACCAAATCCGGAGACTGG
AAGAGCAAGTGCTTCTACACAACAGACACCGAGTGTGATTTAACCGACG
AAATCGTCAAGGACGTCAAGCAAACCTATCTGGCTCGGGTCTTTTCCTA
CCCCGCTGGCAATGTCGAGTCCACCGGCTCCGCTGGCGAGCCTCTCTAC
GAGAATTCCCCCGAATTCACCCCTTATTTAGAGACCAATTTAGGCCAGC
CTACCATCCAGAGCTTCGAGCAAGTTGGCACCAAGGTGAACGTCACCGT
CGAGGATGAAAGGACTTTAGTGCGGCGGAATAACACATTTTTATCCCTC
CGGGATGTGTTCGGCAAAGACCTCATCTACACACTGTACTATTGGAAGT
CCAGCTCCTCCGGCAAAAAGACCGCTAAGACCAACACCAACGAGTTTTT
AATTGACGTGGACAAAGGCGAGAACTACTGCTTCAGCGTGCAAGCCGTG
ATCCCTTCTCGTACCGTCAACCGGAAGAGCACAGATTCCCCCGTTGAGT
GCATGGGCCAAGAAAAGGGCGAGTTCCGGGAGAACTGGGTGAACGTCAT
CAGCGATTTAAAGAAGATCGAAGATTTAATTCAGTCCATGCATATCGAC

-continued
GCCACTTTATACACAGAATCCGACGTGCACCCCTCTTGTAAGGTGACCG
CCATGAAATGTTTTTTACTGGAGCTGCAAGTTATCTCTTTAGAGAGCGG
AGACGCTAGCATCCACGACACCGTGGAGAATTTAATCATTTTAGCCAAT
AACTCTTTATCCAGCAACGGCAACGTGACAGAGTCCGGCTGCAAGGAGT
GCGAAGAGCTGGAGGAGAAGAACATCAAGGAGTTTCTGCAATCCTTTGT
GCACATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 90)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHDFILEDAA
SPKCIMKEKKKPGETFFMCSCSSDECNDNIIFSEEYNTSNPDITCPPPM
SVEHADIWVKSYSLYSRERYICNSGFKRKAGTSSLTECVLNKATNVAHW
TTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 91)
ATCCCCCCCCATGTGCAAAAGAGCGTGAACAACGATATGATCGTGACC
GACAACAACGGCGCCGTGAAGTTTCCCCAGCTCTGCAAGTTCTGCGAT
GTCAGGTTCAGCACCTGCGATAATCAGAAGTCCTGCATGTCCAACTGC
ACGATCACCTCCATCTGCGAGAAGCCCCAAGAAGTGTGCGTGGCCGTG
TGGCGGAAAAAATGACGAGAACATCACCCTGGAGACCGTGTGTCACGAC
CCCAAGCTCCCTTATCACGACTTCATTCTGGAGGACGCTGCCTCCCCC
AAATGCATCATGAAGGAGAAGAAGAAGCCCGGAGAGACCTTCTTTATG
TGTTCCTGTAGCAGCGACGAGTGTAACGACAACATCATCTTCAGCGAA
GAGTACAACACCAGCAACCCTGATGGAGGTGGCGGATCCGGAGGTGGA
GGTTCTGGTGGAGGTGGGAGTATTCCTCCCCACGTGCAGAAGAGCGTG
AATAATGACATGATCGTGACCGATAACAATGGCGCCGTGAAATTTCCC
CAGCTGTGCAAATTCTGCGATGTGAGGTTTTCCACCTGCGACAACCAG
AAGTCCTGTATGAGCAACTGCACAATCACCTCCATCTGTGAGAAGCCT
CAGGAGGTGTGCGTGGCTGTCTGGCGGAAGAATGACGAGAATATCACC
CTGGAAACCGTCTGCCACGATCCCAAGCTGCCCTACCACGATTTCATC

-continued

CTGGAAGACGCCGCCAGCCCTAAGTGCATCATGAAAGAGAAAAAGAAG

CCTGGCGAGACCTTTTTCATGTGCTCCTGCAGCAGCGACGAATGCAAC

GACAATATCATCTTTAGCGAGGAATACAATACCAGCAACCCCGACATC

ACGTGTCCTCCTCCTATGTCCGTGGAACACGCAGACATCTGGGTCAAG

AGCTACAGCTTGTACTCCAGGGAGCGGTACATTTGTAACTCTGGTTTC

AAGCGTAAAGCCGGCACGTCCAGCCTGACGGAGTGCGTGTTGAACAAG

GCCACGAATGTCGCCCACTGGACAACCCCCAGTCTCAAATGTATTAGA.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 92)

MKWVTFISLLFLFSSAYSIPPHVQKSVNNDMIVTDNNGAVKFPQLCKFC

DVRFSTCDNQKSCMSNCSITSICEKPQEVCVAVWRKNDENITLETVCHD

PKLPYHDFILEDAASPKCIMKEKKKPGETFFMCSCSSDECNDNIIFSEE

YNTSNPDGGGGSGGGGSGGGGSIPPHVQKSVNNDMIVTDNNGAVKFPQL

CKFCDVRFSTCDNQKSCMSNCSITSICEKPQEVCVAVWRKNDENITLET

VCHDPKLPYHDFILEDAASPKCIMKEKKKPGETFFMCSCSSDECNDNII

FSEEYNTSNPDITCPPPMSVEHADIWVKSYSLYSRERYICNSGFKRKAG

TSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 93)

ATGAAGTGGGTGACCTTCATCAGCCTGCTGTTCCTGTTCTCCAGCGCC

TACTCCATCCCCCCCCATGTGCAAAAGAGCGTGAACAACGATATGATC

GTGACCGACAACAACGGCGCCGTGAAGTTTCCCCAGCTCTGCAAGTTC

TGCGATGTCAGGTTCAGCACCTGCGATAATCAGAAGTCCTGCATGTCC

AACTGCACGATCACCTCCATCTGCGAGAAGCCCCAAGAAGTGTGCGTG

GCCGTGTGGCGGAAAAATGACGAGAACATCACCCTGGAGACCGTGTGT

CACGACCCCAAGCTCCCTTATCACGACTTCATTCTGGAGGACGCTGCC

TCCCCCAAATGCATCATGAAGGAGAAGAAGAAGCCCGGAGAGACCTTC

TTTATGTGTTCCTGTAGCAGCGACGAGTGTAACGACAACATCATCTTC

AGCGAAGAGTACAACACCAGCAACCCTGATGGAGGTGGCGGATCCGGA

GGTGGAGGTTCTGGTGGAGGTGGGAGTATTCCTCCCCACGTGCAGAAG

AGCGTGAATAATGACATGATCGTGACCGATAACAATGGCGCCGTGAAA

TTTCCCCAGCTGTGCAAATTCTGCGATGTGAGGTTTTCCACCTGCGAC

-continued

AACCAGAAGTCCTGTATGAGCAACTGCACAATCACCTCCATCTGTGAG

AAGCCTCAGGAGGTGTGCGTGGCTGTCTGGCGGAAGAATGACGAGAAT

ATCACCCTGGAAACCGTCTGCCACGATCCCAAGCTGCCCTACCACGAT

TTCATCCTGGAAGACGCCGCCAGCCCTAAGTGCATCATGAAAGAGAAA

AAGAAGCCTGGCGAGACCTTTTTCATGTGCTCCTGCAGCAGCGACGAA

TGCAACGACAATATCATCTTTAGCGAGGAATACAATACCAGCAACCCC

GACATCACGTGTCCTCCTCCTATGTCCGTGGAACACGCAGACATCTGG

GTCAAGAGCTACAGCTTGTACTCCAGGGAGCGGTACATTTGTAACTCT

GGTTTCAAGCGTAAAGCCGGCACGTCCAGCCTGACGGAGTGCGTGTTG

AACAAGGCCACGAATGTCGCCCACTGGACAACCCCCAGTCTCAAATGT

ATTAGA.

Exemplary Multi-Chain Chimeric Polypeptides—Type C

In some embodiments of any of the multi-chain chimeric polypeptides described herein, the first target-binding domain and the second targeting-binding domain each independently bind specifically to a receptor of IL-7 or a receptor of IL-21. In some examples of these multi-chain chimeric polypeptides, the first target-binding domain and the soluble tissue factor domain directly abut each other in the first chimeric polypeptide.

In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is a soluble IL-21 (e.g., a soluble human IL-21 polypeptide) or a soluble IL-7 (e.g., a soluble human IL-7 polypeptide). In some embodiments of these multi-chain chimeric polypeptides, the first target-binding domain and the second target-binding domain are each independently a soluble IL-21 or a soluble IL-7. In some embodiments of these multi-chain chimeric polypeptides, the first target-binding domain and the second target-binding domain both bind specifically to a receptor of IL-21 or a receptor of IL-7. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-21, and the second target-binding domain binds specifically to a receptor for IL-7. In some embodiments of these multi-chain chimeric polypeptides, the first target-binding domain binds specifically to a receptor for IL-7, and the second target-binding domain binds specifically to a receptor for IL-21.

In some embodiments of these multi-chain chimeric polypeptides, the first target-binding domain includes a soluble IL-21 (e.g., a soluble human IL-21).

In some embodiments of these multi-chain chimeric polypeptides, the soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 78)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS.
```

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 94)
CAAGGTCAAGATCGCCACATGATTAGAATGCGTCAACTTATAGATATTG

TTGATCAGCTGAAAAATTATGTGAATGACTTGGTCCCTGAATTTCTGCC

AGCTCCAGAAGATGTAGAGACAAACTGTGAGTGGTCAGCTTTTTCCTGT

TTTCAGAAGGCCCAACTAAAGTCAGCAAATACAGGAAACAATGAAAGGA

TAATCAATGTATCAATTAAAAAGCTGAAGAGGAAACCACCTTCCACAAA

TGCAGGGAGAAGACAGAAACACAGACTAACATGCCCTTCATGTGATTCT

TATGAGAAAAAACCACCCAAAGAATTCCTAGAAAGATTCAAATCACTTC

TCCAAAAGATGATTCATCAGCATCTGTCCTCTAGAACACACGGAAGTGA

AGATTCC.
```

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 79)
CAGGGCCAGGACAGGCACATGATCCGGATGAGGCAGCTCATCGACATC

GTCGACCAGCTGAAGAACTACGTGAACGACCTGGTGCCCGAGTTTCTG

CCTGCCCCCGAGGACGTGGAGACCAACTGCGAGTGGTCCGCCTTCTCC

TGCTTTCAGAAGGCCCAGCTGAAGTCCGCCAACACCGGCAACAACGAG

CGGATCATCAACGTGAGCATCAAGAAGCTGAAGCGGAAGCCTCCCTCC

ACAAACGCCGGCAGGAGGCAGAAGCACAGGCTGACCTGCCCCAGCTGT

GACTCCTACGAGAAGAAGCCCCCCAAGGAGTTCCTGGAGAGGTTCAAG

TCCCTGCTGCAGAAGATGATCCATCAGCACCTGTCCTCCAGGACCCAC

GGCTCCGAGGACTCC.
```

In some embodiments of these multi-chain chimeric polypeptides, the sequence of soluble human IL-7 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 11)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEH.
```

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 95)
GATTGTGATATTGAAGGTAAAGATGGCAAACAATATGAGAGTGTTCTAA

TGGTCAGCATCGATCAATTATTGGACAGCATGAAAGAAATTGGTAGCAA

TTGCCTGAATAATGAATTTAACTTTTTTAAAAGACATATCTGTGATGCT

AATAAGGAAGGTATGTTTTTATTCCGTGCTGCTCGCAAGTTGAGGCAAT

TTCTTAAAATGAATAGCACTGGTGATTTTGATCTCCACTTATTAAAAGT

TTCAGAAGGCACAACAATACTGTTGAACTGCACTGGCCAGGTTAAAGGA

AGAAAACCAGCTGCCCTGGGTGAAGCCCAACCAACAAAGAGTTTGGAAG

AAAATAAATCTTTAAAGGAACAGAAAAAACTGAATGACTTGTGTTTCCT

AAAGAGACTATTACAAGAGATAAAAACTTGTTGGAATAAAATTTTGATG

GGCACTAAAGAACAC.
```

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 96)
QGQDRHMIRMRQLIDIVDQLKNYVNDLVPEFLPAPEDVETNCEWSAFSC
FQKAQLKSANTGNNERIINVSIKKLKRKPPSTNAGRRQKHRLTCPSCDS
YEKKPPKEFLERFKSLLQKMIHQHLSSRTHGSEDSSGTTNTVAAYNLTW
KSTNFKTILEWEPKPVNQVYTVQISTKSGDWKSKCFYTTDTECDLTDEI
VKDVKQTYLARVFSYPAGNVESTGSAGEPLYENSPEFTPYLETNLGQPT
IQSFEQVGTKVNVTVEDERTLVRRNNTFLSLRDVFGKDLIYTLYYWKSS
SSGKKTAKTNTNEFLIDVDKGENYCFSVQAVIPSRTVNRKSTDSPVECM
GQEKGEFRENWVNVISDLKKIEDLIQSMHIDATLYTESDVHPSCKVTAM
KCFLLELQVISLESGDASIHDTVENLIILANNSLSSNGNVTESGCKECE
ELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 97)
CAAGGTCAAGATCGCCACATGATTAGAATGCGTCAACTTATAGATATT
GTTGATCAGCTGAAAAATTATGTGAATGACTTGGTCCCTGAATTTCTG
CCAGCTCCAGAAGATGTAGAGACAAACTGTGAGTGGTCAGCTTTTTCC
TGTTTTCAGAAGGCCCAACTAAAGTCAGCAAATACAGGAAACAATGAA
AGGATAATCAATGTATCAATTAAAAAGCTGAAGAGGAAACCACCTTCC
ACAAATGCAGGGAGAAGACAGAAACACAGACTAACATGCCCTTCATGT
GATTCTTATGAGAAAAAACCACCCAAAGAATTCCTAGAAAGATTCAAA
TCACTTCTCCAAAAGATGATTCATCAGCATCTGTCCTCTAGAACACAC
GGAAGTGAAGATTCCTCAGGCACTACAAATACTGTGGCAGCATATAAT
TTAACTTGGAAATCAACTAATTTCAAGACAATTTTGGAGTGGGAACCC
AAACCCGTCAATCAAGTCTACACTGTTCAAATAAGCACTAAGTCAGGA
GATTGGAAAAGCAAATGCTTTTACACAACAGACACAGAGTGTGACCTC
ACCGACGAGATTGTGAAGGATGTGAAGCAGACGTACTTGGCACGGGTC
TTCTCCTACCCGGCAGGGAATGTGGAGAGCACCGGTTCTGCTGGGGAG
CCTCTGTATGAGAACTCCCCAGAGTTCACACCTTACCTGGAGACAAAC
CTCGGACAGCCAACAATTCAGAGTTTTGAACAGGTGGGAACAAAAGTG
AATGTGACCGTAGAAGATGAACGGACTTTAGTCAGAAGGAACAACACT
TTCCTAAGCCTCCGGGATGTTTTTGGCAAGGACTTAATTTATACACTT
TATTATTGGAAATCTTCAAGTTCAGGAAAGAAAACAGCCAAAACAAAC
ACTAATGAGTTTTTGATTGATGTGGATAAAGGAGAAAACTACTGTTTC
AGTGTTCAAGCAGTGATTCCCTCCCGAACAGTTAACCGGAAGAGTACA
GACAGCCCGGTAGAGTGTATGGGCCAGGAGAAAGGGGAATTCAGAGAA

-continued

AACTGGGTGAACGTCATCAGCGATTTAAAGAAGATCGAAGATTTAATT
CAGTCCATGCATATCGACGCCACTTTATACACAGAATCCGACGTGCAC
CCCTCTTGTAAGGTGACCGCCATGAAATGTTTTTTACTGGAGCTGCAA
GTTATCTCTTTAGAGAGCGGAGACGCTAGCATCCACGACACCGTGGAG
AATTTAATCATTTTAGCCAATAACTCTTTATCCAGCAACGGCAACGTG
ACAGAGTCCGGCTGCAAGGAGTGCGAAGAGCTGGAGGAGAAGAACATC
AAGGAGTTTCTGCAATCCTTTGTGCACATTGTCCAGATGTTCATCAAT
ACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 98)
MGVKVLFALICIAVAEAQGQDRHMIRMRQLIDIVDQLKNYVNDLVPEFL
PAPEDVETNCEWSAFSCFQKAQLKSANTGNNERIINVSIKKLKRKPPST
NAGRRQKHRLTCPSCDSYEKKPPKEFLERFKSLLQKMIHQHLSSRTHGS
EDSSGTTNTVAAYNLTWKSTNFKTILEWEPKPVNQVYTVQISTKSGDWK
SKCFYTTDTECDLTDEIVKDVKQTYLARVFSYPAGNVESTGSAGEPLYE
NSPEFTPYLETNLGQPTIQSFEQVGTKVNVTVEDERTLVRRNNTFLSLR
DVFGKDLIYTLYYWKSSSSGKKTAKTNTNEFLIDVDKGENYCFSVQAVI
PSRTVNRKSTDSPVECMGQEKGEFRENWVNVISDLKKIEDLIQSMHIDA
TLYTESDVHPSCKVTAMKCFLLELQVISLESGDASIHDTVENLIILANN
SLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 99)
ATGGGAGTGAAAGTTCTTTTTGCCCTTATTTGTATTGCTGTGGCCGAGG
CCCAAGGTCAAGATCGCCACATGATTAGAATGCGTCAACTTATAGATAT
TGTTGATCAGCTGAAAAATTATGTGAATGACTTGGTCCCTGAATTTCTG
CCAGCTCCAGAAGATGTAGAGACAAACTGTGAGTGGTCAGCTTTTTCCT
GTTTTCAGAAGGCCCAACTAAAGTCAGCAAATACAGGAAACAATGAAAG
GATAATCAATGTATCAATTAAAAAGCTGAAGAGGAAACCACCTTCCACA
AATGCAGGGAGAAGACAGAAACACAGACTAACATGCCCTTCATGTGATT
CTTATGAGAAAAAACCACCCAAAGAATTCCTAGAAAGATTCAAATCACT
TCTCCAAAAGATGATTCATCAGCATCTGTCCTCTAGAACACACGGAAGT
GAAGATTCCTCAGGCACTACAAATACTGTGGCAGCATATAATTTAACTT

-continued

GGAAATCAACTAATTTCAAGACAATTTTGGAGTGGGAACCCAAACCCGT
CAATCAAGTCTACACTGTTCAAATAAGCACTAAGTCAGGAGATTGGAAA
AGCAAATGCTTTTACACAACAGACACAGAGTGTGACCTCACCGACGAGA
TTGTGAAGGATGTGAAGCAGACGTACTTGGCACGGGTCTTCTCCTACCC
GGCAGGGAATGTGGAGAGCACCGGTTCTGCTGGGGAGCCTCTGTATGAG
AACTCCCCAGAGTTCACACCTTACCTGGAGACAAACCTCGGACAGCCAA
CAATTCAGAGTTTTGAACAGGTGGGAACAAAAGTGAATGTGACCGTAGA
AGATGAACGGACTTTAGTCAGAAGGAACAACACTTTCCTAAGCCTCCGG
GATGTTTTTGGCAAGGACTTAATTTATACACTTTATTATTGGAAATCTT
CAAGTTCAGGAAAGAAAACAGCCAAAACAAACACTAATGAGTTTTTGAT
TGATGTGGATAAAGGAGAAAACTACTGTTTCAGTGTTCAAGCAGTGATT
CCCTCCCGAACAGTTAACCGGAAGAGTACAGACAGCCCGGTAGAGTGTA
TGGGCCAGGAGAAAGGGGAATTCAGAGAAAACTGGGTGAACGTCATCAG
CGATTTAAAGAAGATCGAAGATTTAATTCAGTCCATGCATATCGACGCC
ACTTTATACACAGAATCCGACGTGCACCCCTCTTGTAAGGTGACCGCCA
TGAAATGTTTTTTACTGGAGCTGCAAGTTATCTCTTTAGAGAGCGGAGA
CGCTAGCATCCACGACACCGTGGAGAATTTAATCATTTTAGCCAATAAC
TCTTTATCCAGCAACGGCAACGTGACAGAGTCCGGCTGCAAGGAGTGCG
AAGAGCTGGAGGAGAAGAACATCAAGGAGTTTCTGCAATCCTTTGTGCA
CATTGTCCAGATGTTCATCAATACCTCC

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 100)
DCDIEGKDGKQYESVLMVSIDQLLDSMKEIGSNCLNNEFNFFKRHICDA
NKEGMFLFRAARKLRQFLKMNSTGDFDLHLLKVSEGTTILLNCTGQVKG
RKPAALGEAQPTKSLEENKSLKEQKKLNDLCFLKRLLQEIKTCWNKILM
GTKEHITCPPPMSVEHADIWVKSYSLYSRERYICNSGFKRKAGTSSLTE
CVLNKATNVAHWTTPSLKCIR

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 101)
GATTGTGATATTGAAGGTAAAGATGGCAAACAATATGAGAGTGTTCTAAT
GGTCAGCATCGATCAATTATTGGACAGCATGAAAGAAATTGGTAGCAATT
GCCTGAATAATGAATTTAACTTTTTTAAAAGACATATCTGTGATGCTAAT
AAGGAAGGTATGTTTTTATTCCGTGCTGCTCGCAAGTTGAGGCAATTTCT

-continued

TAAAATGAATAGCACTGGTGATTTTGATCTCCACTTATTAAAAGTTTCAG
AAGGCACAACAATACTGTTGAACTGCACTGGCCAGGTTAAAGGAAGAAAA
CCAGCTGCCCTGGGTGAAGCCCAACCAACAAAGAGTTTGGAAGAAAATAA
ATCTTTAAAGGAACAGAAAAAACTGAATGACTTGTGTTTCCTAAAGAGAC
TATTACAAGAGATAAAAACTTGTTGGAATAAAATTTTGATGGGCACTAAA
GAACACATCACGTGCCCTCCCCCCATGTCCGTGGAACACGCAGACATCTG
GGTCAAGAGCTACAGCTTGTACTCCAGGGAGCGGTACATTTGTAACTCTG
GTTTCAAGCGTAAAGCCGGCACGTCCAGCCTGACGGAGTGCGTGTTGAAC
AAGGCCACGAATGTCGCCCACTGGACAACCCCCAGTCTCAAATGCATTAG
A.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 102)
MGVKVLFALICIAVAEADCDIEGKDGKQYESVLMVSIDQLLDSMKEIGSN
CLNNEFNFFKRHICDANKEGMFLFRAARKLRQFLKMNSTGDFDLHLLKVS
EGTTILLNCTGQVKGRKPAALGEAQPTKSLEENKSLKEQKKLNDLCFLKR
LLQEIKTCWNKILMGTKEHITCPPPMSVEHADIWVKSYSLYSRERYICNS
GFKRKAGTSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 103)
ATGGGAGTGAAAGTTCTTTTTGCCCTTATTTGTATTGCTGTGGCCGAGGC
CGATTGTGATATTGAAGGTAAAGATGGCAAACAATATGAGAGTGTTCTAA
TGGTCAGCATCGATCAATTATTGGACAGCATGAAAGAAATTGGTAGCAAT
TGCCTGAATAATGAATTTAACTTTTTTAAAAGACATATCTGTGATGCTAA
TAAGGAAGGTATGTTTTTATTCCGTGCTGCTCGCAAGTTGAGGCAATTTC
TTAAAATGAATAGCACTGGTGATTTTGATCTCCACTTATTAAAAGTTTCA
GAAGGCACAACAATACTGTTGAACTGCACTGGCCAGGTTAAAGGAAGAAA
ACCAGCTGCCCTGGGTGAAGCCCAACCAACAAAGAGTTTGGAAGAAAATA
AATCTTTAAAGGAACAGAAAAAACTGAATGACTTGTGTTTCCTAAAGAGA
CTATTACAAGAGATAAAAACTTGTTGGAATAAAATTTTGATGGGCACTAA
AGAACACATCACGTGCCCTCCCCCCATGTCCGTGGAACACGCAGACATCT
GGGTCAAGAGCTACAGCTTGTACTCCAGGGAGCGGTACATTTGTAACTCT
GGTTTCAAGCGTAAAGCCGGCACGTCCAGCCTGACGGAGTGCGTGTTGAA

-continued

CAAGGCCACGAATGTCGCCCACTGGACAACCCCCAGTCTCAAATGCATTA

GA.

Exemplary Multi-Chain Chimeric Polypeptides—Type D

In some embodiments of any of the multi-chain chimeric polypeptides described herein, the first target-binding domain and the second targeting-binding domain each independently bind specifically to a receptor of IL-7 or a receptor of IL-21. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is a soluble IL-21 (e.g., a soluble human IL-21 polypeptide) or a soluble IL-7 (e.g., a soluble human IL-7 polypeptide). In some embodiments of these multi-chain chimeric polypeptides, the first target-binding domain and the second target-binding domain are each independently a soluble IL-21 or a soluble IL-7. In some embodiments of these multi-chain chimeric polypeptides, the first target-binding domain and the second target-binding domain both bind specifically to a receptor of IL-21 or a receptor of IL-7. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-21, and the second target-binding domain binds specifically to a receptor for IL-7. In some embodiments of these multi-chain chimeric polypeptides, the first target-binding domain binds specifically to a receptor for IL-7, and the second target-binding domain binds specifically to a receptor for IL-21.

In some embodiments of these multi-chain chimeric polypeptides, the soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 78)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 94)
CAAGGTCAAGATCGCCACATGATTAGAATGCGTCAACTTATAGATATTGT

TGATCAGCTGAAAAATTATGTGAATGACTTGGTCCCTGAATTTCTGCCAG

CTCCAGAAGATGTAGAGACAAACTGTGAGTGGTCAGCTTTTTCCTGTTTT

CAGAAGGCCCAACTAAAGTCAGCAAATACAGGAAACAATGAAAGGATAAT

CAATGTATCAATTAAAAAGCTGAAGAGGAAACCACCTTCCACAAATGCAG

GGAGAAGACAGAAACACAGACTAACATGCCCTTCATGTGATTCTTATGAG

AAAAAACCACCCAAAGAATTCCTAGAAAGATTCAAATCACTTCTCCAAAA

GATGATTCATCAGCATCTGTCCTCTAGAACACACGGAAGTGAAGATTCC.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 79)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCCAAGGAGTTCCTGGAGAGGTTCAAGTCCCTGCTGCAGAA

GATGATCCATCAGCACCTGTCCTCCAGGACCCACGGCTCCGAGGACTCC.

In some embodiments of these multi-chain chimeric polypeptides, the sequence of soluble human IL-7 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 11)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 95)
GATTGTGATATTGAAGGTAAAGATGGCAAACAATATGAGAGTGTTCTAAT

GGTCAGCATCGATCAATTATTGGACAGCATGAAAGAAATTGGTAGCAATT

GCCTGAATAATGAATTTAACTTTTTTAAAAGACATATCTGTGATGCTAAT

AAGGAAGGTATGTTTTTATTCCGTGCTGCTCGCAAGTTGAGGCAATTTCT

TAAAATGAATAGCACTGGTGATTTTGATCTCCACTTATTAAAAGTTTCAG

AAGGCACAACAATACTGTTGAACTGCACTGGCCAGGTTAAAGGAAGAAAA

CCAGCTGCCCTGGGTGAAGCCCAACCAACAAAGAGTTTGGAAGAAAATAA

ATCTTTAAAGGAACAGAAAAAACTGAATGACTTGTGTTTCCTAAAGAGAC

TATTACAAGAGATAAAAACTTGTTGGAATAAAATTTTGATGGGCACTAAA

GAACAC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 104)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EHSGTTNTVAAYNLTWKSTNFKTILEWEPKPVNQVYTVQISTKSGDWKSK

CFYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVFG

KDLIYTLYYWKSSSSGKKTAKTNTNEFLIDVDKGENYCFSVQAVIPSRTV

NRKSTDSPVECMGQEKGEFRENWVNVISDLKKIEDLIQSMHIDATLYTES

DVHPSCKVTAMKCFLLELQVISLESGDASIHDTVENLIILANNSLSSNGN

VTESGCKECEELEEKNIKEFLQSFVHIVQMFINTS .

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 105)
GATTGCGACATCGAGGGCAAGGACGGCAAGCAGTACGAGAGCGTGCTGAT

GGTGTCCATCGACCAGCTGCTGGACAGCATGAAGGAGATCGGCTCCAACT

GCCTCAACAACGAGTTCAACTTCTTCAAGCGGCACATCTGCGACGCCAAC

AAGGAGGGCATGTTCCTGTTCAGGGCCGCCAGGAAACTGCGGCAGTTCCT

GAAGATGAACTCCACCGGCGACTTCGACCTGCACCTGCTGAAGGTGTCCG

AGGGCACCACCATCCTGCTGAACTGCACCGGACAGGTGAAGGGCCGGAAA

CCTGCTGCTCTGGGAGAGGCCCAACCCACCAAGAGCCTGGAGGAGAACAA

GTCCCTGAAGGAGCAGAAGAAGCTGAACGACCTGTGCTTCCTGAAGAGGC

TGCTGCAGGAGATCAAGACCTGCTGGAACAAGATCCTGATGGGCACCAAG

GAGCATAGCGGCACAACCAACACAGTCGCTGCCTATAACCTCACTTGGAA

GAGCACCAACTTCAAAACCATCCTCGAATGGGAACCCAAACCCGTTAACC

AAGTTTACACCGTGCAGATCAGCACCAAGTCCGGCGACTGGAAGTCCAAA

TGTTTCTATACCACCGACACCGAGTGCGATCTCACCGATGAGATCGTGAA

AGATGTGAAACAGACCTACCTCGCCCGGGTGTTTAGCTACCCCGCCGGCA

ATGTGGAGAGCACTGGTTCCGCTGGCGAGCCTTTATACGAGAACAGCCCC

GAATTTACCCCTTACCTCGAGACCAATTTAGGACAGCCCACCATCCAAAG

CTTTGAGCAAGTTGGCACAAAGGTGAATGTGACAGTGGAGGACGAGCGGA

CTTTAGTGCGGCGGAACAACACCTTTCTCAGCCTCCGGGATGTGTTCGGC

AAAGATTTAATCTACACACTGTATTACTGGAAGTCCTCTTCCTCCGGCAA

GAAGACAGCTAAAACCAACACAAACGAGTTTTTAATCGACGTGGATAAAG

GCGAAAACTACTGTTTCAGCGTGCAAGCTGTGATCCCCTCCCGGACCGTG

AATAGGAAAAGCACCGATAGCCCCGTTGAGTGCATGGGCCAAGAAAAGGG

CGAGTTCCGGGAGAACTGGGTGAACGTCATCAGCGATTTAAAGAAGATCG

AAGATTTAATTCAGTCCATGCATATCGACGCCACTTTATACACAGAATCC

GACGTGCACCCCTCTTGTAAGGTGACCGCCATGAAATGTTTTTTACTGGA

GCTGCAAGTTATCTCTTTAGAGAGCGGAGACGCTAGCATCCACGACACCG

TGGAGAATTTAATCATTTTAGCCAATAACTCTTTATCCAGCAACGGCAAC

GTGACAGAGTCCGGCTGCAAGGAGTGCGAAGAGCTGGAGGAGAAGAACAT

CAAGGAGTTTCTGCAATCCTTTGTGCACATTGTCCAGATGTTCATCAATA

CCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 106)
MKWVTFISLLFLFSSAYSDCDIEGKDGKQYESVLMVSIDQLLDSMKEIGS
NCLNNEFNFFKRHICDANKEGMFLFRAARKLRQFLKMNSTGDFDLHLLKV
SEGTTILLNCTGQVKGRKPAALGEAQPTKSLEENKSLKEQKKLNDLCFLK
RLLQEIKTCWNKILMGTKEHSGTTNTVAAYNLTWKSTNFKTILEWEPKPV
NQVYTVQISTKSGDWKSKCFYTTDTECDLTDEIVKDVKQTYLARVFSYPA
GNVESTGSAGEPLYENSPEFTPYLETNLGQPTIQSFEQVGTKVNVTVEDE
RTLVRRNNTFLSLRDVFGKDLIYTLYYWKSSSSGKKTAKTNTNEFLIDVD
KGENYCFSVQAVIPSRTVNRKSTDSPVECMGQEKGEFRENWVNVISDLKK
IEDLIQSMHIDATLYTESDVHPSCKVTAMKCFLLELQVISLESGDASIHD
TVENLIILANNSLSSNGNVTESGCKECEELEEKNIKEFLQSFVHIVQMFI
NTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 107)
ATGAAGTGGGTGACCTTCATCAGCCTGCTGTTCCTGTTCTCCAGCGCCTA
CTCCGATTGCGACATCGAGGGCAAGGACGGCAAGCAGTACGAGAGCGTGC
TGATGGTGTCCATCGACCAGCTGCTGGACAGCATGAAGGAGATCGGCTCC
AACTGCCTCAACAACGAGTTCAACTTCTTCAAGCGGCACATCTGCGACGC
CAACAAGGAGGGCATGTTCCTGTTCAGGGCCGCCAGGAAACTGCGGCAGT
TCCTGAAGATGAACTCCACCGGCGACTTCGACCTGCACCTGCTGAAGGTG
TCCGAGGGCACCACCATCCTGCTGAACTGCACCGGACAGGTGAAGGGCCG
GAAACCTGCTGCTCTGGGAGAGGCCCAACCCACCAAGAGCCTGGAGGAGA
ACAAGTCCCTGAAGGAGCAGAAGAAGCTGAACGACCTGTGCTTCCTGAAG
AGGCTGCTGCAGGAGATCAAGACCTGCTGGAACAAGATCCTGATGGGCAC
CAAGGAGCATAGCGGCACAACCAACACAGTCGCTGCCTATAACCTCACTT
GGAAGAGCACCAACTTCAAAACCATCCTCGAATGGGAACCCAAACCCGTT
AACCAAGTTTACACCGTGCAGATCAGCACCAAGTCCGGCGACTGGAAGTC
CAAATGTTTCTATACCACCGACACCGAGTGCGATCTCACCGATGAGATCG
TGAAAGATGTGAAACAGACCTACCTCGCCCGGGTGTTTAGCTACCCCGCC
GGCAATGTGGAGAGCACTGGTTCCGCTGGCGAGCCTTTATACGAGAACAG
CCCCGAATTTACCCCTTACCTCGAGACCAATTTAGGACAGCCCACCATCC
AAAGCTTTGAGCAAGTTGGCACAAAGGTGAATGTGACAGTGGAGGACGAG
CGGACTTTAGTGCGGCGGAACAACACCTTTCTCAGCCTCCGGGATGTGTT
CGGCAAAGATTTAATCTACACACTGTATTACTGGAAGTCCTCTTCCTCCG
GCAAGAAGACAGCTAAAACCAACACAAACGAGTTTTTAATCGACGTGGAT
AAAGGCGAAAACTACTGTTTCAGCGTGCAAGCTGTGATCCCCTCCCGGAC
CGTGAATAGGAAAAGCACCGATAGCCCCGTTGAGTGCATGGGCCAAGAAA

-continued
AGGGCGAGTTCCGGGAGAACTGGGTGAACGTCATCAGCGATTTAAAGAAG
ATCGAAGATTTAATTCAGTCCATGCATATCGACGCCACTTTATACACAGA
ATCCGACGTGCACCCCTCTTGTAAGGTGACCGCCATGAAATGTTTTTTAC
TGGAGCTGCAAGTTATCTCTTTAGAGAGCGGAGACGCTAGCATCCACGAC
ACCGTGGAGAATTTAATCATTTTAGCCAATAACTCTTTATCCAGCAACGG
CAACGTGACAGAGTCCGGCTGCAAGGAGTGCGAAGAGCTGGAGGAGAAGA
ACATCAAGGAGTTTCTGCAATCCTTTGTGCACATTGTCCAGATGTTCATC
AATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 108)
QGQDRHMIRMRQLIDIVDQLKNYVNDLVPEFLPAPEDVETNCEWSAFSCF
QKAQLKSANTGNNERIINVSIKKLKRKPPSTNAGRRQKHRLTCPSCDSYE
KKPPKEFLERFKSLLQKMIHQHLSSRTHGSEDSITCPPPMSVEHADIWVK
SYSLYSRERYICNSGFKRKAGTSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 109)
CAGGGCCAGGACAGGCACATGATCCGGATGAGGCAGCTCATCGACATCGT
CGACCAGCTGAAGAACTACGTGAACGACCTGGTGCCCGAGTTTCTGCCTG
CCCCCGAGGACGTGGAGACCAACTGCGAGTGGTCCGCCTTCTCCTGCTTT
CAGAAGGCCCAGCTGAAGTCCGCCAACACCGGCAACAACGAGCGGATCAT
CAACGTGAGCATCAAGAAGCTGAAGCGGAAGCCTCCCTCCACAAACGCCG
GCAGGAGGCAGAAGCACAGGCTGACCTGCCCCAGCTGTGACTCCTACGAG
AAGAAGCCCCCCAAGGAGTTCCTGGAGAGGTTCAAGTCCCTGCTGCAGAA
GATGATCCATCAGCACCTGTCCTCCAGGACCCACGGCTCCGAGGACTCCA
TTACATGCCCCCCTCCCATGAGCGTGGAGCACGCCGACATCTGGGTGAAG
AGCTATAGCCTCTACAGCCGGGAGAGGTATATCTGTAACAGCGGCTTCAA
GAGGAAGGCCGGCACCAGCAGCCTCACCGAGTGCGTGCTGAATAAGGCTA
CCAACGTGGCTCACTGGACAACACCCTCTTTAAAGTGCATCCGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 110)
MKWVTFISLLFLFSSAYSQGQDRHMIRMRQLIDIVDQLKNYVNDLVPEFL
PAPEDVETNCEWSAFSCFQKAQLKSANTGNNERIINVSIKKLKRKPPSTN
AGRRQKHRLTCPSCDSYEKKPPKEFLERFKSLLQKMIHQHLSSRTHGSED
SITCPPPMSVEHADIWVKSYSLYSRERYICNSGFKRKAGTSSLTECVLNK
ATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 111)
ATGAAGTGGGTGACCTTCATCAGCCTGCTGTTCCT
GTTCTCCAGCGCCTACTCCCAGGGCCAGGACAGGC
ACATGATCCGGATGAGGCAGCTCATCGACATCGTC
GACCAGCTGAAGAACTACGTGAACGACCTGGTGCC
CGAGTTTCTGCCTGCCCCCGAGGACGTGGAGACCA
ACTGCGAGTGGTCCGCCTTCTCCTGCTTTCAGAAG
GCCCAGCTGAAGTCCGCCAACACCGGCAACAACGA
GCGGATCATCAACGTGAGCATCAAGAAGCTGAAGC
GGAAGCCTCCCTCCACAAACGCCGGCAGGAGGCAG
AAGCACAGGCTGACCTGCCCCAGCTGTGACTCCTA
CGAGAAGAAGCCCCCCAAGGAGTTCCTGGAGAGGT
TCAAGTCCCTGCTGCAGAAGATGATCCATCAGCAC
CTGTCCTCCAGGACCCACGGCTCCGAGGACTCCAT
TACATGCCCCCCTCCCATGAGCGTGGAGCACGCCG
ACATCTGGGTGAAGAGCTATAGCCTCTACAGCCGG
GAGAGGTATATCTGTAACAGCGGCTTCAAGAGGAA
GGCCGGCACCAGCAGCCTCACCGAGTGCGTGCTGA
ATAAGGCTACCAACGTGGCTCACTGGACAACACCC
TCTTTAAAGTGCATCCGG.

Exemplary Multi-Chain Chimeric Polypeptides—Type E

In some embodiments of any of the multi-chain chimeric polypeptides described herein, the first target-binding domain and the second targeting-binding domain each independently bind specifically to a receptor for IL-18 (e.g., a soluble human IL-18), a receptor for IL-12 (e.g., a soluble human IL-12), or CD16 (e.g., an anti-CD16 scFv). In some embodiments of these multi-chain chimeric polypeptides described herein, the first chimeric polypeptide further includes the additional target-binding domain. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 or a receptor for IL-12.

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or more of the first target-binding domain, the second target-binding domain and the additional antigen-binding domain is an agonistic antigen-binding domain. In some embodiments of these multi-chain chimeric polypeptides, the first target-binding domain, the second target-binding domain, and the additional antigen-binding domain are each agonistic antigen-binding domains. In some embodiments of these multi-chain chimeric polypeptides, the antigen-binding domain includes a scFv or single-domain antibody.

In some embodiments of these multi-chain chimeric polypeptides, one or both of the first target-binding domain and the second target-binding domain is a soluble IL-15 or a soluble IL-18. In some embodiments of these multi-chain chimeric polypeptides, the first target-binding domain and the second target-binding domain are each independently a soluble IL-15 or a soluble IL-18. In some embodiments of these multi-chain chimeric polypeptides, the first target-binding domain and the second target-binding domain both bind specifically to a receptor of IL-18 or a receptor of IL-12. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-12, and the second target-binding domain binds specifically to a receptor for IL-18. In some embodiments of these multi-chain chimeric polypeptides, the first target-binding domain binds specifically to a receptor for IL-18, and the second target-binding domain bind specifically to a receptor for IL-12. In some embodiments of these multi-chain chimeric polypeptides, the first target-binding domain binds specifically to CD16, and the second target-binding domain binds specifically to a receptor for IL-18. In some embodiments of these multi-chain chimeric polypeptides, the first target-binding domain binds specifically to a receptor for IL-18, and the second target-binding domain bind specifically to CD16.

In some embodiments of these multi-chain chimeric polypeptides, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence.

In some embodiments of these multi-chain chimeric polypeptides, the first target-binding domain includes a soluble IL-18 (e.g., a soluble human IL-18).

In some embodiments of these multi-chain chimeric polypeptides, the soluble human IL-18 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 16)

```
YFGKLESKLSVIRNLNDQVLFIDQGNRPLFEDMTD

SDCRDNAPRTIFIISMYKDSQPRGMAVTISVKCEK

ISTLSCENKIISFKEMNPPDNIKDTKSDIIFFQRS

VPGHDNKMQFESSSYEGYFLACEKERDLFKLILKK

EDELGDRSIMFTVQNED.
```

In some embodiments of these multi-chain chimeric polypeptides, the soluble human IL-18 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 65)

```
TACTTCGGCAAACTGGAATCCAAGCTGAGCGTGAT

CCGGAATTTAAACGACCAAGTTCTGTTTATCGATC

AAGGTAACCGGCCTCTGTTCGAGGACATGACCGAC

TCCGATTGCCGGGACAATGCCCCCCGGACCATCTT

CATTATCTCCATGTACAAGGACAGCCAGCCCCGGG

GCATGGCTGTGACAATTAGCGTGAAGTGTGAGAAA

ATCAGCACTTTATCTTGTGAGAACAAGATCATCTC

CTTTAAGGAAATGAACCCCCCCGATAACATCAAGG

ACACCAAGTCCGATATCATCTTCTTCCAGCGGTCC

GTGCCCGGTCACGATAACAAGATGCAGTTCGAATC

CTCCTCCTACGAGGGCTACTTTTTAGCTTGTGAAA

AGGAGAGGGATTTATTCAAGCTGATCCTCAAGAAG

GAGGACGAGCTGGGCGATCGTTCCATCATGTTCAC

CGTCCAAAACGAGGAT.
```

In some embodiments of these multi-chain chimeric polypeptides, the second target-binding domain includes a soluble IL-12 (e.g., a soluble human IL-12). In some embodiments of these multi-chain chimeric polypeptides, the soluble human IL-15 includes a sequence of soluble human IL-12β (p40) and a sequence of soluble human IL-12α (p35). In some embodiments of these multi-chain chimeric polypeptides, the soluble IL-15 (e.g., soluble human IL-15) further includes a linker sequence (e.g., any of the exemplary linker sequences described herein) between the sequence of soluble IL-12β (p40) and the sequence of soluble human IL-12α (p35). In some examples of these multi-chain chimeric polypeptides, the linker sequence comprises GGGGSGGGGSGGGGS (SEQ ID NO: 7).

In some embodiments of these multi-chain chimeric polypeptides, the sequence of soluble human IL-12β (p40) comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 66)

```
IWELKKDVYVVELDWYPDAPGEMVVLTCDTPEEDG

ITWTLDQSSEVLGSGKTLTIQVKEFGDAGQYTCHK

GGEVLSHSLLLLHKKEDGIWSTDILKDQKEPKNKT

FLRCEAKNYSGRFTCWWLTTISTDLTF SVKSSRG

S SDPQGVTCGAATLS AERVRGDNKEYEYSVECQ

EDSACPAAEESLPIEVMVDAVHKLKYENYTSSFFI

RDIIKPDPPKNLQLKPLKNSRQVEVSWEYPDTWST
```

-continued

PHSYFSLTFCVQVQGKSKREKKDRVFTDKTSATVI

CRKNASISVRAQDRYYSSSWSEWASVPCS

In some embodiments of these multi-chain chimeric polypeptides, the soluble human IL-12β (p40) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 67)

ATTTGGGAACTGAAGAAGGACGTCTACGTGGTCGA

ACTGGACTGGTATCCCGATGCTCCCGGCGAAATGG

TGGTGCTCACTTGTGACACCCCCGAAGAAGACGGC

ATCACTTGGACCCTCGATCAGAGCAGCGAGGTGCT

GGGCTCCGGAAAGACCCTCACAATCCAAGTTAAGG

AGTTCGGAGACGCTGGCCAATACACATGCCACAAG

GGAGGCGAGGTGCTCAGCCATTCCTTATTATTATT

ACACAAGAAGGAAGACGGAATCTGGTCCACCGACA

TTTTAAAAGATCAGAAGGAGCCCAAGAATAAGACC

TTTTTAAGGTGTGAGGCCAAAAACTACAGCGGTCG

TTTCACTTGTTGGTGGCTGACCACCATTTCCACCG

ATTTAACCTTCTCCGTGAAAAGCAGCCGGGGAAGC

TCCGACCCTCAAGGTGTGACATGTGGAGCCGCTAC

CCTCAGCGCTGAGAGGGTTCGTGGCGATAACAAGG

AATACGAGTACAGCGTGGAGTGCCAAGAAGATAGC

GCTTGTCCCGCTGCCGAAGAATCTTTACCCATTGA

GGTGATGGTGGACGCCGTGCACAAACTCAAGTACG

AGAACTACACCTCCTCCTTCTTTATCCGGGACATC

ATTAAGCCCGATCCTCCTAAGAATTTACAGCTGAA

GCCTCTCAAAAATAGCCGGCAAGTTGAGGTCTCTT

GGGAATATCCCGACACTTGGAGCACACCCCACAGC

TACTTCTCTTTAACCTTTTGTGTGCAAGTTCAAGG

TAAAAGCAAGCGGGAGAAGAAAGACCGGGTGTTTA

CCGACAAAACCAGCGCCACCGTCATCTGTCGGAAG

AACGCCTCCATCAGCGTGAGGGCTCAAGATCGTTA

TTACTCCAGCAGCTGGTCCGAGTGGGCCAGCGTGC

CTTGTTCC.

In some embodiments of these multi-chain chimeric polypeptides, the soluble human IL-12α (p35) includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 68)

RNLPVATPDPGMFPCLHHSQNLLRAVSNMLQKARQ

TLEFYPCTSEEIDHEDITKDKTSTVEACLPLELTK

NESCLNSRETSFITNGSCLASRKTSFMMALCLSSI

YEDLKMYQVEFKTMNAKLLMDPKRQIFLDQNMLAV

IDELMQALNFNSETVPQKSSLEEPDFYKTKIKLCI

LLHAFRIRAVTIDRVMSYLNAS.

In some embodiments of these multi-chain chimeric polypeptides, the soluble human IL-12α (p35) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 69)

CGTAACCTCCCCGTGGCTACCCCCGATCCCGGAAT

GTTCCCTTGTTTACACCACAGCCAGAATTTACTGA

GGGCCGTGAGCAACATGCTGCAGAAAGCTAGGCAG

ACTTTAGAATTTTACCCTTGCACCAGCGAGGAGAT

CGACCATGAAGATATCACCAAGGACAAGACATCCA

CCGTGGAGGCTTGTTTACCTCTGGAGCTGACAAAG

AACGAGTCTTGTCTCAACTCTCGTGAAACCAGCTT

CATCACAAATGGCTCTTGTTTAGCTTCCCGGAAGA

CCTCCTTTATGATGGCTTTATGCCTCAGCTCCATC

TACGAGGATTTAAAGATGTACCAAGTGGAGTTCAA

GACCATGAACGCCAAGCTGCTCATGGACCCTAAAC

GGCAGATCTTTTTAGACCAGAACATGCTGGCTGTG

ATTGATGAGCTGATGCAAGCTTTAAACTTCAACTC

CGAGACCGTCCCTCAGAAGTCCTCCCTCGAGGAGC

CCGATTTTTACAAGACAAAGATCAAACTGTGCATT

TTACTCCACGCCTTTAGGATCCGGGCCGTGACCAT

TGACCGGGTCATGAGCTATTTAAACGCCAGC.

In some embodiments of these multi-chain chimeric polypeptides, the additional target-binding domain includes an scFv that specifically binds to CD16 (e.g., an anti-CD16 scFv).

In some embodiments of these multi-chain chimeric polypeptides, the scFv that binds specifically to CD16 includes a light chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 112)
SELTQDPAVSVALGQTVRITCQGDSLRSYYASWYQ

QKPGQAPVLVIYGKNNRPSGIPDRFSGSSSGNTAS

LTITGAQAEDEADYYCNSRDSSGNHVVFGGGTKLT

VGH

In some embodiments of these multi-chain chimeric polypeptides, the scFv that binds specifically to CD16 is encoded by a light chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 113)
TCCGAGCTGACCCAGGACCCTGCTGTGTCCGTGGC

TCTGGGCCAGACCGTGAGGATCACCTGCCAGGGCG

ACTCCCTGAGGTCCTACTACGCCTCCTGGTACCAG

CAGAAGCCCGGCCAGGCTCCTGTGCTGGTGATCTA

CGGCAAGAACAACAGGCCCTCCGGCATCCCTGACA

GGTTCTCCGGATCCTCCTCCGGCAACACCGCCTCC

CTGACCATCACAGGCGCTCAGGCCGAGGACGAGGC

TGACTACTACTGCAACTCCAGGGACTCCTCCGGCA

ACCATGTGGTGTTCGGCGGCGGCACCAAGCTGACC

GTGGGCCAT.

In some embodiments of these multi-chain chimeric polypeptides, the scFv that binds specifically to CD16 includes a heavy chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 114)
EVQLVESGGGVVRPGGSLRLSCAASGFTFDDYGMS

WVRQAPGKGLEWVSGINWNGGSTGYADSVKGRFTI

SRDNAKNSLYLQMNSLRAEDTAVYYCARGRSLLFD

YWGQGTLVTVSR.

In some embodiments of these multi-chain chimeric polypeptides, the scFv that binds specifically to CD16 is encoded by a heavy chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 115)
GAGGTGCAGCTGGTGGAGTCCGGAGGAGGAGTGGT

GAGGCCTGGAGGCTCCCTGAGGCTGAGCTGTGCTG

-continued

CCTCCGGCTTCACCTTCGACGACTACGGCATGTCC

TGGGTGAGGCAGGCTCCTGGAAAGGGCCTGGAGTG

GGTGTCCGGCATCAACTGGAACGGCGGATCCACCG

GCTACGCCGATTCCGTGAAGGGCAGGTTCACCATC

AGCAGGGACAACGCCAAGAACTCCCTGTACCTGCA

GATGAACTCCCTGAGGGCCGAGGACACCGCCGTGT

ACTACTGCGCCAGGGGCAGGTCCCTGCTGTTCGAC

TACTGGGGACAGGGCACCCTGGTGACCGTGTCCAG

G.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 116)
YFGKLESKLSVIRNLNDQVLFIDQGNRPLFEDMTD

SDCRDNAPRTIFIISMYKDSQPRGMAVTISVKCEK

ISTLSCENKIISFKEMNPPDNIKDTKSDIIFFQRS

VPGHDNKMQFESSSYEGYFLACEKERDLFKLILKK

EDELGDRSIMFTVQNEDSGTTNTVAAYNLTWKSTN

FKTILEWEPKPVNQVYTVQISTKSGDWKSKCFYTT

DTECDLTDEIVKDVKQTYLARVFSYPAGNVESTGS

AGEPLYENSPEFTPYLETNLGQPTIQSFEQVGTKV

NVTVEDERTLVRRNNTFLSLRDVFGKDLIYTLYYW

KSSSSGKKTAKTNTNEFLIDVDKGENYCFSVQAVI

PSRTVNRKSTDSPVECMGQEKGEFRENWVNVISDL

KKIEDLIQSMHIDATLYTESDVHPSCKVTAMKCFL

LELQVISLESGDASIHDTVENLIILANNSLSSNGN

VTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 117)
TACTTCGGCAAACTGGAATCCAAGCTGAGCGTGAT

CCGGAATTTAAACGACCAAGTTCTGTTTATCGATC

AAGGTAACCGGCCTCTGTTCGAGGACATGACCGAC

TCCGATTGCCGGGACAATGCCCCCCGGACCATCTT

CATTATCTCCATGTACAAGGACAGCCAGCCCCGGG

GCATGGCTGTGACAATTAGCGTGAAGTGTGAGAAA

-continued

ATCAGCACTTTATCTTGTGAGAACAAGATCATCTC
CTTTAAGGAAATGAACCCCCCCGATAACATCAAGG
ACACCAAGTCCGATATCATCTTCTTCCAGCGGTCC
GTGCCCGGTCACGATAACAAGATGCAGTTCGAATC
CTCCTCCTACGAGGGCTACTTTTTAGCTTGTGAAA
AGGAGAGGGATTTATTCAAGCTGATCCTCAAGAAG
GAGGACGAGCTGGGCGATCGTTCCATCATGTTCAC
CGTCCAAAACGAGGATAGCGGCACAACCAACACAG
TCGCTGCCTATAACCTCACTTGGAAGAGCACCAAC
TTCAAAACCATCCTCGAATGGGAACCCAAACCCGT
TAACCAAGTTTACACCGTGCAGATCAGCACCAAGT
CCGGCGACTGGAAGTCCAAATGTTTCTATACCACC
GACACCGAGTGCGATCTCACCGATGAGATCGTGAA
AGATGTGAAACAGACCTACCTCGCCCGGGTGTTTA
GCTACCCCGCCGGCAATGTGGAGAGCACTGGTTCC
GCTGGCGAGCCTTTATACGAGAACAGCCCCGAATT
TACCCCTTACCTCGAGACCAATTTAGGACAGCCCA
CCATCCAAAGCTTTGAGCAAGTTGGCACAAAGGTG
AATGTGACAGTGGAGGACGAGCGGACTTTAGTGCG
GCGGAACAACACCTTTCTCAGCCTCCGGGATGTGT
TCGGCAAAGATTTAATCTACACACTGTATTACTGG
AAGTCCTCTTCCTCCGGCAAGAAGACAGCTAAAAC
CAACACAAACGAGTTTTTAATCGACGTGGATAAAG
GCGAAAACTACTGTTTCAGCGTGCAAGCTGTGATC
CCCTCCCGGACCGTGAATAGGAAAAGCACCGATAG
CCCCGTTGAGTGCATGGGCCAAGAAAAGGGCGAGT
TCCGGGAGAACTGGGTGAACGTCATCAGCGATTTA
AAGAAGATCGAAGATTTAATTCAGTCCATGCATAT
CGACGCCACTTTATACACAGAATCCGACGTGCACC
CCTCTTGTAAGGTGACCGCCATGAAATGTTTTTTA
CTGGAGCTGCAAGTTATCTCTTTAGAGAGCGGAGA
CGCTAGCATCCACGACACCGTGGAGAATTTAATCA
TTTTAGCCAATAACTCTTTATCCAGCAACGGCAAC
GTGACAGAGTCCGGCTGCAAGGAGTGCGAAGAGCT
GGAGGAGAAGAACATCAAGGAGTTTCTGCAATCCT
TTGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 118)

MKWVTFISLLFLFSSAYSYFGKLESKLSVIRNLND
QVLFIDQGNRPLFEDMTDSDCRDNAPRTIFIISMY
KDSQPRGMAVTISVKCEKISTLSCENKIISFKEMN
PPDNIKDTKSDIIFFQRSVPGHDNKMQFESSSYEG
YFLACEKERDLFKLILKKEDELGDRSIMFTVQNED
SGTTNTVAAYNLTWKSTNFKTILEWEPKPVNQVYT
VQISTKSGDWKSKCFYTTDTECDLTDEIVKDVKQT
YLARVFSYPAGNVESTGSAGEPLYENSPEFTPYLE
TNLGQPTIQSFEQVGTKVNVTVEDERTLVRRNNTF
LSLRDVFGKDLIYTLYYWKS S S SGKKTAKTNT
NEFLIDVDKGENYCF SVQAVIPSRTVNRKSTDSP
VECMGQEKGEFRENWVNVISDLKKIEDLIQSMHID
ATLYTESDVHPSCKVTAMKCFLLELQVISLESGDA
SIHDTVENLIILANNSLSSNGNVTESGCKECEELE
EKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 119)

ATGAAGTGGGTCACATTTATCTCTTTACTGTTCCT
CTTCTCCAGCGCCTACAGCTACTTCGGCAAACTGG
AATCCAAGCTGAGCGTGATCCGGAATTTAAACGAC
CAAGTTCTGTTTATCGATCAAGGTAACCGGCCTCT
GTTCGAGGACATGACCGACTCCGATTGCCGGGACA
ATGCCCCCCGGACCATCTTCATTATCTCCATGTAC
AAGGACAGCCAGCCCCGGGGCATGGCTGTGACAAT
TAGCGTGAAGTGTGAGAAAATCAGCACTTTATCTT
GTGAGAACAAGATCATCTCCTTTAAGGAAATGAAC
CCCCCCGATAACATCAAGGACACCAAGTCCGATAT
CATCTTCTTCCAGCGGTCCGTGCCCGGTCACGATA
ACAAGATGCAGTTCGAATCCTCCTCCTACGAGGGC
TACTTTTTAGCTTGTGAAAAGGAGAGGGATTTATT
CAAGCTGATCCTCAAGAAGGAGGACGAGCTGGGCG
ATCGTTCCATCATGTTCACCGTCCAAAACGAGGAT
AGCGGCACAACCAACACAGTCGCTGCCTATAACCT
CACTTGGAAGAGCACCAACTTCAAAACCATCCTCG
AATGGGAACCCAAACCCGTTAACCAAGTTTACACC
GTGCAGATCAGCACCAAGTCCGGCGACTGGAAGTC

-continued

CAAATGTTTCTATACCACCGACACCGAGTGCGATC
TCACCGATGAGATCGTGAAAGATGTGAAACAGACC
TACCTCGCCCGGGTGTTTAGCTACCCCGCCGGCAA
TGTGGAGAGCACTGGTTCCGCTGGCGAGCCTTTAT
ACGAGAACAGCCCCGAATTTACCCCTTACCTCGAG
ACCAATTTAGGACAGCCCACCATCCAAAGCTTTGA
GCAAGTTGGCACAAAGGTGAATGTGACAGTGGAGG
ACGAGCGGACTTTAGTGCGGCGGAACAACACCTTT
CTCAGCCTCCGGGATGTGTTCGGCAAAGATTTAAT
CTACACACTGTATTACTGGAAGTCCTCTTCCTCCG
GCAAGAAGACAGCTAAAACCAACACAAACGAGTTT
TTAATCGACGTGGATAAAGGCGAAAACTACTGTTT
CAGCGTGCAAGCTGTGATCCCCTCCCGGACCGTGA
ATAGGAAAAGCACCGATAGCCCCGTTGAGTGCATG
GGCCAAGAAAAGGGCGAGTTCCGGGAGAACTGGGT
GAACGTCATCAGCGATTTAAAGAAGATCGAAGATT
TAATTCAGTCCATGCATATCGACGCCACTTTATAC
ACAGAATCCGACGTGCACCCCTCTTGTAAGGTGAC
CGCCATGAAATGTTTTTTACTGGAGCTGCAAGTTA
TCTCTTTAGAGAGCGGAGACGCTAGCATCCACGAC
ACCGTGGAGAATTTAATCATTTTAGCCAATAACTC
TTTATCCAGCAACGGCAACGTGACAGAGTCCGGCT
GCAAGGAGTGCGAAGAGCTGGAGGAGAAGAACATC
AAGGAGTTTCTGCAATCCTTTGTGCACATTGTCCA
GATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 120)
IWELKKDVYVVELDWYPDAPGEMVVLTCDTPEEDG
ITWTLDQSSEVLGSGKTLTIQVKEFGDAGQYTCHK
GGEVLSHSLLLLHKKEDGIWSTDILKDQKEPKNKT
FLRCEAKNYSGRFTCWWLTTISTDLTFSVKSSRGS
SDPQGVTCGAATLSAERVRGDNKEYEYSVECQEDS
ACPAAEESLPIEVMVDAVHKLKYENYTSSFFIRDI
IKPDPPKNLQLKPLKNSRQVEVSWEYPDTWSTPHS
YFSLTFCVQVQGKSKREKKDRVFTDKTSATVICRK
NASISVRAQDRYYSSSWSEWASVPCSGGGGSGGGG
SGGGGSRNLPVATPDPGMFPCLHHSQNLLRAVSNM

-continued

LQKARQTLEFYPCTSEEIDHEDITKDKTSTVEACL
PLELTKNESCLNSRETSFITNGSCLASRKTSFMMA
LCLSSIYEDLKMYQVEFKTMNAKLLMDPKRQIFLD
QNMLAVIDELMQALNFNSETVPQKSSLEEPDFYKT
KIKLCILLHAFRIRAVTIDRVMSYLNASITCPPPM
SVEHADIWVKSYSLYSRERYICNSGFKRKAGTSSL
TECVLNKATNVAHWTTPSLKCIRSELTQDPAVSVA
LGQTVRITCQGDSLRSYYASWYQQKPGQAPVLVIY
GKNNRPSGIPDRFSGSSSGNTASLTITGAQAEDEA
DYYCNSRDSSGNHVVFGGGTKLTVGHGGGGSGGGG
SGGGGSEVQLVESGGGVVRPGGSLRLSCAASGFTF
DDYGMSWVRQAPGKGLEWVSGINWNGGSTGYADSV
KGRFTISRDNAKNSLYLQMNSLRAEDTAVYYCARG
RSLLFDYWGQGTLVTVSR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 121)
ATTTGGGAACTGAAGAAGGACGTCTACGTGGTCGA
ACTGGACTGGTATCCCGATGCTCCCGGCGAAATGG
TGGTGCTCACTTGTGACACCCCCGAAGAAGACGGC
ATCACTTGGACCCTCGATCAGAGCAGCGAGGTGCT
GGGCTCCGGAAAGACCCTCACAATCCAAGTTAAGG
AGTTCGGAGACGCTGGCCAATACACATGCCACAAG
GGAGGCGAGGTGCTCAGCCATTCCTTATTATTATT
ACACAAGAAGGAAGACGGAATCTGGTCCACCGACA
TTTTAAAAGATCAGAAGGAGCCCAAGAATAAGACC
TTTTTAAGGTGTGAGGCCAAAAACTACAGCGGTCG
TTTCACTTGTTGGTGGCTGACCACCATTTCCACCG
ATTTAACCTTCTCCGTGAAAAGCAGCCGGGGAAGC
TCCGACCCTCAAGGTGTGACATGTGGAGCCGCTAC
CCTCAGCGCTGAGAGGGTTCGTGGCGATAACAAGG
AATACGAGTACAGCGTGGAGTGCCAAGAAGATAGC
GCTTGTCCCGCTGCCGAAGAATCTTTACCCATTGA
GGTGATGGTGGACGCCGTGCACAAACTCAAGTACG
AGAACTACACCTCCTCCTTCTTTATCCGGGACATC
ATTAAGCCCGATCCTCCTAAGAATTTACAGCTGAA
GCCTCTCAAAAATAGCCGGCAAGTTGAGGTCTCTT

-continued

GGGAATATCCCGACACTTGGAGCACACCCCACAGC
TACTTCTCTTTAACCTTTTGTGTGCAAGTTCAAGG
TAAAAGCAAGCGGGAGAAGAAAGACCGGGTGTTTA
CCGACAAAACCAGCGCCACCGTCATCTGTCGGAAG
AACGCCTCCATCAGCGTGAGGGCTCAAGATCGTTA
TTACTCCAGCAGCTGGTCCGAGTGGGCCAGCGTGC
CTTGTTCCGGCGGTGGAGGATCCGGAGGAGGTGGC
TCCGGCGGCGGAGGATCTCGTAACCTCCCCGTGGC
TACCCCCGATCCCGGAATGTTCCCTTGTTTACACC
ACAGCCAGAATTTACTGAGGGCCGTGAGCAACATG
CTGCAGAAAGCTAGGCAGACTTTAGAATTTTACCC
TTGCACCAGCGAGGAGATCGACCATGAAGATATCA
CCAAGGACAAGACATCCACCGTGGAGGCTTGTTTA
CCTCTGGAGCTGACAAAGAACGAGTCTTGTCTCAA
CTCTCGTGAAACCAGCTTCATCACAAATGGCTCTT
GTTTAGCTTCCCGGAAGACCTCCTTTATGATGGCT
TTATGCCTCAGCTCCATCTACGAGGATTTAAAGAT
GTACCAAGTGGAGTTCAAGACCATGAACGCCAAGC
TGCTCATGGACCCTAAACGGCAGATCTTTTTAGAC
CAGAACATGCTGGCTGTGATTGATGAGCTGATGCA
AGCTTTAAACTTCAACTCCGAGACCGTCCCTCAGA
AGTCCTCCCTCGAGGAGCCCGATTTTTACAAGACA
AAGATCAAACTGTGCATTTTACTCCACGCCTTTAG
GATCCGGGCCGTGACCATTGACCGGGTCATGAGCT
ATTTAAACGCCAGCATTACATGCCCCCCTCCCATG
AGCGTGGAGCACGCCGACATCTGGGTGAAGAGCTA
TAGCCTCTACAGCCGGGAGAGGTATATCTGTAACA
GCGGCTTCAAGAGGAAGGCCGGCACCAGCAGCCTC
ACCGAGTGCGTGCTGAATAAGGCTACCAACGTGGC
TCACTGGACAACACCCTCTTTAAAGTGCATCCGGT
CCGAGCTGACCCAGGACCCTGCTGTGTCCGTGGCT
CTGGGCCAGACCGTGAGGATCACCTGCCAGGGCGA
CTCCCTGAGGTCCTACTACGCCTCCTGGTACCAGC
AGAAGCCCGGCCAGGCTCCTGTGCTGGTGATCTAC
GGCAAGAACAACAGGCCCTCCGGCATCCCTGACAG
GTTCTCCGGATCCTCCTCCGGCAACACCGCCTCCC
TGACCATCACAGGCGCTCAGGCCGAGGACGAGGCT
GACTACTACTGCAACTCCAGGGACTCCTCCGGCAA
CCATGTGGTGTTCGGCGGCGGCACCAAGCTGACCG
TGGGCCATGGCGGCGGCGGCTCCGGAGGCGGCGGC
AGCGGCGGAGGAGGATCCGAGGTGCAGCTGGTGGA

-continued

GTCCGGAGGAGGAGTGGTGAGGCCTGGAGGCTCCC
TGAGGCTGAGCTGTGCTGCCTCCGGCTTCACCTTC
GACGACTACGGCATGTCCTGGGTGAGGCAGGCTCC
TGGAAAGGGCCTGGAGTGGGTGTCCGGCATCAACT
GGAACGGCGGATCCACCGGCTACGCCGATTCCGTG
AAGGGCAGGTTCACCATCAGCAGGGACAACGCCAA
GAACTCCCTGTACCTGCAGATGAACTCCCTGAGGG
CCGAGGACACCGCCGTGTACTACTGCGCCAGGGGC
AGGTCCCTGCTGTTCGACTACTGGGGACAGGGCAC
CCTGGTGACCGTGTCCAGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 122)
MKWVTFISLLFLFSSAYSIWELKKDVYVVELDWYP
DAPGEMVVLTCDTPEEDGITWTLDQSSEVLGSGKT
LTIQVKEFGDAGQYTCHKGGEVLSHSLLLLHKKED
GIWSTDILKDQKEPKNKTFLRCEAKNYSGRFTCWW
LTTISTDLTFSVKSSRGSSDPQGVTCGAATLSAER
VRGDNKEYEYSVECQEDSACPAAEESLPIEVMVDA
VHKLKYENYTSSFFIRDIIKPDPPKNLQLKPLKNS
RQVEVSWEYPDTWSTPHSYFSLTFCVQVQGKSKRE
KKDRVFTDKTSATVICRKNASISVRAQDRYYSSSW
SEWASVPCSGGGGSGGGGSGGGGSRNLPVATPDPG
MFPCLHHSQNLLRAVSNMLQKARQTLEFYPCTSEE
IDHEDITKDKTSTVEACLPLELTKNESCLNSRETS
FITNGSCLASRKTSFMMALCLSSIYEDLKMYQVEF
KTMNAKLLMDPKRQIFLDQNMLAVIDELMQALNFN
SETVPQKSSLEEPDFYKTKIKLCILLHAFRIRAVT
IDRVMSYLNASITCPPPMSVEHADIWVKSYSLYSR
ERYICNSGFKRKAGTSSLTECVLNKATNVAHWTTP
SLKCIRSELTQDPAVSVALGQTVRITCQGDSLRSY
YASWYQQKPGQAPVLVIYGKNNRPSGIPDRFSGSS
SGNTASLTITGAQAEDEADYYCNSRDSSGNHVVFG
GGTKLTVGHGGGGSGGGGSGGGGSEVQLVESGGGV

-continued

```
VRPGGSLRLSCAASGFTFDDYGMSWVRQAPGKGLE

WVSGINWNGGSTGYADSVKGRFTISRDNAKNSLYL

QMNSLRAEDTAVYYCARGRSLLFDYWGQGTLVTVS

R.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 123)
ATGAAATGGGTGACCTTTATTTCTTTACTGTTCCT

CTTTAGCAGCGCCTACTCCATTTGGGAACTGAAGA

AGGACGTCTACGTGGTCGAACTGGACTGGTATCCC

GATGCTCCCGGCGAAATGGTGGTGCTCACTTGTGA

CACCCCCGAAGAAGACGGCATCACTTGGACCCTCG

ATCAGAGCAGCGAGGTGCTGGGCTCCGGAAAGACC

CTCACAATCCAAGTTAAGGAGTTCGGAGACGCTGG

CCAATACACATGCCACAAGGGAGGCGAGGTGCTCA

GCCATTCCTTATTATTATTACACAAGAAGGAAGAC

GGAATCTGGTCCACCGACATTTTAAAAGATCAGAA

GGAGCCCAAGAATAAGACCTTTTTAAGGTGTGAGG

CCAAAAACTACAGCGGTCGTTTCACTTGTTGGTGG

CTGACCACCATTTCCACCGATTTAACCTTCTCCGT

GAAAAGCAGCCGGGGAAGCTCCGACCCTCAAGGTG

TGACATGTGGAGCCGCTACCCTCAGCGCTGAGAGG

GTTCGTGGCGATAACAAGGAATACGAGTACAGCGT

GGAGTGCCAAGAAGATAGCGCTTGTCCCGCTGCCG

AAGAATCTTTACCCATTGAGGTGATGGTGGACGCC

GTGCACAAACTCAAGTACGAGAACTACACCTCCTC

CTTCTTTATCCGGGACATCATTAAGCCCGATCCTC

CTAAGAATTTACAGCTGAAGCCTCTCAAAAATAGC

CGGCAAGTTGAGGTCTCTTGGGAATATCCCGACAC

TTGGAGCACACCCCACAGCTACTTCTCTTTAACCT

TTTGTGTGCAAGTTCAAGGTAAAAGCAAGCGGGAG

AAGAAAGACCGGGTGTTTACCGACAAAACCAGCGC

CACCGTCATCTGTCGGAAGAACGCCTCCATCAGCG

TGAGGGCTCAAGATCGTTATTACTCCAGCAGCTGG

TCCGAGTGGGCCAGCGTGCCTTGTTCCGGCGGTGG

AGGATCCGGAGGAGGTGGCTCCGGCGGCGGAGGAT

CTCGTAACCTCCCCGTGGCTACCCCCGATCCCGGA

ATGTTCCCTTGTTTACACCACAGCCAGAATTTACT
```

-continued

```
GAGGGCCGTGAGCAACATGCTGCAGAAAGCTAGGC

AGACTTTAGAATTTTACCCTTGCACCAGCGAGGAG

ATCGACCATGAAGATATCACCAAGGACAAGACATC

CACCGTGGAGGCTTGTTTACCTCTGGAGCTGACAA

AGAACGAGTCTTGTCTCAACTCTCGTGAAACCAGC

TTCATCACAAATGGCTCTTGTTTAGCTTCCCGGAA

GACCTCCTTTATGATGGCTTTATGCCTCAGCTCCA

TCTACGAGGATTTAAAGATGTACCAAGTGGAGTTC

AAGACCATGAACGCCAAGCTGCTCATGGACCCTAA

ACGGCAGATCTTTTTAGACCAGAACATGCTGGCTG

TGATTGATGAGCTGATGCAAGCTTTAAACTTCAAC

TCCGAGACCGTCCCTCAGAAGTCCTCCCTCGAGGA

GCCCGATTTTTACAAGACAAAGATCAAACTGTGCA

TTTTACTCCACGCCTTTAGGATCCGGGCCGTGACC

ATTGACCGGGTCATGAGCTATTTAAACGCCAGCAT

TACATGCCCCCCTCCCATGAGCGTGGAGCACGCCG

ACATCTGGGTGAAGAGCTATAGCCTCTACAGCCGG

GAGAGGTATATCTGTAACAGCGGCTTCAAGAGGAA

GGCCGGCACCAGCAGCCTCACCGAGTGCGTGCTGA

ATAAGGCTACCAACGTGGCTCACTGGACAACACCC

TCTTTAAAGTGCATCCGGTCCGAGCTGACCCAGGA

CCCTGCTGTGTCCGTGGCTCTGGGCCAGACCGTGA

GGATCACCTGCCAGGGCGACTCCCTGAGGTCCTAC

TACGCCTCCTGGTACCAGCAGAAGCCCGGCCAGGC

TCCTGTGCTGGTGATCTACGGCAAGAACAACAGGC

CCTCCGGCATCCCTGACAGGTTCTCCGGATCCTCC

TCCGGCAACACCGCCTCCCTGACCATCACAGGCGC

TCAGGCCGAGGACGAGGCTGACTACTACTGCAACT

CCAGGGACTCCTCCGGCAACCATGTGGTGTTCGGC

GGCGGCACCAAGCTGACCGTGGGCCATGGCGGCGG

CGGCTCCGGAGGCGGCGGCAGCGGCGGAGGAGGAT

CCGAGGTGCAGCTGGTGGAGTCCGGAGGAGGAGTG

GTGAGGCCTGGAGGCTCCCTGAGGCTGAGCTGTGC

TGCCTCCGGCTTCACCTTCGACGACTACGGCATGT

CCTGGGTGAGGCAGGCTCCTGGAAAGGGCCTGGAG

TGGGTGTCCGGCATCAACTGGAACGGCGGATCCAC

CGGCTACGCCGATTCCGTGAAGGGCAGGTTCACCA

TCAGCAGGGACAACGCCAAGAACTCCCTGTACCTG

CAGATGAACTCCCTGAGGGCCGAGGACACCGCCGT

GTACTACTGCGCCAGGGGCAGGTCCCTGCTGTTCG
```

-continued
ACTACTGGGGACAGGGCACCCTGGTGACCGTGTCC

AGG.

Exemplary Multi-Chain Chimeric Polypeptides—Type F

In some embodiments of any of the multi-chain chimeric polypeptides described herein, the first target-binding domain and the second targeting-binding domain each independently bind specifically to a receptor for IL-7 (e.g., a soluble human IL-7), CD16 (e.g., an anti-CD16 scFv), or a receptor for IL-21 (e.g., a soluble human IL-21). In some embodiments of these multi-chain chimeric polypeptides described herein, the first chimeric polypeptide further includes the additional target-binding domain. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 or a receptor for IL-21.

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or more of the first target-binding domain, the second target-binding domain and the additional antigen-binding domain is an agonistic antigen-binding domain. In some embodiments of these multi-chain chimeric polypeptides, the first target-binding domain, the second target-binding domain, and the additional antigen-binding domain are each agonistic antigen-binding domains. In some embodiments of these multi-chain chimeric polypeptides, the antigen-binding domain includes a scFv or single-domain antibody.

In some embodiments of any of the multi-chain chimeric polypeptides described herein, the first target-binding domain binds specifically to a receptor IL-7 and the second target-binding domain binds specifically to CD16 or a receptor for IL-21. In some embodiments of any of the multi-chain chimeric polypeptides described herein, the first target-binding domain includes a soluble IL-7 protein. In some embodiments of any of the multi-chain chimeric polypeptides described herein, the soluble IL-7 protein is a soluble human IL-7. In some embodiments of any of the multi-chain chimeric polypeptides described herein, the second antigen-binding domain includes a target-binding domain that binds specifically to CD16. In some embodiments of any of the multi-chain chimeric polypeptides described herein, the second target-binding domain includes an scFv that binds specifically to CD16. In some embodiments of any of the multi-chain chimeric polypeptides described herein, the second target-binding domain binds specifically to a receptor for IL-21. In some embodiments of any of the multi-chain chimeric polypeptides described herein, the second target-binding domain includes a soluble IL-21. In some embodiments of any of the multi-chain chimeric polypeptides described herein, the soluble IL-21 is a soluble human IL-21. In some embodiments of any of the multi-chain chimeric polypeptides described herein, the second chimeric polypeptide further includes an additional target-binding domain that binds specifically to a receptor for IL-21. In some embodiments of any of the multi-chain chimeric polypeptides described herein, the additional target-binding domain includes a soluble IL-21. In some embodiments of any of the multi-chain chimeric polypeptides described herein, the soluble IL-21 is a soluble human IL-21. In some embodiments of any of the multi-chain chimeric polypeptides described herein, the second chimeric polypeptide further includes an additional target-binding domain that binds specifically to CD16.

In some embodiments of these multi-chain chimeric polypeptides, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence.

In some embodiments of these multi-chain chimeric polypeptides, the first target-binding domain includes a soluble IL-7 (e.g., a soluble human IL-7).

In some embodiments of these multi-chain chimeric polypeptides, the soluble human IL-7 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 11)
DCDIEGKDGKQYESVLMVSIDQLLDSMKEIGSNCL

NNEFNFFKRHICDANKEGMFLFRAARKLRQFLKMN

STGDFDLHLLKVSEGTTILLNCTGQVKGRKPAALG

EAQPTKSLEENKSLKEQKKLNDLCFLKRLLQEIKT

CWNKILMGTKEH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 95)
GATTGTGATATTGAAGGTAAAGATGGCAAACAATA

TGAGAGTGTTCTAATGGTCAGCATCGATCAATTAT

TGGACAGCATGAAAGAAATTGGTAGCAATTGCCTG

AATAATGAATTTAACTTTTTTAAAAGACATATCTG

TGATGCTAATAAGGAAGGTATGTTTTTATTCCGTG

CTGCTCGCAAGTTGAGGCAATTTCTTAAAATGAAT

AGCACTGGTGATTTTGATCTCCACTTATTAAAAGT

TTCAGAAGGCACAACAATACTGTTGAACTGCACTG

GCCAGGTTAAAGGAAGAAAACCAGCTGCCCTGGGT

GAAGCCCAACCAACAAAGAGTTTGGAAGAAAATAA

ATCTTTAAAGGAACAGAAAAAACTGAATGACTTGT

GTTTCCTAAAGAGACTATTACAAGAGATAAAAACT

TGTTGGAATAAAATTTTGATGGGCACTAAAGAACA

C.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 124)
GATTGCGACATCGAGGGCAAGGACGGCAAGCAGTA

CGAGAGCGTGCTGATGGTGTCCATCGACCAGCTGC

TGGACAGCATGAAGGAGATCGGCTCCAACTGCCTC

AACAACGAGTTCAACTTCTTCAAGCGGCACATCTG

CGACGCCAACAAGGAGGGCATGTTCCTGTTCAGGG

CCGCCAGGAAACTGCGGCAGTTCCTGAAGATGAAC

TCCACCGGCGACTTCGACCTGCACCTGCTGAAGGT

GTCCGAGGGCACCACCATCCTGCTGAACTGCACCG

GACAGGTGAAGGGCCGGAAACCTGCTGCTCTGGGA

GAGGCCCAACCCACCAAGAGCCTGGAGGAGAACAA

GTCCCTGAAGGAGCAGAAGAAGCTGAACGACCTGT

GCTTCCTGAAGAGGCTGCTGCAGGAGATCAAGACC

TGCTGGAACAAGATCCTGATGGGCACCAAGGAGCA

T.

In some embodiments of these multi-chain chimeric polypeptides, the sequence of soluble human IL-21 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 78)
QGQDRHMIRMRQLIDIVDQLKNYVNDLVPEFLPAP

EDVETNCEWSAFSCFQKAQLKSANTGNNERIINVS

IKKLKRKPPSTNAGRRQKHRLTCPSCDSYEKKPPK

EFLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 94)
CAAGGTCAAGATCGCCACATGATTAGAATGCGTCA

ACTTATAGATATTGTTGATCAGCTGAAAAATTATG

TGAATGACTTGGTCCCTGAATTTCTGCCAGCTCCA

GAAGATGTAGAGACAAACTGTGAGTGGTCAGCTTT

TTCCTGTTTTCAGAAGGCCCAACTAAAGTCAGCAA

ATACAGGAAACAATGAAAGGATAATCAATGTATCA

ATTAAAAAGCTGAAGAGGAAACCACCTTCCACAAA

TGCAGGGAGAAGACAGAAACACAGACTAACATGCC

CTTCATGTGATTCTTATGAGAAAAAACCACCCAAA

GAATTCCTAGAAAGATTCAAATCACTTCTCCAAAA

-continued

GATGATTCATCAGCATCTGTCCTCTAGAACACACG

GAAGTGAAGATTCC.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 79)
CAGGGCCAGGACAGGCACATGATCCGGATGAGGCA

GCTCATCGACATCGTCGACCAGCTGAAGAACTACG

TGAACGACCTGGTGCCCGAGTTTCTGCCTGCCCCC

GAGGACGTGGAGACCAACTGCGAGTGGTCCGCCTT

CTCCTGCTTTCAGAAGGCCCAGCTGAAGTCCGCCA

ACACCGGCAACAACGAGCGGATCATCAACGTGAGC

ATCAAGAAGCTGAAGCGGAAGCCTCCCTCCACAAA

CGCCGGCAGGAGGCAGAAGCACAGGCTGACCTGCC

CCAGCTGTGACTCCTACGAGAAGAAGCCCCCCAAG

GAGTTCCTGGAGAGGTTCAAGTCCCTGCTGCAGAA

GATGATCCATCAGCACCTGTCCTCCAGGACCCACG

GCTCCGAGGACTCC

In some embodiments of these multi-chain chimeric polypeptides, the additional target-binding domain includes an scFv that specifically binds to CD16 (e.g., an anti-CD16 scFv).

In some embodiments of these multi-chain chimeric polypeptides, the scFv that binds specifically to CD16 includes a light chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 112)
SELTQDPAVSVALGQTVRITCQGDSLRSYYASWYQ

QKPGQAPVLVIYGKNNRPSGIPDRFSGSSSGNTAS

LTITGAQAEDEADYYCNSRDSSGNHVVFGGGTKLT

VGH.

In some embodiments of these multi-chain chimeric polypeptides, the scFv that binds specifically to CD16 is encoded by a light chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 113)
TCCGAGCTGACCCAGGACCCTGCTGTGTCCGTGGC

TCTGGGCCAGACCGTGAGGATCACCTGCCAGGGCG

ACTCCCTGAGGTCCTACTACGCCTCCTGGTACCAG

CAGAAGCCCGGCCAGGCTCCTGTGCTGGTGATCTA

CGGCAAGAACAACAGGCCCTCCGGCATCCCTGACA

GGTTCTCCGGATCCTCCTCCGGCAACACCGCCTCC

CTGACCATCACAGGCGCTCAGGCCGAGGACGAGGC

TGACTACTACTGCAACTCCAGGGACTCCTCCGGCA

ACCATGTGGTGTTCGGCGGCGGCACCAAGCTGACC

GTGGGCCAT.

In some embodiments of these multi-chain chimeric polypeptides, the scFv that binds specifically to CD16 includes a heavy chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 114)
EVQLVESGGGVVRPGGSLRLSCAASGFTFDDYGMS

WVRQAPGKGLEWVSGINWNGGSTGYADSVKGRFTI

SRDNAKNSLYLQMNSLRAEDTAVYYCARGRSLLFD

YWGQGTLVTVSR.

In some embodiments of these multi-chain chimeric polypeptides, the scFv that binds specifically to CD16 is encoded by a heavy chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 115)
GAGGTGCAGCTGGTGGAGTCCGGAGGAGGAGTGGT

GAGGCCTGGAGGCTCCCTGAGGCTGAGCTGTGCTG

CCTCCGGCTTCACCTTCGACGACTACGGCATGTCC

TGGGTGAGGCAGGCTCCTGGAAAGGGCCTGGAGTG

GGTGTCCGGCATCAACTGGAACGGCGGATCCACCG

GCTACGCCGATTCCGTGAAGGGCAGGTTCACCATC

AGCAGGGACAACGCCAAGAACTCCCTGTACCTGCA

GATGAACTCCCTGAGGGCCGAGGACACCGCCGTGT

ACTACTGCGCCAGGGGCAGGTCCCTGCTGTTCGAC

TACTGGGGACAGGGCACCCTGGTGACCGTGTCCAG

G.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 125)
DCDIEGKDGKQYESVLMVSIDQLLDSMKEIGSNCL
NNEFNFFKRHICDANKEGMFLFRAARKLRQFLKMN
STGDFDLHLLKVSEGTTILLNCTGQVKGRKPAALG
EAQPTKSLEENKSLKEQKKLNDLCFLKRLLQEIKT
CWNKILMGTKEHSGTTNTVAAYNLTWKSTNFKTIL
EWEPKPVNQVYTVQISTKSGDWKSKCFYTTDTECD
LTDEIVKDVKQTYLARVFSYPAGNVESTGSAGEPL
YENSPEFTPYLETNLGQPTIQSFEQVGTKVNVTVE
DERTLVRRNNTFLSLRDVFGKDLIYTLYYWKSSSS
GKKTAKTNTNEFLIDVDKGENYCFSVQAVIPSRTV
NRKSTDSPVECMGQEKGEFRENWVNVISDLKKIED
LIQSMHIDATLYTESDVHPSCKVTAMKCFLLELQV
ISLESGDASIHDTVENLIILANNSLSSNGNVTESG
CKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 126)
GATTGCGACATCGAGGGCAAGGACGGCAAGCAGTA
CGAGAGCGTGCTGATGGTGTCCATCGACCAGCTGC
TGGACAGCATGAAGGAGATCGGCTCCAACTGCCTC
AACAACGAGTTCAACTTCTTCAAGCGGCACATCTG
CGACGCCAACAAGGAGGGCATGTTCCTGTTCAGGG
CCGCCAGGAAACTGCGGCAGTTCCTGAAGATGAAC
TCCACCGGCGACTTCGACCTGCACCTGCTGAAGGT
GTCCGAGGGCACCACCATCCTGCTGAACTGCACCG
GACAGGTGAAGGGCCGGAAACCTGCTGCTCTGGGA
GAGGCCCAACCCACCAAGAGCCTGGAGGAGAACAA
GTCCCTGAAGGAGCAGAAGAAGCTGAACGACCTGT
GCTTCCTGAAGAGGCTGCTGCAGGAGATCAAGACC
TGCTGGAACAAGATCCTGATGGGCACCAAGGAGCA
TAGCGGCACAACCAACACAGTCGCTGCCTATAACC
TCACTTGGAAGAGCACCAACTTCAAAACCATCCTC
GAATGGGAACCCAAACCCGTTAACCAAGTTTACAC
CGTGCAGATCAGCACCAAGTCCGGCGACTGGAAGT
CCAAATGTTTCTATACCACCGACACCGAGTGCGAT

-continued

CTCACCGATGAGATCGTGAAAGATGTGAAACAGAC
CTACCTCGCCCGGGTGTTTAGCTACCCCGCCGGCA
ATGTGGAGAGCACTGGTTCCGCTGGCGAGCCTTTA
TACGAGAACAGCCCCGAATTTACCCCTTACCTCGA
GACCAATTTAGGACAGCCCACCATCCAAAGCTTTG
AGCAAGTTGGCACAAAGGTGAATGTGACAGTGGAG
GACGAGCGGACTTTAGTGCGGCGGAACAACACCTT
TCTCAGCCTCCGGGATGTGTTCGGCAAAGATTTAA
TCTACACACTGTATTACTGGAAGTCCTCTTCCTCC
GGCAAGAAGACAGCTAAAACCAACACAAACGAGTT
TTTAATCGACGTGGATAAAGGCGAAAACTACTGTT
TCAGCGTGCAAGCTGTGATCCCCTCCCGGACCGTG
AATAGGAAAAGCACCGATAGCCCCGTTGAGTGCAT
GGGCCAAGAAAAGGGCGAGTTCCGGGAGAACTGGG
TGAACGTCATCAGCGATTTAAAGAAGATCGAAGAT
TTAATTCAGTCCATGCATATCGACGCCACTTTATA
CACAGAATCCGACGTGCACCCCTCTTGTAAGGTGA
CCGCCATGAAATGTTTTTTACTGGAGCTGCAAGTT
ATCTCTTTAGAGAGCGGAGACGCTAGCATCCACGA
CACCGTGGAGAATTTAATCATTTTAGCCAATAACT
CTTTATCCAGCAACGGCAACGTGACAGAGTCCGGC
TGCAAGGAGTGCGAAGAGCTGGAGGAGAAGAACAT
CAAGGAGTTTCTGCAATCCTTTGTGCACATTGTCC
AGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 127)
MKWVTFISLLFLFSSAYSDCDIEGKDGKQYESVLM
VSIDQLLDSMKEIGSNCLNNEFNFFKRHICDANKE
GMFLFRAARKLRQFLKMNSTGDFDLHLLKVSEGTT
ILLNCTGQVKGRKPAALGEAQPTKSLEENKSLKEQ
KKLNDLCFLKRLLQEIKTCWNKILMGTKEHSGTTN
TVAAYNLTWKSTNFKTILEWEPKPVNQVYTVQIST
KSGDWKSKCFYTTDTECDLTDEIVKDVKQTYLARV
FSYPAGNVESTGSAGEPLYENSPEFTPYLETNLGQ
PTIQSFEQVGTKVNVTVEDERTLVRRNNTFLSLRD
VFGKDLIYTLYYWKSSSSGKKTAKTNTNEFLIDVD

-continued

KGENYCFSVQAVIPSRTVNRKSTDSPVECMGQEKG
EFRENWVNVISDLKKIEDLIQSMHIDATLYTESDV
HPSCKVTAMKCFLLELQVISLESGDASIHDTVENL
IILANNSLSSNGNVTESGCKECEELEEKNIKEFLQ
SFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 128)

ATGAAGTGGGTGACCTTCATCAGCCTGCTGTTCCT
GTTCTCCAGCGCCTACTCCGATTGCGACATCGAGG
GCAAGGACGGCAAGCAGTACGAGAGCGTGCTGATG
GTGTCCATCGACCAGCTGCTGGACAGCATGAAGGA
GATCGGCTCCAACTGCCTCAACAACGAGTTCAACT
TCTTCAAGCGGCACATCTGCGACGCCAACAAGGAG
GGCATGTTCCTGTTCAGGGCCGCCAGGAAACTGCG
GCAGTTCCTGAAGATGAACTCCACCGGCGACTTCG
ACCTGCACCTGCTGAAGGTGTCCGAGGGCACCACC
ATCCTGCTGAACTGCACCGGACAGGTGAAGGGCCG
GAAACCTGCTGCTCTGGGAGAGGCCCAACCCACCA
AGAGCCTGGAGGAGAACAAGTCCCTGAAGGAGCAG
AAGAAGCTGAACGACCTGTGCTTCCTGAAGAGGCT
GCTGCAGGAGATCAAGACCTGCTGGAACAAGATCC
TGATGGGCACCAAGGAGCATAGCGGCACAACCAAC
ACAGTCGCTGCCTATAACCTCACTTGGAAGAGCAC
CAACTTCAAAACCATCCTCGAATGGGAACCCAAAC
CCGTTAACCAAGTTTACACCGTGCAGATCAGCACC
AAGTCCGGCGACTGGAAGTCCAAATGTTTCTATAC
CACCGACACCGAGTGCGATCTCACCGATGAGATCG
TGAAAGATGTGAAACAGACCTACCTCGCCCGGGTG
TTTAGCTACCCCGCCGGCAATGTGGAGAGCACTGG
TTCCGCTGGCGAGCCTTTATACGAGAACAGCCCCG
AATTTACCCCTTACCTCGAGACCAATTTAGGACAG
CCCACCATCCAAAGCTTTGAGCAAGTTGGCACAAA
GGTGAATGTGACAGTGGAGGACGAGCGGACTTTAG
TGCGGCGGAACAACACCTTTCTCAGCCTCCGGGAT
GTGTTCGGCAAAGATTTAATCTACACACTGTATTA
CTGGAAGTCCTCTTCCTCCGGCAAGAAGACAGCTA
AAACCAACACAAACGAGTTTTTAATCGACGTGGAT
AAAGGCGAAAACTACTGTTTCAGCGTGCAAGCTGT
GATCCCCTCCCGGACCGTGAATAGGAAAAGCACCG
ATAGCCCCGTTGAGTGCATGGGCCAAGAAAAGGGC
GAGTTCCGGGAGAACTGGGTGAACGTCATCAGCGA
TTTAAAGAAGATCGAAGATTTAATTCAGTCCATGC
ATATCGACGCCACTTTATACACAGAATCCGACGTG
CACCCCTCTTGTAAGGTGACCGCCATGAAATGTTT
TTTACTGGAGCTGCAAGTTATCTCTTTAGAGAGCG
GAGACGCTAGCATCCACGACACCGTGGAGAATTTA
ATCATTTTAGCCAATAACTCTTTATCCAGCAACGG
CAACGTGACAGAGTCCGGCTGCAAGGAGTGCGAAG
AGCTGGAGGAGAAGAACATCAAGGAGTTTCTGCAA
TCCTTTGTGCACATTGTCCAGATGTTCATCAATAC
CTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 129)

SELTQDPAVSVALGQTVRITCQGDSLRSYYASWYQ
QKPGQAPVLVIYGKNNRPSGIPDRFSGSSSGNTAS
LTITGAQAEDEADYYCNSRDSSGNHVVFGGGTKLT
VGHGGGGSGGGGSGGGGSEVQLVESGGGVVRPGGS
LRLSCAASGFTFDDYGMSWVRQAPGKGLEWVSGIN
WNGGSTGYADSVKGRFTISRDNAKNSLYLQMNSLR
AEDTAVYYCARGRSLLFDYWGQGTLVTVSRITCPP
PMSVEHADIWVKSYSLYSRERYICNSGFKRKAGTS
SLTECVLNKATNVAHWTTPSLKCIRQGQDRHMIRM
RQLIDIVDQLKNYVNDLVPEFLPAPEDVETNCEWS
AFSCFQKAQLKSANTGNNERIINVSIKKLKRKPPS
TNAGRRQKHRLTCPSCDSYEKKPPKEFLERFKSLL
QKMIHQHLSSRTHGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 130)
TCCGAGCTGACCCAGGACCCTGCTGTGTCCGTGGC
TCTGGGCCAGACCGTGAGGATCACCTGCCAGGGCG
ACTCCCTGAGGTCCTACTACGCCTCCTGGTACCAG
CAGAAGCCCGGCCAGGCTCCTGTGCTGGTGATCTA
CGGCAAGAACAACAGGCCCTCCGGCATCCCTGACA
GGTTCTCCGGATCCTCCTCCGGCAACACCGCCTCC
CTGACCATCACAGGCGCTCAGGCCGAGGACGAGGC
TGACTACTACTGCAACTCCAGGGACTCCTCCGGCA
ACCATGTGGTGTTCGGCGGCGGCACCAAGCTGACC
GTGGGCCATGGCGGCGGCGGCTCCGGAGGCGGCGG
CAGCGGCGGAGGAGGATCCGAGGTGCAGCTGGTGG
AGTCCGGAGGAGGAGTGGTGAGGCCTGGAGGCTCC
CTGAGGCTGAGCTGTGCTGCCTCCGGCTTCACCTT
CGACGACTACGGCATGTCCTGGGTGAGGCAGGCTC
CTGGAAAGGGCCTGGAGTGGGTGTCCGGCATCAAC
TGGAACGGCGGATCCACCGGCTACGCCGATTCCGT
GAAGGGCAGGTTCACCATCAGCAGGGACAACGCCA
AGAACTCCCTGTACCTGCAGATGAACTCCCTGAGG
GCCGAGGACACCGCCGTGTACTACTGCGCCAGGGG
CAGGTCCCTGCTGTTCGACTACTGGGGACAGGGCA
CCCTGGTGACCGTGTCCAGGATTACATGCCCCCCT
CCCATGAGCGTGGAGCACGCCGACATCTGGGTGAA
GAGCTATAGCCTCTACAGCCGGGAGAGGTATATCT
GTAACAGCGGCTTCAAGAGGAAGGCCGGCACCAGC
AGCCTCACCGAGTGCGTGCTGAATAAGGCTACCAA
CGTGGCTCACTGGACAACACCCTCTTTAAAGTGCA
TCCGGCAGGGCCAGGACAGGCACATGATCCGGATG
AGGCAGCTCATCGACATCGTCGACCAGCTGAAGAA
CTACGTGAACGACCTGGTGCCCGAGTTTCTGCCTG
CCCCCGAGGACGTGGAGACCAACTGCGAGTGGTCC
GCCTTCTCCTGCTTTCAGAAGGCCCAGCTGAAGTC
CGCCAACACCGGCAACAACGAGCGGATCATCAACG
TGAGCATCAAGAAGCTGAAGCGGAAGCCTCCCTCC
ACAAACGCCGGCAGGAGGCAGAAGCACAGGCTGAC
CTGCCCCAGCTGTGACTCCTACGAGAAGAAGCCCC
CCAAGGAGTTCCTGGAGAGGTTCAAGTCCCTGCTG
CAGAAGATGATCCATCAGCACCTGTCCTCCAGGAC
CCACGGCTCCGAGGACTCC.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 131)
MKWVTFISLLFLFSSAYSSELTQDPAVSVALGQTV
RITCQGDSLRSYYASWYQQKPGQAPVLVIYGKNNR
PSGIPDRFSGSSSGNTASLTITGAQAEDEADYYCN
SRDSSGNHVVFGGGTKLTVGHGGGGSGGGGSGGGG
SEVQLVESGGGVVRPGGSLRLSCAASGFTFDDYGM
SWVRQAPGKGLEWVSGINWNGGSTGYADSVKGRFT
ISRDNAKNSLYLQMNSLRAEDTAVYYCARGRSLLF
DYWGQGTLVTVSRITCPPPMSVEHADIWVKSYSLY
SRERYICNSGFKRKAGTSSLTECVLNKATNVAHWT
TPSLKCIRQGQDRHMIRMRQLIDIVDQLKNYVNDL
VPEFLPAPEDVETNCEWSAFSCFQKAQLKSANTGN
NERIINVSIKKLKRKPPSTNAGRRQKHRLTCPSCD
SYEKKPPKEFLERFKSLLQKMIHQHLSSRTHGSED
S.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 132)
ATGAAGTGGGTGACCTTCATCAGCCTGCTGTTCCT
GTTCTCCAGCGCCTACTCCTCCGAGCTGACCCAGG
ACCCTGCTGTGTCCGTGGCTCTGGGCCAGACCGTG
AGGATCACCTGCCAGGGCGACTCCCTGAGGTCCTA
CTACGCCTCCTGGTACCAGCAGAAGCCCGGCCAGG
CTCCTGTGCTGGTGATCTACGGCAAGAACAACAGG
CCCTCCGGCATCCCTGACAGGTTCTCCGGATCCTC
CTCCGGCAACACCGCCTCCCTGACCATCACAGGCG
CTCAGGCCGAGGACGAGGCTGACTACTACTGCAAC
TCCAGGGACTCCTCCGGCAACCATGTGGTGTTCGG
CGGCGGCACCAAGCTGACCGTGGGCCATGGCGGCG
GCGGCTCCGGAGGCGGCGGCAGCGGCGGAGGAGGA
TCCGAGGTGCAGCTGGTGGAGTCCGGAGGAGGAGT
GGTGAGGCCTGGAGGCTCCCTGAGGCTGAGCTGTG
CTGCCTCCGGCTTCACCTTCGACGACTACGGCATG
TCCTGGGTGAGGCAGGCTCCTGGAAAGGGCCTGGA
GTGGGTGTCCGGCATCAACTGGAACGGCGGATCCA
CCGGCTACGCCGATTCCGTGAAGGGCAGGTTCACC

-continued

```
ATCAGCAGGGACAACGCCAAGAACTCCCTGTACCT
GCAGATGAACTCCCTGAGGGCCGAGGACACCGCCG
TGTACTACTGCGCCAGGGGCAGGTCCCTGCTGTTC
GACTACTGGGGACAGGGCACCCTGGTGACCGTGTC
CAGGATTACATGCCCCCCTCCCATGAGCGTGGAGC
ACGCCGACATCTGGGTGAAGAGCTATAGCCTCTAC
AGCCGGGAGAGGTATATCTGTAACAGCGGCTTCAA
GAGGAAGGCCGGCACCAGCAGCCTCACCGAGTGCG
TGCTGAATAAGGCTACCAACGTGGCTCACTGGACA
ACACCCTCTTTAAAGTGCATCCGGCAGGGCCAGGA
CAGGCACATGATCCGGATGAGGCAGCTCATCGACA
TCGTCGACCAGCTGAAGAACTACGTGAACGACCTG
GTGCCCGAGTTTCTGCCTGCCCCCGAGGACGTGGA
GACCAACTGCGAGTGGTCCGCCTTCTCCTGCTTTC
AGAAGGCCCAGCTGAAGTCCGCCAACACCGGCAAC
AACGAGCGGATCATCAACGTGAGCATCAAGAAGCT
GAAGCGGAAGCCTCCCTCCACAAACGCCGGCAGGA
GGCAGAAGCACAGGCTGACCTGCCCCAGCTGTGAC
TCCTACGAGAAGAAGCCCCCCAAGGAGTTCCTGGA
GAGGTTCAAGTCCCTGCTGCAGAAGATGATCCATC
AGCACCTGTCCTCCAGGACCCACGGCTCCGAGGAC
TCC.
```

Exemplary Multi-Chain Chimeric Polypeptides—Type G

In some embodiments of any of the multi-chain chimeric polypeptides described herein, the first target-binding domain and the second targeting-binding domain each independently bind specifically to TGFβ (e.g., a human TGFβRII receptor), CD16 (e.g., an anti-CD16 scFv), or a receptor for IL-21 (e.g., a soluble human IL-21). In some embodiments of these multi-chain chimeric polypeptides described herein, the first chimeric polypeptide further includes the additional target-binding domain. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 or a receptor for IL-21.

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or more of the first target-binding domain, the second target-binding domain and the additional antigen-binding domain is an agonistic antigen-binding domain. In some embodiments of these multi-chain chimeric polypeptides, the first target-binding domain, the second target-binding domain, and the additional antigen-binding domain are each agonistic antigen-binding domains. In some embodiments of these multi-chain chimeric polypeptides, the antigen-binding domain includes a scFv or single-domain antibody.

In some embodiments of any of the multi-chain chimeric polypeptides described herein, the first target-binding domain and the second targeting-binding domain each independently bind specifically to TGF-β, CD16, or a receptor for IL-21. In some embodiments of any of the multi-chain chimeric polypeptides described herein, the first target-binding domain binds specifically to a TGF-β and the second target-binding domain binds specifically to CD16 or a receptor of IL-21. In some embodiments of any of the multi-chain chimeric polypeptides described herein, the first target-binding domain is a soluble TGF-β receptor. In some embodiments of any of the multi-chain chimeric polypeptides described herein, soluble TGF-β receptor is a soluble TGFβRII receptor. In some embodiments of any of the multi-chain chimeric polypeptides described herein, the second target-binding domain binds specifically to CD16. In some embodiments of any of the multi-chain chimeric polypeptides described herein, the second antigen-binding domain includes an antigen-binding domain that binds specifically to CD16. In some embodiments of any of the multi-chain chimeric polypeptides described herein, the second antigen-binding domain includes an scFv that binds specifically to CD16. In some embodiments of any of the multi-chain chimeric polypeptides described herein, the second target-binding domain binds specifically to a receptor for IL-21. In some embodiments of any of the multi-chain chimeric polypeptides described herein, the second target-binding domain includes a soluble IL-21. In some embodiments of any of the multi-chain chimeric polypeptides described herein, the second target-binding domain includes a soluble human IL-21. In some embodiments of any of the multi-chain chimeric polypeptides described herein, the second chimeric polypeptide further includes an additional target-binding domain that binds specifically to a receptor for IL-21. In some embodiments of any of the multi-chain chimeric polypeptides described herein, the additional target-binding domain includes a soluble IL-21. In some embodiments of any of the multi-chain chimeric polypeptides described herein, the soluble IL-21 is a soluble human IL-21. In some embodiments of any of the multi-chain chimeric polypeptides described herein, the second chimeric polypeptide further includes an additional target-binding domain that binds specifically to CD16.

In some embodiments of these multi-chain chimeric polypeptides, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence.

In some embodiments of these multi-chain chimeric polypeptides, the first target-binding domain includes a TGFβRII receptor (e.g., a soluble human TGFβRII receptor). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 80)
IPPHVQKSVNNDMIVTDNNGAVKFPQLCKFCDVRF

STCDNQKSCMSNCSITSICEKPQEVCVAVWRKNDE

NITLETVCHDPKLPYHDFILEDAASPKCIMKEKKK

PGETFFMCSCSSDECNDNIIFSEEYNTSNPD.
```

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 81)
IPPHVQKSVNNDMIVTDNNGAVKFPQLCKFCDVRF

STCDNQKSCMSNCSITSICEKPQEVCVAVWRKNDE

NITLETVCHDPKLPYHDFILEDAASPKCIMKEKKK

PGETFFMCSCSSDECNDNIIFSEEYNTSNPD.
```

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 82)
ATCCCCCCCCATGTGCAAAAGAGCGTGAACAACGA

TATGATCGTGACCGACAACAACGGCGCCGTGAAGT

TTCCCCAGCTCTGCAAGTTCTGCGATGTCAGGTTC

AGCACCTGCGATAATCAGAAGTCCTGCATGTCCAA

CTGCAGCATCACCTCCATCTGCGAGAAGCCCCAAG

AAGTGTGCGTGGCCGTGTGGCGGAAAAATGACGAG

AACATCACCCTGGAGACCGTGTGTCACGACCCCAA

GCTCCCTTATCACGACTTCATTCTGGAGGACGCTG

CCTCCCCCAAATGCATCATGAAGGAGAAGAAGAAG

CCCGGAGAGACCTTCTTTATGTGTTCCTGTAGCAG

CGACGAGTGTAACGACAACATCATCTTCAGCGAAG

AGTACAACACCAGCAACCCTGAT
```

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 83)
ATTCCTCCCCACGTGCAGAAGAGCGTGAATAATGA
CATGATCGTGACCGATAACAATGGCGCCGTGAAAT
TTCCCCAGCTGTGCAAATTCTGCGATGTGAGGTTT
TCCACCTGCGACAACCAGAAGTCCTGTATGAGCAA
CTGCTCCATCACCTCCATCTGTGAGAAGCCTCAGG
AGGTGTGCGTGGCTGTCTGGCGGAAGAATGACGAG
AATATCACCCTGGAAACCGTCTGCCACGATCCCAA
GCTGCCCTACCACGATTTCATCCTGGAAGACGCCG
CCAGCCCTAAGTGCATCATGAAAGAGAAAAAGAAG
CCTGGCGAGACCTTTTTCATGTGCTCCTGCAGCAG
CGACGAATGCAACGACAATATCATCTTTAGCGAGG
AATACAATACCAGCAACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 85)
IPPHVQKSVNNDMIVTDNNGAVKFPQLCKFCDVRF
STCDNQKSCMSNCSITSICEKPQEVCVAVWRKNDE
NITLETVCHDPKLPYHDFILEDAASPKCIMKEKKK
PGETFFMCSCSSDECNDNIIFSEEYNTSNPDGGGG
SGGGGSGGGGSIPPHVQKSVNNDMIVTDNNGAVKF
PQLCKFCDVRFSTCDNQKSCMSNCSITSICEKPQE
VCVAVWRKNDENITLETVCHDPKLPYHDFILEDAA
SPKCIMKEKKKPGETFFMCSCSSDECNDNIIFSEE
YNTSNPD.

In some embodiments of these multi-chain chimeric polypeptides, the soluble human TGFβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 84)
ATCCCCCCCCATGTGCAAAAGAGCGTGAACAACGA
TATGATCGTGACCGACAACAACGGCGCCGTGAAGT
TTCCCCAGCTCTGCAAGTTCTGCGATGTCAGGTTC
AGCACCTGCGATAATCAGAAGTCCTGCATGTCCAA
CTGCAGCATCACCTCCATCTGCGAGAAGCCCCAAG
AAGTGTGCGTGGCCGTGTGGCGGAAAAATGACGAG

-continued

AACATCACCCTGGAGACCGTGTGTCACGACCCCAA
GCTCCCTTATCACGACTTCATTCTGGAGGACGCTG
CCTCCCCCAAATGCATCATGAAGGAGAAGAAGAAG
CCCGGAGAGACCTTCTTTATGTGTTCCTGTAGCAG
CGACGAGTGTAACGACAACATCATCTTCAGCGAAG
AGTACAACACCAGCAACCCTGATGGAGGTGGCGGA
TCCGGAGGTGGAGGTTCTGGTGGAGGTGGGAGTAT
TCCTCCCCACGTGCAGAAGAGCGTGAATAATGACA
TGATCGTGACCGATAACAATGGCGCCGTGAAATTT
CCCCAGCTGTGCAAATTCTGCGATGTGAGGTTTTC
CACCTGCGACAACCAGAAGTCCTGTATGAGCAACT
GCTCCATCACCTCCATCTGTGAGAAGCCTCAGGAG
GTGTGCGTGGCTGTCTGGCGGAAGAATGACGAGAA
TATCACCCTGGAAACCGTCTGCCACGATCCCAAGC
TGCCCTACCACGATTTCATCCTGGAAGACGCCGCC
AGCCCTAAGTGCATCATGAAAGAGAAAAAGAAGCC
TGGCGAGACCTTTTTCATGTGCTCCTGCAGCAGCG
ACGAATGCAACGACAATATCATCTTTAGCGAGGAA
TACAATACCAGCAACCCCGAC.

In some embodiments of these multi-chain chimeric polypeptides, the sequence of soluble human IL-21 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 78)
QGQDRHMIRMRQLIDIVDQLKNYVNDLVPEFLPAPE
DVETNCEWSAFSCFQKAQLKSANTGNNERIINVSI
KKLKRKPPSTNAGRRQKHRLTCPSCDSYEKKPPKE
FLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 94)
CAAGGTCAAGATCGCCACATGATTAGAATGCGTCA
ACTTATAGATATTGTTGATCAGCTGAAAAATTATG
TGAATGACTTGGTCCCTGAATTTCTGCCAGCTCCA
GAAGATGTAGAGACAAACTGTGAGTGGTCAGCTTT
TTCCTGTTTTCAGAAGGCCCAACTAAAGTCAGCAA

-continued

ATACAGGAAACAATGAAAGGATAATCAATGTATCA
ATTAAAAAGCTGAAGAGGAAACCACCTTCCACAAA
TGCAGGGAGAAGACAGAAACACAGACTAACATGCC
CTTCATGTGATTCTTATGAGAAAAAACCACCCAAA
GAATTCCTAGAAAGATTCAAATCACTTCTCCAAAA
GATGATTCATCAGCATCTGTCCTCTAGAACACACG
GAAGTGAAGATTCC.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 79)
CAGGGCCAGGACAGGCACATGATCCGGATGAGGCA
GCTCATCGACATCGTCGACCAGCTGAAGAACTACG
TGAACGACCTGGTGCCCGAGTTTCTGCCTGCCCCC
GAGGACGTGGAGACCAACTGCGAGTGGTCCGCCTT
CTCCTGCTTTCAGAAGGCCCAGCTGAAGTCCGCCA
ACACCGGCAACAACGAGCGGATCATCAACGTGAGC
ATCAAGAAGCTGAAGCGGAAGCCTCCCTCCACAAA
CGCCGGCAGGAGGCAGAAGCACAGGCTGACCTGCC
CCAGCTGTGACTCCTACGAGAAGAAGCCCCCCAAG
GAGTTCCTGGAGAGGTTCAAGTCCCTGCTGCAGAA
GATGATCCATCAGCACCTGTCCTCCAGGACCCACG
GCTCCGAGGACTCC.

In some embodiments of these multi-chain chimeric polypeptides, the scFv that binds specifically to CD16 includes a light chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 112)
SELTQDPAVSVALGQTVRITCQGDSLRSYYASWYQ
QKPGQAPVLVIYGKNNRPSGIPDRFSGSSSGNTAS
LTITGAQAEDEADYYCNSRDSSGNHVVFGGGTKLT
VGH.

In some embodiments of these multi-chain chimeric polypeptides, the scFv that binds specifically to CD16 is encoded by a light chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 113)
TCCGAGCTGACCCAGGACCCTGCTGTGTCCGTGGC
TCTGGGCCAGACCGTGAGGATCACCTGCCAGGGCG
ACTCCCTGAGGTCCTACTACGCCTCCTGGTACCAG
CAGAAGCCCGGCCAGGCTCCTGTGCTGGTGATCTA
CGGCAAGAACAACAGGCCCTCCGGCATCCCTGACA
GGTTCTCCGGATCCTCCTCCGGCAACACCGCCTCC
CTGACCATCACAGGCGCTCAGGCCGAGGACGAGGC
TGACTACTACTGCAACTCCAGGGACTCCTCCGGCA
ACCATGTGGTGTTCGGCGGCGGCACCAAGCTGACC
GTGGGCCAT.

In some embodiments of these multi-chain chimeric polypeptides, the scFv that binds specifically to CD16 includes a heavy chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 114)
EVQLVESGGGVVRPGGSLRLSCAASGFTFDDYGMS
WVRQAPGKGLEWVSGINWNGGSTGYADSVKGRFTI
SRDNAKNSLYLQMNSLRAEDTAVYYCARGRSLLFD
YWGQGTLVTVSR.

In some embodiments of these multi-chain chimeric polypeptides, the scFv that binds specifically to CD16 is encoded by a heavy chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 115)
GAGGTGCAGCTGGTGGAGTCCGGAGGAGGAGTGGT
GAGGCCTGGAGGCTCCCTGAGGCTGAGCTGTGCTG
CCTCCGGCTTCACCTTCGACGACTACGGCATGTCC
TGGGTGAGGCAGGCTCCTGGAAAGGGCCTGGAGTG
GGTGTCCGGCATCAACTGGAACGGCGGATCCACCG
GCTACGCCGATTCCGTGAAGGGCAGGTTCACCATC
AGCAGGGACAACGCCAAGAACTCCCTGTACCTGCA
GATGAACTCCCTGAGGGCCGAGGACACCGCCGTGT
ACTACTGCGCCAGGGGCAGGTCCCTGCTGTTCGAC
TACTGGGGACAGGGCACCCTGGTGACCGTGTCCAG
G.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 133)
IPPHVQKSVNNDMIVTDNNGAVKFPQLCKFCDVRF
STCDNQKSCMSNCSITSICEKPQEVCVAVWRKNDE
NITLETVCHDPKLPYHDFILEDAASPKCIMKEKKK
PGETFFMCSCSSDECNDNIIFSEEYNTSNPDGGGG
SGGGGSGGGGSIPPHVQKSVNNDMIVTDNNGAVKF
PQLCKFCDVRFSTCDNQKSCMSNCSITSICEKPQE
VCVAVWRKNDENITLETVCHDPKLPYHDFILEDAA
SPKCIMKEKKKPGETFFMCSCSSDECNDNIIFSEE
YNTSNPDSGTTNTVAAYNLTWKSTNFKTILEWEPK
PVNQVYTVQISTKSGDWKSKCFYTTDTECDLTDEI
VKDVKQTYLARVFSYPAGNVESTGSAGEPLYENSP
EFTPYLETNLGQPTIQSFEQVGTKVNVTVEDERTL
VRRNNTFLSLRDVFGKDLIYTLYYWKSSSSGK
KTAKTNTNEFLIDVDKGENYCFSVQAVIPSRT
VNRKSTDSPVECMGQEKGEFRENWVNVISDLKKI
EDLIQSMHIDATLYTESDVHPSCKVTAMKCFLLEL
QVISLESGDASIHDTVENLIILANNSLSSNGNVTE
SGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 134)
ATCCCCCCCCATGTGCAAAAGAGCGTGAACAACGA
TATGATCGTGACCGACAACAACGGCGCCGTGAAGT
TTCCCCAGCTCTGCAAGTTCTGCGATGTCAGGTTC
AGCACCTGCGATAATCAGAAGTCCTGCATGTCCAA
CTGCAGCATCACCTCCATCTGCGAGAAGCCCCAAG
AAGTGTGCGTGGCCGTGTGGCGGAAAAATGACGAG
AACATCACCCTGGAGACCGTGTGTCACGACCCCAA
GCTCCCTTATCACGACTTCATTCTGGAGGACGCTG
CCTCCCCCAAATGCATCATGAAGGAGAAGAAGAAG
CCCGGAGAGACCTTCTTTATGTGTTCCTGTAGCAG
CGACGAGTGTAACGACAACATCATCTTCAGCGAAG
AGTACAACACCAGCAACCCTGATGGAGGTGGCGGA
TCCGGAGGTGGAGGTTCTGGTGGAGGTGGGAGTAT
TCCTCCCCACGTGCAGAAGAGCGTGAATAATGACA

-continued

TGATCGTGACCGATAACAATGGCGCCGTGAAATTT
CCCCAGCTGTGCAAATTCTGCGATGTGAGGTTTTC
CACCTGCGACAACCAGAAGTCCTGTATGAGCAACT
GCTCCATCACCTCCATCTGTGAGAAGCCTCAGGAG
GTGTGCGTGGCTGTCTGGCGGAAGAATGACGAGAA
TATCACCCTGGAAACCGTCTGCCACGATCCCAAGC
TGCCCTACCACGATTTCATCCTGGAAGACGCCGCC
AGCCCTAAGTGCATCATGAAAGAGAAAAAGAAGCC
TGGCGAGACCTTTTTCATGTGCTCCTGCAGCAGCG
ACGAATGCAACGACAATATCATCTTTAGCGAGGAA
TACAATACCAGCAACCCCGACAGCGGCACAACCAA
CACAGTCGCTGCCTATAACCTCACTTGGAAGAGCA
CCAACTTCAAAACCATCCTCGAATGGGAACCCAAA
CCCGTTAACCAAGTTTACACCGTGCAGATCAGCAC
CAAGTCCGGCGACTGGAAGTCCAAATGTTTCTATA
CCACCGACACCGAGTGCGATCTCACCGATGAGATC
GTGAAAGATGTGAAACAGACCTACCTCGCCCGGGT
GTTTAGCTACCCCGCCGGCAATGTGGAGAGCACTG
GTTCCGCTGGCGAGCCTTTATACGAGAACAGCCCC
GAATTTACCCCTTACCTCGAGACCAATTTAGGACA
GCCCACCATCCAAAGCTTTGAGCAAGTTGGCACAA
AGGTGAATGTGACAGTGGAGGACGAGCGGACTTTA
GTGCGGCGGAACAACACCTTTCTCAGCCTCCGGGA
TGTGTTCGGCAAAGATTTAATCTACACACTGTATT
ACTGGAAGTCCTCTTCCTCCGGCAAGAAGACAGCT
AAAACCAACACAAACGAGTTTTTAATCGACGTGGA
TAAAGGCGAAAACTACTGTTTCAGCGTGCAAGCTG
TGATCCCCTCCCGGACCGTGAATAGGAAAAGCACC
GATAGCCCCGTTGAGTGCATGGGCCAAGAAAAGGG
CGAGTTCCGGGAGAACTGGGTGAACGTCATCAGCG
ATTTAAAGAAGATCGAAGATTTAATTCAGTCCATG
CATATCGACGCCACTTTATACACAGAATCCGACGT
GCACCCCTCTTGTAAGGTGACCGCCATGAAATGTT
TTTTACTGGAGCTGCAAGTTATCTCTTTAGAGAGC
GGAGACGCTAGCATCCACGACACCGTGGAGAATTT
AATCATTTTAGCCAATAACTCTTTATCCAGCAACG
GCAACGTGACAGAGTCCGGCTGCAAGGAGTGCGAA
GAGCTGGAGGAGAAGAACATCAAGGAGTTTCTGCA
ATCCTTTGTGCACATTGTCCAGATGTTCATCAATA
CCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 135)
MKWVTFISLLFLFSSAYSIPPHVQKSVNNDMIVTD
NNGAVKFPQLCKFCDVRFSTCDNQKSCMSNCSITS
ICEKPQEVCVAVWRKNDENITLETVCHDPKLPYHD
FILEDAASPKCIMKEKKKPGETFFMCSCSSDECND
NIIFSEEYNTSNPDGGGGSGGGGSGGGGSIPPHVQ
KSVNNDMIVTDNNGAVKFPQLCKFCDVRFSTCDNQ
KSCMSNCSITSICEKPQEVCVAVWRKNDENITLET
VCHDPKLPYHDFILEDAASPKCIMKEKKKPGETFF
MCSCSSDECNDNIIFSEEYNTSNPDSGTTNTVAAY
NLTWKSTNFKTILEWEPKPVNQVYTVQISTKSGDW
KSKCFYTTDTECDLTDEIVKDVKQTYLARVFSYPA
GNVESTGSAGEPLYENSPEFTPYLETNLGQPTIQS
FEQVGTKVNVTVEDERTLVRRNNTFLSLRDVFGKD
LIYTLYYWKSSSSGKKTAKTNTNEFLIDVDKG
ENYCF SVQAVIPSRTVNRKSTDSPVECMGQEKGE
FRENWVNVISDLKKIEDLIQSMHIDATLYTESDVH
PSCKVTAMKCFLLELQVISLESGDASIHDTVENLI
ILANNSLSSNGNVTESGCKECEELEEKNIKEFLQS
FVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 136)
ATGAAGTGGGTGACCTTCATCAGCCTGCTGTTCCT
GTTCTCCAGCGCCTACTCCATCCCCCCCCATGTGC
AAAAGAGCGTGAACAACGATATGATCGTGACCGAC
AACAACGGCGCCGTGAAGTTTCCCCAGCTCTGCAA
GTTCTGCGATGTCAGGTTCAGCACCTGCGATAATC
AGAAGTCCTGCATGTCCAACTGCAGCATCACCTCC
ATCTGCGAGAAGCCCCAAGAAGTGTGCGTGGCCGT
GTGGCGGAAAAATGACGAGAACATCACCCTGGAGA
CCGTGTGTCACGACCCCAAGCTCCCTTATCACGAC
TTCATTCTGGAGGACGCTGCCTCCCCCAAATGCAT

-continued

CATGAAGGAGAAGAAGAAGCCCGGAGAGACCTTCT
TTATGTGTTCCTGTAGCAGCGACGAGTGTAACGAC
AACATCATCTTCAGCGAAGAGTACAACACCAGCAA
CCCTGATGGAGGTGGCGGATCCGGAGGTGGAGGTT
CTGGTGGAGGTGGGAGTATTCCTCCCCACGTGCAG
AAGAGCGTGAATAATGACATGATCGTGACCGATAA
CAATGGCGCCGTGAAATTTCCCCAGCTGTGCAAAT
TCTGCGATGTGAGGTTTTCCACCTGCGACAACCAG
AAGTCCTGTATGAGCAACTGCTCCATCACCTCCAT
CTGTGAGAAGCCTCAGGAGGTGTGCGTGGCTGTCT
GGCGGAAGAATGACGAGAATATCACCCTGGAAACC
GTCTGCCACGATCCCAAGCTGCCCTACCACGATTT
CATCCTGGAAGACGCCGCCAGCCCTAAGTGCATCA
TGAAAGAGAAAAAGAAGCCTGGCGAGACCTTTTTC
ATGTGCTCCTGCAGCAGCGACGAATGCAACGACAA
TATCATCTTTAGCGAGGAATACAATACCAGCAACC
CCGACAGCGGCACAACCAACACAGTCGCTGCCTAT
AACCTCACTTGGAAGAGCACCAACTTCAAAACCAT
CCTCGAATGGGAACCCAAACCCGTTAACCAAGTTT
ACACCGTGCAGATCAGCACCAAGTCCGGCGACTGG
AAGTCCAAATGTTTCTATACCACCGACACCGAGTG
CGATCTCACCGATGAGATCGTGAAAGATGTGAAAC
AGACCTACCTCGCCCGGGTGTTTAGCTACCCCGCC
GGCAATGTGGAGAGCACTGGTTCCGCTGGCGAGCC
TTTATACGAGAACAGCCCCGAATTTACCCCTTACC
TCGAGACCAATTTAGGACAGCCCACCATCCAAAGC
TTTGAGCAAGTTGGCACAAAGGTGAATGTGACAGT
GGAGGACGAGCGGACTTTAGTGCGGCGGAACAACA
CCTTTCTCAGCCTCCGGGATGTGTTCGGCAAAGAT
TTAATCTACACACTGTATTACTGGAAGTCCTCTTC
CTCCGGCAAGAAGACAGCTAAAACCAACACAAACG
AGTTTTTAATCGACGTGGATAAAGGCGAAAACTAC
TGTTTCAGCGTGCAAGCTGTGATCCCCTCCCGGAC
CGTGAATAGGAAAAGCACCGATAGCCCCGTTGAGT
GCATGGGCCAAGAAAAGGGCGAGTTCCGGGAGAAC
TGGGTGAACGTCATCAGCGATTTAAAGAAGATCGA
AGATTTAATTCAGTCCATGCATATCGACGCCACTT
TATACACAGAATCCGACGTGCACCCCTCTTGTAAG
GTGACCGCCATGAAATGTTTTTTACTGGAGCTGCA
AGTTATCTCTTTAGAGAGCGGAGACGCTAGCATCC
ACGACACCGTGGAGAATTTAATCATTTTAGCCAAT

-continued

AACTCTTTATCCAGCAACGGCAACGTGACAGAGTC

CGGCTGCAAGGAGTGCGAAGAGCTGGAGGAGAAGA

ACATCAAGGAGTTTCTGCAATCCTTTGTGCACATT

GTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 137)

SELTQDPAVSVALGQTVRITCQGDSLRSYYASWYQ

QKPGQAPVLVIYGKNNRPSGIPDRFSGSSSGNTAS

LTITGAQAEDEADYYCNSRDSSGNHVVFGGGTKLT

VGHGGGGSGGGGSGGGGSEVQLVESGGGVVRPGGS

LRLSCAASGFTFDDYGMSWVRQAPGKGLEWVSGIN

WNGGSTGYADSVKGRFTISRDNAKNSLYLQMNSLR

AEDTAVYYCARGRSLLFDYWGQGTLVTVSRITCPP

PMSVEHADIWVKSYSLYSRERYICNSGFKRKAGTS

SLTECVLNKATNVAHWTTPSLKCIRQGQDRHMIRM

RQLIDIVDQLKNYVNDLVPEFLPAPEDVETNCEWS

AFSCFQKAQLKSANTGNNERIINVSIKKLKRKPPS

TNAGRRQKHRLTCPSCDSYEKKPPKEFLERFKSLL

QKMIHQHLSSRTHGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 138)

TCCGAGCTGACCCAGGACCCTGCTGTGTCCGTGGC

TCTGGGCCAGACCGTGAGGATCACCTGCCAGGGCG

ACTCCCTGAGGTCCTACTACGCCTCCTGGTACCAG

CAGAAGCCCGGCCAGGCTCCTGTGCTGGTGATCTA

CGGCAAGAACAACAGGCCCTCCGGCATCCCTGACA

GGTTCTCCGGATCCTCCTCCGGCAACACCGCCTCC

CTGACCATCACAGGCGCTCAGGCCGAGGACGAGGC

TGACTACTACTGCAACTCCAGGGACTCCTCCGGCA

ACCATGTGGTGTTCGGCGGCGGCACCAAGCTGACC

GTGGGCCATGGCGGCGGCGGCTCCGGAGGCGGCGG

CAGCGGCGGAGGAGGATCCGAGGTGCAGCTGGTGG

-continued

AGTCCGGAGGAGGAGTGGTGAGGCCTGGAGGCTCC

CTGAGGCTGAGCTGTGCTGCCTCCGGCTTCACCTT

CGACGACTACGGCATGTCCTGGGTGAGGCAGGCTC

CTGGAAAGGGCCTGGAGTGGGTGTCCGGCATCAAC

TGGAACGGCGGATCCACCGGCTACGCCGATTCCGT

GAAGGGCAGGTTCACCATCAGCAGGGACAACGCCA

AGAACTCCCTGTACCTGCAGATGAACTCCCTGAGG

GCCGAGGACACCGCCGTGTACTACTGCGCCAGGGG

CAGGTCCCTGCTGTTCGACTACTGGGGACAGGGCA

CCCTGGTGACCGTGTCCAGGATTACATGCCCCCCT

CCCATGAGCGTGGAGCACGCCGACATCTGGGTGAA

GAGCTATAGCCTCTACAGCCGGGAGAGGTATATCT

GTAACAGCGGCTTCAAGAGGAAGGCCGGCACCAGC

AGCCTCACCGAGTGCGTGCTGAATAAGGCTACCAA

CGTGGCTCACTGGACAACACCCTCTTTAAAGTGCA

TCCGGCAGGGCCAGGACAGGCACATGATCCGGATG

AGGCAGCTCATCGACATCGTCGACCAGCTGAAGAA

CTACGTGAACGACCTGGTGCCCGAGTTTCTGCCTG

CCCCCGAGGACGTGGAGACCAACTGCGAGTGGTCC

GCCTTCTCCTGCTTTCAGAAGGCCCAGCTGAAGTC

CGCCAACACCGGCAACAACGAGCGGATCATCAACG

TGAGCATCAAGAAGCTGAAGCGGAAGCCTCCCTCC

ACAAACGCCGGCAGGAGGCAGAAGCACAGGCTGAC

CTGCCCCAGCTGTGACTCCTACGAGAAGAAGCCCC

CCAAGGAGTTCCTGGAGAGGTTCAAGTCCCTGCTG

CAGAAGATGATCCATCAGCACCTGTCCTCCAGGAC

CCACGGCTCCGAGGACTCC.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 139)

MKWVTFISLLFLFSSAYSSELTQDPAVSVALGQTV

RITCQGDSLRSYYASWYQQKPGQAPVLVIYGKNNR

PSGIPDRFSGSSSGNTASLTITGAQAEDEADYYCN

SRDSSGNHVVFGGGTKLTVGHGGGGSGGGGSGGGG

SEVQLVESGGGVVRPGGSLRLSCAASGFTFDDYGM

SWVRQAPGKGLEWVSGINWNGGSTGYADSVKGRFT

ISRDNAKNSLYLQMNSLRAEDTAVYYCARGRSLLF

DYWGQGTLVTVSRITCPPPMSVEHADIWVKSYSLY

-continued

SRERYICNSGFKRKAGTSSLTECVLNKATNVAHWT

TPSLKCIRQGQDRHMIRMRQLIDIVDQLKNYVNDL

VPEFLPAPEDVETNCEWSAFSCFQKAQLKSANTGN

NERIINVSIKKLKRKPPSTNAGRRQKHRLTCPSCD

SYEKKPPKEFLERFKSLLQKMIHQHLSSRTHGSED

S.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 140)

ATGAAGTGGGTGACCTTCATCAGCCTGCTGTTCCT

GTTCTCCAGCGCCTACTCCTCCGAGCTGACCCAGG

ACCCTGCTGTGTCCGTGGCTCTGGGCCAGACCGTG

AGGATCACCTGCCAGGGCGACTCCCTGAGGTCCTA

CTACGCCTCCTGGTACCAGCAGAAGCCCGGCCAGG

CTCCTGTGCTGGTGATCTACGGCAAGAACAACAGG

CCCTCCGGCATCCCTGACAGGTTCTCCGGATCCTC

CTCCGGCAACACCGCCTCCCTGACCATCACAGGCG

CTCAGGCCGAGGACGAGGCTGACTACTACTGCAAC

TCCAGGGACTCCTCCGGCAACCATGTGGTGTTCGG

CGGCGGCACCAAGCTGACCGTGGGCCATGGCGGCG

GCGGCTCCGGAGGCGGCGGCAGCGGCGGAGGAGGA

TCCGAGGTGCAGCTGGTGGAGTCCGGAGGAGGAGT

GGTGAGGCCTGGAGGCTCCCTGAGGCTGAGCTGTG

CTGCCTCCGGCTTCACCTTCGACGACTACGGCATG

TCCTGGGTGAGGCAGGCTCCTGGAAAGGGCCTGGA

GTGGGTGTCCGGCATCAACTGGAACGGCGGATCCA

CCGGCTACGCCGATTCCGTGAAGGGCAGGTTCACC

ATCAGCAGGGACAACGCCAAGAACTCCCTGTACCT

GCAGATGAACTCCCTGAGGGCCGAGGACACCGCCG

TGTACTACTGCGCCAGGGGCAGGTCCCTGCTGTTC

GACTACTGGGGACAGGGCACCCTGGTGACCGTGTC

CAGGATTACATGCCCCCCTCCCATGAGCGTGGAGC

ACGCCGACATCTGGGTGAAGAGCTATAGCCTCTAC

AGCCGGGAGAGGTATATCTGTAACAGCGGCTTCAA

GAGGAAGGCCGGCACCAGCAGCCTCACCGAGTGCG

TGCTGAATAAGGCTACCAACGTGGCTCACTGGACA

ACACCCTCTTTAAAGTGCATCCGGCAGGGCCAGGA

-continued

CAGGCACATGATCCGGATGAGGCAGCTCATCGACA

TCGTCGACCAGCTGAAGAACTACGTGAACGACCTG

GTGCCCGAGTTTCTGCCTGCCCCCGAGGACGTGGA

GACCAACTGCGAGTGGTCCGCCTTCTCCTGCTTTC

AGAAGGCCCAGCTGAAGTCCGCCAACACCGGCAAC

AACGAGCGGATCATCAACGTGAGCATCAAGAAGCT

GAAGCGGAAGCCTCCCTCCACAAACGCCGGCAGGA

GGCAGAAGCACAGGCTGACCTGCCCCAGCTGTGAC

TCCTACGAGAAGAAGCCCCCCAAGGAGTTCCTGGA

GAGGTTCAAGTCCCTGCTGCAGAAGATGATCCAT

CAGCACCTGTCCTCCAGGACCCACGGCTCCGAGG

ACTCC.

Exemplary Multi-Chain Chimeric Polypeptides—Type H

In some embodiments of any of the multi-chain chimeric polypeptides described herein, the first target-binding domain and the second targeting-binding domain each independently bind specifically to a receptor of IL-7. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain and the second target-binding domain each independently bind specifically to a receptor for IL-7. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain and the second target-binding domain include a soluble IL-7 (e.g., a soluble human IL-7). In some embodiments of these multi-chain chimeric polypeptides, the soluble human IL-7 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical at least 99% identical or 100% identical to:

(SEQ ID NO: 11)
DCDIEGKDGKQYESVLMVSIDQLLDSMKEIGSNCL

NNEFNFFKRHICDANKEGMFLFRAARKLRQFLKMN

STGDFDLHLLKVSEGTTILLNCTGQVKGRKPAALG

EAQPTKSLEENKSLKEQKKLNDLCFLKRLLQEIKT

CWNKILMGTKEH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 95)
GATTGCGACATCGAGGGCAAGGACGGCAAGCAGTA

CGAGAGCGTGCTGATGGTGTCCATCGACCAGCTGC

TGGACAGCATGAAGGAGATCGGCTCCAACTGCCTC

AACAACGAGTTCAACTTCTTCAAGCGGCACATCTG

CGACGCCAACAAGGAGGGCATGTTCCTGTTCAGGG

CCGCCAGGAAACTGCGGCAGTTCCTGAAGATGAAC

TCCACCGGCGACTTCGACCTGCACCTGCTGAAGGT

GTCCGAGGGCACCACCATCCTGCTGAACTGCACCG

GACAGGTGAAGGGCCGGAAACCTGCTGCTCTGGGA

GAGGCCCAACCCACCAAGAGCCTGGAGGAGAACAA

GTCCCTGAAGGAGCAGAAGAAGCTGAACGACCTGT

GCTTCCTGAAGAGGCTGCTGCAGGAGATCAAGACC

TGCTGGAACAAGATCCTGATGGGCACCAAGGAGCA

T.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 141)
DCDIEGKDGKQYESVLMVSIDQLLDSMKEIGSNCL

NNEFNFFKRHICDANKEGMFLFRAARKLRQFLKMN

STGDFDLHLLKVSEGTTILLNCTGQVKGRKPAALG

EAQPTKSLEENKSLKEQKKLNDLCFLKRLLQEIKT

CWNKILMGTKEHSGTTNTVAAYNLTWKSTNFKTIL

EWEPKPVNQVYTVQISTKSGDWKSKCFYTTDTECD

LTDEIVKDVKQTYLARVFSYPAGNVESTGSAGEPL

YENSPEFTPYLETNLGQPTIQSFEQVGTKVNVTVE

DERTLVRRNNTFLSLRDVFGKDLIYTLYYWKSSSS

GKKTAKTNTNEFLIDVDKGENYCFSVQAVIPSRTV

NRKSTDSPVECMGQEKGEFRENWVNVISDLKKIED

LIQSMHIDATLYTESDVHPSCKVTAMKCFLLELQV

ISLESGDASIHDTVENLIILANNSLSSNGNVTESG

CKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 142)
GATTGCGACATCGAGGGCAAGGACGGCAAGCAGTA

CGAGAGCGTGCTGATGGTGTCCATCGACCAGCTGC

TGGACAGCATGAAGGAGATCGGCTCCAACTGCCTC

AACAACGAGTTCAACTTCTTCAAGCGGCACATCTG

CGACGCCAACAAGGAGGGCATGTTCCTGTTCAGGG

CCGCCAGGAAACTGCGGCAGTTCCTGAAGATGAAC

TCCACCGGCGACTTCGACCTGCACCTGCTGAAGGT

GTCCGAGGGCACCACCATCCTGCTGAACTGCACCG

GACAGGTGAAGGGCCGGAAACCTGCTGCTCTGGGA

GAGGCCCAACCCACCAAGAGCCTGGAGGAGAACAA

GTCCCTGAAGGAGCAGAAGAAGCTGAACGACCTGT

GCTTCCTGAAGAGGCTGCTGCAGGAGATCAAGACC

TGCTGGAACAAGATCCTGATGGGCACCAAGGAGCA

TAGCGGCACAACCAACACAGTCGCTGCCTATAACC

TCACTTGGAAGAGCACCAACTTCAAAACCATCCTC

GAATGGGAACCCAAACCCGTTAACCAAGTTTACAC

CGTGCAGATCAGCACCAAGTCCGGCGACTGGAAGT

CCAAATGTTTCTATACCACCGACACCGAGTGCGAT

CTCACCGATGAGATCGTGAAAGATGTGAAACAGAC

CTACCTCGCCCGGGTGTTTAGCTACCCCGCCGGCA

-continued

ATGTGGAGAGCACTGGTTCCGCTGGCGAGCCTTTA

TACGAGAACAGCCCCGAATTTACCCCTTACCTCGA

GACCAATTTAGGACAGCCCACCATCCAAAGCTTTG

AGCAAGTTGGCACAAAGGTGAATGTGACAGTGGAG

GACGAGCGGACTTTAGTGCGGCGGAACAACACCTT

TCTCAGCCTCCGGGATGTGTTCGGCAAAGATTTAA

TCTACACACTGTATTACTGGAAGTCCTCTTCCTCC

GGCAAGAAGACAGCTAAAACCAACACAAACGAGTT

TTTAATCGACGTGGATAAAGGCGAAAACTACTGTT

TCAGCGTGCAAGCTGTGATCCCCTCCCGGACCGTG

AATAGGAAAAGCACCGATAGCCCCGTTGAGTGCAT

GGGCCAAGAAAAGGGCGAGTTCCGGGAGAACTGGG

TGAACGTCATCAGCGATTTAAAGAAGATCGAAGAT

TTAATTCAGTCCATGCATATCGACGCCACTTTATA

CACAGAATCCGACGTGCACCCCTCTTGTAAGGTGA

CCGCCATGAAATGTTTTTTACTGGAGCTGCAAGTT

ATCTCTTTAGAGAGCGGAGACGCTAGCATCCACGA

CACCGTGGAGAATTTAATCATTTTAGCCAATAACT

CTTTATCCAGCAACGGCAACGTGACAGAGTCCGGC

TGCAAGGAGTGCGAAGAGCTGGAGGAGAAGAACAT

CAAGGAGTTTCTGCAATCCTTTGTGCACATTGTCC

AGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 143)

MKWVTFISLLFLFSSAYSDCDIEGKDGKQYESVLM

VSIDQLLDSMKEIGSNCLNNEFNFFKRHICDANKE

GMFLFRAARKLRQFLKMNSTGDFDLHLLKVSEGTT

ILLNCTGQVKGRKPAALGEAQPTKSLEENKSLKEQ

KKLNDLCFLKRLLQEIKTCWNKILMGTKEHSGTTN

TVAAYNLTWKSTNFKTILEWEPKPVNQVYTVQIST

KSGDWKSKCFYTTDTECDLTDEIVKDVKQTYLARV

FSYPAGNVESTGSAGEPLYENSPEFTPYLETNLGQ

PTIQSFEQVGTKVNVTVEDERTLVRRNNTFLSLRD

VFGKDLIYTLYYWKSSSSGKKTAKTNTNEFLIDVD

KGENYCFSVQAVIPSRTVNRKSTDSPVECMGQEKG

EFRENWVNVISDLKKIEDLIQSMHIDATLYTESDV

HPSCKVTAMKCFLLELQVISLESGDASIHDTVENL

-continued

IILANNSLSSNGNVTESGCKECEELEEKNIKEFLQ

SFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 144)

ATGAAGTGGGTGACCTTCATCAGCCTGCTGTTCCT

GTTCTCCAGCGCCTACTCCGATTGCGACATCGAGG

GCAAGGACGGCAAGCAGTACGAGAGCGTGCTGATG

GTGTCCATCGACCAGCTGCTGGACAGCATGAAGGA

GATCGGCTCCAACTGCCTCAACAACGAGTTCAACT

TCTTCAAGCGGCACATCTGCGACGCCAACAAGGAG

GGCATGTTCCTGTTCAGGGCCGCCAGGAAACTGCG

GCAGTTCCTGAAGATGAACTCCACCGGCGACTTCG

ACCTGCACCTGCTGAAGGTGTCCGAGGGCACCACC

ATCCTGCTGAACTGCACCGGACAGGTGAAGGGCCG

GAAACCTGCTGCTCTGGGAGAGGCCCAACCCACCA

AGAGCCTGGAGGAGAACAAGTCCCTGAAGGAGCAG

AAGAAGCTGAACGACCTGTGCTTCCTGAAGAGGCT

GCTGCAGGAGATCAAGACCTGCTGGAACAAGATCC

TGATGGGCACCAAGGAGCATAGCGGCACAACCAAC

ACAGTCGCTGCCTATAACCTCACTTGGAAGAGCAC

CAACTTCAAAACCATCCTCGAATGGGAACCCAAAC

CCGTTAACCAAGTTTACACCGTGCAGATCAGCACC

AAGTCCGGCGACTGGAAGTCCAAATGTTTCTATAC

CACCGACACCGAGTGCGATCTCACCGATGAGATCG

TGAAAGATGTGAAACAGACCTACCTCGCCCGGGTG

TTTAGCTACCCCGCCGGCAATGTGGAGAGCACTGG

TTCCGCTGGCGAGCCTTTATACGAGAACAGCCCCG

AATTTACCCCTTACCTCGAGACCAATTTAGGACAG

CCCACCATCCAAAGCTTTGAGCAAGTTGGCACAAA

GGTGAATGTGACAGTGGAGGACGAGCGGACTTTAG

TGCGGCGGAACAACACCTTTCTCAGCCTCCGGGAT

GTGTTCGGCAAAGATTTAATCTACACACTGTATTA

CTGGAAGTCCTCTTCCTCCGGCAAGAAGACAGCTA

AAACCAACACAAACGAGTTTTTAATCGACGTGGAT

AAAGGCGAAAACTACTGTTTCAGCGTGCAAGCTGT

GATCCCCTCCCGGACCGTGAATAGGAAAAGCACCG

-continued

ATAGCCCCGTTGAGTGCATGGGCCAAGAAAAGGGC
GAGTTCCGGGAGAACTGGGTGAACGTCATCAGCGA
TTTAAAGAAGATCGAAGATTTAATTCAGTCCATGC
ATATCGACGCCACTTTATACACAGAATCCGACGTG
CACCCCTCTTGTAAGGTGACCGCCATGAAATGTTT
TTTACTGGAGCTGCAAGTTATCTCTTTAGAGAGCG
GAGACGCTAGCATCCACGACACCGTGGAGAATTTA
ATCATTTTAGCCAATAACTCTTTATCCAGCAACGG
CAACGTGACAGAGTCCGGCTGCAAGGAGTGCGAAG
AGCTGGAGGAGAAGAACATCAAGGAGTTTCTGCAA
TCCTTTGTGCACATTGTCCAGATGTTCATCAATAC
CTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 145)
DCDIEGKDGKQYESVLMVSIDQLLDSMKEIGSNCL
NNEFNFFKRHICDANKEGMFLFRAARKLRQFLKMN
STGDFDLHLLKVSEGTTILLNCTGQVKGRKPAALG
EAQPTKSLEENKSLKEQKKLNDLCFLKRLLQEIKT
CWNKILMGTKEHITCPPPMSVEHADIWVKSYSLYS
RERYICNSGFKRKAGTSSLTECVLNKATNVAHWTT
PSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 146)
GATTGTGATATTGAAGGTAAAGATGGCAAACAATA
TGAGAGTGTTCTAATGGTCAGCATCGATCAATTAT
TGGACAGCATGAAAGAAATTGGTAGCAATTGCCTG
AATAATGAATTTAACTTTTTTAAAAGACATATCTG
TGATGCTAATAAGGAAGGTATGTTTTTATTCCGTG
CTGCTCGCAAGTTGAGGCAATTTCTTAAAATGAAT
AGCACTGGTGATTTTGATCTCCACTTATTAAAAGT
TTCAGAAGGCACAACAATACTGTTGAACTGCACTG
GCCAGGTTAAAGGAAGAAAACCAGCTGCCCTGGGT
GAAGCCCAACCAACAAAGAGTTTGGAAGAAAATAA

-continued

ATCTTTAAAGGAACAGAAAAAACTGAATGACTTGT
GTTTCCTAAAGAGACTATTACAAGAGATAAAAACT
TGTTGGAATAAAATTTTGATGGGCACTAAAGAACA
CATCACGTGCCCTCCCCCCATGTCCGTGGAACACG
CAGACATCTGGGTCAAGAGCTACAGCTTGTACTCC
AGGGAGCGGTACATTTGTAACTCTGGTTTCAAGCG
TAAAGCCGGCACGTCCAGCCTGACGGAGTGCGTGT
TGAACAAGGCCACGAATGTCGCCCACTGGACAACC
CCCAGTCTCAAATGCATTAGA.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 147)
MKWVTFISLLFLFSSAYSDCDIEGKDGKQYESVLM
VSIDQLLDSMKEIGSNCLNNEFNFFKRHICDANKE
GMFLFRAARKLRQFLKMNSTGDFDLHLLKVSEGTT
ILLNCTGQVKGRKPAALGEAQPTKSLEENKSLKEQ
KKLNDLCFLKRLLQEIKTCWNKILMGTKEHITCPP
PMSVEHADIWVKSYSLYSRERYICNSGFKRKAGTS
SLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 148)
ATGAAGTGGGTGACCTTCATCAGCCTGCTGTTCCT
GTTCTCCAGCGCCTACTCCGATTGCGACATCGAGG
GCAAGGACGGCAAGCAGTACGAGAGCGTGCTGATG
GTGTCCATCGACCAGCTGCTGGACAGCATGAAGGA
GATCGGCTCCAACTGCCTCAACAACGAGTTCAACT
TCTTCAAGCGGCACATCTGCGACGCCAACAAGGAG
GGCATGTTCCTGTTCAGGGCCGCCAGGAAACTGCG
GCAGTTCCTGAAGATGAACTCCACCGGCGACTTCG
ACCTGCACCTGCTGAAGGTGTCCGAGGGCACCACC
ATCCTGCTGAACTGCACCGGACAGGTGAAGGGCCG
GAAACCTGCTGCTCTGGGAGAGGCCCAACCCACCA
AGAGCCTGGAGGAGAACAAGTCCCTGAAGGAGCAG

-continued

```
AAGAAGCTGAACGACCTGTGCTTCCTGAAGAGGCT
GCTGCAGGAGATCAAGACCTGCTGGAACAAGATCC
TGATGGGCACCAAGGAGCATATTACATGCCCCCCT
CCCATGAGCGTGGAGCACGCCGACATCTGGGTGAA
GAGCTATAGCCTCTACAGCCGGGAGAGGTATATCT
GTAACAGCGGCTTCAAGAGGAAGGCCGGCACCAGC
AGCCTCACCGAGTGCGTGCTGAATAAGGCTACCAA
CGTGGCTCACTGGACAACACCCTCTTTAAAGTGCA
TCCGG.
```

Exemplary Multi-Chain Chimeric Polypeptides—Type I

In some embodiments of any of the multi-chain chimeric polypeptides described herein, the first target-binding domain and the second targeting-binding domain each independently bind specifically to TGF-β. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain and the second target-binding domain each independently bind specifically to TGF-β. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain and the second target-binding domain is a soluble TGF-β receptor (e.g., a soluble TGFβRII receptor, e.g., a soluble human TGFβRII). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                    (SEQ ID NO: 80)
IPPHVQKSVNNDMIVTDNNGAVKFPQLCKFCDVRF
STCDNQKSCMSNCSITSICEKPQEVCVAVWRKNDE
NITLETVCHDPKLPYHDFILEDAASPKCIMKEKKK
PGETFFMCSCSSDECNDNIIFSEEYNTSNPD.
```

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to: c (SEQ ID NO: 81).

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                    (SEQ ID NO: 82)
ATCCCCCCCCATGTGCAAAAGAGCGTGAACAACGA
TATGATCGTGACCGACAACAACGGCGCCGTGAAGT
TTCCCCAGCTCTGCAAGTTCTGCGATGTCAGGTTC
AGCACCTGCGATAATCAGAAGTCCTGCATGTCCAA
CTGCAGCATCACCTCCATCTGCGAGAAGCCCCAAG
AAGTGTGCGTGGCCGTGTGGCGGAAAAATGACGAG
AACATCACCCTGGAGACCGTGTGTCACGACCCCAA
GCTCCCTTATCACGACTTCATTCTGGAGGACGCTG
CCTCCCCCAAATGCATCATGAAGGAGAAGAAGAAG
CCCGGAGAGACCTTCTTTATGTGTTCCTGTAGCAG
```

-continued

CGACGAGTGTAACGACAACATCATCTTCAGCGAAG

AGTACAACACCAGCAACCCTGAT.

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100%

(SEQ ID NO: 83)
ATTCCTCCCCACGTGCAGAAGAGCGTGAATAATGA

CATGATCGTGACCGATAACAATGGCGCCGTGAAAT

TTCCCCAGCTGTGCAAATTCTGCGATGTGAGGTTT

TCCACCTGCGACAACCAGAAGTCCTGTATGAGCAA

CTGCTCCATCACCTCCATCTGTGAGAAGCCTCAGG

AGGTGTGCGTGGCTGTCTGGCGGAAGAATGACGAG

AATATCACCCTGGAAACCGTCTGCCACGATCCCAA

GCTGCCCTACCACGATTTCATCCTGGAAGACGCCG

CCAGCCCTAAGTGCATCATGAAAGAGAAAAAGAAG

CCTGGCGAGACCTTTTTCATGTGCTCCTGCAGCAG

CGACGAATGCAACGACAATATCATCTTTAGCGAGG

AATACAATACCAGCAACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 85)
IPPHVQKSVNNDMIVTDNNGAVKFPQLCKFCDVRF

STCDNQKSCMSNCSITSICEKPQEVCVAVWRKNDE

NITLETVCHDPKLPYHDFILEDAASPKCIMKEKKK

PGETFFMCSCSSDECNDNIIFSEEYNTSNPDGGGG

SGGGGSGGGGSIPPHVQKSVNNDMIVTDNNGAVKF

PQLCKFCDVRFSTCDNQKSCMSNCSITSICEKPQE

VCVAVWRKNDENITLETVCHDPKLPYHDFILEDAA

SPKCIMKEKKKPGETFFMCSCSSDECNDNIIFSEE

YNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 84)
ATCCCCCCCCATGTGCAAAAGAGCGTGAACAACGA

TATGATCGTGACCGACAACAACGGCGCCGTGAAGT

TTCCCCAGCTCTGCAAGTTCTGCGATGTCAGGTTC

AGCACCTGCGATAATCAGAAGTCCTGCATGTCCAA

CTGCAGCATCACCTCCATCTGCGAGAAGCCCCAAG

AAGTGTGCGTGGCCGTGTGGCGGAAAAATGACGAG

AACATCACCCTGGAGACCGTGTGTCACGACCCCAA

GCTCCCTTATCACGACTTCATTCTGGAGGACGCTG

CCTCCCCCAAATGCATCATGAAGGAGAAGAAGAAG

CCCGGAGAGACCTTCTTTATGTGTTCCTGTAGCAG

CGACGAGTGTAACGACAACATCATCTTCAGCGAAG

AGTACAACACCAGCAACCCTGATGGAGGTGGCGGA

TCCGGAGGTGGAGGTTCTGGTGGAGGTGGGAGTAT

TCCTCCCCACGTGCAGAAGAGCGTGAATAATGACA

TGATCGTGACCGATAACAATGGCGCCGTGAAATTT

CCCCAGCTGTGCAAATTCTGCGATGTGAGGTTTTC

CACCTGCGACAACCAGAAGTCCTGTATGAGCAACT

GCTCCATCACCTCCATCTGTGAGAAGCCTCAGGAG

GTGTGCGTGGCTGTCTGGCGGAAGAATGACGAGAA

TATCACCCTGGAAACCGTCTGCCACGATCCCAAGC

TGCCCTACCACGATTTCATCCTGGAAGACGCCGCC

AGCCCTAAGTGCATCATGAAAGAGAAAAAGAAGCC

TGGCGAGACCTTTTTCATGTGCTCCTGCAGCAGCG

ACGAATGCAACGACAATATCATCTTTAGCGAGGAA

TACAATACCAGCAACCCCGAC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 149)
IPPHVQKSVNNDMIVTDNNGAVKFPQLCKFCDVRF

STCDNQKSCMSNCSITSICEKPQEVCVAVWRKNDE

NITLETVCHDPKLPYHDFILEDAASPKCIMKEKKK

PGETFFMCSCSSDECNDNIIFSEEYNTSNPDGGGG

SGGGGSGGGGSIPPHVQKSVNNDMIVTDNNGAVKF

PQLCKFCDVRFSTCDNQKSCMSNCSITSICEKPQE

VCVAVWRKNDENITLETVCHDPKLPYHDFILEDAA

SPKCIMKEKKKPGETFFMCSCSSDECNDNIIFSEE

YNTSNPDSGTTNTVAAYNLTWKSTNFKTILEWEPK

-continued

PVNQVYTVQISTKSGDWKSKCFYTTDTECDLTDEI

VKDVKQTYLARVFSYPAGNVESTGSAGEPLYENSP

EFTPYLETNLGQPTIQSFEQVGTKVNVTVEDERTL

VRRNNTFLSLRDVFGKDLIYTLYYWKSSSSGKKTA

KTNTNEFLIDVDKGENYCFSVQAVIPSRTVNRKST

DSPVECMGQEKGEFRENWVNVISDLKKIEDLIQSM

HIDATLYTESDVHPSCKVTAMKCFLLELQVISLES

GDASIHDTVENLIILANNSLSSNGNVTESGCKECE

ELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 150)

ATCCCCCCCCATGTGCAAAAGAGCGTGAACAACGA

TATGATCGTGACCGACAACAACGGCGCCGTGAAGT

TTCCCCAGCTCTGCAAGTTCTGCGATGTCAGGTTC

AGCACCTGCGATAATCAGAAGTCCTGCATGTCCAA

CTGCAGCATCACCTCCATCTGCGAGAAGCCCCAAG

AAGTGTGCGTGGCCGTGTGGCGGAAAAATGACGAG

AACATCACCCTGGAGACCGTGTGTCACGACCCCAA

GCTCCCTTATCACGACTTCATTCTGGAGGACGCTG

CCTCCCCCAAATGCATCATGAAGGAGAAGAAGAAG

CCCGGAGAGACCTTCTTTATGTGTTCCTGTAGCAG

CGACGAGTGTAACGACAACATCATCTTCAGCGAAG

AGTACAACACCAGCAACCCTGATGGAGGTGGCGGA

TCCGGAGGTGGAGGTTCTGGTGGAGGTGGGAGTAT

TCCTCCCCACGTGCAGAAGAGCGTGAATAATGACA

TGATCGTGACCGATAACAATGGCGCCGTGAAATTT

CCCCAGCTGTGCAAATTCTGCGATGTGAGGTTTTC

CACCTGCGACAACCAGAAGTCCTGTATGAGCAACT

GCTCCATCACCTCCATCTGTGAGAAGCCTCAGGAG

GTGTGCGTGGCTGTCTGGCGGAAGAATGACGAGAA

TATCACCCTGGAAACCGTCTGCCACGATCCCAAGC

TGCCCTACCACGATTTCATCCTGGAAGACGCCGCC

AGCCCTAAGTGCATCATGAAAGAGAAAAAGAAGCC

TGGCGAGACCTTTTTCATGTGCTCCTGCAGCAGCG

ACGAATGCAACGACAATATCATCTTTAGCGAGGAA

TACAATACCAGCAACCCCGACAGCGGCACAACCAA

CACAGTCGCTGCCTATAACCTCACTTGGAAGAGCA

-continued

CCAACTTCAAAACCATCCTCGAATGGGAACCCAAA

CCCGTTAACCAAGTTTACACCGTGCAGATCAGCAC

CAAGTCCGGCGACTGGAAGTCCAAATGTTTCTATA

CCACCGACACCGAGTGCGATCTCACCGATGAGATC

GTGAAAGATGTGAAACAGACCTACCTCGCCCGGGT

GTTTAGCTACCCCGCCGGCAATGTGGAGAGCACTG

GTTCCGCTGGCGAGCCTTTATACGAGAACAGCCCC

GAATTTACCCCTTACCTCGAGACCAATTTAGGACA

GCCCACCATCCAAAGCTTTGAGCAAGTTGGCACAA

AGGTGAATGTGACAGTGGAGGACGAGCGGACTTTA

GTGCGGCGGAACAACACCTTTCTCAGCCTCCGGGA

TGTGTTCGGCAAAGATTTAATCTACACACTGTATT

ACTGGAAGTCCTCTTCCTCCGGCAAGAAGACAGCT

AAAACCAACACAAACGAGTTTTTAATCGACGTGGA

TAAAGGCGAAAACTACTGTTTCAGCGTGCAAGCTG

TGATCCCCTCCCGGACCGTGAATAGGAAAAGCACC

GATAGCCCCGTTGAGTGCATGGGCCAAGAAAAGGG

CGAGTTCCGGGAGAACTGGGTGAACGTCATCAGCG

ATTTAAAGAAGATCGAAGATTTAATTCAGTCCATG

CATATCGACGCCACTTTATACACAGAATCCGACGT

GCACCCCTCTTGTAAGGTGACCGCCATGAAATGTT

TTTTACTGGAGCTGCAAGTTATCTCTTTAGAGAGC

GGAGACGCTAGCATCCACGACACCGTGGAGAATTT

AATCATTTTAGCCAATAACTCTTTATCCAGCAACG

GCAACGTGACAGAGTCCGGCTGCAAGGAGTGCGAA

GAGCTGGAGGAGAAGAACATCAAGGAGTTTCTGCA

ATCCTTTGTGCACATTGTCCAGATGTTCATCAATA

CCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 151)

MKWVTFISLLFLFSSAYSIPPHVQKSVNNDMIVTD

NNGAVKFPQLCKFCDVRFSTCDNQKSCMSNCSITS

ICEKPQEVCVAVWRKNDENITLETVCHDPKLPYHD

FILEDAASPKCIMKEKKKPGETFFMCSCSSDECND

NIIFSEEYNTSNPDGGGGSGGGGSGGGGSIPPHVQ

KSVNNDMIVTDNNGAVKFPQLCKFCDVRFSTCDNQ

-continued

KSCMSNCSITSICEKPQEVCVAVWRKNDENITLET

VCHDPKLPYHDFILEDAASPKCIMKEKKKPGETFF

MCSCSSDECNDNIIFSEEYNTSNPDSGTTNTVAAY

NLTWKSTNFKTILEWEPKPVNQVYTVQISTKSGDW

KSKCFYTTDTECDLTDEIVKDVKQTYLARVFSYPA

GNVESTGSAGEPLYENSPEFTPYLETNLGQPTIQS

FEQVGTKVNVTVEDERTLVRRNNTFLSLRDVFGKD

LIYTLYYWKSSSSGKKTAKTNTNEFLIDVDKGENY

CFSVQAVIPSRTVNRKSTDSPVECMGQEKGEFREN

WVNVISDLKKIEDLIQSMHIDATLYTESDVHPSCK

VTAMKCFLLELQVISLESGDASIHDTVENLIILAN

NSLSSNGNVTESGCKECEELEEKNIKEFLQSFVHI

VQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 152)

ATGAAGTGGGTGACCTTCATCAGCCTGCTGTTCCT

GTTCTCCAGCGCCTACTCCATCCCCCCCCATGTGC

AAAAGAGCGTGAACAACGATATGATCGTGACCGAC

AACAACGGCGCCGTGAAGTTTCCCCAGCTCTGCAA

GTTCTGCGATGTCAGGTTCAGCACCTGCGATAATC

AGAAGTCCTGCATGTCCAACTGCAGCATCACCTCC

ATCTGCGAGAAGCCCCAAGAAGTGTGCGTGGCCGT

GTGGCGGAAAAATGACGAGAACATCACCCTGGAGA

CCGTGTGTCACGACCCCAAGCTCCCTTATCACGAC

TTCATTCTGGAGGACGCTGCCTCCCCCAAATGCAT

CATGAAGGAGAAGAAGAAGCCCGGAGAGACCTTCT

TTATGTGTTCCTGTAGCAGCGACGAGTGTAACGAC

AACATCATCTTCAGCGAAGAGTACAACACCAGCAA

CCCTGATGGAGGTGGCGGATCCGGAGGTGGAGGTT

CTGGTGGAGGTGGGAGTATTCCTCCCCACGTGCAG

AAGAGCGTGAATAATGACATGATCGTGACCGATAA

CAATGGCGCCGTGAAATTTCCCCAGCTGTGCAAAT

TCTGCGATGTGAGGTTTTCCACCTGCGACAACCAG

AAGTCCTGTATGAGCAACTGCTCCATCACCTCCAT

CTGTGAGAAGCCTCAGGAGGTGTGCGTGGCTGTCT

GGCGGAAGAATGACGAGAATATCACCCTGGAAACC

GTCTGCCACGATCCCAAGCTGCCCTACCACGATTT

-continued

CATCCTGGAAGACGCCGCCAGCCCTAAGTGCATCA

TGAAAGAGAAAAAGAAGCCTGGCGAGACCTTTTTC

ATGTGCTCCTGCAGCAGCGACGAATGCAACGACAA

TATCATCTTTAGCGAGGAATACAATACCAGCAACC

CCGACAGCGGCACAACCAACACAGTCGCTGCCTAT

AACCTCACTTGGAAGAGCACCAACTTCAAAACCAT

CCTCGAATGGGAACCCAAACCCGTTAACCAAGTTT

ACACCGTGCAGATCAGCACCAAGTCCGGCGACTGG

AAGTCCAAATGTTTCTATACCACCGACACCGAGTG

CGATCTCACCGATGAGATCGTGAAAGATGTGAAAC

AGACCTACCTCGCCCGGGTGTTTAGCTACCCCGCC

GGCAATGTGGAGAGCACTGGTTCCGCTGGCGAGCC

TTTATACGAGAACAGCCCCGAATTTACCCCTTACC

TCGAGACCAATTTAGGACAGCCCACCATCCAAAGC

TTTGAGCAAGTTGGCACAAAGGTGAATGTGACAGT

GGAGGACGAGCGGACTTTAGTGCGGCGGAACAACA

CCTTTCTCAGCCTCCGGGATGTGTTCGGCAAAGAT

TTAATCTACACACTGTATTACTGGAAGTCCTCTTC

CTCCGGCAAGAAGACAGCTAAAACCAACACAAACG

AGTTTTTAATCGACGTGGATAAAGGCGAAAACTAC

TGTTTCAGCGTGCAAGCTGTGATCCCCTCCCGGAC

CGTGAATAGGAAAAGCACCGATAGCCCCGTTGAGT

GCATGGGCCAAGAAAAGGGCGAGTTCCGGGAGAAC

TGGGTGAACGTCATCAGCGATTTAAAGAAGATCGA

AGATTTAATTCAGTCCATGCATATCGACGCCACTT

TATACACAGAATCCGACGTGCACCCCTCTTGTAAG

GTGACCGCCATGAAATGTTTTTTACTGGAGCTGCA

AGTTATCTCTTTAGAGAGCGGAGACGCTAGCATCC

ACGACACCGTGGAGAATTTAATCATTTTAGCCAAT

AACTCTTTATCCAGCAACGGCAACGTGACAGAGTC

CGGCTGCAAGGAGTGCGAAGAGCTGGAGGAGAAGA

ACATCAAGGAGTTTCTGCAATCCTTTGTGCACAT

TGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 153)
IPPHVQKSVNNDMIVTDNNGAVKFPQLCKFCDVRF
STCDNQKSCMSNCSITSICEKPQEVCVAVWRKNDE
NITLETVCHDPKLPYHDFILEDAASPKCIMKEKKK
PGETFFMCSCSSDECNDNIIFSEEYNTSNPDGGGG
SGGGGSGGGGSIPPHVQKSVNNDMIVTDNNGAVKF
PQLCKFCDVRFSTCDNQKSCMSNCSITSICEKPQE
VCVAVWRKNDENITLETVCHDPKLPYHDFILEDAA
SPKCIMKEKKKPGETFFMCSCSSDECNDNIIFSEE
YNTSNPDITCPPPMSVEHADIWVKSYSLYSRERYI
CNSGFKRKAGTSSLTECVLNKATNVAHWTTPSLKC
IR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 154)
ATCCCCCCCCATGTGCAAAAGAGCGTGAACAACGA
TATGATCGTGACCGACAACAACGGCGCCGTGAAGT
TTCCCCAGCTCTGCAAGTTCTGCGATGTCAGGTTC
AGCACCTGCGATAATCAGAAGTCCTGCATGTCCAA
CTGCAGCATCACCTCCATCTGCGAGAAGCCCCAAG
AAGTGTGCGTGGCCGTGTGGCGGAAAAATGACGAG
AACATCACCCTGGAGACCGTGTGTCACGACCCCAA
GCTCCCTTATCACGACTTCATTCTGGAGGACGCTG
CCTCCCCCAAATGCATCATGAAGGAGAAGAAGAAG
CCCGGAGAGACCTTCTTTATGTGTTCCTGTAGCAG
CGACGAGTGTAACGACAACATCATCTTCAGCGAAG
AGTACAACACCAGCAACCCTGATGGAGGTGGCGGA
TCCGGAGGTGGAGGTTCTGGTGGAGGTGGGAGTAT
TCCTCCCCACGTGCAGAAGAGCGTGAATAATGACA
TGATCGTGACCGATAACAATGGCGCCGTGAAATTT
CCCCAGCTGTGCAAATTCTGCGATGTGAGGTTTTC
CACCTGCGACAACCAGAAGTCCTGTATGAGCAACT
GCTCCATCACCTCCATCTGTGAGAAGCCTCAGGAG
GTGTGCGTGGCTGTCTGGCGGAAGAATGACGAGAA
TATCACCCTGGAAACCGTCTGCCACGATCCCAAGC
TGCCCTACCACGATTTCATCCTGGAAGACGCCGCC
AGCCCTAAGTGCATCATGAAAGAGAAAAAGAAGCC
TGGCGAGACCTTTTTCATGTGCTCCTGCAGCAGCG

-continued
ACGAATGCAACGACAATATCATCTTTAGCGAGGAA
TACAATACCAGCAACCCCGACATTACATGCCCCCC
TCCCATGAGCGTGGAGCACGCCGACATCTGGGTGA
AGAGCTATAGCCTCTACAGCCGGGAGAGGTATATC
TGTAACAGCGGCTTCAAGAGGAAGGCCGGCACCAG
CAGCCTCACCGAGTGCGTGCTGAATAAGGCTACC
AACGTGGCTCACTGGACAACACCCTCTTTAAAGT
GCATCCGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 155)
MKWVTFISLLFLFSSAYSIPPHVQKSVNNDMIVTD
NNGAVKFPQLCKFCDVRFSTCDNQKSCMSNCSITS
ICEKPQEVCVAVWRKNDENITLETVCHDPKLPYHD
FILEDAASPKCIMKEKKKPGETFFMCSCSSDECND
NIIFSEEYNTSNPDGGGGSGGGGSGGGGSIPPHVQ
KSVNNDMIVTDNNGAVKFPQLCKFCDVRFSTCDNQ
KSCMSNCSITSICEKPQEVCVAVWRKNDENITLET
VCHDPKLPYHDFILEDAASPKCIMKEKKKPGETFF
MCSCSSDECNDNIIFSEEYNTSNPDITCPPPMSVE
HADIWVKSYSLYSRERYICNSGFKRKAGTSSLTEC
VLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 156)
ATGAAGTGGGTGACCTTCATCAGCCTGCTGTTCCT
GTTCTCCAGCGCCTACTCCATCCCCCCCCATGTGC
AAAAGAGCGTGAACAACGATATGATCGTGACCGAC
AACAACGGCGCCGTGAAGTTTCCCCAGCTCTGCAA
GTTCTGCGATGTCAGGTTCAGCACCTGCGATAATC
AGAAGTCCTGCATGTCCAACTGCAGCATCACCTCC
ATCTGCGAGAAGCCCCAAGAAGTGTGCGTGGCCGT
GTGGCGGAAAAATGACGAGAACATCACCCTGGAGA
CCGTGTGTCACGACCCCAAGCTCCCTTATCACGAC
TTCATTCTGGAGGACGCTGCCTCCCCCAAATGCAT

-continued

CATGAAGGAGAAGAAGAAGCCCGGAGAGACCTTCT

TTATGTGTTCCTGTAGCAGCGACGAGTGTAACGAC

AACATCATCTTCAGCGAAGAGTACAACACCAGCAA

CCCTGATGGAGGTGGCGGATCCGGAGGTGGAGGTT

CTGGTGGAGGTGGGAGTATTCCTCCCCACGTGCAG

AAGAGCGTGAATAATGACATGATCGTGACCGATAA

CAATGGCGCCGTGAAATTTCCCCAGCTGTGCAAAT

TCTGCGATGTGAGGTTTTCCACCTGCGACAACCAG

AAGTCCTGTATGAGCAACTGCTCCATCACCTCCAT

CTGTGAGAAGCCTCAGGAGGTGTGCGTGGCTGTCT

GGCGGAAGAATGACGAGAATATCACCCTGGAAACC

GTCTGCCACGATCCCAAGCTGCCCTACCACGATTT

CATCCTGGAAGACGCCGCCAGCCCTAAGTGCATCA

TGAAAGAGAAAAAGAAGCCTGGCGAGACCTTTTTC

ATGTGCTCCTGCAGCAGCGACGAATGCAACGACAA

TATCATCTTTAGCGAGGAATACAATACCAGCAACC

CCGACATTACATGCCCCCCTCCCATGAGCGTGGA

GCACGCCGACATCTGGGTGAAGAGCTATAGCCTCT

ACAGCCGGGAGAGGTATATCTGTAACAGCGGCTT

CAAGAGGAAGGCCGGCACCAGCAGCCTCACCGAG

TGCGTGCTGAATAAGGCTACCAACGTGGCTCACTG

GACAACACCCTCTTTAAAGTGCATCCGG.

Exemplary Multi-Chain Chimeric Polypeptides—Type J

In some embodiments of any of the multi-chain chimeric polypeptides described herein, the first target-binding domain and the second targeting-binding domain each independently bind specifically to a receptor of IL-7, a receptor of IL-21, or a receptor of CD137L. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor for IL-21 (e.g., a soluble IL-21, e.g., a soluble human IL-21) or a receptor for CD137L (e.g., a soluble CD137L, e.g., a soluble human CD137L).

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments, the second chimeric polypeptide can include an additional target-binding domain. In some embodiments, the additional target-binding domain and the In some embodiments of these multi-chain chimeric polypeptides, one or more of the first target-binding domain, the second target-binding domain and the additional target-binding domain is an agonistic antigen-binding domain. In some embodiments of these multi-chain chimeric polypeptides, the first target-binding domain, the second target-binding domain, and the additional target-binding domain are each agonistic antigen-binding domains. In some embodiments of these multi-chain chimeric polypeptides, the antigen-binding domain includes a scFv or single-domain antibody.

In some embodiments of these multi-chain chimeric polypeptides, the first target-binding domain binds specifically to a receptor for IL-7, and the second target-binding domain binds specifically to a receptor for IL-21 or a receptor for CD137L. In some embodiments, the additional target-binding domain binds specifically to a receptor for IL-21 or a receptor for CD137L.

In some embodiments of these multi-chain chimeric polypeptides, the first target-binding domain is a soluble IL-7 (e.g., a soluble human IL-7). In some embodiments of these multi-chain chimeric polypeptides, the soluble human IL-7 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 11)
DCDIEGKDGKQYESVLMVSIDQLLDSMKEIGSNCL

NNEFNFFKRHICDANKEGMFLFRAARKLRQFLKMN

STGDFDLHLLKVSEGTTILLNCTGQVKGRKPAALG

EAQPTKSLEENKSLKEQKKLNDLCFLKRLLQEIKT

CWNKILMGTKEH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 124)
GATTGCGACATCGAGGGCAAGGACGGCAAGCAGTA

CGAGAGCGTGCTGATGGTGTCCATCGACCAGCTGC

TGGACAGCATGAAGGAGATCGGCTCCAACTGCCTC

AACAACGAGTTCAACTTCTTCAAGCGGCACATCTG

CGACGCCAACAAGGAGGGCATGTTCCTGTTCAGGG

CCGCCAGGAAACTGCGGCAGTTCCTGAAGATGAAC

TCCACCGGCGACTTCGACCTGCACCTGCTGAAGGT

GTCCGAGGGCACCACCATCCTGCTGAACTGCACCG

GACAGGTGAAGGGCCGGAAACCTGCTGCTCTGGGA

GAGGCCCAACCCACCAAGAGCCTGGAGGAGAACAA

GTCCCTGAAGGAGCAGAAGAAGCTGAACGACCTGT

GCTTCCTGAAGAGGCTGCTGCAGGAGATCAAGACC

TGCTGGAACAAGATCCTGATGGGCACCAAGGAGCA

T.

In some embodiments of these multi-chain chimeric polypeptides, the second target-binding domain or the additional target-binding domain binds specifically to a receptor for IL-21. In some embodiments of these multi-chain chimeric polypeptides, the second target-binding domain or the additional target-binding domain is a soluble IL-21 (e.g., a soluble human IL-21).

In some embodiments of these multi-chain chimeric polypeptides, a soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 78)
QGQDRHMIRMRQLIDIVDQLKNYVNDLVPEFLPAP

EDVETNCEWSAFSCFQKAQLKSANTGNNERIINVS

IKKLKRKPPSTNAGRRQKHRLTCPSCDSYEKKPPK

EFLERFKSLLQKMIHQHLSSRTHGSEDS.

In some embodiments of these multi-chain chimeric polypeptides, a soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 79)
CAGGGCCAGGACAGGCACATGATCCGGATGAGGCA

GCTCATCGACATCGTCGACCAGCTGAAGAACTACG

TGAACGACCTGGTGCCCGAGTTTCTGCCTGCCCCC

GAGGACGTGGAGACCAACTGCGAGTGGTCCGCCTT

CTCCTGCTTTCAGAAGGCCCAGCTGAAGTCCGCCA

ACACCGGCAACAACGAGCGGATCATCAACGTGAGC

ATCAAGAAGCTGAAGCGGAAGCCTCCCTCCACAAA

CGCCGGCAGGAGGCAGAAGCACAGGCTGACCTGCC

CCAGCTGTGACTCCTACGAGAAGAAGCCCCCCAAG

GAGTTCCTGGAGAGGTTCAAGTCCCTGCTGCAGAA

GATGATCCATCAGCACCTGTCCTCCAGGACCCACG

GCTCCGAGGACTCC.

In some embodiments of these multi-chain chimeric polypeptides, the second target-binding domain binds specifically to a receptor for CD137L. In some embodiments of these multi-chain chimeric polypeptides, the second chimeric polypeptide further comprises an additional target-binding domain that binds specifically to a receptor for CD137L. In some embodiments of these multi-chain chimeric polypeptides, the second target-binding domain and/or the additional target-binding domain is a soluble CD137L (e.g., a soluble human CD137L).

In some embodiments of these multi-chain chimeric polypeptides, a soluble human CD137L includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 157)
REGPELSPDDPAGLLDLRQGMFAQLVAQNVLLIDG

PLSWYSDPGLAGVSLTGGLSYKEDTKELVVAKAGV

YYVFFQLELRRVVAGEGSGSVSLALHLQPLRSAAG

AAALALTVDLPPASSEARNSAFGFQGRLLHLSAGQ

RLGVHLHTEARARHAWQLTQGATVLGLFRVTPEIP

AGLPSPRSE.

In some embodiments of these multi-chain chimeric polypeptides, a soluble human CD137L is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 158)
CGCGAGGGTCCCGAGCTTTCGCCCGACGATCCCGC
CGGCCTCTTGGACCTGCGGCAGGGCATGTTTGCGC
AGCTGGTGGCCCAAAATGTTCTGCTGATCGATGGG
CCCCTGAGCTGGTACAGTGACCCAGGCCTGGCAGG
CGTGTCCCTGACGGGGGGCCTGAGCTACAAAGAGG
ACACGAAGGAGCTGGTGGTGGCCAAGGCTGGAGTC
TACTATGTCTTCTTTCAACTAGAGCTGCGGCGCGT
GGTGGCCGGCGAGGGCTCAGGCTCCGTTTCACTTG
CGCTGCACCTGCAGCCACTGCGCTCTGCTGCTGGG
GCCGCCGCCCTGGCTTTGACCGTGGACCTGCCACC
CGCCTCCTCCGAGGCTCGGAACTCGGCCTTCGGTT
TCCAGGGCCGCTTGCTGCACCTGAGTGCCGGCCAG
CGCCTGGGCGTCCATCTTCACACTGAGGCCAGGGC
ACGCCATGCCTGGCAGCTTACCCAGGGCGCCACAG
TCTTGGGACTCTTCCGGGTGACCCCCGAAATCCCA
GCCGGACTCCCTTCACCGAGGTCGGAA.

In some embodiments of these multi-chain chimeric polypeptides, a soluble human CD137L includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 159)
DPAGLLDLRQGMFAQLVAQNVLLIDGPLSWYSDPG
LAGVSLTGGLSYKEDTKELVVAKAGVYYVFFQLEL
RRVVAGEGSGSVSLALHLQPLRSAAGAAALALTVD
LPPASSEARNSAFGFQGRLLHLSAGQRLGVHLHTE
ARARHAWQLTQGATVLGLFRVTPEI.

In some embodiments of these multi-chain chimeric polypeptides, a soluble human CD137L is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 160)
GATCCCGCCGGCCTCTTGGACCTGCGGCAGGGCAT
GTTTGCGCAGCTGGTGGCCCAAAATGTTCTGCTGA
TCGATGGGCCCCTGAGCTGGTACAGTGACCCAGGC

-continued
CTGGCAGGCGTGTCCCTGACGGGGGGCCTGAGCTA
CAAAGAGGACACGAAGGAGCTGGTGGTGGCCAAGG
CTGGAGTCTACTATGTCTTCTTTCAACTAGAGCTG
CGGCGCGTGGTGGCCGGCGAGGGCTCAGGCTCCGT
TTCACTTGCGCTGCACCTGCAGCCACTGCGCTCTG
CTGCTGGGGCCGCCGCCCTGGCTTTGACCGTGGAC
CTGCCACCCGCCTCCTCCGAGGCTCGGAACTCGGC
CTTCGGTTTCCAGGGCCGCTTGCTGCACCTGAGTG
CCGGCCAGCGCCTGGGCGTCCATCTTCACACTGAG
GCCAGGGCACGCCATGCCTGGCAGCTTACCCAGGG
CGCCACAGTCTTGGGACTCTTCCGGGTGACCCCCG
AAATC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 161)
DCDIEGKDGKQYESVLMVSIDQLLDSMKEIGSNCL
NNEFNFFKRHICDANKEGMFLFRAARKLRQFLKMN
STGDFDLHLLKVSEGTTILLNCTGQVKGRKPAALG
EAQPTKSLEENKSLKEQKKLNDLCFLKRLLQEIKT
CWNKILMGTKEHSGTTNTVAAYNLTWKSTNFKTIL
EWEPKPVNQVYTVQISTKSGDWKSKCFYTTDTECD
LTDEIVKDVKQTYLARVFSYPAGNVESTGSAGEPL
YENSPEFTPYLETNLGQPTIQSFEQVGTKVNVTVE
DERTLVRRNNTFLSLRDVFGKDLIYTLYYWKSSSS
GKKTAKTNTNEFLIDVDKGENYCFSVQAVIPSRTV
NRKSTDSPVECMGQEKGEFRENWVNVISDLKKIED
LIQSMHIDATLYTESDVHPSCKVTAMKCFLLELQV
ISLESGDASIHDTVENLIILANNSLSSNGNVTESG
CKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 162)
GATTGCGACATCGAGGGCAAGGACGGCAAGCAGTA
CGAGAGCGTGCTGATGGTGTCCATCGACCAGCTGC
TGGACAGCATGAAGGAGATCGGCTCCAACTGCCTC

-continued

AACAACGAGTTCAACTTCTTCAAGCGGCACATCTG
CGACGCCAACAAGGAGGGCATGTTCCTGTTCAGGG
CCGCCAGGAAACTGCGGCAGTTCCTGAAGATGAAC
TCCACCGGCGACTTCGACCTGCACCTGCTGAAGGT
GTCCGAGGGCACCACCATCCTGCTGAACTGCACCG
GACAGGTGAAGGGCCGGAAACCTGCTGCTCTGGGA
GAGGCCCAACCCACCAAGAGCCTGGAGGAGAACAA
GTCCCTGAAGGAGCAGAAGAAGCTGAACGACCTGT
GCTTCCTGAAGAGGCTGCTGCAGGAGATCAAGACC
TGCTGGAACAAGATCCTGATGGGCACCAAGGAGCA
TAGCGGCACAACCAACACAGTCGCTGCCTATAACC
TCACTTGGAAGAGCACCAACTTCAAAACCATCCTC
GAATGGGAACCCAAACCCGTTAACCAAGTTTACAC
CGTGCAGATCAGCACCAAGTCCGGCGACTGGAAGT
CCAAATGTTTCTATACCACCGACACCGAGTGCGAT
CTCACCGATGAGATCGTGAAAGATGTGAAACAGAC
CTACCTCGCCCGGGTGTTTAGCTACCCCGCCGGCA
ATGTGGAGAGCACTGGTTCCGCTGGCGAGCCTTTA
TACGAGAACAGCCCCGAATTTACCCCTTACCTCGA
GACCAATTTAGGACAGCCCACCATCCAAAGCTTTG
AGCAAGTTGGCACAAAGGTGAATGTGACAGTGGAG
GACGAGCGGACTTTAGTGCGGCGGAACAACACCTT
TCTCAGCCTCCGGGATGTGTTCGGCAAAGATTTAA
TCTACACACTGTATTACTGGAAGTCCTCTTCCTCC
GGCAAGAAGACAGCTAAAACCAACACAAACGAGTT
TTTAATCGACGTGGATAAAGGCGAAAACTACTGTT
TCAGCGTGCAAGCTGTGATCCCCTCCCGGACCGTG
AATAGGAAAAGCACCGATAGCCCCGTTGAGTGCAT
GGGCCAAGAAAAGGGCGAGTTCCGGGAGAACTGGG
TGAACGTCATCAGCGATTTAAAGAAGATCGAAGAT
TTAATTCAGTCCATGCATATCGACGCCACTTTATA
CACAGAATCCGACGTGCACCCCTCTTGTAAGGTGA
CCGCCATGAAATGTTTTTTACTGGAGCTGCAAGTT
ATCTCTTTAGAGAGCGGAGACGCTAGCATCCACGA
CACCGTGGAGAATTTAATCATTTTAGCCAATAACT
CTTTATCCAGCAACGGCAACGTGACAGAGTCCGGC
TGCAAGGAGTGCGAAGAGCTGGAGGAGAAGAACAT
CAAGGAGTTTCTGCAATCCTTTGTGCACATTGTCC
AGATGTTCATCAATACCTCC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 163)
MKWVTFISLLFLFSSAYSDCDIEGKDGKQYESVLM
VSIDQLLDSMKEIGSNCLNNEFNFFKRHICDANKE
GMFLFRAARKLRQFLKMNSTGDFDLHLLKVSEGTT
ILLNCTGQVKGRKPAALGEAQPTKSLEENKSLKEQ
KKLNDLCFLKRLLQEIKTCWNKILMGTKEHSGTTN
TVAAYNLTWKSTNFKTILEWEPKPVNQVYTVQIST
KSGDWKSKCFYTTDTECDLTDEIVKDVKQTYLARV
FSYPAGNVESTGSAGEPLYENSPEFTPYLETNLGQ
PTIQSFEQVGTKVNVTVEDERTLVRRNNTFLSLRD
VFGKDLIYTLYYWKSSSSGKKTAKTNTNEFLIDVD
KGENYCFSVQAVIPSRTVNRKSTDSPVECMGQEKG
EFRENWVNVISDLKKIEDLIQSMHIDATLYTESDV
HPSCKVTAMKCFLLELQVISLESGDASIHDTVENL
IILANNSLSSNGNVTESGCKECEELEEKNIKEFLQ
SFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 164)
ATGAAGTGGGTGACCTTCATCAGCCTGCTGTTCCT
GTTCTCCAGCGCCTACTCCGATTGCGACATCGAGG
GCAAGGACGGCAAGCAGTACGAGAGCGTGCTGATG
GTGTCCATCGACCAGCTGCTGGACAGCATGAAGGA
GATCGGCTCCAACTGCCTCAACAACGAGTTCAACT
TCTTCAAGCGGCACATCTGCGACGCCAACAAGGAG
GGCATGTTCCTGTTCAGGGCCGCCAGGAAACTGCG
GCAGTTCCTGAAGATGAACTCCACCGGCGACTTCG
ACCTGCACCTGCTGAAGGTGTCCGAGGGCACCACC
ATCCTGCTGAACTGCACCGGACAGGTGAAGGGCCG
GAAACCTGCTGCTCTGGGAGAGGCCCAACCCACCA
AGAGCCTGGAGGAGAACAAGTCCCTGAAGGAGCAG
AAGAAGCTGAACGACCTGTGCTTCCTGAAGAGGCT
GCTGCAGGAGATCAAGACCTGCTGGAACAAGATCC
TGATGGGCACCAAGGAGCATAGCGGCACAACCAAC
ACAGTCGCTGCCTATAACCTCACTTGGAAGAGCAC

-continued

CAACTTCAAAACCATCCTCGAATGGGAACCCAAAC
CCGTTAACCAAGTTTACACCGTGCAGATCAGCACC
AAGTCCGGCGACTGGAAGTCCAAATGTTTCTATAC
CACCGACACCGAGTGCGATCTCACCGATGAGATCG
TGAAAGATGTGAAACAGACCTACCTCGCCCGGGTG
TTTAGCTACCCCGCCGGCAATGTGGAGAGCACTGG
TTCCGCTGGCGAGCCTTTATACGAGAACAGCCCCG
AATTTACCCCTTACCTCGAGACCAATTTAGGACAG
CCCACCATCCAAAGCTTTGAGCAAGTTGGCACAAA
GGTGAATGTGACAGTGGAGGACGAGCGGACTTTAG
TGCGGCGGAACAACACCTTTCTCAGCCTCCGGGAT
GTGTTCGGCAAAGATTTAATCTACACACTGTATTA
CTGGAAGTCCTCTTCCTCCGGCAAGAAGACAGCTA
AAACCAACACAAACGAGTTTTTAATCGACGTGGAT
AAAGGCGAAAACTACTGTTTCAGCGTGCAAGCTGT
GATCCCCTCCCGGACCGTGAATAGGAAAAGCACCG
ATAGCCCCGTTGAGTGCATGGGCCAAGAAAAGGGC
GAGTTCCGGGAGAACTGGGTGAACGTCATCAGCGA
TTTAAAGAAGATCGAAGATTTAATTCAGTCCATGC
ATATCGACGCCACTTTATACACAGAATCCGACGTG
CACCCCTCTTGTAAGGTGACCGCCATGAAATGTTT
TTTACTGGAGCTGCAAGTTATCTCTTTAGAGAGCG
GAGACGCTAGCATCCACGACACCGTGGAGAATTTA
ATCATTTTAGCCAATAACTCTTTATCCAGCAACGG
CAACGTGACAGAGTCCGGCTGCAAGGAGTGCGAAG
AGCTGGAGGAGAAGAACATCAAGGAGTTTCTGCAA
TCCTTTGTGCACATTGTCCAGATGTTCATCAATAC
CTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 165)
QGQDRHMIRMRQLIDIVDQLKNYVNDLVPEFLPAP
EDVETNCEWSAFSCFQKAQLKSANTGNNERIINVS
IKKLKRKPPSTNAGRRQKHRLTCPSCDSYEKKPPK
EFLERFKSLLQKMIHQHLSSRTHGSEDSITCPPPM
SVEHADIWVKSYSLYSRERYICNSGFKRKAGTSSL
TECVLNKATNVAHWTTPSLKCIRGGGGSGGGGSGG
GGSREGPELSPDDPAGLLDLRQGMFAQLVAQNVLL

-continued

IDGPLSWYSDPGLAGVSLTGGLSYKEDTKELVVAK
AGVYYVFFQLELRRVVAGEGSGSVSLALHLQPLRS
AAGAAALALTVDLPPASSEARNSAFGFQGRLLHLS
AGQRLGVHLHTEARARHAWQLTQGATVLGLFRVTP
EIPAGLPSPRSE.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 166)
CAGGGCCAGGACAGGCACATGATCCGGATGAGGCA
GCTCATCGACATCGTCGACCAGCTGAAGAACTACG
TGAACGACCTGGTGCCCGAGTTTCTGCCTGCCCCC
GAGGACGTGGAGACCAACTGCGAGTGGTCCGCCTT
CTCCTGCTTTCAGAAGGCCCAGCTGAAGTCCGCCA
ACACCGGCAACAACGAGCGGATCATCAACGTGAGC
ATCAAGAAGCTGAAGCGGAAGCCTCCCTCCACAAA
CGCCGGCAGGAGGCAGAAGCACAGGCTGACCTGCC
CCAGCTGTGACTCCTACGAGAAGAAGCCCCCCAAG
GAGTTCCTGGAGAGGTTCAAGTCCCTGCTGCAGAA
GATGATCCATCAGCACCTGTCCTCCAGGACCCACG
GCTCCGAGGACTCCATTACATGCCCCCCTCCCATG
AGCGTGGAGCACGCCGACATCTGGGTGAAGAGCTA
TAGCCTCTACAGCCGGGAGAGGTATATCTGTAACA
GCGGCTTCAAGAGGAAGGCCGGCACCAGCAGCCTC
ACCGAGTGCGTGCTGAATAAGGCTACCAACGTGGC
TCACTGGACAACACCCTCTTTAAAGTGCATCCGGG
GCGGTGGAGGATCCGGAGGAGGTGGCTCCGGCGGC
GGAGGATCTCGCGAGGGTCCCGAGCTTTCGCCCGA
CGATCCCGCCGGCCTCTTGGACCTGCGGCAGGGCA
TGTTTGCGCAGCTGGTGGCCCAAAATGTTCTGCTG
ATCGATGGGCCCCTGAGCTGGTACAGTGACCCAGG
CCTGGCAGGCGTGTCCCTGACGGGGGGCCTGAGCT
ACAAAGAGGACACGAAGGAGCTGGTGGTGGCCAAG
GCTGGAGTCTACTATGTCTTCTTTCAACTAGAGCT
GCGGCGCGTGGTGGCCGGCGAGGGCTCAGGCTCCG
TTTCACTTGCGCTGCACCTGCAGCCACTGCGCTCT
GCTGCTGGGGCCGCCGCCCTGGCTTTGACCGTGGA
CCTGCCACCCGCCTCCTCCGAGGCTCGGAACTCGG

-continued

CCTTCGGTTTCCAGGGCCGCTTGCTGCACCTGAGT
GCCGGCCAGCGCCTGGGCGTCCATCTTCACACTGA
GGCCAGGGCACGCCATGCCTGGCAGCTTACCCAGG
GCGCCACAGTCTTGGGACTCTTCCGGGTGACCCCC
GAAATCCCAGCCGGACTCCCTTCACCGAGGTCGGA
A.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 167)
MKWVTFISLLFLFSSAYSQGQDRHMIRMRQLIDIV
DQLKNYVNDLVPEFLPAPEDVETNCEWSAFSCFQK
AQLKSANTGNNERIINVSIKKLKRKPPSTNAGRRQ
KHRLTCPSCDSYEKKPPKEFLERFKSLLQKMIHQH
LSSRTHGSEDSITCPPPMSVEHADIWVKSYSLYSR
ERYICNSGFKRKAGTSSLTECVLNKATNVAHWTTP
SLKCIRGGGGSGGGGSGGGGSREGPELSPDDPAGL
LDLRQGMFAQLVAQNVLLIDGPLSWYSDPGLAGVS
LTGGLSYKEDTKELVVAKAGVYYVFFQLELRRVVA
GEGSGSVSLALHLQPLRSAAGAAALALTVDLPPAS
SEARNSAFGFQGRLLHLSAGQRLGVHLHTEARARH
AWQLTQGATVLGLFRVTPEIPAGLPSPRSE.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 168)
ATGAAGTGGGTGACCTTCATCAGCCTGCTGTTCCT
GTTCTCCAGCGCCTACTCCCAGGGCCAGGACAGGC
ACATGATCCGGATGAGGCAGCTCATCGACATCGTC
GACCAGCTGAAGAACTACGTGAACGACCTGGTGCC
CGAGTTTCTGCCTGCCCCCGAGGACGTGGAGACCA
ACTGCGAGTGGTCCGCCTTCTCCTGCTTTCAGAAG
GCCCAGCTGAAGTCCGCCAACACCGGCAACAACGA
GCGGATCATCAACGTGAGCATCAAGAAGCTGAAGC
GGAAGCCTCCCTCCACAAACGCCGGCAGGAGGCAG
AAGCACAGGCTGACCTGCCCCAGCTGTGACTCCTA
CGAGAAGAAGCCCCCCAAGGAGTTCCTGGAGAGGT

-continued

TCAAGTCCCTGCTGCAGAAGATGATCCATCAGCAC
CTGTCCTCCAGGACCCACGGCTCCGAGGACTCCAT
TACATGCCCCCCTCCCATGAGCGTGGAGCACGCCG
ACATCTGGGTGAAGAGCTATAGCCTCTACAGCCGG
GAGAGGTATATCTGTAACAGCGGCTTCAAGAGGAA
GGCCGGCACCAGCAGCCTCACCGAGTGCGTGCTGA
ATAAGGCTACCAACGTGGCTCACTGGACAACACCC
TCTTTAAAGTGCATCCGGGGCGGTGGAGGATCCGG
AGGAGGTGGCTCCGGCGGCGGAGGATCTCGCGAGG
GTCCCGAGCTTTCGCCCGACGATCCCGCCGGCCTC
TTGGACCTGCGGCAGGGCATGTTTGCGCAGCTGGT
GGCCCAAAATGTTCTGCTGATCGATGGGCCCCTGA
GCTGGTACAGTGACCCAGGCCTGGCAGGCGTGTCC
CTGACGGGGGGCCTGAGCTACAAAGAGGACACGAA
GGAGCTGGTGGTGGCCAAGGCTGGAGTCTACTATG
TCTTCTTTCAACTAGAGCTGCGGCGCGTGGTGGCC
GGCGAGGGCTCAGGCTCCGTTTCACTTGCGCTGCA
CCTGCAGCCACTGCGCTCTGCTGCTGGGGCCGCCG
CCCTGGCTTTGACCGTGGACCTGCCACCCGCCTCC
TCCGAGGCTCGGAACTCGGCCTTCGGTTTCCAGGG
CCGCTTGCTGCACCTGAGTGCCGGCCAGCGCCTGG
GCGTCCATCTTCACACTGAGGCCAGGGCACGCCAT
GCCTGGCAGCTTACCCAGGGCGCCACAGTCTTGGG
ACTCTTCCGGGTGACCCCCGAAATCCCAGCCGGAC
TCCCTTCACCGAGGTCGGAA.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 169)
QGQDRHMIRMRQLIDIVDQLKNYVNDLVPEFLPAP
EDVETNCEWSAFSCFQKAQLKSANTGNNERIINVS
IKKLKRKPPSTNAGRRQKHRLTCPSCDSYEKKPPK
EFLERFKSLLQKMIHQHLSSRTHGSEDSITCPPPM
SVEHADIWVKSYSLYSRERYICNSGFKRKAGTSSL
TECVLNKATNVAHWTTPSLKCIRGGGGSGGGGSGG
GGSDPAGLLDLRQGMFAQLVAQNVLLIDGPLSWYS
DPGLAGVSLTGGLSYKEDTKELVVAKAGVYYVFFQ
LELRRVVAGEGSGSVSLALHLQPLRSAAGAAALAL

-continued

TVDLPPASSEARNSAFGFQGRLLHLSAGQRLGVHL

HTEARARHAWQLTQGATVLGLFRVTPEI.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 170)

CAGGGCCAGGACAGGCACATGATCCGGATGAGGCA

GCTCATCGACATCGTCGACCAGCTGAAGAACTACG

TGAACGACCTGGTGCCCGAGTTTCTGCCTGCCCCC

GAGGACGTGGAGACCAACTGCGAGTGGTCCGCCTT

CTCCTGCTTTCAGAAGGCCCAGCTGAAGTCCGCCA

ACACCGGCAACAACGAGCGGATCATCAACGTGAGC

ATCAAGAAGCTGAAGCGGAAGCCTCCCTCCACAAA

CGCCGGCAGGAGGCAGAAGCACAGGCTGACCTGCC

CCAGCTGTGACTCCTACGAGAAGAAGCCCCCCAAG

GAGTTCCTGGAGAGGTTCAAGTCCCTGCTGCAGAA

GATGATCCATCAGCACCTGTCCTCCAGGACCCACG

GCTCCGAGGACTCCATTACATGCCCCCCTCCCATG

AGCGTGGAGCACGCCGACATCTGGGTGAAGAGCTA

TAGCCTCTACAGCCGGGAGAGGTATATCTGTAACA

GCGGCTTCAAGAGGAAGGCCGGCACCAGCAGCCTC

ACCGAGTGCGTGCTGAATAAGGCTACCAACGTGGC

TCACTGGACAACACCCTCTTTAAAGTGCATCCGGG

GCGGTGGAGGATCCGGAGGAGGTGGCTCCGGCGGC

GGAGGATCTGATCCCGCCGGCCTCTTGGACCTGCG

GCAGGGCATGTTTGCGCAGCTGGTGGCCCAAAATG

TTCTGCTGATCGATGGGCCCCTGAGCTGGTACAGT

GACCCAGGCCTGGCAGGCGTGTCCCTGACGGGGGG

CCTGAGCTACAAAGAGGACACGAAGGAGCTGGTGG

TGGCCAAGGCTGGAGTCTACTATGTCTTCTTTCAA

CTAGAGCTGCGGCGCGTGGTGGCCGGCGAGGGCTC

AGGCTCCGTTTCACTTGCGCTGCACCTGCAGCCAC

TGCGCTCTGCTGCTGGGGCCGCCGCCCTGGCTTTG

ACCGTGGACCTGCCACCCGCCTCCTCCGAGGCTCG

GAACTCGGCCTTCGGTTTCCAGGGCCGCTTGCTGC

ACCTGAGTGCCGGCCAGCGCCTGGGCGTCCATCTT

CACACTGAGGCCAGGGCACGCCATGCCTGGCAGCT

TACCCAGGGCGCCACAGTCTTGGGACTCTTCCGGG

TGACCCCCGAAATC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 171)

MKWVTFISLLFLFSSAYSQGQDRHMIRMRQLIDIV

DQLKNYVNDLVPEFLPAPEDVETNCEWSAFSCFQK

AQLKSANTGNNERIINVSIKKLKRKPPSTNAGRRQ

KHRLTCPSCDSYEKKPPKEFLERFKSLLQKMIHQH

LSSRTHGSEDSITCPPPMSVEHADIWVKSYSLYSR

ERYICNSGFKRKAGTSSLTECVLNKATNVAHWTTP

SLKCIRGGGGSGGGGSGGGGSDPAGLLDLRQGMFA

QLVAQNVLLIDGPLSWYSDPGLAGVSLTGGLSYKE

DTKELVVAKAGVYYVFFQLELRRVVAGEGSGSVSL

ALHLQPLRSAAGAAALALTVDLPPASSEARNSAFG

FQGRLLHLSAGQRLGVHLHTEARARHAWQLTQGAT

VLGLFRVTPEI.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 172)

ATGAAGTGGGTGACCTTCATCAGCCTGCTGTTCCT

GTTCTCCAGCGCCTACTCCCAGGGCCAGGACAGGC

ACATGATCCGGATGAGGCAGCTCATCGACATCGTC

GACCAGCTGAAGAACTACGTGAACGACCTGGTGCC

CGAGTTTCTGCCTGCCCCCGAGGACGTGGAGACCA

ACTGCGAGTGGTCCGCCTTCTCCTGCTTTCAGAAG

GCCCAGCTGAAGTCCGCCAACACCGGCAACAACGA

GCGGATCATCAACGTGAGCATCAAGAAGCTGAAGC

GGAAGCCTCCCTCCACAAACGCCGGCAGGAGGCAG

AAGCACAGGCTGACCTGCCCCAGCTGTGACTCCTA

CGAGAAGAAGCCCCCCAAGGAGTTCCTGGAGAGGT

TCAAGTCCCTGCTGCAGAAGATGATCCATCAGCAC

CTGTCCTCCAGGACCCACGGCTCCGAGGACTCCAT

TACATGCCCCCCTCCCATGAGCGTGGAGCACGCCG

ACATCTGGGTGAAGAGCTATAGCCTCTACAGCCGG

GAGAGGTATATCTGTAACAGCGGCTTCAAGAGGAA

GGCCGGCACCAGCAGCCTCACCGAGTGCGTGCTGA

-continued

ATAAGGCTACCAACGTGGCTCACTGGACAACACCC

TCTTTAAAGTGCATCCGGGGCGGTGGAGGATCCGG

AGGAGGTGGCTCCGGCGGCGGAGGATCTGATCCCG

CCGGCCTCTTGGACCTGCGGCAGGGCATGTTTGCG

CAGCTGGTGGCCCAAAATGTTCTGCTGATCGATGG

GCCCCTGAGCTGGTACAGTGACCCAGGCCTGGCAG

GCGTGTCCCTGACGGGGGGCCTGAGCTACAAAGAG

GACACGAAGGAGCTGGTGGTGGCCAAGGCTGGAGT

CTACTATGTCTTCTTTCAACTAGAGCTGCGGCGCG

TGGTGGCCGGCGAGGGCTCAGGCTCCGTTTCACTT

GCGCTGCACCTGCAGCCACTGCGCTCTGCTGCTGG

GGCCGCCGCCCTGGCTTTGACCGTGGACCTGCCAC

CCGCCTCCTCCGAGGCTCGGAACTCGGCCTTCGGT

TTCCAGGGCCGCTTGCTGCACCTGAGTGCCGGCCA

GCGCCTGGGCGTCCATCTTCACACTGAGGCCAGGG

CACGCCATGCCTGGCAGCTTACCCAGGGCGCCACA

GTCTTGGGACTCTTCCGGGTGACCCCCGAAATC.

Exemplary Multi-Chain Chimeric Polypeptides—Type K

In some embodiments of any of the multi-chain chimeric polypeptides described herein, the first target-binding domain and the second targeting-binding domain each independently bind specifically to a receptor of IL-7 or TGF-β. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain binds specifically to a receptor for IL-7, and the second target-binding domain binds specifically to TGF-β. In some embodiments of these multi-chain chimeric polypeptides, the first target-binding domain binds specifically to TGF-β, and the second target-binding domain binds specifically to a receptor for IL-7.

In some embodiments of these multi-chain chimeric polypeptides, the first target-binding domain includes a soluble IL-7 protein (e.g., a soluble human IL-7 protein). In some embodiments of these multi-chain chimeric polypeptides, the soluble human IL-7 protein includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 11)

DCDIEGKDGKQYESVLMVSIDQLLDSMKEIGSNCL

NNEFNFFKRHICDANKEGMFLFRAARKLRQFLKMN

STGDFDLHLLKVSEGTTILLNCTGQVKGRKPAALG

EAQPTKSLEENKSLKEQKKLNDLCFLKRLLQEIKT

CWNKILMGTKEH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 124)

GATTGCGACATCGAGGGCAAGGACGGCAAGCAGTA

CGAGAGCGTGCTGATGGTGTCCATCGACCAGCTGC

TGGACAGCATGAAGGAGATCGGCTCCAACTGCCTC

AACAACGAGTTCAACTTCTTCAAGCGGCACATCTG

CGACGCCAACAAGGAGGGCATGTTCCTGTTCAGGG

CCGCCAGGAAACTGCGGCAGTTCCTGAAGATGAAC

TCCACCGGCGACTTCGACCTGCACCTGCTGAAGGT

GTCCGAGGGCACCACCATCCTGCTGAACTGCACCG

GACAGGTGAAGGGCCGGAAACCTGCTGCTCTGGGA

GAGGCCCAACCCACCAAGAGCCTGGAGGAGAACAA

GTCCCTGAAGGAGCAGAAGAAGCTGAACGACCTGT

GCTTCCTGAAGAGGCTGCTGCAGGAGATCAAGACC

TGCTGGAACAAGATCCTGATGGGCACCAAGGAGCA

T.

In some embodiments of these multi-chain chimeric polypeptides, the second target-binding domain comprises a target-binding domain that binds specifically to TGF-β. In some embodiments of these multi-chain chimeric polypeptides, the second target-binding domain is a soluble TGF-β receptor (e.g., a soluble TGFβRII receptor, e.g., a soluble human TGFβRII receptor). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 80)
IPPHVQKSVNNDMIVTDNNGAVKFPQLCKFCDVRF

STCDNQKSCMSNCSITSICEKPQEVCVAVWRKNDE

NITLETVCHDPKLPYHDFILEDAASPKCIMKEKKK

PGETFFMCSCSSDECNDNIIFSEEYNTSNPD.

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 81)
IPPHVQKSVNNDMIVTDNNGAVKFPQLCKFCDVRF

STCDNQKSCMSNCSITSICEKPQEVCVAVWRKNDE

NITLETVCHDPKLPYHDFILEDAASPKCIMKEKKK

PGETFFMCSCSSDECNDNIIFSEEYNTSNPD.

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 82)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

-continued

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT.

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 83)
ATTCCTCCCCACGTGCAGAAGAGCGTGAATAATGACATGATCGTGACCGA

TAACAATGGCGCCGTGAAATTTCCCCAGCTGTGCAAATTCTGCGATGTGA

GGTTTTCCACCTGCGACAACCAGAAGTCCTGTATGAGCAACTGCTCCATC

ACCTCCATCTGTGAGAAGCCTCAGGAGGTGTGCGTGGCTGTCTGGCGGAA

GAATGACGAGAATATCACCCTGGAAACCGTCTGCCACGATCCCAAGCTGC

CCTACCACGATTTCATCCTGGAAGACGCCGCCAGCCCTAAGTGCATCATG

AAAGAGAAAAAGAAGCCTGGCGAGACCTTTTTCATGTGCTCCTGCAGCAG

CGACGAATGCAACGACAATATCATCTTTAGCGAGGAATACAATACCAGCA

ACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 85)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 84)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

-continued

ACCTCCATCTGCGAGAAGCCCCAAGAAGTGTGCGTGGCCGTGTGGCGGAA
AAATGACGAGAACATCACCCTGGAGACCGTGTGTCACGACCCCAAGCTCC
CTTATCACGACTTCATTCTGGAGGACGCTGCCTCCCCCAAATGCATCATG
AAGGAGAAGAAGAAGCCCGGAGAGACCTTCTTTATGTGTTCCTGTAGCAG
CGACGAGTGTAACGACAACATCATCTTCAGCGAAGAGTACAACACCAGCA
ACCCTGATGGAGGTGGCGGATCCGGAGGTGGAGGTTCTGGTGGAGGTGGG
AGTATTCCTCCCCACGTGCAGAAGAGCGTGAATAATGACATGATCGTGAC
CGATAACAATGGCGCCGTGAAATTTCCCCAGCTGTGCAAATTCTGCGATG
TGAGGTTTTCCACCTGCGACAACCAGAAGTCCTGTATGAGCAACTGCTCC
ATCACCTCCATCTGTGAGAAGCCTCAGGAGGTGTGCGTGGCTGTCTGGCG
GAAGAATGACGAGAATATCACCCTGGAAACCGTCTGCCACGATCCCAAGC
TGCCCTACCACGATTTCATCCTGGAAGACGCCGCCAGCCCTAAGTGCATC
ATGAAAGAGAAAAAGAAGCCTGGCGAGACCTTTTTCATGTGCTCCTGCAG
CAGCGACGAATGCAACGACAATATCATCTTTAGCGAGGAATACAATACCA
GCAACCCCGAC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 173)
DCDIEGKDGKQYESVLMVSIDQLLDSMKEIGSNCLNNEFNFFKRHICDAN
KEGMFLFRAARKLRQFLKMNSTGDFDLHLLKVSEGTTILLNCTGQVKGRK
PAALGEAQPTKSLEENKSLKEQKKLNDLCFLKRLLQEIKTCWNKILMGTK
EHSGTTNTVAAYNLTWKSTNFKTILEWEPKPVNQVYTVQISTKSGDWKSK
CFYTTDTECDLTDEIVKDVKQTYLARVFSYPAGNVESTGSAGEPLYENSP
EFTPYLETNLGQPTIQSFEQVGTKVNVTVEDERTLVRRNNTFLSLRDVFG
KDLIYTLYYWKSSSSGKKTAKTNTNEFLIDVDKGENYCFSVQAVIPSRTV
NRKSTDSPVECMGQEKGEFRENWVNVISDLKKIEDLIQSMHIDATLYTES
DVHPSCKVTAMKCFLLELQVISLESGDASIHDTVENLIILANNSLSSNGN
VTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 174)
GATTGCGACATCGAGGGCAAGGACGGCAAGCAGTACGAGAGCGTGCTGAT
GGTGTCCATCGACCAGCTGCTGGACAGCATGAAGGAGATCGGCTCCAACT
GCCTCAACAACGAGTTCAACTTCTTCAAGCGGCACATCTGCGACGCCAAC

-continued

AAGGAGGGCATGTTCCTGTTCAGGGCCGCCAGGAAACTGCGGCAGTTCCT
GAAGATGAACTCCACCGGCGACTTCGACCTGCACCTGCTGAAGGTGTCCG
AGGGCACCACCATCCTGCTGAACTGCACCGGACAGGTGAAGGGCCGGAAA
CCTGCTGCTCTGGGAGAGGCCCAACCCACCAAGAGCCTGGAGGAGAACAA
GTCCCTGAAGGAGCAGAAGAAGCTGAACGACCTGTGCTTCCTGAAGAGGC
TGCTGCAGGAGATCAAGACCTGCTGGAACAAGATCCTGATGGGCACCAAG
GAGCATAGCGGCACAACCAACACAGTCGCTGCCTATAACCTCACTTGGAA
GAGCACCAACTTCAAAACCATCCTCGAATGGGAACCCAAACCCGTTAACC
AAGTTTACACCGTGCAGATCAGCACCAAGTCCGGCGACTGGAAGTCCAAA
TGTTTCTATACCACCGACACCGAGTGCGATCTCACCGATGAGATCGTGAA
AGATGTGAAACAGACCTACCTCGCCCGGGTGTTTAGCTACCCCGCCGGCA
ATGTGGAGAGCACTGGTTCCGCTGGCGAGCCTTTATACGAGAACAGCCCC
GAATTTACCCCTTACCTCGAGACCAATTTAGGACAGCCCACCATCCAAAG
CTTTGAGCAAGTTGGCACAAAGGTGAATGTGACAGTGGAGGACGAGCGGA
CTTTAGTGCGGCGGAACAACACCTTTCTCAGCCTCCGGGATGTGTTCGGC
AAAGATTTAATCTACACACTGTATTACTGGAAGTCCTCTTCCTCCGGCAA
GAAGACAGCTAAAACCAACACAAACGAGTTTTTAATCGACGTGGATAAAG
GCGAAAACTACTGTTTCAGCGTGCAAGCTGTGATCCCCTCCCGGACCGTG
AATAGGAAAAGCACCGATAGCCCCGTTGAGTGCATGGGCCAAGAAAAGGG
CGAGTTCCGGGAGAACTGGGTGAACGTCATCAGCGATTTAAAGAAGATCG
AAGATTTAATTCAGTCCATGCATATCGACGCCACTTTATACACAGAATCC
GACGTGCACCCCTCTTGTAAGGTGACCGCCATGAAATGTTTTTTACTGGA
GCTGCAAGTTATCTCTTTAGAGAGCGGAGACGCTAGCATCCACGACACCG
TGGAGAATTTAATCATTTTAGCCAATAACTCTTTATCCAGCAACGGCAAC
GTGACAGAGTCCGGCTGCAAGGAGTGCGAAGAGCTGGAGGAGAAGAACAT
CAAGGAGTTTCTGCAATCCTTTGTGCACATTGTCCAGATGTTCATCAATA
CCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 175)
MKWVTFISLLFLFSSAYSDCDIEGKDGKQYESVLMVSIDQLLDSMKEIGS
NCLNNEFNFFKRHICDANKEGMFLFRAARKLRQFLKMNSTGDFDLHLLKV
SEGTTILLNCTGQVKGRKPAALGEAQPTKSLEENKSLKEQKKLNDLCFLK
RLLQEIKTCWNKILMGTKEHSGTTNTVAAYNLTWKSTNFKTILEWEPKPV
NQVYTVQISTKSGDWKSKCFYTTDTECDLTDEIVKDVKQTYLARVFSYPA
GNVESTGSAGEPLYENSPEFTPYLETNLGQPTIQSFEQVGTKVNVTVEDE
RTLVRRNNTFLSLRDVFGKDLIYTLYYWKSSSSGKKTAKTNTNEFLIDVD
KGENYCFSVQAVIPSRTVNRKSTDSPVECMGQEKGEFRENWVNVISDLKK

-continued

IEDLIQSMHIDATLYTESDVHPSCKVTAMKCFLLELQVISLESGDASIHD

TVENLIILANNSLSSNGNVTESGCKECEELEEKNIKEFLQSFVHIVQMFI

NTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 176)

ATGAAGTGGGTGACCTTCATCAGCCTGCTGTTCCTGTTCTCCAGCGCCTA

CTCCGATTGCGACATCGAGGGCAAGGACGGCAAGCAGTACGAGAGCGTGC

TGATGGTGTCCATCGACCAGCTGCTGGACAGCATGAAGGAGATCGGCTCC

AACTGCCTCAACAACGAGTTCAACTTCTTCAAGCGGCACATCTGCGACGC

CAACAAGGAGGGCATGTTCCTGTTCAGGGCCGCCAGGAAACTGCGGCAGT

TCCTGAAGATGAACTCCACCGGCGACTTCGACCTGCACCTGCTGAAGGTG

TCCGAGGGCACCACCATCCTGCTGAACTGCACCGGACAGGTGAAGGGCCG

GAAACCTGCTGCTCTGGGAGAGGCCCAACCCACCAAGAGCCTGGAGGAGA

ACAAGTCCCTGAAGGAGCAGAAGAAGCTGAACGACCTGTGCTTCCTGAAG

AGGCTGCTGCAGGAGATCAAGACCTGCTGGAACAAGATCCTGATGGGCAC

CAAGGAGCATAGCGGCACAACCAACACAGTCGCTGCCTATAACCTCACTT

GGAAGAGCACCAACTTCAAAACCATCCTCGAATGGGAACCCAAACCCGTT

AACCAAGTTTACACCGTGCAGATCAGCACCAAGTCCGGCGACTGGAAGTC

CAAATGTTTCTATACCACCGACACCGAGTGCGATCTCACCGATGAGATCG

TGAAAGATGTGAAACAGACCTACCTCGCCCGGGTGTTTAGCTACCCCGCC

GGCAATGTGGAGAGCACTGGTTCCGCTGGCGAGCCTTTATACGAGAACAG

CCCCGAATTTACCCCTTACCTCGAGACCAATTTAGGACAGCCCACCATCC

AAAGCTTTGAGCAAGTTGGCACAAAGGTGAATGTGACAGTGGAGGACGAG

CGGACTTTAGTGCGGCGGAACAACACCTTTCTCAGCCTCCGGGATGTGTT

CGGCAAAGATTTAATCTACACACTGTATTACTGGAAGTCCTCTTCCTCCG

GCAAGAAGACAGCTAAAACCAACACAAACGAGTTTTTAATCGACGTGGAT

AAAGGCGAAAACTACTGTTTCAGCGTGCAAGCTGTGATCCCCTCCCGGAC

CGTGAATAGGAAAAGCACCGATAGCCCCGTTGAGTGCATGGGCCAAGAAA

AGGGCGAGTTCCGGGAGAACTGGGTGAACGTCATCAGCGATTTAAAGAAG

ATCGAAGATTTAATTCAGTCCATGCATATCGACGCCACTTTATACACAGA

ATCCGACGTGCACCCCTCTTGTAAGGTGACCGCCATGAAATGTTTTTTAC

TGGAGCTGCAAGTTATCTCTTTAGAGAGCGGAGACGCTAGCATCCACGAC

ACCGTGGAGAATTTAATCATTTTAGCCAATAACTCTTTATCCAGCAACGG

CAACGTGACAGAGTCCGGCTGCAAGGAGTGCGAAGAGCTGGAGGAGAAGA

ACATCAAGGAGTTTCTGCAATCCTTTGTGCACATTGTCCAGATGTTCATC

AATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 177)

IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDITCPPPMSVEHAD

IWVKSYSLYSRERYICNSGFKRKAGTSSLTECVLNKATNVAHWTTPSLKC

IR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 178)

ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGACATTACATGCCCCCCTCCCATGAGCGTGGAGCACGCCGAC

ATCTGGGTGAAGAGCTATAGCCTCTACAGCCGGGAGAGGTATATCTGTAA

-continued

CAGCGGCTTCAAGAGGAAGGCCGGCACCAGCAGCCTCACCGAGTGCGTGC

TGAATAAGGCTACCAACGTGGCTCACTGGACAACACCCTCTTTAAAGTGC

ATCCGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 179)

MKWVTFISLLFLFSSAYSIPPHVQKSVNNDMIVTDNNGAVKFPQLCKFCD

VRFSTCDNQKSCMSNCSITSICEKPQEVCVAVWRKNDENITLETVCHDPK

LPYHDFILEDAASPKCIMKEKKKPGETFFMCSCSSDECNDNIIFSEEYNT

SNPDGGGGSGGGGSGGGGSIPPHVQKSVNNDMIVTDNNGAVKFPQLCKFC

DVRFSTCDNQKSCMSNCSITSICEKPQEVCVAVWRKNDENITLETVCHDP

KLPYHDFILEDAASPKCIMKEKKKPGETFFMCSCSSDECNDNIIFSEEYN

TSNPDITCPPPMSVEHADIWVKSYSLYSRERYICNSGFKRKAGTSSLTEC

VLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 180)

ATGAAGTGGGTGACCTTCATCAGCCTGCTGTTCCTGTTCTCCAGCGCCTA

CTCCATCCCCCCCCATGTGCAAAAGAGCGTGAACAACGATATGATCGTGA

CCGACAACAACGGCGCCGTGAAGTTTCCCCAGCTCTGCAAGTTCTGCGAT

GTCAGGTTCAGCACCTGCGATAATCAGAAGTCCTGCATGTCCAACTGCAG

CATCACCTCCATCTGCGAGAAGCCCCAAGAAGTGTGCGTGGCCGTGTGGC

GGAAAAATGACGAGAACATCACCCTGGAGACCGTGTGTCACGACCCCAAG

CTCCCTTATCACGACTTCATTCTGGAGGACGCTGCCTCCCCCAAATGCAT

CATGAAGGAGAAGAAGAAGCCCGGAGAGACCTTCTTTATGTGTTCCTGTA

GCAGCGACGAGTGTAACGACAACATCATCTTCAGCGAAGAGTACAACACC

AGCAACCCTGATGGAGGTGGCGGATCCGGAGGTGGAGGTTCTGGTGGAGG

TGGGAGTATTCCTCCCCACGTGCAGAAGAGCGTGAATAATGACATGATCG

TGACCGATAACAATGGCGCCGTGAAATTTCCCCAGCTGTGCAAATTCTGC

GATGTGAGGTTTTCCACCTGCGACAACCAGAAGTCCTGTATGAGCAACTG

CTCCATCACCTCCATCTGTGAGAAGCCTCAGGAGGTGTGCGTGGCTGTCT

GGCGGAAGAATGACGAGAATATCACCCTGGAAACCGTCTGCCACGATCCC

AAGCTGCCCTACCACGATTTCATCCTGGAAGACGCCGCCAGCCCTAAGTG

CATCATGAAAGAGAAAAAGAAGCCTGGCGAGACCTTTTTCATGTGCTCCT

GCAGCAGCGACGAATGCAACGACAATATCATCTTTAGCGAGGAATACAAT

-continued

ACCAGCAACCCCGACATTACATGCCCCCCTCCCATGAGCGTGGAGCACGC

CGACATCTGGGTGAAGAGCTATAGCCTCTACAGCCGGGAGAGGTATATCT

GTAACAGCGGCTTCAAGAGGAAGGCCGGCACCAGCAGCCTCACCGAGTGC

GTGCTGAATAAGGCTACCAACGTGGCTCACTGGACAACACCCTCTTTAAA

GTGCATCCGG.

Exemplary Multi-Chain Chimeric Polypeptides—Type L

In some embodiments of any of the multi-chain chimeric polypeptides described herein, the first target-binding domain and the second targeting-binding domain each independently bind specifically to TGF-β, a receptor of IL-21, or a receptor of CD137L. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor for IL-21 (e.g., a soluble IL-21, e.g., a soluble human IL-21) or a receptor for CD137L (e.g., a soluble CD137L, e.g., a soluble human CD137L).

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or more of the first target-binding domain, the second target-binding domain and the additional target-binding domain is an agonistic antigen-binding domain. In some embodiments of these multi-chain chimeric polypeptides, the first target-binding domain, the second target-binding domain, and the additional target-binding domain are each agonistic antigen-binding domains. In some embodiments of these multi-chain chimeric polypeptides, the antigen-binding domain includes a scFv or single-domain antibody.

In some embodiments of these multi-chain chimeric polypeptides, the first target-binding domain binds specifically to TGF-β and the second target-binding domain binds specifically to a receptor for IL-21 or a receptor for CD137L.

In some embodiments of these multi-chain chimeric polypeptides, the first target-binding domain is a soluble TGF-β receptor (e.g., a soluble TGFβRII receptor, e.g., a soluble human TGFβRII receptor). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 80)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.
```

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 81)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.
```

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 82)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT
```

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 83)
ATTCCTCCCCACGTGCAGAAGAGCGTGAATAATGACATGATCGTGACCGA

TAACAATGGCGCCGTGAAATTTCCCCAGCTGTGCAAATTCTGCGATGTGA

GGTTTTCCACCTGCGACAACCAGAAGTCCTGTATGAGCAACTGCTCCATC

ACCTCCATCTGTGAGAAGCCTCAGGAGGTGTGCGTGGCTGTCTGGCGGAA

GAATGACGAGAATATCACCCTGGAAACCGTCTGCCACGATCCCAAGCTGC

CCTACCACGATTTCATCCTGGAAGACGCCGCCAGCCCTAAGTGCATCATG

AAAGAGAAAAAGAAGCCTGGCGAGACCTTTTTCATGTGCTCCTGCAGCAG

CGACGAATGCAACGACAATATCATCTTTAGCGAGGAATACAATACCAGCA

ACCCCGAC.
```

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 85)
IPPHVQKSVNNDMIVTDNNGAVKFPQLCKFCDVRFSTCDNQKSCMSNCSI
TSICEKPQEVCVAVWRKNDENITLETVCHDPKLPYHDFILEDAASPKCIM
KEKKKPGETFFMCSCSSDECNDNIIFSEEYNTSNPDGGGGSGGGGSGGGG
SIPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKCI
MKEKKKPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 84)
ATCCCCCCCCATGTGCAAAAGAGCGTGAACAACGATATGATCGTGACCGA
CAACAACGGCGCCGTGAAGTTTCCCCAGCTCTGCAAGTTCTGCGATGTCA
GGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAA
AAATGACGAGAACATCACCCTGGAGACCGTGTGTCACGACCCCAAGCTCC
CTTATCACGACTTCATTCTGGAGGACGCTGCCTCCCCCAAATGCATCATG
AAGGAGAAGAAGAAGCCCGGAGAGACCTTCTTTATGTGTTCCTGTAGCAG
CGACGAGTGTAACGACAACATCATCTTCAGCGAAGAGTACAACACCAGCA
ACCCTGATGGAGGTGGCGGATCCGGAGGTGGAGGTTCTGGTGGAGGTGGG
AGTATTCCTCCCCACGTGCAGAAGAGCGTGAATAATGACATGATCGTGAC
CGATAACAATGGCGCCGTGAAATTTCCCCAGCTGTGCAAATTCTGCGATG
TGAGGTTTTCCACCTGCGACAACCAGAAGTCCTGTATGAGCAACTGCTCC
ATCACCTCCATCTGTGAGAAGCCTCAGGAGGTGTGCGTGGCTGTCTGGCG
GAAGAATGACGAGAATATCACCCTGGAAACCGTCTGCCACGATCCCAAGC
TGCCCTACCACGATTTCATCCTGGAAGACGCCGCCAGCCCTAAGTGCATC
ATGAAAGAGAAAAAGAAGCCTGGCGAGACCTTTTTCATGTGCTCCTGCAG
CAGCGACGAATGCAACGACAATATCATCTTTAGCGAGGAATACAATACCA
GCAACCCCGAC.

In some embodiments of these multi-chain chimeric polypeptides, the second target-binding domain or the additional target-binding domain binds specifically to a receptor for IL-21. In some embodiments of these multi-chain chimeric polypeptides, the second target-binding domain or the additional target-binding domain includes a soluble IL-21 (e.g., a soluble human IL-21).

In some embodiments of these multi-chain chimeric polypeptides, a soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 78)
QGQDRHMIRMRQLIDIVDQLKNYVNDLVPEFLPAPEDVETNCEWSAFSCF
QKAQLKSANTGNNERIINVSIKKLKRKPPSTNAGRRQKHRLTCPSCDSYE
KKPPKEFLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 79)
CAGGGCCAGGACAGGCACATGATCCGGATGAGGCAGCTCATCGACATCGT
CGACCAGCTGAAGAACTACGTGAACGACCTGGTGCCCGAGTTTCTGCCTG
CCCCCGAGGACGTGGAGACCAACTGCGAGTGGTCCGCCTTCTCCTGCTTT
CAGAAGGCCCAGCTGAAGTCCGCCAACACCGGCAACAACGAGCGGATCAT
CAACGTGAGCATCAAGAAGCTGAAGCGGAAGCCTCCCTCCACAAACGCCG
GCAGGAGGCAGAAGCACAGGCTGACCTGCCCCAGCTGTGACTCCTACGAG
AAGAAGCCCCCCAAGGAGTTCCTGGAGAGGTTCAAGTCCCTGCTGCAGAA
GATGATCCATCAGCACCTGTCCTCCAGGACCCACGGCTCCGAGGACTCC.

In some embodiments of these multi-chain chimeric polypeptides, the second target-binding domain or the additional target-binding domain binds specifically to a receptor for CD137L. In some embodiments of these multi-chain chimeric polypeptides, the second target-binding domain and/or the additional target-binding domain includes a soluble CD137L (e.g., a soluble human CD137L).

In some embodiments of these multi-chain chimeric polypeptides, a soluble CD137L includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 157)
REGPELSPDDPAGLLDLRQGMFAQLVAQNVLLIDGPLSWYSDPGLAGVSL
TGGLSYKEDTKELVVAKAGVYYVFFQLELRRVVAGEGSGSVSLALHLQPL
RSAAGAAALALTVDLPPASSEARNSAFGFQGRLLHLSAGQRLGVHLHTEA
RARHAWQLTQGATVLGLFRVTPEIPAGLPSPRSE.

In some embodiments of these multi-chain chimeric polypeptides, a soluble CD137L is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 158)
CGCGAGGGTCCCGAGCTTTCGCCCGACGATCCCGCCGGCCTCTTGGACCT
GCGGCAGGGCATGTTTGCGCAGCTGGTGGCCCAAAATGTTCTGCTGATCG
ATGGGCCCCTGAGCTGGTACAGTGACCCAGGCCTGGCAGGCGTGTCCCTG

-continued

ACGGGGGGCCTGAGCTACAAAGAGGACACGAAGGAGCTGGTGGTGGCCAA

GGCTGGAGTCTACTATGTCTTCTTTCAACTAGAGCTGCGGCGCGTGGTGG

CCGGCGAGGGCTCAGGCTCCGTTTCACTTGCGCTGCACCTGCAGCCACTG

CGCTCTGCTGCTGGGGCCGCCGCCCTGGCTTTGACCGTGGACCTGCCACC

CGCCTCCTCCGAGGCTCGGAACTCGGCCTTCGGTTTCCAGGGCCGCTTGC

TGCACCTGAGTGCCGGCCAGCGCCTGGGCGTCCATCTTCACACTGAGGCC

AGGGCACGCCATGCCTGGCAGCTTACCCAGGGCGCCACAGTCTTGGGACT

CTTCCGGGTGACCCCCGAAATCCCAGCCGGACTCCCTTCACCGAGGTCGG

AA.

In some embodiments of these multi-chain chimeric polypeptides, a soluble human CD137L includes a sequence that is at least 80% identical (e.g., at least 85%, at least 90%, at least 95%, at least 96%, at least 97%, at least 98%, at least 99%, or 100% identical) to:

(SEQ ID NO: 159)

DPAGLLDLRQGMFAQLVAQNVLLIDGPLSWYSDPGLAGVSLTGGLSYKED

TKELVVAKAGVYYVFFQLELRRVVAGEGSGSVSLALHLQPLRSAAGAAAL

ALTVDLPPASSEARNSAFGFQGRLLHLSAGQRLGVHLHTEARARHAWQLT

QGATVLGLFRVTPEI.

In some embodiments of these multi-chain chimeric polypeptides, a soluble human CD137L is encoded by a sequence that is at least 80% identical (e.g., at least 85%, at least 90%, at least 95%, at least 96%, at least 97%, at least 98%, at least 99%, or 100% identical) to:

(SEQ ID NO: 160)

GATCCCGCCGGCCTCTTGGACCTGCGGCAGGGCATGTTTGCGCAGCTGGT

CGGCCAAAATGTTCTGCTGATCGATGGGCCCCTGAGCTGGTACAGTGACC

CAGGCCTGGCAGGCGTGTCCCTGACGGGGGGCCTGAGCTACAAAGAGGAC

ACGAAGGAGCTGGTGGTGGCCAAGGCTGGAGTCTACTATGTCTTCTTTCA

ACTAGAGCTGCGGCGCGTGGTGGCCGGCGAGGGCTCAGGCTCCGTTTCAC

TTGCGCTGCACCTGCAGCCACTGCGCTCTGCTGCTGGGGCCGCCGCCCTG

GCTTTGACCGTGGACCTGCCACCCGCCTCCTCCGAGGCTCGGAACTCGGC

CTTCGGTTTCCAGGGCCGCTTGCTGCACCTGAGTGCCGGCCAGCGCCTGG

GCGTCCATCTTCACACTGAGGCCAGGGCACGCCATGCCTGGCAGCTTACC

CAGGGCGCCACAGTCTTGGGACTCTTCCGGGTGACCCCCGAAATC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 181)

IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

-continued

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDSGTTNTVAAYNLT

WKSTNFKTILEWEPKPVNQVYTVQISTKSGDWKSKCFYTTDTECDLTDEI

VKDVKQTYLARVFSYPAGNVESTGSAGEPLYENSPEFTPYLETNLGQPTI

QSFEQVGTKVNVTVEDERTLVRRNNTFLSLRDVFGKDLIYTLYYWKSSSS

GKKTAKTNTNEFLIDVDKGENYCFSVQAVIPSRTVNRKSTDSPVECMGQE

KGEFRENWVNVISDLKKIEDLIQSMHIDATLYTESDVHPSCKVTAMKCFL

LELQVISLESGDASIHDTVENLIILANNSLSSNGNVTESGCKECEELEEK

NIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 182)

ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGACAGCGGCACAACCAACACAGTCGCTGCCTATAACCTCACT

TGGAAGAGCACCAACTTCAAAACCATCCTCGAATGGGAACCCAAACCCGT

TAACCAAGTTTACACCGTGCAGATCAGCACCAAGTCCGGCGACTGGAAGT

CCAAATGTTTCTATACCACCGACACCGAGTGCGATCTCACCGATGAGATC

GTGAAAGATGTGAAACAGACCTACCTCGCCCGGGTGTTTAGCTACCCCGC

CGGCAATGTGGAGAGCACTGGTTCCGCTGGCGAGCCTTTATACGAGAACA

-continued

GCCCCGAATTTACCCCTTACCTCGAGACCAATTTAGGACAGCCCACCATC
CAAAGCTTTGAGCAAGTTGGCACAAAGGTGAATGTGACAGTGGAGGACGA
GCGGACTTTAGTGCGGCGGAACAACACCTTTCTCAGCCTCCGGGATGTGT
TCGGCAAAGATTTAATCTACACACTGTATTACTGGAAGTCCTCTTCCTCC
GGCAAGAAGACAGCTAAAACCAACACAAACGAGTTTTTAATCGACGTGGA
TAAAGGCGAAAACTACTGTTTCAGCGTGCAAGCTGTGATCCCCTCCCGGA
CCGTGAATAGGAAAAGCACCGATAGCCCCGTTGAGTGCATGGGCCAAGAA
AAGGGCGAGTTCCGGGAGAACTGGGTGAACGTCATCAGCGATTTAAAGAA
GATCGAAGATTTAATTCAGTCCATGCATATCGACGCCACTTTATACACAG
AATCCGACGTGCACCCCTCTTGTAAGGTGACCGCCATGAAATGTTTTTA
CTGGAGCTGCAAGTTATCTCTTTAGAGAGCGGAGACGCTAGCATCCACGA
CACCGTGGAGAATTTAATCATTTTAGCCAATAACTCTTTATCCAGCAACG
GCAACGTGACAGAGTCCGGCTGCAAGGAGTGCGAAGAGCTGGAGGAGAAG
AACATCAAGGAGTTTCTGCAATCCTTTGTGCACATTGTCCAGATGTTCAT
CAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 183)
MKWVTFISLLFLFSSAYSIPPHVQKSVNNDMIVTDNNGAVKFPQLCKFCD
VRFSTCDNQKSCMSNCSITSICEKPQEVCVAVWRKNDENITLETVCHDPK
LPYHDFILEDAASPKCIMKEKKKPGETFFMCSCSSDECNDNIIFSEEYNT
SNPDGGGGSGGGGSGGGGSIPPHVQKSVNNDMIVTDNNGAVKFPQLCKFC
DVRFSTCDNQKSCMSNCSITSICEKPQEVCVAVWRKNDENITLETVCHDP
KLPYHDFILEDAASPKCIMKEKKKPGETFFMCSCSSDECNDNIIFSEEYN
TSNPDSGTTNTVAAYNLTWKSTNFKTILEWEPKPVNQVYTVQISTKSGDW
KSKCFYTTDTECDLTDEIVKDVKQTYLARVFSYPAGNVESTGSAGEPLYE
NSPEFTPYLETNLGQPTIQSFEQVGTKVNVTVEDERTLVRRNNTFLSLRD
VFGKDLIYTLYYWKSSSSGKKTAKTNTNEFLIDVDKGENYCFSVQAVIPS
RTVNRKSTDSPVECMGQEKGEFRENWVNVISDLKKIEDLIQSMHIDATLY
TESDVHPSCKVTAMKCFLLELQVISLESGDASIHDTVENLIILANNSLSS
NGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 184)
ATGAAGTGGGTGACCTTCATCAGCCTGCTGTTCCTGTTCTCCAGCGCCTA
CTCCATCCCCCCCCATGTGCAAAAGAGCGTGAACAACGATATGATCGTGA
CCGACAACAACGGCGCCGTGAAGTTTCCCCAGCTCTGCAAGTTCTGCGAT
GTCAGGTTCAGCACCTGCGATAATCAGAAGTCCTGCATGTCCAACTGCAG
CATCACCTCCATCTGCGAGAAGCCCCAAGAAGTGTGCGTGGCCGTGTGGC
GGAAAAATGACGAGAACATCACCCTGGAGACCGTGTGTCACGACCCCAAG
CTCCCTTATCACGACTTCATTCTGGAGGACGCTGCCTCCCCCAAATGCAT
CATGAAGGAGAAGAAGAAGCCCGGAGAGACCTTCTTTATGTGTTCCTGTA
GCAGCGACGAGTGTAACGACAACATCATCTTCAGCGAAGAGTACAACACC
AGCAACCCTGATGGAGGTGGCGGATCCGGAGGTGGAGGTTCTGGTGGAGG
TGGGAGTATTCCTCCCCACGTGCAGAAGAGCGTGAATAATGACATGATCG
TGACCGATAACAATGGCGCCGTGAAATTTCCCCAGCTGTGCAAATTCTGC
GATGTGAGGTTTTCCACCTGCGACAACCAGAAGTCCTGTATGAGCAACTG
CTCCATCACCTCCATCTGTGAGAAGCCTCAGGAGGTGTGCGTGGCTGTCT
GGCGGAAGAATGACGAGAATATCACCCTGGAAACCGTCTGCCACGATCCC
AAGCTGCCCTACCACGATTTCATCCTGGAAGACGCCGCCAGCCCTAAGTG
CATCATGAAAGAGAAAAAGAAGCCTGGCGAGACCTTTTTCATGTGCTCCT
GCAGCAGCGACGAATGCAACGACAATATCATCTTTAGCGAGGAATACAAT
ACCAGCAACCCCGACAGCGGCACAACCAACACAGTCGCTGCCTATAACCT
CACTTGGAAGAGCACCAACTTCAAAACCATCCTCGAATGGGAACCCAAAC
CCGTTAACCAAGTTTACACCGTGCAGATCAGCACCAAGTCCGGCGACTGG
AAGTCCAAATGTTTCTATACCACCGACACCGAGTGCGATCTCACCGATGA
GATCGTGAAAGATGTGAAACAGACCTACCTCGCCCGGGTGTTTAGCTACC
CCGCCGGCAATGTGGAGAGCACTGGTTCCGCTGGCGAGCCTTTATACGAG
AACAGCCCCGAATTTACCCCTTACCTCGAGACCAATTTAGGACAGCCCAC
CATCCAAAGCTTTGAGCAAGTTGGCACAAAGGTGAATGTGACAGTGGAGG
ACGAGCGGACTTTAGTGCGGCGGAACAACACCTTTCTCAGCCTCCGGGAT
GTGTTCGGCAAAGATTTAATCTACACACTGTATTACTGGAAGTCCTCTTC
CTCCGGCAAGAAGACAGCTAAAACCAACACAAACGAGTTTTTAATCGACG
TGGATAAAGGCGAAAACTACTGTTTCAGCGTGCAAGCTGTGATCCCCTCC
CGGACCGTGAATAGGAAAAGCACCGATAGCCCCGTTGAGTGCATGGGCCA
AGAAAAGGGCGAGTTCCGGGAGAACTGGGTGAACGTCATCAGCGATTTAA
AGAAGATCGAAGATTTAATTCAGTCCATGCATATCGACGCCACTTTATAC
ACAGAATCCGACGTGCACCCCTCTTGTAAGGTGACCGCCATGAAATGTTT
TTTACTGGAGCTGCAAGTTATCTCTTTAGAGAGCGGAGACGCTAGCATCC
ACGACACCGTGGAGAATTTAATCATTTTAGCCAATAACTCTTTATCCAGC
AACGGCAACGTGACAGAGTCCGGCTGCAAGGAGTGCGAAGAGCTGGAGGA
GAAGAACATCAAGGAGTTTCTGCAATCCTTTGTGCACATTGTCCAGATGT
TCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 185)
QGQDRHMIRMRQLIDIVDQLKNYVNDLVPEFLPAPEDVETNCEWSAFSCF
QKAQLKSANTGNNERIINVSIKKLKRKPPSTNAGRRQKHRLTCPSCDSYE
KKPPKEFLERFKSLLQKMIHQHLSSRTHGSEDSITCPPPMSVEHADIWVK
SYSLYSRERYICNSGFKRKAGTSSLTECVLNKATNVAHWTTPSLKCIRGG
GGSGGGGSGGGGSREGPELSPDDPAGLLDLRQGMFAQLVAQNVLLIDGPL
SWYSDPGLAGVSLTGGLSYKEDTKELVVAKAGVYYVFFQLELRRVVAGEG
SGSVSLALHLQPLRSAAGAAALALTVDLPPASSEARNSAFGFQGRLLHLS
AGQRLGVHLHTEARARHAWQLTQGATVLGLFRVTPEIPAGLPSPRSE.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 186)
CAGGGCCAGGACAGGCACATGATCCGGATGAGGCAGCTCATCGACATCGT
CGACCAGCTGAAGAACTACGTGAACGACCTGGTGCCCGAGTTTCTGCCTG
CCCCCGAGGACGTGGAGACCAACTGCGAGTGGTCCGCCTTCTCCTGCTTT
CAGAAGGCCCAGCTGAAGTCCGCCAACACCGGCAACAACGAGCGGATCAT
CAACGTGAGCATCAAGAAGCTGAAGCGGAAGCCTCCCTCCACAAACGCCG
GCAGGAGGCAGAAGCACAGGCTGACCTGCCCCAGCTGTGACTCCTACGAG
AAGAAGCCCCCCAAGGAGTTCCTGGAGAGGTTCAAGTCCCTGCTGCAGAA
GATGATCCATCAGCACCTGTCCTCCAGGACCCACGGCTCCGAGGACTCCA
TTACATGCCCCCCTCCCATGAGCGTGGAGCACGCCGACATCTGGGTGAAG
AGCTATAGCCTCTACAGCCGGGAGAGGTATATCTGTAACAGCGGCTTCAA
GAGGAAGGCCGGCACCAGCAGCCTCACCGAGTGCGTGCTGAATAAGGCTA
CCAACGTGGCTCACTGGACAACACCCTCTTTAAAGTGCATCCGGGGCGGT
GGAGGATCCGGAGGAGGTGGCTCCGGCGGCGGAGGATCTCGCGAGGGTCC
CGAGCTTTCGCCCGACGATCCCGCCGGCCTCTTGGACCTGCGGCAGGGCA
TGTTTGCGCAGCTGGTGGCCCAAAATGTTCTGCTGATCGATGGGCCCCTG
AGCTGGTACAGTGACCCAGGCCTGGCAGGCGTGTCCCTGACGGGGGGCCT
GAGCTACAAAGAGGACACGAAGGAGCTGGTGGTGGCCAAGGCTGGAGTCT
ACTATGTCTTCTTTCAACTAGAGCTGCGGCGCGTGGTGGCCGGCGAGGGC
TCAGGCTCCGTTTCACTTGCGCTGCACCTGCAGCCACTGCGCTCTGCTGC
GGGGCCGCCGCCCTGGCTTTGACCGTGGACCTGCCACCCGCCTCCTCCGA
GGCTCGGAACTCGGCCTTCGGTTTCCAGGGCCGCTTGCTGCACCTGAGTG

-continued
CCGGCCAGCGCCTGGGCGTCCATCTTCACACTGAGGCCAGGGCACGCCAT
GCCTGGCAGCTTACCCAGGGCGCCACAGTCTTGGGACTCTTCCGGGTGAC
CCCCGAAATCCCAGCCGGACTCCCTTCACCGAGGTCGGAA.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 187)
MKWVTFISLLFLFSSAYSQGQDRHMIRMRQLIDIVDQLKNYVNDLVPEFL
PAPEDVETNCEWSAFSCFQKAQLKSANTGNNERIINVSIKKLKRKPPSTN
AGRRQKHRLTCPSCDSYEKKPPKEFLERFKSLLQKMIHQHLSSRTHGSED
SITCPPPMSVEHADIWVKSYSLYSRERYICNSGFKRKAGTSSLTECVLNK
ATNVAHWTTPSLKCIRGGGGSGGGGSGGGGSREGPELSPDDPAGLLDLRQ
GMFAQLVAQNVLLIDGPLSWYSDPGLAGVSLTGGLSYKEDTKELVVAKAG
VYYVFFQLELRRVVAGEGSGSVSLALHLQPLRSAAGAAALALTVDLPPAS
SEARNSAFGFQGRLLHLSAGQRLGVHLHTEARARHAWQLTQGATVLGLFR
VTPEIPAGLPSPRSE.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 188)
ATGAAGTGGGTGACCTTCATCAGCCTGCTGTTCCTGTTCTCCAGCGCCTA
CTCCCAGGGCCAGGACAGGCACATGATCCGGATGAGGCAGCTCATCGACA
TCGTCGACCAGCTGAAGAACTACGTGAACGACCTGGTGCCCGAGTTTCTG
CCTGCCCCCGAGGACGTGGAGACCAACTGCGAGTGGTCCGCCTTCTCCTG
CTTTCAGAAGGCCCAGCTGAAGTCCGCCAACACCGGCAACAACGAGCGGA
TCATCAACGTGAGCATCAAGAAGCTGAAGCGGAAGCCTCCCTCCACAAAC
GCCGGCAGGAGGCAGAAGCACAGGCTGACCTGCCCCAGCTGTGACTCCTA
CGAGAAGAAGCCCCCCAAGGAGTTCCTGGAGAGGTTCAAGTCCCTGCTGC
AGAAGATGATCCATCAGCACCTGTCCTCCAGGACCCACGGCTCCGAGGAC
TCCATTACATGCCCCCCTCCCATGAGCGTGGAGCACGCCGACATCTGGGT
GAAGAGCTATAGCCTCTACAGCCGGGAGAGGTATATCTGTAACAGCGGCT
TCAAGAGGAAGGCCGGCACCAGCAGCCTCACCGAGTGCGTGCTGAATAAG
GCTACCAACGTGGCTCACTGGACAACACCCTCTTTAAAGTGCATCCGGGG
CGGTGGAGGATCCGGAGGAGGTGGCTCCGGCGGCGGAGGATCTCGCGAGG
GTCCCGAGCTTTCGCCCGACGATCCCGCCGGCCTCTTGGACCTGCGGCAG
GGCATGTTTGCGCAGCTGGTGGCCCAAAATGTTCTGCTGATCGATGGGCC
CCTGAGCTGGTACAGTGACCCAGGCCTGGCAGGCGTGTCCCTGACGGGGG

-continued

GCCTGAGCTACAAAGAGGACACGAAGGAGCTGGTGGTGGCCAAGGCTGGA
GTCTACTATGTCTTCTTTCAACTAGAGCTGCGGCGCGTGGTGGCCGGCGA
GGGCTCAGGCTCCGTTTCACTTGCGCTGCACCTGCAGCCACTGCGCTCTG
CTGCTGGGGCCGCCGCCCTGGCTTTGACCGTGGACCTGCCACCCGCCTCC
TCCGAGGCTCGGAACTCGGCCTTCGGTTTCCAGGGCCGCTTGCTGCACCT
GAGTGCCGGCCAGCGCCTGGGCGTCCATCTTCACACTGAGGCCAGGGCAC
GCCATGCCTGGCAGCTTACCCAGGGCGCCACAGTCTTGGGACTCTTCCGG
GTGACCCCCGAAATCCCAGCCGGACTCCCTTCACCGAGGTCGGAA.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 189)
QGQDRHMIRMRQLIDIVDQLKNYVNDLVPEFLPAPEDVETNCEWSAFSCF
QKAQLKSANTGNNERIINVSIKKLKRKPPSTNAGRRQKHRLTCPSCDSYE
KKPPKEFLERFKSLLQKMIHQHLSSRTHGSEDSITCPPPMSVEHADIWVK
SYSLYSRERYICNSGFKRKAGTSSLTECVLNKATNVAHWTTPSLKCIRGG
GGSGGGGSGGGGSDPAGLLDLRQGMFAQLVAQNVLLIDGPLSWYSDPGLA
GVSLTGGLSYKEDTKELVVAKAGVYYVFFQLELRRVVAGEGSGSVSLALH
LQPLRSAAGAAALALTVDLPPASSEARNSAFGFQGRLLHLSAGQRLGVHL
HTEARARHAWQLTQGATVLGLFRVTPEI.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 190)
CAGGGCCAGGACAGGCACATGATCCGGATGAGGCAGCTCATCGACATCGT
CGACCAGCTGAAGAACTACGTGAACGACCTGGTGCCCGAGTTTCTGCCTG
CCCCCGAGGACGTGGAGACCAACTGCGAGTGGTCCGCCTTCTCCTGCTTT
CAGAAGGCCCAGCTGAAGTCCGCCAACACCGGCAACAACGAGCGGATCAT
CAACGTGAGCATCAAGAAGCTGAAGCGGAAGCCTCCCTCCACAAACGCCG
GCAGGAGGCAGAAGCACAGGCTGACCTGCCCCAGCTGTGACTCCTACGAG
AAGAAGCCCCCCAAGGAGTTCCTGGAGAGGTTCAAGTCCCTGCTGCAGAA
GATGATCCATCAGCACCTGTCCTCCAGGACCCACGGCTCCGAGGACTCCA
TTACATGCCCCCCTCCCATGAGCGTGGAGCACGCCGACATCTGGGTGAAG
AGCTATAGCCTCTACAGCCGGGAGAGGTATATCTGTAACAGCGGCTTCAA
GAGGAAGGCCGGCACCAGCAGCCTCACCGAGTGCGTGCTGAATAAGGCTA
CCAACGTGGCTCACTGGACAACACCCTCTTTAAAGTGCATCCGGGGCGGT
GGAGGATCCGGAGGAGGTGGCTCCGGCGGCGGAGGATCTGATCCCGCCGG
CCTCTTGGACCTGCGGCAGGGCATGTTTGCGCAGCTGGTGGCCCAAAATG
TTCTGCTGATCGATGGGCCCCTGAGCTGGTACAGTGACCCAGGCCTGGCA
GGCGTGTCCCTGACGGGGGGCCTGAGCTACAAAGAGGACACGAAGGAGCT
GGTGGTGGCCAAGGCTGGAGTCTACTATGTCTTCTTTCAACTAGAGCTGC
GGCGCGTGGTGGCCGGCGAGGGCTCAGGCTCCGTTTCACTTGCGCTGCAC
CTGCAGCCACTGCGCTCTGCTGCTGGGGCCGCCGCCCTGGCTTTGACCGT
GGACCTGCCACCCGCCTCCTCCGAGGCTCGGAACTCGGCCTTCGGTTTCC
AGGGCCGCTTGCTGCACCTGAGTGCCGGCCAGCGCCTGGGCGTCCATCTT
CACACTGAGGCCAGGGCACGCCATGCCTGGCAGCTTACCCAGGGCGCCAC
AGTCTTGGGACTCTTCCGGGTGACCCCCGAAATC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 191)
MKWVTFISLLFLFSSAYSQGQDRHMIRMRQLIDIVDQLKNYVNDLVPEFL
PAPEDVETNCEWSAFSCFQKAQLKSANTGNNERIINVSIKKLKRKPPSTN
AGRRQKHRLTCPSCDSYEKKPPKEFLERFKSLLQKMIHQHLSSRTHGSED
SITCPPPMSVEHADIWVKSYSLYSRERYICNSGFKRKAGTSSLTECVLNK
ATNVAHWTTPSLKCIRGGGGSGGGGSGGGGSDPAGLLDLRQGMFAQLVAQ
NVLLIDGPLSWYSDPGLAGVSLTGGLSYKEDTKELVVAKAGVYYVFFQLE
LRRVVAGEGSGSVSLALHLQPLRSAAGAAALALTVDLPPASSEARNSAFG
FQGRLLHLSAGQRLGVHLHTEARARHAWQLTQGATVLGLFRVTPEI.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 192)
ATGAAGTGGGTGACCTTCATCAGCCTGCTGTTCCTGTTCTCCAGCGCCTA
CTCCCAGGGCCAGGACAGGCACATGATCCGGATGAGGCAGCTCATCGACA
TCGTCGACCAGCTGAAGAACTACGTGAACGACCTGGTGCCCGAGTTTCTG
CCTGCCCCCGAGGACGTGGAGACCAACTGCGAGTGGTCCGCCTTCTCCTG
CTTTCAGAAGGCCCAGCTGAAGTCCGCCAACACCGGCAACAACGAGCGGA
TCATCAACGTGAGCATCAAGAAGCTGAAGCGGAAGCCTCCCTCCACAAAC
GCCGGCAGGAGGCAGAAGCACAGGCTGACCTGCCCCAGCTGTGACTCCTA
CGAGAAGAAGCCCCCCAAGGAGTTCCTGGAGAGGTTCAAGTCCCTGCTGC
AGAAGATGATCCATCAGCACCTGTCCTCCAGGACCCACGGCTCCGAGGAC
TCCATTACATGCCCCCCTCCCATGAGCGTGGAGCACGCCGACATCTGGGT

-continued

```
GAAGAGCTATAGCCTCTACAGCCGGGAGAGGTATATCTGTAACAGCGGCT
TCAAGAGGAAGGCCGGCACCAGCAGCCTCACCGAGTGCGTGCTGAATAAG
GCTACCAACGTGGCTCACTGGACAACACCCTCTTTAAAGTGCATCCGGGG
CGGTGGAGGATCCGGAGGAGGTGGCTCCGGCGGCGGAGGATCTGATCCCG
CCGGCCTCTTGGACCTGCGGCAGGGCATGTTTGCGCAGCTGGTGGCCCAA
AATGTTCTGCTGATCGATGGGCCCCTGAGCTGGTACAGTGACCCAGGCCT
GGCAGGCGTGTCCCTGACGGGGGGCCTGAGCTACAAAGAGGACACGAAGG
AGCTGGTGGTGGCCAAGGCTGGAGTCTACTATGTCTTCTTTCAACTAGAG
CTGCGGCGCGTGGTGGCCGGCGAGGGCTCAGGCTCCGTTTCACTTGCGCT
GCACCTGCAGCCACTGCGCTCTGCTGCTGGGGCCGCCGCCCTGGCTTTGA
CCGTGGACCTGCCACCCGCCTCCTCCGAGGCTCGGAACTCGGCCTTCGGT
TTCCAGGGCCGCTTGCTGCACCTGAGTGCCGGCCAGCGCCTGGGCGTCCA
TCTTCACACTGAGGCCAGGGCACGCCATGCCTGGCAGCTTACCCAGGGCG
CCACAGTCTTGGGACTCTTCCGGGTGACCCCCGAAATC.
```

Exemplary Multi-Chain Chimeric Polypeptides—Type M

In some embodiments of any of the multi-chain chimeric polypeptides described herein, the first target-binding domain and the second targeting-binding domain each independently bind specifically to TGF-β or a receptor of IL-21. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor for IL-21 (e.g., a soluble IL-21, e.g., a soluble human IL-21) or a TGF-β (e.g., a soluble TGF-β receptor, e.g., a soluble TGFβRII receptor).

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain binds specifically to TGF-β, and the second target-binding domain binds specifically to TGF-β or a receptor for IL-21. In some embodiments of these multi-chain chimeric polypeptides, the first target-binding domain is a soluble TGF-β receptor (e.g., a soluble TGFβRII receptor, e.g., a soluble human TGFβRII receptor). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                            (SEQ ID NO: 80)
IPPHVQKSVNNDMIVTDNNGAVKFPQLCKFCDVRFSTCDNQKSCMSNCSI
TSICEKPQEVCVAVWRKNDENITLETVCHDPKLPYHDFILEDAASPKCIM
KEKKKPGETFFMCSCSSDECNDNIIFSEEYNTSNPD.
```

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 81)
IPPHVQKSVNNDMIVTDNNGAVKFPQLCKFCDVRFSTCDNQKSCMSNCSI
TSICEKPQEVCVAVWRKNDENITLETVCHDPKLPYHDFILEDAASPKCIM
KEKKKPGETFFMCSCSSDECNDNIIFSEEYNTSNPD.

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 82)
ATCCCCCCCCATGTGCAAAAGAGCGTGAACAACGATATGATCGTGACCGA
CAACAACGGCGCCGTGAAGTTTCCCCAGCTCTGCAAGTTCTGCGATGTCA
GGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAA
AAATGACGAGAACATCACCCTGGAGACCGTGTGTCACGACCCCAAGCTCC
CTTATCACGACTTCATTCTGGAGGACGCTGCCTCCCCCAAATGCATCATG
AAGGAGAAGAAGAAGCCCGGAGAGACCTTCTTTATGTGTTCCTGTAGCAG
CGACGAGTGTAACGACAACATCATCTTCAGCGAAGAGTACAACACCAGCA
ACCCTGAT.

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 83)
ATTCCTCCCCACGTGCAGAAGAGCGTGAATAATGACATGATCGTGACCGA
TAACAATGGCGCCGTGAAATTTCCCCAGCTGTGCAAATTCTGCGATGTGA
GGTTTTCCACCTGCGACAACCAGAAGTCCTGTATGAGCAACTGCTCCATC
ACCTCCATCTGTGAGAAGCCTCAGGAGGTGTGCGTGGCTGTCTGGCGGAA
GAATGACGAGAATATCACCCTGGAAACCGTCTGCCACGATCCCAAGCTGC
CCTACCACGATTTCATCCTGGAAGACGCCGCCAGCCCTAAGTGCATCATG
AAAGAGAAAAAGAAGCCTGGCGAGACCTTTTTCATGTGCTCCTGCAGCAG
CGACGAATGCAACGACAATATCATCTTTAGCGAGGAATACAATACCAGCA
ACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 85)
IPPHVQKSVNNDMIVTDNNGAVKFPQLCKFCDVRFSTCDNQKSCMSNCSI
TSICEKPQEVCVAVWRKNDENITLETVCHDPKLPYHDFILEDAASPKCIM
KEKKKPGETFFMCSCSSDECNDNIIFSEEYNTSNPDGGGGSGGGGSGGGG
SIPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKCI
MKEKKKPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 84)
ATCCCCCCCCATGTGCAAAAGAGCGTGAACAACGATATGATCGTGACCGA
CAACAACGGCGCCGTGAAGTTTCCCCAGCTCTGCAAGTTCTGCGATGTCA
GGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAA
AAATGACGAGAACATCACCCTGGAGACCGTGTGTCACGACCCCAAGCTCC
CTTATCACGACTTCATTCTGGAGGACGCTGCCTCCCCCAAATGCATCATG
AAGGAGAAGAAGAAGCCCGGAGAGACCTTCTTTATGTGTTCCTGTAGCAG
CGACGAGTGTAACGACAACATCATCTTCAGCGAAGAGTACAACACCAGCA
ACCCTGATGGAGGTGGCGGATCCGGAGGTGGAGGTTCTGGTGGAGGTGGG
AGTATTCCTCCCCACGTGCAGAAGAGCGTGAATAATGACATGATCGTGAC
CGATAACAATGGCGCCGTGAAATTTCCCCAGCTGTGCAAATTCTGCGATG
TGAGGTTTTCCACCTGCGACAACCAGAAGTCCTGTATGAGCAACTGCTCC
ATCACCTCCATCTGTGAGAAGCCTCAGGAGGTGTGCGTGGCTGTCTGGCG
GAAGAATGACGAGAATATCACCCTGGAAACCGTCTGCCACGATCCCAAGC
TGCCCTACCACGATTTCATCCTGGAAGACGCCGCCAGCCCTAAGTGCATC
ATGAAAGAGAAAAAGAAGCCTGGCGAGACCTTTTTCATGTGCTCCTGCAG
CAGCGACGAATGCAACGACAATATCATCTTTAGCGAGGAATACAATACCA
GCAACCCCGAC.

In some embodiments of these multi-chain chimeric polypeptides, the second target-binding domain binds specifically to a receptor for IL-21. In some embodiments of these multi-chain chimeric polypeptides, the second target-binding domain includes a soluble IL-21 (e.g., a human soluble IL-21). In some embodiments of these multi-chain chimeric polypeptides, the soluble IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 78)

QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS.

In some embodiments of these multi-chain chimeric polypeptides, the soluble IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 79)

CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCCAAGGAGTTCCTGGAGAGGTTCAAGTCCCTGCTGCAGAA

GATGATCCATCAGCACCTGTCCTCCAGGACCCACGGCTCCGAGGACTCC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 193)

IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDSGTTNTVAAYNLT

WKSTNFKTILEWEPKPVNQVYTVQISTKSGDWKSKCFYTTDTECDLTDEI

VKDVKQTYLARVFSYPAGNVESTGSAGEPLYENSPEFTPYLETNLGQPTI

QSFEQVGTKVNVTVEDERTLVRRNNTFLSLRDVFGKDLIYTLYYWKSSSS

GKKTAKTNTNEFLIDVDKGENYCFSVQAVIPSRTVNRKSTDSPVECMGQE

KGEFRENWVNVISDLKKIEDLIQSMHIDATLYTESDVHPSCKVTAMKCFL

LELQVISLESGDASIHDTVENLIILANNSLSSNGNVTESGCKECEELEEK

NIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 194)

ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGACAGCGGCACAACCAACACAGTC

GCTGCCTATAACCTCACTTGGAAGAGCACCAACTTCAAAACCATCCTCG

AATGGGAACCCAAACCCGTTAACCAAGTTTACACCGTGCAGATCAGCAC

CAAGTCCGGCGACTGGAAGTCCAAATGTTTCTATACCACCGACACCGAG

TGCGATCTCACCGATGAGATCGTGAAAGATGTGAAACAGACCTACCTCG

CCCGGGTGTTTAGCTACCCCGCCGGCAATGTGGAGAGCACTGGTTCCGC

TGGCGAGCCTTTATACGAGAACAGCCCCGAATTTACCCCTTACCTCGAG

ACCAATTTAGGACAGCCCACCATCCAAAGCTTTGAGCAAGTTGGCACAA

AGGTGAATGTGACAGTGGAGGACGAGCGGACTTTAGTGCGGCGGAACAA

CACCTTTCTCAGCCTCCGGGATGTGTTCGGCAAAGATTTAATCTACACA

CTGTATTACTGGAAGTCCTCTTCCTCCGGCAAGAAGACAGCTAAAACCA

ACACAAACGAGTTTTTAATCGACGTGGATAAAGGCGAAAACTACTGTTT

CAGCGTGCAAGCTGTGATCCCCTCCCGGACCGTGAATAGGAAAAGCACC

GATAGCCCCGTTGAGTGCATGGGCCAAGAAAAGGGCGAGTTCCGGGAGA

ACTGGGTGAACGTCATCAGCGATTTAAAGAAGATCGAAGATTTAATTCA

GTCCATGCATATCGACGCCACTTTATACACAGAATCCGACGTGCACCCC

TCTTGTAAGGTGACCGCCATGAAATGTTTTTTACTGGAGCTGCAAGTTA

TCTCTTTAGAGAGCGGAGACGCTAGCATCCACGACACCGTGGAGAATTT

AATCATTTTAGCCAATAACTCTTTATCCAGCAACGGCAACGTGACAGAG

TCCGGCTGCAAGGAGTGCGAAGAGCTGGAGGAGAAGAACATCAAGGAGT

TTCTGCAATCCTTTGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 195)
MKWVTFISLLFLFSSAYSIPPHVQKSVNNDMIVTDNNGAVKFPQLCKFC
DVRFSTCDNQKSCMSNCSITSICEKPQEVCVAVWRKNDENITLETVCHD
PKLPYHDFILEDAASPKCIMKEKKKPGETFFMCSCSSDECNDNIIFSEE
YNTSNPDGGGGSGGGGSGGGGSIPPHVQKSVNNDMIVTDNNGAVKFPQL
CKFCDVRFSTCDNQKSCMSNCSITSICEKPQEVCVAVWRKNDENITLET
VCHDPKLPYHDFILEDAASPKCIMKEKKKPGETFFMCSCSSDECNDNII
FSEEYNTSNPDSGTTNTVAAYNLTWKSTNFKTILEWEPKPVNQVYTVQI
STKSGDWKSKCFYTTDTECDLTDEIVKDVKQTYLARVFSYPAGNVESTG
SAGEPLYENSPEFTPYLETNLGQPTIQSFEQVGTKVNVTVEDERTLVRR
NNTFLSLRDVFGKDLIYTLYYWKSSSSGKKTAKTNTNEFLIDVDKGENY
CFSVQAVIPSRTVNRKSTDSPVECMGQEKGEFRENWVNVISDLKKIEDL
IQSMHIDATLYTESDVHPSCKVTAMKCFLLELQVISLESGDASIHDTVE
NLIILANNSLSSNGNVTESGCKECEELEEKNIKEFLQSFVHIVQMFINT
S.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 196)
ATGAAGTGGGTGACCTTCATCAGCCTGCTGTTCCTGTTCTCCAGCGCCT
ACTCCATCCCCCCCCATGTGCAAAAGAGCGTGAACAACGATATGATCGT
GACCGACAACAACGGCGCCGTGAAGTTTCCCCAGCTCTGCAAGTTCTGC
GATGTCAGGTTCAGCACCTGCGATAATCAGAAGTCCTGCATGTCCAACT
GCAGCATCACCTCCATCTGCGAGAAGCCCCAAGAAGTGTGCGTGGCCGT
GTGGCGGAAAAATGACGAGAACATCACCCTGGAGACCGTGTGTCACGAC
CCCAAGCTCCCTTATCACGACTTCATTCTGGAGGACGCTGCCTCCCCCA
AATGCATCATGAAGGAGAAGAAGAAGCCCGGAGAGACCTTCTTTATGTG
TTCCTGTAGCAGCGACGAGTGTAACGACAACATCATCTTCAGCGAAGAG
TACAACACCAGCAACCCTGATGGAGGTGGCGGATCCGGAGGTGGAGGTT
CTGGTGGAGGTGGGAGTATTCCTCCCCACGTGCAGAAGAGCGTGAATAA
TGACATGATCGTGACCGATAACAATGGCGCCGTGAAATTTCCCCAGCTG
TGCAAATTCTGCGATGTGAGGTTTTCCACCTGCGACAACCAGAAGTCCT
GTATGAGCAACTGCTCCATCACCTCCATCTGTGAGAAGCCTCAGGAGGT
GTGCGTGGCTGTCTGGCGGAAGAATGACGAGAATATCACCCTGGAAACC
GTCTGCCACGATCCCAAGCTGCCCTACCACGATTTCATCCTGGAAGACG
CCGCCAGCCCTAAGTGCATCATGAAAGAGAAAAAGAAGCCTGGCGAGAC
CTTTTTCATGTGCTCCTGCAGCAGCGACGAATGCAACGACAATATCATC

-continued

TTTAGCGAGGAATACAATACCAGCAACCCCGACAGCGGCACAACCAACA
CAGTCGCTGCCTATAACCTCACTTGGAAGAGCACCAACTTCAAAACCAT
CCTCGAATGGGAACCCAAACCCGTTAACCAAGTTTACACCGTGCAGATC
AGCACCAAGTCCGGCGACTGGAAGTCCAAATGTTTCTATACCACCGACA
CCGAGTGCGATCTCACCGATGAGATCGTGAAAGATGTGAAACAGACCTA
CCTCGCCCGGGTGTTTAGCTACCCCGCCGGCAATGTGGAGAGCACTGGT
TCCGCTGGCGAGCCTTTATACGAGAACAGCCCCGAATTTACCCCTTACC
TCGAGACCAATTTAGGACAGCCCACCATCCAAAGCTTTGAGCAAGTTGG
CACAAAGGTGAATGTGACAGTGGAGGACGAGCGGACTTTAGTGCGGCGG
AACAACACCTTTCTCAGCCTCCGGGATGTGTTCGGCAAAGATTTAATCT
ACACACTGTATTACTGGAAGTCCTCTTCCTCCGGCAAGAAGACAGCTAA
AACCAACACAAACGAGTTTTTAATCGACGTGGATAAAGGCGAAAACTAC
TGTTTCAGCGTGCAAGCTGTGATCCCCTCCCGGACCGTGAATAGGAAAA
GCACCGATAGCCCCGTTGAGTGCATGGGCCAAGAAAAGGGCGAGTTCCG
GGAGAACTGGGTGAACGTCATCAGCGATTTAAAGAAGATCGAAGATTTA
ATTCAGTCCATGCATATCGACGCCACTTTATACACAGAATCCGACGTGC
ACCCCTCTTGTAAGGTGACCGCCATGAAATGTTTTTTACTGGAGCTGCA
AGTTATCTCTTTAGAGAGCGGAGACGCTAGCATCCACGACACCGTGGAG
AATTTAATCATTTTAGCCAATAACTCTTTATCCAGCAACGGCAACGTGA
CAGAGTCCGGCTGCAAGGAGTGCGAAGAGCTGGAGGAGAAGAACATCAA
GGAGTTTCTGCAATCCTTTGTGCACATTGTCCAGATGTTCATCAATACC
TCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 197)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHDFILEDAA
SPKCIMKEKKKPGETFFMCSCSSDECNDNIIFSEEYNTSNPDITCPPPM
SVEHADIWVKSYSLYSRERYICNSGFKRKAGTSSLTECVLNKATNVAHW
TTPSLKCIRQGQDRHMIRMRQLIDIVDQLKNYVNDLVPEFLPAPEDVET
NCEWSAFSCFQKAQLKSANTGNNERIINVSIKKLKRKPPSTNAGRRQKH
RLTCPSCDSYEKKPPKEFLERFKSLLQKMIHQHLSSRTHGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 198)

ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGATGGAGGTGGCGGATCCGGAGGTGGAGGTTCTGGT
GGAGGTGGGAGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCTCCATCACCTCCATCTGTGAGAAGCCTCAGGAGGTGTGCG
TGGCTGTCTGGCGGAAGAATGACGAGAATATCACCCTGGAAACCGTCTG
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGTGCTCCTGCAGCAGCGACGAATGCAACGACAATATCATCTTTAG
CGAGGAATACAATACCAGCAACCCCGACATTACATGCCCCCCTCCCATG
AGCGTGGAGCACGCCGACATCTGGGTGAAGAGCTATAGCCTCTACAGCC
GGGAGAGGTATATCTGTAACAGCGGCTTCAAGAGGAAGGCCGGCACCAG
CAGCCTCACCGAGTGCGTGCTGAATAAGGCTACCAACGTGGCTCACTGG
ACAACACCCTCTTTAAAGTGCATCCGGCAGGGCCAGGACAGGCACATGA
TCCGGATGAGGCAGCTCATCGACATCGTCGACCAGCTGAAGAACTACGT
GAACGACCTGGTGCCCGAGTTTCTGCCTGCCCCCGAGGACGTGGAGACC
AACTGCGAGTGGTCCGCCTTCTCCTGCTTTCAGAAGGCCCAGCTGAAGT
CCGCCAACACCGGCAACAACGAGCGGATCATCAACGTGAGCATCAAGAA
GCTGAAGCGGAAGCCTCCCTCCACAAACGCCGGCAGGAGGCAGAAGCAC
AGGCTGACCTGCCCCAGCTGTGACTCCTACGAGAAGAAGCCCCCCAAGG
AGTTCCTGGAGAGGTTCAAGTCCCTGCTGCAGAAGATGATCCATCAGCA
CCTGTCCTCCAGGACCCACGGCTCCGAGGACTCC.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 199)

MKWVTFISLLFLFSSAYSIPPHVQKSVNNDMIVTDNNGAVKFPQLCKFC
DVRFSTCDNQKSCMSNCSITSICEKPQEVCVAVWRKNDENITLETVCHD

-continued

PKLPYHDFILEDAASPKCIMKEKKKPGETFFMCSCSSDECNDNIIFSEE
YNTSNPDGGGGSGGGGSGGGGSIPPHVQKSVNNDMIVTDNNGAVKFPQL
CKFCDVRFSTCDNQKSCMSNCSITSICEKPQEVCVAVWRKNDENITLET
VCHDPKLPYHDFILEDAASPKCIMKEKKKPGETFFMCSCSSDECNDNII
FSEEYNTSNPDITCPPPMSVEHADIWVKSYSLYSRERYICNSGFKRKAG
TSSLTECVLNKATNVAHWTTPSLKCIRQGQDRHMIRMRQLIDIVDQLKN
YVNDLVPEFLPAPEDVETNCEWSAFSCFQKAQLKSANTGNNERIINVSI
KKLKRKPPSTNAGRRQKHRLTCPSCDSYEKKPPKEFLERFKSLLQKMIH
QHLSSRTHGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 200)

ATGAAGTGGGTGACCTTCATCAGCCTGCTGTTCCTGTTCTCCAGCGCCT
ACTCCATCCCCCCCCATGTGCAAAAGAGCGTGAACAACGATATGATCGT
GACCGACAACAACGGCGCCGTGAAGTTTCCCCAGCTCTGCAAGTTCTGC
GATGTCAGGTTCAGCACCTGCGATAATCAGAAGTCCTGCATGTCCAACT
GCAGCATCACCTCCATCTGCGAGAAGCCCCAAGAAGTGTGCGTGGCCGT
GTGGCGGAAAAATGACGAGAACATCACCCTGGAGACCGTGTGTCACGAC
CCCAAGCTCCCTTATCACGACTTCATTCTGGAGGACGCTGCCTCCCCCA
AATGCATCATGAAGGAGAAGAAGAAGCCCGGAGAGACCTTCTTTATGTG
TTCCTGTAGCAGCGACGAGTGTAACGACAACATCATCTTCAGCGAAGAG
TACAACACCAGCAACCCTGATGGAGGTGGCGGATCCGGAGGTGGAGGTT
CTGGTGGAGGTGGGAGTATTCCTCCCCACGTGCAGAAGAGCGTGAATAA
TGACATGATCGTGACCGATAACAATGGCGCCGTGAAATTTCCCCAGCTG
TGCAAATTCTGCGATGTGAGGTTTTCCACCTGCGACAACCAGAAGTCCT
GTATGAGCAACTGCTCCATCACCTCCATCTGTGAGAAGCCTCAGGAGGT
GTGCGTGGCTGTCTGGCGGAAGAATGACGAGAATATCACCCTGGAAACC
GTCTGCCACGATCCCAAGCTGCCCTACCACGATTTCATCCTGGAAGACG
CCGCCAGCCCTAAGTGCATCATGAAAGAGAAAAAGAAGCCTGGCGAGAC
CTTTTTCATGTGCTCCTGCAGCAGCGACGAATGCAACGACAATATCATC
TTTAGCGAGGAATACAATACCAGCAACCCCGACATTACATGCCCCCCTC
CCATGAGCGTGGAGCACGCCGACATCTGGGTGAAGAGCTATAGCCTCTA
CAGCCGGGAGAGGTATATCTGTAACAGCGGCTTCAAGAGGAAGGCCGGC
ACCAGCAGCCTCACCGAGTGCGTGCTGAATAAGGCTACCAACGTGGCTC
ACTGGACAACACCCTCTTTAAAGTGCATCCGGCAGGGCCAGGACAGGCA
CATGATCCGGATGAGGCAGCTCATCGACATCGTCGACCAGCTGAAGAAC
TACGTGAACGACCTGGTGCCCGAGTTTCTGCCTGCCCCCGAGGACGTGG

-continued

```
AGACCAACTGCGAGTGGTCCGCCTTCTCCTGCTTTCAGAAGGCCCAGCT

GAAGTCCGCCAACACCGGCAACAACGAGCGGATCATCAACGTGAGCATC

AAGAAGCTGAAGCGGAAGCCTCCCTCCACAAACGCCGGCAGGAGGCAGA

AGCACAGGCTGACCTGCCCCAGCTGTGACTCCTACGAGAAGAAGCCCCC

CAAGGAGTTCCTGGAGAGGTTCAAGTCCCTGCTGCAGAAGATGATCCAT

CAGCACCTGTCCTCCAGGACCCACGGCTCCGAGGACTCC.
```

Exemplary Multi-Chain Chimeric Polypeptides—Type N

In some embodiments of any of the multi-chain chimeric polypeptides described herein, the first target-binding domain and the second targeting-binding domain each independently bind specifically to TGF-β or CD16. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 (e.g., an anti-CD16 scFv) or a TGF-β (e.g., a soluble TGF-β receptor, e.g., a soluble TGFβRII receptor).

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain binds specifically to TGF-β, and the second target-binding domain binds specifically to TGF-β or CD16. In some embodiments of these multi-chain chimeric polypeptides, the first target-binding domain is a soluble TGF-β receptor (e.g., a soluble TGFβRII receptor, e.g., a soluble human TGFβRII receptor). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
(SEQ ID NO: 80)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.
```

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
(SEQ ID NO: 81)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.
```

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 82)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGAT.

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 83)
ATTCCTCCCCACGTGCAGAAGAGCGTGAATAATGACATGATCGTGACC

GATAACAATGGCGCCGTGAAATTTCCCCAGCTGTGCAAATTCTGCGAT

GTGAGGTTTTCCACCTGCGACAACCAGAAGTCCTGTATGAGCAACTGC

TCCATCACCTCCATCTGTGAGAAGCCTCAGGAGGTGTGCGTGGCTGTC

TGGCGGAAGAATGACGAGAATATCACCCTGGAAACCGTCTGCCACGAT

CCCAAGCTGCCCTACCACGATTTCATCCTGGAAGACGCCGCCAGCCCT

AAGTGCATCATGAAAGAGAAAAAGAAGCCTGGCGAGACCTTTTTCATG

TGCTCCTGCAGCAGCGACGAATGCAACGACAATATCATCTTTAGCGAG

GAATACAATACCAGCAACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 85)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 84)
ATCCCCCCCCATGTGCAAAAGAGCGTGAACAACGATATGATCGTGACC

GACAACAACGGCGCCGTGAAGTTTCCCCAGCTCTGCAAGTTCTGCGAT

GTCAGGTTCAGCACCTGCGATAATCAGAAGTCCTGCATGTCCAACTGC

AGCATCACCTCCATCTGCGAGAAGCCCCAAGAAGTGTGCGTGGCCGTG

TGGCGGAAAAATGACGAGAACATCACCCTGGAGACCGTGTGTCACGAC

CCCAAGCTCCCTTATCACGACTTCATTCTGGAGGACGCTGCCTCCCCC

AAATGCATCATGAAGGAGAAGAAGAAGCCCGGAGAGACCTTCTTTATG

TGTTCCTGTAGCAGCGACGAGTGTAACGACAACATCATCTTCAGCGAA

GAGTACAACACCAGCAACCCTGATGGAGGTGGCGGATCCGGAGGTGGA

GGTTCTGGTGGAGGTGGGAGTATTCCTCCCCACGTGCAGAAGAGCGTG

AATAATGACATGATCGTGACCGATAACAATGGCGCCGTGAAATTTCCC

CAGCTGTGCAAATTCTGCGATGTGAGGTTTTCCACCTGCGACAACCAG

AAGTCCTGTATGAGCAACTGCTCCATCACCTCCATCTGTGAGAAGCCT

CAGGAGGTGTGCGTGGCTGTCTGGCGGAAGAATGACGAGAATATCACC

CTGGAAACCGTCTGCCACGATCCCAAGCTGCCCTACCACGATTTCATC

CTGGAAGACGCCGCCAGCCCTAAGTGCATCATGAAAGAGAAAAAGAAG

CCTGGCGAGACCTTTTTCATGTGCTCCTGCAGCAGCGACGAATGCAAC

GACAATATCATCTTTAGCGAGGAATACAATACCAGCAACCCCGAC.

In some embodiments of these multi-chain chimeric polypeptides, the second target-binding domain binds specifically to CD16. In some embodiments of these multi-chain chimeric polypeptides, the second target-binding domain includes an anti-CD16 scFv. In some embodiments of these multi-chain chimeric polypeptides, the scFv that binds specifically to CD16 includes a light chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 112)
SELTQDPAVSVALGQTVRITCQGDSLRSYYASWYQQKPGQAPVLVIYGK

NNRPSGIPDRFSGSSSGNTASLTITGAQAEDEADYYCNSRDSSGNHVVF

GGGTKLTVGH.

In some embodiments of these multi-chain chimeric polypeptides, the scFv that binds specifically to CD16 is encoded by a light chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 113)
TCCGAGCTGACCCAGGACCCTGCTGTGTCCGTGGCTCTGGGCCAGACCG
TGAGGATCACCTGCCAGGGCGACTCCCTGAGGTCCTACTACGCCTCCTG
GTACCAGCAGAAGCCCGGCCAGGCTCCTGTGCTGGTGATCTACGGCAAG
AACAACAGGCCCTCCGGCATCCCTGACAGGTTCTCCGGATCCTCCTCCG
GCAACACCGCCTCCCTGACCATCACAGGCGCTCAGGCCGAGGACGAGGC
TGACTACTACTGCAACTCCAGGGACTCCTCCGGCAACCATGTGGTGTTC
GGCGGCGGCACCAAGCTGACCGTGGGCCAT.

In some embodiments of these multi-chain chimeric polypeptides, the scFv that binds specifically to CD16 includes a heavy chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 114)
EVQLVESGGGVVRPGGSLRLSCAASGFTFDDYGMSWVRQAPGKGLEWVSG
INWNGGSTGYADSVKGRFTISRDNAKNSLYLQMNSLRAEDTAVYYCARGR
SLLFDYWGQGTLVTVSR.

In some embodiments of these multi-chain chimeric polypeptides, the scFv that binds specifically to CD16 is encoded by a heavy chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 115)
GAGGTGCAGCTGGTGGAGTCCGGAGGAGGAGTGGTGAGGCCTGGAGGCTC
CCTGAGGCTGAGCTGTGCTGCCTCCGGCTTCACCTTCGACGACTACGGCA
TGTCCTGGGTGAGGCAGGCTCCTGGAAAGGGCCTGGAGTGGGTGTCCGGC
ATCAACTGGAACGGCGGATCCACCGGCTACGCCGATTCCGTGAAGGGCAG
GTTCACCATCAGCAGGGACAACGCCAAGAACTCCCTGTACCTGCAGATGA
ACTCCCTGAGGGCCGAGGACACCGCCGTGTACTACTGCGCCAGGGGCAGG
TCCCTGCTGTTCGACTACTGGGGACAGGGCACCCTGGTGACCGTGTCCAG
G.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 201)
IPPHVQKSVNNDMIVTDNNGAVKFPQLCKFCDVRFSTCDNQKSCMSNCSI
TSICEKPQEVCVAVWRKNDENITLETVCHDPKLPYHDFILEDAASPKCIM
KEKKKPGETFFMCSCSSDECNDNIIFSEEYNTSNPDGGGGSGGGGSGGGG

-continued

SIPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKCI
MKEKKKPGETFFMCSCSSDECNDNIIFSEEYNTSNPDSGTTNTVAAYNLT
WKSTNFKTILEWEPKPVNQVYTVQISTKSGDWKSKCFYTTDTECDLTDEI
VKDVKQTYLARVFSYPAGNVESTGSAGEPLYENSPEFTPYLETNLGQPTI
QSFEQVGTKVNVTVEDERTLVRRNNTFLSLRDVFGKDLIYTLYYWKSSSS
GKKTAKTNTNEFLIDVDKGENYCFSVQAVIPSRTVNRKSTDSPVECMGQE
KGEFRENWVNVISDLKKIEDLIQSMHIDATLYTESDVHPSCKVTAMKCFL
LELQVISLESGDASIHDTVENLIILANNSLSSNGNVTESGCKECEELEEK
NIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 202)
ATCCCCCCCCATGTGCAAAAGAGCGTGAACAACGATATGATCGTGACCGA
CAACAACGGCGCCGTGAAGTTTCCCCAGCTCTGCAAGTTCTGCGATGTCA
GGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAA
AAATGACGAGAACATCACCCTGGAGACCGTGTGTCACGACCCCAAGCTCC
CTTATCACGACTTCATTCTGGAGGACGCTGCCTCCCCCAAATGCATCATG
AAGGAGAAGAAGAAGCCCGGAGAGACCTTCTTTATGTGTTCCTGTAGCAG
CGACGAGTGTAACGACAACATCATCTTCAGCGAAGAGTACAACACCAGCA
ACCCTGATGGAGGTGGCGGATCCGGAGGTGGAGGTTCTGGTGGAGGTGGG
AGTATTCCTCCCCACGTGCAGAAGAGCGTGAATAATGACATGATCGTGAC
CGATAACAATGGCGCCGTGAAATTTCCCCAGCTGTGCAAATTCTGCGATG
TGAGGTTTTCCACCTGCGACAACCAGAAGTCCTGTATGAGCAACTGCTCC
ATCACCTCCATCTGTGAGAAGCCTCAGGAGGTGTGCGTGGCTGTCTGGCG
GAAGAATGACGAGAATATCACCCTGGAAACCGTCTGCCACGATCCCAAGC
TGCCCTACCACGATTTCATCCTGGAAGACGCCGCCAGCCCTAAGTGCATC
ATGAAAGAGAAAAAGAAGCCTGGCGAGACCTTTTTCATGTGCTCCTGCAG
CAGCGACGAATGCAACGACAATATCATCTTTAGCGAGGAATACAATACCA
GCAACCCCGACAGCGGCACAACCAACACAGTCGCTGCCTATAACCTCACT
TGGAAGAGCACCAACTTCAAAACCATCCTCGAATGGGAACCCAAACCCGT
TAACCAAGTTTACACCGTGCAGATCAGCACCAAGTCCGGCGACTGGAAGT
CCAAATGTTTCTATACCACCGACACCGAGTGCGATCTCACCGATGAGATC
GTGAAAGATGTGAAACAGACCTACCTCGCCCGGGTGTTTAGCTACCCCGC
CGGCAATGTGGAGAGCACTGGTTCCGCTGGCGAGCCTTTATACGAGAACA
GCCCCGAATTTACCCCTTACCTCGAGACCAATTTAGGACAGCCCACCATC

CAAAGCTTTGAGCAAGTTGGCACAAAGGTGAATGTGACAGTGGAGGACGA

GCGGACTTTAGTGCGGCGGAACAACACCTTTCTCAGCCTCCGGGATGTGT

TCGGCAAAGATTTAATCTACACACTGTATTACTGGAAGTCCTCTTCCTCC

GGCAAGAAGACAGCTAAAACCAACACAAACGAGTTTTTAATCGACGTGGA

TAAAGGCGAAAACTACTGTTTCAGCGTGCAAGCTGTGATCCCCTCCCGGA

CCGTGAATAGGAAAAGCACCGATAGCCCCGTTGAGTGCATGGGCCAAGAA

AAGGGCGAGTTCCGGGAGAACTGGGTGAACGTCATCAGCGATTTAAAGAA

GATCGAAGATTTAATTCAGTCCATGCATATCGACGCCACTTTATACACAG

AATCCGACGTGCACCCCTCTTGTAAGGTGACCGCCATGAAATGTTTTTTA

CTGGAGCTGCAAGTTATCTCTTTAGAGAGCGGAGACGCTAGCATCCACGA

CACCGTGGAGAATTTAATCATTTTAGCCAATAACTCTTTATCCAGCAACG

GCAACGTGACAGAGTCCGGCTGCAAGGAGTGCGAAGAGCTGGAGGAGAAG

AACATCAAGGAGTTTCTGCAATCCTTTGTGCACATTGTCCAGATGTTCAT

CAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 203)
MKWVTFISLLFLFSSAYSIPPHVQKSVNNDMIVTDNNGAVKFPQLCKFCD

VRFSTCDNQKSCMSNCSITSICEKPQEVCVAVWRKNDENITLETVCHDPK

LPYHDFILEDAASPKCIMKEKKKPGETFFMCSCSSDECNDNIIFSEEYNT

SNPDGGGGSGGGGSGGGGSIPPHVQKSVNNDMIVTDNNGAVKFPQLCKFC

DVRFSTCDNQKSCMSNCSITSICEKPQEVCVAVWRKNDENITLETVCHDP

KLPYHDFILEDAASPKCIMKEKKKPGETFFMCSCSSDECNDNIIFSEEYN

TSNPDSGTTNTVAAYNLTWKSTNFKTILEWEPKPVNQVYTVQISTKSGDW

KSKCFYTTDTECDLTDEIVKDVKQTYLARVFSYPAGNVESTGSAGEPLYE

NSPEFTPYLETNLGQPTIQSFEQVGTKVNVTVEDERTLVRRNNTFLSLRD

VFGKDLIYTLYYWKSSSSGKKTAKTNTNEFLIDVDKGENYCFSVQAVIPS

RTVNRKSTDSPVECMGQEKGEFRENWVNVISDLKKIEDLIQSMHIDATLY

TESDVHPSCKVTAMKCFLLELQVISLESGDASIHDTVENLIILANNSLSS

NGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 204)
ATGAAGTGGGTGACCTTCATCAGCCTGCTGTTCCTGTTCTCCAGCGCCTA

CTCCATCCCCCCCCATGTGCAAAAGAGCGTGAACAACGATATGATCGTGA

CCGACAACAACGGCGCCGTGAAGTTTCCCCAGCTCTGCAAGTTCTGCGAT

GTCAGGTTCAGCACCTGCGATAATCAGAAGTCCTGCATGTCCAACTGCAG

CATCACCTCCATCTGCGAGAAGCCCCAAGAAGTGTGCGTGGCCGTGTGGC

GGAAAAATGACGAGAACATCACCCTGGAGACCGTGTGTCACGACCCCAAG

CTCCCTTATCACGACTTCATTCTGGAGGACGCTGCCTCCCCCAAATGCAT

CATGAAGGAGAAGAAGAAGCCCGGAGAGACCTTCTTTATGTGTTCCTGTA

GCAGCGACGAGTGTAACGACAACATCATCTTCAGCGAAGAGTACAACACC

AGCAACCCTGATGGAGGTGGCGGATCCGGAGGTGGAGGTTCTGGTGGAGG

TGGGAGTATTCCTCCCCACGTGCAGAAGAGCGTGAATAATGACATGATCG

TGACCGATAACAATGGCGCCGTGAAATTTCCCCAGCTGTGCAAATTCTGC

GATGTGAGGTTTTCCACCTGCGACAACCAGAAGTCCTGTATGAGCAACTG

CTCCATCACCTCCATCTGTGAGAAGCCTCAGGAGGTGTGCGTGGCTGTCT

GGCGGAAGAATGACGAGAATATCACCCTGGAAACCGTCTGCCACGATCCC

AAGCTGCCCTACCACGATTTCATCCTGGAAGACGCCGCCAGCCCTAAGTG

CATCATGAAAGAGAAAAAGAAGCCTGGCGAGACCTTTTTCATGTGCTCCT

GCAGCAGCGACGAATGCAACGACAATATCATCTTTAGCGAGGAATACAAT

ACCAGCAACCCCGACAGCGGCACAACCAACACAGTCGCTGCCTATAACCT

CACTTGGAAGAGCACCAACTTCAAAACCATCCTCGAATGGGAACCCAAAC

CCGTTAACCAAGTTTACACCGTGCAGATCAGCACCAAGTCCGGCGACTGG

AAGTCCAAATGTTTCTATACCACCGACACCGAGTGCGATCTCACCGATGA

GATCGTGAAAGATGTGAAACAGACCTACCTCGCCCGGGTGTTTAGCTACC

CCGCCGGCAATGTGGAGAGCACTGGTTCCGCTGGCGAGCCTTTATACGAG

AACAGCCCCGAATTTACCCCTTACCTCGAGACCAATTTAGGACAGCCCAC

CATCCAAAGCTTTGAGCAAGTTGGCACAAAGGTGAATGTGACAGTGGAGG

ACGAGCGGACTTTAGTGCGGCGGAACAACACCTTTCTCAGCCTCCGGGAT

GTGTTCGGCAAAGATTTAATCTACACACTGTATTACTGGAAGTCCTCTTC

CTCCGGCAAGAAGACAGCTAAAACCAACACAAACGAGTTTTTAATCGACG

TGGATAAAGGCGAAAACTACTGTTTCAGCGTGCAAGCTGTGATCCCCTCC

CGGACCGTGAATAGGAAAAGCACCGATAGCCCCGTTGAGTGCATGGGCCA

AGAAAAGGGCGAGTTCCGGGAGAACTGGGTGAACGTCATCAGCGATTTAA

AGAAGATCGAAGATTTAATTCAGTCCATGCATATCGACGCCACTTTATAC

ACAGAATCCGACGTGCACCCCTCTTGTAAGGTGACCGCCATGAAATGTTT

TTTACTGGAGCTGCAAGTTATCTCTTTAGAGAGCGGAGACGCTAGCATCC

ACGACACCGTGGAGAATTTAATCATTTTAGCCAATAACTCTTTATCCAGC

AACGGCAACGTGACAGAGTCCGGCTGCAAGGAGTGCGAAGAGCTGGAGGA

GAAGAACATCAAGGAGTTTCTGCAATCCTTTGTGCACATTGTCCAGATGT

TCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 205)
IPPHVQKSVNNDMIVTDNNGAVKFPQLCKFCDVRFSTCDNQKSCMSNCSI
TSICEKPQEVCVAVWRKNDENITLETVCHDPKLPYHDFILEDAASPKCIM
KEKKKPGETFFMCSCSSDECNDNIIFSEEYNTSNPDGGGGSGGGGSGGGG
SIPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKCI
MKEKKKPGETFFMCSCSSDECNDNIIFSEEYNTSNPDITCPPPMSVEHAD
IWVKSYSLYSRERYICNSGFKRKAGTSSLTECVLNKATNVAHWTTPSLKC
IRSELTQDPAVSVALGQTVRITCQGDSLRSYYASWYQQKPGQAPVLVIYG
KNNRPSGIPDRFSGSSSGNTASLTITGAQAEDEADYYCNSRDSSGNHVVF
GGGTKLTVGHGGGGSGGGGSGGGGSEVQLVESGGGVVRPGGSLRLSCAAS
GFTFDDYGMSWVRQAPGKGLEWVSGINWNGGSTGYADSVKGRFTISRDNA
KNSLYLQMNSLRAEDTAVYYCARGRSLLFDYWGQGTLVTVSR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 206)
ATCCCCCCCCATGTGCAAAAGAGCGTGAACAACGATATGATCGTGACCGA
CAACAACGGCGCCGTGAAGTTTCCCCAGCTCTGCAAGTTCTGCGATGTCA
GGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAA
AAATGACGAGAACATCACCCTGGAGACCGTGTGTCACGACCCCAAGCTCC
CTTATCACGACTTCATTCTGGAGGACGCTGCCTCCCCCAAATGCATCATG
AAGGAGAAGAAGAAGCCCGGAGAGACCTTCTTTATGTGTTCCTGTAGCAG
CGACGAGTGTAACGACAACATCATCTTCAGCGAAGAGTACAACACCAGCA
ACCCTGATGGAGGTGGCGGATCCGGAGGTGGAGGTTCTGGTGGAGGTGGG
AGTATTCCTCCCCACGTGCAGAAGAGCGTGAATAATGACATGATCGTGAC
CGATAACAATGGCGCCGTGAAATTTCCCCAGCTGTGCAAATTCTGCGATG
TGAGGTTTTCCACCTGCGACAACCAGAAGTCCTGTATGAGCAACTGCTCC
ATCACCTCCATCTGTGAGAAGCCTCAGGAGGTGTGCGTGGCTGTCTGGCG
GAAGAATGACGAGAATATCACCCTGGAAACCGTCTGCCACGATCCCAAGC
TGCCCTACCACGATTTCATCCTGGAAGACGCCGCCAGCCCTAAGTGCATC
ATGAAAGAGAAAAAGAAGCCTGGCGAGACCTTTTTCATGTGCTCCTGCAG
CAGCGACGAATGCAACGACAATATCATCTTTAGCGAGGAATACAATACCA
GCAACCCCGACATTACATGCCCCCCTCCCATGAGCGTGGAGCACGCCGAC
ATCTGGGTGAAGAGCTATAGCCTCTACAGCCGGGAGAGGTATATCTGTAA
CAGCGGCTTCAAGAGGAAGGCCGGCACCAGCAGCCTCACCGAGTGCGTGC

-continued
TGAATAAGGCTACCAACGTGGCTCACTGGACAACACCCTCTTTAAAGTGC
ATCCGGTCCGAGCTGACCCAGGACCCTGCTGTGTCCGTGGCTCTGGGCCA
GACCGTGAGGATCACCTGCCAGGGCGACTCCCTGAGGTCCTACTACGCCT
CCTGGTACCAGCAGAAGCCCGGCCAGGCTCCTGTGCTGGTGATCTACGGC
AAGAACAACAGGCCCTCCGGCATCCCTGACAGGTTCTCCGGATCCTCCTC
CGGCAACACCGCCTCCCTGACCATCACAGGCGCTCAGGCCGAGGACGAGG
CTGACTACTACTGCAACTCCAGGGACTCCTCCGGCAACCATGTGGTGTTC
GGCGGCGGCACCAAGCTGACCGTGGGCCATGGCGGCGGCGGCTCCGGAGG
CGGCGGCAGCGGCGGAGGAGGATCCGAGGTGCAGCTGGTGGAGTCCGGAG
GAGGAGTGGTGAGGCCTGGAGGCTCCCTGAGGCTGAGCTGTGCTGCCTCC
GGCTTCACCTTCGACGACTACGGCATGTCCTGGGTGAGGCAGGCTCCTGG
AAAGGGCCTGGAGTGGGTGTCCGGCATCAACTGGAACGGCGGATCCACCG
GCTACGCCGATTCCGTGAAGGGCAGGTTCACCATCAGCAGGGACAACGCC
AAGAACTCCCTGTACCTGCAGATGAACTCCCTGAGGGCCGAGGACACCGC
CGTGTACTACTGCGCCAGGGGCAGGTCCCTGCTGTTCGACTACTGGGGAC
AGGGCACCCTGGTGACCGTGTCCAGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 207)
MKWVTFISLLFLFSSAYSIPPHVQKSVNNDMIVTDNNGAVKFPQLCKFCD
VRFSTCDNQKSCMSNCSITSICEKPQEVCVAVWRKNDENITLETVCHDPK
LPYHDFILEDAASPKCIMKEKKKPGETFFMCSCSSDECNDNIIFSEEYNT
SNPDGGGGSGGGGSGGGGSIPPHVQKSVNNDMIVTDNNGAVKFPQLCKFC
DVRFSTCDNQKSCMSNCSITSICEKPQEVCVAVWRKNDENITLETVCHDP
KLPYHDFILEDAASPKCIMKEKKKPGETFFMCSCSSDECNDNIIFSEEYN
TSNPDITCPPPMSVEHADIWVKSYSLYSRERYICNSGFKRKAGTSSLTEC
VLNKATNVAHWTTPSLKCIRSELTQDPAVSVALGQTVRITCQGDSLRSYY
ASWYQQKPGQAPVLVIYGKNNRPSGIPDRFSGSSSGNTASLTITGAQAED
EADYYCNSRDSSGNHVVFGGGTKLTVGHGGGGSGGGGSGGGGSEVQLVES
GGGVVRPGGSLRLSCAASGFTFDDYGMSWVRQAPGKGLEWVSGINWNGGS
TGYADSVKGRFTISRDNAKNSLYLQMNSLRAEDTAVYYCARGRSLLFDYW
GQGTLVTVSR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 208)

```
ATGAAGTGGGTGACCTTCATCAGCCTGCTGTTCCTGTTCTCCAGCGCCTA
CTCCATCCCCCCCCATGTGCAAAAGAGCGTGAACAACGATATGATCGTGA
CCGACAACAACGGCGCCGTGAAGTTTCCCCAGCTCTGCAAGTTCTGCGAT
GTCAGGTTCAGCACCTGCGATAATCAGAAGTCCTGCATGTCCAACTGCAG
CATCACCTCCATCTGCGAGAAGCCCCAAGAAGTGTGCGTGGCCGTGTGGC
GGAAAAATGACGAGAACATCACCCTGGAGACCGTGTGTCACGACCCCAAG
CTCCCTTATCACGACTTCATTCTGGAGGACGCTGCCTCCCCCAAATGCAT
CATGAAGGAGAAGAAGAAGCCCGGAGAGACCTTCTTTATGTGTTCCTGTA
GCAGCGACGAGTGTAACGACAACATCATCTTCAGCGAAGAGTACAACACC
AGCAACCCTGATGGAGGTGGCGGATCCGGAGGTGGAGGTTCTGGTGGAGG
TGGGAGTATTCCTCCCCACGTGCAGAAGAGCGTGAATAATGACATGATCG
TGACCGATAACAATGGCGCCGTGAAATTTCCCCAGCTGTGCAAATTCTGC
GATGTGAGGTTTTCCACCTGCGACAACCAGAAGTCCTGTATGAGCAACTG
CTCCATCACCTCCATCTGTGAGAAGCCTCAGGAGGTGTGCGTGGCTGTCT
GGCGGAAGAATGACGAGAATATCACCCTGGAAACCGTCTGCCACGATCCC
AAGCTGCCCTACCACGATTTCATCCTGGAAGACGCCGCCAGCCCTAAGTG
CATCATGAAAGAGAAAAAGAAGCCTGGCGAGACCTTTTTCATGTGCTCCT
GCAGCAGCGACGAATGCAACGACAATATCATCTTTAGCGAGGAATACAAT
ACCAGCAACCCCGACATTACATGCCCCCCTCCCATGAGCGTGGAGCACGC
CGACATCTGGGTGAAGAGCTATAGCCTCTACAGCCGGGAGAGGTATATCT
GTAACAGCGGCTTCAAGAGGAAGGCCGGCACCAGCAGCCTCACCGAGTGC
GTGCTGAATAAGGCTACCAACGTGGCTCACTGGACAACACCCTCTTTAAA
GTGCATCCGGTCCGAGCTGACCCAGGACCCTGCTGTGTCCGTGGCTCTGG
GCCAGACCGTGAGGATCACCTGCCAGGGCGACTCCCTGAGGTCCTACTAC
GCCTCCTGGTACCAGCAGAAGCCCGGCCAGGCTCCTGTGCTGGTGATCTA
CGGCAAGAACAACAGGCCCTCCGGCATCCCTGACAGGTTCTCCGGATCCT
CCTCCGGCAACACCGCCTCCCTGACCATCACAGGCGCTCAGGCCGAGGAC
GAGGCTGACTACTACTGCAACTCCAGGGACTCCTCCGGCAACCATGTGGT
GTTCGGCGGCGGCACCAAGCTGACCGTGGGCCATGGCGGCGGCGGCTCCG
GAGGCGGCGGCAGCGGCGGAGGAGGATCCGAGGTGCAGCTGGTGGAGTCC
GGAGGAGGAGTGGTGAGGCCTGGAGGCTCCCTGAGGCTGAGCTGTGCTGC
CTCCGGCTTCACCTTCGACGACTACGGCATGTCCTGGGTGAGGCAGGCTC
CTGGAAAGGGCCTGGAGTGGGTGTCCGGCATCAACTGGAACGGCGGATCC
ACCGGCTACGCCGATTCCGTGAAGGGCAGGTTCACCATCAGCAGGGACAA
CGCCAAGAACTCCCTGTACCTGCAGATGAACTCCCTGAGGGCCGAGGACA
CCGCCGTGTACTACTGCGCCAGGGGCAGGTCCCTGCTGTTCGACTACTGG
GGACAGGGCACCCTGGTGACCGTGTCCAGG.
```

Exemplary Multi-Chain Chimeric Polypeptides—Type O

In some embodiments of any of the multi-chain chimeric polypeptides described herein, the first target-binding domain and the second targeting-binding domain each independently bind specifically to TGF-β or a receptor of CD137L. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor to TGF-β (e.g., a soluble TGF-β receptor, e.g., a soluble TGFβRII receptor) or CD137L.

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain binds specifically to TGF-β, and the second target-binding domain binds specifically to CD137L. In some embodiments of these multi-chain chimeric polypeptides, the first target-binding domain or the additional target-binding domain is a soluble TGF-β receptor (e.g., a soluble TGFβRII receptor, e.g., a soluble human TGFβRII receptor).

In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                            (SEQ ID NO: 80)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.
```

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                            (SEQ ID NO: 81)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.
```

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                            (SEQ ID NO: 82)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC
```

-continued

```
CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT.
```

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                            (SEQ ID NO: 83)
ATTCCTCCCCACGTGCAGAAGAGCGTGAATAATGACATGATCGTGACCGA

TAACAATGGCGCCGTGAAATTTCCCCAGCTGTGCAAATTCTGCGATGTGA

GGTTTTCCACCTGCGACAACCAGAAGTCCTGTATGAGCAACTGCTCCATC

ACCTCCATCTGTGAGAAGCCTCAGGAGGTGTGCGTGGCTGTCTGGCGGAA

GAATGACGAGAATATCACCCTGGAAACCGTCTGCCACGATCCCAAGCTGC

CCTACCACGATTTCATCCTGGAAGACGCCGCCAGCCCTAAGTGCATCATG

AAAGAGAAAAAGAAGCCTGGCGAGACCTTTTTCATGTGCTCCTGCAGCAG

CGACGAATGCAACGACAATATCATCTTTAGCGAGGAATACAATACCAGCA

ACCCCGAC.
```

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                            (SEQ ID NO: 85)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD.
```

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                            (SEQ ID NO: 84)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT
```

-continued

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGAC.

In some embodiments of these multi-chain chimeric polypeptides, the second target-binding domain includes a soluble CD137L protein (e.g., a soluble human CD137L protein). In some embodiments of these multi-chain chimeric polypeptides, a soluble human CD137L includes a sequence that is at least 80% identical (e.g., at least 85%, at least 90%, at least 95%, at least 96%, at least 97%, at least 98%, at least 99%, or 100% identical) to:

(SEQ ID NO: 157)

REGPELSPDDPAGLLDLRQGMFAQLVAQNVLLIDGPLSWYSDPGLAGVS

LTGGLSYKEDTKELVVAKAGVYYVFFQLELRRVVAGEGSGSVSLALHLQ

PLRSAAGAAALALTVDLPPASSEARNSAFGFQGRLLHLSAGQRLGVHLH

TEARARHAWQLTQGATVLGLFRVTPEIPAGLPSPRSE.

In some embodiments of these multi-chain chimeric polypeptides, a soluble human CD137L is encoded by a sequence that is at least 80% identical (e.g., at least 85%, at least 90%, at least 95%, at least 96%, at least 97%, at least 98%, at least 99%, or 100% identical) to:

(SEQ ID NO: 158)

CGCGAGGGTCCCGAGCTTTCGCCCGACGATCCCGCCGGCCTCTTGGACC

TGCGGCAGGGCATGTTTGCGCAGCTGGTGGCCCAAAATGTTCTGCTGAT

CGATGGGCCCCTGAGCTGGTACAGTGACCCAGGCCTGGCAGGCGTGTCC

CTGACGGGGGGCCTGAGCTACAAAGAGGACACGAAGGAGCTGGTGGTGG

CCAAGGCTGGAGTCTACTATGTCTTCTTTCAACTAGAGCTGCGGCGCGT

GGTGGCCGGCGAGGGCTCAGGCTCCGTTTCACTTGCGCTGCACCTGCAG

CCACTGCGCTCTGCTGCTGGGGCCGCCGCCCTGGCTTTGACCGTGGACC

TGCCACCCGCCTCCTCCGAGGCTCGGAACTCGGCCTTCGGTTTCCAGGG

CCGCTTGCTGCACCTGAGTGCCGGCCAGCGCCTGGGCGTCCATCTTCAC

-continued

ACTGAGGCCAGGGCACGCCATGCCTGGCAGCTTACCCAGGGCGCCACAG

TCTTGGGACTCTTCCGGGTGACCCCCGAAATCCCAGCCGGACTCCCTTC

ACCGAGGTCGGAA.

In some embodiments of these multi-chain chimeric polypeptides, a soluble human CD137L includes a sequence that is at least 80% identical (e.g., at least 85%, at least 90%, at least 95%, at least 96%, at least 97%, at least 98%, at least 99%, or 100% identical) to:

(SEQ ID NO: 159)

DPAGLLDLRQGMFAQLVAQNVLLIDGPLSWYSDPGLAGVSLTGGLSYKE

DTKELVVAKAGVYYVFFQLELRRVVAGEGSGSVSLALHLQPLRSAAGAA

ALALTVDLPPASSEARNSAFGFQGRLLHLSAGQRLGVHLHTEARARHAW

QLTQGATVLGLFRVTPEI.

In some embodiments of these multi-chain chimeric polypeptides, a soluble human CD137L is encoded by a sequence that is at least 80% identical (e.g., at least 85%, at least 90%, at least 95%, at least 96%, at least 97%, at least 98%, at least 99%, or 100% identical) to:

(SEQ ID NO: 160)

GATCCCGCCGGCCTCTTGGACCTGCGGCAGGGCATGTTTGCGCAGCTGG

TGGCCCAAAATGTTCTGCTGATCGATGGGCCCCTGAGCTGGTACAGTGA

CCCAGGCCTGGCAGGCGTGTCCCTGACGGGGGGCCTGAGCTACAAAGAG

GACACGAAGGAGCTGGTGGTGGCCAAGGCTGGAGTCTACTATGTCTTCT

TTCAACTAGAGCTGCGGCGCGTGGTGGCCGGCGAGGGCTCAGGCTCCGT

TTCACTTGCGCTGCACCTGCAGCCACTGCGCTCTGCTGCTGGGGCCGCC

GCCCTGGCTTTGACCGTGGACCTGCCACCCGCCTCCTCCGAGGCTCGGA

ACTCGGCCTTCGGTTTCCAGGGCCGCTTGCTGCACCTGAGTGCCGGCCA

GCGCCTGGGCGTCCATCTTCACACTGAGGCCAGGGCACGCCATGCCTGG

CAGCTTACCCAGGGCGCCACAGTCTTGGGACTCTTCCGGGTGACCCCCG

AAATC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 209)

IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPDSGTTNTV

AAYNLTWKSTNFKTILEWEPKPVNQVYTVQISTKSGDWKSKCFYTTDTE

-continued

CDLTDEIVKDVKQTYLARVFSYPAGNVESTGSAGEPLYENSPEFTPYLE

TNLGQPTIQSFEQVGTKVNVTVEDERTLVRRNNTFLSLRDVFGKDLIYT

LYYWKSSSSGKKTAKTNTNEFLIDVDKGENYCFSVQAVIPSRTVNRKST

DSPVECMGQEKGEFRENWVNVISDLKKIEDLIQSMHIDATLYTESDVHP

SCKVTAMKCFLLELQVISLESGDASIHDTVENLIILANNSLSSNGNVTE

SGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 210)

ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGACAGCGGCACAACCAACACAGTC

GCTGCCTATAACCTCACTTGGAAGAGCACCAACTTCAAAACCATCCTCG

AATGGGAACCCAAACCCGTTAACCAAGTTTACACCGTGCAGATCAGCAC

CAAGTCCGGCGACTGGAAGTCCAAATGTTTCTATACCACCGACACCGAG

TGCGATCTCACCGATGAGATCGTGAAAGATGTGAAACAGACCTACCTCG

CCCGGGTGTTTAGCTACCCCGCCGGCAATGTGGAGAGCACTGGTTCCGC

TGGCGAGCCTTTATACGAGAACAGCCCCGAATTTACCCCTTACCTCGAG

ACCAATTTAGGACAGCCCACCATCCAAAGCTTTGAGCAAGTTGGCACAA

AGGTGAATGTGACAGTGGAGGACGAGCGGACTTTAGTGCGGCGGAACAA

CACCTTTCTCAGCCTCCGGGATGTGTTCGGCAAAGATTTAATCTACACA

CTGTATTACTGGAAGTCCTCTTCCTCCGGCAAGAAGACAGCTAAAACCA

-continued

ACACAAACGAGTTTTTAATCGACGTGGATAAAGGCGAAAACTACTGTTT

CAGCGTGCAAGCTGTGATCCCCTCCCGGACCGTGAATAGGAAAAGCACC

GATAGCCCCGTTGAGTGCATGGGCCAAGAAAAGGGCGAGTTCCGGGAGA

ACTGGGTGAACGTCATCAGCGATTTAAAGAAGATCGAAGATTTAATTCA

GTCCATGCATATCGACGCCACTTTATACACAGAATCCGACGTGCACCCC

TCTTGTAAGGTGACCGCCATGAAATGTTTTTTACTGGAGCTGCAAGTTA

TCTCTTTAGAGAGCGGAGACGCTAGCATCCACGACACCGTGGAGAATTT

AATCATTTTAGCCAATAACTCTTTATCCAGCAACGGCAACGTGACAGAG

TCCGGCTGCAAGGAGTGCGAAGAGCTGGAGGAGAAGAACATCAAGGAGT

TTCTGCAATCCTTTGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 211)

MKWVTFISLLFLFSSAYSIPPHVQKSVNNDMIVTDNNGAVKFPQLCKFC

DVRFSTCDNQKSCMSNCSITSICEKPQEVCVAVWRKNDENITLETVCHD

PKLPYHDFILEDAASPKCIMKEKKKPGETFFMCSCSSDECNDNIIFSEE

YNTSNPDGGGGSGGGGSGGGGSIPPHVQKSVNNDMIVTDNNGAVKFPQL

CKFCDVRFSTCDNQKSCMSNCSITSICEKPQEVCVAVWRKNDENITLET

VCHDPKLPYHDFILEDAASPKCIMKEKKKPGETFFMCSCSSDECNDNII

FSEEYNTSNPDSGTTNTVAAYNLTWKSTNFKTILEWEPKPVNQVYTVQI

STKSGDWKSKCFYTTDTECDLTDEIVKDVKQTYLARVFSYPAGNVESTG

SAGEPLYENSPEFTPYLETNLGQPTIQSFEQVGTKVNVTVEDERTLVRR

NNTFLSLRDVFGKDLIYTLYYWKSSSSGKKTAKTNTNEFLIDVDKGENY

CFSVQAVIPSRTVNRKSTDSPVECMGQEKGEFRENWVNVISDLKKIEDL

IQSMHIDATLYTESDVHPSCKVTAMKCFLLELQVISLESGDASIHDTVE

NLIILANNSLSSNGNVTESGCKECEELEEKNIKEFLQSFVHIVQMFINT

S.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 212)

ATGAAGTGGGTGACCTTCATCAGCCTGCTGTTCCTGTTCTCCAGCGCCTAC

TCCATCCCCCCCCATGTGCAAAAGAGCGTGAACAACGATATGATCGTGACC

GACAACAACGGCGCCGTGAAGTTTCCCCAGCTCTGCAAGTTCTGCGATGTC

AGGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAAA

```
AATGACGAGAACATCACCCTGGAGACCGTGTGTCACGACCCCAAGCTCCCT

TATCACGACTTCATTCTGGAGGACGCTGCCTCCCCCAAATGCATCATGAAG

GAGAAGAAGAAGCCCGGAGAGACCTTCTTTATGTGTTCCTGTAGCAGCGAC

GAGTGTAACGACAACATCATCTTCAGCGAAGAGTACAACACCAGCAACCCT

GATGGAGGTGGCGGATCCGGAGGTGGAGGTTCTGGTGGAGGTGGGAGTATT

CCTCCCCACGTGCAGAAGAGCGTGAATAATGACATGATCGTGACCGATAAC

AATGGCGCCGTGAAATTTCCCCAGCTGTGCAAATTCTGCGATGTGAGGTTT

TCCACCTGCGACAACCAGAAGTCCTGTATGAGCAACTGCTCCATCACCTCC

ATCTGTGAGAAGCCTCAGGAGGTGTGCGTGGCTGTCTGGCGGAAGAATGAC

GAGAATATCACCCTGGAAACCGTCTGCCACGATCCCAAGCTGCCCTACCAC

GATTTCATCCTGGAAGACGCCGCCAGCCCTAAGTGCATCATGAAAGAGAAA

AAGAAGCCTGGCGAGACCTTTTTCATGTGCTCCTGCAGCAGCGACGAATGC

AACGACAATATCATCTTTAGCGAGGAATACAATACCAGCAACCCCGACAGC

GGCACAACCAACACAGTCGCTGCCTATAACCTCACTTGGAAGAGCACCAAC

TTCAAAACCATCCTCGAATGGGAACCCAAACCCGTTAACCAAGTTTACACC

GTGCAGATCAGCACCAAGTCCGGCGACTGGAAGTCCAAATGTTTCTATACC

ACCGACACCGAGTGCGATCTCACCGATGAGATCGTGAAAGATGTGAAACAG

ACCTACCTCGCCCGGGTGTTTAGCTACCCCGCCGGCAATGTGGAGAGCACT

GGTTCCGCTGGCGAGCCTTTATACGAGAACAGCCCCGAATTTACCCCTTAC

CTCGAGACCAATTTAGGACAGCCCACCATCCAAAGCTTTGAGCAAGTTGGC

ACAAAGGTGAATGTGACAGTGGAGGACGAGCGGACTTTAGTGCGGCGGAAC

AACACCTTTCTCAGCCTCCGGGATGTGTTCGGCAAAGATTTAATCTACACA

CTGTATTACTGGAAGTCCTCTTCCTCCGGCAAGAAGACAGCTAAAACCAAC

ACAAACGAGTTTTTAATCGACGTGGATAAAGGCGAAAACTACTGTTTCAGC

GTGCAAGCTGTGATCCCCTCCCGGACCGTGAATAGGAAAAGCACCGATAGC

CCCGTTGAGTGCATGGGCCAAGAAAAGGGCGAGTTCCGGGAGAACTGGGTG

AACGTCATCAGCGATTTAAAGAAGATCGAAGATTTAATTCAGTCCATGCAT

ATCGACGCCACTTTATACACAGAATCCGACGTGCACCCCTCTTGTAAGGTG

ACCGCCATGAAATGTTTTTTACTGGAGCTGCAAGTTATCTCTTTAGAGAGC

GGAGACGCTAGCATCCACGACACCGTGGAGAATTTAATCATTTTAGCCAAT

AACTCTTTATCCAGCAACGGCAACGTGACAGAGTCCGGCTGCAAGGAGTGC

GAAGAGCTGGAGGAGAAGAACATCAAGGAGTTTCTGCAATCCTTTGTGCAC

ATTGTCCAGATGTTCATCAATACCTCC.
```

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 213)
```
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPDITCPPPM

SVEHADIWVKSYSLYSRERYICNSGFKRKAGTSSLTECVLNKATNVAHW

TTPSLKCIRGGGGSGGGGSGGGGSREGPELSPDDPAGLLDLRQGMFAQL

VAQNVLLIDGPLSWYSDPGLAGVSLTGGLSYKEDTKELVVAKAGVYYVF

FQLELRRVVAGEGSGSVSLALHLQPLRSAAGAAALALTVDLPPASSEAR

NSAFGFQGRLLHLSAGQRLGVHLHTEARARHAWQLTQGATVLGLFRVTP

EIPAGLPSPRSE.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 214)
```
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGACATTACATGCCCCCCTCCCATG

AGCGTGGAGCACGCCGACATCTGGGTGAAGAGCTATAGCCTCTACAGCC

GGGAGAGGTATATCTGTAACAGCGGCTTCAAGAGGAAGGCCGGCACCAG

CAGCCTCACCGAGTGCGTGCTGAATAAGGCTACCAACGTGGCTCACTGG

ACAACACCCTCTTTAAAGTGCATCCGGGGCGGTGGAGGATCCGGAGGAG
```

-continued

```
GTGGCTCCGGCGGCGGAGGATCTCGCGAGGGTCCCGAGCTTTCGCCCGA
CGATCCCGCCGGCCTCTTGGACCTGCGGCAGGGCATGTTTGCGCAGCTG
GTGGCCCAAAATGTTCTGCTGATCGATGGGCCCCTGAGCTGGTACAGTG
ACCCAGGCCTGGCAGGCGTGTCCCTGACGGGGGGCCTGAGCTACAAAGA
GGACACGAAGGAGCTGGTGGTGGCCAAGGCTGGAGTCTACTATGTCTTC
TTTCAACTAGAGCTGCGGCGCGTGGTGGCCGGCGAGGGCTCAGGCTCCG
TTTCACTTGCGCTGCACCTGCAGCCACTGCGCTCTGCTGCTGGGGCCGC
CGCCCTGGCTTTGACCGTGGACCTGCCACCCGCCTCCTCCGAGGCTCGG
AACTCGGCCTTCGGTTTCCAGGGCCGCTTGCTGCACCTGAGTGCCGGCC
AGCGCCTGGGCGTCCATCTTCACACTGAGGCCAGGGCACGCCATGCCTG
GCAGCTTACCCAGGGCGCCACAGTCTTGGGACTCTTCCGGGTGACCCCC
GAAATCCCAGCCGGACTCCCTTCACCGAGGTCGGAA.
```

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 215)
MKWVTFISLLFLFSSAYSIPPHVQKSVNNDMIVTDNNGAVKFPQLCKFC
DVRFSTCDNQKSCMSNCSITSICEKPQEVCVAVWRKNDENITLETVCHD
PKLPYHDFILEDAASPKCIMKEKKKPGETFFMCSCSSDECNDNIIFSEE
YNTSNPDGGGGSGGGGSGGGGSIPPHVQKSVNNDMIVTDNNGAVKFPQL
CKFCDVRFSTCDNQKSCMSNCSITSICEKPQEVCVAVWRKNDENITLET
VCHDPKLPYHDFILEDAASPKCIMKEKKKPGETFFMCSCSSDECNDNII
FSEEYNTSNPDITCPPPMSVEHADIWVKSYSLYSRERYICNSGFKRKAG
TSSLTECVLNKATNVAHWTTPSLKCIRGGGGSGGGGSGGGGSREGPELS
PDDPAGLLDLRQGMFAQLVAQNVLLIDGPLSWYSDPGLAGVSLTGGLSY
KEDTKELVVAKAGVYYVFFQLELRRVVAGEGSGSVSLALHLQPLRSAAG
AAALALTVDLPPASSEARNSAFGFQGRLLHLSAGQRLGVHLHTEARARH
AWQLTQGATVLGLFRVTPEIPAGLPSPRSE .
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 216)
ATGAAGTGGGTGACCTTCATCAGCCTGCTGTTCCTGTTCTCCAGCGCCT
ACTCCATCCCCCCCCATGTGCAAAAGAGCGTGAACAACGATATGATCGT
GACCGACAACAACGGCGCCGTGAAGTTTCCCCAGCTCTGCAAGTTCTGC
GATGTCAGGTTCAGCACCTGCGATAATCAGAAGTCCTGCATGTCCAACT
GCAGCATCACCTCCATCTGCGAGAAGCCCCAAGAAGTGTGCGTGGCCGT
```

-continued

```
GTGGCGGAAAAATGACGAGAACATCACCCTGGAGACCGTGTGTCACGAC
CCCAAGCTCCCTTATCACGACTTCATTCTGGAGGACGCTGCCTCCCCCA
AATGCATCATGAAGGAGAAGAAGAAGCCCGGAGAGACCTTCTTTATGTG
TTCCTGTAGCAGCGACGAGTGTAACGACAACATCATCTTCAGCGAAGAG
TACAACACCAGCAACCCTGATGGAGGTGGCGGATCCGGAGGTGGAGGTT
CTGGTGGAGGTGGGAGTATTCCTCCCCACGTGCAGAAGAGCGTGAATAA
TGACATGATCGTGACCGATAACAATGGCGCCGTGAAATTTCCCCAGCTG
TGCAAATTCTGCGATGTGAGGTTTTCCACCTGCGACAACCAGAAGTCCT
GTATGAGCAACTGCTCCATCACCTCCATCTGTGAGAAGCCTCAGGAGGT
GTGCGTGGCTGTCTGGCGGAAGAATGACGAGAATATCACCCTGGAAACC
GTCTGCCACGATCCCAAGCTGCCCTACCACGATTTCATCCTGGAAGACG
CCGCCAGCCCTAAGTGCATCATGAAAGAGAAAAAGAAGCCTGGCGAGAC
CTTTTTCATGTGCTCCTGCAGCAGCGACGAATGCAACGACAATATCATC
TTTAGCGAGGAATACAATACCAGCAACCCCGACATTACATGCCCCCCTC
CCATGAGCGTGGAGCACGCCGACATCTGGGTGAAGAGCTATAGCCTCTA
CAGCCGGGAGAGGTATATCTGTAACAGCGGCTTCAAGAGGAAGGCCGGC
ACCAGCAGCCTCACCGAGTGCGTGCTGAATAAGGCTACCAACGTGGCTC
ACTGGACAACACCCTCTTTAAAGTGCATCCGGGGCGGTGGAGGATCCGG
AGGAGGTGGCTCCGGCGGCGGAGGATCTCGCGAGGGTCCCGAGCTTTCG
CCCGACGATCCCGCCGGCCTCTTGGACCTGCGGCAGGGCATGTTTGCGC
AGCTGGTGGCCCAAAATGTTCTGCTGATCGATGGGCCCCTGAGCTGGTA
CAGTGACCCAGGCCTGGCAGGCGTGTCCCTGACGGGGGGCCTGAGCTAC
AAAGAGGACACGAAGGAGCTGGTGGTGGCCAAGGCTGGAGTCTACTATG
TCTTCTTTCAACTAGAGCTGCGGCGCGTGGTGGCCGGCGAGGGCTCAGG
CTCCGTTTCACTTGCGCTGCACCTGCAGCCACTGCGCTCTGCTGCTGGG
GCCGCCGCCCTGGCTTTGACCGTGGACCTGCCACCCGCCTCCTCCGAGG
CTCGGAACTCGGCCTTCGGTTTCCAGGGCCGCTTGCTGCACCTGAGTGC
CGGCCAGCGCCTGGGCGTCCATCTTCACACTGAGGCCAGGGCACGCCAT
GCCTGGCAGCTTACCCAGGGCGCCACAGTCTTGGGACTCTTCCGGGTGA
CCCCCGAAATCCCAGCCGGACTCCCTTCACCGAGGTCGGAA.
```

Compositions/Kits

Also provided herein are compositions (e.g., pharmaceutical compositions) that include at least one of any multi-chain chimeric polypeptides, any of the cells, or any of the nucleic acids described herein. In some embodiments, the compositions include at least one of any of the multi-chain chimeric polypeptides described herein. In some embodiments, the compositions include any of the immune cells (e.g., any of the immune cells described herein, e.g., any of the immune cells produced using any of the methods described herein).

In some embodiments, the pharmaceutical compositions are formulated for different routes of administration (e.g., intravenous, subcutaneous). In some embodiments, the pharmaceutical compositions can include a pharmaceutically acceptable carrier (e.g., phosphate buffered saline).

Single or multiple administrations of pharmaceutical compositions can be given to a subject in need thereof depending on for example: the dosage and frequency as required and tolerated by the subject. The formulation should provide a sufficient quantity of active agent to effectively treat, prevent or ameliorate conditions, diseases or symptoms.

Also provided herein are kits that include any of the multi-chain chimeric polypeptides, compositions, nucleic acids, or cells (e.g., immune cells) described herein. In some embodiments, the kits can include instructions for performing any of the methods described herein. In some embodiments, the kits can include at least one dose of any of the pharmaceutical compositions described herein.

Nucleic Acids/Vectors

Also provided herein are nucleic acids that encode any of the multi-chain chimeric polypeptides described herein. In some embodiments, a first nucleic acid can encode the first chimeric polypeptide and a second nucleic acid can encode the second chimeric polypeptide. In some embodiments, a single nucleic acid can encode both the first chimeric polypeptide and the second chimeric polypeptide.

Also provided herein are vectors that include any of the nucleic acids encoding any of the multi-chain chimeric polypeptides described herein. In some embodiments, a first vector can include a nucleic acid encoding the first chimeric polypeptide and a second vector can include a nucleic acid encoding the second chimeric polypeptide. In some embodiments, a single vector can include a first nucleic acid encoding the first chimeric polypeptide and a second nucleic acid encoding the second chimeric polypeptide.

Any of the vectors described herein can be an expression vector. For example, an expression vector can include a promoter sequence operably linked to the sequence encoding the first chimeric polypeptide and the second chimeric polypeptide.

Non-limiting examples of vectors include plasmids, transposons, cosmids, and viral vectors (e.g., any adenoviral vectors (e.g., pSV or pCMV vectors), adeno-associated virus (AAV) vectors, lentivirus vectors, and retroviral vectors), and any Gateway® vectors. A vector can, e.g., include sufficient cis-acting elements for expression; other elements for expression can be supplied by the host mammalian cell or in an in vitro expression system. Skilled practitioners will be capable of selecting suitable vectors and mammalian cells for making any of the multi-chain chimeric polypeptides described herein.

Cells

Also provided herein are cells (e.g., any of the exemplary cells described herein or known in the art) comprising any of the nucleic acids described herein that encode any of the multi-chain chimeric polypeptides described herein (e.g., encoding both the first and second chimeric polypeptides). Also provided herein are cells (e.g., any of the exemplary cells described herein or known in the art) comprising any of the nucleic acids described herein that encode any of the first chimeric polypeptides described herein. Also provided are cells (e.g., any of the exemplary cells described herein or known in the art) comprising any of the nucleic acids described herein that encode any of the second chimeric polypeptides described herein.

Also provided herein are cells (e.g., any of the exemplary cells described herein or known in the art) that include any of the vectors described herein that encode any of the multi-chain chimeric polypeptides described herein (e.g., encoding both the first and second chimeric polypeptides). Also provided herein are cells (e.g., any of the exemplary cells described herein or known in the art) that include any of the vectors described herein that encode any of the first chimeric polypeptides described herein. Also provided herein are cells (e.g., any of the exemplary cells described herein or known in the art) that include any of the vectors described herein that encode any of the second chimeric polypeptides described herein).

In some embodiments of any of the methods described herein, the cell can be a eukaryotic cell. As used herein, the term "eukaryotic cell" refers to a cell having a distinct, membrane-bound nucleus. Such cells may include, for example, mammalian (e.g., rodent, non-human primate, or human), insect, fungal, or plant cells. In some embodiments, the eukaryotic cell is a yeast cell, such as *Saccharomyces cerevisiae*. In some embodiments, the eukaryotic cell is a higher eukaryote, such as mammalian, avian, plant, or insect cells. Non-limiting examples of mammalian cells include Chinese hamster ovary cells and human embryonic kidney cells (e.g., HEK293 cells).

Methods of introducing nucleic acids and expression vectors into a cell (e.g., a eukaryotic cell) are known in the art. Non-limiting examples of methods that can be used to introduce a nucleic acid into a cell include lipofection, transfection, electroporation, microinjection, calcium phosphate transfection, dendrimer-based transfection, cationic polymer transfection, cell squeezing, sonoporation, optical transfection, impalefection, hydrodynamic delivery, magnetofection, viral transduction (e.g., adenoviral and lentiviral transduction), and nanoparticle transfection.

Methods of Producing Multi-Chain Chimeric Polypeptides

Also provided herein are methods of producing any of the multi-chain chimeric polypeptides described herein that include culturing any of the cells described herein in a culture medium under conditions sufficient to result in the production of the multi-chain chimeric polypeptide; and recovering the multi-chain chimeric polypeptide from the cell and/or the culture medium.

Also provided herein are method of producing any of the multi-chain chimeric polypeptides described herein that include: culturing any of cells described herein in a first culture medium under conditions sufficient to result in the production of the first chimeric polypeptide; recovering the first chimeric polypeptide from the cell and/or the first culture medium; culturing any of the cells described herein in a second culture medium under conditions sufficient to result in the production of the second chimeric polypeptide; recovering the second chimeric polypeptide from the cell and/or the second culture medium; and combining (e.g., mixing) the recovered first chimeric polypeptide and the recovered second chimeric polypeptide to form the multi-chain chimeric polypeptide (e.g., any of the multi-chain chimeric polypeptides described herein).

The recovery of the multi-chain chimeric polypeptide, the first chimeric polypeptide, or the second chimeric polypeptide from a cell (e.g., a eukaryotic cell) can be performed using techniques well-known in the art (e.g., ammonium sulfate precipitation, polyethylene glycol precipitation, ion-exchange chromatography (anion or cation), chromatography based on hydrophobic interaction, metal-affinity chromatography, ligand-affinity chromatography, and size exclusion chromatography).

Methods of culturing cells are well known in the art. Cells can be maintained in vitro under conditions that favor proliferation, differentiation and growth. Briefly, cells can be cultured by contacting a cell (e.g., any cell) with a cell culture medium that includes the necessary growth factors and supplements to support cell viability and growth.

Also provided herein are multi-chain chimeric polypeptides (e.g., any of the multi-chain chimeric polypeptides described herein), first chimeric polypeptides (e.g., any of the first chimeric polypeptides), or second chimeric polypeptides (e.g., any of the second chimeric polypeptides described herein) produced by any of the methods described herein.

Methods of Stimulating an Immune Cell

Also provided herein are methods of stimulating an immune cell (e.g., any of the exemplary immune cells described herein or known in the art) that include contacting an immune cell with an effective amount of any of the multi-chain chimeric polypeptides described herein or any of the compositions (e.g., pharmaceutical compositions) described herein. In some examples, the immune cell is contacted in vitro (e.g., in a suitable liquid culture medium under conditions sufficient to result in stimulation of the immune cell).

In some examples, the immune cell has been previously obtained from a subject (e.g., a mammal, e.g., a human). Some embodiments of these methods further include obtaining the immune cell from the subject prior to the contacting step.

In some examples, the immune cell is contacted in vivo. In such embodiments, the multi-chain chimeric polypeptide is administered to a subject (e.g., a mammal, e.g., a human) in an amount sufficient to result in stimulation of an immune cell in the subject.

In some examples of any of the methods described herein, the immune cell can be an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8$^+$ T cell, a CD4$^+$ T cell, a natural killer T cell, a mast cell, a macrophage, a neutrophil, a dendritic cell, a basophil, an eosinophil, or a natural killer cell, or a combination thereof.

In some examples, the immune cell has previously been genetically-modified to express a chimeric antigen receptor or a recombinant T-cell receptor. In some examples, the immune cell (e.g., any of the immune cells described herein) has previously been genetically-modified to express a co-stimulatory molecule (e.g., CD28).

Some embodiments of these methods can further include, after the contacting step, introducing into the immune cell (e.g., any of the immune cells described herein) a nucleic acid encoding a chimeric antigen-receptor or a recombinant T-cell receptor.

Some embodiments of these methods can further include, after the contacting step, introducing into the immune cell (e.g., any of the immune cells described herein) a nucleic acid encoding a co-stimulatory molecule (e.g., CD28).

Some embodiments of these methods can further include administering a therapeutically effective amount of the immune cell to a subject in need thereof (e.g., any of the exemplary subjects described herein).

In some examples, the subject can be a subject identified or diagnosed as having an age-related disease or condition. Non-limiting examples of age-related diseases or disorders include: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples, the subject can be a subject that has been identified or diagnosed as having a cancer. Non-limiting examples of cancers include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CMIL), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples, the subject can be a subject that has been diagnosed or identified as having an infectious disease. Non-limiting examples of infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

Activation of an immune cell can be determined using methods known in the art. For example, activation of an immune cell can be determined by detecting the levels of cytokines and chemokines that are secreted or cytotoxicity granules and regulatory molecules that are upregulated upon activation of an immune cell. Non-limiting examples of cytokines, chemokines, cytotoxicity granules, and regulatory molecules that are secreted or upregulated upon activation of an immune cell include: IL-2, IFN-γ, IL-1, IL-4, IL-5, IL-6, IL-7, IL-9, IL-10, IL-12, IL-13, IL-15, IL-17, IL-18, IL-22, IL-33, leukotriene B4, CCL5, TNFα, granzymes, perforin, TGFβ, STAT3, STAT4, STAT5, RORγT, FOXP3, STAT6, and GATA3. The detection of these cytokines, chemokines, cytotoxicity granules, or regulatory molecules can be performed using an immunoassay (e.g., an enzyme-linked immunosorbent assay) and quantitative PCR. For example, activation of an immune cell can result in an increase of about 1% to about 800% (e.g., about 1% to about 750%, about 1% to about 700%, about 1% to about 650%, about 1% to about 600%, about 1% to about 550%, about 1% to about 500%, about 1% to about 450%, about 1% to about 400%, about 1% to about 350%, about 1% to about 300%, about 1% to about 280%, about 1% to about 260%, about 1% to about 240%, about 1% to about 220%, about 1% to about 200%, about 1% to about 180%, about 1% to about 160%, about 1% to about 140%, about 1% to about 120%, about 1% to about 100%, about 1% to about 90%, about 1% to about 80%, about 1% to about 70%, about 1% to about 60%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 5%, about 5% to about 800%, about 5% to about 750%, about 5% to about 700%, about 5% to about 650%, about 5% to about 600%, about 5% to about 550%, about 5% to about 500%, about 5% to about 450%, about 5% to about 400%, about 5% to about 350%, about 5% to about 300%, about 5% to about 280%, about 5% to about 260%, about 5% to about 240%, about 5% to about 220%, about 5% to about 200%, about 5% to about 180%, about 5% to about 160%, about 5% to about 140%, about 5% to about 120%, about 5% to about 100%, about 5% to about 90%, about 5% to about 80%, about 5% to about 70%, about 5% to about 60%, about 5% to about 50%, about 5% to about 45%, about 5% to about 40%, about 5% to about 35%, about 5% to about 30%, about 5% to about 25%, about 5% to about 20%, about 5% to about 15%, about 5% to about 10%, about 10% to about 800%, about 10% to about 750%, about 10% to about 700%, about 10% to about 650%, about 10% to about 600%, about 10% to about 550%, about 10% to about 500%, about 10% to about 450%, about 10% to about 400%, about 10% to about 350%, about 10% to about 300%, about 10% to about 280%, about 10% to about 260%, about 10% to about 240%, about 10% to about 220%, about 10% to about 200%, about 10% to about 180%, about 10% to about 160%, about 10% to about 140%, about 10% to about 120%, about 10% to about 100%, about 10% to about 90%, about 10% to about 80%, about 10% to about 70%, about 10% to about 60%, about 10% to about 50%, about 10% to about 45%, about 10% to about 40%, about 10% to about 35%, about 10% to about 30%, about 10% to about 25%, about 10% to about 20%, about 10% to about 15%, about 15% to about 800%, about 15% to about 750%, about 15% to about 700%, about 15% to about 650%, about 15% to about 600%, about 15% to about 550%, about 15% to about 500%, about 15% to about 450%, about 15% to about 400%, about 15% to about 350%, about 15% to about 300%, about 15% to about 280%, about 15% to about 260%, about 15% to about 240%, about 15% to about 220%, about 15% to about 200%, about 15% to about 180%, about 15% to about 160%, about 15% to about 140%, about 15% to about 120%, about 15% to about 100%, about 15% to about 90%, about 15% to about 80%, about 15% to about 70%, about 15% to about 60%, about 15% to about 50%, about 15% to about 45%, about 15% to about 40%, about 15% to about 35%, about 15% to about 30%, about 15% to about 25%, about 15% to about 20%, about 20% to about 800%, about 20% to about 750%, about 20% to about 700%, about 20% to about 650%, about 20% to about 600%, about 20% to about 550%, about 20% to about 500%, about 20% to about 450%, about 20% to about 400%, about 20% to about 350%, about 20% to about 300%, about 20% to about 280%, about 20% to about 260%, about 20% to about 240%, about 20% to about 220%, about 20% to about 200%, about 20% to about 180%, about 20% to about 160%, about 20% to about 140%, about 20% to about 120%, about 20% to about 100%, about 20% to about 90%, about 20% to about 80%, about 20% to about 70%, about 20% to about 60%, about 20% to about 50%, about 20% to about 45%, about 20% to about 40%, about 20% to about 35%, about 20% to about 30%, about 20% to about 25%, about 25% to about 800%, about 25% to about 750%, about 25% to about 700%, about 25% to about 650%, about 25% to about 600%, about 25% to about 550%, about 25% to about 500%, about 25% to about 450%, about 25% to about 400%, about 25% to about 350%, about 25% to about 300%, about 25% to about 280%, about 25% to about 260%, about 25% to about 240%, about 25% to about 220%, about 25% to about 200%, about 25% to about 180%, about 25% to about 160%, about 25% to about 140%, about 25% to about 120%, about 25% to about 100%, about 25% to about 90%, about 25% to about 80%, about 25% to about 70%, about 25% to about 60%, about 25% to about 50%, about 25% to about 45%, about 25% to about 40%, about 25% to about 35%, about 35% to about 800%, about 35% to about 750%, about 35% to about 700%, about 35% to about 650%, about 35% to about 600%, about 35% to about 550%, about 35% to about 500%, about 35% to about 450%, about 35% to about 400%, about 35% to about 350%, about 35% to about 300%, about 35% to about 280%, about 35% to about 260%, about 35% to about 240%, about 35% to about 220%, about 35% to about 200%, about 35% to about 180%, about 35% to about 160%, about 35% to about 140%, about 35% to about 120%, about 35% to about 100%, about 35% to about 90%, about 35% to about 80%, about 35% to about 70%, about 35% to about 60%, about 35% to about 50%, about 35% to about 45%, about 35% to about 40%, about 40% to about 800%, about 40% to about 750%, about 40% to about 700%, about 40% to about 650%, about 40% to about 600%, about 40% to about 550%, about 40% to about 500%, about 40% to about 450%, about 40% to about 400%, about 40% to about 350%, about 40% to about 300%, about 40% to about 280%, about 40% to about 260%, about 40% to about 240%, about 40% to about 220%, about 40% to about 200%, about 40% to about 180%, about 40% to about 160%, about 40% to about 140%, about 40% to about 120%, about 40% to about 100%, about 40% to about 90%, about 40% to about 80%, about 40% to about 70%, about 40% to about 60%, about 40% to about 50%, about 40% to about 45%, about 45% to about 800%, about 45% to about 750%, about 45% to about 700%, about 45% to about 650%, about 45% to about 600%, about 45% to about 550%, about 45% to about 500%, about 45% to about 450%, about 45% to about 400%, about 45% to about 350%, about 45% to about 300%, about 45% to about 280%, about 45% to about 260%, about 45% to about 240%, about 45% to about 220%, about 45% to about 200%, about 45% to about 180%, about 45% to about 160%, about 45% to about 140%, about 45% to about 120%, about 45% to about 100%, about 45% to about 90%, about 45% to about 80%, about 45% to about 70%, about 45% to about 60%, about 45% to about 50%, about 50% to about 800%, about 50% to about 750%, about 50% to about 700%, about 50% to about 650%, about 50% to about 600%, about 50% to about 550%, about 50% to about 500%, about 50% to about 450%, about 50% to about 400%, about 50% to about 350%, about 50% to about 300%, about 50% to about 280%, about 50% to about 260%, about 50% to about 240%, about 50% to about 220%, about 50% to about 200%, about 50% to about 180%, about 50% to about 160%, about 50% to about 140%, about 50% to about 120%, about 50% to about 100%, about 50% to about 90%, about 50% to about 80%, about 50% to about 70%, about 50% to about 60%, about 60% to about 800%, about 60% to about 750%, about 60% to about 700%, about 60% to about 650%, about 60% to about 600%, about 60% to about 550%, about 60% to about 500%, about 60% to about 450%, about 60% to about 400%, about 60% to about 350%, about 60% to about 300%, about 60% to about 280%, about 60% to about 260%, about 60% to about 240%, about 60% to about 220%, about 60% to about 200%, about 60% to about 180%, about 60% to about 160%, about 60% to about 140%, about 60% to about 120%, about 60% to about 100%, about 60% to about 90%, about 60% to about 80%, about 60% to about 70%, about 70% to about 800%, about 70% to about 750%, about 70% to about 700%, about 70% to about 650%, about 70% to about 600%, about 70% to about 550%, about 70% to about 500%, about 70% to about 450%, about 70% to about 400%, about 70% to about 350%, about 70% to about 300%, about 70% to about 280%, about 70% to about 260%, about 70% to about 240%, about 70% to about 220%, about 70% to about 200%, about 70% to about 180%, about 70% to about 160%, about 70% to about 140%, about 70% to about 120%, about 70% to about 100%, about 70% to about 90%, about 70% to about 80%, about 80% to about 800%, about 80% to about 750%, about 80% to about 700%, about 80% to about 650%, about 80% to about 600%, about 80% to about 550%, about 80% to about 500%, about 80% to about 450%, about 80% to about 400%, about 80% to about 350%, about 80% to about 300%, about 80% to about 280%, about 80% to about 260%, about 80% to about 240%, about 80% to about 220%, about 80% to about 200%, about 80% to about 180%, about 80% to about 160%, about 80% to about 140%, about 80% to about 120%, about 80% to about 100%, about 80% to about 90%, about 90% to about 800%, about 90% to about 750%, about 90% to about 700%, about 90% to about 650%, about 90% to about 600%, about 90% to about 550%, about 90% to about 500%, about 90% to about 450%, about 90% to about 400%, about 90% to about 350%, about 90% to about 300%, about 90% to about 280%, about 90% to about 260%, about 90% to about 240%, about 90% to about 220%, about 90% to about 200%, about 90% to about 180%, about 90% to about 160%, about 90% to about 140%, about 90% to about 120%, about 90% to about 100%, about 100% to about 800%, about 100% to about 750%, about 100% to about 700%, about 100% to about 650%, about 100% to about 600%, about 100% to about 550%, about 100% to about 500%, about 100% to about 450%, about 100% to about 400%, about 100% to about 350%, about 100% to about 300%, about 100% to about 280%, about 100% to about 260%, about 100% to about 240%, about 100% to about 220%, about 100% to about 200%, about 100% to about 180%, about 100% to about 160%, about 100% to about 140%, about 100% to about 120%, about 120% to about 800%, about 120% to about 750%, about 120% to about 700%, about 120% to about 650%, about 120% to about 600%, about 120% to about 550%, about 120% to about 500%, about 120% to about 450%, about 120% to about 400%, about 120% to about 350%, about 120% to about 300%, about 120% to about 280%, about 120% to about 260%, about 120% to about 240%, about 120% to about 220%, about 120% to about 200%, about 120% to about 180%, about 120% to about 160%, about 120% to about 140%, about 140% to about 800%, about 140% to about 750%, about 140% to about 700%, about 140% to about 650%, about 140% to about 600%, about 140% to about 550%, about 140% to about 500%, about 140% to about 450%, about 140% to about 400%, about 140% to about 350%, about 140% to about 300%, about 140% to about 280%, about 140% to about 260%, about 140% to about 240%, about 140% to about 220%, about 140% to about 200%, about 140% to about 180%, about 140% to about 160%, about 160% to about 800%, about 160% to about 750%, about 160% to about 700%, about 160% to about 650%, about 160% to about 600%, about 160% to about 550%, about 160% to about 500%, about 160% to about 450%, about 160% to about 400%, about 160% to about 350%, about 160% to about 300%, about 160% to about 280%, about 160% to about 260%, about 160% to about 240%, about 160% to about 220%, about 160% to about 200%, about 160% to about 180%, about 180% to about 800%, about 180% to about 750%, about 180% to about 700%, about 180% to about 650%, about 180% to about 600%, about 180% to about 550%, about 180% to about 500%, about 180% to about 450%, about 180% to about 400%, about 180% to about 350%, about 180% to about 300%, about 180% to about 280%, about 180% to about 260%, about 180% to about 240%, about 180% to about 220%, about 180% to about 200%, about 200% to about 800%, about 200% to about 750%, about 200% to about 700%, about 200% to about 650%, about 200% to about 600%, about 200% to about 550%, about 200% to about 500%, about 200% to about 450%, about 200% to about 400%, about 200% to about 350%, about 200% to about 300%, about 200% to about 280%, about 200% to about 260%, about 200% to about 240%, about 200% to about 220%, about 220% to about 800%, about 220% to about 750%, about 220% to about 700%, about 220% to about 650%, about 220% to about 600%, about 220% to about 550%, about 220% to about 500%, about 220% to about 450%, about 220% to about 400%, about 220% to about 350%, about 220% to about 300%, about 220% to about 280%, about 220% to about 260%, about 220% to about 240%, about 240% to about 800%, about 240% to about 750%, about 240% to about 700%, about 240% to about 650%, about 240% to about 600%, about 240% to about 550%, about 240% to about 500%, about 240% to about 450%, about 240% to about 400%, about 240% to about 350%, about 240% to about 300%, about 240% to about 280%, about 240% to about 260%, about 260% to about 800%, about 260% to about 750%, about 260% to about 700%, about 260% to about 650%, about 260% to about 600%, about 260% to about 550%, about 260% to about 500%, about 260% to about 450%, about 260% to about 400%, about 260% to about 350%, about 260% to about 300%, about 260% to about 280%, about 280% to about 800%, about 280% to about 750%, about 280% to about 700%, about 280% to about 650%, about 280% to about 600%, about 280% to about 550%, about 280% to about 500%, about 280% to about 450%, about 280% to about 400%, about 280% to about 350%, about 280% to about 300%, about 300% to about 800%, about 300% to about 750%, about 300% to about 700%, about 300% to about 650%, about 300% to about 600%, about 300% to about 550%, about 300% to about 500%, about 300% to about 450%, about 300% to about 400%, about 300% to about 350%, about 350% to about 800%, about 350% to about 750%, about 350% to about 700%, about 350% to about 650%, about 350% to about 600%, about 350% to about 550%, about 350% to about 500%, about 350% to about 450%, about 350% to about 400%, about 400% to about 800%, about 400% to about 750%, about 400% to about 700%, about 400% to about 650%, about 400% to about 600%, about 400% to about 550%, about 400% to about 500%, about 400% to about 450%, about 450% to about 800%, about 450% to about 750%, about 450% to about 700%, about 450% to about 650%, about 450% to about 600%, about 450% to about 550%, about 450% to about 500%, about 500% to about 800%, about 500% to about 750%, about 500% to about 700%, about 500% to about 650%, about 500% to about 600%, about 500% to about 550%, about 550% to about 800%, about 550% to about 750%, about 550% to about 700%, about 550% to about 650%, about 550% to about 600%, about 600% to about 800%, about 600% to about 750%, about 600% to about 700%, about 600% to about 650%, about 650% to about 800%, about 650% to about 750%, about 650% to about 700%, about 700% to about 800%, about 700% to about 750%, or about 750% to about 800%) of one or more of any of the cytokines or chemokines or cytotoxicity granules or regulatory molecules described herein (e.g., one or more of any of IL-2, IFN-γ, IL-1, IL-4, IL-5, IL-6, IL-7, IL-9, IL-10, IL-12, IL-13, IL-15, IL-17, IL-18, IL-22, IL-33, leukotriene B4, CCL5, TNFα, granzymes, perforin, TGFβ, STAT3, STAT4, STAT5, RORγT, FOXP3, and GATA3) (e.g., as compared to the level of the one or more cytokines, chemokines, cytotoxicity granules, and regulatory molecules in a control not contacted with any of the multi-chain chimeric polypeptides described herein).

Methods of Inducing or Increasing Proliferation of an Immune Cell

Also provided herein are methods of inducing or increasing proliferation of an immune cell (e.g., any of the exemplary immune cells described herein or known in the art) that include contacting an immune cell with an effective amount of any of the multi-chain chimeric polypeptides described herein or any of the compositions (e.g., pharmaceutical compositions) described herein. In some examples, the immune cell is contacted in vitro (e.g., in a suitable liquid culture medium under conditions sufficient to result in stimulation of the immune cell).

In some examples, the immune cell has been previously obtained from a subject (e.g., a mammal, e.g., a human). Some embodiments of these methods further include obtaining the immune cell from the subject prior to the contacting step.

In some examples, the immune cell is contacted in vivo. In such embodiments, the multi-chain chimeric polypeptide is administered to a subject (e.g., a mammal, e.g., a human) in an amount sufficient to result in stimulation of an immune cell in the subject.

In some examples of any of the methods described herein, the immune cell can be an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a $CD8^+$ T cell, a $CD4^+$ T cell, a natural killer T cell, a mast cell, a macrophage, a neutrophil, a dendritic cell, a basophil, an eosinophil, or a natural killer cell, or a combination thereof.

In some examples, the immune cell has previously been genetically-modified to express a chimeric antigen receptor or a recombinant T-cell receptor. In some examples, the immune cell (e.g., any of the immune cells described herein) has previously been genetically-modified to express a co-stimulatory molecule (e.g., CD28).

Some embodiments of these methods can further include, after the contacting step, introducing into the immune cell (e.g., any of the immune cells described herein) a nucleic acid encoding a chimeric antigen-receptor or a recombinant T-cell receptor. Some embodiments of these methods can further include, after the contacting step, introducing into the immune cell (e.g., any of the immune cells described herein) a nucleic acid encoding a co-stimulatory molecule (e.g., CD28).

Some embodiments of these methods can further include administering a therapeutically effective amount of the immune cell to a subject in need thereof (e.g., any of the exemplary subjects described herein).

In some examples, the subject can be a subject identified or diagnosed as having an age-related disease or condition. Non-limiting examples of age-related diseases or disorders include: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples, the subject can be a subject that has been identified or diagnosed as having a cancer. Non-limiting examples of cancers include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CMIL), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples, the subject can be a subject that has been diagnosed or identified as having an infectious disease. Non-limiting examples of infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

Detection of the proliferation of an immune cell can be performed using methods known in the art, e.g., cytometry (e.g., fluorescence-assisted flow cytometry), microscopy, and immunofluorescence microscopy, e.g., by comparing the rate of increase in the concentration of the immune cell in a sample not contacted with a multi-chain chimeric polypeptide to the rate of increase in the concentration of the immune cell in a similar sample contacted with any of the multi-chain chimeric polypeptides described herein).

In other examples, the proliferation of an immune cell can be indirectly detected by detecting an increase in the level of one or more cytokines or chemokines or cytotoxicity granules or regulatory molecules secreted or upregulated by proliferating immune cells (e.g., one or more of IL-2, IFN-7, IL-1, IL-4, IL-5, IL-6, IL-7, IL-9, IL-10, IL-12, IL-13, IL-15, IL-17, IL-18, IL-22, IL-33, leukotriene B4, CCL5, TNFα, granzymes, perforin, TGFβ, STAT3, STAT4, STAT5, RORγT, FOXP3, and GATA3) (e.g., as compared to the level of the one or more cytokines, chemokines, cytotoxicity granules, and regulatory molecules in a control not contacted with any of the multi-chain chimeric polypeptides described herein).

In some embodiments, the methods provided herein can result in an increase (e.g., about 1% to about 800% increase, or any of the subranges of this range described herein) in the rate of increase in the concentration of the immune cell in a sample contacted with any of the multi-chain chimeric polypeptides described herein as compared to the rate of increase in a similar control sample not contacted with any of the multi-chain chimeric polypeptides described herein.

Methods of Inducing Differentiation of an Immune Cell

Also provided herein are method of inducing differentiation of an immune cell (e.g., any of the exemplary immune cells described herein or known in the art) into a memory or memory-like immune cell that include contacting an immune cell with an effective amount of any of the multi-chain chimeric polypeptides described herein or any of the compositions (e.g., pharmaceutical compositions) described herein. In some examples, the immune cell is contacted in vitro (e.g., in a suitable liquid culture medium under conditions sufficient to result in stimulation of the immune cell).

In some examples, the immune cell has been previously obtained from a subject (e.g., a mammal, e.g., a human). Some embodiments of these methods further include obtaining the immune cell from the subject prior to the contacting step.

In some examples, the immune cell is contacted in vivo. In such embodiments, the multi-chain chimeric polypeptide is administered to a subject (e.g., a mammal, e.g., a human) in an amount sufficient to result in stimulation of an immune cell in the subject.

In some examples of any of the methods described herein, the immune cell can be an immature thymocyte, a peripheral blood lymphocyte, a naïve T cell, a pluripotent Th cell precursor, a lymphoid progenitor cell, a Treg cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, or a natural killer cell, or a combination thereof.

In some examples, the immune cell has previously been genetically-modified to express a chimeric antigen receptor or a recombinant T-cell receptor. In some examples, the immune cell (e.g., any of the immune cells described herein) has previously been genetically-modified to express a co-stimulatory molecule (e.g., CD28).

In some examples, an effective amount of any of the multi-chain chimeric polypeptides described herein or any of the compositions (e.g., pharmaceutical compositions) described herein is combined with an anti-TF IgG1 antibody to create a memory or memory like immune cell.

Some embodiments of these methods can further include, after the contacting step, introducing into the immune cell (e.g., any of the immune cells described herein) a nucleic acid encoding a chimeric antigen-receptor or a recombinant T-cell receptor.

Some embodiments of these methods can further include, after the contacting step, introducing into the immune cell (e.g., any of the immune cells described herein) a nucleic acid encoding a co-stimulatory molecule (e.g., CD28).

Some embodiments of these methods can further include administering a therapeutically effective amount of the immune cell to a subject in need thereof (e.g., any of the exemplary subjects described herein).

In some examples, the subject can be a subject identified or diagnosed as having an age-related disease or condition. Non-limiting examples of age-related diseases or disorders include: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples, the subject can be a subject that has been identified or diagnosed as having a cancer. Non-limiting examples of cancers include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CMIL), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples, the subject can be a subject that has been diagnosed or identified as having an infectious disease. Non-limiting examples of infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

In some examples, the immune cell is a NK cell, and the detection of a memory NK cell can include, e.g., the detection of the level of one or more of IL-12, IL-18, IL-33, CD25, CD69, CD62L, STAT4, Zbtb32, DNAM-1, NKp30, NKp44, NKp46, BIM, Noxa, SOCS1, BNIP3, BNIP3L, IFN-7, CXCL16, CXCR6, NKG2D, TRAIL, CD49, Ly49D, CD49b, and Ly79H. A description of NK memory cells and methods of detecting the same is described in O'Sullivan et al., *Immunity* 43:634-645, 2015.

In some examples, the immune cell is a T cell, and the detection of memory T cells can include, e.g., the detection of the level of expression of one or more of CD45RO, CCR7, L-selectin (CD62L), CD44, CD45RA, integrin αeβ7, CD43, CD27, CD28, IL-7Rα, CD95, IL-2Rβ, CXCR3, and LFA-1. In some examples, the immune cell is a B cell and the detection of memory B cells can include, e.g., the detection of the level of expression of CD27. Other types and markers of memory or memory-like immune cells are known in the art.

Methods of Treatment

Also provided herein are methods of treating a subject in need thereof (e.g., any of the exemplary subjects described herein or known in the art) that include administering to the subject a therapeutically effective amount of any of the multi-chain chimeric polypeptides described herein or any of the compositions (e.g., pharmaceutical compositions) described herein.

In some embodiments of these methods, the subject has been identified or diagnosed as having a cancer. Non-limiting examples of cancer include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, these methods can result in a reduction in the number, severity, or frequency of one or more symptoms of the cancer in the subject (e.g., as compared to the number, severity, or frequency of the one or more symptoms of the cancer in the subject prior to treatment). In some embodiments, these methods can result in a reduction (e.g., about 1% reduction to about 99% reduction, about 1% reduction to about 95% reduction, about 1% reduction to about 90% reduction, about 1% reduction to about 85% reduction, about 1% reduction to about 80% reduction, about 1% reduction to about 75% reduction, about 1% reduction to about 70% reduction, about 1% reduction to about 65% reduction, about 1% reduction to about 60% reduction, about 1% reduction to about 55% reduction, about 1% reduction to about 50% reduction, about 1% reduction to about 45% reduction, about 1% reduction to about 40% reduction, about 1% reduction to about 35% reduction, about 1% reduction to about 30% reduction, about 1% reduction to about 25% reduction, about 1% reduction to about 20% reduction, about 1% reduction to about 15% reduction, about 1% reduction to about 10% reduction, about 1% reduction to about 5% reduction, about 5% reduction to about 99% reduction, about 5% reduction to about 95% reduction, about 5% reduction to about 90% reduction, about 5% reduction to about 85% reduction, about 5% reduction to about 80% reduction, about 5% reduction to about 75% reduction, about 5% reduction to about 70% reduction, about 5% reduction to about 65% reduction, about 5% reduction to about 60% reduction, about 5% reduction to about 55% reduction, about 5% reduction to about 50% reduction, about 5% reduction to about 45% reduction, about 5% reduction to about 40% reduction, about 5% reduction to about 35% reduction, about 5% reduction to about 30% reduction, about 5% reduction to about 25% reduction, about 5% reduction to about 20% reduction, about 5% reduction to about 15% reduction, about 5% reduction to about 10% reduction, about 10% reduction to about 99% reduction, about 10% reduction to about 95% reduction, about 10% reduction to about 90% reduction, about 10% reduction to about 85% reduction, about 10% reduction to about 80% reduction, about 10% reduction to about 75% reduction, about 10% reduction to about 70% reduction, about 10% reduction to about 65% reduction, about 10% reduction to about 60% reduction, about 10% reduction to about 55% reduction, about 10% reduction to about 50% reduction, about 10% reduction to about 45% reduction, about 10% reduction to about 40% reduction, about 10% reduction to about 35% reduction, about 10% reduction to about 30% reduction, about 10% reduction to about 25% reduction, about 10% reduction to about 20% reduction, about 10% reduction to about 15% reduction, about 15% reduction to about 99% reduction, about 15% reduction to about 95% reduction, about 15% reduction to about 90% reduction, about 15% reduction to about 85% reduction, about 15% reduction to about 80% reduction, about 15% reduction to about 75% reduction, about 15% reduction to about 70% reduction, about 15% reduction to about 65% reduction, about 15% reduction to about 60% reduction, about 15% reduction to about 55% reduction, about 15% reduction to about 50% reduction, about 15% reduction to about 45% reduction, about 15% reduction to about 40% reduction, about 15% reduction to about 35% reduction, about 15% reduction to about 30% reduction, about 15% reduction to about 25% reduction, about 15% reduction to about 20% reduction, about 20% reduction to about 99% reduction, about 20% reduction to about 95% reduction, about 20% reduction to about 90% reduction, about 20% reduction to about 85% reduction, about 20% reduction to about 80% reduction, about 20% reduction to about 75% reduction, about 20% reduction to about 70% reduction, about 20% reduction to about 65% reduction, about 20% reduction to about 60% reduction, about 20% reduction to about 55% reduction, about 20% reduction to about 50% reduction, about 20% reduction to about 45% reduction, about 20% reduction to about 40% reduction, about 20% reduction to about 35% reduction, about 20% reduction to about 30% reduction, about 20% reduction to about 25% reduction, about 25% reduction to about 99% reduction, about 25% reduction to about 95% reduction, about 25% reduction to about 90% reduction, about 25% reduction to about 85% reduction, about 25% reduction to about 80% reduction, about 25% reduction to about 75% reduction, about 25% reduction to about 70% reduction, about 25% reduction to about 65% reduction, about 25% reduction to about 60% reduction, about 25% reduction to about 55% reduction, about 25% reduction to about 50% reduction, about 25% reduction to about 45% reduction, about 25% reduction to about 40% reduction, about 25% reduction to about 35% reduction, about 25% reduction to about 30% reduction, about 30% reduction to about 99% reduction, about 30% reduction to about 95% reduction, about 30% reduction to about 90% reduction, about 30% reduction to about 85% reduction, about 30% reduction to about 80% reduction, about 30% reduction to about 75% reduction, about 30% reduction to about 70% reduction, about 30% reduction to about 65% reduction, about 30% reduction to about 60% reduction, about 30% reduction to about 55% reduction, about 30% reduction to about 50% reduction, about 30% reduction to about 45% reduction, about 30% reduction to about 40% reduction, about 30% reduction to about 35% reduction, about 35% reduction to about 99% reduction, about 35% reduction to about 95% reduction, about 35% reduction to about 90% reduction, about 35% reduction to about 85% reduction, about 35% reduction to about 80% reduction, about 35% reduction to about 75% reduction, about 35% reduction to about 70% reduction, about 35% reduction to about 65% reduction, about 35% reduction to about 60% reduction, about 35% reduction to about 55% reduction, about 35% reduction to about 50% reduction, about 35% reduction to about 45% reduction, about 35% reduction to about 40% reduction, about 40% reduction to about 99% reduction, about 40% reduction to about 95% reduction, about 40% reduction to about 90% reduction, about 40% reduction to about 85% reduction, about 40% reduction to about 80% reduction, about 40% reduction to about 75% reduction, about 40% reduction to about 70% reduction, about 40% reduction to about 65% reduction, about 40% reduction to about 60% reduction, about 40% reduction to about 55% reduction, about 40% reduction to about 50% reduction, about 40% reduction to about 45% reduction, about 45% reduction to about 99% reduction, about 45% reduction to about 95% reduction, about 45% reduction to about 90% reduction, about 45% reduction to about 85% reduction, about 45% reduction to about 80% reduction, about 45% reduction to about 75% reduction, about 45% reduction to about 70% reduction, about 45% reduction to about 65% reduction, about 45% reduction to about 60% reduction, about 45% reduction to about 55% reduction, about 45% reduction to about 50% reduction, about 50% reduction to about 99% reduction, about 50% reduction to about 95% reduction, about 50% reduction to about 90% reduction, about 50% reduction to about 85% reduction, about 50% reduction to about 80% reduction, about 50% reduction to about 75% reduction, about 50% reduction to about 70% reduction, about 50% reduction to about 65% reduction, about 50% reduction to about 60% reduction, about 50% reduction to about 55% reduction, about 55% reduction to about 99% reduction, about 55% reduction to about 95% reduction, about 55% reduction to about 90% reduction, about 55% reduction to about 85% reduction, about 55% reduction to about 80% reduction, about 55% reduction to about 75% reduction, about 55% reduction to about 70% reduction, about 55% reduction to about 65% reduction, about 55% reduction to about 60% reduction, about 60% reduction to about 99% reduction, about 60% reduction to about 95% reduction, about 60% reduction to about 90% reduction, about 60% reduction to about 85% reduction, about 60% reduction to about 80% reduction, about 60% reduction to about 75% reduction, about 60% reduction to about 70% reduction, about 60% reduction to about 65% reduction, about 65% reduction to about 99% reduction, about 65% reduction to about 95% reduction, about 65% reduction to about 90% reduction, about 65% reduction to about 85% reduction, about 65% reduction to about 80% reduction, about 65% reduction to about 75% reduction, about 65% reduction to about 70% reduction, about 70% reduction to about 99% reduction, about 70% reduction to about 95% reduction, about 70% reduction to about 90% reduction, about 70% reduction to about 85% reduction, about 70% reduction to about 80% reduction, about 70% reduction to about 75% reduction, about 75% reduction to about 99% reduction, about 75% reduction to about 95% reduction, about 75% reduction to about 90% reduction, about 75% reduction to about 85% reduction, about 75% reduction to about 80% reduction, about 80% reduction to about 99% reduction, about 80% reduction to about 95% reduction, about 80% reduction to about 90% reduction, about 80% reduction to about 85% reduction, about 85% reduction to about 99% reduction, about 85% reduction to about 95% reduction, about 85% reduction to about 90% reduction, about 90% reduction to about 99% reduction, about 90% reduction to about 95% reduction, or about 95% reduction to about 99% reduction) in the volume of one or more solid tumors in the subject (e.g., as compared to the volume of the one or more solid tumors prior to treatment or at the start of treatment). In some embodiments, the these methods can reduce (e.g., about 1% reduction to about 99% reduction, or any of the subranges of this range described herein) the risk of developing a metastasis or developing one or more additional metastasis in a subject (e.g., as compared to the risk of developing a metastasis or developing one or more additional metastasis in a subject prior to treatment or in a similar subject or a population of subjects administered a different treatment).

In some examples of these methods, the subject has been identified or diagnosed as having an aging-related disease or condition. Non-limiting examples of aging-related diseases and conditions include Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some examples, these methods can result in a reduction in the number, severity, or frequency of one or more symptoms of the aging-related disease or condition in the subject (e.g., as compared to the number, severity, or frequency of the one or more symptoms of the aging-related disease or condition in the subject prior to treatment). In some examples, the methods can result in a decrease (e.g., about 1% decrease to about 99% decrease, an about 1% decrease to about 95% decrease, about 1% decrease to about 90% decrease, about 1% decrease to about 85% decrease, about 1% decrease to about 80% decrease, about 1% decrease to about 75% decrease, about 1% to about 70% decrease, about 1% decrease to about 65% decrease, about 1% decrease to about 60% decrease, about 1% decrease to about 55% decrease, about 1% decrease to about 50% decrease, about 1% decrease to about 45% decrease, about 1% decrease to about 40% decrease, about 1% decrease to about 35% decrease, about 1% decrease to about 30% decrease, about 1% decrease to about 25% decrease, about 1% decrease to about 20% decrease, about 1% decrease to about 15% decrease, about 1% decrease to about 10% decrease, about 1% decrease to about 5% decrease, about 5% decrease to about 99% decrease, an about 5% decrease to about 95% decrease, about 5% decrease to about 90% decrease, about 5% decrease to about 85% decrease, about 5% decrease to about 80% decrease, about 5% decrease to about 75% decrease, about 5% to about 70% decrease, about 5% decrease to about 65% decrease, about 5% decrease to about 60% decrease, about 5% decrease to about 55% decrease, about 5% decrease to about 50% decrease, about 5% decrease to about 45% decrease, about 5% decrease to about 40% decrease, about 5% decrease to about 35% decrease, about 5% decrease to about 30% decrease, about 5% decrease to about 25% decrease, about 5% decrease to about 20% decrease, about 5% decrease to about 15% decrease, about 5% decrease to about 10% decrease, about 10% decrease to about 99% decrease, an about 10% decrease to about 95% decrease, about 10% decrease to about 90% decrease, about 10% decrease to about 85% decrease, about 10% decrease to about 80% decrease, about 10% decrease to about 75% decrease, about 10% to about 70% decrease, about 10% decrease to about 65% decrease, about 10% decrease to about 60% decrease, about 10% decrease to about 55% decrease, about 10% decrease to about 50% decrease, about 10% decrease to about 45% decrease, about 10% decrease to about 40% decrease, about 10% decrease to about 35% decrease, about 10% decrease to about 30% decrease, about 10% decrease to about 25% decrease, about 10% decrease to about 20% decrease, about 10% decrease to about 15% decrease, about 15% decrease to about 99% decrease, an about 15% decrease to about 95% decrease, about 15% decrease to about 90% decrease, about 15% decrease to about 85% decrease, about 15% decrease to about 80% decrease, about 15% decrease to about 75% decrease, about 15% to about 70% decrease, about 15% decrease to about 65% decrease, about 15% decrease to about 60% decrease, about 15% decrease to about 55% decrease, about 15% decrease to about 50% decrease, about 15% decrease to about 45% decrease, about 15% decrease to about 40% decrease, about 15% decrease to about 35% decrease, about 15% decrease to about 30% decrease, about 15% decrease to about 25% decrease, about 15% decrease to about 20% decrease, about 20% decrease to about 99% decrease, an about 20% decrease to about 95% decrease, about 20% decrease to about 90% decrease, about 20% decrease to about 85% decrease, about 20% decrease to about 80% decrease, about 20% decrease to about 75% decrease, about 20% to about 70% decrease, about 20% decrease to about 65% decrease, about 20% decrease to about 60% decrease, about 20% decrease to about 55% decrease, about 20% decrease to about 50% decrease, about 20% decrease to about 45% decrease, about 20% decrease to about 40% decrease, about 20% decrease to about 35% decrease, about 20% decrease to about 30% decrease, about 20% decrease to about 25% decrease, about 25% decrease to about 99% decrease, an about 25% decrease to about 95% decrease, about 25% decrease to about 90% decrease, about 25% decrease to about 85% decrease, about 25% decrease to about 80% decrease, about 25% decrease to about 75% decrease, about 25% to about 70% decrease, about 25% decrease to about 65% decrease, about 25% decrease to about 60% decrease, about 25% decrease to about 55% decrease, about 25% decrease to about 50% decrease, about 25% decrease to about 45% decrease, about 25% decrease to about 40% decrease, about 25% decrease to about 35% decrease, about 25% decrease to about 30% decrease, about 30% decrease to about 99% decrease, an about 30% decrease to about 95% decrease, about 30% decrease to about 90% decrease, about 30% decrease to about 85% decrease, about 30% decrease to about 80% decrease, about 30% decrease to about 75% decrease, about 30% to about 70% decrease, about 30% decrease to about 65% decrease, about 30% decrease to about 60% decrease, about 30% decrease to about 55% decrease, about 30% decrease to about 50% decrease, about 30% decrease to about 45% decrease, about 30% decrease to about 40% decrease, about 30% decrease to about 35% decrease, about 35% decrease to about 99% decrease, an about 35% decrease to about 95% decrease, about 35% decrease to about 90% decrease, about 35% decrease to about 85% decrease, about 35% decrease to about 80% decrease, about 35% decrease to about 75% decrease, about 35% to about 70% decrease, about 35% decrease to about 65% decrease, about 35% decrease to about 60% decrease, about 35% decrease to about 55% decrease, about 35% decrease to about 50% decrease, about 35% decrease to about 45% decrease, about 35% decrease to about 40% decrease, about 40% decrease to about 99% decrease, an about 40% decrease to about 95% decrease, about 40% decrease to about 90% decrease, about 40% decrease to about 85% decrease, about 40% decrease to about 80% decrease, about 40% decrease to about 75% decrease, about 40% to about 70% decrease, about 40% decrease to about 65% decrease, about 40% decrease to about 60% decrease, about 40% decrease to about 55% decrease, about 40% decrease to about 50% decrease, about 40% decrease to about 45% decrease, about 45% decrease to about 99% decrease, an about 45% decrease to about 95% decrease, about 45% decrease to about 90% decrease, about 45% decrease to about 85% decrease, about 45% decrease to about 80% decrease, about 45% decrease to about 75% decrease, about 45% to about 70% decrease, about 45% decrease to about 65% decrease, about 45% decrease to about 60% decrease, about 45% decrease to about 55% decrease, about 45% decrease to about 50% decrease, about 50% decrease to about 99% decrease, an about 50% decrease to about 95% decrease, about 50% decrease to about 90% decrease, about 50% decrease to about 85% decrease, about 50% decrease to about 80% decrease, about 50% decrease to about 75% decrease, about 50% to about 70% decrease, about 50% decrease to about 65% decrease, about 50% decrease to about 60% decrease, about 50% decrease to about 55% decrease, about 55% decrease to about 99% decrease, an about 55% decrease to about 95% decrease, about 55% decrease to about 90% decrease, about 55% decrease to about 85% decrease, about 55% decrease to about 80% decrease, about 55% decrease to about 75% decrease, about 55% to about 70% decrease, about 55% decrease to about 65% decrease, about 55% decrease to about 60% decrease, about 60% decrease to about 99% decrease, an about 60% decrease to about 95% decrease, about 60% decrease to about 90% decrease, about 60% decrease to about 85% decrease, about 60% decrease to about 80% decrease, about 60% decrease to about 75% decrease, about 60% to about 70% decrease, about 60% decrease to about 65% decrease, about 65% decrease to about 99% decrease, an about 65% decrease to about 95% decrease, about 65% decrease to about 90% decrease, about 65% decrease to about 85% decrease, about 65% decrease to about 80% decrease, about 65% decrease to about 75% decrease, about 65% to about 70% decrease, about 70% decrease to about 99% decrease, an about 70% decrease to about 95% decrease, about 70% decrease to about 90% decrease, about 70% decrease to about 85% decrease, about 70% decrease to about 80% decrease, about 70% decrease to about 75% decrease, about 75% decrease to about 99% decrease, an about 75% decrease to about 95% decrease, about 75% decrease to about 90% decrease, about 75% decrease to about 85% decrease, about 75% decrease to about 80% decrease, about 80% decrease to about 99% decrease, an about 80% decrease to about 95% decrease, about 80% decrease to about 90% decrease, about 80% decrease to about 85% decrease, about 85% decrease to about 99% decrease, an about 85% decrease to about 95% decrease, about 85% decrease to about 90% decrease, about 90% decrease to about 99% decrease, an about 90% decrease to about 95% decrease, or about 95% decrease to about 99% decrease) in the number of senescent cells in the subject (e.g., a decrease in the number of senescent cells in one or more specific tissues involved and/or implicated in the aging-related disease or disorder in the subject), e.g., as compared to the number of senescent cells in the subject prior to treatment.

In some examples of these methods, the subject has been diagnosed or identified as having an infectious disease. Non-limiting examples of infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus. In some embodiments, these methods can result in a decrease in the infectious titer (e.g., viral titer) in a subject (e.g., as compared to the infectious titer in the subject prior to treatment). In some embodiments, these methods can result in a reduction in the number, severity, or frequency of one or more symptoms of the infectious disease (e.g., viral infection) in the subject (e.g., as compared to the number, severity, or frequency of the one or more symptoms of the infectious disease in the subject prior to treatment).

The term "subject" refers to any mammal. In some embodiments, the subject or "subject in need of treatment" may be a canine (e.g., a dog), feline (e.g., a cat), equine (e.g., a horse), ovine, bovine, porcine, caprine, primate, e.g., a simian (e.g., a monkey (e.g., marmoset, baboon), or an ape (e.g., a gorilla, chimpanzee, orangutan, or gibbon) or a human; or rodent (e.g., a mouse, a guinea pig, a hamster, or a rat). In some embodiments, the subject or "subject in need of treatment" may be a non-human mammal, especially mammals that are conventionally used as models for demonstrating therapeutic efficacy in humans (e.g., murine, lapine, porcine, canine or primate animals) may be employed.

Methods of Killing a Cancer Cell, an Infected Cell, or a Senescent Cell

Also provided herein are methods of killing a cancer cell (e.g., any of the exemplary types of cancer described herein or known in the art), an infected cell (e.g., a cell infected with any of the exemplary viruses described herein or known in the art), or a senescent cell (e.g., a senescent cancer cell, a senescent fibroblast, or a senescent endothelial cell) in a subject in need thereof (e.g., any of the exemplary subjects described herein or known in the art) that include administering to the subject a therapeutically effective amount of any of the multi-chain chimeric polypeptides described herein or any of the compositions (e.g., pharmaceutical compositions) described herein.

In some embodiments of these methods, the subject has been identified or diagnosed as having a cancer. Non-limiting examples of cancer include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CMIL), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been identified or diagnosed as having an aging-related disease or condition. Non-limiting examples of aging-related diseases and conditions include Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been diagnosed or identified as having an infectious disease. Non-limiting examples of an infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Senescent Cells

Senescence is a form of irreversible growth arrest accompanied by phenotypic changes, resistance to apoptosis and activation of damage-sensing signaling pathways. Cellular senescence was first described in cultured human fibroblast cells that lost their ability to proliferate, reaching permanent arrest after about 50 population doublings (referred to as the Hayflick limit). Senescence is considered a stress response that can be induced by a wide range of intrinsic and extrinsic insults, including oxidative and genotoxic stress, DNA damage, telomere attrition, oncogenic activation, mitochondrial dysfunction, or chemotherapeutic agents.

Senescent cells remain metabolically active and can influence the tissue hemostasis, disease and aging through their secretory phenotype. Senescence is considered as a physiologic process and is important in promoting wound healing, tissue homeostasis, regeneration, and fibrosis regulation. For instance, transient induction of senescent cells is observed during would healing and contributes to wound resolution. Perhaps one of the most important roles of senescence is its role in tumor suppression. However, the accumulation of senescent cells also drives aging- and aging-related diseases and conditions. The senescent phenotype also can trigger chronic inflammatory responses and consequently augment chronic inflammatory conditions to promote tumor growth. The connection between senescence and aging was initially based on observations that senescent cells accumulate in aged tissue. The use of transgenic models has enabled the detection of senescent cells systematically in many age-related pathologies. Strategies to selectively eliminate senescent cells has demonstrated that senescent cells can indeed play a causal role in aging and related pathologies.

Senescent cells display important and unique properties which include changes in morphology, chromatin organization, gene expression, and metabolism. There are several biochemical and functional properties associated with cellular senescence, such as (i) increased expression of p16 and p21, inhibitors of cyclin-dependent kinases, (ii) presence of senescence-associated β-galactosidase, a marker of lysosomal activity, (iii) appearance of senescence-associated heterochromatin foci and downregulation of lamin B1 levels, (iv) resistance to apoptosis caused by an increased expression of anti-apoptotic BCL-family protein, and (v) upregulation of CD26 (DPP4), CD36 (Scavenger receptor), forkhead box 4 (FOXO4), and secretory carrier membrane protein 4 (SCAMP4). Senescent cells also express an inflammatory signature, the so-called senescence-associated secretory phenotype (SASP). Through SASP, the senescent cells produce a wide range of inflammatory cytokines (IL-6, IL-8), growth factors (TGF-0), chemokines (CCL-2), and matrix metalloproteinases (MMP-3, MMP-9) that operate in a cell-autonomous manner to reinforce senescence (autocrine effects) and communicate with and modify the microenvironment (paracrine effects). SASP factors can contribute to tumor suppression by triggering senescence surveillance, an immune-mediated clearance of senescent cells. However, chronic inflammation is also a known driver of tumorigenesis, and accumulating evidence indicates that chronic SASP can also boost cancer and aging-related diseases.

The secretion profile of senescent cells is context dependent. For instance, the mitochondrial dysfunction-associated senescence (MiDAS), induced by different mitochondrial dysfunction in human fibroblasts, led to the appearance of a SASP that was deficient in IL-1-dependent inflammatory factors. A decrease in the NAD+/NADH ratio activated AMPK signaling which induced MiDAS through the activation of p53. As a result, p53 inhibited NF-xB signaling which is a crucial inducer of pro-inflammatory SASP. In contrast, the cellular senescence caused by persistent DNA damage in human cells induced an inflammatory SASP, which was dependent on the activation of ataxia-telangiectasia mutated (ATM) kinase but not on that of p53. In particular, the expression and secretion levels of IL-6 and IL-8 were increased. It was also demonstrated that cellular senescence caused by the ectopic expression p16INK4a and p21CIP1 induced the senescent phenotype in human fibroblasts without an inflammatory SASP indicating that the growth arrest itself did not stimulate SASP.

One of the most defining characteristics of senescence is stable growth arrest. This is achieved by two important pathways, the p16/Rb and the p53/p21, both of which are central in tumor suppression. DNA damage results in: (1) high deposition of γH2Ax (histone coding gene) and 53BP1 (involved in DNA damage response) in chromatin: this leads to activation of a kinase cascade eventually resulting in p53 activation, and (2) activation of p16INK4a and ARF (both encoded by CDKN2A) and P15INK4b (encoded by CDKN2B): p53 induces transcription of cyclin-dependent kinase inhibitor (p21) and along with both p16INK4a and p15INK4b block genes for cell cycle progression (CDK4 and CDK6). This eventually leads to hypophosphorylation of Retinoblastoma protein (Rb) and cell cycle arrest at the G1 phase.

Selectively killing senescent cells has been shown to significantly improve the health span of mice in the context of normal aging and ameliorates the consequences of age-related disease or cancer therapy (Ovadya, *J Clin Invest.* 128(4):1247-1254, 2018). In nature, the senescent cells are normally removed by the innate immune cells. Induction of senescence not only prevents the potential proliferation and transformation of damaged/altered cells, but also favors tissue repair through the production of SASP factors that function as chemoattractants mainly for Natural Killer (NK) cells (such as IL-15 and CCL2) and macrophages (such as CFS-1 and CCL2). These innate immune cells mediate the immunosurveillance mechanism for eliminating stressed cells. Senescent cells usually up-regulate the NK-cell activating receptor NKG2D and DNAM-1 ligands, which belong to a family of stress-inducible ligands: an important component of the frontline immune defense against infectious diseases and malignancies. Upon receptor activation, NK cells can then specifically induce the death of senescent cells through their cytolytic machinery. A role for NK cells in the immune surveillance of senescent cells has been pointed out in liver fibrosis (Sagiv, *Oncogene* 32(15): 1971-1977, 2013), hepatocellular carcinoma (Iannello, *J Exp Med* 210(10): 2057-2069, 2013), multiple myeloma (Soriani, *Blood* 113(15): 3503-3511, 2009), and glioma cells stressed by dysfunction of the mevalonate pathway (Ciaglia, *Int J Cancer* 142(1): 176-190, 2018). Endometrial cells undergo acute cellular senescence and do not differentiate into decidual cells. The differentiated decidual cells secrete IL-15 and thereby recruit uterine NK cells to target and eliminate the undifferentiated senescent cells thus helping to re-model and rejuvenate the endometrium (Brighton, *Elife* 6: e31274, 2017). With a similar mechanism, during liver fibrosis, p53-expressing senescent liver satellite cells skewed the polarization of resident Kupfer macrophages and freshly infiltrated macrophages toward the pro-inflammatory M1 phenotype, which display senolytic activity. F4/80+ macrophages have been shown to play a key role in the clearance of mouse uterine senescent cells to maintain postpartum uterine function.

Senescent cells recruit NK cells by mainly upregulating ligands to NKG2D (expressed on NK cells), chemokines, and other SASP factors. In vivo models of liver fibrosis have shown effective clearance of senescent cells by activated NK cells (Krizhanovsky, *Cell* 134(4): 657-667, 2008). Studies have described various models to study senescence including liver fibrosis (Krizhanovsky, Cell 134(4): 657-667, 2008), osteoarthritis (Xu, *J Gerontol A Biol Sci Med Sci* 72(6): 780-785, 2017), and Parkinson's disease (Chinta, *Cell Rep* 22(4): 930-940, 2018). Animal models for studying senescent cells are described in: Krizhanovsky, Cell 134(4): 657-667, 2008; Baker, *Nature* 479(7372): 232-236, 2011; Farr, *Nat Med* 23(9): 1072-1079, 2017; Bourgeois, *FEBS Lett* 592(12): 2083-2097, 2018; Xu, *Nat Med* 24(8): 1246-1256, 2018).

Additional Therapeutic Agents

Some embodiments of any of the methods described herein can further include administering to a subject (e.g., any of the subjects described herein) a therapeutically effective amount of one or more additional therapeutic agents. The one or more additional therapeutic agents can be administered to the subject at substantially the same time as the multi-chain chimeric polypeptide (e.g., any of the multi-chain chimeric polypeptides described herein) or immune cell (e.g., administered as a single formulation or two or more formulations to the subject). In some embodiments, one or more additional therapeutic agents can be administered to the subject prior to administration of the multi-chain chimeric polypeptide (e.g., any of the multi-chain chimeric polypeptides described herein) or immune cell. In some embodiments, one or more additional therapeutic agents can be administered to the subject after administration of the multi-chain chimeric polypeptide (e.g., any of the multi-chain chimeric polypeptides described herein) or immune cell to the subject.

Non-limiting examples of additional therapeutic agents include: anti-cancer drugs, activating receptor agonists, immune checkpoint inhibitors, agents for blocking HLA-specific inhibitory receptors, Glucogen Synthase Kinase (GSK) 3 inhibitors, and antibodies.

Non-limiting examples of anticancer drugs include antimetabolic drugs (e.g., 5-fluorouracil (5-FU), 6-mercaptopurine (6-MP), capecitabine, cytarabine, floxuridine, fludarabine, gemcitabine, hydroxycarbamide, methotrexate, 6-thioguanine, cladribine, nelarabine, pentostatin, or pemetrexed), plant alkaloids (e.g., vinblastine, vincristine, vindesine, camptothecin, 9-methoxycamptothecin, coronaridine, taxol, naucleaorals, diprenylated indole alkaloid, montamine, schischkiniin, protoberberine, berberine, sanguinarine, chelerythrine, chelidonine, liriodenine, clivorine, β-carboline, antofine, tylophorine, cryptolepine, neocryptolepine, corynoline, sampangine, carbazole, crinamine, montanine, ellipticine, paclitaxel, docetaxel, etoposide, tenisopide, irinotecan, topotecan, or acridone alkaloids), proteasome inhibitors (e.g., lactacystin, disulfiram, epigallocatechin-3-gallate, marizomib (salinosporamide A), oprozomib (ONX-0912), delanzomib (CEP-18770), epoxomicin, MG132, beta-hydroxy beta-methylbutyrate, bortezomib, carfilzomib, or ixazomib), antitumor antibiotics (e.g., doxorubicin, daunorubicin, epirubicin, mitoxantrone, idarubicin, actinomycin, plicamycin, mitomycin, or bleomycin), histone deacetylase inhibitors (e.g., vorinostat, panobinostat, belinostat, givinostat, abexinostat, depsipeptide, entinostat, phenyl butyrate, valproic acid, trichostatin A, dacinostat, mocetinostat, pracinostat, nicotinamide, cambinol, tenovin 1, tenovin 6, sirtinol, ricolinostat, tefinostat, kevetrin, quisinostat, resminostat, tacedinaline, chidamide, or selisistat), tyrosine kinase inhibitors (e.g., axitinib, dasatinib, encorafinib, erlotinib, imatinib, nilotinib, pazopanib, and sunitinib), and chemotherapeutic agents (e.g., all-trans retinoic acid, azacitidine, azathioprine, doxifluridine, epothilone, hydroxyurea, imatinib, teniposide, tioguanine, valrubicin, vemurafenib, and lenalidomide). Additional examples of chemotherapeutic agents include alkylating agents, e.g., mechlorethamine, cyclophosphamide, chlorambucil, melphalan, ifosfamide, thiotepa, hexamethylmelamine, busulfan, altretamine, procarbazine, dacarbazine, temozolomide, carmustine, lumustine, streptozocin, carboplatin, cisplatin, and oxaliplatin.

Non-limiting examples of activating receptor agonists include any agonists for activating receptors which activate and enhance the cytotoxicity of NK cells, including anti-CD16 antibodies (e.g., anti-CD16/CD30 bispecific monoclonal antibody (BiMAb)) and Fc-based fusion proteins. Non-limiting examples of checkpoint inhibitors include anti-PD-1 antibodies (e.g., MEDIO680), anti-PD-L1 antibodies (e.g., BCD-135, BGB-A333, CBT-502, CK-301, CS1001, FAZ053, KN035, MDX-1105, MSB2311, SHR-1316, anti-PD-L1/CTLA-4 bispecific antibody KN046, anti-PD-L1/TGFβRII fusion protein M7824, anti-PD-L1/TIM-3 bispecific antibody LY3415244, atezolizumab, or avelumab), anti-TIM3 antibodies (e.g., TSR-022, Sym023, or MBG453) and anti-CTLA-4 antibodies (e.g., AGEN1884, MK-1308, or an anti-CTLA-4/OX40 bispecific antibody ATOR-1015). Non-limiting examples of agents for blocking HLA-specific inhibitory receptors include monalizumab (e.g., an anti-HLA-E NKG2A inhibitory receptor monoclonal antibody). Non-limiting examples of GSK3 inhibitor include tideglusib or CHIR99021. Non-limiting examples of antibodies that can be used as additional therapeutic agents include anti-CD26 antibodies (e.g., YS110), anti-CD36 antibodies, and any other antibody or antibody construct that can bind to and activate an Fc receptor (e.g., CD16) on a NK cell. In some embodiments, an additional therapeutic agent can be insulin or metformin.

EXAMPLES

The invention is further described in the following examples, which do not limit the scope of the invention described in the claims.

Example 1. Construction of Exemplary Multi-Chain Chimeric Polypeptides and Evaluation of Properties Thereof Two multi-chain chimeric polypeptides were generated and their properties were evaluated. Each of the two multi-chain chimeric polypeptides includes a first chimeric polypeptide that includes a soluble tissue factor domain covalently linked a first target-binding domain and a first domain of an affinity pair of domains. The second chimeric polypeptide in each of the two multi-chain chimeric polypeptides includes a second domain of the affinity pair of domains, and a second target-binding domain.

Description of Logic Underlying Construction of Multi-Chain Chimeric Polypeptides Tissue Factor (TF) is a stable, transmembrane protein containing 236 amino acid residues. The truncated, recombinant 219-amino-acid extracellular domain of tissue factor is soluble and is known to be expressed at high levels in bacteria or mammalian cells. Without wishing to be bound to a particular theory, the applicants speculated that the 219-aa tissue factor could be used as a connector linker for creation of unique multi-chain chimeric polypeptides.

First chimeric polypeptides including soluble tissue factor domain were produced at high levels by CHO cells grown in fermentation broth. These first chimeric polypeptides were purified by an anti-tissue factor monoclonal antibody (mAb) coupled on a solid matrix. Notably, tissue factor contains binding sites for FVIIa and FX. The catalytic activity of the tissue factor-FVIIa complex for FX is approximately 1 million-fold lower when tissue factor is not anchored to a phospholipid bilayer. Thus, without wishing to be bound to a particular theory, applicants speculated that using the 219-aa extracellular domain of tissue factor without the transmembrane in construction of the first chimeric polypeptides may eliminate the pro-coagulation activity of tissue factor in the first chimeric polypeptides. In an effort to further reduce or eliminate the pro-coagulation activity of the 219-aa tissue factor, select mutations in tissue factor can be made, specifically at seven amino acid residues that are known to contribute to binding energy of the FVIIa binding site.

Characterization of Binding Interactions for Described Chimeric Polypeptides

To determine if the first and second chimeric polypeptides bind to each other to form multi-chain chimeric polypeptides, in vitro binding assays were performed. To determine if the first chimeric polypeptide comprising soluble tissue factor domain are recognized and bound by anti-TF mAb, in vitro binding assays were performed. Notably, the data indicated that the mutated tissue factor proteins are still recognized and selectively bound by the anti-TF mAb which is known to bind to the FX binding site on tissue factor. To determine if the first chimeric polypeptides comprising soluble tissue factor domain covalently linked to scFvs or cytokines (see FIG. 1 and FIG. 2) possess functional scFvs or cytokines, in vitro binding assays were performed. The data from the aforementioned assays were consistent with the purified first chimeric polypeptides having the expected biological activities (e.g. scFvs selectively bind expected target antigens or cytokines selectively bind expected receptors or binding proteins).

In addition, experiments performed using the two multi-chain chimeric polypeptides including a first and second chimeric polypeptide bound to each other demonstrate the expected target binding activity (e.g., the multi-chain chimeric polypeptide binds specifically to the target specifically recognized by the first target-binding domain and the target specifically recognized by the second target-binding domain).

Based on the aforementioned results, applicants concluded that the soluble tissue factor connecter linker provided or enabled appropriate display of the polypeptides encoding either scFvs, interleukins, cytokines, interleukin receptors, or cytokine receptors in three-dimensional space relative to soluble tissue factor domain and relative to one another such that each retained expected biological properties and activities.

When both the first and second chimeric polypeptides were co-expressed, the heterodimeric complexes were secreted into the fermentation broths at high levels. The complexes were captured and readily purified by anti-TF mAb conjugated to a solid matrix using affinity chromatography. The first and second target-binding domains of these multi-chain chimeric polypeptides retained their expected biological activities as assayed by in vitro binding assays. Thus, the assembly of the multi-chain chimeric polypeptides provides the appropriate spatial display and folding of the domains for biological activities. Importantly, the spatial arrangement of the multi-chain chimeric polypeptides does not interfere with the FX binding site on tissue factor which enables the use of anti-TF mAb for affinity purification.

Characterization of Stability for Described Chimeric Polypeptides

Both purified multi-chain chimeric polypeptides are stable. These multi-chain chimeric polypeptides are structurally intact and fully biologically active when they are incubated in human serum at 37° C. for 72 hours.

Characterization of Propensity of Described Chimeric Polypeptides to Aggregate

Both purified multi-chain chimeric polypeptides developed do not form aggregates when stored at 4° C. in PBS.

Characterization of Viscosity of Described Chimeric Polypeptides

There is no viscosity issue when the multi-chain chimeric polypeptides are formulated at a concentration as high as 50 mg/mL in PBS.

Additional Applications of the Multi-Chain Chimeric Polypeptide Platform

The data from these studies show that the platform technologies described herein can be utilized to create molecules that could be fused to target-binding domains derived from antibodies, in any of the formats as described herein including, without limitation, adhesion molecules, receptors, cytokines, ligands, and chemokines. With the appropriate target-binding domain, the resulting multi-chain chimeric polypeptides could promote conjugation of various immune effector cells and mediate destruction of target cells, including cancer cells, virally-infected cells, or senescent cells. Other domains in the multi-chain chimeric polypeptides stimulate, activate, and attract the immune system for enhancing cytotoxicity of effector cells for the targeted cells.

Example 2: Creation of an IL-12/IL-15RαSu DNA Construct

Figure 3:
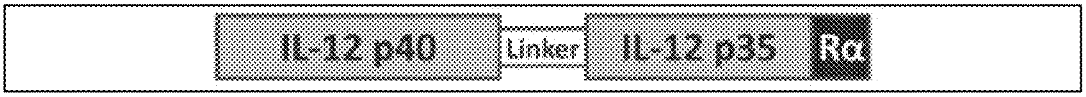
FIG. 3 shows a schematic diagram of an exemplary IL-12/IL-15RαSu DNA construct.

In a non-limiting example, an IL-12/IL-15RαSu DNA construct was created (FIG. 3). The human IL-12 subunit sequences, human IL-15RαSu sequence, human IL-15 sequence, human tissue factor 219 sequence, and human IL-18 sequence were obtained from the UniProt website and DNA for these sequences was synthesized by Genewiz. A DNA construct was made linking the IL-12 subunit beta (p40) to IL-12 subunit alpha (p35) with a GS (3) linker to generate a single chain version of IL-12 and then directly linking the IL-12 sequence to the IL-15RαSu sequence. The final IL-12/IL-15RαSu DNA construct sequence was synthesized by Genewiz.

The nucleic acid sequence of the IL12/IL-15RαSu construct (including signal peptide sequence) is as follows (SEQ ID NO: 77):

```
(Signal peptide)
ATGAAATGGGTGACCTTTATTTCTTTACTGTTCCTCTTTAGCAGCGCCT

ACTCC

(Human IL-12 subunit beta (p40))
ATTTGGGAACTGAAGAAGGACGTCTACGTGGTCGAACTGGACTGGTAT

CCCGATGCTCCCGGCGAAATGGTGGTGCTCACTTGTGACACCCCCGAAG

AAGACGGCATCACTTGGACCCTCGATCAGAGCAGCGAGGTGCTGGGCTC

CGGAAAGACCCTCACAATCCAAGTTAAGGAGTTCGGAGACGCTGGCCAA

TACACATGCCACAAGGGAGGCGAGGTGCTCAGCCATTCCTTATTATTAT

TACACAAGAAGGAAGACGGAATCTGGTCCACCGACATTTTAAAAGATCA

GAAGGAGCCCAAGAATAAGACCTTTTTAAGGTGTGAGGCCAAAAACTAC

AGCGGTCGTTTCACTTGTTGGTGGCTGACCACCATTTCCACCGATTTAA

CCTTCTCCGTGAAAAGCAGCCGGGGAAGCTCCGACCCTCAAGGTGTGAC

ATGTGGAGCCGCTACCCTCAGCGCTGAGAGGGTTCGTGGCGATAACAAG
```

-continued

```
GAATACGAGTACAGCGTGGAGTGCCAAGAAGATAGCGCTTGTCCCGCTG

CCGAAGAATCTTTACCCATTGAGGTGATGGTGGACGCCGTGCACAAACT

CAAGTACGAGAACTACACCTCCTCCTTCTTTATCCGGGACATCATTAAG

CCCGATCCTCCTAAGAATTTACAGCTGAAGCCTCTCAAAAATAGCCGGC

AAGTTGAGGTCTCTTGGGAATATCCCGACACTTGGAGCACACCCCACAG

CTACTTCTCTTTAACCTTTTGTGTGCAAGTTCAAGGTAAAAGCAAGCGG

GAGAAGAAAGACCGGGTGTTTACCGACAAAACCAGCGCCACCGTCATCT

GTCGGAAGAACGCCTCCATCAGCGTGAGGGCTCAAGATCGTTATTACTC

CAGCAGCTGGTCCGAGTGGGCCAGCGTGCCTTGTTCC

(Linker)
GGCGGTGGAGGATCCGGAGGAGGTGGCTCCGGCGGCGGAGGATCT

(Human IL-12 subunit alpha (p35))
CGTAACCTCCCCGTGGCTACCCCCGATCCCGGAATGTTCCCTTGTTTAC

ACCACAGCCAGAATTTACTGAGGGCCGTGAGCAACATGCTGCAGAAAGC

TAGGCAGACTTTAGAATTTTACCCTTGCACCAGCGAGGAGATCGACCAT

GAAGATATCACCAAGGACAAGACATCCACCGTGGAGGCTTGTTTACCTC

TGGAGCTGACAAAGAACGAGTCTTGTCTCAACTCTCGTGAAACCAGCTT

CATCACAAATGGCTCTTGTTTAGCTTCCCGGAAGACCTCCTTTATGATG

GCTTTATGCCTCAGCTCCATCTACGAGGATTTAAAGATGTACCAAGTGG

AGTTCAAGACCATGAACGCCAAGCTGCTCATGGACCCTAAACGGCAGAT

CTTTTTAGACCAGAACATGCTGGCTGTGATTGATGAGCTGATGCAAGCT

TTAAACTTCAACTCCGAGACCGTCCCTCAGAAGTCCTCCCTCGAGGAGC

CCGATTTTTACAAGACAAAGATCAAACTGTGCATTTTACTCCACGCCTT

TAGGATCCGGGCCGTGACCATTGACCGGGTCATGAGCTATTTAAACGCC

AGC

(Human IL-15Rα sushi domain)
ATTACATGCCCCCCTCCCATGAGCGTGGAGCACGCCGACATCTGGGTG

AAGAGCTATAGCCTCTACAGCCGGGAGAGGTATATCTGTAACAGCGGCTTC

AGAGGAAGGCCGGCACCAGCAGCCTCACCGAGTGCGTGCTGAATAAGGCTA

ACCAACGTGGCTCACTGGACAACACCCTCTTTAAAGTGCATCCGG
```

Example 3: Creation of an IL-18/TF/IL-15 DNA Construct

Figure 4:
FIG. 4 shows a schematic diagram of an exemplary IL-18/TF/IL-15 DNA construct.

In a non-limiting example, an IL-18/TF/IL-15 construct was made (FIG. 4) linking the IL-18 sequence to the N-terminus coding region of tissue factor 219, and further linking the IL-18/TF construct with the N-terminus coding region of IL-15. The nucleic acid sequence of the IL-18/TF/IL-15 construct (including leader sequence), synthesized by Genewiz, is as follows (SEQ ID NO: 73):

```
(Signal peptide)
ATGAAGTGGGTCACATTTATCTCTTTACTGTTCCTCTTCTCCAGCGCCT

ACAGC
```

-continued (Human IL-18)
TACTTCGGCAAACTGGAATCCAAGCTGAGCGTGATCCGGAATTTAAAC

GACCAAGTTCTGTTTATCGATCAAGGTAACCGGCCTCTGTTCGAGGACATG

ACCGACTCCGATTGCCGGGACAATGCCCCCCGGACCATCTTCATTATCTCC

ATGTACAAGGACAGCCAGCCCCGGGGCATGGCTGTGACAATTAGCGTGAAG

TGTGAGAAAATCAGCACTTTATCTTGTGAGAACAAGATCATCTCCTTTAAG

GAAATGAACCCCCCCGATAACATCAAGGACACCAAGTCCGATATCATCTTC

TTCCAGCGGTCCGTGCCCGGTCACGATAACAAGATGCAGTTCGAATCCTCC

TCCTACGAGGGCTACTTTTTAGCTTGTGAAAAGGAGAGGGATTTATTCAAG

CTGATCCTCAAGAAGGAGGACGAGCTGGGCGATCGTTCCATCATGTTCACC

GTCCAAAACGAGGAT (Human Tissue Factor 219)
AGCGGCACAACCAACACAGTCGCTGCCTATAACCTCACTTGGAAGAG

CACCAACTTCAAAACCATCCTCGAATGGGAACCCAAACCCGTTAACCAAGT

TTACACCGTGCAGATCAGCACCAAGTCCGGCGACTGGAAGTCCAAATGTTT

CTATACCACCGACACCGAGTGCGATCTCACCGATGAGATCGTGAAAGATGT

GAAACAGACCTACCTCGCCCGGGTGTTTAGCTACCCCGCCGGCAATGTGGA

GAGCACTGGTTCCGCTGGCGAGCCTTTATACGAGAACAGCCCCGAATTTAC

CCCTTACCTCGAGACCAATTTAGGACAGCCCACCATCCAAAGCTTTGAGCA

AGTTGGCACAAAGGTGAATGTGACAGTGGAGGACGAGCGGACTTTAGTGCG

GCGGAACAACACCTTTCTCAGCCTCCGGGATGTGTTCGGCAAAGATTTAAT

CTACACACTGTATTACTGGAAGTCCTCTTCCTCCGGCAAGAAGACAGCTAA

AACCAACACAAACGAGTTTTTAATCGACGTGGATAAAGGCGAAAACTACTG

TTTCAGCGTGCAAGCTGTGATCCCCTCCCGGACCGTGAATAGGAAAAGCAC

CGATAGCCCCGTTGAGTGCATGGGCCAAGAAAAGGGCGAGTTCCGGGAG (Human IL-15)
AACTGGGTGAACGTCATCAGCGATTTAAAGAAGATCGAAGATTTAATT

CAGTCCATGCATATCGACGCCACTTTATACACAGAATCCGACGTGCACCCC

TCTTGTAAGGTGACCGCCATGAAATGTTTTTTACTGGAGCTGCAAGTTATC

TCTTTAGAGAGCGGAGACGCTAGCATCCACGACACCGTGGAGAATTTAATC

ATTTTAGCCAATAACTCTTTATCCAGCAACGGCAACGTGACAGAGTCCGGC

TGCAAGGAGTGCGAAGAGCTGGAGGAGAAGAACATCAAGGAGTTTCTGCAA

TCCTTTGTGCACATTGTCCAGATGTTCATCAATACCTCC

Example 4: Secretion of IL-12/IL-15RαSu and IL-18/TF/IL-15 Fusion Proteins

Figure 5:
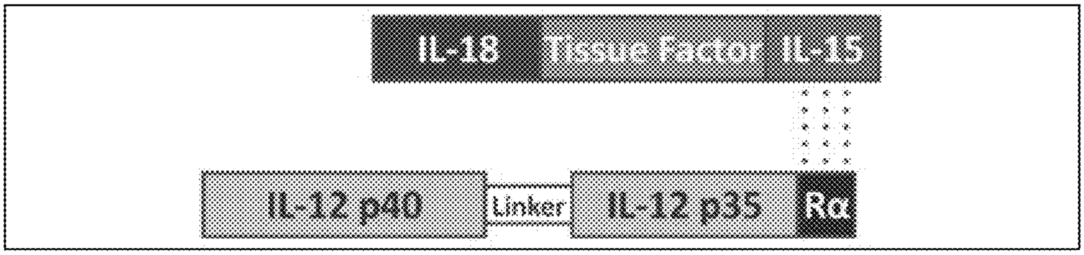
FIG. 5 shows a schematic diagram of the interaction between the exemplary IL-12/IL-15RαSu and IL-18/TF/IL-15 DNA constructs.
Figure 6:
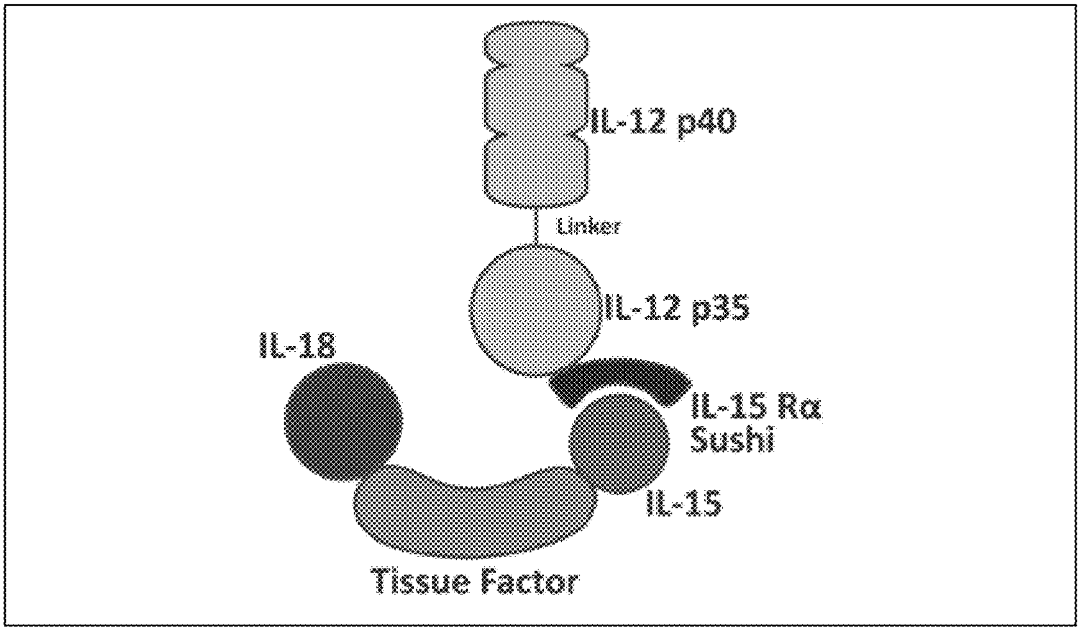
FIG. 6 shows a schematic diagram of the interaction between the exemplary IL-12/IL-15RαSu and IL-18/TF/IL-15 fusion proteins resulting in IL-18/TF/IL-15:IL-12/IL-15RαSu complex (18t15-12s).

The IL-12/IL-15RαSu and IL-18/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-18/TF/IL-15:IL-12/IL-15RαSu protein complex (referred to as 18t15-12s; FIG. 5 and FIG. 6). The 18t15-12s protein was purified from CHO-K1 cell culture supernatant using anti-TF antibody affinity chromatography and size exclusion chromatography resulting in soluble (non-aggregated) protein complexes consisting of IL-12/IL-15RαSu and IL-18/TF/IL-15 fusion proteins.

The amino acid sequence of the IL12/IL-15RαSu fusion protein (including signal peptide sequence) is as follows (SEQ ID NO: 76):

(Signal peptide)
MKWVTFISLLFLFSSAYS (Human IL-12 subunit beta (p40))
IWELKKDVYVVELDWYPDAPGEMVVLTCDTPEEDGITWTLDQSSEVLGS

GKTLTIQVKEFGDAGQYTCHKGGEVLSHSLLLLHKKEDGIWSTDILKDQ

KEPKNKTFLRCEAKNYSGRFTCWWLTTISTDLTFSVKSSRGSSDPQGVT

CGAATLSAERVRGDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSKREKKDRVFTDKTSATVICRKNASISVRAQDRYYS

SSWSEWASVPCS (Linker)
GGGGSGGGGSGGGGS (Human IL-12 subunit alpha (p35))
RNLPVATPDPGMFPCLHHSQNLLRAVSNMLQKARQTLEFYPCTSEEIDH

EDITKDKTSTVEACLPLELTKNESCLNSRETSFITNGSCLASRKTSFMM

ALCLSSIYEDLKMYQVEFKTMNAKLLMDPKRQIFLDQNMLAVIDELMQA

LNFNSETVPQKSSLEEPDFYKTKIKLCILLHAFRIRAVTIDRVMSYLNA

S (Human IL-15Rα sushi domain)
ITCPPPMSVEHADIWVKSYSLYSRERYICNSGFKRKAGTSSLTECVLNK

ATNVAHWTTPSLKCIR

The amino acid sequence of the IL-18/TF/IL-15 fusion protein (including signal peptide sequence) is as follows (SEQ ID NO: 72):

(Signal peptide)
MKWVTFISLLFLFSSAYS (Human IL-18)
YFGKLESKLSVIRNLNDQVLFIDQGNRPLFEDMTDSDCRDNAPRTIFIIS

MYKDSQPRGMAVTISVKCEKISTLSCENKIISFKEMNPPDNIKDTKSDII

FFQRSVPGHDNKMQFESSSYEGYFLACEKERDLFKLILKKEDELGDRSIM

FTVQNED (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSPE

FTPYLETNLGQPTIQSFEQVGTKVNVTVEDERTLVRRNNTFLSLRDVFGK

DLIYTLYYWKSSSSGKKTAKTNTNEFLIDVDKGENYCFSVQAVIPSRTVN

RKSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

In some cases, the leader (signal sequence) peptide is cleaved from the intact polypeptide to generate the mature form that may be soluble or secreted.

Example 5: Purification of 18t15-12s by Immunoaffinity Chromatography

An anti-TF antibody affinity column was connected to a GE Healthcare™ AKTA Avant protein purification system. The flow rate was 4 mL/min for all steps except the elution step, which was 2 mL/min.

Figure 7:
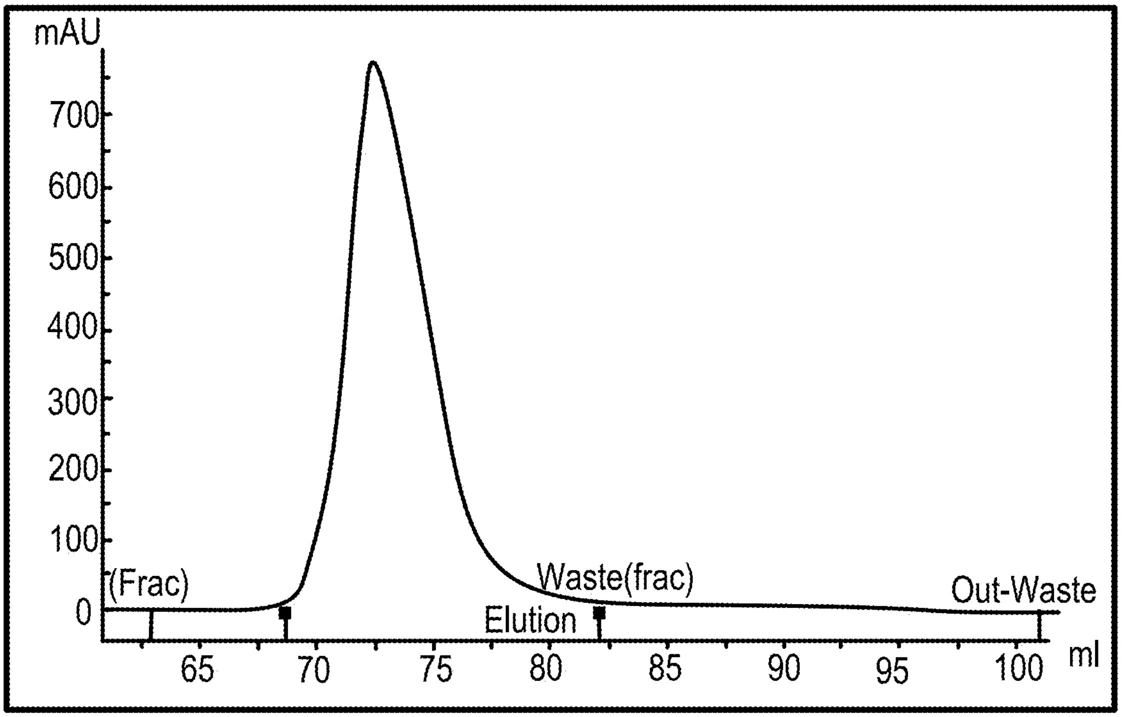
FIG. 7 shows a chromatograph of 18t15-12s purification elution from an anti-TF antibody affinity column.

Cell culture harvest of 18t15-12s was adjusted to pH 7.4 with 1M Tris base and loaded onto the anti-TF antibody affinity column equilibrated with 5 column volumes of PBS. After loading the sample, the column was washed with 5 column volumes PBS, followed by elution with 6 column volumes 0.1M acetic acid, pH 2.9. Absorbance at 280 nm was collected and then the sample was neutralized to pH 7.5-8.0 by adding 1M Tris base. The neutralized sample was then buffer exchanged into PBS using Amicon® centrifugal filters with a 30 KDa molecular weight cutoff. FIG. 7 shows that the 18t15-12s complex binds the anti-TF antibody affinity column, wherein TF is an 18t15-12s binding partner. The buffer-exchanged protein sample is stored at 2-8° C. for further biochemical analysis and biological activity testing.

After each elution, the anti-TF antibody affinity column was then stripped using 6 column volumes 0.1M glycine, pH 2.5. The column was then neutralized using 10 column volumes PBS, 0.05% sodium azide and stored at 2-8° C.

Example 6: Size Exclusion Chromatography of 18t15-12s

Figure 8:
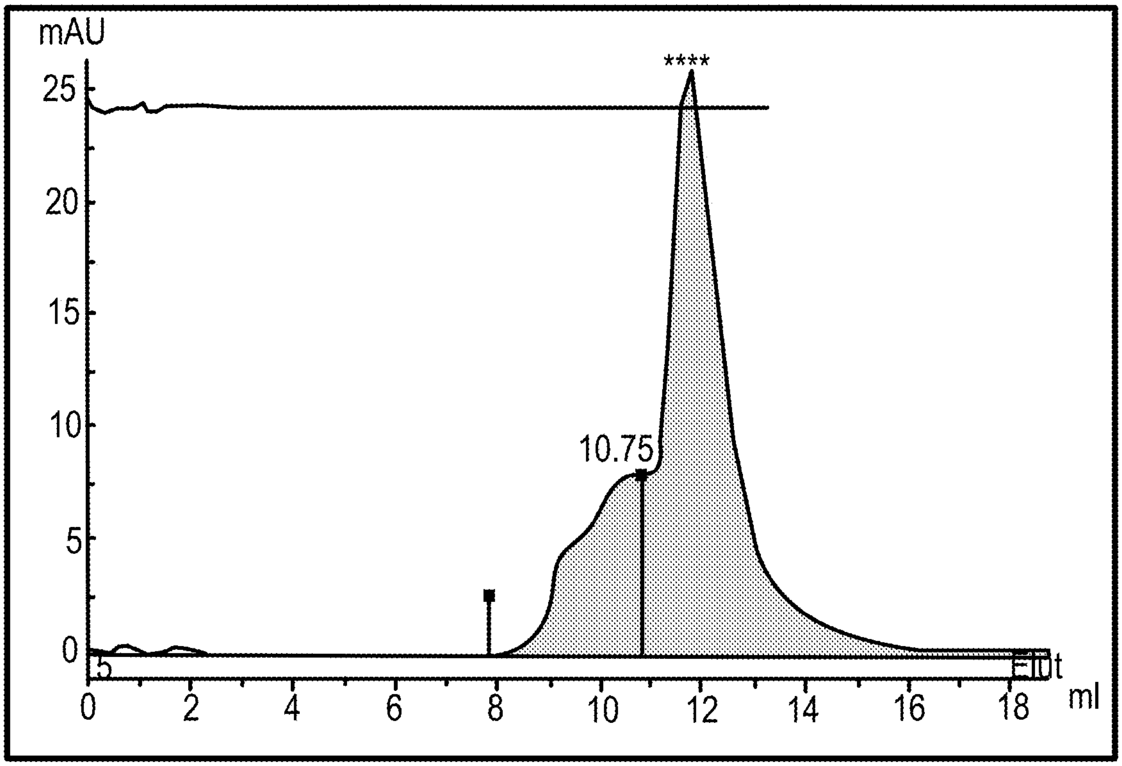
FIG. 8 shows an exemplary chromatographic profile of anti-TF Ab/SEC-purified 18t15-12s protein following elution on an analytical size exclusion column, demonstrating separation of monomeric multiprotein 18t15-12s complexes from protein aggregates.

A GE Healthcare Superdex® 200 Increase 10/300 GL gel filtration column was connected to a GE Healthcare AKTA™ Avant protein purification system. The column was equilibrated with 2 column volumes of PBS. The flow rate was 0.8 mL/min. A capillary loop was used to inject 200 μL of 1 mg/mL of 18t15-12s complex onto the column. The injection was chased with 1.25 column volumes of PBS. The SEC chromatograph is shown in FIG. 8. There is a main 18t15-12s protein peak with a minor high molecular weight peak, likely due to differing degrees of glycosylation of 18t15-12s dimers or aggregates.

Example 7: SDS-PAGE of 18t15-12s

Figure 9:
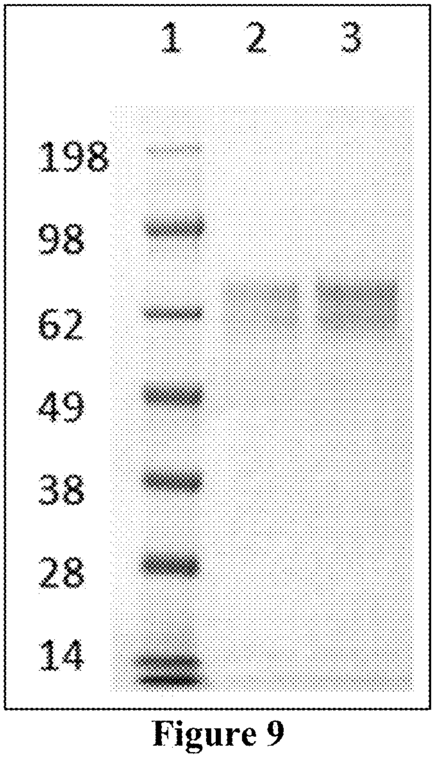
FIG. 9 shows an example of a 4-12% SDS-PAGE of the 18t15-12s complex following disulfide bond reduction. Lane 1: SeeBlue Plus2 marker; Lane 2: an anti-tissue factor antibody affinity column-purified 18t15-12s (0.5 μg); Lane 3: an anti-tissue factor antibody affinity column-purified 18t15-12s (1 μg).

To determine the purity and protein molecular weight, the purified 18t15-12s protein sample was analyzed using 4-12% NuPage Bis-Tris protein gel SDS-PAGE. The gel was stained with InstantBlue™ for about 30 min, followed by destaining overnight in purified water. FIG. 9 shows an example SDS gel of anti-TF antibody affinity purified 18t15-12s, with bands at the expected molecular weights (66 kDa and 56 kDa).

Example 8: Glycosylation of 18t15-12s in CHO-K1 Cells

Figure 10:
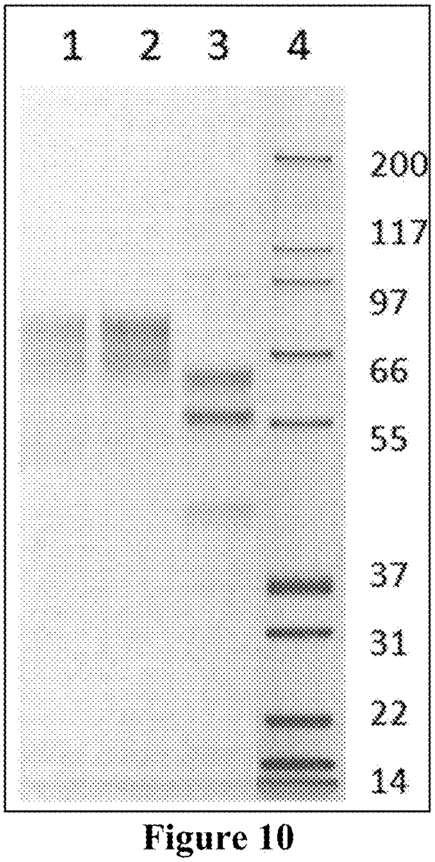
FIG. 10 shows SDS PAGE analysis of deglycosylated and non-deglycosylated 18t15-12s. Lane 1: an anti-tissue factor antibody affinity column-purified 18t15-12s (0.5 μg), non-deglycosylated; Lane 2: anti-TF Ab-purified 18t15-12s (1 μg), non-deglycosylated; Lane 3: 18t15-12s (1 μg), deglycosylated, Lane 4: Mark12 unstained maker.
Figure 11:
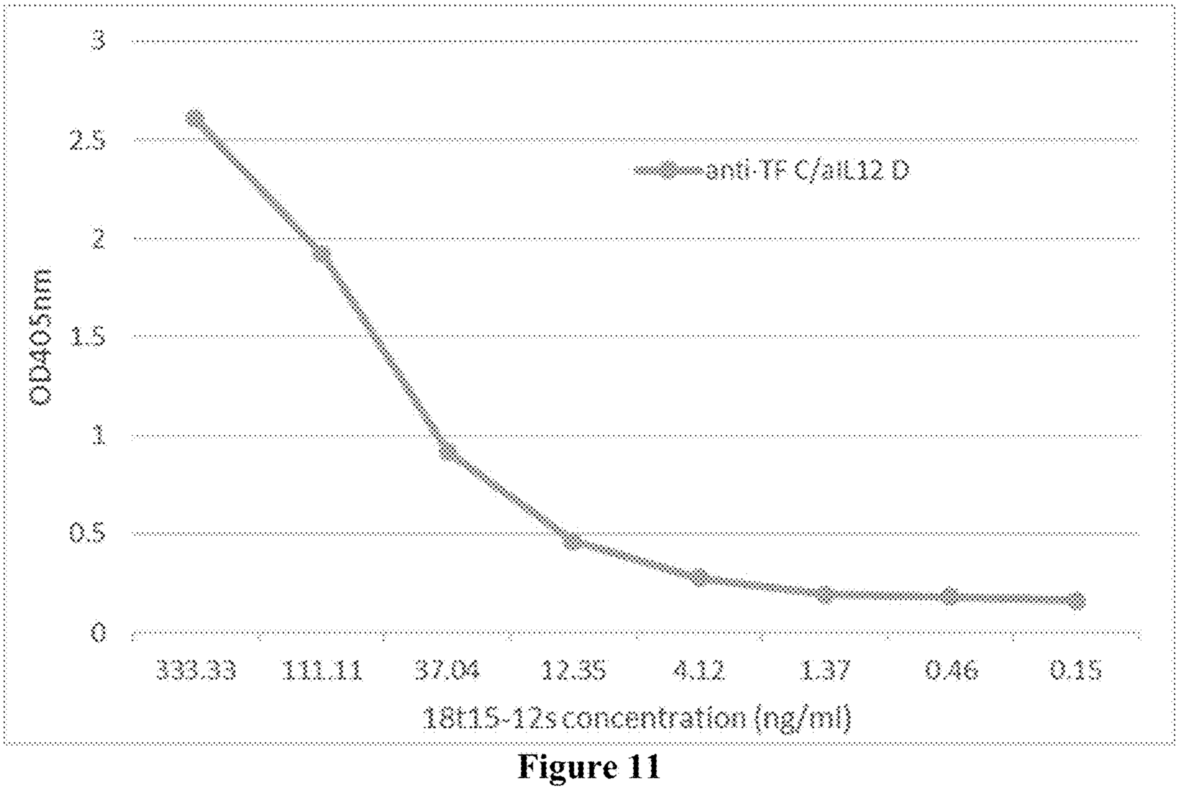
FIG. 11 shows a sandwich ELISA for the 18t15-12s complex, comprising an anti-human tissue factor capture antibody and a biotinylated anti-human IL-12 detection antibody (BAF 219).
Figure 12:
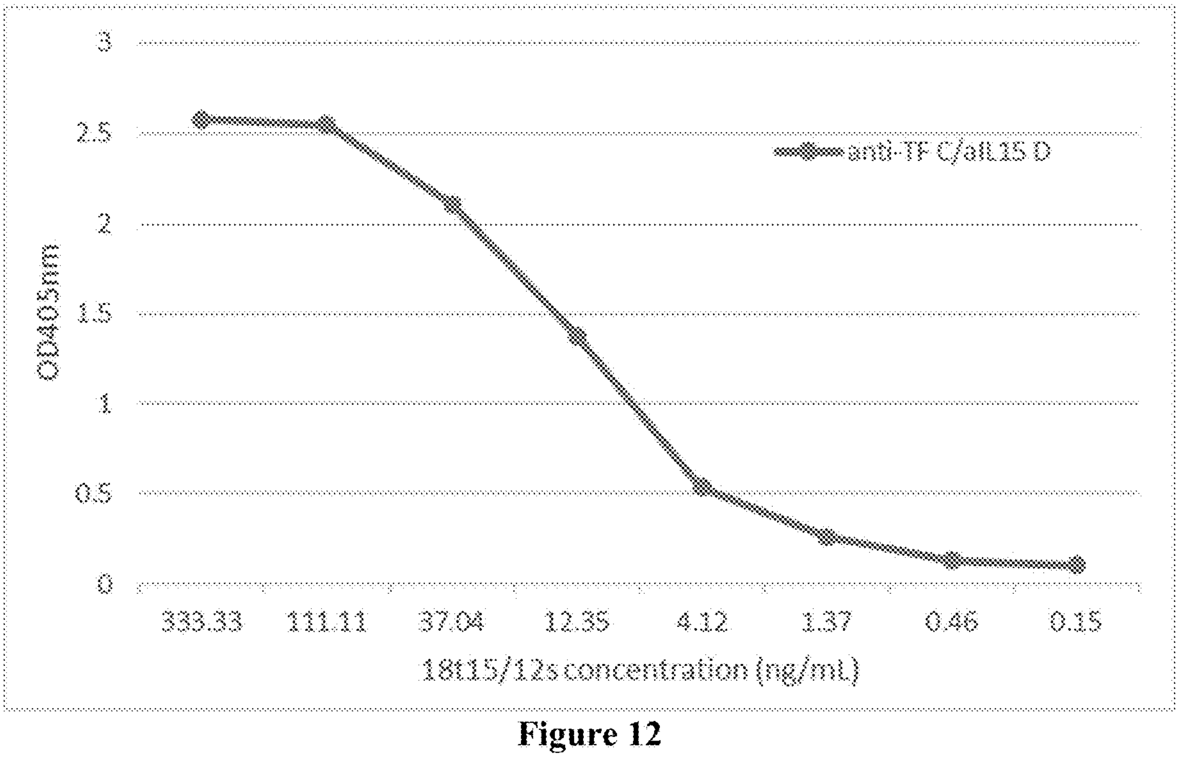
FIG. 12 shows a sandwich ELISA for the 18t15-12s complex, comprising an anti-human tissue factor capture antibody and a biotinylated anti-human IL-15 detection antibody (BAM 247).
Figure 13:
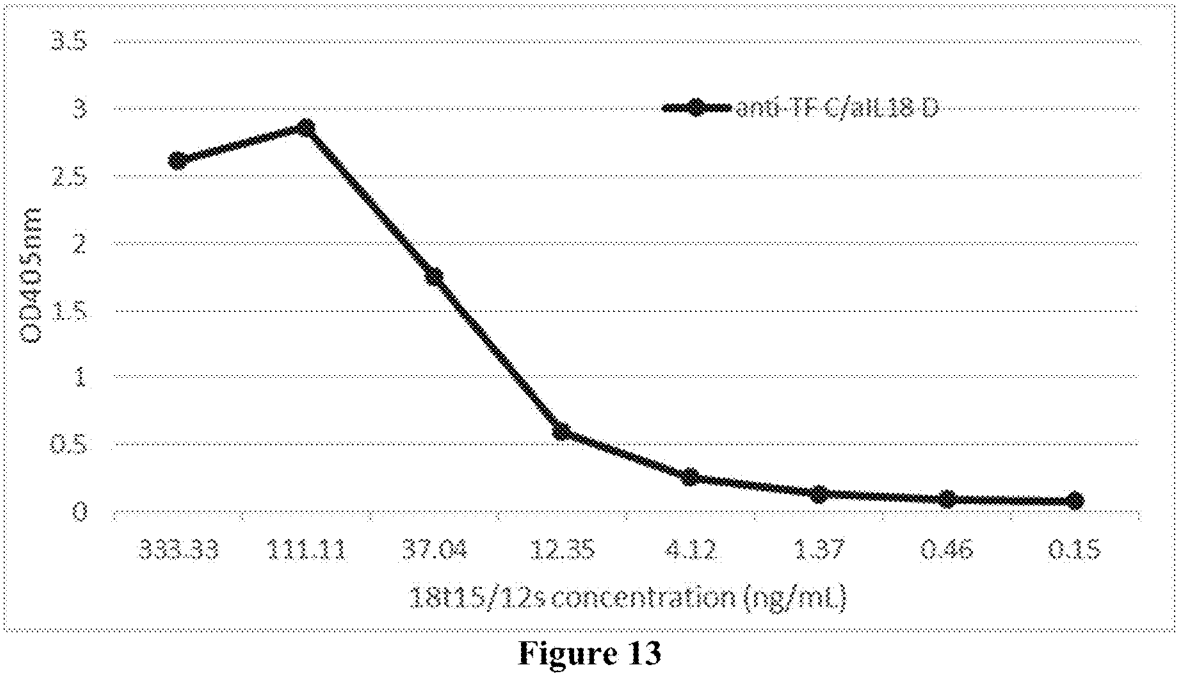
FIG. 13 shows a sandwich ELISA for the 18t15-12s complex, comprising an anti-human tissue factor capture antibody and a biotinylated anti-human IL-18 detection antibody (D045-6).
Figure 14:
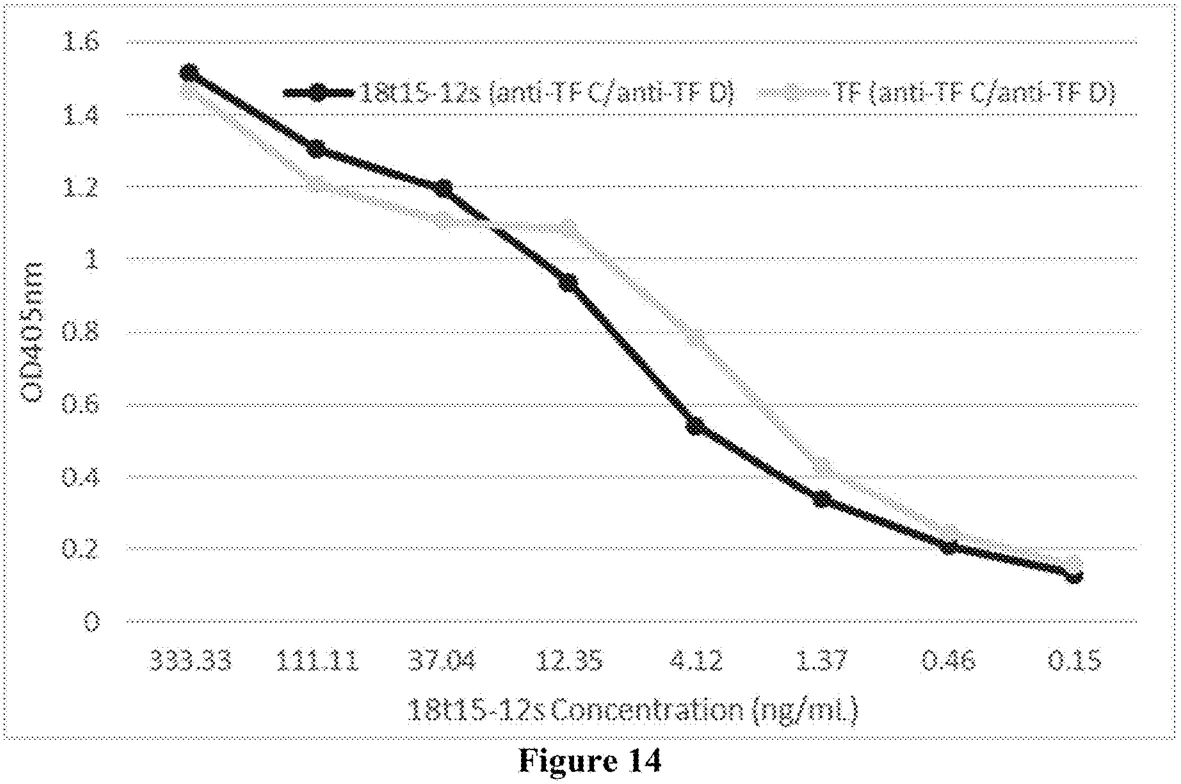
FIG. 14 shows a sandwich ELISA for the 18t15-12s complex, comprising an anti-human tissue factor (I43) capture antibody and an anti-human tissue factor detection antibody.

Glycosylation of 18t15-12s in CHO-K1 cells was confirmed using the Protein Deglycosylation Mix II kit (New England Biolabs), according to the manufacturer's instructions. FIG. 10 shows an example SDS PAGE of deglycosylated and non-deglycosylated 18t15-12s. Deglycosylation reduces the molecular weight of 18t15-12s as seen in FIG. 10, lane 4.

Example 9: Recombinant Protein Quantitation of 18t15-12s Complexes

The 18t15-12s complex was detected and quantified using standard sandwich ELISA methods (FIGS. 11-14). Anti-human tissue factor antibody served as the capture antibody and biotinylated anti-human IL-12, IL-15, or IL-18 antibody (BAF 219, BAM 247, D045-6, all R&D Systems) served as the detection antibody. Tissue factor in purified 18t15-12s protein complexes was also detected using an anti-human tissue factor capture antibody (I43), and anti-human tissue factor antibody detection antibody. The I43/anti-TF antibody ELISA was compared to purified tissue factor at similar concentrations.

Example 10: Immunostimulatory Capacity of the 18t15-12s Complex

Figure 15:
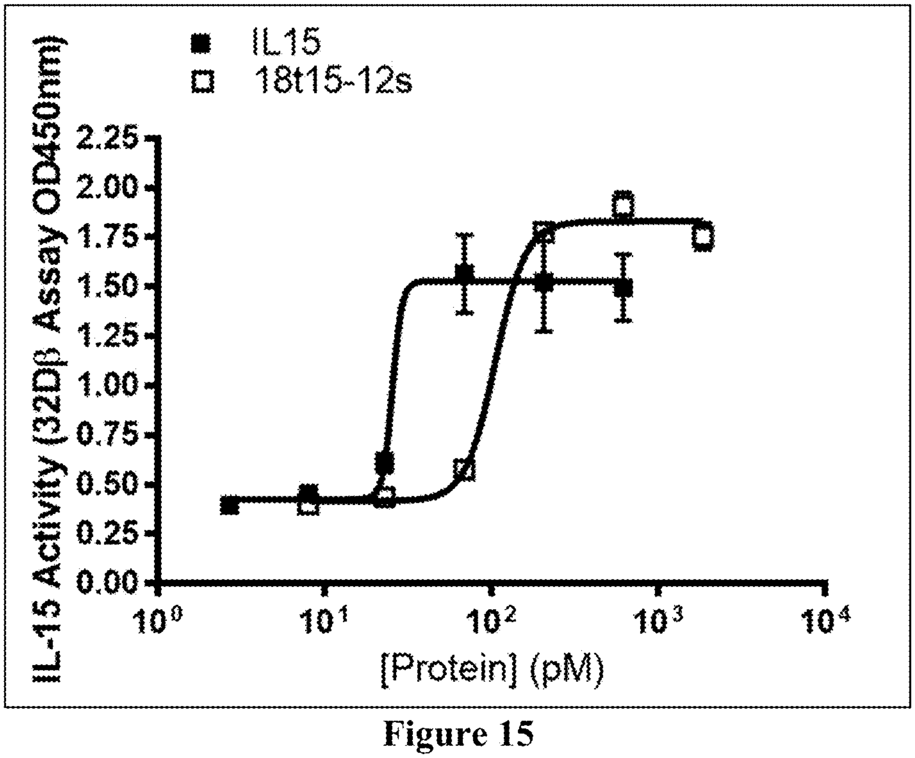
FIG. 15 shows proliferation of IL-15-dependent 32Dβ cells mediated by the 18t15-12s complex (open squares) and recombinant IL-15 (black squares).

To assess the IL-15 immunostimulatory activity of the 18t15-12s complex, increasing concentrations of 18t15-12s was added to 32Dβ cells (104 cell/well) in 200 μL IMDM: 10% FBS media. The 32Dβ cells were incubated for 3 days at 37° C. On the fourth day, WST-1 proliferation reagent (10 μL/well) was added and after 4 hours, absorbance was measured at 450 nm to determine cell proliferation based on cleavage of WST-1 to a soluble formazan dye. Bioactivity of human recombinant IL-15 was assessed as a positive control. As shown in FIG. 15, 18t15-12s demonstrated IL-15-dependent cell proliferation of 32Dβ cells. The 18t15-12s complex demonstrated reduced activity compared to human recombinant IL-15, possibly due to the linkage of IL-18 and tissue factor to the IL-15 domain.

Figure 16:
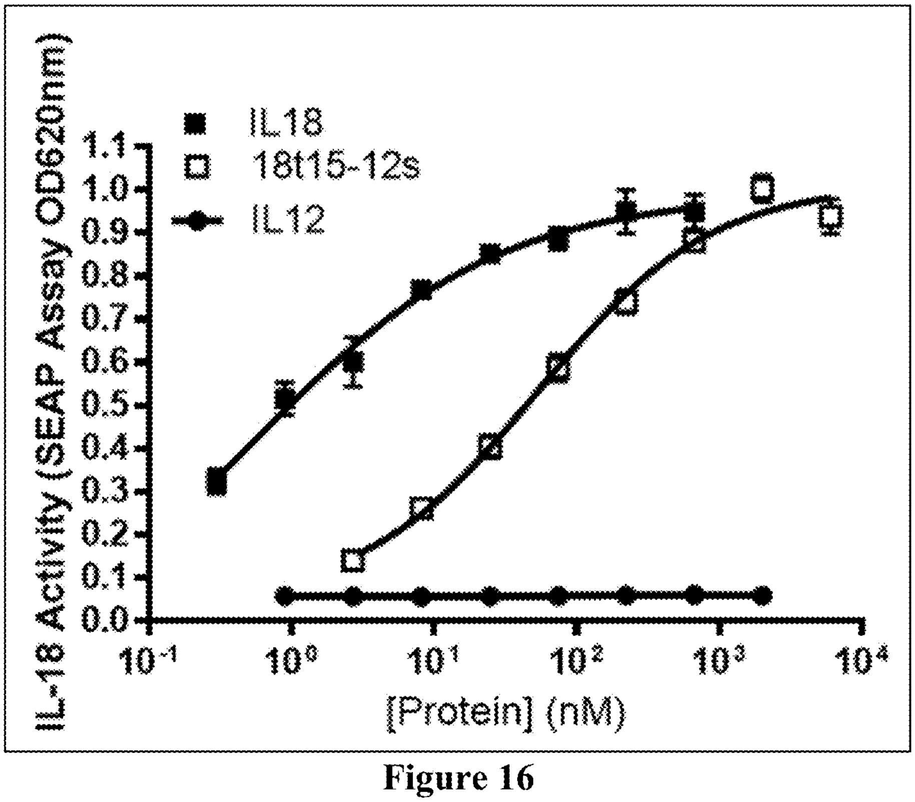
FIG. 16 shows biological activity of IL-18 within the 18t15-12s complex (open squares), where recombinant IL-18 (black squares) and recombinant IL-12 (black circles) serve as positive and negative controls, respectively.
Figure 17:
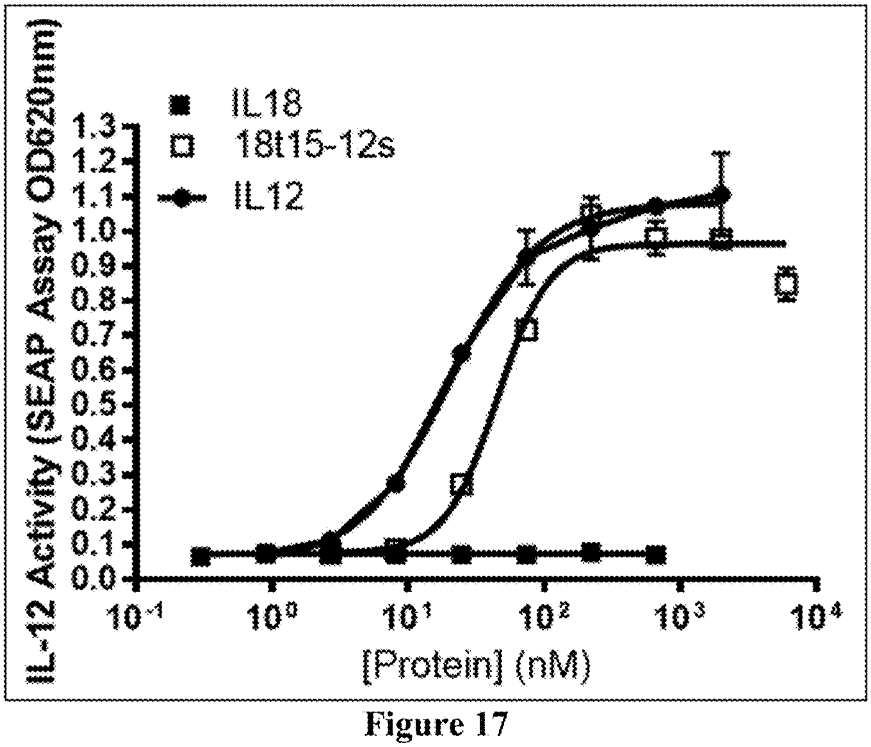
FIG. 17 shows biological activity of IL-12 within the 18t15-12s complex (open squares), where recombinant IL-12 (black circles) and recombinant IL-18 (open squares) serve as positive and negative controls, respectively.

In order to assess the individual activities of IL-12 and IL-18 in the 18t15-12s complex, 18t15-12s was added to HEK-Blue IL-12 and HEK-Blue IL-18 reporter cells ($5\times10^4$ cell/well; hkb-il12 and hkb-hmil18, InvivoGen) in 200 μL IMDM:10% heat-inactivated FBS media. Cells were incubated for overnight at 37° C. 20 μl of induced HEK-Blue IL-12 and HEK-Blue IL-18 reporter cell supernatant was added to 180 μl of QUANTI-Blue (InvivoGen), and incubated for 1-3 hours at 37° C. IL-12 or IL-18 activity was assessed by measuring absorbance at 620 nm. Human recombinant IL-12 or IL-18 was assessed as a positive or negative control. As shown in FIG. 16 and FIG. 17, each of the cytokine domains of the 18t15-12s complex retain specific biological activity. The activity of 18t15-12s was reduced compared to that of human recombinant IL-18 or IL-12, possibly due to linkage of IL-15 and tissue factor to the IL-18 domain and linkage of IL-12 to the IL-15Rα, sushi domain.

Example 11: Induction of Cytokine-Induced Memory-Like NK Cells by the 18t15-12s Complex Cytokine-induced memory-like NK cells can be induced ex vivo following overnight stimulation of purified NK cells with saturating amounts of IL-12 (10 ng/mL), IL-15 (50 ng/mL), and IL-18 (50 ng/mL). These memory-like properties have been measured through expression of IL-2 receptor α (IL-2Rα, CD25), CD69 (and other activation markers), and increased IFN-γ production. To evaluate the ability of 18t15-12s complexes to promote generation of cytokine-induced memory-like NK cells, purified human NK cells (>95% CD56+) were stimulated for 14-18 hours with 0.01 nM to 10000 nM of the 18t15-12s complex or a combination of individual cytokines (recombinant IL-12 (10 ng/mL), IL-18 (50 ng/mL), and IL-15 (50 ng/mL)). Cell-surface CD25 and CD 69 expression and intracellular IFN-7 levels were assessed by antibody-staining and flow cytometry.

Figure 18A:
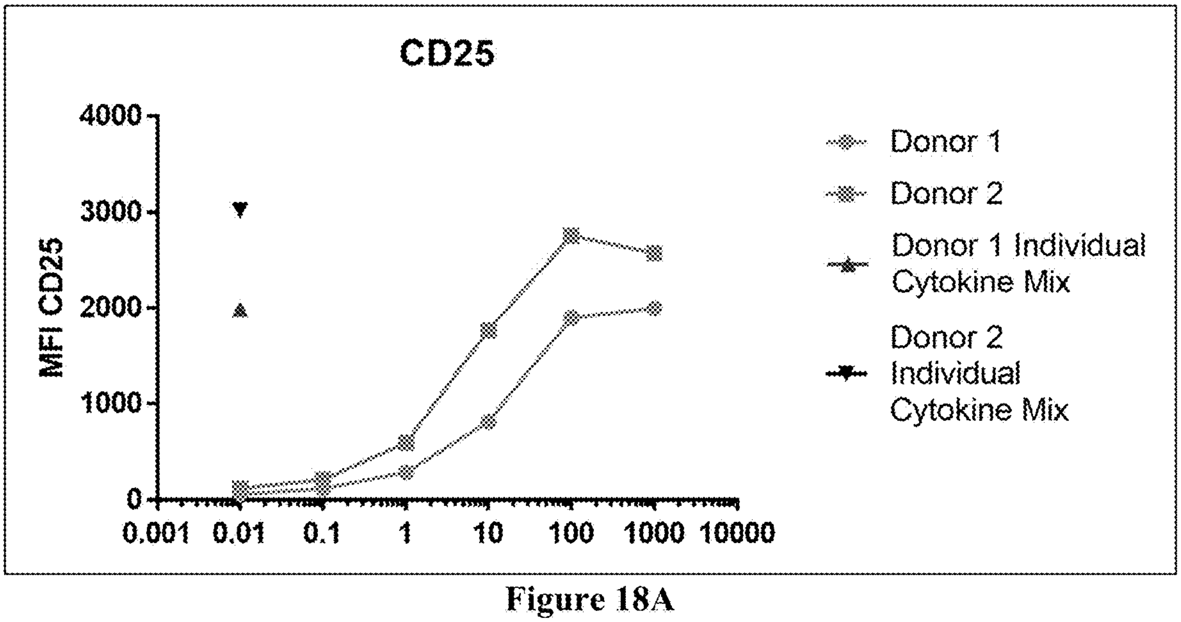
FIGS. 18A and 18B show cell-surface expression of CD25 on NK cells induced by the 18t15-12s complex and cell-surface CD69 expression of NK cells induced by the 18t15-12s complex.
Figure 18B:
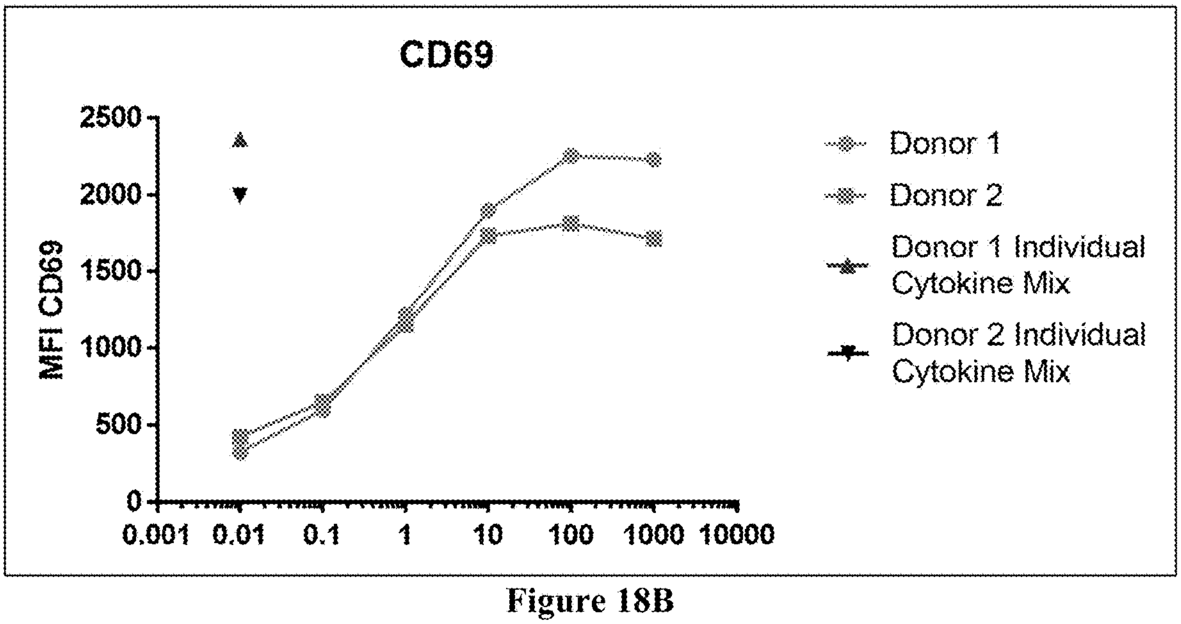

Fresh human leukocytes were obtained from a blood bank and CD56+NK cells were isolated with the RosetteSep/human NK cell reagent (StemCell Technologies). The purity of NK cells was >70% and confirmed by staining with antibodies specific to CD56-BV421, CD16-BV510, CD25-PE, CD69-APCFire750 (BioLegend). Cells were counted and resuspended in $0.2\times10^6$/mL in a 96 well flat bottom plate in 0.2 mL of complete media (RPMI 1640 (Gibco), supplemented with 2 mM L-glutamine (Thermo Life Technologies), penicillin (Thermo Life Technologies), streptomycin (Thermo Life Technologies), and 10% FBS (Hyclone)). Cells were stimulated with either a mixture of cytokines hIL-12 (10 ng/mL) (Biolegend), hIL-18 (50 ng/mL) (R&D Systems) and hIL-15 (50 ng/mL) (NCI) or with 0.01 nM to 10000 nM of the 18t15-12s at 37° C., 5% $CO_2$ for 14-18 hrs. The cells were then harvested and surface stained with antibodies specific to CD56-BV421, CD16-BV510, CD25-PE, CD69-APCFire750 (BioLegend) for 30 minutes. After staining, cells were washed (1500 RPM for 5 minutes at room temperature) in FACS buffer (1×PBS (Hyclone), with 0.5% BSA (EMD Millipore) and 0.001% sodium azide (Sigma)). After two washes, cells were analyzed using a BD FACSCelesta™ flow cytometer (Plotted Data-Mean Fluorescence Intensity; FIG. 18A and FIG. 18B).

Figure 19:
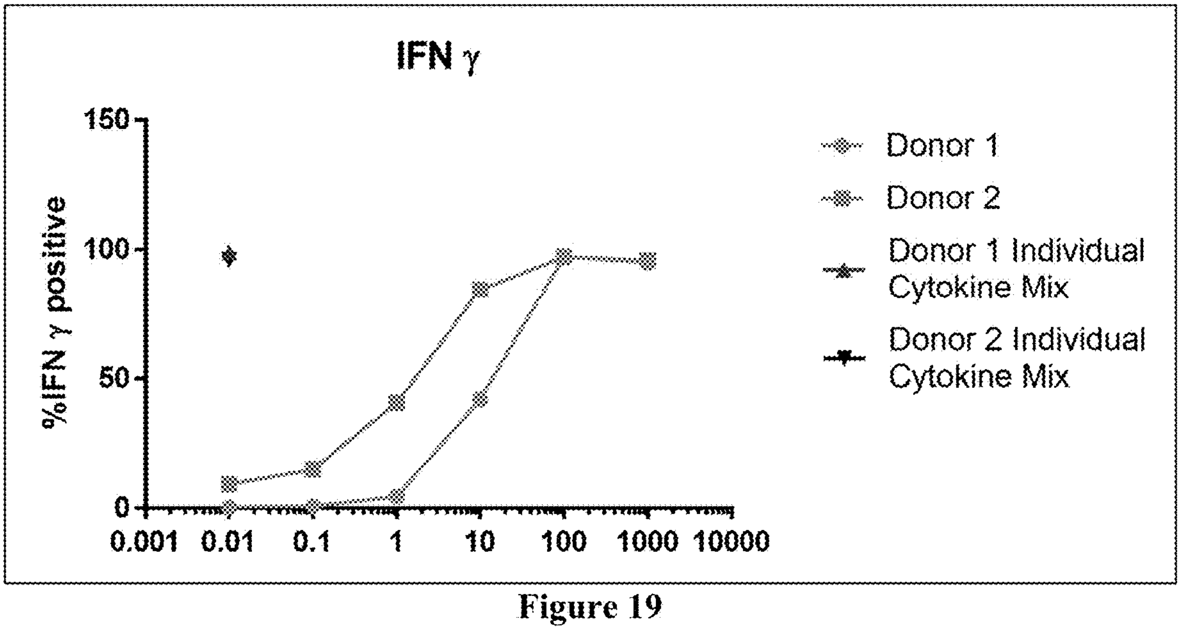
FIG. 19 shows a flow cytometry graph of intracellular interferon gamma expression of NK cells induced by the 18t15-12s complex.

Fresh human leukocytes were obtained from a blood bank and CD56+NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 specific antibodies (BioLegend). Cells were counted and resuspended in $0.2\times10^6$/mL in a 96 well flat bottom plate in 0.2 mL of complete media (RPMI 1640 (Gibco), supplemented with 2 mM L-glutamine (Thermo Life Technologies), penicillin (Thermo Life Technologies), streptomycin (Thermo Life Technologies), and 10% FBS (Hyclone)). Cells were stimulated with either a cytokine mix of hIL-12 (10 ng/mL) (Biolegend), hIL-18 (50 ng/mL) (R&D), and hIL-15 (50 ng/mL) (NCI), or 0.01 nM to 10000 nM of the 18t15-12s complex at 37° C., 5% CO2 for 14-18 hrs. The cells were then treated with 10 μg/mL of Brefeldin A (Sigma) and 1× of Monensin (eBioscience) for 4 hrs before harvesting and staining with antibodies specific to CD56-BV421, CD16-BV510, CD25-PE, CD69-APCFire750 for 30 minutes. After staining, cells were washed (1500 RPM for 5 minutes in room temperature) in FACS buffer (1×PBS (Hyclone), with 0.5% BSA (EID Millipore) and 0.001% sodium azide (Sigma)) and fixed for 10 minutes at room temperature. After fixation, cells were washed (1500 RPM for 5 minutes in room temperature) in 1× permeabilized buffer (eBioscience) and stained with IFN-γ-PE Ab (Biolegend) for 30 minutes at room temperature. Cells were washed once again with 1× permeabilized buffer and then washed with FACS buffer. Cell pellets were resuspended in 300 μls of FACS buffer and analyzed using a BD FACSCelesta™ flow cytometer (Plotted % of IFN-7 Positive Cells; FIG. 19).

Example 12: In Vitro Cytotoxicity of NK Cells Against Human Tumor Cells

Figure 20:
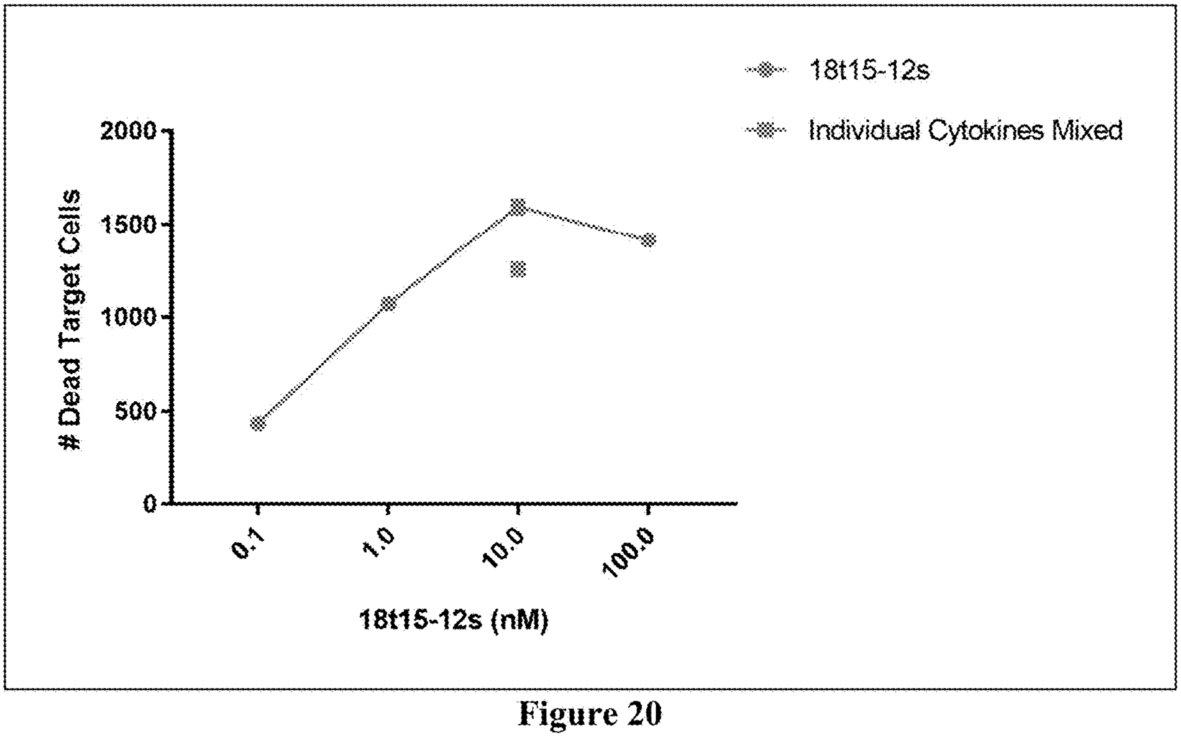
FIG. 20 shows cytotoxicity of 18t15-12s induced human NK cells against K562 cells.

Human myelogenous leukemia cells, K562 (CELLTRACE®, violet dye, labelled), were incubated with purified human NK cells in the presence of increasing concentrations of the 18t15-12s complex or a mixture of cytokines as a control. After 20 hours, the cultures were harvested, stained with propidium iodide (PI), and assessed by flow cytometry. As shown in FIG. 20, the 18t15-12s complex induced human NK cytotoxicity against K562, at levels similar or greater than the cytokine mixture, wherein both the 18t15-12s complex and the cytokine mixture induced greater cytotoxicity than the medium control.

Figure 21:
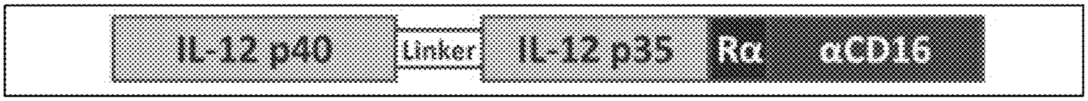
FIG. 21 shows a schematic diagram of an exemplary IL-12/IL-15RαSu/αCD16 DNA construct.
Figure 22:
FIG. 22 shows a schematic diagram of an exemplary IL-18/TF/IL-15 DNA construct.

Example 13: Creation of IL-12/IL-15RαSu/αCD16scFv and IL-18/TF/IL-15 DNA Constructs In a non-limiting example, IL-12/IL-15RαSu/αCD16scFv and IL-18/TF/IL-15 DNA constructs were created (FIG. 21 and FIG. 22). The human IL-12 subunit sequences, human IL-15RαSu sequence, human IL-15 sequence, human tissue factor 219 sequence, and human IL-18 sequence were synthesized by Genewiz. A DNA construct was made linking the IL-12 subunit beta (p40) to IL-12 subunit alpha (p35) with a GS (3) linker to generate a single chain version of IL-12, directly linking the IL-12 sequence to the IL-15RαSu sequence, and directly linking the IL-12/IL-15RαSu construct to the N-terminus coding region of αCD16scFv.

The nucleic acid sequence of the IL-12/IL-15RαSu/αCD16scFv construct is as follows (SEQ ID NO: 123):

```
(Signal peptide)
ATGAAATGGGTGACCTTTATTTCTTTACTGTTCCTCTTTAGCAGCGCCT

ACTCC

(Human IL-12 subunit beta (p40))
ATTTGGGAACTGAAGAAGGACGTCTACGTGGTCGAACTGGACTGGTAT

CCCGATGCTCCCGGCGAAATGGTGGTGCTCACTTGTGACACCCCCGAAG

AAGACGGCATCACTTGGACCCTCGATCAGAGCAGCGAGGTGCTGGGCTC

CGGAAAGACCCTCACAATCCAAGTTAAGGAGTTCGGAGACGCTGGCCAA

TACACATGCCACAAGGGAGGCGAGGTGCTCAGCCATTCCTTATTATTAT

TACACAAGAAGGAAGACGGAATCTGGTCCACCGACATTTTAAAAGATCA

GAAGGAGCCCAAGAATAAGACCTTTTTAAGGTGTGAGGCCAAAAACTAC

AGCGGTCGTTTCACTTGTTGGTGGCTGACCACCATTTCCACCGATTTAA

CCTTCTCCGTGAAAAGCAGCCGGGGAAGCTCCGACCCTCAAGGTGTGAC

ATGTGGAGCCGCTACCCTCAGCGCTGAGAGGGTTCGTGGCGATAACAAG

GAATACGAGTACAGCGTGGAGTGCCAAGAAGATAGCGCTTGTCCCGCTG

CCGAAGAATCTTTACCCATTGAGGTGATGGTGGACGCCGTGCACAAACT

CAAGTACGAGAACTACACCTCCTCCTTCTTTATCCGGGACATCATTAAG

CCCGATCCTCCCTAAGAATTTACAGCTGAAGCCTCTCAAAAATAGCCGGC

AAGTTGAGGTCTCTTGGGAATATCCCGACACTTGGAGCACACCCCACAG

CTACTTCTCTTTAACCTTTTGTGTGCAAGTTCAAGGTAAAAGCAAGCGG

GAGAAGAAAGACCGGGTGTTTACCGACAAAACCAGCGCCACCGTCATCT

GTCGGAAGAACGCCTCCATCAGCGTGAGGGCTCAAGATCGTTATTACTC

CAGCAGCTGGTCCGAGTGGGCCAGCGTGCCTTGTTCC
```

-continued (Linker)
GGCGGTGGAGGATCCGGAGGAGGTGGCTCCGGCGGCGGAGGATCT (Human IL-12 subunit alpha (p35))
CGTAACCTCCCCGTGGCTACCCCCGATCCCGGAATGTTCCCTTGTTTAC

ACCACAGCCAGAATTTACTGAGGGCCGTGAGCAACATGCTGCAGAAAGC

TAGGCAGACTTTAGAATTTTACCCTTGCACCAGCGAGGAGATCGACCAT

GAAGATATCACCAAGGACAAGACATCCACCGTGGAGGCTTGTTTACCTC

TGGAGCTGACAAAGAACGAGTCTTGTCTCAACTCTCGTGAAACCAGCTT

CATCACAAATGGCTCTTGTTTAGCTTCCCGGAAGACCTCCTTTATGATG

GCTTTATGCCTCAGCTCCATCTACGAGGATTTAAAGATGTACCAAGTGG

AGTTCAAGACCATGAACGCCAAGCTGCTCATGGACCCTAAACGGCAGAT

CTTTTTAGACCAGAACATGCTGGCTGTGATTGATGAGCTGATGCAAGCT

TTAAACTTCAACTCCGAGACCGTCCCTCAGAAGTCCTCCCTCGAGGAGC

CCGATTTTTACAAGACAAAGATCAAACTGTGCATTTTACTCCACGCCTT

TAGGATCCGGGCCGTGACCATTGACCGGGTCATGAGCTATTTAAACGCC

AGC (Human IL-15Rα sushi domain)
ATTACATGCCCCCCTCCCATGAGCGTGGAGCACGCCGACATCTGGGTG

AAGAGCTATAGCCTCTACAGCCGGGAGAGGTATATCTGTAACAGCGGCT

TCAAGAGGAAGGCCGGCACCAGCAGCCTCACCGAGTGCGTGCTGAATAA

GGCTACCAACGTGGCTCACTGGACAACACCCTCTTTAAAGTGCATCCGG (anti-Human CD16 light chain variable domain)
TCCGAGCTGACCCAGGACCCTGCTGTGTCCGTGGCTCTGGGCCAGACC

GTGAGGATCACCTGCCAGGGCGACTCCCTGAGGTCCTACTACGCCTCCT

GGTACCAGCAGAAGCCCGGCCAGGCTCCTGTGCTGGTGATCTACGGCAA

GAACAACAGGCCCTCCGGCATCCCTGACAGGTTCTCCGGATCCTCCTCC

GGCAACACCGCCTCCCTGACCATCACAGGCGCTCAGGCCGAGGACGAGG

CTGACTACTACTGCAACTCCAGGGACTCCTCCGGCAACCATGTGGTGTT

CGGCGGCGGCACCAAGCTGACCGTGGGCCAT (Linker)
GGCGGCGGCGGCTCCGGAGGCGGCGGCAGCGGCGGAGGAGGATCC (anti-Human CD16 heavy chain variable domain)
GAGGTGCAGCTGGTGGAGTCCGGAGGAGGAGTGGTGAGGCCTGGAGG

CTCCCTGAGGCTGAGCTGTGCTGCCTCCGGCTTCACCTTCGACGACTAC

GGCATGTCCTGGGTGAGGCAGGCTCCTGGAAAGGGCCTGGAGTGGGTGT

CCGGCATCAACTGGAACGGCGGATCCACCGGCTACGCCGATTCCGTGAA

GGGCAGGTTCACCATCAGCAGGGACAACGCCAAGAACTCCCTGTACCTG

CAGATGAACTCCCTGAGGGCCGAGGACACCGCCGTGTACTACTGCGCCA

GGGGCAGGTCCCTGCTGTTCGACTACTGGGGACAGGGCACCCTGGTGAC

CGTGTCCAGG

Constructs were also made linking the IL-18 sequence to the N-terminus coding region of tissue factor 219, and linking the IL-18/TF construct with the N-terminus coding region of IL-15 (FIG. 22). The nucleic acid sequence of the IL-18/TF/IL-15 construct (including leader sequence) is as follows (SEQ ID NO: 73):

(Signal peptide)
ATGAAGTGGGTCACATTTATCTCTTTACTGTTCCTCTTCTCCAGCGCCT

ACAGC (Human IL-18)
TACTTCGGCAAACTGGAATCCAAGCTGAGCGTGATCCGGAATTTAAAC

GACCAAGTTCTGTTTATCGATCAAGGTAACCGGCCTCTGTTCGAGGACA

TGACCGACTCCGATTGCCGGGACAATGCCCCCCGGACCATCTTCATTAT

CTCCATGTACAAGGACAGCCAGCCCCGGGGCATGGCTGTGACAATTAGC

GTGAAGTGTGAGAAAATCAGCACTTTATCTTGTGAGAACAAGATCATCT

CCTTTAAGGAAATGAACCCCCCCGATAACATCAAGGACACCAAGTCCGA

TATCATCTTCTTCCAGCGGTCCGTGCCCGGTCACGATAACAAGATGCAG

TTCGAATCCTCCTCCTACGAGGGCTACTTTTTAGCTTGTGAAAAGGAGA

GGGATTTATTCAAGCTGATCCTCAAGAAGGAGGACGAGCTGGGCGATCG

TTCCATCATGTTCACCGTCCAAAACGAGGAT (Human Tissue Factor 219)
AGCGGCACAACCAACACAGTCGCTGCCTATAACCTCACTTGGAAGAG

CACCAACTTCAAAACCATCCTCGAATGGGAACCCAAACCCGTTAACCAA

GTTTACACCGTGCAGATCAGCACCAAGTCCGGCGACTGGAAGTCCAAAT

GTTTCTATACCACCGACACCGAGTGCGATCTCACCGATGAGATCGTGAA

AGATGTGAAACAGACCTACCTCGCCCGGGTGTTTAGCTACCCCGCCGGC

AATGTGGAGAGCACTGGTTCCGCTGGCGAGCCTTTATACGAGAACAGCC

CCGAATTTACCCCTTACCTCGAGACCAATTTAGGACAGCCCACCATCCA

AAGCTTTGAGCAAGTTGGCACAAAGGTGAATGTGACAGTGGAGGACGAG

CGGACTTTAGTGCGGCGGAACAACACCTTTCTCAGCCTCCGGGATGTGT

TCGGCAAAGATTTAATCTACACACTGTATTACTGGAAGTCCTCTTCCTC

CGGCAAGAAGACAGCTAAAACCAACACAAACGAGTTTTTAATCGACGTG

GATAAAGGCGAAAACTACTGTTTCAGCGTGCAAGCTGTGATCCCCTCCC

GGACCGTGAATAGGAAAAGCACCGATAGCCCCGTTGAGTGCATGGGCCA

AGAAAAGGGCGAGTTCCGGGAG (Human IL-15)
AACTGGGTGAACGTCATCAGCGATTTAAAGAAGATCGAAGATTTAATT

CAGTCCATGCATATCGACGCCACTTTATACACAGAATCCGACGTGCACC

CCTCTTGTAAGGTGACCGCCATGAAATGTTTTTTACTGGAGCTGCAAGT

TATCTCTTTAGAGAGCGGAGACGCTAGCATCCACGACACCGTGGAGAAT

TTAATCATTTTAGCCAATAACTCTTTATCCAGCAACGGCAACGTGACAG

AGTCCGGCTGCAAGGAGTGCGAAGAGCTGGAGGAGAAGAACATCAAGGA

GTTTCTGCAATCCTTTGTGCACATTGTCCAGATGTTCATCAATACCTCC

Figure 23:
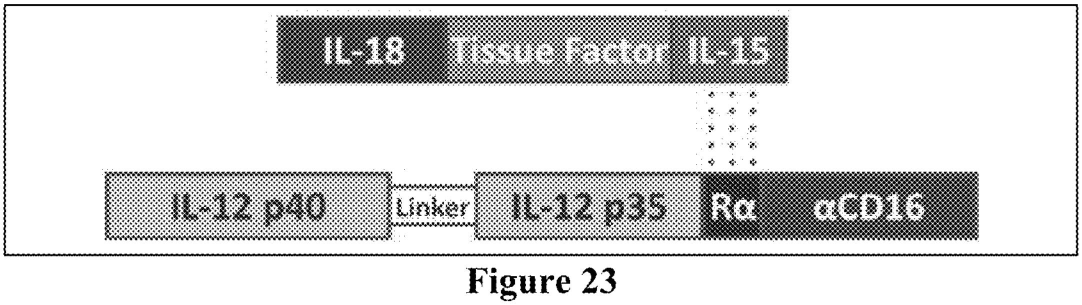
FIG. 23 shows a schematic diagram of the interaction between the exemplary IL-12/IL-15RαSu/αCD16scFv and IL-18/TF/IL-15 DNA constructs.
Figure 24:
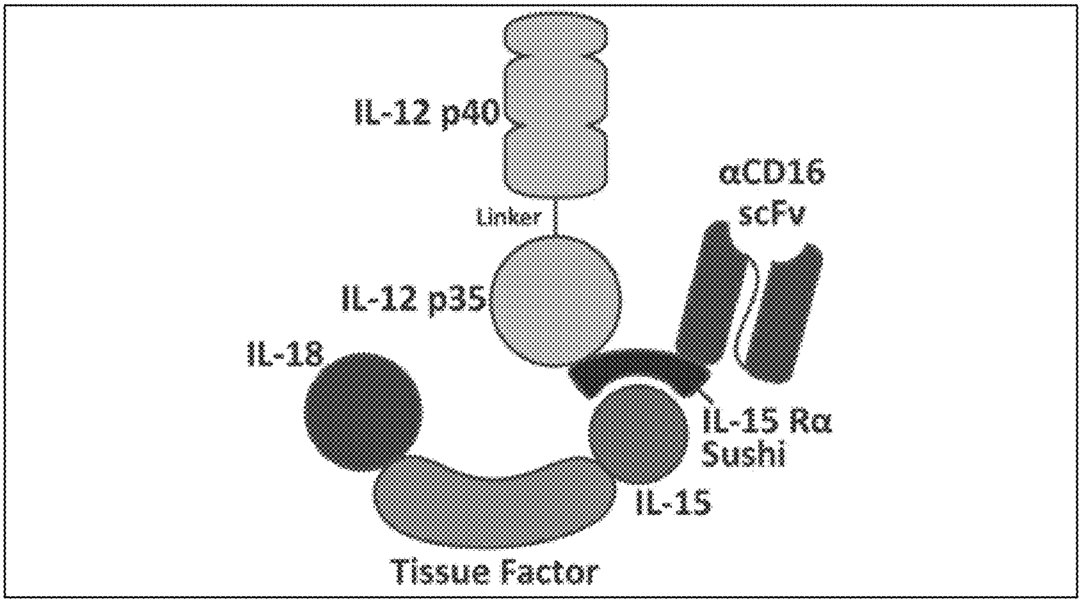
FIG. 24 shows a schematic diagram of an exemplary 18t15-12s/αCD16 protein complex.

Example 14: Secretion of IL-12/IL-15RαSu/αCD16scFv and IL-18/TF/IL-15 Fusion Proteins The IL-12/IL-15RαSu/αCD16scFv and IL-18/TF/IL-15 constructs were cloned into a pMSGV-1 modified retrovirus expression vector (Hughes, *Hum Gene Ther* 16:457-72, 2005, herein incorporated by reference), and the expression vector was transfected into CHO-K1 cells. Co-expression of the two constructs in CHO-K1 cells resulted in secretion of a soluble IL-18/TF/IL-15:IL-12/IL-15RαSu/αCD16scFv protein complex (referred to as 18t15-12s/αCD16; FIGS. 23 and 24). Co-expression of the two constructs in CHO-K1 cells resulted in secretion of the soluble IL-18/TF/IL-15:IL-12/IL-15RαSu/αCD16scFv protein complex (referred to as 18t15-12s/αCD16; FIG. 23 and FIG. 24), which can be purified by anti-TF Ab affinity and other chromatography methods. In some cases, the signal peptide is cleaved from the intact polypeptide to generate the mature form.

The amino acid sequence of the IL-12/IL-15RαSu/αCD16scFv fusion protein (including signal peptide sequence) is as follows (SEQ ID NO: 122):

```
(Signal peptide)
MKWVTFISLLFLFSSAYS

(Human IL-12 subunit beta (p40))
IWELKKDVYVVELDWYPDAPGEMVVLTCDTPEEDGITWTLDQSSEVLGS

GKTLTIQVKEFGDAGQYTCHKGGEVLSHSLLLLHKKEDGIWSTDILKDQ

KEPKNKTFLRCEAKNYSGRFTCWWLTTISTDLTFSVKSSRGSSDPQGVT

CGAATLSAERVRGDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSKREKKDRVFTDKTSATVICRKNASISVRAQDRYYS

SSWSEWASVPCS

(Linker)
GGGGSGGGGSGGGGS

(Human IL-12 subunit alpha (p35))
RNLPVATPDPGMFPCLHHSQNLLRAVSNMLQKARQTLEFYPCTSEEIDH

EDITKDKTSTVEACLPLELTKNESCLNSRETSFITNGSCLASRKTSFMM

ALCLSSIYEDLKMYQVEFKTMNAKLLMDPKRQIFLDQNMLAVIDELMQA

LNFNSETVPQKSSLEEPDFYKTKIKLCILLHAFRIRAVTIDRVMSYLNA

S

(Human IL-15Rα sushi domain)
ITCPPPMSVEHADIWVKSYSLYSRERYICNSGFKRKAGTSSLTECVLNK

ATNVAHWTTPSLKCIR

(anti-Human CD16 light chain variable domain)
SELTQDPAVSVALGQTVRITCQGDSLRSYYASWYQQKPGQAPVLVIYGK

NNRPSGIPDRFSGSSSGNTASLTITGAQAEDEADYYCNSRDSSGNHVVF

GGGTKLTVGH

(Linker)
GGGGSGGGGSGGGGS

(anti-Human CD16 heavy chain variable domain)
EVQLVESGGGVVRPGGSLRLSCAASGFTFDDYGMSWVRQAPGKGLEWV

SGINWNGGSTGYADSVKGRFTISRDNAKNSLYLQMNSLRAEDTAVYYC

ARGRSLLFDYWGQGTLVTVSR
```

The amino acid sequence of the IL-18/TF/IL-15 fusion protein (including leader sequence) is as follows (SEQ ID NO: 72):

```
(Signal peptide)
MKWVTFISLLFLFSSAYS

(Human IL-18)
YFGKLESKLSVIRNLNDQVLFIDQGNRPLFEDMTDSDCRDNAPRTIFII

SMYKDSQPRGMAVTISVKCEKISTLSCENKIISFKEMNPPDNIKDTKSD

IIFFQRSVPGHDNKMQFESSSYEGYFLACEKERDLFKLILKKEDELGDR

SIMFTVQNED

(Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE

(Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS
```

Example 15: Creation of IL-18/IL-15RαSu and IL-12/TF/IL-15 DNA Constructs

In a non-limiting example, IL-18/IL-15RαSu and IL-12/TF/IL-15 DNA constructs were created. The human IL-18 subunit sequences, human IL-15RαSu sequence, human IL-12 sequence, human tissue factor 219 sequence, and human IL-15 sequence were synthesized by Genewiz. A DNA construct was made linking IL-18 directly to IL-15RαSu. An additional construct was also made linking IL-12 sequence to the N-terminus coding region of human tissue factor 219 form, and further linking the IL-12/TF construct to the N-terminus coding region of IL-15. As described above, a single-chain version of IL-12 (p40-linker-p35) was used.

The nucleic acid sequence of the IL-18/IL-15RαSu construct (including signal peptide sequence) is as follows (SEQ ID NO: 217):

```
(Signal peptide)
ATGAAGTGGGTCACATTTATCTCTTTACTGTTCCTCTTCTCCAGCGCCT

ACAGC

(Human IL-18)
TACTTCGGCAAACTGGAATCCAAGCTGAGCGTGATCCGGAATTTAAAC

GACCAAGTTCTGTTTATCGATCAAGGTAACCGGCCTCTGTTCGAGGACA

TGACCGACTCCGATTGCCGGGACAATGCCCCCCGGACCATCTTCATTAT

CTCCATGTACAAGGACAGCCAGCCCCGGGGCATGGCTGTGACAATTAGC

GTGAAGTGTGAGAAAATCAGCACTTTATCTTGTGAGAACAAGATCATCT

CCTTTAAGGAAATGAACCCCCCCGATAACATCAAGGACACCAAGTCCGA

TATCATCTTCTTCCAGCGGTCCGTGCCCGGTCACGATAACAAGATGCAG
```

-continued

TTCGAATCCTCCTCCTACGAGGGCTACTTTTTAGCTTGTGAAAAGGAGA

GGGATTTATTCAAGCTGATCCTCAAGAAGGAGGACGAGCTGGGCGATCG

TTCCATCATGTTCACCGTCCAAAACGAGGAT (Human IL-15α sushi domain)
ATTACATGCCCCCCTCCCATGAGCGTGGAGCACGCCGACATCTGGGTG

AAGAGCTATAGCCTCTACAGCCGGGAGAGGTATATCTGTAACAGCGGCT

TCAAGAGGAAGGCCGGCACCAGCAGCCTCACCGAGTGCGTGCTGAATAA

GGCTACCAACGTGGCTCACTGGACAACACCCTCTTTAAAGTGCATCCGG

The nucleic acid sequence of the IL-12/TF/IL-15 construct (including leader sequence) is as follows (SEQ ID NO: 218):

(Signal peptide)
ATGAAATGGGTGACCTTTATTTCTTTACTGTTCCTCTTTAGCAGCGCCT

ACTCC (Human IL-12 subunit beta (p40))
ATTTGGGAACTGAAGAAGGACGTCTACGTGGTCGAACTGGACTGGTAT

CCCGATGCTCCCGGCGAAATGGTGGTGCTCACTTGTGACACCCCCGAAG

AAGACGGCATCACTTGGACCCTCGATCAGAGCAGCGAGGTGCTGGGCTC

CGGAAAGACCCTCACAATCCAAGTTAAGGAGTTCGGAGACGCTGGCCAA

TACACATGCCACAAGGGAGGCGAGGTGCTCAGCCATTCCTTATTATTAT

TACACAAGAAGGAAGACGGAATCTGGTCCACCGACATTTTAAAAGATCA

GAAGGAGCCCAAGAATAAGACCTTTTTAAGGTGTGAGGCCAAAAACTAC

AGCGGTCGTTTCACTTGTTGGTGGCTGACCACCATTTCCACCGATTTAA

CCTTCTCCGTGAAAAGCAGCCGGGGAAGCTCCGACCCTCAAGGTGTGAC

ATGTGGAGCCGCTACCCTCAGCGCTGAGAGGGTTCGTGGCGATAACAAG

GAATACGAGTACAGCGTGGAGTGCCAAGAAGATAGCGCTTGTCCCGCTG

CCGAAGAATCTTTACCCATTGAGGTGATGGTGGACGCCGTGCACAAACT

CAAGTACGAGAACTACACCTCCTCCTTCTTTATCCGGGACATCATTAAG

CCCGATCCTCCTAAGAATTTACAGCTGAAGCCTCTCAAAAATAGCCGGC

AAGTTGAGGTCTCTTGGGAATATCCCGACACTTGGAGCACACCCCACAG

CTACTTCTCTTTAACCTTTTGTGTGCAAGTTCAAGGTAAAAGCAAGCGG

GAGAAGAAAGACCGGGTGTTTACCGACAAAACCAGCGCCACCGTCATCT

GTCGGAAGAACGCCTCCATCAGCGTGAGGGCTCAAGATCGTTATTACTC

CAGCAGCTGGTCCGAGTGGGCCAGCGTGCCTTGTTCC (Linker)
GGCGGTGGAGGATCCGGAGGAGGTGGCTCCGGCGGCGGAGGATCT (Human IL-12 subunit alpha (p35j)
CGTAACCTCCCCGTGGCTACCCCCGATCCCGGAATGTTCCCTTGTTTAC

ACCACAGCCAGAATTTACTGAGGGCCGTGAGCAACATGCTGCAGAAAGC

TAGGCAGACTTTAGAATTTTACCCTTGCACCAGCGAGGAGATCGACCAT

GAAGATATCACCAAGGACAAGACATCCACCGTGGAGGCTTGTTTACCTC

TGGAGCTGACAAAGAACGAGTCTTGTCTCAACTCTCGTGAAACCAGCTT

CATCACAAATGGCTCTTGTTTAGCTTCCCGGAAGACCTCCTTTATGATG

-continued

GCTTTATGCCTCAGCTCCATCTACGAGGATTTAAAGATGTACCAAGTGG

AGTTCAAGACCATGAACGCCAAGCTGCTCATGGACCCTAAACGGCAGAT

CTTTTTAGACCAGAACATGCTGGCTGTGATTGATGAGCTGATGCAAGCT

TTAAACTTCAACTCCGAGACCGTCCCTCAGAAGTCCTCCCTCGAGGAGC

CCGATTTTTACAAGACAAAGATCAAACTGTGCATTTTACTCCACGCCTT

TAGGATCCGGGCCGTGACCATTGACCGGGTCATGAGCTATTTAAACGCC

AGC (Human Tissue Factor 219)
AGCGGCACAACCAACACAGTCGCTGCCTATAACCTCACTTGGAAGAG

CACCAACTTCAAAACCATCCTCGAATGGGAACCCAAACCCGTTAACCAA

GTTTACACCGTGCAGATCAGCACCAAGTCCGGCGACTGGAAGTCCAAAT

GTTTCTATACCACCGACACCGAGTGCGATCTCACCGATGAGATCGTGAA

AGATGTGAAACAGACCTACCTCGCCCGGGTGTTTAGCTACCCCGCCGGC

AATGTGGAGAGCACTGGTTCCGCTGGCGAGCCTTTATACGAGAACAGCC

CCGAATTTACCCCTTACCTCGAGACCAATTTAGGACAGCCCACCATCCA

AAGCTTTGAGCAAGTTGGCACAAAGGTGAATGTGACAGTGGAGGACGAG

CGGACTTTAGTGCGGCGGAACAACACCTTTCTCAGCCTCCGGGATGTGT

TCGGCAAAGATTTAATCTACACACTGTATTACTGGAAGTCCTCTTCCTC

CGGCAAGAAGACAGCTAAAACCAACACAAACGAGTTTTTAATCGACGTG

GATAAAGGCGAAAACTACTGTTTCAGCGTGCAAGCTGTGATCCCCTCCC

GGACCGTGAATAGGAAAAGCACCGATAGCCCCGTTGAGTGCATGGGCCA

AGAAAAGGGCGAGTTCCGGGAG (Human IL-15)
AACTGGGTGAACGTCATCAGCGATTTAAAGAAGATCGAAGATTTAATT

CAGTCCATGCATATCGACGCCACTTTATACACAGAATCCGACGTGCACC

CCTCTTGTAAGGTGACCGCCATGAAATGTTTTTTACTGGAGCTGCAAGT

TATCTCTTTAGAGAGCGGAGACGCTAGCATCCACGACACCGTGGAGAAT

TTAATCATTTTAGCCAATAACTCTTTATCCAGCAACGGCAACGTGACAG

AGTCCGGCTGCAAGGAGTGCGAAGAGCTGGAGGAGAAGAACATCAAGGA

GTTTCTGCAATCCTTTGTGCACATTGTCCAGATGTTCATCAATACCTCC

Example 16: Secretion of IL-18/IL-15RαSu and IL-12/TF/IL-15 Fusion Proteins

The IL-18/IL-15RαSu and IL-12/TF/IL-15 constructs were cloned into a pMSGV-1 modified retrovirus expression vector (Hughes, *Hum Gene Ther* 16:457-72, 2005 herein incorporated by reference), and the expression vector was transfected into CHO-K1 cells. Co-expression of the two constructs in CHO-K1 cells resulted in secretion of a soluble IL-12/TF/IL-15:IL-18/IL-15RαSu protein complex (referred to as 12t15/s18), which can be purified by anti-TF Ab affinity and other chromatography methods.

The amino acid sequence of the IL-18/IL-15RαSu fusion protein (including signal peptide sequence) is as follows (SEQ ID NO: 219):

(Signal peptide)
MKWVTFISLLFLFSSAYS (Human IL-18)
YFGKLESKLSVIRNLNDQVLFIDQGNRPLFEDMTDSDCRDNAPRTIFII

SMYKDSQPRGMAVTISVKCEKISTLSCENKIISFKEMNPPDNIKDTKSD

IIFFQRSVPGHDNKMQFESSSYEGYFLACEKERDLFKLILKKEDELGDR

SIMFTVQNED (Human IL-15Rα sushi domain)
ITCPPPMSVEHADIWVKSYSLYSRERYICNSGFKRKAGTSSLTECVLNK

ATNVAHWTTPSLKCIR

The amino acid sequence of the IL-12/TF/IL-15 fusion protein (including leader sequence) is as follows (SEQ ID NO: 220):

(Signal peptide)
MKWVTFISLLFLFSSAYS (Human IL-12 subunit beta (p40))
IWELKKDVYVVELDWYPDAPGEMVVLTCDTPEEDGITWTLDQSSEVLGS

GKTLTIQVKEFGDAGQYTCHKGGEVLSHSLLLLHKKEDGIWSTDILKDQ

KEPKNKTFLRCEAKNYSGRFTCWWLTTISTDLTFSVKSSRGSSDPQGVT

CGAATLSAERVRGDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSKREKKDRVFTDKTSATVICRKNASISVRAQDRYYS

SSWSEWASVPCS (Linker)
GGGGSGGGGSGGGGS (Human IL-12 subunit alpha (p35))
RNLPVATPDPGMFPCLHHSQNLLRAVSNMLQKARQTLEFYPCTSEEIDH

EDITKDKTSTVEACLPLELTKNESCLNSRETSFITNGSCLASRKTSFMM

ALCLSSIYEDLKMYQVEFKTMNAKLLMDPKRQIFLDQNMLAVIDELMQA

LNFNSETVPQKSSLEEPDFYKTKIKLCILLHAFRIRAVTIDRVMSYLNA

S (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS

In some cases, the leader peptide is cleaved from the intact polypeptide to generate the mature form that may be soluble or secreted.

Example 17: Recombinant Protein Quantitation of the 18t15-12s16 Complex

Figure 25:
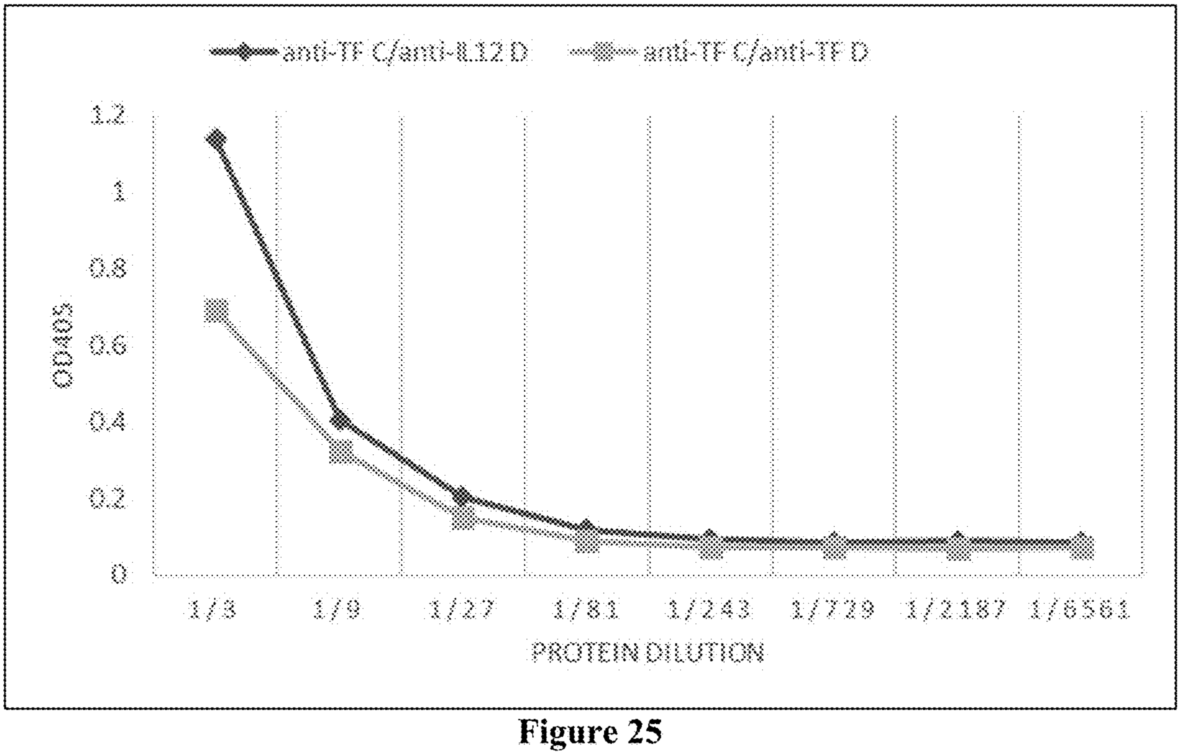
FIG. 25 shows a sandwich ELISA for the 18t15-12s16 complex, comprising an anti-human tissue factor capture antibody and a biotinylated anti-human IL-12 or IL-18 detection antibody.

The 18t15-12s16 complex (comprising IL-12/IL-15RαSu/αCD16scFv; IL-18/TF/IL-15) was detected and quantified using standard sandwich ELISA methods (FIG. 25). Anti-human tissue factor antibody/IL-2 or anti-TF Ab/IL-18 served as the capture antibody and biotinylated anti-human IL-12 or IL-18 antibody (BAF 219, D045-6, both R&D Systems) served as the detection antibody. Tissue factor was also detected using an anti-human tissue factor antibody (I43), and anti-human tissue factor antibody detection antibody.

Example 18: Creation of TGFβRII/IL-15RαSu and IL-21/TF/IL-15 DNA Constructs

Figure 26:
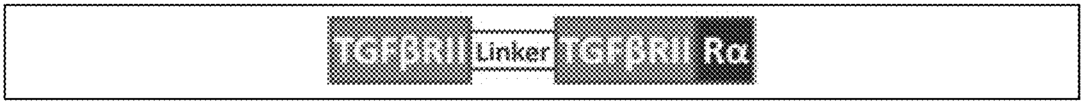
FIG. 26 shows a schematic diagram of an exemplary TGFβRII/IL-15RαSu DNA construct.

In a non-limiting example, a TGFβRII/IL-15RαSu DNA construct was created (FIG. 26). The human TGFβRII dimer and human IL-21 sequences were obtained from the UniProt website and DNA for these sequences was synthesized by Genewiz. A DNA construct was made linking the TGFβRII to another TGFβRII with a linker to generate a single chain version of TGFβRII and then directly linking the TGFβRII single chain dimer sequence to the N-terminal coding region of IL-15RαSu.

The nucleic acid sequences of the TGFβRII/IL-15RαSu construct (including signal sequence) is as follows (SEQ ID NO: 93):

(Signal peptide)
ATGAAGTGGGTGACCTTCATCAGCCTGCTGTTCCTGTTCTCCAGCGCCT

ACTCC (Human TGFβRII-1st fragment)
ATCCCCCCCCATGTGCAAAAGAGCGTGAACAACGATATGATCGTGACC

GACAACAACGGCGCCGTGAAGTTTCCCCAGCTCTGCAAGTTCTGCGATG

TCAGGTTCAGCACCTGCGATAATCAGAAGTCCTGCATGTCCAACTGCAC

GATCACCTCCATCTGCGAGAAGCCCCAAGAAGTGTGCGTGGCCGTGTGG

CGGAAAAATGACGAGAACATCACCCTGGAGACCGTGTGTCACGACCCCA

AGCTCCCTTATCACGACTTCATTCTGGAGGACGCTGCCTCCCCCAAATG

CATCATGAAGGAGAAGAAGAAGCCCGGAGAGACCTTCTTTATGTGTTCC

TGTAGCAGCGACGAGTGTAACGACAACATCATCTTCAGCGAAGAGTACA

ACACCAGCAACCCTGAT (Linker)
GGAGGTGGCGGATCCGGAGGTGGAGGTTCTGGTGGAGGTGGGAGT (Human TGFβRII-2nd fragment)
ATTCCTCCCCACGTGCAGAAGAGCGTGAATAATGACATGATCGTGACC

GATAACAATGGCGCCGTGAAATTTCCCCAGCTGTGCAAATTCTGCGATG

TGAGGTTTTCCACCTGCGACAACCAGAAGTCCTGTATGAGCAACTGCAC

AATCACCTCCATCTGTGAGAAGCCTCAGGAGGTGTGCGTGGCTGTCTGG

CGGAAGAATGACGAGAATATCACCCTGGAAACCGTCTGCCACGATCCCA

AGCTGCCCTACCACGATTTCATCCTGGAAGACGCCGCCAGCCCTAAGTG

-continued

CATCATGAAAGAGAAAAAGAAGCCTGGCGAGACCTTTTTCATGTGCTCC

TGCAGCAGCGACGAATGCAACGACAATATCATCTTTAGCGAGGAATACA

ATACCAGCAACCCCGAC (Human IL-15Rα sushi domain)
ATCACGTGTCCTCCTCCTATGTCCGTGGAACACGCAGACATCTGGGTC

AAGAGCTACAGCTTGTACTCCAGGGAGCGGTACATTTGTAACTCTGGTT

TCAAGCGTAAAGCCGGCACGTCCAGCCTGACGGAGTGCGTGTTGAACAA

GGCCACGAATGTCGCCCACTGGACAACCCCCAGTCTCAAATGTATTAGA

Figure 27:
FIG. 27 shows a schematic diagram of an exemplary IL-21/TF/IL-15 construct.

Additionally, an IL-21/TF/IL-15 construct was made linking the IL-21 sequence to the N-terminus coding region of tissue factor 219, and further linking the IL-21/TF construct to the N-terminus coding region of IL-15 (FIG. 27). The nucleic acid sequence of the IL-21/TF/IL-15 construct (including leader sequence) is as follows (SEQ ID NO: 89):

(Signal peptide)
ATGAAGTGGGTGACCTTCATCAGCCTGCTGTTCCTGTTCTCCAGCGCCT

ACTCC (Human IL-21)
CAGGGCCAGGACAGGCACATGATCCGGATGAGGCAGCTCATCGACAT

CGTCGACCAGCTGAAGAACTACGTGAACGACCTGGTGCCCGAGTTTCTG

CCTGCCCCCGAGGACGTGGAGACCAACTGCGAGTGGTCCGCCTTCTCCT

GCTTTCAGAAGGCCCAGCTGAAGTCCGCCAACACCGGCAACAACGAGCG

GATCATCAACGTGAGCATCAAGAAGCTGAAGCGGAAGCCTCCCTCCACA

AACGCCGGCAGGAGGCAGAAGCACAGGCTGACCTGCCCCAGCTGTGACT

CCTACGAGAAGAAGCCCCCCAAGGAGTTCCTGGAGAGGTTCAAGTCCCT

GCTGCAGAAGATGATCCATCAGCACCTGTCCTCCAGGACCCACGGCTCC

GAGGACTCC (Human Tissue Factor 219)
TCCGGCACCACCAATACCGTGGCCGCTTATAACCTCACATGGAAGAGC

ACCAACTTCAAGACAATTCTGGAATGGGAACCCAAGCCCGTCAATCAAG

TTTACACCGTGCAGATCTCCACCAAATCCGGAGACTGGAAGAGCAAGTG

CTTCTACACAACAGACACCGAGTGTGATTTAACCGACGAAATCGTCAAG

GACGTCAAGCAAACCTATCTGGCTCGGGTCTTTTCCTACCCCGCTGGCA

ATGTCGAGTCCACCGGCTCCGCTGGCGAGCCTCTCTACGAGAATTCCCC

CGAATTCACCCCTTATTTAGAGACCAATTTAGGCCAGCCTACCATCCAG

AGCTTCGAGCAAGTTGGCACCAAGGTGAACGTCACCGTCGAGGATGAAA

GGACTTTAGTGCGGCGGAATAACACATTTTTATCCCTCCGGGATGTGTT

CGGCAAAGACCTCATCTACACACTGTACTATTGGAAGTCCAGCTCCTCC

GGCAAAAAGACCGCTAAGACCAACACCAACGAGTTTTTAATTGACGTGG

ACAAAGGCGAGAACTACTGCTTCAGCGTGCAAGCCGTGATCCCTTCTCG

TACCGTCAACCGGAAGAGCACAGATTCCCCCGTTGAGTGCATGGGCCAA

GAAAAGGGCGAGTTCCGGGAG

-continued (Human IL-15)
AACTGGGTGAACGTCATCAGCGATTTAAAGAAGATCGAAGATTTAATT

CAGTCCATGCATATCGACGCCACTTTATACACAGAATCCGACGTGCACC

CCTCTTGTAAGGTGACCGCCATGAAATGTTTTTTACTGGAGCTGCAAGT

TATCTCTTTAGAGAGCGGAGACGCTAGCATCCACGACACCGTGGAGAAT

TTAATCATTTTAGCCAATAACTCTTTATCCAGCAACGGCAACGTGACAG

AGTCCGGCTGCAAGGAGTGCGAAGAGCTGGAGGAGAAGAACATCAAGGA

GTTTCTGCAATCCTTTGTGCACATTGTCCAGATGTTCATCAATACCTCC

Figure 28:
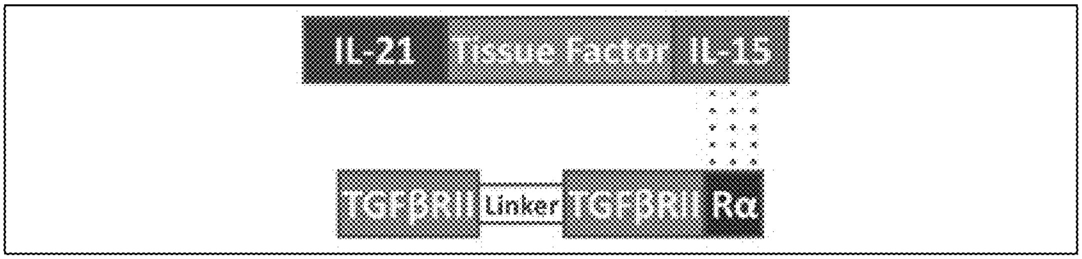
FIG. 28 shows a schematic diagram of the interaction between the exemplary IL-IL-21/TF/IL-15 and TGFβRII/IL-15RαSu constructs.
Figure 29:
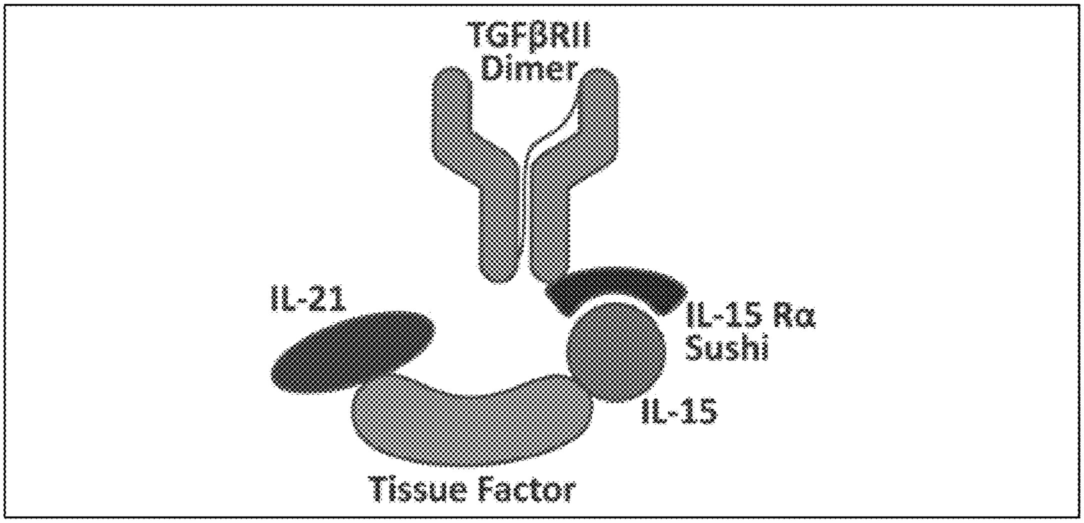
FIG. 29 shows a schematic diagram of the interaction between the exemplary TGFβRII/IL-15RαSu and IL-21/TF/IL-15 fusion proteins, resulting in an IL-21/TF/IL-15/TGFβRII/IL-15RαSu complex (21t15-TGFRs).

Example 19: Secretion of TGFβRII/IL-15RαSu and IL-21/TF/IL-15 Fusion Proteins The TGFβRII/IL-15RαSu and IL-21/TF/IL-15 DNA constructs were cloned into a pMSGV-1 modified retrovirus expression vector (as described in Hughes et al., *Hum Gene Ther* 16:457-72, 2005, herein incorporated by reference), and the expression vector was transfected into CHO-K1 cells. Co-expression of the two constructs in CHO-K1 cells resulted in secretion of the soluble IL-21/TF/IL-15:TGFβRII/IL-15RαSu protein complex (referred to as 21t15-TGFRs; FIG. 28 and FIG. 29). The 21t15-TGFRs complex was purified from CHO-K1 cell culture supernatant using anti-TF antibody affinity chromatography and other chromatography methods.

The amino acid sequence of the TGFβRII/IL-15RαSu construct (including signal peptide sequence) is as follows (SEQ ID NO: 92):

(Signal peptide)
MKWVTFISLLFLFSSAYS (Human TGFβRII-1$^{st}$ fragment)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD (Linker)
GGGGSGGGGSGGGGS (Human TGFβRII-2$^{nd}$ fragment)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD (Human IL-15Rα sushi domain)
ITCPPPMSVEHADIWVKSYSLYSRERYICNSGFKRKAGTSSLTECVLNK

ATNVAHWTTPSLKCIR

The amino acid sequence of the mature IL-21/TF/IL-15 fusion protein (including signal peptide sequence) is as follows (SEQ ID NO: 88):

(Signal peptide)
MKWVTFISLLFLFSSAYS (Human IL-21)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS

-continued

```
(Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE

(Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS
```

In some cases, the leader peptide is cleaved from the intact polypeptide to generate a mature form that may be soluble or secreted.

Example 20: Purification of 21t15-TGFRs by Immunoaffinity Chromatography

An anti-TF antibody affinity column was connected to a GE Healthcare AKTA™ Avant protein purification system. The flow rate was 4 mL/min for all steps except the elution step, which was 2 mL/min.

Figure 30:
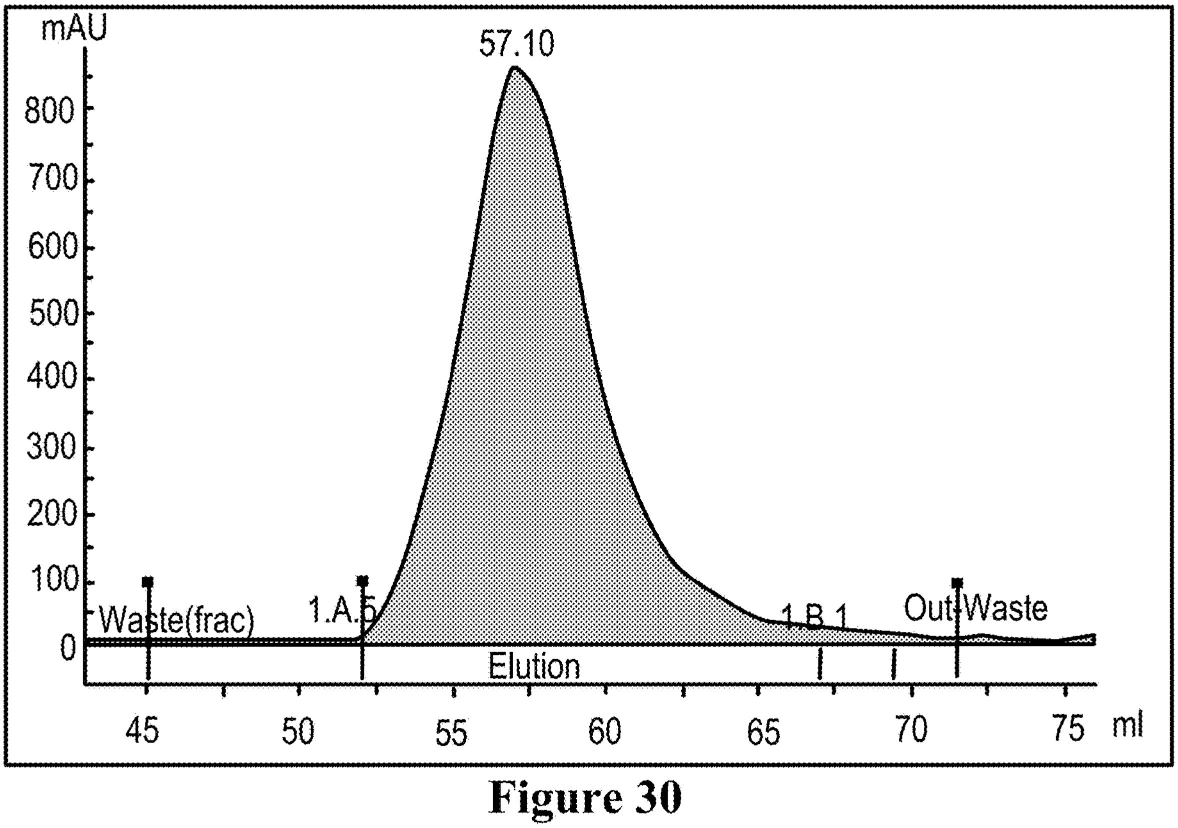
FIG. 30 shows a chromatograph of 21t15-TGFRs purification elution from an anti-TF antibody affinity column.

Cell culture harvest of 21t15-TGFRs was adjusted to pH 7.4 with 1M Tris base and loaded onto the anti-TF antibody affinity column equilibrated with 5 column volumes of PBS. After loading the sample, the column was washed with 5 column volumes PBS, followed by elution with 6 column volumes 0.1M acetic acid, pH 2.9. Absorbance at 280 nm was collected and then the sample was then neutralized to pH 7.5-8.0 by adding 1M Tris base. The neutralized sample was then buffer exchanged into PBS using Amicon® centrifugal filters with a 30 KDa molecular weight cutoff. FIG. 30 shows that the 21t15-TGFRs complex binds anti-TF antibody affinity column, wherein TF is a 21t15-TGFRs binding partner. The buffer-exchanged protein sample is stored at 2-8° C. for further biochemical analysis and biological activity testing.

After each elution, the anti-TF antibody affinity column was then stripped using 6 column volumes 0.1M glycine, pH 2.5. The column was then neutralized using 10 column volumes PBS, 0.05% sodium azide, and stored at 2-8° C.

Example 21: Size Exclusion Chromatography of 21t15-TGFRs

Figure 31:
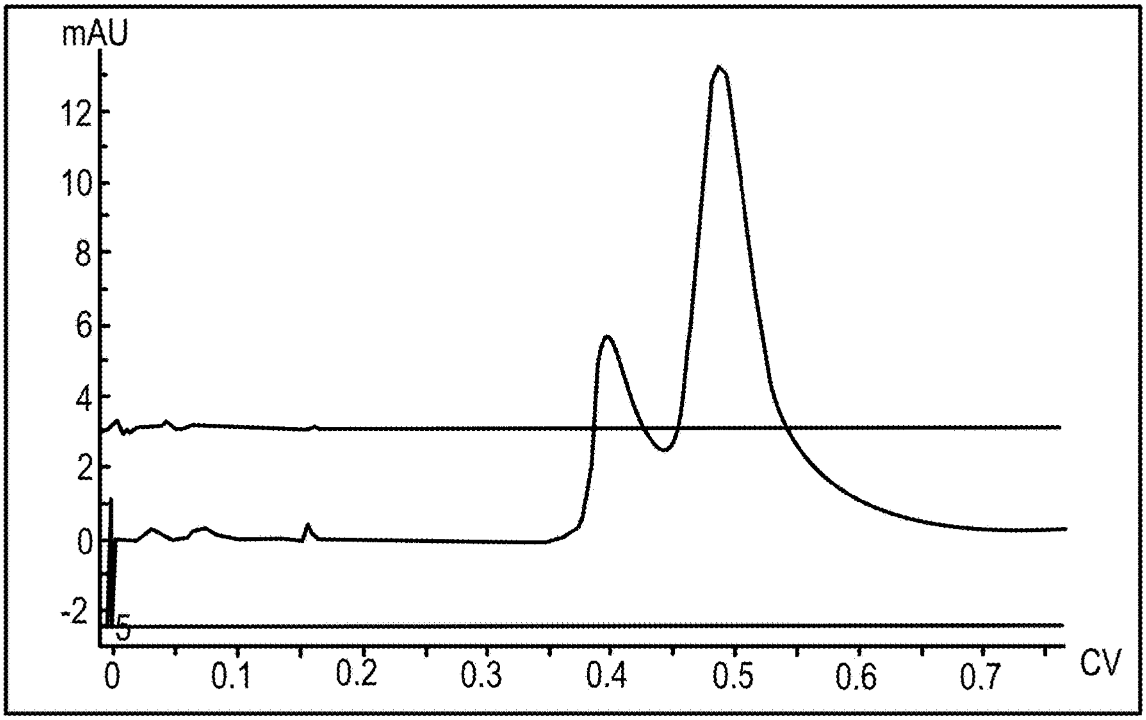
FIG. 31 shows an exemplary 21t15-TGFRs size exclusion chromatograph showing a main protein peak and a high molecular weight peak

A GE Healthcare Superdex® 200 Increase 10/300 GL gel filtration column was connected to a GE Healthcare AKTA™ Avant protein purification system. The column was equilibrated with 2 column volumes of PBS. The flow rate was 0.8 mL/min. A capillary loop was used to inject 200 μL of 1 mg/mL of 21t15-TGFRs complex onto the column. The injection was then chased with 1.25 column volumes of PBS. The SEC chromatograph was shown in FIG. 31. There were two protein peaks, likely representing a monomer and dimer forms of 21t15-TGFRs.

Example 22: SDS-PAGE of 21t15-TGFRs

Figure 32:
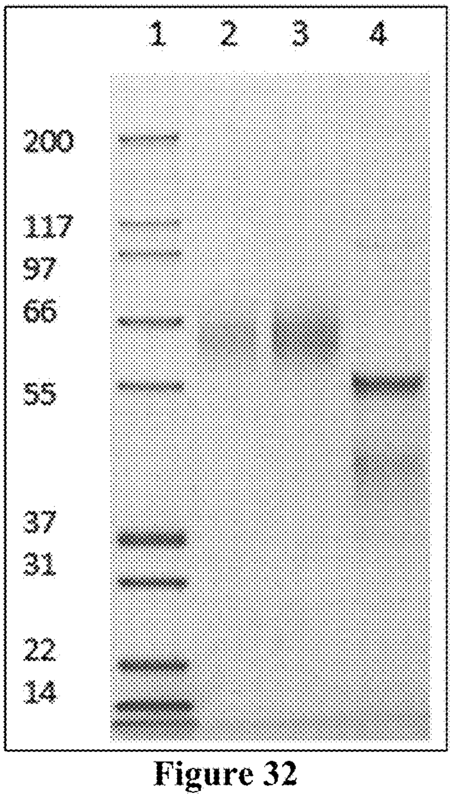
FIG. 32 shows an example of a 4-12% SDS-PAGE of the 21t15-TGFRs complex following disulfide bond reduction. Lane 1: Mark12 unstained marker (numbers on the left side indicate molecular weights in kDa); Lane 2: 21t15-TGFRs (0.5 μg); Lane 3: 21t15-TGFRs (1 μg); Lane 4: 21t15-TGFRs, deglycosylated (1 μg), wherein the MW was the expected size of 53 kDa and 39.08 kDa.
Figure 33:
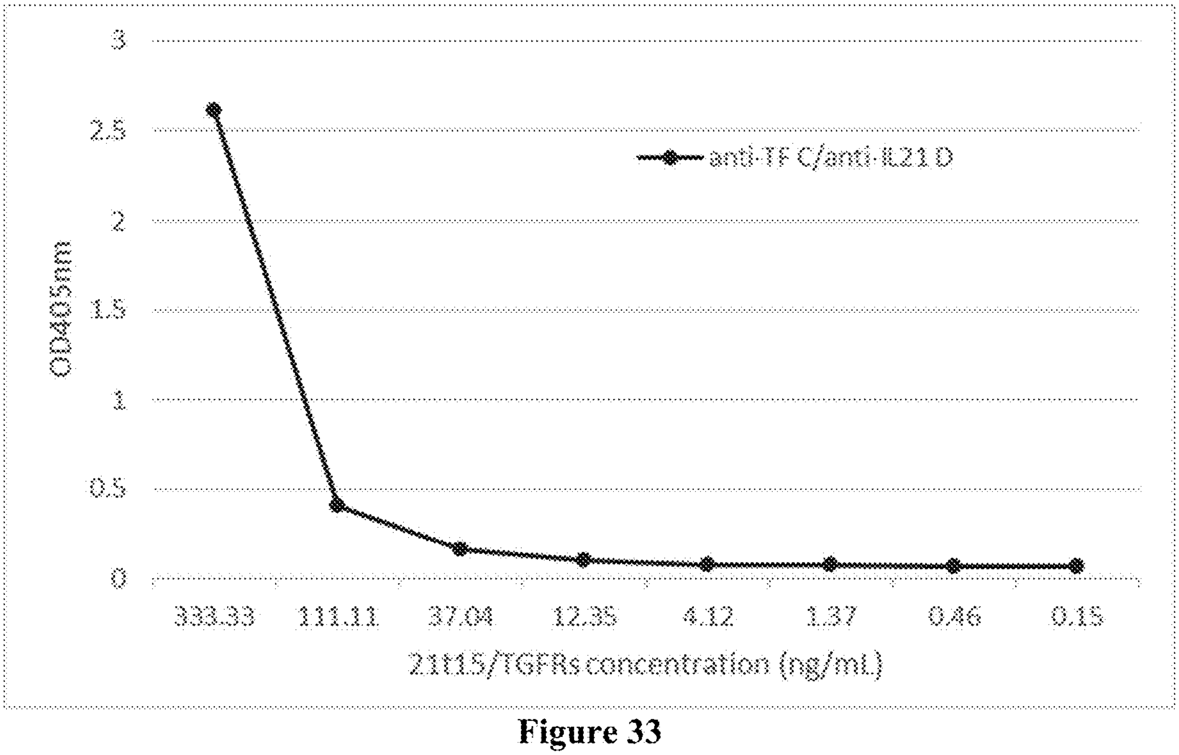
FIG. 33 shows a sandwich ELISA for the 21t15-TGFRs complex, comprising an anti-human tissue factor capture antibody and a biotinylated anti-human IL-21 detection antibody (13-7218-81, BioLegend).
Figure 34:
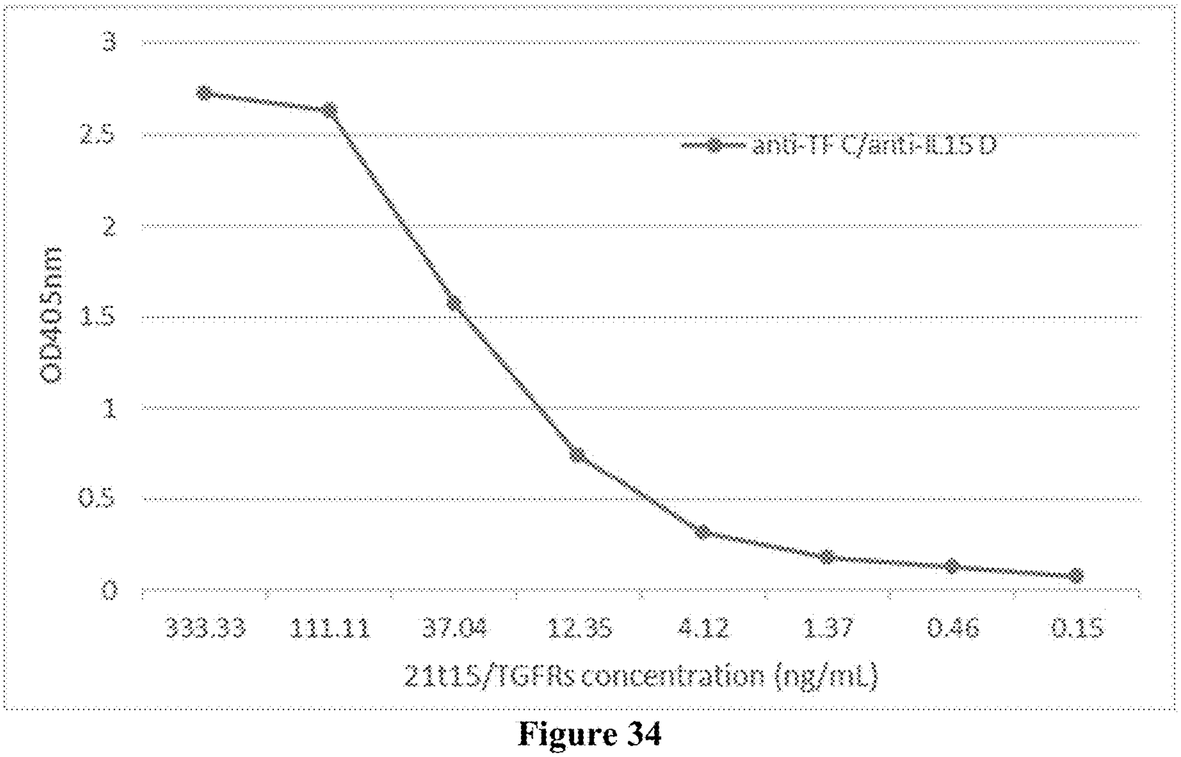
FIG. 34 shows a sandwich ELISA for the 21t15-TGFRs complex, comprising an anti-human tissue factor capture antibody and a biotinylated anti-human IL-15 detection antibody (BAM 247, R&D Systems).
Figure 35:
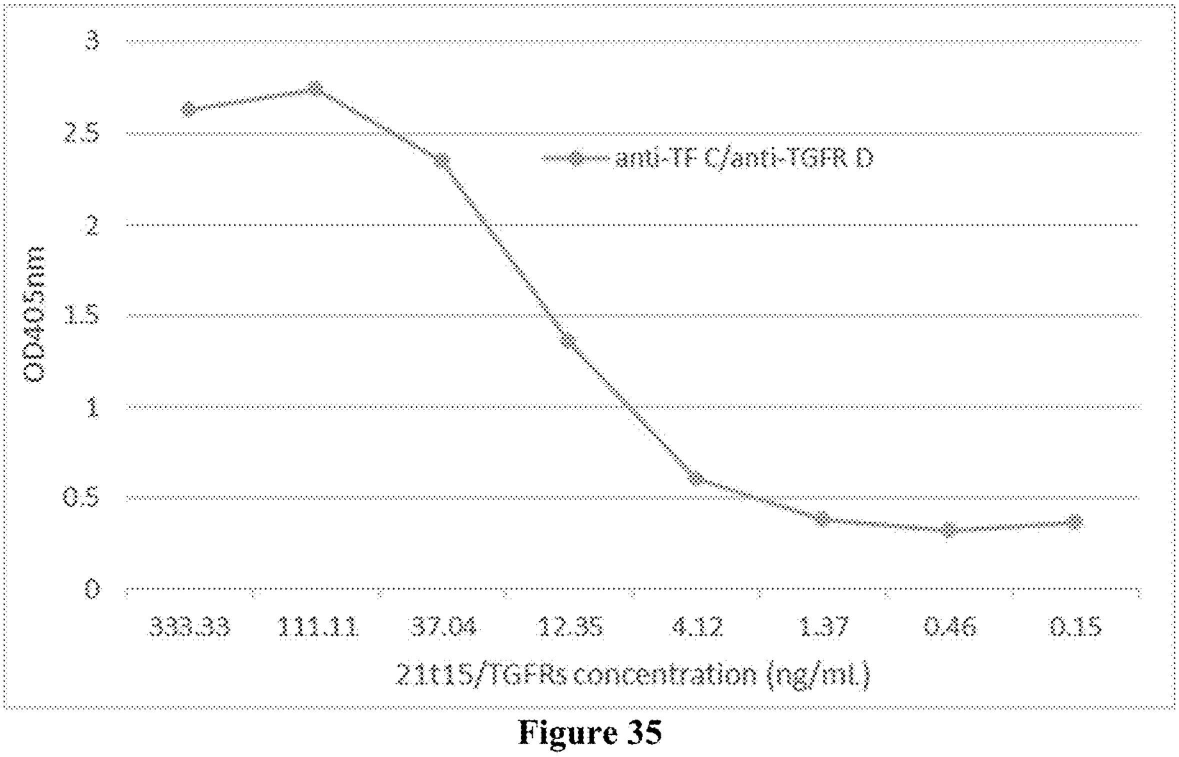
FIG. 35 shows a sandwich ELISA for the 21t15-TGFRs complex, comprising an anti-human tissue factor capture antibody and a biotinylated anti-human TGFβRII detection antibody (BAF241, R&D Systems).
Figure 36:
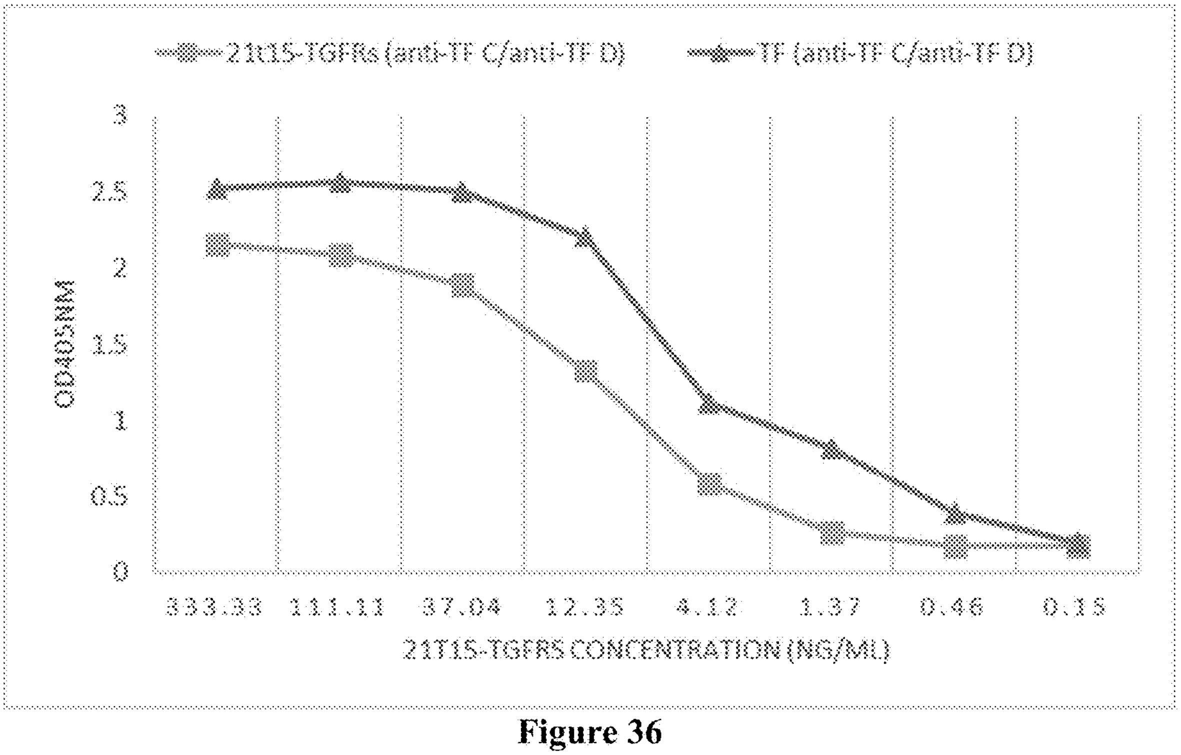
FIG. 36 shows a sandwich ELISA for the 21t15-TGFRs complex, comprising an anti-human tissue factor (I43) capture antibody and an anti-human tissue factor detection antibody.

To determine the purity and protein molecular weight, the purified 21t15-TGFRs complex protein sample was analyzed using 4-12% NuPage Bis-Tris protein gel SDS-PAGE under reduced conditions. The gel was stained with InstantBlue™ for about 30 min, followed by destaining overnight in purified water. FIG. 32 shows an example SDS gel of anti-TF antibody affinity purified 21t15-TGFRs, with bands at 39.08 kDa and 53 kDa Glycosylation of 21t15-TGFRs in CHO cells was confirmed using the Protein Deglycosylation Mix II kit (New England Biolabs) and the manufacturer's instructions. Deglycosylation reduces the molecular weight of 21t15-TGFRs, as seen in lane 4 of FIG. 32.

Example 23: Recombinant Protein Quantitation of 21t15-TGFRs Complexes

The 21t15-TGFRs complex was detected and quantified using standard sandwich ELISA methods (Figures. 33-37). Anti-human tissue factor antibody served as the capture antibody and biotinylated anti-human IL-21, IL-15, or TGFβRII served as the detection antibody. Tissue factor was also detected using an anti-human tissue factor capture antibody (I43), and anti-human tissue factor antibody detection antibody. The I43/anti-TF antibody ELISA was compared to purified tissue factor at similar concentrations.

Example 24: Immunostimulatory Capacity of the 21t15-TGFRs Complex

Figure 37:
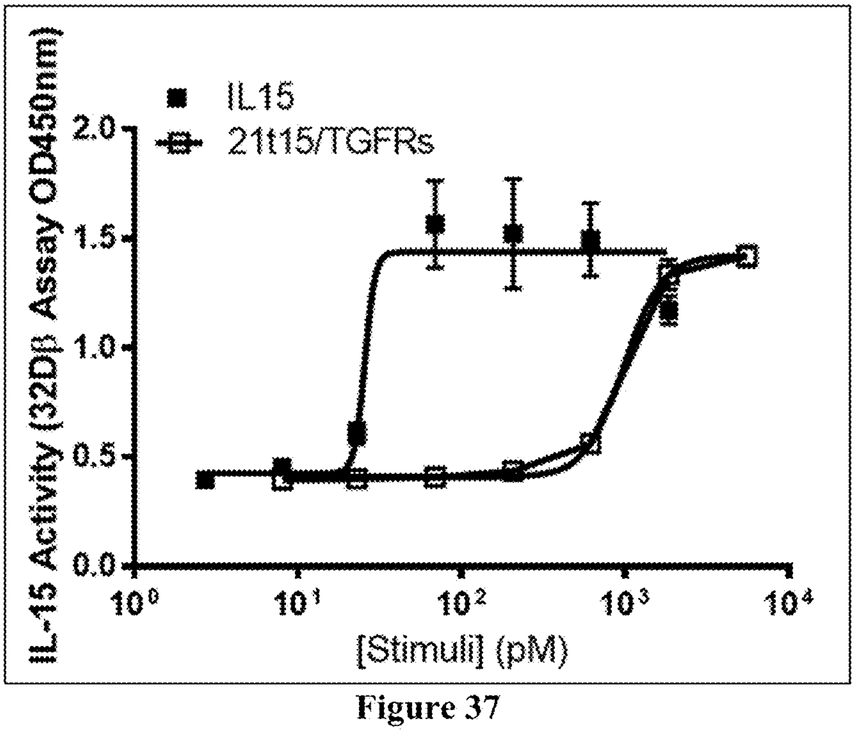
FIG. 37 shows IL-15-dependent proliferation of 32Dβ cells mediated by the 21t15-TGFRs complex (open squares) compared to IL-15 (black squares).

To assess the IL-15 immunostimulatory activity of the 21t15-TGFRs complexes, increasing concentrations of 21t15-TGFRs was added to 32Dβ cells ($10^4$ cell/well) in 200 μL IMDM:10% FBS media and cells were incubated for 3 days at 37° C. On the fourth day, WST-1 proliferation reagent (10 μL/well) then was added and after 4 hours, absorbance was measured at 450 nm to determine cell proliferation based on cleavage of WST-1 to a soluble formazan dye. Bioactivity of the human recombinant IL-15 was assessed as a positive control. As shown in FIG. 37, 21t15-TGFRs demonstrated IL-15-dependent 32Dβ cell proliferation. The 21t15-TGFRs complex was reduced compared to that of human recombinant IL-15, possibly due to the linkage of IL-21 and tissue factor to the IL-15 domain.

Figure 38:
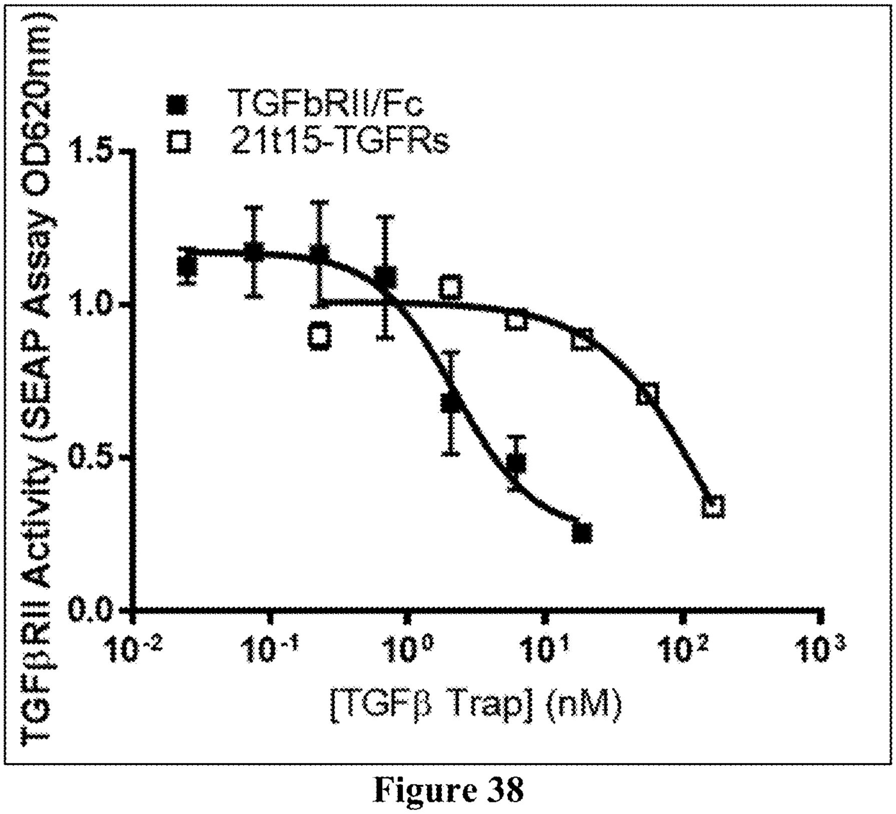
FIG. 38 shows biological activity of the TGFβRII domain within the 21t15-TGFRs complex (open squares). TGFβRII/Fc (black squares) served as a positive control.

Additionally, HEK-Blue TGFβ reporter cells (hkb-tgfb, InvivoGen) were used to measure the ability of 21t15-TGFRs to block TGFβ1 activity (FIG. 38). Increasing concentrations of 21t15-TGFRs were mixed with 0.1 nM of TGFβ1 and added to HEK-Blue TGFβ reporter cells (2.5×$10^4$ cell/well) in 200 μL IMDM:10% heat-inactivated FBS media. Cells were incubated overnight at 37° C. The next day, 20 μl of induced HEK-Blue TGFβ reporter cell supernatant was added to 180 μl of QUANTI-Blue (InvivoGen) and incubated for 1-3 hours at 37° C. 21t15-TGFRs activity was assessed by measuring absorbance at 620 nm. Human recombinant TGFβRII/Fc activity was assessed as a positive control.

These results demonstrate that TGFβRII domain of the 21t15-TGFRs complex retains its ability to trap TGFβ1. The ability of 21t15-TGFRs to block TGFβ1 activity was reduced compared to that of human recombinant TGFβRII/Fc, possibly due to the linkage of TGFβRII to the IL-15Rα sushi domain.

Example 25: Induction of Cytokine-Induced Memory-Like NK Cells by the 21t15-TGFRs Complex Cytokine-induced memory-like NK cells can be induced ex vivo following overnight stimulation of purified NK cells with saturating amounts of cytokines. These memory-like properties can be measured through expression of IL-2 receptor α (IL-2Rα, CD25), CD69 (and other activation markers), and increased IFN-γ production. To evaluate the ability of 21t15-TGFRs complexes to promote generation of cytokine-induced memory-like NK cells, purified human NK cells (>95% CD56+) were stimulated for 14-18 hours with 1 nM to 100 nM of the 21t15-TGFRs complex. Cell-surface CD25 and CD 69 expression and intracellular IFN-7 levels were assessed by antibody-staining and flow cytometry.

Figure 39:
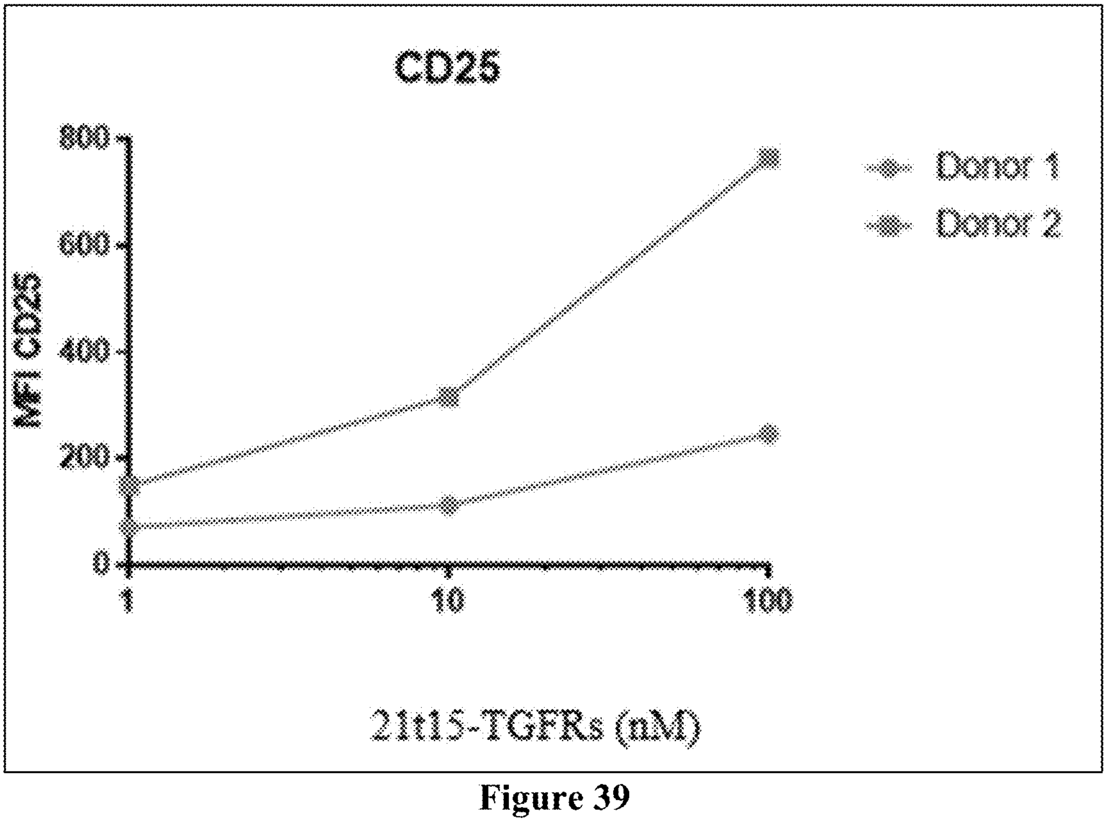
FIG. 39 A shows a flow cytometry graph of cell-surface CD25 expression of NK cells induced by the 21t15-TGFRs complex.
Figure 40:
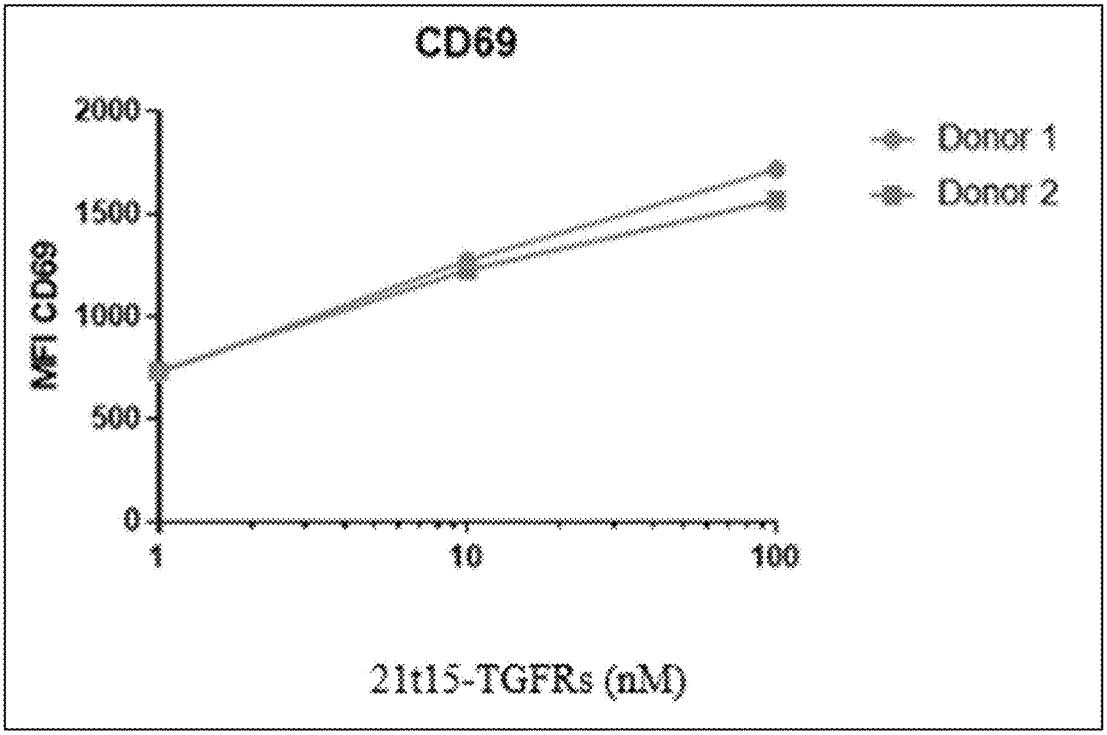
FIG. 40 shows a flow cytometry graph of cell-surface CD69 expression of NK cells induced by the 21t15-TGFRs complex.

Fresh human leukocytes were obtained from a blood bank and CD56+NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 specific antibodies (BioLegend). Cells were counted and resuspended in $0.2\times10^6$/mL in a 96 well flat bottom plate in 0.2 mL of complete media (RPMI 1640 (Gibco), supplemented with 2 mM L-glutamine (Thermo Life Technologies), penicillin (Thermo Life Technologies), streptomycin (Thermo Life Technologies), and 10% FBS (Hyclone)). Cells were stimulated with either mix-cytokines of hIL-21 (50 ng/mL) (Biolegend) and hIL-15 (50 ng/mL) (NCI) or with 1 nM, 10 nM, or 100 nM 21t15-TGFRs complex overnight at 37° C., 5% $CO_2$ for 14-18 hrs. The cells were then harvested and surface stained with CD56-BV421, CD16-BV510, CD25-PE, CD69-APCFire750 specific antibodies for 30 minutes. After staining, cells were washed (1500 RPM for 5 minutes at room temperature) in FACS buffer (1×PBS (Hyclone) with 0.5% BSA (EMD Millipore) and 0.001% sodium azide (Sigma)). After two washes, cells were analyzed using a BD FACSCelesta™ flow cytometer. (Plotted Data-Mean Fluorescence Intensity; FIG. 39 and FIG. 40).

Figure 41:
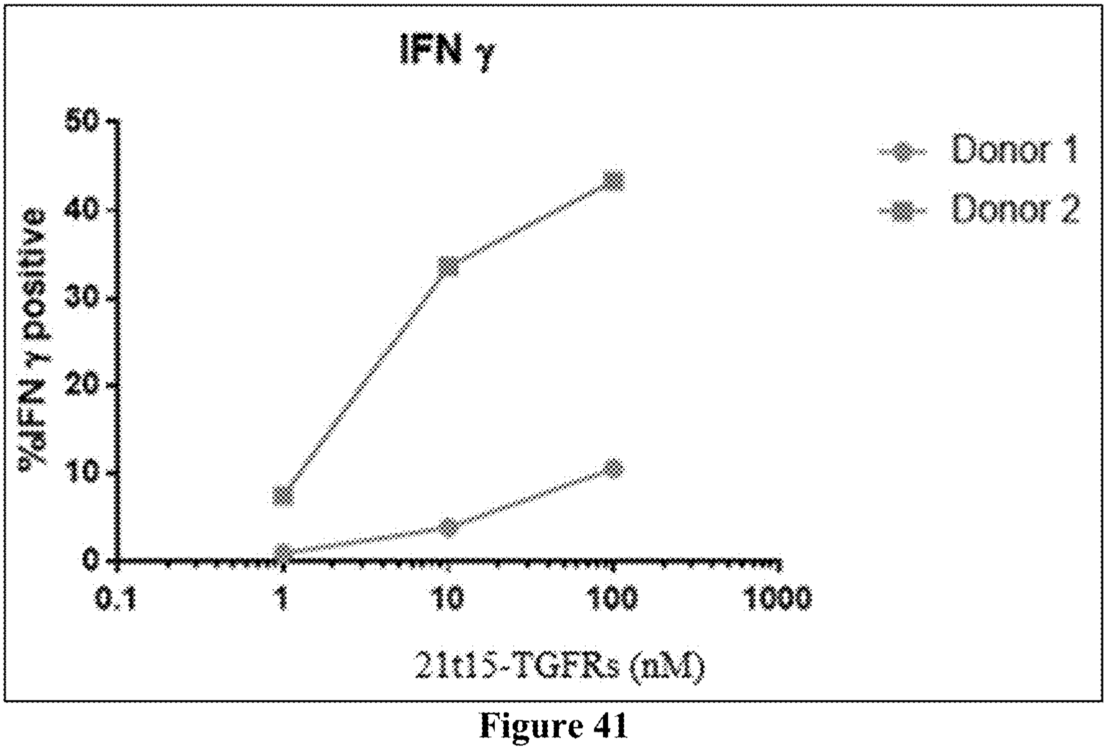
FIG. 41 shows a flow cytometry graph of intracellular interferon gamma expression of NK cells induced by the 21t15-TGFRs complex.

Fresh human leukocytes were obtained from a blood bank and CD56+NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 specific antibodies (BioLegend). Cells were counted and resuspended in 0.2×106/mL in a 96 well flat bottom plate in 0.2 mL of complete media (RPMI 1640 (Gibco), supplemented with 2 mM L-glutamine (Thermo Life Technologies), penicillin (Thermo Life Technologies), streptomycin (Thermo Life Technologies), and 10% FBS (Hyclone)). Cells were stimulated with either mix-cytokines of hIL-21 (50 ng/mL) (Biolegend) and hIL-15 (50 ng/mL) (NCI) or with 1 nM, 10 nM, or 100 nM 21t15-TGFRs complex overnight at 37° C., 5% $CO_2$ for 14-18 hrs. The cells were then treated with 10 μg/mL of Brefeldin A (Sigma) and 1× of Monensin (eBioscience) for 4 hrs. Cells were harvested and surface stained with CD56-BV421, CD16-BV510, CD25-PE, CD69-APCFire750 specific antibodies for 30 minutes. After staining, cells were washed (1500 RPM for 5 minutes at room temperature) in FACS buffer (1×PBS (Hyclone) with 0.5% BSA (EMD Millipore) and 0.001% sodium azide (Sigma)) and fixed for 10 minutes at room temperature. After fixation, cells were washed (1500 RPM for 5 minutes at room temperature) with 1× permeabilized buffer (eBioscience) and stained for intracellular IFN-γ-PE Ab (Biolegend) for 30 minutes at room temperature. Cells were washed once again with 1× permeabilized buffer and then washed with FACS buffer. Cell pellets were resuspended in 300 μls of FACS Buffer and analyzed using a BD FACSCelesta™ flow cytometer. (Plotted % of IFN-γ Positive Cells; FIG. 41).

Example 26: In Vitro Cytotoxicity of NK Cells Against Human Tumor Cells

Figure 42:
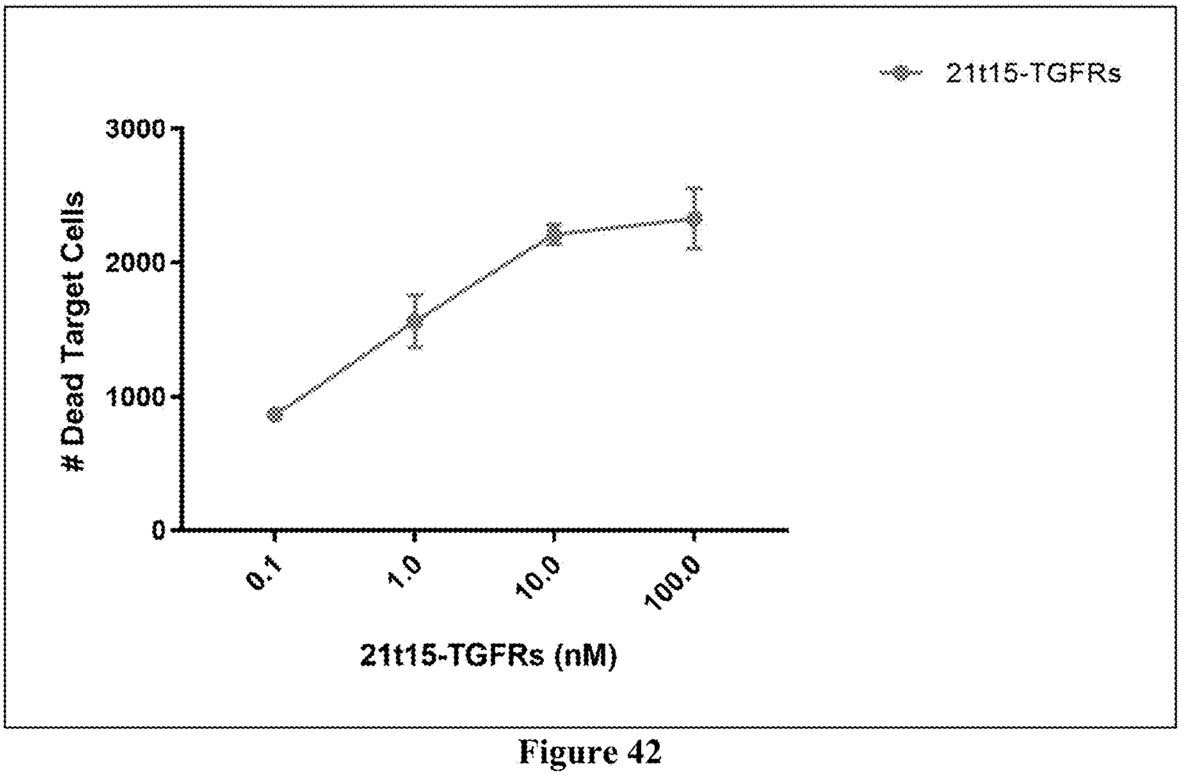
FIG. 42 shows cytotoxicity of 21t15-TGFRs-induced human NK cells against K562 cells.

K562 (CELLTRACE®, violet dye, labelled), human myelogenous leukemia cells, were incubated with purified human NK cells (using StemCell human NK cell purification kit (E:T ratio; 2:1)) in the presence of increasing concentrations of the 21t15-TGFRs complex. After 20 hours, the cultures were harvested, stained with propidium iodide (PI), and assessed by flow cytometry. As shown in FIG. 42, the 21t15-TGFRs complex induced human NK cytotoxicity against K562, as compared to control.

Example 27: Creation of an IL-21/TF Mutant/IL-15 DNA Construct and Resulting Fusion Protein Complex with TGFβRII/IL-15RαSu In a non-limiting example, an IL-21/TF mutant/IL-15 DNA construct was made by linking IL-21 directly to the N-terminus coding region of a tissue factor 219 mutant, and further linking the IL-21/TF mutant to the N-terminus coding region of IL-15.

The nucleic acid sequence of the IL-21/TF mutant/IL-15 construct (including signal peptide sequence) is as follows (SEQ ID NO: 221, shaded nucleotides are mutant and the mutant codons are underlined):

```
(Signal sequence)
ATGAAGTGGGTGACCTTCATCAGCCTGCTGTTCCTGTTCTCCAGCGCCTA

CTCC

(Human IL-21)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCCAAGGAGTTCCTGGAGAGGTTCAAGTCCCTGCTGCAGAA

GATGATCCATCAGCACCTGTCCTCCAGGACCCACGGCTCCGAGGACTCC

(Human Tissue Factor 219 mutants)
TCCGGCACCACCAATACCGTGGCCGCTTATAACCTCACATGGAAGAGCAC

CAACTTCGCGACAGCTCTGGAATGGGAACCCAAGCCCGTCAATCAAGTTT

ACACCGTGCAGATCTCCACCAAATCCGGAGACTGGAAGAGCAAGTGCTTC

TACACAACAGACACCGAGTGTGCTTTAACCGACGAAATCGTCAAGGACGT

CAAGCAAACCTATCTGGCTCGGGTCTTTTCCTACCCCGCTGGCAATGTCG

AGTCCACCGGCTCCGCTGGCGAGCCTCTCTACGAGAATTCCCCCGAATTC

ACCCCTTATTTAGAGACCAATTTAGGCCAGCCTACCATCCAGAGCTTCGA

GCAAGTTGGCACCAAGGTGAACGTCACCGTCGAGGATGAAAGGACTTTAG

TGGCGCGGAATAACACAGCTTTATCCCTCCGGGATGTGTTCGGCAAAGAC

CTCATCTACACACTGTACTATTGGAAGTCCAGCTCCTCCGGCAAAAAGAC

CGCTAAGACCAACACCAACGAGTTTTTAATTGACGTGGACAAAGGCGAGA

ACTACTGCTTCAGCGTGCAAGCCGTGATCCCTTCTCGTACCGTCAACCGG
```

-continued

```
AAGAGCACAGATTCCCCCGTTGAGTGCATGGGCCAAGAAAAGGGCGAGTT

CCGGGAG

(Human IL-15)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC
```

The amino acid sequence of the IL-21/TF mutant/IL-15 construct (including signal peptide sequence) is as follows (SEQ ID NO: 222, substituted residues are shaded):

```
(Signal peptide)
MKWVTFISLLFLFSSAYS

(Human IL-21)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS

(Human Tissue Factor 219)
SGTTNTVAAYNLTWKSTNFATALEWEPKPVNQVYTVQISTKSGDWKSKCF

YTTDTECALTDEIVKDVKQTYLARVFSYPAGNVESTGSAGEPLYENSPEF

TPYLETNLGQPTIQSFEQVGTKVNVTVEDERTLVARNNTALSLRDVFGKDL

YIYTLYYWKSSSSGKKTAKTNTNEFLIDVDKGENYCFSVQAVIPSRTVNR

KSTDSPVECMGQEKGEFRE

(Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS
```

In some cases, the leader peptide is cleaved from the intact polypeptide to generate a mature form that may be soluble or secreted.

In some embodiments, the IL-21/TF mutant/IL-15 DNA construct may be combined with an TGFβRII/IL-15RαSu DNA construct, transfected into cells using a retroviral vector as described above, and expressed as IL-21/TF mutant/IL-15 and TGFβRII/IL-15RαSu fusion proteins. The IL-15RαSu domain of the TGFβRII/IL-15RαSu fusion protein binds to the IL-15 domain of the IL-21/TF mutant/IL-15 fusion protein to create an IL-21/TF mutant/IL-15:TGFβRII/IL-15RαSu complex.

Example 28: Creation of IL-21/IL-15RαSu and TGFβRII/TF/IL-15 DNA Constructs and the Resulting Fusion Protein Complex In a non-limiting example, an IL-21/IL-15RαSu DNA construct was made by linking IL-21 directly to the IL-15RαSu subunit sequence. The nucleic acid sequence of the IL-21/IL-15RαSu construct (including signal sequence) is as follows (SEQ ID NO: 111):

```
(Signal sequence)
ATGAAGTGGGTGACCTTCATCAGCCTGCTGTTCCTGTTCTCCAGCGCCT

ACTCC

(Human IL-21)
CAGGGCCAGGACAGGCACATGATCCGGATGAGGCAGCTCATCGACAT

CGTCGACCAGCTGAAGAACTACGTGAACGACCTGGTGCCCGAGTTTCTG

CCTGCCCCCGAGGACGTGGAGACCAACTGCGAGTGGTCCGCCTTCTCCT

GCTTTCAGAAGGCCCAGCTGAAGTCCGCCAACACCGGCAACAACGAGCG

GATCATCAACGTGAGCATCAAGAAGCTGAAGCGGAAGCCTCCCTCCACA

AACGCCGGCAGGAGGCAGAAGCACAGGCTGACCTGCCCCAGCTGTGACT

CCTACGAGAAGAAGCCCCCCAAGGAGTTCCTGGAGAGGTTCAAGTCCCT

GCTGCAGAAGATGATCCATCAGCACCTGTCCTCCAGGACCCACGGCTCC

GAGGACTCC

(Human IL-15Rα sushi domain)
ATTACATGCCCCCCTCCCATGAGCGTGGAGCACGCCGACATCTGGGTG

AAGAGCTATAGCCTCTACAGCCGGGAGAGGTATATCTGTAACAGCGGCT

TCAAGAGGAAGGCCGGCACCAGCAGCCTCACCGAGTGCGTGCTGAATAA

GGCTACCAACGTGGCTCACTGGACAACACCCTCTTTAAAGTGCATCCGG
```

The amino acid sequence of the IL-21/IL-15RαSu construct (including signal peptide sequence) is as follows (SEQ ID NO: 110):

```
(Signal peptide)
MKWVTFISLLFLFSSAYS

(Human IL-21)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS

(Human IL-15Rα sushi domain)
ITCPPPMSVEHADIWVKSYSLYSRERYICNSGFKRKAGTSSLTECVLN

KATNVAHWTTPSLKCIR
```

In some cases, the leader peptide is cleaved from the intact polypeptide to generate a mature form that may be soluble or secreted.

In some embodiments, the IL-21/IL-15RαSu DNA construct may be combined with a TGFβRII/TF/IL-15 DNA construct, transfected into a retroviral vector as described above, and expressed as IL-21/IL-15RαSu and TGFβRII/TF/IL-15 fusion proteins. The IL-15RαSu domain of the IL-21/IL-15RαSu fusion protein binds to the IL-15 domain of the TGFβRII/TF/IL-15 fusion protein to create a TGFβRII/TF/IL-15:IL-21/IL-15RαSu complex.

The TGFβRII/TF/IL-15RαSu DNA construct was created by linking the TGFβRII sequence to the N-terminus coding region of human tissue factor 219 form, and then linking the TGFβRII/TF construct to the N-terminus coding region of IL-15. As described above, a single-chain version of TGFβRII (TGFβRII-linker-TGFβRII) was used. The nucleic acid sequence of the TGFβRII/TF/IL-15 construct (including leader sequence) is as follows (SEQ ID NO: 136):

(Signal peptide)
ATGAAGTGGGTGACCTTCATCAGCCTGCTGTTCCTGTTCTCCAGCGCCT

ACTCC (Human TGFβRII-1st fragment)
ATCCCCCCCCATGTGCAAAAGAGCGTGAACAACGATATGATCGTGACC

GACAACAACGGCGCCGTGAAGTTTCCCCAGCTCTGCAAGTTCTGCGATG

TCAGGTTCAGCACCTGCGATAATCAGAAGTCCTGCATGTCCAACTGCAC

GATCACCTCCATCTGCGAGAAGCCCCAAGAAGTGTGCGTGGCCGTGTGG

CGGAAAAATGACGAGAACATCACCCTGGAGACCGTGTGTCACGACCCCA

AGCTCCCTTATCACGACTTCATTCTGGAGGACGCTGCCTCCCCCAAATG

CATCATGAAGGAGAAGAAGAAGCCCGGAGAGACCTTCTTTATGTGTTCC

TGTAGCAGCGACGAGTGTAACGACAACATCATCTTCAGCGAAGAGTACA

ACACCAGCAACCCTGAT (Linker)
GGAGGTGGCGGATCCGGAGGTGGAGGTTCTGGTGGAGGTGGGAGT (Human TGFβRII-2nd fragment)
ATTCCTCCCCACGTGCAGAAGAGCGTGAATAATGACATGATCGTGACC

GATAACAATGGCGCCGTGAAATTTCCCCAGCTGTGCAAATTCTGCGATG

TGAGGTTTTCCACCTGCGACAACCAGAAGTCCTGTATGAGCAACTGCAC

AATCACCTCCATCTGTGAGAAGCCTCAGGAGGTGTGCGTGGCTGTCTGG

CGGAAGAATGACGAGAATATCACCCTGGAAACCGTCTGCCACGATCCCA

AGCTGCCCTACCACGATTTCATCCTGGAAGACGCCGCCAGCCCTAAGTG

CATCATGAAAGAGAAAAAGAAGCCTGGCGAGACCTTTTTCATGTGCTCC

TGCAGCAGCGACGAATGCAACGACAATATCATCTTTAGCGAGGAATACA

ATACCAGCAACCCCGAC (Human Tissue Factor 219)
TCCGGCACCACCAATACCGTGGCCGCTTATAACCTCACATGGAAGAGC

ACCAACTTCAAGACAATTCTGGAATGGGAACCCAAGCCCGTCAATCAAG

TTTACACCGTGCAGATCTCCACCAAATCCGGAGACTGGAAGAGCAAGTG

CTTCTACACAACAGACACCGAGTGTGATTTAACCGACGAAATCGTCAAG

GACGTCAAGCAAACCTATCTGGCTCGGGTCTTTTCCTACCCCGCTGGCA

ATGTCGAGTCCACCGGCTCCGCTGGCGAGCCTCTCTACGAGAATTCCCC

CGAATTCACCCCTTATTTAGAGACCAATTTAGGCCAGCCTACCATCCAG

AGCTTCGAGCAAGTTGGCACCAAGGTGAACGTCACCGTCGAGGATGAAA

GGACTTTAGTGCGGCGGAATAACACATTTTTATCCCTCCGGGATGTGTT

CGGCAAAGACCTCATCTACACACTGTACTATTGGAAGTCCAGCTCCTCC

GGCAAAAAGACCGCTAAGACCAACACCAACGAGTTTTTAATTGACGTGG

ACAAAGGCGAGAACTACTGCTTCAGCGTGCAAGCCGTGATCCCTTCTCG

TACCGTCAACCGGAAGAGCACAGATTCCCCCGTTGAGTGCATGGGCCAA

GAAAAGGGCGAGTTCCGGGAG (Human IL-15)
AACTGGGTGAACGTCATCAGCGATTTAAAGAAGATCGAAGATTTAATT

CAGTCCATGCATATCGACGCCACTTTATACACAGAATCCGACGTGCACC

CCTCTTGTAAGGTGACCGCCATGAAATGTTTTTTACTGGAGCTGCAAGT

-continued

TATCTCTTTAGAGAGCGGAGACGCTAGCATCCACGACACCGTGGAGAAT

TTAATCATTTTAGCCAATAACTCTTTATCCAGCAACGGCAACGTGACAG

AGTCCGGCTGCAAGGAGTGCGAAGAGCTGGAGGAGAAGAACATCAAGGA

GTTTCTGCAATCCTTTGTGCACATTGTCCAGATGTTCATCAATACCTCC

The amino acid sequence of the TGFβRII/TF/IL-15 fusion protein (including signal peptide) is as follows (SEQ ID NO: 135):

(Signal peptide)
MKWVTFISLLFLFSSAYS (Human TGFβRII-1st fragment)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD (Linker)
GGGGSGGGGSGGGGS (Human TGFβRII-2nd fragment)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS

Example 29: Creation of an IL-7/IL-15RαSu DNA Construct

Figure 43:
FIG. 43 shows a schematic diagram of an exemplary IL-7/IL-15RαSu DNA construct.

In a non-limiting example, an IL-7/IL-15RαSu DNA construct was created (see FIG. 43). The human IL-7 sequence, human IL-15RαSu sequence, human IL-15 sequence, and human tissue factor 219 sequence were obtained from the UniProt website and DNA for these sequences was synthesized by Genewiz. A DNA construct was made linking the IL-7 sequence to the IL-15RαSu sequence. The final IL-7/IL-15RαSu DNA construct sequence was synthesized by Genewiz.

The nucleic acid sequence encoding the second chimeric polypeptide of IL-7/IL-15RαSu construct (including signal peptide sequence) is as follows (SEQ ID NO: 103):

(Signal peptide)
ATGGGAGTGAAAGTTCTTTTTGCCCTTATTTGTATTGCTGTGGCCGAGG
CC (Human IL-7)
GATTGTGATATTGAAGGTAAAGATGGCAAACAATATGAGAGTGTTCTA

ATGGTCAGCATCGATCAATTATTGGACAGCATGAAAGAAATTGGTAGCA

ATTGCCTGAATAATGAATTTAACTTTTTTAAAAGACATATCTGTGATGC

TAATAAGGAAGGTATGTTTTTATTCCGTGCTGCTCGCAAGTTGAGGCAA

TTTCTTAAAATGAATAGCACTGGTGATTTTGATCTCCACTTATTAAAAG

TTTCAGAAGGCACAACAATACTGTTGAACTGCACTGGCCAGGTTAAAGG

AAGAAAACCAGCTGCCCTGGGTGAAGCCCAACCAACAAAGAGTTTGGAA

GAAAATAAATCTTTAAAGGAACAGAAAAAACTGAATGACTTGTGTTTCC

TAAAGAGACTATTACAAGAGATAAAAACTTGTTGGAATAAAATTTTGAT

GGGCACTAAAGAACAC (Human IL-15Rα sushi domain)
ATCACGTGCCCTCCCCCCATGTCCGTGGAACACGCAGACATCTGGGTC

AAGAGCTACAGCTTGTACTCCAGGGAGCGGTACATTTGTAACTCTGGTT

TCAAGCGTAAAGCCGGCACGTCCAGCCTGACGGAGTGCGTGTTGAACAA

GGCCACGAATGTCGCCCACTGGACAACCCCCAGTCTCAAATGCATTAGA

The second chimeric polypeptide of IL-7/IL-15RαSu construct (including signal peptide sequence) is as follows (SEQ ID NO: 102):

(Signal peptide)
MKWVTFISLLFLFSSAYS (Human IL-7)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEH (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS

Example 30: Creation of an IL-21/TF/IL-15 DNA Construct

Figure 44:
FIG. 44 shows a schematic diagram of an exemplary IL-21/TF/IL-15 DNA construct.

In a non-limiting example, an IL-21/TF/IL-15 construct was made (FIG. 44) by linking the IL-21 sequence to the N-terminus coding region of tissue factor 219, and further linking the IL-21/TF construct with the N-terminus coding region of IL-15.

The nucleic acid sequence encoding the first chimeric polypeptide of IL-21/TF/IL-15 construct (including leader sequence), synthesized by Genewiz, is as follows (SEQ ID NO: 89):

(Signal peptide)
ATGGGAGTGAAAGTTCTTTTTGCCCTTATTTGTATTGCTGTGGCCGAGG

CC (Human IL-21 fragment)
CAAGGTCAAGATCGCCACATGATTAGAATGCGTCAACTTATAGATATT

GTTGATCAGCTGAAAAATTATGTGAATGACTTGGTCCCTGAATTTCTGC

CAGCTCCAGAAGATGTAGAGACAAACTGTGAGTGGTCAGCTTTTTCCTG

TTTTCAGAAGGCCCAACTAAAGTCAGCAAATACAGGAAACAATGAAAGG

ATAATCAATGTATCAATTAAAAAGCTGAAGAGGAAACCACCTTCCACAA

ATGCAGGGAGAAGACAGAAACACAGACTAACATGCCCTTCATGTGATTC

TTATGAGAAAAAACCACCCAAAGAATTCCTAGAAAGATTCAAATCACTT

CTCCAAAAGATGATTCATCAGCATCTGTCCTCTAGAACACACGGAAGTG

AAGATTCC (Human Tissue Factor 219)
TCAGGCACTACAAATACTGTGGCAGCATATAATTTAACTTGGAAATCA

ACTAATTTCAAGACAATTTTGGAGTGGGAACCCAAACCCGTCAATCAAG

TCTACACTGTTCAAATAAGCACTAAGTCAGGAGATTGGAAAAGCAAATG

CTTTTACACAACAGACACAGAGTGTGACCTCACCGACGAGATTGTGAAG

GATGTGAAGCAGACGTACTTGGCACGGGTCTTCTCCTACCCGGCAGGGA

ATGTGGAGAGCACCGGTTCTGCTGGGGAGCCTCTGTATGAGAACTCCCC

AGAGTTCACACCTTACCTGGAGACAAACCTCGGACAGCCAACAATTCAG

AGTTTTGAACAGGTGGGAACAAAAGTGAATGTGACCGTAGAAGATGAAC

GGACTTTAGTCAGAAGGAACAACACTTTCCTAAGCCTCCGGGATGTTTT

TGGCAAGGACTTAATTTATACACTTTATTATTGGAAATCTTCAAGTTCA

GGAAAGAAAACAGCCAAAACAAACACTAATGAGTTTTTGATTGATGTGG

ATAAAGGAGAAAACTACTGTTTCAGTGTTCAAGCAGTGATTCCCTCCCG

AACAGTTAACCGGAAGAGTACAGACAGCCCGGTAGAGTGTATGGGCCAG

GAGAAAGGGGAATTCAGAGAA (Human IL-15)
AACTGGGTGAACGTCATCAGCGATTTAAAGAAGATCGAAGATTTAATT

CAGTCCATGCATATCGACGCCACTTTATACACAGAATCCGACGTGCACC

CCTCTTGTAAGGTGACCGCCATGAAATGTTTTTTACTGGAGCTGCAAGT

TATCTCTTTAGAGAGCGGAGACGCTAGCATCCACGACACCGTGGAGAAT

TTAATCATTTTAGCCAATAACTCTTTATCCAGCAACGGCAACGTGACAG

AGTCCGGCTGCAAGGAGTGCGAAGAGCTGGAGGAGAAGAACATCAAGGA

GTTTCTGCAATCCTTTGTGCACATTGTCCAGATGTTCATCAATACCTCC

The first chimeric polypeptide of IL-21/TF/IL-15 construct including leader sequence is SEQ ID NO: 88:

```
(Signal peptide)
                                        (SEQ ID NO: 223)
MGVKVLFALICIAVAEA

(Human IL-21)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS

(Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE

(Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS
```

Example 31: Secretion of IL-7/IL-15RαSu and IL-21/TF/IL-15 Fusion Proteins

Figure 45:
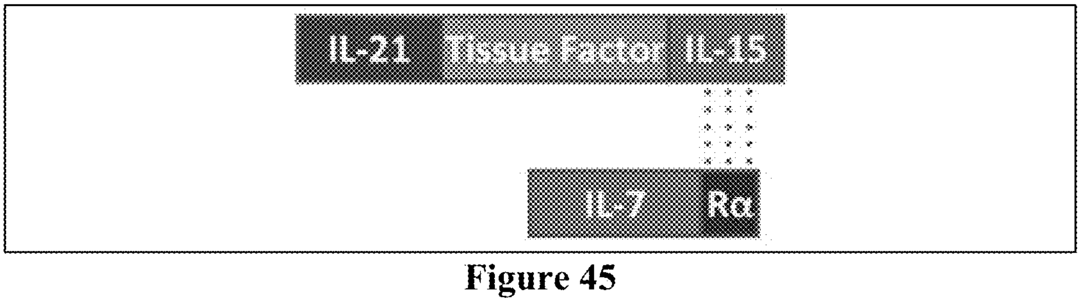
FIG. 45 shows a schematic diagram of the interaction between the exemplary IL-7/IL-15RαSu and IL-21/TF/IL-15 DNA constructs.
Figure 46:
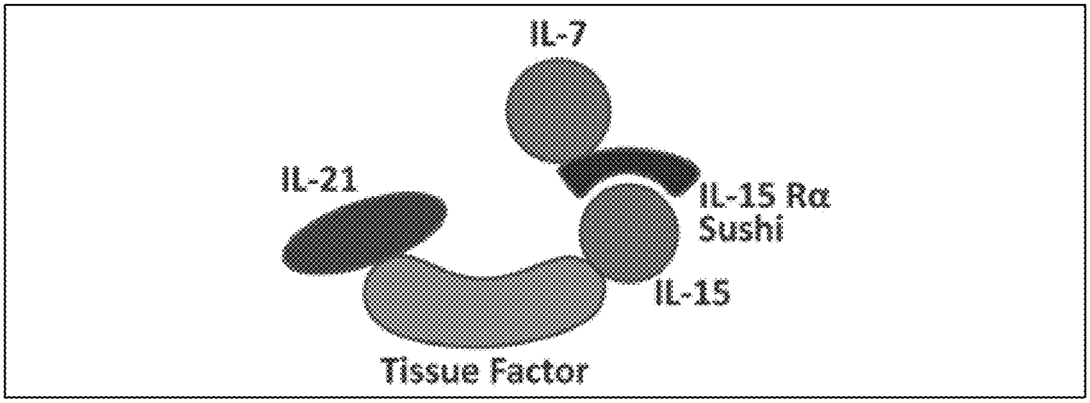
FIG. 46 shows a schematic diagram of the interaction between the exemplary IL-7/IL-15RαSu and IL-21/TF/IL-15 fusion proteins resulting in an IL-21/TF/IL-15:IL-7/IL-15RαSu complex (21t15-7s).

The IL-7/IL-15RαSu and IL-21/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-21/TF/IL-15:IL-7/IL-15RαSu protein complex (referred to as 21t15-7s; FIG. 45 and FIG. 46). The 21t15-7s protein was purified from CHO-K1 cell culture supernatant using anti-TF antibody affinity chromatography and size exclusion chromatography resulting in soluble (non-aggregated) protein complexes consisting of IL-7/IL-15RαSu and IL-21/TF/IL-15 fusion proteins.

In some cases, the leader (signal sequence) peptide is cleaved from the intact polypeptide to generate the mature form that may be soluble or secreted.

Example 32: Purification of 21t15-7s by Immunoaffinity Chromatography

An anti-TF antibody affinity column was connected to a GE Healthcare™ AKTA Avant protein purification system. The flow rate was 4 mL/min for all steps except the elution step, which was 2 mL/min.

Cell culture harvest of 21t15-7s was adjusted to pH 7.4 with 1M Tris base and loaded onto the anti-TF antibody affinity column equilibrated with 5 column volumes of PBS. After loading the sample, the column was washed with 5 column volumes PBS, followed by elution with 6 column volumes 0.1M acetic acid, pH 2.9. Absorbance at 280 nm was collected and then the sample was neutralized to pH 7.5-8.0 by adding 1M Tris base. The neutralized sample was then buffer exchanged into PBS using Amicon® centrifugal filters with a 30 KDa molecular weight cutoff. The buffer-exchanged protein sample was stored at 2-8° C. for further biochemical analysis and biological activity testing.

After each elution, the anti-TF antibody affinity column was then stripped using 6 column volumes 0.1M glycine, pH 2.5. The column was then neutralized using 10 column volumes PBS, 0.05% sodium azide and stored at 2-8° C.

Example 33: Size Exclusion Chromatography

A GE Healthcare Superdex® 200 Increase 10/300 GL gel filtration column was connected to a GE Healthcare AKTA™ Avant protein purification system. The column was equilibrated with 2 column volumes of PBS. The flow rate was 0.7 mL/min. A capillary loop was used to inject 200 μL of 1 mg/mL of 7t15-21s complex onto the column. The injection was chased with 1.25 column volumes of PBS.

Example 34: SDS-PAGE of 21t15-7s and 21t15-TGFRs

To determine the purity and protein molecular weight, the purified 21t15-7s or 21t15-TGFRs protein sample were analyzed using 4-12% NuPage Bis-Tris protein gel SDS-PAGE. The gel will be stained with InstantBlue™ for about 30 mi, followed by destaining overnight in purified water.

Example 35: Glycosylation of 21t15-7s and 21t15-TGFRs in CHO-K1 Cells

Glycosylation of 21t15-7s in CHO-K1 cells or 21t15-TGFRs in CHO-K1 cells were confirmed using the Protein Deglycosylation Mix II kit (New England Biolabs), according to the manufacturer's instructions.

Example 36: Recombinant Protein Quantitation of 21t15-7s and 21t15-TGFRs Complexes The 21t15-7s complex or the 21t15-TGFRs complex were detected and quantified using standard sandwich ELISA methods. Anti-human tissue factor antibody (IgG1) served as the capture antibody and biotinylated anti-human IL-21, IL-15, or IL-7 antibody (21t15-7s) or biotinylated anti-human IL-21, IL-15, or TGF-βRII antibody (21t15-TGFRs) served as the detection antibody. Tissue factor in purified 21t15-7s or 21t15-TGFRs protein complexes was detected using an anti-human tissue factor capture antibody, and anti-human tissue factor antibody (IgG1) detection antibody. The anti-TF antibody ELISA will be compared to purified tissue factor at similar concentrations.

Figure 47:
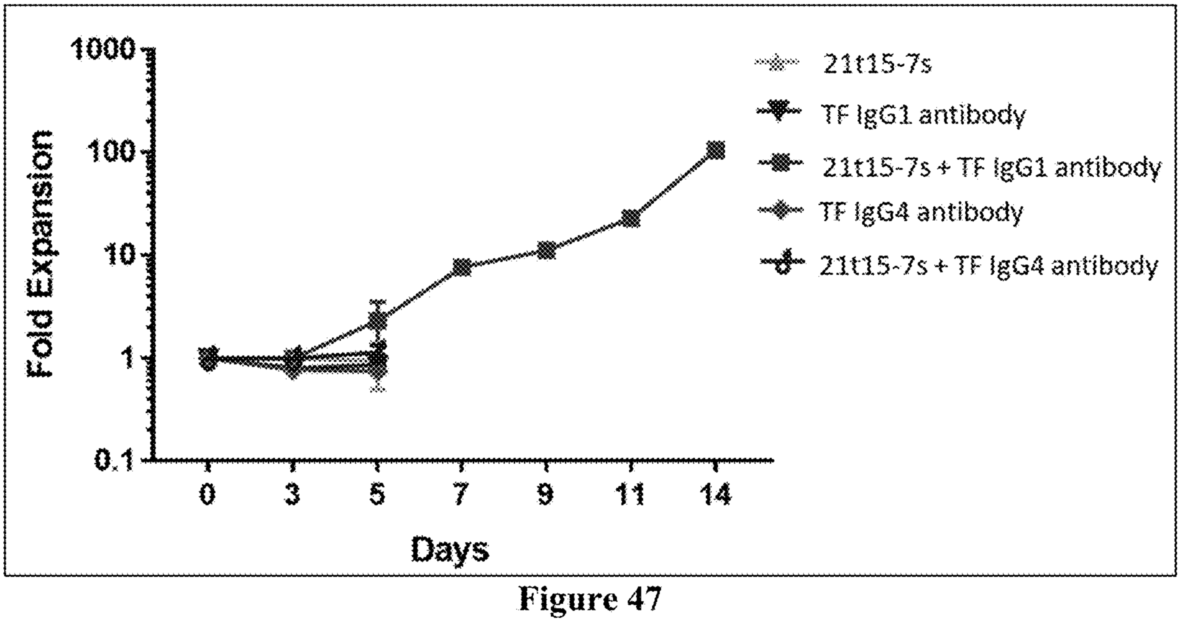
FIG. 47 shows the expansion of primary natural killer (NK) cells by stimulation with 21t15-7s+anti-TF IgG1 antibody.
Figure 54:
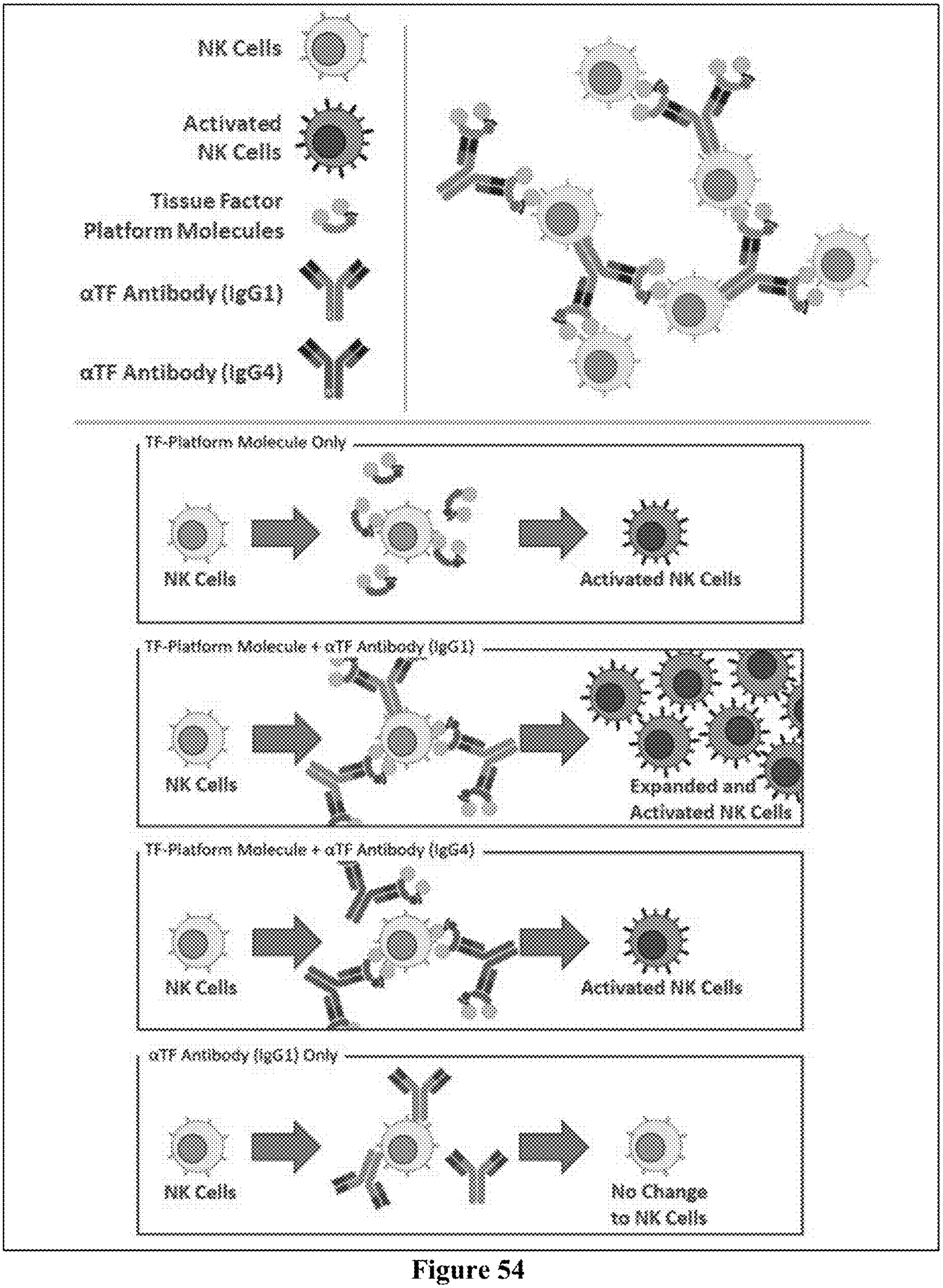
FIG. 54 shows in diagrammatic form the activation and expansion of primary natural killer (NK) cells by stimulation with 21t15-TGFRs+anti-TF IgG1 antibody.

Example 37: Expansion Capacity of Primary Natural Killer (NK) Cells by 21t15-7s Complex+Anti-TF IgG1 Antibody or 21t15-TGFRs Complex+Anti-TF IgG1 Antibody To assess the 21t15-7s complex's ability to expand primary natural killer (NK) cells, 21t15-7s complex and 21t15-7s complex+anti-TF IgG1 antibody was added to NK cells obtained from samples of fresh human leukocytes. Cells were stimulated with 50 nM of 21t15-7s complex with or without 25 nM of anti-TF IgG1 or anti-TF IgG4 antibody at 37° C. and 5% $CO_2$. Cells were maintained at concentration at $0.5\times10^6$/mL not exceeding $2.0\times10^6$/mL by counting every 48-72 hours and media was replenished with fresh stimulator. Cells stimulated with 21t15-7s complex or anti-TF IgG1 antibody or anti-TF IgG4 antibody, or anti-TF IgG4+21t15-7s complex were maintained up to day 5. FIG. 47 shows expansion of primary NK cells upon incubation with 21t15-7s complex+anti-TF IgG1 antibody. FIG. 54 also shows a schematic of the results.

Figure 48:
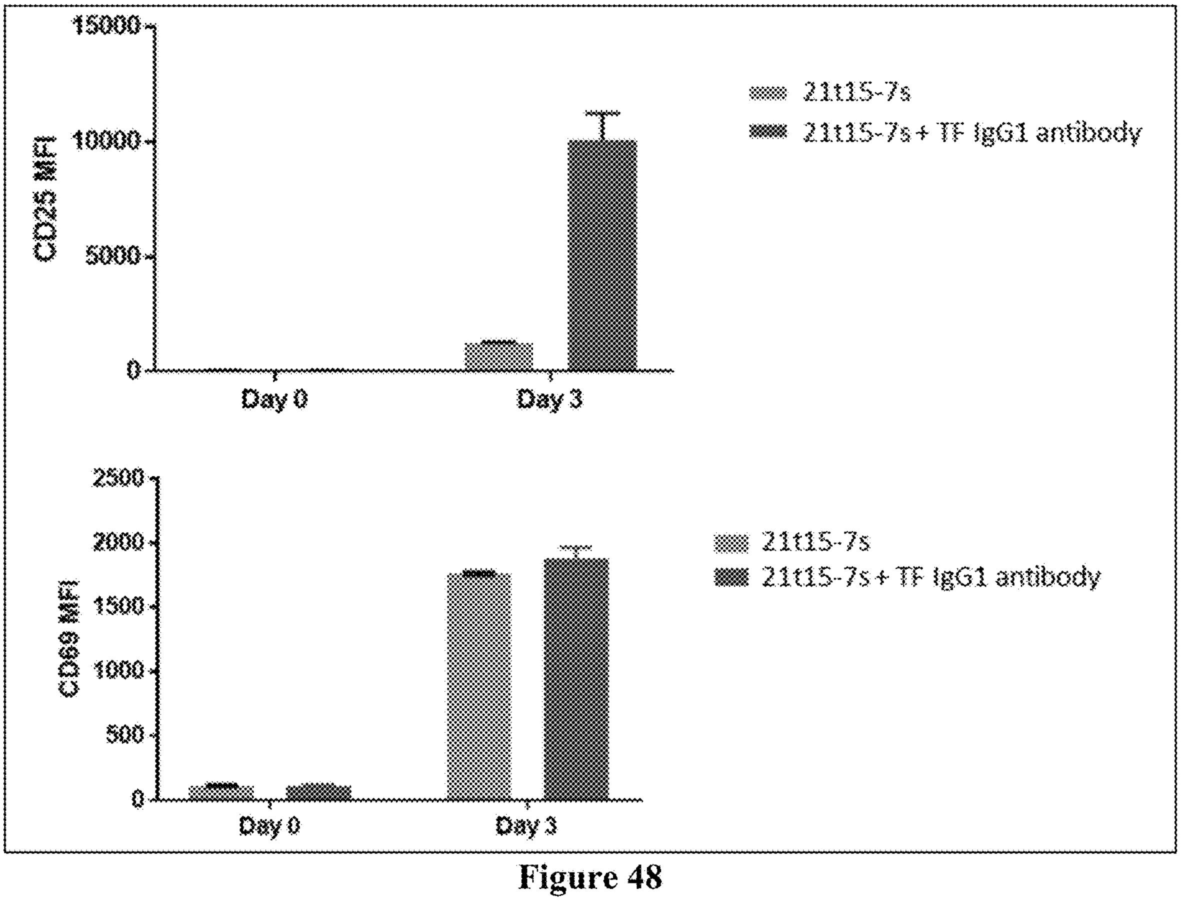
FIG. 48 shows activation of expanded primary NK cells, using CD25 MFI and CD69 MFI as markers of NK cell activation.

Example 38: Activation of Expanded NK Cells by the 21t15-7s Complex+Anti-TF IgG1 Antibody or the 21t15-TGFRs Complex+Anti-TF IgG1 Antibody Primary NK cells can be induced ex vivo following overnight stimulation of purified NK cells with 21t15-7s complex+anti-TF IgG1 antibody. Fresh human leukocytes were obtained from a blood bank and CD56+NK cells were isolated with the RosetteSep/human NK cell reagent (StemCell Technologies). The purity of NK cells was >80% and confirmed by staining with CD56-BV421 and CD16-BV510 specific antibodies (BioLegend). Cells were counted and resuspended in $1\times10^6$/mL in a 24 well flat bottom plate in 1 mL of complete media (RPMI 1640 (Gibco), supplemented with 4 mM L-glutamine (Thermo Life Technologies), penicillin (Thermo Life Technologies), streptomycin (Thermo Life Technologies), non-essential amino acid (Thermo Life Technologies), sodium pyruvate (Thermo Life Technologies), and 10% FBS (Hyclone)). Cells were stimulated with 50 nM of 21t15-7s with or without 25 nM of anti-TF IgG1 antibody at 37° C. and 5% $CO_2$. Cells were counted every 48-72 hours and maintained at a concentration of $0.5\times10^6$/mL to $2.0\times10^6$/mL until day 14. Media was periodically replenished with fresh stimulator. Cells were harvested and surface stained at day 3 with CD56-BV421, CD16-BV510, CD25-PE, CD69-APCFire750 specific antibodies (Biolegend and analyzed by Flow Cytometry-Celeste-BD Bioscience). FIG. 48 shows the activation markers CD25 MFI and CD69 MFI. The activation marker CD25 MFI increased with 21t15-7s complex+anti-TF IgG1 antibody stimulation, but not 21t15-7s complex stimulation. The activation marker CD69 MFI increased with both 21t15-7s complex+anti-TF IgG1 antibody and with 21t15-7s complex, alone.

Example 39: Cytotoxicity of NK Cells Against Human Tumor Cells

Figure 49:
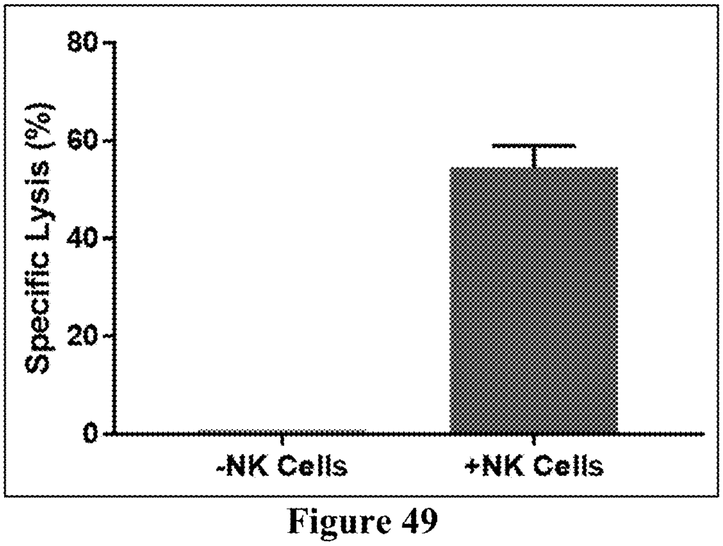
FIG. 49 shows cytotoxic activity of expanded NK cells against K562 human tumor cells, wherein NK cells stimulated with 21t15-7s+anti-TF IgG1 antibody demonstrate greater specific lysis of K562 cells than NK cells not stimulated with 21t15-7s+anti-TF IgG1 antibody.

Fresh human blood buffy coat was obtained from a blood bank. NK cells were isolated via negative selection using the RosetteSep/human NK cell reagent (StemCell Technologies). The NK cells were cultured in complete RPMI-1640 medium with 21t15-7s 100 nM and 50 nM of anti-TF IgG1 antibody for up to 11 days at 37° C. and 5% $CO_2$. The activated NK cells were mixed with CELLTRACE®, violet dye, labeled K562 cells at E:T ratio equal to 2:1 and incubated at 37° C. for 4 hours. The mixture was harvested and the percentage of dead K562 cells were determined by propidium iodide staining and flow cytometry. FIG. 49 shows increased specific lysis of K562 cells when incubated with expanded NK cells.

Example 40: Creation of an IL-21/IL-15RαSu DNA Construct

Figure 50:
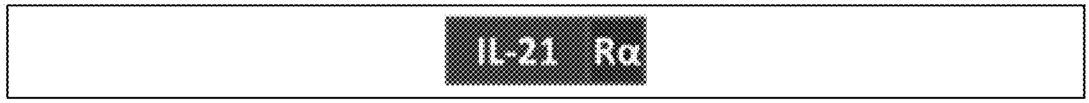
FIG. 50 shows a schematic diagram of an exemplary IL-21/IL-15RαSu DNA construct.

In a non-limiting example, an IL-21/IL-15RαSu DNA construct was created. The human IL-21 sequence and human IL-15RαSu sequence were obtained from the UniProt website and DNA for these sequences was synthesized by Genewiz. A DNA construct was made linking the IL-21 sequence to the IL-15RαSu sequence. The final IL-21/IL-15RαSu DNA construct sequence was synthesized by Genewiz. See FIG. 50.

Example 41: Creation of an IL-7/TF/IL-15 DNA Construct

Figure 51:
FIG. 51 shows a schematic diagram of an exemplary IL-7/TF/IL-15 DNA construct.

In a non-limiting example, an IL-7/TF/IL-15 construct was made by linking the IL-7 sequence to the N-terminus coding region of tissue factor 219, and further linking the IL-7/TF construct with the N-terminus coding region of IL-15. See FIG. 51.

Example 42: Creation of an IL-21/IL-15Rα Sushi DNA Construct

In a non-limiting example, a second chimeric polypeptide of IL-21/IL-15RαSu was generated. The human IL-21 and human IL-15Rα sushi sequences were obtained from the UniProt website and DNA for these sequences was synthesized by Genewiz. A DNA construct was made linking the IL-21 sequence to the IL-15Rα sushi sequence. The final IL-21/IL-15RαSu DNA construct sequence was synthesized by Genewiz.

The nucleic acid sequence encoding the second chimeric polypeptide of IL-21/IL-15RαSu domain (including leader sequence), synthesized by Genewiz, is as follows (SEQ ID NO: 111):

```
(Signal peptide)
ATGAAGTGGGTGACCTTCATCAGCCTGCTGTTCCTGTTCTCCAGCGCCT
ACTCC

(Human IL-21)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC

(Human IL-15Rα sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG
```

The second chimeric polypeptide of IL-21/IL-15Rα sushi domain (including leader sequence) is as follows (SEQ ID NO: 110):

```
(Signal Sequence)
MKWVTFISLLFLFSSAYS

(Human IL-21)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS
```

-continued (Human IL-15Rα sushi domain)
ITCPPPMSVEHADIWVKSYSLYSRERYICNSGFKRKAGTSSLTECVLNK

ATNVAHWTTPSLKCIR

Example 43: Creation of an IL-7/TF/IL-15 DNA Construct

In a non-limiting example, an exemplary first chimeric polypeptide of IL-7/TF/IL-15 was made by linking the IL-7 sequence to the N-terminus coding region of tissue factor 219, and further linking the IL-7/TF construct with the N-terminus coding region of IL-15. The nucleic acid sequence encoding the first chimeric polypeptide of IL-7/TF/IL-15 (including leader sequence), synthesized by Genewiz, is as follows (SEQ ID NO: 107):

(Signal peptide)
ATGAAGTGGGTGACCTTCATCAGCCTGCTGTTCCTGTTCTCCAGCGCCT

ACTCC (Human IL-7 fragment)
GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

GAAGAGGCTGCTGCAGGAGATCAAGACCTGCTGGAACAAGATCCTGATG

GGCACCAAGGAGCAT (Human Tissue Factor 219)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG (Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

-continued

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC

The first chimeric polypeptide of IL-7/TF/IL-15 (including leader sequence), is as follows (SEQ ID NO: 106):

(Signal peptide)
MKWVTFISLLFLFSSAYS (Human IL-7)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEH (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS

Example 44: Secretion of IL-21/IL-15RαSu and IL-7/TF/IL-15 Fusion Proteins

Figure 52:
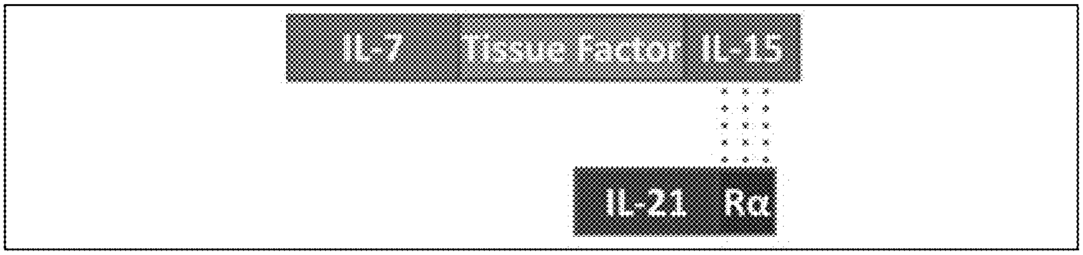
FIG. 52 shows a schematic diagram of the interaction between the exemplary IL-21/IL-15RαSu and IL-7/TF/IL-15 DNA constructs.
Figure 53:
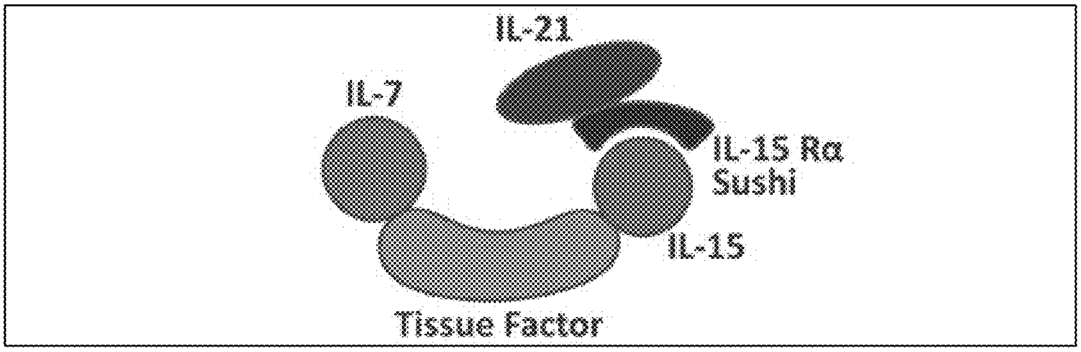
FIG. 53 shows a schematic diagram of the interaction between the exemplary IL-21/IL-15RαSu and IL-7/TF/IL-15 fusion proteins resulting in an IL-7/TF/IL-15:IL-21/IL-15RαSU complex (7t15-21s).

The IL-21/IL-15RαSu and IL-7/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-7/TF/IL-15:IL-21/IL-15RαSu protein complex (referred to as 7t15-21s). The 7t15-21s protein was purified from CHO-K1 cell culture supernatant using anti-TF antibody (IgG1) affinity chromatography and size exclusion chromatography resulting in soluble (non-aggregated) protein complexes consisting of IL-21/IL-15RαSu and IL-7/TF/IL-15 fusion proteins. See FIG. 52 and FIG. 53.

Figure 55:
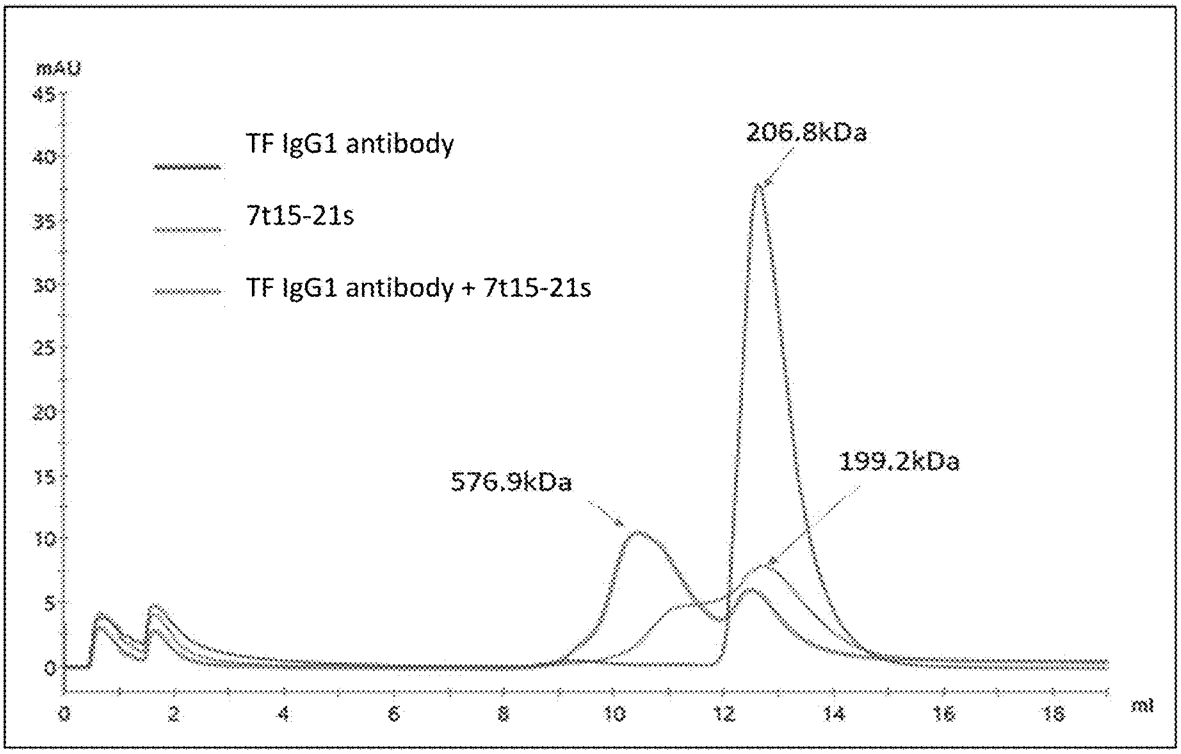
FIG. 55 shows size exclusion chromatography (SEC) profiles of anti-TF IgG1 antibody, 7t15-21s and the complex containing equal amounts of anti-TF IgG1 antibody and 7t15-21s.

Example 45: Analytical Size Exclusion Chromatography (SEC) Analysis of IL-21/IL-15RαSu and IL-7/TF/IL-15 Fusion Proteins To determine if anti-tissue factor monoclonal antibody and 7t15-21s can form an antibody-fusion-molecule complex, analytical size exclusion chromatography (SEC) was performed. A Superdex 200 Increase 10/300 GL gel filtration column (from GE Healthcare) was connected to an AKTA Avant system (from GE Healthcare). The column was equilibrated with 2 column volumes of PBS. The flow rate was 0.7 mL/min. Samples of the anti-TF mAb (1 mg/mL), 7t15-21s (1 mg/mL), and a mixture of combined at a 1:1 ratio, so the final concentration of each protein is 0.5 mg/mL) were in PBS. Each sample was injected into the Superdex 200 column using a capillary loop, and analyzed by SEC. The SEC chromatograph of each sample was shown in FIG. 55. The SEC results indicated that there are two protein peaks for 7t15-21s, likely representing a dimer (with an apparent molecular weight of 199.2 kDa) and a higher oligomer of 7t15-21s, and there is one peak (with an apparent molecular weight of 206.8 kDa) for the anti-TF mAb. However, as expected, a new protein peak with a higher molecular weight (with an apparent molecular weight of 576.9 kDa) was formed in the mixture sample containing the anti-TF mAb and 7t15-21s, indicating that the anti-TF mAb and 7t15-21s form an antibody-antigen complex through the binding of anti-TF mAb to TF in the fusion protein complex.

Example 46: Expansion Capacity of Primary Natural Killer (NK) Cells by 7t15-21s Complex+Anti-TF IgG1 Antibody To assess the 7t15-21s complex's ability to expand primary natural killer (NK) cells, 7t15-21s complex and 7t15-21s complex+anti-TF IgG1 antibody are added to NK cells obtained from samples of fresh human leukocytes. Cells are stimulated with 50 nM of 7t15-21s complex with or without 25 nM of anti-TF IgG1 or anti-TF IgG4 antibody at 37° C. and 5% $CO_2$. Cells are maintained at concentration at $0.5\times10^6$/mL not exceeding $2.0\times10^6$/mL by counting every 48-72 hours and media is replenished with fresh stimulator. Cells stimulated with 7t15-21s complex or anti-TF IgG1 antibody or anti-TF IgG4 antibody or anti-TF IgG4+7t15-21s complex are maintained up to day 5. Expansion of primary NK cells upon incubation with 21t15-7s complex+anti-TF IgG1 antibody is observed.

Example 47: Activation of Expanded NK Cells by the 7t15-21s Complex+Anti-TF IgG1 Antibody Primary NK cells are induced ex vivo following overnight stimulation of purified NK cells with 7t15-21s complex+anti-TF IgG1 antibody. Fresh human leukocytes are obtained from a blood bank and CD56+NK cells are isolated with the RosetteSep/human NK cell reagent (StemCell Technologies). The purity of NK cells is >80% and is confirmed by staining with CD56-BV421 and CD16-BV510 specific antibodies (BioLegend). Cells are counted and resuspended in $1\times10^6$/mL in a 24 well flat bottom plate in 1 mL of complete media (RPMI 1640 (Gibco), supplemented with 4 mM L-glutamine (Thermo Life Technologies), penicillin (Thermo Life Technologies), streptomycin (Thermo Life Technologies), non-essential amino acid (Thermo Life Technologies), sodium pyruvate (Thermo Life Technologies), and 10% FBS (Hyclone)). Cells are stimulated with 50 nM of 7t15-21s with or without 25 nM of anti-TF IgG1 antibody at 37° C. and 5% $CO_2$. Cells are counted every 48-72 hours and maintained at a concentration of $0.5\times10^6$/mL to $2.0\times10^6$/mL until day 14. Media is periodically replenished with fresh stimulator. Cells are harvested and surface stained at day 3 with CD56-BV421, CD16-BV510, CD25-PE, CD69-APCFire750 specific antibodies (Biolegend) and analyzed by Flow Cytometry-Celeste-BD Bioscience). The activation marker CD25 MFI are observed to increase with 7t15-21s complex+anti-TF IgG1 antibody stimulation, but not 7t15-21s complex stimulation. The activation marker CD69 MFI is observed to increase with both 7t15-21s complex+anti-TF IgG1 antibody and with 7t15-21s complex, alone.

Example 48: Increase in Glucose Metabolism in NK Cells Using 18t15-12s

A set of experiments was performed to determine the effect of the construct of 18t15-12s (FIG. 6) on oxygen consumption rate and extracellular acidification rate (ECAR) on NK cells purified from human blood.

In these experiments, fresh human leukocytes were obtained from the blood bank from two different human donors and NK cells were isolated via negative selection using the RosetteSep/human NK cell reagent (StemCell Technologies). The purity of NK cells was >80% and confirmed by staining with CD56-BV421 and CD16-BV510 specific Abs (BioLegend). The cells were counted and resuspended in $2\times10^6$/mL in 24-well, flat-bottom plates in 1 mL of complete media (RPMI 1640 (Gibco) supplemented with 4 mM L-glutamine (Thermo Life Technologies), penicillin (Thermo Life Technologies), streptomycin (Thermo Life Technologies), non-essential amino acid (Thermo Life Technologies), sodium pyruvate (Thermo Life Technologies) and 10% FBS (Hyclone)). The cells were stimulated with either (1) media alone, (2) 100 nM 18t15-12s, or (3) mixture of single cytokines recombinant human IL-12 (0.25 μg), recombinant human IL-15 (1.25 μg), and recombinant human IL-18 (1.25 μg) overnight at 37° C. and 5% $CO_2$. On the next day, the cells were harvested and extracellular flux assays on expanded NK cells were performed using a XFp Analyzer (Seahorse Bioscience). The harvested cells washed and plated $2.0\times10^5$ cells/well in at least duplicate for extracellular flux analysis of OCR (Oxygen Consumption Rate) and ECAR (Extracellular Acidification Rate). The glycolysis stress tests were performed in Seahorse Media contain 2 mM of glutamine. The following were used during the assay: 10 mM glucose; 100 nM oligomycin; and 100 mM 2-deoxy-D-glycose (2DG).

Figure 56:
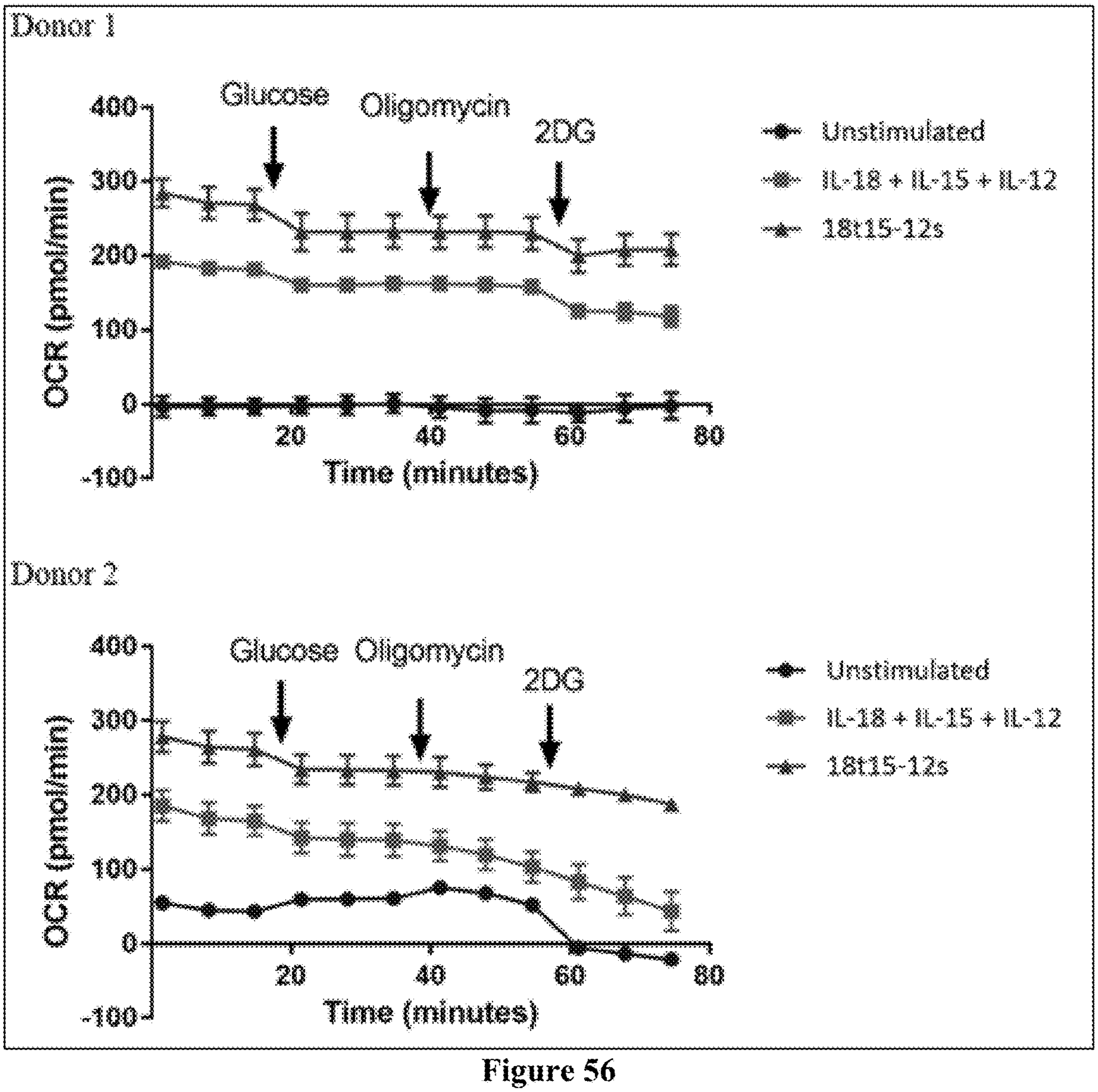
FIG. 56 shows the oxygen consumption rate (OCR) in pmoles/min for human NK cells isolated from blood ($2\times10^6$ cells/mL) of two different donors.
Figure 57:
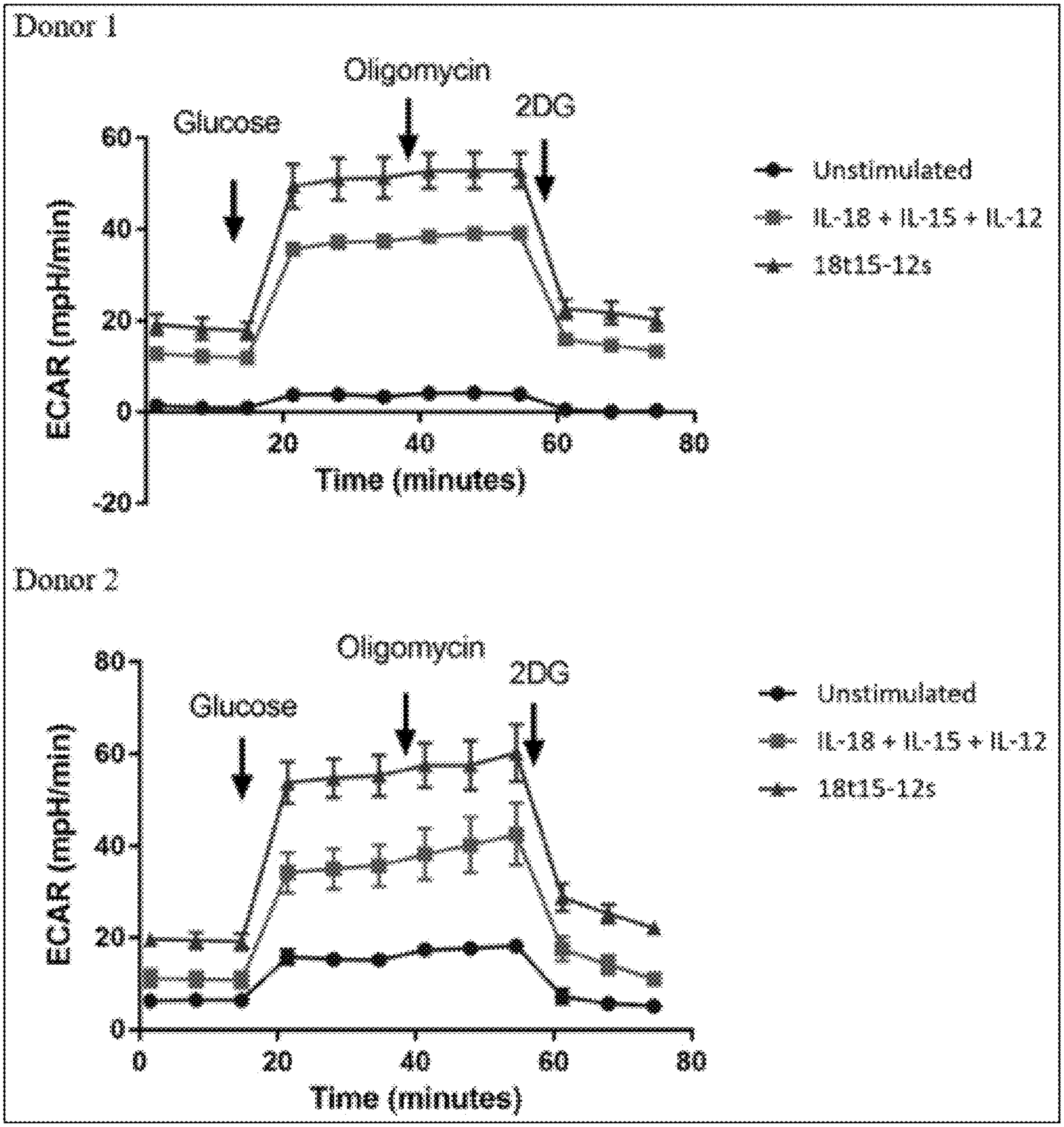
FIG. 57 shows the extracellular acidification rate (ECAR) in mpH/minute for human NK cells isolated from blood ($2\times10^6$ cells/mL) of two different donors.

The data show that the 18t15-12s results in significantly increased oxygen consumption rate (FIG. 56) and extracellular acidification rate (ECAR) as compared to the same cells activated with a combination of recombinant human IL-12, recombinant human IL-15, and recombinant human IL-18 (FIG. 57).

Example 49: 7t15-16s21 Fusion Protein Generation and Characterization

A fusion protein complex was generated comprising of anti-CD16scFv/IL-15RαSu/IL-21 and IL-7/TF/IL-15 fusion proteins. The human IL-7 and IL-21 sequences were obtained from the UniProt website and DNA for these sequences was synthesized by Genewiz. Specifically, a construct was made linking the IL-7 sequence to the N-terminus coding region of tissue factor 219 followed by the N-terminus coding region of IL-15.

The nucleic acid and protein sequences of a construct comprising IL-7 linked to the N-terminus of tissue factor 219 following with the N-terminus of IL-15 are shown below.

The nucleic acid sequence of the IL-7/TF/IL-15 construct (including signal peptide sequence) is as follows:

(Signal peptide)
ATGAAGTGGGTGACCTTCATCAGCCTGCTGTTCCTGTTCTCCAGCGCCT

ACTCC (Human IL-7)
GATTGCGACATCGAGGGCAAGGACGGCAAGCAGTACGAGAGCGTGCT

GATGGTGTCCATCGACCAGCTGCTGGACAGCATGAAGGAGATCGGCTCC

AACTGCCTCAACAACGAGTTCAACTTCTTCAAGCGGCACATCTGCGACG

CCAACAAGGAGGGCATGTTCCTGTTCAGGGCCGCCAGGAAACTGCGGCA

GTTCCTGAAGATGAACTCCACCGGCGACTTCGACCTGCACCTGCTGAAG

GTGTCCGAGGGCACCACCATCCTGCTGAACTGCACCGGACAGGTGAAGG

GCCGGAAACCTGCTGCTCTGGGAGAGGCCCAACCCACCAAGAGCCTGGA

GGAGAACAAGTCCCTGAAGGAGCAGAAGAAGCTGAACGACCTGTGCTTC

CTGAAGAGGCTGCTGCAGGAGATCAAGACCTGCTGGAACAAGATCCTGA

TGGGCACCAAGGAGCAT (Human Tissue Factor 219)
AGCGGCACAACCAACACAGTCGCTGCCTATAACCTCACTTGGAAGAG

CACCAACTTCAAAACCATCCTCGAATGGGAACCCAAACCCGTTAACCAA

GTTTACACCGTGCAGATCAGCACCAAGTCCGGCGACTGGAAGTCCAAAT

GTTTCTATACCACCGACACCGAGTGCGATCTCACCGATGAGATCGTGAA

AGATGTGAAACAGACCTACCTCGCCCGGGTGTTTAGCTACCCCGCCGGC

AATGTGGAGAGCACTGGTTCCGCTGGCGAGCCTTTATACGAGAACAGCC

CCGAATTTACCCCTTACCTCGAGACCAATTTAGGACAGCCCACCATCCA

AAGCTTTGAGCAAGTTGGCACAAAGGTGAATGTGACAGTGGAGGACGAG

CGGACTTTAGTGCGGCGGAACAACACCTTTCTCAGCCTCCGGGATGTGT

TCGGCAAAGATTTAATCTACACACTGTATTACTGGAAGTCCTCTTCCTC

CGGCAAGAAGACAGCTAAAACCAACACAAACGAGTTTTTAATCGACGTG

GATAAAGGCGAAAACTACTGTTTCAGCGTGCAAGCTGTGATCCCCTCCC

GGACCGTGAATAGGAAAAGCACCGATAGCCCCGTTGAGTGCATGGGCCA

AGAAAAGGGCGAGTTCCGGGAG (Human IL-15)
AACTGGGTGAACGTCATCAGCGATTTAAAGAAGATCGAAGATTTAATT

CAGTCCATGCATATCGACGCCACTTTATACACAGAATCCGACGTGCACC

CCTCTTGTAAGGTGACCGCCATGAAATGTTTTTTACTGGAGCTGCAAGT

TATCTCTTTAGAGAGCGGAGACGCTAGCATCCACGACACCGTGGAGAAT

TTAATCATTTTAGCCAATAACTCTTTATCCAGCAACGGCAACGTGACAG

AGTCCGGCTGCAAGGAGTGCGAAGAGCTGGAGGAGAAGAACATCAAGGA

GTTTCTGCAATCCTTTGTGCACATTGTCCAGATGTTCATCAATACCTCC

The amino acid sequence of IL-7/TF/IL-15 fusion protein (including the leader sequence) is as follows:

(Signal peptide)
MKWVTFISLLFLFSSAYS (Human IL-7)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEH (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS

Constructs were also made by linking the anti-CD16scFv sequence to the N-terminus coding region of IL-15RαSu chain followed by the N-terminus coding region of IL-21 which was synthesized by Genewiz. The nucleic acid and protein sequences of a construct comprising the anti-CD16scFv linked to the N-terminus of IL-15RαSu chain followed by the N-terminus coding region of IL-21 are shown below.

The nucleic acid sequence of the anti-CD16SscFv/IL-15 RαSu/IL-21 construct (including signal peptide sequence) is as follows:

(Signal peptide)
ATGAAGTGGGTGACCTTCATCAGCCTGCTGTTCCTGTTCTCCAGCGCCT

ACTCC ((Anti-human CD16scFv)
TCCGAGCTGACCCAGGACCCTGCTGTGTCCGTGGCTCTGGGCCAGACC

GTGAGGATCACCTGCCAGGGCGACTCCCTGAGGTCCTACTACGCCTCCT

GGTACCAGCAGAAGCCCGGCCAGGCTCCTGTGCTGGTGATCTACGGCAA

GAACAACAGGCCCTCCGGCATCCCTGACAGGTTCTCCGGATCCTCCTCC

GGCAACACCGCCTCCCTGACCATCACAGGCGCTCAGGCCGAGGACGAGG

CTGACTACTACTGCAACTCCAGGGACTCCTCCGGCAACCATGTGGTGTT

CGGCGGCGGCACCAAGCTGACCGTGGGCCATGGCGGCGGCGGCTCCGGA

GGCGGCGGCAGCGGCGGAGGAGGATCCGAGGTGCAGCTGGTGGAGTCCG

GAGGAGGAGTGGTGAGGCCTGGAGGCTCCCTGAGGCTGAGCTGTGCTGC

CTCCGGCTTCACCTTCGACGACTACGGCATGTCCTGGGTGAGGCAGGCT

CCTGGAAAGGGCCTGGAGTGGGTGTCCGGCATCAACTGGAACGGCGGAT

CCACCGGCTACGCCGATTCCGTGAAGGGCAGGTTCACCATCAGCAGGGA

CAACGCCAAGAACTCCCTGTACCTGCAGATGAACTCCCTGAGGGCCGAG

-continued

GACACCGCCGTGTACTACTGCGCCAGGGGCAGGTCCCTGCTGTTCGACT

ACTGGGGACAGGGCACCCTGGTGACCGTGTCCAGG (Human IL-15Rα sushi domain)
ATTACATGCCCCCCTCCCATGAGCGTGGAGCACGCCGACATCTGGGTG

AAGAGCTATAGCCTCTACAGCCGGGAGAGGTATATCTGTAACAGCGGCT

TCAAGAGGAAGGCCGGCACCAGCAGCCTCACCGAGTGCGTGCTGAATAA

GGCTACCAACGTGGCTCACTGGACAACACCCTCTTTAAAGTGCATCCGG (Human IL-21)
CAGGGCCAGGACAGGCACATGATCCGGATGAGGCAGCTCATCGACAT

CGTCGACCAGCTGAAGAACTACGTGAACGACCTGGTGCCCGAGTTTCTG

CCTGCCCCCGAGGACGTGGAGACCAACTGCGAGTGGTCCGCCTTCTCCT

GCTTTCAGAAGGCCCAGCTGAAGTCCGCCAACACCGGCAACAACGAGCG

GATCATCAACGTGAGCATCAAGAAGCTGAAGCGGAAGCCTCCCTCCACA

AACGCCGGCAGGAGGCAGAAGCACAGGCTGACCTGCCCCAGCTGTGACT

CCTACGAGAAGAAGCCCCCCAAGGAGTTCCTGGAGAGGTTCAAGTCCCT

GCTGCAGAAGATGATCCATCAGCACCTGTCCTCCAGGACCCACGGCTCC

GAGGACTCC

The amino acid sequence of the anti-CD16scFv/IL-15RαSu/IL-21 construct (including signal peptide sequence) is as follows:

(Signal peptide)
MKWVTFISLLFLFSSAYS (Anti-human CD16scFv)
SELTQDPAVSVALGQTVRITCQGDSLRSYYASWYQQKPGQAPVLVIYGK

NNRPSGIPDRFSGSSSGNTASLTITGAQAEDEADYYCNSRDSSGNHVVF

GGGTKLTVGHGGGGSGGGGSGGGGSEVQLVESGGGVVRPGGSLRLSCAA

SGFTFDDYGMSWVRQAPGKGLEWVSGINWNGGSTGYADSVKGRFTISRD

NAKNSLYLQMNSLRAEDTAVYYCARGRSLLFDYWGQGTLVTVSR (Human IL-15Rα sushi domain)
ITCPPPMSVEHADIWVKSYSLYSRERYICNSGFKRKAGTSSLTECVLNK

ATNVAHWTTPSLKCIR (Human IL-21)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS

In some cases, the leader peptide is cleaved from the intact polypeptide to generate the mature form that may be soluble or secreted.

Figure 58:
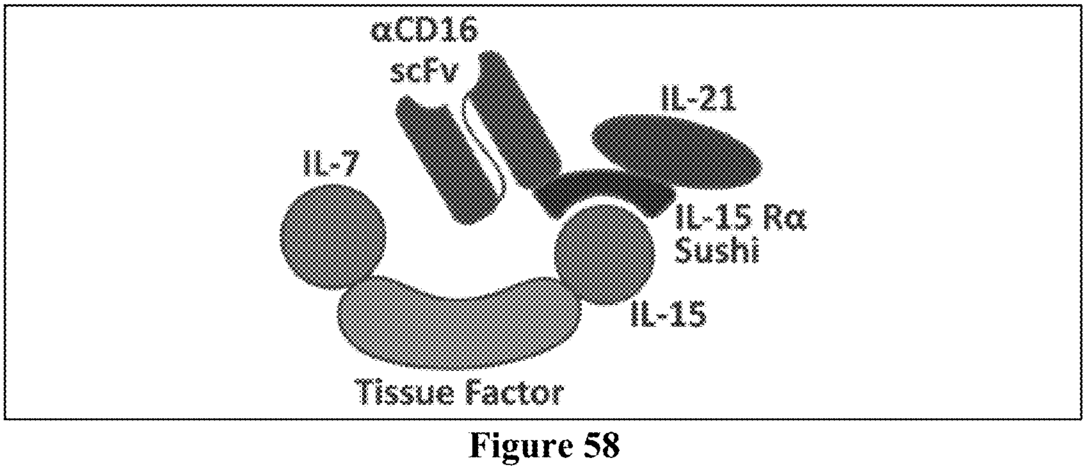
FIG. 58 shows a schematic of the 7t15-16s21 construct.
Figure 59:
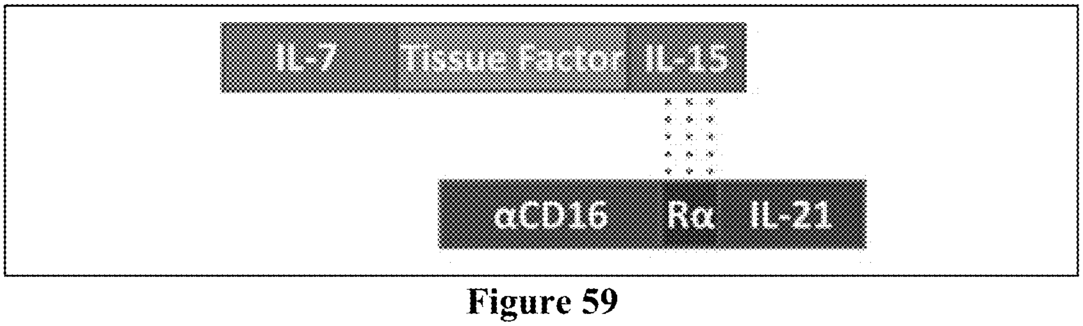
FIG. 59 shows an additional schematic of the 7t15-16s21 construct.

The anti-CD16scFv/IL-15RαSu/IL-21 and IL-7/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble IL-7/TF/IL-15:anti-CD16scFv/IL-15RαSu/IL-21 protein complex (referred to as 7t15-16s21; FIG. 58 and FIG. 59), which can be purified by anti-TF IgG1-based affinity and other chromatography methods.

Binding of 7t15-16s21 to CHO Cells Expressing Human CD16b

Figure 60A:
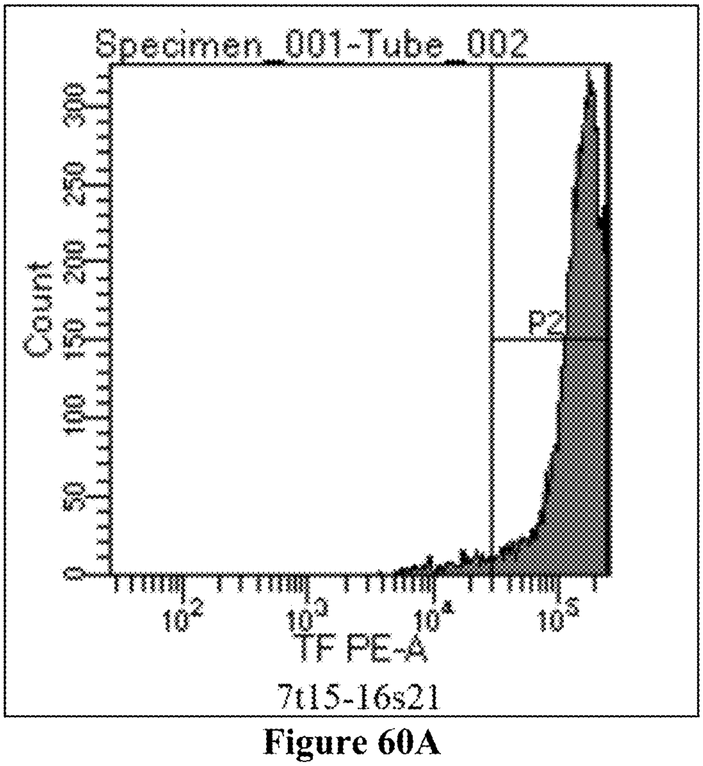
FIGS. 60A and 60B show binding of 7t15-16s21 to CHO cells expressing human CD16b as compared to a control protein.
Figure 60B:
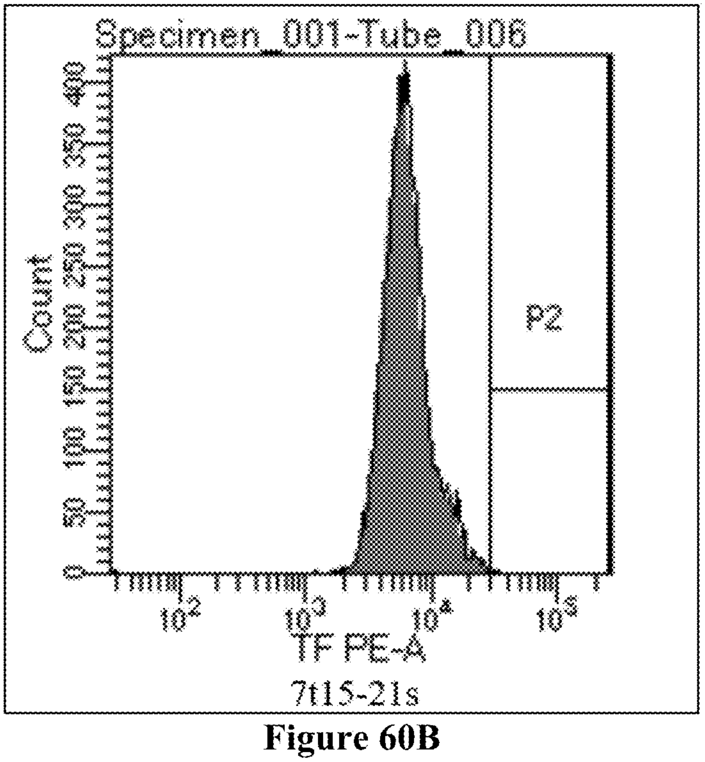

CHO cells were transfected with human CD16b in a pMC plasmid and selected with 10 μg/mL of blasticidin for 10 days. The CHO cells stably expressing CD16b were stained with 1.2 μg/mL of 7t15-16s21, containing anti-human CD16 scFv or 18t15-12s, which does not contain anti-human CD16 scFv, as a negative control, and then stained with biotinylated anti-human tissue factor Ab and PE conjugated streptavidin. Only anti-human CD16scFv containing 7t15-16s21 stained the cells as shown in FIG. 60A. 18t15-12s did not stain the CHO cells expressing human CD16b as showed in FIG. 60B.

Detection of IL-15, IL-21, and IL-7 in 7t15-16s21 Using ELISA

Figure 61A:
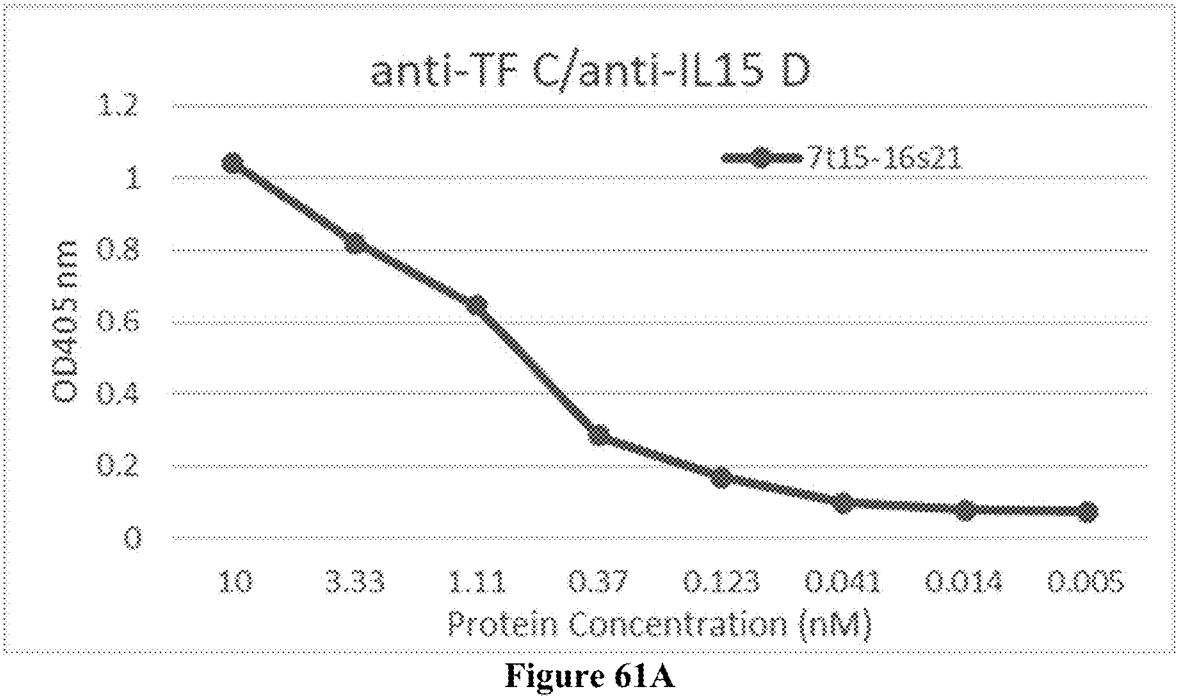
FIGS. 61A-61C are results from ELISA experiments using antibodies against IL-15, IL-21, and IL-7 in detecting 7t15-16s21.
Figure 61B:
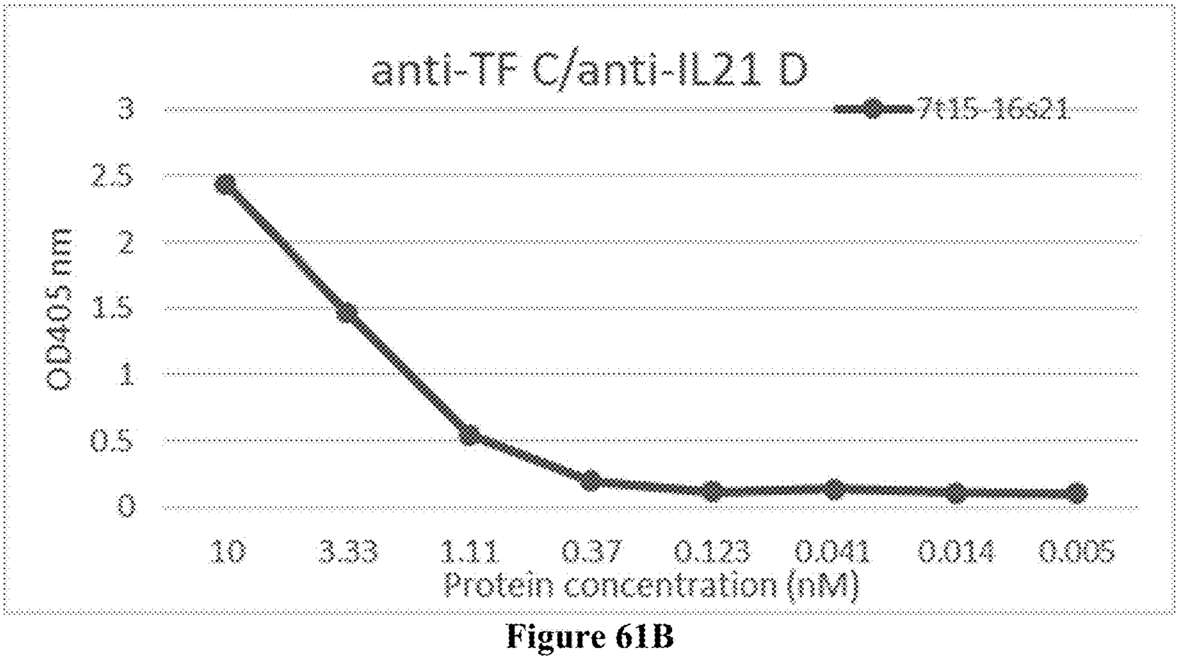
Figure 61C:
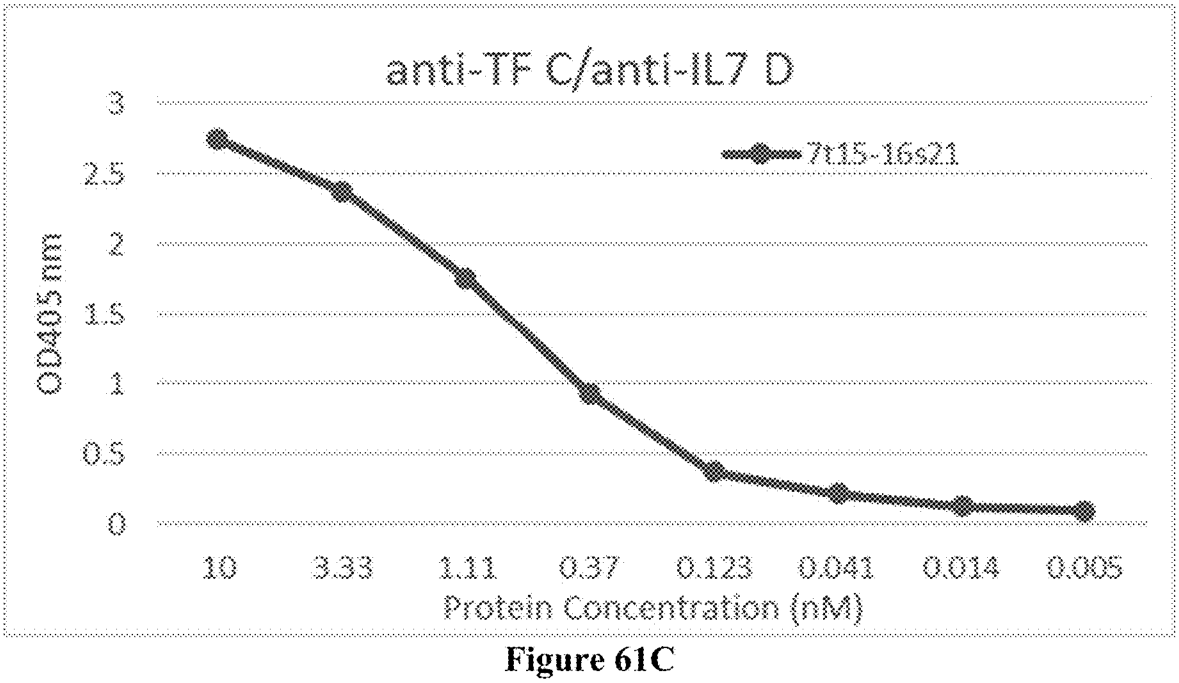

A 96-well plate was coated with 100 μL (8 μg/mL) of anti-TF IgG1 in R5 (coating buffer) and incubated at room temperature (RT) for 2 hrs. The plates were washed 3 times and blocked with 100 μL of 1% BSA in PBS. Serial dilution of 7t15-16s21 (at a 1:3 ratio) were added to the wells, and incubated at RT for 60 min. Following 3 washes, 50 ng/mL of biotinylated-anti-IL15 antibody (BAM247, R&D Systems), 500 ng/mL of biotinylated-anti-IL-21 antibody (13-7218-81, R&D Systems), or 500 ng/mL of biotinylated-anti-IL-7 antibody (506602, R&D Systems) was added to the wells and incubated at RT for 60 min. The plate was washed 3 times, and incubated with 0.25 μg/mL of HRP-SA (Jackson ImmunoResearch) at 100 μL per well for 30 min at RT, followed by 4 washes and incubation with 100 μl of ABTS for 2 mins at RT. Absorbance was read at 405 nm. As shown in FIGS. 61A-61C, the IL-15, IL-21, and IL-7 domains in 7t15-16s21 were detected by the individual antibodies.

Figure 62:
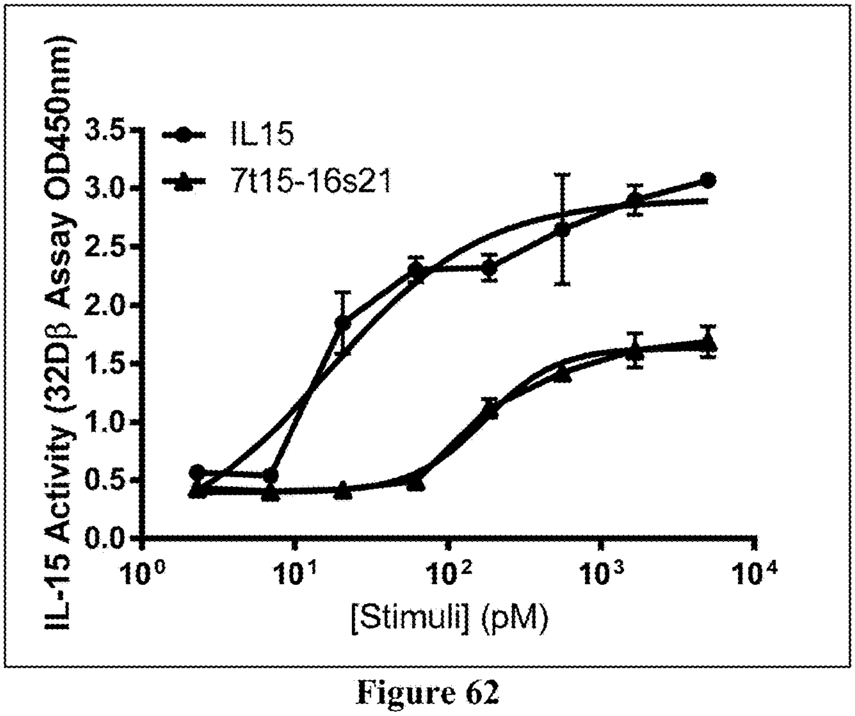
FIG. 62 shows results of the 32Dβ cell proliferation assay with 7t15-16s21 or recombinant IL-15.

The IL-15 in 7t15-16s21 Promotes IL-2Rβ and Common γ Chain Containing 32Dβ Cell Proliferation To analyze the activity of IL-15 in 7t15-16s21, the IL-15 activity of 7t15-16s21 was compared to recombinant IL-15 using 32Dβ cells that express IL2Rβ and common γ chain, and evaluating their effects on promoting cell proliferation. IL-15 dependent 32Dβ cells were washed 5 times with IMDM-10% FBS and seeded in the wells at $2\times10^4$ cells/well. Serially-diluted 7t15-16s21 or IL-15 were added to the cells (FIG. 62). Cells were incubated in a $CO_2$ incubator at 37° C. for 3 days. Cell proliferation was detected by adding 10 μl of WST1 to each well on day 3 and incubating for an additional 3 hours in a $CO_2$ incubator at 37° C. The absorbance at 450 nm was measured by analyzing the amount of formazan dye produced. As shown in FIG. 62, 7t15-16s21 and IL-15 promoted 32Dβ cell proliferation, with the $EC_{50}$ of 7t15-16s21 and IL-15 being 172.2 pM and 16.63 pM, respectively.

Figure 63:
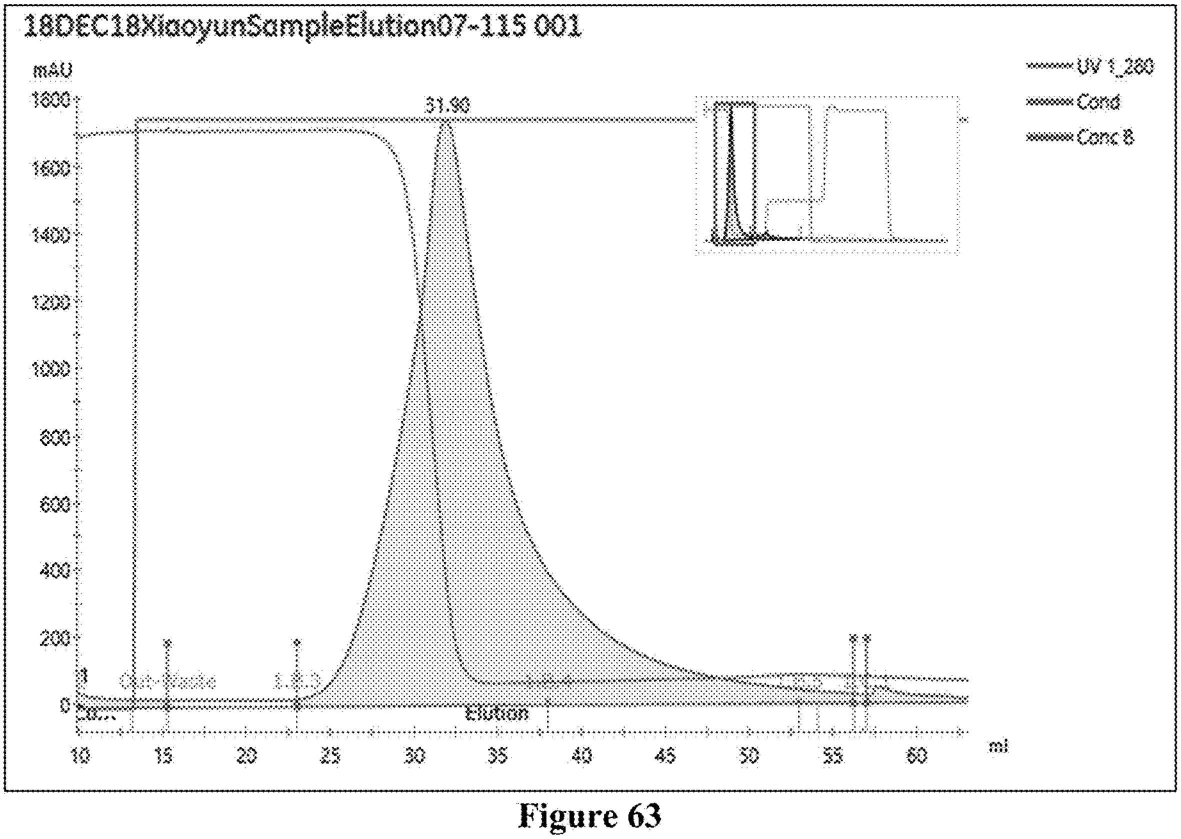
FIG. 63 shows the chromatographic profile of 7t15-16s21 protein containing cell culture supernatant following binding and elution on anti-TF antibody resin.

Purification Elution Chromatograph of 7t15-16s21 from Anti-TF Antibody Affinity Column 7t15-16s21 harvested from cell culture was loaded onto the anti-TF antibody affinity column equilibrated with 5 column volumes of PBS. The column was then washed with 5 column volumes of PBS, followed by elution with 6 column volumes of 0.1M acetic acid (pH 2.9). A280 elution peak was collected and neutralized to pH 7.5-8.0 with 1M Tris base. The neutralized sample was buffer exchanged into PBS using Amicon centrifugal filters with a 30 KDa molecular weight cutoff. FIG. 63 is a line graph showing the chromatographic profile of 7t15-16s21 protein containing cell culture supernatant following binding and elution on anti-TF antibody resin. As shown in FIG. 63, the anti-TF antibody affinity column bound 7t15-16s21 which contains TF. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Analytical Size Exclusion Chromatography (SEC) Analysis of 7t15-16s21

Figure 64:
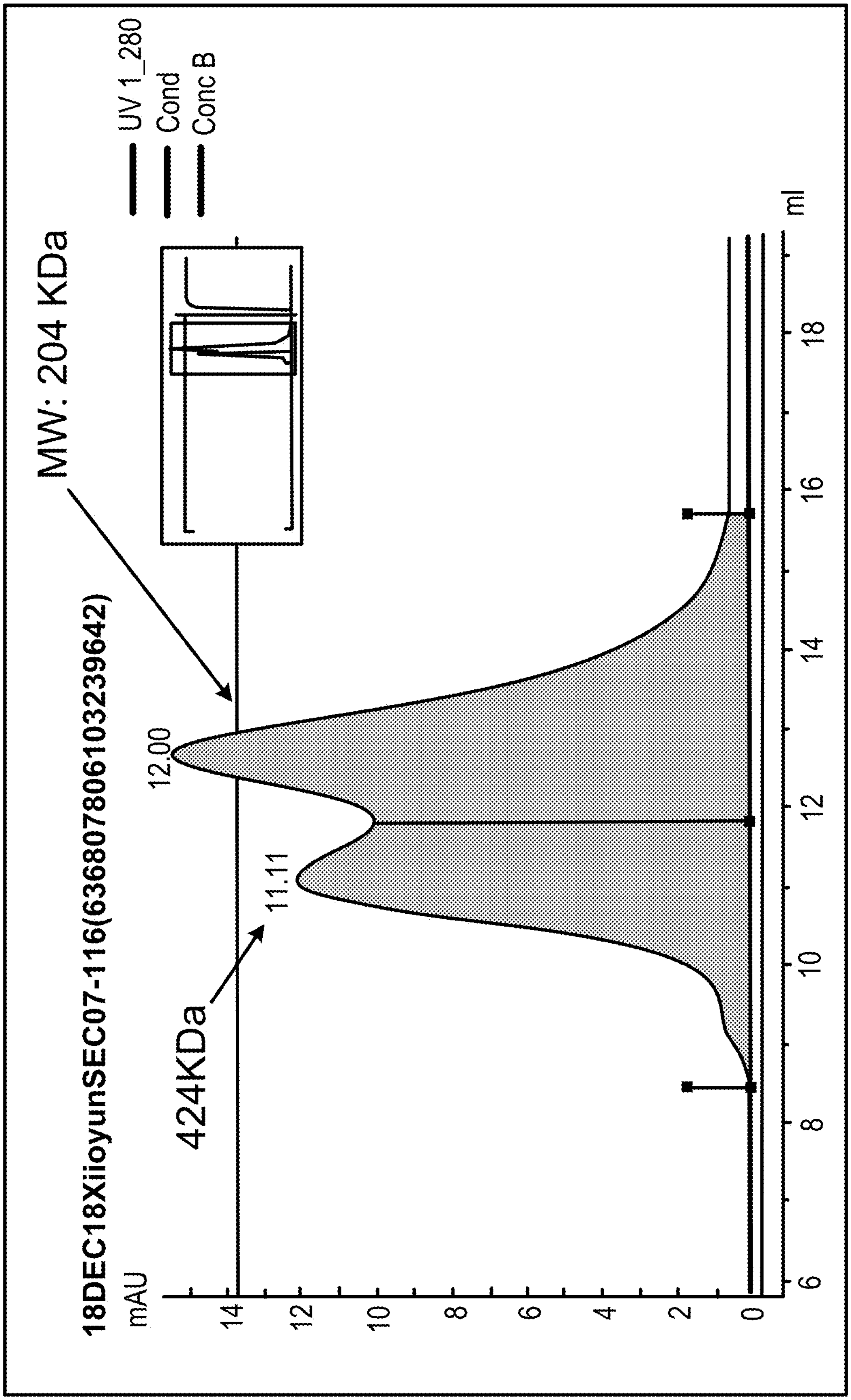
FIG. 64 shows the analytical SEC Profile of 7t15-16s21.

To perform size exclusion chromatography (SEC) analysis for 7t15-16s21, a Superdex 200 Increase 10/300 GL gel filtration column (GE Healthcare) connected to an AKTA Avant system (GE Healthcare) was used. The column was equilibrated with 2 column volumes of PBS. The flow rate was 0.7 mL/min. A sample containing 7t15-16s21 in PBS was injected into the Superdex 200 column using a capillary loop, and analyzed by SEC. As shown in FIG. 64, the SEC results showed two protein peaks for 7t15-16s21.

Example 50: TGFRt15-16s21 Fusion Protein Generation and Characterization

Figure 65:
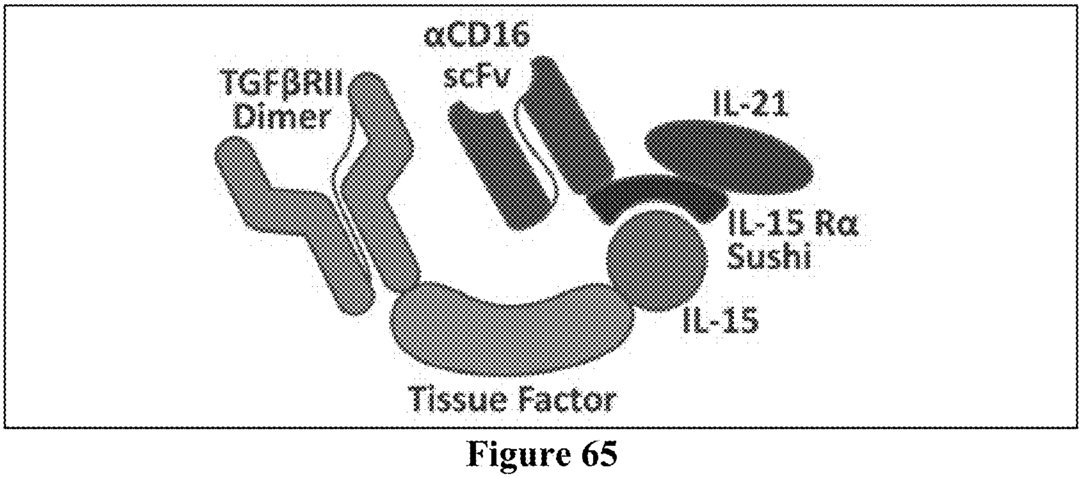
FIG. 65 shows a schematic of the TGFRt15-16s21 construct.
Figure 66:
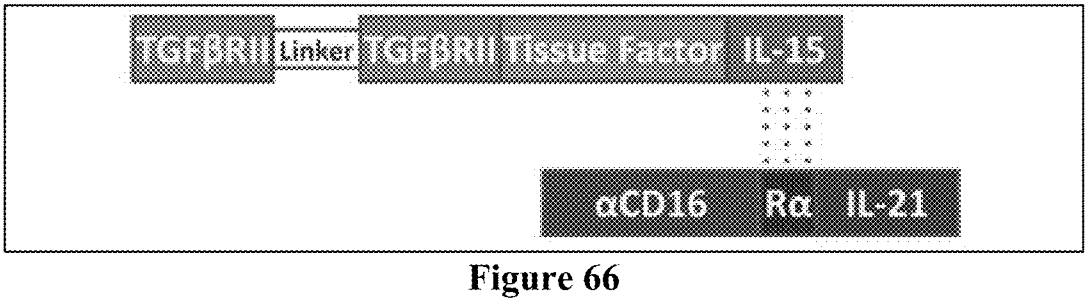
FIG. 66 shows an additional schematic of the TGFRt15-16s21 construct.

A fusion protein complex was generated comprising anti-human CD16scFv/IL-15RαSu/IL21 and TGFβ Receptor II/TF/IL-15 fusion proteins (FIGS. 65 and 66). The human TGFβ Receptor II (Ile24-Asp159), tissue factor 219, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the two TGFβ Receptor II/TF/IL-15 construct (including signal peptide sequence) is as follows:

```
(Signal peptide)
ATGAAGTGGGTGACCTTCATCAGCCTGCTGTTCCT

GTTCTCCAGCGCCTACTCC

(Two Human TGFβ Receptor II fragments)
ATCCCCCCCCATGTGCAAAAGAGCGTGAACAACGA

TATGATCGTGACCGACAACAACGGCGCCGTGAAGT

TTCCCCAGCTCTGCAAGTTCTGCGATGTCAGGTTC

AGCACCTGCGATAATCAGAAGTCCTGCATGTCCAA

CTGCAGCATCACCTCCATCTGCGAGAAGCCCCAAG

AAGTGTGCGTGGCCGTGTGGCGGAAAAATGACGAG

AACATCACCCTGGAGACCGTGTGTCACGACCCCAA

GCTCCCTTATCACGACTTCATTCTGGAGGACGCTG

CCTCCCCCAAATGCATCATGAAGGAGAAGAAGAAG

CCCGGAGAGACCTTCTTTATGTGTTCCTGTAGCAG
```

-continued

```
CGACGAGTGTAACGACAACATCATCTTCAGCGAAG

AGTACAACACCAGCAACCCTGATGGAGGTGGCGGA

TCCGGAGGTGGAGGTTCTGGTGGAGGTGGGAGTAT

TCCTCCCCACGTGCAGAAGAGCGTGAATAATGACA

TGATCGTGACCGATAACAATGGCGCCGTGAAATTT

CCCCAGCTGTGCAAATTCTGCGATGTGAGGTTTTC

CACCTGCGACAACCAGAAGTCCTGTATGAGCAACT

GCTCCATCACCTCCATCTGTGAGAAGCCTCAGGAG

GTGTGCGTGGCTGTCTGGCGGAAGAATGACGAGAA

TATCACCCTGGAAACCGTCTGCCACGATCCCAAGC

TGCCCTACCACGATTTCATCCTGGAAGACGCCGCCA

GCCCTAAGTGCATCATGAAAGAGAAAAAGAAGCCTG

GCGAGACCTTTTTCATGTGCTCCTGCAGCAGCGACG

AATGCAACGACAATATCATCTTTAGCGAGGAATACA

ATACCAGCAACCCCGAC

(Human Tissue Factor 219)
AGCGGCACAACCAACACAGTCGCTGCCTATAACCT

CACTTGGAAGAGCACCAACTTCAAAACCATCCTCG

AATGGGAACCCAAACCCGTTAACCAAGTTTACACC

GTGCAGATCAGCACCAAGTCCGGCGACTGGAAGTC

CAAATGTTTCTATACCACCGACACCGAGTGCGATC

TCACCGATGAGATCGTGAAAGATGTGAAACAGACC

TACCTCGCCCGGGTGTTTAGCTACCCCGCCGGCAA

TGTGGAGAGCACTGGTTCCGCTGGCGAGCCTTTAT

ACGAGAACAGCCCCGAATTTACCCCTTACCTCGAG

ACCAATTTAGGACAGCCCACCATCCAAAGCTTTGA

GCAAGTTGGCACAAAGGTGAATGTGACAGTGGAGG

ACGAGCGGACTTTAGTGCGGCGGAACAACACCTTT

CTCAGCCTCCGGGATGTGTTCGGCAAAGATTTAAT

CTACACACTGTATTACTGGAAGTCCTCTTCCTCCG

GCAAGAAGACAGCTAAAACCAACACAAACGAGTTT

TTAATCGACGTGGATAAAGGCGAAAACTACTGTTT

CAGCGTGCAAGCTGTGATCCCCTCCCGGACCGTGA

ATAGGAAAAGCACCGATAGCCCCGTTGAGTGCATG

GGCCAAGAAAAGGGCGAGTTCCGGGAG

(Human IL-15)
AACTGGGTGAACGTCATCAGCGATTTAAAGAAGAT

CGAAGATTTAATTCAGTCCATGCATATCGACGCCA

CTTTATACACAGAATCCGACGTGCACCCCTCTTGT

AAGGTGACCGCCATGAAATGTTTTTTACTGGAGCT

GCAAGTTATCTCTTTAGAGAGCGGAGACGCTAGCA
```

TCCACGACACCGTGGAGAATTTAATCATTTTAGCC

AATAACTCTTTATCCAGCAACGGCAACGTGACAGA

GTCCGGCTGCAAGGAGTGCGAAGAGCTGGAGGAGA

AGAACATCAAGGAGTTTCTGCAATCCTTTGTGCAC

ATTGTCCAGATGTTCATCAATACCTCC

The amino acid sequence of TGFβ Receptor II/TF/IL-15 fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRF

STCDNQKSCMSNCSITSICEKPQEVCVAVWRKNDE

NITLETVCHDPKLPYHDFILEDAASPKCIMKEKKK

PGETFFMCSCSSDECNDNIIFSEEYNTSNPDGGGG

SGGGGSGGGGSIPPHVQKSVNNDMIVTDNNGAVKF

PQLCKFCDVRFSTCDNQKSCMSNCSITSICEKPQE

VCVAVWRKNDENITLETVCHDPKLPYHDFILEDAA

SPKCIMKEKKKPGETFFMCSCSSDECNDNIIFSEE

YNTSNPD (Human Tissue Factor 219)
SGTTNTVAAYNLTWKSTNFKTILEWEPKPVNQVYT

VQISTKSGDWKSKCFYTTDTECDLTDEIVKDVKQT

YLARVFSYPAGNVESTGSAGEPLYENSPEFTPYLE

TNLGQPTIQSFEQVGTKVNVTVEDERTLVRRNNTF

LSLRDVFGKDLIYTLYYWKSSSSGKKTAKTNTNEF

LIDVDKGENYCFSVQAVIPSRTVNRKSTDSPVECM

GQEKGEFRE (Human IL-15)
NWVNVISDLKKIEDLIQSMHIDATLYTESDVHPSC

KVTAMKCFLLELQVISLESGDASIHDTVENLIILA

NNSLSSNGNVTESGCKECEELEEKNIKEFLQSFVH

IVQMFINTS

Constructs were also made by attaching anti-human CD16scFv directly linking to the N-terminus coding region of IL-15RαSu chain followed by the N-terminus coding region of IL-21 which was synthesized by Genewiz. The nucleic acid and protein sequences of a construct comprising the anti-human CD16scFv linked to the N-terminus of IL-15RαSu followed by the N-terminus coding region of IL-21 are shown below.

The nucleic acid sequence of the anti-CD16scFv/IL-15 RαSu/IL-21 construct (including signal peptide sequence) is as follows:

(Signal peptide)
ATGAAGTGGGTGACCTTCATCAGCCTGCTGTTCCT

GTTCTCCAGCGCCTACTCC (Anti-human CD16scFv)
TCCGAGCTGACCCAGGACCCTGCTGTGTCCGTGGC

TCTGGGCCAGACCGTGAGGATCACCTGCCAGGGCG

ACTCCCTGAGGTCCTACTACGCCTCCTGGTACCAG

CAGAAGCCCGGCCAGGCTCCTGTGCTGGTGATCTA

CGGCAAGAACAACAGGCCCTCCGGCATCCCTGACA

GGTTCTCCGGATCCTCCTCCGGCAACACCGCCTCC

CTGACCATCACAGGCGCTCAGGCCGAGGACGAGGC

TGACTACTACTGCAACTCCAGGGACTCCTCCGGCA

ACCATGTGGTGTTCGGCGGCGGCACCAAGCTGACC

GTGGGCCATGGCGGCGGCGGCTCCGGAGGCGGCGG

CAGCGGCGGAGGAGGATCCGAGGTGCAGCTGGTGG

AGTCCGGAGGAGGAGTGGTGAGGCCTGGAGGCTCC

CTGAGGCTGAGCTGTGCTGCCTCCGGCTTCACCTT

CGACGACTACGGCATGTCCTGGGTGAGGCAGGCTC

CTGGAAAGGGCCTGGAGTGGGTGTCCGGCATCAAC

TGGAACGGCGGATCCACCGGCTACGCCGATTCCGT

GAAGGGCAGGTTCACCATCAGCAGGGACAACGCCA

AGAACTCCCTGTACCTGCAGATGAACTCCCTGAGG

GCCGAGGACACCGCCGTGTACTACTGCGCCAGGGG

CAGGTCCCTGCTGTTCGACTACTGGGGACAGGGCA

CCCTGGTGACCGTGTCCAGG (Human IL-15R α sushi domain)
ATTACATGCCCCCCTCCCATGAGCGTGGAGCACGC

CGACATCTGGGTGAAGAGCTATAGCCTCTACAGCC

GGGAGAGGTATATCTGTAACAGCGGCTTCAAGAGG

AAGGCCGGCACCAGCAGCCTCACCGAGTGCGTGCT

GAATAAGGCTACCAACGTGGCTCACTGGACAACAC

CCTCTTTAAAGTGCATCCGG (Human IL-21)
CAGGGCCAGGACAGGCACATGATCCGGATGAGGCA

GCTCATCGACATCGTCGACCAGCTGAAGAACTACG

TGAACGACCTGGTGCCCGAGTTTCTGCCTGCCCCC

GAGGACGTGGAGACCAACTGCGAGTGGTCCGCCTT

CTCCTGCTTTCAGAAGGCCCAGCTGAAGTCCGCCA

ACACCGGCAACAACGAGCGGATCATCAACGTGAGC

ATCAAGAAGCTGAAGCGGAAGCCTCCCTCCACAAA

CGCCGGCAGGAGGCAGAAGCACAGGCTGACCTGCC

CCAGCTGTGACTCCTACGAGAAGAAGCCCCCCAAG

GAGTTCCTGGAGAGGTTCAAGTCCCTGCTGCAGAA

GATGATCCATCAGCACCTGTCCTCCAGGACCCACG

GCTCCGAGGACTCC

The amino acid sequence of the anti-CD16scFv/IL-15RαSu/IL-21 construct (including signal peptide sequence) is as follows:

```
(Signal peptide)
MKWVTFISLLFLFSSAYS

(Anti-human CD16scFv)
SELTQDPAVSVALGQTVRITCQGDSLRSYYASWYQ

QKPGQAPVLVIYGKNNRPSGIPDRFSGSSSGNTAS

LTITGAQAEDEADYYCNSRDSSGNHVVFGGGTKLT

VGHGGGGSGGGGSGGGGSEVQLVESGGGVVRPGGS

LRLSCAASGFTFDDYGMSWVRQAPGKGLEWVSGIN

WNGGSTGYADSVKGRFTISRDNAKNSLYLQMNSLR

AEDTAVYYCARGRSLLFDYWGQGTLVTVSR

(Human IL-15R α sushi domain)
ITCPPPMSVEHADIWVKSYSLYSRERYICNSGFKR

KAGTSSLTECVLNKATNVAHWTTPSLKCIR

(Human IL-21)
QGQDRHMIRMRQLIDIVDQLKNYVNDLVPEFLPAP

EDVETNCEWSAFSCFQKAQLKSANTGNNERIINVS

IKKLKRKPPSTNAGRRQKHRLTCPSCDSYEKKPPK

EFLERFKSLLQKMIHQHLSSRTHGSEDS
```

In some cases, the leader peptide is cleaved from the intact polypeptide to generate the mature form that may be soluble or secreted.

The anti-CD16scFv/IL-15RαSu/IL-21 and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFR/TF/IL-15:CD16scFv/IL-15RαSu/IL-21 protein complex (referred to as TGFRt15-16s21), which can be purified by anti-TF IgG1-based affinity and other chromatography methods.

Interaction Between TGFRt15-16s21 and CHO Cells Expressing Human CD16b

Figure 67A:
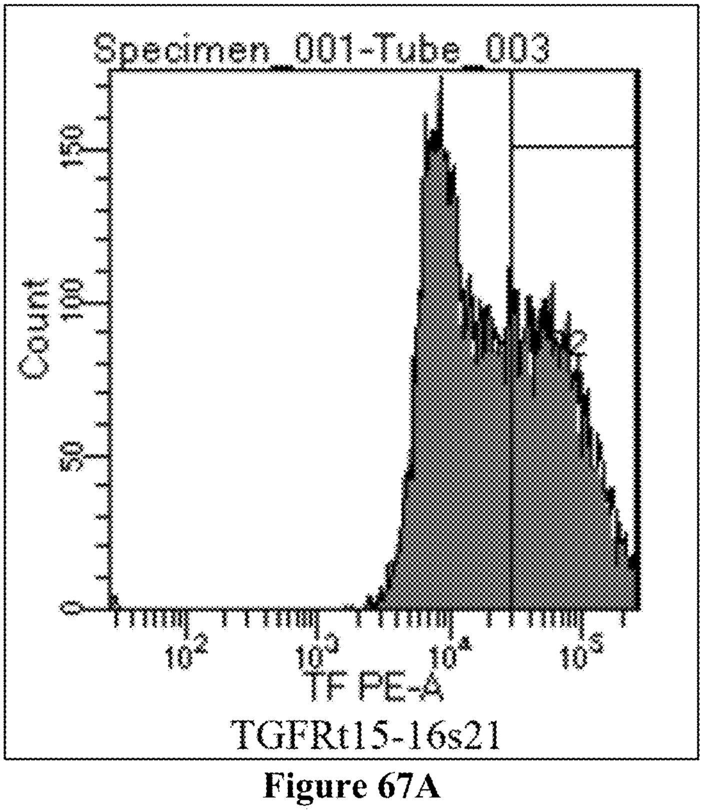
FIGS. 67A and 67B show binding affinity of TGFRt15-16S21 and 7t15-21s with CHO cells expressing human CD16b.
Figure 67B:
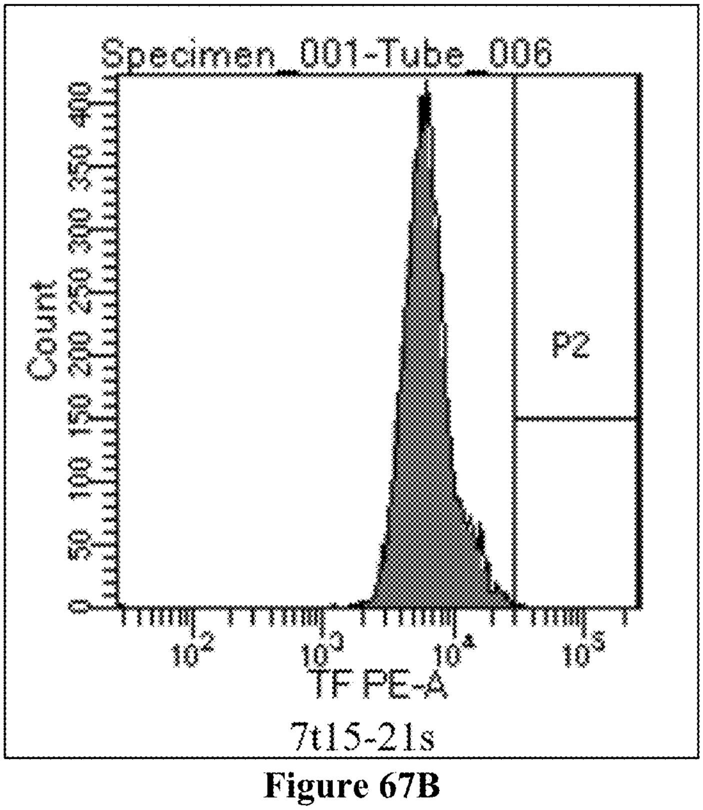

CHO cells were transfected with human CD16b in a pMC plasmid and selected with 10 μg/mL of blasticidin for 10 days. Cells stably expressing CD16b were stained with 1.2 μg/mL of TGFRt15-16s21, containing anti-human CD16 scFv, or 7t15-21s, not containing anti-human CD16 scFv, as a negative control, and with biotinylated anti-human tissue factor antibody and PE conjugated streptavidin. As shown in FIGS. 67A and 67B, TGFRt15-16s21, which contains anti-human CD16scFv, showed positive binding, while 7t15-21s did not show binding.

Effect of TGFRt15-16s21 on TGFβ1 Activity in HEK-Blue TGFβ Cells

To evaluate the activity of TGFβRII in TGFRt15-16s21, the effect of TGFRt15-16s21 on the activity of TGFβ1 in HEK-Blue TGFβ cells was analyzed. HEK-Blue TGFβ cells (Invivogen) were washed twice with pre-warmed PBS and resuspended in the testing medium (DMEM, 10% heat-inactivated FCS, 1× glutamine, 1× anti-anti, and 2× glutamine) at $5\times10^5$ cells/mL. In a flat-bottom 96-well plate, 50 μl cells were added to each well ($2.5\times10^4$ cells/well) and followed with 50 μL 0.1 nM TGFβ1 (R&D systems). TGFRt15-16s21 or TGFR-Fc (R&D Systems) prepared at a 1:3 serial dilution was then added to the plate to reach a total volume of 200 μL. After 24 hrs of incubation at 37° C., 40 μL of induced HEK-Blue TGFβ cell supernatant was added to 160 μL pre-warmed QUANTI-Blue (Invivogen) in a flat-bottom 96-well plate, and incubated at 37° C. for 1-3 hrs. The OD values were then determined using a plate reader (Multiscan Sky) at 620-655 nM. The $IC_{50}$ of each protein sample was calculated with GraphPad Prism 7.04. The $IC_{50}$ of TGFRt15-16s21 and TGFR-Fc were 9127 pM and 460.6 pM respectively. These results showed that the TGFβRII domain in TGFRt15-16s21 was able to block the activity of TGFβ-1 in HEK-Blue TGFβ cells.

Figure 68:
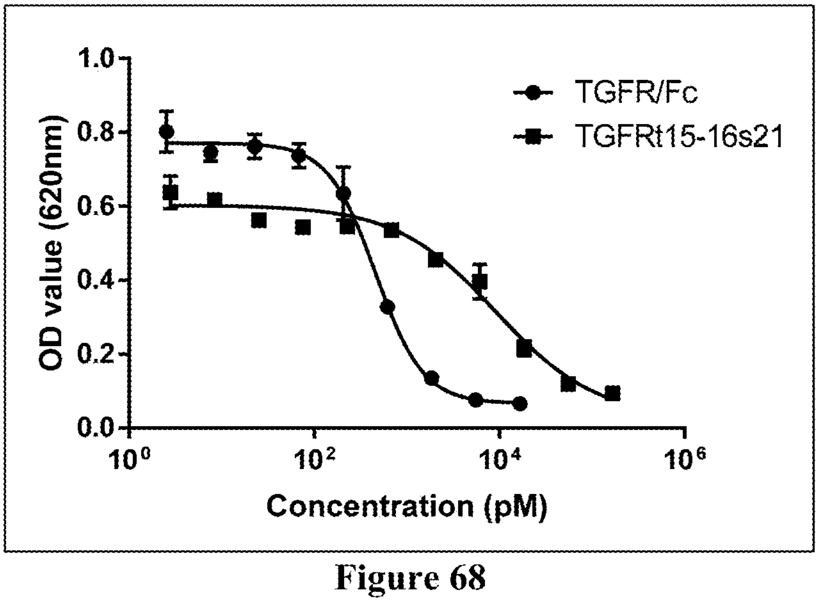
FIG. 68 shows results of TGFβ1 inhibition by TGFRt15-16s21 and TGFR-Fc.

The IL-15 in TGFRt15-16s21 Promotes IL-2Rβ and Common γ Chain Containing 32Dβ Cell Proliferation To analyze the activity of IL-15 in TGFRt15-16s21, the IL-15 activity of TGFRt15-16s21 was compared to recombinant IL-15 using 32Dβ cells that express IL2Rβ and common γ chain, and evaluating their effects on promoting cell proliferation. IL-15 dependent 32Dβ cells were washed 5 times with IMDM-10% FBS and seeded in the wells at $2\times10^4$ cells/well. Serially-diluted TGFRt15-16s21 or IL-15 were added to the cells (FIG. 68). Cells were incubated in a $CO_2$ incubator at 37° C. for 3 days. Cell proliferation was detected by adding 10 μL of WST1 to each well on day 3 and incubating for an additional 3 hours in a $CO_2$ incubator at 37° C. The absorbance at 450 nm was measured by analyzing the amount of formazan dye produced. As shown in FIG. 68, TGFRt15-16s21 and IL-15 promoted 32Dβ cell proliferation, with the $EC_{50}$ of TGFRt15-16s21 and IL-15 being 51298 pM and 10.63 pM, respectively.

Detection of IL-15, IL-21, and TGFβRII in TGFRt15-16s21 Using ELISA

Figure 69:
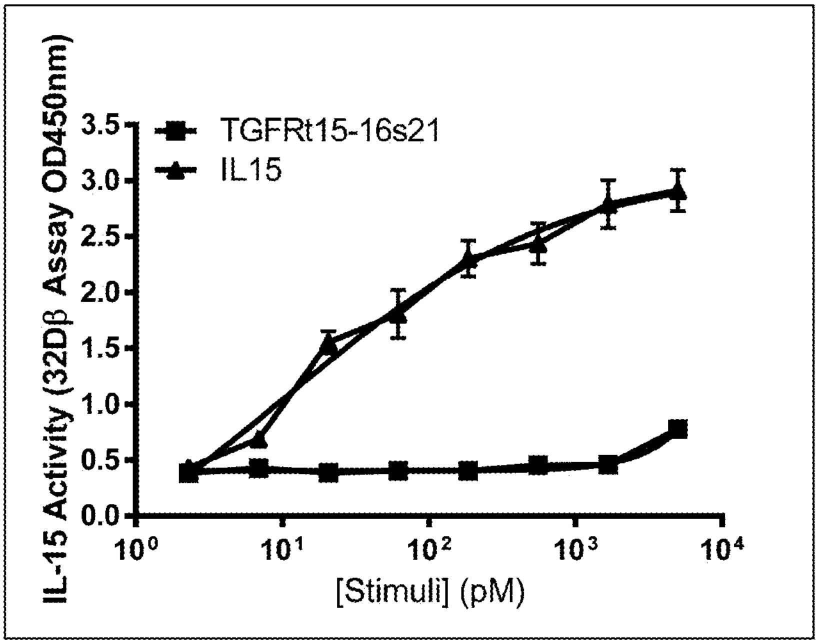
FIG. 69 shows results of 32Dβ cell proliferation assay with TGFRt15-16s21 or recombinant IL-15.
Figure 70A:
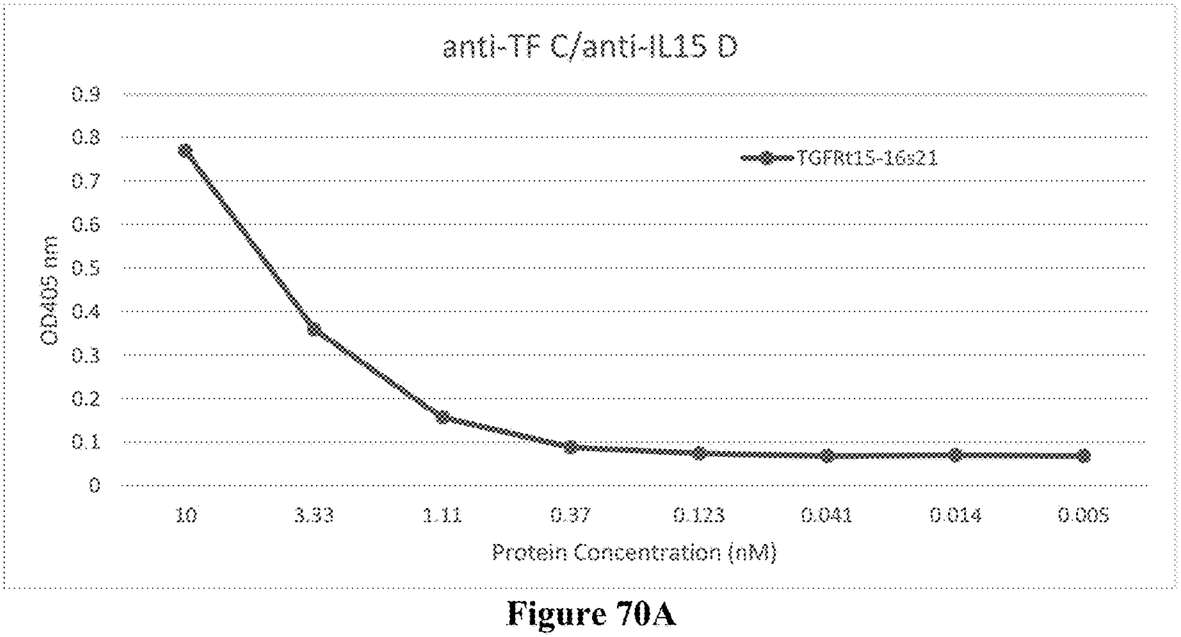
FIGS. 70A-70C show results of detecting IL-15, IL-21, and TGFβRII in TGFRt15-16s21 with corresponding antibodies using ELISA.
Figure 70B:
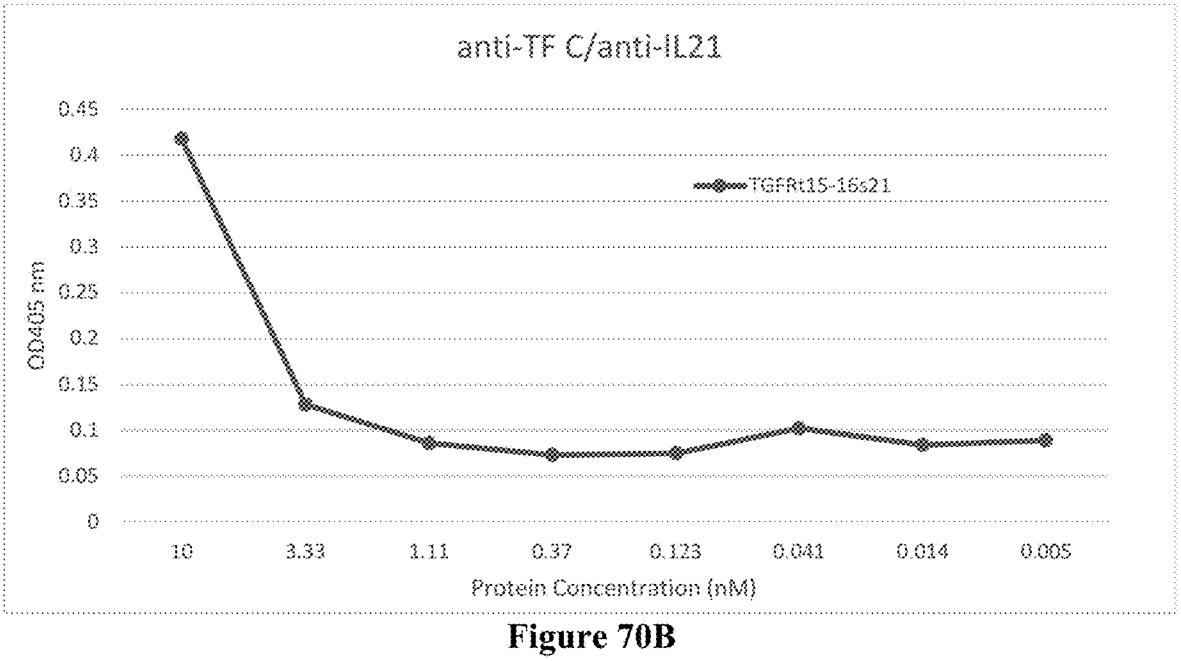
Figure 70C:
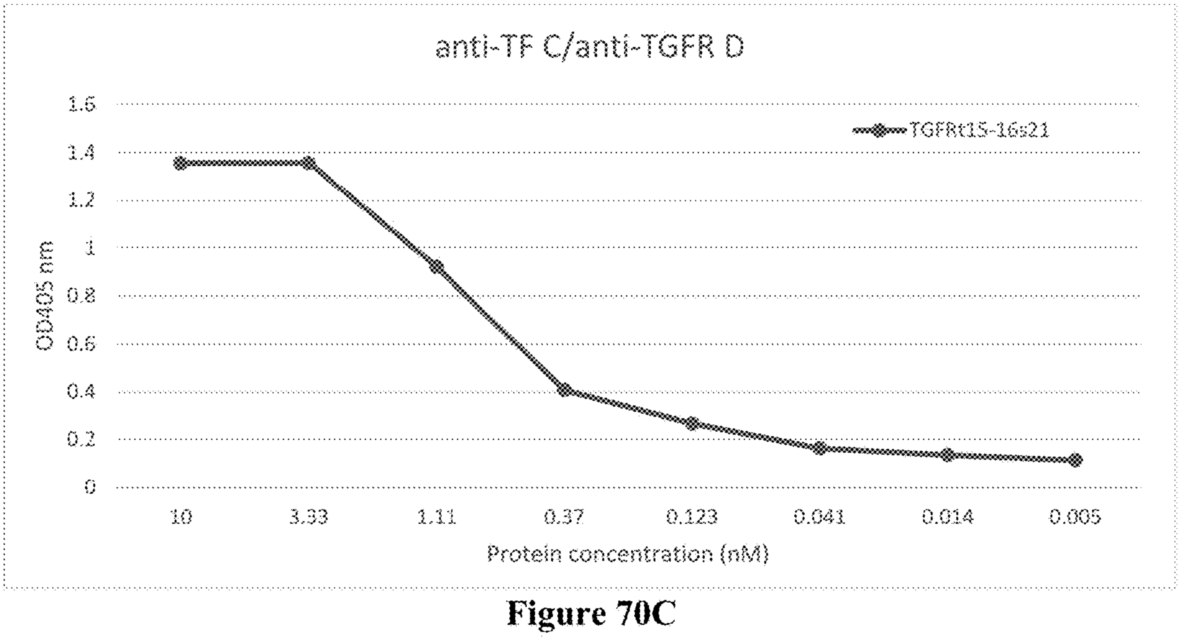

A 96-well plate was coated with 100 μL (8 μg/mL) of anti-TF IgG1 in R5 (coating buffer) and incubated at room temperature (RT) for 2 hrs. The plates were washed 3 times and blocked with 100 μL of 1% BSA in PBS. TGFRt15-16s21 serially diluted at a 1:3 ratio was added and incubated at RT for 60 min. Following three washes, 50 ng/mL of biotinylated-anti-IL-15 antibody (BAM247, R&D Systems), 500 ng/mL of biotinylated-anti-IL-21 antibody (13-7218-81, R&D Systems), or 200 ng/mL of biotinylated-anti-TGFβRII antibody (BAF241, R&D Systems) was applied per well, and incubated at RT for 60 min. Following three washes, incubation with 0.25 μg/mL of HRP-SA (Jackson ImmunoResearch at 100 μL per well for 30 min at RT was carried out, followed by 4 washes and incubation with 100 μL of ABTS for 2 mins at RT. Absorbance was read at 405 nm. The data are shown in FIG. 69. As shown in FIGS. 70A-70C, the IL-15, IL-21, and TGFβRII domains in TGFRt15-16s21 were detected by the respective antibodies.

Figure 71:
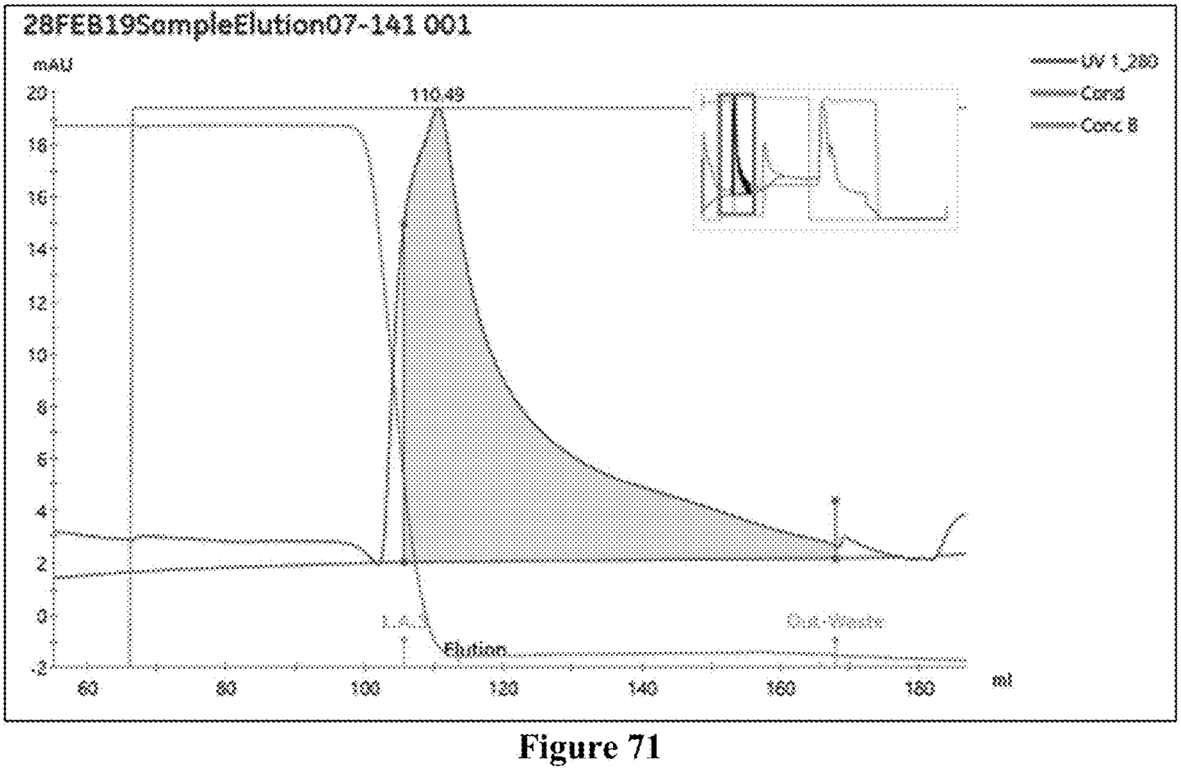
FIG. 71 shows the chromatographic profile of TGFRt15-16s21 protein containing cell culture supernatant following binding and elution on anti-TF antibody resin.

Purification Elution Chromatograph of TGFRt15-16s21 Using Anti-TF Antibody Affinity Column TGFRt15-16s21 harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 71, the anti-TF antibody affinity column bound to TGFRt15-16s21, which contains tissue factor as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Reduced SDS-PAGE of TGFRt15-16s21

To determine the purity and molecular weight of the TGFRt15-16s21 protein, protein sample purified with anti-TF antibody affinity column was analyzed by sodium dodecyl sulfate polyacrylamide gel (4-12% NuPage Bis-Tris gel) electrophoresis (SDS-PAGE) under reduced condition. After electrophoresis, the gel was stained with InstantBlue for about 30 min, followed by destaining overnight in purified water.

Figure 72:
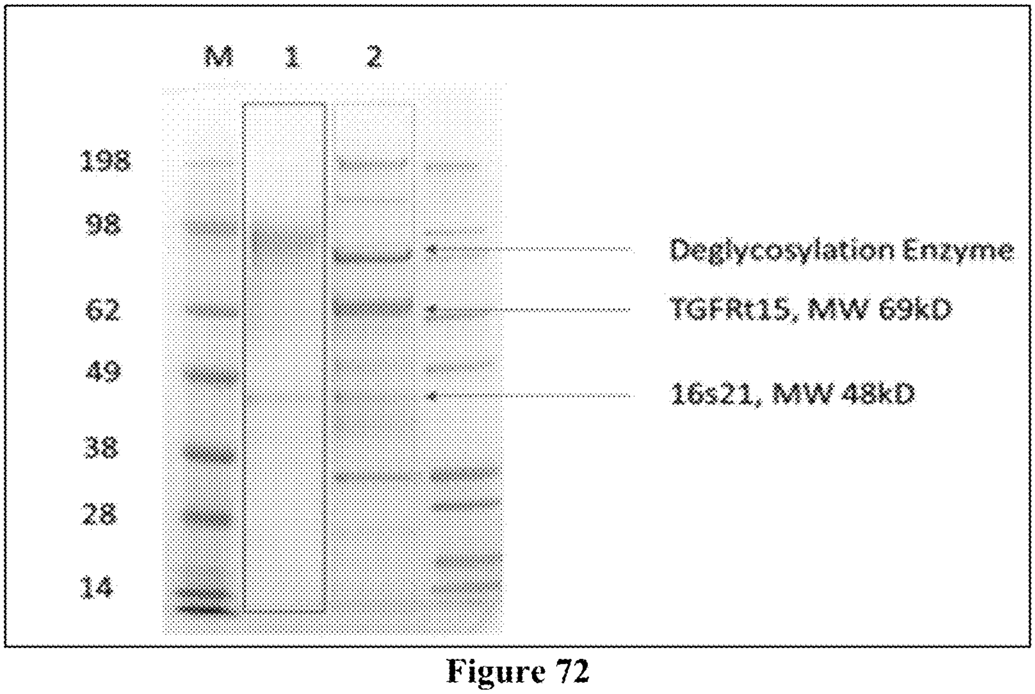
FIG. 72 shows results of a reduced SDS-PAGE analysis of TGFRt15-16s21.

To verify that the TGFRt15-16s21 protein undergoes glycosylation after translation in CHO cells, a deglycosylation experiment was conducted using the Protein Deglycosylation Mix II kit from New England Biolabs according to the manufacturer's instructions. FIG. 72 shows results from the reduced SDS-PAGE analysis of the sample in non-deglycosylated (lane 1 in red outline) and deglycosylated (lane 2 in yellow outline) state. The results showed that the TGFRt15-16s21 protein is glycosylated when expressed in CHO cells. After deglycosylation, the purified sample showed expected molecular weights (69 kDa and 48 kDa) in the reduced SDS gel. Lane M was loaded with 10 μL of SeeBlue Plus2 Prestained Standard.

Example 51: 7t15-7s Fusion Protein Generation and Characterization

Figure 73:
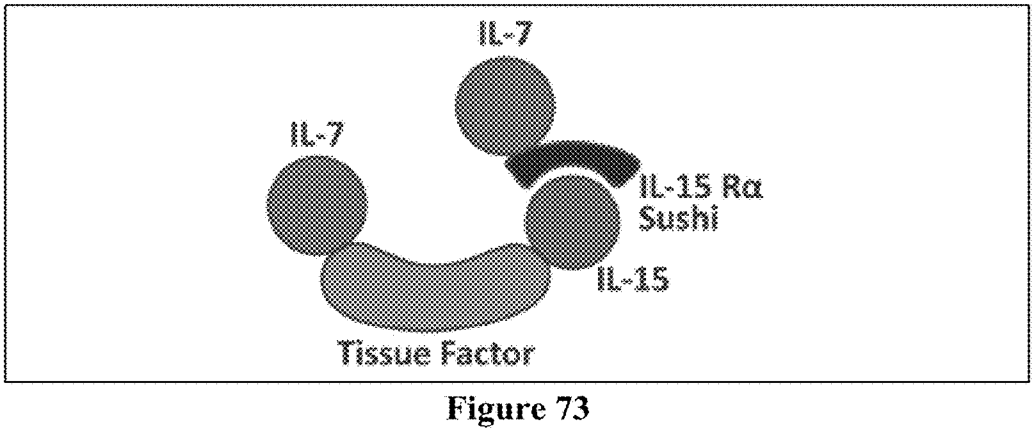
FIG. 73 shows a schematic of the 7t15-7s construct.
Figure 74:
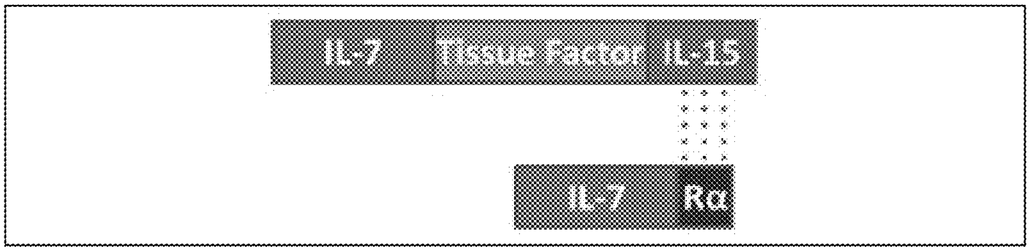
FIG. 74 shows an additional schematic of the 7t15-7s construct.

A fusion protein complex was generated comprising IL-7/TF/IL-15 and IL-7/IL-15RαSu fusion proteins (FIG. 73 and FIG. 74). The human IL-7, tissue factor 219, and IL-15 sequences were obtained from the UniProt website and DNA for these sequences was synthesized by Genewiz. Specifically, a construct was made linking the IL-7 sequence to the N-terminus coding region of tissue factor 219 followed by the N-terminus coding region of IL-15.

The nucleic acid and protein sequences of a construct comprising IL-7 linked to the N-terminus of tissue factor 219 following with the N-terminus of IL-15 are shown below.

The nucleic acid sequence of 7t15 construct (including signal peptide sequence) is as follows:

```
(Signal peptide)
ATGAAGTGGGTGACCTTCATCAGCCTGCTGTTCCT

GTTCTCCAGCGCCTACTCC

(Human IL7)
GATTGCGACATCGAGGGCAAGGACGGCAAGCAGTA

CGAGAGCGTGCTGATGGTGTCCATCGACCAGCTGC

TGGACAGCATGAAGGAGATCGGCTCCAACTGCCTC

AACAACGAGTTCAACTTCTTCAAGCGGCACATCTG

CGACGCCAACAAGGAGGGCATGTTCCTGTTCAGGG

CCGCCAGGAAACTGCGGCAGTTCCTGAAGATGAAC
```

-continued

```
TCCACCGGCGACTTCGACCTGCACCTGCTGAAGGT

GTCCGAGGGCACCACCATCCTGCTGAACTGCACCG

GACAGGTGAAGGGCCGGAAACCTGCTGCTCTGGGA

GAGGCCCAACCCACCAAGAGCCTGGAGGAGAACAA

GTCCCTGAAGGAGCAGAAGAAGCTGAACGACCTGT

GCTTCCTGAAGAGGCTGCTGCAGGAGATCAAGACC

TGCTGGAACAAGATCCTGATGGGCACCAAGGAGCA

T

(Human Tissue Factor 219)
AGCGGCACAACCAACACAGTCGCTGCCTATAACCT

CACTTGGAAGAGCACCAACTTCAAAACCATCCTCG

AATGGGAACCCAAACCCGTTAACCAAGTTTACACC

GTGCAGATCAGCACCAAGTCCGGCGACTGGAAGTC

CAAATGTTTCTATACCACCGACACCGAGTGCGATC

TCACCGATGAGATCGTGAAAGATGTGAAACAGACC

TACCTCGCCCGGGTGTTTAGCTACCCCGCCGGCAA

TGTGGAGAGCACTGGTTCCGCTGGCGAGCCTTTAT

ACGAGAACAGCCCCGAATTTACCCCTTACCTCGAG

ACCAATTTAGGACAGCCCACCATCCAAAGCTTTGA

GCAAGTTGGCACAAAGGTGAATGTGACAGTGGAGG

ACGAGCGGACTTTAGTGCGGCGGAACAACACCTTT

CTCAGCCTCCGGGATGTGTTCGGCAAAGATTTAAT

CTACACACTGTATTACTGGAAGTCCTCTTCCTCCG

GCAAGAAGACAGCTAAAACCAACACAAACGAGTTT

TTAATCGACGTGGATAAAGGCGAAAACTACTGTTT

CAGCGTGCAAGCTGTGATCCCCTCCCGGACCGTGA

ATAGGAAAAGCACCGATAGCCCCGTTGAGTGCATG

GGCCAAGAAAAGGGCGAGTTCCGGGAG

(Human IL-15)
AACTGGGTGAACGTCATCAGCGATTTAAAGAAGAT

CGAAGATTTAATTCAGTCCATGCATATCGACGCCA

CTTTATACACAGAATCCGACGTGCACCCCTCTTGT

AAGGTGACCGCCATGAAATGTTTTTTACTGGAGCT

GCAAGTTATCTCTTTAGAGAGCGGAGACGCTAGCA

TCCACGACACCGTGGAGAATTTAATCATTTTAGCC

AATAACTCTTTATCCAGCAACGGCAACGTGACAGA

GTCCGGCTGCAAGGAGTGCGAAGAGCTGGAGGAGA

AGAACATCAAGGAGTTTCTGCAATCCTTTGTGCAC

ATTGTCCAGATGTTCATCAATACCTCC
```

The amino acid sequence of 7t15 fusion protein (including the leader sequence) is as follows.

(Signal peptide)
MKWVTFISLLFLFSSAYS (Human IL7)
DCDIEGKDGKQYESVLMVSIDQLLDSMKEIGSNCL

NNEFNFFKRHICDANKEGMFLFRAARKLRQFLKMN

STGDFDLHLLKVSEGTTILLNCTGQVKGRKPAALG

EAQPTKSLEENKSLKEQKKLNDLCFLKRLLQEIKT

CWNKILMGTKEH (Human Tissue Factor 219)
SGTTNTVAAYNLTWKSTNFKTILEWEPKPVNQVYT

VQISTKSGDWKSKCFYTTDTECDLTDEIVKDVKQT

YLARVFSYPAGNVESTGSAGEPLYENSPEFTPYLE

TNLGQPTIQSFEQVGTKVNVTVEDERTLVRRNNTF

LSLRDVFGKDLIYTLYYWKSSSSGKKTAKTNTNEF

LIDVDKGENYCFSVQAVIPSRTVNRKSTDSPVECM

GQEKGEFRE (Human IL-15)
NWVNVISDLKKIEDLIQSMHIDATLYTESDVHPSC

KVTAMKCFLLELQVISLESGDASIHDTVENLIILA

NNSLSSNGNVTESGCKECEELEEKNIKEFLQSFVH

IVQMFINTS

Constructs were also made by linking the IL-7 sequence to the N-terminus coding region of IL-15RαSu chain which was synthesized by Genewiz. The nucleic acid and protein sequences of a construct comprising the IL-7 linked to the N-terminus of IL-15RαSu chain are shown below.

The nucleic acid sequence of 7s construct (including signal peptide sequence) is as follows.

(Signal peptide)
ATGGGAGTGAAAGTTCTTTTTGCCCTTATTTGTAT

TGCTGTGGCCGAGGCC (Human IL7)
GATTGTGATATTGAAGGTAAAGATGGCAAACAATA

TGAGAGTGTTCTAATGGTCAGCATCGATCAATTAT

TGGACAGCATGAAAGAAATTGGTAGCAATTGCCTG

AATAATGAATTTAACTTTTTTAAAAGACATATCTG

TGATGCTAATAAGGAAGGTATGTTTTTATTCCGTG

CTGCTCGCAAGTTGAGGCAATTTCTTAAAATGAAT

AGCACTGGTGATTTTGATCTCCACTTATTAAAAGT

TTCAGAAGGCACAACAATACTGTTGAACTGCACTG

GCCAGGTTAAAGGAAGAAAACCAGCTGCCCTGGGT

GAAGCCCAACCAACAAAGAGTTTGGAAGAAAATAA

ATCTTTAAAGGAACAGAAAAAACTGAATGACTTGT

-continued

GTTTCCTAAAGAGACTATTACAAGAGATAAAAACT

TGTTGGAATAAAATTTTGATGGGCACTAAAGAACA

C (Human IL-15R α sushi domain)
ATCACGTGCCCTCCCCCCATGTCCGTGGAACACGC

AGACATCTGGGTCAAGAGCTACAGCTTGTACTCCA

GGGAGCGGTACATTTGTAACTCTGGTTTCAAGCGT

AAAGCCGGCACGTCCAGCCTGACGGAGTGCGTGTT

GAACAAGGCCACGAATGTCGCCCACTGGACAACCC

CCAGTCTCAAATGCATTAGA

The amino acid sequence of 7s fusion protein (including the leader sequence) is as follows:

(Signal peptide)
MGVKVLFALICIAVAEA (Human IL7)
DCDIEGKDGKQYESVLMVSIDQLLDSMKEIGSNCL

NNEFNFFKRHICDANKEGMFLFRAARKLRQFLKMN

STGDFDLHLLKVSEGTTILLNCTGQVKGRKPAALG

EAQPTKSLEENKSLKEQKKLNDLCFLKRLLQEIKT

CWNKILMGTKEH (Human IL-15R α sushi domain)
ITCPPPMSVEHADIWVKSYSLYSRERYICNSGFKR

KAGTSSLTECVLNKATNVAHWTTPSLKCIR

The IL-7/TF/IL-15 and IL-7/IL-15RαSu constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble IL-7/TF/IL-15:IL-7/IL-15RαSu protein complex referred to as 7t15-7s, which can be purified by anti-TF IgG1 affinity and other chromatography methods.

Figure 75:
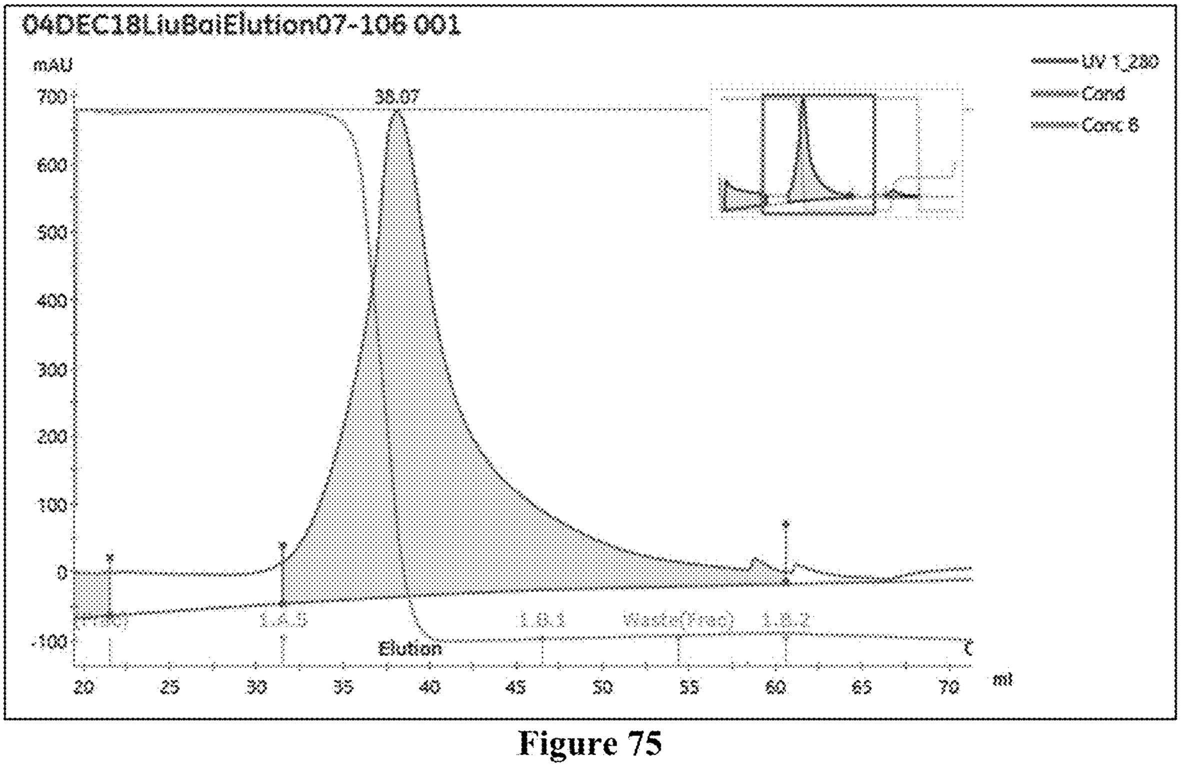
FIG. 75 shows the chromatographic profile of 7t15-7s protein containing cell culture supernatant following binding and elution on anti-TF antibody resin.

Purification Elution Chromatograph of 7t15-7s Using Anti-TF Antibody Affinity Column 7t15-7s harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 75, the anti-TF antibody affinity column bound to 7t15-7s which contains tissue factor (TF) as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except the elution step, which was 2 mL/min.

Immunostimulation of 7t15-7s in C57BL 6 Mice

7t15-7s is a multi-chain polypeptide (a type A multi-chain polypeptide described herein) that includes the first polypeptide that is a soluble fusion of human IL-7, human tissue factor 219 fragment and human IL-15 (7t15), and the second polypeptide that is a soluble fusion of human IL-7 and sushi domain of human IL-15 receptor alpha chain (7s).

Figure 76:
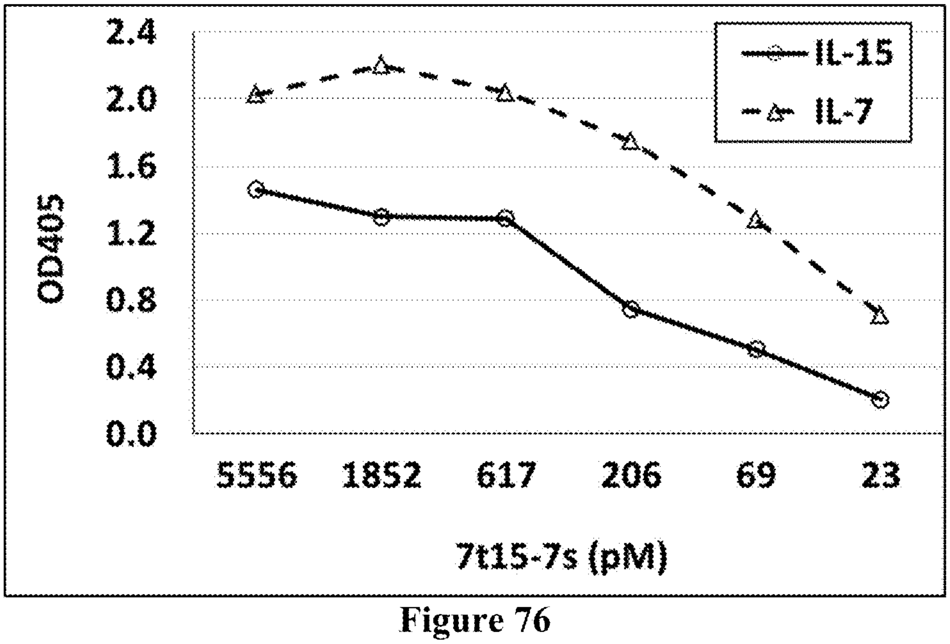
FIG. 76 shows detection of TF, IL-15 and IL-7 in 7t15-7s using ELISA.

CHO cells were co-transfected with the IL7-TF-IL15 (7t15) and IL7-IL15Rα sushi domain (7s) vectors. The 7t15-7s complex was purified from the transfected CHO cell culture supernatant. The IL-7, IL-15 and tissue factor (TF) components were demonstrated in the complex by ELISA as shown in FIG. 76. A humanized anti-TF monoclonal antibody (anti-TF IgG1) was used as the capture antibody to determine TF in 7t15-7s, and biotinylated anti-human IL-15 antibody (R&D systems) and biotinylated anti-human IL-7 antibody (R&D Systems) were used as the detection antibodies to respectively detect IL-15 and IL-7 in 7t15-7s, followed by peroxidase conjugated streptavidin (Jackson ImmunoResearch Lab) and ABTS substrate (Surmodics IVD, Inc.).

Example 52: TGFRt15-TGFRs Fusion Protein Generation and Characterization

Figure 77:
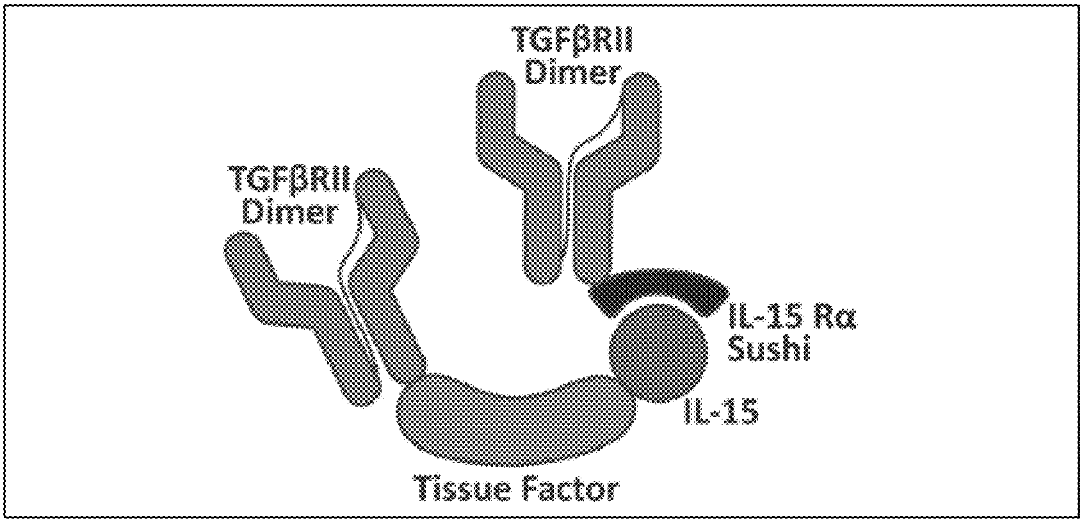
FIG. 77 shows a schematic of the TGFRt15-TGFRs construct.
Figure 78:
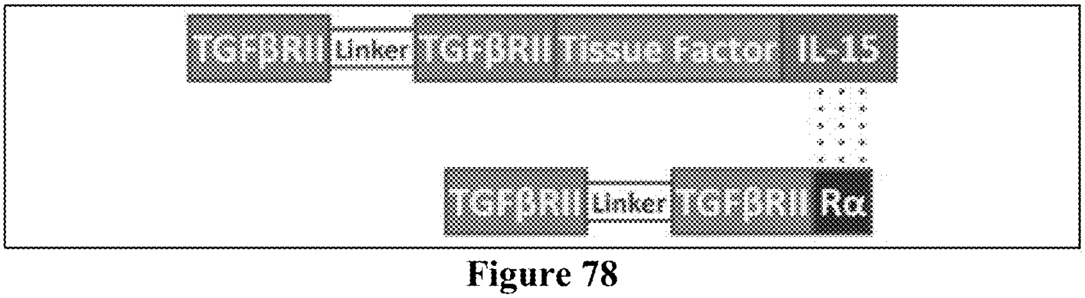
FIG. 78 shows an additional schematic of the TGFRt15-TGFRs construct.

A fusion protein complex was generated comprising of TGFβ Receptor II/IL-15RαSu and TGFβ Receptor II/TF/IL-15 fusion proteins (FIG. 77 and FIG. 78). The human TGFβ Receptor II (Ile24-Asp159), tissue factor 219, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the two TGFβ Receptor II/TF/IL-15 construct (including signal peptide sequence) is as follows:

```
(Signal peptide)
ATGAAGTGGGTGACCTTCATCAGCCTGCTGTTCCT

GTTCTCCAGCGCCTACTCC

(Two Human TGFβ Receptor IIfragments)
ATCCCCCCCCATGTGCAAAAGAGCGTGAACAACGA

TATGATCGTGACCGACAACAACGGCGCCGTGAAGT

TTCCCCAGCTCTGCAAGTTCTGCGATGTCAGGTTC

AGCACCTGCGATAATCAGAAGTCCTGCATGTCCAA

CTGCAGCATCACCTCCATCTGCGAGAAGCCCCAAG

AAGTGTGCGTGGCCGTGTGGCGGAAAAATGACGAG

AACATCACCCTGGAGACCGTGTGTCACGACCCCAA

GCTCCCTTATCACGACTTCATTCTGGAGGACGCTG
```

-continued

```
CCTCCCCCAAATGCATCATGAAGGAGAAGAAGAAG

CCCGGAGAGACCTTCTTTATGTGTTCCTGTAGCAG

CGACGAGTGTAACGACAACATCATCTTCAGCGAAG

AGTACAACACCAGCAACCCTGATGGAGGTGGCGGA

TCCGGAGGTGGAGGTTCTGGTGGAGGTGGGAGTAT

TCCTCCCCACGTGCAGAAGAGCGTGAATAATGACA

TGATCGTGACCGATAACAATGGCGCCGTGAAATTT

CCCCAGCTGTGCAAATTCTGCGATGTGAGGTTTTC

CACCTGCGACAACCAGAAGTCCTGTATGAGCAACT

GCTCCATCACCTCCATCTGTGAGAAGCCTCAGGAG

GTGTGCGTGGCTGTCTGGCGGAAGAATGACGAGAA

TATCACCCTGGAAACCGTCTGCCACGATCCCAAGC

TGCCCTACCACGATTTCATCCTGGAAGACGCCGCC

AGCCCTAAGTGCATCATGAAAGAGAAAAAGAAGCC

TGGCGAGACCTTTTTCATGTGCTCCTGCAGCAGCG

ACGAATGCAACGACAATATCATCTTTAGCGAGGAA

TACAATACCAGCAACCCCGAC

(Human Tissue Factor 219)
AGCGGCACAACCAACACAGTCGCTGCCTATAACCT

CACTTGGAAGAGCACCAACTTCAAAACCATCCTCG

AATGGGAACCCAAACCCGTTAACCAAGTTTACACC

GTGCAGATCAGCACCAAGTCCGGCGACTGGAAGTC

CAAATGTTTCTATACCACCGACACCGAGTGCGATC

TCACCGATGAGATCGTGAAAGATGTGAAACAGACC

TACCTCGCCCGGGTGTTTAGCTACCCCGCCGGCAA

TGTGGAGAGCACTGGTTCCGCTGGCGAGCCTTTAT

ACGAGAACAGCCCCGAATTTACCCCTTACCTCGAG

ACCAATTTAGGACAGCCCACCATCCAAAGCTTTGA

GCAAGTTGGCACAAAGGTGAATGTGACAGTGGAGG

ACGAGCGGACTTTAGTGCGGCGGAACAACACCTTT

CTCAGCCTCCGGGATGTGTTCGGCAAAGATTTAAT

CTACACACTGTATTACTGGAAGTCCTCTTCCTCCG

GCAAGAAGACAGCTAAAACCAACACAAACGAGTTT

TTAATCGACGTGGATAAAGGCGAAAACTACTGTTT

CAGCGTGCAAGCTGTGATCCCCTCCCGGACCGTGA

ATAGGAAAAGCACCGATAGCCCCGTTGAGTGCATG

GGCCAAGAAAAGGGCGAGTTCCGGGAG

(Human IL-15)
AACTGGGTGAACGTCATCAGCGATTTAAAGAAGAT

CGAAGATTTAATTCAGTCCATGCATATCGACGCCA

CTTTATACACAGAATCCGACGTGCACCCCTCTTGT
```

-continued

```
AAGGTGACCGCCATGAAATGTTTTTACTGGAGCT

GCAAGTTATCTCTTTAGAGAGCGGAGACGCTAGCA

TCCACGACACCGTGGAGAATTTAATCATTTTAGCC

AATAACTCTTTATCCAGCAACGGCAACGTGACAGA

GTCCGGCTGCAAGGAGTGCGAAGAGCTGGAGGAGA

AGAACATCAAGGAGTTTCTGCAATCCTTTGTGCAC

ATTGTCCAGATGTTCATCAATACCTCC
```

The amino acid sequence of TGFβ Receptor II/TF/IL-15 fusion protein (including the leader sequence) is as follows:

```
(Signal peptide)
MKWVTFISLLFLFSSAYS

(Human TGFβ Receptor II)
IPPHVQKSVNNDMIVTDNNGAVKFPQLCKFCDVRF

STCDNQKSCMSNCSITSICEKPQEVCVAVWRKNDE

NITLETVCHDPKLPYHDFILEDAASPKCIMKEKKK

PGETFFMCSCSSDECNDNIIFSEEYNTSNPDGGGG

SGGGGSGGGGSIPPHVQKSVNNDMIVTDNNGAVKF

PQLCKFCDVRFSTCDNQKSCMSNCSITSICEKPQE

VCVAVWRKNDENITLETVCHDPKLPYHDFILEDAA

SPKCIMKEKKKPGETFFMCSCSSDECNDNIIFSEE

YNTSNPD

(Human Tissue Factor 219)
SGTTNTVAAYNLTWKSTNFKTILEWEPKPVNQVYTV

QISTKSGDWKSKCFYTTDTECDLTDEIVKDVKQTY

LARVFSYPAGNVESTGSAGEPLYENSPEFTPYLET

NLGQPTIQSFEQVGTKVNVTVEDERTLVRRNNTFL

SLRDVFGKDLIYTLYYWKSSSSGKKTAKTNTNEFL

IDVDKGENYCFSVQAVIPSRTVNRKSTDSPVECMG

QEKGEFRE

(Human IL-15)
NWVNVISDLKKIEDLIQSMHIDATLYTESDVHPSC

KVTAMKCFLLELQVISLESGDASIHDTVENLIILA

NNSLSSNGNVTESGCKECEELEEKNIKEFLQSFVH

IVQMFINTS
```

Constructs were also made by attaching two TGFβ Receptor II directly to the IL-15RαSu chain which was synthesized by Genewiz. The nucleic acid and protein sequences of a construct comprising the TGFβ Receptor II linked to the N-terminus of IL-15RαSu are shown below.

The nucleic acid sequence of the TGFβ Receptor II/IL-15 RαSu construct (including signal peptide sequence) is as follows:

```
(Signal peptide)
ATGAAGTGGGTGACCTTCATCAGCCTGCTGTTCCT

GTTCTCCAGCGCCTACTCC

(Two human TGFβ Receptor IIfragments)
ATCCCCCCCCATGTGCAAAAGAGCGTGAACAACGA

TATGATCGTGACCGACAACAACGGCGCCGTGAAGT

TTCCCCAGCTCTGCAAGTTCTGCGATGTCAGGTTC

AGCACCTGCGATAATCAGAAGTCCTGCATGTCCAA

CTGCAGCATCACCTCCATCTGCGAGAAGCCCCAAG

AAGTGTGCGTGGCCGTGTGGCGGAAAAATGACGAG

AACATCACCCTGGAGACCGTGTGTCACGACCCCAA

GCTCCCTTATCACGACTTCATTCTGGAGGACGCTG

CCTCCCCCAAATGCATCATGAAGGAGAAGAAGAAG

CCCGGAGAGACCTTCTTTATGTGTTCCTGTAGCAG

CGACGAGTGTAACGACAACATCATCTTCAGCGAAG

AGTACAACACCAGCAACCCTGATGGAGGTGGCGGA

TCCGGAGGTGGAGGTTCTGGTGGAGGTGGGAGTAT

TCCTCCCCACGTGCAGAAGAGCGTGAATAATGACA

TGATCGTGACCGATAACAATGGCGCCGTGAAATTT

CCCCAGCTGTGCAAATTCTGCGATGTGAGGTTTTC

CACCTGCGACAACCAGAAGTCCTGTATGAGCAACT

GCTCCATCACCTCCATCTGTGAGAAGCCTCAGGAG

GTGTGCGTGGCTGTCTGGCGGAAGAATGACGAGAA

TATCACCCTGGAAACCGTCTGCCACGATCCCAAGC

TGCCCTACCACGATTTCATCCTGGAAGACGCCGCC

AGCCCTAAGTGCATCATGAAAGAGAAAAAGAAGCC

TGGCGAGACCTTTTTCATGTGCTCCTGCAGCAGCG

ACGAATGCAACGACAATATCATCTTTAGCGAGGAA

TACAATACCAGCAACCCCGAC

(Human IL-15R α sushi domain)
ATTACATGCCCCCCTCCCATGAGCGTGGAGCACGC

CGACATCTGGGTGAAGAGCTATAGCCTCTACAGCC

GGGAGAGGTATATCTGTAACAGCGGCTTCAAGAGG

AAGGCCGGCACCAGCAGCCTCACCGAGTGCGTGCT

GAATAAGGCTACCAACGTGGCTCACTGGACAACAC

CCTCTTTAAAGTGCATCCGG
```

The amino acid sequence of the two TGFβ Receptor II/IL-15RαSu construct (including signal peptide sequence) is as follows:

```
(Signal peptide)
MKWVTFISLLFLFSSAYS

(Two human TGFβ Receptor II
extra-cellular domains)
IPPHVQKSVNNDMIVTDNNGAVKFPQLCKFCDVRF

STCDNQKSCMSNCSITSICEKPQEVCVAVWRKNDE

NITLETVCHDPKLPYHDFILEDAASPKCIMKEKKK
```

-continued

```
PGETFFMCSCSSDECNDNIIFSEEYNTSNPDGGGG

SGGGGSGGGGSIPPHVQKSVNNDMIVTDNNGAVKF

PQLCKFCDVRFSTCDNQKSCMSNCSITSICEKPQE

VCVAVWRKNDENITLETVCHDPKLPYHDFILEDAA

SPKCIMKEKKKPGETFFMCSCSSDECNDNIIFSEE

YNTSNPD

(Human IL-15R α sushi domain)
ITCPPPMSVEHADIWVKSYSLYSRERYICNSGFKR

KAGTSSLTECVLNKAT NVAHWTTPSLKCIR
```

In some cases, the leader peptide is cleaved from the intact polypeptide to generate the mature form that may be soluble or secreted.

The TGFβR/IL-15RαSu and TGFβR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFβR/TF/IL-15:TGFβR/IL-15RαSu protein complex (referred to as TGFRt15-TGFRs), which can be purified by anti-TF IgG1 affinity and other chromatography methods.

Effect of TGFRt15-TGFRs on TGFβ1 Activity in HEK-Blue TGFβ Cells

To evaluate the activity of TGFβRII in TGFRt15-TGFRs, the effect of TGFRt15-TGFRs on the activity of TGFβ1 in HEK-Blue TGFβ cells was analyzed. HEK-Blue TGFβ cells (Invivogen) were washed twice with pre-warmed PBS and resuspended in the testing medium (DMEM, 10% heat-inactivated FCS, 1× glutamine, 1× anti-anti, and 2× glutamine) at $5\times10^5$ cells/mL. In a flat-bottom 96-well plate, 50 μL cells were added to each well ($2.5\times10^4$ cells/well) and followed with 50 μL 0.1 nM TGFβ1 (R&D systems). TGFRt15-TGFRs or TGFR-Fc (R&D Systems) prepared at a 1:3 serial dilution was then added to the plate to reach a total volume of 200 μL. After 24 hrs of incubation at 37° C., 40 μL of induced HEK-Blue TGFβ cell supernatant was added to 160 μL pre-warmed QUANTI-Blue (Invivogen) in a flat-bottom 96-well plate, and incubated at 37° C. for 1-3 hrs. The OD values were then determined using a plate reader (Multiscan Sky) at 620-655 nM. The $IC_{50}$ of each protein sample was calculated with GraphPad Prism 7.04. The $IC_{50}$ of TGFRt15-TGFRs and TGFR-Fc were 216.9 pM and 460.6 pM respectively. These results showed that the TGFβRII domain in TGFRt15-TGFRs was able to block the activity of TGFβ1 in HEK-Blue TGFβ cells.

Figure 79:
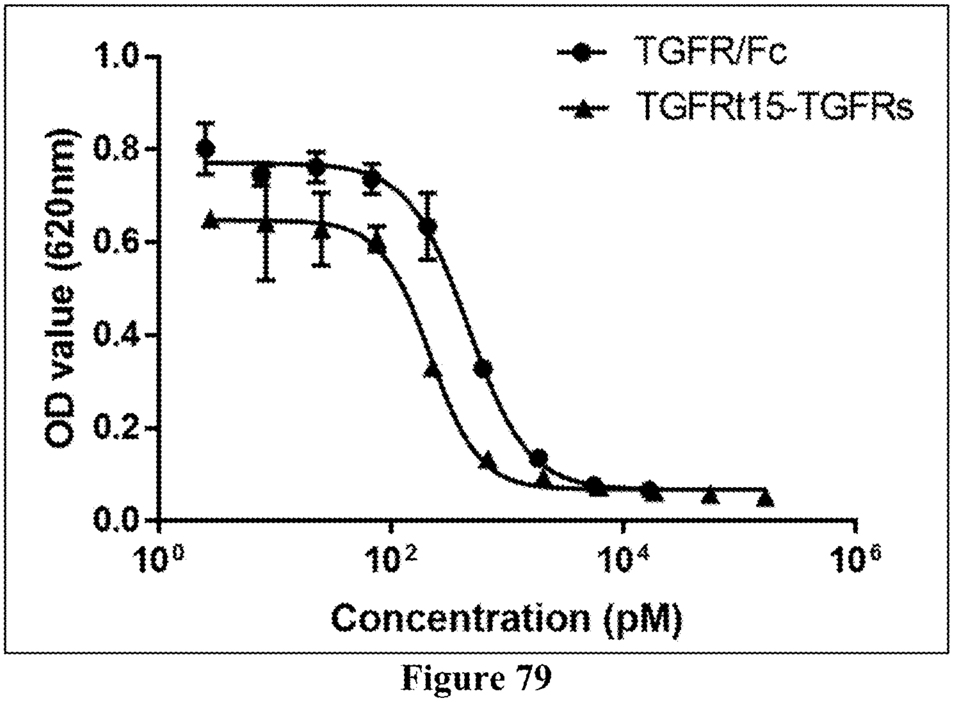
FIG. 79 shows results of TGFβ1 inhibition by TGFRt15-TGFRs and TGFR-Fc.
Figure 80:
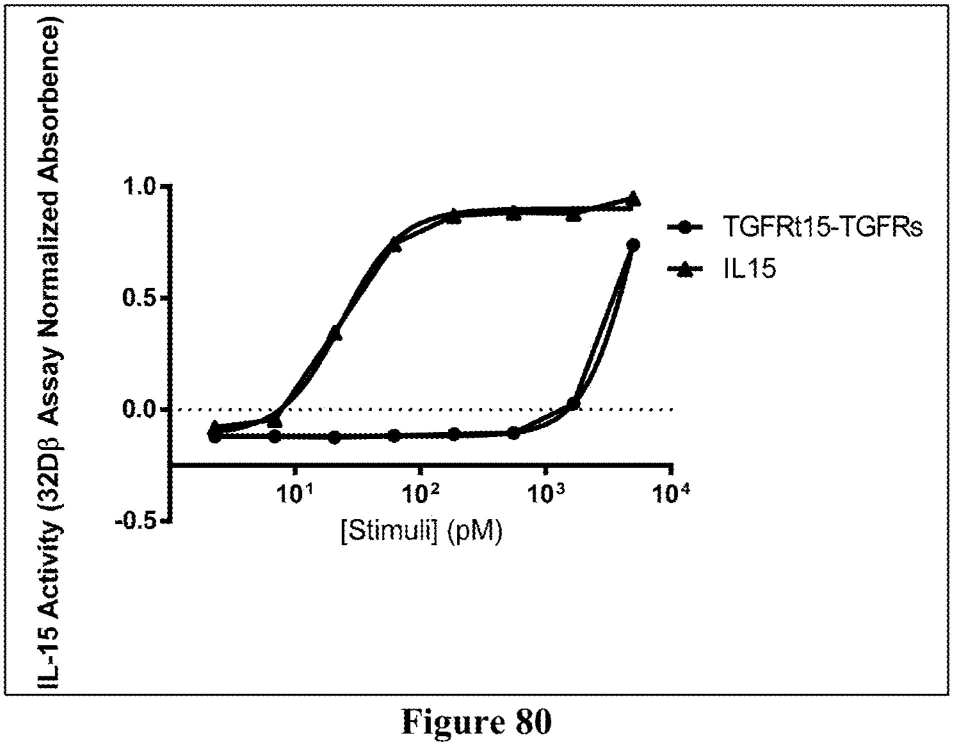
FIG. 80 shows results of 32Dβ cell proliferation assay with TGFRt15-TGFRs or recombinant IL-15

The IL-15 in TGFRt15-TGFRs Promotes IL-2Rβ and Common γ Chain Containing 32Dβ Cell Proliferation To evaluate the activity of IL-15 in TGFRt15-TGFRs, the IL-15 activity of TGFRt15-TGFRs was compared to recombinant IL-15 using 32Dβ cells that express IL2Rβ and common γ chain, and evaluating their effects on promoting cell proliferation. IL-15 dependent 32Dβ cells were washed 5 times with IMDM-10% FBS and seeded in the wells at $2\times10^4$ cells/well. Serially-diluted TGFRt15-TGFRs or IL-15 were added to the cells (FIG. 79). Cells were incubated in a $CO_2$ incubator at 37° C. for 3 days. Cell proliferation was detected by adding 10 μL of WST1 to each well on day 3 and incubating for an additional 3 hours in a $CO_2$ incubator at 37° C. The absorbance at 450 nm was measured by analyzing the amount of formazan dye produced. As shown in FIG. 79, TGFRt15-TGFRs and IL-15 promoted 32Dβ cell proliferation, with the $EC_{50}$ of TGFRt15-TGFRs and IL-15 being 1901 pM and 10.63 pM, respectively.

Figure 81A:
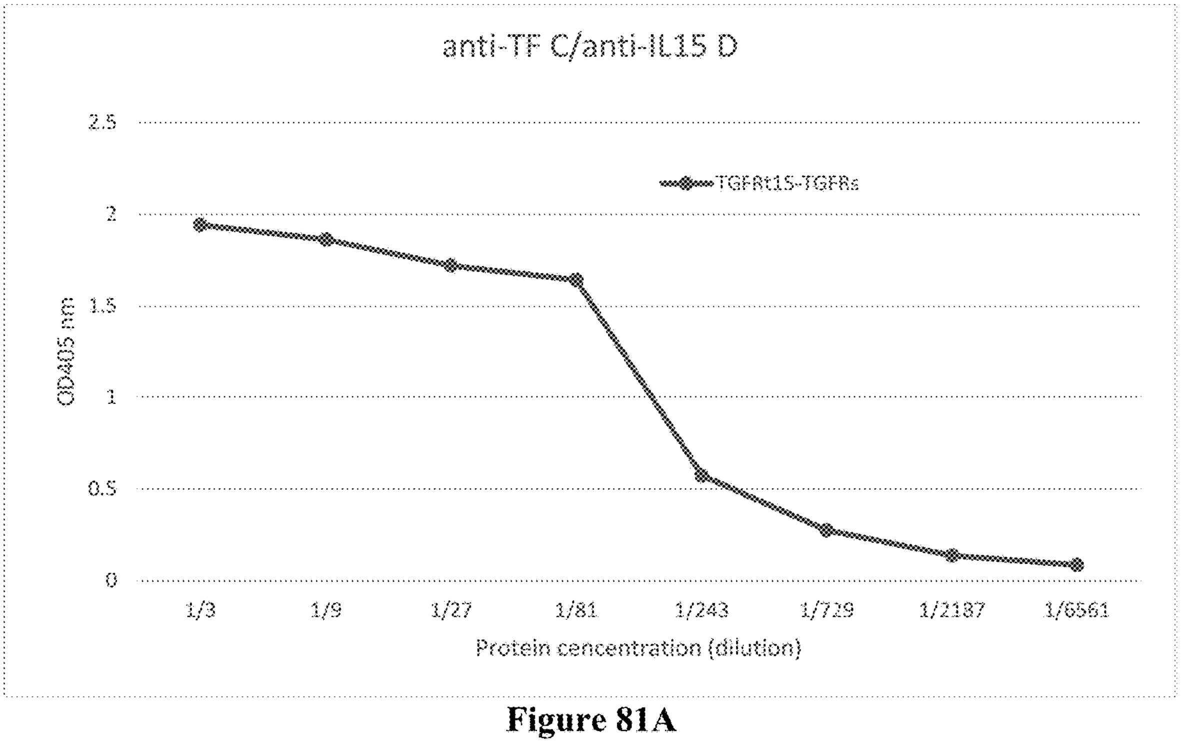
FIGS. 81A and 81B show results of detecting IL-15 and TGFβRII in TGFRt15-TGFRs with corresponding antibodies using ELISA.
Figure 81B:
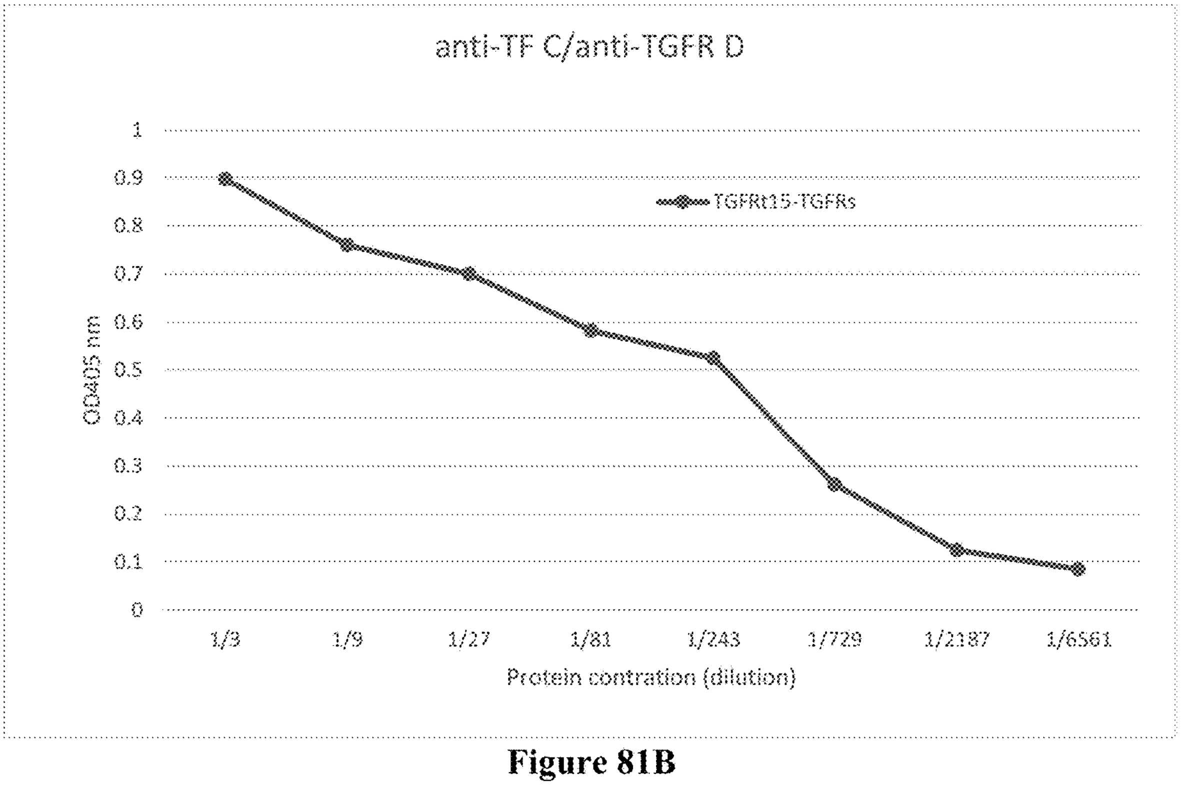

Detection of IL-15 and TGFβRII Domains in TGFRt15-TGFRs with Corresponding Antibodies Using ELISA A 96-well plate was coated with 100 μL (8 μg/mL) of anti-TF IgG1 in R5 (coating buffer) and incubated at room temperature (RT) for 2 hrs. The plates were washed 3 times and blocked with 100 μL of 1% BSA in PBS. TGFRt15-TGFRs was added at a 1:3 serial dilution, and incubated at RT for 60 min. After 3 washes, 50 ng/mL of biotinylated-anti-IL-15 antibody (BAM247, R&D Systems), or 200 ng/mL of biotinylated-anti-TGFβRII antibody (BAF241, R&D Systems) was added to the wells and incubated at RT for 60 min. Next the plates were washed 3 times, and 0.25 μg/mL of HRP-SA (Jackson ImmunoResearch) at 100 μL per well was added and incubated for 30 min at RT, followed by 4 washes and incubation with 100 μL of ABTS for 2 mins at RT. Absorbance at 405 nm was read. As shown in FIGS. 81A and 81B, the IL-15 and TGFβRII domains in TGFRt15-TGFRs were detected by the individual antibodies.

Figure 82:
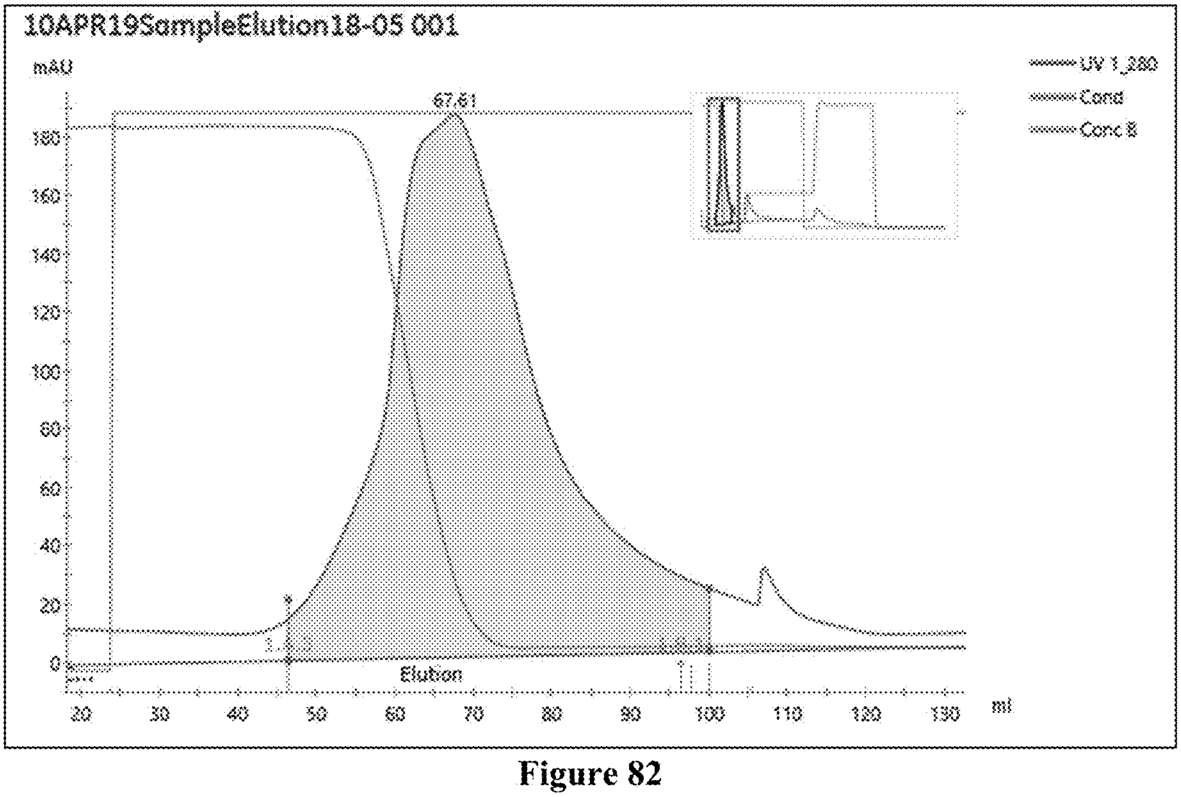
FIG. 82 is a line graph showing the chromatographic profile of TGFRt15-TGFRs protein containing cell culture supernatant following binding and elution on anti-TF antibody resin.

Purification Elution Chromatograph of TGFRt15-TGFRs from Anti-TF Antibody Affinity Column TGFRt15-TGFRs harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 82, the anti-TF antibody affinity column bound to TGFRt15-TGFRs which contains TF as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Analytical Size Exclusion Chromatography (SEC) Analysis of TGFRt15-TGFRs

Figure 83:
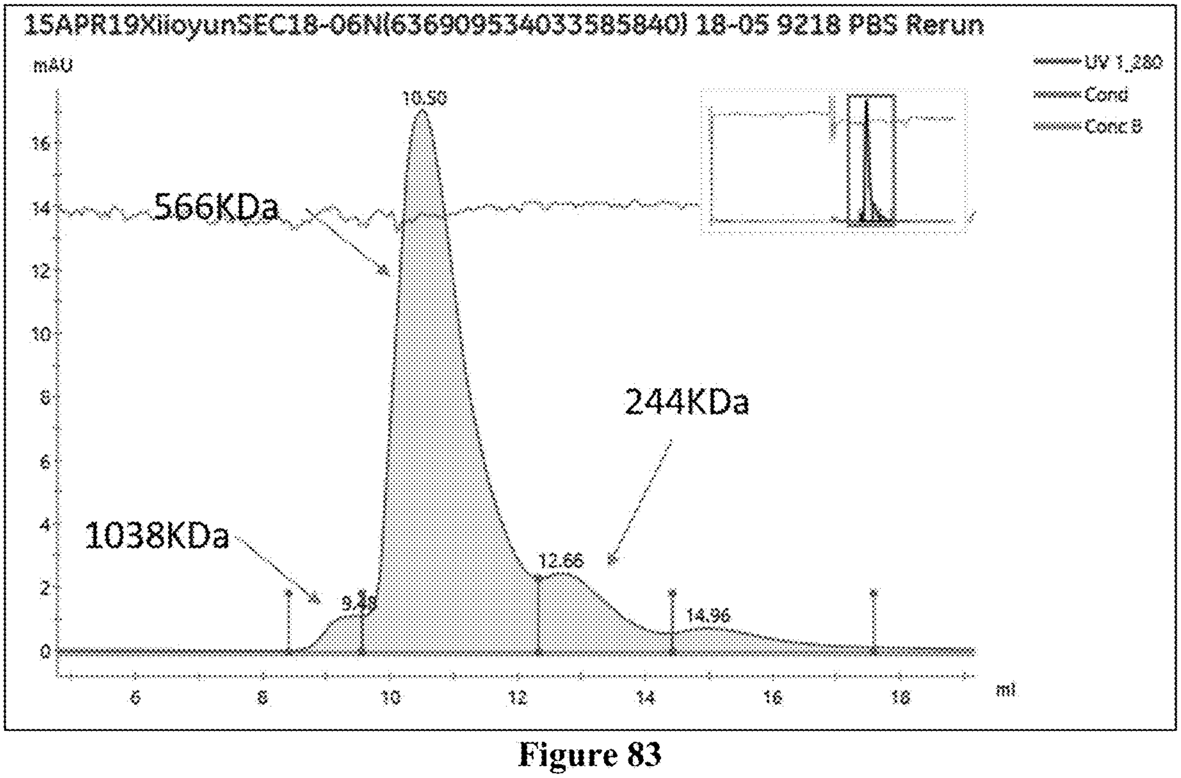
FIG. 83 shows the analytical SEC profile of TGFRt15-TGFRs.

A Superdex 200 Increase 10/300 GL gel filtration column (from GE Healthcare) was connected to an AKTA Avant system (from GE Healthcare). The column was equilibrated with 2 column volumes of PBS. The flow rate was 0.7 mL/min. A sample containing TGFRt15-TGFRs in PBS was injected into the Superdex 200 column using a capillary loop, and analyzed by SEC. The SEC chromatograph of the sample is shown in FIG. 83. The SEC results showed four protein peaks for TGFRt15-TGFRs.

Reduced SDS-PAGE Analysis of TGFRt15-TGFRs

To determine the purity and molecular weight of the TGFRt15-TGFRs protein, protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

Figure 84:
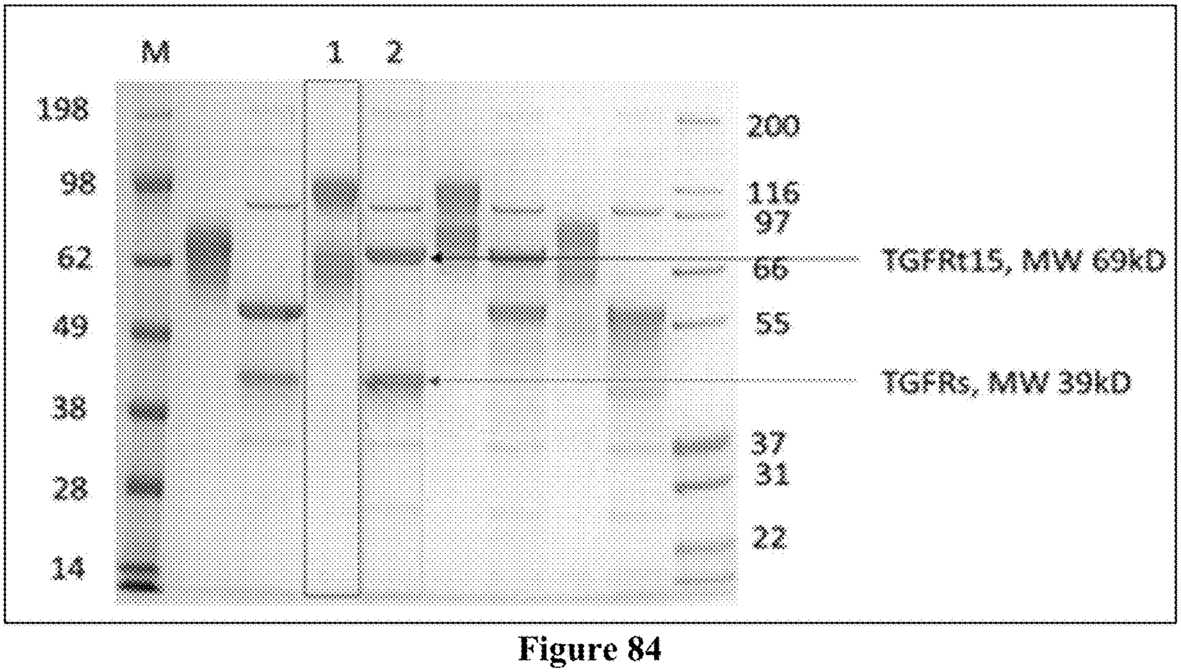
FIG. 84 shows TGFRt15-TGFRs before and after deglycosylation as analyzed by reduced SDS-PAGE.

To verify that the TGFRt15-TGFRs protein undergoes glycosylation after translation in CHO cells, a deglycosylation experiment was conducted using the Protein Deglycosylation Mix II kit from New England Biolabs and the manufacturer's instructions. FIG. 84 shows the reduced SDS-PAGE analysis of the sample in non-deglycosylated (lane 1 in red outline) and deglycosylated (lane 2 in yellow outline) state. The results showed that the TGFRt15-TGFRs protein is glycosylated when expressed in CHO cells. After deglycosylation, the purified sample showed expected molecular weights (69 kDa and 39 kDa) in the reduced SDS gel. Lane M was loaded with 10 ul of SeeBlue Plus2 Prestained Standard.

Immunostimulatory Activity of TGFRt15-TGFRs in C57BL 6 Mice

TGFRt15-TGFRs is a multi-chain polypeptide (a type A multi-chain polypeptide described herein) that includes a first polypeptide that is a soluble fusion of two TGFβRII domains, human tissue factor 219 fragment and human IL-15, and the second polypeptide that is a soluble fusion of two TGFβRII domains and sushi domain of human IL-15 receptor alpha chain.

Figure 85A:
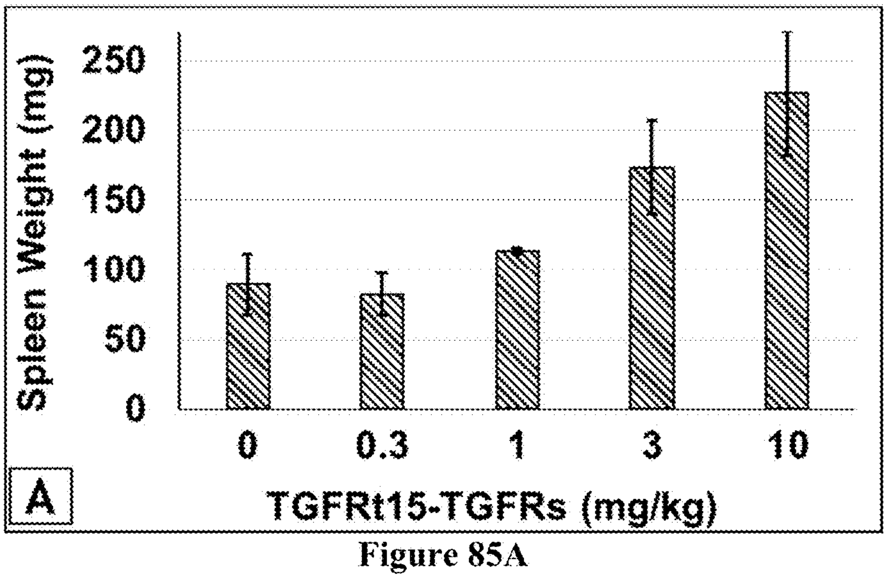
FIGS. 85A and 85B show spleen weight and the percentages of immune cell types in TGFRt15-TGFRs-treated and control-treated mice.
Figure 85B:
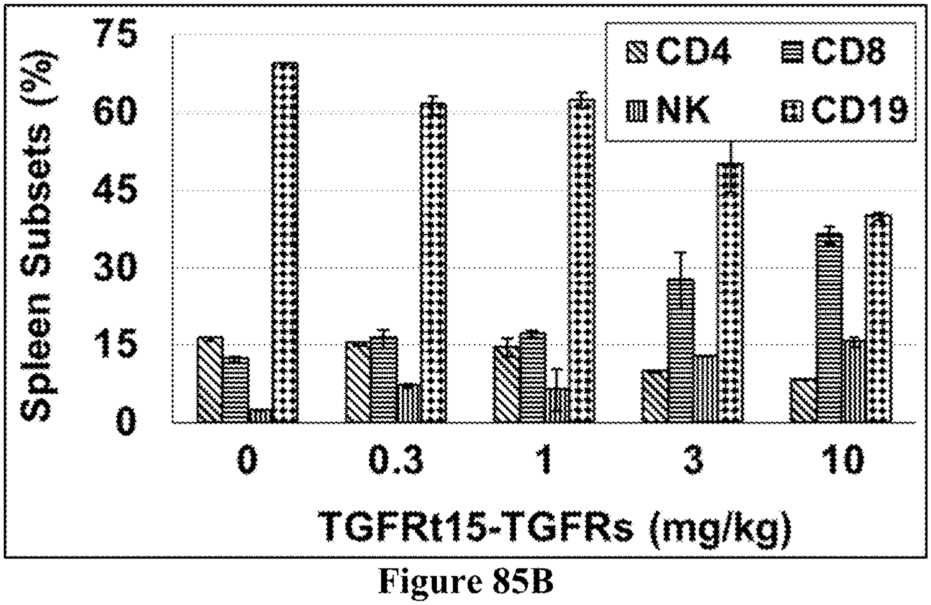

Wild type C57BL/6 mice were treated subcutaneously with either control solution or with TGFRt15-TGFRs at a dosage of 0.3 mg/kg, 1 mg/kg, 3 mg/kg, or 10 mg/kg. Four days after treatment, spleen weight and the percentages of various immune cell types present in the spleen were evaluated. As shown in FIG. 85A, the spleen weight in mice treated with TGFRt15-TGFRs increased with increasing dosage of TGFRt15-TGFRs. Moreover, the spleen weight in mice treated with 1 mg/kg, 3 mg/kg, and 10 mg/kg of TGFRt15-TGFRs were higher as compared to mice treated with the control solution, respectively. In addition, the percentages of $CD4^+$ T cells, $CD8^+$ T cells, NK cells, and $CD19^+$ B cells present in the spleen of control-treated and TGFRt15-TGFRs-treated mice were evaluated. As shown in FIG. 85B, in the spleens of mice treated with TGFRt15-TGFRs, the percentages of $CD8^+$ T cells and NK cells both increased with increasing dosage of TGFRt15-TGFRs. Specifically, the percentages of $CD8^+$ T cells were higher in mice treated with 0.3 mg/kg, 3 mg/kg, and 10 mg/kg of TGFRt15-TGFRs compared to control-treated mice, and the percentages of NK cells were higher in mice treated with 0.3 mg/kg, 1 mg/kg, 3 mg/kg, and 10 mg/kg of TGFRt15-TGFRs compared to control-treated mice. These results demonstrate that TGFRt15-TGFRs is able to stimulate immune cells in the spleen, in particular $CD8^+$ T cells and NK cells.

The pharmacokinetics of TGFRt15-TGFRs molecules were evaluated in wild type C57BL/6 mice. The mice were treated subcutaneously with TGFRt15-TGFRs at a dosage of 3 mg/kg. The mouse blood was drained from tail vein at various time points and the serum was prepared. The TGFRt15-TGFRs concentrations in mouse serum was determined with ELISA (capture: anti-human tissue factor antibody; detection: biotinylated anti-human TGFβ receptor antibody and followed by peroxidase conjugated streptavidin and ABTS substrate). The results showed that the half-life of TGFRt15-TGFRs was 12.66 hours in C57BL/6 mice.

Figure 86A:
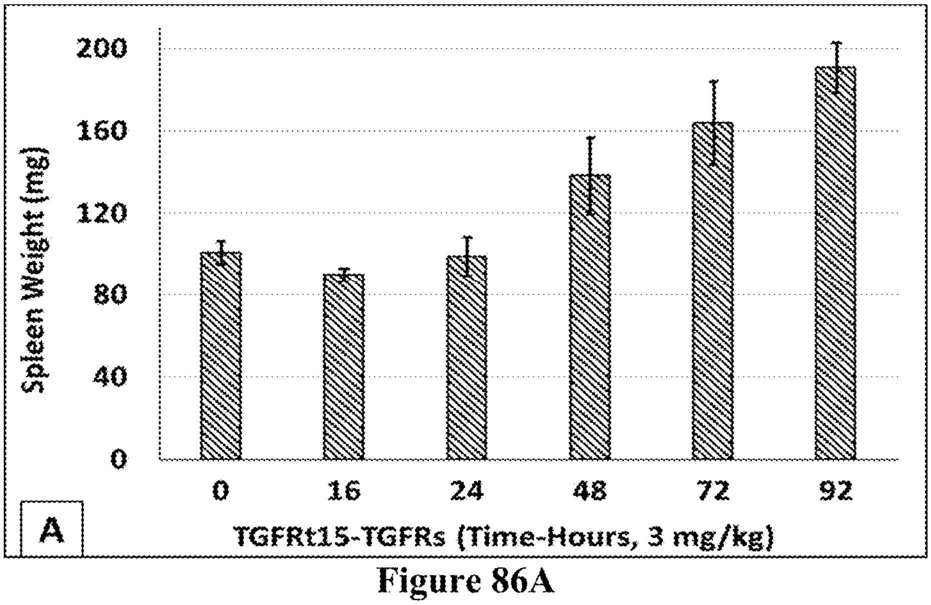
FIGS. 86A and 86B show the spleen weight and immunostimulation over 92 hours in mice treated with TGFRt15-TGFRs.
Figure 86B:
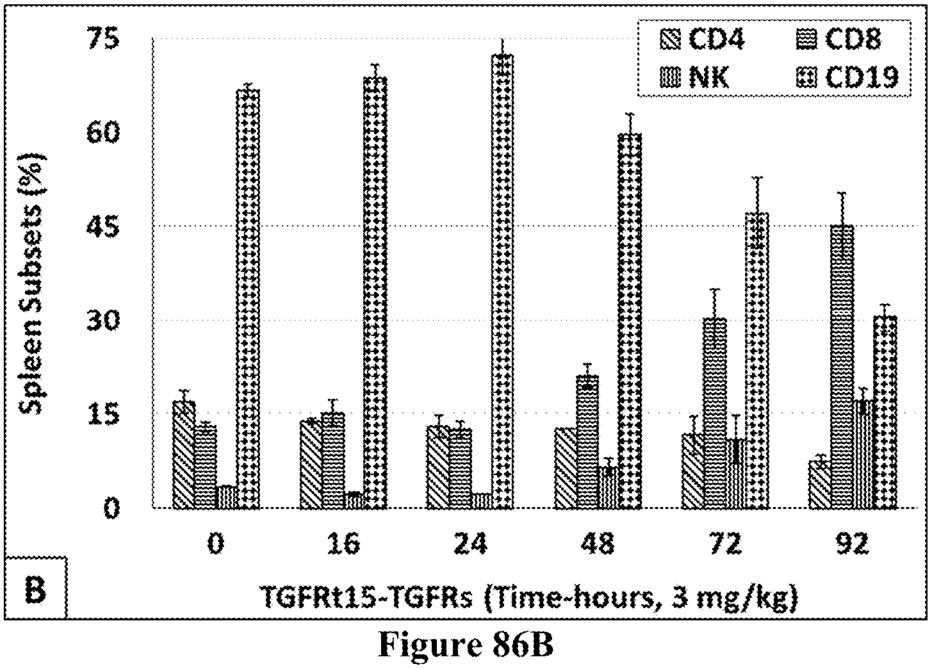

The mouse splenocytes were prepared in order to evaluate the immunostimulatory activity of TGFRt15-TGFRs over time in mice. As shown in FIG. 86A, the spleen weight in mice treated with TGFRt15-TGFRs increased 48 hours posttreatment and continued to increase over time. In addition, the percentages of $CD4^+$ T cells, $CD8^+$ T cells, NK cells, and $CD19^+$ B cells present in the spleen of control-treated and TGFRt15-TGFRs-treated mice were evaluated. As shown in FIG. 86B, in the spleens of mice treated with TGFRt15-TGFRs, the percentages of $CD8^+$ T cells and NK cells both increased at 48 hours after treatment and were higher and higher overtime after the single dose treatment. These results further demonstrate that TGFRt15-TGFRs is able to stimulate immune cells in the spleen, in particular $CD8^+$ T cells and NK cells.

Figure 87A:
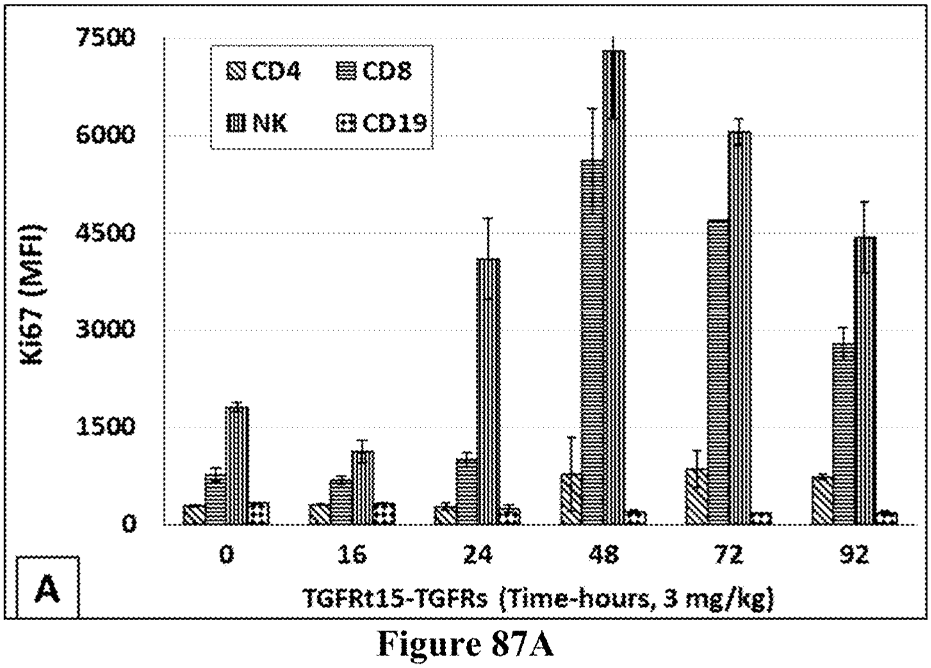
FIGS. 87A and 87B show Ki67 and Granzyme B expression in mice treated with TGFRt15-TGFRs over time.
Figure 87B:
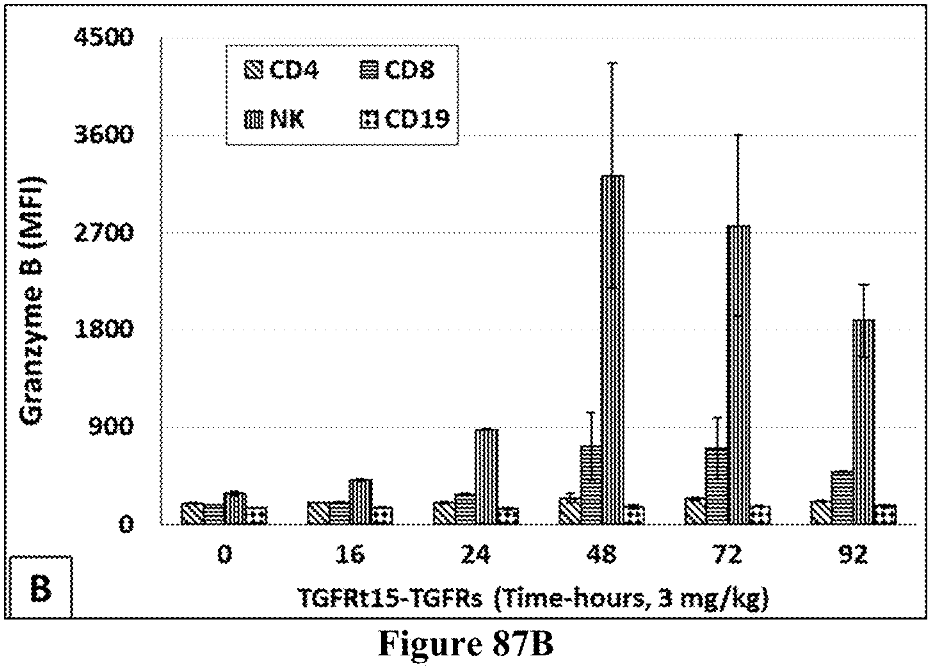

Furthermore, the dynamic proliferation of immune cells based on Ki67 expression of splenocytes and cytotoxicity potential based on granzyme B expression were evaluated in splenocytes isolated from mice following a single dose (3 mg/kg) of TGFRt15-TGFRs. As shown in FIGS. 87A and 87B, in the spleens of mice treated with TGFRt15-TGFRs, the expression of Ki67 and granzyme B by NK cells increased at 24 hours after treatment and its expression of $CD8^+$ T cells and NK cells both increased at 48 hours and later time points after the single dose treatment. These results demonstrate that TGFRt15-TGFRs not only increases the numbers of $CD8^+$ T cells and NK cells but also enhance the cytotoxicity of these cells. The single dose treatment of TGFRt15-TGFRs led $CD8^+$ T cells and NK cells to proliferate for at least 4 days.

Figure 88:
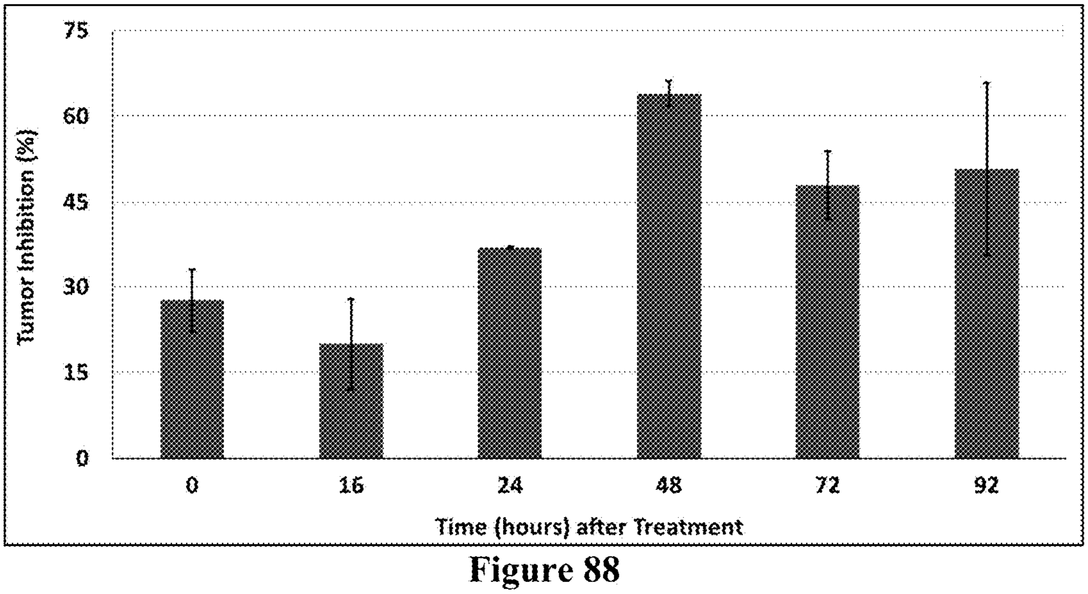
FIG. 88 shows enhancement of cytotoxicity of splenocytes by TGFRt15-TGFRs in C57BL/6 Mice.

The cytotoxicity of the splenocytes from TGFRt15-TGFRs-treated mice against tumor cells was also evaluated. Mouse Moloney leukemia cells (Yac-1) were labeled with CELLTRACE®, violet dye, and were used as tumor target cells. Splenocytes were prepared from TGFRt15-TGFRs (3 mg/kg)-treated mouse spleens at various time points post treatment and were used as effector cells. The target cells were mixed with effector cells at an E:T ratio=10:1 and incubated at 37° C. for 20 hours. Target cell viability was assessed by analysis of propidium iodide positive, violet-labeled Yac-1 cells using flow cytometry. Percentage of Yac-1 tumor inhibition was calculated using the formula, (1-[viable Yac-1 cell number in experimental sample]/[viable Yac-1 cell number in the sample without splenocytes])×100. As shown in FIG. 88, splenocytes from TGFRt15-TGFRs-treated mice had stronger cytotoxicity against Yac-1 cells than the control mouse splenocytes.

Tumor Size Analysis in Response to Chemotherapy and/or TGFRt15-TGFRs

Figure 89:
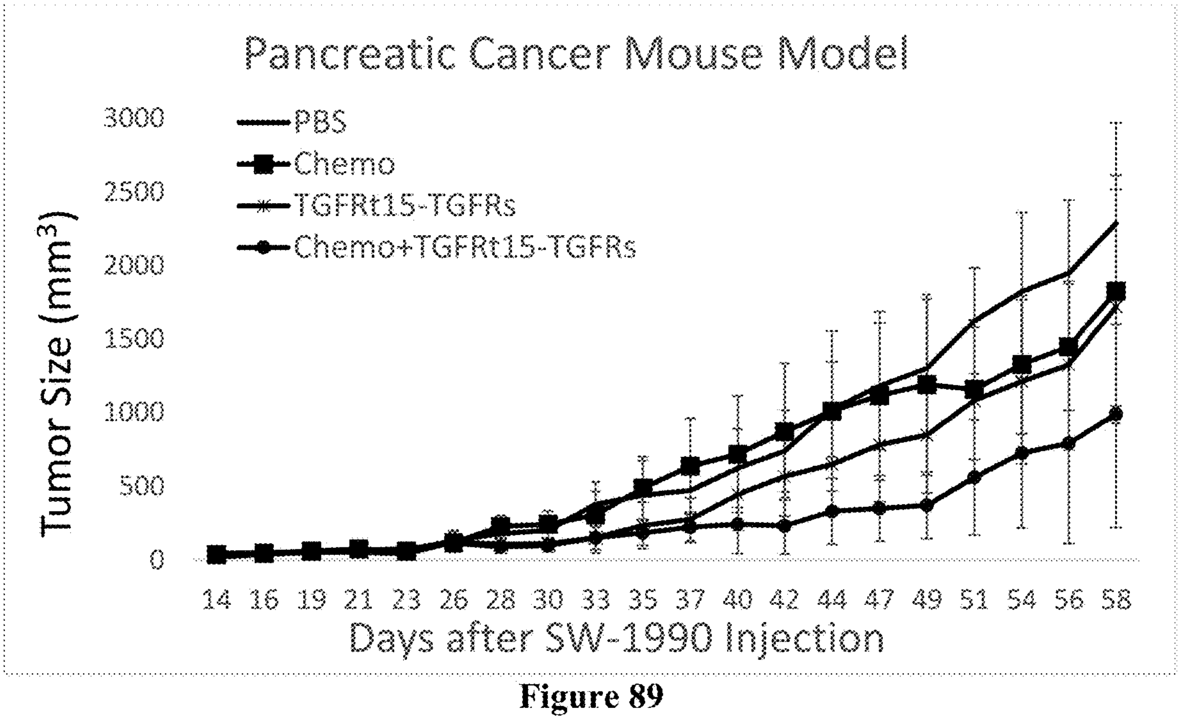
FIG. 89 shows changes in tumor size in response to PBS treatment, chemotherapy alone, TGFRt15-TGFRs alone, or chemotherapy and TGFRt15-TGFRs combination, in a pancreatic cancer mouse model.

Pancreatic cancer cells (SW1990, ATCC® CRL-2172) were subcutaneously (s.c.) injected into C57BL/6 scid mice (The Jackson Laboratory, 001913, $2\times10^6$ cells/mouse, in 100 μL HBSS) to establish the pancreatic cancer mouse model. Two weeks after tumor cell injection, chemotherapy was initiated in these mice intraperitoneally with a combination of Abraxane (Celgene, 68817-134, 5 mg/kg, i.p.) and Gemcitabine (Sigma Aldrich, G6423, 40 mg/kg, i.p.), followed by immunotherapy with TGFRt15-TGFRs (3 mg/kg, s.c.) in 2 days. The procedure above was considered one treatment cycle and was repeated for another 3 cycles (1 cycle/week). Control groups were set up as the SW1990-injected mice that received PBS, chemotherapy (Gemcitabine and Abraxane), or TGFRt15-TGFRs alone. Along with the treatment cycles, tumor size of each animal was measured and recorded every other day, until the termination of the experiment 2 months after the SW1990 cells were injected. Measurement of the tumor volumes were analyzed by group and the results indicated that the animals receiving a combination of chemotherapy and TGFRt15-TGFRs had significantly smaller tumors comparing to the PBS group, whereas neither chemotherapy nor TGFRt15-TGFRs therapy alone work as sufficiently as the combination (FIG. 89).

In Vitro Senescent B16F10 Melanoma Model

Figure 90:
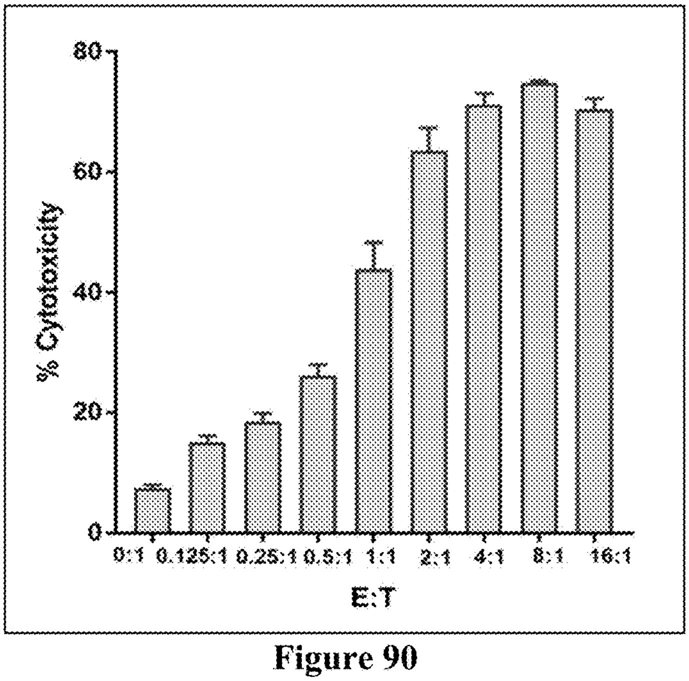
FIG. 90 shows the cytotoxicity of NK cells isolated from mice treated with TGFRt15-TGFRs.

Next, in vitro killing of senescent B16F10 melanoma cells by activated mouse NK cells was evaluated. B16F10 senescence cells (B16F10-SNC) cells were labelled with CELLTRACE®, violet dye, and incubated for 16 hrs with different E:T ratio of in vitro 2t2-activated mouse NK cells (isolated from spleen of C57BL/6 mice injected with TGFRt15-TGFRs10 mg/kg for 4 days). The cells were trypsinized, washed and resuspended in complete media containing propidium iodide (PI) solution. The cytotoxicity was assessed by flow cytometry (FIG. 90).

Figure 91:
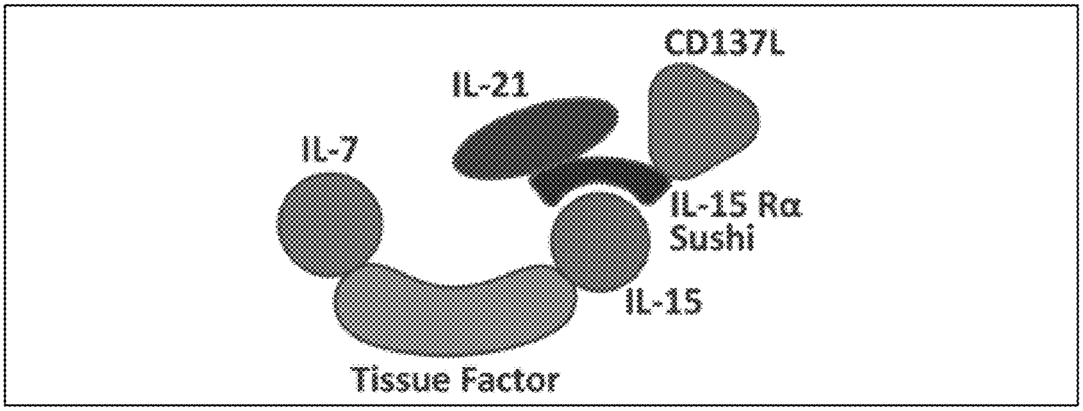
FIG. 91 shows a schematic of the 7t15-21s137L (long version) construct.
Figure 92:
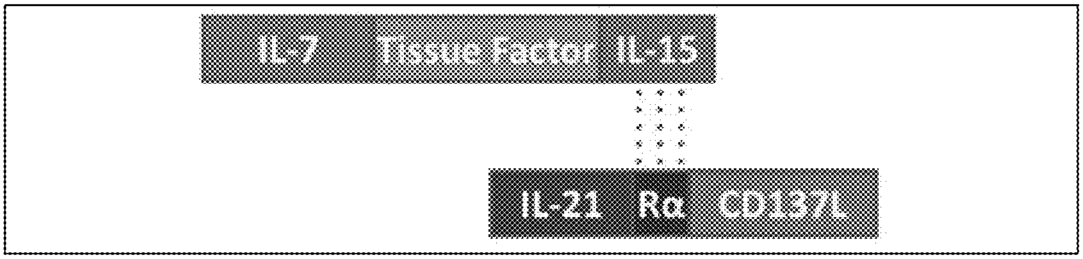
FIG. 92 shows an additional schematic of the 7t15-21s137L (long version) construct.

Example 53: 7t15-21s137L (Long Version) Fusion Protein Creation and Characterization A fusion protein complex was generated comprising of IL-21/IL-15RαSu/CD137L and IL-7/TF/IL-15 fusion proteins (FIG. 91 and FIG. 92). Specifically, a construct was made linking the IL-7 sequence to the N-terminus coding region of tissue factor 219 followed by the N-terminus coding region of IL-15. The nucleic acid and protein sequences of a construct comprising IL-7 linked to the N-terminus of tissue factor 219 following with the N-terminus of IL-15 are shown below.

The nucleic acid sequence of the 7t15 construct (including signal peptide sequence) is as follows:

```
(Signal peptide)
ATGAAGTGGGTGACCTTCATCAGCCTGCTGTTCCT

GTTCTCCAGCGCCTACTCC

(Human IL7)
GATTGCGACATCGAGGGCAAGGACGGCAAGCAGTA

CGAGAGCGTGCTGATGGTGTCCATCGACCAGCTGC

TGGACAGCATGAAGGAGATCGGCTCCAACTGCCTC

AACAACGAGTTCAACTTCTTCAAGCGGCACATCTG

CGACGCCAACAAGGAGGGCATGTTCCTGTTCAGGG

CCGCCAGGAAACTGCGGCAGTTCCTGAAGATGAAC

TCCACCGGCGACTTCGACCTGCACCTGCTGAAGGT

GTCCGAGGGCACCACCATCCTGCTGAACTGCACCG

GACAGGTGAAGGGCCGGAAACCTGCTGCTCTGGGA

GAGGCCCAACCCACCAAGAGCCTGGAGGAGAACAA

GTCCCTGAAGGAGCAGAAGAAGCTGAACGACCTGT

GCTTCCTGAAGAGGCTGCTGCAGGAGATCAAGACC

TGCTGGAACAAGATCCTGATGGGCACCAAGGAGCA

T

(Human Tissue Factor 219)
AGCGGCACAACCAACACAGTCGCTGCCTATAACCT

CACTTGGAAGAGCACCAACTTCAAAACCATCCTCG

AATGGGAACCCAAACCCGTTAACCAAGTTTACACC

GTGCAGATCAGCACCAAGTCCGGCGACTGGAAGTC
```

-continued

```
CAAATGTTTCTATACCACCGACACCGAGTGCGATC

TCACCGATGAGATCGTGAAAGATGTGAAACAGACC

TACCTCGCCCGGGTGTTTAGCTACCCCGCCGGCAA

TGTGGAGAGCACTGGTTCCGCTGGCGAGCCTTTAT

ACGAGAACAGCCCCGAATTTACCCCTTACCTCGAG

ACCAATTTAGGACAGCCCACCATCCAAAGCTTTGA

GCAAGTTGGCACAAAGGTGAATGTGACAGTGGAGG

ACGAGCGGACTTTAGTGCGGCGGAACAACACCTTT

CTCAGCCTCCGGGATGTGTTCGGCAAAGATTTAAT

CTACACACTGTATTACTGGAAGTCCTCTTCCTCCG

GCAAGAAGACAGCTAAAACCAACACAAACGAGTTT

TTAATCGACGTGGATAAAGGCGAAAACTACTGTTT

CAGCGTGCAAGCTGTGATCCCCTCCCGGACCGTGA

ATAGGAAAAGCACCGATAGCCCCGTTGAGTGCATG

GGCCAAGAAAAGGGCGAGTTCCGGGAG

(Human IL-15)
AACTGGGTGAACGTCATCAGCGATTTAAAGAAGAT

CGAAGATTTAATTCAGTCCATGCATATCGACGCCA

CTTTATACACAGAATCCGACGTGCACCCCTCTTGT

AAGGTGACCGCCATGAAATGTTTTTTACTGGAGCT

GCAAGTTATCTCTTTAGAGAGCGGAGACGCTAGCA

TCCACGACACCGTGGAGAATTTAATCATTTTAGCC

AATAACTCTTTATCCAGCAACGGCAACGTGACAGA

GTCCGGCTGCAAGGAGTGCGAAGAGCTGGAGGAGA

AGAACATCAAGGAGTTTCTGCAATCCTTTGTGCAC

ATTGTCCAGATGTTCATCAATACCTCC
```

The amino acid sequence of 7t15 fusion protein (including the leader sequence) is as follows:

```
(Signal peptide)
MKWVTFISLLFLFSSAYS

(Human IL7)
DCDIEGKDGKQYESVLMVSIDQLLDSMKEIGSNCL

NNEFNFFKRHICDANKEGMFLFRAARKLRQFLKMN

STGDFDLHLLKVSEGTTILLNCTGQVKGRKPAALG

EAQPTKSLEENKSLKEQKKLNDLCFLKRLLQEIKT

CWNKILMGTKEH

(Human Tissue Factor 219)
SGTTNTVAAYNLTWKSTNFKTILEWEPKPVNQVYT

VQISTKSGDWKSKCFYTTDTECDLTDEIVKDVKQT

YLARVFSYPAGNVESTGSAGEPLYENSPEFTPYLE

TNLGQPTIQSFEQVGTKVNVTVEDERTLVRRNNTF

LSLRDVFGKDLIYTLYYWKSSSSGKKTAKTNTNEF
```

-continued

LIDVDKGENYCFSVQAVIPSRTVNRKSTDSPVECM

GQEKGEFRE (Human IL-15)
NWVNVISDLKKIEDLIQSMHIDATLYTESDVHPSC

KVTAMKCFLLELQVISLESGDASIHDTVENLIILA

NNSLSSNGNVTESGCKECEELEEKNIKEFLQSFVH

IVQMFINTS

The nucleic acid and protein sequences of the 21s137L are shown below. The nucleic acid sequence of the 21s137L construct (including signal peptide sequence) is as follows:

(Signal peptide)
ATGAAGTGGGTGACCTTCATCAGCCTGCTGTTCCT

GTTCTCCAGCGCCTACTCC (Human IL-21)
CAGGGCCAGGACAGGCACATGATCCGGATGAGGCA

GCTCATCGACATCGTCGACCAGCTGAAGAACTACG

TGAACGACCTGGTGCCCGAGTTTCTGCCTGCCCCC

GAGGACGTGGAGACCAACTGCGAGTGGTCCGCCTT

CTCCTGCTTTCAGAAGGCCCAGCTGAAGTCCGCCA

ACACCGGCAACAACGAGCGGATCATCAACGTGAGC

ATCAAGAAGCTGAAGCGGAAGCCTCCCTCCACAAA

CGCCGGCAGGAGGCAGAAGCACAGGCTGACCTGCC

CCAGCTGTGACTCCTACGAGAAGAAGCCCCCCAAG

GAGTTCCTGGAGAGGTTCAAGTCCCTGCTGCAGAA

GATGATCCATCAGCACCTGTCCTCCAGGACCCACG

GCTCCGAGGACTCC (Human IL-15R α sushi domain)
ATTACATGCCCCCCTCCCATGAGCGTGGAGCACGC

CGACATCTGGGTGAAGAGCTATAGCCTCTACAGCC

GGGAGAGGTATATCTGTAACAGCGGCTTCAAGAGG

AAGGCCGGCACCAGCAGCCTCACCGAGTGCGTGCT

GAATAAGGCTACCAACGTGGCTCACTGGACAACAC

CCTCTTTAAAGTGCATCCGG ((G4S)3 linker)
GGCGGTGGAGGATCCGGAGGAGGTGGCTCCGGCGG

CGGAGGATCT (Human CD137L)
CGCGAGGGTCCCGAGCTTTCGCCCGACGATCCCGC

CGGCCTCTTGGACCTGCGGCAGGGCATGTTTGCGC

AGCTGGTGGCCCAAAATGTTCTGCTGATCGATGGG

CCCCTGAGCTGGTACAGTGACCCAGGCCTGGCAGG

CGTGTCCCTGACGGGGGGCCTGAGCTACAAAGAGG

ACACGAAGGAGCTGGTGGTGGCCAAGGCTGGAGTC

TACTATGTCTTCTTTCAACTAGAGCTGCGGCGCGT

-continued

GGTGGCCGGCGAGGGCTCAGGCTCCGTTTCACTTG

CGCTGCACCTGCAGCCACTGCGCTCTGCTGCTGGG

GCCGCCGCCCTGGCTTTGACCGTGGACCTGCCACC

CGCCTCCTCCGAGGCTCGGAACTCGGCCTTCGGTT

TCCAGGGCCGCTTGCTGCACCTGAGTGCCGGCCAG

CGCCTGGGCGTCCATCTTCACACTGAGGCCAGGGC

ACGCCATGCCTGGCAGCTTACCCAGGGCGCCACAG

TCTTGGGACTCTTCCGGGTGACCCCCGAAATCCCA

GCCGGACTCCCTTCACCGAGGTCGGAA

The amino acid sequence of 21s137L fusion protein (including the leader sequence) is as follows:

(Signal peptide)
MKWVTFISLLFLFSSAYS (Human IL-21)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS (Human IL-15Rα sushi domain)
ITCPPPMSVEHADIWVKSYSLYSRERYICNSGFKRKAGTSSLTECVLN

KATNVAHWTTPSLKCIR ((G4S)3 linker)
GGGGSGGGGSGGGGS (Human CD137L)
REGPELSPDDPAGLLDLRQGMFAQLVAQNVLLIDGPLSWYSDPGLAGV

SLTGGLSYKEDTKELVVAKAGVYYVFFQLELRRVVAGEGSGSVSLALH

LQPLRSAAGAAALALTVDLPPASSEARNSAFGFQGRLLHLSAGQRLGV

HLHTEARARHAWQLTQGATVLGLFRVTPEIPAGLPSPRSE

In some cases, the leader peptide is cleaved from the intact polypeptide to generate the mature form that may be soluble or secreted.

The IL-21/IL-15RαSu/CD137L and IL-7/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble IL-7/TF/IL-15: IL-21/IL-15RαSu/CD137L protein complex (referred to as 7t15-21s137L), which can be purified by anti-TF IgG1 affinity and other chromatography methods.

Figure 93:
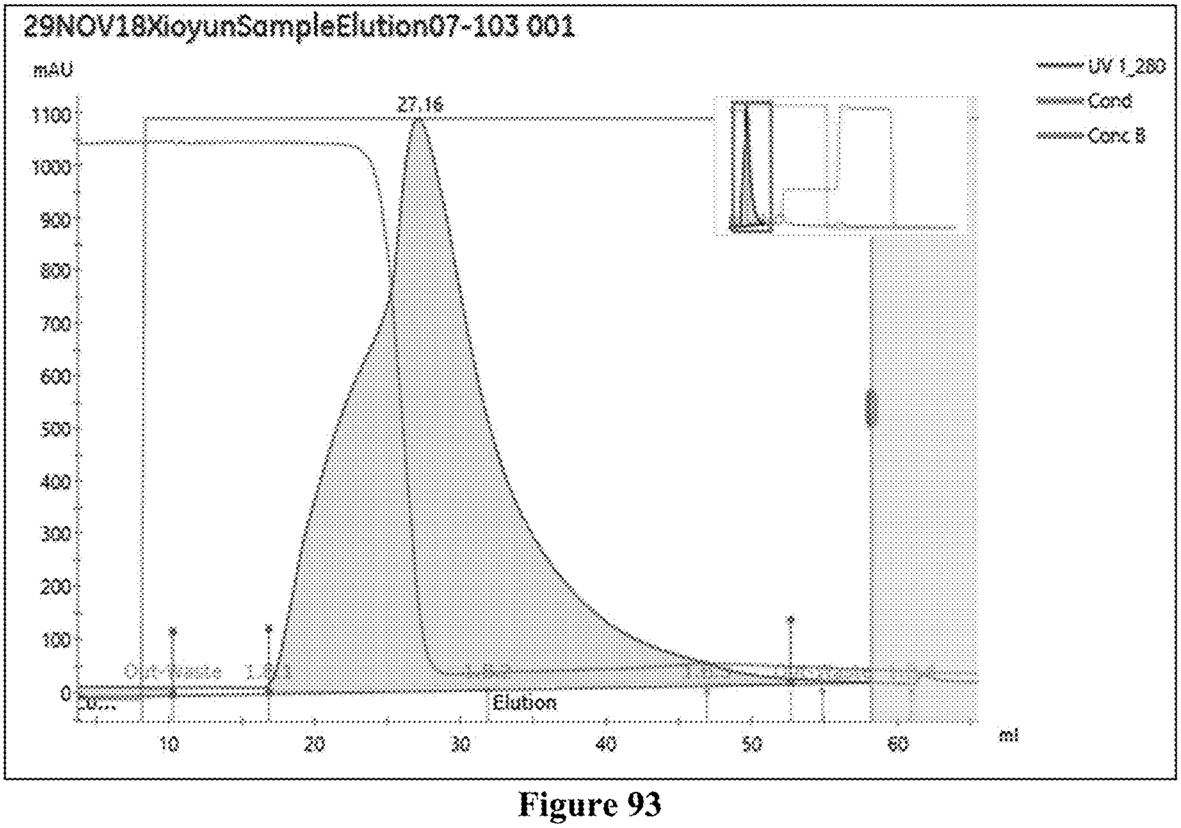
FIG. 93 is a line graph showing the chromatographic profile of 7t15-21s137L (long version) protein containing cell culture supernatant following binding and elution on anti-TF antibody resin.
Figure 94:
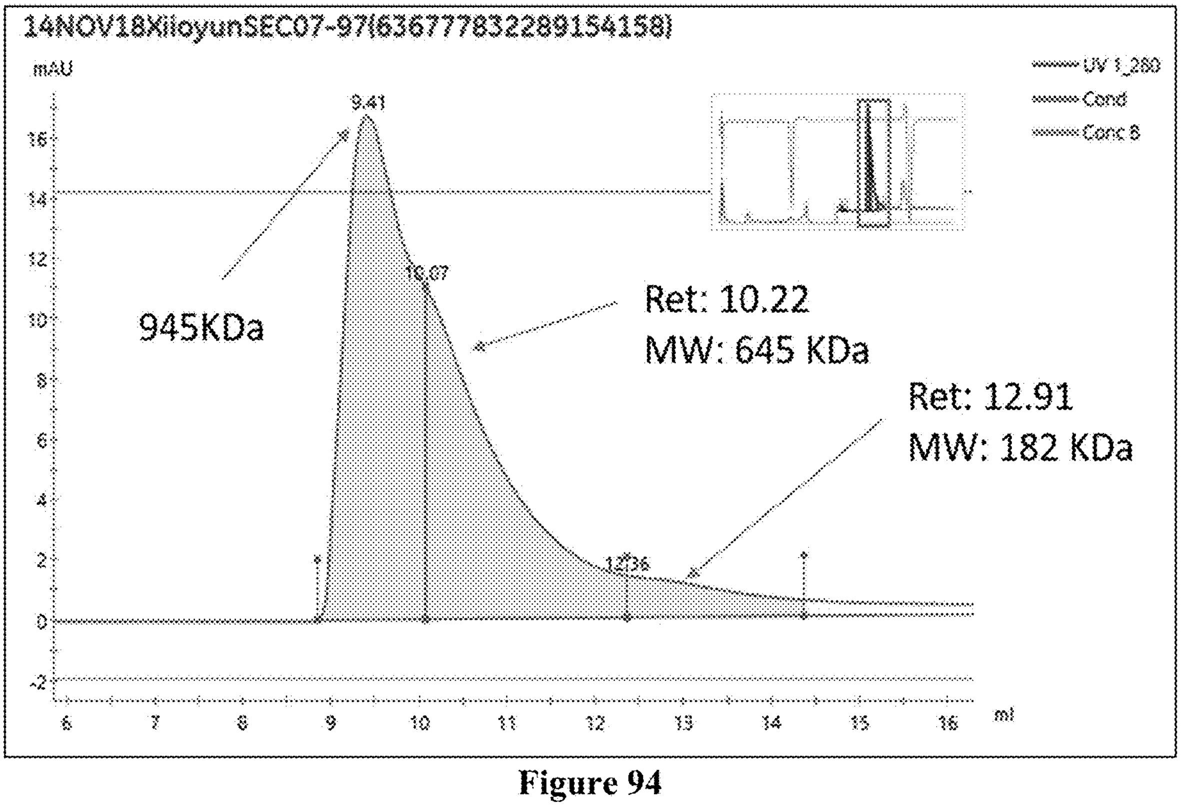
FIG. 94 shows the analytical SEC profile of 7t15-21s137L (long version).
Figure 95:
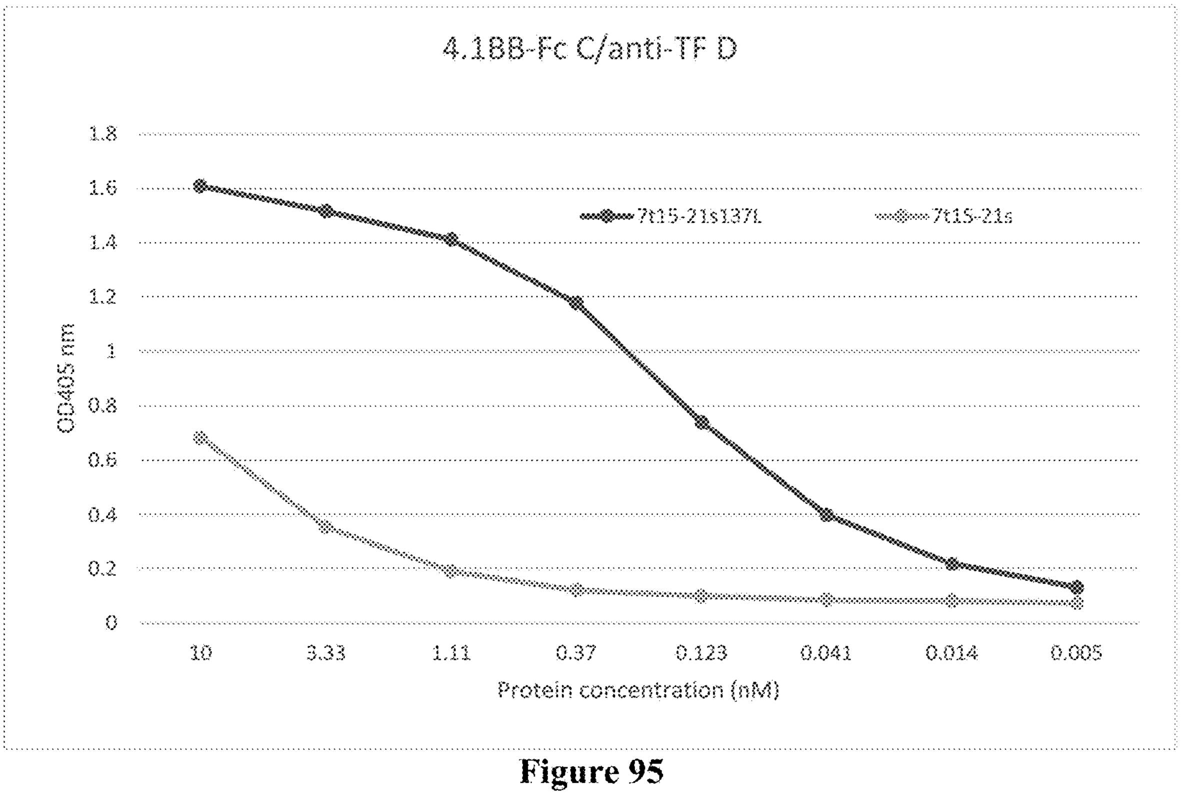
FIG. 95 shows binding of 7t15-21s137L (short version) to CD137L (4.1BBL)

Purification Elution Chromatograph of 7t15-21s137L Using Anti-TF Antibody Affinity Column 7t15-21s137L harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 93, the anti-TF antibody affinity column bound to 7t15-21s137L which contains TF as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min. FIG. 94 shows the analytical SEC profile of 7t15-21s137L.

Example 54: 7t15-21s137L (Short Version) Fusion Protein Generation and Characterization A fusion protein complex was generated comprising of IL-21/IL-15RαSu/CD137L and IL-7/TF/IL-15 fusion proteins. Specifically, a construct was made linking the IL-7 sequence to the N-terminus coding region of tissue factor 219 followed by the N-terminus coding region of IL-15. The nucleic acid and protein sequences of a construct comprising IL-7 linked to the N-terminus of tissue factor 219 following with the N-terminus of IL-15 are shown below.

The nucleic acid sequence of 7t15 construct (including signal peptide sequence) is as follows:

```
(Signal peptide)
ATGAAGTGGGTGACCTTCATCAGCCTGCTGTTCCTGTTCTCCAGCGCCT

ACTCC

(Human IL7)
GATTGCGACATCGAGGGCAAGGACGGCAAGCAGTACGAGAGCGTGCT

GATGGTGTCCATCGACCAGCTGCTGGACAGCATGAAGGAGATCGGCTCC

AACTGCCTCAACAACGAGTTCAACTTCTTCAAGCGGCACATCTGCGACG

CCAACAAGGAGGGCATGTTCCTGTTCAGGGCCGCCAGGAAACTGCGGCA

GTTCCTGAAGATGAACTCCACCGGCGACTTCGACCTGCACCTGCTGAAG

GTGTCCGAGGGCACCACCATCCTGCTGAACTGCACCGGACAGGTGAAGG

GCCGGAAACCTGCTGCTCTGGGAGAGGCCCAACCCACCAAGAGCCTGGA

GGAGAACAAGTCCCTGAAGGAGCAGAAGAAGCTGAACGACCTGTGCTTC

CTGAAGAGGCTGCTGCAGGAGATCAAGACCTGCTGGAACAAGATCCTGA

TGGGCACCAAGGAGCAT

(Human Tissue Factor 219)
AGCGGCACAACCAACACAGTCGCTGCCTATAACCTCACTTGGAAGAG

CACCAACTTCAAAACCATCCTCGAATGGGAACCCAAACCCGTTAACCAA

GTTTACACCGTGCAGATCAGCACCAAGTCCGGCGACTGGAAGTCCAAAT

GTTTCTATACCACCGACACCGAGTGCGATCTCACCGATGAGATCGTGAA

AGATGTGAAACAGACCTACCTCGCCCGGGTGTTTAGCTACCCCGCCGGC

AATGTGGAGAGCACTGGTTCCGCTGGCGAGCCTTTATACGAGAACAGCC

CCGAATTTACCCCTTACCTCGAGACCAATTTAGGACAGCCCACCATCCA

AAGCTTTGAGCAAGTTGGCACAAAGGTGAATGTGACAGTGGAGGACGAG
```

-continued

```
CGGACTTTAGTGCGGCGGAACAACACCTTTCTCAGCCTCCGGGATGTGT

TCGGCAAAGATTTAATCTACACACTGTATTACTGGAAGTCCTCTTCCTC

CGGCAAGAAGACAGCTAAAACCAACACAAACGAGTTTTTAATCGACGTG

GATAAAGGCGAAAACTACTGTTTCAGCGTGCAAGCTGTGATCCCCTCCC

GGACCGTGAATAGGAAAAGCACCGATAGCCCCGTTGAGTGCATGGGCCA

AGAAAAGGGCGAGTTCCGGGAG

(Human IL-15)
AACTGGGTGAACGTCATCAGCGATTTAAAGAAGATCGAAGATTTAATT

CAGTCCATGCATATCGACGCCACTTTATACACAGAATCCGACGTGCACC

CCTCTTGTAAGGTGACCGCCATGAAATGTTTTTTACTGGAGCTGCAAGT

TATCTCTTTAGAGAGCGGAGACGCTAGCATCCACGACACCGTGGAGAAT

TTAATCATTTTAGCCAATAACTCTTTATCCAGCAACGGCAACGTGACAG

AGTCCGGCTGCAAGGAGTGCGAAGAGCTGGAGGAGAAGAACATCAAGGA

GTTTCTGCAATCCTTTGTGCACATTGTCCAGATGTTCATCAATACCTCC
```

The amino acid sequence of 7t15 fusion protein (including the leader sequence) is as follows:

```
(Signal peptide)
MKWVTFISLLFLFSSAYS

(Human IL7)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEH

(Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE

(Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS
```

The nucleic acid and protein sequences of the 21s137L (short version) are shown below. The nucleic acid sequence of 21s137L (short version) construct (including signal peptide sequence) is as follows:

```
(Signal peptide)
ATGAAGTGGGTGACCTTCATCAGCCTGCTGTTCCTGTTCTCCAGCGCCT

ACTCC

(Human IL-21)
CAGGGCCAGGACAGGCACATGATCCGGATGAGGCAGCTCATCGACAT

CGTCGACCAGCTGAAGAACTACGTGAACGACCTGGTGCCCGAGTTTCTG

CCTGCCCCCGAGGACGTGGAGACCAACTGCGAGTGGTCCGCCTTCTCCT
```

-continued

```
GCTTTCAGAAGGCCCAGCTGAAGTCCGCCAACACCGGCAACAACGAGCG

GATCATCAACGTGAGCATCAAGAAGCTGAAGCGGAAGCCTCCCTCCACA

AACGCCGGCAGGAGGCAGAAGCACAGGCTGACCTGCCCCAGCTGTGACT

CCTACGAGAAGAAGCCCCCCAAGGAGTTCCTGGAGAGGTTCAAGTCCCT

GCTGCAGAAGATGATCCATCAGCACCTGTCCTCCAGGACCCACGGCTCC

GAGGACTCC

(Human IL-15Rα sushi domain)
ATTACATGCCCCCCTCCCATGAGCGTGGAGCACGCCGACATCTGGGTG

AAGAGCTATAGCCTCTACAGCCGGGAGAGGTATATCTGTAACAGCGGCT

TCAAGAGGAAGGCCGGCACCAGCAGCCTCACCGAGTGCGTGCTGAATAA

GGCTACCAACGTGGCTCACTGGACAACACCCTCTTTAAAGTGCATCCGG

((G4S)3 linker)
GGCGGTGGAGGATCCGGAGGAGGTGGCTCCGGCGGCGGAGGATCT

(Human CD137 Ligand short version)
GATCCCGCCGGCCTCTTGGACCTGCGGCAGGGCATGTTTGCGCAGCTG

GTGGCCCAAAATGTTCTGCTGATCGATGGGCCCCTGAGCTGGTACAGTG

ACCCAGGCCTGGCAGGCGTGTCCCTGACGGGGGGCCTGAGCTACAAAGA

GGACACGAAGGAGCTGGTGGTGGCCAAGGCTGGAGTCTACTATGTCTTC

TTTCAACTAGAGCTGCGGCGCGTGGTGGCCGGCGAGGGCTCAGGCTCCG

TTTCACTTGCGCTGCACCTGCAGCCACTGCGCTCTGCTGCTGGGGCCGC

CGCCCTGGCTTTGACCGTGGACCTGCCACCCGCCTCCTCCGAGGCTCGG

AACTCGGCCTTCGGTTTCCAGGGCCGCTTGCTGCACCTGAGTGCCGGCC

AGCGCCTGGGCGTCCATCTTCACACTGAGGCCAGGGCACGCCATGCCTG

GCAGCTTACCCAGGGCGCCACAGTCTTGGGACTCTTCCGGGTGACCCCC

GAAATC
```

The amino acid sequence of the 21s137L (short version) construct (including signal peptide sequence) is as follows:

```
(Signal peptide)
MKWVTFISLLFLFSSAYS

(Human IL-21)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS

(Human IL-15Rα sushi domain)
ITCPPPMSVEHADIWVKSYSLYSRERYICNSGFKRKAGTSSLTECVLNK

ATNVAHWTTPSLKCIR

((G4S)3 linker)
GGGGSGGGGSGGGGS

(Human CD137 Ligand short version)
DPAGLLDLRQGMFAQLVAQNVLLIDGPLSWYSDPGLAGVSLTGGLSYKE

DTKELVVAKAGVYYVFFQLELRRVVAGEGSGSVSLALHLQPLRSAAGAA

ALALTVDLPPASSEARNSAFGFQGRLLHLSAGQRLGVHLHTEARARHAW

QLTQGATVLGLFRVTPEI
```

The IL-21/IL-15RαSu/CD137L (short version) and IL-7/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble IL-7/TF/IL-15: IL-21/IL-15RαSu/CD137L protein complex (referred to as 7t15-21s137L (short version)), which can be purified by anti-TF IgG1 affinity and other chromatography methods.

Binding of 7t15-21s137L (Short Version) to CD137 (4.1BB)

On day 1, a 96-well plate was coated with 100 μL (2.5 μg/mL) of GAH IgG Fc (G-102-C, R&D Systems) in R5 (coating buffer) or R5 only and incubated at 4° C., overnight. On day 2, the plates were washed three times and blocked with 300 μL of 1% BSA in PBS at 37° C. for 2 hrs. 10 ng/mL of 4.1BB/Fc (838-4B, R&D Systems) was added at 100 μL/well and incubated for 2 hrs at RT. After three washes, the 7t15-21s137L or 7t15-21s serially diluted at a 1/3 ratio (starting at 10 nM), and incubated at 4° C. overnight. On day 3, following 3 washes, 300 ng/mL of biotinylated-anti-hTF antibody (BAF2339, R&D Systems) was added at 100 μL per well and incubated at RT for 2 hrs. The plate was then washed three times and incubated with 0.25 μg/mL of HRP-SA (Jackson ImmuneResearch) at 100 μL per well for 30 min, followed by 3 washes and incubation with 100 μL of ABTS for 2 mins at RT. Absorbance was read at 405 nm. As shown in FIG. 95, 7t15-21s137L (short version) showed significant interaction with 4.1BB/Fc (blue line) as compared to 7t15-21s.

Detection of IL-15, IL-21, and IL-7 in 7t15-21s137L (Short Version) with ELISA

Figure 96A:
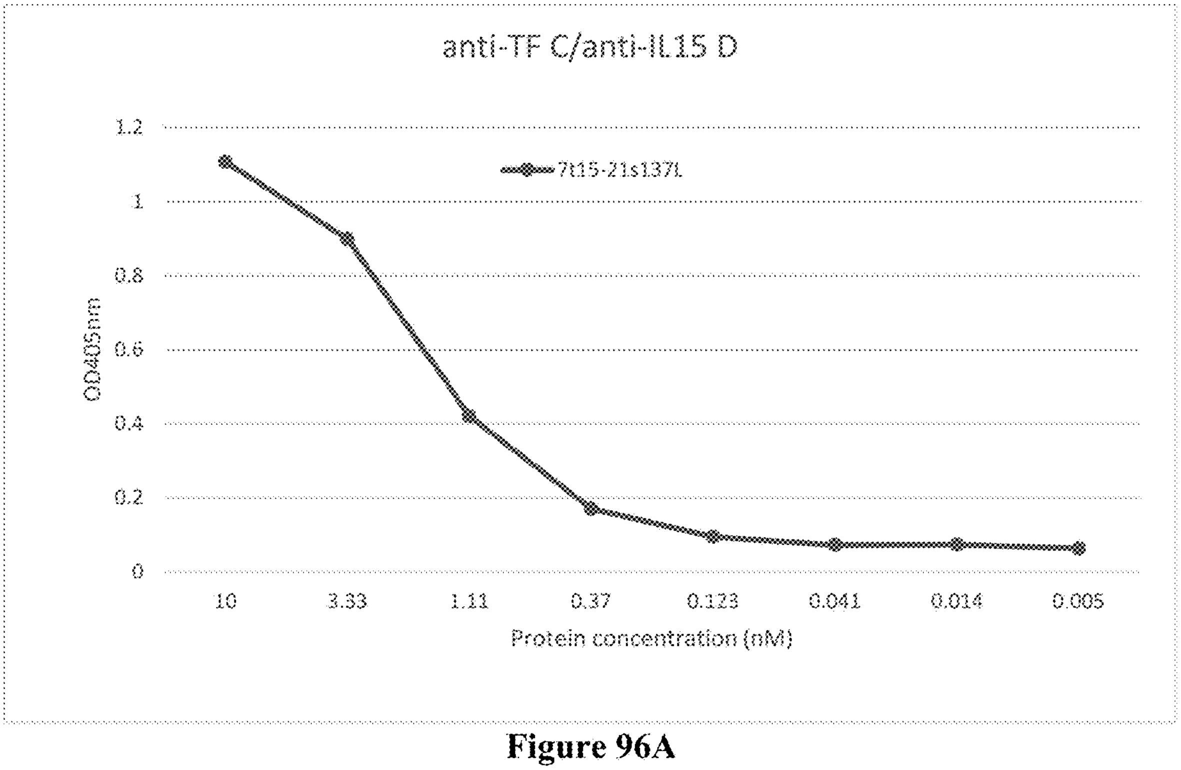
FIGS. 96A-96C show detection of IL15, IL21, and IL7 in 7t15-21s137L (short version) with ELISA.
Figure 96B:
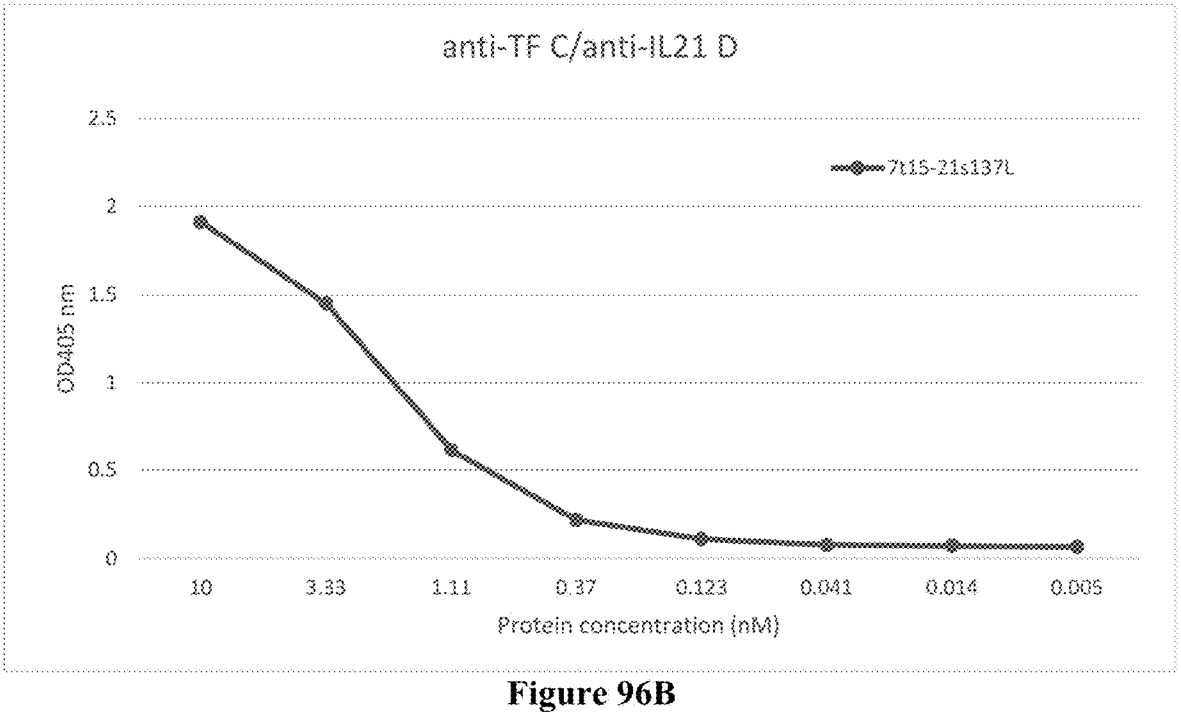
Figure 96C:
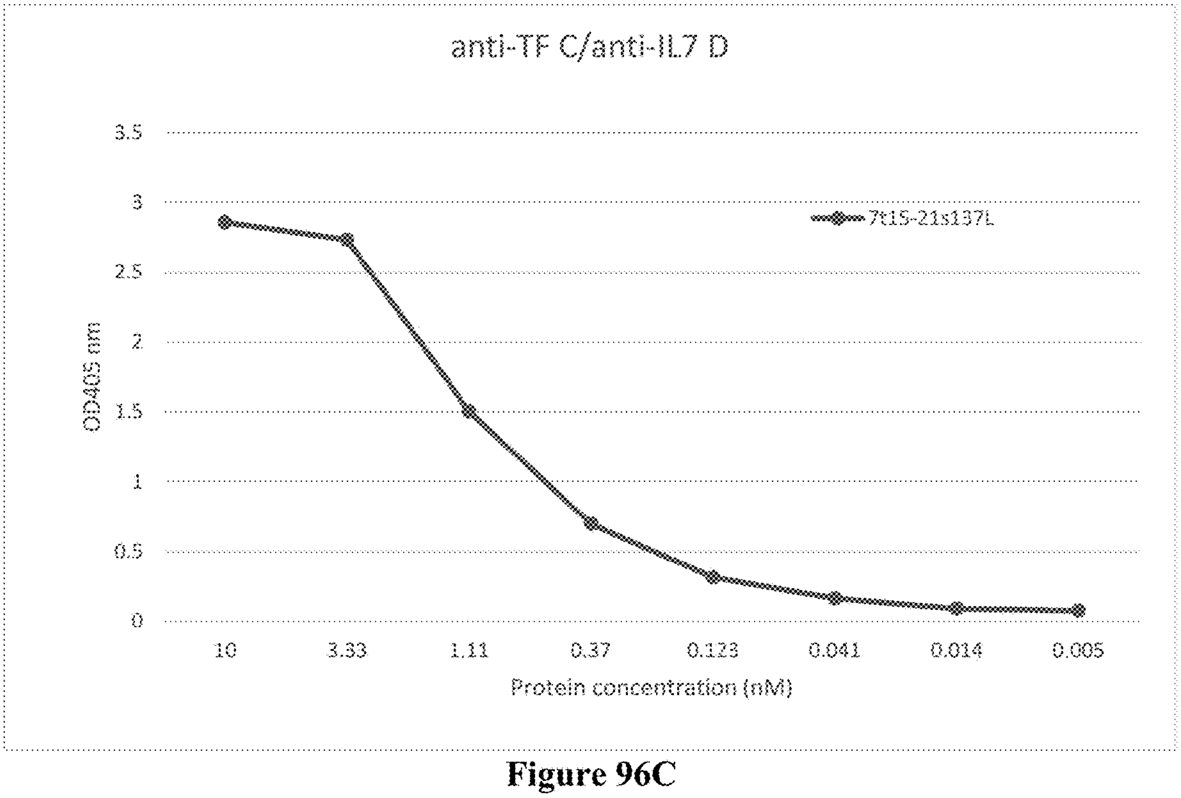

A 96-well plate was coated with 100 μL (8 μg/mL) of anti-TF IgG1 in R5 (coating buffer) and incubated at RT for 2 hrs. The plates were washed 3 times and blocked with 100 μL of 1% BSA in PBS. 7t15-21s137L (short version), serially diluted at a 1:3 ratio was added, and incubated at RT for 60 min. After three washes, 50 ng/mL of biotinylated-anti-IL15 antibody (BAM247, R&D Systems), 500 ng/mL of biotinylated-anti-IL21 antibody (13-7218-81, R&D Systems), or 500 ng/mL of biotinylated-anti-IL7 antibody (506602, R&D Systems) was added to the wells and incubated at RT for 60 min. After three washes and incubation with 0.25 μg/mL of HRP-SA (Jackson ImmunoResearch) at 100 μL per well was carried out for 30 min at RT, followed by four washes and incubation with 100 μL of ABTS for 2 mins at RT. Absorbance was read at 405 nm. As shown in FIGS. 96A-96C, the IL-15, IL-21, and IL-7 domains in 7t15-21s137L (short version) were detected by the respective antibodies.

Figure 97:
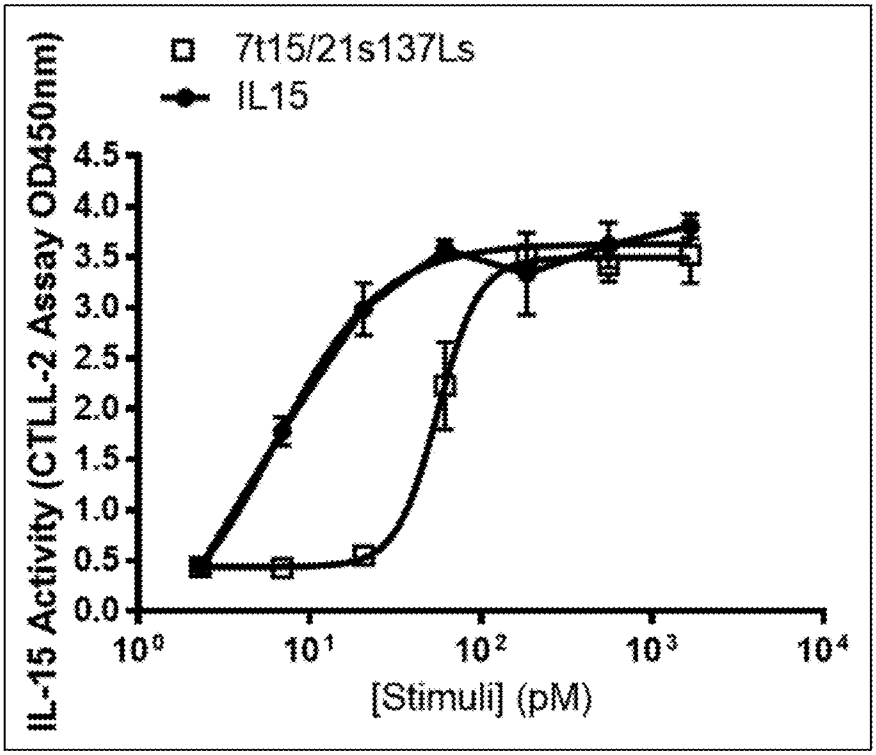
FIG. 97 shows results from a CTLL-2 cell proliferation assay.

The IL-15 in 7t15-1s137L (Short Version) Promotes IL2Rαβγ Containing CTLL2 Cell proliferation To evaluate the IL-15 activity of 7t15-21s137L (short version), 7t15-21s137L (short version) was compared with recombinant IL15 in promoting proliferation of IL2Rαβγ expressing CTLL2 cells. IL-15-dependent CTLL2 cells were washed 5 times with IMDM-10% FBS and seeded to the wells at $2\times10^4$ cells/well. Serially diluted 7t15-21s137L (short version) or IL-15 were added to the cells (FIG. 97). Cells were incubated in a $CO_2$ incubator at 37° C. for 3 days. Cell proliferation was detected by adding 10 μL of WST1 to each well on day 3 and incubated for an additional 3 hours in a $CO_2$ incubator at 37° C. The amount of formazan dye produced was analyzed by measuring the absorbance at 450 nm. As shown in FIG. 97, 7t15-21s137L (short version) and IL-15 promoted CTLL2 cell proliferation. The $EC_{50}$ of 7t15-21s137L (short version) and IL-15 was 55.91 pM and 6.22 pM, respectively.

Figure 98:
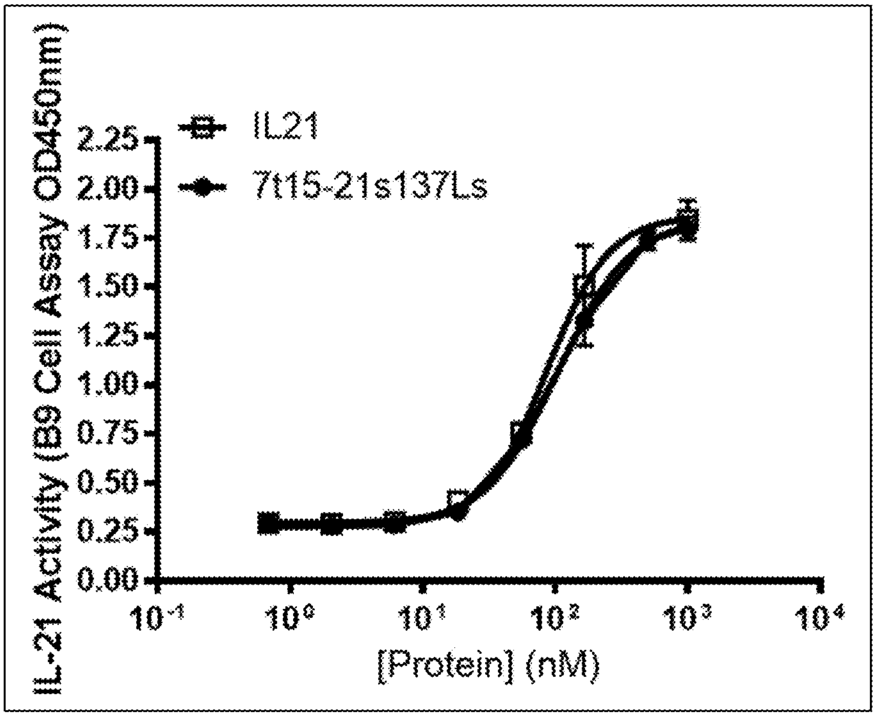
FIG. 98 shows the activity of 7t15-1s137L (short version) in promoting IL21R containing B9 cell proliferation.

The IL-21 in 7t15-1s137L (Short Version) Promotes IL21R Containing B9 Cell Proliferation To evaluate the IL-21 activity of 7t15-21s137L (short version), 7t15-21s137L (short version) was compared with recombinant IL-21 in promoting proliferation of IL-21R expressing B9 cells. IL-21R containing B9 cells were washed 5 times with RPMI-10% FBS and seeded to the wells at $1\times10^4$ cells/well. Serially diluted 7t15-21s137L (short version) or IL-21 were added to the cells (FIG. 98). Cells were incubated in a $CO_2$ incubator at 37° C. for 5 days. Cell proliferation was detected by adding 10 μL of WST1 to each well on day 5 and incubated for an additional 4 hours in a $CO_2$ incubator at 37° C. The amount of formazan dye produced was analyzed by measuring the absorbance at 450 nm. As shown in FIG. 98, 7t15-21s137L (short version) and IL-21 promoted B9 cell proliferation. The $EC_{50}$ of 7t15-21s137L (short version) and IL-21 was 104.1 nM and 72.55 nM, respectively.

Example 55: 7t15-TGFRs Fusion Protein Generation and Characterization

Figure 99:
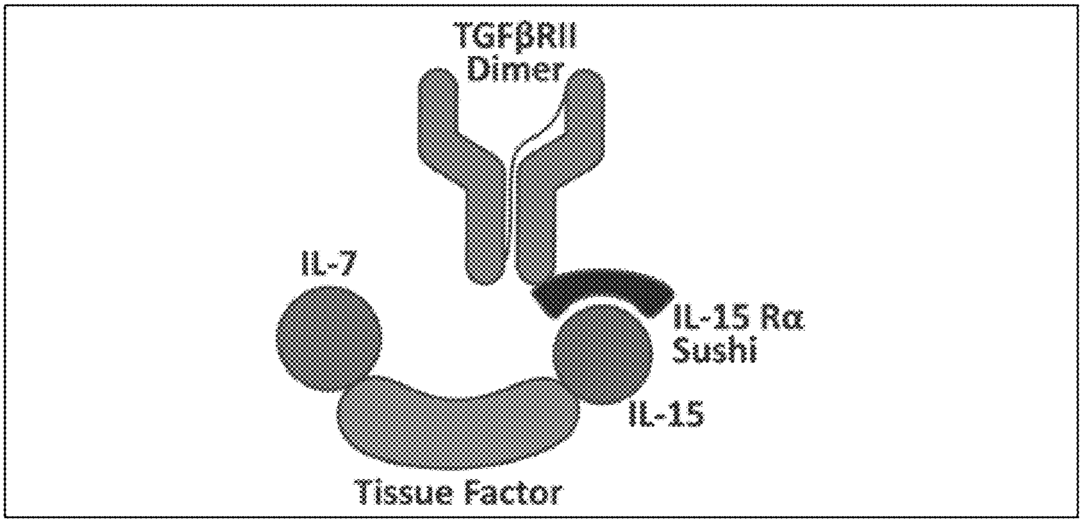
FIG. 99 shows a schematic of the 7t15-TGFRs construct.
Figure 100:
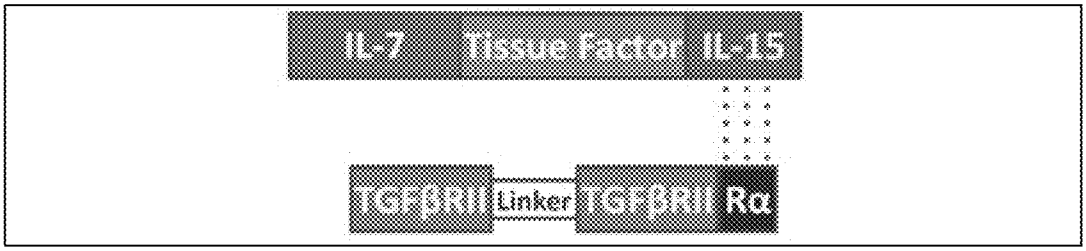
FIG. 100 shows an additional schematic of the 7t15-TGFRs construct.

A fusion protein complex was generated comprising of TGFβ Receptor II/IL-15RαSu and IL-7/TF/IL-15 fusion proteins (FIG. 99 and FIG. 100). The human TGFβ Receptor II (Ile24-Asp159), tissue factor 219, IL-15, and IL-7 sequences were obtained from the UniProt website and DNA for these sequences was synthesized by Genewiz. Specifically, a construct was made linking the IL-7 sequence to the N-terminus coding region of tissue factor 219 followed by the N-terminus coding region of IL-15. The nucleic acid and protein sequences of a construct comprising IL-7 linked to the N-terminus of tissue factor 219 following with the N-terminus of IL-15 are shown below.

The nucleic acid sequence of the 7t15 construct (including signal peptide sequence) is as follows:

```
(Signal peptide)
ATGAAGTGGGTGACCTTCATCAGCCTGCTGTTCCTGTTCTCCAGCGCCT
ACTCC

(Human IL7)
GATTGCGACATCGAGGGCAAGGACGGCAAGCAGTACGAGAGCGTGCT
GATGGTGTCCATCGACCAGCTGCTGGACAGCATGAAGGAGATCGGCTCC
AACTGCCTCAACAACGAGTTCAACTTCTTCAAGCGGCACATCTGCGACG
CCAACAAGGAGGGCATGTTCCTGTTCAGGGCCGCCAGGAAACTGCGGCA
GTTCCTGAAGATGAACTCCACCGGCGACTTCGACCTGCACCTGCTGAAG
GTGTCCGAGGGCACCACCATCCTGCTGAACTGCACCGGACAGGTGAAGG
GCCGGAAACCTGCTGCTCTGGGAGAGGCCCAACCCACCAAGAGCCTGGA
GGAGAACAAGTCCCTGAAGGAGCAGAAGAAGCTGAACGACCTGTGCTTC
CTGAAGAGGCTGCTGCAGGAGATCAAGACCTGCTGGAACAAGATCCTGA
TGGGCACCAAGGAGCAT

(Human Tissue Factor 219)
AGCGGCACAACCAACACAGTCGCTGCCTATAACCTCACTTGGAAGAG
CACCAACTTCAAAACCATCCTCGAATGGGAACCCAAACCCGTTAACCAA
```

-continued

```
GTTTACACCGTGCAGATCAGCACCAAGTCCGGCGACTGGAAGTCCAAAT
GTTTCTATACCACCGACACCGAGTGCGATCTCACCGATGAGATCGTGAA
AGATGTGAAACAGACCTACCTCGCCCGGGTGTTTAGCTACCCCGCCGGC
AATGTGGAGAGCACTGGTTCCGCTGGCGAGCCTTTATACGAGAACAGCC
CCGAATTTACCCCTTACCTCGAGACCAATTTAGGACAGCCCACCATCCA
AAGCTTTGAGCAAGTTGGCACAAAGGTGAATGTGACAGTGGAGGACGAG
CGGACTTTAGTGCGGCGGAACAACACCTTTCTCAGCCTCCGGGATGTGT
TCGGCAAAGATTTAATCTACACACTGTATTACTGGAAGTCCTCTTCCTC
CGGCAAGAAGACAGCTAAAACCAACACAAACGAGTTTTTAATCGACGTG
GATAAAGGCGAAAACTACTGTTTCAGCGTGCAAGCTGTGATCCCCTCCC
GGACCGTGAATAGGAAAAGCACCGATAGCCCCGTTGAGTGCATGGGCCA
AGAAAAGGGCGAGTTCCGGGAG

(Human IL-15)
AACTGGGTGAACGTCATCAGCGATTTAAAGAAGATCGAAGATTTAATT
CAGTCCATGCATATCGACGCCACTTTATACACAGAATCCGACGTGCACC
CCTCTTGTAAGGTGACCGCCATGAAATGTTTTTTACTGGAGCTGCAAGT
TATCTCTTTAGAGAGCGGAGACGCTAGCATCCACGACACCGTGGAGAAT
TTAATCATTTTAGCCAATAACTCTTTATCCAGCAACGGCAACGTGACAG
AGTCCGGCTGCAAGGAGTGCGAAGAGCTGGAGGAGAAGAACATCAAGGA
GTTTCTGCAATCCTTTGTGCACATTGTCCAGATGTTCATCAATACCTCC
```

The amino acid sequence of 7t15 fusion protein (including the leader sequence) is as follows:

```
(Signal peptide)
MKWVTFISLLFLFSSAYS

(Human IL7)
DCDIEGKDGKQYESVLMVSIDQLLDSMKEIGSNCLNNEFNFFKRHICDA
NKEGMFLFRAARKLRQFLKMNSTGDFDLHLLKVSEGTTILLNCTGQVKG
RKPAALGEAQPTKSLEENKSLKEQKKLNDLCFLKRLLQEIKTCWNKILM
GTKEH

(Human Tissue Factor 219)
SGTTNTVAAYNLTWKSTNFKTILEWEPKPVNQVYTVQISTKSGDWKSKC
FYTTDTECDLTDEIVKDVKQTYLARVFSYPAGNVESTGSAGEPLYENSP
EFTPYLETNLGQPTIQSFEQVGTKVNVTVEDERTLVRRNNTFLSLRDVF
GKDLIYTLYYWKSSSSGKKTAKTNTNEFLIDVDKGENYCFSVQAVIPSR
TVNRKSTDSPVECMGQEKGEFRE

(Human IL-15)
NWVNVISDLKKIEDLIQSMHIDATLYTESDVHPSCKVTAMKCFLLELQV
ISLESGDASIHDTVENLIILANNSLSSNGNVTESGCKECEELEEKNIKE
FLQSFVHIVQMFINTS
```

Constructs were also made by attaching two TGFβ Receptor II directly to the IL-15RαSu chain which was synthesized by Genewiz. The nucleic acid and protein sequences of a construct comprising the TGFβ Receptor II linked to the N-terminus of IL-15RαSu are shown below.

The nucleic acid sequence of the TGFRs construct (including signal peptide sequence) is as follows:

(Signal peptide)
ATGAAGTGGGTGACCTTCATCAGCCTGCTGTTCCTGTTCTCCAGCGCCT

ACTCC (Human TGFβ Receptor II fragments)
ATCCCCCCCCATGTGCAAAAGAGCGTGAACAACGATATGATCGTGACC

GACAACAACGGCGCCGTGAAGTTTCCCCAGCTCTGCAAGTTCTGCGATG

TCAGGTTCAGCACCTGCGATAATCAGAAGTCCTGCATGTCCAACTGCAG

CATCACCTCCATCTGCGAGAAGCCCCAAGAAGTGTGCGTGGCCGTGTGG

CGGAAAAATGACGAGAACATCACCCTGGAGACCGTGTGTCACGACCCCA

AGCTCCCTTATCACGACTTCATTCTGGAGGACGCTGCCTCCCCCAAATG

CATCATGAAGGAGAAGAAGAAGCCCGGAGAGACCTTCTTTATGTGTTCC

TGTAGCAGCGACGAGTGTAACGACAACATCATCTTCAGCGAAGAGTACA

ACACCAGCAACCCTGATGGAGGTGGCGGATCCGGAGGTGGAGGTTCTGG

TGGAGGTGGGAGTATTCCTCCCCACGTGCAGAAGAGCGTGAATAATGAC

ATGATCGTGACCGATAACAATGGCGCCGTGAAATTTCCCCAGCTGTGCA

AATTCTGCGATGTGAGGTTTTCCACCTGCGACAACCAGAAGTCCTGTAT

GAGCAACTGCTCCATCACCTCCATCTGTGAGAAGCCTCAGGAGGTGTGC

GTGGCTGTCTGGCGGAAGAATGACGAGAATATCACCCTGGAAACCGTCT

GCCACGATCCCAAGCTGCCCTACCACGATTTCATCCTGGAAGACGCCGC

CAGCCCTAAGTGCATCATGAAAGAGAAAAAGAAGCCTGGCGAGACCTTT

TTCATGTGCTCCTGCAGCAGCGACGAATGCAACGACAATATCATCTTTA

GCGAGGAATACAATACCAGCAACCCCGAC (Human IL-15Rα sushi domain)
ATTACATGCCCCCCTCCCATGAGCGTGGAGCACGCCGACATCTGGGTG

AAGAGCTATAGCCTCTACAGCCGGGAGAGGTATATCTGTAACAGCGGCT

TCAAGAGGAAGGCCGGCACCAGCAGCCTCACCGAGTGCGTGCTGAATAA

GGCTACCAACGTGGCTCACTGGACAACACCCTCTTTAAAGTGCATCCGG

The amino acid sequence of TGFRs fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD (Human IL-15Rα sushi domain)
ITCPPPMSVEHADIWVKSYSLYSRERYICNSGFKRKAGTSSLTECVLNK

ATNVAHWTTPSLKCIR

Effect of 7t15-TGFRs on TGFβ1 Activity in HEK-Blue TGFβ Cells

To evaluate the activity of TGFβR in 7t15-TGFRs, the effect of 7t15-TGFRs on the activity of TGFβ1 in HEK-Blue TGFβ cells was analyzed. HEK-Blue TGFβ cells (Invivogen) were washed twice with pre-warmed PBS and resuspended in the testing medium (DMEM, 10% heat-inactivated FCS, 1× glutamine, 1× anti-anti, and 2× glutamine) at $5\times10^5$ cells/mL. In a flat-bottom 96-well plate, 50 μL cells were added to each well ($2.5\times10^4$ cells/well) and followed with 50 μL 0.1 nM TGFβ1 (R&D systems). 7t15-TGFRs or TGFR-Fc (R&D Systems) prepared at a1:3 serial dilution was then added to the plate to reach a total volume of 200 μL. After 24 hrs of incubation at 37° C., 40 μL of induced HEK-Blue TGFβ cell supernatant was added to 160 μL pre-warmed QUANTI-Blue (Invivogen) in a flat-bottom 96-well plate, and incubated at 37° C. for 1-3 hrs. The OD values were then determined using a plate reader (Multiscan Sky) at 620-655 nM. The $IC_{50}$ of each protein sample was calculated with GraphPad Prism 7.04. The $IC_{50}$ of 7t15-TGFRs and TGFR-Fc were 1142 pM and 558.6 pM respectively. These results showed that the TGFβR in 7t15-TGFRs was able to block the activity of TGFβ1 in HEK-Blue TGFβ cells.

Detection of IL-15, TGFβRII, and IL-7 in 7t15-TGFRs with ELISA

Figure 101:
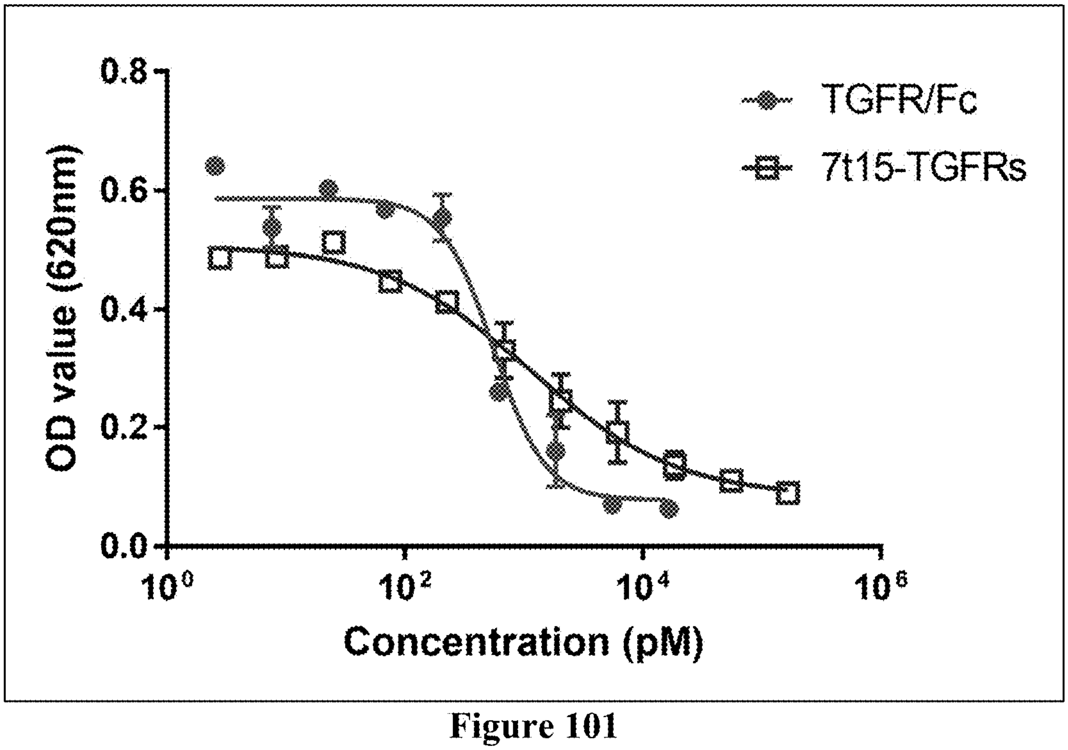
FIG. 101 shows results of TGFβ1 inhibition by 7t15-TGFRs and TGFR-Fc.
Figure 102A:
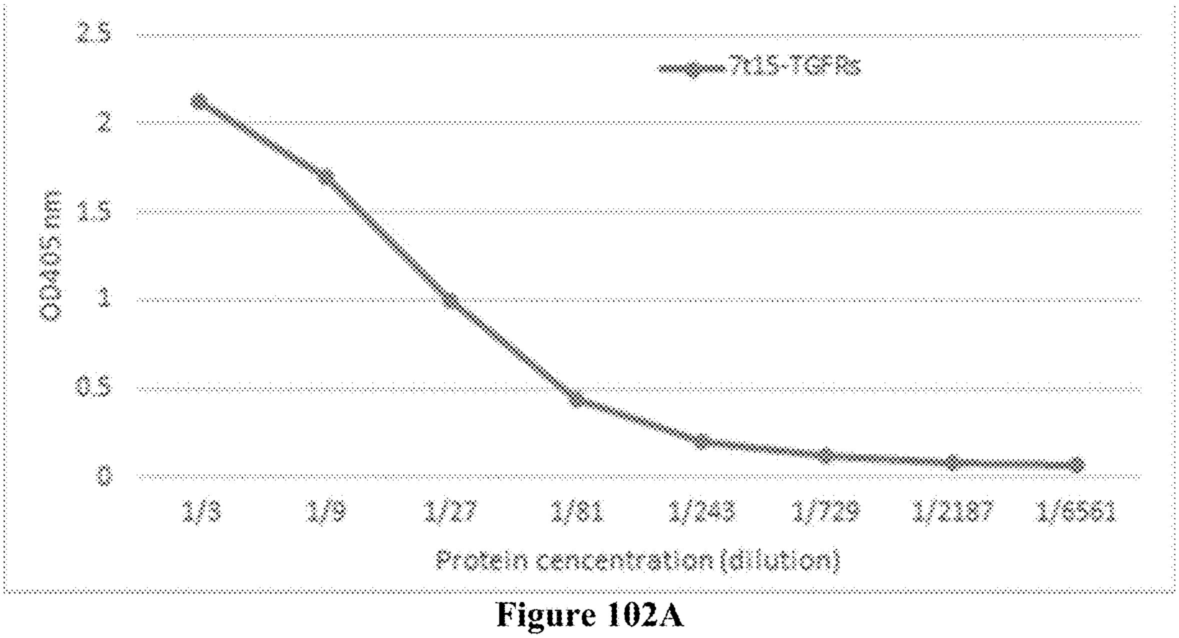
FIGS. 102A-102C show detection of IL-15, TGFβRII, and IL-7 in 7t15-TGFRs with ELISA.
Figure 102B:
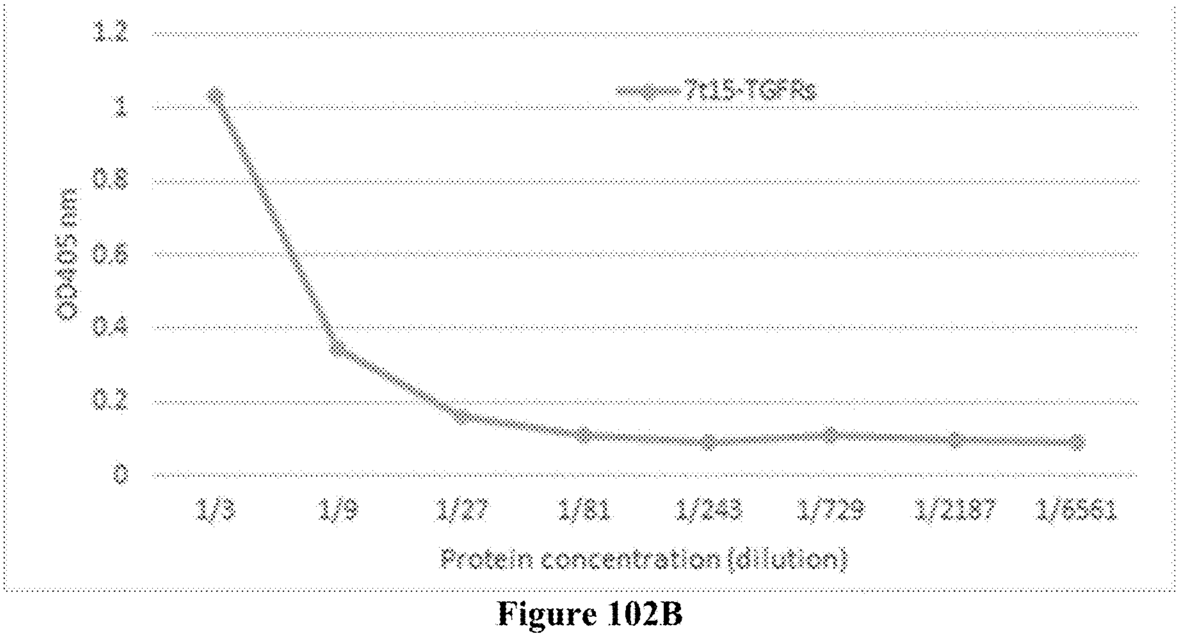
Figure 102C:
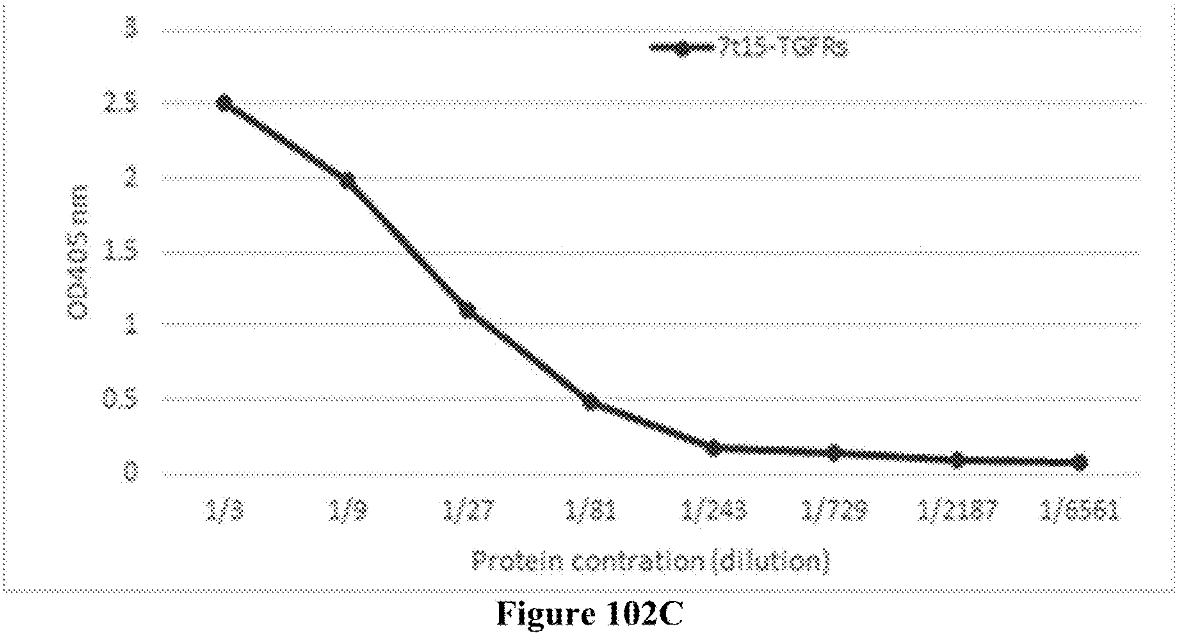

A 96-well plate was coated with 100 μL (8 μg/mL) of anti-TF IgG1 in R5 (coating buffer) and incubated at room temperature (RT) for 2 hrs. The plates were washed three times and blocked with 100 μL of 1% BSA in PBS. Serial dilution of 7t15-TGFRs (1:3 ratio) was added, and incubated at RT for 60 mins. After 3 washes, 50 ng/mL of biotinylated-anti-IL-15 antibody (BAM247, R&D Systems), 200 ng/mL of biotinylated-anti-TGFbRII antibody (BAF241, R&D Systems), or 500 ng/mL of biotinylated-anti-IL-7 antibody (506602, R&D Systems) was added and incubated at RT for 60 min. Following three washes, incubation with 0.25 μg/mL of HRP-SA (Jackson ImmunoResearch) at 100 μL per well was carried out for 30 min at RT, followed by 4 washes and incubation with 100 μL of ABTS for 2 mins at RT. Absorbance was read at 405 nm. The data are shown in FIG. 101. As shown in FIGS. 102A-102C, the IL-15, TGFR, and IL-7 in 7t15-TGFRs were detected by the respective antibodies.

Figure 103:
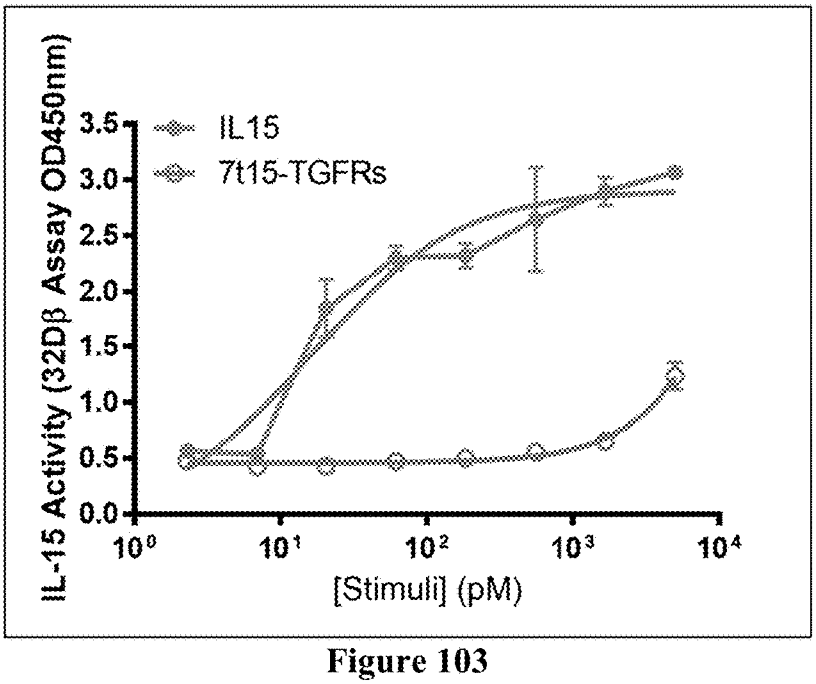
FIG. 103 shows results of a 32Dβ cell proliferation assay with 7t15-TGFRs or recombinant IL-15.

The IL-15 in 7t15-TGFRs Promotes IL-2Rβ and Common γ Chain Containing 32Dβ Cell Proliferation To evaluate the activity of IL-15 in 7t15-TGFRs, 7t15-TGFRs was compared to recombinant IL-15 using 32Dβ cells that express IL2Rβ and common γ chain, and evaluating their effects on promoting cell proliferation. IL-15 dependent 32Dβ cells were washed 5 times with IMDM-10% FBS and seeded in the wells at $2\times10^4$ cells/well. Serially-diluted 7t15-TGFRs or IL-15 were added to the cells (FIG. 103). Cells were incubated in a $CO_2$ incubator at 37° C. for 3 days. Cell proliferation was detected by adding 10 μL of WST1 to each well on day 3 and incubating for an additional 3 hours in a $CO_2$ incubator at 37° C. The amount of formazan dye produced was analyzed by measuring the absorbance at 450 nm. As shown in FIG. 103, 7t15-TGFRs and IL-15 promoted 32Dβ cell proliferation, with the $EC_{50}$ of 7t15-TGFRs and IL-15 being 126 nM and 16.63 pM, respectively.

Figure 104:
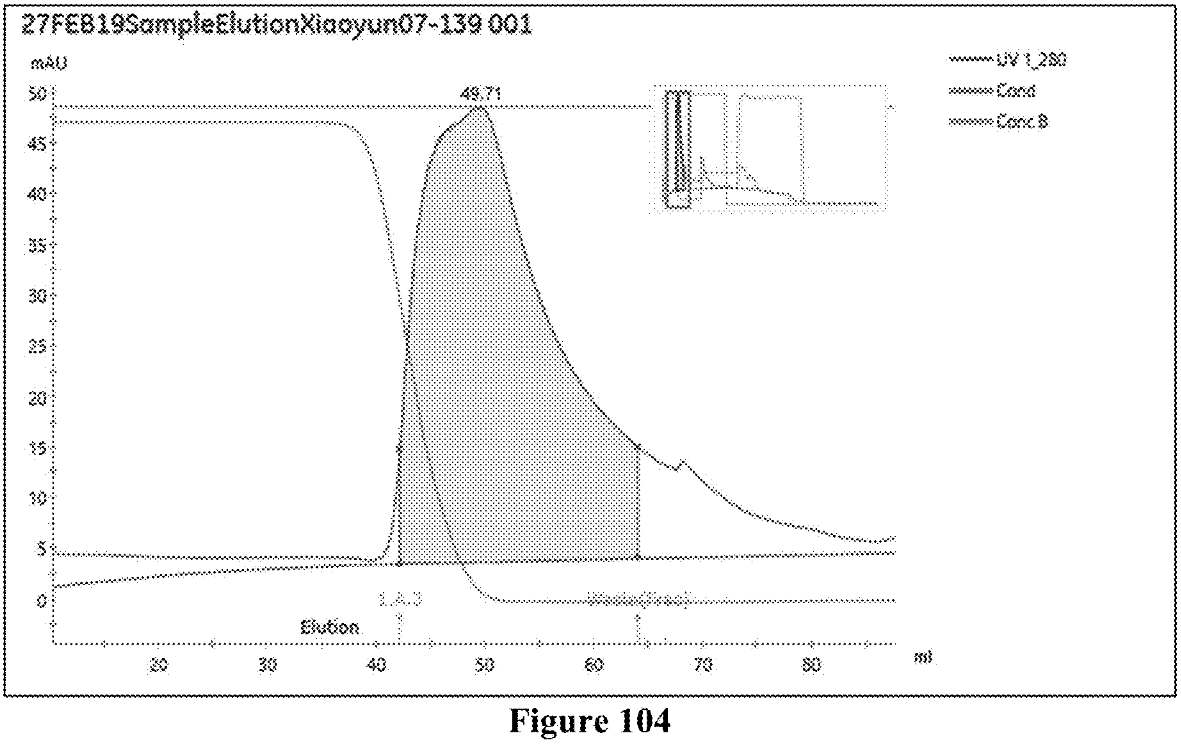
FIG. 104 is a line graph showing the chromatographic profile of 7t15-TGFRs protein containing cell culture supernatant following binding and elution on anti-TF antibody affinity column.

Purification Elution Chromatograph of 7t15-TGFRs Using Anti-TF Antibody Affinity Column 7t15-TGFRs harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 104, the anti-TF antibody affinity column can bind 7t15-TGFRs which contains TF as a fusion partner of 7t15-TGFRs. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Reduced SDS-PAGE Analysis of 7t15-TGFRs

To determine the purity and molecular weight of the protein, 7t15-TGFRs protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

Figure 105:
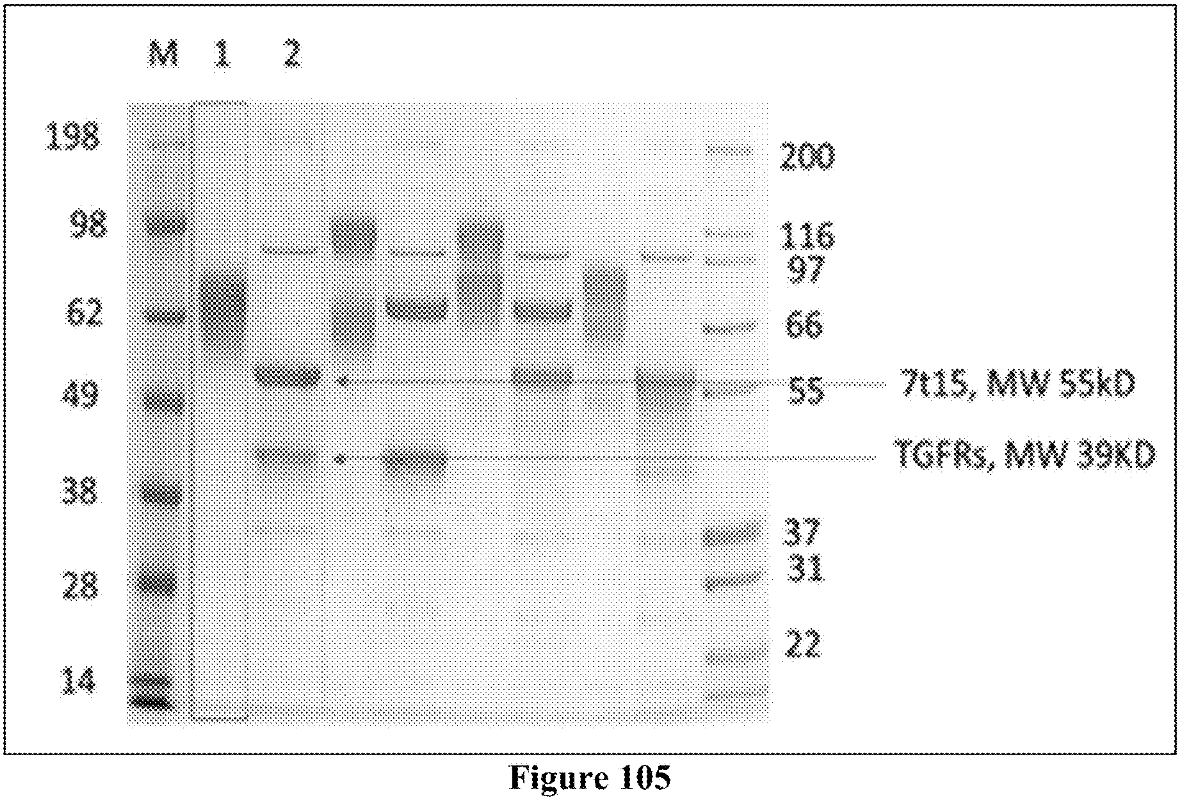
FIG. 105 shows 7t15-TGFRs before and after deglycosylation as analyzed using reduced SDS-PAGE.

To verify that the 7t15-TGFRs protein undergoes glycosylation after translation in CHO cells, a deglycosylation experiment was conducted using the Protein Deglycosylation Mix II kit from New England Biolabs and the manufacturer's instructions. FIG. 105 shows reduced SDS-PAGE analysis of the sample in non-deglycosylated (lane 1 in red outline) and deglycosylated (lane 2 in yellow outline) state. These results showed that the protein is glycosylated when it is expressed in CHO cells. After deglycosylation, the purified sample showed expected molecular weights (55 kDa and 39 kDa) in reduced SDS gel. Lane M was loaded with 10 ul of SeeBlue Plus2 Prestained Standard.

Characterization of 7t15-TGFRs

7t15-TGFRs is a multi-chain polypeptide (a type A multi-chain polypeptide described herein) that includes the first polypeptide that is a soluble fusion of human IL-7, human tissue factor 219 fragment and human IL-15 (7t15), and the second polypeptide that is a soluble fusion of single chain two TGFβRII domains and sushi domain of human IL-15 receptor alpha chain (TGFRs).

Figure 106:
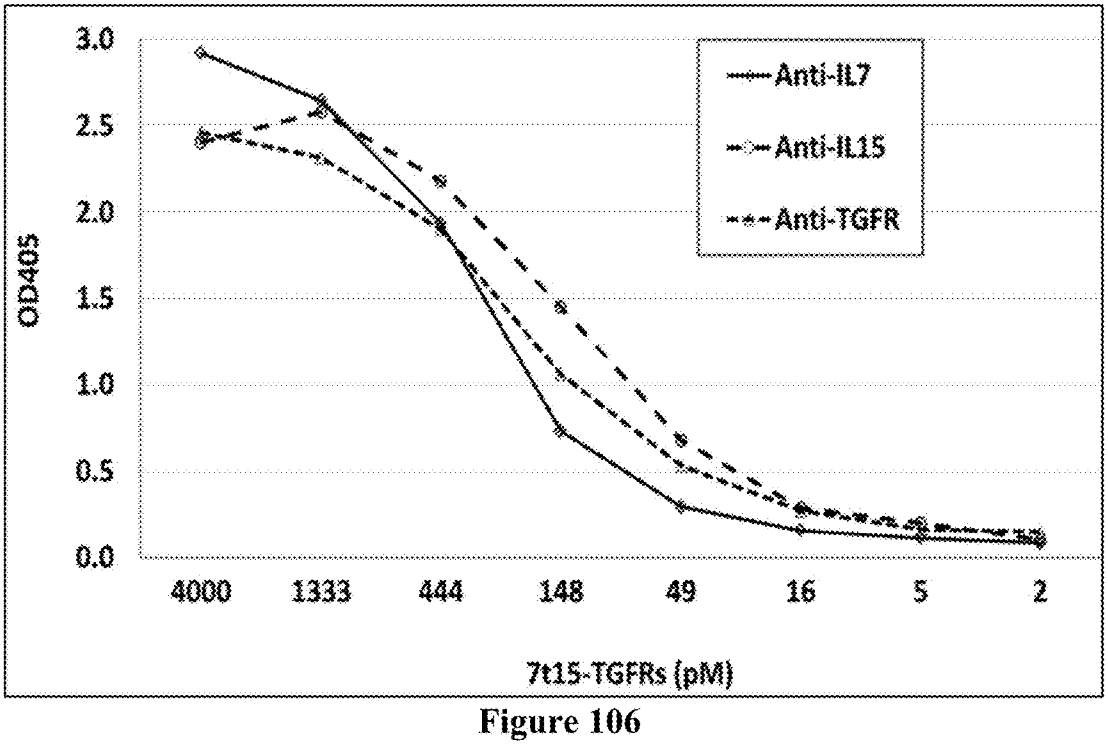
FIG. 106 shows ELISA detection of IL-7, IL-15 and TGFβRII in the 7t15-TGFRs protein.

CHO cells were co-transfected with 7t15 and TGFRs vectors. The 7t15-TGFRs complex was purified from the transfected CHO cell culture supernatant. The IL-7, IL-15, TGFβ receptor and tissue factor (TF) components were demonstrated in the complex by ELISA as shown in FIG. 106. A humanized anti-TF monoclonal antibody (anti-TF IgG1) was used as the capture antibody to determine TF in 7t15-TGFRs, and biotinylated antibodies against human IL-15 antibody (R&D systems), human IL-7 (Biolegend), anti-TGFβ receptor (R&D Systems) were used as the detection antibodies to respectively determine IL-7, IL-15 and TGFβ receptor in 7t15-TGFRs. Peroxidase conjugated streptavidin (Jackson ImmunoResearch Lab) and ABTS substrate (Surmodics IVD, Inc.) were then used to detect the bound biotinylated antibodies. The results were analyzed by ELISA (FIG. 106).

In Vivo Characterization of 7t15-TGFRs in C57BL 6 Mice

Figure 107A:
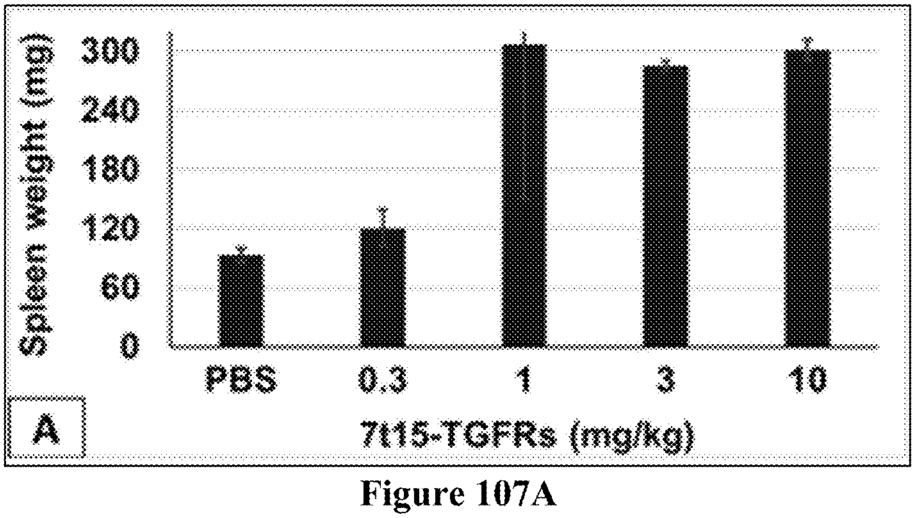
FIGS. 107A and 107B show spleen weight and the percentages of immune cell types in 7t15-TGFRs-treated and control-treated mice.
Figure 107B:
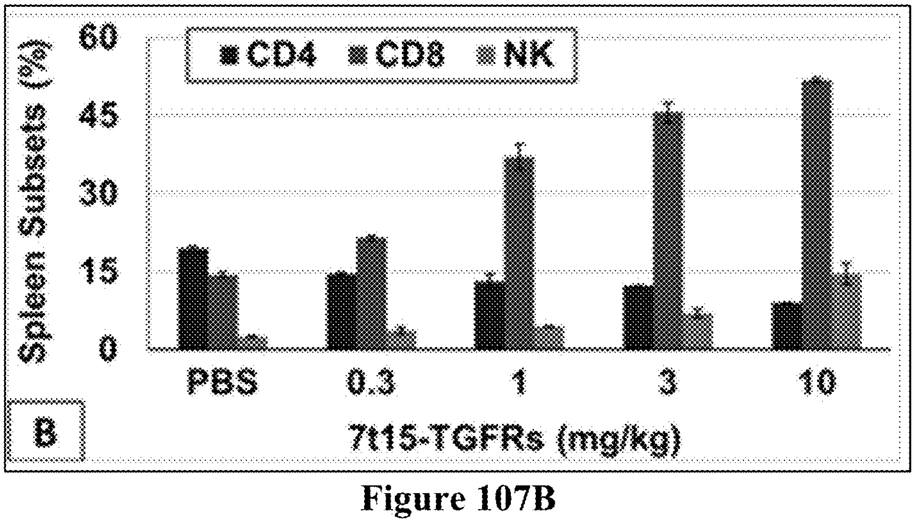
Figure 108A:
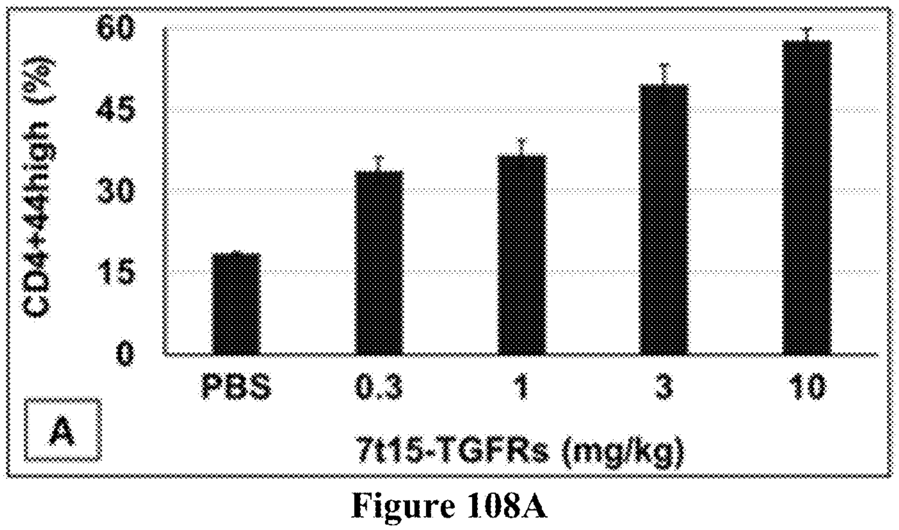
FIGS. 108A and 108B show upregulation of CD44 expression of $CD4^+$ and $CD8^+$ T cells by 7t15-TGFRs in C57BL/6 mice.
Figure 108B:
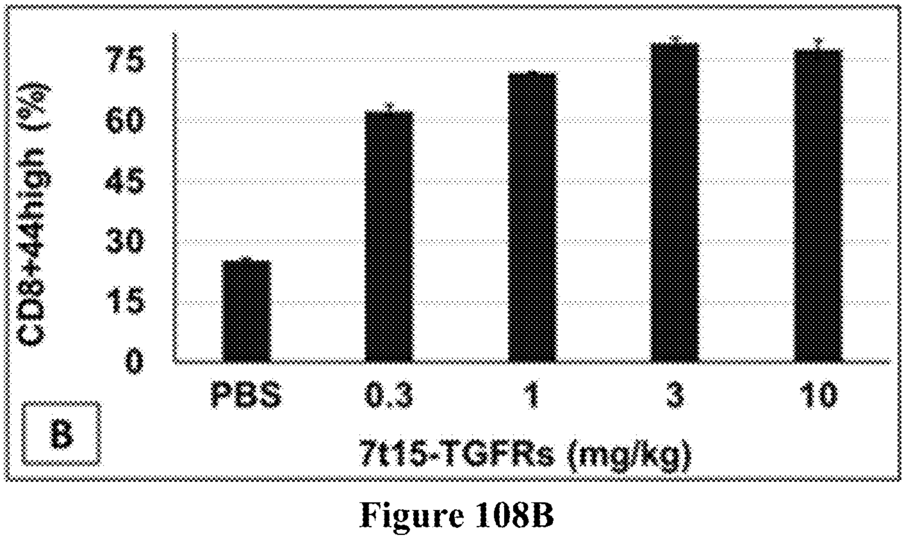

To determine the immunostimulatory activity of 7t15-TGFRs in vivo, C57BL/6 mice were subcutaneously treated with control solution (PBS) or 7t15-TGFRs at 0.3, 1, 3 and 10 mg/kg. The treated mice were euthanized. The mouse spleens were collected and weighed day 4 post treatment. Single splenocyte suspensions were prepared and stained with fluorochrome-conjugated anti-CD4, anti-CD8, and anti-NK1.1 antibodies and the percentage of $CD4^+$ T cells, $CD8^+$ T cells, and NK cells was analyzed by flow cytometry. The results showed that 7t15-TGFRs was effective at expanding splenocytes based on spleen weight (FIG. 107A), especially at 1-10 mg/kg. The percentages of $CD8^+$ T cells and NK cells were higher compared to control-treated mice (FIG. 107B) at all doses tested.

CD44 Expression of $CD4^+$ and $CD8^+$ T Cells

It has been known that IL-15 induces CD44 expression on T cells and development of memory T cells. CD44 expression of $CD4^+$ and $CD8^+$ T cells in the 7t15-TGFRs treated mice were assessed. C57BL/6 mice were subcutaneously treated with 7t15-TGFRs. The splenocytes were stained with fluorochrome-conjugated anti-CD4, anti-CD8 and anti-CD44 monoclonal antibodies for immunocyte subsets. The percentages of $CD4^+CD44^{high}$ T cells of total $CD4^+$ T cells and $CD8^+CD44^{high}$ T cells of total $CD8^+$ T cells were analyzed by flow cytometry. As shown in FIGS. 108A and 108B, 7t15-TGFRs significantly activated $CD4^+$ and $CD8^+$ T cells to differentiate into memory T cells.

Figure 109A:
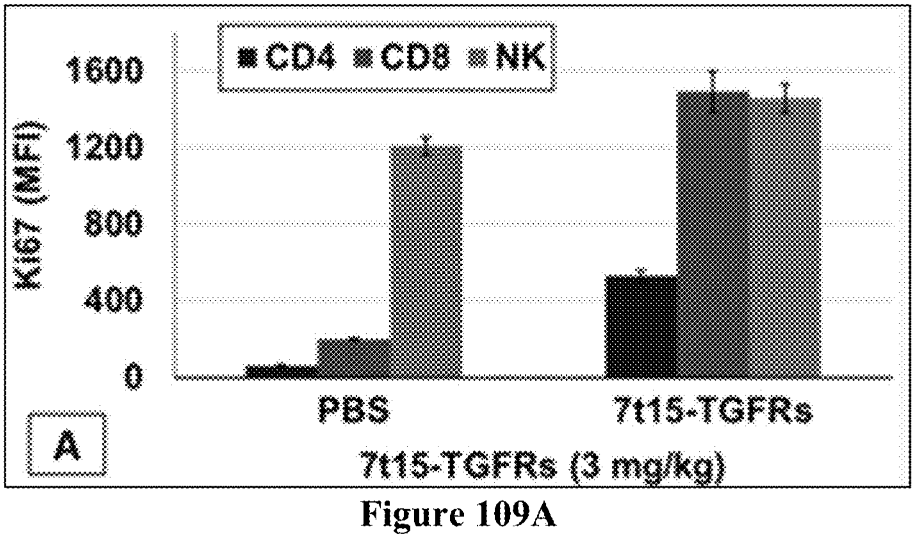
FIGS. 109A and 109B show upregulation of Ki67 expression and Granzyme B expression of $CD8^+$ T cells and NK Cells by 7t15-TGFRs in C57BL/6 mice.
Figure 109B:
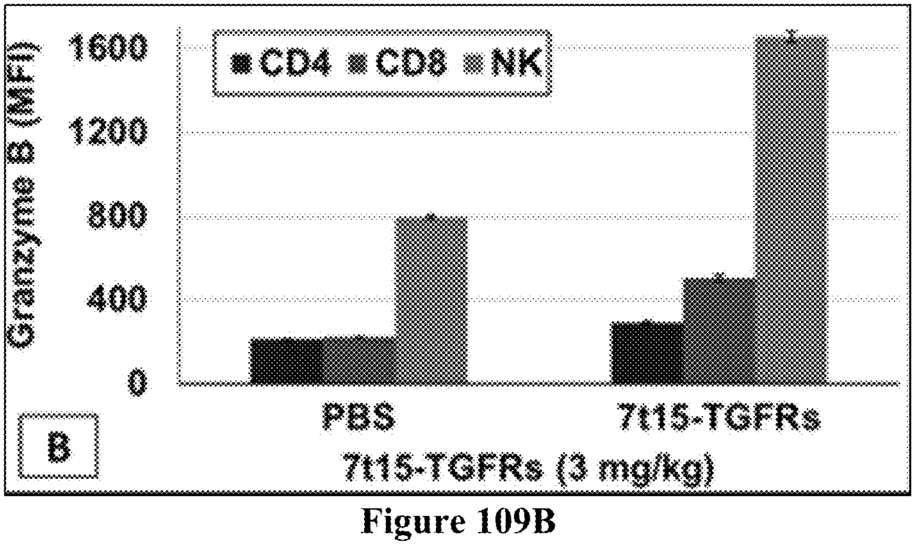

Furthermore, the dynamic proliferation of immune cells based on Ki67 expression of splenocytes and cytotoxicity potential based on granzyme B expression of the splenocytes induced by 7t15-TGFRs after the single dose treatment of mouse were also evaluated. C57BL/6 mice were subcutaneously treated with 7t15-TGFRs at 3 mg/kg. The treated mice were euthanized and the splenocytes were prepared. The prepared splenocytes were stained with fluorochrome-conjugated anti-CD4, anti-CD8, and anti-NK1.1 (NK) antibodies for immunocyte subsets and then intracellularly stained with anti-Ki67 antibody for cell proliferation and anti-granzyme B antibody for cytotoxic marker. The mean fluorescent intensity (MFI) of Ki67 and granzyme B of corresponding immunocyte subsets was analyzed by flow cytometry. As shown in FIGS. 109A and 109B, in the spleens of mice treated with 7t15-TGFRs, the expression of Ki67 and granzyme B by $CD8^+$ T cells and NK cells increased compared with PBS control treatment. These results demonstrate that 7t15-TGFRs is not only to increase numbers of $CD8^+$ T cells and NK cells but also enhance potential cytotoxicity of these cells.

Figure 110:
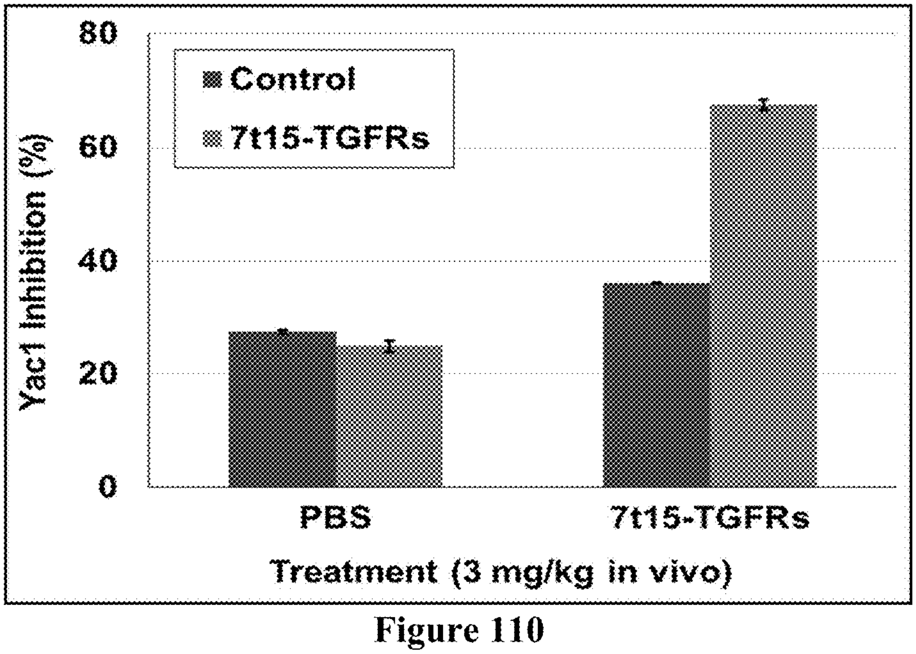
FIG. 110 shows enhancement of cytotoxicity of splenocytes by 7t15-TGFRs in C57BL/6 mice.

Additionally, cytotoxicity of the mouse splenocytes against tumor cells was also evaluated. Mouse Yac-1 cells were labeled with CELLTRACE®, violet dye, and used as tumor target cells. The splenocytes were prepared from 7t15-TGFRs-treated mice and used as effector cells. The target cells were mixed with effector cells at E:T ratio=10:1 in RPMI-10 medium with or without 7t15-TGFRs at 100 nM and incubated at 37° C. for 20 hours. Target Yac-1 cell inhibition was assessed by analysis of viable violet-labeled Yac-1 cells using flow cytometry. Percentage of Yac-1 inhibition was calculated using a formula, (1-viable Yac-1 cell number in experimental sample/viable Yac-1 cell number in the sample without splenocytes)×100. As shown in FIG. 110, 7t15-TGFRs-treated mouse splenocytes had stronger cytotoxicity against Yac-1 cells than the control mouse splenocytes and addition of 7t15-TGFRs during cytotoxic assay further enhanced cytotoxicity of splenocytes against Yac-1 target cells.

Example 56: TGFRt15-21s137L Fusion Protein Generation and Characterization

Figure 111:
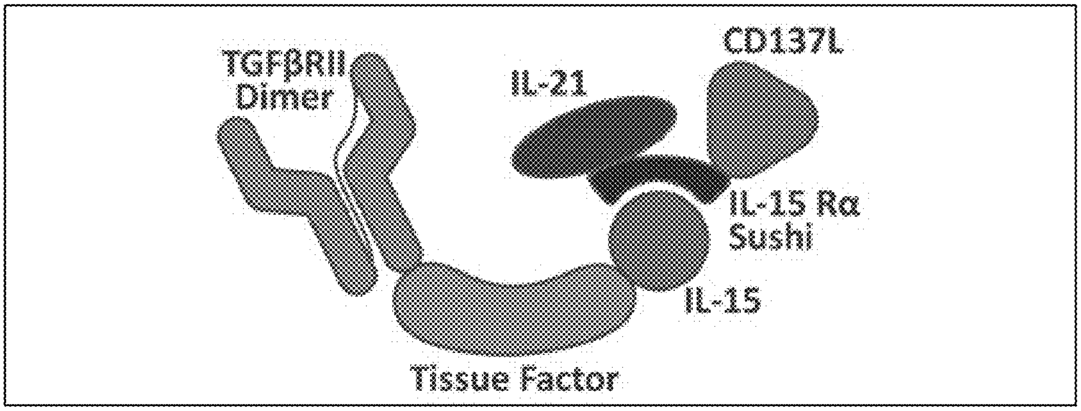
FIG. 111 shows a schematic of the TGFRt15-21s137L construct.
Figure 112:
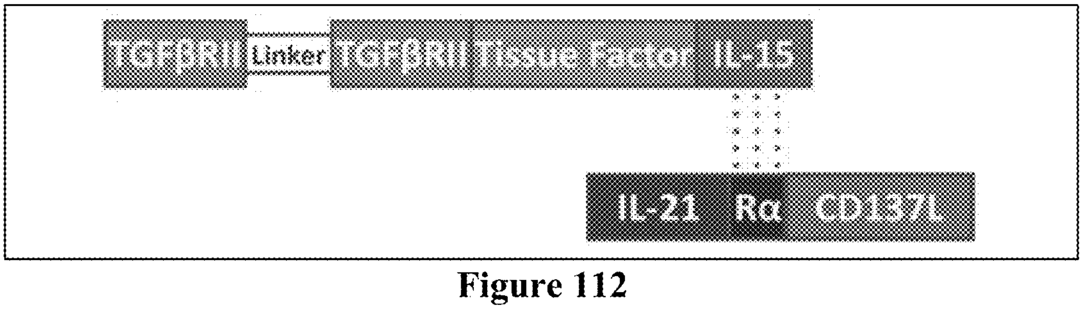
FIG. 112 shows an additional schematic of the TGFRt15-21s137L construct.

A fusion protein complex was generated comprising IL-21/IL-15RαSu/CD137L and TGFβ Receptor II/TF/IL-15 fusion proteins (FIG. 111 and FIG. 112). The human TGFβ Receptor II (Ile24-Asp159), tissue factor 219, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid sequence of the TGFRt15 construct (including signal peptide sequence) is as follows:

```
(Signal peptide)
ATGAAGTGGGTGACCTTCATCAGCCTGCTGTTCCTGTTCTCCAGCGCCT

ACTCC

(Human TGFβ Receptor II fragments)
ATCCCCCCCCATGTGCAAAAGAGCGTGAACAACGATATGATCGTGACC

GACAACAACGGCGCCGTGAAGTTTCCCCAGCTCTGCAAGTTCTGCGATG

TCAGGTTCAGCACCTGCGATAATCAGAAGTCCTGCATGTCCAACTGCAG

CATCACCTCCATCTGCGAGAAGCCCCAAGAAGTGTGCGTGGCCGTGTGG

CGGAAAAATGACGAGAACATCACCCTGGAGACCGTGTGTCACGACCCCA

AGCTCCCTTATCACGACTTCATTCTGGAGGACGCTGCCTCCCCCAAATG

CATCATGAAGGAGAAGAAGAAGCCCGGAGAGACCTTCTTTATGTGTTCC

TGTAGCAGCGACGAGTGTAACGACAACATCATCTTCAGCGAAGAGTACA

ACACCAGCAACCCTGATGGAGGTGGCGGATCCGGAGGTGGAGGTTCTGG

TGGAGGTGGGAGTATTCCTCCCCACGTGCAGAAGAGCGTGAATAATGAC

ATGATCGTGACCGATAACAATGGCGCCGTGAAATTTCCCCAGCTGTGCA

AATTCTGCGATGTGAGGTTTTCCACCTGCGACAACCAGAAGTCCTGTAT

GAGCAACTGCTCCATCACCTCCATCTGTGAGAAGCCTCAGGAGGTGTGC

GTGGCTGTCTGGCGGAAGAATGACGAGAATATCACCCTGGAAACCGTCT

GCCACGATCCCAAGCTGCCCTACCACGATTTCATCCTGGAAGACGCCGC

CAGCCCTAAGTGCATCATGAAAGAGAAAAAGAAGCCTGGCGAGACCTTT

TTCATGTGCTCCTGCAGCAGCGACGAATGCAACGACAATATCATCTTTA

GCGAGGAATACAATACCAGCAACCCCGAC

(Human Tissue Factor 219)
AGCGGCACAACCAACACAGTCGCTGCCTATAACCTCACTTGGAAGAG

CACCAACTTCAAAACCATCCTCGAATGGGAACCCAAACCCGTTAACCAA

GTTTACACCGTGCAGATCAGCACCAAGTCCGGCGACTGGAAGTCCAAAT

GTTTCTATACCACCGACACCGAGTGCGATCTCACCGATGAGATCGTGAA

AGATGTGAAACAGACCTACCTCGCCCGGGTGTTTAGCTACCCCGCCGGC

AATGTGGAGAGCACTGGTTCCGCTGGCGAGCCTTTATACGAGAACAGCC

CCGAATTTACCCCTTACCTCGAGACCAATTTAGGACAGCCCACCATCCA

AAGCTTTGAGCAAGTTGGCACAAAGGTGAATGTGACAGTGGAGGACGAG

CGGACTTTAGTGCGGCGGAACAACACCTTTCTCAGCCTCCGGGATGTGT

TCGGCAAAGATTTAATCTACACACTGTATTACTGGAAGTCCTCTTCCTC

CGGCAAGAAGACAGCTAAAACCAACACAAACGAGTTTTTAATCGACGTG

GATAAAGGCGAAAACTACTGTTTCAGCGTGCAAGCTGTGATCCCCTCCC

GGACCGTGAATAGGAAAAGCACCGATAGCCCCGTTGAGTGCATGGGCCA

AGAAAAGGGCGAGTTCCGGGAG
```

-continued

```
(Human IL-15)
AACTGGGTGAACGTCATCAGCGATTTAAAGAAGATCGAAGATTTAATT

CAGTCCATGCATATCGACGCCACTTTATACACAGAATCCGACGTGCACC

CCTCTTGTAAGGTGACCGCCATGAAATGTTTTTTACTGGAGCTGCAAGT

TATCTCTTTAGAGAGCGGAGACGCTAGCATCCACGACACCGTGGAGAAT

TTAATCATTTTAGCCAATAACTCTTTATCCAGCAACGGCAACGTGACAG

AGTCCGGCTGCAAGGAGTGCGAAGAGCTGGAGGAGAAGAACATCAAGGA

GTTTCTGCAATCCTTTGTGCACATTGTCCAGATGTTCATCAATACCTCC
```

The amino acid sequence of TGFRt15 fusion protein (including the leader sequence) is as follows:

```
(Signal peptide)
MKWVTFISLLFLFSSAYS

(Human TGFβ Receptor II)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD

(Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE

(Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS
```

The nucleic acid and protein sequences of the 21s137L are shown below. The nucleic acid sequence of the 21s137L construct (including signal peptide sequence) is as follows:

```
(Signal peptide)
ATGAAGTGGGTGACCTTCATCAGCCTGCTGTTCCTGTTCTCCAGCGCCT

ACTCC

(Human IL-21)
CAGGGCCAGGACAGGCACATGATCCGGATGAGGCAGCTCATCGACAT

CGTCGACCAGCTGAAGAACTACGTGAACGACCTGGTGCCCGAGTTTCTG

CCTGCCCCCGAGGACGTGGAGACCAACTGCGAGTGGTCCGCCTTCTCCT

GCTTTCAGAAGGCCCAGCTGAAGTCCGCCAACACCGGCAACAACGAGCG

GATCATCAACGTGAGCATCAAGAAGCTGAAGCGGAAGCCTCCCTCCACA

AACGCCGGCAGGAGGCAGAAGCACAGGCTGACCTGCCCCAGCTGTGACT

CCTACGAGAAGAAGCCCCCCAAGGAGTTCCTGGAGAGGTTCAAGTCCCT
```

-continued

GCTGCAGAAGATGATCCATCAGCACCTGTCCTCCAGGACCCACGGCTCC

GAGGACTCC (Human IL-15R a sushi domain)
ATTACATGCCCCCCTCCCATGAGCGTGGAGCACGCCGACATCTGGGTG

AAGAGCTATAGCCTCTACAGCCGGGAGAGGTATATCTGTAACAGCGGCT

TCAAGAGGAAGGCCGGCACCAGCAGCCTCACCGAGTGCGTGCTGAATAA

GGCTACCAACGTGGCTCACTGGACAACACCCTCTTTAAAGTGCATCCGG ((G4S)3 linker)
GGCGGTGGAGGATCCGGAGGAGGTGGCTCCGGCGGCGGAGGATCT (Human CD137L)
CGCGAGGGTCCCGAGCTTTCGCCCGACGATCCCGCCGGCCTCTTGGAC

CTGCGGCAGGGCATGTTTGCGCAGCTGGTGGCCCAAAATGTTCTGCTGA

TCGATGGGCCCCTGAGCTGGTACAGTGACCCAGGCCTGGCAGGCGTGTC

CCTGACGGGGGGCCTGAGCTACAAAGAGGACACGAAGGAGCTGGTGGTG

GCCAAGGCTGGAGTCTACTATGTCTTCTTTCAACTAGAGCTGCGGCGCG

TGGTGGCCGGCGAGGGCTCAGGCTCCGTTTCACTTGCGCTGCACCTGCA

GCCACTGCGCTCTGCTGCTGGGGCCGCCGCCCTGGCTTTGACCGTGGAC

CTGCCACCCGCCTCCTCCGAGGCTCGGAACTCGGCCTTCGGTTTCCAGG

GCCGCTTGCTGCACCTGAGTGCCGGCCAGCGCCTGGGCGTCCATCTTCA

CACTGAGGCCAGGGCACGCCATGCCTGGCAGCTTACCCAGGGCGCCACA

GTCTTGGGACTCTTCCGGGTGACCCCCGAAATCCCAGCCGGACTCCCTT

CACCGAGGTCGGAA

The amino acid sequence of 21s137L fusion protein (including the leader sequence) is as follows:

(Signal peptide)
MKWVTFISLLFLFSSAYS (Human IL-21)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS (Human IL-15Rα sushi domain)
ITCPPPMSVEHADIWVKSYSLYSRERYICNSGFKRKAGTSSLTECVLNK

ATNVAHWTTPSLKCIR ((G4S)3 linker)
GGGGSGGGGSGGGGS (Human CD137L)
REGPELSPDDPAGLLDLRQGMFAQLVAQNVLLIDGPLSWYSDPGLAGVS

LTGGLSYKEDTKELVVAKAGVYYVFFQLELRRVVAGEGSGSVSLALHLQ

PLRSAAGAAALALTVDLPPASSEARNSAFGFQGRLLHLSAGQRLGVHLH

TEARARHAWQLTQGATVLGLFRVTPEIPAGLPSPRSE

In some cases, the leader peptide is cleaved from the intact polypeptide to generate the mature form that may be soluble or secreted.

The IL-21/IL-15RαSu/CD137L and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFR/TF/IL-15: IL-21/IL-15RαSu/CD137L protein complex (referred to as TGFRt15-21s137L), which can be purified by anti-TF IgG1 affinity and other chromatography methods.

Figure 113:
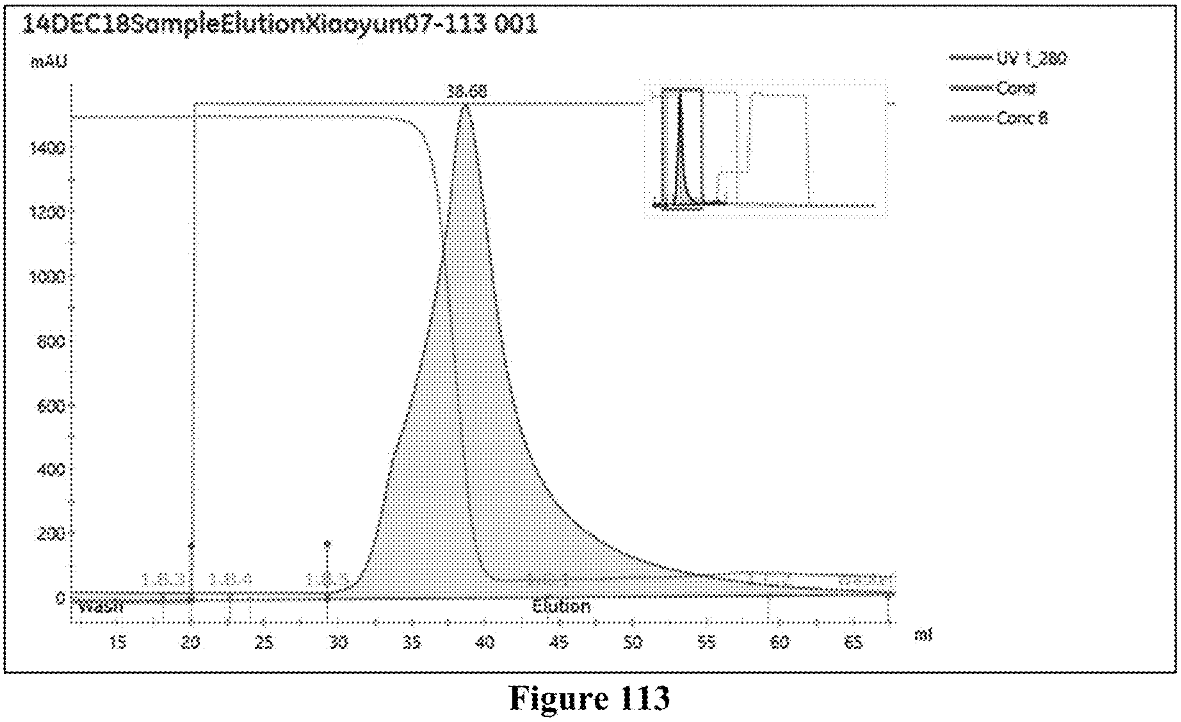
FIG. 113 is a line graph showing the chromatographic profile of TGFRt15-21s137L protein containing cell culture supernatant following binding and elution on anti-TF antibody affinity column.

Purification Elution Chromatograph of TGFRt15-21s137L Using Anti-TF Antibody Affinity Column TGFRt15-21s137L harvest from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 113, the anti-TF antibody affinity column bound to TGFRt15-21s137L which contains TF as a fusion partner of TGFRt15-21s137L. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Example 57: TGFRt15-TGFRs21 Fusion Protein Generation and Characterization

Figure 114:
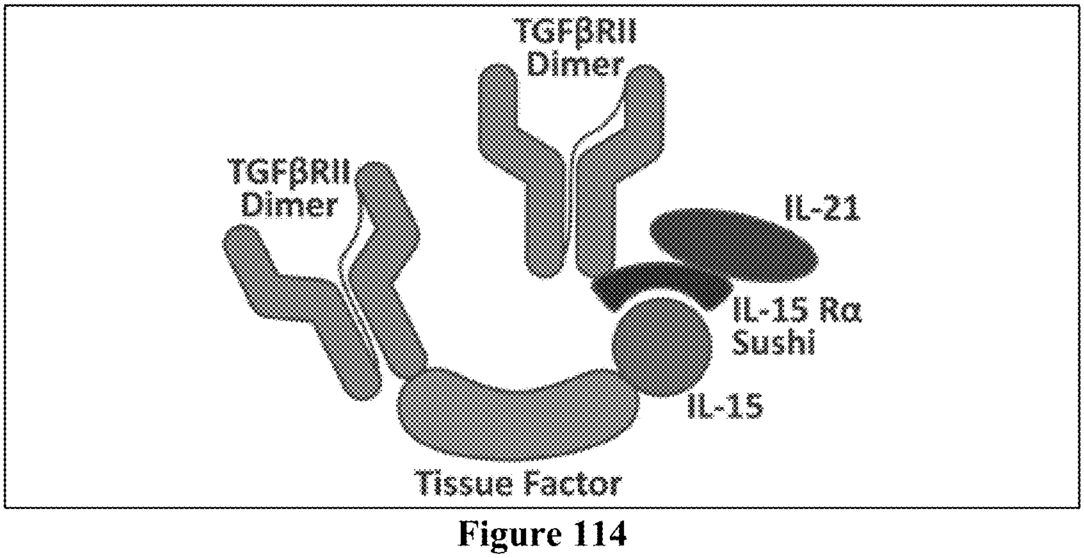
FIG. 114 shows a schematic of the TGFRt15-TGFRs21 construct.
Figure 115:
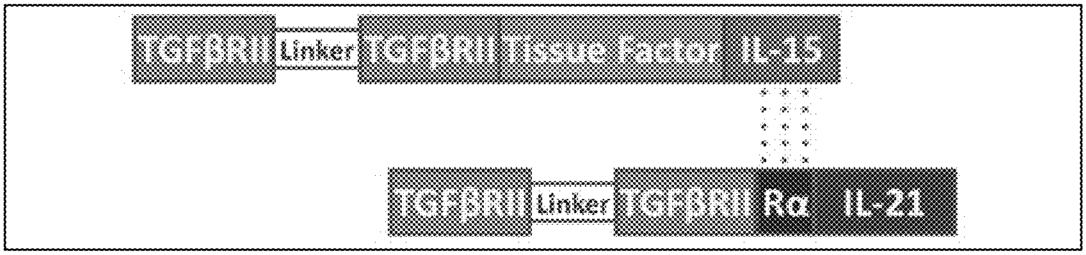
FIG. 115 shows an additional schematic of the TGFRt15-TGFRs21 construct.

A fusion protein complex was generated comprising of TGFβ Receptor II/IL-15RαSu/IL-21 and TGFβ Receptor II/TF/IL-15 fusion proteins (FIG. 114 and FIG. 115). The human TGFβ Receptor II (Ile24-Asp159), tissue factor 219, IL-21, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the TGFRt15 construct (including signal peptide sequence) is as follows:

(Signal peptide)
ATGAAGTGGGTGACCTTCATCAGCCTGCTGTTCCTGTTCTCCAGCGCCT

ACTCC (Human TGFβ Receptor II fragments)
ATCCCCCCCCATGTGCAAAAGAGCGTGAACAACGATATGATCGTGACC

GACAACAACGGCGCCGTGAAGTTTCCCCAGCTCTGCAAGTTCTGCGATG

TCAGGTTCAGCACCTGCGATAATCAGAAGTCCTGCATGTCCAACTGCAG

CATCACCTCCATCTGCGAGAAGCCCCAAGAAGTGTGCGTGGCCGTGTGG

-continued

CGGAAAAATGACGAGAACATCACCCTGGAGACCGTGTGTCACGACCCCA

AGCTCCCTTATCACGACTTCATTCTGGAGGACGCTGCCTCCCCCAAATG

CATCATGAAGGAGAAGAAGAAGCCCGGAGAGACCTTCTTTATGTGTTCC

TGTAGCAGCGACGAGTGTAACGACAACATCATCTTCAGCGAAGAGTACA

ACACCAGCAACCCTGATGGAGGTGGCGGATCCGGAGGTGGAGGTTCTGG

TGGAGGTGGGAGTATTCCTCCCCACGTGCAGAAGAGCGTGAATAATGAC

ATGATCGTGACCGATAACAATGGCGCCGTGAAATTTCCCCAGCTGTGCA

AATTCTGCGATGTGAGGTTTTCCACCTGCGACAACCAGAAGTCCTGTAT

GAGCAACTGCTCCATCACCTCCATCTGTGAGAAGCCTCAGGAGGTGTGC

GTGGCTGTCTGGCGGAAGAATGACGAGAATATCACCCTGGAAACCGTCT

GCCACGATCCCAAGCTGCCCTACCACGATTTCATCCTGGAAGACGCCGC

CAGCCCTAAGTGCATCATGAAAGAGAAAAAGAAGCCTGGCGAGACCTTT

TTCATGTGCTCCTGCAGCAGCGACGAATGCAACGACAATATCATCTTTA

GCGAGGAATACAATACCAGCAACCCCGAC (Human Tissue Factor 219)
AGCGGCACAACCAACACAGTCGCTGCCTATAACCTCACTTGGAAGAG

CACCAACTTCAAAACCATCCTCGAATGGGAACCCAAACCCGTTAACCAA

GTTTACACCGTGCAGATCAGCACCAAGTCCGGCGACTGGAAGTCCAAAT

GTTTCTATACCACCGACACCGAGTGCGATCTCACCGATGAGATCGTGAA

AGATGTGAAACAGACCTACCTCGCCCGGGTGTTTAGCTACCCCGCCGGC

AATGTGGAGAGCACTGGTTCCGCTGGCGAGCCTTTATACGAGAACAGCC

CCGAATTTACCCCTTACCTCGAGACCAATTTAGGACAGCCCACCATCCA

AAGCTTTGAGCAAGTTGGCACAAAGGTGAATGTGACAGTGGAGGACGAG

CGGACTTTAGTGCGGCGGAACAACACCTTTCTCAGCCTCCGGGATGTGT

TCGGCAAAGATTTAATCTACACACTGTATTACTGGAAGTCCTCTTCCTC

CGGCAAGAAGACAGCTAAAACCAACACAAACGAGTTTTTAATCGACGTG

GATAAAGGCGAAAACTACTGTTTCAGCGTGCAAGCTGTGATCCCCTCCC

GGACCGTGAATAGGAAAAGCACCGATAGCCCCGTTGAGTGCATGGGCCA

AGAAAAGGGCGAGTTCCGGGAG (Human IL-15)
AACTGGGTGAACGTCATCAGCGATTTAAAGAAGATCGAAGATTTAATT

CAGTCCATGCATATCGACGCCACTTTATACACAGAATCCGACGTGCACC

CCTCTTGTAAGGTGACCGCCATGAAATGTTTTTTACTGGAGCTGCAAGT

TATCTCTTTAGAGAGCGGAGACGCTAGCATCCACGACACCGTGGAGAAT

TTAATCATTTTAGCCAATAACTCTTTATCCAGCAACGGCAACGTGACAG

AGTCCGGCTGCAAGGAGTGCGAAGAGCTGGAGGAGAAGAACATCAAGGA

GTTTCTGCAATCCTTTGTGCACATTGTCCAGATGTTCATCAATACCTCC

The amino acid sequence of TGFRt15 fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS

Constructs were also made by attaching two TGFβ Receptor II directly to the IL-15RαSu chain, followed by the N-terminus coding region of IL-21, which was synthesized by Genewiz. The nucleic acid and protein sequences of a construct comprising the TGFβ Receptor II linked to the N-terminus of IL-15RαSu following with the N-terminus of IL-21 are shown below.

The nucleic acid sequence of the TGFRs21 construct (including signal peptide sequence) is as follows:

(Signal peptide)
ATGAAGTGGGTGACCTTCATCAGCCTGCTGTTCCTGTTCTCCAGCGCCT

ACTCC (Human TGFβ Receptor II fragments)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

-continued

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGAC (Human IL-15R α sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG (Human IL-21)
CAAGGTCAAGATCGCCACATGATTAGAATGCGTCAACTTATAGATATTG

TTGATCAGCTGAAAAATTATGTGAATGACTTGGTCCCTGAATTTCTGCC

AGCTCCAGAAGATGTAGAGACAAACTGTGAGTGGTCAGCTTTTTCCTGT

TTTCAGAAGGCCCAACTAAAGTCAGCAAATACAGGAAACAATGAAAGGA

TAATCAATGTATCAATTAAAAAGCTGAAGAGGAAACCACCTTCCACAAA

TGCAGGGAGAAGACAGAAACACAGACTAACATGCCCTTCATGTGATTCT

TATGAGAAAAAACCACCCAAAGAATTCCTAGAAAGATTCAAATCACTTC

TCCAAAAGATGATTCATCAGCATCTGTCCTCTAGAACACACGGAAGTGA

AGATTCC

The amino acid sequence of TGFRs21 fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD (Human IL-15R α sushi domain)
ITCPPPMSVEHADIWVKSYSLYSRERYICNSGFKRKAGTSSLTECVLNK

ATNVAHWTTPSLKCIR (Human IL-21)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS

In some cases, the leader peptide is cleaved from the intact polypeptide to generate the mature form that may be soluble or secreted.

The TGFR/IL-15RαSu/IL-21 and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFR/TF/IL-15:TGFR/IL-15RαSu/IL-21 protein complex (referred to as TGFRt15-TGFRs21), which can be purified by anti-TF antibody IgG1 affinity and other chromatography methods.

Figure 116:
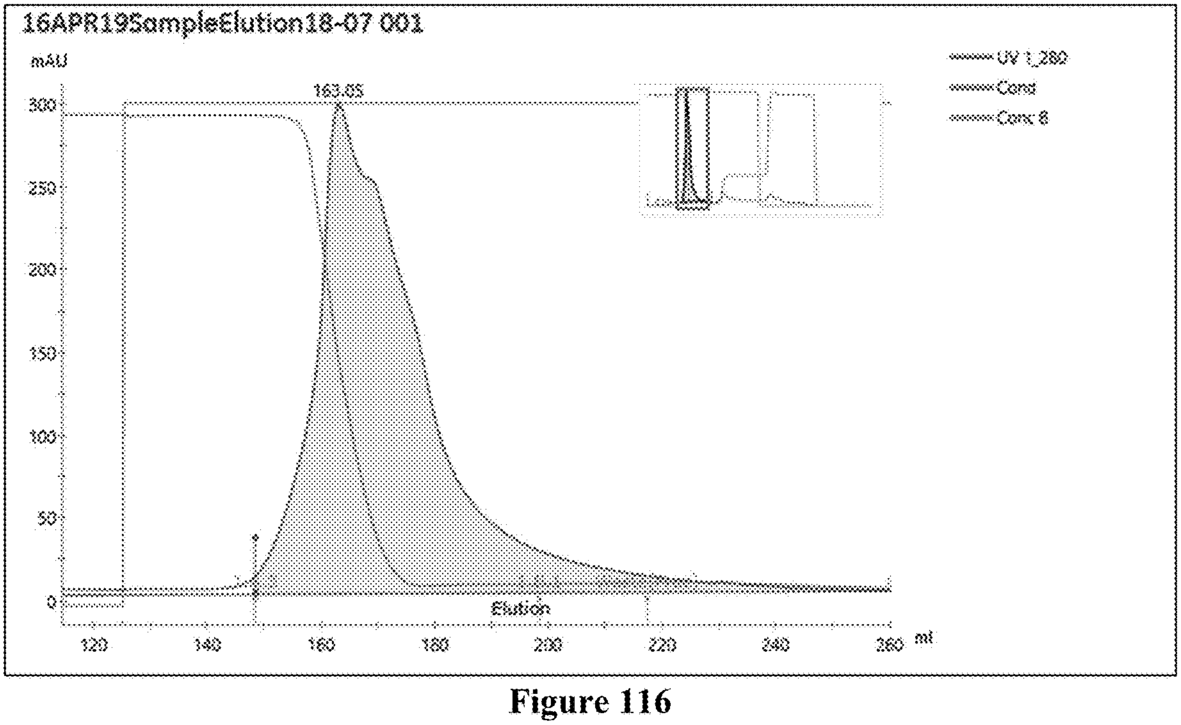
FIG. 116 is a line graph showing the chromatographic profile of TGFRt15-TGFRs21 protein containing cell culture supernatant following binding and elution on anti-TF antibody affinity column.

Purification Elution Chromatograph of TGFRt15-TGFRs21 Using Anti-TF Antibody Affinity Column TGFRt15-TGFRs21 harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 116, the anti-TF antibody affinity column bound to TGFRt15-TGFRs21 which contains TF as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Reduced SDS-PAGE Analysis of TGFRt15-TGFRs21

To determine the purity and molecular weight of the protein, TGFRt15-TGFRs21 protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

Figure 117:
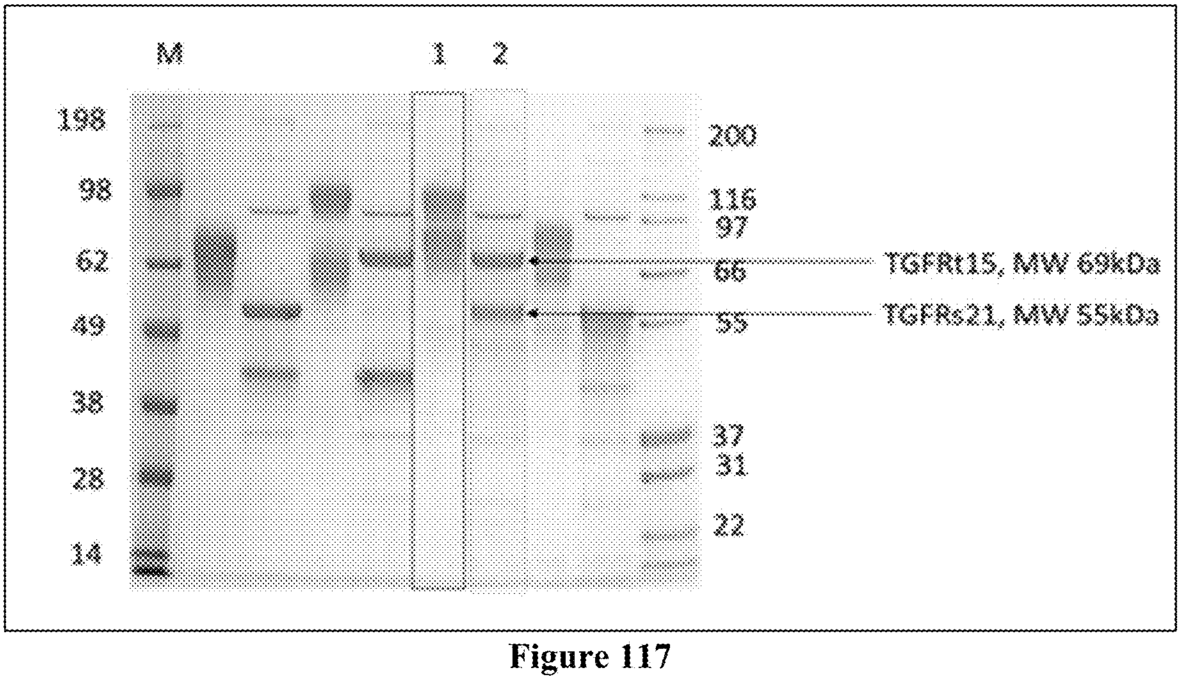
FIG. 117 shows TGFRt15-TGFRs21 before and after deglycosylation as analyzed by reduced SDS-PAGE.

To verify that the TGFRt15-TGFRs21 protein undergoes glycosylation after translation in CHO cells, a deglycosylation experiment was conducted using the Protein Deglycosylation Mix II kit from New England Biolabs and the manufacturer's instructions. FIG. 117 shows the reduced SDS-PAGE analysis of the sample in non-deglycosylated (lane 1 in red outline) and deglycosylated (lane 2 in yellow outline) state. It is clear that the protein is glycosylated when it is expressed in CHO cells. After deglycosylation, the purified sample showed expected molecular weights (69 kDa and 55 kDa) in reduced SDS gel. Lane M was loaded with 10 ul of SeeBlue Plus2 Prestained Standard.

Immunostimulation of TGFRt15-TGFRs21 in C57BL 6 Mice

TGFRt15-TGFRs21 is a multi-chain polypeptide (a type A multi-chain polypeptide described herein) that includes the first polypeptide that is a soluble fusion of single chain two TGFβRII domains, human tissue factor 219 fragment and human IL-15 (TGFRt15), and the second polypeptide that is a soluble fusion of single chain two TGFβRII domains, sushi domain of human IL-15 receptor alpha chain and human IL-21 (TGFRs21).

Figure 118A:
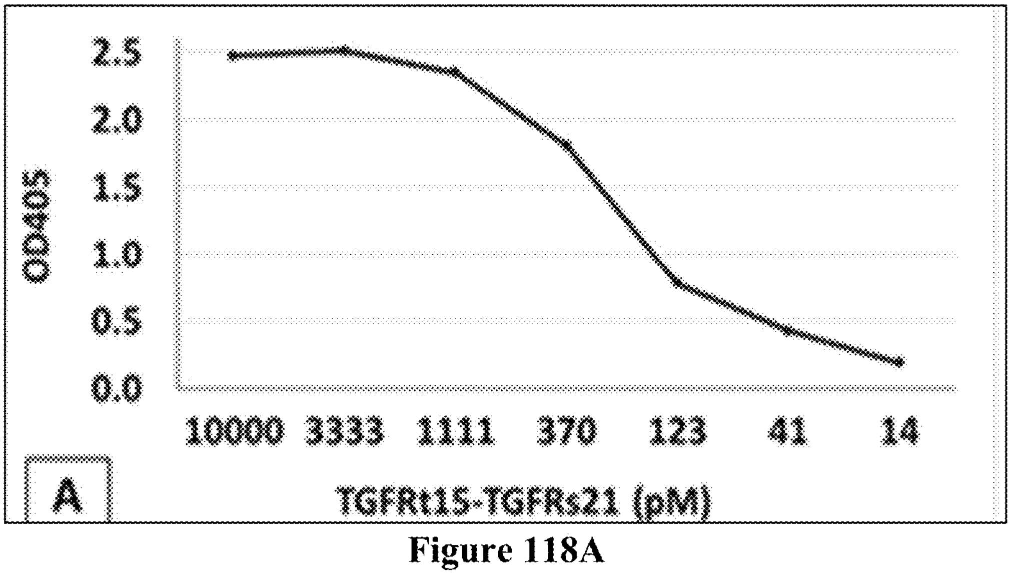
FIGS. 118A and 118B show detection of components of TGFRt15-TGFRs21 using ELISA.
Figure 118B:
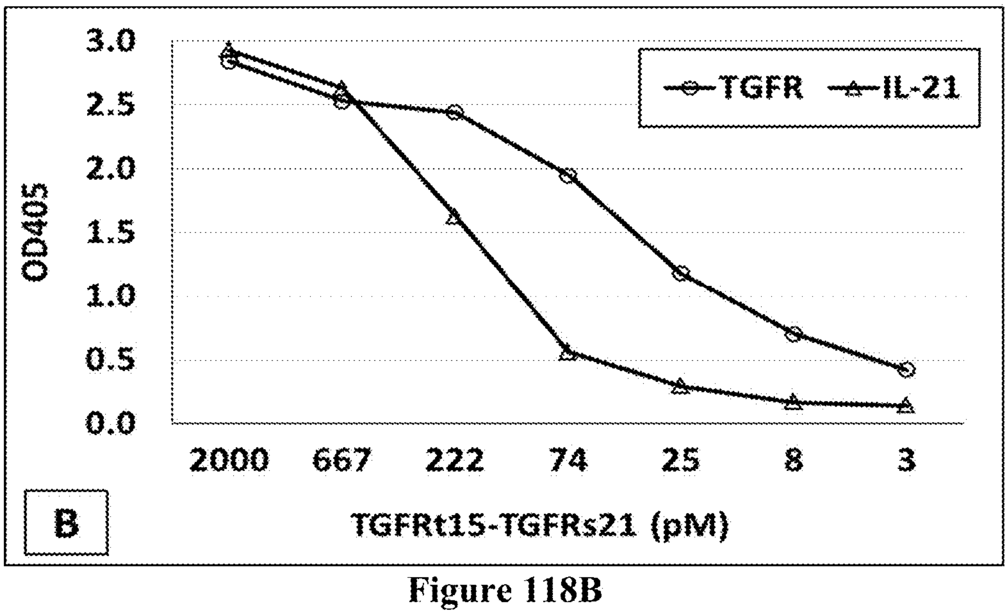

CHO cells were co-transfected with TGFRt15 and TGFRs21 vectors. The TGFRt15-TGFRs21 complex was purified from the transfected CHO cell culture supernatant. The TGFβ receptor, IL-15, IL-21 and tissue factor (TF) components were demonstrated in the complex by ELISA as shown in FIG. 118A-B. A humanized anti-TF monoclonal antibody (anti-TF IgG1) was used as the capture antibody to determine TF in TGFRt15-TGFRs21, biotinylated anti-human IL-15 antibody (R&D systems), biotinylated anti-human TGFβ receptor antibody (R&D systems, and biotinylated anti-human IL-21 antibody (R&D Systems) were used as the detection antibodies to respectively determine IL-15, TGFβ receptor, and IL-21 in TGFRt15-TGFRs21. For detection, peroxidase conjugated streptavidin (Jackson ImmunoResearch Lab) and ABTS were used.

Figure 119A:
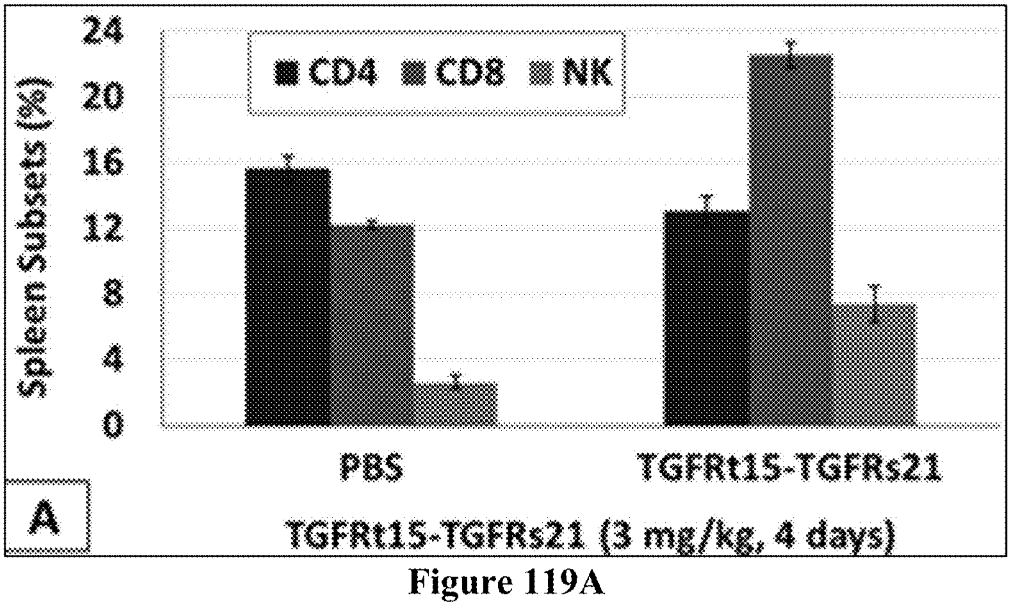
FIGS. 119A and 119B show the percentages and proliferation of $CD4^+$ T cells, $CD8^+$ T cells, and natural killer (NK) cells present in the spleen of control-treated and TGFRt15-TGFRs21-treated mice.
Figure 119B:
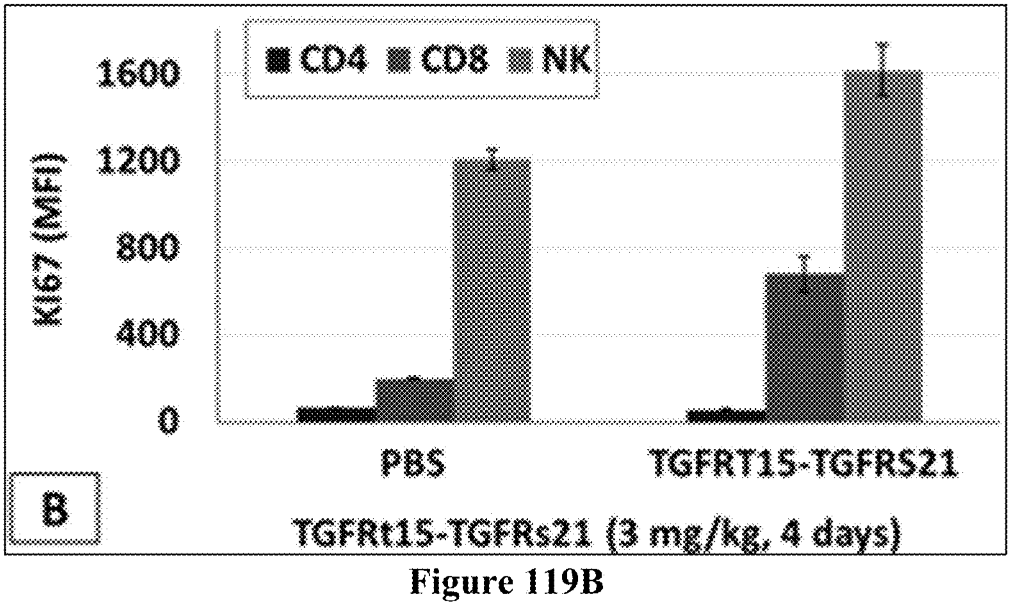
Figure 120:
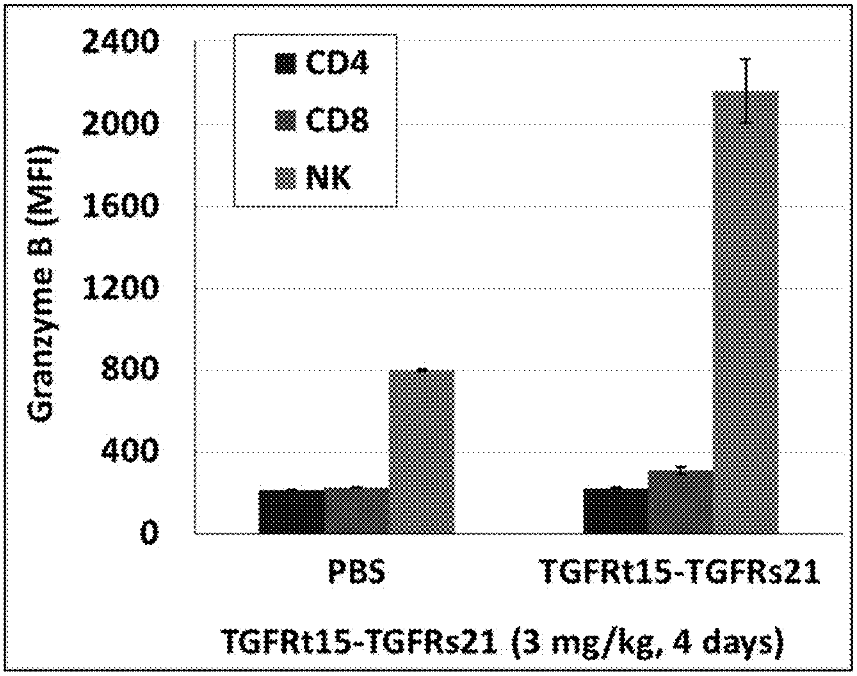
FIG. 120 shows upregulation of Granzyme B expression of splenocytes in mice treated with TGFRt15-TGFRs21.

Wild type C57BL/6 mice were treated subcutaneously with either control solution (PBS) or with TGFRt15-TGFRs21 at 3 mg/kg. Four days after treatment, spleen weight and the percentages of various immune cell types present in the spleen were evaluated. As shown in FIG. 119A, the percentages of $CD4^+$ T cells, $CD8^+$ T cells, and NK cells present in the spleen of control-treated and TGFRt15-TGFRs21-treated mice were evaluated. The dynamic proliferation of immune cells based on Ki67 expression after TGFRt15-TGFRs21 treatment was also evaluated. The splenocytes were stained with fluorochrome-conjugated anti-CD4, anti-CD8, and anti-NK1.1 (NK) antibodies and then intracellularly stained with anti-Ki67 antibody. The percentage of $CD4^+$ T cells, $CD8^+$ T cells, and NK cells and the mean fluorescent intensity (MFI) of Ki67 of corresponding immunocyte subsets were analyzed by flow cytometry (FIGS. 119A and 119B). Furthermore, cytotoxicity potential based on granzyme B expression of the splenocytes induced by TGFRt15-TGFRs21 after the single dose treatment of mouse was also evaluated. As shown in FIG. 120, in the spleens of mice treated with TGFRt15-TGFRs21, the expression of granzyme B by NK cells increased after treatment. The splenocytes from TGFRt15-TGFRs21-treated mice were stained with fluorochrome-conjugated anti-CD4, anti-CD8, and anti-NK1.1 (NK) antibodies and then intracellularly stained with anti-granzyme B antibody. The mean fluorescent intensity (MFI) of granzyme B of corresponding immunocyte subsets was analyzed by flow cytometry (FIG. 120).

As shown in FIG. 119A, in the spleens of mice treated with TGFRt15-TGFRs21, the percentages of $CD8^+$ T cells and NK cells both increased on day 4 after a single TGFRt15-TGFRs21 treatment. These results demonstrate that TGFRt15-TGFRs21 is able to induce immune cells to proliferate in mouse spleen, in particular $CD8^+$ T cells and NK cells.

Figure 121:
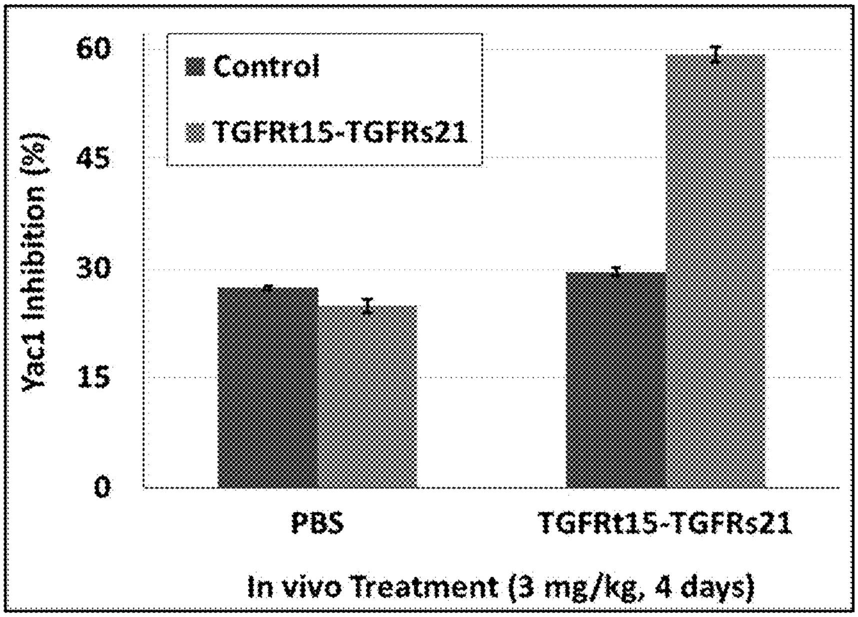

Additionally, cytotoxicity of the mouse splenocytes against tumor cells was also evaluated. Mouse Yac-1 cells were labeled with CELLTRACE®, violet dye, and used as tumor target cells. The splenocytes were prepared from TGFRt15-TGFRs21-treated mice and used as effector cells. The target cells were mixed with effector cells at E:T ratio=10:1 in RPMI-10 medium with or without TGFRt15-TGFRs21 at 100 nM and incubated at 37° C. for 24 hours. Target Yac-1 cell inhibition was assessed by analysis of viable violet-labeled Yac-1 cells using flow cytometry. Percentage of Yac-1 inhibition was calculated using a formula, (1-[viable Yac-1 cell number in experimental sample]/[viable Yac-1 cell number in the sample without splenocytes])×100. As shown in FIG. 121, TGFRt15-TGFRs21-treated mouse splenocytes had stronger cytotoxicity against Yac-1 cells than the control mouse cells in the presence of TGFRt15-TGFRs21 during cytotoxic assay (FIG. 121).

Example 58: TGFRt15-TGFRs16 Fusion Protein Generation

Figure 122:
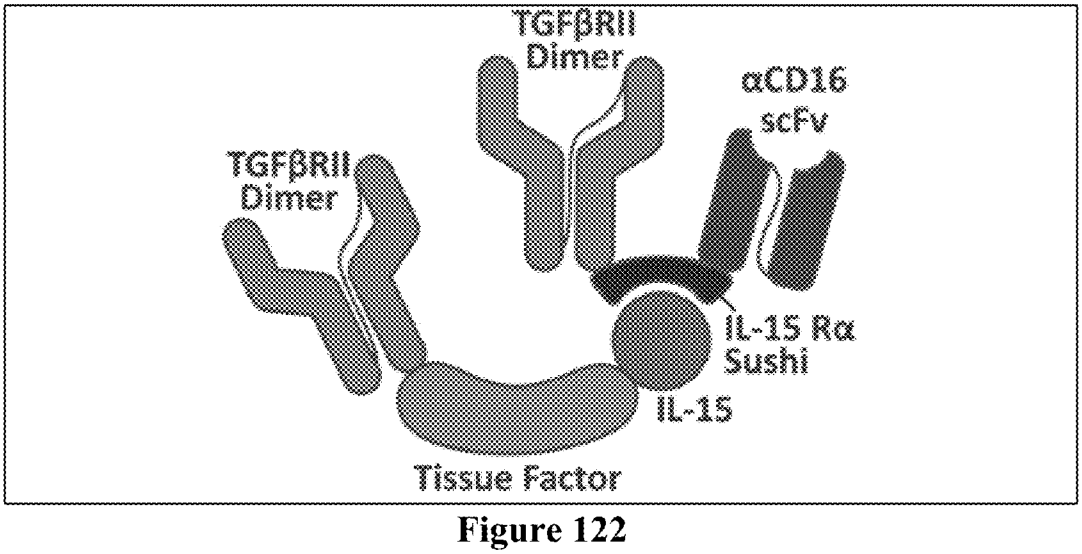
Figure 123:
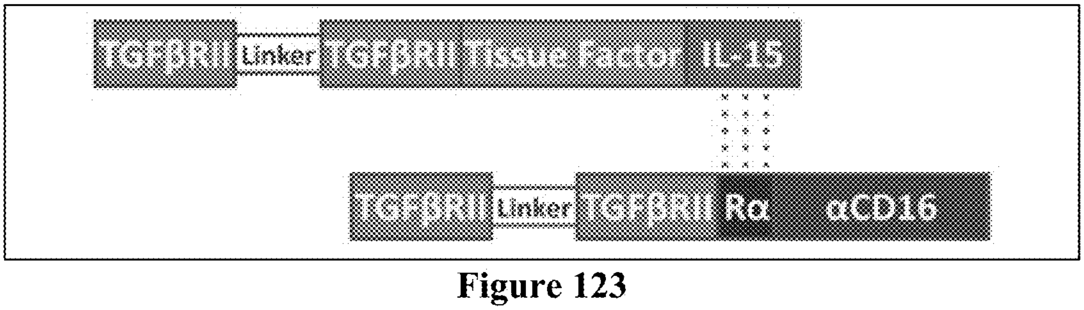

A fusion protein complex was generated comprising of TGFβ Receptor II/IL-15RαSu/anti-CD16scFv and TGFβ Receptor II/TF/IL-15 fusion proteins (FIG. 122 and FIG. 123). The human TGFβ Receptor II (Ile24-Asp159), tissue factor 219, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the TGFRt15 construct (including signal peptide sequence) is as follows:

```
(Signal peptide)
ATGAAGTGGGTGACCTTCATCAGCCTGCTGTTCCTGTTCTCCAGCGCCT

ACTCC

(Human TGFβ Receptor II fragments)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGAC

(Human Tissue Factor 219)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC
```

-continued

GGCAAAGATTTAATCTACACACTGTATTACTGGAAGTCCTCTTCCTCCG

GCAAGAAGACAGCTAAAACCAACACAAACGAGTTTTTAATCGACGTGGA

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG (Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC

The amino acid sequence of TGFRt15 fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS

Constructs were also made by attaching two TGFβ Receptor II directly to the IL-15RαSu chain, followed by the anti-CD16scFv sequence, which was synthesized by Genewiz. The nucleic acid and protein sequences of a construct comprising the TGFβ Receptor II linked to the N-terminus of IL-15RαSu following with the anti-CD16scFv sequence are shown below.

The nucleic acid sequence of the TGFRs16 construct (including signal peptide sequence) is as follows:

(Signal peptide)
ATGAAGTGGGTGACCTTCATCAGCCTGCTGTTCCTGTTCTCCAGCGCCT

ACTCC (Human TGFβ Receptor II fragments)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGAC (Human IL-15R α sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG (Anti-human CD16scFv)
TCCGAGCTGACCCAGGACCCTGCTGTGTCCGTGGCTCTGGGCCAGACCG

TGAGGATCACCTGCCAGGGCGACTCCCTGAGGTCCTACTACGCCTCCTG

GTACCAGCAGAAGCCCGGCCAGGCTCCTGTGCTGGTGATCTACGGCAAG

AACAACAGGCCCTCCGGCATCCCTGACAGGTTCTCCGGATCCTCCTCCG

GCAACACCGCCTCCCTGACCATCACAGGCGCTCAGGCCGAGGACGAGGC

TGACTACTACTGCAACTCCAGGGACTCCTCCGGCAACCATGTGGTGTTC

GGCGGCGGCACCAAGCTGACCGTGGGCCATGGCGGCGGCGGCTCCGGAG

GCGGCGGCAGCGGCGGAGGAGGATCCGAGGTGCAGCTGGTGGAGTCCGG

AGGAGGAGTGGTGAGGCCTGGAGGCTCCCTGAGGCTGAGCTGTGCTGCC

TCCGGCTTCACCTTCGACGACTACGGCATGTCCTGGGTGAGGCAGGCTC

CTGGAAAGGGCCTGGAGTGGGTGTCCGGCATCAACTGGAACGGCGGATC

-continued

CACCGGCTACGCCGATTCCGTGAAGGGCAGGTTCACCATCAGCAGGGAC

AACGCCAAGAACTCCCTGTACCTGCAGATGAACTCCCTGAGGGCCGAGG

ACACCGCCGTGTACTACTGCGCCAGGGGCAGGTCCCTGCTGTTCGACTA

CTGGGGACAGGGCACCCTGGTGACCGTGTCCAGG

The amino acid sequence of TGFRs16 fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD (Human IL-15R α sushi domain)
ITCPPPMSVEHADIWVKSYSLYSRERYICNSGFKRKAGTSSLTECVLNK

ATNVAHWTTPSLKCIR (Anti-human CD16scFv)
SELTQDPAVSVALGQTVRITCQGDSLRSYYASWYQQKPGQAPVLVIYGK

NNRPSGIPDRFSGSSSGNTASLTITGAQAEDEADYYCNSRDSSGNHVVF

GGGTKLTVGHGGGGSGGGGSGGGGSEVQLVESGGGVVRPGGSLRLSCAA

SGFTFDDYGMSWVRQAPGKGLEWVSGINWNGGSTGYADSVKGRFTISRD

NAKNSLYLQMNSLRAEDTAVYYCARGRSLLFDYWGQGTLVTVSR

In some cases, the leader peptide is cleaved from the intact polypeptide to generate the mature form that may be soluble or secreted.

The TGFR/IL-15RαSu/anti-CD16scFv and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFR/TF/IL-15:TGFR/IL-15RαSu/anti-CD16scFv protein complex (referred to as TGFRt15-TGFRs16), which can be purified by anti-TF IgG1 affinity and other chromatography methods.

Figure 124:
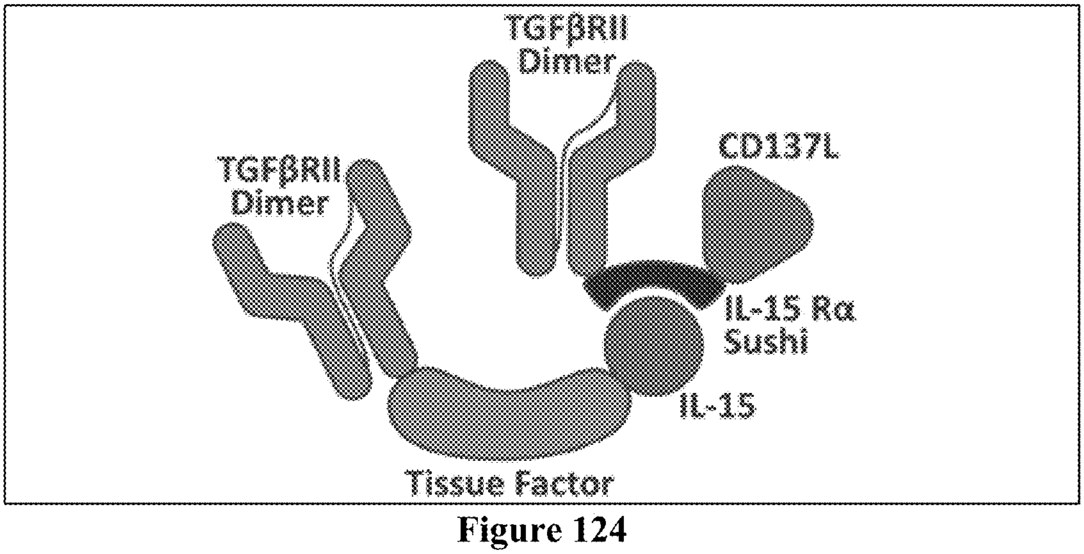
Figure 125:
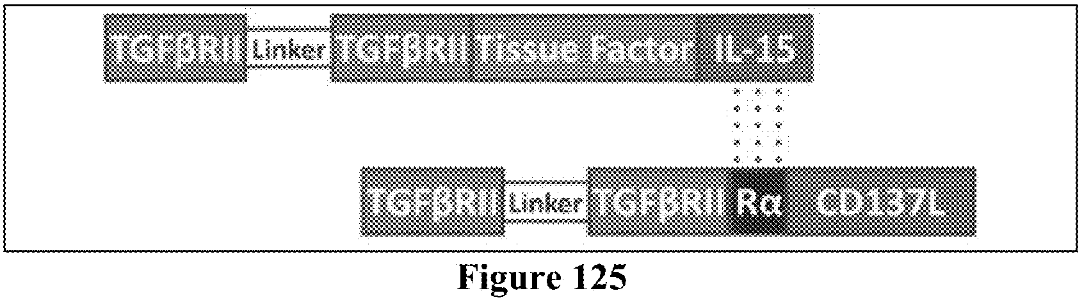

Example 59: The TGFRt15-TGFRs137L fusion protein generation A fusion protein complex was generated comprising of TGFβ Receptor II/IL-15RαSu/CD137L and TGFβ Receptor II/TF/IL-15 fusion proteins (FIG. 124 and FIG. 125). The human TGFβ Receptor II (Ile24-Asp159), tissue factor 219, CD137L, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the TGFRt15 construct (including signal peptide sequence) is as follows:

(Signal peptide)
ATGAAGTGGGTGACCTTCATCAGCCTGCTGTTCCTGTTCTCCAGCGCCT

ACTCC (Human TGFβ Receptor II fragments)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGAC (Human Tissue Factor 219)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA

-continued

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG (Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC

The amino acid sequence of TGFRt15 fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS

Constructs were also made by attaching two TGFβ Receptor II directly to the IL-15RαSu chain, followed by a (G4S)3 linker and the CD137L sequence, which was synthesized by Genewiz. The nucleic acid and protein sequences of a construct comprising the TGFβ Receptor II linked to the N-terminus of IL-15RαSu following with a (G4S)3 linker and the CD137L sequence are shown below.

The nucleic acid sequence of the TGFRs137L construct (including signal peptide sequence) is as follows:

(Signal peptide)
ATGAAGTGGGTGACCTTCATCAGCCTGCTGTTCCTGTTCTCCAGCGCCT

ACTCC

-continued (Human TGFβ Receptor II fragments)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGAC (Human IL-15R α sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG ((G4S)3 linker)
GGCGGTGGAGGATCCGGAGGAGGTGGCTCCGGCGGCGGAGGATCT (Human CD137L)
CGCGAGGGTCCCGAGCTTTCGCCCGACGATCCCGCCGGCCTCTTGGACC

TGCGGCAGGGCATGTTTGCGCAGCTGGTGGCCCAAAATGTTCTGCTGAT

CGATGGGCCCCTGAGCTGGTACAGTGACCCAGGCCTGGCAGGCGTGTCC

CTGACGGGGGGCCTGAGCTACAAAGAGGACACGAAGGAGCTGGTGGTGG

CCAAGGCTGGAGTCTACTATGTCTTCTTTCAACTAGAGCTGCGGCGCGT

GGTGGCCGGCGAGGGCTCAGGCTCCGTTTCACTTGCGCTGCACCTGCAG

CCACTGCGCTCTGCTGCTGGGGCCGCCGCCCTGGCTTTGACCGTGGACC

TGCCACCCGCCTCCTCCGAGGCTCGGAACTCGGCCTTCGGTTTCCAGGG

CCGCTTGCTGCACCTGAGTGCCGGCCAGCGCCTGGGCGTCCATCTTCAC

ACTGAGGCCAGGGCACGCCATGCCTGGCAGCTTACCCAGGGCGCCACAG

TCTTGGGACTCTTCCGGGTGACCCCCGAAATCCCAGCCGGACTCCCTTC

ACCGAGGTCGGAA

The amino acid sequence of TGFRs137L fusion protein (including the leader sequence) is as follows:

```
(Signal peptide)
MKWVTFISLLFLFSSAYS

(Human TGFβ Receptor II)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD

(Human IL-15R α sushi domain)
ITCPPPMSVEHADIWVKSYSLYSRERYICNSGFKRKAGTSSLTECVLNK

ATNVAHWTTPSLKCIR

((G4S)3 linker)
GGGGSGGGGSGGGGS

(Human CD137L)
REGPELSPDDPAGLLDLRQGMFAQLVAQNVLLIDGPLSWYSDPGLAGVS

LTGGLSYKEDTKELVVAKAGVYYVFFQLELRRVVAGEGSGSVSLALHLQ

PLRSAAGAAALALTVDLPPASSEARNSAFGFQGRLLHLSAGQRLGVHLH

TEARARHAWQLTQGATVLGLFRVTPEIPAGLPSPRSE
```

In some cases, the leader peptide is cleaved from the intact polypeptide to generate the mature form that may be soluble or secreted.

The TGFR/IL-15RαSu/CD137L and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. Hum Gene Ther 2005; 16:457-72), and the expression vectors were transfected into CHO-K1 cells. Co-expression of the two constructs in CHO-K1 cells allowed for formation and secretion of the soluble TGFR/TF/IL-15:TGFR/IL-15RαSu/CD137L protein complex (referred to as TGFRt15-TGFRs137L), which can be purified by anti-TF IgG1 affinity and other chromatography methods.

Figure 126:
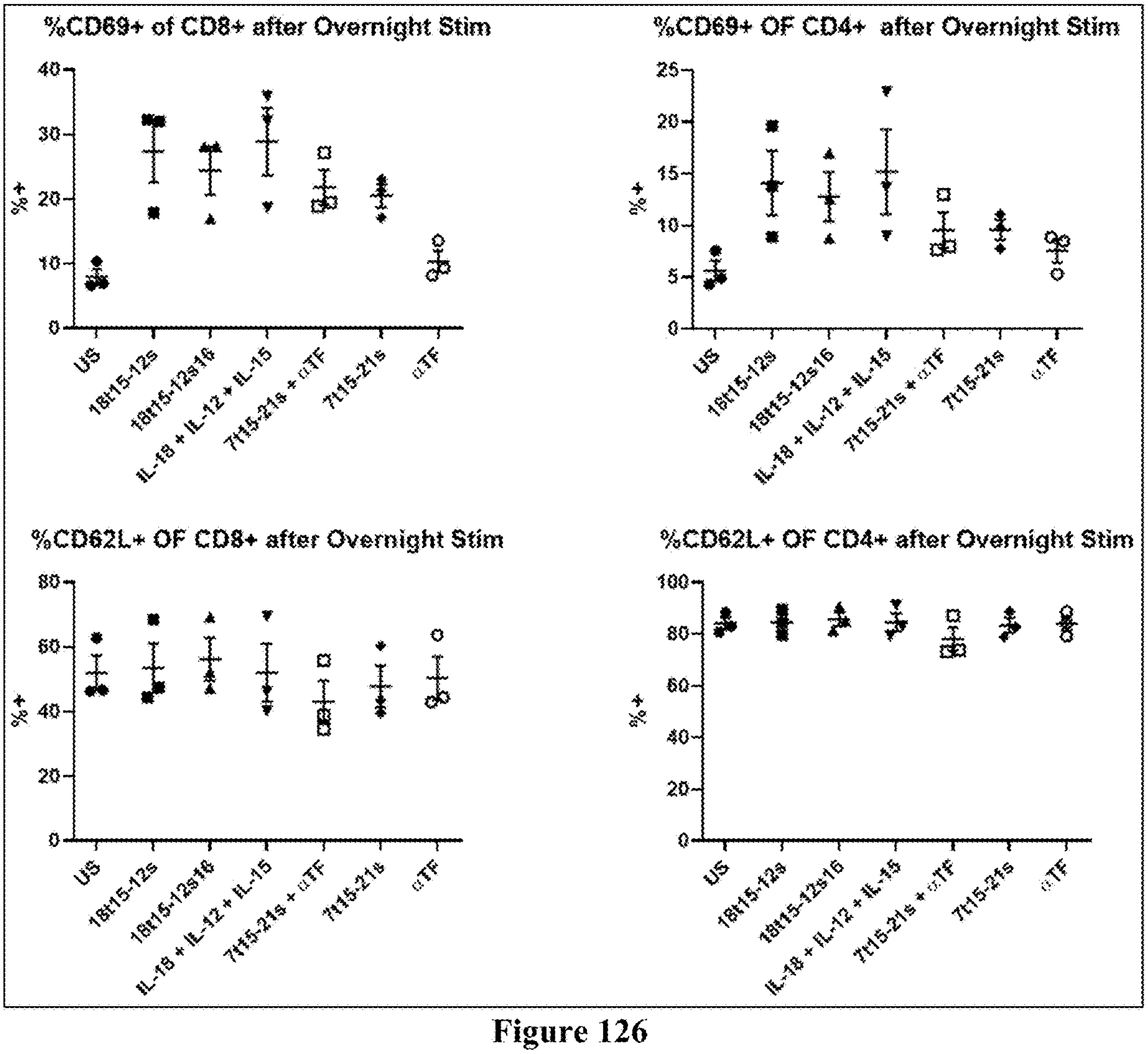

Example 60: Stimulation of NK Cells In Vitro by Multi-Chain Chimeric Polypeptide Constructs A set of experiments was performed to assess changes in the surface phenotype of lymphocyte populations after stimulation with 18t15-12s, 18t15-12s16, and 7t15-21s. In these experiments, fresh human leukocytes were obtained from the blood bank. Peripheral blood lymphocytes were isolated with the Ficoll-PAQUE Plus (GE Healthcare) density gradient media. The cells were counted and resuspended at $0.2\times10^6$/mL in a 96-well flat-bottom plate in 0.2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with: 18t15-12s (100 nM); 18t15-12s16 (100 nM), a mixture of single cytokines rhIL15 (50 ng/mL) (Miltenyi), rhIL18 (50 ng/mL) (Invivogen), and rhIL-12 (10 ng/mL) (Peprotech); 7t15-21s (100 nM)+anti-TF antibody (50 nM); 7t15-21s (100 nM); or anti-TF antibody (50 nM) at 37° C. and 5% $CO_2$ for 16 hours. The next day, the cells were harvested and surface stained for 30 minutes with antibodies specific for CD4 or CD8, CD62L, and CD69. After surface staining, cells were washed (1500 RPM for 5 minutes at room temperature) in FACS buffer (1×PBS (Hyclone) with 0.5% BSA (EMD Millipore) and 0.001% sodium azide (Sigma)). After two washes, the cells were analyzed by flow cytometry (Celesta-BD Bioscience). FIG. 126 shows that overnight incubation of purified lymphocyte populations (CD4 and CD8 T cells) with 18t15-12s, 18t15-12s16, or 7t15-21s+anti-TF antibody resulted in an increase in the percentage of CD8 and CD4 T cells expressing CD69. Additionally, incubation with 7t15-21s+anti-TF antibody resulted in an increase in the percentage of CD8 and CD4 T cells expressing CD62L (FIG. 126).

Figure 127:
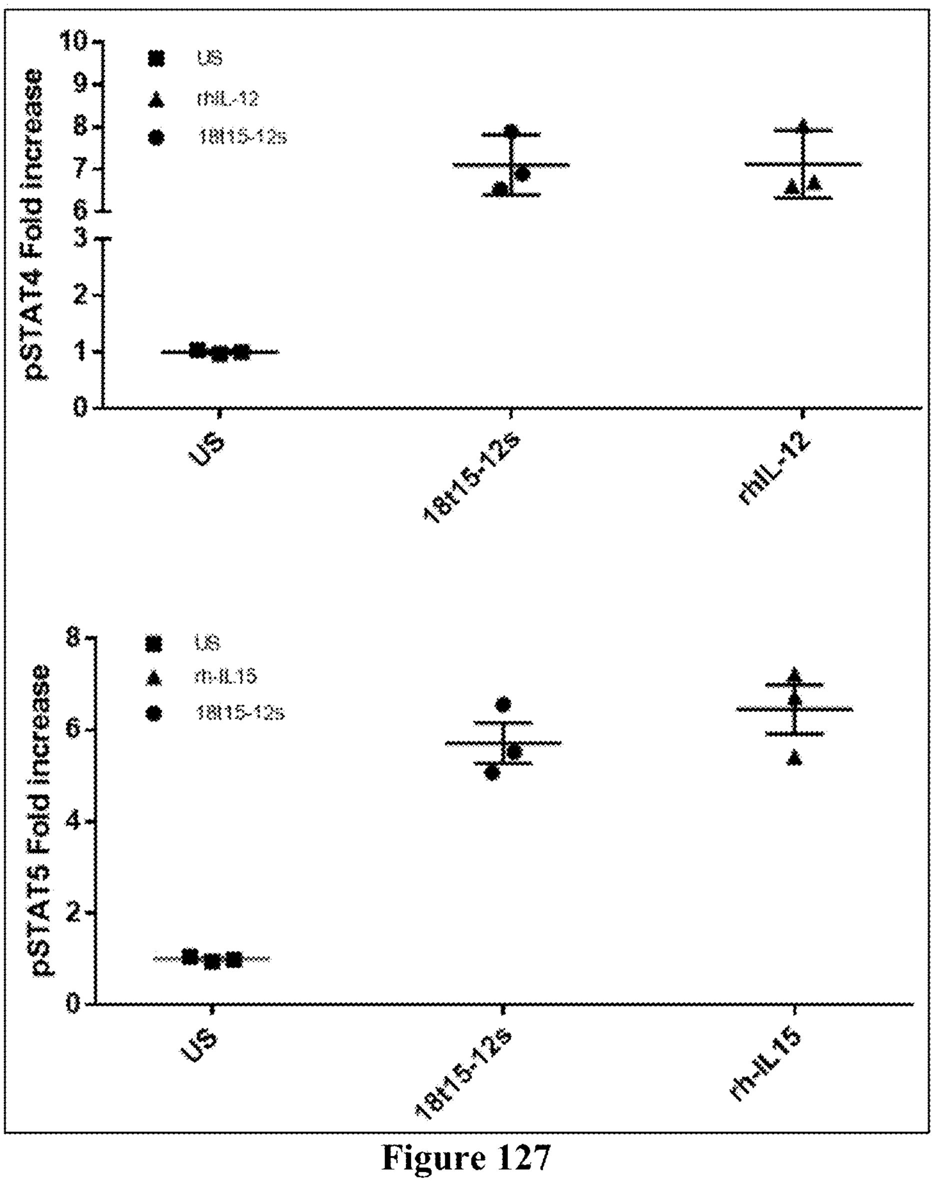

A set of experiments was performed to determine the increase in phospho-STAT4 and phospho-STAT5 levels in NK cells after stimulation with 18t15-12s. In these experiments, fresh human leukocytes were obtained from the blood bank and $CD56^+$ NK cells were isolated with the RosetteSep/human NK cell reagent (StemCell Technologies). The purity of NK cells was >70% and confirmed by staining with CD56-BV421, CD16-BV510, CD25-PE, and CD69-APCFire750 specific antibodies (BioLegend). The cells were counted and resuspended in $0.05\times10^6$/mL in a 96-well flat-bottom plate in 0.1 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with hIL-12 (10 ng/mL) (Biolegend) or hIL-15 (50 ng/mL) (NCI) (Single cytokines), or 18t15-12s (100 nM) at 37° C. and 5% $CO_2$ for 90 minutes. Unstimulated NK cells (US) were used as a control. The cells were harvested and fixed in paraformaldehyde (Sigma) to a final concentration of 1.6%. Plates were incubated in the dark at room temperature for 10 minutes. FACS buffer (1×PBS (Hyclone) with 0.5% BSA (EMD Millipore) and 0.001% sodium azide (Sigma)) (100 μL) was added and cells were transferred to 96-well "V" bottom plate. The cells were washed for 1500 RPM for 5 minutes at room temperature. The cell pellet was mixed with 100 μL chilled methanol by gently pipetting up and down, and cells were incubated for 30 minutes at 4° C. The cells were mixed with 100 mL of FACS buffer and washed for 1500 RPM for 5 minutes at room temperature. The cell pellets were mixed with 50 mL of FACS buffer containing 4 mL of pSTAT4 (BD Bioscience) and pSTAT5 antibodies (BD Bioscience) followed by incubation for 30 minutes at room temperature in the dark. The cells were mixed with 100 mL of FACS buffer and washed for 1500 RPM for 5 minutes at room temperature. The cell pellets were mixed with 50 mL of FACS buffer and cells were analyzed by flow cytometry (Celesta-BD Bioscience). FIG. 127 shows that incubation of NK cells with 18t15-12s induced an increase in pSTAT4 and pSTAT5 (plotted data, normalized fold-change).

Example 61: Stimulation of NK Cells In Vivo by TGFRt15-TGFRs

Figure 128A:
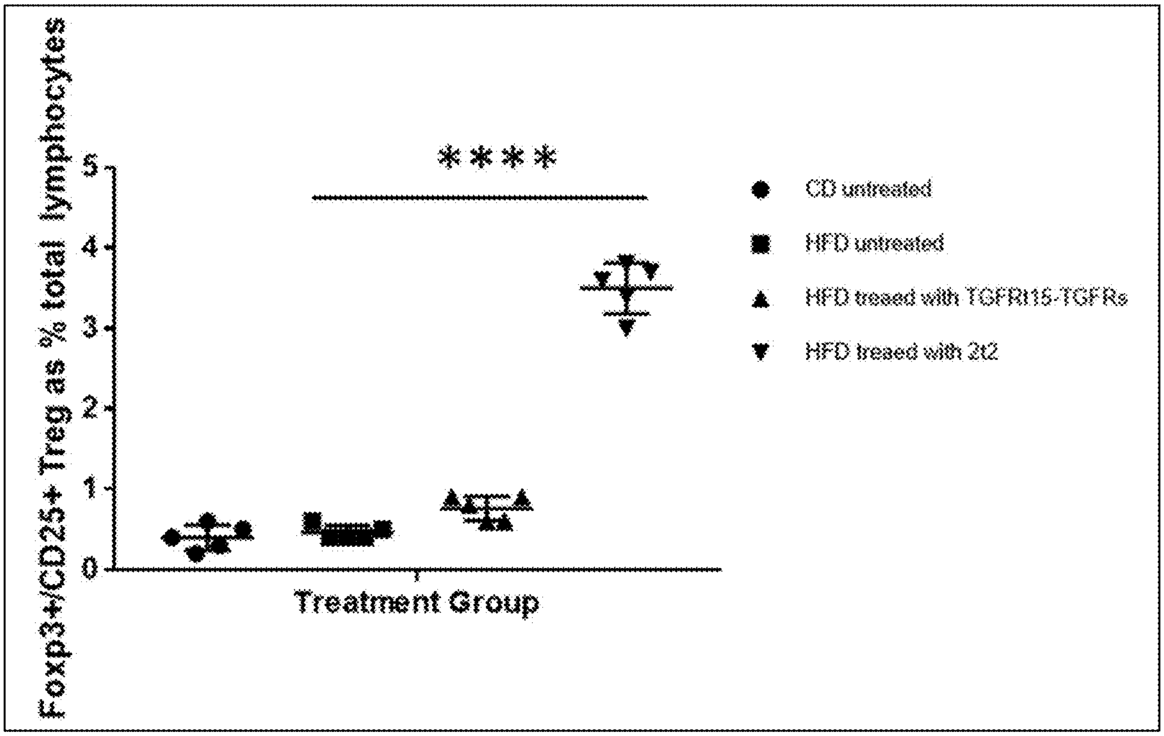
Figure 128B:
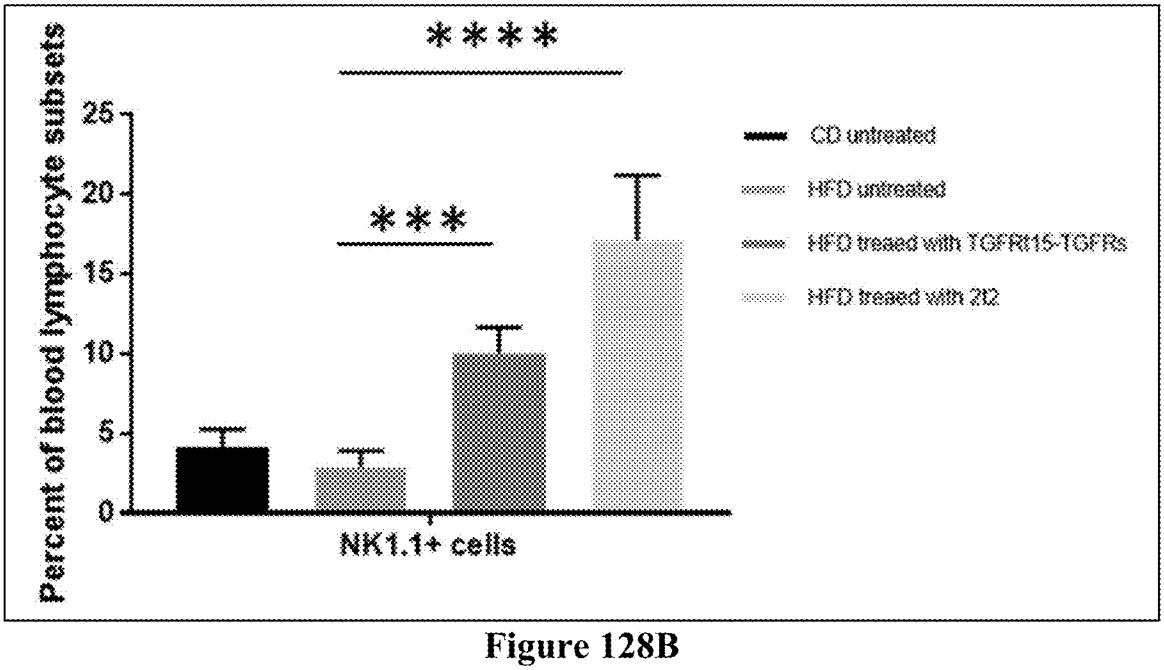
Figure 128C:
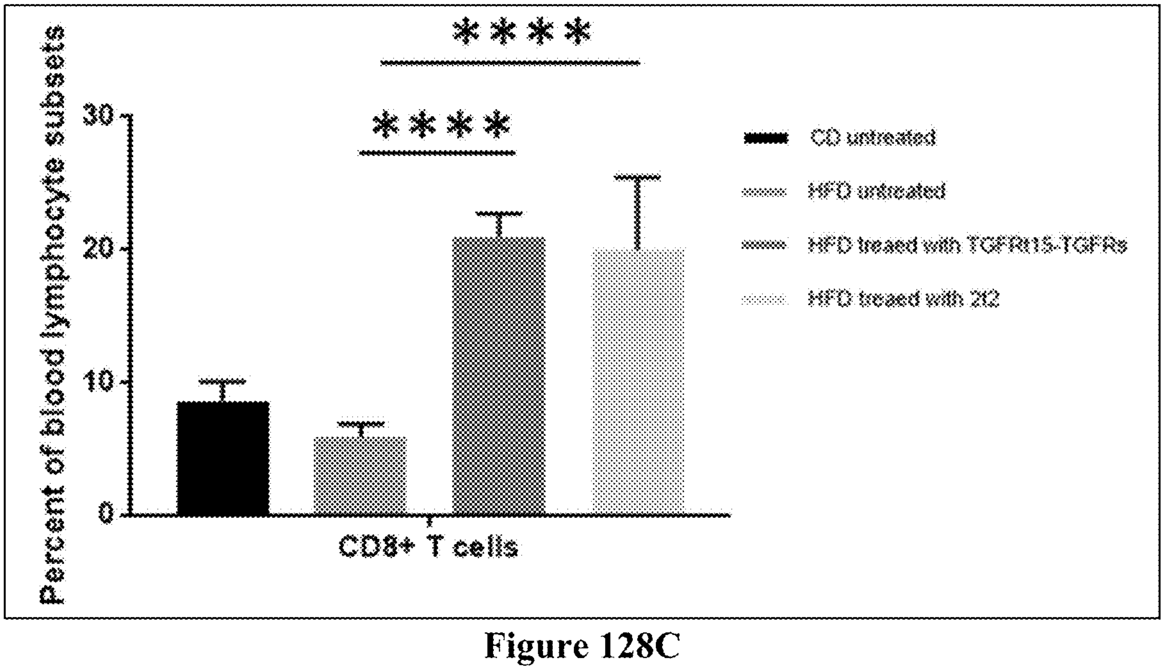

A set of experiments was performed to determine the effect of the TGFRt15-TGFRs construct on immune stimulation in $ApoE^{-/-}$ mice fed with a Western diet. In these experiments, 6-week old female B6.129P2-$ApoE^{tm1Unc}$/J mice (Jackson Laboratory) were fed with a Western diet containing 21% fat, 0.15% cholesterol, 34.1% sucrose, 19.5% casein, and 15% starch (TD88137, Envigo Laboratories). After 8-weeks of the Western diet, the mice were injected subcutaneously with TGFRt15-TGFRs at 3 mg/kg. Three days post treatment, mice were fasted for 16 hours and then blood samples were collected through retro-orbital venous plexus puncture. The blood was mixed with 10 μL 0.5 M EDTA, and 20 μL blood was taken for lymphocyte subsets analysis. The red blood cells were lysed with ACK (0.15 M $NH_4Cl$, 1.0 mM $KHCO_3$, 0.1 mM $Na_2EDTA$, 30 pH 7.4) and the lymphocytes were stained with anti-mouse CD8a and anti-mouse NK1.1 antibodies for 30 minutes at 4° C. in FACS staining buffer (1% BSA in PBS). The cells were washed once and analyzed with a BD FACS Celesta. For Treg staining, ACK treated blood lymphocytes were stained with anti-mouse CD4 and anti-mouse CD25 antibodies for 30 minutes at 4° C. in FACS staining buffer. The cells were washed once and resuspended in fixation/permeabilization working solution and incubated at room temperature for 60 minutes. The cells were washed once and resuspended in permeabilization buffer. The samples were centrifuged at 300-400×g for 5 minutes at room temperature and the supernatant was then discarded. The cell pellet was resuspended in residual volume and the volume adjusted to about 100 μL with 1×permeabilization buffer. Anti-Foxp3 antibody was added to the cells, and the cells were incubated for 30 minutes at room temperature. Permeabilization buffer (200 μL) was added to the cells, and the cells were centrifuged at 300-400×g for 5 minutes at room temperature. The cells were resuspended in flow cytometry staining buffer and analyzed on a flow cytometer. FIGS. 128A-128C show that treatment with TGFRt15-TGFRs increased the percentage of NK cells and $CD8^+$ T cells in $ApoE^{-/-}$ mice fed with Western diet.

Example 62: Induction of Proliferation of Immune Cells In Vivo

Figure 129A:
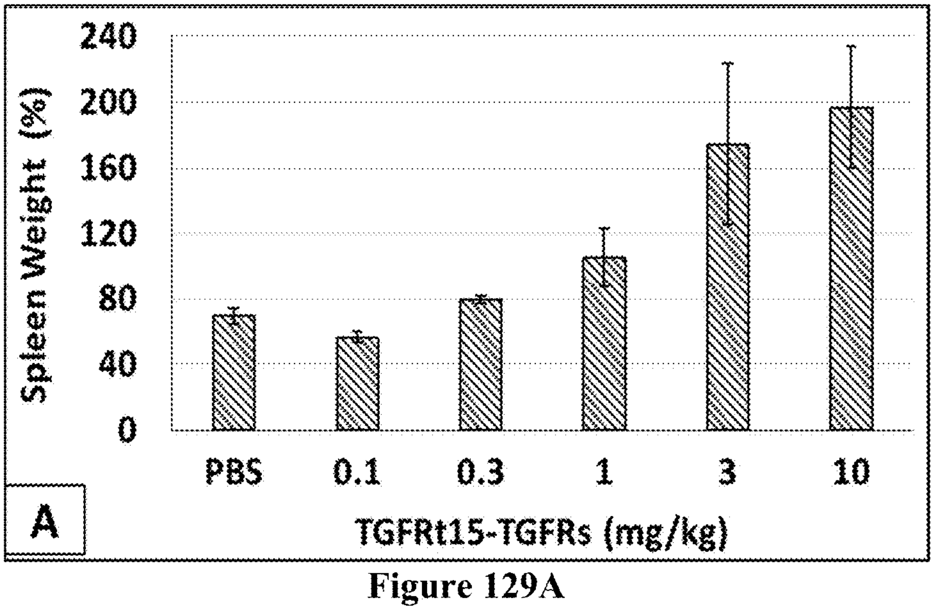
Figure 129B:
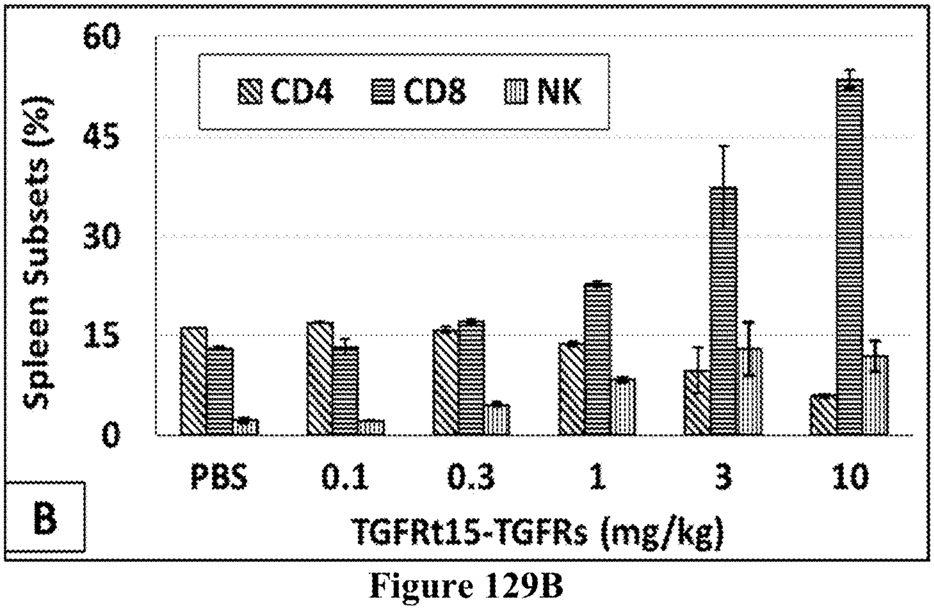
Figure 129C:
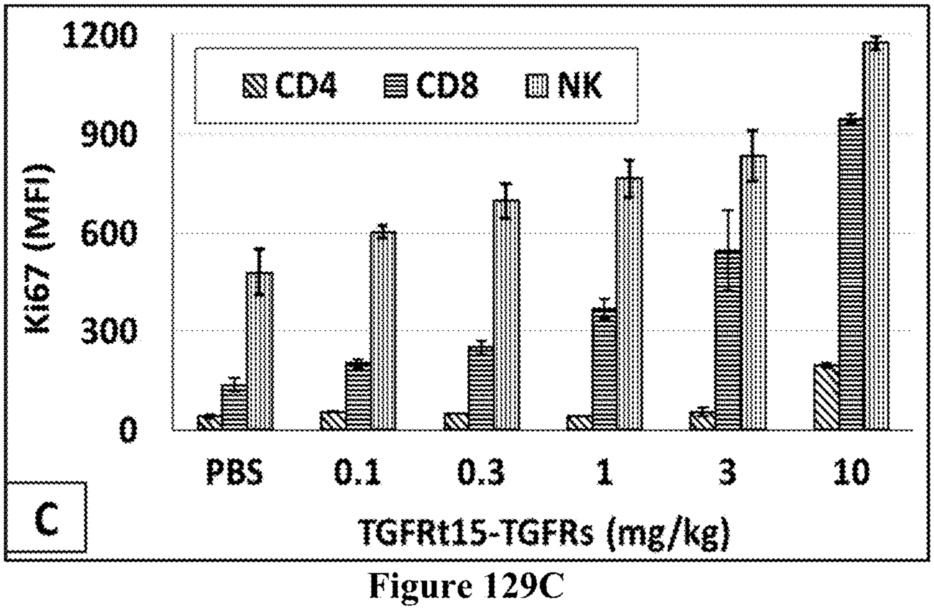

A set of experiments was performed to determine the effect of the TGFRt15-TGFRs construct on immune stimulation in C57BL/6 mice. In these experiments, C57BL/6 mice were subcutaneously treated with control solution (PBS) or TGFRt15-TGFRs at 0.1, 0.3, 1, 3, and 10 mg/kg. The treated mice were euthanized 4 days post-treatment. Spleen weight was measured and splenocyte suspensions were prepared. The splenocyte suspensions were stained with conjugated anti-CD4, anti-CD8, and anti-NK1.1 (NK) antibodies. The cells were additionally stained for proliferation marker Ki67. FIG. 129A shows that spleen weight in mice treated with TGFRt15-TGFRs increased with increasing dosage of TGFRt15-TGFRs. Additionally, spleen weight in mice treated with 1 mg/kg, 3 mg/kg, and 10 mg/kg of TGFRt15-TGFRs was higher as compared to mice treated with just the control solution. The percentages of $CD8^+$ T cells and NK cells both increased with increasing dosage of TGFRt15-TGFRs (FIG. 129B). Finally, TGFRt15-TGFRs significantly upregulated expression of cell proliferation marker Ki67 in both $CD8^+$ T cells and NK cells at all doses of TGFRt15-TGFRs tested (FIG. 129C). These results demonstrate that TGFRt15-TGFRs treatment induced proliferation of both $CD8^+$ T cells and NK cells in C57BL/6 mice.

Figure 130A:
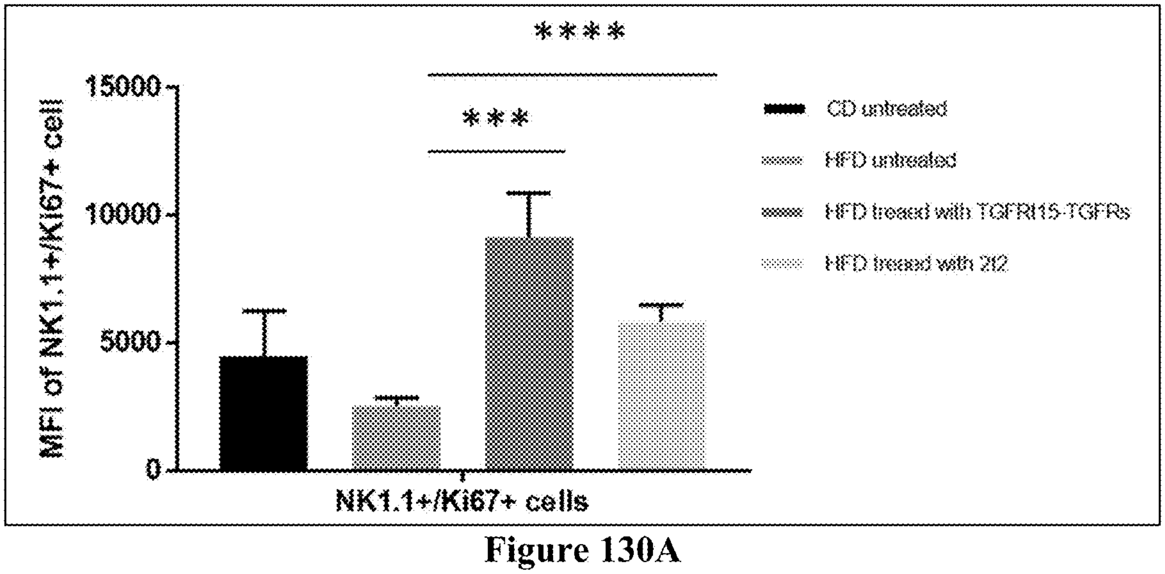
Figure 130B:
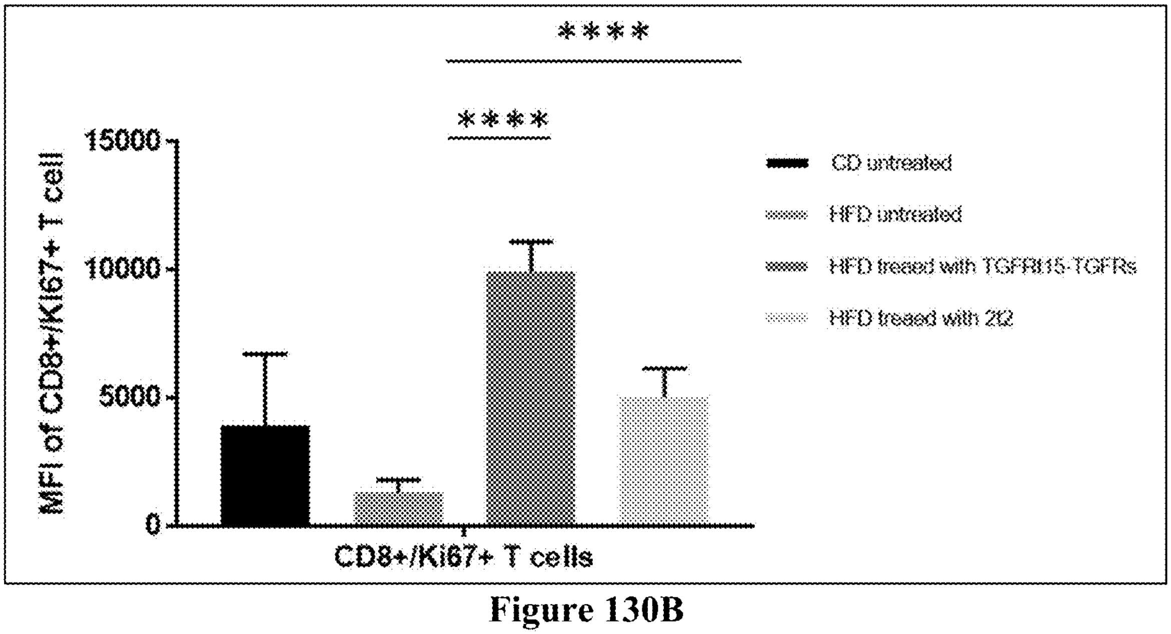

A set of experiments was performed to determine the effect of the TGFRt15-TGFRs construct on immune stimulation in $ApoE^{-/-}$ mice fed with a Western diet. In these experiments, 6-week old female B6.129P2-$ApoE^{tm1Unc}$/J mice (Jackson Laboratory) were fed with a Western diet containing 21% fat, 0.15% cholesterol, 34.1% sucrose, 19.5% casein, and 15% starch (TD88137, Envigo Laboratories). After 8-week of the Western diet, the mice were injected subcutaneously with TGFRt15-TGFRs at 3 mg/kg. Three days post-treatment, the mice were fasted for 16 hours and then blood samples were collected through retro-orbital venous plexus puncture. The blood was mixed with 10 μL 0.5 M EDTA and 20 μL blood was taken for lymphocyte subsets analysis. The red blood cells were lysed with ACK (0.15 M $NH_4Cl$, 1.0 mM $KHCO_3$, 0.1 mM $Na_2EDTA$, pH 7.4) and the lymphocytes were stained with anti-mouse CD8a and anti-mouse NK1.1 antibodies for 30 minutes at 4° C. in FACS staining buffer (1% BSA in PBS). The cells were washed once and resuspended in Fixation Buffer (BioLegend Cat #420801) for 20 minutes at room temperature. The cells were centrifuged at 350×g for 5 minutes, the fixed cells were resuspended in Intracellular Staining Permeabilization Wash Buffer (BioLegend Cat #421002) and then centrifuged at 350×g for 5 minutes. The cells were then stained with anti-Ki67 antibody for 20 minutes at RT. The cells were washed twice with Intracellular Staining Permeabilization Wash Buffer and centrifuged at 350×g for 5 minutes. The cells were then resuspended in FACS staining buffer. Lymphocyte subsets were analyzed with a BD FACS Celesta. As described in FIGS. 130A and 130B, treatment of $ApoE^{-/-}$ mice with TGFRt15-TGFRs induced proliferation (Ki67-positive staining) in NK and $CD8^+$ T cells.

Figure 131A:
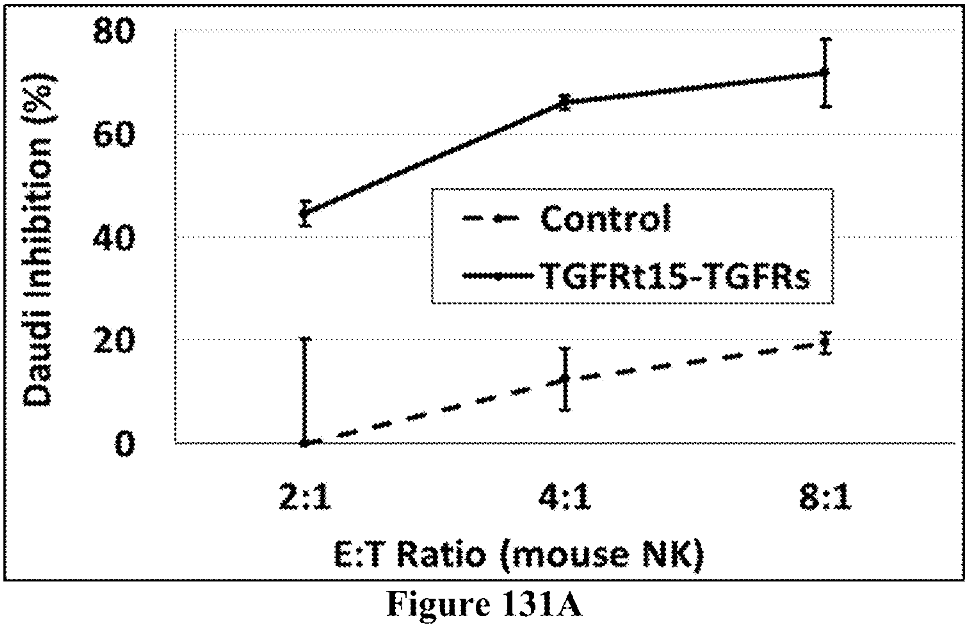
Figure 131B:
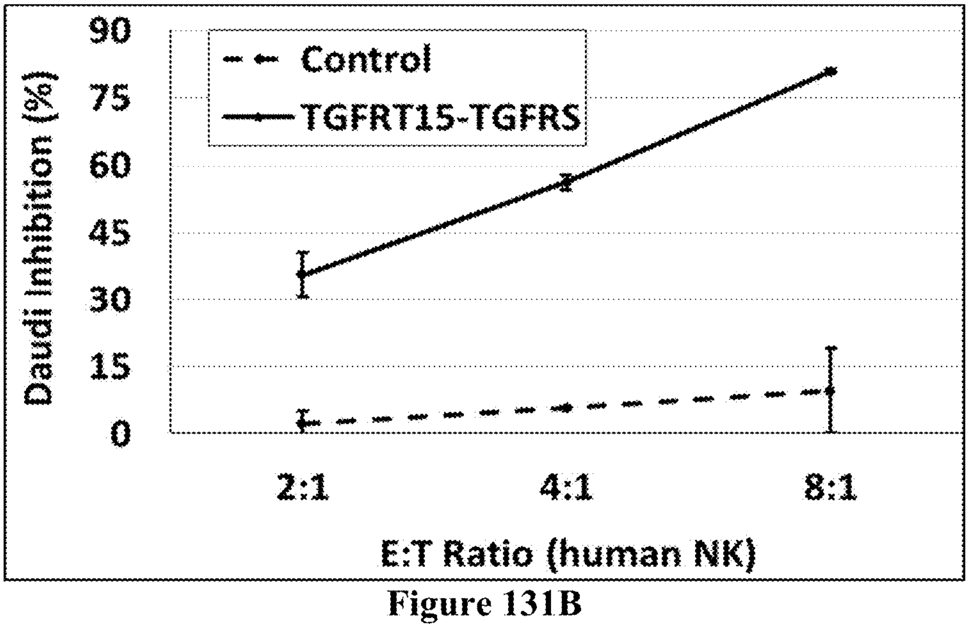

Example 63: NK-Mediated Cytotoxicity Following Treatment with Multi-Chain Construct A set of experiments was performed to determine if treatment of NK cells with TGFRt15-TGFRs enhanced cytotoxicity of NK cells. In these experiments, Human Daudi B lymphoma cells were labeled with CELLTRACE®, violet dye (CTV), and used as tumor target cells. Mouse NK effector cells were isolated with NK1.1-positive selection using a magnetic cell sorting method (Miltenyi Biotec) of C57BL/6 female mouse spleens 4 days post TGFRt15-TGFRs subcutaneous treatment at 3 mg/kg. Human NK effector cells were isolated from peripheral blood mononuclear cells derived from human blood buffy coats with the RosetteSep/human NK cell reagent (Stemcell Technologies). The target cells (Human Daudi B lymphoma cells) were mixed with effector cells (either mouse NK effector cells or human NK effector cells) in the presence of 50 nM TGFRt15-TGFRs or in the absence of TGFRt15-TGFRs (control) and incubated at 37° C. for 44 hours for mouse NK cells and for 20 hours for human NK cells. Target cell (Daudi) viability was assessed by analysis of propidium iodide-positive, CTV-labeled cells using flow cytometry. The percentage of Daudi inhibition was calculated using the formula (1-viable tumor cell number in experimental sample/viable tumor cell number in the sample without NK cells)×100. FIG. 131 shows that mouse (FIG. 131A) and human (FIG. 131B) NK cells had significantly stronger cytotoxicity against Daudi B cells following NK cell activation with TGFRt15-TGFRs than in the absence of TGFRt15-TGFRs activation.

Figure 132A:
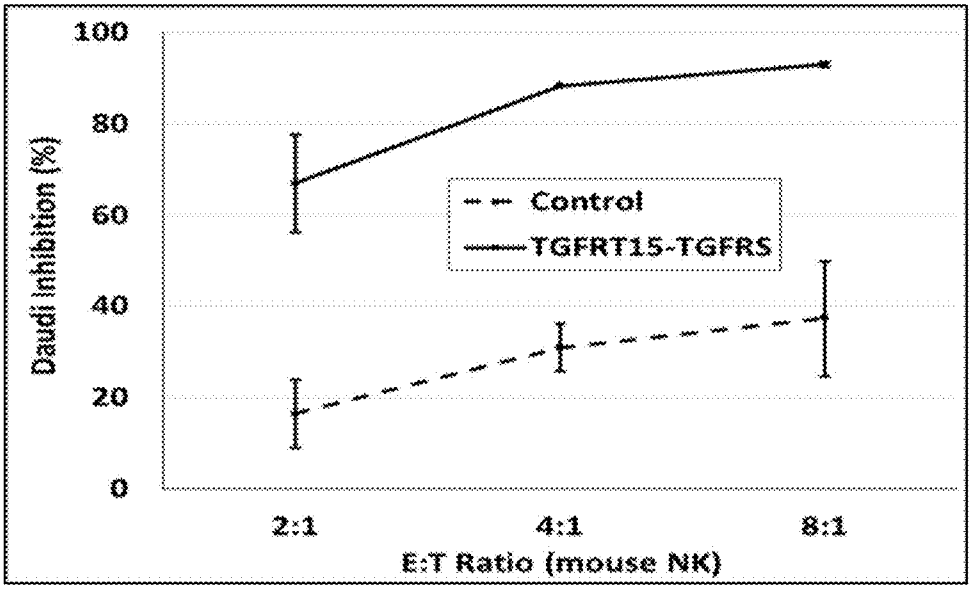
Figure 132B:
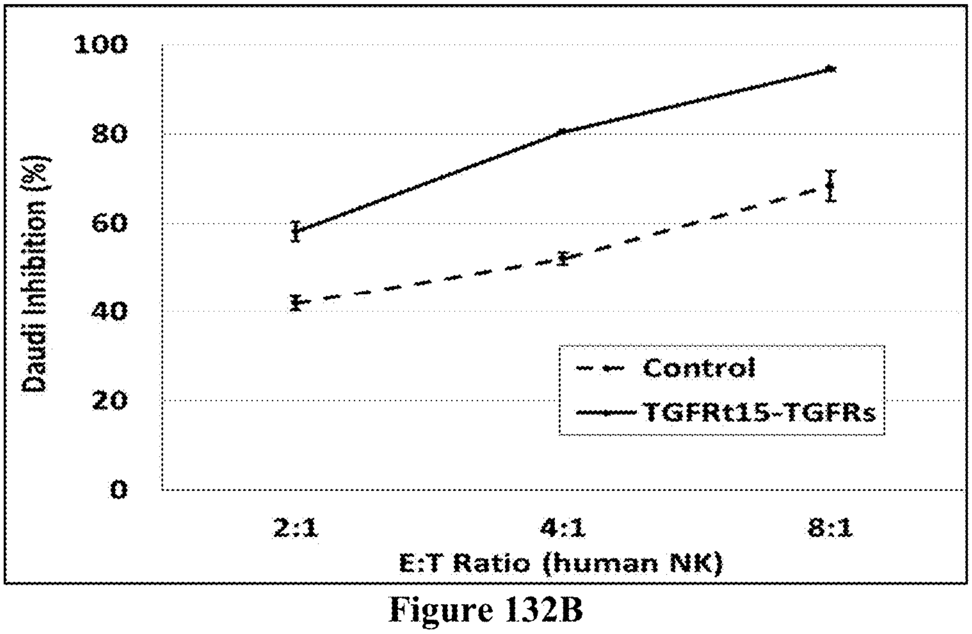

A set of experiments was performed to determine antibody-dependent cellular cytotoxicity (ADCC) of mouse and human NK cells following treatment with TGFRt15-TGFRs. In these experiments, human Daudi B lymphoma cells were labeled with CELLTRACE®, violet dye (CTV), and used as tumor target cells. Mouse NK effector cells were isolated with NK1.1-positive selection using a magnetic cell sorting method (Miltenyi Biotec) of C57BL/6 female mouse spleens 4 days post-TGFRt15-TGFRs subcutaneous treatment at 3 mg/kg. Human NK effector cells were isolated from peripheral blood mononuclear cells derived from human blood buffy coats with the RosetteSep/human NK cell reagent (Stemcell Technologies). The target cells (Daudi B cells) were mixed with effector cells (either mouse NK effector cells or human NK effector cells) in the presence of anti-CD20 antibody (10 nM Rituximab, Genentech) and in the presence of 50 nM TGFRt15-TGFRs, or in the absence of TGFRt15-TGFRs (control) and incubated at 37° C. for 44 hours for mouse NK cells and for 20 hours for human NK cells. The Daudi B cells express the CD20 targets for the anti-CD20 antibody. Target cell viability was assessed after incubation by analysis of propidium iodide-positive, CTV-labeled target cells using flow cytometry. The percentage of Daudi inhibition was calculated using the formula (1-viable tumor cell number in experimental sample/viable tumor cell number in the sample without NK cells)×100. FIG. 132 shows that mouse NK cells (FIG. 132A) and human NK cells (FIG. 132B) had stronger ADCC activity against Daudi B cells following NK cell activation with TGFRt15-TGFRs than in the absence of TGFRt15-TGFRs activation.

Example 64: Treatment of Cancer

Figure 133A:
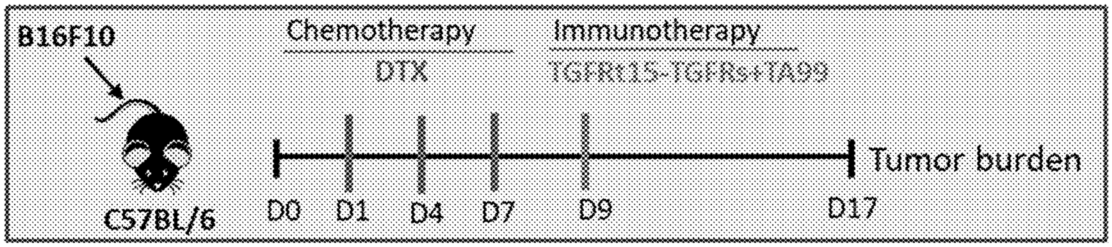
Figure 133B:
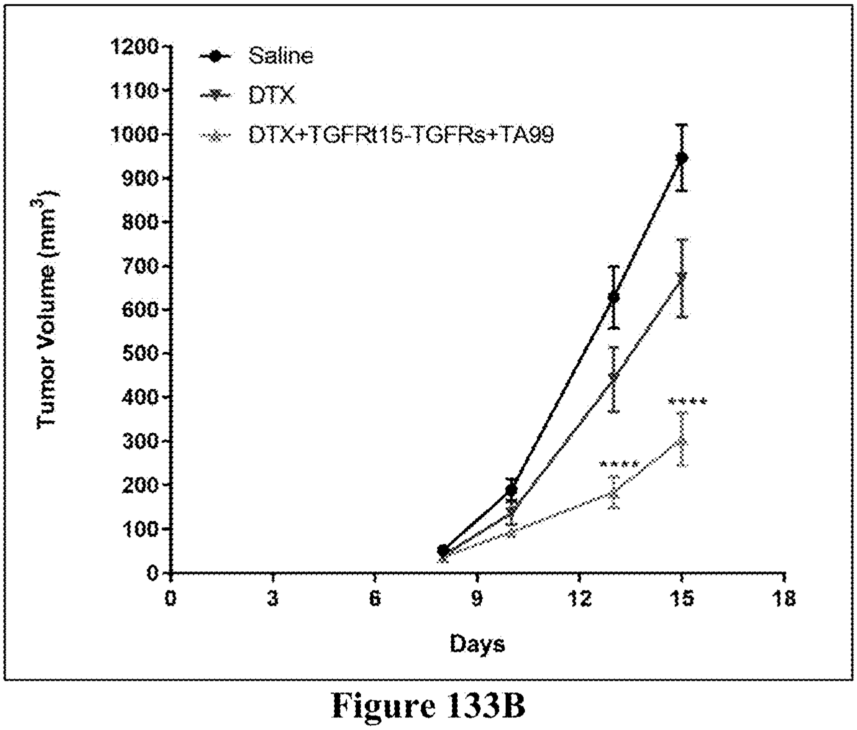

A set of experiments was performed to assess antitumor activity of TGFRt15-TGFRs plus anti-TRP1 antibody (TA99) in combination with chemotherapy in a melanoma mouse model. In these experiments, C57BL/6 mice were subcutaneously injected with $0.5\times10^6$ B16F10 melanoma cells. The mice were treated with three doses of chemotherapy docetaxel (10 mg/kg) (DTX) on day 1, day 4, and day 7, followed by treatment with single dose of combination immunotherapy TGFRt15-TGFRs (3 mg/kg)+anti-TRP1 antibody TA99 (200 μg) on day 9. FIG. 133A shows a schematic of the treatment regimen. Tumor growth was monitored by caliper measurement, and tumor volume was calculated using the formula $V=(L\times W^2)/2$, where L is the largest tumor diameter and W is the perpendicular tumor diameter. FIG. 133B shows that treatment with DTX+TGFRt15-TGFRs+TA99 significantly reduced tumor growth compared to saline control and DTX treatment groups (N=10, ****$p<0.001$, Multiple t test analyses).

Figure 133C:
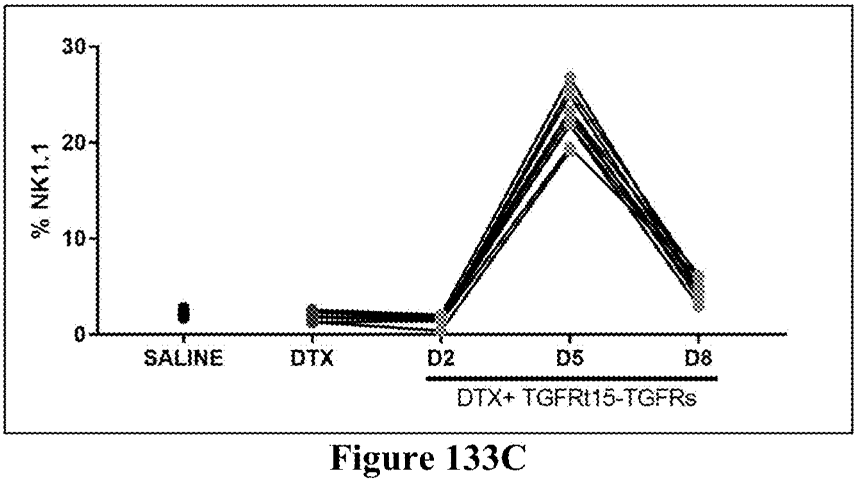
Figure 133D:
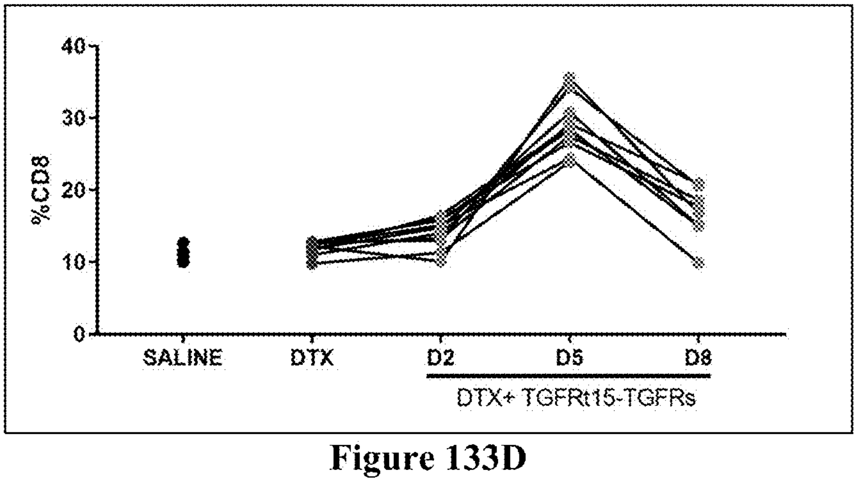
Figure 133E:
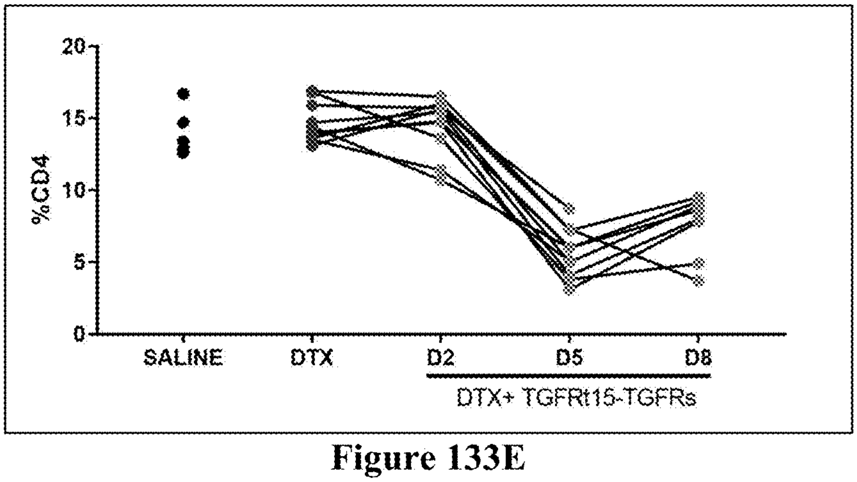

To assess immune cell subsets in the B16F10 tumor model, peripheral blood analysis was performed. In these experiments, C57BL/6 mice were injected with B16F10 cells and treated with DTX, DTX+TGFRt15-TGFRs+TA99, or saline. Blood was drawn from the submandibular vein of B16F10 tumor-bearing mice on days 2, 5, and 8 post-immunotherapy for the DTX+TGFRt15-TGFRs+TA99 group and day 11 post-tumor injection for the DTX and saline groups. RBCs were lysed in ACK lysis buffer and the lymphocytes were washed and stained with anti-NK1.1, anti-CD8, and anti-CD4 antibodies. The cells were analyzed by flow cytometry (Celesta-BD Bioscience). FIGS. 133C-133E show that DTX+TGFRt15-TGFRs+TA99 treatment induced an increase in the percentage of NK cells and $CD8^+$ T cells in the tumors compared to the saline and DTX treatment groups.

Figure 133F:
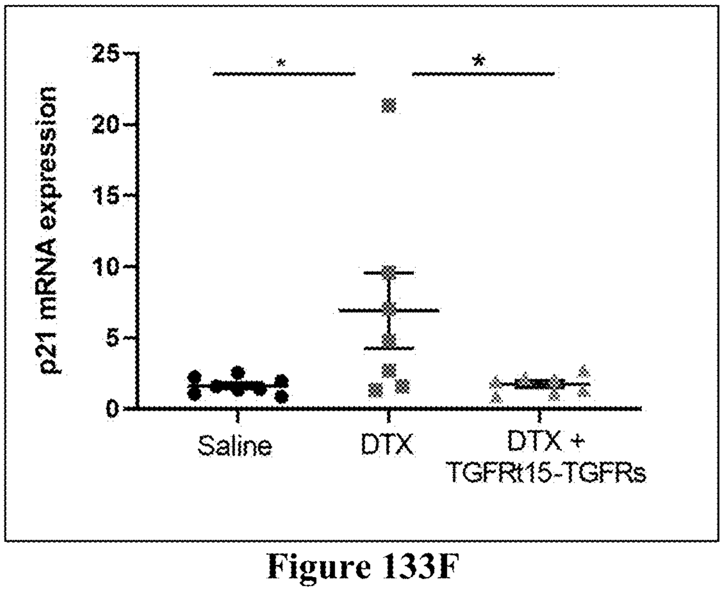
Figure 133G:
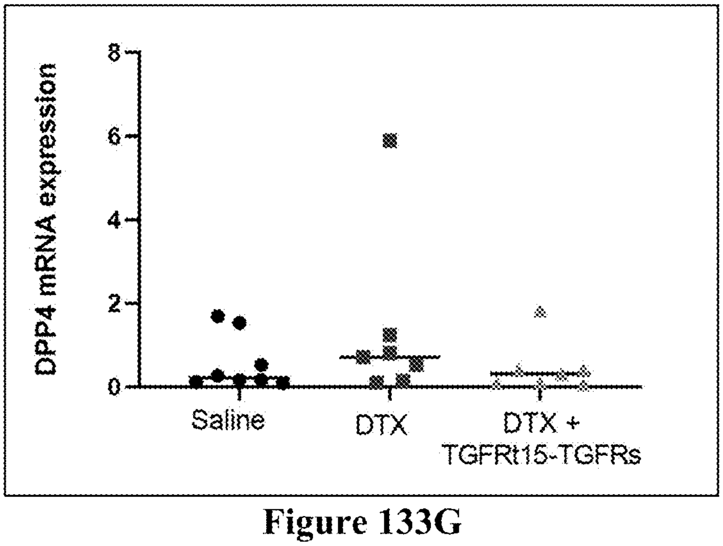
Figure 133H:
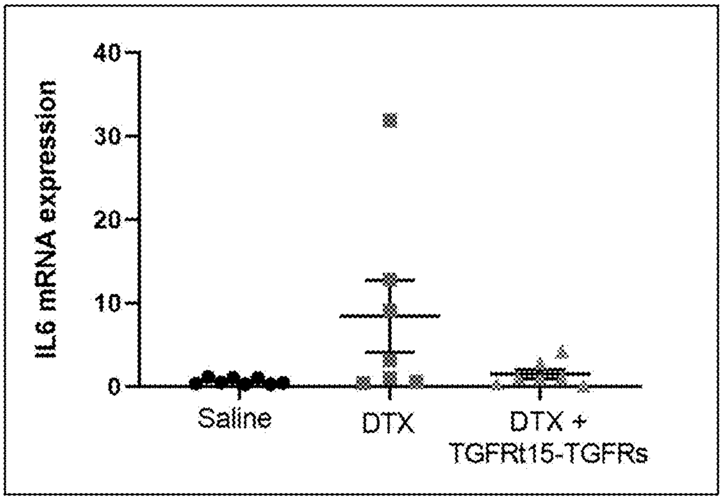

On day 17, total RNA was extracted from tumors of mice treated with saline, DTX or DTX+TGFRt15-TGFRs+TA99 using Trizol. Total RNA (1 μg) was used for cDNA synthesis using the QUANTITECT® Reverse Transcription Kit (Qiagen). Real-time PCR was carried out with CFX96 Detection System (Bio-Rad) using FAM-labeled predesigned primers for senescence cell markers, (F) p21 (G) DPP4 and (H) IL6. The housekeeping gene 18S ribosomal RNA was used as an internal control to normalize the variability in expression levels. The expression of each target mRNA relative to 18S rRNA was calculated based on Ct as $2-\Delta(\Delta Ct)$, in which $\Delta Ct=Cttarget-Ct18S$. The data is presented as fold-change as compared to saline control. FIG. 133F-133H show that DTX treatment induced an increase in senescent tumor cells that were subsequently reduced following treatment with TGFRt15-TGFRs+TA99 immunotherapy.

A set of experiments was performed to investigate amelioration of Western diet-induced hyperglycemia in $ApoE^{-/-}$ mice by TGFRt15-TGFRs. In these experiments, 6-week old female B6.129P2-$ApoE^{tm1Unc}$/J mice (Jackson Laboratory) were fed with a Western diet containing 21% fat, 0.15% cholesterol, 34.1% sucrose, 19.5% casein, and 15% starch (TD88137, Envigo Laboratories). After 8-weeks of the Western diet, the mice were injected subcutaneously with TGFRt15-TGFRs at 3 mg/kg. Three days post-treatment, the mice were fasted for 16 hours and then blood samples were collected through retro-orbital venous plexus puncture. Blood glucose was detected with a glucose meter (OneTouch UltraMini) and GenUltimated test strips using a drop of fresh blood. As shown in FIG. 134A, TGFRt15-TGFRs treatment reduced hyperglycemia induced by the Western diet. The plasma insulin and resistin levels were analyzed with Mouse Rat Metabolic Array by Eve Technologies. HOMA-IR was calculated using the following formula: homeostatic model assessment-insulin resistance=Glucose (mg/dL)*Insulin (mU/mL)/405. As shown in FIG. 134B, TGFRt15-TGFRs treatment reduced insulin resistance compared to the untreated group. TGFRt15-TGFRs ($p<0.05$) reduced resistin levels significantly compared to the untreated group as shown in FIG. 142C, which may relate to the reduced insulin resistance induced by TGFRt15-TGFRs (FIG. 134B).

Example 65: Induction of Differentiation of NK Cells into Cytokine-Induced Memory Like NK Cells A set of experiments was performed to assess the differentiation of NK cells into cytokine-induced memory like NK Cells (CIMK-NK Cells) after stimulation with 18t15-12s. In these experiments, fresh human leukocytes were obtained from the blood bank and $CD56^+$ NK cells were isolated with the RosetteSep/human NK cell reagent (StemCell Technologies). The purity of NK cells was >90% and confirmed by staining with CD56-BV421, CD16-BV510, CD25-PE, and CD69-APCFire750 antibodies (BioLegend). The cells were counted and resuspended in $2\times10^6$/mL in a 24-well flat-bottom plate in 2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were unstimulated ("No Spike") or stimulated with 18t15-12s (100 nM) or a mixture of single cytokines including rhIL15 (50 ng/mL) (Miltenyi), rhIL18 (50 ng/mL) (Invivogen), and rhIL-12 (10 ng/mL) (Peprotech) ("single cytokines") at 37° C. and 5% $CO_2$ for 16 hrs. The next day, the cells were harvested, and washed two times with warm complete media at 1000 RPM for 10 minutes at room temperature. The cells were resuspended at $2\times10^6$/mL in a 24-well flat-bottom plate in 2 mL of complete media with rhIL15 (1 ng/mL). After every 2 days, half of the medium was replaced with fresh complete media containing rhIL15.

To assess the change in memory phenotype of NK cells at day 7, the cells were stained with antibodies to cell-surface CD56, CD16, CD27, CD62L, NKp30, and NKp44 (BioLegend). After surface staining, the cells were washed (1500 RPM for 5 minutes at room temperature) in FACS buffer (1×PBS (Hyclone) with 0.5% BSA (EMD Millipore) and 0.001% sodium azide (Sigma)). After two washes, the cells were analyzed by flow cytometry (Celesta-BD Bioscience). FIG. 135 shows that incubation of NK cells with 18t15-12s resulted in an increase in the percentage of $CD16^+CD56^+$ NK cells expressing CD27, CD62L, and NKp44, and an increase in the levels (MFI) of NKp30 in $CD16^+CD56^+$ NK cells.

Example 66: Upregulation of CD44 Memory T Cells

A set of experiments was performed to assess upregulation of CD44 memory T cells upon treatment with TGFRt15-TGFRs. In these experiments, C57BL/6 mice were subcutaneously treated with TGFRt15-TGFRs. The treated mice were euthanized and the single splenocyte suspensions were prepared 4 days (TGFRt15-TGFRs) following the treatment. The prepared splenocytes were stained with fluorochrome-conjugated anti-CD4, anti-CD8 and anti-CD44 antibodies and the percentages of $CD44^{high}$ T cells in $CD4^+$ T cells or $CD8^+$ T cells were analyzed by flow cytometry. The results show that TGFRt15-TGFRs upregulated expression of the memory marker CD44 on $CD4^+$ and $CD8^+$ T cells (FIG. 136). These findings indicate that TGFRt15-TGFRs was able to induce mouse T cells to differentiate into memory T cells.

Example 67: Tissue Factor Coagulation Assays Following Treatment with Single-Chain or Multi-Chain Chimeric Polypeptides A set of experiments was performed to assess blood coagulation following treatment with single-chain or multi-chain chimeric polypeptides. To initiate the blood coagulation cascade pathway, tissue factor (TF) binds to Factor VIIa (FVIIa) to form a TF/FVIIa complex. The TF/FVIIa complex then binds Factor X (FX) and converts FX to FXa.

Factor VIIa (FVIIa) Activity Assay

One assay to measure blood coagulation involves measuring Factor VIIa (FVIIa) activity. This type of assay requires the presence of tissue factor and calcium. The TF/FVIIa complex activity can be measured by a small substrate or by a natural protein substrate, for example, Factor X (FX). When FX is used as a substrate, phospholipids are also required for TF/FVIIa activity. In this assay, FVIIa activity is determined with FVIIa-specific chromogenic substrate S-2288 (Diapharma, West Chester, OH). The color change of the S-2288 substrate can be measured spectrophotometrically and is proportional to the proteolytic activity of FVIIa (e.g., the TF/FVIIa complex).

In these experiments, the FVIIa activity of the following groups were compared: the 219-amino acid extracellular domain of tissue factor domain ($TF_{219}$), a multi-chain chimeric polypeptide with a wild-type tissue factor domain, and a multi-chain chimeric polypeptide with a mutant tissue factor domain. The chimeric polypeptides containing mutant tissue factor molecules were constructed with mutations to the TF domain at amino acid sites: Lys20, Ile22, Asp58, Arg135, and Phe140.

In order to assess activity of FVIIa, FVIIa, and $TF_{219}$ or a $TF_{219}$-containing multi-chain chimeric polypeptide were mixed at an equal molar concentration (10 nM) in all wells of a 96-well ELISA plate in a total volume of 70 μL. After incubation for 10 minutes at 37° C., 10 μL of 8 mM S-2288 substrate was added to start the reaction. The incubation was then kept at 37° C. for 20 minutes. Finally, color change was monitored by reading absorbance at 405 nm. The OD values of different TF/VIIa complexes are shown in Table 1 and Table 2. Table 1 shows a comparison of $TF_{219}$, 21t15-21s wild-type (WT) and 21t15-21s mutant (Mut). Table 2 shows a comparison of $TF_{219}$, 21t15-TGFRs wild-type (WT), and 21t15-TGFRs mutant (Mut). These data show that $TF_{219}$-containing multi-chain chimeric polypeptides (e.g., 21t15-21s-WT, 21t15-21s-Mut, 21t15-TGFRS-WT, and 21t15-TGFRS-Mut) have lower FVIIa activity than $TF_{219}$ when the chromogenic S-2288 was used as a substrate. Notably, the multi-chain chimeric polypeptides containing $TF_{219}$ mutations showed much lower FVIIa activity when compared to multi-chain chimeric polypeptides containing wild type $TF_{219}$.

TABLE 1

| FVIIa activity | |
|---|---|
| Molecule | OD value at 405 nm |
| $TF_{219}$ | 0.307 |
| 21t15/21S-WT | 0.136 |
| 21t15/21S-Mut | 0.095 |

WT: wild type of $TF_{219}$,
Mut: $TF_{219}$ containing mutations.

TABLE 2

| FVIIa activity | |
|---|---|
| Molecule | OD value at 405 nm |
| $TF_{219}$ | 0.345 |
| 21t15/TGFRS-WT | 0.227 |
| 21t15/TGFRS-Mut | 0.100 |

WT: wild type of $TF_{219}$,
Mut: $TF_{219}$ containing mutations.

Factor X (FX) Activation Assay

An additional assay to measure blood coagulation involves measuring activation of Factor X (FX). Briefly, TF/VIIa activates blood coagulation Factor X (FX) to Factor Xa (FXa) in the presence of calcium and phospholipids. $TF_{243}$, which contains the transmembrane domain of TF, has much higher activity in activating FX to FXa than $TF_{219}$, which does not contain the transmembrane domain. TF/VIIa dependent activation of FX is determined by measuring FXa activity using an FXa-specific chromogenic substrate S-2765 (Diapharma, West Chester, OH). The color change of S-2765 can be monitored spectrophotometrically and is proportional to the proteolytic activity of FXa.

In these experiments, FX activation with a multi-chain chimeric polypeptide (18t15-12s, mouse (m)21t15, 21t15-TGFRs, and 21t15-7s) was compared with a positive control (Innovin) or $TF_{219}$. $TF_{219}$ (or $TF_{219}$-containing multi-chain chimeric polypeptides)/FVIIa complexes were mixed at an equal molar concentration (0.1 nM each) in a volume of 50 μL in round bottom wells of a 96-well ELISA plate, after which 10 μL of 180 nM FX was added. After 15 minutes of incubation at 37° C., during which time FX was converted to FXa, 8 μL of 0.5 M EDTA (which chelates calcium and thus terminates FX activation by TF/VIIa) was added to each well to stop FX activation. Next, 10 μL of 3.2 mM S-2765 substrate was added to the reaction mixture. Immediately, the plate absorbance was measured at 405 nm and was recorded as the absorbance at time 0. The plate was then incubated for 10-20 minutes at 37° C. The color change was monitored by reading absorbance at 405 nm following the incubation. Results of FX activation as measured by FXa activity using chromogenic substrate S-2765 are shown in FIG. 137. In this experiment, Innovin, which is a commercial prothrombin reagent containing lipidated recombinant human $TF_{243}$, was used as a positive control for FX activation. Innovin was reconstituted with purified water to about 10 nM of $TF_{243}$. Next, 0.1 nM TF/VIIa complex was made by mixing an equal volume of 0.2 nM of FVIIa with 0.2 nM of Innovin. Innovin demonstrated very potent FX activation activity, while $TF_{219}$ and $TF_{219}$-containing multi-chain chimeric polypeptides had very low FX activation activity, confirming that $TF_{219}$ is not active in a TF/FVIIa complex for activating natural substrate FX in vivo.

Prothrombin Time Test

A third assay to measure blood coagulation is the prothrombin time (PT) test, which measures blood clotting activity. Here, the PT test was performed using commercially available normal human plasma (Ci-Trol Coagulation Control, Level I). For a standard PT test, clot reactions were initiated by addition of Innovin, a lipidated recombinant human $TF_{243}$, in the presence of calcium. Clotting time was monitored and reported by STart PT analyzer (Diagnostica Stago, Parsippany, N.J.). PT assays were started by injecting 0.2 mL of various dilutions of Innovin diluted in PT assay buffer (50 mM Tris-HCl, pH 7.5, 14.6 mM $CaCl_2$), 0.1% BSA) into cuvettes containing 0.1 mL of normal human plasma prewarmed at 37° C. In the PT assay, shorter PT time (clotting time) indicates a higher TF-dependent clotting activity while longer PT (clotting time) means lower TF-dependent clotting activity.

As seen in FIG. 138, addition of different amounts of Innovin (e.g., Innovin reconstituted with purified water equivalent to 10 nM of lipidated recombinant human $TF_{243}$ was considered to be 100% Innovin) to the PT assay demonstrated a dose-response relationship, where lower concentrations of $TF_{243}$ resulted in a longer PT time (lower clotting activity). For example, 0.001% Innovin had a PT time greater than 110 seconds, which was almost the same as buffer alone.

In another experiment, the PT test was conducted on $TF_{219}$ and multi-chain chimeric polypeptides including: 18t15-12s, 7t15-21s, 21t15-TGFRs-WT, and 21t15-TGFRs-Mut. FIG. 139 show that $TF_{219}$ and $TF_{219}$-containing multi-chain chimeric polypeptides (at a concentration of 100 nM) had prolonged PT times indicating extremely low or no clotting activity.

Studies were also conducted to evaluate whether incubating the multi-chain chimeric polypeptides in the presence of other cells carrying receptors for the cytokine components of the multi-chain chimeric polypeptide (32Dβ or human PBMCs) would affect the clotting time in the PT assay. To examine whether cells that express IL-15 receptor (32Dβ cells) or IL-15 and IL-21 receptors (PBMCs) would bind IL-15-containing multi-chain chimeric polypeptides to mimic natural TF as a cellular FVIIa receptor, $TF_{219}$-containing multi-chain chimeric polypeptides (at a concentration of 100 nM for each molecule) were diluted in the PT assay buffer and preincubated with 32Dβ cells (at $2\times10^5$ cells/mL) or PBMC (at $1\times10^5$ cells/mL) for 20-30 minutes at room temperature. The PT assay was then conducted as described above. FIGS. 140 and 141 shows that $TF_{219}$ and $TF_{219}$-containing multi-chain chimeric polypeptides mixed with 32Dβ cells (FIG. 140) or PBMC (FIG. 141) at a final concentration of 100 nM had prolonged PT times similar to 0.001-0.01% Innovin (equivalent to 0.1 pM to 1.0 pM of $TF_{243}$). Expressed in percentage of relative $TF_{243}$ activity, $TF_{219}$-containing multi-chain chimeric polypeptides had 100,000 to 1,000,000 times lower TF dependent clotting activity when compared to Innovin. This demonstrated that $TF_{219}$-containing multi-chain chimeric polypeptides had extremely low or no TF-dependent clotting activity, even while the molecules were bound to an intact cell membrane surface, such as 32Dβ or PBMCs.

Example 68: Characterization of 7t15-21s137L (Long Version)

The nucleic acid sequence of the 7t15 construct (including signal peptide sequence) is as follows (SEQ ID NO: 107):

```
(Signal peptide)
ATGAAGTGGGTGACCTTCATCAGCCTGCTGTTCCTGTTCTCCAGCGCCT

ACTCC

(Human IL7)
GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

GAAGAGGCTGCTGCAGGAGATCAAGACCTGCTGGAACAAGATCCTGATG

GGCACCAAGGAGCAT

(Human Tissue Factor 219)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG

(Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA
```

-continued

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC

The amino acid sequence of 7t15 fusion protein (including the leader sequence) is as follows (SEQ ID NO: 106):

(Signal peptide)
MKWVTFISLLFLFSSAYS (Human IL7)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEH (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS

The nucleic acid sequence of the 21s137L construct (including signal peptide sequence) is as follows (SEQ ID NO: 225):

(Signal peptide)
ATGAAGTGGGTGACCTTCATCAGCCTGCTGTTCCTGTTCTCCAGCGCCT

ACTCC (Human IL-21)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC (Human IL-15R α sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG ((G4S)3 linker)
GGCGGTGGAGGATCCGGAGGAGGTGGCTCCGGCGGCGGAGGATCT -continued (Human CD137L)
CGCGAGGGTCCCGAGCTTTCGCCCGACGATCCCGCCGGCCTCTTGGACC

TGCGGCAGGGCATGTTTGCGCAGCTGGTGGCCCAAAATGTTCTGCTGAT

CGATGGGCCCCTGAGCTGGTACAGTGACCCAGGCCTGGCAGGCGTGTCC

CTGACGGGGGGCCTGAGCTACAAAGAGGACACGAAGGAGCTGGTGGTGG

CCAAGGCTGGAGTCTACTATGTCTTCTTTCAACTAGAGCTGCGGCGCGT

GGTGGCCGGCGAGGGCTCAGGCTCCGTTTCACTTGCGCTGCACCTGCAG

CCACTGCGCTCTGCTGCTGGGGCCGCCGCCCTGGCTTTGACCGTGGACC

TGCCACCCGCCTCCTCCGAGGCTCGGAACTCGGCCTTCGGTTTCCAGGG

CCGCTTGCTGCACCTGAGTGCCGGCCAGCGCCTGGGCGTCCATCTTCAC

ACTGAGGCCAGGGCACGCCATGCCTGGCAGCTTACCCAGGGCGCCACAG

TCTTGGGACTCTTCCGGGTGACCCCCGAAATCCCAGCCGGACTCCCTTC

ACCGAGGTCGGAA

The amino acid sequence of 21s137L fusion protein (including the leader sequence) is as follows (SEQ ID NO: 226):

(Signal peptide)
MKWVTFISLLFLFSSAYS (Human IL-21)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS (Human IL-15R α sushi domain)
ITCPPPMSVEHADIWVKSYSLYSRERYICNSGFKRKAGTSSLTECVLNK

ATNVAHWTTPSLKCIR ((G4S)3 linker)
GGGGSGGGGSGGGGS (Human CD137L)
REGPELSPDDPAGLLDLRQGMFAQLVAQNVLLIDGPLSWYSDPGLAGVS

LTGGLSYKEDTKELVVAKAGVYYVFFQLELRRVVAGEGSGSVSLALHLQ

PLRSAAGAAALALTVDLPPASSEARNSAFGFQGRLLHLSAGQRLGVHLH

TEARARHAWQLTQGATVLGLFRVTPEIPAGLPSPRSE

The following experiment was conducted to evaluate whether the CD137L portion in 7t15-21s137L was intact to bind to CD137 (4.1BB). On day 1, a 96-well plate was coated with 100 μL (2.5 μg/mL) of GAH IgG Fc (G-102-C, R&D Systems) in R5 (coating buffer), overnight. On day 2, the plates were washed three times and blocked with 300 μL of 1% BSA in PBS at 37° C. for 2 hrs. 10 ng/ml of 4.1BB/Fc (838-4B, R&D Systems) was added at 100 μl/well for 2 hrs at room temperature. Following three washes, 7t15-21s137L (long version) or 7t15-21s137Ls (short version) was added starting at 10 nM, or recombinant human 4.1BBL starting at 180 ng/mL, with 1/3 dilution, followed by incubation at 4° C. overnight. On day 3, the plates were washed three times, and 500 ng/mL of biotinylate-goat anti-human 4.1BBL (BAF2295, R&D Systems) was applied at 100 μL per well, followed by incubation at RT for 2 hrs. The plates were washed three times, and incubated with 0.25 μg/mL of HRP-SA (Jackson ImmuneResearch) at 100 μL per well for 30 min. The plates were then washed three times, and incubated with 100 μL of ABTS for 2 mins at RT. The results were read at 405 nm. As shown in FIG. 142, both 7t15-

21s137L (long version) and 7t15-21s137L (short version) could interact with 4.1BB/Fc (dark diamond and gray square) compared to the recombinant human 4.1BB ligand (rhCD137L, light gray star). 7t15-21s137L (long version) (dark diamond) interacted better with 4.1BB/Fc as compared to 7t15-21s137L (short version) (gray square).

The following experiments were conducted to evaluate whether the components IL7, IL21, IL15, and 4.1BBL in 7t15-21s137L (long version) were intact to be detected by the individual antibody using ELISA. A 96-well plate was coated with 100 μL (4 μg/mL) of anti-TF (human IgG1) in R5 (coating buffer) and incubated at RT for 2 hrs. The plates were washed three times, and blocked with 100 μL of 1% BSA in PBS. Purified 7t15-21s137L (long version) was added starting at 10 nM, and at 1/3 dilution, followed by incubation at RT for 60 min. The plates were washed three times, and 500 ng/mL of biotinylate-anti-IL7 (506602, R&D Systems), 500 ng/mL of biotinylate-anti-IL21 (13-7218-81, R&D Systems), 50 ng/mL of biotinylate-anti-IL15 (BAM247, R&D Systems), or 500 ng/ml of biotinylate-goat anti-human 4.1BBL (BAF2295, R&D Systems) was added per well and incubated at room temperature for 60 min. The plates were washed three times and incubated with 0.25 μg/mL of HRP-SA (Jackson ImmunoResearch) at 100 μL per well for 30 min at RT. The plates were washed four times, and incubated with 100 μL of ABTS for 2 mins at room temperature. The absorbance results were read at 405 nm. As shown in FIG. 143A-143D, the components including IL7, IL21, IL15, and 4.1BBL in 7t15-21s137L (long version) were detected by the individual antibodies.

The following experiment was conducted to evaluate the activity of IL15 in 7t15-21s137L (long version) and 7t15-21s137L (short version). The ability of 7t15-21s137L (long version) and 7t15-21s137L (short version) to promote proliferation of IL2Rαβγ-expressing CTLL2 cells was compared with that of recombinant IL15. IL15 dependent CTLL2 cells were washed five times with IMDM-10% FBS and seeded to the wells at $2\times10^4$ cells/well. Serially diluted 7t15-21s137L (long version), 7t15-21s137L (short version), or IL15 were added to the cells. Cells were incubated in a $CO_2$ incubator at 37° C. for 3 days. Cell proliferation was detected by adding 20 μL of PrestoBlue (A13261, ThermoFisher) to each well on day 3 and incubated for an additional 4 hours in a $CO_2$ incubator at 37° C. Raw absorbance at 570-610 nm was read in a micro-titer plate reader. As shown in FIG. 144, 7t15-21s137L (long version), 7t15-21s137L (short version), and IL15 all promoted CTLL2 cell proliferation. The $EC_{50}$ of 7t15-21s137L (long version), 7t15-21s137L (short version), and IL15 is 51.19 pM, 55.75 pM, and 4.947 pM, respectively.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Exemplary Embodiments

Embodiment A1. A multi-chain chimeric polypeptide comprising:

(a) a first chimeric polypeptide comprising:
 (i) a first target-binding domain;
 (ii) a soluble tissue factor domain; and
 (iii) a first domain of a pair of affinity domains;
(b) a second chimeric polypeptide comprising:
 (i) a second domain of a pair of affinity domains; and
 (ii) a second target-binding domain, wherein the first chimeric polypeptide and the second chimeric polypeptide associate through the binding of the first domain and the second domain of the pair of affinity domains.

Embodiment A2. The multi-chain chimeric polypeptide of embodiment A1, wherein the first target-binding domain and the soluble tissue factor domain directly abut each other in the first chimeric polypeptide.

Embodiment A3. The multi-chain chimeric polypeptide of embodiment A1, wherein the first chimeric polypeptide further comprises a linker sequence between the first target-binding domain and the soluble tissue factor domain in the first chimeric polypeptide.

Embodiment A4. The multi-chain chimeric polypeptide of any one of embodiments A1-A3, wherein the soluble tissue factor domain and the first domain of the pair of affinity domains directly abut each other in the first chimeric polypeptide.

Embodiment A5. The multi-chain chimeric polypeptide of any one of embodiments A1-A3, wherein the first chimeric polypeptide further comprises a linker sequence between the soluble tissue factor domain and the first domain of the pair of affinity domains in the first chimeric polypeptide.

Embodiment A6. The multi-chain chimeric polypeptide of any one of embodiments A1-A5, wherein the second domain of the pair of affinity domains and the second target-binding domain directly abut each other in the second chimeric polypeptide.

Embodiment A7. The multi-chain chimeric polypeptide of any one of embodiments A1-A5, wherein second chimeric polypeptide further comprises a linker sequence between the second domain of the pair of affinity domains and the second target-binding domain in the second chimeric polypeptide.

Embodiment A8. The multi-chain chimeric polypeptide of any one of embodiments A1-A7, wherein the first target-binding domain and the second target-binding domain bind specifically to the same antigen.

Embodiment A9. The multi-chain chimeric polypeptide of embodiment A8, wherein the first target-binding domain and the second target-binding domain bind specifically to the same epitope.

Embodiment A10. The multi-chain chimeric polypeptide of embodiment A9, wherein the first target-binding domain and the second target-binding domain comprise the same amino acid sequence.

Embodiment A11. The multi-chain chimeric polypeptide of any one of embodiments A1-A7, wherein the first target-binding domain and the second target-binding domain bind specifically to different antigens.

Embodiment A12. The multi-chain chimeric polypeptide of any one of embodiments A1-A11, wherein one or both of the first target-binding domain and the second target-binding domain is an antigen-binding domain.

Embodiment A13. The multi-chain chimeric polypeptide of embodiment A12, wherein the first target-binding domain and the second target-binding domain are each antigen-binding domains.

Embodiment A14. The multi-chain chimeric polypeptide of embodiment A12 or A13, wherein antigen-binding domain comprises a scFv or a single domain antibody.

Embodiment A15. The multi-chain chimeric polypeptide of any one of embodiments A1-A14, wherein one or both of the first target-binding domain and the second target-binding domain bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKP30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment A16. The multi-chain chimeric polypeptide of any one of embodiments A1-A14, wherein one or both of the first target-binding domain and the second target-binding domain is a soluble interleukin or cytokine protein.

Embodiment A17. The multi-chain chimeric polypeptide of embodiment A16, wherein the soluble interleukin, cytokine, or ligand protein is selected from the group consisting of: IL-1, IL-2, IL-3, IL-7, IL-8, IL-10, IL-12, IL-15, IL-17, IL-18, IL-21, PDGF-DD, SCF, and FLT3L.

Embodiment A18. The multi-chain chimeric polypeptide of any one of embodiments A1-A14, wherein one or both of the first target-binding domain and the second target-binding domain is a soluble interleukin or cytokine receptor.

Embodiment A19. The multi-chain chimeric polypeptide of embodiment A18, wherein the soluble receptor is a soluble TGF-β receptor II (TGF-β RII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, or a soluble CD28.

Embodiment A20. The multi-chain chimeric polypeptide of any one of embodiments A1-A19, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment A21. The multi-chain chimeric polypeptide of embodiment A20, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment A22. The multi-chain chimeric polypeptide of any one of embodiments A1-A19, wherein the first chimeric polypeptide further comprises one or more additional target-binding domains at the N-terminal and/or C-terminal end of the first chimeric polypeptide.

Embodiment A23. The multi-chain chimeric polypeptide of embodiment A22, wherein at least one of the one or more additional target-binding domains directly abuts the first domain of the pair of affinity domains in the first chimeric polypeptide.

Embodiment A24. The multi-chain chimeric polypeptide of embodiment A22, wherein the first chimeric polypeptide further comprises a linker sequence between the at least one of the one or more additional target-binding domains and the first domain of the pair of affinity domains.

Embodiment A25. The multi-chain chimeric polypeptide of embodiment A22, wherein the at least one of the one or more additional target-binding domains directly abuts the first target-binding domain in the first chimeric polypeptide.

Embodiment A26. The multi-chain chimeric polypeptide of embodiment A22, wherein the first chimeric polypeptide further comprises a linker sequence between the at least one of the one or more additional target-binding domains and the first target-binding domain.

Embodiment A27. The multi-chain chimeric polypeptide of embodiment A22, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment A28. The multi-chain chimeric polypeptide of embodiment A27, wherein the at least one additional target-binding domain of the one or more additional target-binding domains disposed at the N-terminus directly abuts the first target-binding domain or the first domain of the pair of affinity domains in the first chimeric polypeptide.

Embodiment A29. The multi-chain chimeric polypeptide of embodiment A27, wherein the first chimeric polypeptide further comprises a linker sequence disposed between the at least one additional target-binding domain and the first target-binding domain or the first domain of the pair of affinity domains in the first chimeric polypeptide.

Embodiment A30. The multi-chain chimeric polypeptide of embodiment A27, wherein the at least one additional target-binding domain of the one or more additional target-binding domains disposed at the C-terminus directly abuts the first target-binding domain or the first domain of the pair of affinity domains in the first chimeric polypeptide.

Embodiment A31. The multi-chain chimeric polypeptide of embodiment A27, wherein the first chimeric polypeptide further comprises a linker sequence disposed between the at least one additional target-binding domain and the first target-binding domain or the first domain of the pair of affinity domains in the first chimeric polypeptide.

Embodiment A32. The multi-chain chimeric polypeptide of embodiment A27, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment A33. The multi-chain chimeric polypeptide of embodiment A27, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment A34. The multi-chain chimeric polypeptide of any one of embodiments A1-A33, wherein the second chimeric polypeptide further comprises one or more additional target-binding domains at the N-terminal end or the C-terminal end of the second chimeric polypeptide.

Embodiment A35. The multi-chain chimeric polypeptide of embodiment A34, wherein at least one of the one or more additional target-binding domains directly abuts the second domain of the pair of affinity domains in the second chimeric polypeptide.

Embodiment A36. The multi-chain chimeric polypeptide of embodiment A34, wherein the second chimeric polypeptide further comprises a linker sequence between at least one of the one or more additional target-binding domains and the second domain of the pair of affinity domains in the second chimeric polypeptide.

Embodiment A37. The multi-chain chimeric polypeptide of embodiment A34, wherein at least one of the one or more additional target-binding domains directly abuts the second target-binding domain in the second chimeric polypeptide.

Embodiment A38. The multi-chain chimeric polypeptide of embodiment A34, wherein the second chimeric polypeptide further comprises a linker sequence between at least one of the one or more additional target-binding domains and the second target-binding domain in the second chimeric polypeptide.

Embodiment A39. The multi-chain chimeric polypeptide of any one of embodiments A20-A38, wherein two or more of the first target-binding domain, the second target-binding domain, and the one or more additional target-binding domains bind specifically to the same antigen.

Embodiment A40. The multi-chain chimeric polypeptide of embodiment A39, wherein two or more of the first target-binding domain, the second target-binding domain, and the one or more additional target-binding domains bind specifically to the same epitope.

Embodiment A41. The multi-chain chimeric polypeptide of embodiment A40, wherein two or more of the first target-binding domain, the second target-binding domain, and the one or more additional target-binding domains comprise the same amino acid sequence.

Embodiment A42. The multi-chain chimeric polypeptide of embodiment A39, wherein the first target-binding domain, the second target-binding domain, and the one or more additional target-binding domains each bind specifically to the same antigen.

Embodiment A43. The multi-chain chimeric polypeptide of embodiment A42, wherein the first target-binding domain, the second target-binding domain, and the one or more additional target-binding domains each bind specifically to the same epitope.

Embodiment A44. The multi-chain chimeric polypeptide of embodiment A43, wherein the first target-binding domain, the second target-binding domain, and the one or more additional target-binding domains each comprise the same amino acid sequence.

Embodiment A45. The multi-chain chimeric polypeptide of any one of embodiments A20-A38, wherein the first target-binding domain, the second target-binding domain, and the one or more additional target-binding domains bind specifically to different antigens.

Embodiment A46. The multi-chain chimeric polypeptide of any one of embodiments A20-A45, wherein one or more of the first target-binding domain, the second target-binding domain, and the one or more target-binding domains is an antigen-binding domain.

Embodiment A47. The multi-chain chimeric polypeptide of embodiment A46, wherein the first target-binding domain, the second target-binding domain, and the one or more additional target-binding domains are each an antigen-binding domain.

Embodiment A48. The multi-chain chimeric polypeptide of embodiment A47, wherein antigen-binding domain comprises a scFv.

Embodiment A49. The multi-chain chimeric polypeptide of any one of embodiments A20-A48, wherein one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKP30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD3, and a receptor for CD28.

Embodiment A50. The multi-chain chimeric polypeptide of any one of embodiments A20-A48, wherein one or more of the first target-binding domain, the second target-binding domain, and the one or more additional target-binding domains is a soluble interleukin or cytokine protein.

Embodiment A51. The multi-chain chimeric polypeptide of embodiment A50, wherein the soluble interleukin, cytokine, or ligand protein is selected from the group consisting of: IL-1, IL-2, IL-3, IL-7, IL-8, IL-10, IL-12, IL-15, IL-17, IL-18, IL-21, PDGF-DD, SCF, and FLT3L.

Embodiment A52. The multi-chain chimeric polypeptide of any one of embodiments A20-A48, wherein one or more of the first target-binding domain, the second target-binding domain, and the one or more additional target-binding domains is a soluble interleukin or cytokine receptor.

Embodiment A53. The multi-chain chimeric polypeptide of embodiment A52, wherein the soluble receptor is a soluble TGF-β receptor II (TGF-β RII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

Embodiment A54. The multi-chain chimeric polypeptide of any one of embodiments A1-A53, wherein the first chimeric polypeptide further comprises a peptide tag at the N-terminal end or the C-terminal end of the first chimeric polypeptide.

Embodiment A55. The multi-chain chimeric polypeptide of any one of embodiments A1-A53, wherein the second chimeric polypeptide further comprises a peptide tag at the N-terminal end or the C-terminal end of the second chimeric polypeptide.

Embodiment A56. The multi-chain chimeric polypeptide of any one of embodiments A1-A55, wherein the soluble tissue factor domain is a soluble human tissue factor domain.

Embodiment A57. The multi-chain chimeric polypeptide of embodiment A56, wherein the soluble human tissue factor domain comprises a sequence that is at least 80% identical to SEQ ID NO: 1.

Embodiment A58. The multi-chain chimeric polypeptide of embodiment A57, wherein the soluble human tissue factor domain comprises a sequence that is at least 90% identical to SEQ ID NO: 1.

Embodiment A59. The multi-chain chimeric polypeptide of embodiment A58, wherein the soluble human tissue factor domain comprises a sequence that is at least 95% identical to SEQ ID NO: 1.

Embodiment A60. The multi-chain chimeric polypeptide of any one of embodiments A56-A59, wherein the soluble human tissue factor domain does not comprise one or more of:

- a lysine at an amino acid position that corresponds to amino acid position 20 of mature wildtype human tissue factor protein;
- an isoleucine at an amino acid position that corresponds to amino acid position 22 of mature wildtype human tissue factor protein;
- a tryptophan at an amino acid position that corresponds to amino acid position 45 of mature wildtype human tissue factor protein;
- an aspartic acid at an amino acid position that corresponds to amino acid position 58 of mature wildtype human tissue factor protein;
- a tyrosine at an amino acid position that corresponds to amino acid position 94 of mature wildtype human tissue factor protein;
- an arginine at an amino acid position that corresponds to amino acid position 135 of mature wildtype human tissue factor protein; and
- a phenylalanine at an amino acid position that corresponds to amino acid position 140 of mature wildtype human tissue factor protein.

Embodiment A61. The multi-chain chimeric polypeptide of embodiment A60, wherein the soluble human tissue factor domain does not comprise any of:

- a lysine at an amino acid position that corresponds to amino acid position 20 of mature wildtype human tissue factor protein;
- an isoleucine at an amino acid position that corresponds to amino acid position 22 of mature wildtype human tissue factor protein;
- a tryptophan at an amino acid position that corresponds to amino acid position 45 of mature wildtype human tissue factor protein;
- an aspartic acid at an amino acid position that corresponds to amino acid position 58 of mature wildtype human tissue factor protein;
- a tyrosine at an amino acid position that corresponds to amino acid position 94 of mature wildtype human tissue factor protein;
- an arginine at an amino acid position that corresponds to amino acid position 135 of mature wildtype human tissue factor protein; and
- a phenylalanine at an amino acid position that corresponds to amino acid position 140 of mature wildtype human tissue factor protein.

Embodiment A62. The multi-chain chimeric polypeptide of any one of embodiments A1-A61, wherein the soluble tissue factor domain is not capable of binding to Factor VIIa.

Embodiment A63. The multi-chain chimeric polypeptide of any one of embodiments A1-A62, wherein the soluble tissue factor domain does not convert inactive Factor X into Factor Xa.

Embodiment A64. The multi-chain chimeric polypeptide of any one of embodiments A1-A63, wherein the multi-chain chimeric polypeptide does not stimulate blood coagulation in a mammal.

Embodiment A65. The multi-chain chimeric polypeptide of any one of embodiments A1-A64, wherein the pair of affinity domains is a sushi domain from an alpha chain of human IL-15 receptor (IL15Rα) and a soluble IL-15.

Embodiment A66. The multi-chain chimeric polypeptide of embodiment A65, wherein the soluble IL15 has a D8N or D8A amino acid substitution.

Embodiment A67. The multi-chain chimeric polypeptide of embodiment A65 or A66, wherein the human IL15Rα is a mature full-length IL15Rα.

Embodiment A68. The multi-chain chimeric polypeptide of any one of embodiments A1-A64, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment A69. The multi-chain chimeric polypeptide of any one of embodiments A1-A68, wherein the first chimeric polypeptide and/or the second chimeric polypeptide further comprises a signal sequence at its N-terminal end.

Embodiment A70. A composition comprising any of the multi-chain chimeric polypeptides of embodiments A1-A69.

Embodiment A71. The composition of embodiment A70, wherein the composition is a pharmaceutical composition.

Embodiment A72. A kit comprising at least one dose of the composition of embodiment A70 or A71.

Embodiment A73. A method of stimulating an immune cell, the method comprising:

- contacting an immune cell with an effective amount of any of the multi-chain chimeric polypeptides of embodiments A1-A69 or the composition of embodiment A70 or A71.

Embodiment A74. The method of embodiment A73, wherein the immune cell is contacted in vitro.

Embodiment A75. The method of embodiment A74, wherein the immune cell was previously obtained from a subject.

Embodiment A76. The method of embodiment A75, wherein the method further comprises obtaining the immune cell from the subject prior to the contacting step.

Embodiment A77. The method of embodiment A73, wherein the immune cell is contacted in vivo.

Embodiment A78. The method of any one of embodiments A73-A77, wherein the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a $CD8^+$ T cell, a $CD4^+$ T cell, a natural killer T cell, a mast cell, a macrophage, a neutrophil, a dendritic cell, a basophil, an eosinophil, and a natural killer cell.

Embodiment A79. The method of any one of embodiments A73-A78, wherein the immune cell has previously been genetically modified to express a chimeric antigen receptor or a recombinant T-cell receptor.

Embodiment A80. The method of any one of embodiments A73-A78, wherein the method further comprises, after the contacting step, introducing into the immune cell a nucleic acid encoding a chimeric antigen-receptor or a recombinant T-cell receptor.

Embodiment A81. The method of any one of embodiments A73-A80, wherein the method further comprises administering the immune cell to a subject in need thereof.

Embodiment A82. The method of embodiment A81, wherein the subject has been identified or diagnosed as having an age-related disease or condition.

Embodiment A83. The method of embodiment A82, wherein the age-related disease or condition is selected from the group consisting of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment A84. The method of embodiment A81, wherein the subject has been identified or diagnosed as having a cancer.

Embodiment A85. The method of embodiment A84, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment A86. The method of embodiment A81, wherein the subject has been diagnosed or identified as having an infectious disease.

Embodiment A87. The method of embodiment A86, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment A88. A method of inducing or increasing proliferation of an immune cell, the method comprising:

contacting an immune cell with an effective amount of any of the multi-chain chimeric polypeptides of embodiments A1-A69 or the composition of embodiment A70 or A71.

Embodiment A89. The method of embodiment A88, wherein the immune cell is contacted in vitro.

Embodiment A90. The method of embodiment A89, wherein the immune cell was previously obtained from a subject.

Embodiment A91. The method of embodiment A90, wherein the method further comprises obtaining the immune cell from the subject prior to the contacting step.

Embodiment A92. The method of embodiment A88, wherein the immune cell is contacted in vivo.

Embodiment A93. The method of any one of embodiments A88-A92, wherein the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a $CD8^+$ T cell, a $CD4^+$ T cell, a natural killer T cell, a mast cell, a macrophage, a neutrophil, a dendritic cell, a basophil, an eosinophil, and a natural killer cell.

Embodiment A94. The method of any one of embodiments A88-A93, wherein the immune cell has previously been genetically modified to express a chimeric antigen receptor or a recombinant T-cell receptor.

Embodiment A95. The method of any one of embodiments A88-A93, wherein the method further comprises, after the contacting step, introducing into the immune cell a nucleic acid encoding a chimeric antigen-receptor or a recombinant T-cell receptor.

Embodiment A96. The method of any one of embodiments A88-A95, wherein the method further comprises administering the immune cell to a subject in need thereof.

Embodiment A97. The method of embodiment A96, wherein the subject has been identified or diagnosed as having an age-related disease or condition.

Embodiment A98. The method of embodiment A97, wherein the age-related disease or condition is selected from the group consisting of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment A99. The method of embodiment A96, wherein the subject has been identified or diagnosed as having a cancer.

Embodiment A100. The method of embodiment A99, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment A101. The method of embodiment A96, wherein the subject has been diagnosed or identified as having an infectious disease.

Embodiment A102. The method of embodiment A96, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment A103. A method of inducing differentiation of an immune cell into a memory or memory-like immune cell, the method comprising:

contacting an immune cell with an effective amount of any of the multi-chain chimeric polypeptides of embodiments A1-A69 or the composition of embodiment A70 or A71.

Embodiment A104. The method of embodiment A103, wherein the immune cell is contacted in vitro.

Embodiment A105. The method of embodiment A104, wherein the immune cell was previously obtained from a subject.

Embodiment A106. The method of embodiment A105, wherein the method further comprises obtaining the immune cell from the subject prior to the contacting step.

Embodiment A107. The method of embodiment A103, wherein the immune cell is contacted in vivo.

Embodiment A108. The method of any one of embodiments A103-A107, wherein the immune cell is selected from the group consisting of: an immature thymocyte, a peripheral blood lymphocyte, a naïve T cell, a pluripotent Th cell precursor, a lymphoid progenitor cell, a Treg cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell.

Embodiment A109. The method of any one of embodiments A103-A108, wherein the immune cell has previously been genetically modified to express a chimeric antigen receptor or a recombinant T-cell receptor.

Embodiment A110. The method of any one of embodiments A103-A108, wherein the method further comprises, after the contacting step, introducing into the immune cell a nucleic acid encoding a chimeric antigen-receptor or a recombinant T-cell receptor.

Embodiment A111. The method of any one of embodiments A103-A110, wherein the method further comprises administering the immune cell to a subject in need thereof.

Embodiment A112. The method of embodiment A111, wherein the subject has been identified or diagnosed as having an age-related disease or condition.

Embodiment A113. The method of embodiment A112, wherein the age-related disease or condition is selected from the group consisting of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment A114. The method of embodiment A111, wherein the subject has been identified or diagnosed as having a cancer.

Embodiment A115. The method of embodiment A114, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment A116. The method of embodiment A111, wherein the subject has been diagnosed or identified as having an infectious disease.

Embodiment A117. The method of embodiment A116, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment A118. A method of killing a cancer cell, an infected cell, or a senescent cell in a subject in need thereof, the method comprising administering to the subject a therapeutically effective amount of any of the multi-chain chimeric polypeptides of embodiments A1-A69 or the composition of embodiment A70 or A71.

Embodiment A119. The method of embodiment A118, wherein the subject has been identified or diagnosed as having a cancer.

Embodiment A120. The method of embodiment A119, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment A121. The method of embodiment A118, wherein the subject has been identified or diagnosed as having an aging-related disease or condition.

Embodiment A122. The method of embodiment A121, wherein the aging-related disease or condition is selected from the group consisting of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment A123. A method of treating a subject in need thereof, the method comprising administering to the subject a therapeutically effective amount of any of the multi-chain chimeric polypeptides of embodiments A1-A69 or the composition of embodiment A70 or A71.

Embodiment A124. The method of embodiment A123, wherein the subject has been identified or diagnosed as having a cancer.

Embodiment A125. The method of embodiment A124, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment A126. The method of embodiment A123, wherein the subject has been identified or diagnosed as having an aging-related disease or condition.

Embodiment A127. The method of embodiment A126, wherein the aging-related disease or condition is selected from the group consisting of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment A128. The method of embodiment A123, wherein the subject has been diagnosed or identified as having an infectious disease.

Embodiment A129. The method of embodiment A128, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment A130. Nucleic acid encoding any of the multi-chain chimeric polypeptides of any one of embodiments A1-A69.

Embodiment A131. A vector comprising the nucleic acid of embodiment A130.

Embodiment A132. The vector of embodiment A131, wherein the vector is an expression vector.

Embodiment A133. A cell comprising the nucleic acid of embodiment A130 or the vector of embodiment A131 or A132.

Embodiment A134. A method of producing a multi-chain chimeric polypeptide, the method comprising:

culturing the cell of embodiment A133 in a culture medium under conditions sufficient to result in the production of the multi-chain chimeric polypeptide; and recovering the multi-chain chimeric polypeptide from the cell and/or the culture medium.

Embodiment A135. A multi-chain chimeric polypeptide produced by the method of embodiment A134.

Embodiment A136. The multi-chain chimeric polypeptide of embodiment A56, wherein the soluble human tissue factor domain comprises a sequence that is at least 80% identical to SEQ ID NO: 3.

Embodiment A137. The multi-chain chimeric polypeptide of embodiment A136, wherein the soluble human tissue factor domain comprises a sequence that is at least 90% identical to SEQ ID NO: 3.

Embodiment A138. The multi-chain chimeric polypeptide of embodiment A137, wherein the soluble human tissue factor domain comprises a sequence that is at least 95% identical to SEQ ID NO: 3.

Embodiment A139. The multi-chain chimeric polypeptide of embodiment A138, wherein the soluble human tissue factor domain comprises a sequence that is 100% identical to SEQ ID NO: 3.

Embodiment A140. The multi-chain chimeric polypeptide of embodiment A56, wherein the soluble human tissue factor domain comprises a sequence that is at least 80% identical to SEQ ID NO: 4.

Embodiment A141. The multi-chain chimeric polypeptide of embodiment A140, wherein the soluble human tissue factor domain comprises a sequence that is at least 90% identical to SEQ ID NO: 4.

Embodiment A142. The multi-chain chimeric polypeptide of embodiment A141, wherein the soluble human tissue factor domain comprises a sequence that is at least 95% identical to SEQ ID NO: 4.

Embodiment A143. The multi-chain chimeric polypeptide of embodiment A142, wherein the soluble human tissue factor domain comprises a sequence that is 100% identical to SEQ ID NO: 4.

Embodiment A144. The multi-chain chimeric polypeptide of embodiment 56, wherein the human soluble tissue factor domain does not initiate coagulation.

Embodiment A145. The multi-chain chimeric polypeptide of any one of claims 1-59, wherein the soluble tissue factor domain comprises or consists of a sequence from a wildtype soluble human tissue factor.

B. Exemplary Embodiments

Embodiment B1. A multi-chain chimeric polypeptide comprising:

(a) a first chimeric polypeptide comprising:
  (i) a first target-binding domain;
  (ii) a soluble tissue factor domain; and
  (iii) a first domain of a pair of affinity domains;
(b) a second chimeric polypeptide comprising:
  (i) a second domain of a pair of affinity domains; and
  (ii) a second target-binding domain, wherein:

the first chimeric polypeptide and the second chimeric polypeptide associate through the binding of the first domain and the second domain of the pair of affinity domains;

the first target-binding domain and the second targeting-binding domain each independently bind specifically to a receptor of IL-18 or a receptor of IL-12.

Embodiment B2. The multi-chain chimeric polypeptide of embodiment B1, wherein the first target-binding domain and the soluble tissue factor domain directly abut each other in the first chimeric polypeptide.

Embodiment B3. The multi-chain chimeric polypeptide of embodiment B1, wherein the first chimeric polypeptide further comprises a linker sequence between the first target-binding domain and the soluble tissue factor domain in the first chimeric polypeptide.

Embodiment B4. The multi-chain chimeric polypeptide of any one of embodiments B1-B3, wherein the soluble tissue factor domain and the first domain of the pair of affinity domains directly abut each other in the first chimeric polypeptide.

Embodiment B5. The multi-chain chimeric polypeptide of any one of embodiments B1-B3, wherein the first chimeric polypeptide further comprises a linker sequence between the soluble tissue factor domain and the first domain of the pair of affinity domains in the first chimeric polypeptide.

Embodiment B6. The multi-chain chimeric polypeptide of any one of embodiments B1-B5, wherein the second domain of the pair of affinity domains and the second target-binding domain directly abut each other in the second chimeric polypeptide.

Embodiment B7. The multi-chain chimeric polypeptide of any one of embodiments B1-B5, wherein second chimeric polypeptide further comprises a linker sequence between the second domain of the pair of affinity domains and the second target-binding domain in the second chimeric polypeptide.

Embodiment B8. The multi-chain chimeric polypeptide of any one of embodiments B1-B7, wherein the soluble tissue factor domain is a soluble human tissue factor domain.

Embodiment B9. The multi-chain chimeric polypeptide of embodiment B8, wherein the soluble human tissue factor domain comprises a sequence that is at least 80% identical to SEQ ID NO: 1.

Embodiment B10. The multi-chain chimeric polypeptide of embodiment B9, wherein the soluble human tissue factor domain comprises a sequence that is at least 90% identical to SEQ ID NO: 1.

Embodiment B11. The multi-chain chimeric polypeptide of embodiment B10, wherein the soluble human tissue factor domain comprises a sequence that is at least 95% identical to SEQ ID NO: 1.

Embodiment B12. The multi-chain chimeric polypeptide of any one of embodiments B8-B11, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment B13. The multi-chain chimeric polypeptide of embodiment B12, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment B14. The multi-chain chimeric polypeptide of any one of embodiments B1-B13, wherein the soluble tissue factor domain is not capable of binding to Factor VIIa.

Embodiment B15. The multi-chain chimeric polypeptide of any one of embodiments B1-B14, wherein the soluble tissue factor domain does not convert inactive Factor X into Factor Xa.

Embodiment B16. The multi-chain chimeric polypeptide of any one of embodiments B1-B15, wherein the multi-chain chimeric polypeptide does not stimulate coagulation in a mammal.

Embodiment B17. The multi-chain chimeric polypeptide of any one of embodiments B1-B16, wherein the first chimeric polypeptide further comprises a peptide tag at the N-terminal end or the C-terminal end of the first chimeric polypeptide.

Embodiment B18. The multi-chain chimeric polypeptide of any one of embodiments B1-B17, wherein the second chimeric polypeptide further comprises a peptide tag at the N-terminal end or the C-terminal end of the second chimeric polypeptide.

Embodiment B19. The multi-chain chimeric polypeptide of any one of embodiments B1-18, wherein the first chimeric polypeptide and/or the second chimeric polypeptide further comprises a signal sequence at its N-terminal end.

Embodiment B20. The multi-chain chimeric polypeptide of embodiment B19, wherein the signal sequence comprises SEQ ID NO: 31.

Embodiment B21. The multi-chain chimeric polypeptide of embodiment B20, wherein the signal sequence is SEQ ID NO: 31.

Embodiment B22. The multi-chain chimeric polypeptide of any one of embodiments B1-B21, wherein the pair of affinity domains is a sushi domain from an alpha chain of human IL-15 receptor (IL15Rα) and a soluble IL-15.

Embodiment B23. The multi-chain chimeric polypeptide of embodiment B22, wherein the soluble IL-15 has a D8N or D8A amino acid substitution.

Embodiment B24. The multi-chain chimeric polypeptide of embodiment B22, wherein the soluble IL-15 comprises a sequence that is 80% identical to SEQ ID NO: 14.

Embodiment B25. The multi-chain chimeric polypeptide of embodiment B24, wherein the soluble IL-15 comprises a sequence that is 90% identical to SEQ ID NO: 14.

Embodiment B26. The multi-chain chimeric polypeptide of embodiment B25, wherein the soluble IL-15 comprises a sequence that is 95% identical to SEQ ID NO: 14.

Embodiment B27. The multi-chain chimeric polypeptide of embodiment B26, wherein the soluble IL-15 comprises SEQ ID NO: 14.

Embodiment B28. The multi-chain chimeric polypeptide of any one of embodiments B22-B27, wherein the sushi domain of IL15Rα comprises a sushi domain from human IL15Rα.

Embodiment B29. The multi-chain chimeric polypeptide of embodiment B28, wherein the sushi domain from human IL15Rα comprises a sequence that is 80% identical to SEQ ID NO: 28.

Embodiment B30. The multi-chain chimeric polypeptide of embodiment B29, wherein the sushi domain from human IL15Rα comprises a sequence that is 90% identical to SEQ ID NO: 28.

Embodiment B31. The multi-chain chimeric polypeptide of embodiment B30, wherein the sushi domain from human IL15Rα comprises a sequence that is 95% identical to SEQ ID NO: 28.

Embodiment B32. The multi-chain chimeric polypeptide of embodiment B31, wherein the sushi domain from human IL15Rα comprises SEQ ID NO: 28.

Embodiment B33. The multi-chain chimeric polypeptide of embodiment B28, wherein the sushi domain from human IL15Rα is a mature full-length IL15Rα.

Embodiment B34. The multi-chain chimeric polypeptide of any one of embodiments B1-B21, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment B35. The multi-chain chimeric polypeptide of any one of embodiments B1-B34, wherein one or both of the first target-binding domain and the second target-binding domain is an agonistic antigen-binding domain.

Embodiment B36. The multi-chain chimeric polypeptide of embodiment B35, wherein the first target-binding domain and the second target-binding domain are each agonistic antigen-binding domains.

Embodiment B37. The multi-chain chimeric polypeptide of embodiment B35 or B36, wherein antigen-binding domain comprises a scFv or single-domain antibody.

Embodiment B38. The multi-chain chimeric polypeptide of any one of embodiments B1-B34, wherein one or both of the first target-binding domain and the second target-binding domain is a soluble IL-15 or a soluble IL-18.

Embodiment B39. The multi-chain chimeric polypeptide of embodiment B38, wherein the first target-binding domain and the second target-binding domain are each independently a soluble IL-15 or a soluble IL-18.

Embodiment B40. The multi-chain chimeric polypeptide of any one of embodiments B1-B39, wherein the first target-binding domain and the second target-binding domain both bind specifically to a receptor of IL-18 or a receptor of IL-12.

Embodiment B41. The multi-chain chimeric polypeptide of embodiment B40, wherein the first target-binding domain and the second target-binding domain bind specifically to the same epitope.

Embodiment B42. The multi-chain chimeric polypeptide of embodiment B41, wherein the first target-binding domain and the second target-binding domain comprise the same amino acid sequence.

Embodiment B43. The multi-chain chimeric polypeptide of any one of embodiments B1-B39, wherein the first target-binding domain binds specifically to a receptor for IL-12, and the second target-binding domain binds specifically to a receptor for IL-18.

Embodiment B44. The multi-chain chimeric polypeptide of any one of embodiments B1-B39, wherein the first target-binding domain binds specifically to a receptor for IL-18, and the second target-binding domain bind specifically to a receptor for IL-12.

Embodiment B45. The multi-chain chimeric polypeptide of embodiment B44, wherein the first target-binding domain comprises a soluble IL-18.

Embodiment B46. The multi-chain chimeric polypeptide of embodiment B45, wherein the soluble IL-18 is a soluble human IL-18.

Embodiment B47. The multi-chain chimeric polypeptide of embodiment B46, wherein the soluble human IL-18 comprises a sequence at least 80% identical to SEQ ID NO: 16.

Embodiment B48. The multi-chain chimeric polypeptide of embodiment B47, wherein the soluble human IL-18 comprises a sequence at least 90% identical to SEQ ID NO: 16.

Embodiment B49. The multi-chain chimeric polypeptide of embodiment B48, wherein the soluble human IL-18 comprises a sequence at least 95% identical to SEQ ID NO: 16.

Embodiment B50. The multi-chain chimeric polypeptide of embodiment B49, wherein the soluble human IL-18 comprises a sequence of SEQ ID NO: 16.

Embodiment B51. The multi-chain chimeric polypeptide of any one of embodiments B44-B50, wherein the second target-binding domain comprises a soluble IL-12.

Embodiment B52. The multi-chain chimeric polypeptide of embodiment B51, wherein the soluble IL-18 is a soluble human IL-12.

Embodiment B53. The multi-chain chimeric polypeptide of embodiment B52, wherein the soluble human IL-15 comprises a sequence of soluble human IL-12β (p40) and a sequence of soluble human IL-12α (p35).

Embodiment B54. The multi-chain chimeric polypeptide of embodiment B53, wherein the soluble human IL-15 further comprises a linker sequence between the sequence of soluble IL-12β (p40) and the sequence of soluble human IL-12α (p35).

Embodiment B55. The multi-chain chimeric polypeptide of embodiment B54, wherein the linker sequence comprises SEQ ID NO: 7.

Embodiment B56. The multi-chain chimeric polypeptide of any one of embodiments B53-B55, wherein the sequence of soluble human IL-12β (p40) comprises a sequence that is at least 80% identical to SEQ ID NO: 66.

Embodiment B57. The multi-chain chimeric polypeptide of embodiment B56, wherein the sequence of soluble human IL-12β (p40) comprises a sequence that is at least 90% identical to SEQ ID NO: 66.

Embodiment B58. The multi-chain chimeric polypeptide of embodiment B57, wherein the sequence of soluble human IL-12β (p40) comprises a sequence that is at least 95% identical to SEQ ID NO: 66.

Embodiment B59. The multi-chain chimeric polypeptide of embodiment B58, wherein the sequence of soluble human IL-12β (p40) comprises SEQ ID NO: 66.

Embodiment B60. The multi-chain chimeric polypeptide of any one of embodiments B53-B59, wherein the sequence of soluble human IL-12α (p35) comprises a sequence that is at least 80% identical to SEQ ID NO: 68.

Embodiment B61. The multi-chain chimeric polypeptide of embodiment B60, wherein the sequence of soluble human IL-12α (p35) comprises a sequence that is at least 90% identical to SEQ ID NO: 68.

Embodiment B62. The mule-chain chimeric polypeptide of embodiment B61, wherein the sequence of soluble human IL-12α (p35) comprises a sequence that is at least 95% identical to SEQ ID NO: 68.

Embodiment B63. The multi-chain chimeric polypeptide of embodiment B62, wherein the sequence of soluble human IL-12α (p35) comprises SEQ ID NO: 68.

Embodiment B64. The multi-chain chimeric polypeptide of embodiment B1, wherein the first chimeric polypeptide comprises a sequence that is at least 80% identical to SEQ ID NO: 70.

Embodiment B65. The multi-chain chimeric polypeptide of embodiment B64, wherein the first chimeric polypeptide comprises a sequence that is at least 90% identical to SEQ ID NO: 70.

Embodiment B66. The multi-chain chimeric polypeptide of embodiment B65, wherein the first chimeric polypeptide comprises a sequence that is at least 95% identical to SEQ ID NO: 70.

Embodiment B67. The multi-chain chimeric polypeptide of embodiment B66, wherein the first chimeric polypeptide comprises SEQ ID NO: 70.

Embodiment B68. The multi-chain chimeric polypeptide of embodiment B67, wherein the first chimeric polypeptide comprises SEQ ID NO: 72.

Embodiment B69. The multi-chain chimeric polypeptide of any one of embodiments B1 and B64-B68, wherein the second chimeric polypeptide comprises a sequence that is at least 80% identical to SEQ ID NO: 74.

Embodiment B70. The multi-chain chimeric polypeptide of embodiment B69, wherein the second chimeric polypeptide comprises a sequence that is at least 90% identical to SEQ ID NO: 74.

Embodiment B71. The multi-chain chimeric polypeptide of embodiment B70, wherein the second chimeric polypeptide comprises a sequence that is at least 95% identical to SEQ ID NO: 74.

Embodiment B72. The multi-chain chimeric polypeptide of embodiment B71, wherein the second chimeric polypeptide comprises SEQ ID NO: 74.

Embodiment B73. The multi-chain chimeric polypeptide of embodiment B72, wherein the second chimeric polypeptide comprises SEQ ID NO: 74.

Embodiment B74. The multi-chain chimeric polypeptide of any one of embodiments B1-B63, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment B75. The multi-chain chimeric polypeptide of embodiment B74, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment B76. The multi-chain chimeric polypeptide of any one of embodiments B1-B63, wherein the first chimeric polypeptide further comprises one or more additional target-binding domains at the N-terminal and/or C-terminal end of the first chimeric polypeptide.

Embodiment B77. The multi-chain chimeric polypeptide of embodiment B76, wherein at least one of the one or more additional target-binding domains directly abuts the first domain of the pair of affinity domains in the first chimeric polypeptide.

Embodiment B78. The multi-chain chimeric polypeptide of embodiment B76, wherein the first chimeric polypeptide further comprises a linker sequence between the at least one of the one or more additional target-binding domains and the first domain of the pair of affinity domains.

Embodiment B79. The multi-chain chimeric polypeptide of embodiment B76, wherein the at least one of the one or more additional target-binding domains directly abuts the first target-binding domain in the first chimeric polypeptide.

Embodiment B80. The multi-chain chimeric polypeptide of embodiment B76, wherein the first chimeric polypeptide further comprises a linker sequence between the at least one of the one or more additional target-binding domains and the first target-binding domain.

Embodiment B81. The multi-chain chimeric polypeptide of embodiment B76, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment B82. The multi-chain chimeric polypeptide of embodiment B81, wherein the at least one additional target-binding domain of the one or more additional target-binding domains disposed at the N-terminus directly abuts the first target-binding domain or the first domain of the pair of affinity domains in the first chimeric polypeptide.

Embodiment B83. The multi-chain chimeric polypeptide of embodiment B81, wherein the first chimeric polypeptide further comprises a linker sequence disposed between the at least one additional target-binding domain and the first target-binding domain or the first domain of the pair of affinity domains in the first chimeric polypeptide.

Embodiment B84. The multi-chain chimeric polypeptide of embodiment B81, wherein the at least one additional target-binding domain of the one or more additional target-binding domains disposed at the C-terminus directly abuts the first target-binding domain or the first domain of the pair of affinity domains in the first chimeric polypeptide.

Embodiment B85. The multi-chain chimeric polypeptide of embodiment B81, wherein the first chimeric polypeptide further comprises a linker sequence disposed between the at least one additional target-binding domain and the first target-binding domain or the first domain of the pair of affinity domains in the first chimeric polypeptide.

Embodiment B86. The multi-chain chimeric polypeptide of embodiment B81, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment B87. The multi-chain chimeric polypeptide of embodiment B81, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment B88. The multi-chain chimeric polypeptide of any one of embodiments B1-B63 and B74-B87, wherein the second chimeric polypeptide further comprises one or more additional target-binding domains at the N-terminal end or the C-terminal end of the second chimeric polypeptide.

Embodiment B89. The multi-chain chimeric polypeptide of embodiment B88, wherein at least one of the one or more additional target-binding domains directly abuts the second domain of the pair of affinity domains in the second chimeric polypeptide.

Embodiment B90. The multi-chain chimeric polypeptide of embodiment B88, wherein the second chimeric polypeptide further comprises a linker sequence between at least one of the one or more additional target-binding domains and the second domain of the pair of affinity domains in the second chimeric polypeptide.

Embodiment B91. The multi-chain chimeric polypeptide of embodiment B88, wherein at least one of the one or more additional target-binding domains directly abuts the second target-binding domain in the second chimeric polypeptide.

Embodiment B92. The multi-chain chimeric polypeptide of embodiment B88, wherein the second chimeric polypeptide further comprises a linker sequence between at least one of the one or more additional target-binding domains and the second target-binding domain in the second chimeric polypeptide.

Embodiment B93. The multi-chain chimeric polypeptide of any one of embodiments B74-B92, wherein two or more of the first target-binding domain, the second target-binding domain, and the one or more additional target-binding domains bind specifically to the same antigen.

Embodiment B94. The multi-chain chimeric polypeptide of embodiment B93, wherein two or more of the first target-binding domain, the second target-binding domain, and the one or more additional target-binding domains bind specifically to the same epitope.

Embodiment B95. The multi-chain chimeric polypeptide of embodiment B94, wherein two or more of the first target-binding domain, the second target-binding domain, and the one or more additional target-binding domains comprise the same amino acid sequence.

Embodiment B96. The multi-chain chimeric polypeptide of any one of embodiments B74-B92, wherein the first target-binding domain, the second target-binding domain, and the one or more additional target-binding domains bind specifically to different antigens.

Embodiment B97. The multi-chain chimeric polypeptide of any one of embodiments B74-B96, wherein the one or more additional antigen-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKP30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD28.

Embodiment B98. The multi-chain chimeric polypeptide of any one of embodiments B74-B96, wherein the one or more additional target-binding domains is a soluble interleukin or cytokine protein.

Embodiment B99. The multi-chain chimeric polypeptide of embodiment B98, wherein the soluble interleukin, cytokine, or ligand protein is selected from the group consisting of: IL-1, IL-2, IL-3, IL-7, IL-8, IL-10, IL-12, IL-15, IL-17, IL-18, IL-21, PDGF-DD, SCF, and FLT3L.

Embodiment B100. The multi-chain chimeric polypeptide of any one of embodiments B74-B96, wherein the one or more additional target-binding domains is a soluble interleukin or cytokine receptor.

Embodiment B101. The multi-chain chimeric polypeptide of embodiment B100, wherein the soluble receptor is a soluble TGF-β receptor II (TGF-β RII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, a soluble CD122, or a soluble CD28.

Embodiment B102. A composition comprising any of the multi-chain chimeric polypeptides of embodiments B1-B101.

Embodiment B103. The composition of embodiment B102, wherein the composition is a pharmaceutical composition.

Embodiment B104. A kit comprising at least one dose of the composition of embodiment B102 or B103.

Embodiment B105. A method of stimulating an immune cell, the method comprising:

contacting an immune cell with an effective amount of any of the multi-chain chimeric polypeptides of embodiments B1-B101 or the composition of embodiment B102 or B103.

Embodiment B106. The method of embodiment B105, wherein the immune cell is contacted in vitro.

Embodiment B107. The method of embodiment B106, wherein the immune cell was previously obtained from a subject.

Embodiment B108. The method of embodiment B107, wherein the method further comprises obtaining the immune cell from the subject prior to the contacting step. Embodiment B109. The method of embodiment B105, wherein the immune cell is contacted in vivo.

Embodiment B110. The method of any one of embodiments B105-B109, wherein the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a $CD8^{+}$ T cell, a $CD4^{+}$ T cell, a natural killer T cell, a mast cell, a macrophage, a neutrophil, a dendritic cell, a basophil, an eosinophil, and a natural killer cell.

Embodiment B111. The method of any one of embodiments B105-B110, wherein the immune cell has previously been genetically modified to express a chimeric antigen receptor or a recombinant T-cell receptor.

Embodiment B112. The method of any one of embodiments B105-B110, wherein the method further comprises, after the contacting step, introducing into the immune cell a nucleic acid encoding a chimeric antigen-receptor or a recombinant T-cell receptor.

Embodiment B113. The method of any one of embodiments B105-B112, wherein the method further comprises administering the immune cell to a subject in need thereof.

Embodiment B114. The method of embodiment B113, wherein the subject has been identified or diagnosed as having age-related disease or condition.

Embodiment B115. The method of embodiment B114, wherein the age-related disease or condition is selected from the group consisting of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment B116. The method of embodiment B113, wherein the subject has been identified or diagnosed as having a cancer.

Embodiment B117. The method of embodiment B116, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment B118. The method of embodiment B113, wherein the subject has been diagnosed or identified as having an infectious disease.

Embodiment B119. The method of embodiment B118, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment B120. A method of inducing or increasing proliferation of an immune cell, the method comprising:

contacting an immune cell with an effective amount of any of the multi-chain chimeric polypeptides of embodiments B1-B101 or the composition of embodiment B102 or B103.

Embodiment B121. The method of embodiment B120, wherein the immune cell is contacted in vitro.

Embodiment B122. The method of embodiment B121, wherein the immune cell was previously obtained from a subject.

Embodiment B123. The method of embodiment B122, wherein the method further comprises obtaining the immune cell from the subject prior to the contacting step.

Embodiment B124. The method of embodiment B120, wherein the immune cell is contacted in vivo.

Embodiment B125. The method of any one of embodiments B120-B124, wherein the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell.

Embodiment B126. The method of any one of embodiments B120-B125, wherein the immune cell has previously been genetically modified to express a chimeric antigen receptor or a recombinant T-cell receptor.

Embodiment B127. The method of any one of embodiments B120-B125, wherein the method further comprises, after the contacting step, introducing into the immune cell a nucleic acid encoding a chimeric antigen-receptor or a recombinant T-cell receptor.

Embodiment B128. The method of any one of embodiments B120-B127, wherein the method further comprises administering the immune cell to a subject in need thereof.

Embodiment B129. The method of embodiment B128, wherein the subject has been identified or diagnosed as having an age-related disease or condition.

Embodiment B130. The method of embodiment B129, wherein the age-related disease or condition is selected from the group consisting of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment B131. The method of embodiment B128, wherein the subject has been identified or diagnosed as having a cancer.

Embodiment B132. The method of embodiment B131, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment B133. The method of embodiment B128, wherein the subject has been diagnosed or identified as having an infectious disease.

Embodiment B134. The method of embodiment B128, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment B135. A method of inducing differentiation of an immune cell into a memory or memory-like immune cell, the method comprising:

contacting an immune cell with an effective amount of any of the multi-chain chimeric polypeptides of embodiments B1-B101 or the composition of embodiment B102 or B103.

Embodiment B136. The method of embodiment B135, wherein the immune cell is contacted in vitro.

Embodiment B137. The method of embodiment B136, wherein the immune cell was previously obtained from a subject.

Embodiment B138. The method of embodiment B137, wherein the method further comprises obtaining the immune cell from the subject prior to the contacting step. Embodiment B139. The method of embodiment B135, wherein the immune cell is contacted in vivo.

Embodiment B140. The method of any one of embodiments B135-B139, wherein the immune cell is selected from the group consisting of: an immature thymocyte, a peripheral blood lymphocyte, a naïve T cell, a pluripotent Th cell precursor, a lymphoid progenitor cell, a Treg cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell.

Embodiment B141. The method of any one of embodiments B135-B140, wherein the immune cell has previously been genetically modified to express a chimeric antigen receptor or a recombinant T-cell receptor.

Embodiment B142. The method of any one of embodiments B135-B140, wherein the method further comprises, after the contacting step, introducing into the immune cell a nucleic acid encoding a chimeric antigen-receptor or a recombinant T-cell receptor.

Embodiment B143. The method of any one of embodiments B135-B142, wherein the method further comprises administering the immune cell to a subject in need thereof.

Embodiment B144. The method of embodiment B143, wherein the subject has been identified or diagnosed as having an age-related disease or condition.

Embodiment B145. The method of embodiment B144, wherein the age-related disease or condition is selected from the group consisting of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment B146. The method of embodiment B143, wherein the subject has been identified or diagnosed as having a cancer.

Embodiment B147. The method of embodiment B146, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment B148. The method of embodiment B143, wherein the subject has been diagnosed or identified as having an infectious disease.

Embodiment B149. The method of embodiment B148, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment B150. A method of killing a cancer cell, an infected cell, or a senescent cell in a subject in need thereof, the method comprising administering to the subject a therapeutically effective amount of any of the multi-chain chimeric polypeptides of embodiments B1-B101 or the composition of embodiment B102 or B103.

Embodiment B151. The method of embodiment B150, wherein the subject has been identified or diagnosed as having a cancer.

Embodiment B152. The method of embodiment B151, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment B153. The method of embodiment B150, wherein the subject has been identified or diagnosed as having an aging-related disease or condition.

Embodiment B154. The method of embodiment B153, wherein the aging-related disease or condition is selected from the group consisting of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Embodiment B155. A method of treating a subject in need thereof, the method comprising administering to the subject a therapeutically effective amount of any of the multi-chain chimeric polypeptides of embodiments B1-B101 or the composition of embodiment B102 or B103.

Embodiment B156. The method of embodiment B155, wherein the subject has been identified or diagnosed as having a cancer or infectious disease.

Embodiment B157. The method of embodiment B156, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment B158. The method of embodiment B155, wherein the subject has been identified or diagnosed as having age-related disease or condition.

Embodiment B159. The method of embodiment B158, wherein the age-related disease or condition is selected from the group consisting of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment B160. The method of embodiment B155, wherein the subject has been diagnosed or identified as having an infectious disease.

Embodiment B161. The method of embodiment B160, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment B162. Nucleic acid encoding any of the multi-chain chimeric polypeptides of any one of embodiments B1-B101.

Embodiment B163. A vector comprising the nucleic acid of embodiment B162.

Embodiment B164. The vector of embodiment B163, wherein the vector is an expression vector.

Embodiment B165. A cell comprising the nucleic acid of embodiment B162 or the vector of embodiment B163 or B164.

Embodiment B166. A method of producing a multi-chain chimeric polypeptide, the method comprising:

culturing the cell of embodiment B165 in a culture medium under conditions sufficient to result in the production of the multi-chain chimeric polypeptide; and recovering the multi-chain chimeric polypeptide from the cell and/or the culture medium.

Embodiment B167. A multi-chain chimeric polypeptide produced by the method of embodiment B166.

Embodiment B168. The multi-chain chimeric polypeptide of embodiment B8, wherein the soluble human tissue factor domain comprises a sequence that is at least 80% identical to SEQ ID NO: 3.

Embodiment B169. The multi-chain chimeric polypeptide of embodiment B168, wherein the soluble human tissue factor domain comprises a sequence that is at least 90% identical to SEQ ID NO: 3.

Embodiment B170. The multi-chain chimeric polypeptide of embodiment B169, wherein the soluble human tissue factor domain comprises a sequence that is at least 95% identical to SEQ ID NO: 3.

Embodiment B171. The multi-chain chimeric polypeptide of embodiment B170, wherein the soluble human tissue factor domain comprises a sequence that is 100% identical to SEQ ID NO: 3.

Embodiment B172. The multi-chain chimeric polypeptide of embodiment B8, wherein the soluble human tissue factor domain comprises a sequence that is at least 80% identical to SEQ ID NO: 4.

Embodiment B173. The multi-chain chimeric polypeptide of embodiment B172, wherein the soluble human tissue factor domain comprises a sequence that is at least 90% identical to SEQ ID NO: 4.

Embodiment B174. The multi-chain chimeric polypeptide of embodiment B173, wherein the soluble human tissue factor domain comprises a sequence that is at least 95% identical to SEQ ID NO: 4.

Embodiment B175. The multi-chain chimeric polypeptide of embodiment B174, wherein the soluble human tissue factor domain comprises a sequence that is 100% identical to SEQ ID NO: 4.

C. Exemplary Embodiments

Embodiment C1. A multi-chain chimeric polypeptide comprising:

(a) a first chimeric polypeptide comprising:
(i) a first target-binding domain;
(ii) a soluble tissue factor domain; and
(iii) a first domain of a pair of affinity domains;
(b) a second chimeric polypeptide comprising:
(i) a second domain of a pair of affinity domains; and
(ii) a second target-binding domain,
wherein:
the first chimeric polypeptide and the second chimeric polypeptide associate through the binding of the first domain and the second domain of the pair of affinity domains; and
the first target-binding domain and the second targeting-binding domain each independently bind specifically to a receptor of IL-21 or a ligand of tumor growth factor receptor β II (TGFβRII).

Embodiment C2. The multi-chain chimeric polypeptide of embodiment C1, wherein the first target-binding domain and the soluble tissue factor domain directly abut each other in the first chimeric polypeptide.

Embodiment C3. The multi-chain chimeric polypeptide of embodiments C1, wherein the first chimeric polypeptide further comprises a linker sequence between the first target-binding domain and the soluble tissue factor domain in the first chimeric polypeptide.

Embodiment C4. The multi-chain chimeric polypeptide of any one of embodiments C1-C3, wherein the soluble tissue factor domain and the first domain of the pair of affinity domains directly abut each other in the first chimeric polypeptide.

Embodiment C5. The multi-chain chimeric polypeptide of any one of embodiments C1-C3, wherein the first chimeric polypeptide further comprises a linker sequence between the soluble tissue factor domain and the first domain of the pair of affinity domains in the first chimeric polypeptide.

Embodiment C6. The multi-chain chimeric polypeptide of any one of embodiments C1-C5, wherein the second domain of the pair of affinity domains and the second target-binding domain directly abut each other in the second chimeric polypeptide.

Embodiment C7. The multi-chain chimeric polypeptide of any one of embodiments C1-C5, wherein second chimeric polypeptide further comprises a linker sequence between the second domain of the pair of affinity domains and the second target-binding domain in the second chimeric polypeptide.

Embodiment C8. The multi-chain chimeric polypeptide of any one of embodiments C1-C7, wherein the soluble tissue factor domain is a soluble human tissue factor domain.

Embodiment C9. The multi-chain chimeric polypeptide of embodiment C8, wherein the soluble human tissue factor domain comprises a sequence that is at least 80% identical to SEQ ID NO: 1.

Embodiment C10. The multi-chain chimeric polypeptide of embodiment C9, wherein the soluble human tissue factor domain comprises a sequence that is at least 90% identical to SEQ ID NO: 1.

Embodiment C11. The multi-chain chimeric polypeptide of embodiment C10, wherein the soluble human tissue factor domain comprises a sequence that is at least 95% identical to SEQ ID NO: 1.

Embodiment C12. The multi-chain chimeric polypeptide of any one of embodiments C8-C11, wherein the soluble human tissue factor domain does not comprise one or more of:
a lysine at an amino acid position that corresponds to amino acid position 20 of mature wildtype human tissue factor protein;

an isoleucine at an amino acid position that corresponds to amino acid position 22 of mature wildtype human tissue factor protein;
a tryptophan at an amino acid position that corresponds to amino acid position 45 of mature wildtype human tissue factor protein;
an aspartic acid at an amino acid position that corresponds to amino acid position 58 of mature wildtype human tissue factor protein;
a tyrosine at an amino acid position that corresponds to amino acid position 94 of mature wildtype human tissue factor protein;
an arginine at an amino acid position that corresponds to amino acid position 135 of mature wildtype human tissue factor protein; and
a phenylalanine at an amino acid position that corresponds to amino acid position 140 of mature wildtype human tissue factor protein.

Embodiment C13. The multi-chain chimeric polypeptide of embodiment C12, wherein the soluble human tissue factor domain does not comprise any of:
a lysine at an amino acid position that corresponds to amino acid position 20 of mature wildtype human tissue factor protein;
an isoleucine at an amino acid position that corresponds to amino acid position 22 of mature wildtype human tissue factor protein;
a tryptophan at an amino acid position that corresponds to amino acid position 45 of mature wildtype human tissue factor protein;
an aspartic acid at an amino acid position that corresponds to amino acid position 58 of mature wildtype human tissue factor protein;
a tyrosine at an amino acid position that corresponds to amino acid position 94 of mature wildtype human tissue factor protein;
an arginine at an amino acid position that corresponds to amino acid position 135 of mature wildtype human tissue factor protein; and
a phenylalanine at an amino acid position that corresponds to amino acid position 140 of mature wildtype human tissue factor protein.

Embodiment C14. The multi-chain chimeric polypeptide of any one of embodiments C1-C13, wherein the soluble tissue factor domain is not capable of binding to Factor VIIa.

Embodiment C15. The multi-chain chimeric polypeptide of any one of embodiments C1-C14, wherein the soluble tissue factor domain does not convert inactive Factor X into Factor Xa.

Embodiment C16. The multi-chain chimeric polypeptide of any one of embodiments C1-C15, wherein the multi-chain chimeric polypeptide does not stimulate blood coagulation in a mammal.

Embodiment C17. The multi-chain chimeric polypeptide of any one of embodiments C1-C16, wherein the first chimeric polypeptide further comprises a peptide tag at the N-terminal end or the C-terminal end of the first chimeric polypeptide.

Embodiment C18. The multi-chain chimeric polypeptide of any one of embodiments C1-C17, wherein the second chimeric polypeptide further comprises a peptide tag at the N-terminal end or the C-terminal end of the second chimeric polypeptide.

Embodiment C19. The multi-chain chimeric polypeptide of any one of embodiments C1-C18, wherein the first chimeric polypeptide and/or the second chimeric polypeptide further comprises a signal sequence at its N-terminal end.

Embodiment C20. The multi-chain chimeric polypeptide of embodiment C19, wherein the signal sequence comprises SEQ ID NO: 31.

Embodiment C21. The multi-chain chimeric polypeptide of embodiment C20, wherein the signal sequence is SEQ ID NO: 31.

Embodiment C22. The multi-chain chimeric polypeptide of any one of embodiments C1-C21, wherein the pair of affinity domains is a sushi domain from an alpha chain of human IL-15 receptor (IL15Rα and a soluble IL-15.

Embodiment C23. The multi-chain chimeric polypeptide of embodiment C22, wherein the soluble IL-15 has a D8N or D8A amino acid substitution.

Embodiment C24. The multi-chain chimeric polypeptide of embodiment C22, wherein the soluble IL-15 comprises a sequence that is 80% identical to SEQ ID NO: 14.

Embodiment C25. The multi-chain chimeric polypeptide of embodiment C24, wherein the soluble IL-15 comprises a sequence that is 90% identical to SEQ ID NO: 14.

Embodiment C26. The multi-chain chimeric polypeptide of embodiment C25, wherein the soluble IL-15 comprises a sequence that is 95% identical to SEQ ID NO: 14.

Embodiment C27. The multi-chain chimeric polypeptide of embodiment C26, wherein the soluble IL-15 comprises SEQ ID NO: 14.

Embodiment C28. The multi-chain chimeric polypeptide of any one of embodiments C22-C27, wherein the sushi domain of IL15Rα comprises a sushi domain from human IL15Rα.

Embodiment C29. The multi-chain chimeric polypeptide of embodiment C28, wherein the sushi domain from human IL15Rα comprises a sequence that is 80% identical to SEQ ID NO: 28.

Embodiment C30. The multi-chain chimeric polypeptide of embodiment C29, wherein the sushi domain from human IL15Rα comprises a sequence that is 90% identical to SEQ ID NO: 28.

Embodiment C31. The multi-chain chimeric polypeptide of embodiment C30, wherein the sushi domain from human IL15Rα comprises a sequence that is 95% identical to SEQ ID NO: 28.

Embodiment C32. The multi-chain chimeric polypeptide of embodiment C31, wherein the sushi domain from human IL15Rα comprises SEQ ID NO: 28.

Embodiment C33. The multi-chain chimeric polypeptide of embodiment C28, wherein the sushi domain from human IL15Rα is a mature full-length IL15Rα.

Embodiment C34. The multi-chain chimeric polypeptide of any one of embodiments C1-C21, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment C35. The multi-chain chimeric polypeptide of any one of embodiments C1-C34, wherein one or both of the first target-binding domain and the second target-binding domain is an antigen-binding domain.

Embodiment C36. The multi-chain chimeric polypeptide of embodiment C35, wherein the first target-binding domain and the second target-binding domain are antigen-binding domains.

Embodiment C37. The multi-chain chimeric polypeptide of embodiment C35 or C36, wherein antigen-binding domain comprises a scFv or single-domain antibody.

Embodiment C38. The multi-chain chimeric polypeptide of any one of embodiments C1-C34, wherein one or both of the first target-binding domain and the second target-binding domain is a soluble IL-21 or a soluble TGFβRII.

Embodiment C39. The multi-chain chimeric polypeptide of any one of embodiments C1-C38, wherein the first target-binding domain and the second target-binding domain both bind specifically to a receptor of IL-21 or a ligand of TGFβRII.

Embodiment C40. The multi-chain chimeric polypeptide of embodiment C39, wherein the first target-binding domain and the second target-binding domain bind specifically to the same epitope.

Embodiment C41. The multi-chain chimeric polypeptide of embodiment C40, wherein the first target-binding domain and the second target-binding domain comprise the same amino acid sequence.

Embodiment C42. The multi-chain chimeric polypeptide of any one of embodiments C1-C38, wherein the first target-binding domain binds specifically to a ligand of TGFβRII, and the second target-binding domain binds specifically to a receptor for IL-21.

Embodiment C43. The multi-chain chimeric polypeptide of any one of embodiments C1-C38, wherein the first target-binding domain binds specifically to a receptor for IL-21, and the second target-binding domain bind specifically to a ligand of TGFβRII.

Embodiment C44. The multi-chain chimeric polypeptide of embodiment C43, wherein the first target-binding domain comprises a soluble IL-21.

Embodiment C45. The multi-chain chimeric polypeptide of embodiment C44, wherein the soluble IL-21 is a soluble human IL-21.

Embodiment C46. The multi-chain chimeric polypeptide of embodiment C45, wherein the soluble human IL-21 comprises a sequence at least 80% identical to SEQ ID NO: 78.

Embodiment C47. The multi-chain chimeric polypeptide of embodiment C46, wherein the soluble human IL-21 comprises a sequence at least 90% identical to SEQ ID NO: 78.

Embodiment C48. The multi-chain chimeric polypeptide of embodiment C47, wherein the soluble human IL-21 comprises a sequence at least 95% identical to SEQ ID NO: 78.

Embodiment C49. The multi-chain chimeric polypeptide of embodiment C48, wherein the soluble human IL-21 comprises a sequence of SEQ ID NO: 78.

Embodiment C50. The multi-chain chimeric polypeptide of any one of embodiments C43-C49, wherein the second target-binding domain comprises a soluble TGFβRII.

Embodiment C51. The multi-chain chimeric polypeptide of embodiment C50, wherein the soluble TGFβRII is a soluble human TGFβRII.

Embodiment C52. The multi-chain chimeric polypeptide of embodiment C51, wherein the soluble human TGFβRII comprises a first sequence of soluble human TGFβRII and a second sequence of soluble human TGFβRII.

Embodiment C53. The multi-chain chimeric polypeptide of embodiment C52, wherein the soluble human TGFβRII further comprises a linker sequence between the first sequence of soluble human TGFβRII and the second sequence of soluble human TGFβRII.

Embodiment C54. The multi-chain chimeric polypeptide of embodiment C53, wherein the linker sequence comprises SEQ ID NO: 7.

Embodiment C55. The multi-chain chimeric polypeptide of any one of embodiments C52-C54, wherein the first sequence of soluble human TGFβRII comprises a sequence that is at least 80% identical to SEQ ID NO: 80.

Embodiment C56. The multi-chain chimeric polypeptide of embodiment C55, wherein the first sequence of soluble human TGFβRII comprises a sequence that is at least 90% identical to SEQ ID NO: 80.

Embodiment C57. The multi-chain chimeric polypeptide of embodiment C56, wherein the first sequence of soluble human TGFβRII comprises a sequence that is at least 95% identical to SEQ ID NO: 80.

Embodiment C58. The multi-chain chimeric polypeptide of embodiment C57, wherein the first sequence of soluble human TGFβRII comprises SEQ ID NO: 80.

Embodiment C59. The multi-chain chimeric polypeptide of any one of embodiments C52-C58, wherein the second sequence of soluble human TGFβRII comprises a sequence that is at least 80% identical to SEQ ID NO: 81.

Embodiment C60. The multi-chain chimeric polypeptide of embodiment C59, wherein the second sequence of soluble human TGFβRII comprises a sequence that is at least 90% identical to SEQ ID NO: 81.

Embodiment C61. The mule-chain chimeric polypeptide of embodiment C60, wherein the second sequence of soluble human TGFβRII comprises a sequence that is at least 95% identical to SEQ ID NO: 81.

Embodiment C62. The multi-chain chimeric polypeptide of embodiment C61, wherein the second sequence of soluble human TGFβRII comprises SEQ ID NO: 81.

Embodiment C63. The multi-chain chimeric polypeptide of embodiment C1, wherein the first chimeric polypeptide comprises a sequence that is at least 80% identical to SEQ ID NO: 86.

Embodiment C64. The multi-chain chimeric polypeptide of embodiment C63, wherein the first chimeric polypeptide comprises a sequence that is at least 90% identical to SEQ ID NO: 86.

Embodiment C65. The multi-chain chimeric polypeptide of embodiment C64, wherein the first chimeric polypeptide comprises a sequence that is at least 95% identical to SEQ ID NO: 86.

Embodiment C66. The multi-chain chimeric polypeptide of embodiment C65, wherein the first chimeric polypeptide comprises SEQ ID NO: 86.

Embodiment C67. The multi-chain chimeric polypeptide of embodiment C66, wherein the first chimeric polypeptide comprises SEQ ID NO: 88.

Embodiment C68. The multi-chain chimeric polypeptide of any one of embodiments C1 and C63-C67, wherein the second chimeric polypeptide comprises a sequence that is at least 80% identical to SEQ ID NO: 90.

Embodiment C69. The multi-chain chimeric polypeptide of embodiment C68, wherein the second chimeric polypeptide comprises a sequence that is at least 90% identical to SEQ ID NO: 90.

Embodiment C70. The multi-chain chimeric polypeptide of embodiment C69, wherein the second chimeric polypeptide comprises a sequence that is at least 95% identical to SEQ ID NO: 90.

Embodiment C71. The multi-chain chimeric polypeptide of embodiment C70, wherein the second chimeric polypeptide comprises SEQ ID NO: 90.

Embodiment C72. The multi-chain chimeric polypeptide of embodiment C71, wherein the second chimeric polypeptide comprises SEQ ID NO: 92.

Embodiment C73. The multi-chain chimeric polypeptide of any one of embodiments C1-C62, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment C74. The multi-chain chimeric polypeptide of embodiment C73, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains. Embodiment C75. The multi-chain chimeric polypeptide of any one of embodiments C1-C62, wherein the first chimeric polypeptide further comprises one or more additional target-binding domains at the N-terminal and/or C-terminal end of the first chimeric polypeptide.

Embodiment C76. The multi-chain chimeric polypeptide of embodiment C75, wherein at least one of the one or more additional target-binding domains directly abuts the first domain of the pair of affinity domains in the first chimeric polypeptide.

Embodiment C77. The multi-chain chimeric polypeptide of embodiment C75, wherein the first chimeric polypeptide further comprises a linker sequence between the at least one of the one or more additional target-binding domains and the first domain of the pair of affinity domains.

Embodiment C78. The multi-chain chimeric polypeptide of embodiment C75, wherein the at least one of the one or more additional target-binding domains directly abuts the first target-binding domain in the first chimeric polypeptide.

Embodiment C79. The multi-chain chimeric polypeptide of embodiment C75, wherein the first chimeric polypeptide further comprises a linker sequence between the at least one of the one or more additional target-binding domains and the first target-binding domain.

Embodiment C80. The multi-chain chimeric polypeptide of embodiment C75, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment C81. The multi-chain chimeric polypeptide of embodiment C80, wherein the at least one additional target-binding domain of the one or more additional target-binding domains disposed at the N-terminus directly abuts the first target-binding domain or the first domain of the pair of affinity domains in the first chimeric polypeptide.

Embodiment C82. The multi-chain chimeric polypeptide of embodiment C80, wherein the first chimeric polypeptide further comprises a linker sequence disposed between the at least one additional target-binding domain and the first target-binding domain or the first domain of the pair of affinity domains in the first chimeric polypeptide.

Embodiment C83. The multi-chain chimeric polypeptide of embodiment C80, wherein the at least one additional target-binding domain of the one or more additional target-binding domains disposed at the C-terminus directly abuts the first target-binding domain or the first domain of the pair of affinity domains in the first chimeric polypeptide.

Embodiment C84. The multi-chain chimeric polypeptide of embodiment C80, wherein the first chimeric polypeptide further comprises a linker sequence disposed between the at least one additional target-binding domain and the first target-binding domain or the first domain of the pair of affinity domains in the first chimeric polypeptide.

Embodiment C85. The multi-chain chimeric polypeptide of embodiment C80, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment C86. The multi-chain chimeric polypeptide of embodiment C80, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment C87. The multi-chain chimeric polypeptide of any one of embodiments C1-C62 and C73-C86, wherein the second chimeric polypeptide further comprises one or more additional target-binding domains at the N-terminal end or the C-terminal end of the second chimeric polypeptide.

Embodiment C88. The multi-chain chimeric polypeptide of embodiment C87, wherein at least one of the one or more additional target-binding domains directly abuts the second domain of the pair of affinity domains in the second chimeric polypeptide.

Embodiment C89. The multi-chain chimeric polypeptide of embodiment C87, wherein the second chimeric polypeptide further comprises a linker sequence between at least one of the one or more additional target-binding domains and the second domain of the pair of affinity domains in the second chimeric polypeptide.

Embodiment C90. The multi-chain chimeric polypeptide of embodiment C87, wherein at least one of the one or more additional target-binding domains directly abuts the second target-binding domain in the second chimeric polypeptide.

Embodiment C91. The multi-chain chimeric polypeptide of embodiment C87, wherein the second chimeric polypeptide further comprises a linker sequence between at least one of the one or more additional target-binding domains and the second target-binding domain in the second chimeric polypeptide.

Embodiment C92. The multi-chain chimeric polypeptide of any one of embodiments C73-C91, wherein two or more of the first target-binding domain, the second target-binding domain, and the one or more additional target-binding domains bind specifically to the same antigen.

Embodiment C93. The multi-chain chimeric polypeptide of embodiment C92, wherein two or more of the first target-binding domain, the second target-binding domain, and the one or more additional target-binding domains bind specifically to the same epitope.

Embodiment C94. The multi-chain chimeric polypeptide of embodiment C93, wherein two or more of the first target-binding domain, the second target-binding domain, and the one or more additional target-binding domains comprise the same amino acid sequence.

Embodiment C95. The multi-chain chimeric polypeptide of any one of embodiments C73-C91, wherein the first target-binding domain, the second target-binding domain, and the one or more additional target-binding domains bind specifically to different antigens.

Embodiment C96. The multi-chain chimeric polypeptide of any one of embodiments C73-C95, wherein the one or more additional antigen-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-D, a ligand of TGF-β receptor II (TGF-βII), a ligand of TGF-βRIII, a ligand of DNAM-1, a ligand of NKp46, a ligand of NKp44, a ligand of NKG2D, a ligand of NKp30, a ligand for a scMHICI, a ligand for a scMHICII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD28.

Embodiment C97. The multi-chain chimeric polypeptide of any one of embodiments C73-C95, wherein the one or more additional target-binding domains is a soluble interleukin or cytokine protein.

Embodiment C98. The multi-chain chimeric polypeptide of embodiment C97, wherein the soluble interleukin, cytokine, or ligand protein is selected from the group consisting of: IL-1, IL-2, IL-3, IL-7, IL-8, IL-10, IL-12, IL-15, IL-17, IL-18, IL-21, PDGF-DD, SCF, and FLT3L.

Embodiment C99. The multi-chain chimeric polypeptide of any one of embodiments C73-C95, wherein the one or more additional target-binding domains is a soluble interleukin or cytokine receptor.

Embodiment C100. The multi-chain chimeric polypeptide of embodiment C99, wherein the soluble receptor is a soluble TGF-β receptor II (TGF-β RII), a soluble TGF-βRIII, a soluble NKG2D, a soluble NKp30, a soluble NKp44, a soluble NKp46, a soluble DNAM-1, a scMHICI, a scMHICII, a scTCR, a soluble CD155, or a soluble CD28.

Embodiment C101. A composition comprising any of the multi-chain chimeric polypeptides of embodiments C1-C100.

Embodiment C102. The composition of embodiment C101, wherein the composition is a pharmaceutical composition.

Embodiment C103. A kit comprising at least one dose of the composition of embodiment C101 or C102.

Embodiment C104. A method of stimulating an immune cell, the method comprising:

contacting an immune cell with an effective amount of any of the multi-chain chimeric polypeptides of embodiments C1-C100 or the composition of embodiment C101 or C102.

Embodiment C105. The method of embodiment C104, wherein the immune cell is contacted in vitro.

Embodiment C106. The method of embodiment C105, wherein the immune cell was previously obtained from a subject.

Embodiment C107. The method of embodiment C106, wherein the method further comprises obtaining the immune cell from the subject prior to the contacting step.

Embodiment C108. The method of embodiment C104, wherein the immune cell is contacted in vivo.

Embodiment C109. The method of any one of embodiments C104-C108, wherein the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a $CD8^+$ T cell, a $CD4^+$ T cell, a natural killer T cell, a mast cell, a macrophage, a neutrophil, a dendritic cell, a basophil, an eosinophil, and a natural killer cell.

Embodiment C110. The method of any one of embodiments C104-C109, wherein the immune cell has previously been genetically modified to express a chimeric antigen receptor or a recombinant T-cell receptor.

Embodiment C111. The method of any one of embodiments C104-C109, wherein the method further comprises, after the contacting step, introducing into the immune cell a nucleic acid encoding a chimeric antigen-receptor or a recombinant T-cell receptor.

Embodiment C112. The method of any one of embodiments C104-C111, wherein the method further comprises administering the immune cell to a subject in need thereof.

Embodiment C113. The method of embodiment C112, wherein the subject has been identified or diagnosed as having age-related disease or condition.

Embodiment C114. The method of embodiment C113, wherein the age-related disease or condition is selected from the group consisting of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment C115. The method of embodiment C112, wherein the subject has been identified or diagnosed as having a cancer.

Embodiment C116. The method of embodiment C115, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment C117. The method of embodiment C112, wherein the subject has been diagnosed or identified as having an infectious disease.

Embodiment C118. The method of embodiment C117, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment C119. A method of inducing or increasing proliferation of an immune cell, the method comprising:

contacting an immune cell with an effective amount of any of the multi-chain chimeric polypeptides of embodiments C1-C100 or the composition of embodiment C101 or C102.

Embodiment C120. The method of embodiment C119, wherein the immune cell is contacted in vitro.

Embodiment C121. The method of embodiment C120, wherein the immune cell was previously obtained from a subject.

Embodiment C122. The method of embodiment C121, wherein the method further comprises obtaining the immune cell from the subject prior to the contacting step.

Embodiment C123. The method of embodiment C119, wherein the immune cell is contacted in vivo.

Embodiment C124. The method of any one of embodiments C119-C123, wherein the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell.

Embodiment C125. The method of any one of embodiments C119-C124, wherein the immune cell has previously been genetically modified to express a chimeric antigen receptor or a recombinant T-cell receptor.

Embodiment C126. The method of any one of embodiments C119-C124, wherein the method further comprises, after the contacting step, introducing into the immune cell a nucleic acid encoding a chimeric antigen-receptor or a recombinant T-cell receptor.

Embodiment C127. The method of any one of embodiments C119-C126, wherein the method further comprises administering the immune cell to a subject in need thereof.

Embodiment C128. The method of embodiment C127, wherein the subject has been identified or diagnosed as having an age-related disease or condition.

Embodiment C129. The method of embodiment C128, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment C130. The method of embodiment C127, wherein the subject has been identified or diagnosed as having a cancer.

Embodiment C131. The method of embodiment C130, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment C132. The method of embodiment C127, wherein the subject has been diagnosed or identified as having an infectious disease.

Embodiment C133. The method of embodiment C127, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment C134. A method of inducing differentiation of an immune cell into a memory or memory-like immune cell, the method comprising:

contacting an immune cell with an effective amount of any of the multi-chain chimeric polypeptides of embodiments C1-C100 or the composition of embodiment C101 or C102.

Embodiment C135. The method of embodiment C134, wherein the immune cell is contacted in vitro.

Embodiment C136. The method of embodiment C135, wherein the immune cell was previously obtained from a subject.

Embodiment C137. The method of embodiment C136, wherein the method further comprises obtaining the immune cell from the subject prior to the contacting step.

Embodiment C138. The method of embodiment C134, wherein the immune cell is contacted in vivo.

Embodiment C139. The method of any one of embodiments C134-C138, wherein the immune cell is selected from the group consisting of: an immature thymocyte, a peripheral blood lymphocyte, a naïve T cell, a pluripotent Th cell precursor, a lymphoid progenitor cell, a Treg cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell.

Embodiment C140. The method of any one of embodiments C134-C139, wherein the immune cell has previously been genetically modified to express a chimeric antigen receptor or a recombinant T-cell receptor.

Embodiment C141. The method of any one of embodiments C134-C139, wherein the method further comprises, after the contacting step, introducing into the immune cell a nucleic acid encoding a chimeric antigen-receptor or a recombinant T-cell receptor.

Embodiment C142. The method of any one of embodiments C134-C141, wherein the method further comprises administering the immune cell to a subject in need thereof.

Embodiment C143. The method of embodiment C142, wherein the subject has been identified or diagnosed as having an age-related disease or condition.

Embodiment C144. The method of embodiment C143, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment C145. The method of embodiment C142, wherein the subject has been identified or diagnosed as having a cancer.

Embodiment C146. The method of embodiment C145, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment C147. The method of embodiment C142, wherein the subject has been diagnosed or identified as having an infectious disease.

Embodiment C148. The method of embodiment C147, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment C149. A method of killing a cancer cell, an infected cell, or a senescent cell in a subject in need thereof, the method comprising administering to the subject a therapeutically effective amount of any of the multi-chain chimeric polypeptides of embodiments C1-C100 or the composition of embodiment C101 or C102.

Embodiment C150. The method of embodiment C149, wherein the subject has been identified or diagnosed as having a cancer.

Embodiment C151. The method of embodiment C150, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment C152. The method of embodiment C149, wherein the subject has been identified or diagnosed as having an aging-related disease or condition.

Embodiment C153. The method of embodiment C152, wherein the aging-related disease or condition is selected from the group consisting of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Embodiment C154. A method of treating a subject in need thereof, the method comprising administering to the subject a therapeutically effective amount of any of the multi-chain chimeric polypeptides of embodiments C1-C100 or the composition of embodiment C101 or C102.

Embodiment C155. The method of embodiment C154, wherein the subject has been identified or diagnosed as having a cancer or infectious disease.

Embodiment C156. The method of embodiment C157, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment C157. The method of embodiment C154, wherein the subject has been identified or diagnosed as having age-related disease or condition.

Embodiment C158. The method of embodiment C157, wherein the age-related disease or condition is selected from the group consisting of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment C159. The method of embodiment C154, wherein the subject has been diagnosed or identified as having an infectious disease.

Embodiment C160. The method of embodiment C159, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment C161. Nucleic acid encoding any of the multi-chain chimeric polypeptides of any one of embodiments C1-C100.

Embodiment C162. A vector comprising the nucleic acid of embodiment C161.

Embodiment C163. The vector of embodiment C162, wherein the vector is an expression vector.

Embodiment C164. A cell comprising the nucleic acid of embodiment C161 or the vector of embodiment C162 or C163.

Embodiment C165. A method of producing a multi-chain chimeric polypeptide, the method comprising:

culturing the cell of embodiment C164 in a culture medium under conditions sufficient to result in the production of the multi-chain chimeric polypeptide; and recovering the multi-chain chimeric polypeptide from the cell and/or the culture medium.

Embodiment C166. A multi-chain chimeric polypeptide produced by the method of embodiment C165.

Embodiment C167. The multi-chain chimeric polypeptide of embodiment C12, wherein the soluble human tissue factor domain comprises a sequence that is at least 80% identical to SEQ ID NO: 3.

Embodiment C168. The multi-chain chimeric polypeptide of embodiment C167, wherein the soluble human tissue factor domain comprises a sequence that is at least 90% identical to SEQ ID NO: 3.

Embodiment C169. The multi-chain chimeric polypeptide of embodiment C168, wherein the soluble human tissue factor domain comprises a sequence that is at least 95% identical to SEQ ID NO: 3.

Embodiment C170. The multi-chain chimeric polypeptide of embodiment C169, wherein the soluble human tissue factor domain comprises a sequence that is 100% identical to SEQ ID NO: 3.

Embodiment C171. The multi-chain chimeric polypeptide of embodiment C12, wherein the soluble human tissue factor domain comprises a sequence that is at least 80% identical to SEQ ID NO: 4.

Embodiment C172. The multi-chain chimeric polypeptide of embodiment C171, wherein the soluble human tissue factor domain comprises a sequence that is at least 90% identical to SEQ ID NO: 4.

Embodiment C173. The multi-chain chimeric polypeptide of embodiment C172, wherein the soluble human tissue factor domain comprises a sequence that is at least 95% identical to SEQ ID NO: 4.

Embodiment C174. The multi-chain chimeric polypeptide of embodiment C173, wherein the soluble human tissue factor domain comprises a sequence that is 100% identical to SEQ ID NO: 4.

D. Exemplary Embodiments

Embodiment D1. A multi-chain chimeric polypeptide comprising:

(c) a first chimeric polypeptide comprising:
 (i) a first target-binding domain;
 (ii) a soluble tissue factor domain; and
 (iii) a first domain of a pair of affinity domains;
(d) a second chimeric polypeptide comprising:
 (i) a second domain of a pair of affinity domains; and
 (ii) a second target-binding domain, wherein:

the first chimeric polypeptide and the second chimeric polypeptide associate through the binding of the first domain and the second domain of the pair of affinity domains;

the first target-binding domain and the second targeting-binding domain each independently bind specifically to a receptor of IL-21 or a receptor of IL-7.

Embodiment D2. The multi-chain chimeric polypeptide of embodiment D1, wherein the first target-binding domain and the soluble tissue factor domain directly abut each other in the first chimeric polypeptide.

Embodiment D3. The multi-chain chimeric polypeptide of embodiment D1, wherein the first chimeric polypeptide further comprises a linker sequence between the first target-binding domain and the soluble tissue factor domain in the first chimeric polypeptide.

Embodiment D4. The multi-chain chimeric polypeptide of any one of embodiments D1-D3, wherein the soluble tissue factor domain and the first domain of the pair of affinity domains directly abut each other in the first chimeric polypeptide.

Embodiment D5. The multi-chain chimeric polypeptide of any one of embodiments D1-D3, wherein the first chimeric polypeptide further comprises a linker sequence between the soluble tissue factor domain and the first domain of the pair of affinity domains in the first chimeric polypeptide.

Embodiment D6. The multi-chain chimeric polypeptide of any one of embodiments D1-D5, wherein the second domain of the pair of affinity domains and the second target-binding domain directly abut each other in the second chimeric polypeptide.

Embodiment D7. The multi-chain chimeric polypeptide of any one of embodiments D1-D5, wherein second chimeric polypeptide further comprises a linker sequence between the second domain of the pair of affinity domains and the second target-binding domain in the second chimeric polypeptide.

Embodiment D8. The multi-chain chimeric polypeptide of any one of embodiments D1-D7, wherein the soluble tissue factor domain is a soluble human tissue factor domain.

Embodiment D9. The multi-chain chimeric polypeptide of embodiment D8, wherein the soluble human tissue factor domain comprises a sequence that is at least 80% identical to SEQ ID NO: 1.

Embodiment D10. The multi-chain chimeric polypeptide of embodiment D9, wherein the soluble human tissue factor domain comprises a sequence that is at least 90% identical to SEQ ID NO: 1.

Embodiment D11. The multi-chain chimeric polypeptide of embodiment D10, wherein the soluble human tissue factor domain comprises a sequence that is at least 95% identical to SEQ ID NO: 1.

Embodiment D12. The multi-chain chimeric polypeptide of embodiment D11, wherein the soluble human tissue factor domain comprises SEQ ID NO: 1.

Embodiment D13. The multi-chain chimeric polypeptide of embodiment D8, wherein the soluble human tissue factor domain comprises a sequence that is at least 80% identical to SEQ ID NO: 3.

Embodiment D14. The multi-chain chimeric polypeptide of embodiment D13, wherein the soluble human tissue factor domain comprises a sequence that is at least 90% identical to SEQ ID NO: 3.

Embodiment D15. The multi-chain chimeric polypeptide of embodiment D14, wherein the soluble human tissue factor domain comprises a sequence that is at least 95% identical to SEQ ID NO: 3.

Embodiment D16. The multi-chain chimeric polypeptide of embodiment D15, wherein the soluble human tissue factor domain comprises SEQ ID NO: 3.

Embodiment D17. The multi-chain chimeric polypeptide of embodiment D8, wherein the soluble human tissue factor domain comprises a sequence that is at least 80% identical to SEQ ID NO: 4.

Embodiment D18. The multi-chain chimeric polypeptide of embodiment D17, wherein the soluble human tissue factor domain comprises a sequence that is at least 90% identical to SEQ ID NO: 4.

Embodiment D19. The multi-chain chimeric polypeptide of embodiment D18, wherein the soluble human tissue factor domain comprises a sequence that is at least 95% identical to SEQ ID NO: 4.

Embodiment D20. The multi-chain chimeric polypeptide of embodiment D19, wherein the soluble human tissue factor domain comprises SEQ ID NO: 4.

Embodiment D21. The multi-chain chimeric polypeptide of any one of embodiments D8-D11, D13-D15, and D17-D19, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment D22. The multi-chain chimeric polypeptide of embodiment D21, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment D23. The multi-chain chimeric polypeptide of any one of embodiments D1-D22, wherein the soluble tissue factor domain is not capable of binding to Factor VIIa.

Embodiment D24. The multi-chain chimeric polypeptide of any one of embodiments D1-D23, wherein the soluble tissue factor domain does not convert inactive Factor X into Factor Xa.

Embodiment D25. The multi-chain chimeric polypeptide of any one of embodiments D1-D24, wherein the multi-chain chimeric polypeptide does not stimulate coagulation in a mammal.

Embodiment D26. The multi-chain chimeric polypeptide of any one of embodiments D1-D25, wherein the first chimeric polypeptide further comprises a peptide tag at the N-terminal end or the C-terminal end of the first chimeric polypeptide.

Embodiment D27. The multi-chain chimeric polypeptide of any one of embodiments D1-D26, wherein the second chimeric polypeptide further comprises a peptide tag at the N-terminal end or the C-terminal end of the second chimeric polypeptide.

Embodiment D28. The multi-chain chimeric polypeptide of any one of embodiments D1-D27, wherein the first chimeric polypeptide and/or the second chimeric polypeptide further comprises a signal sequence at its N-terminal end.

Embodiment D29. The multi-chain chimeric polypeptide of embodiment D28, wherein the signal sequence comprises SEQ ID NO: 31.

Embodiment D30. The multi-chain chimeric polypeptide of embodiment D28, wherein the signal sequence is SEQ ID NO: 223.

Embodiment D31. The multi-chain chimeric polypeptide of any one of embodiments D1-D30, wherein the pair of affinity domains is a sushi domain from an alpha chain of human IL-15 receptor (IL15Rα) and a soluble IL-15.

Embodiment D32. The multi-chain chimeric polypeptide of embodiment D31, wherein the soluble IL-15 has a D8N or D8A amino acid substitution.

Embodiment D33. The multi-chain chimeric polypeptide of embodiment D31, wherein the soluble IL-15 comprises a sequence that is at least 80% identical to SEQ ID NO: 14.

Embodiment D34. The multi-chain chimeric polypeptide of embodiment D33, wherein the soluble IL-15 comprises a sequence that is at least 90% identical to SEQ ID NO: 14.

Embodiment D35. The multi-chain chimeric polypeptide of embodiment D34, wherein the soluble IL-15 comprises a sequence that is at least 95% identical to SEQ ID NO: 14.

Embodiment D36. The multi-chain chimeric polypeptide of embodiment D35, wherein the soluble IL-15 comprises SEQ ID NO: 14.

Embodiment D37. The multi-chain chimeric polypeptide of any one of embodiments D31-D36, wherein the sushi domain of IL15Rα comprises a sushi domain from human IL15Rα.

Embodiment D38. The multi-chain chimeric polypeptide of embodiment D37, wherein the sushi domain from human IL15Rα comprises a sequence that is at least 80% identical to SEQ ID NO: 28.

Embodiment D39. The multi-chain chimeric polypeptide of embodiment D38, wherein the sushi domain from human IL15Rα comprises a sequence that is at least 90% identical to SEQ ID NO: 28.

Embodiment D40. The multi-chain chimeric polypeptide of embodiment D39, wherein the sushi domain from human IL15Rα comprises a sequence that is at least 95% identical to SEQ ID NO: 28.

Embodiment D41. The multi-chain chimeric polypeptide of embodiment D40, wherein the sushi domain from human IL15Rα comprises SEQ ID NO: 28.

Embodiment D42. The multi-chain chimeric polypeptide of embodiment D37, wherein the sushi domain from human IL15Rα is a mature full-length IL15Rα.

Embodiment D43. The multi-chain chimeric polypeptide of any one of embodiments D1-D30, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment D44. The multi-chain chimeric polypeptide of any one of embodiments D1-D43, wherein one or both of the first target-binding domain and the second target-binding domain is an agonistic antigen-binding domain.

Embodiment D45. The multi-chain chimeric polypeptide of embodiment D44, wherein the first target-binding domain and the second target-binding domain are each agonistic antigen-binding domains.

Embodiment D46. The multi-chain chimeric polypeptide of embodiment D44 or D45, wherein antigen-binding domain comprises a scFv or single-domain antibody.

Embodiment D47. The multi-chain chimeric polypeptide of any one of embodiments D1-D43, wherein one or both of the first target-binding domain and the second target-binding domain is a soluble IL-21 or a soluble IL-7.

Embodiment D48. The multi-chain chimeric polypeptide of embodiment D47, wherein the first target-binding domain and the second target-binding domain are each independently a soluble IL-21 or a soluble IL-7.

Embodiment D49. The multi-chain chimeric polypeptide of any one of embodiments D1-D48, wherein the first target-binding domain and the second target-binding domain both bind specifically to a receptor of IL-21 or a receptor of IL-7.

Embodiment D50. The multi-chain chimeric polypeptide of embodiment D49, wherein the first target-binding domain and the second target-binding domain bind specifically to the same epitope.

Embodiment D51. The multi-chain chimeric polypeptide of embodiment D50, wherein the first target-binding domain and the second target-binding domain comprise the same amino acid sequence.

Embodiment D52. The multi-chain chimeric polypeptide of any one of embodiments D1-D48, wherein the first target-binding domain binds specifically to a receptor for IL-21, and the second target-binding domain binds specifically to a receptor for IL-7.

Embodiment D53. The multi-chain chimeric polypeptide of any one of embodiments D1-D48, wherein the first target-binding domain binds specifically to a receptor for IL-7, and the second target-binding domain bind specifically to a receptor for IL-21.

Embodiment D54. The multi-chain chimeric polypeptide of embodiment D53, wherein the first target-binding domain comprises a soluble IL-21.

Embodiment D55. The multi-chain chimeric polypeptide of embodiment D54, wherein the soluble IL-21 is a soluble human IL-21.

Embodiment D56. The multi-chain chimeric polypeptide of embodiment D55, wherein the soluble human IL-21 comprises a sequence at least 80% identical to SEQ ID NO: 78.

Embodiment D57. The multi-chain chimeric polypeptide of embodiment D56, wherein the soluble human IL-21 comprises a sequence at least 90% identical to SEQ ID NO: 78.

Embodiment D58. The multi-chain chimeric polypeptide of embodiment D57, wherein the soluble human IL-21 comprises a sequence at least 95% identical to SEQ ID NO: 78.

Embodiment D59. The multi-chain chimeric polypeptide of embodiment D58, wherein the soluble human IL-21 comprises a sequence of SEQ ID NO: 78.

Embodiment D60. The multi-chain chimeric polypeptide of any one of embodiments D53-D59, wherein the second target-binding domain comprises a soluble IL-7.

Embodiment D61. The multi-chain chimeric polypeptide of embodiment D60, wherein the soluble IL-7 is a soluble human TL-7.

Embodiment D62. The multi-chain chimeric polypeptide of embodiment D61, wherein the soluble human IL-7 comprises a sequence at least 80% identical to SEQ ID NO: 11.

Embodiment D63. The multi-chain chimeric polypeptide of embodiment D62, wherein the soluble human IL-7 comprises a sequence at least 90% identical to SEQ ID NO: 11.

Embodiment D64. The multi-chain chimeric polypeptide of embodiment D63, wherein the soluble human IL-7 comprises a sequence at least 95% identical to SEQ ID NO: 11.

Embodiment D65. The multi-chain chimeric polypeptide of embodiment D64, wherein the soluble human IL-7 comprises a sequence of SEQ ID NO: 11.

Embodiment D66. The multi-chain chimeric polypeptide of embodiment D1, wherein the first chimeric polypeptide comprises a sequence that is at least 80% identical to SEQ ID NO: 104.

Embodiment D67. The multi-chain chimeric polypeptide of embodiment D66, wherein the first chimeric polypeptide comprises a sequence that is at least 90% identical to SEQ ID NO: 104.

Embodiment D68. The multi-chain chimeric polypeptide of embodiment D67, wherein the first chimeric polypeptide comprises a sequence that is at least 95% identical to SEQ ID NO: 104.

Embodiment D69. The multi-chain chimeric polypeptide of embodiment D68, wherein the first chimeric polypeptide comprises SEQ ID NO: 104.

Embodiment D70. The multi-chain chimeric polypeptide of embodiment D69, wherein the first chimeric polypeptide comprises SEQ ID NO: 106.

Embodiment D71. The multi-chain chimeric polypeptide of any one of embodiments D1 and D66-D70, wherein the second chimeric polypeptide comprises a sequence that is at least 80% identical to SEQ ID NO: 108.

Embodiment D72. The multi-chain chimeric polypeptide of embodiment D71, wherein the second chimeric polypeptide comprises a sequence that is at least 90% identical to SEQ ID NO: 108.

Embodiment D73. The multi-chain chimeric polypeptide of embodiment D72, wherein the second chimeric polypeptide comprises a sequence that is at least 95% identical to SEQ ID NO: 108.

Embodiment D74. The multi-chain chimeric polypeptide of embodiment D73, wherein the second chimeric polypeptide comprises SEQ ID NO: 108.

Embodiment D75. The multi-chain chimeric polypeptide of embodiment D74, wherein the second chimeric polypeptide comprises SEQ ID NO: 110.

Embodiment D76. The multi-chain chimeric polypeptide of embodiment D1, wherein the first chimeric polypeptide comprises a sequence that is at least 80% identical to SEQ ID NO: 96.

Embodiment D77. The multi-chain chimeric polypeptide of embodiment D76, wherein the first chimeric polypeptide comprises a sequence that is at least 90% identical to SEQ ID NO: 96.

Embodiment D78. The multi-chain chimeric polypeptide of embodiment D77, wherein the first chimeric polypeptide comprises a sequence that is at least 95% identical to SEQ ID NO: 96.

Embodiment D79. The multi-chain chimeric polypeptide of embodiment D68, wherein the first chimeric polypeptide comprises SEQ ID NO: 96.

Embodiment D80. The multi-chain chimeric polypeptide of embodiment D69, wherein the first chimeric polypeptide comprises SEQ ID NO: 98.

Embodiment D81. The multi-chain chimeric polypeptide of any one of embodiments D1 and D76-D80, wherein the second chimeric polypeptide comprises a sequence that is at least 80% identical to SEQ ID NO: 100.

Embodiment D82. The multi-chain chimeric polypeptide of embodiment D81, wherein the second chimeric polypeptide comprises a sequence that is at least 90% identical to SEQ ID NO: 100.

Embodiment D83. The multi-chain chimeric polypeptide of embodiment D82, wherein the second chimeric polypeptide comprises a sequence that is at least 95% identical to SEQ ID NO: 100.

Embodiment D84. The multi-chain chimeric polypeptide of embodiment D83, wherein the second chimeric polypeptide comprises SEQ ID NO: 100.

Embodiment D85. The multi-chain chimeric polypeptide of embodiment D84, wherein the second chimeric polypeptide comprises SEQ ID NO: 106.

Embodiment D86. The multi-chain chimeric polypeptide of any one of embodiments D1-D65, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment D87. The multi-chain chimeric polypeptide of embodiment D86, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment D88. The multi-chain chimeric polypeptide of any one of embodiments D1-D65, wherein the first chimeric polypeptide further comprises one or more additional target-binding domains at the N-terminal and/or C-terminal end of the first chimeric polypeptide.

Embodiment D89. The multi-chain chimeric polypeptide of embodiment D88, wherein at least one of the one or more additional target-binding domains directly abuts the first domain of the pair of affinity domains in the first chimeric polypeptide.

Embodiment D90. The multi-chain chimeric polypeptide of embodiment D88, wherein the first chimeric polypeptide further comprises a linker sequence between the at least one of the one or more additional target-binding domains and the first domain of the pair of affinity domains.

Embodiment D91. The multi-chain chimeric polypeptide of embodiment D88, wherein the at least one of the one or more additional target-binding domains directly abuts the first target-binding domain in the first chimeric polypeptide.

Embodiment D92. The multi-chain chimeric polypeptide of embodiment D88, wherein the first chimeric polypeptide further comprises a linker sequence between the at least one of the one or more additional target-binding domains and the first target-binding domain.

Embodiment D93. The multi-chain chimeric polypeptide of embodiment D88, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment D94. The multi-chain chimeric polypeptide of embodiment D93, wherein the at least one additional target-binding domain of the one or more additional target-binding domains disposed at the N-terminus directly abuts the first target-binding domain or the first domain of the pair of affinity domains in the first chimeric polypeptide.

Embodiment D95. The multi-chain chimeric polypeptide of embodiment D93, wherein the first chimeric polypeptide further comprises a linker sequence disposed between the at least one additional target-binding domain and the first target-binding domain or the first domain of the pair of affinity domains in the first chimeric polypeptide.

Embodiment D96. The multi-chain chimeric polypeptide of embodiment D93, wherein the at least one additional target-binding domain of the one or more additional target-binding domains disposed at the C-terminus directly abuts the first target-binding domain or the first domain of the pair of affinity domains in the first chimeric polypeptide.

Embodiment D97. The multi-chain chimeric polypeptide of embodiment D93, wherein the first chimeric polypeptide further comprises a linker sequence disposed between the at least one additional target-binding domain and the first target-binding domain or the first domain of the pair of affinity domains in the first chimeric polypeptide.

Embodiment D98. The multi-chain chimeric polypeptide of embodiment D93, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment D99. The multi-chain chimeric polypeptide of embodiment D93, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment D100. The multi-chain chimeric polypeptide of any one of embodiments D1-D65 and D86-D99, wherein the second chimeric polypeptide further comprises one or more additional target-binding domains at the N-terminal end or the C-terminal end of the second chimeric polypeptide.

Embodiment D101. The multi-chain chimeric polypeptide of embodiment D100, wherein at least one of the one or more additional target-binding domains directly abuts the second domain of the pair of affinity domains in the second chimeric polypeptide.

Embodiment D102. The multi-chain chimeric polypeptide of embodiment D100, wherein the second chimeric polypeptide further comprises a linker sequence between at least one of the one or more additional target-binding domains and the second domain of the pair of affinity domains in the second chimeric polypeptide.

Embodiment D103. The multi-chain chimeric polypeptide of embodiment D100, wherein at least one of the one or more additional target-binding domains directly abuts the second target-binding domain in the second chimeric polypeptide.

Embodiment D104. The multi-chain chimeric polypeptide of embodiment D100, wherein the second chimeric polypeptide further comprises a linker sequence between at least one of the one or more additional target-binding domains and the second target-binding domain in the second chimeric polypeptide.

Embodiment D105. The multi-chain chimeric polypeptide of any one of embodiments D86-D104, wherein two or more of the first target-binding domain, the second target-binding domain, and the one or more additional target-binding domains bind specifically to the same antigen.

Embodiment D106. The multi-chain chimeric polypeptide of embodiment D105, wherein two or more of the first target-binding domain, the second target-binding domain, and the one or more additional target-binding domains bind specifically to the same epitope.

Embodiment D107. The multi-chain chimeric polypeptide of embodiment D106, wherein two or more of the first target-binding domain, the second target-binding domain, and the one or more additional target-binding domains comprise the same amino acid sequence.

Embodiment D108. The multi-chain chimeric polypeptide of any one of embodiments D86-D104, wherein the first target-binding domain, the second target-binding domain, and the one or more additional target-binding domains bind specifically to different antigens.

Embodiment D109. The multi-chain chimeric polypeptide of any one of embodiments D86-D108, wherein the one or more additional antigen-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD28.

Embodiment D110. The multi-chain chimeric polypeptide of any one of embodiments D86-D108, wherein the one or more additional target-binding domains is a soluble interleukin or cytokine protein.

Embodiment D111. The multi-chain chimeric polypeptide of embodiment D110, wherein the soluble interleukin, cytokine, or ligand protein is selected from the group consisting of: IL-1, IL-2, IL-3, IL-7, IL-8, IL-10, IL-12, IL-15, IL-17, IL-18, IL-21, PDGF-DD, SCF, and FLT3L.

Embodiment D112. The multi-chain chimeric polypeptide of any one of embodiments D86-D108, wherein the one or more additional target-binding domains is a soluble interleukin or cytokine receptor.

Embodiment D113. The multi-chain chimeric polypeptide of embodiment D112, wherein the soluble receptor is a soluble TGF-β receptor II (TGF-βRII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, a soluble CD122, or a soluble CD28.

Embodiment D114. A composition comprising any of the multi-chain chimeric polypeptides of embodiments D1-D113.

Embodiment D115. The composition of embodiment D114, wherein the composition is a pharmaceutical composition.

Embodiment D116. A kit comprising at least one dose of the composition of embodiment D114 or D115.

Embodiment D117. A method of stimulating an immune cell, the method comprising:

contacting an immune cell with an effective amount of any of the multi-chain chimeric polypeptides of embodiments D1-D113 or the composition of embodiment D114 or D115.

Embodiment D118. The method of embodiment D117, wherein the immune cell is contacted in vitro.

Embodiment D119. The method of embodiment D118, wherein the immune cell was previously obtained from a subject.

Embodiment D120. The method of embodiment D119, wherein the method further comprises obtaining the immune cell from the subject prior to the contacting step.

Embodiment D121. The method of embodiment D117, wherein the immune cell is contacted in vivo.

Embodiment D122. The method of any one of embodiments D117-D121, wherein the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a $CD8^+$ T cell, a $CD4^+$ T cell, a natural killer T cell, a mast cell, a macrophage, a neutrophil, a dendritic cell, a basophil, an eosinophil, and a natural killer cell.

Embodiment D123. The method of any one of embodiments D117-D122, wherein the immune cell has previously been genetically modified to express a chimeric antigen receptor or a recombinant T-cell receptor.

Embodiment D124. The method of any one of embodiments D117-D122, wherein the method further comprises, after the contacting step, introducing into the immune cell a nucleic acid encoding a chimeric antigen-receptor or a recombinant T-cell receptor.

Embodiment D125. The method of any one of embodiments D117-D124, wherein the method further comprises administering the immune cell to a subject in need thereof.

Embodiment D126. The method of embodiment D125, wherein the subject has been identified or diagnosed as having age-related disease or condition.

Embodiment D127. The method of embodiment D126, wherein the age-related disease or condition is selected from the group consisting of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment D128. The method of embodiment D125, wherein the subject has been identified or diagnosed as having a cancer.

Embodiment D129. The method of embodiment D128, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment D130. The method of embodiment D125, wherein the subject has been diagnosed or identified as having an infectious disease.

Embodiment D131. The method of embodiment D130, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Embodiment D132. A method of inducing or increasing proliferation of an immune cell, the method comprising:

contacting an immune cell with an effective amount of any of the multi-chain chimeric polypeptides of embodiments D1-D113 or the composition of embodiment D114 or D115.

Embodiment D133. The method of embodiment D132, wherein the immune cell is contacted in vitro.

Embodiment D134. The method of embodiment D133, wherein the immune cell was previously obtained from a subject.

Embodiment D135. The method of embodiment D134, wherein the method further comprises obtaining the immune cell from the subject prior to the contacting step.

Embodiment D136. The method of embodiment D132, wherein the immune cell is contacted in vivo.

Embodiment D137. The method of any one of embodiments D132-D136, wherein the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell.

Embodiment D138. The method of any one of embodiments D132-D137, wherein the immune cell has previously been genetically modified to express a chimeric antigen receptor or a recombinant T-cell receptor.

Embodiment D139. The method of any one of embodiments D132-D137, wherein the method further comprises, after the contacting step, introducing into the immune cell a nucleic acid encoding a chimeric antigen-receptor or a recombinant T-cell receptor.

Embodiment D140. The method of any one of embodiments D132-D139, wherein the method further comprises administering the immune cell to a subject in need thereof.

Embodiment D141. The method of embodiment D140, wherein the subject has been identified or diagnosed as having an age-related disease or condition.

Embodiment D142. The method of embodiment D141, wherein the age-related disease or condition is selected from the group consisting of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment D143. The method of embodiment D140, wherein the subject has been identified or diagnosed as having a cancer.

Embodiment D144. The method of embodiment D143, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment D145. The method of embodiment D140, wherein the subject has been diagnosed or identified as having an infectious disease.

Embodiment D146. The method of embodiment D140, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Embodiment D147. A method of inducing differentiation of an immune cell into a memory or memory-like immune cell, the method comprising:

contacting an immune cell with an effective amount of any of the multi-chain chimeric polypeptides of embodiments D1-D113 or the composition of embodiment D114 or D115.

Embodiment D148. The method of embodiment D147, wherein the immune cell is contacted in vitro.

Embodiment D149. The method of embodiment D148, wherein the immune cell was previously obtained from a subject.

Embodiment D150. The method of embodiment D149, wherein the method further comprises obtaining the immune cell from the subject prior to the contacting step.

Embodiment D151. The method of embodiment D147, wherein the immune cell is contacted in vivo.

Embodiment D152. The method of any one of embodiments D147-D151, wherein the immune cell is selected from the group consisting of: an immature thymocyte, a peripheral blood lymphocyte, a naïve T cell, a pluripotent Th cell precursor, a lymphoid progenitor cell, a Treg cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell.

Embodiment D153. The method of any one of embodiments D147-D152, wherein the immune cell has previously been genetically modified to express a chimeric antigen receptor or a recombinant T-cell receptor.

Embodiment D154. The method of any one of embodiments D147-D152, wherein the method further comprises, after the contacting step, introducing into the immune cell a nucleic acid encoding a chimeric antigen-receptor or a recombinant T-cell receptor.

Embodiment D155: The method of any one of embodiments D147-D153, wherein the immune cell is contacted with anti-TF IgG antibody to create a memory or memory like immune cell.

Embodiment D156. The method of any one of embodiments D147-D155, wherein the method further comprises administering the immune cell to a subject in need thereof.

Embodiment D157. The method of embodiment D156, wherein the subject has been identified or diagnosed as having an age-related disease or condition.

Embodiment D158. The method of embodiment D156, wherein the age-related disease or condition is selected from the group consisting of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment D159. The method of embodiment D156, wherein the subject has been identified or diagnosed as having a cancer.

Embodiment D160. The method of embodiment D159, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment D161. The method of embodiment D156, wherein the subject has been diagnosed or identified as having an infectious disease.

Embodiment D162. The method of embodiment D161, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Embodiment D163. A method of killing a cancer cell, an infected cell, or a senescent cell in a subject in need thereof, the method comprising administering to the subject a therapeutically effective amount of any of the multi-chain chimeric polypeptides of embodiments D1-D113 or the composition of embodiment D114 or D115.

Embodiment D164. The method of embodiment D163, wherein the subject has been identified or diagnosed as having a cancer.

Embodiment D165. The method of embodiment D164, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment D166. The method of embodiment D163, wherein the subject has been identified or diagnosed as having an aging-related disease or condition.

Embodiment D167. The method of embodiment D166, wherein the aging-related disease or condition is selected from the group consisting of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Embodiment D168. A method of treating a subject in need thereof, the method comprising administering to the subject a therapeutically effective amount of any of the multi-chain chimeric polypeptides of embodiments D1-D113 or the composition of embodiment D114 or D115.

Embodiment D169. The method of embodiment D168, wherein the subject has been identified or diagnosed as having a cancer or infectious disease.

Embodiment D170. The method of embodiment D169, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment D171. The method of embodiment D168, wherein the subject has been identified or diagnosed as having age-related disease or condition.

Embodiment D172. The method of embodiment D171, wherein the age-related disease or condition is selected from the group consisting of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment D173. The method of embodiment D168, wherein the subject has been diagnosed or identified as having an infectious disease.

Embodiment D174. The method of embodiment D173, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Embodiment D175. Nucleic acid encoding any of the multi-chain chimeric polypeptides of any one of embodiments D1-D113.

Embodiment D176. A vector comprising the nucleic acid of embodiment D174.

Embodiment D177. The vector of embodiment D176, wherein the vector is an expression vector.

Embodiment D178. A cell comprising the nucleic acid of embodiment D175 or the vector of embodiment D175 or D176.

Embodiment D179. A method of producing a multi-chain chimeric polypeptide, the method comprising:

culturing the cell of embodiment D177 in a culture medium under conditions sufficient to result in the production of the multi-chain chimeric polypeptide; and recovering the multi-chain chimeric polypeptide from the cell and/or the culture medium.

Embodiment D180. A multi-chain chimeric polypeptide produced by the method of embodiment D179.

E. Exemplary Embodiments

Embodiment E1. A multi-chain chimeric polypeptide comprising:

(e) a first chimeric polypeptide comprising:
  (i) a first target-binding domain;
  (ii) a soluble tissue factor domain; and
  (iii) a first domain of a pair of affinity domains;
(f) a second chimeric polypeptide comprising:
  (i) a second domain of a pair of affinity domains; and
  (ii) a second target-binding domain, wherein:

the first chimeric polypeptide and the second chimeric polypeptide associate through the binding of the first domain and the second domain of the pair of affinity domains; and the first target-binding domain and the second targeting-binding domain each independently bind specifically to: a receptor for IL-7, CD16, a receptor for IL-21, TGF-3, or a receptor for CD137L.

Embodiment E2. The multi-chain chimeric polypeptide of embodiment E1, wherein the first target-binding domain and the soluble tissue factor domain directly abut each other in the first chimeric polypeptide.

Embodiment E3. The multi-chain chimeric polypeptide of embodiment E1, wherein the first chimeric polypeptide further comprises a linker sequence between the first target-binding domain and the soluble tissue factor domain in the first chimeric polypeptide.

Embodiment E4. The multi-chain chimeric polypeptide of any one of embodiments E1-E3, wherein the soluble tissue factor domain and the first domain of the pair of affinity domains directly abut each other in the first chimeric polypeptide.

Embodiment E5. The multi-chain chimeric polypeptide of any one of embodiments E1-E3, wherein the first chimeric polypeptide further comprises a linker sequence between the soluble tissue factor domain and the first domain of the pair of affinity domains in the first chimeric polypeptide.

Embodiment E6. The multi-chain chimeric polypeptide of any one of embodiments E1-E5, wherein the second domain of the pair of affinity domains and the second target-binding domain directly abut each other in the second chimeric polypeptide.

Embodiment E7. The multi-chain chimeric polypeptide of any one of embodiments E1-E5, wherein second chimeric polypeptide further comprises a linker sequence between the second domain of the pair of affinity domains and the second target-binding domain in the second chimeric polypeptide.

Embodiment E8. The multi-chain chimeric polypeptide of any one of embodiments E1-E7, wherein the soluble tissue factor domain is a soluble human tissue factor domain.

Embodiment E9. The multi-chain chimeric polypeptide of embodiment E8, wherein the soluble human tissue factor domain comprises a sequence that is at least 80% identical to SEQ ID NO: 1.

Embodiment E10. The multi-chain chimeric polypeptide of embodiment E9, wherein the soluble human tissue factor domain comprises a sequence that is at least 90% identical to SEQ ID NO: 1.

Embodiment E11. The multi-chain chimeric polypeptide of embodiment E10, wherein the soluble human tissue factor domain comprises a sequence that is at least 95% identical to SEQ ID NO: 1.

Embodiment E12. The multi-chain chimeric polypeptide of any one of embodiments E8-E11, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment E13. The multi-chain chimeric polypeptide of embodiment E12, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment E14. The multi-chain chimeric polypeptide of any one of embodiments E1-E13, wherein the soluble tissue factor domain is not capable of binding to Factor VIIa.

Embodiment E15. The multi-chain chimeric polypeptide of any one of embodiments E1-E14, wherein the soluble tissue factor domain does not convert inactive Factor X into Factor Xa.

Embodiment E16. The multi-chain chimeric polypeptide of any one of embodiments E1-E15, wherein the multi-chain chimeric polypeptide does not stimulate coagulation in a mammal.

Embodiment E17. The multi-chain chimeric polypeptide of any one of embodiments E1-E16, wherein the first chimeric polypeptide further comprises a peptide tag at the N-terminal end or the C-terminal end of the first chimeric polypeptide.

Embodiment E18. The multi-chain chimeric polypeptide of any one of embodiments E1-E17, wherein the second chimeric polypeptide further comprises a peptide tag at the N-terminal end or the C-terminal end of the second chimeric polypeptide.

Embodiment E19. The multi-chain chimeric polypeptide of any one of embodiments E1-E18, wherein the first chimeric polypeptide and/or the second chimeric polypeptide further comprises a signal sequence at its N-terminal end.

Embodiment E20. The multi-chain chimeric polypeptide of embodiment E19, wherein the signal sequence comprises SEQ ID NO: 31.

Embodiment E21. The multi-chain chimeric polypeptide of embodiment E20, wherein the signal sequence is SEQ ID NO: 31.

Embodiment E22. The multi-chain chimeric polypeptide of any one of embodiments E1-E21, wherein the pair of affinity domains is a sushi domain from an alpha chain of human IL-15 receptor (IL15Rα) and a soluble IL-15.

Embodiment E23. The multi-chain chimeric polypeptide of embodiment E22, wherein the soluble IL-15 has a D8N or D8A amino acid substitution.

Embodiment E24. The multi-chain chimeric polypeptide of embodiment E22, wherein the soluble IL-15 comprises a sequence that is 80% identical to SEQ ID NO: 14.

Embodiment E25. The multi-chain chimeric polypeptide of embodiment E24, wherein the soluble IL-15 comprises a sequence that is 90% identical to SEQ ID NO: 14.

Embodiment E26. The multi-chain chimeric polypeptide of embodiment E25, wherein the soluble IL-15 comprises a sequence that is 95% identical to SEQ ID NO: 14.

Embodiment E27. The multi-chain chimeric polypeptide of embodiment E26, wherein the soluble IL-15 comprises SEQ ID NO: 14.

Embodiment E28. The multi-chain chimeric polypeptide of any one of embodiments E22-E27, wherein the sushi domain of IL15Rα comprises a sushi domain from human IL15Rα.

Embodiment E29. The multi-chain chimeric polypeptide of embodiment E28, wherein the sushi domain from human IL15Rα comprises a sequence that is 80% identical to SEQ ID NO: 28.

Embodiment E30. The multi-chain chimeric polypeptide of embodiment E29, wherein the sushi domain from human IL15Rα comprises a sequence that is 90% identical to SEQ ID NO: 28.

Embodiment E31. The multi-chain chimeric polypeptide of embodiment E30, wherein the sushi domain from human IL15Rα comprises a sequence that is 95% identical to SEQ ID NO: 28.

Embodiment E32. The multi-chain chimeric polypeptide of embodiment E31, wherein the sushi domain from human IL15Rα comprises SEQ ID NO: 28.

Embodiment E33. The multi-chain chimeric polypeptide of embodiment E28, wherein the sushi domain from human IL15Rα is a mature full-length IL15Rα.

Embodiment E34. The multi-chain chimeric polypeptide of any one of embodiments E1-E21, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment E35. The multi-chain chimeric polypeptide of any one of embodiments E1-E34, wherein the first target-binding domain and the second targeting-binding domain each independently bind specifically to a receptor for IL-7, CD16, or a receptor for IL-21.

Embodiment E36. The multi-chain chimeric polypeptide of embodiment E35, wherein the first target-binding domain binds specifically to a receptor IL-7 and the second target-binding domain binds specifically to CD16 or a receptor for IL-21.

Embodiment E37. The multi-chain chimeric polypeptide of embodiment E36, wherein the first target-binding domain comprises a soluble IL-7 protein.

Embodiment E38. The multi-chain chimeric polypeptide of embodiment E37, wherein the soluble IL-7 protein is a soluble human IL-7.

Embodiment E39. The multi-chain chimeric polypeptide of any one of embodiments E36-E38, wherein the second antigen-binding domain comprises an antigen-binding domain that binds specifically to CD16.

Embodiment E40. The multi-chain chimeric polypeptide of embodiment E39, wherein the second antigen-binding domain comprises an scFv that binds specifically to CD16.

Embodiment E41. The multi-chain chimeric polypeptide of any one of embodiments E36-E38, wherein the second antigen-binding domain bind specifically to a receptor for IL-21.

Embodiment E42. The multi-chain chimeric polypeptide of embodiment E41, wherein the second antigen-binding domain comprises a soluble IL-21.

Embodiment E43. The multi-chain chimeric polypeptide of embodiment E42, wherein the soluble IL-21 is a soluble human IL-21.

Embodiment E44. The multi-chain chimeric polypeptide of any one of embodiments E36-E40, wherein the second chimeric polypeptide further comprises an additional target-binding domain that binds specifically to a receptor for IL-21.

Embodiment E45. The multi-chain chimeric polypeptide of embodiment E44, wherein the additional target-binding domain comprises a soluble IL-21.

Embodiment E46. The multi-chain chimeric polypeptide of embodiment E45, wherein the soluble IL-21 is a soluble human IL-12.

Embodiment E47. The multi-chain chimeric polypeptide of any one of embodiments E1-E34, wherein the first target-binding domain and the second targeting-binding domain each independently bind specifically to TGF-β, CD16, or a receptor for IL-21.

Embodiment E48. The multi-chain chimeric polypeptide of embodiment E47, wherein the first target-binding domain binds specifically to a TGF-β and the second target-binding domain binds specifically to CD16 or a receptor of IL-21.

Embodiment E49. The multi-specific chimeric polypeptide of embodiment E48, wherein the first target-binding domain is a soluble TGF-β receptor.

Embodiment E50. The multi-specific chimeric polypeptide of embodiment E49, wherein soluble TGF-β receptor is a soluble TGFβRII receptor.

Embodiment E51. The multi-specific chimeric polypeptide of any one of embodiments E48-E50, wherein the second target-binding domain binds specifically to CD16.

Embodiment E52. The multi-specific chimeric polypeptide of embodiment E51, wherein the second antigen-binding domain comprises an antigen-binding domain that binds specifically to CD16.

Embodiment E53. The multi-chain chimeric polypeptide of embodiment E52, wherein the second antigen-binding domain comprises an scFv that binds specifically to CD16.

Embodiment E54. The multi-chain chimeric polypeptide of any one of embodiments E48-E50, wherein the second target-binding domain binds specifically to a receptor for IL-21.

Embodiment E55. The multi-chain chimeric polypeptide of embodiment E54, wherein the second target-binding domain comprises a soluble IL-21.

Embodiment E56. The multi-chain chimeric polypeptide of embodiment E55, wherein the second target-binding domain comprises a soluble human IL-21.

Embodiment E57. The multi-chain chimeric polypeptide of any one of embodiments E48-E53, wherein the second chimeric polypeptide further comprises an additional target-binding domain that binds specifically to a receptor for IL-21.

Embodiment E58. The multi-chain chimeric polypeptide of embodiment E57, wherein the additional target-binding domain comprises a soluble IL-21.

Embodiment E59. The multi-chain chimeric polypeptide of embodiment E58, wherein the soluble IL-21 is a soluble human IL-21.

Embodiment E60. The multi-chain chimeric polypeptide of any one of embodiments E1-E34, wherein the first target-binding domain and the second target-binding domain each independently bind specifically to a receptor for IL-7.

Embodiment E61. The multi-chain chimeric polypeptide of embodiment E60, wherein the first target-binding domain and the second target-binding domain include a soluble IL-7.

Embodiment E62. The multi-chain chimeric polypeptide of embodiment E61, wherein the soluble IL-7 is a soluble human IL-7.

Embodiment E63. The multi-chain chimeric polypeptide of any one of embodiments E1-E34, wherein the first target-binding domain and the second target-binding domain each independently bind specifically to TGF-β.

Embodiment E64. The multi-specific chimeric polypeptide of embodiment E63, wherein the first target-binding domain and the second target-binding domain is a soluble TGF-β receptor.

Embodiment E65. The multi-specific chimeric polypeptide of embodiment E64, wherein the soluble TGF-β receptor is a soluble TGFβRII receptor.

Embodiment E66. The multi-specific chimeric polypeptide of any one of embodiments E1-E34, wherein the first target-binding domain and the second targeting-binding domain each independently bind specifically to a receptor for IL-7, a receptor for IL-21, or a receptor for CD137L.

Embodiment E67. The multi-chain chimeric polypeptide of embodiment E66, wherein the first target-binding domain binds specifically to a receptor for IL-7 and the second target-binding domain binds specifically to a receptor for IL-21 or a receptor for CD137L.

Embodiment E68. The multi-specific chimeric polypeptide of embodiment E67, wherein the first target-binding domain is a soluble IL-7.

Embodiment E69. The multi-specific chimeric polypeptide of embodiment E68, wherein the soluble IL-7 is a soluble human IL-7.

Embodiment E70. The multi-chain chimeric polypeptide of any one of embodiments E67-E69, wherein the second target-binding domain binds specifically to a receptor for IL-21.

Embodiment E71. The multi-chain chimeric polypeptide of embodiment E70, wherein the second target-binding domain is a soluble IL-21.

Embodiment E72. The multi-chain chimeric polypeptide of embodiment E71, wherein the soluble IL-21 is a soluble human IL-21.

Embodiment E73. The multi-chain chimeric polypeptide of any one of embodiments E67-E69, wherein the second antigen-binding domain binds specifically to a receptor for CD137L.

Embodiment E74. The multi-chain chimeric polypeptide of embodiment E73, wherein the second antigen-binding domain is a soluble CD137L.

Embodiment E75. The multi-chain chimeric polypeptide of embodiment E74, wherein the soluble CD137L is a soluble human CD137L.

Embodiment E76. The multi-chain chimeric polypeptide of any one of embodiments E67-E72, wherein the second chimeric polypeptide further comprises an additional target-binding domain that binds specifically to a receptor for CD137L.

Embodiment E77. The multi-chain chimeric polypeptide of embodiment E76, wherein the additional target-binding domain comprises a soluble CD137L.

Embodiment E78. The multi-chain chimeric polypeptide of embodiment E77, wherein the soluble CD137L is a soluble human CD137L.

Embodiment E79. The multi-chain chimeric polypeptide of any one of embodiments E1-E34, wherein the first target-binding domain and the second targeting-binding domain each independently bind specifically to a receptor for IL-7 or TGF-β.

Embodiment E80. The multi-chain chimeric polypeptide of embodiment E79, wherein the first target-binding domain binds specifically to a receptor IL-7 and the second target-binding domain binds specifically to TGF-β.

Embodiment E81. The multi-chain chimeric polypeptide of embodiment E80, wherein the first target-binding domain comprises a soluble IL-7 protein.

Embodiment E82. The multi-chain chimeric polypeptide of embodiment E81, wherein the soluble IL-7 protein is a soluble human IL-7.

Embodiment E83. The multi-chain chimeric polypeptide of any one of embodiments E80-E82, wherein the second antigen-binding domain comprises an antigen-binding domain that binds specifically to TGF-β.

Embodiment E84. The multi-specific chimeric polypeptide of embodiment E83, wherein the second target-binding domain is a soluble TGF-β receptor.

Embodiment E85. The multi-specific chimeric polypeptide of embodiment E84, wherein the soluble TGF-β receptor is a soluble TGFβRII receptor.

Embodiment E86. The multi-chain chimeric polypeptide of any one of embodiments E1-E34, wherein the first target-binding domain and the second targeting-binding domain each independently bind specifically to TGF-β, a receptor for IL-21, or a receptor for CD137L.

Embodiment E87. The multi-chain chimeric polypeptide of embodiment E86, wherein the first target-binding domain binds specifically to a TGF-β and the second target-binding domain binds specifically to a receptor for IL-21 or a receptor for CD137L.

Embodiment E88. The multi-specific chimeric polypeptide of embodiment E87, wherein the first target-binding domain is a soluble TGF-β receptor.

Embodiment E89. The multi-specific chimeric polypeptide of embodiment E88, wherein the soluble TGF-β receptor is a soluble TGFβRII receptor.

Embodiment E90. The multi-specific chimeric polypeptide of any one of embodiments E87-E89, wherein the second target-binding domain binds specifically to a receptor for IL-21.

Embodiment E91. The multi-chain chimeric polypeptide of embodiment E90, wherein the second target-binding domain comprises a soluble IL-21.

Embodiment E92. The multi-chain chimeric polypeptide of embodiment E91, wherein the second target-binding domain comprises a soluble human IL-21.

Embodiment E93. The multi-specific chimeric polypeptide of any one of embodiments E87-E89, wherein the second target-binding domain binds specifically to a receptor for CD137L.

Embodiment E94. The multi-chain chimeric polypeptide of embodiment E93, wherein the second target-binding domain comprises a soluble CD137L.

Embodiment E95. The multi-chain chimeric polypeptide of embodiment E94, wherein the second target-binding domain comprises a soluble human CD137L.

Embodiment E96. The multi-chain chimeric polypeptide of any one of embodiments E87-E92, wherein the second chimeric polypeptide further comprises an additional target-binding domain that binds specifically to a receptor for CD137L.

Embodiment E97. The multi-chain chimeric polypeptide of embodiment E96, wherein the additional target-binding domain comprises a soluble CD137L.

Embodiment E98. The multi-chain chimeric polypeptide of embodiment E97, wherein the soluble CD137L is a soluble human CD137L.

Embodiment E99. The multi-chain chimeric polypeptide of any one of embodiments E1-E34, wherein the first target-binding domain and the second targeting-binding domain each independently bind specifically to TGF-β or a receptor for IL-21.

Embodiment E100. The multi-chain chimeric polypeptide of embodiment E99, wherein the first target-binding domain binds specifically to a TGF-β and the second target-binding domain binds specifically to TGF-β or a receptor for IL-21.

Embodiment E101. The multi-specific chimeric polypeptide of embodiment E100, wherein the first target-binding domain is a soluble TGF-β receptor.

Embodiment E102. The multi-specific chimeric polypeptide of embodiment E101, wherein the soluble TGF-β receptor is a soluble TGFβRII receptor.

Embodiment E103. The multi-specific chimeric polypeptide of any one of embodiments E100-E102, wherein the second target-binding domain binds specifically to a receptor for IL-21.

Embodiment E104. The multi-chain chimeric polypeptide of embodiment E103, wherein the second target-binding domain comprises a soluble IL-21.

Embodiment E105. The multi-chain chimeric polypeptide of embodiment E104, wherein the second target-binding domain comprises a soluble human IL-21.

Embodiment E106. The multi-specific chimeric polypeptide of any one of embodiments E100-E102, wherein the second target-binding domain binds specifically to TGF-β.

Embodiment E107. The multi-specific chimeric polypeptide of embodiment E106, wherein the first target-binding domain is a soluble TGF-β receptor.

Embodiment E108. The multi-specific chimeric polypeptide of embodiment E107, wherein the soluble TGF-β receptor is a soluble TGFβRII receptor.

Embodiment E109. The multi-specific chimeric polypeptide of any one of embodiments E100-E105, wherein the second polypeptide further comprises an additional target-binding domain that binds specifically to TGF-β.

Embodiment E110. The multi-specific chimeric polypeptide of embodiment E109, wherein the first target-binding domain is a soluble TGF-β receptor.

Embodiment E111. The multi-specific chimeric polypeptide of embodiment E110, wherein the soluble TGF-β receptor is a soluble TGFβRII receptor.

Embodiment E112. The multi-chain chimeric polypeptide of any one of embodiments E1-E34, wherein the first target-binding domain and the second targeting-binding domain each independently bind specifically to TGF-β or IL-16.

Embodiment E113. The multi-chain chimeric polypeptide of embodiment E112, wherein the first target-binding domain binds specifically to a TGF-β and the second target-binding domain binds specifically to TGF-β or IL-16.

Embodiment E114. The multi-specific chimeric polypeptide of embodiment E113, wherein the first target-binding domain is a soluble TGF-β receptor.

Embodiment E115. The multi-specific chimeric polypeptide of embodiment E114, wherein the soluble TGF-β receptor is a soluble TGFβRII receptor.

Embodiment E116. The multi-specific chimeric polypeptide of any one of embodiments E113-E115, wherein the second target-binding domain binds specifically to IL-16.

Embodiment E117. The multi-specific chimeric polypeptide of embodiment E116, wherein the second antigen-binding domain comprises an antigen-binding domain that binds specifically to CD16.

Embodiment E118. The multi-chain chimeric polypeptide of embodiment E117, wherein the second antigen-binding domain comprises an scFv that binds specifically to CD16.

Embodiment E119. The multi-specific chimeric polypeptide of any one of embodiments E113-E115, wherein the second target-binding domain binds specifically to TGF-3.

Embodiment E120. The multi-specific chimeric polypeptide of embodiment E119, wherein the first target-binding domain is a soluble TGF-β receptor.

Embodiment E121. The multi-specific chimeric polypeptide of embodiment E120, wherein the soluble TGF-β receptor is a soluble TGFβRII receptor.

Embodiment E122. The multi-specific chimeric polypeptide of any one of embodiments E113-E118, wherein the second chimeric polypeptide further comprises an additional target-binding domain that binds specifically to TGF-β.

Embodiment E123. The multi-specific chimeric polypeptide of embodiment E122, wherein the first target-binding domain is a soluble TGF-β receptor.

Embodiment E124. The multi-specific chimeric polypeptide of embodiment E123, wherein the soluble TGF-β receptor is a soluble TGFβRII receptor.

Embodiment E125. The multi-chain chimeric polypeptide of any one of embodiments E1-E34, wherein the first target-binding domain and the second targeting-binding domain each independently bind specifically to a TGF-β or a receptor for CD137L.

Embodiment E126. The multi-chain chimeric polypeptide of embodiment E125, wherein the first target-binding domain binds specifically to TGF-β and the second target-binding domain binds specifically to a receptor for CD137L.

Embodiment E127. The multi-specific chimeric polypeptide of embodiment E126, wherein the first target-binding domain is a soluble TGF-β receptor.

Embodiment E128. The multi-specific chimeric polypeptide of embodiment E127, wherein the soluble TGF-β receptor is a soluble TGFβRII receptor.

Embodiment E129. The multi-chain chimeric polypeptide of embodiment E128, wherein the second target-binding domain comprises a soluble CD137L protein.

Embodiment E130. The multi-chain chimeric polypeptide of embodiment E129, wherein the soluble CD137L protein is a soluble human CD137L.

Embodiment E131. The multi-chain chimeric polypeptide of any one of embodiments E126-E130, wherein the second chimeric polypeptide further comprises an additional target-binding domain that binds specifically to TGF-β.

Embodiment E132. The multi-specific chimeric polypeptide of embodiment E131, wherein the additional target-binding domain is a soluble TGF-β receptor.

Embodiment E133. The multi-specific chimeric polypeptide of embodiment E132, wherein the soluble TGF-β receptor is a soluble TGFβRII receptor.

Embodiment E134. The multi-chain chimeric polypeptide of embodiment E1, wherein the first chimeric polypeptide comprises a sequence that is at least 80% identical to SEQ ID NO: 104.

Embodiment E135. The multi-chain chimeric polypeptide of embodiment E134, wherein the first chimeric polypeptide comprises a sequence that is at least 90% identical to SEQ ID NO: 104.

Embodiment E136. The multi-chain chimeric polypeptide of embodiment E135, wherein the first chimeric polypeptide comprises a sequence that is at least 95% identical to SEQ ID NO: 104.

Embodiment E137. The multi-chain chimeric polypeptide of embodiment E136, wherein the first chimeric polypeptide comprises SEQ ID NO: 104.

Embodiment E138. The multi-chain chimeric polypeptide of embodiment E137, wherein the first chimeric polypeptide comprises SEQ ID NO: 106.

Embodiment E139. The multi-chain chimeric polypeptide of any one of embodiments E1 and E134-E138, wherein the second chimeric polypeptide comprises a sequence that is at least 80% identical to SEQ ID NO: 129.

Embodiment E140. The multi-chain chimeric polypeptide of embodiment E139, wherein the second chimeric polypeptide comprises a sequence that is at least 90% identical to SEQ ID NO: 129.

Embodiment E141. The multi-chain chimeric polypeptide of embodiment E140, wherein the second chimeric polypeptide comprises a sequence that is at least 95% identical to SEQ ID NO: 129.

Embodiment E142. The multi-chain chimeric polypeptide of embodiment E141, wherein the second chimeric polypeptide comprises SEQ ID NO: 129.

Embodiment E143. The multi-chain chimeric polypeptide of embodiment E142, wherein the second chimeric polypeptide comprises SEQ ID NO: 131.

Embodiment E144. The multi-chain chimeric polypeptide of embodiment E1, wherein the first chimeric polypeptide comprises a sequence that is at least 80% identical to SEQ ID NO: 133.

Embodiment E145. The multi-chain chimeric polypeptide of embodiment E144, wherein the first chimeric polypeptide comprises a sequence that is at least 90% identical to SEQ ID NO: 133.

Embodiment E146. The multi-chain chimeric polypeptide of embodiment E145, wherein the first chimeric polypeptide comprises a sequence that is at least 95% identical to SEQ ID NO: 133.

Embodiment E147. The multi-chain chimeric polypeptide of embodiment E146, wherein the first chimeric polypeptide comprises SEQ ID NO: 133.

Embodiment E148. The multi-chain chimeric polypeptide of embodiment E147, wherein the first chimeric polypeptide comprises SEQ ID NO: 135.

Embodiment E149. The multi-chain chimeric polypeptide of any one of embodiments E1 and E144-E148, wherein the second chimeric polypeptide comprises a sequence that is at least 80% identical to SEQ ID NO: 137.

Embodiment E150. The multi-chain chimeric polypeptide of embodiment E149, wherein the second chimeric polypeptide comprises a sequence that is at least 90% identical to SEQ ID NO: 137.

Embodiment E151. The multi-chain chimeric polypeptide of embodiment E150, wherein the second chimeric polypeptide comprises a sequence that is at least 95% identical to SEQ ID NO: 137.

Embodiment E152. The multi-chain chimeric polypeptide of embodiment E151, wherein the second chimeric polypeptide comprises SEQ ID NO: 137.

Embodiment E153. The multi-chain chimeric polypeptide of embodiment E152, wherein the second chimeric polypeptide comprises SEQ ID NO: 139.

Embodiment E154. The multi-chain chimeric polypeptide of embodiment E1, wherein the first chimeric polypeptide comprises a sequence that is at least 80% identical to SEQ ID NO: 141.

Embodiment E155. The multi-chain chimeric polypeptide of embodiment E154, wherein the first chimeric polypeptide comprises a sequence that is at least 90% identical to SEQ ID NO: 141.

Embodiment E156. The multi-chain chimeric polypeptide of embodiment E155, wherein the first chimeric polypeptide comprises a sequence that is at least 95% identical to SEQ ID NO: 141.

Embodiment E157. The multi-chain chimeric polypeptide of embodiment E156, wherein the first chimeric polypeptide comprises SEQ ID NO: 141.

Embodiment E158. The multi-chain chimeric polypeptide of embodiment E157, wherein the first chimeric polypeptide comprises SEQ ID NO: 143.

Embodiment E159. The multi-chain chimeric polypeptide of any one of embodiments E1 and E154-E158, wherein the second chimeric polypeptide comprises a sequence that is at least 80% identical to SEQ ID NO: 145.

Embodiment E160. The multi-chain chimeric polypeptide of embodiment E159, wherein the second chimeric polypeptide comprises a sequence that is at least 90% identical to SEQ ID NO: 145.

Embodiment E161. The multi-chain chimeric polypeptide of embodiment E160, wherein the second chimeric polypeptide comprises a sequence that is at least 95% identical to SEQ ID NO: 145.

Embodiment E162. The multi-chain chimeric polypeptide of embodiment E161, wherein the second chimeric polypeptide comprises SEQ ID NO: 145.

Embodiment E163. The multi-chain chimeric polypeptide of embodiment E162, wherein the second chimeric polypeptide comprises SEQ ID NO: 147.

Embodiment E164. The multi-chain chimeric polypeptide of embodiment E1, wherein the first chimeric polypeptide comprises a sequence that is at least 80% identical to SEQ ID NO: 149.

Embodiment E165. The multi-chain chimeric polypeptide of embodiment E164, wherein the first chimeric polypeptide comprises a sequence that is at least 90% identical to SEQ ID NO: 149.

Embodiment E166. The multi-chain chimeric polypeptide of embodiment E165, wherein the first chimeric polypeptide comprises a sequence that is at least 95% identical to SEQ ID NO: 149.

Embodiment E167. The multi-chain chimeric polypeptide of embodiment E166, wherein the first chimeric polypeptide comprises SEQ ID NO: 149.

Embodiment E168. The multi-chain chimeric polypeptide of embodiment E167, wherein the first chimeric polypeptide comprises SEQ ID NO: 151.

Embodiment E169. The multi-chain chimeric polypeptide of any one of embodiments E1 and E164-E168, wherein the second chimeric polypeptide comprises a sequence that is at least 80% identical to SEQ ID NO: 153.

Embodiment E170. The multi-chain chimeric polypeptide of embodiment E169, wherein the second chimeric polypeptide comprises a sequence that is at least 90% identical to SEQ ID NO: 153.

Embodiment E171. The multi-chain chimeric polypeptide of embodiment E170, wherein the second chimeric polypeptide comprises a sequence that is at least 95% identical to SEQ ID NO: 153.

Embodiment E172. The multi-chain chimeric polypeptide of embodiment E171, wherein the second chimeric polypeptide comprises SEQ ID NO: 153.

Embodiment E173. The multi-chain chimeric polypeptide of embodiment E172, wherein the second chimeric polypeptide comprises SEQ ID NO: 155.

Embodiment E174. The multi-chain chimeric polypeptide of embodiment E1, wherein the first chimeric polypeptide comprises a sequence that is at least 80% identical to SEQ ID NO: 161.

Embodiment E175. The multi-chain chimeric polypeptide of embodiment E174, wherein the first chimeric polypeptide comprises a sequence that is at least 90% identical to SEQ ID NO: 161.

Embodiment E176. The multi-chain chimeric polypeptide of embodiment E175, wherein the first chimeric polypeptide comprises a sequence that is at least 95% identical to SEQ ID NO: 161.

Embodiment E177. The multi-chain chimeric polypeptide of embodiment E176, wherein the first chimeric polypeptide comprises SEQ ID NO: 161.

Embodiment E178. The multi-chain chimeric polypeptide of embodiment E177, wherein the first chimeric polypeptide comprises SEQ ID NO: 163.

Embodiment E179. The multi-chain chimeric polypeptide of any one of embodiments E1 and E174-E178, wherein the second chimeric polypeptide comprises a sequence that is at least 80% identical to SEQ ID NO: 165.

Embodiment E180. The multi-chain chimeric polypeptide of embodiment E179, wherein the second chimeric polypeptide comprises a sequence that is at least 90% identical to SEQ ID NO: 165.

Embodiment E181. The multi-chain chimeric polypeptide of embodiment E180, wherein the second chimeric polypeptide comprises a sequence that is at least 95% identical to SEQ ID NO: 165.

Embodiment E182. The multi-chain chimeric polypeptide of embodiment E181, wherein the second chimeric polypeptide comprises SEQ ID NO: 165.

Embodiment E183. The multi-chain chimeric polypeptide of embodiment E182, wherein the second chimeric polypeptide comprises SEQ ID NO: 167.

Embodiment E184. The multi-chain chimeric polypeptide of embodiment E1, wherein the first chimeric polypeptide comprises a sequence that is at least 80% identical to SEQ ID NO: 173.

Embodiment E185. The multi-chain chimeric polypeptide of embodiment E184, wherein the first chimeric polypeptide comprises a sequence that is at least 90% identical to SEQ ID NO: 173.

Embodiment E186. The multi-chain chimeric polypeptide of embodiment E185, wherein the first chimeric polypeptide comprises a sequence that is at least 95% identical to SEQ ID NO: 173.

Embodiment E187. The multi-chain chimeric polypeptide of embodiment E186, wherein the first chimeric polypeptide comprises SEQ ID NO: 173.

Embodiment E188. The multi-chain chimeric polypeptide of embodiment E187, wherein the first chimeric polypeptide comprises SEQ ID NO: 175.

Embodiment E189. The multi-chain chimeric polypeptide of any one of embodiments E1 and E184-E188, wherein the second chimeric polypeptide comprises a sequence that is at least 80% identical to SEQ ID NO: 189.

Embodiment E190. The multi-chain chimeric polypeptide of embodiment E189, wherein the second chimeric polypeptide comprises a sequence that is at least 90% identical to SEQ ID NO: 189.

Embodiment E191. The multi-chain chimeric polypeptide of embodiment E190, wherein the second chimeric polypeptide comprises a sequence that is at least 95% identical to SEQ ID NO: 189.

Embodiment E192. The multi-chain chimeric polypeptide of embodiment E191, wherein the second chimeric polypeptide comprises SEQ ID NO: 189.

Embodiment E193. The multi-chain chimeric polypeptide of embodiment E192, wherein the second chimeric polypeptide comprises SEQ ID NO: 191.

Embodiment E194. The multi-chain chimeric polypeptide of embodiment E1, wherein the first chimeric polypeptide comprises a sequence that is at least 80% identical to SEQ ID NO: 173.

Embodiment E195. The multi-chain chimeric polypeptide of embodiment E194, wherein the first chimeric polypeptide comprises a sequence that is at least 90% identical to SEQ ID NO: 173.

Embodiment E196. The multi-chain chimeric polypeptide of embodiment E195, wherein the first chimeric polypeptide comprises a sequence that is at least 95% identical to SEQ ID NO: 173.

Embodiment E197. The multi-chain chimeric polypeptide of embodiment E196, wherein the first chimeric polypeptide comprises SEQ ID NO: 173.

Embodiment E198. The multi-chain chimeric polypeptide of embodiment E197, wherein the first chimeric polypeptide comprises SEQ ID NO: 175.

Embodiment E199. The multi-chain chimeric polypeptide of any one of embodiments E1 and E194-E198, wherein the second chimeric polypeptide comprises a sequence that is at least 80% identical to SEQ ID NO: 177.

Embodiment E200. The multi-chain chimeric polypeptide of embodiment E199, wherein the second chimeric polypeptide comprises a sequence that is at least 90% identical to SEQ ID NO: 177.

Embodiment E201. The multi-chain chimeric polypeptide of embodiment E200, wherein the second chimeric polypeptide comprises a sequence that is at least 95% identical to SEQ ID NO: 177.

Embodiment E202. The multi-chain chimeric polypeptide of embodiment E201, wherein the second chimeric polypeptide comprises SEQ ID NO: 177.

Embodiment E203. The multi-chain chimeric polypeptide of embodiment E202, wherein the second chimeric polypeptide comprises SEQ ID NO: 179.

Embodiment E204. The multi-chain chimeric polypeptide of embodiment E1, wherein the first chimeric polypeptide comprises a sequence that is at least 80% identical to SEQ ID NO: 181.

Embodiment E205. The multi-chain chimeric polypeptide of embodiment E204, wherein the first chimeric polypeptide comprises a sequence that is at least 90% identical to SEQ ID NO: 181.

Embodiment E206. The multi-chain chimeric polypeptide of embodiment E205, wherein the first chimeric polypeptide comprises a sequence that is at least 95% identical to SEQ ID NO: 181.

Embodiment E207. The multi-chain chimeric polypeptide of embodiment E206, wherein the first chimeric polypeptide comprises SEQ ID NO: 181.

Embodiment E208. The multi-chain chimeric polypeptide of embodiment E207, wherein the first chimeric polypeptide comprises SEQ ID NO: 183.

Embodiment E209. The multi-chain chimeric polypeptide of any one of embodiments E1 and E204-E208, wherein the second chimeric polypeptide comprises a sequence that is at least 80% identical to SEQ ID NO: 185.

Embodiment E210. The multi-chain chimeric polypeptide of embodiment E209, wherein the second chimeric polypeptide comprises a sequence that is at least 90% identical to SEQ ID NO: 185.

Embodiment E211. The multi-chain chimeric polypeptide of embodiment E210, wherein the second chimeric polypeptide comprises a sequence that is at least 95% identical to SEQ ID NO: 185.

Embodiment E212. The multi-chain chimeric polypeptide of embodiment E211, wherein the second chimeric polypeptide comprises SEQ ID NO: 185.

Embodiment E213. The multi-chain chimeric polypeptide of embodiment E212, wherein the second chimeric polypeptide comprises SEQ ID NO: 187.

Embodiment E214. The multi-chain chimeric polypeptide of embodiment E1, wherein the first chimeric polypeptide comprises a sequence that is at least 80% identical to SEQ ID NO: 193.

Embodiment E215. The multi-chain chimeric polypeptide of embodiment E214, wherein the first chimeric polypeptide comprises a sequence that is at least 90% identical to SEQ ID NO: 193.

Embodiment E216. The multi-chain chimeric polypeptide of embodiment E215, wherein the first chimeric polypeptide comprises a sequence that is at least 95% identical to SEQ ID NO: 193.

Embodiment E217. The multi-chain chimeric polypeptide of embodiment E216, wherein the first chimeric polypeptide comprises SEQ ID NO: 193.

Embodiment E218. The multi-chain chimeric polypeptide of embodiment E217, wherein the first chimeric polypeptide comprises SEQ ID NO: 195.

Embodiment E219. The multi-chain chimeric polypeptide of any one of embodiments E1 and E214-E218, wherein the second chimeric polypeptide comprises a sequence that is at least 80% identical to SEQ ID NO: 197.

Embodiment E220. The multi-chain chimeric polypeptide of embodiment E219, wherein the second chimeric polypeptide comprises a sequence that is at least 90% identical to SEQ ID NO: 197.

Embodiment E221. The multi-chain chimeric polypeptide of embodiment E220, wherein the second chimeric polypeptide comprises a sequence that is at least 95% identical to SEQ ID NO: 197.

Embodiment E222. The multi-chain chimeric polypeptide of embodiment E221, wherein the second chimeric polypeptide comprises SEQ ID NO: 197.

Embodiment E223. The multi-chain chimeric polypeptide of embodiment E222, wherein the second chimeric polypeptide comprises SEQ ID NO: 199.

Embodiment E224. The multi-chain chimeric polypeptide of embodiment E1, wherein the first chimeric polypeptide comprises a sequence that is at least 80% identical to SEQ ID NO: 201.

Embodiment E225. The multi-chain chimeric polypeptide of embodiment E224, wherein the first chimeric polypeptide comprises a sequence that is at least 90% identical to SEQ ID NO: 201.

Embodiment E226. The multi-chain chimeric polypeptide of embodiment E225, wherein the first chimeric polypeptide comprises a sequence that is at least 95% identical to SEQ ID NO: 201.

Embodiment E227. The multi-chain chimeric polypeptide of embodiment E226, wherein the first chimeric polypeptide comprises SEQ ID NO: 201.

Embodiment E228. The multi-chain chimeric polypeptide of embodiment E227, wherein the first chimeric polypeptide comprises SEQ ID NO: 203.

Embodiment E229. The multi-chain chimeric polypeptide of any one of embodiments E1 and E224-E228, wherein the second chimeric polypeptide comprises a sequence that is at least 80% identical to SEQ ID NO: 205.

Embodiment E230. The multi-chain chimeric polypeptide of embodiment E229, wherein the second chimeric polypeptide comprises a sequence that is at least 90% identical to SEQ ID NO: 205.

Embodiment E231. The multi-chain chimeric polypeptide of embodiment E230, wherein the second chimeric polypeptide comprises a sequence that is at least 95% identical to SEQ ID NO: 205.

Embodiment E232. The multi-chain chimeric polypeptide of embodiment E231, wherein the second chimeric polypeptide comprises SEQ ID NO: 205.

Embodiment E233. The multi-chain chimeric polypeptide of embodiment E232, wherein the second chimeric polypeptide comprises SEQ ID NO: 207.

Embodiment E234. The multi-chain chimeric polypeptide of embodiment E1, wherein the first chimeric polypeptide comprises a sequence that is at least 80% identical to SEQ ID NO: 209.

Embodiment E235. The multi-chain chimeric polypeptide of embodiment E234, wherein the first chimeric polypeptide comprises a sequence that is at least 90% identical to SEQ ID NO: 209.

Embodiment E236. The multi-chain chimeric polypeptide of embodiment E235, wherein the first chimeric polypeptide comprises a sequence that is at least 95% identical to SEQ ID NO: 209.

Embodiment E237. The multi-chain chimeric polypeptide of embodiment E236, wherein the first chimeric polypeptide comprises SEQ ID NO: 209.

Embodiment E238. The multi-chain chimeric polypeptide of embodiment E237, wherein the first chimeric polypeptide comprises SEQ ID NO: 211.

Embodiment E239. The multi-chain chimeric polypeptide of any one of embodiments E1 and E234-E238, wherein the second chimeric polypeptide comprises a sequence that is at least 80% identical to SEQ ID NO: 213.

Embodiment E240. The multi-chain chimeric polypeptide of embodiment E239, wherein the second chimeric polypeptide comprises a sequence that is at least 90% identical to SEQ ID NO: 213.

Embodiment E241. The multi-chain chimeric polypeptide of embodiment E240, wherein the second chimeric polypeptide comprises a sequence that is at least 95% identical to SEQ ID NO: 213.

Embodiment E242. The multi-chain chimeric polypeptide of embodiment E241, wherein the second chimeric polypeptide comprises SEQ ID NO: 213.

Embodiment E243. The multi-chain chimeric polypeptide of embodiment E242, wherein the second chimeric polypeptide comprises SEQ ID NO: 215.

Embodiment E244. The multi-chain chimeric polypeptide of any one of embodiments E1-E133, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment E245. The multi-chain chimeric polypeptide of embodiment E244, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment E246. The multi-chain chimeric polypeptide of any one of embodiments E1-E133, wherein the first chimeric polypeptide further comprises one or more additional target-binding domains at the N-terminal and/or C-terminal end of the first chimeric polypeptide.

Embodiment E247. The multi-chain chimeric polypeptide of embodiment E246, wherein at least one of the one or more additional target-binding domains directly abuts the first domain of the pair of affinity domains in the first chimeric polypeptide.

Embodiment E248. The multi-chain chimeric polypeptide of embodiment E246, wherein the first chimeric polypeptide further comprises a linker sequence between the at least one of the one or more additional target-binding domains and the first domain of the pair of affinity domains.

Embodiment E249. The multi-chain chimeric polypeptide of embodiment E246, wherein the at least one of the one or more additional target-binding domains directly abuts the first target-binding domain in the first chimeric polypeptide.

Embodiment E250. The multi-chain chimeric polypeptide of embodiment E246, wherein the first chimeric polypeptide further comprises a linker sequence between the at least one of the one or more additional target-binding domains and the first target-binding domain.

Embodiment E251. The multi-chain chimeric polypeptide of embodiment E246, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment E252. The multi-chain chimeric polypeptide of embodiment E251, wherein the at least one additional target-binding domain of the one or more additional target-binding domains disposed at the N-terminus directly abuts the first target-binding domain or the first domain of the pair of affinity domains in the first chimeric polypeptide.

Embodiment E253. The multi-chain chimeric polypeptide of embodiment E251, wherein the first chimeric polypeptide further comprises a linker sequence disposed between the at least one additional target-binding domain and the first target-binding domain or the first domain of the pair of affinity domains in the first chimeric polypeptide.

Embodiment E254. The multi-chain chimeric polypeptide of embodiment E251, wherein the at least one additional target-binding domain of the one or more additional target-binding domains disposed at the C-terminus directly abuts the first target-binding domain or the first domain of the pair of affinity domains in the first chimeric polypeptide.

Embodiment E255. The multi-chain chimeric polypeptide of embodiment E251, wherein the first chimeric polypeptide further comprises a linker sequence disposed between the at least one additional target-binding domain and the first target-binding domain or the first domain of the pair of affinity domains in the first chimeric polypeptide.

Embodiment E256. The multi-chain chimeric polypeptide of embodiment E251, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment E257. The multi-chain chimeric polypeptide of embodiment E251, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment E258. The multi-chain chimeric polypeptide of any one of embodiments E44-E46, E57-E59, E76-E78, E96-E98, E109-E111, E122-E124, and E131-E133, wherein the second chimeric polypeptide further comprises the additional target-binding domain at the N-terminal end or the C-terminal end of the second chimeric polypeptide.

Embodiment E259. The multi-chain chimeric polypeptide of embodiment E258, wherein the additional target-binding domain directly abuts the second domain of the pair of affinity domains in the second chimeric polypeptide.

Embodiment E260. The multi-chain chimeric polypeptide of embodiment E258, wherein the second chimeric polypeptide further comprises a linker sequence between the additional target-binding domain and the second domain of the pair of affinity domains in the second chimeric polypeptide.

Embodiment E261. The multi-chain chimeric polypeptide of embodiment E258, wherein the additional target-binding domain directly abuts the second target-binding domain in the second chimeric polypeptide.

Embodiment E262. The multi-chain chimeric polypeptide of embodiment E258, wherein the second chimeric polypeptide further comprises a linker sequence between the additional target-binding domain and the second target-binding domain in the second chimeric polypeptide.

Embodiment E263. A composition comprising any of the multi-chain chimeric polypeptides of embodiments E1-E262.

Embodiment E264. The composition of embodiment E263, wherein the composition is a pharmaceutical composition.

Embodiment E265. A kit comprising at least one dose of the composition of embodiment E263 or E264.

Embodiment E266. A method of stimulating an immune cell, the method comprising:

contacting an immune cell with an effective amount of any of the multi-chain chimeric polypeptides of embodiments E1-E262 or the composition of embodiment E263 or E264.

Embodiment E267. The method of embodiment E266, wherein the immune cell is contacted in vitro.

Embodiment E268. The method of embodiment E267, wherein the immune cell was previously obtained from a subject.

Embodiment E269. The method of embodiment E268, wherein the method further comprises obtaining the immune cell from the subject prior to the contacting step.

Embodiment E270. The method of embodiment E266, wherein the immune cell is contacted in vivo.

Embodiment E271. The method of any one of embodiments E266-E270, wherein the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a $CD8^+$ T cell, a $CD4^+$ T cell, a natural killer T cell, a mast cell, a macrophage, a neutrophil, a dendritic cell, a basophil, an eosinophil, and a natural killer cell.

Embodiment E272. The method of any one of embodiments E266-E271, wherein the immune cell has previously been genetically modified to express a chimeric antigen receptor or a recombinant T-cell receptor.

Embodiment E273. The method of any one of embodiments E266-E271, wherein the method further comprises, after the contacting step, introducing into the immune cell a nucleic acid encoding a chimeric antigen-receptor or a recombinant T-cell receptor.

Embodiment E274. The method of any one of embodiments E266-E273, wherein the method further comprises administering the immune cell to a subject in need thereof.

Embodiment E275. The method of embodiment E274, wherein the subject has been identified or diagnosed as having age-related disease or condition.

Embodiment E276. The method of embodiment E275, wherein the age-related disease or condition is selected from the group consisting of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. Embodiment E277. The method of embodiment E274, wherein the subject has been identified or diagnosed as having a cancer.

Embodiment E278. The method of embodiment E277, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment E279. The method of embodiment E274, wherein the subject has been diagnosed or identified as having an infectious disease.

Embodiment E280. The method of embodiment E279, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment E281. A method of inducing or increasing proliferation of an immune cell, the method comprising:

contacting an immune cell with an effective amount of any of the multi-chain chimeric polypeptides of embodiments E1-E262 or the composition of embodiment E263 or E264.

Embodiment E282. The method of embodiment E281, wherein the immune cell is contacted in vitro.

Embodiment E283. The method of embodiment E282, wherein the immune cell was previously obtained from a subject.

Embodiment E284. The method of embodiment E283, wherein the method further comprises obtaining the immune cell from the subject prior to the contacting step.

Embodiment E285. The method of embodiment E281, wherein the immune cell is contacted in vivo.

Embodiment E286. The method of any one of embodiments E281-E285, wherein the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell.

Embodiment E287. The method of any one of embodiments E281-E286, wherein the immune cell has previously been genetically modified to express a chimeric antigen receptor or a recombinant T-cell receptor.

Embodiment E288. The method of any one of embodiments E281-E286, wherein the method further comprises, after the contacting step, introducing into the immune cell a nucleic acid encoding a chimeric antigen-receptor or a recombinant T-cell receptor.

Embodiment E289. The method of any one of embodiments E281-E288, wherein the method further comprises administering the immune cell to a subject in need thereof.

Embodiment E290. The method of embodiment E289, wherein the subject has been identified or diagnosed as having an age-related disease or condition.

Embodiment E291. The method of embodiment E290, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment E292. The method of embodiment E289, wherein the subject has been identified or diagnosed as having a cancer.

Embodiment E293. The method of embodiment E292, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment E294. The method of embodiment E289, wherein the subject has been diagnosed or identified as having an infectious disease.

Embodiment E295. The method of embodiment E289, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment E296. A method of inducing differentiation of an immune cell into a memory or memory-like immune cell, the method comprising:

contacting an immune cell with an effective amount of any of the multi-chain chimeric polypeptides of embodiments E1-E262 or the composition of embodiment E263 or E264.

Embodiment E297. The method of embodiment E296, wherein the immune cell is contacted in vitro.

Embodiment E298. The method of embodiment E297, wherein the immune cell was previously obtained from a subject.

Embodiment E299. The method of embodiment E298, wherein the method further comprises obtaining the immune cell from the subject prior to the contacting step.

Embodiment E300. The method of embodiment E296, wherein the immune cell is contacted in vivo.

Embodiment E301. The method of any one of embodiments E296-E300, wherein the immune cell is selected from the group consisting of: an immature thymocyte, a peripheral blood lymphocyte, a naïve T cell, a pluripotent Th cell precursor, a lymphoid progenitor cell, a Treg cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell.

Embodiment E302. The method of any one of embodiments E296-E301, wherein the immune cell has previously been genetically modified to express a chimeric antigen receptor or a recombinant T-cell receptor.

Embodiment E303. The method of any one of embodiments E296-E301, wherein the method further comprises, after the contacting step, introducing into the immune cell a nucleic acid encoding a chimeric antigen-receptor or a recombinant T-cell receptor.

Embodiment E304. The method of any one of embodiments E296-E303, wherein the method further comprises administering the immune cell to a subject in need thereof.

Embodiment E305. The method of embodiment E304, wherein the subject has been identified or diagnosed as having an age-related disease or condition.

Embodiment E306. The method of embodiment E305, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment E307. The method of embodiment E304, wherein the subject has been identified or diagnosed as having a cancer.

Embodiment E308. The method of embodiment E307, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment E309. The method of embodiment E304, wherein the subject has been diagnosed or identified as having an infectious disease.

Embodiment E310. The method of embodiment E309, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment E311. A method of killing a cancer cell, an infected cell, or a senescent cell in a subject in need thereof, the method comprising administering to the subject a therapeutically effective amount of any of the multi-chain chimeric polypeptides of embodiments E1-E262 or the composition of embodiment E263 or E264.

Embodiment E312. The method of embodiment E311, wherein the subject has been identified or diagnosed as having a cancer.

Embodiment E313. The method of embodiment E312, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment E314. The method of embodiment E311, wherein the subject has been identified or diagnosed as having an aging-related disease or condition.

Embodiment E315. The method of embodiment E314, wherein the aging-related disease or condition is selected from the group consisting of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment E316. A method of treating a subject in need thereof, the method comprising administering to the subject a therapeutically effective amount of any of the multi-chain chimeric polypeptides of embodiments E1-E262 or the composition of embodiment E263 or E264.

Embodiment E317. The method of embodiment E316, wherein the subject has been identified or diagnosed as having a cancer or infectious disease.

Embodiment E318. The method of embodiment E317, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment E319. The method of embodiment E316, wherein the subject has been identified or diagnosed as having age-related disease or condition.

Embodiment E320. The method of embodiment E319, wherein the age-related disease or condition is selected from the group consisting of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment E321. The method of embodiment E316, wherein the subject has been diagnosed or identified as having an infectious disease.

Embodiment E322. The method of embodiment E321, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment E323. Nucleic acid encoding any of the multi-chain chimeric polypeptides of any one of embodiments E1-E262.

Embodiment E324. A vector comprising the nucleic acid of embodiment E323.

Embodiment E325. The vector of embodiment E324, wherein the vector is an expression vector.

Embodiment E326. A cell comprising the nucleic acid of embodiment E323 or the vector of embodiment E324 or E325.

Embodiment E327. A method of producing a multi-chain chimeric polypeptide, the method comprising:

culturing the cell of embodiment E326 in a culture medium under conditions sufficient to result in the production of the multi-chain chimeric polypeptide; and recovering the multi-chain chimeric polypeptide from the cell and/or the culture medium.

Embodiment E328. A multi-chain chimeric polypeptide produced by the method of embodiment E327.

Embodiment E329. The multi-chain chimeric polypeptide of embodiment E8, wherein the soluble human tissue factor domain comprises a sequence that is at least 80% identical to SEQ ID NO: 3.

Embodiment E330. The multi-chain chimeric polypeptide of embodiment E329, wherein the soluble human tissue factor domain comprises a sequence that is at least 90% identical to SEQ ID NO: 3.

Embodiment E331. The multi-chain chimeric polypeptide of embodiment E330, wherein the soluble human tissue factor domain comprises a sequence that is at least 95% identical to SEQ ID NO: 3.

Embodiment E332. The multi-chain chimeric polypeptide of embodiment E331, wherein the soluble human tissue factor domain comprises a sequence that is 100% identical to SEQ ID NO: 3.

Embodiment E333. The multi-chain chimeric polypeptide of embodiment E8, wherein the soluble human tissue factor domain comprises a sequence that is at least 80% identical to SEQ ID NO: 4.

Embodiment E334. The multi-chain chimeric polypeptide of embodiment E333, wherein the soluble human tissue factor domain comprises a sequence that is at least 90% identical to SEQ ID NO: 4.

Embodiment E335. The multi-chain chimeric polypeptide of embodiment E334, wherein the soluble human tissue factor domain comprises a sequence that is at least 95% identical to SEQ ID NO: 4.

Embodiment E336. The multi-chain chimeric polypeptide of embodiment E335, wherein the soluble human tissue factor domain comprises a sequence that is 100% identical to SEQ ID NO: 4.

F. Exemplary Embodiments

Embodiment F1. A multi-chain chimeric polypeptide comprising:

(a) a first chimeric polypeptide comprising:
  (i) a first target-binding domain;
  (ii) a linker domain; and
  (iii) a first domain of a pair of affinity domains;
(b) a second chimeric polypeptide comprising:
  (i) a second domain of a pair of affinity domains; and
  (ii) a second target-binding domain,
  wherein the first chimeric polypeptide and the second chimeric polypeptide associate through the binding of the first domain and the second domain of the pair of affinity domains.

Embodiment F2. The multi-chain chimeric polypeptide of embodiment F1, wherein the first target-binding domain and the linker domain directly abut each other in the first chimeric polypeptide.

Embodiment F3. The multi-chain chimeric polypeptide of embodiment F1, wherein the first chimeric polypeptide further comprises a linker sequence between the first target-binding domain and the linker domain in the first chimeric polypeptide.

Embodiment F4. The multi-chain chimeric polypeptide of any one of embodiments F1-F3, wherein the linker domain and the first domain of the pair of affinity domains directly abut each other in the first chimeric polypeptide.

Embodiment F5. The multi-chain chimeric polypeptide of any one of embodiments F1-F3, wherein the first chimeric polypeptide further comprises a linker sequence between the linker domain and the first domain of the pair of affinity domains in the first chimeric polypeptide.

Embodiment F6. The multi-chain chimeric polypeptide of any one of embodiments F1-F5, wherein the second domain of the pair of affinity domains and the second target-binding domain directly abut each other in the second chimeric polypeptide.

Embodiment F7. The multi-chain chimeric polypeptide of any one of embodiments F1-F5, wherein the second chimeric polypeptide further comprises a linker sequence between the second domain of the pair of affinity domains and the second target-binding domain in the second chimeric polypeptide.

Embodiment F8. The multi-chain chimeric polypeptide of any one of embodiments F1-F7, wherein the first target-binding domain and the second target-binding domain bind specifically to the same antigen.

Embodiment F9. The multi-chain chimeric polypeptide of embodiment F8, wherein the first target-binding domain and the second target-binding domain bind specifically to the same epitope.

Embodiment F10. The multi-chain chimeric polypeptide of embodiment F9, wherein the first target-binding domain and the second target-binding domain comprise the same amino acid sequence.

Embodiment F11. The multi-chain chimeric polypeptide of any one of embodiments F1-F7, wherein the first target-binding domain and the second target-binding domain bind specifically to different antigens.

Embodiment F12. The multi-chain chimeric polypeptide of any one of embodiments F1-F11, wherein one or both of the first target-binding domain and the second target-binding domain is an antigen-binding domain.

Embodiment F13. The multi-chain chimeric polypeptide of embodiment F12, wherein the first target-binding domain and the second target-binding domain are each antigen-binding domains.

Embodiment F14. The multi-chain chimeric polypeptide of embodiment F12 or F13, wherein the antigen-binding domain comprises a scFv or a single domain antibody.

Embodiment F15. The multi-chain chimeric polypeptide of any one of embodiments F1-F14, wherein one or both of the first target-binding domain and the second target-binding domain bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment F16. The multi-chain chimeric polypeptide of any one of embodiments F1-F14, wherein one or both of the first target-binding domain and the second target-binding domain is a soluble interleukin or cytokine protein.

Embodiment F17. The multi-chain chimeric polypeptide of embodiment F16, wherein the soluble interleukin, cytokine, or ligand protein is selected from the group consisting of: IL-1, IL-2, IL-3, IL-7, IL-8, IL-10, IL-12, IL-15, IL-17, IL-18, IL-21, PDGF-DD, SCF, and FLT3L.

Embodiment F18. The multi-chain chimeric polypeptide of any one of embodiments F1-F14, wherein one or both of the first target-binding domain and the second target-binding domain is a soluble interleukin or cytokine receptor.

Embodiment F19. The multi-chain chimeric polypeptide of embodiment F18, wherein the soluble receptor is a soluble TGF-β receptor II (TGF-β RII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, or a soluble CD28.

Embodiment F20. The multi-chain chimeric polypeptide of any one of embodiments F1-F19, wherein the first chimeric polypeptide further comprises one or more additional target-binding domain(s), where at least one of the one or more target-binding domain(s) is positioned between the linker domain and the first domain of the pair of affinity domains.

Embodiment F21. The multi-chain chimeric polypeptide of embodiment F20, wherein the first chimeric polypeptide further comprises a linker sequence between the linker domain and the at least one of the one or more target antigen-binding domain(s), and/or a linker sequence between the at least one of the one or more target antigen-binding domain(s) and the first domain of the pair of affinity domains.

Embodiment F22. The multi-chain chimeric polypeptide of any one of embodiments F1-F19, wherein the first chimeric polypeptide further comprises one or more additional target-binding domains at the N-terminal and/or C-terminal end of the first chimeric polypeptide.

Embodiment F23. The multi-chain chimeric polypeptide of embodiment F22, wherein at least one of the one or more additional target-binding domains directly abuts the first domain of the pair of affinity domains in the first chimeric polypeptide.

Embodiment F24. The multi-chain chimeric polypeptide of embodiment F22, wherein the first chimeric polypeptide further comprises a linker sequence between the at least one of the one or more additional target-binding domains and the first domain of the pair of affinity domains.

Embodiment F25. The multi-chain chimeric polypeptide of embodiment F22, wherein the at least one of the one or more additional target-binding domains directly abuts the first target-binding domain in the first chimeric polypeptide.

Embodiment F26. The multi-chain chimeric polypeptide of embodiment F22, wherein the first chimeric polypeptide further comprises a linker sequence between the at least one of the one or more additional target-binding domains and the first target-binding domain.

Embodiment F27. The multi-chain chimeric polypeptide of embodiment F22, wherein at least one of the one or more additional target-binding domains is disposed at the N- and/or C-terminus of the first chimeric polypeptide, and at least one of the one or more additional target-binding domains is positioned between the linker domain and the first domain of the pair of affinity domains in the first chimeric polypeptide.

Embodiment F28. The multi-chain chimeric polypeptide of embodiment F27, wherein the at least one additional target-binding domain of the one or more additional target-binding domains disposed at the N-terminus directly abuts the first target-binding domain or the first domain of the pair of affinity domains in the first chimeric polypeptide.

Embodiment F29. The multi-chain chimeric polypeptide of embodiment F27, wherein the first chimeric polypeptide further comprises a linker sequence disposed between the at least one additional target-binding domain and the first target-binding domain or the first domain of the pair of affinity domains in the first chimeric polypeptide.

Embodiment F30. The multi-chain chimeric polypeptide of embodiment F27, wherein the at least one additional target-binding domain of the one or more additional target-binding domains disposed at the C-terminus directly abuts the first target-binding domain or the first domain of the pair of affinity domains in the first chimeric polypeptide.

Embodiment F31. The multi-chain chimeric polypeptide of embodiment F27, wherein the first chimeric polypeptide further comprises a linker sequence disposed between the at least one additional target-binding domain and the first target-binding domain or the first domain of the pair of affinity domains in the first chimeric polypeptide.

Embodiment F32. The multi-chain chimeric polypeptide of embodiment F27, wherein the at least one of the one or more additional target-binding domains positioned between the linker domain and the first domain of the pair of affinity domains, directly abuts the linker domain and/or the first domain of the pair of affinity domains.

Embodiment F33. The multi-chain chimeric polypeptide of embodiment F27, wherein the first chimeric polypeptide further comprises a linker sequence disposed (i) between the linker domain and the at least one of the one or more additional target-binding domains positioned between the linker domain and the first domain of the pair of affinity domains, and/or (ii) between the first domain of the pair of affinity domains and the at least one of the one or more additional target-binding domains positioned between the linker domain and the first domain of the pair of affinity domains.

Embodiment F34. The multi-chain chimeric polypeptide of any one of embodiments F1-F33, wherein the second chimeric polypeptide further comprises one or more additional target-binding domains at the N-terminal end and/or the C-terminal end of the second chimeric polypeptide.

Embodiment F35. The multi-chain chimeric polypeptide of embodiment F34, wherein at least one of the one or more additional target-binding domains directly abuts the second domain of the pair of affinity domains in the second chimeric polypeptide.

Embodiment F36. The multi-chain chimeric polypeptide of embodiment F34, wherein the second chimeric polypeptide further comprises a linker sequence between at least one of the one or more additional target-binding domains and the second domain of the pair of affinity domains in the second chimeric polypeptide.

Embodiment F37. The multi-chain chimeric polypeptide of embodiment F34, wherein at least one of the one or more additional target-binding domains directly abuts the second target-binding domain in the second chimeric polypeptide.

Embodiment F38. The multi-chain chimeric polypeptide of embodiment F34, wherein the second chimeric polypeptide further comprises a linker sequence between at least one of the one or more additional target-binding domains and the second target-binding domain in the second chimeric polypeptide.

Embodiment F39. The multi-chain chimeric polypeptide of any one of embodiments F20-F38, wherein two or more of the first target-binding domain, the second target-binding domain, and the one or more additional target-binding domains bind specifically to the same antigen.

Embodiment F40. The multi-chain chimeric polypeptide of embodiment F39, wherein two or more of the first target-binding domain, the second target-binding domain, and the one or more additional target-binding domains bind specifically to the same epitope.

Embodiment F41. The multi-chain chimeric polypeptide of embodiment F40, wherein two or more of the first target-binding domain, the second target-binding domain, and the one or more additional target-binding domains comprise the same amino acid sequence.

Embodiment F42. The multi-chain chimeric polypeptide of embodiment F39, wherein the first target-binding domain, the second target-binding domain, and the one or more additional target-binding domains each bind specifically to the same antigen.

Embodiment F43. The multi-chain chimeric polypeptide of embodiment F42, wherein the first target-binding domain, the second target-binding domain, and the one or more additional target-binding domains each bind specifically to the same epitope.

Embodiment F44. The multi-chain chimeric polypeptide of embodiment F43, wherein the first target-binding domain, the second target-binding domain, and the one or more additional target-binding domains each comprise the same amino acid sequence.

Embodiment F45. The multi-chain chimeric polypeptide of any one of embodiments F20-F38, wherein the first target-binding domain, the second target-binding domain, and the one or more additional target-binding domains bind specifically to different antigens.

Embodiment F46. The multi-chain chimeric polypeptide of any one of embodiments F20-F45, wherein one or more of the first target-binding domain, the second target-binding domain, and the one or more target-binding domains is an antigen-binding domain.

Embodiment F47. The multi-chain chimeric polypeptide of embodiment F46, wherein the first target-binding domain, the second target-binding domain, and the one or more additional target-binding domains are each an antigen-binding domain.

Embodiment F48. The multi-chain chimeric polypeptide of embodiment F46 or F47, wherein the antigen-binding domain comprises a scFv.

Embodiment F49. The multi-chain chimeric polypeptide of any one of embodiments F20-F48, wherein one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD3, and a receptor for CD28.

Embodiment F50. The multi-chain chimeric polypeptide of any one of embodiments F20-F48, wherein one or more of the first target-binding domain, the second target-binding domain, and the one or more additional target-binding domains is a soluble interleukin or cytokine protein.

Embodiment F52. The multi-chain chimeric polypeptide of any one of embodiments F20-F48, wherein one or more of the first target-binding domain, the second target-binding domain, and the one or more additional target-binding domains is a soluble interleukin or cytokine receptor.

Embodiment F53. The multi-chain chimeric polypeptide of embodiment F52, wherein the soluble receptor is a soluble TGF-β receptor II (TGF-β RII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

Embodiment F54. The multi-chain chimeric polypeptide of any one of embodiments F1-F53, wherein the first chimeric polypeptide further comprises a peptide tag at the N-terminal end or the C-terminal end of the first chimeric polypeptide.

Embodiment F55. The multi-chain chimeric polypeptide of any one of embodiments F1-F53, wherein the second chimeric polypeptide further comprises a peptide tag at the N-terminal end or the C-terminal end of the second chimeric polypeptide.

Embodiment F56. The multi-chain chimeric polypeptide of any one of embodiments F1-F55, wherein the linker domain is a soluble tissue factor domain.

Embodiment F57. The multi-chain chimeric polypeptide of embodiment F56, wherein the soluble tissue factor domain is a soluble human tissue factor domain.

Embodiment F58. The multi-chain chimeric polypeptide of embodiment F57, wherein the soluble human tissue factor domain comprises a sequence that is at least 80% identical to SEQ ID NO: 1.

Embodiment F59. The multi-chain chimeric polypeptide of embodiment F58, wherein the soluble human tissue factor domain comprises a sequence that is at least 90% identical to SEQ ID NO: 1.

Embodiment F60. The multi-chain chimeric polypeptide of embodiment F59, wherein the soluble human tissue factor domain comprises a sequence that is at least 95% identical to SEQ ID NO: 1.

Embodiment F61. The multi-chain chimeric polypeptide of any one of embodiments F57-F60, wherein the soluble human tissue factor domain does not comprise one or more of:

- a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment F62. The multi-chain chimeric polypeptide of embodiment F61, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment F63. The multi-chain chimeric polypeptide of any one of embodiments F56-F62, wherein the soluble tissue factor domain is not capable of binding to Factor VIIa.

Embodiment F64. The multi-chain chimeric polypeptide of any one of embodiments F56-F63, wherein the soluble tissue factor domain does not convert inactive Factor X into Factor Xa.

Embodiment F65. The multi-chain chimeric polypeptide of any one of embodiments F56-F64, wherein the multi-chain chimeric polypeptide does not stimulate blood coagulation in a mammal.

Embodiment F66. The multi-chain chimeric polypeptide of any one of embodiments F1-F55, wherein the linker domain is selected from the group consisting of: a kappa chain and a lambda chain.

Embodiment F67. The multi-chain chimeric polypeptide of any one of embodiments F1-F66, wherein the pair of affinity domains is a sushi domain from an alpha chain of human IL-15 receptor (IL15Rα) and a soluble IL-15.

Embodiment F68. The multi-chain chimeric polypeptide of embodiment F67, wherein the soluble IL15 has a D8N or D8A amino acid substitution.

Embodiment F69. The multi-chain chimeric polypeptide of embodiment F67 or F68, wherein the human IL15Rα is a mature full-length IL15Rα.

Embodiment F70. The multi-chain chimeric polypeptide of any one of embodiments F1-F66, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment F71. The multi-chain chimeric polypeptide of any one of embodiments F1-F70, wherein the first chimeric polypeptide and/or the second chimeric polypeptide further comprises a signal sequence at its N-terminal end.

Embodiment F72. The multi-chain chimeric polypeptide of any one of embodiments F1-F70, wherein the first chimeric polypeptide and/or the second chimeric polypeptide lacks a signal sequence at its N-terminal end.

Embodiment F73. A composition comprising any of the multi-chain chimeric polypeptides of embodiments F1-F72.

Embodiment F74. The composition of embodiment F73, wherein the composition is a pharmaceutical composition.

Embodiment F75. A kit comprising at least one dose of the composition of embodiment F73 or F74.

Embodiment F76. Nucleic acid encoding any of the multi-chain chimeric polypeptides of any one of embodiments F1-F72.

Embodiment F77. A vector comprising the nucleic acid of embodiment F76.

Embodiment F78. The vector of embodiment F77, wherein the vector is an expression vector.

Embodiment F79. A cell comprising the nucleic acid of embodiment F76 or the vector of embodiment F77 or F78.

Embodiment F80. A method of producing a multi-chain chimeric polypeptide, the method comprising:

culturing the cell of embodiment F79 in a culture medium under conditions sufficient to result in the production of the multi-chain chimeric polypeptide; and recovering the multi-chain chimeric polypeptide from the cell and/or the culture medium.

Embodiment F81. A multi-chain chimeric polypeptide produced by the method of embodiment F80.

What is claimed is:

1. A nucleic acid encoding a multi-chain chimeric polypeptide, wherein the multi-chain chimeric polypeptide comprises:

(a) a first chimeric polypeptide comprising:
   (i) a first target-binding domain;
   (ii) a soluble tissue factor domain comprising a sequence that is at least 90% identical to SEQ ID NO: 1; and
   (iii) a first domain of a pair of affinity domains comprising a sequence that is at least 90% identical to SEQ ID NO: 14; and (b) a second chimeric polypeptide comprising:
   (i) a second domain of a pair of affinity domains comprising a sequence that is at least 90% identical to SEQ ID NO: 28; and
   (ii) a second target-binding domain, wherein:

the first chimeric polypeptide and the second chimeric polypeptide associate through the binding of the first domain and the second domain of the pair of affinity domains; and the first target-binding domain and the second target-binding domain each comprise a soluble TGF-β receptor II (TGF-βRII) and each comprise a sequence that is at least 90% identical to SEQ ID NO: 85.

2. The nucleic acid of claim 1, wherein the first target-binding domain and the soluble tissue factor domain directly abut each other in the first chimeric polypeptide.

3. The nucleic acid of claim 1, wherein the first chimeric polypeptide further comprises a linker sequence between the first target-binding domain and the soluble tissue factor domain in the first chimeric polypeptide.

4. The nucleic acid of claim 1, wherein the soluble tissue factor domain and the first domain of the pair of affinity domains directly abut each other in the first chimeric polypeptide.

5. The nucleic acid of claim 1, wherein the first chimeric polypeptide further comprises a linker sequence between the soluble tissue factor domain and the first domain of the pair of affinity domains in the first chimeric polypeptide.

6. The nucleic acid of claim 1, wherein the second domain of the pair of affinity domains and the second target-binding domain directly abut each other in the second chimeric polypeptide.

7. The nucleic acid of claim 1, wherein the second chimeric polypeptide further comprises a linker sequence between the second domain of the pair of affinity domains and the second target-binding domain in the second chimeric polypeptide.

8. The nucleic acid of claim 1, wherein the first chimeric polypeptide further comprises one or more additional target-binding domain(s).

9. The nucleic acid of claim 1, wherein the second chimeric polypeptide further comprises one or more additional target-binding domain(s).

10. The nucleic acid of claim 1, wherein the soluble human tissue factor domain comprises a sequence that is at least 95% identical to SEQ ID NO: 1.

11. The nucleic acid of claim 1, wherein the first target-binding domain comprises a sequence that is at least 95% identical to SEQ ID NO: 85.

12. The nucleic acid of claim 1, wherein the first target-binding domain comprises a sequence that is at least 99% identical to SEQ ID NO: 85.

13. The nucleic acid of claim 1, wherein the first target-binding domain comprises a sequence of SEQ ID NO: 85.

14. The nucleic acid of claim 1, wherein:

the first chimeric polypeptide comprises a sequence of SEQ ID NO: 133; and the second chimeric polypeptide comprises a sequence of SEQ ID NO: 177.

15. The nucleic acid of claim 14, wherein:

the first chimeric polypeptide comprises a sequence of SEQ ID NO: 135; and the second chimeric polypeptide comprises a sequence of SEQ ID NO: 92.

16. The nucleic acid of claim 1, wherein the second target-binding domain comprises a sequence that is at least 95% identical to SEQ ID NO: 85.

17. The nucleic acid of claim 1, wherein the second target-binding domain comprises a sequence that is at least 99% identical to SEQ ID NO: 85.

18. The nucleic acid of claim 1, wherein the second target-binding domain comprises a sequence of SEQ ID NO: 85.

19. The nucleic acid of claim 1, wherein:

the first and second target-binding domain each comprise a sequence that is at least 95% identical to SEQ ID NO: 85;

the soluble tissue factor domain is at least 95% identical to SEQ ID NO: 1;

the first domain of the pair of affinity domains comprises a sequence that is at least 95% identical to SEQ ID NO: 14; and the second domain of the pair of affinity domains comprises a sequence that is at least 95% identical to SEQ ID NO: 28.

20. The nucleic acid of claim 1, wherein the first domain of the pair of affinity domains comprises a sequence that is at least 95% identical to SEQ ID NO: 14, and the second domain of the pair of affinity domains comprises a sequence that is at least 95% identical to SEQ ID NO: 28.

21. The nucleic acid of claim 1, wherein:

the first and second target-binding domain each comprise a sequence that is at least 99% identical to SEQ ID NO: 85;

the soluble tissue factor domain is at least 99% identical to SEQ ID NO: 1;

the first domain of the pair of affinity domains comprises a sequence that is at least 99% identical to SEQ ID NO: 14; and the second domain of the pair of affinity domains comprises a sequence that is at least 99% identical to SEQ ID NO: 28.

22. The nucleic acid of claim 1, wherein the first domain of the pair of affinity domains comprises a sequence that is at least 99% identical to SEQ ID NO: 14, and the second domain of the pair of affinity domains comprises a sequence that is at least 99% identical to SEQ ID NO: 28.

23. The nucleic acid of claim 1, wherein the first chimeric polypeptide comprises a sequence that is at least 90% identical to SEQ ID NO: 133, and the second chimeric polypeptide comprises a sequence that is at least 90% identical to SEQ ID NO: 177.

24. The nucleic acid of claim 1, wherein the first chimeric polypeptide comprises a sequence that is at least 95% identical to SEQ ID NO: 133, and the second chimeric polypeptide comprises a sequence that is at least 95% identical to SEQ ID NO: 177.

25. The nucleic acid of claim 1, wherein the first chimeric polypeptide comprises a sequence that is at least 99% identical to SEQ ID NO: 133, and the second chimeric polypeptide comprises a sequence that is at least 99% identical to SEQ ID NO: 177.

26. A vector comprising the nucleic acid of claim 1.

27. A first vector and a second vector that together comprise the nucleic acid of claim 1, wherein the first vector comprises a nucleic acid encoding the first chimeric polypeptide, and wherein the second vector comprises a nucleic acid encoding the second chimeric polypeptide.

28. A cell comprising the nucleic acid of claim 1.

29. A method of producing a multi-chain chimeric polypeptide, the method comprising:

culturing the cell of claim 28 in a culture medium under conditions sufficient to result in the production of the multi-chain chimeric polypeptide; and recovering the multi-chain chimeric polypeptide from the cell and/or the culture medium.

* * * * *